US012747241B2

(12) United States Patent
Guckian et al.

(10) Patent No.: US 12,747,241 B2
(45) Date of Patent: Sep. 29, 2026

(54) COMPOUNDS FOR TARGETING DEGRADATION OF BRUTON'S TYROSINE KINASE

(71) Applicants: BIOGEN MA INC., Cambridge, MA (US); C4 THERAPEUTICS, INC., Watertown, MA (US)

(72) Inventors: Kevin M. Guckian, Northborough, MA (US); Eric Stefan, Watertown, MA (US); Corey Don Anderson, Brighton, MA (US); Jae Young Ahn, Somerville, MA (US); Morgan Welzel O'Shea, Waltham, MA (US); Jeremy L Yap, Sudbury, MA (US); Xinpeng Cheng, Watertown, MA (US); Brian T. Hopkins, Newton, MA (US); Isaac Marx, Arlington, MA (US); Marta Nevalainen, Holliston, MA (US)

(73) Assignee: BIOGEN MA INC., Cambridge, MA (US)

( * ) Notice: Subject to any disclaimer, the term of this patent is extended or adjusted under 35 U.S.C. 154(b) by 401 days.

(21) Appl. No.: 18/289,438

(22) PCT Filed: May 5, 2022

(86) PCT No.: PCT/US2022/027888

§ 371 (c)(1),
(2) Date: Nov. 3, 2023

(87) PCT Pub. No.: WO2022/235945

PCT Pub. Date: Nov. 10, 2022

(65) Prior Publication Data

US 2024/0287076 A1 Aug. 29, 2024

Related U.S. Application Data

(60) Provisional application No. 63/184,439, filed on May 5, 2021.

(51) Int. Cl.
*C07D 487/04* (2006.01)
*A61K 31/53* (2006.01)

(52) U.S. Cl.
CPC ............ *C07D 487/04* (2013.01); *A61K 31/53* (2013.01)

(58) Field of Classification Search
CPC .................................................... C07D 487/04
See application file for complete search history.

(56) References Cited

U.S. PATENT DOCUMENTS 12,391,697 B2 * 8/2025 Marx .................. C07D 519/00
2018/0194762 A1 7/2018 Atallah et al.

(Continued)

FOREIGN PATENT DOCUMENTS

JP 2023-523130 A 6/2023
WO 2013/010380 A1 1/2013

(Continued)

OTHER PUBLICATIONS

Ott et al., Pyrrolo[2,1-f][1,2,4]triazines: From C-nucleosides to kinases and back again, the remarkable journey of a versatile nitrogen heterocycle. Bioorg Med Chem Lett. Sep. 15, 2017;27(18):4238-4246.

(Continued)

*Primary Examiner* — Rei Tsang Shiao
(74) *Attorney, Agent, or Firm* — McCarter & English, LLP; Xin Zhang; James M. Alburger

(57) ABSTRACT

This disclosure relates to compounds of Formula (A): BTK-L-DSM (A) or a pharmaceutically acceptable salt thereof, wherein DSM is a degradation signaling moiety that is covalently attached to the linker L, L is a linker that covalently attaches BTK to DSM, and BTK is a Btk binding moiety represented by Formula (I) or Formula (II) that is covalently attached to linker L: in which all of the variables are as defined in the application. Compounds or pharmaceutically acceptable salts thereof as described herein are capable of activating the selective ubiqitination of Btk proteins via the ubiquitin-proteasome pathways (UPP) and cause degradation of Btk proteins. The present disclosure also provides methods of treating disorders responsive to modulation of Btk activity and/or degradation of Btk with at least one compound described herein.

BTK—L—DSM, (A)

(I)

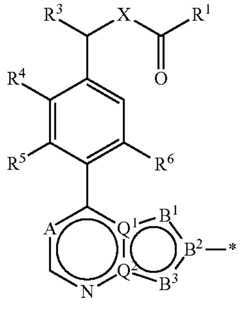

(II)

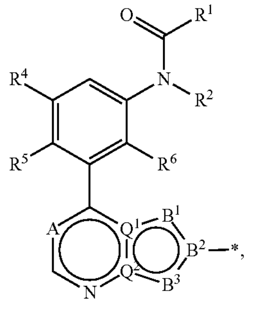

20 Claims, No Drawings

(56) References Cited

U.S. PATENT DOCUMENTS

| | | | | |
|---|---|---|---|---|
| 2022/0344443 | A1 | 10/2022 | Yamazaki et al. | |
| 2023/0025892 | A1* | 1/2023 | Marx .................. | C07D 519/00 |
| 2023/0137118 | A1 | 5/2023 | Dan et al. | |
| 2023/0167118 | A1† | 6/2023 | Wang | |

FOREIGN PATENT DOCUMENTS

| | | | |
|---|---|---|---|
| WO | 2017/019442 | A1 | 2/2017 |
| WO | 2017/197046 | A1 | 11/2017 |
| WO | 2019/186343 | A1 | 10/2019 |
| WO | 2019/186358 | A1 | 10/2019 |
| WO | 2021/053495 | A1 | 3/2021 |
| WO | 2021/087086 | A1 | 5/2021 |
| WO | 2021/087112 | A1 | 5/2021 |
| WO | 2021/219070 | A1 | 11/2021 |
| WO | 2021/243421 | A1 | 12/2021 |
| WO | 2022/060836 | A1 | 3/2022 |
| WO | 2022/235725 | A1 | 11/2022 |
| WO | 2022/235864 | A1 | 11/2022 |
| WO | 2022/235870 | A1 | 11/2022 |

OTHER PUBLICATIONS

International Search Report and Written Opinion for Application No. PCT/US2022/027888, dated Aug. 24, 2022, 12 pages.

* cited by examiner
† cited by third party

COMPOUNDS FOR TARGETING DEGRADATION OF BRUTON'S TYROSINE KINASE

RELATED APPLICATION

This application is a 35 U.S.C. § 371 national stage filing of International Application No. PCT/US2022/027888, filed on May 5, 2022, which in turn claims the benefit of the filing date, under 35 U.S.C. § 119 (e), of U.S. Provisional Application No. 63/184,439, filed on May 5, 2021. The entire contents of each of the foregoing applications are incorporated herein by reference.

TECHNICAL FIELD

Provided are certain agents that target the degradation of Bruton's tyrosine kinase (Btk), and methods of making and using such agents.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. There are over 600 E3 ubiquitin ligases which facilitate the ubiquitination of different proteins in vivo, which can be divided into four families: HECT-domain E3s, U-box E3s, monomeric RING E3s and multi-subunit E3s.

It is known that the ubiquitin-proteasome pathway (UPP) can be harnessed for therapeutic intervention by using chimeric compounds capable of activating the ubiquitination of a Target Protein, where the chimeric compound comprises a Target Protein binding element that is covalently linked to ubiquitination recognition element. Such chimeric compounds that are capable of binding a Target Protein and a ubiquitin ligase may cause the Target Protein to be selectively degraded via the UPP. The discovery, for example, that thalidomide binds to the cereblon E3 ubiquitin ligase has led to research investigating the incorporatation of thalidomide and certain derivatives into chimeric compounds for the targeted destruction of proteins.

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell finvolved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Because Tec kinases play critical roles in both B-cell and T-cell signaling, Tec kinases are targets of interest for autoimmune disorders.

Given that Btk plays an important role in B-cell signalling, there is a great need to develop chimeric compounds capable of activating the ubiquitination and degradation of Btk proteins. It is an object of the present disclosure to provide new compounds, methods, compositions and methods of manufacture that are useful for the selective degradation of Btk protein in vivo via the ubiquitin-proteasome pathway (UPP).

SUMMARY

A first aspect of the present disclosure is a compound of Formula (A):

BTK-L-DSM (A), or a pharmaceutically acceptable salt thereof, wherein:

DSM is a degradation signaling moiety that is covalently attached to the linker L, L is a linker that covalently attaches BTK to DSM; and BTK is a Btk binding moiety represented by Formula (I) or Formula (II) that is covalently attached to linker L:

(I)

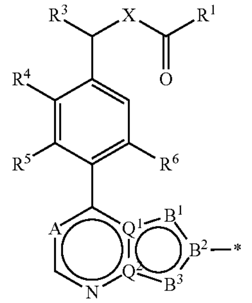

(II)

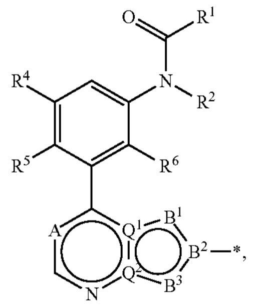

or a pharmaceutically acceptable salt thereof, wherein:

A is selected from $CR^7$ and N;

$B^1$ is selected from $CR^8$, N, and $NR^8$;

$B^2$ is C or N;

$B^3$ is selected from $CR^8$, N, $NR^8$ and S;

one of $Q^1$ and $Q^2$ is N, and the other one is C; or both of $Q^1$ and $Q^2$ are C;

X is selected from O and $NR^2$;

$R^1$ is selected from —$N(R^{1a})_2$, $C_{1-10}$ alkyl, 3- to 7-membered monocyclic carbocyclyl, 3- to 7-membered monocyclic heterocyclyl, 7- to 10-membered bicyclic carbocyclyl, and 7- to 10-membered bicyclic heterocyclyl; wherein the $C_{1-10}$ alkyl, 3- to 7-membered monocyclic carbocyclyl, 3- to 7-membered monocyclic heterocyclyl, 7- to 10-membered bicyclic carbocyclyl, and 7- to 10-membered bicyclic heterocyclyl represented by $R^1$ are each optionally substituted with one or more (e.g., 1 to 6, 1 to 3, or 1, 2, 3, 4, 5, or 6) $R^{10}$;

$R^{1a}$, for each occurrence, is independently selected from H, $C_{1-6}$ alkyl, $C_{2-6}$ alkenyl, $C_{2-6}$alkynyl, wherein the $C_{1-6}$ alkyl, $C_{2-6}$ alkenyl, and $C_{2-6}$ alkynyl represented by $R^{1a}$ are each optionally substituted with one or more (e.g., 1 to 6, 1 to 3, or 1, 2, 3, 4, 5, or 6) $R^{10}$;

or alternatively two $R^{1a}$, taken together with their intervening atoms, form a 3- to 7-membered monocyclic heterocyclyl which is optionally substituted with one or more (e.g., 1 to 6, 1 to 3, or 1, 2, 3, 4, 5, or 6) $R^{10}$;

$R^{10}$, for each occurrence, is independently selected from H, halogen, —$OR^{10a}$, —$S(O)_2R^{10a}$, —CN, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{10}$ are each optionally substituted with one or more (e.g., 1 to 6, 1 to 3, or 1, 2, 3, 4, 5, or 6) $R^{15}$;

or alternatively two $R^{10}$, taken together with their intervening atoms, form a Ring A that is selected from 3- to 7-membered monocyclic carbocyclyl, 3- to 7-membered monocyclic heterocyclyl, 7- to 10-membered bicyclic carbocyclyl, and 7- to 10-membered bicyclic heterocyclyl, wherein the Ring A is optionally substituted with one or more (e.g., 1 to 6, 1 to 3, or 1, 2, 3, 4, 5, or 6) $R^{15}$;

$R^{10a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl;

$R^{15}$, for each occurrence, is independently selected from $C_{1-6}$ alkyl, halogen, —CN, 3- to 7-membered monocyclic carbocyclyl and —$OR^{15a}$; wherein the $C_{1-6}$ alkyl and 3- to 7-membered monocyclic carbocyclyl represented by $R^{15}$ is optionally substituted with one or more (e.g., 1 to 6, 1 to 3, or 1, 2, 3, 4, 5, or 6) $R^{15a}$; or two $R^{15}$, taken together with their intervening atom, form 3- to 7-membered monocyclic carbocyclyl or 4- to 6-membered monocyclic heterocyclyl;

$R^{15a}$ is selected from H, halogen and $C_{1-6}$ alkyl optionally substituted with at least one halogen;

$R^2$ is selected from H, $C_{1-6}$ alkyl, $C_{2-6}$ alkenyl, and $C_{2-6}$ alkynyl;

$R^3$ is selected from H, $C_{1-6}$ alkyl, $C_{2-6}$ alkenyl, $C_{2-6}$ alkynyl, —$C(O)N(R^{3a})_2$, —$C(O)OR^{3a}$, and —$C(O)R^{3a}$, wherein the $C_{1-6}$ alkyl, $C_{2-6}$ alkenyl, and $C_{2-6}$alkynyl represented by $R^3$ are each optionally substituted with one or more (e.g., 1 to 6, 1 to 3, or 1, 2, 3, 4, 5, or 6) $R^{30}$;

$R^{3a}$, for each occurrence, is independently selected from H, $C_{1-6}$ alkyl, $C_{2-6}$ alkenyl, $C_{2-6}$ alkynyl, wherein the $C_{1-6}$ alkyl, $C_{2-6}$ alkenyl, and $C_{2-6}$ alkynyl represented by $R^{3a}$ are each optionally substituted with one or more (e.g., 1 to 6, 1 to 3, or 1, 2, 3, 4, 5, or 6) $R^{30}$;

$R^{30}$, for each occurrence, is independently selected from halogen, —$OR^{30a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl;

$R^{30a}$ is selected from H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl;

or alternatively $R^1$ and $R^2$, taken together with their intervening atoms, form a Ring B that is selected from 3- to 7-membered monocyclic heterocyclyl and 7- to 14-membered bicyclic heterocyclyl; wherein the Ring B is optionally substituted with one or more (e.g., 1 to 6, 1 to 3, or 1, 2, 3, 4, 5, or 6) $R^{200}$;

or alternatively $R^2$ and $R^3$, taken together with their intervening atoms, form a Ring C that is selected from 3- to 7-membered monocyclic heterocyclyl and 7- to 10-membered bicyclic heterocyclyl; wherein the Ring C is optionally substituted with one or more (e.g., 1 to 6, 1 to 3, or 1, 2, 3, 4, 5, or 6) $R^{200}$;

$R^{200}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, —CN, —$C(O)R^{200a}$, —$C(O)_2R^{200a}$; —$C(O)N(R^{200a})_2$, —$N(R^{200a})_2$, —$N(R^{200a})C(O)R^{200a}$, —$N(R^{200a})C(O)_2R^{200a}$, —$N(R^{200a})C(O)N(R^{200a})_2$, —$N(R^{200a})S(O)_2R^{200a}$, —$OR^{200a}$, —$OC(O)R^{200a}$, —$OC(O)N(R^{200a})_2$, —$SR^{200a}$, —$S(O)R^{200a}$, —$S(O)_2R^{200a}$, —$S(O)N(R^{200a})_2$, —$S(O)_2N(R^{200a})_2$; wherein the $C_{1-6}$alkyl, $C_{2-6}$alkenyl, $C_{2-6}$alkynyl, 3- to 7-membered monocyclic carbocyclyl, 4- to 6-membered monocyclic heterocyclyl represented by $R^{200}$ are each optionally substituted with one or more (e.g., 1 to 6, 1 to 3, or 1, 2, 3, 4, 5, or 6) $R^{250}$; or two $R^{200}$ taken together with their intervening atom, form 4- to 6-membered monocyclic heterocyclyl or 3- to 7-membered monocyclic carbocyclyl, each of which is optionally substituted with one or more (e.g., 1 to 6, 1 to 3, or 1, 2, 3, 4, 5, or 6) $R^{250}$;

$R^{200a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{200a}$ are each optionally substituted with one or more (e.g., 1 to 6, 1 to 3, or 1, 2, 3, 4, 5, or 6) $R^{250}$;

$R^{250}$, for each occurrence, is independently selected from $C_{1-6}$ alkyl, halogen and —$OR^{250a}$;

$R^{250a}$ is H or $C_{1-6}$ alkyl;

$R^4$ is selected from H, $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, —$NO_2$, —CN, —$OR^{4a}$, —$SR^{4a}$, —$N(R^{4a})_2$, —$C(O)R^{4a}$, —$C(O)OR^{4a}$, —$S(O)R^{4a}$, —$S(O)_2R^{4a}$, —$C(O)N(R^{4a})_2$, —$SO_2N(R^{4a})_2$, —$OC(O)R^{4a}$, —$N(R)C(O)R^{4a}$, —$N(R)C(O)OR^{4a}$, —$N(R)SO_2R^{4a}$, and —$OC(O)N(R^{4a})_2$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^4$ are each optionally substituted with one or more (e.g., 1 to 6, 1 to 3, or 1, 2, 3, 4, 5, or 6) $R^{40}$;

$R^{4a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{4a}$ are each optionally substituted with one or more (e.g., 1 to 6, 1 to 3, or 1, 2, 3, 4, 5, or 6) $R^{40}$;

$R^{40}$, for each occurrence, is independently selected from halogen, —$OR^{40a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{40}$ are each optionally substituted with one or more (e.g., 1 to 6, 1 to 3, or 1, 2, 3, 4, 5, or 6) $R^{45}$;

$R^{40a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl are each optionally substituted with one or more (e.g., 1 to 6, 1 to 3, or 1, 2, 3, 4, 5, or 6) $R^{45}$;

$R^{45}$, for each occurrence, is independently selected from $C_{1-6}$ alkyl, halogen and —$OR^{45a}$;

$R^{45a}$ is H or $C_{1-6}$ alkyl;

or alternatively $R^3$ and $R^4$, taken together with their intervening atoms form Ring D that is selected from 5- to 7-membered monocyclic carbocyclyl and 5- to 7-membered monocyclic heterocyclyl having 1-2 heteroatoms independently selected from O, N and S; wherein the Ring D is optionally substituted with one or more (e.g., 1 to 6, 1 to 3, or 1, 2, 3, 4, 5, or 6) $R^{300}$;

$R^{300}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, —$C(O)R^{300a}$, —$OR^{300a}$, and —$S(O)_2R^{300a}$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300}$ are each optionally substituted with one or more (e.g., 1 to 6, 1 to 3, or 1, 2, 3, 4, 5, or 6) $R^{350}$;

$R^{300a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300a}$ are each optionally substituted with one or more (e.g., 1 to 6, 1 to 3, or 1, 2, 3, 4, 5, or 6) $R^{350}$;

$R^{350}$, for each occurrence, is independently selected from $C_{1-6}$ alkyl, halogen, —CN, —$C(O)R^{350a}$, —$C(O)N(R^{350a})_2$, —$C(R^{350a})_2N(R^{350a})_2$, and —$OR^{350a}$;

$R^{350a}$, for each occurrence, is independently H or $C_{1-6}$ alkyl optionally substituted with one to three halogen, or two $R^{350a}$ together with the N atom from which they are attached form 4 to 6-membered monocyclic heterocyclyl with 1-2 heteroatoms selected from N and O;

$R^5$ is selected from H, $C_{1-6}$ alkyl, $C_{2-6}$ alkenyl, $C_{2-6}$ alkynyl, halogen, and —$OR^{15a}$; wherein the $C_{1-6}$ alkyl, $C_{2-6}$ alkenyl, and $C_{2-6}$ alkynyl represented by $R^5$ are optionally substituted with one or more (e.g., 1 to 6, 1 to 3, or 1, 2, 3, 4, 5, or 6) halogen;

$R^{5a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl represented by $R^{5a}$ are each optionally substituted with one or more (e.g., 1 to 6, 1 to 3, or 1, 2, 3, 4, 5, or 6) halogen;

$R^6$ is selected from H, $C_{1-6}$ alkyl, $C_{2-6}$ alkenyl, $C_{2-6}$ alkynyl, halogen, —$OR^{6a}$; wherein the $C_{1-6}$ alkyl, $C_{2-6}$ alkenyl and $C_{2-6}$ alkynyl represented by $R^6$ are each optionally substituted with one or more (e.g., 1 to 6, 1 to 3, or 1, 2, 3, 4, 5, or 6) halogen;

$R^{6a}$ is H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl and 4- to 6-membered monocyclic heterocyclyl represented by $R^{6a}$ are each optionally substituted with one or more (e.g., 1 to 6, 1 to 3, or 1, 2, 3, 4, 5, or 6) halogen;

$R^7$ is selected from H, $C_{1-6}$ alkyl, $C_{2-6}$ alkenyl, $C_{2-6}$ alkynyl, —CN, —$OR^{7a}$, —$C(O)N(R^{7a})_2$, —$C(O)OR^{7a}$, and —$C(O)R^{7a}$; wherein the $C_{1-6}$ alkyl, $C_{2-6}$ alkenyl, and $C_{2-6}$ alkynyl represented by $R^7$ are each optionally substituted one or more (e.g., 1 to 6, 1 to 3, or 1, 2, 3, 4, 5, or 6) $R^{70}$;

$R^{7a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{7a}$ are each optionally substituted with one or more (e.g., 1 to 6, 1 to 3, or 1, 2, 3, 4, 5, or 6) $R^{70}$;

$R^{70}$, for each occurrence, is independently selected from halogen, —$OR^{70a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$alkyl, $C_{2-6}$alkenyl, $C_{2-6}$alkynyl, 3- to 7-membered monocyclic carbocyclyl and 4- to 6-membered monocyclic heterocyclyl represented by $R^{70}$ are optionally substituted with one or more (e.g., 1 to 6, 1 to 3, or 1, 2, 3, 4, 5, or 6) $R^{75}$;

$R^{70a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{70a}$ are each optionally substituted one or more (e.g., 1 to 6, 1 to 3, or 1, 2, 3, 4, 5, or 6) $R^{75}$;

$R^{75}$, for each occurrence, is independently selected from $C_{1-6}$ alkyl, halogen and —$OR^{75a}$;

$R^{75a}$ is H or $C_{1-6}$ alkyl;

$R^8$, for each occurrence, is independently selected from H, halogen, $C_{1-6}$ alkyl, $C_{2-6}$ alkenyl, $C_{2-6}$ alkynyl, —CN, —$C(O)R^{8a}$, —$C(O)_2R^{8a}$, —$C(O)N(R^{8a})_2$, —$N(R^{8a})_2$, —$N(R^{8a})C(O)R^{8a}$, —$N(R^{8a})C(O)_2R^{8a}$, —$N(R^{8a})C(O)N(R^{8a})_2$, —$N(R^{8a})S(O)_2R^{8a}$, —$OR^{8a}$, —$OC(O)R^{8a}$, —$OC(O)N(R^{8a})_2$, —$SR^{8a}$, —$S(O)R^{8a}$, —$S(O)_2R^{8a}$, —$S(O)N(R^{8a})_2$, —$S(O)_2N(R^{8a})_2$, 3- to 7-membered monocyclic carbocyclyl, 4- to 6-membered monocyclic heterocyclyl, and 7- to 10-membered bicyclic heterocyclyl; wherein the $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl and 7- to 10-membered bicyclic heterocyclyl represented by $R^8$ are each optionally substituted with one or more (e.g., 1 to 6, 1 to 3, or 1, 2, 3, 4, 5, or 6) $R^{80}$;

$R^{8a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{8a}$ are each optionally substituted with one or more (e.g., 1 to 6, 1 to 3, or 1, 2, 3, 4, 5, or 6) $R^{80}$; or two $R^{8a}$, taken together with their intervening atom, form 4- to 6-membered monocyclic heterocyclyl optionally substituted with one or more (e.g., 1 to 6, 1 to 3, or 1, 2, 3, 4, 5, or 6) $R^{80}$;

$R^{80}$, for each occurrence, is independently selected from halogen, $C_{1-6}$ alkyl, $C_{2-6}$ alkenyl, $C_{2-6}$ alkynyl, —CN, —$C(O)R^{80a}$, —$C(O)_2R^{80a}$, —$C(O)N(R^{80a})_2$, —$N(R^{80a})_2$, —$N(R^{80a})C(O)R^{80a}$, —$N(R^{80a})C(O)_2R^{80a}$, —$N(R^{80a})C(O)N(R^{80a})_2$, —$N(R^{80a})S(O)_2R^{80a}$, —$OR^{8a}$, —$OC(O)R^{80a}$, —$OC(O)N(R^{80a})_2$, —$SR^{8a}$, —$S(O)R^{80a}$, $S(O)_2R^{80a}$, —$S(O)N(R^{80a})_2$, —$S(O)_2N(R^{80a})_2$, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{80}$ are each optionally substituted with one or more (e.g., 1 to 6, 1 to 3, or 1, 2, 3, 4, 5, or 6) $R^{85}$; or two $R^{80}$ together the carbon atom from which they are attached form an oxo group (—C(=O)—);

$R^{80a}$, for each occurrence, is independently selected from H, $C_{1-6}$ alkyl, $C_{2-6}$ alkenyl, $C_{2-6}$alkynyl, 3- to 6-membered monocyclic carbocyclyl, and 4- to 6-membered monocyclic heterocyclyl; wherein the $C_{1-6}$ alkyl, $C_{2-6}$ alkenyl, $C_{2-6}$alkynyl, 3- to 6-membered monocyclic carbocyclyl, and 4- to 6-membered monocyclic heterocyclyl represented by $R^{80a}$ are each optionally substituted with one or more (e.g., 1 to 6, 1 to 3, or 1, 2, 3, 4, 5, or 6) $R^{85}$;

$R^{85}$, for each occurrence, is independently $C_{1-6}$ alkyl, halogen and —$OR^{85a}$;

$R^{85a}$ is H or $C_{1-6}$ alkyl; and

~~~* represents a bond to the linker L.

In another aspect, the present disclosure provides methods of treating a disorder responsive to modulation of Btk activity and/or degradation of Btk in a subject comprising administering to the subject an effective amount of at least one compound described herein. The present disclosure also includes the use of at least one compound described herein, or a pharmaceutically acceptable salt thereof, for the manufacture of a medicament for the treatment of a disorder responsive to modulation of Btk activity and/or degradation of Btk. Also provided are compounds described herein, or pharmaceutically acceptable salts thereof, for use in treating a disorder responsive to modulation of Btk activity and/or degradation of Btk. Methods of making the compounds described herein and any synthetic intermediates are also included in the present disclosure.

Other features or advantages will be apparent from the following detailed description of several embodiments, and also from the appended claims.

## DETAILED DESCRIPTION

Compounds or pharmaceutically acceptable salts thereof as described herein are capable of activating the selective ubiqitination of Btk proteins via the ubiquitin-proteasome pathways (UPP) and cause degradation of Btk proteins. In some embodiments, compounds or pharmaceutically acceptable salts thereof as described herein can modulate Btk activities.

### I. Definitions

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

As used herein, the term "alkyl" refers to a fully saturated branched or unbranched hydrocarbon moiety. In some embodiments, the alkyl comprises 1 to 20 carbon atoms, 1 to 10 carbon atoms, 1 to 8 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. In some embodiments, alkenyl groups have 2 to 20 carbon atoms, 2 to 10 carbon atoms or 2-6 carbon atoms. The alkenyl group may contain 1, 2 or 3 carbon-carbon double bonds, or more. Examples of alkenyl groups include ethenyl, n-propenyl, iso-propenyl, n-but-2-enyl, n-hex-3-enyl and the like.

"Alkynyl" refers to an unsaturated hydrocarbon group which may be linear or branched and has at least one carbon-carbon triple bond. In some embodiments, alkynyl groups have 2 to 20 carbon atoms, 2 to 10 carbon atoms or 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

In some embodiments, the number of carbon atoms in a group is specified herein by the prefix "$C_{x-xx}$", wherein x and xx are integers. For example, "$C_{1-4}$alkyl" is an alkyl group which has from 1 to 4 carbon atoms.

As used herein, the term "carbocyclyl", "carbocycle" or "carbocyclic ring" refers to saturated or unsaturated monocyclic or bicyclic hydrocarbon groups of 3-10, 3-8, 3-7, 3-5, 3-6, 4-6, 5-7 or 7-10 carbon atoms. The term "carbocyclyl" encompasses cycloalkyl groups and aromatic groups (i.e., aryl). The term "cycloalkyl" refers to completely saturated monocyclic or bicyclic or spiro hydrocarbon groups of 3-7 carbon atoms, 3-6 carbon atoms, or 5-7 carbon atoms. In some embodiments, cycloalkyl is a 3- to 6-membered monocyclic cycloalkyl. Exemplary bicyclic carbocyclyl groups
~~~

include bicyclo[2.1.1]hexyl, bicyclo[2.2.1]heptyl, bicyclo [2.2.1]heptenyl, 6,6-dimethylbicyclo-[3.1.1]heptyl, 2,6,6-trimethylbicyclo[3.1.1]heptyl, spiro[2.2]pentanyl, and spiro [3.3]heptanyl.

In one embodiment, the carbocyclyl is a 7- to 10-membered bicyclic carbocyclyl. Exemplary 7- to 10-membered bicyclic carbocyclyls include, but are not limited to, bicyclo [2.2.1]heptyl, bicyclo[2.2.1]heptenyl, 6,6-dimethylbicyclo [3.1.1]heptyl, 2,6,6-trimethylbicyclo[3.1.1]heptyl, spiro [3.3]heptanyl, spiro[2.5]octanyl, bicyclo[3.3.0]octanyl, bicyclo[2.2.2]octanyl, bicyclo[3.3.1] nonanyl, bicyclo [3.3.2]decanyl, decalinyl, naphthyl and indanyl. In one embodiment, the carbocyclyl is a 3- to 7-membered monocyclic carbocyclyl. Exemplary 3- to 7-membered monocyclic carbocyclyls include, but are not limited to, cyclopropyl, cyclobutyl, cyclopentyl, cyclohexyl, cycloheptyl, cyclopropenyl, cyclobutenyl, cyclopentenyl, cyclohexenyl, cycloheptenyl, cyclobutadienyl, cyclopentadienyl, cyclohexadienyl, cycloheptadienyl, phenyl and cycloheptatrienyl. In one embodiment, the carbocyclyl is a 5- to 7-membered monocyclic carbocyclyl, such as but not limited to cyclopentyl, cyclohexyl, cycloheptyl, cyclopentenyl, cyclohexenyl, cycloheptenyl, cyclopentadienyl, cyclohexadienyl, cycloheptadienyl, phenyl or cycloheptatrienyl. In another embodiment, the carbocyclyl is a 4- to 6-membered monocyclic carbocyclyl, such as but not limited to cyclobutyl, cyclopentyl, cyclohexyl, cyclobutenyl, cyclopentenyl, cyclohexenyl, cyclobutadienyl, cyclopentadienyl, cyclohexadienyl or phenyl. In another embodiment, the carbocyclyl is a 3- to 6-membered carbocyclyl, such as but not limited to cyclopropyl, cyclobutyl, cyclopentyl, cyclohexyl, cyclopropenyl, cyclobutenyl, cyclopentenyl, cyclohexenyl, cyclobutadienyl, cyclopentadienyl, cyclohexadienyl or phenyl. In another embodiment, the carbocyclyl is a 3- to 6-membered monocyclic cycloalkyl, such as but not limited to cyclopropyl, cyclobutyl, cyclopentyl or cyclohexyl. In yet another embodiment, the carbocyclyl is phenyl. In yet another embodiment, the carbocyclyl is cyclopropyl.

"Halogen" or "halo" may be fluoro, chloro, bromo or iodo.

As used herein, the term "heterocyclyl" refers to a saturated or unsaturated, monocyclic or polycyclic (e.g., bicyclic or tricyclic) ring system (e.g., fused, bridged or spiro ring systems) which has from 3- to 14-ring members, or in particular 3- to 8-ring members, 3- to 7-ring members, 3- to 6-ring members or 5- to 7-ring members, 4- to 7-ring members or 4- to 6-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. The heterocyclyl group can be attached to the rest of a compound of the invention at a heteroatom or a carbon atom. The term azacyclic refers to a non-aromatic heterocyclyl, which has at least one nitrogen ring atom. The examples of azacyclic include, but are not limited to, azetidine, pyrrolidine, piperidine, piperazine, and morpholine.

In one embodiment, a heterocyclyl is a 3- to 7-membered monocyclic heterocyclyl (saturated or partially unsaturated (i.e., non-aromatic)) having 1-2 heteroatoms selected from O, S and N. Examples of 3- to 7-membered monocyclic heterocyclyl include, but are not limited to, aziridinyl, oxiranyl, thirranyl, oxaziridinyl, oxazepanyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, and dihydropyranyl. In one embodiment, a heterocyclyl is a 5 to 7-membered monocyclic heterocyclyl (saturated or partially unsaturated). Examples include pyrrolidinyl, tetrahydrofuranyl, thiolanyl, imidazolidinyl, pyrazolidinyl, oxazolidinyl, oxazepanyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, and dihydropyranyl.

In another embodiment, a heterocyclyl is a 4- to 7-membered monocyclic heterocyclyl (saturated or partially unsaturated) having 1-2 heteroatoms selected from O, S and N. Examples of a 4- to 7-membered monocyclic heterocyclic include, but are not limited to azetidinyl, diazetidinyl, oxetanyl, thietanyl, pyrrolidinyl, tetrahydrofuranyl, thiolanyl, imidazolidinyl, pyrazolidinyl, oxazolidinyl, oxazepanyl, oxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, and dihydropyranyl.

In one embodiment, a heterocyclyl is a 4- to 6-membered monocyclic heterocyclyl (saturated or partially unsaturated) having 1-2 heteroatoms selected from O, S and N. Examples of a 4- to 6-membered monocyclic heterocyclic include, but are not limited to azetidinyl, diazetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl.

In another embodiment, a heterocyclyl is a saturated 4- to 6-membered monocyclic heterocyclyl having 1-2 heteroatoms selected from O, S and N. Examples of saturated 4- to 6-membered monocyclic heterocyclic ring systems include, but are not limited to azetidinyl, diazetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, and dithiinyl. In one embodiment, a saturated 4- to 6-membered monocyclic heterocyclyl is azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, or dioxinyl. In another embodiment, a saturated 4- to 6-membered monocyclic heterocyclyl is oxetanyl, tetrahydrofuranyl, or tetrahydropyranyl.

In one embodiment, a heterocyclyl is a 4- to 6-membered monocyclic heterocyclyl selected from

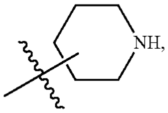, 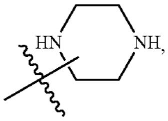, 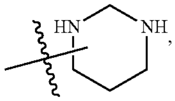, 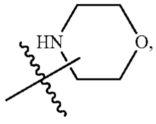, 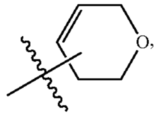, 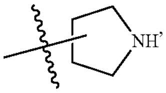, 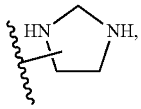, 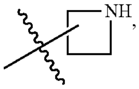, 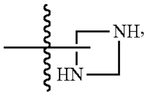, 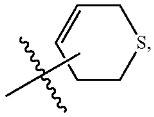, 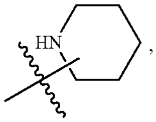, 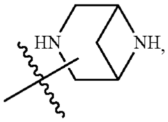, 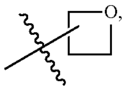, 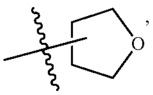, 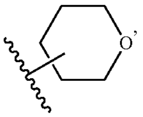, 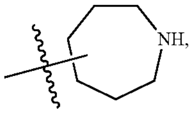, 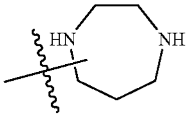 and 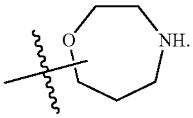.

In one embodiment, a heterocyclyl is a 4- to 6-membered monocyclic heterocyclyl selected from

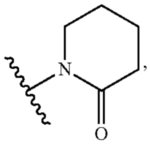, 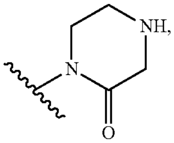, 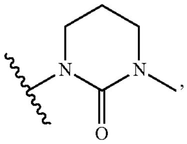, 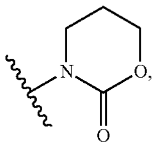, 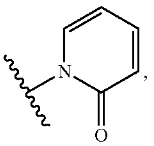, 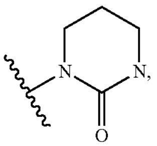, 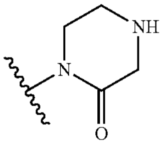 and 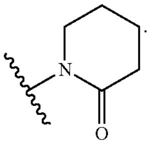.

In one embodiment, a heterocyclyl is a 7-membered monocyclic heterocyclyl (saturated or partially unsaturated), such as a 7-membered monocyclic heterocyclyl having one heteroatom selected from O and N. Examples of a 7-membered monocyclic heterocyclyl include, but are not limited to, azepanyl, azepinyl, oxepanyl, oxepinyl, thiepanyl, thiepinyl, diazepanyl, diazepinyl, and thiazepinyl.

In another embodiment, a heterocyclyl is a 7- to 11-membered or 7- to 10-membered bicyclic heterocyclyl. In yet another embodiment, a heterocyclyl is a 9- to 10-membered non-aromatic saturated or unsaturated bicyclic heterocyclyl. In another embodiment, a heterocyclyl is 9- to 10-membered fused non-aromatic saturated or unsaturated bicyclic heterocyclyl. In another embodiments, a heterocyclyl is 7- to 11-membered or 7- to 10-membered bicyclic heterocyclyl selected from 1,2,3,4-tetrahydroisoquinoline, 3,4-dihydro-1H-2$\lambda^2$-isoquinolinyl, hexahydro-2H-thieno[2,3-c]pyrrolyl, hexahydro-2H-thieno[2,3-c]pyrrole-1,1-dioxide-yl, 2,3-dihydrobenzo[b][1,4]dioxinyl, azaspiro[4.4] nonanyl, azabicyclo[3.2.1]octanyl, azaspiro[2.5]octanyl, azaspiro[2.4]heptanyl, 5-azaspiro[2.4]heptanyl, azaspiro[3.4]octanyl, 6-oxa-2-azaspiro [3.4]octanyl, 2-azaspiro[3.3] heptanyl, azaspiro [5.5]undecanyl, indolinyl and isoindolinyl. The heterocyclyl group can be attached to the rest of a compound of the invention at a heteroatom or a carbon atom.

In one embodiment, a heterocyclyl is an 8- to 11-membered bicyclic heterocyclyl selected from

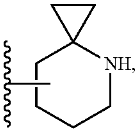, 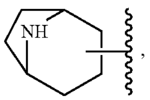, 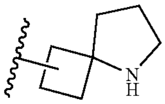, 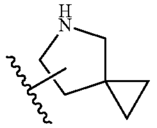, 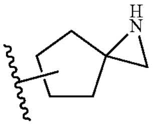, 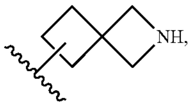, 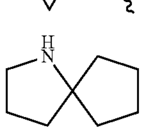, 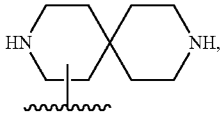, 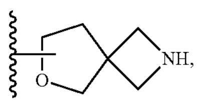, 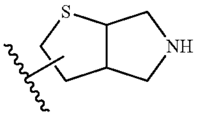 and 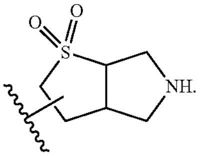.

In one embodiment, a heterocyclyl is an 9- to 10-membered, non-aromatic unsaturated fused bicyclic heterocyclyl selected from

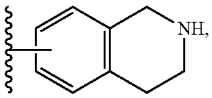, 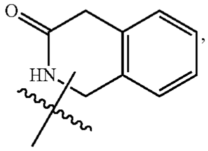, 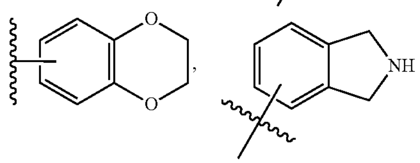 and

-continued

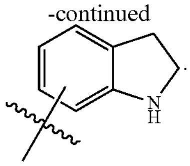

In one embodiment, a heterocyclyl is a 9- to 11-membered fused non-aromatic bicyclic heterocyclyl selected from

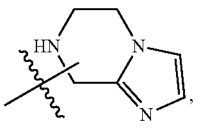, 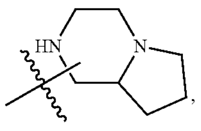, and

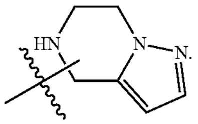

In one embodiment, a heterocyclyl is a 7- to 11-membered bridged non-aromatic saturated or unsaturated bicyclic and/or fused heterocyclyl, such as

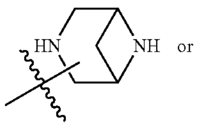 or 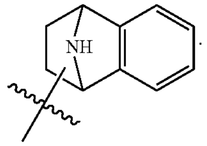

As used herein, the term "aryl" refers to a carbocyclic (all carbon) aromatic monocyclic or bicyclic ring system containing 6-10 carbon atoms. Examples of 6-10 membered aryl groups include phenyl and naphthyl. In some embodiments, the aryl is phenyl.

As used herein, the term "heteroaryl" refers to an aromatic 5- to 6-membered monocyclic or an 8- to 10-membered bicyclic ring system, having 1 to 4 heteroatoms independently selected from O, N and S, and wherein N can be oxidized (e.g., N(O)) or quaternized, and S can be optionally oxidized to sulfoxide and sulfone. Examples of 5- to 6-membered monocyclic heteroaryls include, but are not limited to, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyrazinyl, pyrimidinyl, pyridazinyl, triazinyl, tetrazinyl, and the like. In one embodiment, a heteroaryl is a 5-membered heteroaryl. Examples of a 5-membered heteroaryl include, but are not limited to, pyrazolyl, imidazolyl, oxazolyl, isoxazolyl, 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl. Examples of 8- to 10-membered bicyclic heteroaryls include, but are not limited to, imidazolthiazolyl, imidazopyridinyl, imidazo[1,2-a]pyridinyl, imidazo[2,1-b]thiazolyl, indazolyl, 2H-indazolyl, indolyl, isoindolyl, 2$\lambda^2$-isoindolinyl, benzimidazolyl, benzofuranyl, benzothiophenyl, benzothiazolyl, quinolinyl, isoquinolinyl, quinazolinyl, purinyl, thienopyridinyl and thieno[3,2-b]pyridinyl. Examples of 9- to 10-membered bicyclic heteroaryls include, but are not limited to, imidazopyridinyl, imidazo[1,2-a]pyridinyl, indazolyl, 2H-indazolyl, indolyl, isoindolyl, 2$\lambda^2$-isoindolinyl, benzimidazolyl, benzofuranyl, benzothiophenyl, benzothiazolyl, quinolinyl, isoquinolinyl, quinazolinyl, purinyl, thienopyridinyl and thieno[3,2-b]pyridinyl.

In another embodiment, a heteroaryl is an 8- to 9-membered bicyclic heteroaryl selected from

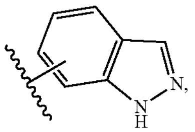 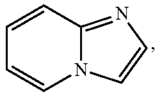, 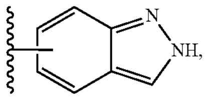

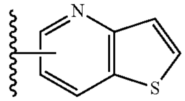 and 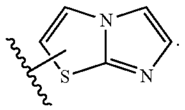

In one embodiment, a 5-membered heteroaryl is selected from

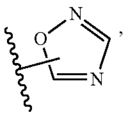, 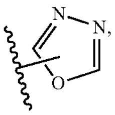 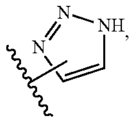 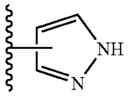

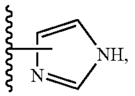 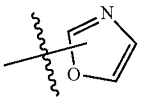, 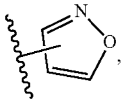

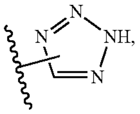 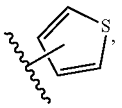 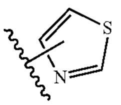 and

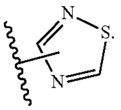

In one embodiment, a 5-membered heteroaryl is selected from

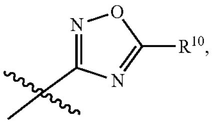 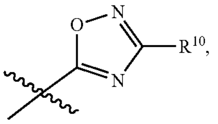

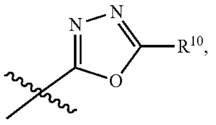 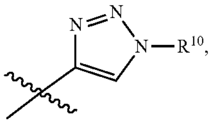

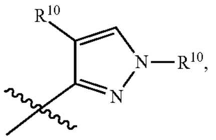 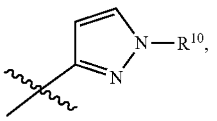

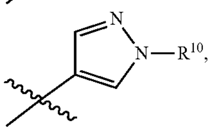 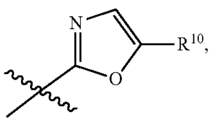

-continued

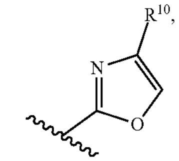
,
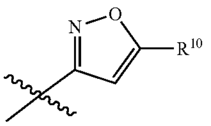
,
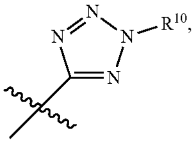
,
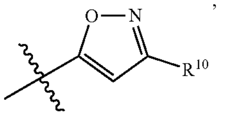
,
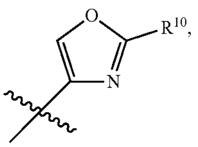
,
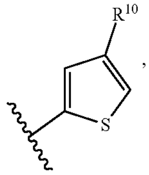
,
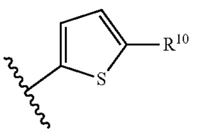
and
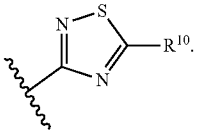

In one embodiment, a 6-membered heteroaryl is selected from

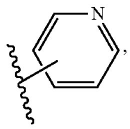
,
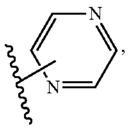
,
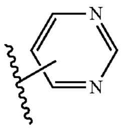
and
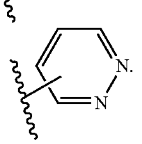

The term "fused ring system", as used herein, is a ring system that has two rings each of which are independently selected from a carbocyclyl or a heterocyclyl, wherein the two ring structures share two adjacent ring atoms. In one embodiment, a fused ring system have from 8 to 12 ring members.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, and S. In one embodiment, a bridged ring system have from 6 to 8 ring members.

The term "spiro ring system," as used herein, is a ring system that has two rings each of which are independently selected from a carbocyclyl or a heterocyclyl, wherein the two ring structures having one ring atom in common. In one embodiment, spiro ring systems have from 5 to 8 ring members.

The term "oxo", as used herein, refers to the double-bond oxygen group (=O) of a carbonyl group (C=O).

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. In addition, some compounds may exhibit polymorphism.

In one embodiment, the invention provides deuterated compounds disclosed herein, in which any or more positions occupied by hydrogen can include enrichment by deuterium above the natural abundance of deuterium. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

II. Compounds of the Disclosure

The compounds of the present disclosure comprise a degradation signaling moiety (DSM) that can bind to an E3 ligase (e.g., the cereblon protein), a Btk binding or targeting moiety and optionally a Linker that covalently links the DSM to the Btk binding or targeting moiety.

In a first embodiment, the compound of the present disclosure is a compound of Formula (A):

BTK-L-DSM (A), or a pharmaceutically acceptable salt thereof, wherein the BTK, L and DSM portions in Formula (A) as described in the first embodiment above. In some embodiments, the DSM, BTK and Linker portions in Formula (A) are as described below.

A. Btk Binding or Targeting Moiety

In a second embodiment of the present disclosure, for the compound of formula (A), or a pharmaceutically acceptable salt thereof, the Btk binding moiety or targeting moiety (represented by BTK in formula (A)) is represented by Formula (I) or Formula (II):

(I)

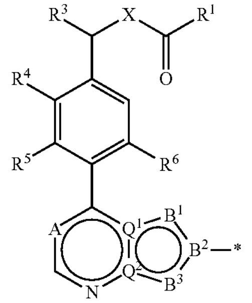

(II)

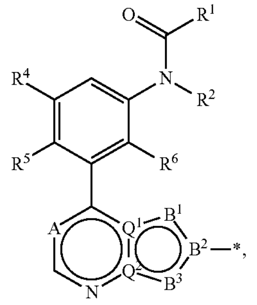

or a pharmaceutically acceptable salt thereof, wherein: (i) A is N, $Q^1$ is C, and $Q^2$ is N; (ii) A is CH, $Q^1$ is C, and $Q^2$ is C; (iii) A is CH, $Q^1$ is N, and $Q^2$ is C; or (iv) A is CH, $Q^1$ is C, and $Q^2$ is N; and the definitions for the other variables are as defined in the first embodiment.

In a third embodiment of the present disclosure, for the compound of formula (A), or a pharmaceutically acceptable salt thereof, the Btk binding moiety or targeting moiety BTK is represented by Formula (I) or Formula (II) wherein (i) $B^1$ is CH, $B^2$ is C, and $B^3$ is CH; (ii) $B^1$ is CH, $B^2$ is C, and $B^3$ is S; (iii) $B^1$ is N, $B^2$ is C, and $B^3$ is CH; (iv) $B^1$ is CH, $B^2$ is C, and $B^3$ is $NR^8$; (v) $B^1$ is N, $B^2$ is N, and $B^3$ is CH; or (vi) $B^1$ is CH, $B^2$ is N, and $B^3$ is N; and the definitions for the other variables are as defined in the first or second embodiment.

In a fourth embodiment of the present disclosure, for the compound of formula (A), or a pharmaceutically acceptable salt thereof, the Btk binding moiety or targeting moiety BTK is represented by Formula (I) or Formula (II) wherein X is $NR^2$; and wherein the definitions for the other variables are as defined in the first, second or third embodiment.

In a fifth embodiment of the present disclosure, for the compound of formula (A), or a pharmaceutically acceptable salt thereof, BTK in formula (A) is a Btk binding moiety or targeting moiety represented by one of the following formulae:

(IA)

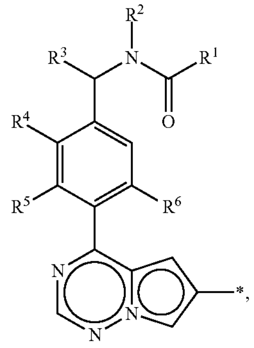

(IB)

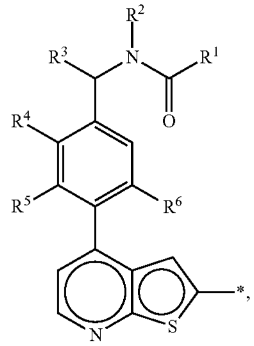

(IC)

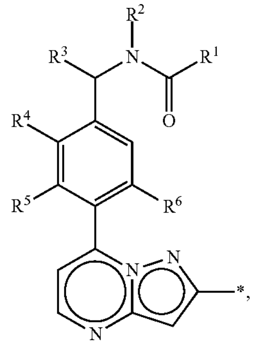

(ID)

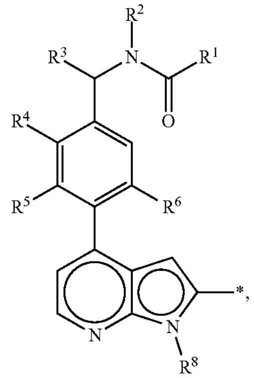

-continued (IE)

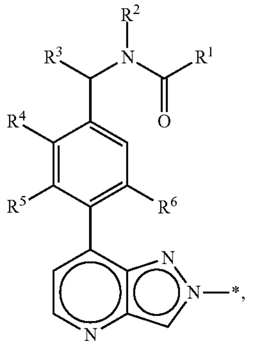

(IF)

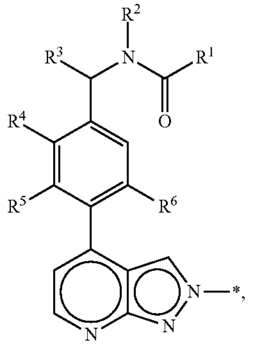

(IG)

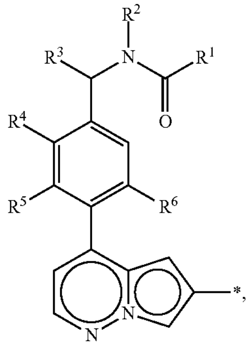

and (IIA)

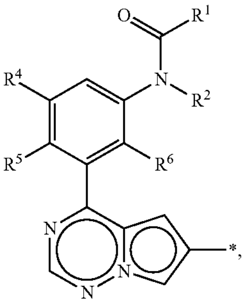

and wherein the definitions for the other variables are as defined in the first embodiment.

In a sixth embodiment of the present disclosure, for the compound of formula (A), or a pharmaceutically acceptable salt thereof, BTK in formula (A) is a Btk binding moiety represented by formula (IA) or (IC); and the definitions for the other variables are as defined in the first embodiment.

In a seventh embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^1$ is selected from a $C_{1-6}$ alkyl, 3- to 6-membered monocyclic or bicyclic carbocyclyl, 4- to 6-membered saturated monocyclic heterocyclyl, 5- to 6-membered monocyclic heteroaryl, and 9 to 10-membered bicyclic heteroaryl; wherein the $C_{1-6}$ alkyl, phenyl, monocyclic or bicyclic $C_{3-7}$ cycloalkyl, 4- to 6-membered saturated heterocyclyl, 5- to 6-membered monocyclic heteroaryl, and 9 to 10-membered bicyclic heteroaryl represented by $R^1$ are each optionally substituted with one or more (e.g., 1 to 6, 1 to 3, or 1, 2, 3, 4, 5, or 6) $R^{10}$; and the definitions for the other variables are as defined in the first, second, third, fourth, fifth or sixth embodiment.

In an eighth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^1$ is 5-membered monocyclic heteroaryl optionally substituted with one to three $R^{10}$; and the definitions for the other variables are as defined in the first, second, third, fourth, fifth, sixth or seventh embodiment.

In a ninth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^1$ is selected from methyl, butyl, pentyl, phenyl, bicyclo[1.1.1]pentanyl, azetidinyl, isoxazolyl, 1,2,4-oxadiazolyl, oxazolyl, pyrazolyl, triazolyl, piperidinyl, piperazinyl, pyrazinyl, pyridinyl, pyrimidinyl, pyrrolidinyl, pyridazinyl, 1,2,4-thiadiazolyl, thiophenyl, benzothiophenyl, each of which is optionally substituted with one to three $R^{10}$; and the definitions for the other variables are as defined in the first, second, third, fourth, fifth, sixth or seventh embodiment.

In a tenth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^1$ is selected from methyl, butyl, pentyl, phenyl, bicyclo[1.1.1]pentanyl, azetidinyl, isoxazolyl, 1,2,4-oxadiazolyl, oxazolyl, pyrazolyl, piperidinyl, piperazinyl, pyrazinyl, pyridinyl, pyrimidinyl, pyrrolidinyl, pyridazinyl, 1,2,4-thiadiazolyl, thiophenyl, benzothiophenyl, each of which is optionally substituted with one or three $R^{10}$; and the definitions for the other variables are as defined in the first, second, third, fourth, fifth, sixth or seventh embodiment.

In an eleventh embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^1$ is represented by one of the following formulae:

(C1)

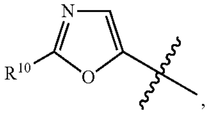

, (C2)

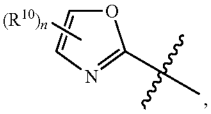

,

-continued (C3)

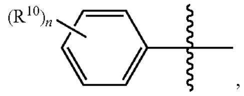

, (C4)

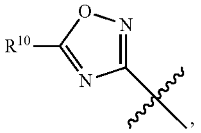

, (C5)

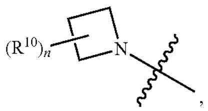

, (C6)

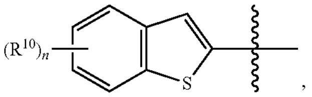

, (C7)

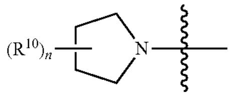

, (C8)

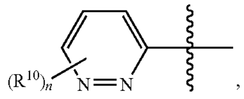

, (C9)

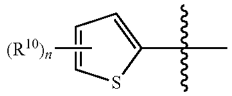

, (C10)

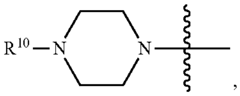

, (C11)

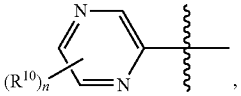

, (C12)

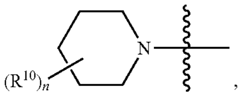

, (C13)

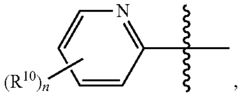

, (C14)

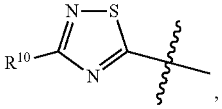

, (C15)

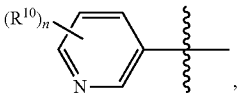

, (C16)

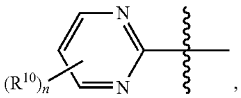

,

-continued (C17)

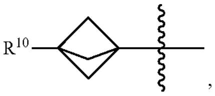
, (C18)

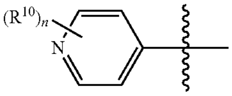
, (C19)

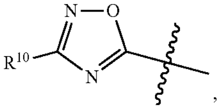
, (C22)

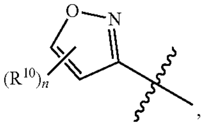
, (C23)

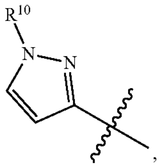
, (C24)

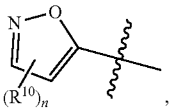
, (C25)

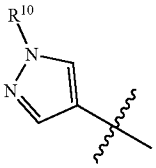
or (C26)

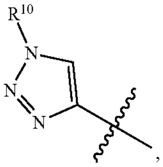
, wherein n represents an integer ranging from 0 to 3; and the definitions for the other variables are as defined in the first, second, third, fourth, fifth, sixth or seventh embodiment.

In a twelfth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^1$ is represented by one of the following formulae:

(C1)

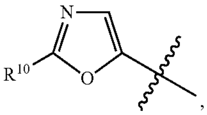
,

-continued (C2)

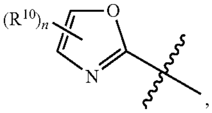
, (C3)

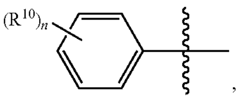
, (C4)

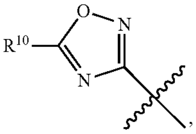
, (C5)

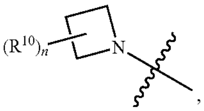
, (C6)

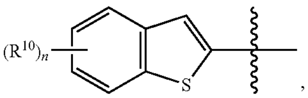
, (C7)

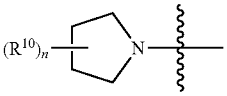
, (C8)

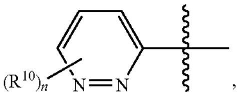
, (C9)

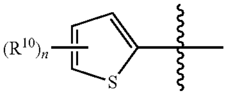
, (C10)

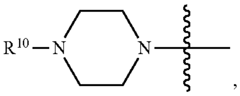
, (C11)

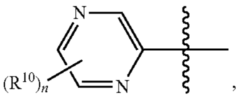
, (C12)

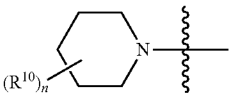
, (C13)

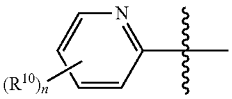
, (C14)

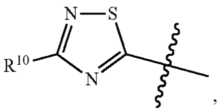
, (C15)

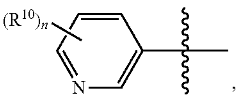
,

-continued (C16)

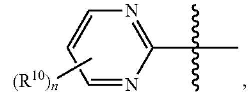

, (C17)

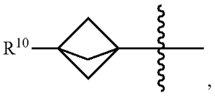

, (C18)

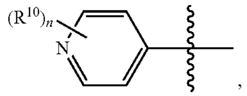

, (C19)

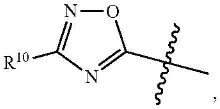

, (C22)

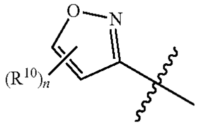

, or (C23)

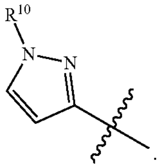

.

wherein: n represents an integer ranging from 0 to 3, with the proviso that a maximum valency of $R^1$ is not exceeded; and the definitions for the other variables are as defined in the first, second, third, fourth, fifth, sixth or seventh embodiment.

In a thirteenth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein: $R^{10}$, for each occurrence, is independently selected from halogen, —$OR^{10a}$, —$S(O)_2R^{10a}$, $C_{1-6}$ alkyl, and 3- to 7-membered monocyclic carbocyclyl, wherein the $C_{1-6}$ alkyl and 3- to 7-membered monocyclic carbocyclyl represented by $R^{10}$ are each optionally substituted with one or more (e.g., 1 to 6, 1 to 3, or 1, 2, 3, 4, 5, or 6) $R^{15}$; or alternatively two $R^{10}$, taken together with their intervening atoms, form a 5- to 7-membered monocyclic carbocyclyl that is optionally substituted with one or more (e.g., 1 to 6, 1 to 3, or 1, 2, 3, 4, 5, or 6) $R^{15}$; $R^{10a}$, for each occurrence, is H or $C_{1-6}$ alkyl; $R^{15}$, for each occurrence, is independently selected from $C_{1-6}$ alkyl, halogen, —$OR^{15a}$, and 3- to 7-membered monocyclic carbocyclyl; wherein the $C_{1-6}$ alkyl and the 3- to 7-membered monocyclic carbocyclyl represented by $R^{15}$ is optionally substituted with one or more (e.g., 1 to 6, 1 to 3, or 1, 2, 3, 4, 5, or 6) $R^{15a}$; and $R^{15a}$ is selected from H, halogen and $C_{1-6}$ alkyl optionally substituted with at least one (e.g., 1 to 6, 1 to 3, or 1, 2, 3, 4, 5, or 6) halogen; and the definitions for the other variables are as defined in the first, second, third, fourth, fifth, sixth, seventh, eighth, ninth, tenth, eleventh or twelfth embodiment.

In a fourteenth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein: $R^{10}$, for each occurrence, is independently selected from halogen, —$OR^{10a}$, —$S(O)_2R^{10a}C_{1-6}$ alkyl and $C_{3-6}$ cycloalkyl, wherein the $C_{1-6}$ alkyl and $C_{3-6}$ cycloalkyl are optionally substituted with one to three $R^{15}$, or alternatively two $R^{10}$, taken together with their intervening atoms, form a 5- to 7-membered monocyclic carbocyclyl that is optionally substituted with one or three $R^{15}$; $R^{10a}$, for each occurrence, is H or $C_{1-6}$ alkyl; $R^{15}$, for each occurrence, is independently selected from $C_{1-6}$ alkyl, halogen, —$OR^{15a}$, and $C_{3-6}$ cycloalkyl; wherein the $C_{1-6}$ alkyl and the $C_{3-6}$ cycloalkyl represented by $R^{15}$ is optionally substituted with one to three $R^{15a}$; and $R^{15a}$ is selected from H, halogen and $C_{1-3}$ alkyl optionally substituted with one to three halogen; and the definitions for the other variables are as defined in the first, second, third, fourth, fifth, sixth, seventh, eighth, ninth, tenth, eleventh or twelfth embodiment.

In a fifteenth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^{10}$, for each occurrence, is independently selected from Cl, F, —$CH_3$, —$CF_3$, —$CH_2$—$CH_3$, —$CH(CH_3)_2$, —$CHF_2$, —$C(CH_3)F_2$, —$CH_2$—$CF_3$, —$CH_2$—$C(CH_3)_3$, —$OCH_3$, —$C(CH_3)_3$, —O—$CH(CH_3)_2$, —O—$C(CH_3)_3$, —O—$CH_2$—$C(CH_3)_3$, —$C(CH_3)_2OH$, -cyclopropyl-$CF_3$, —$CH_2$-cyclopropyl-$CF_3$,

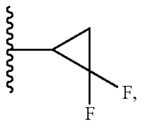 [SMILES: *C1CC1(F)F]

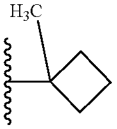

and —$S(O)_2$—$CH_3$; or alternatively two $R^{10}$, taken together with their intervening atoms, form a cyclohexane; and the definitions for the other variables are as defined in the first, second, third, fourth, fifth, sixth, seventh, eighth, ninth, tenth, eleventh or twelfth embodiment.

In a sixteenth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein: $R^{10}$, for each occurrence, is independently selected from Cl, F, —$CH_3$, —$CF_3$, —$CH_2$—$CH_3$, —$CH(CH_3)_2$, —$CHF_2$, —$C(CH_3)F_2$, —$CH_2$—$CF_3$, —$CH_2$—$C(CH_3)_3$, —$OCH_3$, —$C(CH_3)_3$, —O—$CH(CH_3)_2$, —O—$C(CH_3)_3$, —O—$CH_2$—$C(CH_3)_3$, —$C(CH_3)_2OH$, -cyclopropyl-$CF_3$, —$CH_2$-cyclopropyl-$CF_3$,

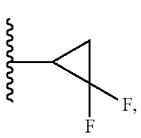 [SMILES: *C1CC1(F)F]

and $-S(O)_2-CH_3$; or alternatively two $R^{10}$, taken together with their intervening atoms, form a cyclohexane; and the definitions for the other variables are as defined in the first, second, third, fourth, fifth, sixth, seventh, eighth, ninth, tenth, eleventh or twelfth embodiment.

In a seventeenth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^2$ is H or $C_{1-3}$ alkyl; and the definitions for the other variables are as defined in the first, second, third, fourth, fifth, sixth, seventh, eighth, ninth, tenth, eleventh, twelfth, thirteenth, fourteenth, fifteenth or sixteenth embodiment.

In an eighteenth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^2$ is H; and the definitions for the other variables are as defined in the first, second, third, fourth, fifth, sixth, seventh, eighth, ninth, tenth, eleventh, twelfth, thirteenth, fourteenth, fifteenth or sixteenth embodiment.

In a nineteenth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^1$ and $R^2$, taken together with their intervening atoms, form the Ring B that is selected from 3- to 7-membered monocyclic heterocyclyl and 9- to 10-membered bicyclic heterocyclyl; wherein the Ring B is optionally substituted with one to three $R^{200}$; and the definitions for the other variables are as defined in the first, second, third, fourth, fifth or sixth embodiment.

In a twentieth embodiment of the present disclosure, for the compound or a pharmaceutically acceptable salt thereof described in the sixteenth embodiment, the Ring B is represented by the following formula:

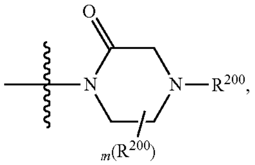

or

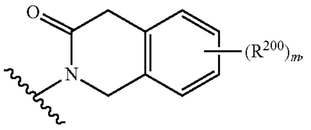

wherein m is 0, 1, 2 or 3; and the definitions for the other variables are as defined in the nineteenth embodiment.

In a twenty-first embodiment of the present disclosure, for the compound or a pharmaceutically acceptable salt thereof described in the sixteenth or seventeenth embodiment, $R^{200}$ is halo or $C_{1-6}$ alkyl optionally substituted with one to three halogen; and the definitions for the other variables are as defined in the nineteenth or twentieth embodiment.

In a twenty-second embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein X is O; and the definitions for the other variables are as defined in the first, second or third embodiment.

In a twenty-third embodiment of the present disclosure, for the compound or a pharmaceutically acceptable salt thereof described in the nineteenth embodiment, $R^1$ is a 4- to 6-membered monocyclic heterocyclyl that is optionally substituted with one to three $R^{10}$; and wherein the definitions for the other variables are as defined in the twenty-second embodiment.

In a twenty-fourth embodiment of the present disclosure, for the compound or a pharmaceutically acceptable salt thereof described in the nineteenth embodiment, $R^1$ is pyrrolidinyl, piperidinyl or piperazinyl, each of which is optionally substituted with one or three $R^{10}$; and wherein the definitions for the other variables are as defined in the twenty-second embodiment.

In a twenty-fifth embodiment of the present disclosure, for the compound or a pharmaceutically acceptable salt thereof described in the nineteenth, twentieth or twenty-first embodiment, $R^{10}$ for each occurrence is independently $-OR^{10a}$ or $C_{1-6}$ alkyl optionally substituted with one to three halogen; and $R^{10a}$ is $C_{1-6}$ alkyl; and the definitions for the other variables are as defined in the twenty-second, twenty-third or twenty-fourth embodiment.

In a twenty-sixth embodiment of the present disclosure, for the compound or a pharmaceutically acceptable salt thereof described in the nineteenth, twentieth or twenty-first embodiment, $R^{10}$ is selected from $-CH_2-C(CH_3)_3$, $-CH_2-CF_3$ and $-O-C(CH_3)_3$; and wherein the definitions for the other variables are as defined in the twenty-second, twenty-third or twenty-fourth embodiment.

In a twenty-seventh embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^3$ is H or $C_{1-4}$ alkyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth or twenty-sixth embodiment.

In a twenty-eighth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^3$ is H; and definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth or twenty-sixth embodiment.

In a twenty-ninth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^4$ is selected from H, $C_{1-6}$ alkyl, $C_{3-6}$ cycloalkyl, halogen and $-OR^{4a}$; and $R^{4a}$ is H, $C_{1-6}$ alkyl or $C_{1-6}$ haloalkyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh or twenty-eighth embodiment.

In a thirtieth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^4$ is selected from H, $C_{1-4}$ alkyl, halogen and —$OR^{4a}$; and $R^{4a}$ is $C_{1-4}$ alkyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh or twenty-eighth embodiment.

In a thirty-first embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^4$ is selected from H, F, Cl, —$CH_3$, $CH(CH_3)_2$ and —$OCH_3$; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth or thirtieth embodiment.

In a thirty-second embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^3$ and $R^4$ together with their intervening atoms form Ring D that is a 7-membered monocyclic heterocyclyl having 1 heteroatom selected from N and O, and Ring D is optionally substituted with $R^{300}$; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth or twenty-sixth embodiment.

In a thirty-third embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein Ring D is oxepane or azepane, each of which is optionally substituted with $R^{300}$; and $R^{300}$ is $C_{1-6}$ alkyl, 3- to 7-membered monocyclic carbocyclyl, or 4- to 6-membered monocyclic heterocyclyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth or twenty-sixth embodiment.

In a thirty-fourth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^5$ is H, $C_{1-4}$ alkyl or halogen; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second or thirty-third embodiment.

In a thirty-fifth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^5$ is H; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second or thirty-third embodiment.

In a thirty-sixth embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^6$ is H, $C_{1-4}$ alkyl or halogen; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth or thirty-fifth embodiment.

In a thirty-seventh embodiment of the present disclosure, for the compound of formula (A), or a pharmaceutically acceptable salt thereof, the Btk binding moiety or targeting moiety BTK in formula (A) is represented by Formula (I), (II), (IA), (IB), (IC), (ID), (IE), (IF), (IG) or (IIA), wherein $R^6$ is H, —$CH_3$ or F; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth or thirty-fifth embodiment.

In a thirty-eighth embodiment of the present disclosure, for the compound of formula (A), or a pharmaceutically acceptable salt thereof, the Btk binding moiety or targeting moiety BTK in formula (A) is represented by Formula (III) or Formula (IV):

(III)

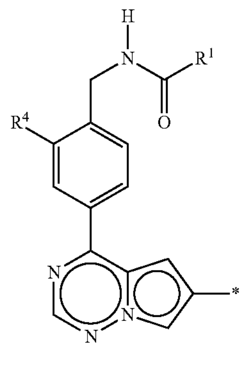

-continued (IV)

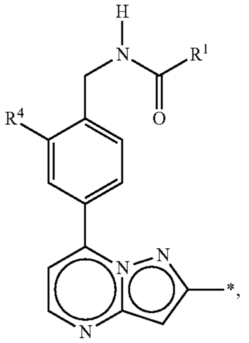

, or a pharmaceutically acceptable salt thereof, wherein: $R^1$ is phenyl, 4- to 6-membered saturated monocyclic heterocyclyl, or 5- or 6-membered heteroaryl, each of which is optionally substituted with 1 to 3 $R^{10}$; $R^{10}$, for each occurrence, is independently selected from halogen, $—OR^{10a}$, $—S(O)_2R^{10a}$, $C_{1-6}$ alkyl and $C_{3-6}$ cycloalkyl, wherein the $C_1$-6 alkyl and $C_{3-6}$ cycloalkyl are optionally substituted with one to three $R^{15}$, or alternatively two $R^{10}$, taken together with their intervening atoms, form a 5- to 7-membered monocyclic carbocyclyl that is optionally substituted with one to three $R^{15}$; $R^{10a}$, for each occurrence, is H or $C_{1-6}$ alkyl; $R^{15}$, for each occurrence, is independently selected from $C_{1-6}$ alkyl, halogen, $—OR^{15}$a, and $C_{3-6}$ cycloalkyl; wherein the $C_{1-6}$ alkyl and the $C_{3-6}$ cycloalkyl represented by $R^{15}$ is optionally substituted with one to three $R^{15a}$; $R^{15a}$ is selected from H, halogen and $C_{1-3}$ alkyl optionally substituted with one to three halogen; and the definitions for the other variables are as defined in the first embodiment.

In a thirty-ninth embodiment of the present disclosure, for the compound of formula (A), or a pharmaceutically acceptable salt thereof, the Btk binding moiety or targeting moiety BTK in formula (A) is represented by Formula (III) or Formula (IV), wherein $R^1$ is phenyl, isoxazolyl, 1,2,4-oxadiazolyl, pyrazolyl, triazolyl or azetidinyl, each of which is optionally substituted with 1 to 3 $R^{10}$; and the definitions for the other variables are as defined in the third-eighth embodiment.

In a fortieth embodiment of the present disclosure, for the compound of formula (A), or a pharmaceutically acceptable salt thereof, the Btk binding moiety or targeting moiety BTK in formula (A) is represented by Formula (III) or Formula (IV), wherein $R^1$ is phenyl, 1,2,4-oxadiazolyl, pyrazolyl, or azetidinyl, each of which is optionally substituted with 1 to 3 $R^{10}$; and the definitions for the other variables are as defined in the thirty-eighth embodiment.

In a forty-first embodiment of the present disclosure, for the compound of formula (A), or a pharmaceutically acceptable salt thereof, the Btk binding moiety or targeting moiety BTK in formula (A) is represented by Formula (III) or Formula (IV), wherein $R^1$ is represented by the following formula:

(C4)

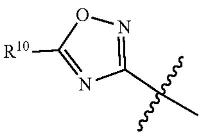

,

-continued (C23)

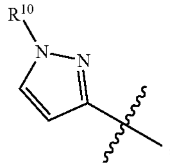

, (C24)

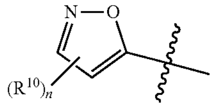

, (C25)

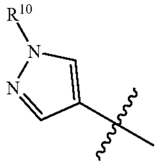

or (C26)

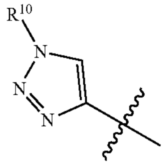

, wherein $R^{10}$ is $C_{1-4}$ alkyl, $C_{1-4}$ haloalkyl or $C_{3-6}$ cycloalkyl optionally substituted with 1 to 3 halogen, and n is 0 or 1; and the definitions for the other variables are as defined in the thirty-eighth embodiment.

In a forty-second embodiment of the present disclosure, for the compound of formula (A), or a pharmaceutically acceptable salt thereof, the Btk binding moiety or targeting moiety BTK in formula (A) is represented by Formula (III) or Formula (IV), wherein $R^1$ is represented by the following formula:

(C4)

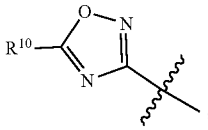

, or (C23)

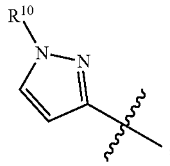

, wherein $R^{10}$ is $C_{1-4}$ alkyl, $C_{1-4}$ haloalkyl or $C_{3-6}$ cycloalkyl optionally substituted with 1 to 3 halogen; and the definitions for the other variables are as defined in the thirty-eighth embodiment.

In a forty-third embodiment of the present disclosure, for the compound of formula (A), or a pharmaceutically acceptable salt thereof, the Btk binding moiety or targeting moiety BTK in formula (A) is represented by Formula (III) or Formula (IV), wherein $R^{10}$ is $—C(CH_3)_3$ or

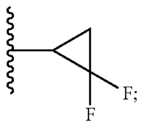

and the definitions for the other variables are as defined in the thirty-eighth, thirty-ninth, fortieth, forty-first or forty-second embodiment.

In a forty-fourth embodiment of the present disclosure, for the compound of formula (A), or a pharmaceutically acceptable salt thereof, the Btk binding moiety or targeting moiety BTK in formula (A) is represented by Formula (III) or Formula (IV), wherein $R^4$ is $C_{1-3}$ alkyl or halogen; and the definitions for the other variables are as defined in the thirty-eighth, thirty-ninth, fortieth, forty-first, forty-second or forty-third embodiment.

In a forty-fifth embodiment of the present disclosure, for the compound of formula (A), or a pharmaceutically acceptable salt thereof, the Btk binding moiety or targeting moiety BTK in formula (A) is represented by Formula (III) or Formula (IV), wherein $R^4$ is —$CH_3$ or F; and the definitions for the other variables are as defined in the thirty-eighth, thirty-ninth, fortieth, forty-first, forty-second, forty-third or forty-fourth embodiment.

B. Degradation Signaling Moiety (DSM)

The degradation signaling moiety (DSM) in compounds of formula (A) or a pharmaceutically acceptable salt thereof can be a suitable moiety that binds to an E3 ubiquitin ligase (e.g., the cereblon protein), for example, a degron or E3 ubiquitin ligase binding or targeting moiety described in WO2020/210630 titled "Tricyclic Degraders of Ikaros and Aiolos"; WO2020/181232 titled "Heterocyclic Compounds for Medical Treatment"; WO2020/132561 titled "Targeted Protein Degradation"; WO2019/204354 titled "Spirocyclic Compounds"; WO2019/099868 titled "Degraders and Degrons for Targeted Protein Degradation"; WO2018/237026 titled "N/O-Linked Degrons and Degronimers for Protein Degradation"; WO2017/197051 titled "Amine-Linked C3-Glutarimide Degronimers for Target Protein Degradation"; WO2017/197055 titled "Heterocyclic Degronimers for Target Protein Degradation"; WO2017/197036 titled "Spirocyclic Degronimers for Target Protein Degradation"; WO2017/197046 titled "C3-Carbon Linked Glutarimide Degronimers for Target Protein Degradation"; and WO2017/197056 titled "Bromodomain Targeting Degronimers for Target Protein Degradation". Other degradation signaling moiety or E3 ubiquitin ligase binding or targeting moiety that can be used are those described in WO2015/160845; WO2016/105518; WO2016/118666; WO2016/149668; WO2016/197032; WO2016/197114; WO2017/007612; WO2017/011371; WO2017/011590; WO2017/030814; WO2017/046036; WO2017/176708; WO2017/176957; WO2017/180417; WO2018/053354; WO2018/071606; WO2018/102067; WO2018/102725; WO2018/118598; WO2018/119357; WO2018/119441; WO2018/119448; WO2018/140809; WO2018/144649; WO2018/119448; WO2018/226542; WO2019/023553, WO2019/195201, WO2019/199816, and WO2019/099926. The entire teachings of the above-referenced PCT publications are incorporated herein by reference.

In a forty-sixth embodiment of the present disclosure, for the compound of formula (A), or a pharmaceutically acceptable salt thereof, DSM is a degradation signaling moiety of formula (D):

(D)

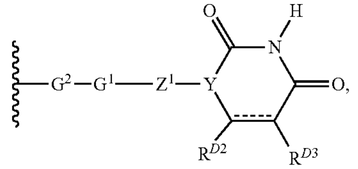

wherein:

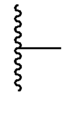

represents a bond to the linker L; ----- represents an optional double bond; Y is $CR^{D1}$ or N; $Z^1$ is selected from bond, —$NR^{D6}$—, —O—, —$CH_2$—, *—C(O)—$CH_2$—‡, *—$C_{1-8}$ alkyl-$NR^{D6}$—‡, *—$NR^{D6}$—$C_{1-8}$alkyl-‡; wherein *– represents a bond to $G^1$, and ‡– represents a bond to Y; $G^1$ is selected from bond, 3- to 7-membered monocyclic carbocyclyl, 5- to 6-membered monocyclic heterocyclyl, 9- to 14-membered bicyclic or tricyclic heterocyclyl; wherein the 3- to 7-membered monocyclic carbocyclyl, 5- to 6-membered monocyclic heterocyclyl, 9- to 14-membered bicyclic or tricyclic heterocyclyl represented by $G^1$ are each optionally substituted with one or more (e.g., 1 to 6, 1 to 3, or 1, 2, 3, 4, 5, or 6) $R^{D4}$; $G^2$ is selected from bond, —$NR^{D6}$—, —C(O)—, *—$NR^{D6}$—$C_{1-4}$ alkyl-‡, *—$NR^{D6}$—$C_{1-4}$ alkyl-O‡, 3- to 7-membered monocyclic carbocyclyl, Het, *—$NR^{D6}$-Het-‡, and *-Het-$C_{1-4}$ alkyl-‡; wherein *– represents a bond to the linker L, and ‡– represents a bond to $G^1$; and wherein the 3- to 7-membered monocyclic carbocyclyl and Het represented by $G^2$ are each optionally substituted with one or more (e.g., 1 to 6, 1 to 3, or 1, 2, 3, 4, 5, or 6) $R^{D5}$; Het is 4- to 7-membered monocyclic heterocyclyl or 9- to 11-membered bicyclic heterocyclyl, $R^{D4}$, $R^{D2}$ and $R^{D3}$ are each independently H or $C_{1-6}$ alkyl; or alternatively $R^{D1}$ and $R^{D3}$, taken together with their intervening atoms when the optional double bond is not present, form a 4- to 6-membered carbocyclyl; $R^{D4}$ is, for each occurrence, independently selected from H, halogen, oxo, $C_{1-4}$ alkyl, $C_{1-4}$haloalkyl, and $C_{1-4}$ alkoxy; or alternatively two $R^{D4}$, taken together with their intervening atoms, form a 4- to 6-membered monocyclic heterocyclyl; and $R^{D5}$ is, for each occurrence, independently selected from H, halogen, OH, $C_{1-4}$ alkyl, $C_{1-4}$haloalkyl and $C_{1-4}$ alkoxy; or alternatively two $R^{D5}$, taken together with their intervening atoms, form a 3- to 6-membered monocyclic carbocyclyl or 4- to 6-membered monocyclic heterocyclyl; $R^{D6}$ is H or $C_{1-3}$ alkyl, provided at least one of $Z^1$, $G^1$ and $G^2$ is not a bond; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first, forty-second, forty-third, forty-fourth or forty-fifth embodiment.

In a forty-seventh embodiment of the present disclosure, for the compound of formula (A), or a pharmaceutically acceptable salt thereof, DSM is a degradation signaling moiety of formula (D), wherein Y is $CR^{D1}$ or N; $Z^1$ is selected from bond, —$NR^{D6}$—, —O—, —$CH_2$—, *—C(O—$CH_2$-‡, *—$C_{1-8}$ alkyl-$NR^{D6}$-‡, *—$NR^{D6}$—$C_{1-8}$ alkyl-‡; wherein *– represents a bond to $G^1$, and ‡– represents a bond to Y; $G^1$ is selected from bond, 3- to 7-membered monocyclic carbocyclyl, 5- to 6-membered monocyclic heterocyclyl and 9- to 11-membered bicyclic heterocyclyl; wherein the 3- to 7-membered monocyclic carbocyclyl, 5- to 6-membered monocyclic heterocyclyl and 9- to 11-membered bicyclic heterocyclyl represented by $G^1$ are each optionally substituted with one or more (e.g., 1 to 6, 1 to 3, or 1, 2, 3, 4, 5, or 6) $R^{D4}$; $G^2$ is selected from bond, —$NR^{D6}$—, —C(O)—, *—$NR^{D6}$—$C_{1-4}$ alkyl-‡, *—$NR^{D6}$—$C_{1-4}$ alkyl-O-‡, 3- to 7-membered monocyclic carbocyclyl, Het, *—$NR^{D6}$-Het-‡, and *-Het-$C_{1-4}$ alkyl-‡; wherein *– represents a bond to the linker L, and ‡– represents a bond to $G^1$; and wherein the 3- to 7-membered monocyclic carbocyclyl and Het represented by $G^2$ are each optionally substituted with one or more (e.g., 1 to 6, 1 to 3, or 1, 2, 3, 4, 5, or 6) $R^{D5}$; Het is 4- to 7-membered monocyclic heterocyclyl or 9- to 11-membered bicyclic heterocyclyl; $R^{D1}$, $R^{D2}$ and $R^{D3}$ are each independently H or $C_{1-6}$ alkyl; or alternatively $R^{D1}$ and $R^{D3}$, taken together with their intervening atoms when the optional double bond is not present, form a 4- to 6-membered carbocyclyl; $R^{D4}$ is, for each occurrence, independently selected from H, halogen, oxo, $C_{1-4}$ alkyl, $C_{1-4}$haloalkyl, and $C_{1-4}$ alkoxy; or alternatively two $R^{D4}$, taken together with their intervening atoms, form a 4- to 6-membered monocyclic heterocyclyl; and $R^{D5}$ is, for each occurrence, independently selected from H, halogen, $C_{1-4}$ alkyl, $C_{1-4}$haloalkyl and $C_{1-4}$ alkoxy; or alternatively two $R^{D5}$, taken together with their intervening atoms, form a 3- to 6-membered monocyclic carbocyclyl or 4- to 6-membered monocyclic heterocyclyl; $R^{D6}$ is H or $C_{1-3}$ alkyl, provided at least one of $Z^1$, $G^1$ and $G^2$ is not a bond; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first, forty-second, forty-third, forty-fourth, forty-fifth or forty-sixth embodiment.

In a forty-eighth embodiment of the present disclosure, for the compound of formula (A), or a pharmaceutically acceptable salt thereof, DSM is a degradation signaling moiety of formula (D-I), (D-II), (D-III) or (D-IV):

(D-I)

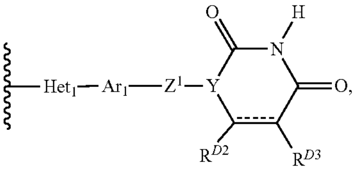

(D-II)

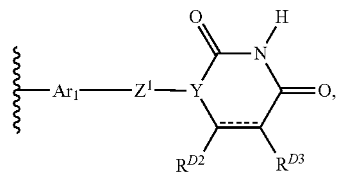

-continued (D-III)

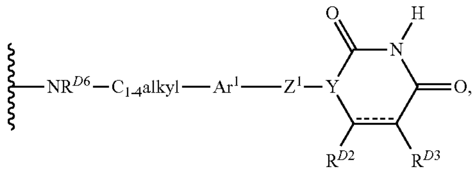

or (D-IV)

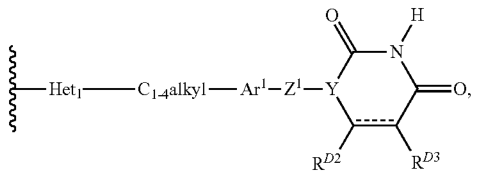

wherein: $Het_1$ is represented by the following formula:

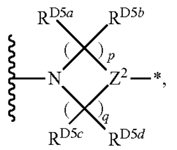

or

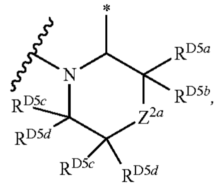

wherein * indicates the connection point to $Ar_1$ in formula (D-I) or the $C_{1-4}$alkyl group in formula (D-IV); p is 1 or 2; q is 1, 2 or 3; $Z^2$ is CH or N; $Z^{2a}$ is $CH_2$ or O; $R^{D5a}$ and $R^{D5b}$, for each occurrence, are each independently H, $C_{1-4}$ alkyl, halogen, OH or $C_{1-4}$ alkoxy; or $R^{D5a}$ and $R^{D5b}$ together with the carbon atom from which they are attached from a $C_{3-6}$ cycloalkyl; $R^{D5c}$ and $R^{D5}$d, for each occurrence, are each independently H, $C_{1-4}$ alkyl, halogen, OH or $C_{1-4}$ alkoxy; or $R^{D5a}$ and $R^{D5c}$ together form —$(CH_2)_t$—; t is 1, 2 or 3; $Ar_1$ is phenyl, phenyl fused with 5- to 7-membered heterocyclyl, naphthalenyl fused with 5- to 7-membered heterocyclyl, 5- to 6-membered monocyclic heteroaryl or 9- to 10-membered bicyclic heteroaryl, wherein the phenyl, phenyl fused with 5- to 7-membered heterocyclyl, 5- to 6-membered monocyclic heteroaryl and 9- to 10-membered bicyclic heteroaryl are each optionally substituted with 1 to 3 $R^{D4}$; $Z^1$ is a bond, $NR^{D6}$, or O; $R^{D6}$ is H or $C_{1-4}$ alkyl; and the definitions for the other variables are as defined in the forty-sixth embodiment.

In a forty-ninth embodiment of the present disclosure, for the compound of formula (A), or a pharmaceutically acceptable salt thereof, DSM is a degradation signaling moiety of formula (D-I), (D-II), (D-III) or (D-IV), wherein: $Het_1$ is represented by the following formula:

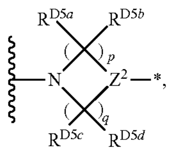

or

-continued

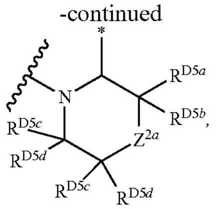

wherein * indicates the connection point to $Ar_1$; p is 1 or 2; q is 1, 2 or 3; $Z^2$ is CH or N; $Z^{2a}$ is $CH_2$ or O; $R^{D5a}$ and $R^{D5b}$, for each occurrence, are each independently H, $C_{1-4}$ alkyl or halogen; or $R^{D5a}$ and $R^{D5}$b together with the carbon atom from which they are attached from a $C_{3-6}$ cycloalkyl; $R^{D5c}$ and $R^{D5d}$, for each occurrence, are each independently H, $C_{1-4}$ alkyl or halogen; or $R^{D5a}$ and $R^{D5c}$ together form $-(CH_2)_t-$; t is 1, 2 or 3; $Ar_1$ is phenyl, phenyl fused with 5- to 7-membered heterocyclyl, 5- to 6-membered monocyclic heteroaryl or 9- to 10-membered bicyclic heteroaryl, wherein the phenyl, phenyl fused with 5- to 7-membered heterocyclyl, 5- to 6-membered monocyclic heteroaryl and 9- to 10-membered bicyclic heteroaryl are each optionally substituted with 1 to 3 $R^{D4}$; $Z^1$ is a bond, $NR^{D6}$, or O; and $R^{D6}$ is H or $C_{1-4}$ alkyl; and the definitions for the other variables are as defined in the forty-sixth embodiment.

In a fiftieth embodiment of the present disclosure, for the compound of formula (A), or a pharmaceutically acceptable salt thereof, DSM is a degradation signaling moiety of formula (D-I), (D-II), (D-III) or (D-IV), wherein $Ar_1$ is phenyl, pyrazol, pyrazolo-pyridinyl, pyridinyl, pyrimidinyl, pyridazinyl, benzoisoxazolyl, benzo[cd]indol-2(1H)-onyl, imidazo-pyridinyl or indazolyl, each or which is optionally substituted with 1 to 3 $R^{D4}$; and the definitions for the other variables are as defined in forty-eighth or forty-ninth embodiment.

In a fifty-first embodiment of the present disclosure, for the compound of formula (A), or a pharmaceutically acceptable salt thereof, DSM is a degradation signaling moiety of formula (D-I), (D-II), (D-III) or (D-IV), wherein $Ar_1$ is phenyl, pyrazol, pyridinyl, pyrimidinyl, pyridazinyl, or indazolyl, each or which is optionally substituted with 1 to 3 $R^{D4}$; and the definitions for the other variables are as defined in the forty-eighth or forty-ninth embodiment.

In a fifty-second embodiment of the present disclosure, for the compound of formula (A), or a pharmaceutically acceptable salt thereof, DSM is a degradation signaling moiety of formula (D-I), (D-II), (D-III) or (D-IV), wherein $Ar_1$ is represented by the following formula:

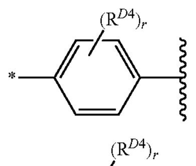
,
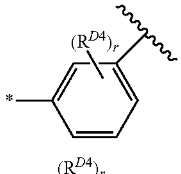
,
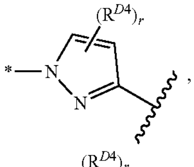
,
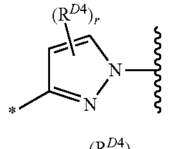
,
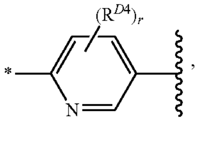
,
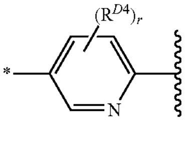
, -continued

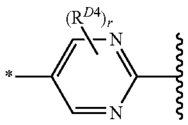
,
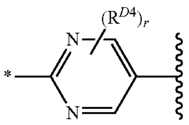
,
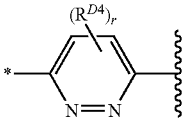
,
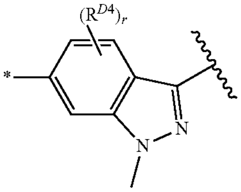
,
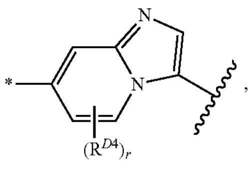
,
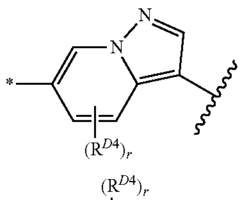
,
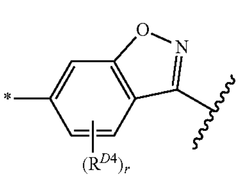
,
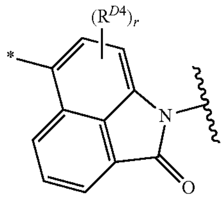
,
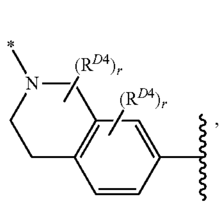
,
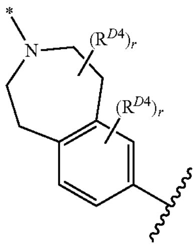
, or
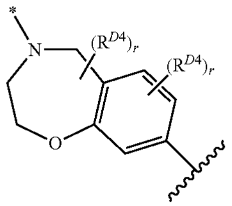
, wherein: *— represents a bond to $Het_1$;

represents a bond to $Z^1$; $R^{D4}$, for each occurrence, is independently selected from $C_{1-4}$ alkyl, $C_{1-4}$ haloalkyl, halogen and $C_{1-4}$ alkoxy; and r is 0, 1 or 2; and the definitions for the other variables are as defined in the forty-eighth embodiment. In a fifty-third embodiment of the present disclosure, for the compound of formula (A), or a pharmaceutically acceptable salt thereof, DSM is a degradation signaling moiety of formula (D-I), (D-II), (D-III) or (D-IV), wherein $Ar_1$ is represented by the following formula:

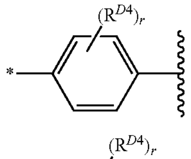, 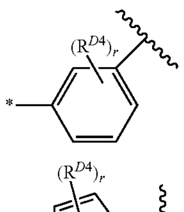,

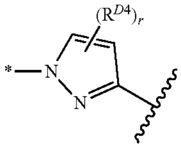, 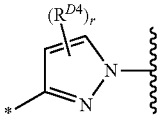,

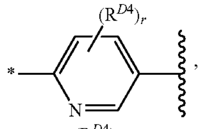, 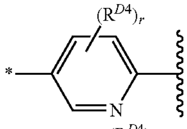,

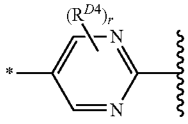, 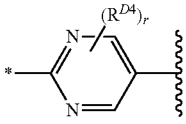,

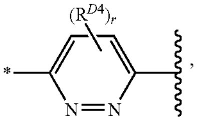, 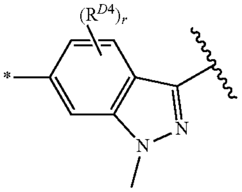,

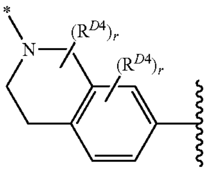, 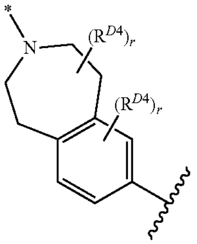, or

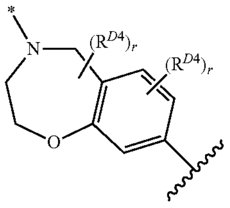, wherein: *— represents a bond to $Het_1$;

represents a bond to $Z^1$; $R^{D4}$, for each occurrence, is independently selected from $C_{1-4}$ alkyl, $C_{1-4}$ haloalkyl, halogen and $C_{1-4}$ alkoxy; and r is 0, 1 or 2; and the definitions for the other variables are as defined in the forty-eighth or forty-ninth embodiment.

In a fifty-fourth embodiment of the present disclosure, for the compound of formula (A), or a pharmaceutically acceptable salt thereof, DSM is a degradation signaling moiety of formula (D-I), (D-II), (D-III) or (D-IV), wherein $R^{D4}$, for each occurrence, is independently selected from —$CH_3$, F, Cl, $CF_3$, and —$OCH_3$; and the definitions for the other variables are as defined in the fifty-second or fifty-third embodiment.

In a fifty-fifth embodiment of the present disclosure, for the compound of formula (A), or a pharmaceutically acceptable salt thereof, DSM is a degradation signaling moiety of formula (D-I), (D-II), (D-III) or (D-IV), wherein: (i) p is 1 and q is 1; (ii) p is 2 and q is 2; or (iii) p is 1 and q is 3; and the definitions for the other variables are as defined in the forty-eighth, forty-ninth, fiftieth, fifty-first, fifty-second, fifty-third or fifty-fourth embodiment.

In a fifty-sixth embodiment of the present disclosure, for the compound of formula (A), or a pharmaceutically acceptable salt thereof, DSM is a degradation signaling moiety of formula (D-I), (D-II), (D-III) or (D-IV), wherein $Het_1$ is azetidine, piperidine, piperazine, pyrrolidine, azabicyclo[3.2.1]octane, or azaspiro[2.5]octane, each of which is optionally substituted with 1 to 3 substituents independently selected from $C_{1-3}$ alkyl, halogen, OH and $C_{1-3}$ alkoxy, or two of the substituents together with the carbon atom from which they are attached form a $C_{3-6}$ cycloalkyl; and the definitions for the other variables are as defined in the forty-eighth, forty-ninth, fiftieth, fifty-first, fifty-second, fifty-third or fifty-fourth embodiment.

In a fifty-seventh embodiment of the present disclosure, for the compound of formula (A), or a pharmaceutically acceptable salt thereof, DSM is a degradation signaling moiety of formula (D-I), (D-II), (D-III) or (D-IV), wherein $Het_1$ is azetidine, piperidine, piperazine, pyrrolidine, azabicyclo[3.2.1]octane, or azaspiro [2.5]octane, each of which is optionally substituted with 1 to 3 substituents independently selected from $C_{1-3}$ alkyl and halogen, or two of the substituents together with the carbon atom from which they are attached form a $C_{3-6}$ cycloalkyl; and the definitions for the other variables are as defined in the forty-eights, forty-ninth, fiftieth, fifty-first, fifty-second, fifty-third or fifty-fourth embodiment.

In a fifty-eighth embodiment of the present disclosure, for the compound of formula (A), or a pharmaceutically acceptable salt thereof, DSM is a degradation signaling moiety of formula (D-I), (D-II), (D-III) or (D-IV), wherein the substituent is independently selected from —$CH_3$, F, $C_1$, OH and —$OCH_3$; and the definitions for the other variables are as defined in the fifty-sixth or fifty-seventh embodiment.

In a fifty-ninth embodiment of the present disclosure, for the compound of formula (A), or a pharmaceutically acceptable salt thereof, DSM is a degradation signaling moiety of formula (D-I), (D-II), (D-III) or (D-IV), wherein the substituent is independently selected from —$CH_3$, F and Cl; and the definitions for the other variables are as defined in the fifty-sixth or fifty-seventh embodiment.

In a sixtieth embodiment of the present disclosure, for the compound of formula (A), or a pharmaceutically acceptable salt thereof, DSM is a degradation signaling moiety of formula (D-I), (D-II), (D-III) or (D-IV), wherein $Het_1$ is represented by the following formula:

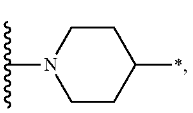, 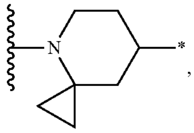,

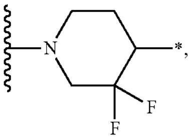, 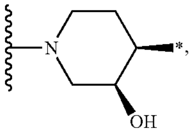,

-continued

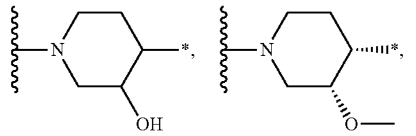

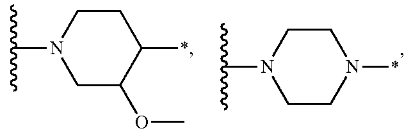

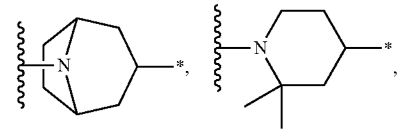

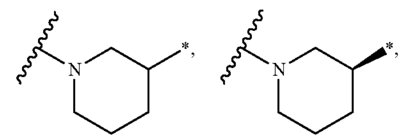

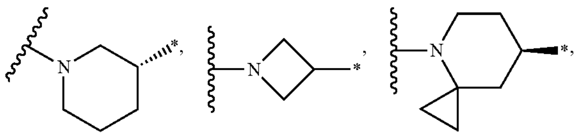

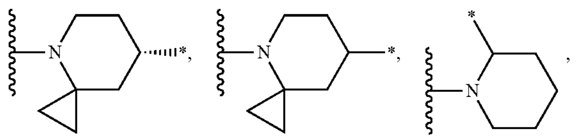

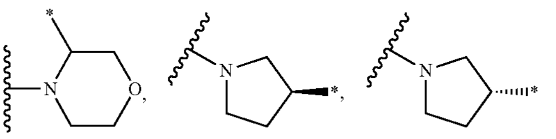

or

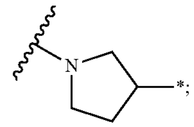

and the definitions for the other variables are as defined in the forty-eighth, forty-ninth, fiftieth, fifty-first, fifty-second, fifty-third or fifty-fourth embodiment.

In a sixty-first embodiment of the present disclosure, for the compound of formula (A), or a pharmaceutically acceptable salt thereof, DSM is a degradation signaling moiety of formula (D-I), (D-II), (D-III) or (D-IV), wherein $Het_1$ is represented by the following formula:

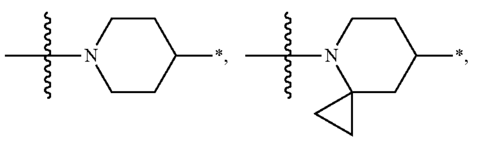

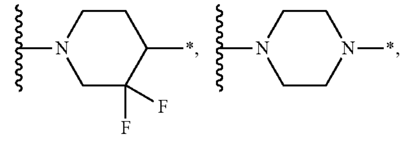

-continued

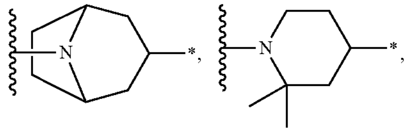

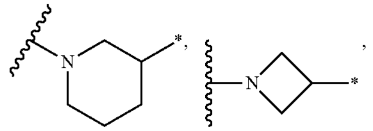

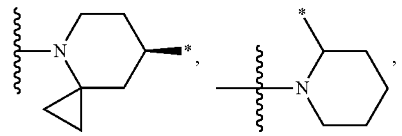

or

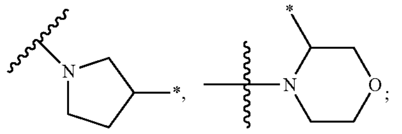

and the definitions for the other variables are as defined in the forty-eighth, forty-ninth, fiftieth, fifty-first, fifty-second, fifty-third or fifty-fourth embodiment.

In a sixty-second embodiment of the present disclosure, for the compound of formula (A), or a pharmaceutically acceptable salt thereof, DSM is a degradation signaling moiety of formula (D), (D-I), (D-II), (D-III) or (D-IV), wherein $R^{D1}$, $R^{D2}$, $R^{D3}$ are each independently H or $-CH_3$; and the definitions for the other variables are as defined in the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth or sixty-first embodiment.

In a sixty-third embodiment of the present disclosure, for the compound of formula (A), or a pharmaceutically acceptable salt thereof, DSM is a degradation signaling moiety of formula (D), (D-I), (D-II), (D-III) or (D-IV), wherein $R^{D1}$, $R^{D2}$, $R^{D3}$ are H; and the definitions for the other variables are as defined in the sixty-second embodiment.

In a sixty-fourth embodiment of the present disclosure, for the compound of formula (A), or a pharmaceutically acceptable salt thereof, DSM is a degradation signaling moiety of formula (D), (D-I), (D-II), (D-III) or (D-IV), wherein $R^{D6}$ is H or $-CH_3$; and the definitions for the other variables are as defined in the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second or sixty-third embodiment.

In a sixty-fifth embodiment of the present disclosure, for the compound of formula (A), or a pharmaceutically acceptable salt thereof, DSM is a degradation signaling moiety of formula (D), (D-I), (D-II), (D-III) or (D-IV), wherein $R^{D6}$ is H; and the definitions for the other variables are as defined in the sixty-fourth embodiment.

In a sixty-sixth embodiment of the present disclosure, for the compound of formula (A), or a pharmaceutically acceptable salt thereof, DSM is a degradation signaling moiety represented by Formula (D-IA1-1), (D-IA3), (D-IIA), (D-IIIA) or (D-IVA):

(D-IA1-1)

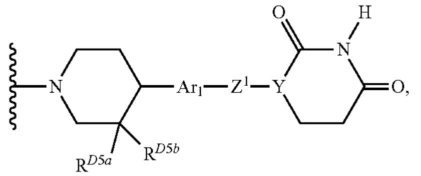

(D-IA3)

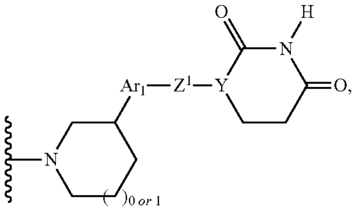

(D-IIA)

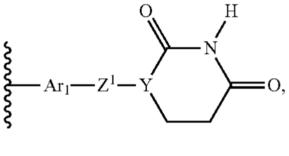

(D-IIIA)

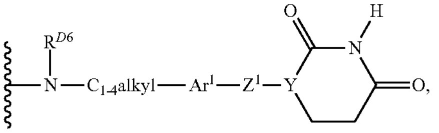

or (D-IVA)

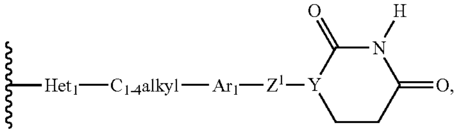

wherein: $Ar^1$ is phenyl, pyrazol, pyrazolo-pyridinyl, pyridinyl, pyrimidinyl, pyridazinyl, benzoisoxazolyl, benzo[cd]indol-2(1H)-onyl, imidazo-pyridinyl or indazolyl, each or which is optionally substituted with 1 or 2 substituents independently selected from halogen and $C_{1-3}$ alkyl; $Z^1$ is a bond, NH or O; $R^{D5a}$ and $R^{D5}$b are each independently H, OH, F or —$OCH_3$; $R^{D6}$ is H or $CH_3$; $Het_1$ is piperidine, piperazine, or pyrrolidine, and Y is CH, $C(CH_3)$ or —N—; and the definitions for the other variables are as defined in the forty-sixth embodiment.

In a sixty-seventh embodiment of the present disclosure, for the compound of formula (A), or a pharmaceutically acceptable salt thereof, DSM is a degradation signaling moiety represented by Formula (D-IA1), (D-IA2), (D-IIA), (D-IIIA) or (D-IVA):

(D-IA1)

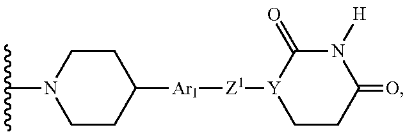

-continued (D-IA2)

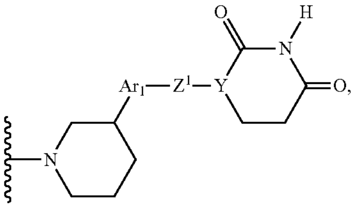

(D-IIA)

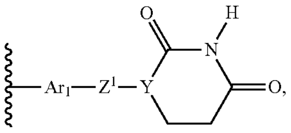

or (D-IIIA)

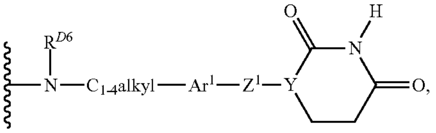

(D-IVA)

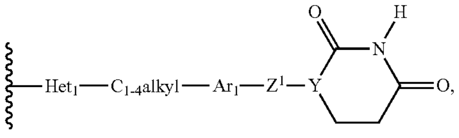

wherein: $Ar^1$ is phenyl, pyrazol, pyridinyl, pyrimidinyl, pyridazinyl, or indazolyl, each or which is optionally substituted with 1 or 2 halogen; $Z^1$ is a bond, NH or O; $R^{D6}$ is H or $CH_3$; $Het_1$ is piperidine, piperazine, or pyrrolidine, and Y is CH, $C(CH_3)$ or —N—; and the definitions for the other variables are as defined in the forty-seventh embodiment.

In a sixty-eighth embodiment of the present disclosure, for the compound of formula (A), or a pharmaceutically acceptable salt thereof, DSM is a degradation signaling moiety represented by Formula (D-IA1), (D-IA1-1), (D-IA2), (D-IA3), (D-IIA), (D-IIIA) or (D-IVA), wherein $Ar^1$ is phenyl, pyrazolo-pyridinyl, pyridinyl, benzoisoxazolyl, benzo[cd]indol-2(1H)-onyl, imidazo-pyridinyl or indazolyl, each of which is optionally substituted with one or two substituents independently selected from halogen and $C_{1-3}$alkyl; and the definitions for the other variables are as defined in the sixty-sixth or sixty-seventh embodiment.

In a sixty-ninth embodiment of the present disclosure, for the compound of formula (A), or a pharmaceutically acceptable salt thereof, DSM is a degradation signaling moiety represented by Formula (D-IA1), (D-IA1-1), (D-IA2), (D-IA3), (D-IIA), (D-IIIA) or (D-IVA), wherein $Ar^1$ is phenyl or indazolyl; and the definitions for the other variables are as defined in the sixty-sixth or sixty-seventh embodiment.

In a seventieth embodiment of the present disclosure, for the compound of formula (A), or a pharmaceutically acceptable salt thereof, DSM is a degradation signaling moiety represented by Formula (D-IA1), (D-IA1-1), (D-IA2), (D-IA3), (D-IIA), (D-IIIA) or (D-IVA), wherein $Ar^1$ is represented by the following formula:

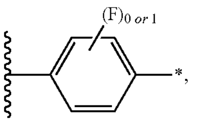

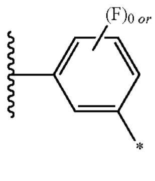

,

-continued

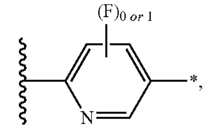,
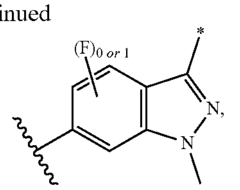,
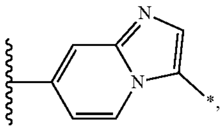,
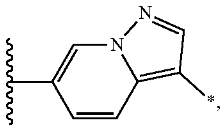,
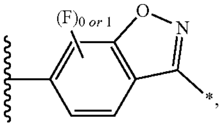, or
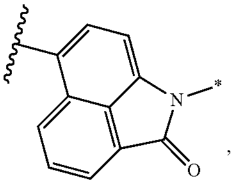, wherein *— represents a bond to $Z^1$; and the definitions for the other variables are as defined in the sixty-seventh or sixty-eighth embodiment.

In a seventy-first embodiment of the present disclosure, for the compound of formula (A), or a pharmaceutically acceptable salt thereof, DSM is a degradation signaling moiety represented by Formula (D-IA1), (D-IA1-1), (D-IA2), (D-IA3), (D-IIA), (D-IIIA) or (D-IVA), wherein $Ar^1$ is represented by the following formula:

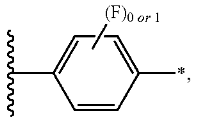,
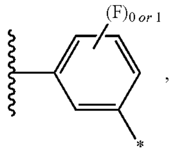, or
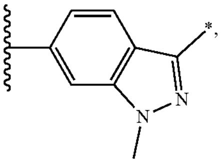, wherein *— represents a bond to $Z^1$; and the definitions for the other variables are as defined in the sixty-seventh or sixty-eighth embodiment.

In a seventy-second embodiment of the present disclosure, for the compound of formula (A), or a pharmaceutically acceptable salt thereof, DSM is a degradation signaling moiety represented by Formula (D-IA1), (D-IA1-1), (D-IA2), (D-IA3), (D-IIA), (D-IIIA) or (D-IVA), wherein $Het_1$ is represented by the following formula:

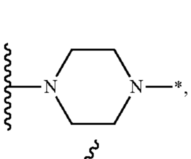,
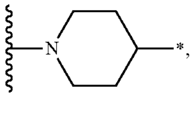,
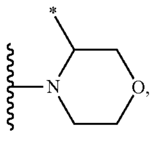,
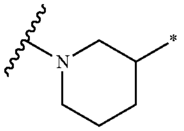 or
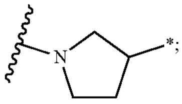;

and the definitions for the other variables are as defined in the sixty-sixth, sixty-seventh, sixty-eighth, sixty-ninth, seventieth or seventy-first embodiment.

In a seventy-third embodiment of the present disclosure, for the compound of formula (A), or a pharmaceutically acceptable salt thereof, DSM is a degradation signaling moiety represented by Formula (D-IA1), (D-IA1-1), (D-IA2), (D-IA3), (D-IIA), (D-IIIA) or (D-IVA), wherein $Het_1$ is represented by the following formula:

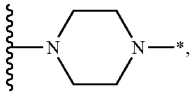,
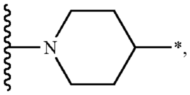,
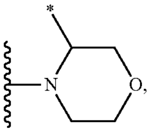, or
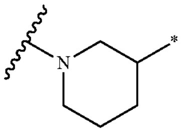;

and the definitions for the other variables are as defined in sixty-sixth, sixty-seventh, sixty-eighth, sixty-ninth, seventieth or seventy-first embodiment.

In a seventy-fourth embodiment of the present disclosure, for the compound of formula (A), or a pharmaceutically acceptable salt thereof, wherein DSM represented by any one of the following attached to L:

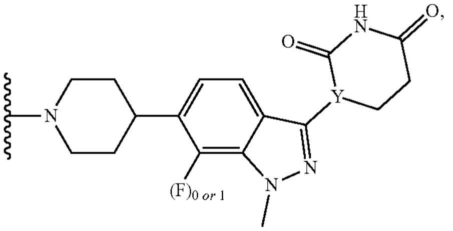,
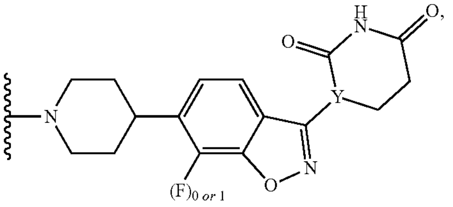

wherein Y is CH or N; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first, forty-second, forty-third, forty-fourth or forty-fifth embodiment.

In a seventy-fifth embodiment of the present disclosure, for the compound of formula (A), or a pharmaceutically acceptable salt thereof, DSM is a degradation signaling moiety represented by one of the following formulae attached to L:

(D1)
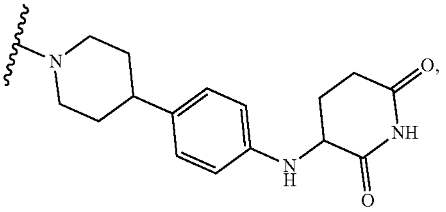
(D2)
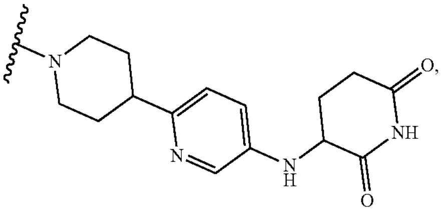
(D3)
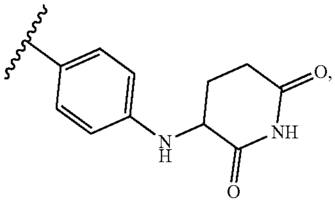
(D4)
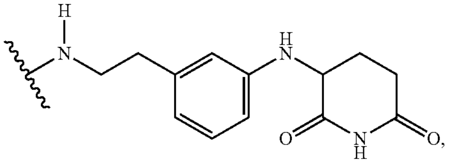
(D5)
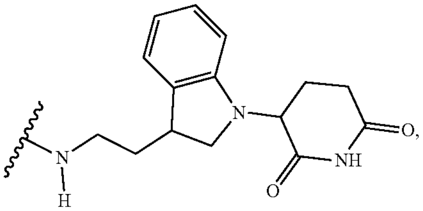
(D6)
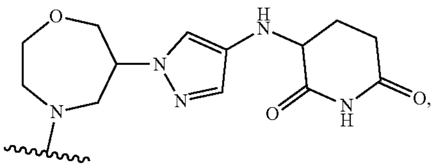
(D7)
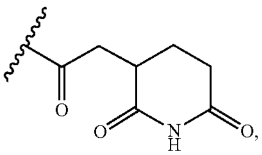
(D8)
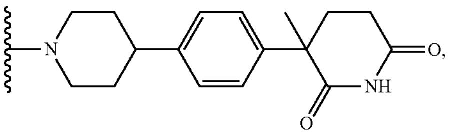
-continued
(8a)
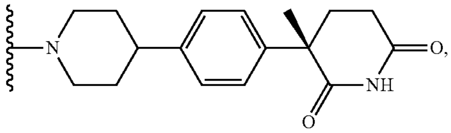
(D8b)
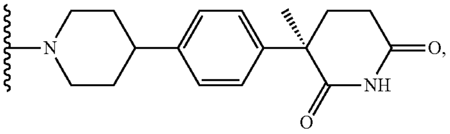
(D9)
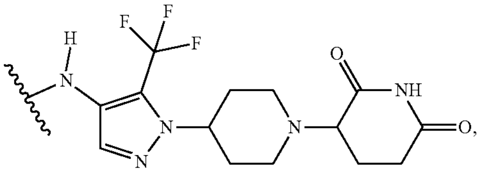
(D10)
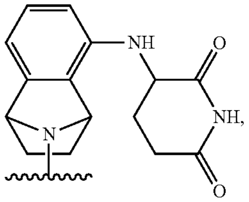
(D11)
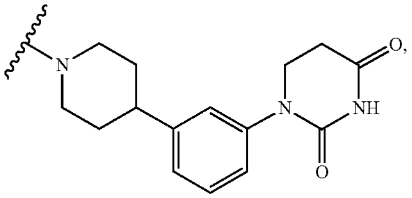
(D12)
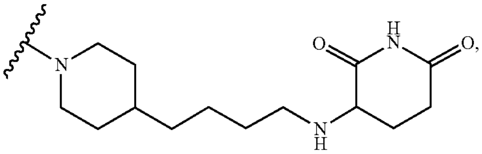
(D113)
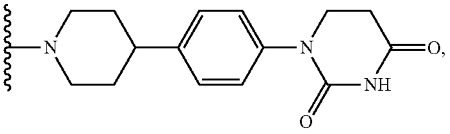
(D14)
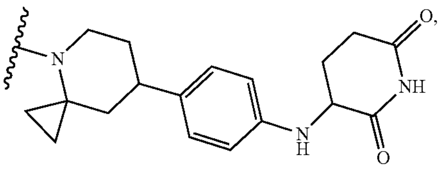
(D15)
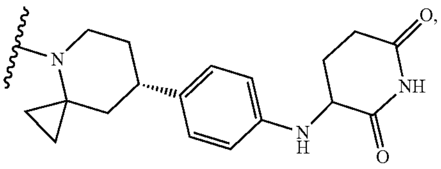

-continued
(D16)
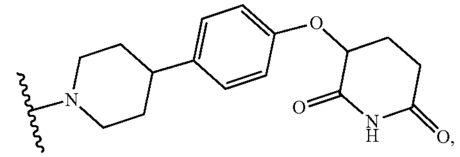
(D17)
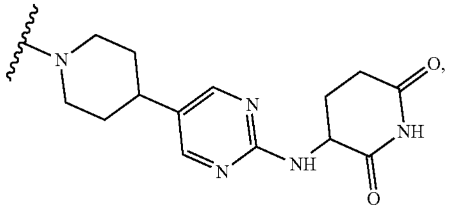
(D18)
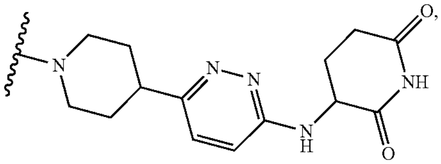
(D19)
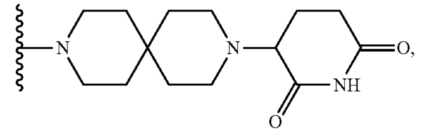
(D20)
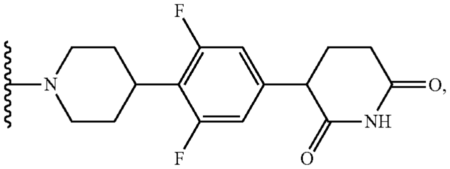
(D21)
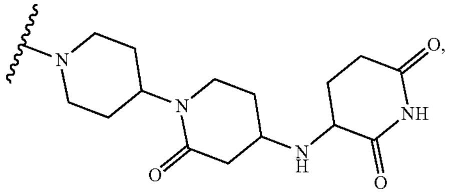
(D22)
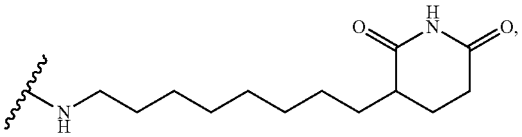
(D23)
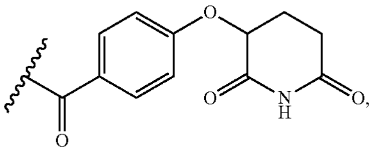
(D24)
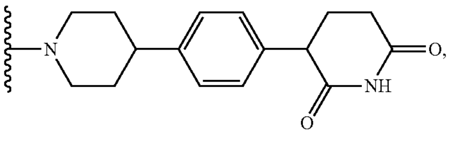
-continued
(D25)
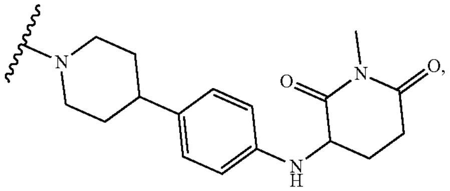
(D26)
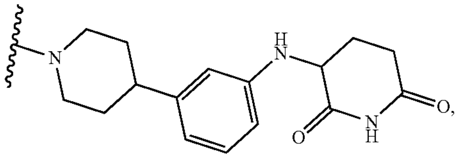
(D27)
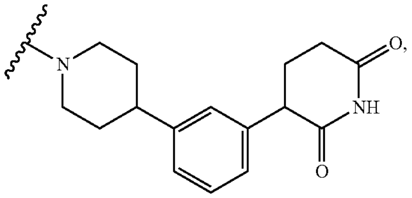
(D28)
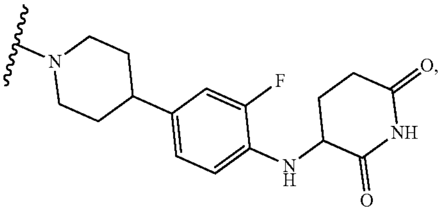
(D29)
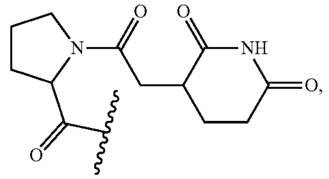
(D30)
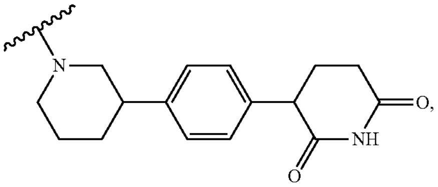
(D31)
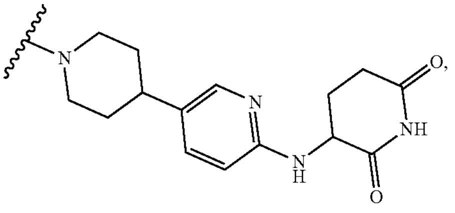
(D32)
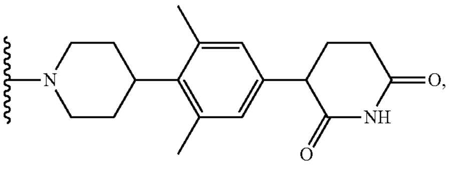

-continued
(D33)
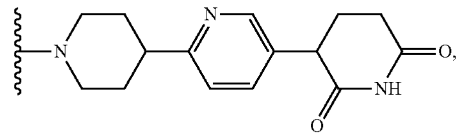
(D34)
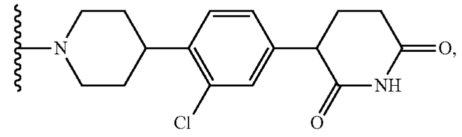
(D35)
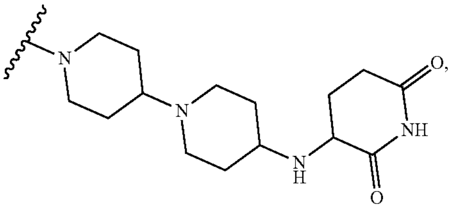
(D36)
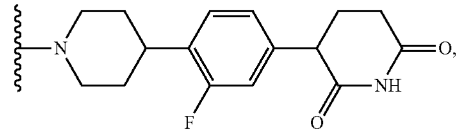
(D37)
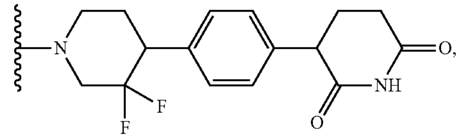
(D38)
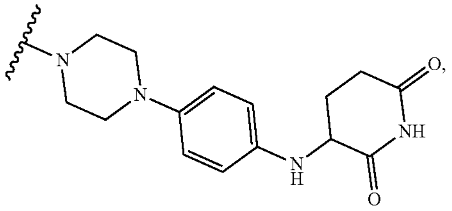
(D39)
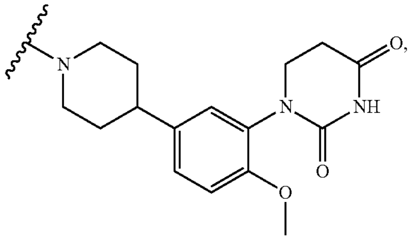
(D40a)
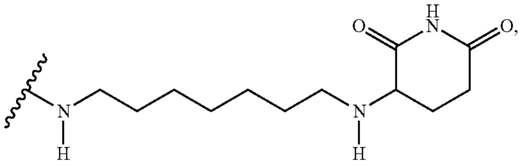
-continued
(D41)
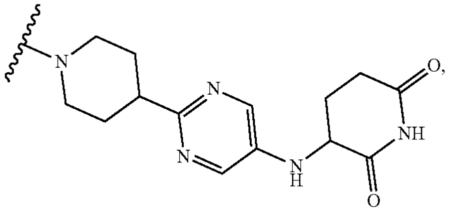
(D42)
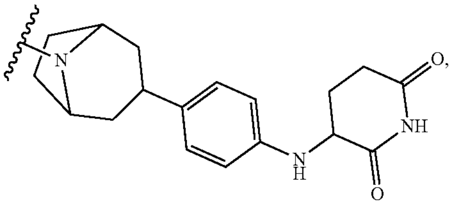
(D43)
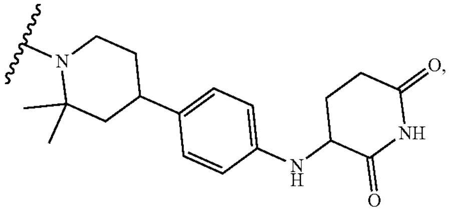
(D44)
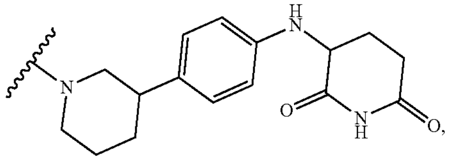
(D45)
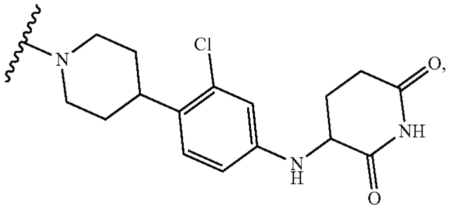
(D46)
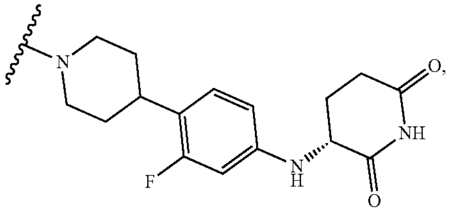
(D47)
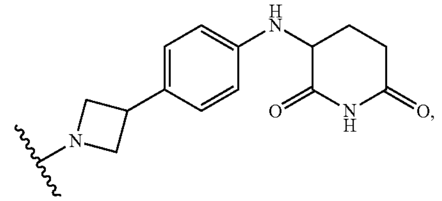

-continued
(D48)
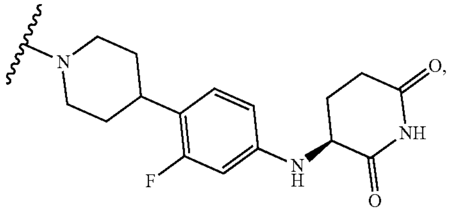
(D49)
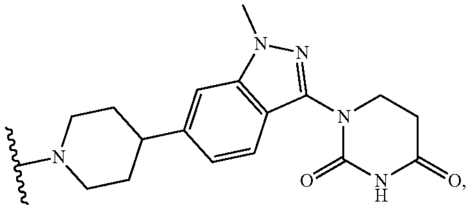
(D50)
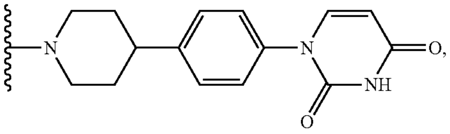
(D51)
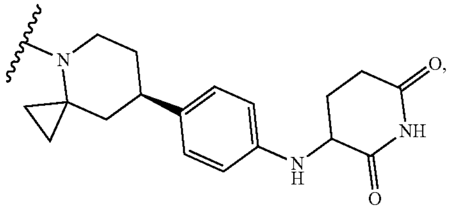
(D52)
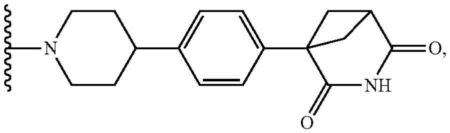
(D53)
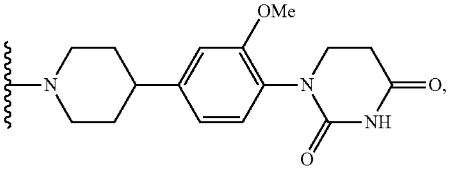
(D54)
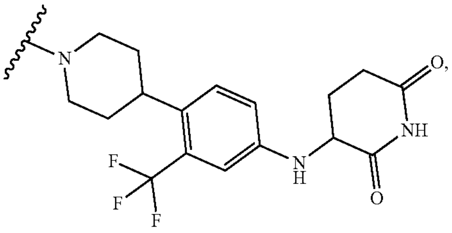
(D55)
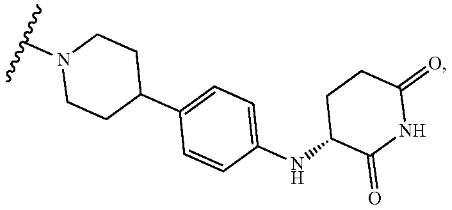
-continued
(D56)
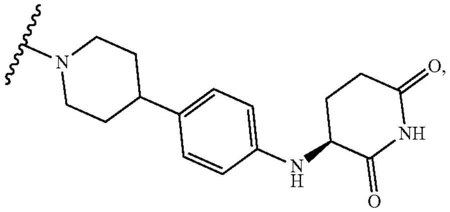
(D57)
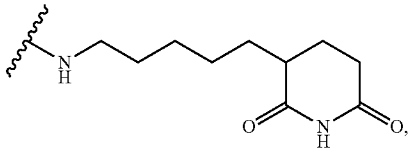
(D58)
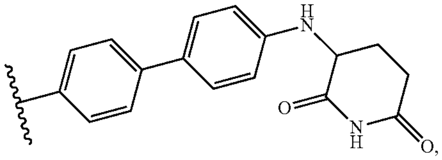
(D59)
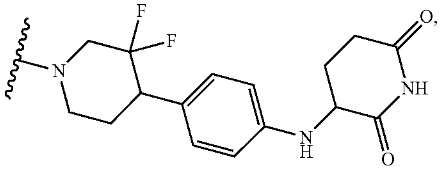
(D60)
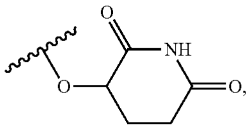
(D61)
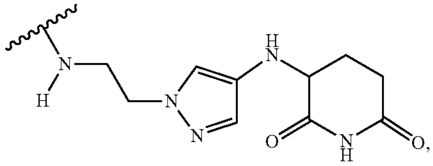
(D62)
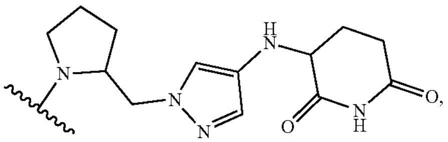
(D63a)
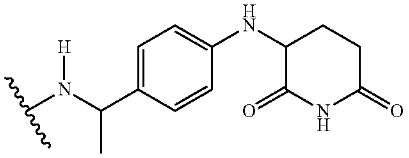
(D63)
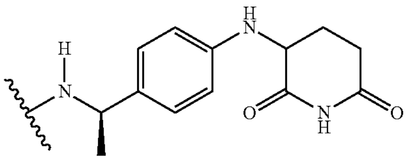

-continued
(D64)
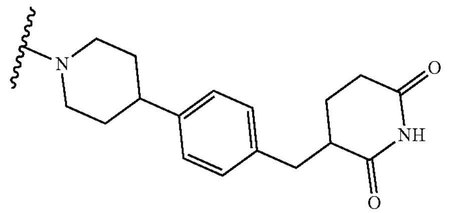
(D65)
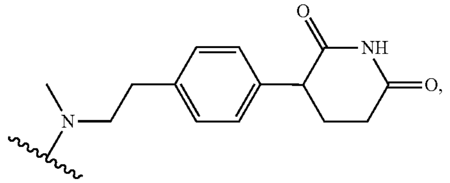
(D66)
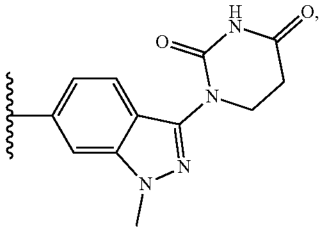
(D67)
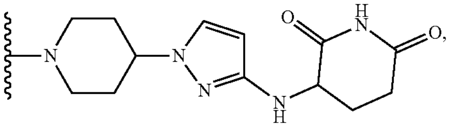
(D68)
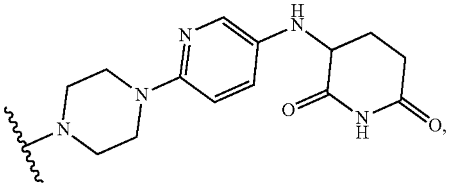
(D69)
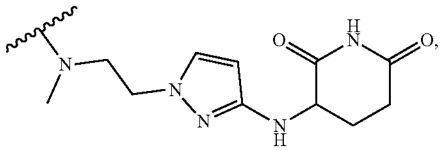
(D70)
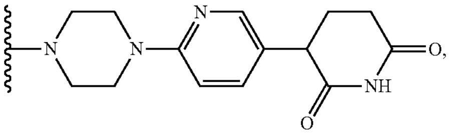
(D71)
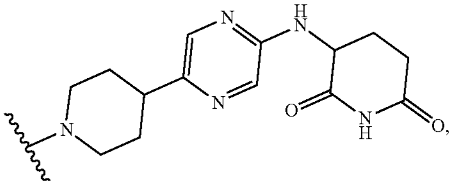
-continued
(D72)
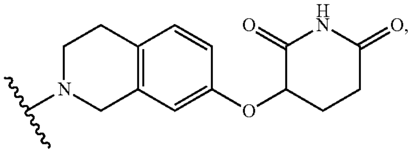
(D73)
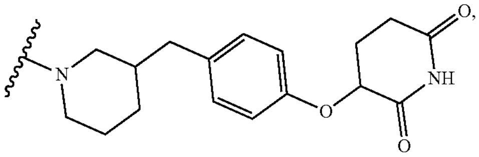
(D74)
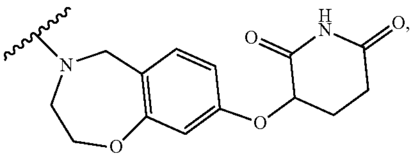
(D75)
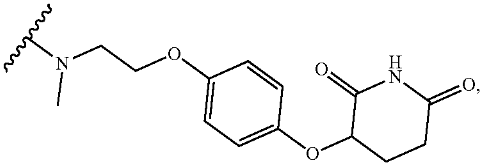
(D76)
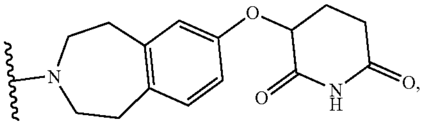
(D77)
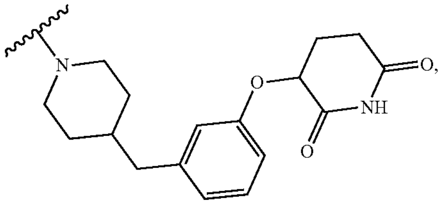
(D78)
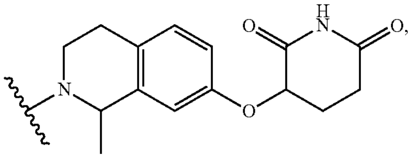
(D79)
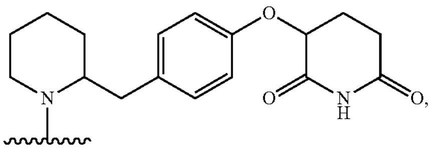
(D80)
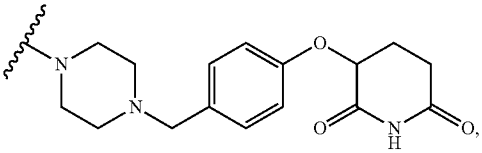

-continued
(D81)
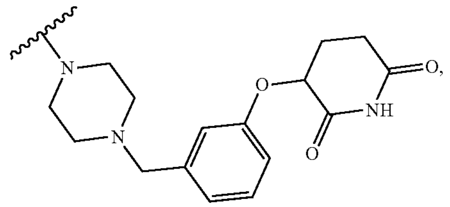
(D82)
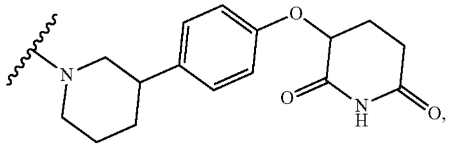
(D83)
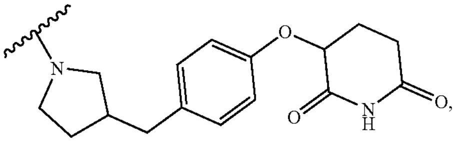
(D84)
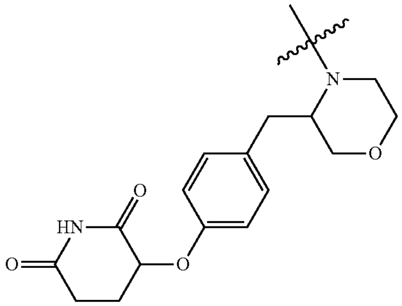
(D85)
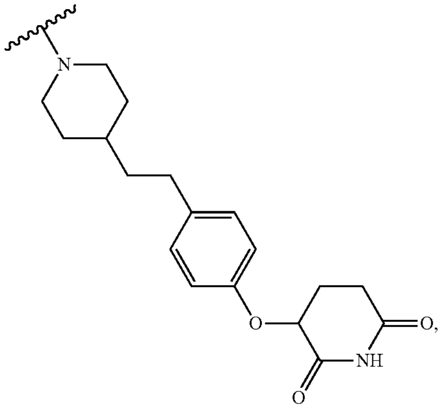
(D86)
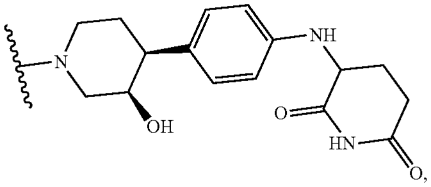
-continued
(D86a)
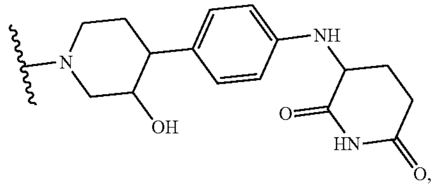
(D87)
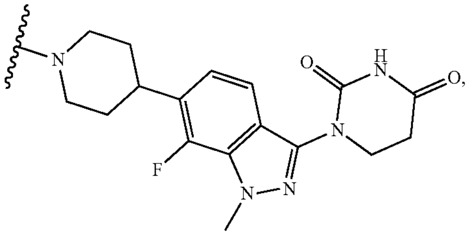
(D88)
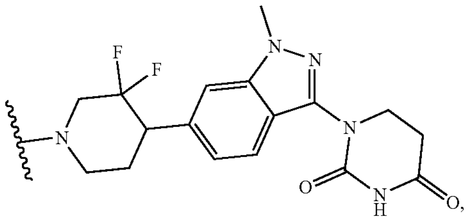
(D89)
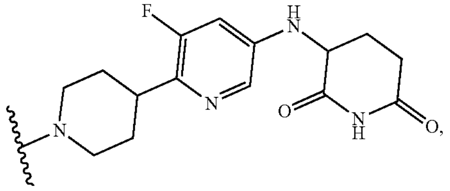
(D90)
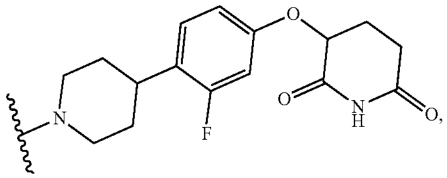
(D91)
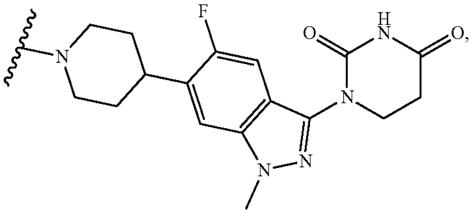
(D92)
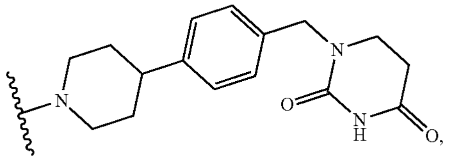

-continued (D93)

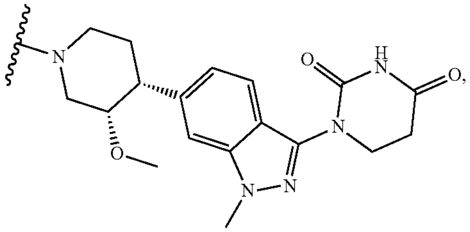

(D93a)

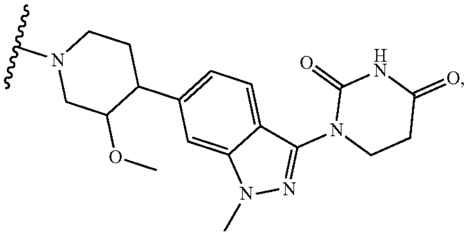

(D94)

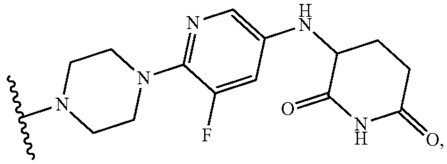

(D96)

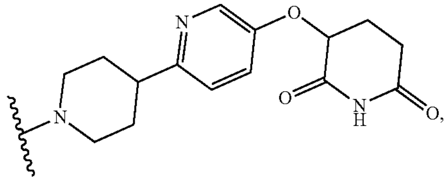

(D96a)

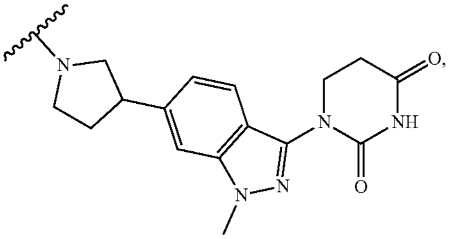

(D96)

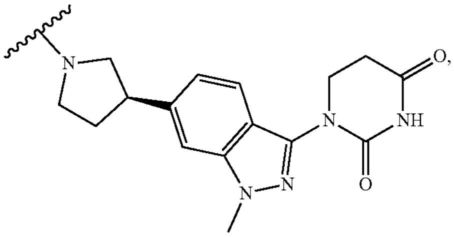

(D97)

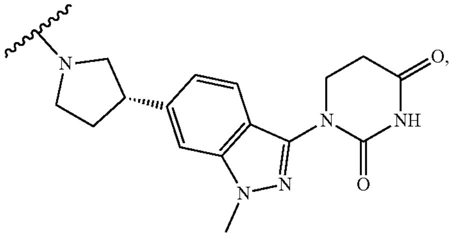

-continued (D98)

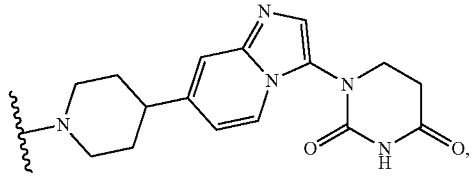

(D99)

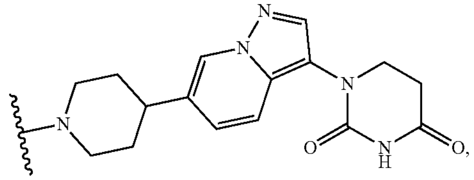

(D100)

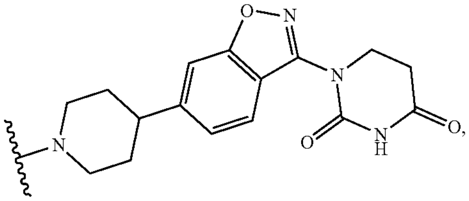

(D101)

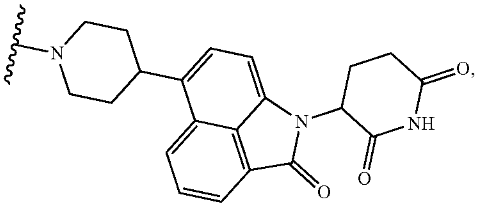

(D102)

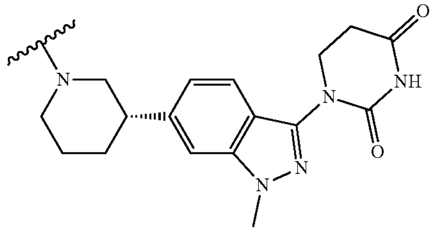

or (D103)

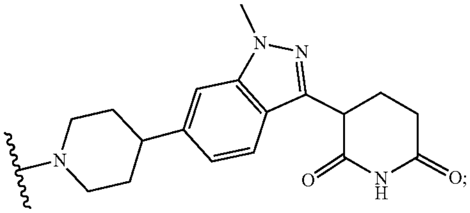

and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first, forty-second, forty-third, forty-fourth or forty-fifth embodiment.

In a seventy-sixth embodiment of the present disclosure, the compound of formula (A), or a pharmaceutically acceptable salt thereof, is represented by one of Formula (A-Ia-1), (A-Ib), (A-Ic), (A-II), (A-III) or (A-IV):

(A-Ia-1)

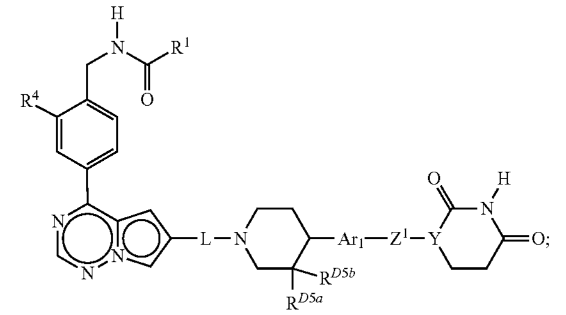

(A-Ib)

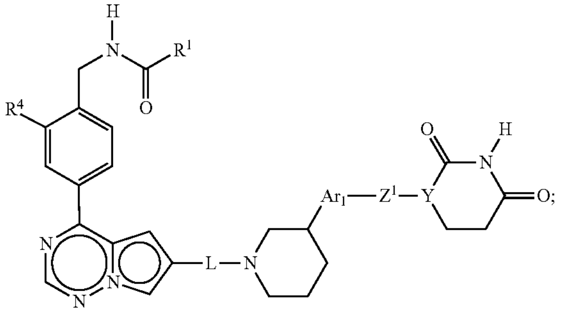

(A-Ic)

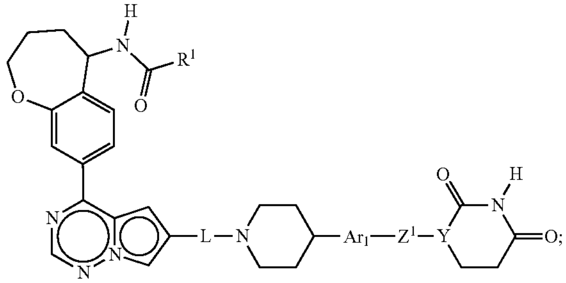

(A-II)

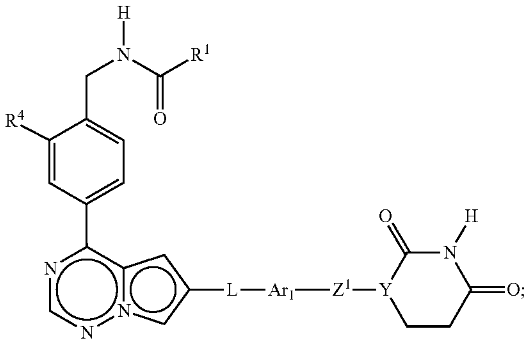

(A-III)

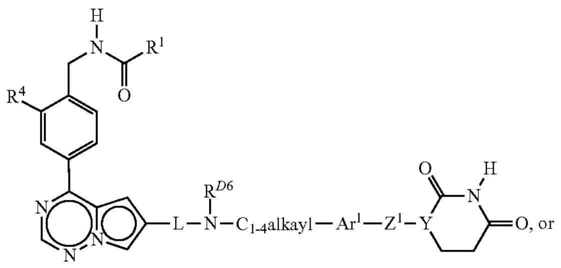

-continued (A-IV)

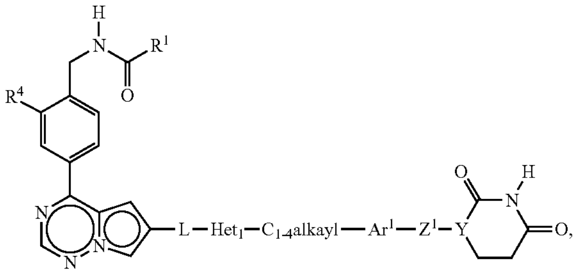

or a pharmaceutically acceptable salt thereof, wherein: $R^1$ is phenyl, 1,2,4-oxadiazolyl, pyrazolyl, triazolyl, or azetidinyl, each of which is optionally substituted with 1 to 3 $R^{10}$; $R^{10}$ is $C_{1-4}$ alkyl, $C_{1-4}$ haloalkyl or $C_{3-6}$ cycloalkyl optionally substituted with 1 to 3 halogen; $R^4$ is selected from H, $C_{1-4}$ alkyl, halogen and —$OR^{4a}$; $R^{4a}$ is $C_{1-4}$ alkyl; $Ar^1$ is phenyl, pyrazol, pyrazolo-pyridinyl, pyridinyl, pyrimidinyl, pyridazinyl, benzoisoxazolyl, benzo[cd]indol-2(1H)-onyl, imidazo-pyridinyl or indazolyl, each or which is optionally substituted with 1 or 2 halogen; $Z^1$ is a bond, $CH_2$, NH or O; $R^{D5a}$ and $R^{D5}b$ are each independently H, OH, F or —$OCH_3$; $R^{D6}$ is H or $CH_3$; $Het_1$ is piperidine or piperazine; and Y is CH, $C(CH_3)$ or —N—; and the definitions for the other variables are as defined in the first embodiment.

In a seventy-seventh embodiment of the present disclosure, the compound of formula (A), or a pharmaceutically acceptable salt thereof, is represented by one of Formula (A-Ia), (A-Ib), (A-II), (A-III) or (A-IV):

(A-Ia)

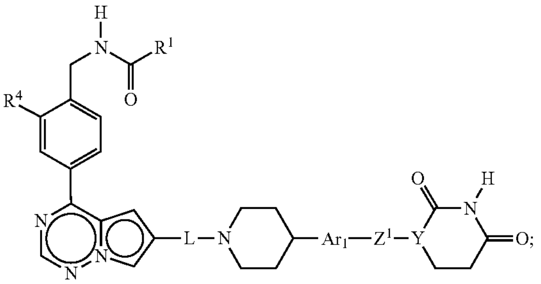

(A-Ib)

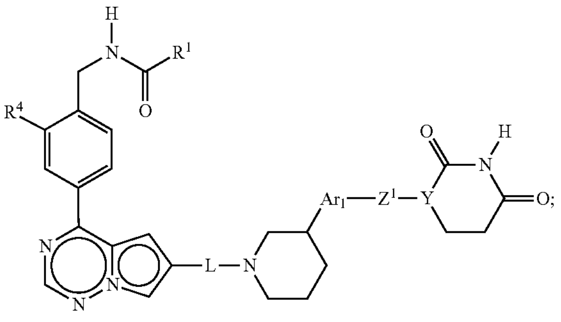

-continued (A-II)

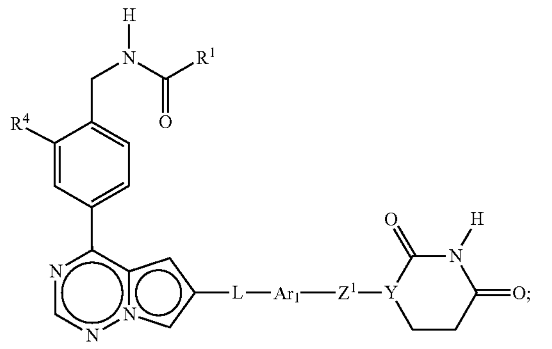

(A-III)

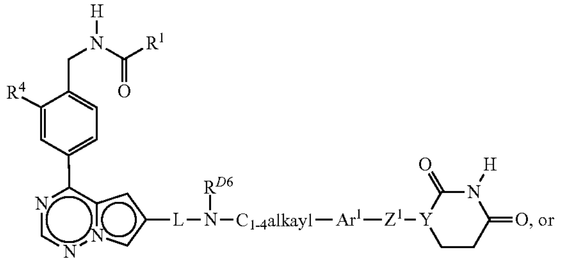

(A-IV)

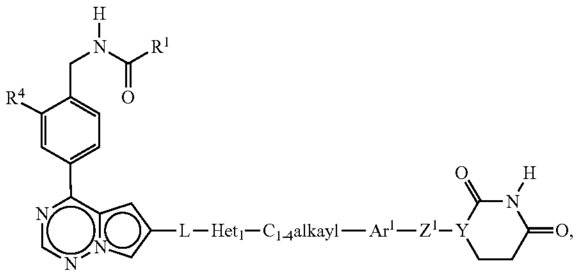

wherein: $R^1$ is phenyl, 1,2,4-oxadiazolyl, pyrazolyl, or azetidinyl, each of which is optionally substituted with 1 to 3 $R^{10}$; $R^{10}$ is $C_{1-4}$ alkyl, $C_{1-4}$haloalkyl or $C_{3-6}$ cycloalkyl optionally substituted with 1 to 3 halogen; $R^4$ is selected from H, $C_{1-4}$ alkyl, halogen and —$OR^{4a}$; $R^{4a}$ is $C_{1-4}$ alkyl; $Ar^1$ is phenyl, pyrazol, pyridinyl, pyrimidinyl, pyridazinyl, or indazolyl, each or which is optionally substituted with 1 or 2 halogen; $Z^1$ is a bond, NH or O; $R^{D6}$ is H or $CH_3$; $Het_1$ is piperidine or piperazine; and Y is CH, $C(CH_3)$ or —N—; and the definitions for the other variables are as defined in the first embodiment.

In a seventy-eighth embodiment of the present disclosure, the compound of formula (A), or a pharmaceutically acceptable salt thereof, is represented by one of Formula (A-Ia-1), (A-Ib), (A-Ic), (A-II), (A-III) or (A-IV), wherein $R^1$ is represented by the following formula:

(C4)

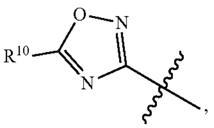

-continued (C23)

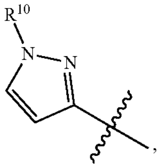

(C24)

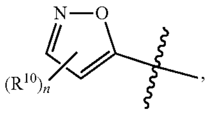

(C25)

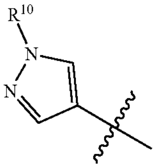

or (C26)

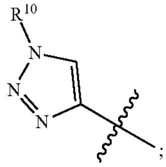

$Ar^1$ is

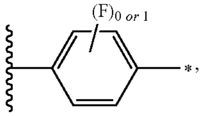

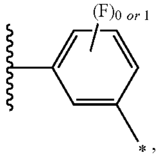

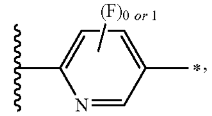

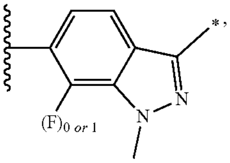

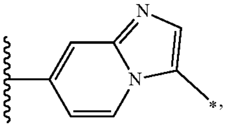

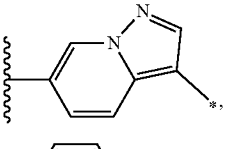

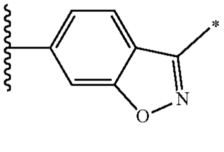

or

-continued

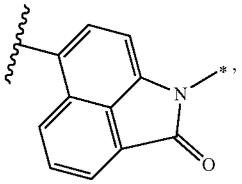

wherein ∗— represents a bond to $Z^1$; and $Het_1$ is

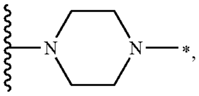 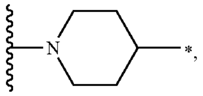

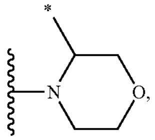 or 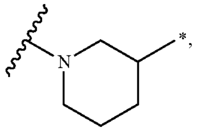

wherein ∗— represents a bond to $C_{1-4}$ alkyl; and the definitions for the other variables are as defined in the seventy-sixth or seventy-seventh embodiment.

In a seventy-ninth embodiment of the present disclosure, the compound of formula (A), or a pharmaceutically acceptable salt thereof, is represented by one of Formula (A-Ia), (A-Ia-1), (A-Ib), (A-Ic), (A-II), (A-III) or (A-IV), wherein: $R^1$ is represented by the following formula:

$Ar^1$ is (C4)

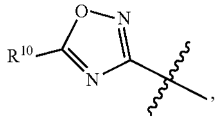 or (C23)

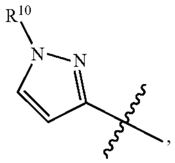

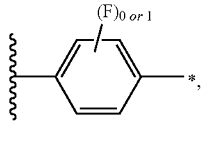

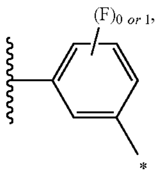 or

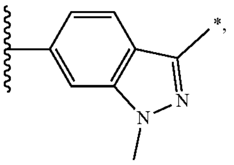

wherein ∗— represents a bond to $Z^1$;

$Het_1$ is

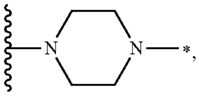 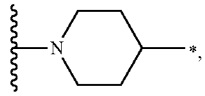

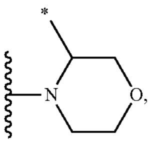 or 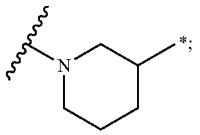

$R^{10}$ is $C_{1-4}$ alkyl, $C_{1-4}$ haloalkyl or $C_{3-6}$ cycloalkyl optionally substituted with 1 to 3 halogen; and the definitions for the other variables are as defined in the seventy-sixth or seventy-seventh embodiment.

In an eightieth embodiment of the present disclosure, the compound of formula (A), or a pharmaceutically acceptable salt thereof, is represented by one of Formula (A-Ia), (A-Ia-1), (A-Ib), (A-Ic), (A-II), (A-III) or (A-IV), wherein $R^{10}$ is $—C(CH_3)_3$ or

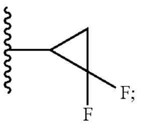

$R^4$ is F or $—CH_3$; and Y is CH or N; and the definitions for the other variables are as defined in the seventy-sixth, seventy-seventh, seventy-eighth or seventy-ninth embodiment.

C. Linker

In an eighty-first embodiment of the present disclosure, for the compound of formula (A), or a pharmaceutically acceptable salt thereof, L is represented by Formula (L-1), (L-2), (L-3), (L-4) or (L-5):

(a)

(L-1)

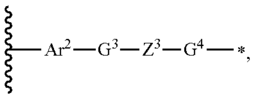

(b)

(L-2)

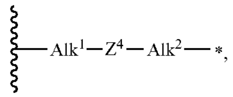

(c)

(L-3)

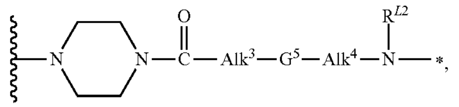

(d)

(L-4)

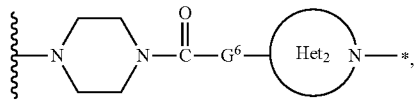 or

-continued (e)

(L-5)

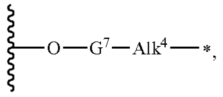

wherein:

$Ar^2$ is phenyl, naphthyl, phenyl fused with 5- or 6-membered heterocycle, 5- or 6-membered monocyclic heteroaryl or 9- to 10-membered bicyclic heteroaryl, each of which is optionally substituted with 1 to 3 $R^U$;

$G^3$ is a bond, $C_{1-6}$ alkyl, —O— or —O—$C_{1-6}$alkyl-O—;

$Z^3$ is a bond, —$NR^{L2}$—, —O—, —C(═O)—, $C_{4-6}$ cycloalkyl, phenyl, 4- to 6-membered saturated monocyclic heterocyclyl, or 5- to 6-membered monocyclic heteroaryl, wherein the phenyl, 4- to 6-membered saturated monocyclic heterocyclyl, and 5- to 6-membered monocyclic heteroaryl are each optionally substituted with 1 to 3 $R^{L1}$;

$G^4$ is a bond or $C_{1-8}$ alkyl;

$R^{L1}$, for each occurrence, is independently H, halogen, $C_{1-4}$ alkyl, $C_{1-4}$haloalkyl, or $C_{1-4}$ alkoxy;

$R^{L2}$ is H or $C_{1-3}$ alkyl; $Alk^1$ is a bond, $C_{1-4}$ alkyl, $C_{2-4}$ alkynyl or $C_{3-6}$ cycloalkyl, wherein the $C_{1-4}$ alkyl, $C_{2-4}$ alkynyl and $C_{3-6}$ cycloalkyl are each optionally substituted with 1 to 3 halogen; $Z^4$ is a bond, —O—, —$NR^{L2}$, or 4- to 10-membered saturated monocyclic or bicyclic heterocyclyl;

$Alk^2$ is a bond or $C_{1-8}$ alkyl optionally substituted with 1 to 3 halogen;

$G^5$ is bond, phenyl, naphthyl, a 5- or 6-membered heteroaryl, a 4- to 10-membered monocyclic or bicyclic saturated heterocyclyl, 3- to 10-membered monocyclic or bicylic saturated carbocyclyl, or —$(O—CH_2—CH_2)_t$—, wherein the phenyl, naphthyl, a 5- or 6-membered heteroaryl, a 4- to 10-membered monocyclic or bicyclic saturated heterocyclyl, 3- to 10-membered monocyclic and bicylic saturated carbocyclyl are each optionally substituted with 1 to 3 $R^L$; t is an integer from 2 to 8;

$Alk^3$ is a bond or $C_{1-6}$ alkyl optionally substituted with 1 to 3 halogen or $C_{3-6}$ cycloalkyl; $Alk^4$ is a bond or $C_{1-6}$ alkyl optionally substituted with 1 to 3 halogen;

$G^6$ is a bond, $C_{1-6}$ alkyl, or —$C_{1-4}$ alkyl-NH—C(═O)—, wherein - represents a bond to $Het_2$;

$Het_2$ is 4- to 10-membered saturated monocyclic or bicyclic heterocyclcyl; $G^7$ is $C_{3-7}$ cycloalkyl;

*— represents a bond to DSM;

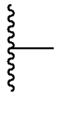

represents a bond to BTK, provided that for formula (L-2), one of $Alk^1$ and $Alk^2$ is not a bond; and for formula (L-3), at least one of $Alk^3$, $G^5$ and $Alk^4$ is not a bond; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first, forty-second, forty-third, forty-fourth, forty-fifth, forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth, sixty-seventh, sixty-eighth, sixty-ninth, seventieth, seventy-first, seventy-second, seventy-third, seventy-fourth, seventy-fifth, seventy-sixth, seventy-seventh, seventy-eighth, seventy-ninth or eightieth embodiment.

In an eighty-second embodiment of the present disclosure, for the compound of formula (A), or a pharmaceutically acceptable salt thereof, L is represented by Formula (L-1), (L-2), (L-3) or (L-4), wherein $Ar^2$ is phenyl, naphthyl, phenyl fused with 5- or 6-membered heterocycle, 5- or 6-membered monocyclic heteroaryl or 9- to 10-membered bicyclic heteroaryl, each of which is optionally substituted with 1 to 3 $R^{L1}$; $G^3$ is a bond, $C_{1-6}$ alkyl, —O— or —O—$C_{1-6}$alkyl-O—; $Z^3$ is a bond, —$NR^{L2}$_, —O—, —C(═O)—, $C_{4-6}$ cycloalkyl, phenyl, 4- to 6-membered saturated monocyclic heterocyclyl, or 5- to 6-membered monocyclic heteroaryl, wherein the phenyl, 4- to 6-membered saturated monocyclic heterocyclyl, and 5- to 6-membered monocyclic heteroaryl are each optionally substituted with 1 to 3 $R^{L1}$; $G^4$ is a bond or $C_{1-6}$ alkyl, $R^{L1}$, for each occurrence, is independently H, halogen, $C_{1-4}$ alkyl, $C_{1-4}$ haloalkyl, or $C_{1-4}$ alkoxy; $R^{L2}$ is H or $C_{1-3}$ alkyl; $Alk^1$ is a bond, $C_{1-4}$ alkyl, $C_{2-4}$ alkynyl or $C_{3-6}$ cycloalkyl, wherein the $C_{1-4}$ alkyl, $C_{2-4}$ alkynyl and $C_{3-6}$ cycloalkyl are each optionally substituted with 1 to 3 halogen; $Z^4$ is a bond, —O—, —$NR^{L2}$, or 4- to 10-membered saturated monocyclic or bicyclic heterocyclyl; $Alk^2$ is a bond or $C_{1-8}$ alkyl optionally substituted with 1 to 3 halogen; $G^5$ is bond, phenyl, naphthyl, a 5- or 6-membered heteroaryl, a 4- to 10-membered monocyclic or bicyclic saturated heterocyclyl, 3- to 10-membered monocyclic or bicylic saturated carbocyclyl, or —$(O—CH_2—CH_2)_t$—, wherein the phenyl, naphthyl, a 5- or 6-membered heteroaryl, a 4- to 10-membered monocyclic or bicyclic saturated heterocyclyl, 3- to 10-membered monocyclic and bicylic saturated carbocyclyl are each optionally substituted with 1 to 3 $R^{L1}$; t is an integer from 2 to 8; $Alk^3$ is a bond or $C_{1-6}$ alkyl optionally substituted with 1 to 3 halogen or $C_{3-6}$ cycloalkyl; $Alk^4$ is a bond or $C_{1-6}$ alkyl optionally substituted with 1 to 3 halogen; $G^6$ is a bond, $C_{1-6}$ alkyl, or —$C_{1-4}$ alkyl-NH—C(═O)—, wherein - represents a bond to $Het_2$; $Het_2$ is 4- to 10-membered saturated monocyclic or bicyclic heterocyclyl; *— represents a bond to DSM;

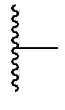

represents a bond to BTK, provided that for formula (L-2), one of $Alk^1$ and $Alk^2$ is not a bond; and for formula (L-3), at least one of $Alk_3$, $G^5$ and $Alk_4$ is not a bond; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first, forty-second, forty-third, forty-fourth, forty-fifth, forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth, sixty-seventh, sixty-eighth, sixty-ninth, seventieth, seventy-first, seventy-second, seventy-third, seventy-fourth, seventy-fifth, seventy-sixth, seventy-seventh, seventy-eighth, seventy-ninth or eightieth embodiment.

In an eighty-third embodiment of the present disclosure, for the compound of formula (A), or a pharmaceutically acceptable salt thereof, L is represented by Formula (L-1), (L-2), (L-3), (L-4) or (L-5), wherein: $Ar^2$ is phenyl, naphthyl, pyridinyl, pyrimidinyl, pyrazolyl, thiazolyl, thiophenyl, imidazolyl, oxazolyl, imidazolthiazolyl, imidazopyridinyl, indazolyl, thienopyridinyl, $2\lambda^2$-isoindolinyl, 2,3-dihydrobenzo[b][1,4]dioxinyl, or 3,4-dihydro-1H-$2\lambda^2$-isoquinolinyl, each or which is optionally substituted with 1 or 2 $R^{L1}$; $Z^3$ is a bond, —$NR^{L2}$—, —O—, —C(═O)—, cyclobutyl, piperazinyl, or pyrazolyl; $G^5$ is phenyl, naphthyl, cyclopropyl, cyclobutyl, cyclohexyl, tetrahydrofuranyl, azetidinyl, oxazolyl, pyrazolyl, or pyridinyl, each of which is optionally substituted with 1 or 2 $R^U$; $Z^4$ is a bond, —O—, —$NR^{L2}$, azaspiro[3.3]heptanyl, or piperazinyl; and $Het_2$ is azaspiro[5.5]undecanyl, azaspiro[2.4]heptanyl, azaspiro[4.4]nonanyl, azaspiro[3.4]octanyl, 6-oxa-azaspiro[3.4]octanyl, hexahydro-2H-thieno[2,3-c]pyrrolyl 1,1-dioxide, pyrrolidinyl, morpholinyl, piperidinyl, or azepanyl; and the definitions for the other variables are as defined in the eighty-first or eighty-second embodiment.

In an eighty-fourth embodiment of the present disclosure, for the compound of formula (A), or a pharmaceutically acceptable salt thereof, L is represented by Formula (L-1), (L-2), (L-3), (L-4) or (L-5), wherein: $Ar^2$ is phenyl, naphthyl, pyridinyl, pyrimidinyl, thiazolyl, thiophenyl, imidazolyl, oxazolyl, imidazolthiazolyl, imidazopyridinyl, indazolyl, thienopyridinyl, $2\lambda^2$-isoindolinyl, 2,3-dihydrobenzo[b][1,4]dioxinyl, or 3,4-dihydro-1H-$2\lambda^2$-isoquinolinyl, each or which is optionally substituted with 1 or 2 $R^{L1}$; $Z^3$ is a bond, —$NR^2$—, —O—, —C(═O)—, cyclobutyl, piperazinyl, or pyrazolyl, $G^5$ is phenyl, naphthyl, cyclopropyl, cyclobutyl, cyclohexyl, tetrahydrofuranyl, azetidinyl, oxazolyl, pyrazolyl, or pyridinyl, each of which is optionally substituted with 1 or 2 $R^{L1}$; $Z^4$ is a bond, —O—, —$NR^{L2}$, azaspiro[3.3]heptanyl, or piperazinyl; and $Het_2$ is azaspiro[5.5]undecanyl, azaspiro[2.4]heptanyl, azaspiro[4.4]nonanyl, azaspiro[3.4]octanyl, 6-oxa-azaspiro[3.4]octanyl, hexahydro-2H-thieno[2,3-c]pyrrolyl 1,1-dioxide, pyrrolidinyl, morpholinyl, piperidinyl, or azepanyl; and the definitions for the other variables are as defined in the eighty-first or eighty-second embodiment.

In a eighty-fifth embodiment of the present disclosure, for the compound of formula (A), or a pharmaceutically acceptable salt thereof, L is represented by Formula (L-1), (L-2), (L-3), (L-4) or (L-5), wherein: $R^{L1}$, for each occurrence, is independently F, Cl, $CH_3$ or $OCH_3$; and $R^{L2}$ is H or $CH_3$; and the definitions for the other variables are as defined in the eighty-first, eighty-second, eighty-third or eighty-fourth embodiment.

In an eighty-sixth embodiment of the present disclosure, for the compound of formula (A), or a pharmaceutically acceptable salt thereof, L is represented by the following formula:

(L-1A)

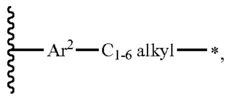

(L-1B)

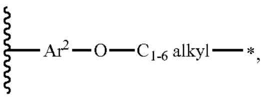

(L-1C)

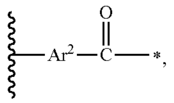

(L-2A)

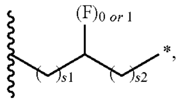

(L-2B)

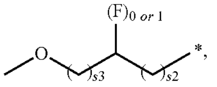

or (L-3)

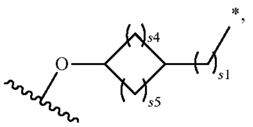

wherein: $Ar^2$ is phenyl, phenyl fused with 5-membered heterocycle, 6-membered saturated monocyclic heterocyclyl or 6-membered heteroaryl, each of which is optionally substituted with 1 or 2 halogen; s1 is 0 or an integer from 1 to 4; s2 is 0 or an integer from 1 to 4; s3 is an integer from 1 to 3; s4 and s5 are each independently 0 or an integer from 1 to 3, provided at least one of s4 and s5 is not 0; and the definitions for the other variables are as defined in the eighty-first embodiment.

In an eighty-seventh embodiment of the present disclosure, for the compound of formula (A), or a pharmaceutically acceptable salt thereof, L is represented by the following formula:

(L-1A)

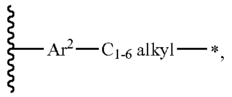

(L-1B)

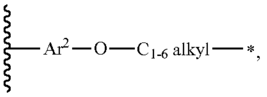

(L-1C)

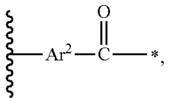

or

-continued (L-2A)

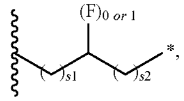

wherein: $Ar^2$ is phenyl, phenyl fused with 5-membered heterocycle, 6-membered saturated monocyclic heterocyclyl or 6-membered heteroaryl, each of which is optionally substituted with 1 or 2 halogen; s1 is 0 or an integer from 1 to 4; and s2 is 0 or an integer form 1 to 4; and the definitions for the other variables are as defined in the eighty-first embodiment.

In a eighty-eighth embodiment of the present disclosure, for the compound of formula (A), or a pharmaceutically acceptable salt thereof, L is represented by Formula (L-1A), (L-1B), (L-1C) or (L-2A), wherein $Ar^2$ is piperazinyl, phenyl, pyridine, pyrimidine, or $2\lambda^2$-isoindoline, each of which is optionally substituted with 1 or 2 F; and the definitions for the other variables are as defined in the eighty-sixth or eighty-seventh embodiment.

In an eighty-ninth embodiment of the present disclosure, for the compound of formula (A), or a pharmaceutically acceptable salt thereof, wherein L represents any one of the following:

(L1)

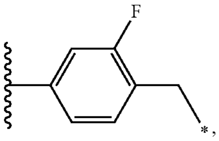

(L2)

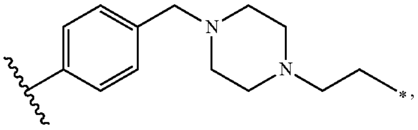

(L3)

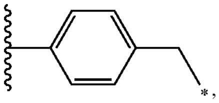

(L4)

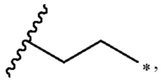

(L5)

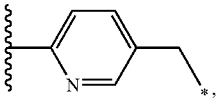

(L6)

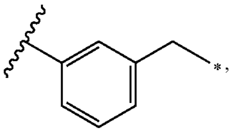

(L7)

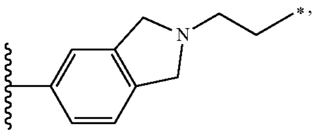

-continued (L8)

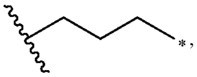

(L9)

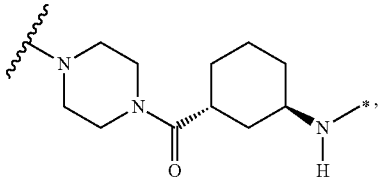

(L9a)

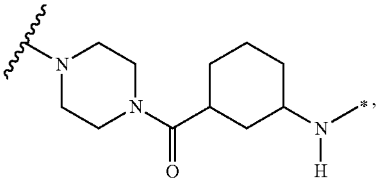

(L10)

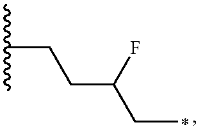

(L11)

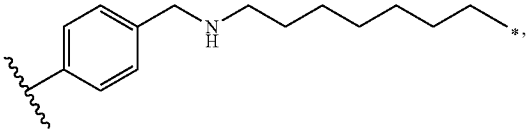

(L12)

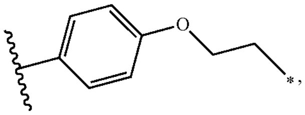

(L13)

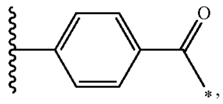

(L14)

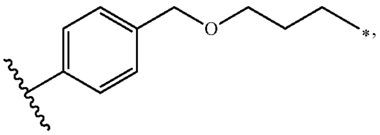

(L15)

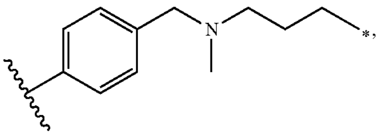

(L16)

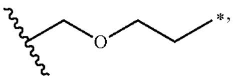

(L17)

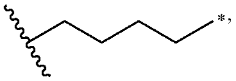

-continued
(L18)
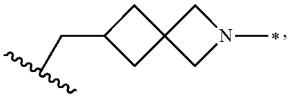
(L19)
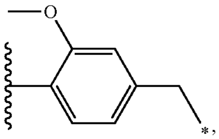
(L20)
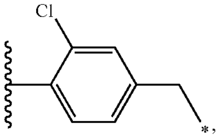
(L21)
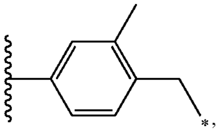
(L22)
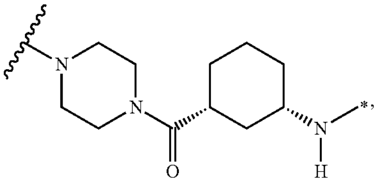
(L23)
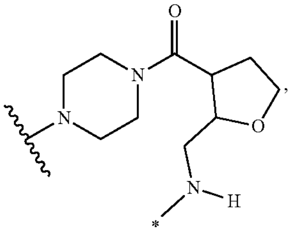
(L24)
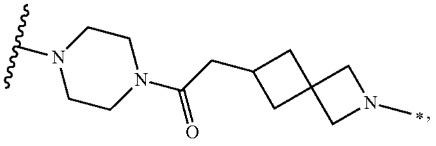
(L25)
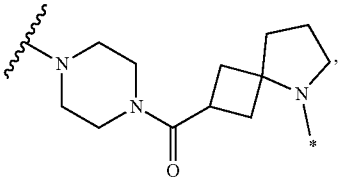
(L26)
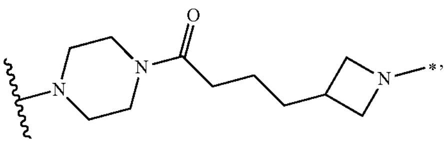
-continued
(L27)
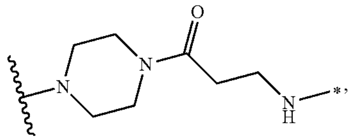
(L28)
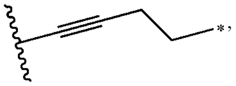
(L29)
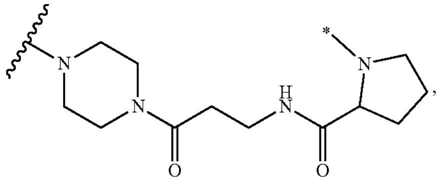
(L30)
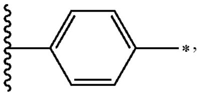
(L31)
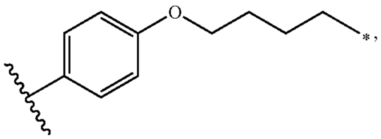
(L32)
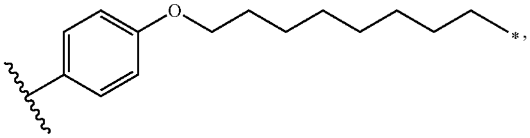
(L33)
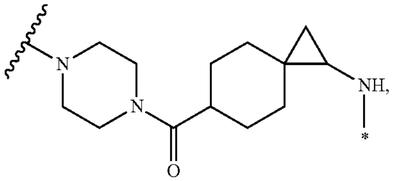
(L34)
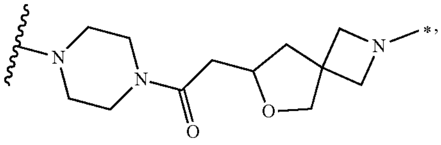
(L35)
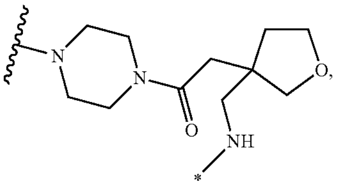
(L36)
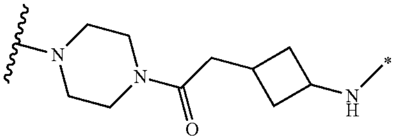

-continued
(L37)
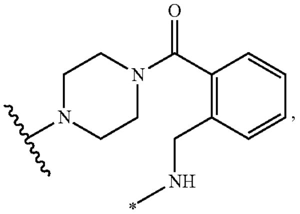
(L38)
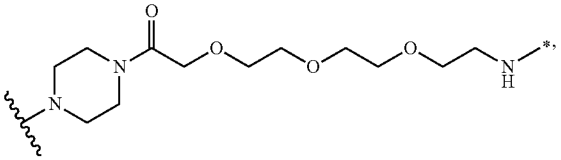
(L39)
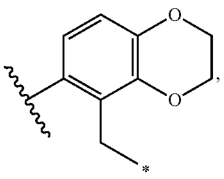
(L40)
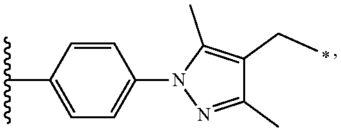
(L41)
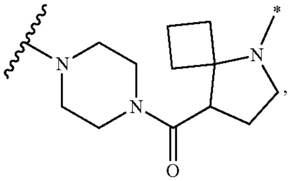
(L42)
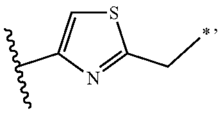
(L43)
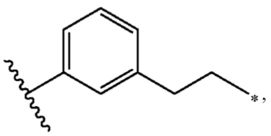
(L44)
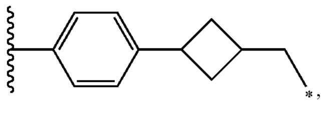
(L45)
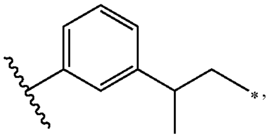
-continued
(L46)
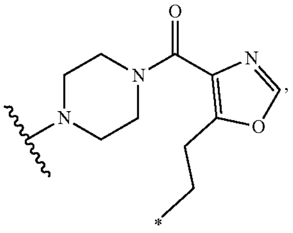
(L47)
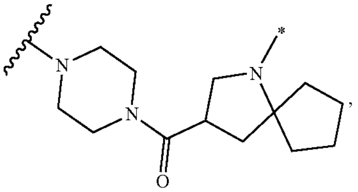
(L48)
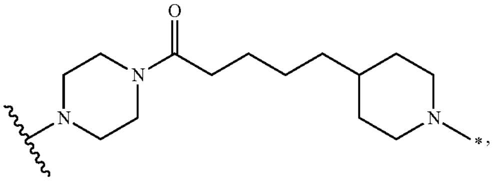
(L49)
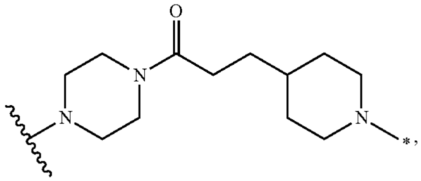
(L50)
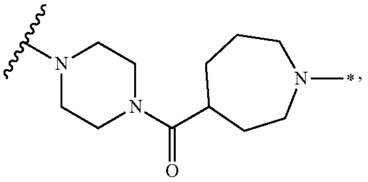
(L51)
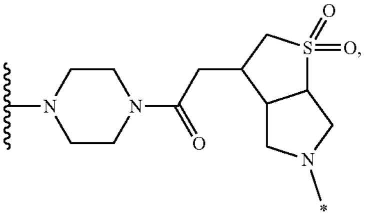
(L52)
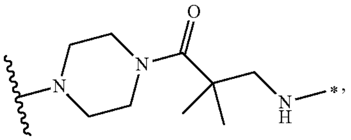
(L53)
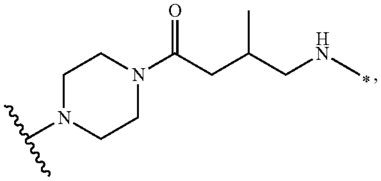

-continued
(L54)
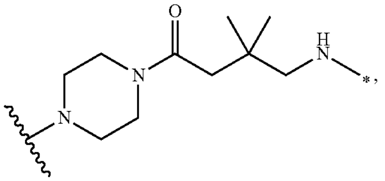
(L55)
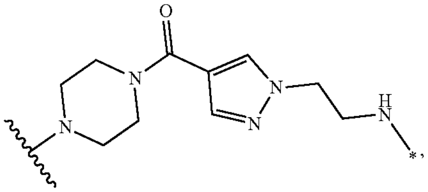
(L56)
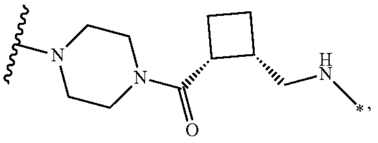
(L56a)
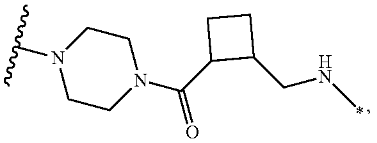
(L57)
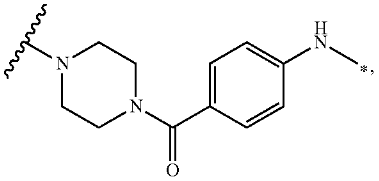
(L58)
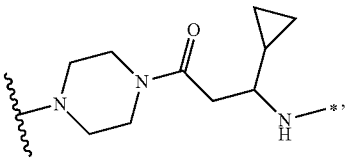
(L59)
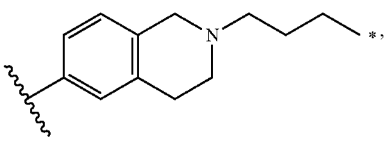
(L60)
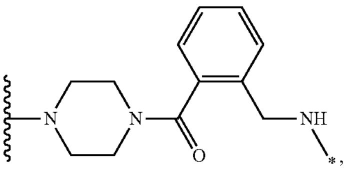
(L61)
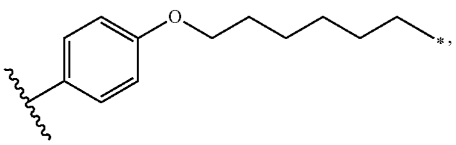
-continued
(L62)
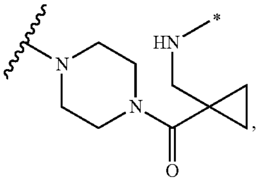
(L63)
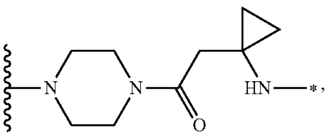
(L64)
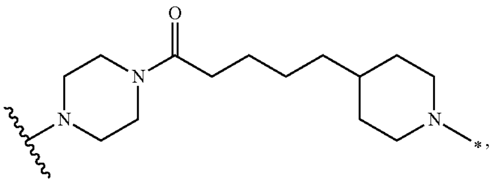
(L65)
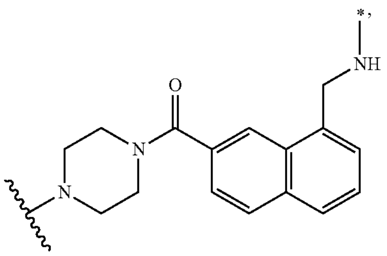
(L66)
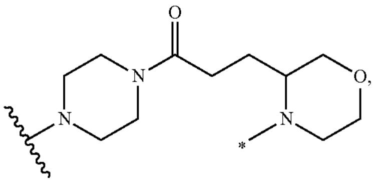
(L67)
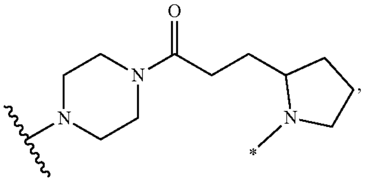
(L68)
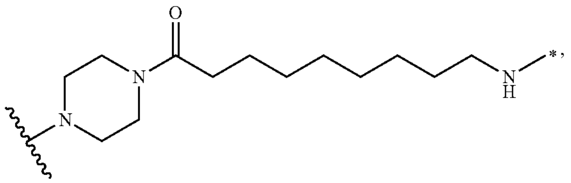
(L69)
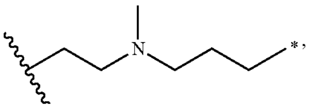

-continued
(L70)
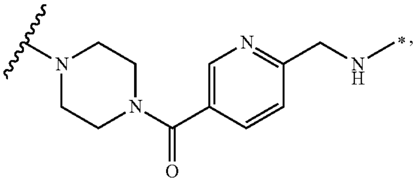
(L71)
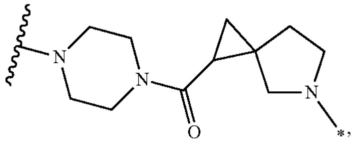
(L72)
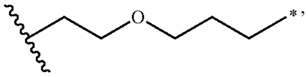
(L&3)
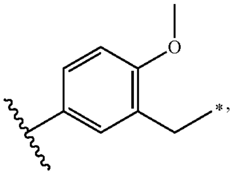
(L74)
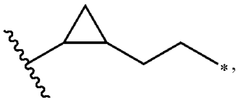
(L75)
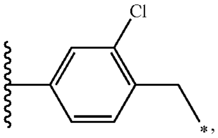
(L76)
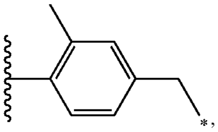
(L77)
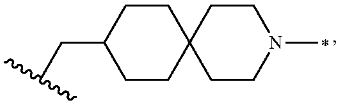
(L78)
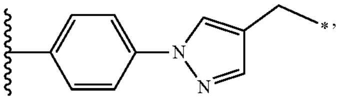
(L79)
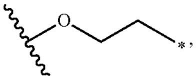
(L80)
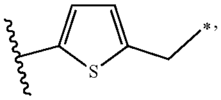
-continued
(L81)
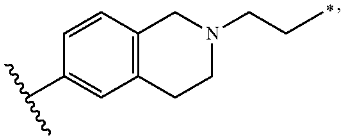
(L82)
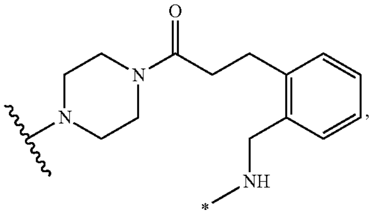
(L83)
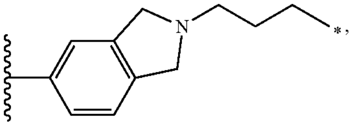
(L84)
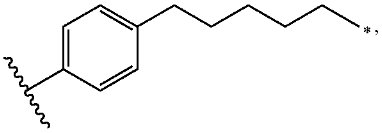
(L85)
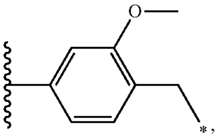
(L86)
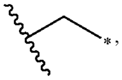
(L87)
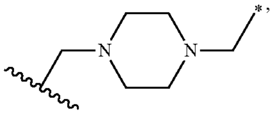
(L88)
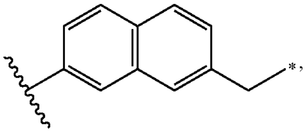
(L89)
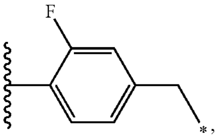
(L90)
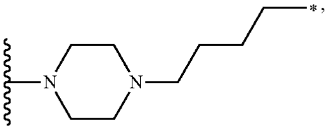

(L91)
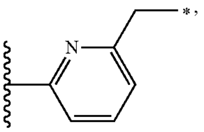
(L92)
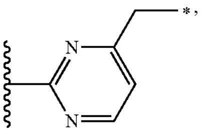
(L93)
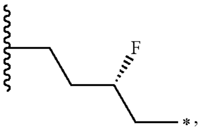
(L94)
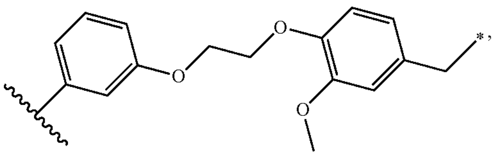
(L95)
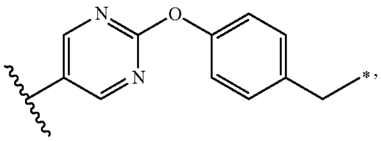
(L96)
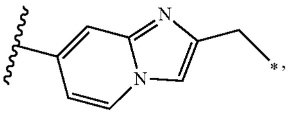
(L97)
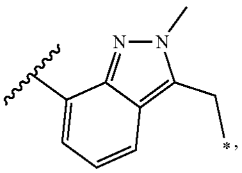
(L98)
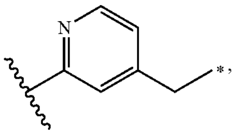
(L99)
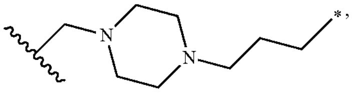
(L100)
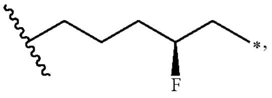
(L100a)
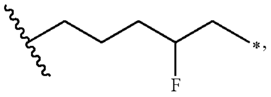
(L101)
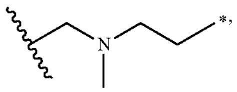
(L102)
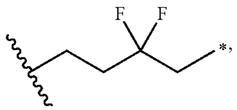
(L103)
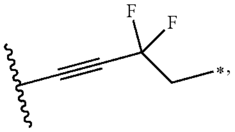
(L104)
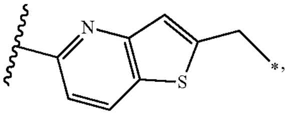
(L105)
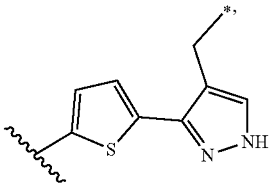
(L106)
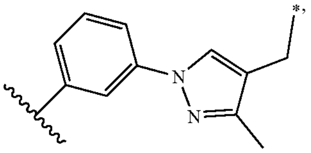
(L107)
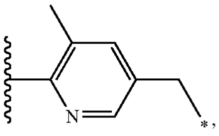
(L108)
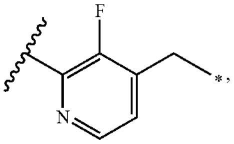
(L109)
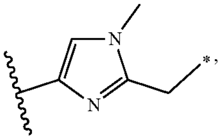
(L110)
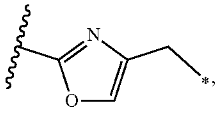

-continued (L111)

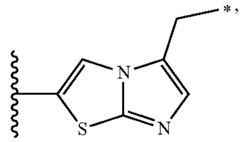

(L112)

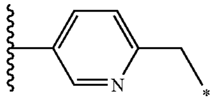

(L113)

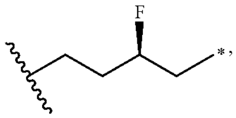

(L114)

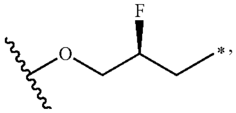

(L114a)

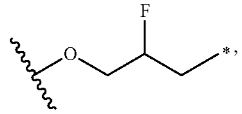

(L115)

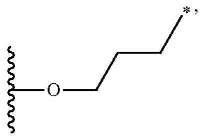

(L116)

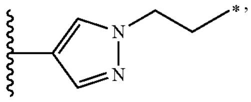

or (L117)

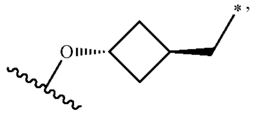

wherein *— represents a bond to DSM;

represents a bond to BTK; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first, forty-second, forty-third, forty-fourth, forty-fifth, forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth, sixty-seventh, sixty-eighth, sixty-ninth, seventieth, seventy-first, seventy-second, seventy-third, seventy-fourth, seventy-fifth, seventy-sixth, seventy-seventh, seventy-eighth, seventy-ninth or eightieth embodiment.

In a ninetieth embodiment, the compound is represented by the following formula:

(A-V)

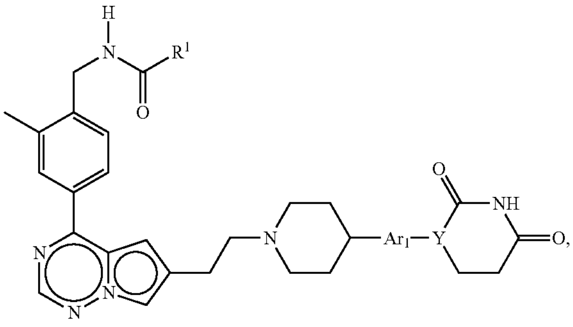

or a pharmaceutically acceptable salt thereof, wherein: $R^1$ is 1,2,4-oxadiazolyl or triazolyl, each of which is substituted with $R^{10}$, wherein $R^{10}$ is $C_{1-4}$alkyl; Y is N or CH; and $Ar_1$ is indozolyl or benzoisoxazolyl, each of which is optionally substituted with 1 or 2 substituents independently selected from halo and $C_{1-2}$alkyl.

In a ninety-first embodiment, the compound is represented by formula (A-V), or a pharmaceutically acceptable salt thereof, wherein $R^1$ is (C4)

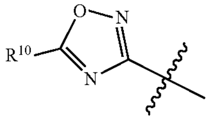

or (C26)

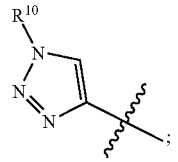

;

and $Ar_1$ is

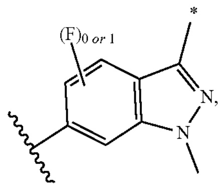

or

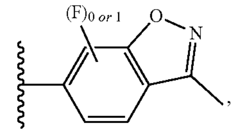

, wherein *— represents a bond to Y; and the definitions for the other variables are as defined in the ninetieth embodiment.

In a ninety-second embodiment, the compound is represented by formula (A-V), or a pharmaceutically acceptable salt thereof, wherein $R^{10}$ is —$C(CH_3)_3$; and the definitions for the other variables are as defined in the ninetieth or ninety-first embodiment.

In a ninety-third embodiment of the present disclosure, the compound of formula (A), or a pharmaceutically acceptable salt thereof is a compound of any one of Examples 1-300 or a pharmaceutically acceptable salt thereof.

III. Pharmaceutical Composition and Methods of Uses

Another aspect of the present disclosure is a pharmaceutical composition comprising at least one compound described herein (e.g., a compound or a pharmaceutically acceptable salt thereof described in any one of the first to sixth embodiments described above), and at least one pharmaceutically acceptable carrier.

In some embodiments, the compounds described herein (e.g., a compound or a pharmaceutically acceptable salt thereof described in any one of the first to sixth embodiments described above) can be used to cause the degradation of Btk proteins. In some embodiments, the compounds described herein (e.g., a compound or a pharmaceutically acceptable salt thereof described in any one of the first to sixth embodiments described above) can be used to modulate (e.g., decrease) the level of Btk proteins. In some embodiments, the compounds or pharmaceutically acceptable salts thereof described herein (e.g., a compound or a pharmaceutically acceptable salt thereof described in any one of the first to sixth embodiments described above) can be used to modulate (e.g., decrease) the activity of Btk, or to otherwise affect the properties and/or behavior of Btk, e.g., stability, phosphorylation, kinase activity, interactions with other proteins, etc.

In some embodiments, the present disclosure provides methods of decreasing protein levels of Btk and/or Btk enzymatic activity. In some embodiments, such methods include contacting a cell with an effective amount of a compound described herein (e.g., a compound or a pharmaceutically acceptable salt thereof described in any one of the first to sixth embodiments described above).

One aspect of the present disclosure includes a method of treating a disorder responsive to degradation of Btk and/or inhibition of Btk activity in a subject comprising administering to the subject an effective amount of at least one compound described herein (e.g., a compound or a pharmaceutically acceptable salt thereof described in any one of the first to sixth embodiments described above), or a pharmaceutical composition described herein.

In one embodiment, the present invention provides methods of treating autoimmune disorders, inflammatory disorders, and cancers in a subject in need thereof comprising administering to the subject an effective amount of at least one compound described herein (e.g., a compound or a pharmaceutically acceptable salt thereof described in any one of the first to sixth embodiments described above), or a pharmaceutical composition described herein.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus. In some embodiments, the present invention provides a method of treating multiple sclerosis. In some embodiments, the present invention provides a method of treating systemic lupus erythematosus or atopic dermatitis.

The compounds of the present disclosure (e.g., a compound or a pharmaceutically acceptable salt thereof described in any one of the first to sixth embodiments described above) may be useful in the treatment of cancer, for example a cancer selected from solid tumor cancers and hematopoietic cancers.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present disclosure provides a method of treating leukemia or lymphoma.

Examples of solid tumor cancers include central nervous system cancer, brain cancer, breast cancer, head and neck cancer, lung cancer; esophageal and esophagogastric junction cancer, gastric cancer, colorectal cancer, rectal cancer, anal cancer, hepatobiliary cancer, pancreatic cancer, non-melanoma skin cancer, melanoma, renal cancer, prostate cancer, bladder cancer, uterine cancer, cervical cancer, ovarian cancer, bone cancer, neuroendocrine cancer, mesothelioma cancer, testicular cancer, thymoma and thymic carcinoma, and thyroid cancer.

Examples of hematopoietic cancers include B-cell neoplasms (including rare B-cell malignancies), Hodgkin lymphoma, non-Hodgkin lymphoma, post-transplant lymphoproliferative disorder, hairy cell leukemia, histiocytic and dendritic neoplasms.

Examples of B-cell neoplasms include chronic lymphocytic leukemia (CLL), mantle cell lymphoma (MCL), small lymphocytic lymphoma (SLL). Waldenstrom's macroglobulinemia, diffuse large B-cell lymphoma (DLBCL), follicular lymphoma, Burkitt lymphoma, Marginal Zone Lymphoma, immunoblastic large cell lymphoma, Richter Syndrome, and precursor B-lymphoblastic lymphoma, primary and secondary multiple myeloma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, lymphomatoid granulomatosis, and acute lymphoblastic leukemia.

In some embodiments, the cancer is selected from chronic lymphocytic leukemia (CLL), diffuse large B-cell lymphoma (DLBCL), mantle cell lymphoma (MCL), small lymphocytic lymphoma (SLL), and Waldenstrom's macroglobulinemia.

In one embodiment, the cancer is chronic lymphocytic leukemia (CLL). In another embodiment, the cancer is diffuse large B-cell lymphoma (DLBCL).

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 μg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXEMPLIFICATIONS

Abbreviations and acronyms used herein include the following:

AcOH=acetic acid;
Aq.=aqueous;
Bn=benzyl;
Boc=tert-butoxy carbonyl;
br=broad;
° C.=degrees Celsius;
CDCl3=deutero-chloroform;
$CO_2$=carbon dioxide;
$Cs_2CO_3$=cesium carbonate;
δ=chemical shift;
d=doublet;
dd=double doublet;
DCE=1,2-Dichloroethane
DCM=dichloromethane;
DIPEA=N-ethyldiisopropylamine or N,N-diisopropylethylamine;
DMF=N,N-dimethylformamide;
DMSO=dimethylsulfoxide;
DMSO-d6=hexadeuterodimethyl sulfoxide;
Et=ethyl;
$Et_2O$=ether;
EtOH=ethanol;
EtOAc=ethyl acetate;
Equiv.=equivalent;
g=gram;
HATU=(1-[bis(dimethylamino)methylene]-1H-1,2,3-triazolo[4,5-b]pyridinium 3-oxide hexafluorophosphate
HBr=hydrogen bromide;
HCl=hydrochloric acid;
$^1$H NMR=proton nuclear magnetic resonance;
$H_2O$=water;
HPLC=high pressure liquid chromatography;
h=hour;
$K_2CO_3$=potassium carbonate;
$KHSO_4$=potassium bisulfate;
KOAc=potassium acetate;
$K_3PO_4$=potassium phosphate tribasic;
L=litre;
LCMS=liquid chromatography mass spectrometry;
m=multiplet;
M=molar;
Me=methyl;
MeCN=acetonitrile;
MeOH=methanol;
mg=milligram;
MHz=mega Hertz;
mins=minutes;
mL=millilitres;
mmol=millimole;
MS m/z=mass spectrum peak;
$N_2$=nitrogen;
$Na_2CO_3$=sodium carbonate;
$NaHCO_3$=sodium bicarbonate;
NaOH=sodium hydroxide;
$Na_2SO_4$=sodium sulfate;
$NH_3$=ammonia;
$NH_4Cl$=ammonium chloride;
Pd(amphos)$Cl_2$=Bis(di-tert-butyl(4-dimethylaminophenyl)phosphine) dichloropalladium(II)
Pd/C=palladium on carbon;
Pd(dppf)$Cl_2$=[1,1'-bis(diphenylphosphino)ferrocene]dichloropalladium(II);
$POC_3$=phosphoryl chloride
PyBOP=benzotriazol-1-yloxytripyrrolidinophosphonium hexafluorophosphate
q=quartet;
RT=room temperature;
s=singlet;
sat.=saturated;
SFC=supercritical fluid chromatography;
Si—CBH=silica-bound cyanoborohydride
$SiO_2$=silicon dioxide;
SOR=specific rotation
soln. or sol.=solution;
t=triplet;
TBAI=tetra-n-butylammonium iodide
TBAF=tetrabutylammonium fluoride;
TEA=triethylamine;
TFA=trifluoroacetic acid;
$Tf_2O$=trifluoromethanesulfonic anhydride;
THF=tetrahydrofuran;
TLC=thin layer chromatography;
μL=micro litres;
μmol=micromole.

I. Analytical Methods

NMR
Instrument Specifications:
Bruker AVANCE DRX 500
Varian UNITYplus 400
LC/MS
Instrument Specifications:
Agilent 1200 Series LC/MSD system with DADELSD Alltech 3300 and Agilent LCMSD G6130A, G6120B mass-spectrometer.
Agilent Technologies 1260 Infinity LC/MSD system with DADELSD Alltech 3300 and Agilent LCMSD G6120B mass-spectrometer.
Agilent Technologies 1260 Infinity II LC/MSD system with DADELSD G7102A 1290 Infinity II and Agilent LCMSD G6120B mass-spectrometer.
Agilent 1260 Series LC/MSD system with DADELSD and Agilent LCMSD (G6120B) mass-spectrometer.
UHPLC Agilent 1290 Series LC/MSD system with DADELSD and Agilent LCMSD (G6125B) mass-spectrometer.
LC Method 2 Min:
Inject volume: 0.5 μl
Column Temperature: 60° C.
UV scan: 207-223 nM
246-262 nM
272-288 nM
Agilent Poroshell 120 SB-C18 4.6×30 mm 2.7 μm
with UHPLC Guard Infinity Lab Poroshell 120 SB-C18 4.6×5 mm 2.7 μm
Mobile phase A: 0.1% FA in Water
Mobile phase B: 0.1% FA in Acetonitrile Details of Elution

| Time (min) | Flow (mL/min) | % A | % B |
|---|---|---|---|
| 0.00 | 3.00 | 99 | 1 |
| 0.01 | 3.00 | 99 | 1 |
| 1.5 | 3.00 | 0 | 100 |
| 1.73 | 3.00 | 0 | 100 |
| 1.74 | 3.00 | 99 | 1 |

Method 6 Min:
- Inject volume: 0.5 μl
- Column Temperature: 60° C.
- UV scan: 207-223 nM
  - 246-262 nM
  - 272-288 nM
- Agilent Poroshell 120 SB-C18 4.6×30 mm 2.7 μm with UHPLC Guard Infinity Lab Poroshell 120 SB-C18 4.6×5 mm 2.7 μm
- Mobile phase A: 0.1% FA in Water
- Mobile phase B: 0.1% FA in Acetonitrile Details of Elution

| Time (min) | Flow (mL/min) | % A | % B |
|---|---|---|---|
| 0.00 | 1.5 | 99 | 1 |
| 0.01 | 1.5 | 99 | 1 |
| 5.00 | 1.5 | 0 | 100 |
| 5.99 | 1.5 | 0 | 100 |
| 6.00 | 1.5 | 99 | 1 |

II. Synthesis of BTK-Linker Precursors

Synthesis of N-(4-(6-bromopyrrolo[2,1-f][1,2,4]triazin-4-yl)-2-methylbenzyl)-5-(tert-butyl)-1,2,4-oxadiazole-3-carboxamide

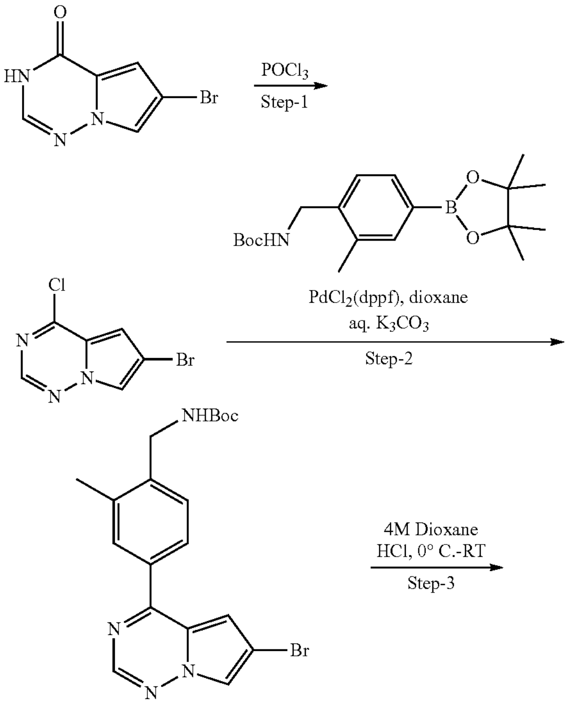

-continued

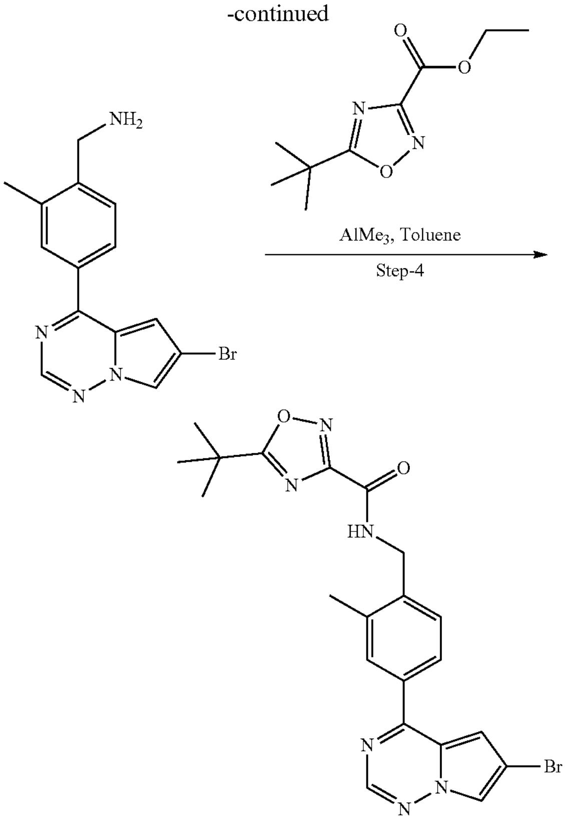

Step-1:

To a stirred solution of 6-bromo-3H-pyrrolo[2,1-f][1,2,4]triazin-4-one (20 g, 93.45 mmol) in toluene (75 mL) was added $POCl_3$ (659.12 g, 4.30 mol) at room temperature. The reaction mixture was warmed to 100° C. and stirred for 12 hours. Then the reaction mixture was concentrated in vacuo and quenched by a saturated solution of $NaHCO_3$. The reaction mixture was portioned between water and ethyl acetate. The organic layer was separated, washed with brine, dried over $Na_2SO_4$, and concentrated to give the crude product. The crude product was purified by flash column chromatography (silica gel 60-120 mesh, 0-5% ethyl acetate in pet ether) to afford the product 6-bromo-4-chloro-pyrrolo[2,1-f][1,2,4]triazine (18 g, 76.66 mmol, 82.03% yield) as an off-white solid. LC-MS ($ES^+$): m/z 232.25 $[M+H]^+$.

Step-2:

To a stirred solution of tert-butyl (2-methyl-4-(4,4,5,5-tetramethyl-1,3,2-dioxaborolan-2-yl)benzyl)carbamate (80 g, 230.38 mmol) in dioxane (350 mL) was added 6-bromo-4-chloropyrrolo[2,1-f][1,2,4]triazine (69.62 g, 299.49 mmol) at room temperature followed by potassium carbonate (95.52 g, 691.13 mmol) in water (90 mL) under argon atmosphere. The reaction mixture was degassed with argon gas repeatedly and $Pd(dppf)Cl_2{\cdot}CH_2Cl_2$ (8.43 g, 11.52 mmol) was added to the reaction mixture in one portion. The reaction mixture was degassed again with argon gas before it was heated at 50° C. for 16 hours. The crude product was purified by flash column chromatography (0-100% ethyl acetate in pet ether) to afford tert-butyl (4-(6-bromopyrrolo[2,1-f][1,2,4]triazin-4-yl)-2-methylbenzyl)carbamate (76 g, 173.02 mmol, 75.10% yield) as a yellow solid. LC-MS ($ES^+$): m/z 417.0.3 $[M+H]^+$.

Step-3:

To a stirred solution of tert-butyl N-[[4-(6-bromopyrrolo[2,1-f][1,2,4]triazin-4-yl)-2-methyl-phenyl]methyl]carbamate (15 g, 35.95 mmol) in DCM (200 mL) at 0° C., 4 M HCl in dioxane. (120 mL) was added dropwise. The reaction was stirred at 27° C. for 3 hours. The reaction was concentrated under reduced pressure, basified with saturated bicarbonate solution, and extracted with ethyl acetate (100 mL×4). The organic layer was separated, dried over anhydrous sodium sulfate, and concentrated under reduced pressure. The crude product was purified by flash column chromatography (silica gel 230-400 mesh, 0-20% MeOH in DCM) to afford [4-(6-bromopyrrolo[2,1-f][1,2,4]triazin-4-yl)-2-methyl-phenyl]methanamine (11 g, 33.64 mmol, 93.57% yield). LC-MS ($ES^+$): m/z 316.95 [M+H]+.

Step-4:

To a stirred solution of (4-(6-bromopyrrolo[2,1-f][1,2,4]triazin-4-yl)-2-methylphenyl)methanamine HCl salt (10 g, 28.28 mmol) in toluene (100 mL) was added ethyl 5-(tert-butyl)-1,2,4-oxadiazole-3-carboxylate (6.73 g, 33.93 mmol), and the reaction mixture was cooled to 0° C. Trimethylaluminum (2.04 g, 28.28 mmol, 2.72 mL) was added, and the reaction was heated at 90° C. for 12 hours. After completion, the reaction was cooled down, diluted with water, and extracted with ethyl acetate. The combined organic layers were dried over anhydrous sodium sulfate and concentrated under the high vacuum to give the crude product. The resulting crude product was purified via column chromatography (silica gel) to afford N-(4-(6-bromopyrrolo[2,1-f][1,2,4]triazin-4-yl)-2-methylbenzyl)-5-(tert-butyl)-1,2,4-oxadiazole-3-carboxamide (8.6 g, 17.41 mmol, 61.56% yield) as a yellow solid. LC-MS ($ES^+$): m/z 469.21 $[M+H]^+$.

Synthesis of 5-(tert-butyl)-N-(2-methyl-4-(6-(4,4,5,5-tetramethyl-1,3,2-dioxaborolan-2-yl)pyrrolo[2,1-f][1,2,4]triazin-4-yl)benzyl)-1,2,4-oxadiazole-3-carboxamide

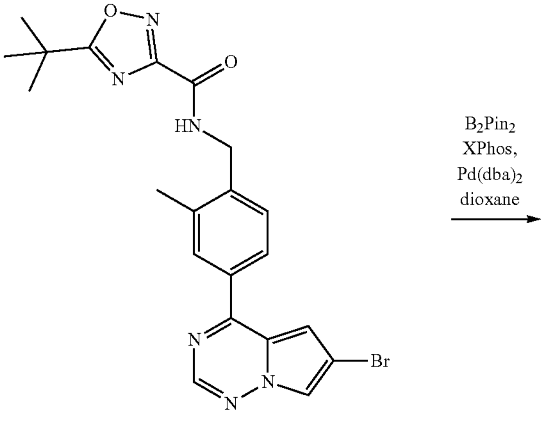

-continued

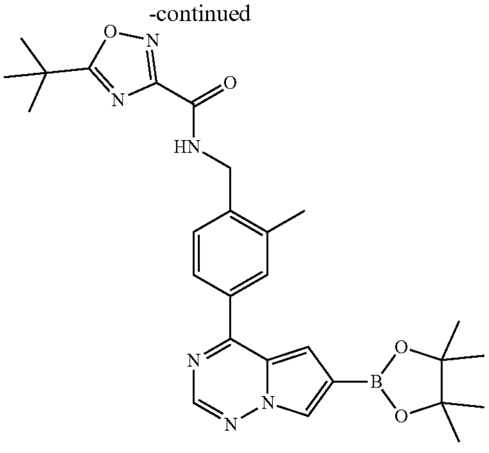

A mixture of N-(4-(6-bromopyrrolo[2,1-f][1,2,4]triazin-4-yl)-2-methylbenzyl)-5-(tert-butyl)-1,2,4-oxadiazole-3-carboxamide (100 mg, 213.07 μmol), 4,4,4',4',5,5,5',5'-octamethyl-2,2'-bi(1,3,2-dioxaborolane) (216.42 mg, 852.27 μmol), potassium acetate (41.82 mg, 426.14 μmol, 26.64 μL) and dicyclohexyl-[2-(2,4,6-triisopropylphenyl)phenyl]phosphane (20.31 mg, 42.61 μmol) in dioxane (2 mL) was degassed and purged with $N_2$ 3 times, and then the mixture was stirred at 100° C. for 1 h under $N_2$ atmosphere. The reaction mixture was filtered and concentrated under reduced pressure to give a residue. The residue was purified by prep-TLC ($SiO_2$, PE:EA=1:1). 5-(tert-butyl)-N-(2-methyl-4-(6-(4,4,5,5-tetramethyl-1,3,2-dioxaborolan-2-yl)pyrrolo[2,1-f][1,2,4]triazin-4-yl)benzyl)-1,2,4-oxadiazole-3-carboxamide (92 mg, 113.66 μmol, 53.35% yield) was obtained as a yellow solid. LC-MS ($ES^+$): m/z 517.5 $[M+H]^+$.

Synthesis of 5-(tert-butyl)-N-(4-(6-(5-formylpyridin-2-yl)pyrrolo[2,1-f][1,2,4]triazin-4-yl)-2-methylbenzyl)-1,2,4-oxadiazole-3-carboxamide

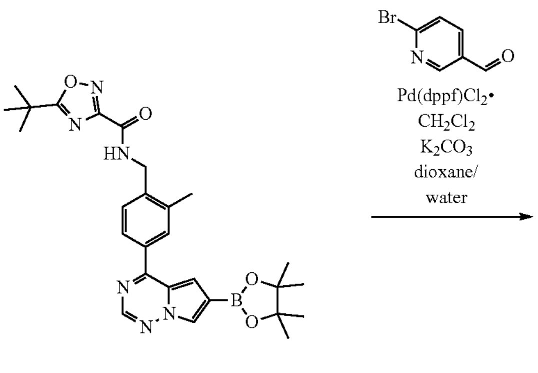

-continued

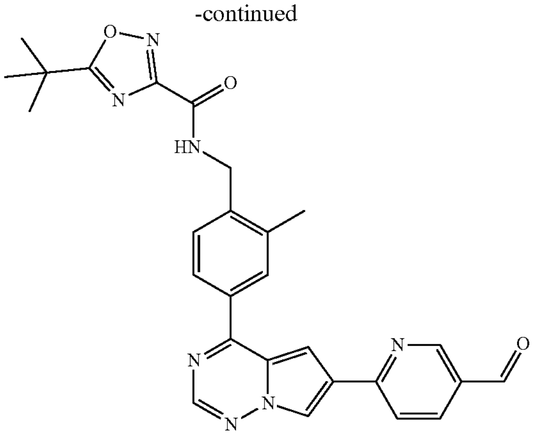

A mixture of 5-(tert-butyl)-N-(2-methyl-4-(6-(4,4,5,5-tetramethyl-1,3,2-dioxaborolan-2-yl)pyrrolo[2,1-f][1,2,4]triazin-4-yl)benzyl)-1,2,4-oxadiazole-3-carboxamide (92 mg, 178.16 μmol), 6-bromonicotinaldehyde (66.28 mg, 356.31 μmol), Pd(dppf)$Cl_2$·$CH_2Cl_2$ (14.55 mg, 17.82 μmol) and $K_2CO_3$ (73.87 mg, 534.47 μmol, 32.26 μL) in dioxane (1.6 mL) was degassed and purged with $N_2$ 3 times, and then the mixture was stirred at 100° C. for 3 h under $N_2$ atmosphere. The reaction mixture was under reduced pressure to give a residue. The residue was purified by prep-TLC ($SiO_2$, PE:EA=2:3). 5-(tert-butyl)-N-(4-(6-(5-formylpyridin-2-yl)pyrrolo[2,1-f][1,2,4]triazin-4-yl)-2-methylbenzyl)-1,2,4-oxadiazole-3-carboxamide (40 mg, 66.92 μmol, 37.56% yield) was obtained as a yellow solid. LC-MS ($ES^+$): m/z 496.5 $[M+H]^+$.

Synthesis of 5-tert-butyl-N-[[4-[6-(4-formylphenyl)pyrrolo[2,1-f][1,2,4]triazin-4-yl]-2-methyl-phenyl]methyl]-1,2,4-oxadiazole-3-carboxamide

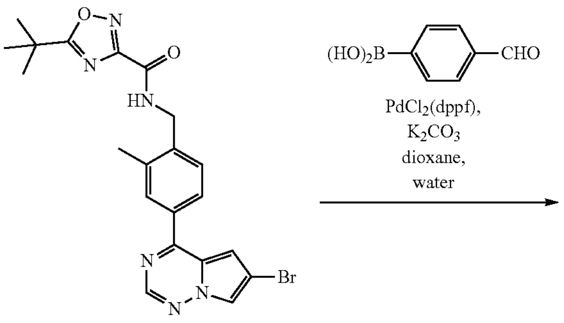

-continued

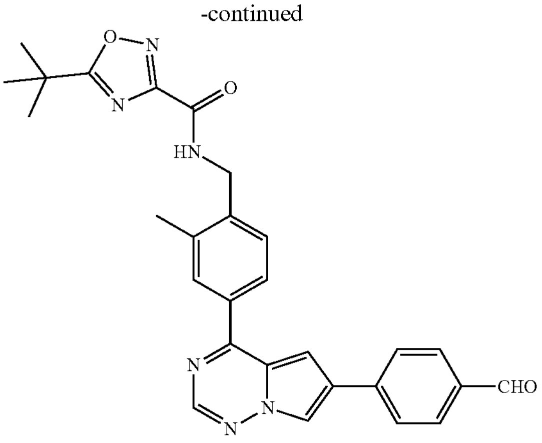

To a stirred solution of N-[[4-(6-bromopyrrolo[2,1-f][1,2,4]triazin-4-yl)-2-methyl-phenyl]methyl]-5-tert-butyl-1,2,4-oxadiazole-3-carboxamide (3.0 g, 6.39 mmol) in dioxane (40 mL) and water (10 mL) purged with argon gas, potassium carbonate (2.65 g, 19.18 mmol) and (4-formylphenyl) boronic acid (1.73 g, 11.51 mmol) were added at room temperature and the reaction mixture was stirred at this temperature for 10 minutes. Pd(dppf)$Cl_2$·$CH_2Cl_2$ (467.71 mg, 639.20 μmol) was added, and the reaction was heated at 85° C. for 16 hours while the reaction progress was monitored by TLC and LC-MS. After completion of the reaction, the reaction was quenched with water (50 mL) and extracted with ethyl acetate (30 mL×3). The combined organic layers were washed with brine solution (50 mL), dried over anhydrous sodium sulfate, filtered, and concentrated under reduced pressure. The crude compound was purified by flash column chromatography (silica gel 230-400 mesh, 0-100% ethyl acetate in pet-ether) to afford 5-tert-butyl-N-[[4-[6-(4-formylphenyl)pyrrolo[2,1-f][1,2,4]triazin-4-yl]-2-methyl-phenyl]methyl]-1,2,4-oxadiazole-3-carboxamide (2.57 g, 4.57 mmol, 71.54% yield). LC-MS ($ES^+$): m/z 495.30 $[M+H]^+$.

Synthesis of 5-(tert-butyl)-N-(4-(6-(3-chloro-4-formylphenyl)pyrrolo[2,1-f][1,2,4]triazin-4-yl)-2-methylbenzyl)-1,2,4-oxadiazole-3-carboxamide

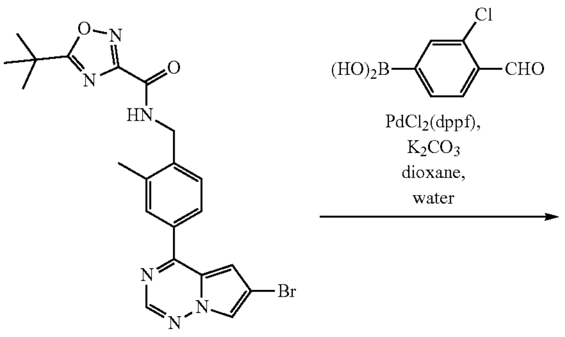

-continued

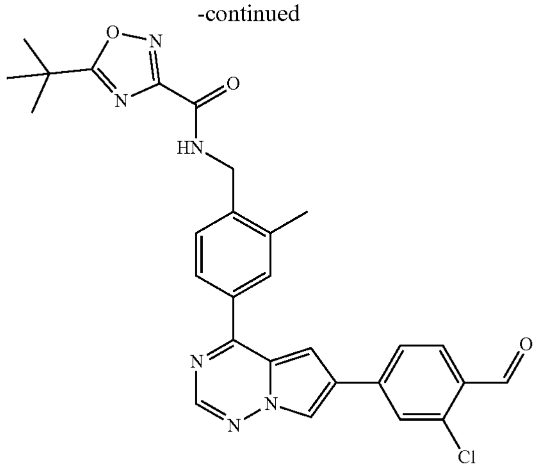

A solution of N-(4-(6-bromopyrrolo[2,1-f][1,2,4]triazin-4-yl)-2-methylbenzyl)-5-(tert-butyl)-1,2,4-oxadiazole-3-carboxamide (100 mg, 213.07 μmol), 2-chloro-4-(4,4,5,5-tetramethyl-1,3,2-dioxaborolan-2-yl)benzaldehyde (85.18 mg, 319.60 μmol) and sodium carbonate (22.58 mg, 213.07 μmol) in $H_2O$ (0.2 mL) and dioxane (0.8 mL) was added cyclopentyl(diphenyl)phosphane; dichloropalladium; iron (15.59 mg, 21.31 μmol), and the mixture was stirred at 100° C. for 12 hours under $N_2$ atmosphere. The progress of the reaction was monitored by LC-MS. The reaction mixture was concentrated under reduced pressure to remove dioxane, poured into saturated $NH_4Cl$ aqueous solution (3 mL), and extracted with ethyl acetate (5 mL×3). The combined organic layers were washed with brine (10 mL), dried over anhydrous sodium sulfate, filtered, and concentrated in vacuo. The residue was purified by flash column chromatography (silica gel, petroleum ether/ethyl acetate=10/1 to 1/1) to afford 5-(tert-butyl)-N-(4-(6-(3-chloro-4-formylphenyl)pyrrolo[2,1-f][1,2,4]triazin-4-yl)-2-methylbenzyl)-1,2,4-oxadiazole-3-carboxamide (80 mg, 127.34 μmol, 59.76% yield) was obtained as a yellow solid. $^1H$ NMR (400 MHz, $CDCl_3$) δ=10.50 (s, 1H), 8.60 (s, 1H), 8.32 (s, 1H), 8.01 (d, J=1.6 Hz, 2H), 7.97 (br d, J=11.2 Hz, 1H), 7.79 (d, J=1.6 Hz, 1H), 7.71 (d, J=8.4 Hz, 1H), 7.59 (br d, J=7.9 Hz, 1H), 7.43 (s, 1H), 4.84-4.75 (m, 2H), 2.55 (s, 3H), 1.49 (s, 9H). LC-MS ($ES^+$): m/z, 529.3 $[M+H]^+$.

Synthesis of 5-(tert-butyl)-N-(4-(6-(4-formyl-3-methoxyphenyl)pyrrolo[2,1-f][1,2,4]triazin-4-yl)-2-methylbenzyl)-1,2,4-oxadiazole-3-carboxamide

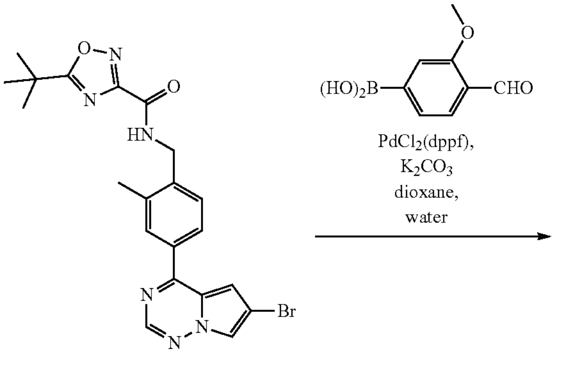

-continued

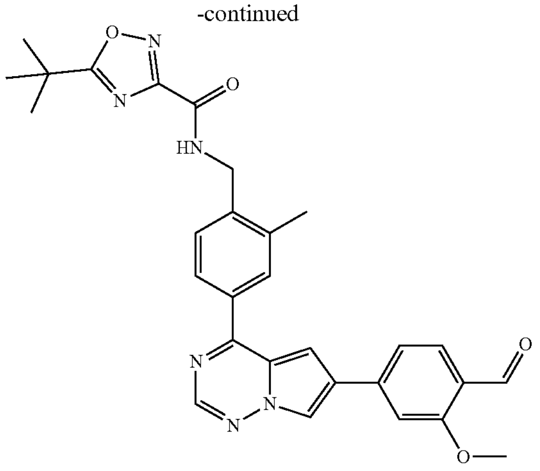

A solution of N-(4-(6-bromopyrrolo[2,1-f][1,2,4]triazin-4-yl)-2-methylbenzyl)-5-(tert-butyl)-1,2,4-oxadiazole-3-carboxamide (100 mg, 213.07 μmol), 2-methoxy-4-(4,4,5,5-tetramethyl-1,3,2-dioxaborolan-2-yl)benzaldehyde (83.77 mg, 319.60 μmol), and sodium carbonate (22.58 mg, 213.07 μmol) in $H_2O$ (0.2 mL) and dioxane (0.8 mL) was added $Pd(dppf)Cl_2{\cdot}CH_2Cl_2$ (15.59 mg, 21.31 μmol). The mixture was stirred at 100° C. for 12 hours under $N_2$ atmosphere and the progress of the reaction was monitored by LC-MS. The reaction mixture was concentrated under reduced pressure to remove dioxane, poured into saturated $NH_4Cl$ aqueous solution (3 mL), and extracted with ethyl acetate (5 mL×3). The combined organic layers were washed with brine (10 mL), dried over anhydrous sodium sulfate, filtered, and concentrated in vacuo. The residue was purified by flash column chromatography (silica gel, petroleum ether/ethyl acetate=10/1 to 1/1). Compound 5-(tert-butyl)-N-(4-(6-(4-formyl-3-methoxyphenyl)pyrrolo[2,1-f][1,2,4]triazin-4-yl)-2-methylbenzyl)-1,2,4-oxadiazole-3-carboxamide (100 mg, 168.52 μmol, 79.09% yield) was obtained as a yellow oil. $^1H$ NMR (400 MHz, $CDCl_3$) δ=10.44 (s, 1H), 8.52 (d, J=1.2 Hz, 1H), 8.22 (d, J=1.6 Hz, 1H), 7.93 (br s, 2H), 7.87 (dd, J=1.2, 8.0 Hz, 1H), 7.52 (d, J=8.4 Hz, 1H), 7.33 (d, J=8.0 Hz, 1H), 7.29 (d, J=1.6 Hz, 1H), 7.23 (s, 1H), 4.76 (d, J=6.0 Hz, 2H), 4.02 (s, 3H), 2.50 (s, 3H), 1.47 (d, J=0.8 Hz, 9H). LC-MS ($ES^+$): m/z 525.3 $[M+H]^+$.

Synthesis of 5-tert-butyl-N-[[4-[6-(3-fluoro-4-formyl-phenyl)pyrrolo[2,1-f][1,2,4]triazin-4-yl]-2-methyl-phenyl]methyl]-1,2,4-oxadiazole-3-carboxamide

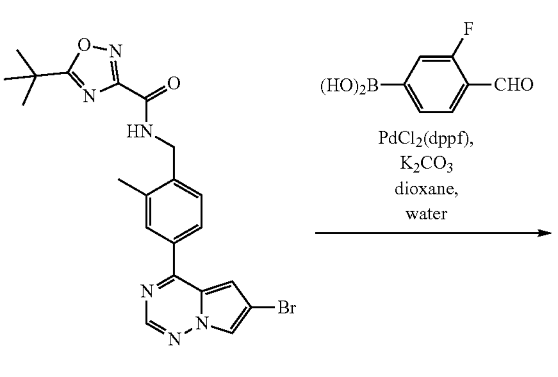

-continued

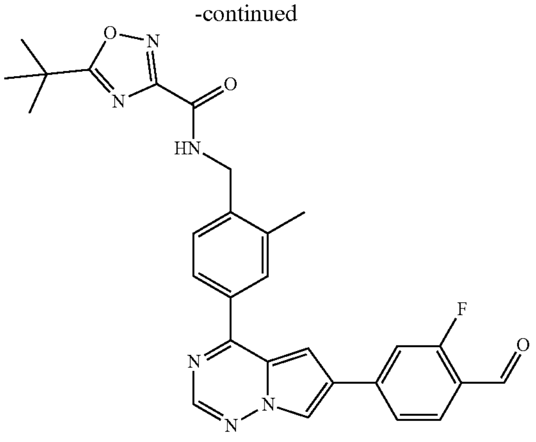

To a solution of N-[[4-(6-bromopyrrolo[2,1-f][1,2,4]triazin-4-yl)-2-methyl-phenyl]methyl]-5-tert-butyl-1,2,4-oxadiazole-3-carboxamide (100 mg, 213.07 μmol) and (3-fluoro-4-formyl-phenyl)boronic acid (39.36 mg, 234.37 μmol) in dioxane (1 mL) and water (0.2 mL) was added $Pd(dppf)Cl_2{\cdot}CH_2Cl_2$ (7.80 mg, 10.65 μmol) and sodium carbonate (67.75 mg, 639.20 μmol). The mixture was stirred at 100° C. for 12 hours. The reaction progress was monitored by LC-MS. After completion, the reaction mixture was concentrated under reduced pressure, and the residue was purified by prep-TLC (silica gel, petroleum ether/ethyl acetate=3/1). Compound 5-tert-butyl-N-[[4-[6-(3-fluoro-4-formyl-phenyl)pyrrolo[2,1-f][1,2,4]triazin-4-yl]-2-methyl-phenyl]methyl]-1,2,4-oxadiazole-3-carboxamide (60 mg, 117.07 μmol, 54.94% yield) was obtained as a yellow solid. $^1H$ NMR (400 MHz, $CDCl_3$) δ=10.30 (s, 1H), 8.48 (s, 1H), 8.16 (d, J=1.3 Hz, 1H), 7.91-7.83 (m, 3H), 7.55-7.38 (m, 3H), 7.24 (d, J=1.3 Hz, 1H), 4.71 (br s, 2H), 2.46 (s, 3H), 1.41 (s, 9H). LC-MS ($ES^+$): m/z 513.4 $[M+H]^+$.

Synthesis of 5-tert-butyl-N-[[4-[6-(4-formyl-2-methoxy-phenyl)pyrrolo[2,1-f][1,2,4]triazin-4-yl]-2-methyl-phenyl]methyl]-1,2,4-oxadiazole-3-carboxamide

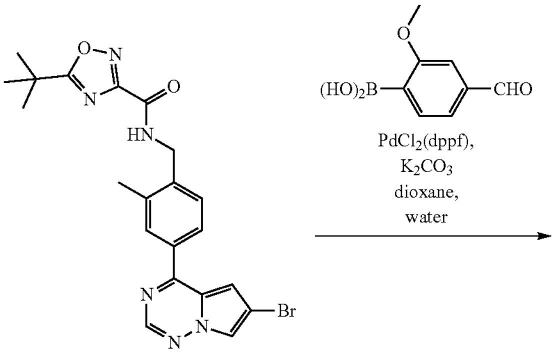

-continued

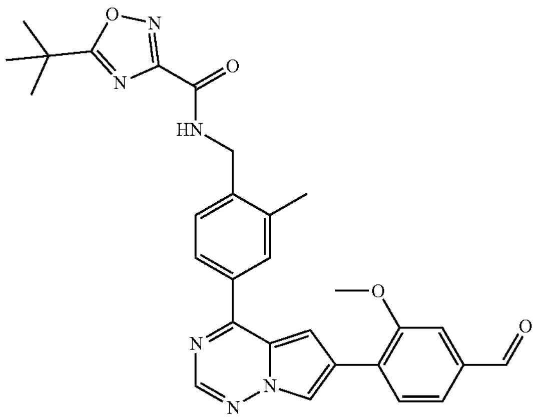

To a solution of N-[[4-(6-bromopyrrolo[2,1-f][1,2,4]triazin-4-yl)-2-methyl-phenyl]methyl]-5-tert-butyl-1,2,4-oxadiazole-3-carboxamide (200 mg, 426.14 μmol) and (4-formyl-2-methoxy-phenyl)boronic acid (84.36 mg, 468.75 μmol) in dioxane (2 mL) and water (0.4 mL) was added $Pd(dppf)Cl_2{\cdot}CH_2Cl_2$ (15.59 mg, 21.31 μmol) and sodium carbonate (135.50 mg, 1.28 mmol). The mixture was stirred at 100° C. for 12 hours. The progress of the reaction was monitored by LC-MS. The reaction mixture was quenched by adding $H_2O$ (20 mL), and extracted with ethyl acetate (50 mL×2). The combined organic layers were washed with brine (50 mL), dried over anhydrous sodium sulfate, filtered, and concentrated under reduced pressure. The residue was purified by prep-TLC (silica gel, petroleum ether/ethyl acetate=3/1). Compound 5-tert-butyl-N-[[4-[6-(4-formyl-2-methoxy-phenyl)pyrrolo[2,1-f][1,2,4]triazin-4-yl]-2-methyl-phenyl]methyl]-1,2,4-oxadiazole-3-carboxamide (120 mg, 228.76 μmol, 53.68% yield) was obtained as a yellow solid. LC-MS ($ES^+$): m/z 525.4 $[M+H]^+$.

Synthesis of 5-(tert-butyl)-N-(4-(6-(4-formyl-2-methylphenyl)pyrrolo[2,1-f][1,2,4]triazin-4-yl)-2-methylbenzyl)-1,2,4-oxadiazole-3-carboxamide

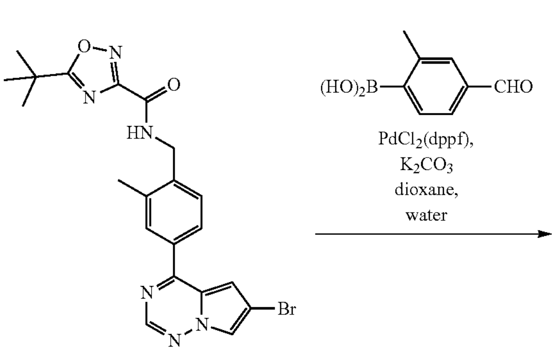

-continued

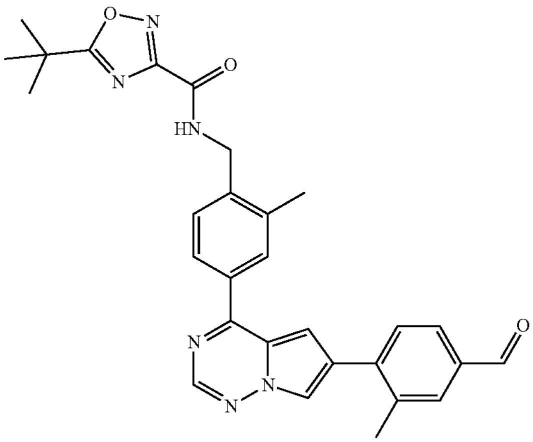

A mixture of N-(4-(6-bromopyrrolo[2,1-f][1,2,4]triazin-4-yl)-2-methylbenzyl)-5-(tert-butyl)-1,2,4-oxadiazole-3-carboxamide (100 mg, 213.07 μmol), 3-methyl-4-(4,4,5,5-tetramethyl-1,3,2-dioxaborolan-2-yl)benzaldehyde (83.90 mg, 340.91 μmol), Pd(dppf)$Cl_2$·$CH_2Cl_2$ (15.59 mg, 21.31 μmol) and sodium carbonate (50 mg, 471.75 μmol) in dioxane (1 mL) and water (81 μL) was degassed and purged with $N_2$ three times. The mixture was stirred at 100° C. for 12 hours under $N_2$ atmosphere. The progress of the reaction was monitored by LC-MS. After completion, the reaction mixture was concentrated under reduced pressure to remove water and dioxane, and the residue was purified by flash column chromatography (silica gel, petroleum ether/ethyl acetate=6/1 to 5/1). Compound 5-(tert-butyl)-N-(4-(6-(4-formyl-2-methylphenyl)pyrrolo[2,1-f][1,2,4]triazin-4-yl)-2-methylbenzyl)-1,2,4-oxadiazole-3-carboxamide (81 mg, 130.41 μmol, 61.21% yield) was obtained as a yellow solid.

$^1$H NMR (400 MHz, DMSO-$d_6$) δ ppm 1.44 (s, 9H) 2.47 (s, 3H) 2.58 (s, 3H) 4.56 (d, J=6.0 Hz, 2H) 7.44-7.50 (m, 2H) 7.81 (s, 2H) 7.87 (s, 1H) 8.00-8.09 (m, 2H) 8.55 (d, J=1.2 Hz, 1H) 8.67 (s, 1H) 9.53 (t, J=6.0 Hz, 1H) 10.02 (s, 1H). LC-MS ($ES^+$): m/z 509.3 $[M+H]^+$. z Synthesis of tert-butyl (4-(6-bromopyrrolo[2,1-f][1,2,4]triazin-4-yl)-2-fluorobenzyl)carbamate

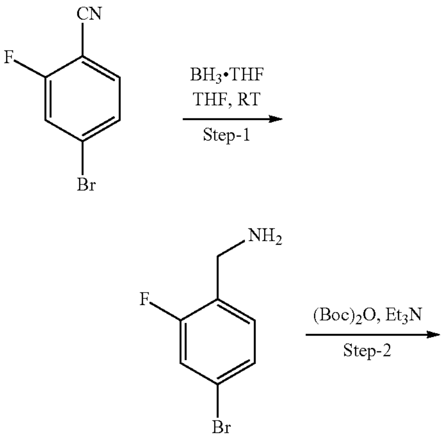

-continued

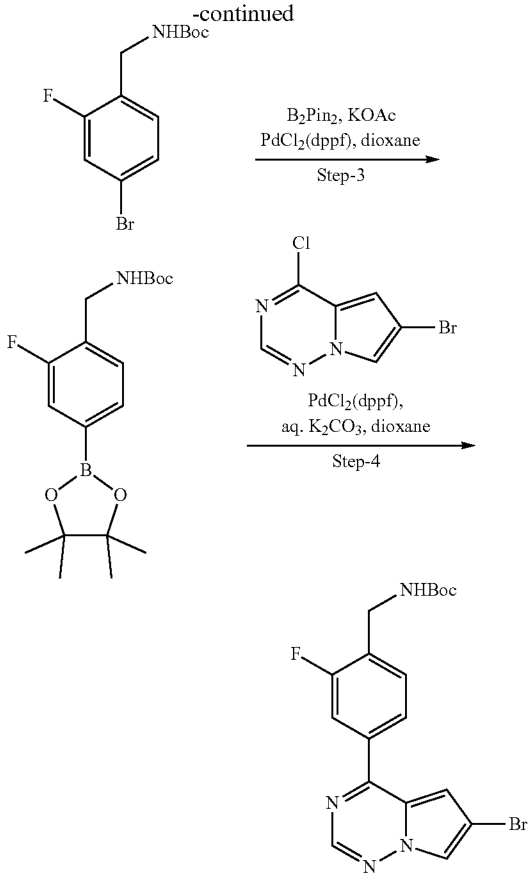

Step-1:

To the stirred solution of 4-bromo-2-fluorobenzonitrile (65 g, 324.99 mmol) in dry THF (500 mL) was added borane; tetrahydrofuran (1 M solution) (83.79 g, 974.97 mmol, 95.43 mL) dropwise at 0° C. under $N_2$ atmosphere. The reaction mixture was slowly warmed to room temperature over 1 hour and heated at 80° C. for 12 hours. After completion of the reaction, the reaction mixture was cooled to 0° C. and quenched carefully with methanol (750 ml) at 0° C. with stirring for over 1 hour (Note: The exothermicity and evolution of gas were controlled carefully by slow addition as well as external cooling). The quenched reaction mixture was concentrated to obtain the residual mass, which was then dissolved in ethyl acetate (500 ml) and HCl (g) in 1,4-dioxane (4M solution) (59.25 g, 1.62 mol, 74.06 mL) was added dropwise at 0° C. The reaction mixture was stirred for 30 minutes, and the solidified mass was filtered-off, washed with diethyl ether (500 ml), dried to afford (4-bromo-2-fluorophenyl)methanamine HCl salt (62 g, 244.91 mmol, 75.36% yield) as a colorless solid. LC-MS ($ES^+$): m/z 187.32 $[M+H-NH_3]^+$.

Step-2:

To the stirred solution of (4-bromo-2-fluorophenyl)methanamine HCl salt (70 g, 291.06 mmol) in dry DCM (2000 mL), triethylamine (73.63 g, 727.65 mmol, 101.42 mL) was added dropwise at 20° C. under $N_2$ atmosphere. The reaction mixture was stirred at the same temperature for 30 minutes, and tert-butoxycarbonyl tert-butyl carbonate (69.88 g, 320.17 mmol, 73.48 mL) in DCM (500 ml) was added dropwise for 1 hour. The reaction mixture was warmed to room temperature over a period of 1 hour and stirred at ambient temperature for 12 hours while the reaction progress was monitored by TLC. Upon reaction completion, the reaction mixture was quenched with ice-cold water (500 ml), and the organic layer was partitioned. The organic layer was further washed with water (3×500 ml), brine (1×200 ml), dried over anhydrous sodium sulfate, filtered, concentrated in vacuo to get the crude compound. The crude product was purified by flash column chromatography (silica gel 100/200 mesh, 2-5% ethyl acetate in hexane) to afford tert-butyl N-[(4-bromo-2-fluoro-phenyl)methyl]carbamate (64 g, 199.90 mmol, 68.68% yield) as a colorless solid. LC-MS ($ES^+$): m/z 247.88 $[M-56+H]^+$.

Step-3:

To the stirred solution of tert-butyl N-[(4-bromo-2-fluoro-phenyl)methyl]carbamate (64 g, 210.42 mmol) in dry 1,4-dioxane (640 mL) was added 4,4,5,5-tetramethyl-2-(4,4,5,5-tetramethyl-1,3,2-dioxaborolan-2-yl)-1,3,2-dioxaborolane (69.46 g, 273.54 mmol) followed by potassium acetate (51.63 g, 526.05 mmol) at room temperature under argon atmosphere. The reaction mixture was degassed with argon gas for 10 minutes, and $Pd(dppf)Cl_2$ (1.54 g, 2.10 mmol) was added in one portion. The reaction mixture was degassed again with argon gas for another 15 minutes before it was heated to 90° C. for 12 hours. The reaction mixture was filtered through a celite bed, washed with ethyl acetate (100 ml). The filtrate was concentrated to a residual mass, which was dissolved in ethyl acetate (500 ml), washed with water (2×300 ml), brine (1×100 ml), dried over anhydrous sodium sulfate, filtered, and concentrated to get the crude compound. The crude product was purified by flash column chromatography (silica gel 100/200 mesh, 5-25% ethyl acetate in hexane) to obtain the tert-butyl N-[[2-fluoro-4-(4,4,5,5-tetramethyl-1,3,2-dioxaborolan-2-yl)phenyl]methyl] carbamate (70 g, 179.37 mmol, 85.25% yield) as a white solid. LC-MS ($ES^+$): m/z 296.36 $[M-56+H]^+$.

Step-4:

To the stirred solution of 6-bromo-4-chloropyrrolo[2,1-f][1,2,4]triazine (25 g, 107.54 mmol) and tert-butyl (2-fluoro-4-(4,4,5,5-tetramethyl-1,3,2-dioxaborolan-2-yl)benzyl)carbamate (30.22 g, 86.03 mmol) in dry dioxane (500 mL) was added potassium carbonate (29.73 g, 215.09 mmol) followed by water (125 mL) at room temperature under argon atmosphere. The reaction mixture was degassed with argon gas for 10 minutes, and $Pd(dppf)Cl_2$ (786.90 mg, 1.08 mmol) was added in one portion. The reaction mixture was degassed again with argon gas for another 15 minutes before being heated at 60° C. for 5 hours. The reaction mixture was filtered through a celite bed and washed with ethyl acetate (100 ml). The filtrate was concentrated to a residual mass, which was dissolved in ethyl acetate (500 ml), washed with water (2×100 ml), brine (1×100 ml), dried over anhydrous sodium sulfate, filtered, and concentrated to get the crude compound. The crude product was purified by flash column chromatography (silica gel 100-200 mesh, 20-30% ethyl acetate in hexane) to afford tert-butyl (4-(6-bromopyrrolo[2,1-f][1,2,4]triazin-4-yl)-2-fluorobenzyl)carbamate (26 g, 60.78 mmol, 56.52% yield) as a yellow solid. LC-MS ($ES^+$): m/z 422.48 $[M+H]^+$.

Synthesis of N-[[4-(6-bromopyrrolo[2,1-f][1,2,4]triazin-4-yl)-2-fluoro-phenyl]methyl]-5-tert-butyl-1,2,4-oxadiazole-3-carboxamide

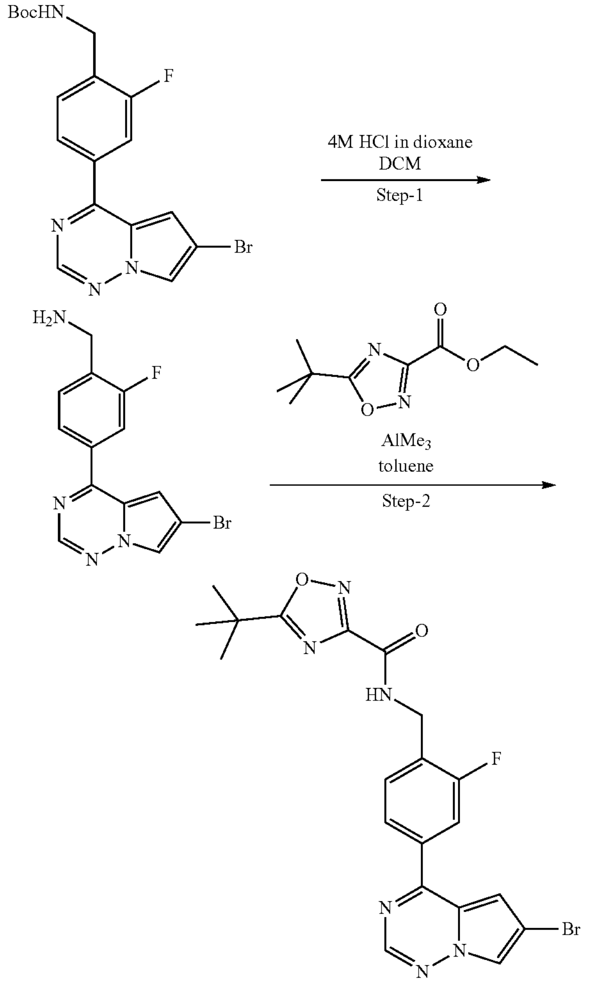

Step-1:

To a solution of tert-butyl (4-(6-bromopyrrolo[2,1-f][1,2,4]triazin-4-yl)-2-fluorobenzyl)carbamate (10 g, 23.74 mmol) in DCM (100 mL) was added 4 M hydrogen chloride in 1,4-dioxane (50 mL) at 0° C. and the reaction mixture was stirred at room temperature for 2 hours. The reaction mixture was concentrated in vacuo to get the crude product, which was neutralized with saturated sodium bicarbonate solution and extracted with 10% MeOH/DCM. The organic layer was concentrated to afford [4-(6-bromopyrrolo[2,1-f][1,2,4]triazin-4-yl)-2-fluoro-phenyl]methanamine (7.5 g, 23.31 mmol, 98.19% yield). LC-MS ($ES^+$): m/z 321.28 $[M+H]^+$.

Step-2:

To a stirred solution of [4-(6-bromopyrrolo[2,1-f][1,2,4]triazin-4-yl)-2-fluoro-phenyl]methanamine (7.5 g, 23.35 mmol) in toluene (150 mL) was added ethyl 5-tert-butyl-1,2,4-oxadiazole-3-carboxylate (9.26 g, 46.71 mmol) at 0° C. Trimethylaluminum 2M in toluene (4.21 g, 58.38 mmol) was then added, and the reaction was allowed to equilibrate to room temperature for 5 minutes. The reaction was heated for 3 hours at 80° C., and the progress was monitored by TLC. After the reaction was complete, the reaction mixture was diluted with water and extracted with ethyl acetate. The organic layer was concentrated in vacuo to obtain the crude product, which was purified by flash column chromatography (silica gel 230-400 mesh, 80% ethyl acetate/petroleum ether) to afford N-[[4-(6-bromopyrrolo[2,1-f][1,2,4]triazin-4-yl)-2-fluoro-phenyl]methyl]-5-tert-butyl-1,2,4-oxadiazole-3-carboxamide (4.5 g, 7.67 mmol, 32.84% yield). LC-MS ($ES^+$): m/z 473.27 $[M+H]^+$.

Synthesis of 5-tert-butyl-N-[[2-fluoro-4-[6-(4-formylphenyl)pyrrolo[2,1-f][1,2,4]triazin-4-yl]phenyl]methyl]-1,2,4-oxadiazole-3-carboxamide

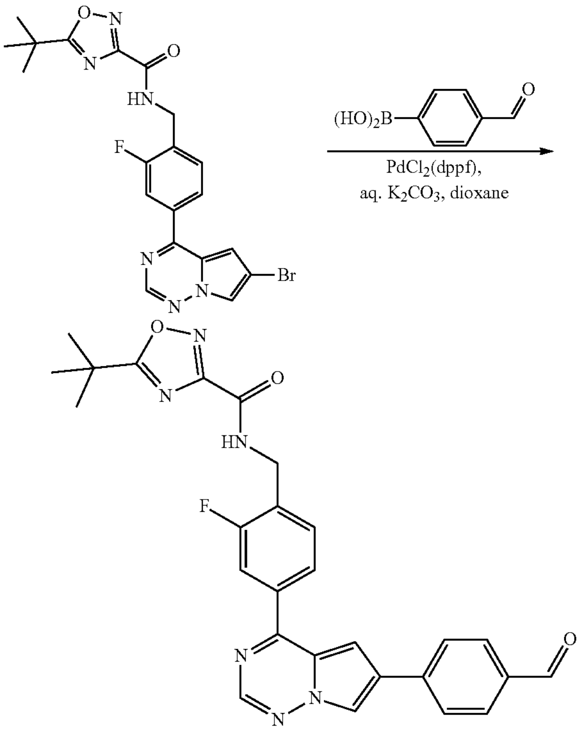

To a stirred solution of N-[[4-(6-bromopyrrolo[2,1-f][1,2,4]triazin-4-yl)-2-fluoro-phenyl]methyl]-5-tert-butyl-1,2,4-oxadiazole-3-carboxamide (1 g, 2.11 mmol) in dioxane (16 mL) and water (4 mL) purged with argon gas, potassium carbonate (876.02 mg, 6.34 mmol) and (4-formylphenyl) boronic acid (506.88 mg, 3.38 mmol) were added and the reaction mixture was stirred at room temperature for 10 minutes. After the addition of $Pd(dppf)Cl_2{\cdot}CH_2Cl_2$ (154.60 mg, 211.28 μmol), the reaction mixture was heated at 90° C. for 16 hours. The reaction progress was monitored by TLC and LC-MS. Upon completion, the reaction was quenched with water (50 mL) and extracted with ethyl acetate (30 mL×3). The combined organic layers were washed with brine solution (50 mL), dried over anhydrous sodium sulfate, filtered, and concentrated under reduced pressure. The crude product was purified by flash column chromatography (silica gel 100-200 mesh, 0-100% ethyl acetate in pet ether) to afford 5-tert-butyl-N-[[2-fluoro-4-[6-(4-formylphenyl)pyrrolo[2,1-f][1,2,4]triazin-4-yl]phenyl]methyl]-1,2,4-oxadiazole-3-carboxamide (0.9 g, 1.75 mmol, 82.68% yield). LC-MS ($ES^+$): m/z 499.43 $[M+H]^+$.

Synthesis of 5-tert-butyl-N-[[2-fluoro-4-[6-(3-fluoro-4-formyl-phenyl)pyrrolo[2,1-f][1,2,4]triazin-4-yl]phenyl]methyl]-1,2,4-oxadiazole-3-carboxamide

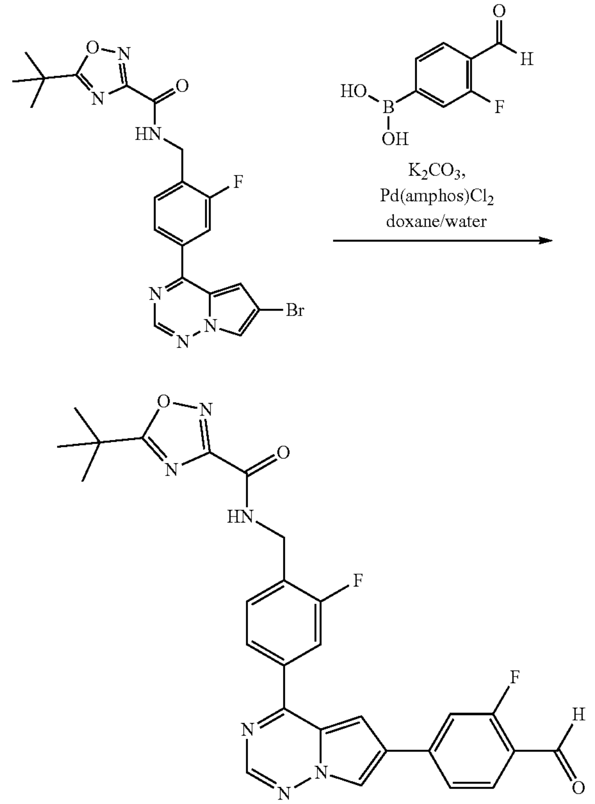

To a stirred solution of N-[[4-(6-bromopyrrolo[2,1-f][1,2,4]triazin-4-yl)-2-fluoro-phenyl]methyl]-5-tert-butyl-1,2,4-oxadiazole-3-carboxamide (1.5 g, 3.17 mmol) and (3-fluoro-4-formyl-phenyl)boronic acid (798.32 mg, 4.75 mmol) in dioxane (16 mL) and water (4 mL) was added potassium carbonate (1.31 g, 9.51 mmol) at room temperature. The reaction mixture was degassed with argon for 10 minutes before $Pd(amphos)Cl_2$ (224.41 mg, 316.93 μmol) was added. The reaction mixture was degassed with argon for an additional 5 minutes and it was stirred at 90° C. for 16 hours. Subsequently, the reaction mixture was concentrated under reduced pressure to give the crude product, which was purified by column chromatography (silica gel 100-200 mesh, 20% ethyl acetate in pet ether) to afford 5-tert-butyl-N-[[2-fluoro-4-[6-(3-fluoro-4-formyl-phenyl)pyrrolo[2,1-f][1,2,4]triazin-4-yl]phenyl]methyl]-1,2,4-oxadiazole-3-carboxamide (1.9 g, 3.08 mmol, 97.30% yield) as a yellow solid. LC-MS ($ES^+$): m/z 517.62 $[M+H]^+$.

Synthesis of 5-tert-butyl-N-[[2-fluoro-4-[6-(4-formylphenyl)pyrrolo[2,1-f][1,2,4]triazin-4-yl]phenyl]methyl]-N-methyl-1,2,4-oxadiazole-3-carboxamide

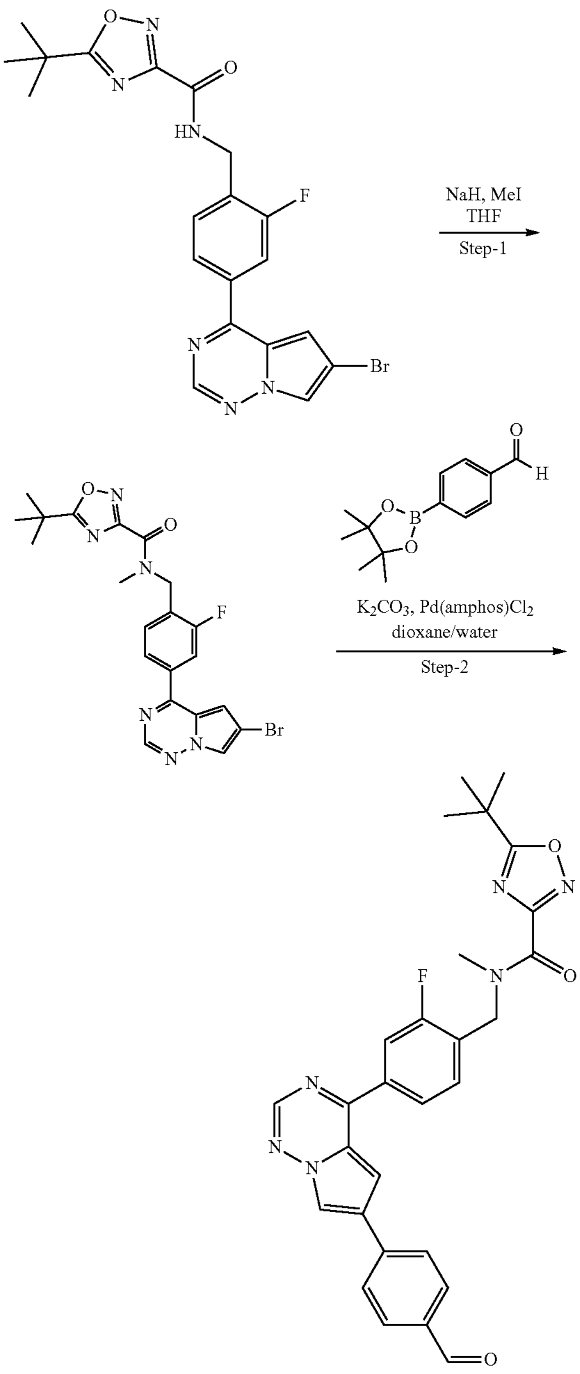

Step-1:

To a stirred a solution of N-[[4-(6-bromopyrrolo[2,1-f][1,2,4]triazin-4-yl)-2-fluoro-phenyl]methyl]-5-tert-butyl-1,2,4-oxadiazole-3-carboxamide (0.5 g, 1.06 mmol) in THF (10 mL) was added sodium hydride (41.22 mg, 1.58 mmol) followed by iodomethane (149.95 mg, 1.06 mmol, 65.77 μL). The reaction mixture was stirred at 0° C. for 4 hours. After completion of the reaction, the reaction mixture was diluted with ice-water and extracted with ethyl acetate (30 ml×2). The organic layer was dried over anhydrous sodium sulfate, filtered, and concentrated under reduced pressure to give the crude product, which was purified by column chromatography (silica gel 100-200 mesh, 20% ethyl acetate in pet ether) to afford N-[[4-(6-bromopyrrolo[2,1-f][1,2,4]triazin-4-yl)-2-fluoro-phenyl]methyl]-5-tert-butyl-N-methyl-1,2,4-oxadiazole-3-carboxamide (0.3 g, 548.57 μmol, 51.93% yield). LC-MS ($ES^+$): m/z 487.44 $[M+H]^+$.

Step-2:

To a stirred solution of N-[[4-(6-bromopyrrolo[2,1-f][1,2,4]triazin-4-yl)-2-fluoro-phenyl]methyl]-5-tert-butyl-N-methyl-1,2,4-oxadiazole-3-carboxamide (0.3 g, 615.61 mol) and 4-(4,4,5,5-tetramethyl-1,3,2-dioxaborolan-2-yl)benzaldehyde (214.31 mg, 923.41 mol) in dioxane (8 mL) and water (2 mL) was added potassium carbonate (255.24 mg, 1.85 mmol) at room temperature. The reaction mixture was degassed with argon for 10 minutes before Pd(amphos)$Cl_2$ (43.59 mg, 61.56 μmol) was added. The reaction mixture was then degassed with argon for an additional 5 minutes and it was stirred at 90° C. for 16 hours. Subsequently, the reaction mixture was concentrated under reduced pressure to give the crude product, which was purified by column chromatography (silica gel 100-200 mesh, 20% ethyl acetate in pet ether) to afford 5-tert-butyl-N-[[2-fluoro-4-[6-(4-formylphenyl)pyrrolo[2,1-f][1,2,4]triazin-4-yl]phenyl]methyl]-N-methyl-1,2,4-oxadiazole-3-carboxamide (0.350 g, 390.68 mol, 63.46% yield) as a yellow solid.

Synthesis of 5-(tert-butyl)-N-(2-chloro-4-(6-(4-formylphenyl)pyrrolo[2,1-f][1,2,4]triazin-4-yl)benzyl)-1,2,4-oxadiazole-3-carboxamide

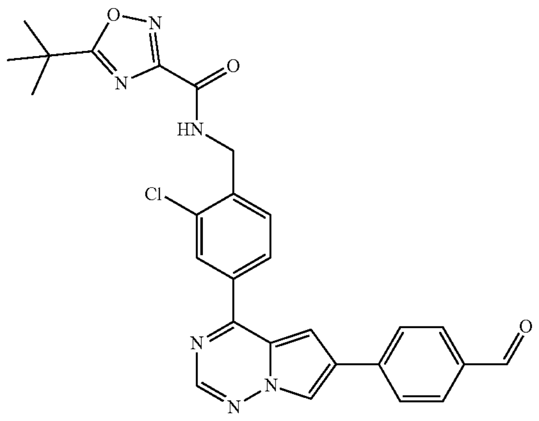 [SMILES: CC(C)(C)c1nc(C(=O)NCc2ccc(-c3ncnn4cc(-c5ccc(C=O)cc5)cc34)cc2Cl)no1]

The procedures used are substantially identical to those of 5-tert-butyl-N-[[2-fluoro-4-[6-(4-formylphenyl)pyrrolo[2,1-f][1,2,4]triazin-4-yl]phenyl]methyl]-1,2,4-oxadiazole-3-carboxamide, except 4-bromo-2-chloro-benzonitrile was used instead of 4-bromo-2-fluorobenzonitrile.

5-(tert-butyl)-N-(2-chloro-4-(6-(4-formylphenyl)pyrrolo[2,1-f][1,2,4]triazin-4-yl)benzyl)-1,2,4-oxadiazole-3-carboxamide. LC-MS ($ES^+$): m/z 515.17 $[M+H]^+$.

Synthesis of 5-(tert-butyl)-N-(4-(6-(4-formylphenyl) pyrrolo[2,1-f][1,2,4]triazin-4-yl)-2-methoxybenzyl)-1,2,4-oxadiazole-3-carboxamide

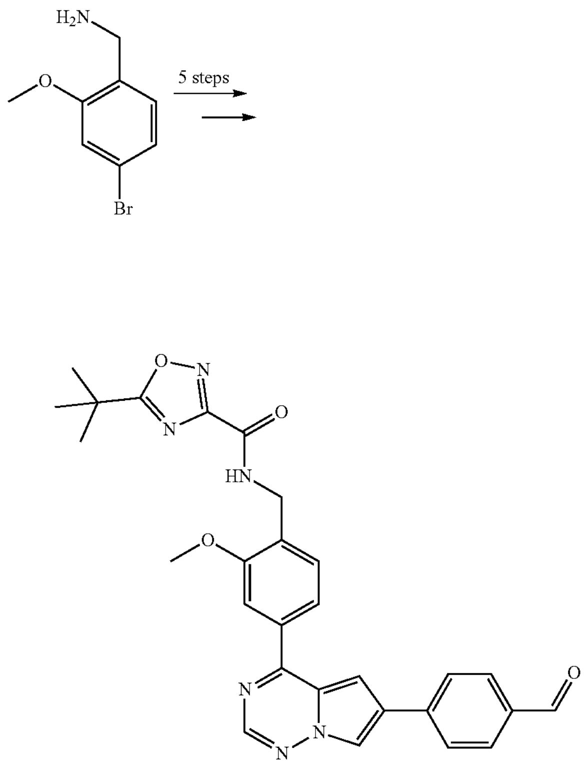

The procedures used are substantially similar to those of 5-tert-butyl-N-[[2-fluoro-4-[6-(4-formylphenyl)pyrrolo[2,1-f][1,2,4]triazin-4-yl]phenyl]methyl]-1,2,4-oxadiazole-3-carboxamide, except the synthesis began with (4-bromo-2-methoxy-phenyl)methanamine instead of (4-bromo-2-fluorophenyl)methanamine.

5-tert-butyl-N-[[4-[6-(4-formylphenyl)pyrrolo[2,1-f][1,2,4]triazin-4-yl]-2-methoxy-phenyl]methyl]-1,2,4-oxadiazole-3-carboxamide. LC-MS ($ES^+$): m/z 511.30 $[M+H]^+$.

Synthesis of 5-(tert-butyl)-N-(2-chloro-5-fluoro-4-(6-(4-formylphenyl)pyrrolo[2,1-f][1,2,4]triazin-4-yl) benzyl)-1,2,4-oxadiazole-3-carboxamide

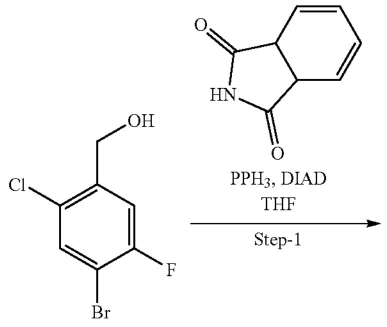

-continued

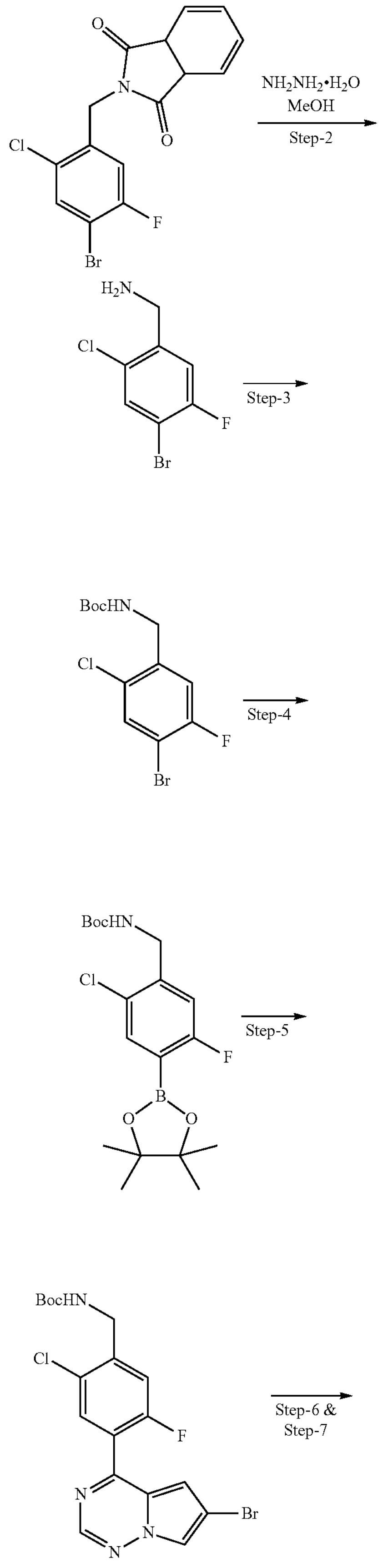

-continued

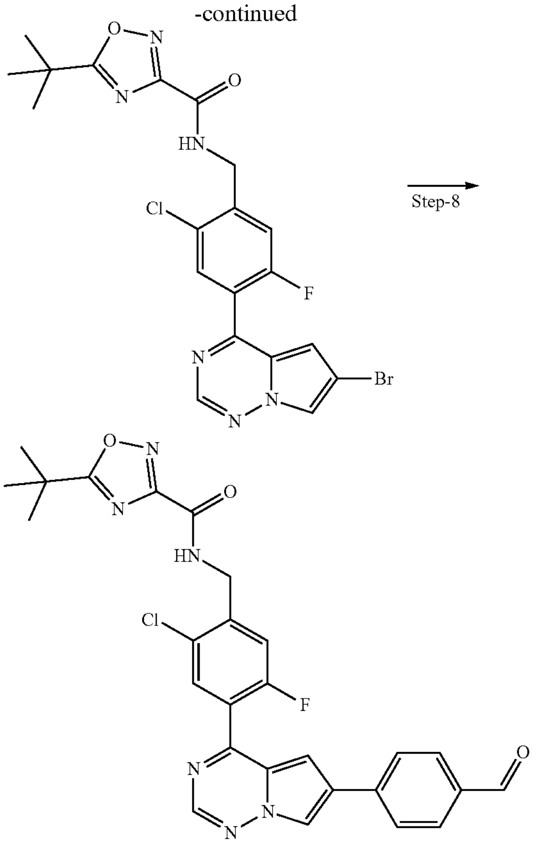

Step-1:

A solution of (4-bromo-2-chloro-5-fluoro-phenyl)methanol (94.0 g, 392.53 mmol) and isoindoline-1,3-dione (86.63 g, 588.80 mmol, 71.60 mL) in THF (1000 mL) was cooled to 0° C. before triphenyl phosphine (154.44 g, 588.80 mmol) was added. This was followed by the dropwise addition of isopropyl (NE)-N-isopropoxycarbonyliminocarbamate (119.06 g, 588.80 mmol, 115.59 mL) at 0° C. and the reaction mixture was stirred at room temperature for 16 hours. The reaction was monitored by TLC. After completion, the volatiles were removed under reduced pressure, and DCM (100 mL) was added to the residue. The precipitate was filtered and washed with diethyl ether (100 mL). The filtrate was then concentrated, and the crude product was purified by column chromatography (silica gel 230-400 mesh, 0-50% ethyl acetate in pet-ether) to afford 2-[(4-bromo-2-chloro-5-fluoro-phenyl)methyl]-3a,7a-dihydroisoindole-1,3-dione (190.0 g, 314.53 mmol, 80.13% yield) as an off-white solid. LC-MS ($ES^+$): m/z 368.07 $[M+H]^+$.

Step-2:

To a stirred solution of 2-[(4-bromo-2-chloro-5-fluoro-phenyl)methyl]isoindoline-1,3-dione (190.0 g, 515.49 mmol) in methanol (4000 mL) was added hydrazine hydrate (129.03 g, 2.58 mol, 125.27 mL). The reaction mixture was stirred for 2 hours at 70° C. The reaction was monitored by TLC. The reaction mixture was cooled to room temperature, diluted with water (200 mL), and most of the methanol or volatiles were removed under reduced pressure. The aqueous suspension was acidified with 1 N HCl solution (1000 mL) and filtered. The filtrate (aq. layer) was washed with DCM (200 mL×3) and basified with 1 N NaOH until pH was 12 and extracted with DCM (200 mL×3) and 9:1 DCM/MeOH (200 mL×3). The combined organic layers were washed with brine solution (100 mL×2), dried over anhydrous sodium sulfate, filtered, and concentrated under reduced pressure. The residue was purified by column chromatography (silica gel 230-400 mesh, 0-10% ethyl acetate in pet ether) to afford (4-bromo-2-chloro-5-fluoro-phenyl)methanamine (65.0 g, 239.55 mmol, 46.47% yield) as a light grey liquid. LC-MS ($ES^+$): m/z 238.22 $[M+H]^+$.

Step-3 to Step-8 have procedures identical to those of 5-tert-butyl-N-[[2-fluoro-4-[6-(4-formylphenyl)pyrrolo[2,1-f][1,2,4]triazin-4-yl]phenyl]methyl]-1,2,4-oxadiazole-3-carboxamide.

Step-3:

tert-butyl N-[(4-bromo-2-chloro-5-fluoro-phenyl)methyl]carbamate.

LC-MS ($ES^+$): m/z 238.22 $[M-tBu+H]^+$.

Step-4:

tert-butyl-N-[[2-chloro-5-fluoro-4-(4,4,5,5-tetramethyl-1,3,2-dioxaborolan-2-yl)phenyl]methyl]carbamate. LC-MS ($ES^+$): m/z 330.41 $[M-tBu+H]^+$.

Step-5:

tert-butyl (4-(6-bromopyrrolo[2,1-f][1,2,4]triazin-4-yl)-2-chloro-5-fluorobenzyl)carbamate.

LC-MS ($ES^+$): m/z 455.31$[M+H]^+$.

Step-6: (4-(6-bromopyrrolo[2,1-f][1,2,4]triazin-4-yl)-2-chloro-5-fluorophenyl)methanamine.

LC-MS ($ES^+$): m/z 355.32 $[M+H]^+$.

Step-7:

N-(4-(6-bromopyrrolo[2,1-f][1,2,4]triazin-4-yl)-2-chloro-5-fluorobenzyl)-5-(tert-butyl)-1,2,4-oxadiazole-3-carboxamide. LC-MS ($ES^+$): m/z 507.43 $[M+H]^+$.

Step-8:

5-(tert-butyl)-N-(2-chloro-5-fluoro-4-(6-(4-formylphenyl)pyrrolo[2,1-f][1,2,4]triazin-4-yl)benzyl)-1,2,4-oxadiazole-3-carboxamide. LC-MS ($ES^+$): m/z 533.18 $[M+H]^+$.

Synthesis of tert-butyl N-[[4-[6-(4-hydroxybut-1-ynyl)pyrrolo[2,1-f][1,2,4]triazin-4-yl]-2-methyl-phenyl]methyl]carbamate

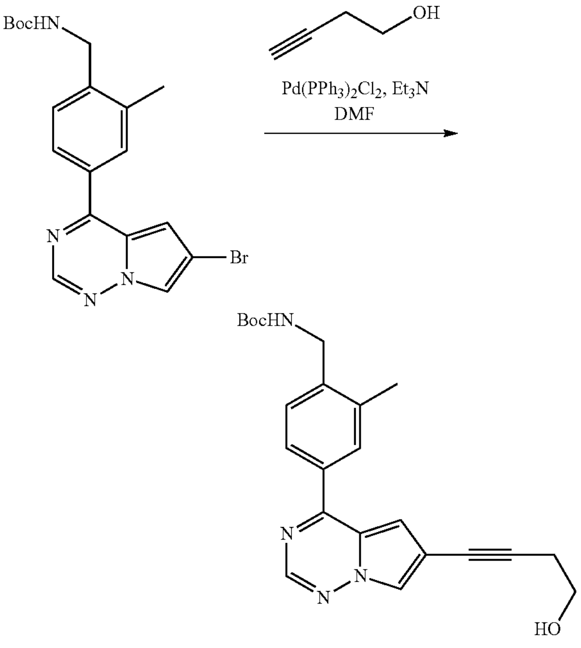

A solution of tert-butyl N-[[4-(6-bromopyrrolo[2,1-f][1,2,4]triazin-4-yl)-2-methyl-phenyl]methyl]carbamate (5 g, 11.98 mmol), but-3-yn-1-ol (4.20 g, 59.90 mmol, 4.53 mL) and triethylamine (12.12 g, 119.80 mmol, 16.70 mL) in 1,4-dioxane (50 mL) was purged with argon gas for 15 minutes. Copper iodide (760.38 mg, 2.40 mmol) and bis(triphenylphosphine)palladium(II) dichloride (1.68 g, 2.40 mmol) were then added to the reaction mixture, which was stirred at 110° C. for 16 hours. The reaction mixture was filtered through a celite bed and washed with ethyl acetate (100 mL×2). The filtrate was washed with water (100 mL) and brine solution (100 mL). The combined organic layers were dried over anhydrous sodium sulfate, filtered, and concentrated under reduced pressure. The crude product was purified by flash column chromatography (silica gel 230-400 mesh, 0-100% ethyl acetate in pet-ether) to afford tert-butyl N-[[4-[6-(4-hydroxybut-1-ynyl)pyrrolo[2,1-f][1,2,4]triazin-4-yl]-2-methyl-phenyl]methyl]carbamate (4 g, 9.54 mmol, 79.64% yield). LC-MS (ES+): m/z 407.46 [M+H]+.

Synthesis of tert-butyl N-[[2-methyl-4-[6-(4-oxobutyl)pyrrolo[2,1-f][1,2,4]triazin-4-yl]phenyl]methyl]carbamate

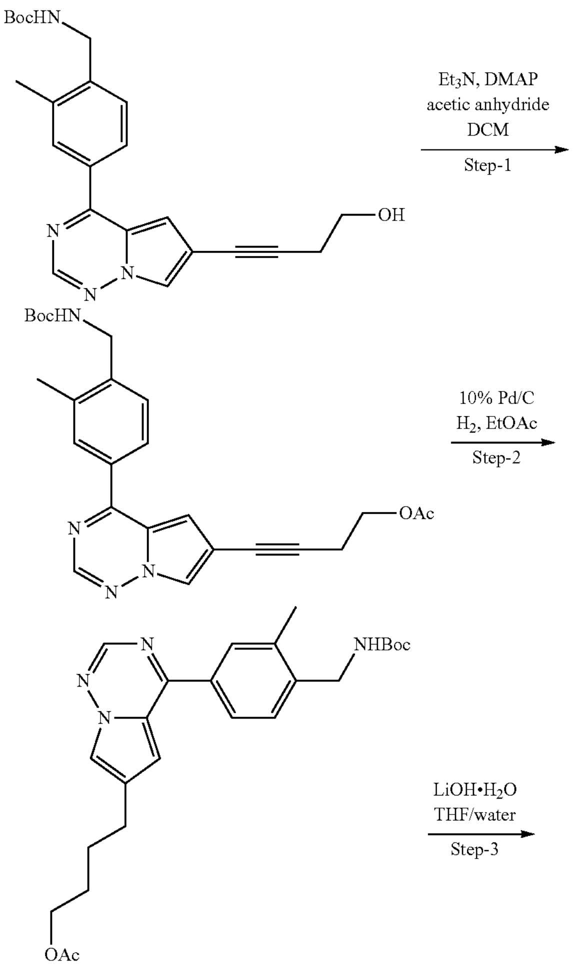

-continued

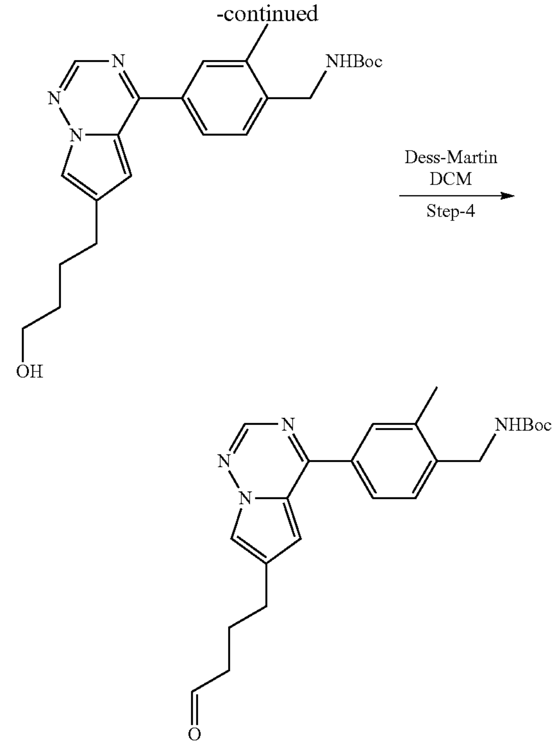

Step-1

To a solution of tert-butyl N-[[4-[6-(4-hydroxybut-1-ynyl)pyrrolo[2,1-f][1,2,4]triazin-4-yl]-2-methyl-phenyl]methyl]carbamate (0.5 g, 1.23 mmol) in DCM (9.40 mL) were added triethylamine (622.36 mg, 6.15 mmol, 857.25 μL), DMAP (15.03 mg, 123.01 μmol) and acetic anhydride (251.15 mg, 2.46 mmol, 232.12 μL) at 0° C. The reaction mixture was then stirred for 2 hours at room temperature. After completion of the reaction, the reaction mixture was poured into water and extracted with DCM. The organic layer was washed with brine solution, dried over anhydrous sodium sulfate and concentrated in vacuo to afford the crude product 4-[4-[4-[(tert-butoxycarbonylamino)methyl]-3-methyl-phenyl]pyrrolo[2,1-f][1,2,4]triazin-6-yl]but-3-ynyl acetate (0.5 g, 1.05 mmol, 85.00% yield). LC-MS (ES+): m/z 449.45 [M+H]+.

Step-2:

Palladium on charcoal (10% wt. by wt.) (9.08 g, 85.28 mmol) was added to a solution of 4-[4-[4-[(tert-butoxycarbonylamino)methyl]-3-methyl-phenyl]pyrrolo[2,1-f][1,2,4]triazin-6-yl]but-3-ynyl acetate (9 g, 20.07 mmol) in ethyl acetate (100 mL) at 27° C. under hydrogen atmosphere. The reaction mixture was stirred at 27° C. for 6 hours. Upon completion of the reaction, the reaction mixture was filtered through celite and washed with ethyl acetate (100 mL×2). The organic layer was concentrated under reduced pressure to obtain the crude compound, which was purified by column chromatography (silica gel 230-400 mesh, 0-100% ethyl acetate in pet-ether) to afford 4-[4-[4-[(tert-butoxycarbonylamino)methyl]-3-methyl-phenyl]pyrrolo[2,1-f][1,2,4]triazin-6-yl]butyl acetate (7.5 g, 14.58 mmol, 72.68% yield) as a yellow gummy liquid. LC-MS (ES+): m/z 453.90 [M+H]+.

Step-3:

To a solution of 4-[4-[4-[(tert-butoxycarbonylamino)methyl]-3-methyl-phenyl]pyrrolo[2,1-f][1,2,4]triazin-6-yl]butyl acetate (7.5 g, 16.57 mmol) in THF (80 mL) and water (20 mL) was added lithium hydroxide monohydrate, 98% (6.95 g, 165.73 mmol) at 0° C. The reaction mixture was stirred for 10 hours at 60° C., while the reaction progress was monitored by TLC and LC-MS. After consumption of the starting material, the reaction was diluted with ethyl acetate (100 mL) and washed with water (100 mL) and brine solution (100 mL). The organic layer was dried over sodium sulfate and concentrated in vacuo to give the crude product, which was purified by column chromatography (silica gel 230-400 mesh, 0-10% ethyl acetate in pet-ether) to afford tert-butyl N-[[4-[6-(4-hydroxybutyl)pyrrolo[2,1-f][1,2,4]triazin-4-yl]-2-methyl-phenyl]methyl]carbamate (5 g, 11.21 mmol, 67.61% yield). LC-MS ($ES^+$): m/z 411.48 $[M+H]^+$.

Step-4:

To a solution of tert-butyl N-[[4-[6-(4-hydroxybutyl)pyrrolo[2,1-f][1,2,4]triazin-4-yl]-2-methyl-phenyl]methyl]carbamate (1.01 g, 2.46 mmol) was added Dess-Martin periodinane (1.57 g, 3.69 mmol) at 0° C. The reaction mixture was stirred for 1 hour at 0° C. while being monitored by TLC and LC-MS. After consumption of the starting material, the reaction was diluted with DCM and filtered through a pad of celite. The reaction mixture was then washed with saturated sodium bicarbonate solution (100 mL) and brine solution (100 mL). The organic layer was dried over sodium sulfate and concentrated in vacuo to give the crude product, which was purified by column chromatography (silica gel 230-400 mesh, 0-100% ethyl acetate in pet-ether) to afford tert-butyl N-[[2-methyl-4-[6-(4-oxobutyl)pyrrolo[2,1-f][1,2,4]triazin-4-yl]phenyl]methyl]carbamate (0.7 g, 1.37 mmol, 55.73% yield). LC-MS ($ES^+$): m/z 409.46 $[M+H]^+$.

Synthesis of 4-(4-(4-((5-(tert-butyl)-1,2,4-oxadiazole-3-carboxamido)methyl)-3-methylphenyl)pyrrolo[2,1-f][1,2,4]triazin-6-yl)but-3-yn-1-yl methanesulfonate

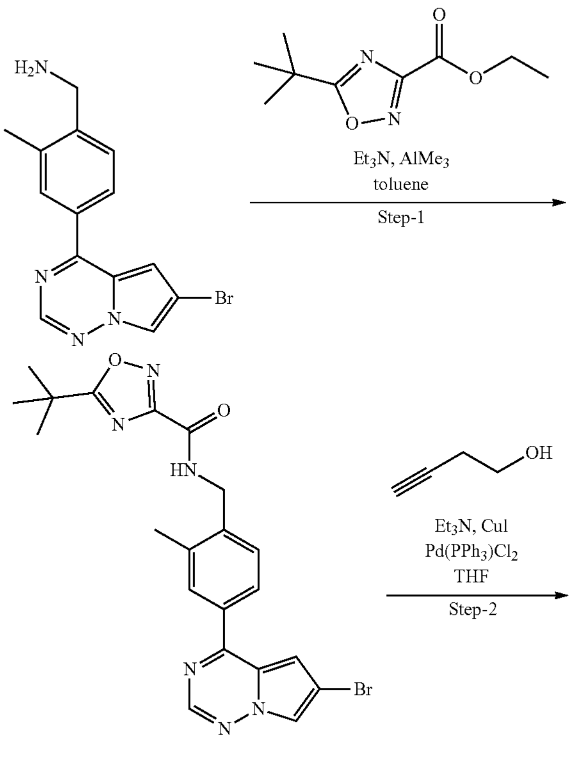

-continued

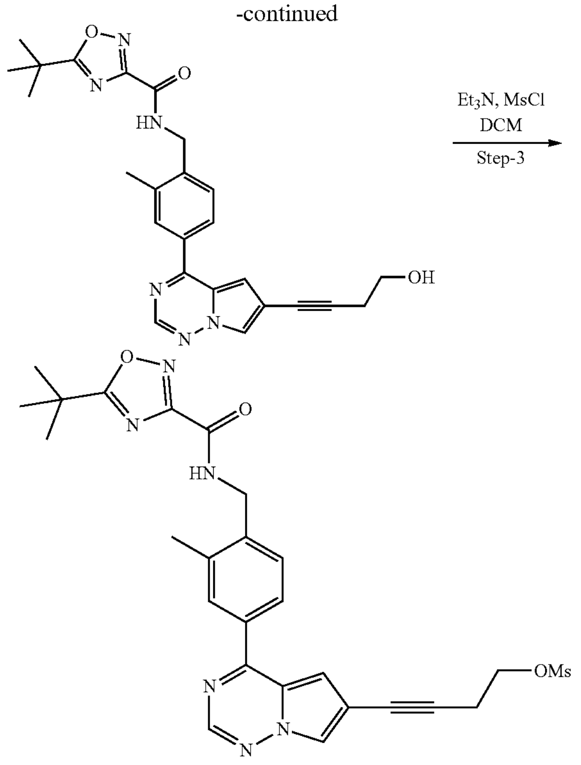

Step-1:

To a stirred solution of [4-(6-bromopyrrolo[2,1-f][1,2,4]triazin-4-yl)-2-methyl-phenyl]methanamine (2.8 g, 8.83 mmol) in toluene (60 mL) at 0° C. was added triethylamine (2.68 g, 26.48 mmol, 3.69 mL) and stirred for 10 min. Trimethylalumane (1.27 g, 17.66 mmol, 1.57 mL) was added dropwise and the reaction mass was stirred at 27° C. for 30 min, followed by the addition of a solution of ethyl 5-(tert-butyl)-1,2,4-oxadiazole-3-carboxylate (1.75 g, 8.83 mmol) in toluene (2 mL). Finally, the reaction mass was allowed to stir at 120° C. for 2 hr in a sealed tube. The reaction mixture was quenched with ice-cold water (50 mL) and extracted with EtOAc (100 mL×3). The combined organic layers were dried over anhydrous sodium sulfate, filtered, and concentrated under reduced pressure to give the crude product, which was purified by column chromatography over silica gel (100-200 mesh silica 0-50% EA:Pet ether solvent gradient) to afford N-(4-(6-bromopyrrolo[2,1-f][1,2,4]triazin-4-yl)-2-methylbenzyl)-5-(tert-butyl)-1,2,4-oxadiazole-3-carboxamide (2.9 g, 6.13 mmol, 69.46% yield) as a yellow solid. LC-MS($ES^+$): m/z 470.55 $[M+H]^+$.

Step-2:

To a stirred solution of N-(4-(6-bromopyrrolo[2,1-f][1,2,4]triazin-4-yl)-2-methylbenzyl)-5-(tert-butyl)-1,2,4-oxadiazole-3-carboxamide (500 mg, 1.07 mmol) in THF (5 mL), but-3-yn-1-ol (89.60 mg, 1.28 mmol, 96.66 μL), copper (I) iodide (24.35 mg, 127.84 μmol, 4.33 L) and triethylamine (215.60 mg, 2.13 mmol, 296.97 μL) was added. The reaction mixture was purged with argon for 10 minutes and added $Pd(PPh_3)Cl_2$ (17.95 mg, 25.57 μmol) and heated at 90° C. for 16 h. The reaction mixture was cooled to ambient temperature and diluted with water (10 mL) and extracted with ethyl acetate (2×30 mL). The combined organic extracts were dried over anhydrous sodium sulfate, filtered and evaporated under reduce pressure. The resulting crude was purified by reverse phase (0-100% gradient of 0.1% FA in water:ACN) to obtain 5-tert-butyl-N-[[4-[6-(4-hydroxy-but-1-ynyl)pyrrolo[2,1-f][1,2,4]triazin-4-yl]-2-methyl-phenyl]methyl]-1,2,4-oxadiazole-3-carboxamide (220 mg, 0.372 mmol, 34.93% yield) as a yellow gummy solid. LC-MS(ES$^+$): m/z 459.78 [M+H]$^+$.

Step-3:

To a suspension of 5-tert-butyl-N-[[4-[6-(4-hydroxybut-1-ynyl)pyrrolo[2,1-f][1,2,4]triazin-4-yl]-2-methyl-phenyl]methyl]-1,2,4-oxadiazole-3-carboxamide (220 mg, 479.81 mol) in DCM (3 mL) was added methanesulfonyl chloride (54.96 mg, 479.81 μmol, 37.14 L) at 0° C. and stirred at room temperature for 2 h. After completion of the reaction, the reaction mixture was quenched with saturated $NaHCO_3$ solution and extracted with ethyl acetate. The combined organic layers were concentrated under vacuum and the obtained crude was purified by column chromatography (100-200 mesh silica; 0-30% EA:PE solvent gradient) to obtain 4-[4-[4-[[(5-tert-butyl-1,2,4-oxadiazole-3-carbonyl)amino]methyl]-3-methyl-phenyl]pyrrolo[2,1-f][1,2,4]triazin-6-yl]but-3-ynyl methanesulfonate (200 mg, 324.08 μmol, 67.54% yield). LC-MS(ES$^+$): m/z 537.19 [M+H]$^+$.

Tert-butyl N-[[2-fluoro-4-[6-(4-oxobutyl)pyrrolo[2,1-f][1,2,4]triazin-4-yl]phenyl]methyl]carbamate was Prepared Following the Synthesis of tert-butyl N-[[2-methyl-4-[6-(4-oxobutyl)pyrrolo[2,1-f][1,2,4]triazin-4-yl]phenyl]methyl]carbamate

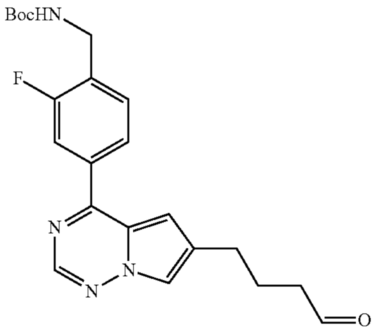

LC-MS (ES$^+$): m/z 413.46 [M+H]$^+$.

Synthesis of 5-tert-butyl-N-[[2-fluoro-4-[6-(2-oxoethyl)pyrrolo[2,1-f][1,2,4]triazin-4-yl]phenyl]methyl]-1,2,4-oxadiazole-3-carboxamide

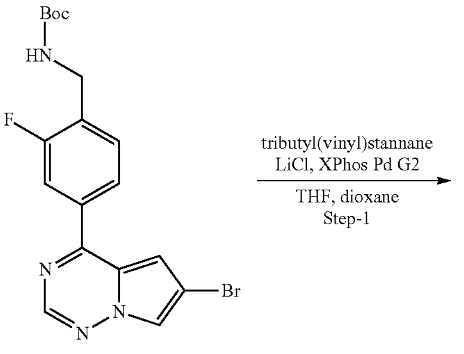

-continued

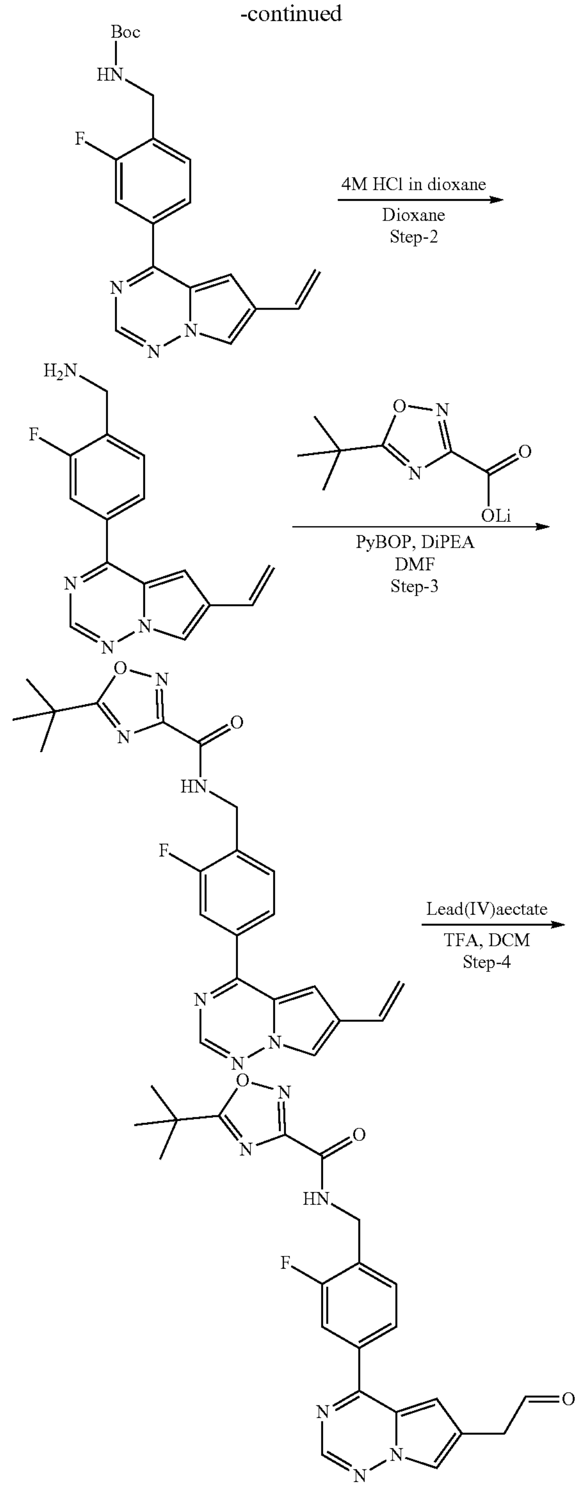

Step-1:

To a stirred solution of tert-butyl N-[[4-(6-bromopyrrolo[2,1-f][1,2,4]triazin-4-yl)-2-fluoro-phenyl]methyl]carbamate (4.3 g, 10.21 mmol) in THF (20 mL) was added tributyl(vinyl)stannane (12.95 g, 40.83 mmol, 11.88 mL) and degassed for 15 minutes. The solution was cooled to 0° C. before adding XPhos Pd G2 (1.20 g, 1.53 mmol), then the reaction mixture was stirred at 90° C. After completion of the reaction, the reaction mixture was filtered through celite and washed with ethyl acetate. The filtrate was distilled under reduced pressure and purification by column chromatography (10% ethyl acetate in pet ether) to afford tert-butyl N-[[2-fluoro-4-(6-vinylpyrrolo[2,1-f][1,2,4]triazin-4-yl) phenyl]methyl]carbamate (3.6 g, 9.09 mmol, 89.03% yield). LC-MS ($ES^+$): m/z 369.41 $[M+H]^+$.

Step-2:

To a stirred solution of tert-butyl N-[[2-fluoro-4-(6-vinylpyrrolo[2,1-f][1,2,4]triazin-4-yl)phenyl]methyl]carbamate (2 g, 5.43 mmol) in dioxane (10 mL) under inert atmosphere was added 4 M HCl in 1,4-dioxane (20 mL) at 0° C. Then, the reaction mixture was stirred at room temperature for 2 hours and monitored by TLC and LC-MS. After completion, the crude material was concentrated under reduced pressure and triturated with diethyl ether (2*100 mL), then dried to obtain [2-fluoro-4-(6-vinylpyrrolo[2,1-f][1,2,4]triazin-4-yl)phenyl]methanamine hydrochloride (1.7 g, 5.39 mmol, 99.36% yield) as light yellow solid. LC-MS ($ES^+$): m/z 269.36 $[M+H]^+$.

Step-3:

To a stirred solution of (5-tert-butyl-1,2,4-oxadiazole-3-carbonyl)oxylithium (2.02 g, 11.48 mmol) in DMF (10 mL) was added DIPEA (4.45 g, 34.45 mmol, 6.00 mL) and stirred for 5 mins followed by the addition of (5-tert-butyl-1,2,4-oxadiazole-3-carbonyl)oxylithium (2.02 g, 11.48 mmol). Finally, PyBOP (4.48 g, 8.61 mmol) was added to the reaction mixture and stirred at room temperature for 2 hours. After completion, the reaction mixture was quenched with ice flakes to obtain a solid. The solid was filtered and purified by normal phase column chromatography (silica gel, 25% ethyl acetate in pet ether) to obtain 5-tert-butyl-N-[[2-fluoro-4-(6-vinylpyrrolo[2,1-f][1,2,4]triazin-4-yl) phenyl]methyl]-1,2,4-oxadiazole-3-carboxamide (1 g, 2.11 mmol, 36.81% yield) as a light yellow solid. LC-MS ($ES^+$): m/z 421.95 $[M+H]^+$.

Step-4:

To a stirred solution of 5-tert-butyl-N-[[2-fluoro-4-(6-vinylpyrrolo[2,1-f][1,2,4]triazin-4-yl)phenyl]methyl]-1,2,4-oxadiazole-3-carboxamide (1 g, 2.38 mmol) in DCM (5 mL) was added trifluoroacetic acid (13.56 g, 118.92 mmol, 9.16 mL) at 0° C. followed by the addition of lead (IV) tetraacetate (1.05 g, 2.38 mmol) at the same temperature and allowed to stir at room temperature for 3 hours. After completion, the reaction mixture was concentrated under reduced pressure. The crude was quenched with sodium bi-carbonate solution and extracted with ethyl acetate. The combined organic layer was dried over anhydrous sodium sulfate and concentrated under reduced pressure to obtain 5-tert-butyl-N-[[2-fluoro-4-[6-(2-oxoethyl)pyrrolo[2,1-f][1,2,4]triazin-4-yl]phenyl]methyl]-1,2,4-oxadiazole-3-carboxamide (0.9 g, 1.44 mmol, 60.69% yield), which was used without further purification. LC-MS ($ES^+$): m/z 435.21 $[M-H]^-$.

Synthesis of tert-butyl N-[[4-(6-formylpyrrolo[2,1-f][1,2,4]triazin-4-yl)-2-methyl-phenyl]methyl]carbamate

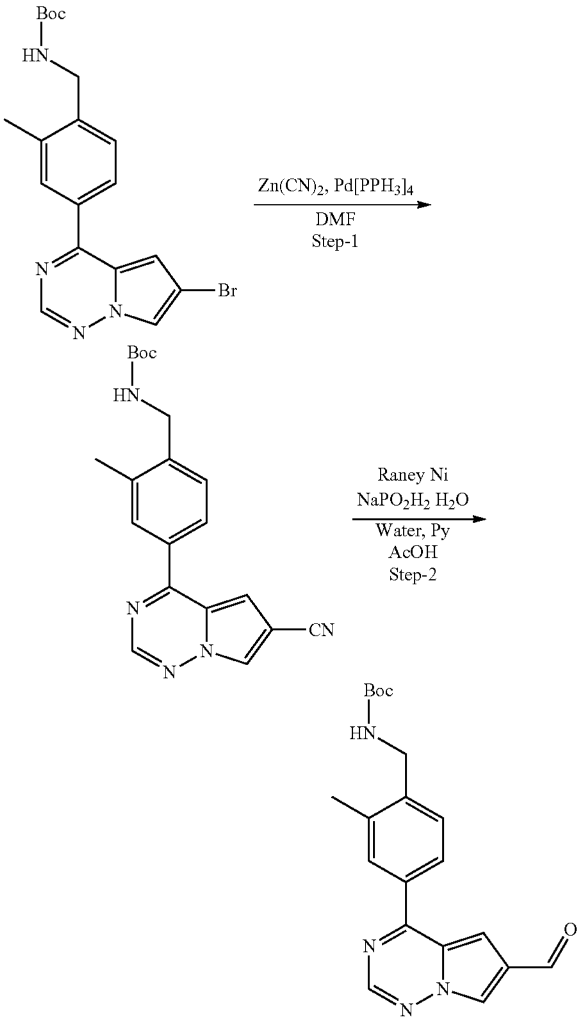

Step-1:

To a solution tert-butyl N-[[4-(6-bromopyrrolo[2,1-f][1,2,4]triazin-4-yl)-2-methyl-phenyl]methyl]carbamate (5 g, 11.98 mmol) and zinc dicyanide (2.81 g, 23.96 mmol) in DMF (50 mL) at room temperature was added tetrakis (triphenylphosphine)-palladium(0) (1.38 g, 1.20 mmol) and the reaction mixture was stirred at 120° C. for 40 minutes. A saturated sodium bicarbonate solution was added to the reaction mixture, and extraction was carried out using ethyl acetate (50 mL×3). The combined organic layers were washed with water, brine solution, dried over anhydrous sodium sulfate, filtered, and concentrated under reduced pressure. The crude material was purified by column chromatography (silica gel 230-400 mesh, 0-30% ethyl acetate in pet ether) to afford tert-butyl N-[[4-(6-cyanopyrrolo[2,1-f][1,2,4]triazin-4-yl)-2-methyl-phenyl]methyl]carbamate (3.8 g, 10.20 mmol, 85.13% yield). LC-MS ($ES^+$): m/z 364.42 $[M+H]^+$.

Step-2:

To a stirred solution of tert-butyl N-[[4-(6-cyanopyrrolo[2,1-f][1,2,4]triazin-4-yl)-2-methyl-phenyl]methyl]carbamate (3.4 g, 9.36 mmol) in water (8 mL), pyridine (16 mL) and AcOH (8 mL) at 0° C. was added sodium hypophosphite monohydrate (8.27 g, 79.52 mmol) and the reaction mixture was stirred at 0° C. for 30 minutes. Raney nickel (3.4 g, 57.93 mmol) was added portion-wise, and the reaction mixture was stirred at 65° C. for 2 hours. The reaction mixture was then filtered through celite and washed with ethyl acetate. The filtrate was concentrated under reduced pressure. The residue was quenched with water (60 mL), and extraction was carried out using ethyl acetate (50 mL×3). The combined organic layers were washed with brine solution (100 mL), dried over anhydrous sodium sulfate, filtered, and concentrated under reduced pressure. The residue was purified by column chromatography (silica gel 230-400 mesh, 0-10% ethyl acetate in pet-ether) to afford tert-butyl N-[[4-(6-formylpyrrolo[2,1-f][1,2,4]triazin-4-yl)-2-methyl-phenyl]methyl]carbamate (1.2 g, 3.05 mmol, 32.56% yield). LC-MS ($ES^+$): m/z 367.24 $[M+H]^+$.

Synthesis of tert-butyl N-[[4-(6-bromopyrrolo[1,2-b]pyridazin-4-yl)-2-methyl-phenyl]methyl]carbamate

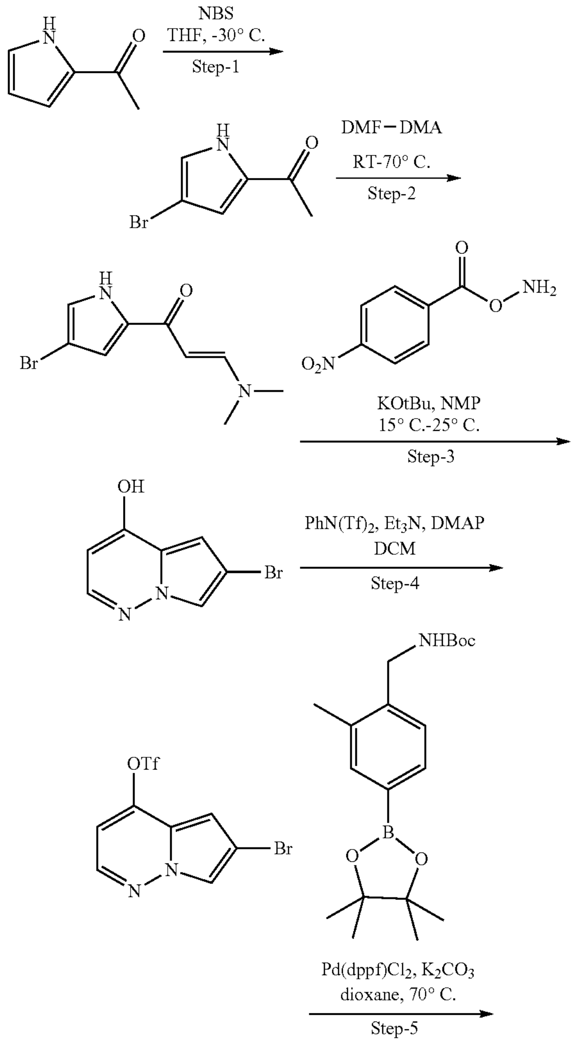

-continued

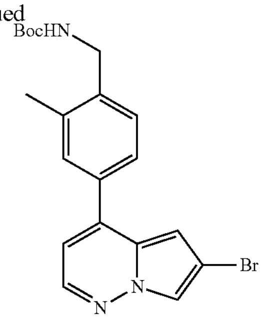

Step-1:

To the stirred solution of 2-acetylpyrrole (95 g, 870.56 mmol) in THF (10 mL) was added amberlyst (0.09 g, 870.56 mmol), 1-bromopyrrolidine-2,5-dione (154.95 g, 870.56 mmol, 73.78 mL) at −25° C. under nitrogen atmosphere. The reaction was monitored by TLC and LC-MS. After the completion of the reaction, the residual mass was dissolved in ethyl acetate (500 mL), washed with water (1×100 mL), brine (1×100 mL), dried over anhydrous $Na_2SO_4$, and concentrated to get the crude product. The crude product was further purified by column chromatography over silica gel (100/200 mesh), and the product was eluted at 30-50% EtOAc/Hexane to afford the product 1-(4-bromo-1H-pyrrol-2-yl)ethan-1-one (154 g, 655.24 mmol, 75.27% yield) as a white solid. $^1H$ NMR (400 MHz, DMSO-$d_6$) δ=12.12 (s, 1H), 7.20 (s, 1H), 7.08 (s, 1H), 2.34 (s, 3H).

Step-2:

To a stirred solution of 1-(4-bromo-1H-pyrrol-2-yl)ethan-1-one (30 g, 159.56 mmol) was added toluene (150 mL) and then heated at 80° C. for 16 h. After the completion of the reaction, the reaction mixture was cooled to room temperature and filtered off through celite, washed with ethyl acetate (100 mL). The organic layer was partitioned from the filtrate and concentrated. The resultant crude product was purified by column chromatography using 10% Methanol/DCM as the eluent gradient to afford (E)-1-(4-bromo-1H-pyrrol-2-yl)-3-(dimethylamino)prop-2-en-1-one (24.5 g, 65.51 mmol, 41.06% yield) as a yellow solid. LC-MS ($ES^+$): m/z 242.9 $[M+H]^+$.

Step-3:

To a stirred solution of potassium tert-butoxide (83.08 g, 740.44 mmol) in NMP (1 L) was added (E)-1-(4-bromo-1H-pyrrol-2-yl)-3-(dimethylamino)prop-2-en-1-one (120.0 g, 493.62 mmol) and the reaction mixture was stirred at room temperature for 1-2 hours. Then, the reaction mixture was cooled to −5° C. Amino 4-nitrobenzoate (143.85 g, 789.80 mmol) was added and stirred at 0 to −5° C. for 16 hr. The progress of the reaction was monitored by LCMS and TLC. After the completion of the reaction, pH was maintained to 2-3 and extracted with ethyl acetate (3×50 mL). The combined organic layer was concentrated under reduced pressure, and the crude material was purified by column chromatography (30% ethyl acetate in pet ether) to afford 6-bromopyrrolo[1,2-b]pyridazin-4-ol (40.0 g, 184.84 mmol, 37.44% yield) as a yellow solid. LC-MS ($ES^+$): m/z 211.1 $[M-H]^-$.

Step-4:

A stirred solution of 6-bromopyrrolo[1,2-b]pyridazin-4-ol (7.0 g, 32.86 mmol) in DCM (500 mL), the reaction mixture was cooled 0° C. Triethylamine (9.98 g, 98.58 mmol, 13.74 mL), 4-Dimethylaminopyridine (401.44 mg, 3.29 mmol), and trifluoromethyl N-phenyl-N-(trifluoromethoxysulfonyl) sulfamate (19.19 g, 49.29 mmol) were added sequentially and the reaction was monitored by LC-MS. Upon the completion of the reaction, the mixture was quenched by citric acid and extracted with DCM. The organic layer was separated, washed with brine, dried over $Na_2SO_4$, and concentrated to give the crude product. The crude mixture was purified by column chromatography to afford (6-bromopyrrolo[1,2-b]pyridazin-4-yl) trifluoromethanesulfonate (4.0 g, 11.51 mmol, 35.02% yield) as a colorless liquid. LC-MS ($ES^+$): m/z 343.1 $[M-H]^-$.

Step-5:

Under the argon atmosphere, to a stirred solution of (6-bromopyrrolo[1,2-b]pyridazin-4-yl) trifluoromethanesulfonate (6.0 g, 17.39 mmol) and tert-butyl N-[[2-methyl-4-(4,4,5,5-tetramethyl-1,3,2-dioxaborolan-2-yl)phenyl]methyl]carbamate (4.83 g, 13.91 mmol) in dioxane (80 mL)/water (20 mL) was added potassium carbonate (7.21 g, 52.16 mmol), $Pd(dppf)Cl_2$ (1.27 g, 1.74 mmol). The reaction mixture was stirred at 50° C. for 16 hours, and the reaction was monitored by TLC and LC-MS. After completion of the reaction, the reaction mixture was washed with water and extracted with ethyl acetate (3×100 mL). The combined organic layer was dried over anhydrous sodium sulfate, concentrated under reduced pressure in vacuo. The crude was purified by column chromatography (230-400 mesh silica gel) using ethyl acetate in pet ether as an eluent to afford tert-butyl N-[[4-(6-bromopyrrolo[1,2-b]pyridazin-4-yl)-2-methyl-phenyl]methyl]carbamate (5.5 g, 13.15 mmol, 75.61% yield) as a green gummy solid. LC-MS ($ES^+$): m/z 416.3 $[M+H]^+$.

Synthesis of tert-butyl N-[[4-(2-bromopyrazolo[1,5-a]pyrimidin-7-yl)-2-fluoro-phenyl]methyl]carbamate

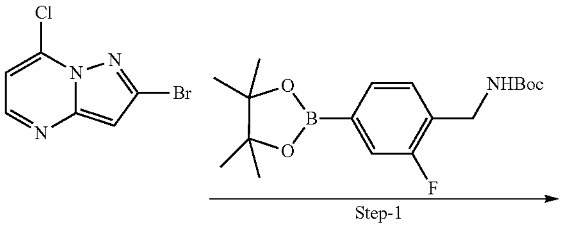

-continued

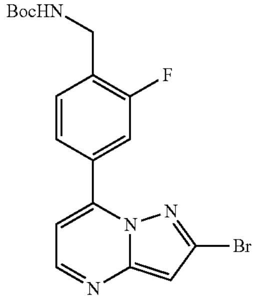

Step-1:

To a solution of 2-bromo-7-chloro-pyrazolo[1,5-a]pyrimidine (2 g, 8.60 mmol) and tert-butyl N-[[2-fluoro-4-(4,4,5,5-tetramethyl-1,3,2-dioxaborolan-2-yl)phenyl]methyl]carbamate (2.42 g, 6.88 mmol) in dioxane (40 mL) was added potassium carbonate—granular (2.38 g, 17.21 mmol) in Water (8 mL) and purged with $N_2$ for 15 mins. Then, $Pd(dppf)Cl_2$ (314.76 mg, 430.17 μmol) was added and purged with nitrogen gas for 5 minutes. Then the reaction mixture was heated to 60° C. for 2 hours and monitored by TLC and LC-MS. After the completion, the mixture was filtered through a celite bed, and the filtrate was concentrated to obtain the crude.

The crude was purified by normal phase column chromatography (Devisil silica, 20% ethyl acetate/petroleum ether) using Biotage® to obtain tert-butyl N-[[4-(2-bromopyrazolo[1,5-a]pyrimidin-7-yl)-2-fluoro-phenyl]methyl]carbamate (1.6 g, 3.29 mmol, 38.26% yield). LC-MS ($ES^+$): m/z 421.5 $[M+H]^+$.

Synthesis of 5-(tert-butyl)-N-(2-methyl-4-(6-(piperazin-1-yl)pyrrolo[2,1-f][1,2,4]triazin-4-yl)benzyl)-1,2,4-oxadiazole-3-carboxamide

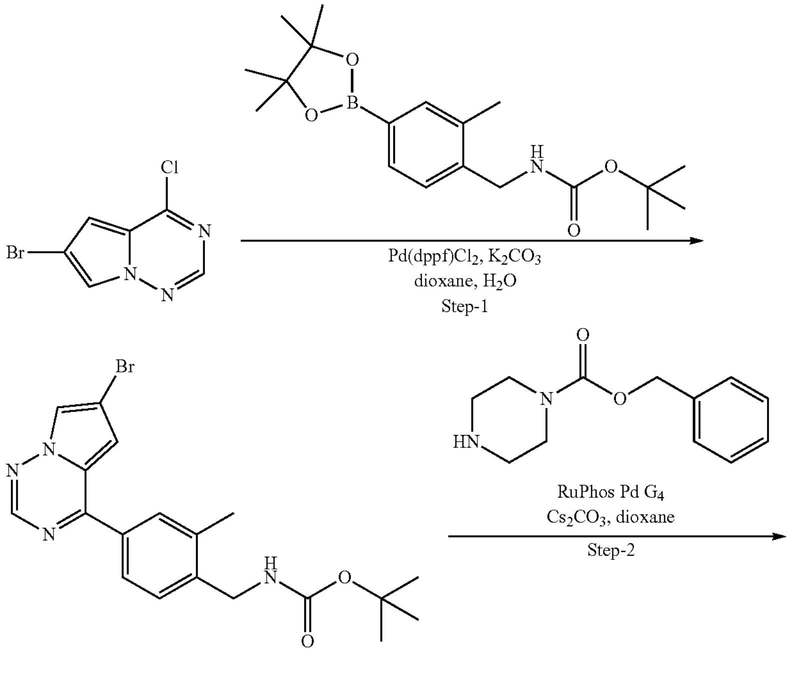

-continued
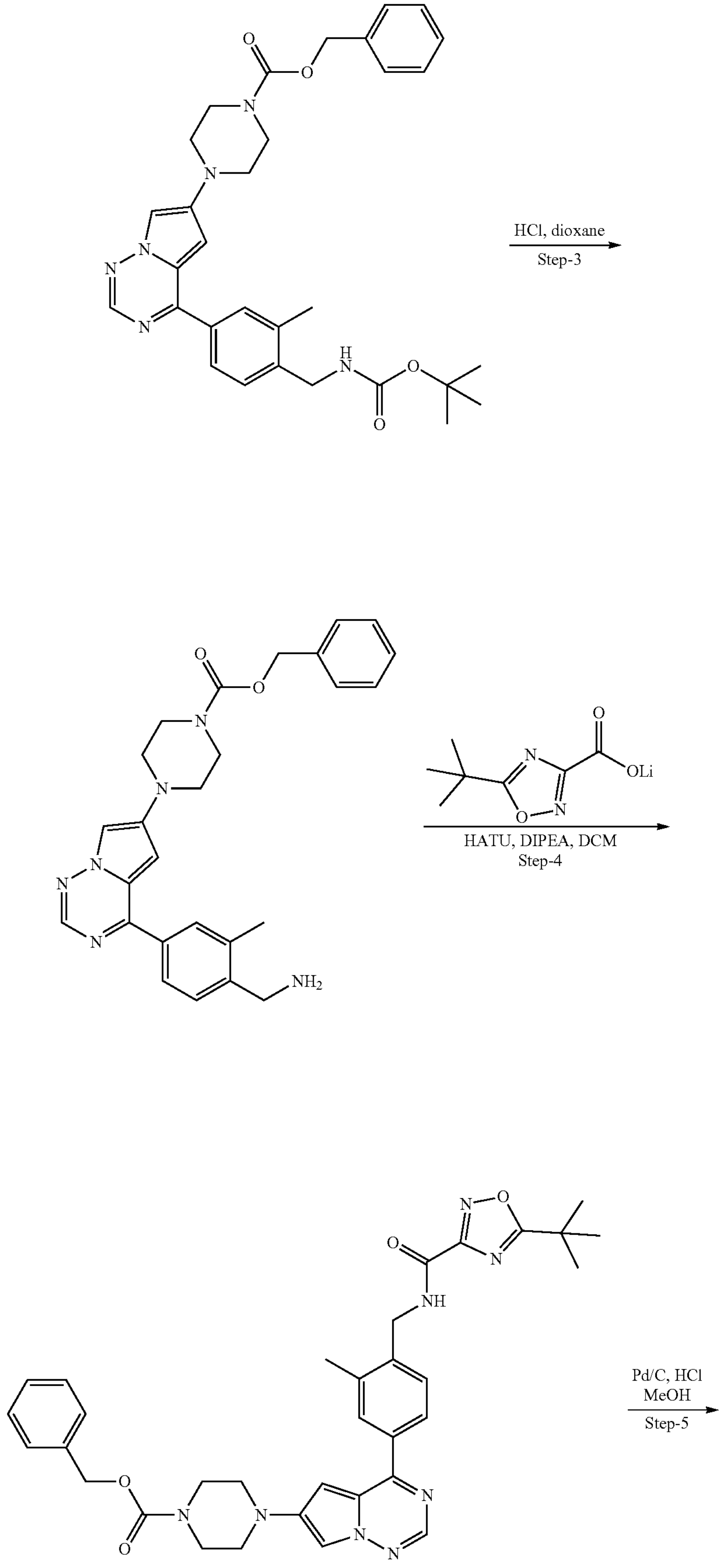

-continued

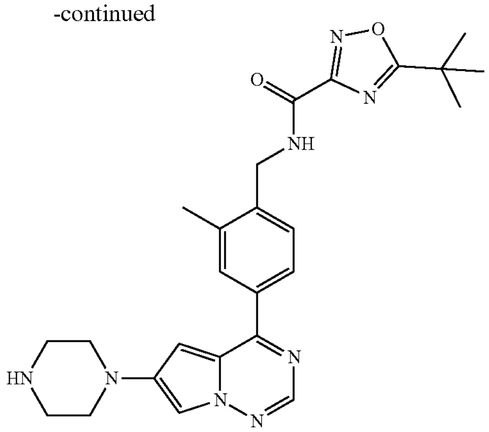

Step-1: A solution of tert-butyl N-[[2-methyl-4-(4,4,5,5-tetramethyl-1,3,2-dioxaborolan-2-yl)phenyl]methyl]carbamate (41.3 g, 118.93 mmol), 6-bromo-4-chloro-pyrrolo[2,1-f][1,2,4]triazine (27.65 g, 118.93 mmol), $K_2CO_3$ (49.31 g, 356.80 mmol) and Pd(dppf)$Cl_2$—$CH_2Cl_2$ (4.86 g, 5.95 mmol) in 1,4-dioxane (450 mL) and $H_2O$ (90 mL) was stirred at 80° C. for 18 h under inert atmosphere. After cooling to rt, the mixture was diluted in water (400 mL) and extracted with Ethyl acetate (250 mL×3). The combined organic layers were washed with brine, dried and concentrated. The residue was purified by column chromatography (Companion combiflash; 720 g $SiO_2$; petroleum ether/EtOAc) to give tert-butyl (4-(6-bromopyrrolo[2,1-f][1,2,4]triazin-4-yl)-2-methylbenzyl)carbamate (30.1 g, 68.52 mmol, 58% yield). $^1$H NMR (500 MHz, $CDCl_3$) δ=8.49 (s, 1H), 7.85 (m, 3H), 7.42 (br d, J=8.2 Hz, 1H), 7.07 (s, 1H), 4.92 (br s, 1H), 4.40 (br s, 2H), 2.43 (s, 3H), 1.49 (s, 9H).

Step-2:

tert-butyl N-[[4-(6-bromopyrrolo[2,1-f][1,2,4]triazin-4-yl)-2-methylphenyl]methyl]carbamate (29 g, 69.49 mmol), benzyl piperazine-1-carboxylate (45.92 g, 208.48 mmol, 40.21 mL), $Cs_2CO_3$ (67.93 g, 208.48 mmol) were dissolved in 1,4-dioxane (350 mL). The solution was degassed under reduced pressure, followed by the addition of RuPhos Pd G4 (3.54 g, 4.17 mmol). The reaction mixture was heated at 80° C. under an argon atmosphere overnight. After cooling to rt, the mixture was diluted with $H_2O$ (300 mL) and extracted with Ethyl acetate (250 mL×3). The combined organic layers were washed with brine, dried and concentrated. The residue was purified by column chromatography (Companion combiflash; 720 g $SiO_2$; petroleum ether/EtOAc) to give benzyl 4-(4-(4-(((tert-butoxycarbonyl)amino)methyl)-3-methylphenyl)pyrrolo[2,1-f][1,2,4]triazin-6-yl)piperazine-1-carboxylate (22.1 g, 38.83 mmol, 56% yield) as a yellow oil. LC-MS($ES^+$): $m/z$=557.4 $[M+H]^+$.

Step-3:

To a solution of benzyl 4-[4-[4-[(2,2-dimethylpropanoylamino)methyl]-3-methylphenyl]pyrrolo[2,1-f][1,2,4]triazin-6-yl]piperazine-1-carboxylate (10.6 g, 19.61 mmol) in 1,4-dioxane (40 mL) was added 24.51 mL HCl in dioxane (4 M in dioxane, 24.51 mL) at room temperature and stirred for 7 h. The reaction mixture was evaporated in vacuo and triturated with MTBE (50 ml) and filtered to give benzyl 4-[4-[4-(aminomethyl)-3-methyl-phenyl]pyrrolo[2,1-f][1,2,4]triazin-6-yl]piperazine-1-carboxylate (8.95 g, 16.52 mmol, 84% yield, Hydrochloride) as a red solid. LC-MS ($ES^+$): $m/z$=457.0 $[M+H]^+$.

Step-4:

To a solution of benzyl 4-[4-[4-(aminomethyl)-3-methylphenyl]pyrrolo[2,1-f][1,2,4]triazin-6-yl]piperazine-1-carboxylate (19.05 g, 38.64 mmol) in DCM (500 mL) and DMF (50 mL) were added 5-tert-butyl-1,2,4-oxadiazole-3-carboxylate (10.21 g, 57.96 mmol), HATU (22.10 g, 57.96 mmol) and DIPEA (14.98 g, 115.92 mmol, 20.19 mL). The mixture was stirred at 20° C. for overnight. The mixture was poured into water (250 mL), and extracted with DCM (100 mL×3). The combined organic layers were washed with brine (2×150 mL), dried and concentrated. The residue was purified by column chromatography (Companion combiflash; 240 g $SiO_2$, petroleum ether/MTBE with MTBE from 0~100%, flow rate=80 mL/min. Rv=50-130) to give benzyl 4-[4-[4-[[(5-tert-butyl-1,2,4-oxadiazole-3-carbonyl)amino]methyl]-3-methyl-phenyl]pyrrolo[2,1-f][1,2,4]triazin-6-yl]piperazine-1-carboxylate (7.2 g, 11.24 mmol, 29% yield) as a yellow solid. LC-MS($ES^+$): $m/z$=609.2 [M+H]+.

Step-5:

A solution of benzyl 4-[4-[4-[[(5-tert-butyl-1,2,4-oxadiazole-3-carbonyl)amino]methyl]-3-methylphenyl]pyrrolo[2,1-f][1,2,4]triazin-6-yl]piperazine-1-carboxylate (2.05 g, 3.37 mmol) and 10 wt. % palladium on carbon (358.41 mg, 336.79 μmol) in methanol (120 mL) and HCl in water (1 M, 16.84 mL) was stirred for 14 h at room temperature under hydrogen atmosphere (1 atm). The solution was filtered and concentrated in vacuo. 1M potassium carbonate (1M in water) was added for neutralization and the solution was extracted with DCM (25 mL×3) and evaporated. The crude material was purified by chromatography (Companion combiflash; 40 g $SiO_2$, chloroform/methanol+TEA (2%) with methanol+TEA (2%) from 5-8% flow rate=40 mL/min, Rv=5-12 CV) to give 5-tert-butyl-N-[[2-methyl-4-(6-piperazin-1-ylpyrrolo[2,1-f][1,2,4]triazin-4-yl)phenyl]methyl]-1,2,4-oxadiazole-3-carboxamide (0.75 g, 1.45 mmol, 43% yield) as a yellow solid. LC-MS($ES^+$): $m/z$=475.2 [M+H]+.

4-(4-(4-((5-(tert-butyl)-1,2,4-oxadiazole-3-carboxamido)methyl)-3-methylphenyl)pyrrolo[2,1-f][1,2,4]triazin-6-yl)benzoic acid

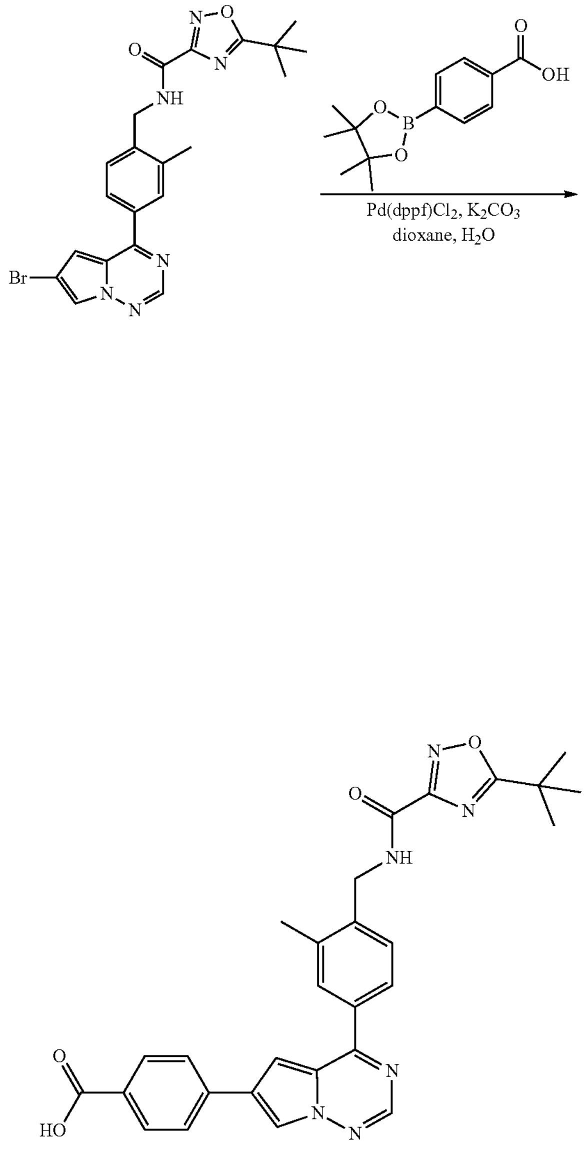

A solution of N-[[4-(6-bromopyrrolo[2,1-f][1,2,4]triazin-4-yl)-2-methyl-phenyl]methyl]-5-tert-butyl-1,2,4-oxadiazole-3-carboxamide (4.01 g, 8.54 mmol), 4-(4,4,5,5-tetramethyl-1,3,2-dioxaborolan-2-yl)benzoic acid (2.33 g, 9.40 mmol), $Pd(dppf)Cl_2 \cdot CH_2Cl_2$ (697.74 mg, 854.40 μmol) and $K_2CO_3$ (3.54 g, 25.63 mmol) in 1,4-dioxane (40 mL) and water (10 mL), was stirred at 90° C. for 12 h under inert atmosphere. After cooling to rt, the mixture was concentrated, then was diluted in water (250 ml) and filtered. The filtrates were acidified with 1M $NaHSO_4$ (pH 3-4) and filtered. The solid was dried, refluxed in $CH_3CN$ (40 ml) and filtered. The cake was washed with $CH_3CN$ (20 ml) and dried to provide 4-[4-[4-[[(5-tert-butyl-1,2,4-oxadiazole-3-carbonyl)amino]methyl]-3-methyl-phenyl]pyrrolo[2,1-f][1,2,4]triazin-6-yl]benzoic acid (3.7 g, 6.59 mmol, 77% yield) as a yellow solid. LC-MS($ES^+$): m/z=511.2 [M+H]+.

5-(tert-butyl)-N-(4-(6-(4-formylphenyl)pyrrolo[2,1-f][1,2,4]triazin-4-yl)-2-methylbenzyl)-1,2,4-oxadiazole-3-carboxamide

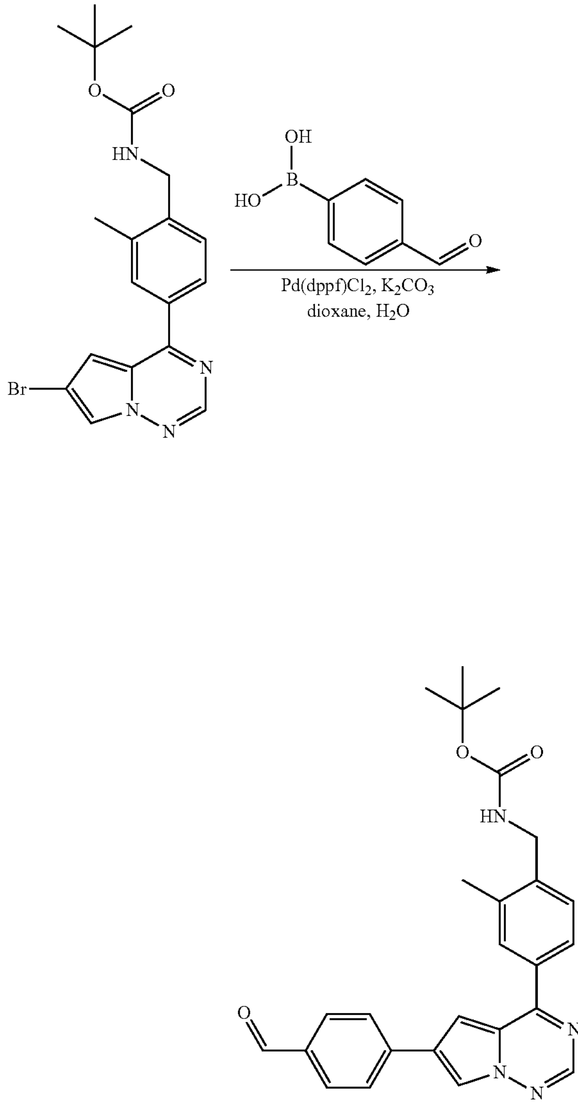

To a solution of tert-butyl N-[[4-(6-bromopyrrolo[2,1-f][1,2,4]triazin-4-yl)-2-methyl-phenyl]methyl]carbamate (3.65 g, 8.75 mmol) in 1,4-dioxane (75 mL) and $H_2O$ (7.5 mL), (4-formylphenyl)boronic acid (1.44 g, 9.62 mmol), $K_2CO_3$ (3.63 g, 26.24 mmol) and $Pd(dppf)Cl_2CH_2Cl_2$ (357.15 mg, 437.34 μmol) were added under inert atmosphere. The mixture was stirred at 80° C. for 18 h. After cooling to rt, the mixture was diluted with water (200 mL) and extracted with ethyl acetate (150 mL×3). The combined organic layers were washed with brine, dried, filtered, and concentrated. The residue was purified by column chromatography (Companion combiflash; 120 g $SiO_2$; petroleum ether/EtOAc flow rate=75 ml/min, Rv=40-80 cv.) to give tert-butyl N-[[4-[6-(4-formylphenyl)pyrrolo[2,1-f][1,2,4]triazin-4-yl]-2-methyl-phenyl]methyl]carbamate (1.72 g, 3.69 mmol, 42% yield) as a yellow solid. LC-MS($ES^+$): m/z=495.1 [M+H]+.

5-(tert-butyl)-N-(2-methyl-4-(6-(4,4,5,5-tetramethyl-1,3,2-dioxaborolan-2-yl)pyrrolo[2,1-f][1,2,4]triazin-4-yl)benzyl)-1,2,4-oxadiazole-3-carboxamide

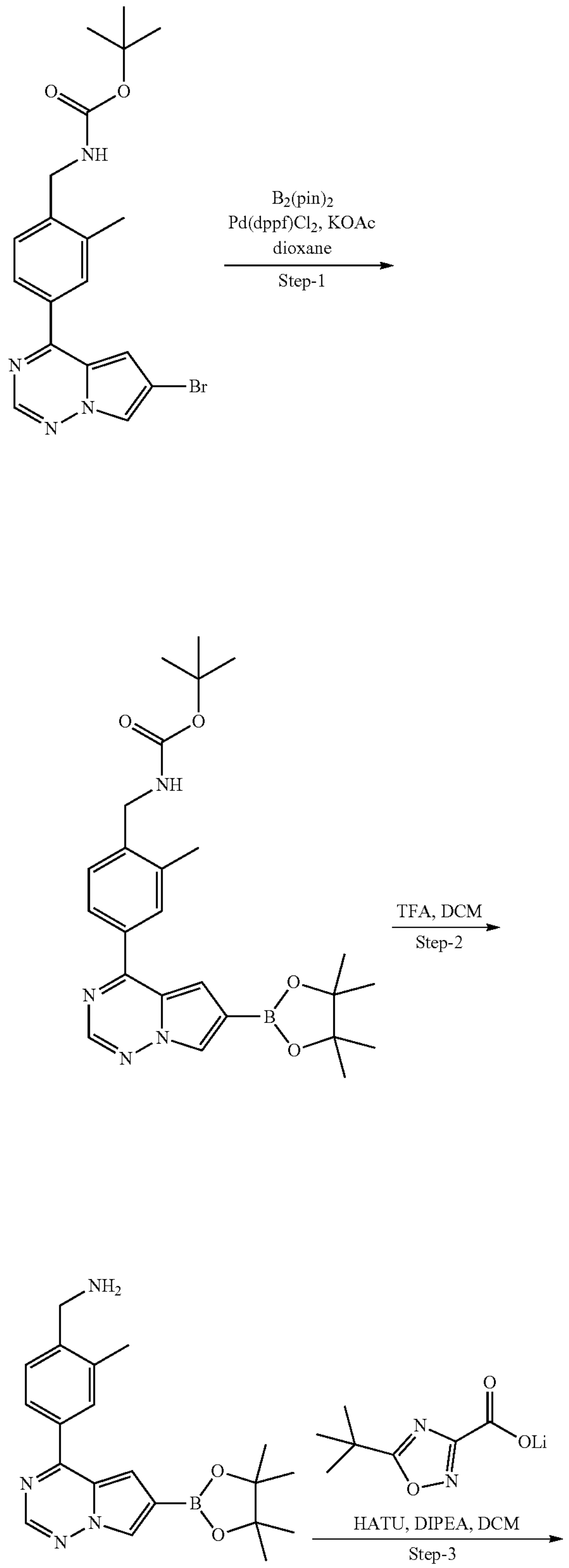

-continued

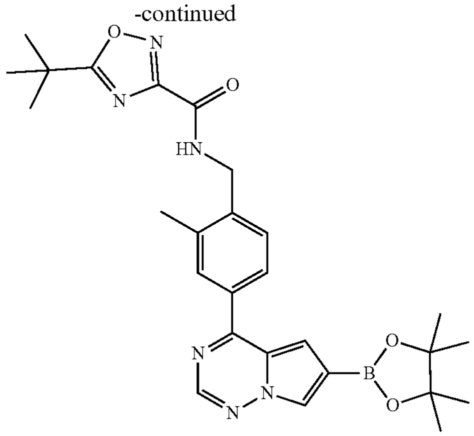

Step-1:

A solution of tert-butyl N-[[4-(6-bromopyrrolo[2,1-f][1,2,4]triazin-4-yl)-2-methylphenyl]methyl]carbamate (10 g, 21.81 mmol) 4,4,5,5-tetramethyl-2-(4,4,5,5-tetramethyl-1,3,2-dioxaborolan-2-yl)-1,3,2-dioxaborolane (6.65 g, 26.17 mmol) and KOAc (6.42 g, 65.42 mmol) in 1,4-dioxane (150 mL) was degassed and then heated overnight at 80° C. under an argon atmosphere. The reaction mixture was cooled to RT and concentrated. The residue was dissolved in EtOAc (200 ml), filtered and washed with brine (200 ml×2). The organic layer was dried over $Na_2SO_4$ filtered and concentrated in vacuo. The residue was purified by column chromatography (Companion; 120 g $SiO_2$; petroleum ether/MtBE with MtBE from 0 to 50%, flow rate=85 ml/min, Rv=8-9 cv.) to give tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (5 g, 9.69 mmol, 44% yield) as a yellow solid. $^1$H NMR (500 MHz, $CDCl_3$) δ=8.55-8.42 (m, 1H), 8.14 (m, 1H), 8.02-7.83 (m, 2H), 7.50-7.33 (m, 2H), 4.82 (br s, 1H), 4.40 (br s, 2H), 2.54-2.33 (m, 3H), 1.48-1.27 (m, 21H).

Step-2:

To a stirred solution of tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (0.5 g, 1.08 mmol) in DCM (10 mL) was added TFA (5 mL) at 0° C. and the reaction mixture was stirred at RT for 2 h. The reaction mixture was concentrated under reduced pressure to get the crude product, which was triturated with diethyl ether (50 mL) to afford [2-methyl-4-[6-(4,4,5,5-tetramethyl-1,3,2-dioxaborolan-2-yl)pyrrolo[2,1-f][1,2,4]triazin-4-yl]phenyl]methanamine (0.4 g, 355.53 mol, 33.02% yield, TFA salt) as yellow solid.

Step-3:

To a solution of tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (5 g, 10.77 mmol) in DCM (50 mL) was added TFA (33.09 g, 290.20 mmol, 22.22 mL) at room temperature. The solution was stirred for 48 h, then was concentrated to provide [2-methyl-4-[6-(4,4,5,5-tetramethyl-1,3,2-dioxaborolan-2-yl)pyrrolo[2,1-f][1,2,4]triazin-4-yl]phenyl]methanamine (5 g, 8.90 mmol, 83% yield Trifluoroacetate) as a dark yellow oil and used in the next step without purification. A solution of [2-methyl-4-[6-(4,4,5,5-tetramethyl-1,3,2-dioxaborolan-2-yl)pyrrolo[2,1-f][1,2,4]triazin-4-yl]phenyl]methanamine (2.4 g, 5.03 mmol, Trifluoroacetate), (5-tert-butyl-1,2,4-oxadiazole-3-carbonyl)oxylithium (1.33 g, 7.26 mmol, Lithium), HATU (2.88 g, 7.54 mmol) and DIPEA (1.95 g, 15.09 mmol, 2.63 mL) in DCM (50 ml) was stirred at room temperature overnight. The solution was washed with water, brine (50 ml×2), dried over $Na_2SO_4$, filtered and concentrated. The residue was crystalized from i-PrOH\Ether (2:1), to give 5-tert-butyl-N-[[2-methyl-4-[6-(4,4,5,5-tetramethyl-1,3,2-dioxaborolan-2-yl)pyrrolo[2,1-f][1,2,4]triazin-4-yl]phenyl]methyl]-1,2,4-oxadiazole-3-carboxamide (0.91 g, 1.59 mmol, 31.54% yield). LC-MS(ES$^+$): m/z=517.2 [M+H]$^+$.

Synthesis of 2-(4-(4-(4-((5-(tert-butyl)-1,2,4-oxadiazole-3-carboxamido)methyl)-3-methylphenyl)pyrrolo[2,1-f][1,2,4]triazin-6-yl)-1H-pyrazol-1-yl)ethyl methanesulfonate

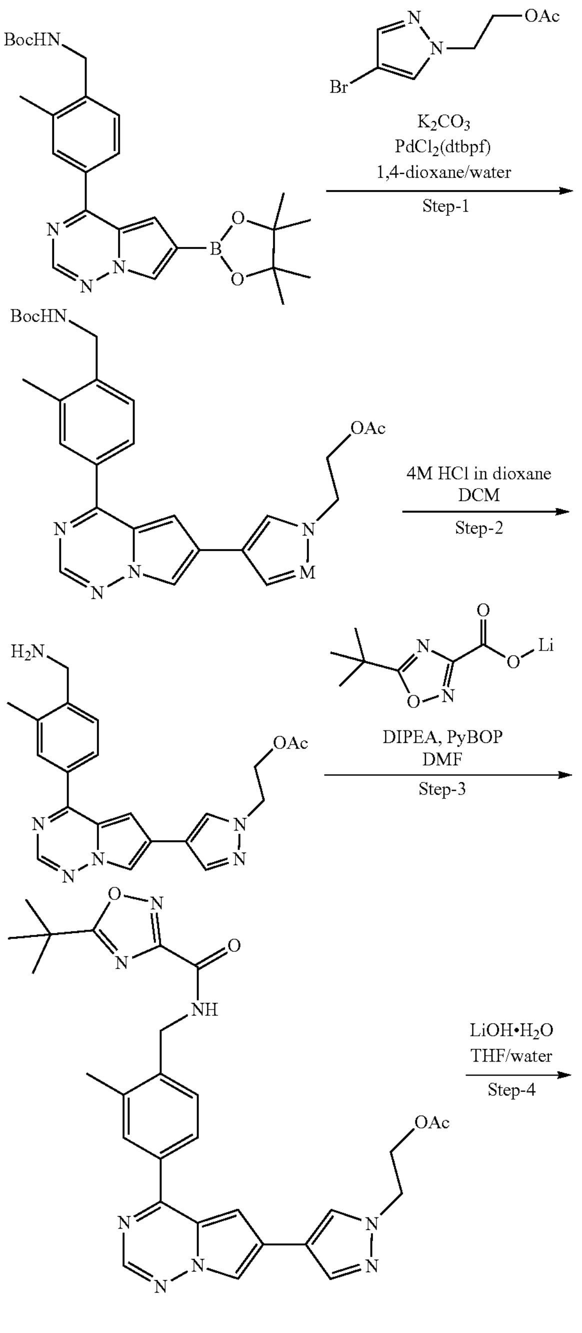

-continued

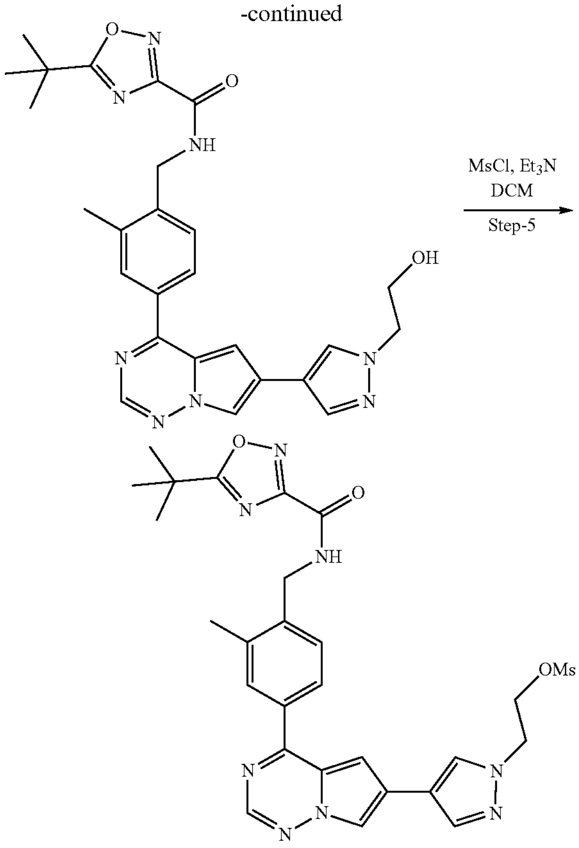

Step-1:

Under argon atmosphere, to stirred solution of tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (2.0 g, 4.31 mmol) and 2-(4-bromopyrazol-1-yl) ethyl acetate (1.00 g, 4.31 mmol) in 1,4-dioxane (24 mL)/water (6 mL) was added, followed by the addition of $K_2CO_3$ (1.79 g, 12.92 mmol) and $PdCl_2$(dtbpf) (280.71 mg, 430.70 μmol). The resulting mixture was stirred at 80° C. for 2 hours, and the progress of the reaction was monitored by TLC and LCMS. After completion of the reaction, washed with water and extracted with ethyl acetate (3×100 mL), the combined organic layer was dried over anhydrous sodium sulfate and concentrated under reduced pressure to get crude. The crude was purified by column over (230-400 silica) EtOAc in PE as an eluent to afforded 2-[4-[4-[4-[(tert-butoxycarbonylamino)methyl]-3-methyl-phenyl]pyrrolo[2,1-f][1,2,4]triazin-6-yl]pyrazol-1-yl]ethyl acetate (1.4 g, 2.68 mmol, 62.21% yield) as a yellow solid. LC-MS(ES$^+$): m/z 491.66 [M+H]$^+$.

Step-2:

To a stirred solution of 2-[4-[4-[4-[(tert-butoxycarbonylamino)methyl]-3-methyl-phenyl]pyrrolo[2,1-f][1,2,4]triazin-6-yl]pyrazol-1-yl]ethyl acetate (1.4 g, 2.85 mmol) in DCM (30.0 mL) under inert atmosphere was added hydrogen chloride solution 4.0 M in dioxane (7.13 mL) at 0° C. Then, the reaction mixture was stirred at RT for 2 hrs while monitoring by TLC and LCMS. After completion, the crude was concentrated under reduced pressure and triturated with diethyl ether (2×50 mL), then again dried to obtain 2-[4-[4-[4-(aminomethyl)-3-methyl-phenyl]pyrrolo[2,1-f][1,2,4]triazin-6-yl]pyrazol-1-yl]ethyl acetate (1.4 g, 3.28 mmol) as a light yellow solid. LC-MS(ES$^+$): m/z 391.35 [M+H]$^+$.

Step-3:

To a stirred solution of 2-[4-[4-[4-(aminomethyl)-3-methyl-phenyl]pyrrolo[2,1-f][1,2,4]triazin-6-yl]pyrazol-1-yl]ethyl acetate (1.4 g, 3.28 mmol) and (5-tert-butyl-1,2,4-oxadiazole-3-carbonyl)oxylithium (866.26 mg, 4.92 mmol) in DMF (15 mL) was added DIPEA (2.12 g, 16.40 mmol, 2.86 mL) and PyBOP (3.41 g, 6.56 mmol) was added. The reaction mixture was stirred at rt for 1 hr. The reaction mixture was concentrated under reduced pressure to get crude. The crude was washed with water and extracted with ethyl acetate (3×50 mL), the combined organic layer was concentrated under reduced pressure to get crude, the crude was purified by column chromatography using 230-400 mesh silica and ethyl acetate/pet ether as an eluent to afford 2-[4-[4-[4-[[(5-tert-butyl-1,2,4-oxadiazole-3-carbonyl) amino]methyl]-3-methyl-phenyl]pyrrolo[2,1-f][1,2,4]triazin-6-yl]pyrazol-1-yl]ethyl acetate (0.8 g, 1.29 mmol, 39.26% yield) as a yellow solid. LC-MS(ES$^+$): m/z 543.50 $[M+H]^+$.

Step-4:

To a stirred solution of 2-[4-[4-[4-[[(5-tert-butyl-1,2,4-oxadiazole-3-carbonyl)amino]methyl]-3-methyl-phenyl] pyrrolo[2,1-f][1,2,4]triazin-6-yl]pyrazol-1-yl]ethyl acetate (0.8 g, 1.47 mmol) in tetrahydrofuran (8 mL)/water (2 mL) was added lithium hydroxide monohydrate (92.80 mg, 2.21 mmol) at room temperature and stirred for 2 hr. Solvents were reduced under pressure and the crude product was washed with 1N HCl solution to afford 5-tert-butyl-N-[[4-[6-[1-(2-hydroxyethyl)pyrazol-4-yl]pyrrolo[2,1-f][1,2,4]triazin-4-yl]-2-methyl-phenyl]methyl]-1,2,4-oxadiazole-3-carboxamide (0.5 g, 864.25 μmol, 58.62% yield) as a yellow solid. LC-MS(ES$^+$): m/z 501.57 $[M+H]^+$.

Step-5:

To a solution of 5-tert-butyl-N-[[4-[6-[1-(2-hydroxyethyl) pyrazol-4-yl]pyrrolo[2,1-f][1,2,4]triazin-4-yl]-2-methyl-phenyl]methyl]-1,2,4-oxadiazole-3-carboxamide (0.55 g, 1.10 mmol) in DCM (5 mL) was added methanesulfonyl chloride (188.80 mg, 1.65 mmol, 127.83 L) at RT and the reaction mixture was cooled to 0° C. Triethylamine (222.37 mg, 2.20 mmol, 306.30 μL) was added dropwise and the reaction mixture was stirred at RT for 1 h. The reaction mixture was diluted with DCM (20 mL) and washed with saturated $NaHCO_3$ solution (10 mL) and brine solution (5 mL). The organic layer was dried over sodium sulfate, and concentrated in vacuo to get 2-[4-[4-[4-[[(5-tert-butyl-1,2,4-oxadiazole-3-carbonyl)amino]methyl]-3-methyl-phenyl] pyrrolo[2,1-f][1,2,4]triazin-6-yl]pyrazol-1-yl]ethyl methanesulfonate (0.5 g, 713.22 mol, 64.91% yield), which was used in the next step without any purification. LC-MS(ES$^+$): m/z 579.61 $[M+H]^+$.

Synthesis of 3-((4-(4-(((tert-butoxycarbonyl)amino) methyl)-3-methylphenyl)pyrrolo[2,1-f][1,2,4]triazin-6-yl)oxy)propyl methanesulfonate

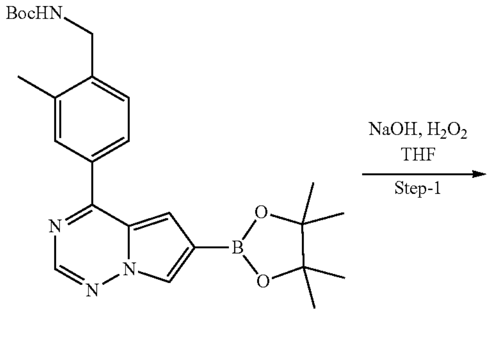

-continued

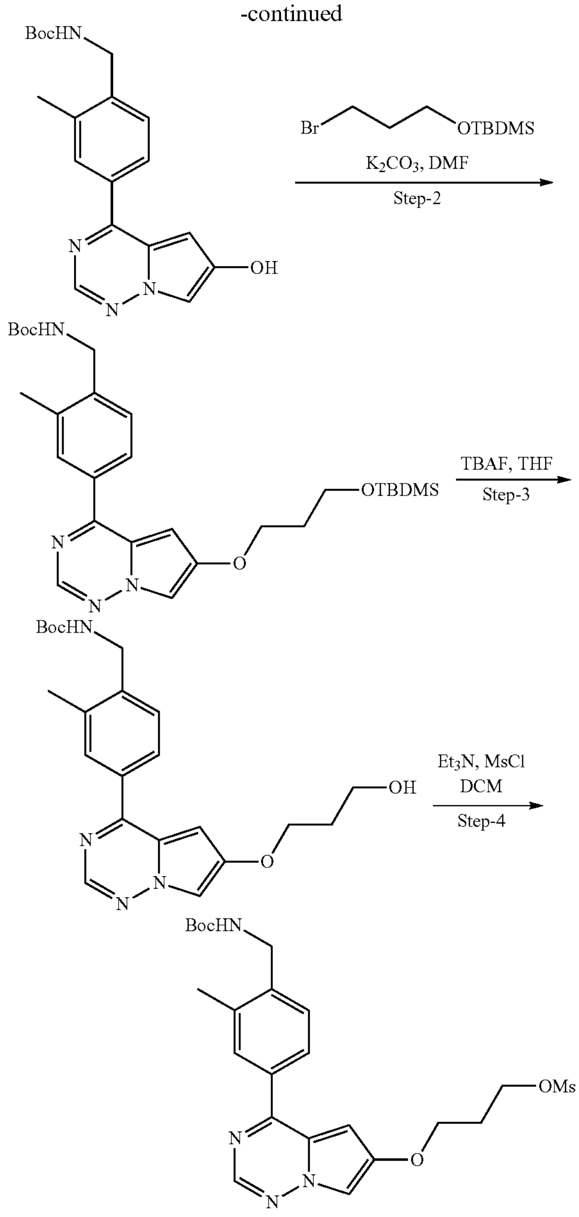

Step-1:

To a stirred solution of tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (1 g, 2.15 mmol) in THF (15 mL) was added sodium hydroxide (1.72 g, 43.07 mmol) in water slowly. After that, the reaction mixture was stirred for 10 mins and added 35% hydrogen peroxide (1.47 g, 43.07 mmol, 1.33 mL) dropwise (while the addition reaction mixture turned to dark red and fluorescence was observed) and stirred for 16 hr at room temperature while monitoring by TLC and LC-MS. After completion, it was neutralized with 1.5N HCl solution and extracted with ethyl acetate. The resulting organic layer was washed with brine solution, dried over $Na_2SO_4$, concentrated under reduced pressure. The crude product was purified by silica gel column chromatography using 0-60% EA in PE to afford tert-butyl N-[[4-(6-hydroxypyrrolo[2,1-f][1,2,4]triazin-4-yl)-2-methyl-phenyl]methyl]carbamate (0.6 g, 1.46 mmol, 67.61% yield) as a dark pink liquid. LC-MS(ES$^+$): m/z 355.45 $[M+H]^+$.

Step-2:

In a solution of tert-butyl N-[[4-(6-hydroxypyrrolo[2,1-f][1,2,4]triazin-4-yl)-2-methyl-phenyl]methyl]carbamate (1.5 g, 4.23 mmol) and 3-bromopropoxy-tert-butyl-dimethyl-silane (2.14 g, 8.46 mmol) in DMF (20 mL), potassium carbonate (1.75 g, 12.69 mmol) was added and stirred at 80° C. for 5 hr. The reaction mixture was quenched with ice-cold water (100 mL) and extracted with ethyl acetate (50 mL×3). The organic was washed with water (100 mL) and brine solution (50 mL). The combined organic layers was dried over anhydrous sodium sulfate, filtered and concentrated under reduced pressure to afford tert-butyl N-[[4-[6-[3-[tert-butyl(dimethyl)silyl]oxypropoxy]pyrrolo[2,1-f][1,2,4]triazin-4-yl]-2-methyl-phenyl]methyl]carbamate (2 g, 2.24 mmol, 52.88% yield). LC-MS(ES$^+$): m/z 527.58 [M+H]$^+$.

Step-3:

Argon gas was purged through a solution of tert-butyl N-[[4-[6-[3-[tert butyl(dimethyl)silyl]oxypropoxy]pyrrolo[2,1-f][1,2,4]triazin-4-yl]-2-methyl-phenyl]methyl]carbamate (2 g, 3.80 mmol) in THF (40 mL) for 5 min followed by the addition of Tetrabutylammonium fluoride (1 M, 5.70 mL) to reaction mixture at 0° C. The resulting mixture was stirred at 27° C. for 2 hr. The reaction was monitored by TLC and LCMS. After consuming the starting material. The reaction was diluted with ethyl acetate (100 mL) and washed with water (100 mL) and brine solution (100 mL). The organic layer was dried over sodium sulfate and concentrated in vacuo to get a crude product. The crude was purified by column chromatography over silica gel (230-400 mesh) (using 0-10% EtOAc in pet-ether as an eluent) to afford tert-butyl N-[[4-[6-(3-hydroxypropoxy)pyrrolo[2,1-f][1,2,4]triazin-4-yl]-2-methyl-phenyl]methyl]carbamate (0.9 g, 1.75 mmol, 45.97% yield). LC-MS(ES$^+$): m/z 413.62 [M+H]$^+$.

Step-4:

In a solution of tert-butyl N-[[4-[6-(3-hydroxypropoxy)pyrrolo[2,1-f][1,2,4]triazin-4-yl]-2-methyl-phenyl]methyl]carbamate (0.9 g, 2.18 mmol) in DCM (10 mL), triethylamine (1.10 g, 10.90 mmol, 1.52 mL) was added and stirred for 5 min before MsCl (374.58 mg, 3.27 mmol, 253.61 μL) was added to reaction mixture at 0° C. The resulting mixture was stirred at 27° C. for 3 hr. The reaction mixture was quenched with saturated bicarbonate solution (50 mL) and extracted with DCM (50 mL×3). The DCM layer was washed with water (50 mL) and brine solution (50 mL). The combined organic layers were dried over anhydrous sodium sulfate, filtered and concentrated under reduced pressure to afford 3-[4-[4-[(tert-butoxycarbonylamino)methyl]-3-methyl-phenyl]pyrrolo[2,1-f][1,2,4]triazin-6-yl]oxypropyl methanesulfonate (0.9 g, 1.36 mmol, 62.28% yield). LC-MS (ES$^+$): m/z 491.73 [M+H]$^+$.

Synthesis of (R)-3-((4-(4-(((tert-butoxycarbonyl)amino)methyl)-3-methylphenyl)pyrrolo[2,1-f][1,2,4]triazin-6-yl)oxy)-2-fluoropropyl trifluoromethanesulfonate

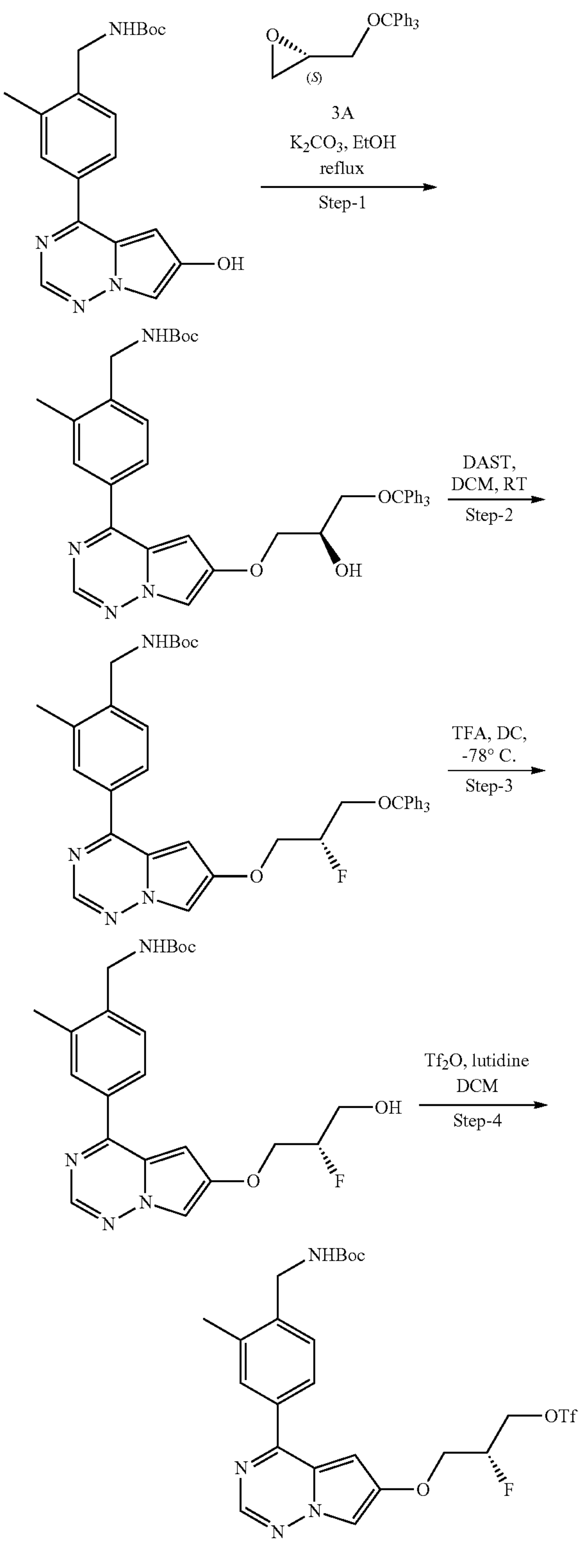

Step-1:

To a stirred solution of tert-butyl N-[[4-(6-hydroxypyrrolo[2,1-f][1,2,4]triazin-4-yl)-2-methyl-phenyl]methyl]carbamate (10 g, 28.22 mmol) in ethanol (100 mL) was added potassium carbonate (11.70 g, 84.65 mmol, 5.11 mL) followed by the addition of (2S)-2-(trityloxymethyl)oxirane (8.93 g, 28.22 mmol) and heated the reaction mixture at 70° C. for 16 hr. After completion, the reaction mixture was concentrated under reduced pressure to get the crude product. The resulting crude was diluted with water (200 mL) and extracted with ethyl acetate (200×3 mL). The combined organic layer was washed with brine solution (100×3 mL), dried over sodium sulfate, and concentrated under reduced pressure to get the crude product. The resulting crude product was purified by silica gel (100-200 mesh, 25% ethyl acetate in pet ether as mobile phase) to afforded tert-butyl N-[[2-methyl-4-[6-[(2S)-2-hydroxy-3-trityloxy-propoxy]pyrrolo[2,1-f][1,2,4]triazin-4-yl]phenyl]methyl]carbamate (6 g, 7.78 mmol, 27.58% yield) as yellow solid. LC-MS ($ES^+$): m/z 671.51 $[M+H]^+$.

Step-2:

To a stirred solution of tert-butyl N-[[2-methyl-4-[6-[rac-(2S)-2-hydroxy-3-trityloxy-propoxy]pyrrolo[2,1-f][1,2,4]triazin-4-yl]phenyl]methyl]carbamate (6.00 g, 8.94 mmol) in DCM (60 mL) was added (diethylamino)sulfur trifluoride (3.60 g, 22.36 mmol, 2.95 mL) at −78° C., stirred at same temperature for 20 minutes and then warm up to room temperature for 10 minutes. After completion, the reaction mixture was quenched with a saturated sodium bicarbonate solution (20 mL) and extracted with DCM. The combined organic layer was dried over sodium sulfate and concentrated under reduced pressure to get the crude product. The resulting crude was purified by silica gel (100-200 mesh, 25% ethyl acetate in pet ether as mobile phase) to afford tert-butyl N-[[2-methyl-4-[6-[(2R)-2-fluoro-3-trityloxy-propoxy]pyrrolo[2,1-f][1,2,4]triazin-4-yl]phenyl]methyl]carbamate (2.5 g, 2.86 mmol, 31.99% yield) as an yellow solid. LC-MS($ES^+$): m/z 673.73 $[M+H]^+$.

Step-3:

To a stirred solution of tert-butyl N-[[2-methyl-4-[6-[(2R)-2-fluoro-3-trityloxy-propoxy]pyrrolo[2,1-f][1,2,4]triazin-4-yl]phenyl]methyl]carbamate (4.00 g, 5.95 mmol) in DCM was added trifluoroacetic acid at −78° C. and stirred at same temperature for 1 hr.

After completion, the reaction mixture was quenched with a saturated sodium bicarbonate solution (20 mL) and extracted with DCM. The combined organic layer was dried over sodium sulfate and concentrated under reduced pressure to get the crude product. The resulting crude was purified by silica gel (100-200 mesh, 40% ethyl acetate in pet ether as mobile phase) to afforded tert-butyl N-[[2-methyl-4-[6-[rac-(2S)-2-fluoro-3-hydroxy-propoxy]pyrrolo[2,1-f][1,2,4]triazin-4-yl]phenyl]methyl]carbamate (2 g, 4.46 mmol, 75.02% yield) as yellow solid. LC-MS($ES^+$): m/z 431.23 $[M+H]^+$.

Step-4:

To a stirred solution of tert-butyl N-[[2-methyl-4-[6-[rac-(2S)-2-fluoro-3-hydroxy-propoxy]pyrrolo[2,1-f][1,2,4]triazin-4-yl]phenyl]methyl]carbamate (1 g, 2.32 mmol) in DCM (10 mL) was added 2,6-lutidine (622.30 mg, 5.81 mmol, 674.21 μL) followed by the addition of triflic anhydride (1.18 g, 4.18 mmol, 703.49 μL) at −10° C. and stirred the reaction mixture at same temperature for 30 min. After completion, the reaction mixture was diluted with water and extracted with DCM. The combined organic layer was dried over sodium sulfate and concentrated under high vacuum to get the crud product. The resulting crude was purified over silica gel (230-400 mesh, 10% ethyl acetate in pet ether as mobile phase) to afford [(2R)-3-[4-[4-[(tert-butoxycarbonylamino)methyl]-3-methyl-phenyl]pyrrolo[2,1-f][1,2,4]triazin-6-yl]oxy-2-fluoro-propyl] trifluoromethanesulfonate (0.7 g, 1.02 mmol, 43.92% yield) as yellow oil. LC-MS ($ES^+$): m/z 563.57 $[M+H]^+$.

Synthesis of tert-butyl (2-methyl-4-(6-(2-oxoethoxy)pyrrolo[2,1-f][1,2,4]triazin-4-yl)benzyl)carbamate

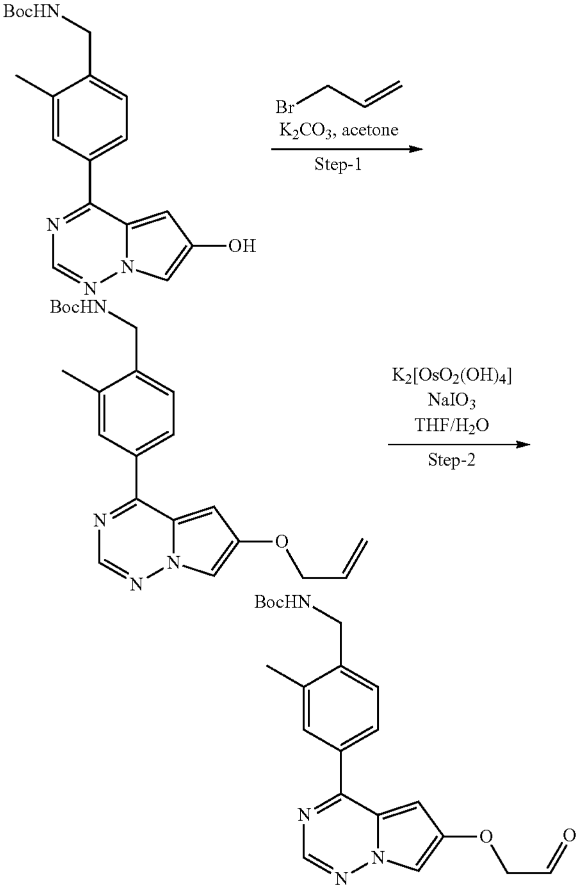

Step-1:

To a stirred solution of tert-butyl N-[[4-(6-hydroxypyrrolo[2,1-f][1,2,4]triazin-4-yl)-2-methyl-phenyl]methyl]carbamate (0.6 g, 1.69 mmol) in acetone (15 mL) was added Potassium carbonate, anhydrous, 99% (701.95 mg, 5.08 mmol) and stirred for 30 min at RT. Then 3-bromoprop-1-ene (307.22 mg, 2.54 mmol, 219.44 μL) was added and allowed to stir at RT for 16 hrs. After completion, the reaction mass was concentrated under reduced pressure and the crude was purified by normal phase column chromatography (Davisil silica, 10% Ethyl acetate/PE as eluent) using Biotage to obtain tert-butyl N-[[4-(6-allyloxypyrrolo[2,1-f][1,2,4]triazin-4-yl)-2-methyl-phenyl]methyl]carbamate (0.45 g, 1.04 mmol, 61.47% yield). LC-MS($ES^+$): m/z 395.48 $[M+H]^+$.

Step-2:

To a stirred solution of tert-butyl N-[[4-(6-allyloxypyrrolo[2,1-f][1,2,4]triazin-4-yl)-2-methyl-phenyl]methyl]carbamate (0.42 g, 1.06 mmol) in THF (2 mL) was added potassium osmate(VI) dihydrate (19.62 mg, 53.24 μmol) followed by sodium periodate (1.14 g, 5.32 mmol) in water (2 mL) and stirred for 1 hr while monitoring by TLC. After completion, quenched with water and extracted with ethyl acetate, concentrated, and the resulting residue was taken in THF (2 mL) and added sodium periodate (1.14 g, 5.32 mmol) in water (2 mL) and stirred for 1 hr while monitoring by TLC and LCMS analysis. Again, it was quenched with water and extracted with Ethyl acetate. The organic layer was dried over $Na_2SO_4$ and concentrated under reduced pressure to obtain tert-butyl N-[[2-methyl-4-[6-(2-oxoethoxy)pyrrolo[2,1-f][1,2,4]triazin-4-yl]phenyl]methyl]carbamate (0.2 g, 200.03 μmol, 18.79% yield) as a light yellow compound. LC-MS(ES$^+$): m/z397.41 [M+H]$^+$.

Synthesis of tert-butyl (4-(6-(3-formylcyclobutoxy) pyrrolo[2,1-f][1,2,4]triazin-4-yl)-2-methylbenzyl) carbamate

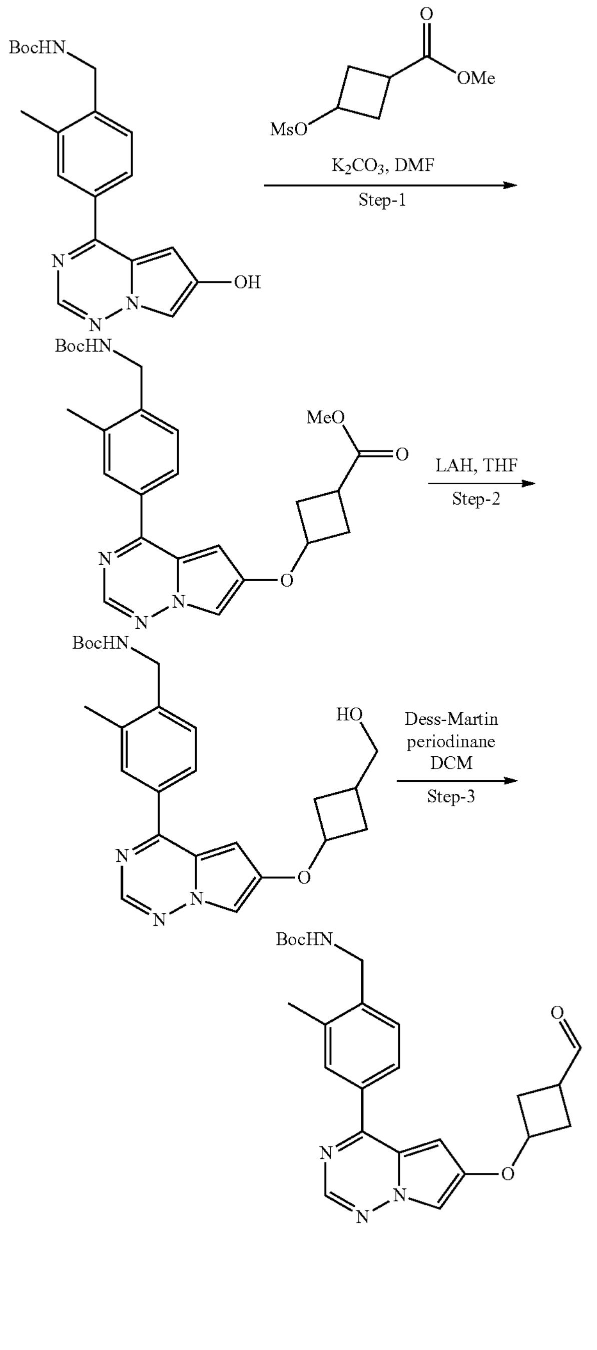

Step-1:

To a stirred solution of tert-butyl N-[[4-(6-hydroxypyrrolo[2,1-f][1,2,4]triazin-4-yl)-2-methyl-phenyl]methyl]carbamate (1.5 g, 4.23 mmol) in DMF (25 mL) was added methyl 3-((methylsulfonyl)oxy)cyclobutane-1-carboxylate (1.32 g, 6.35 mmol) at rt then potassium carbonate (1.75 g, 12.70 mmol) was added heated at 80° C. for 18 hr. The reaction progress was monitored by LC-MS and TLC. Upon completion, the reaction was diluted with water (50 mL) and extracted with DCM (2×50 mL). The combined organic layer was washed with brine solution (50 mL), then the organic layer was dried over anhydrous $Na_2SO_4$ and concentrated to obtain the crude product. The crude was purified by column chromatography by using silica gel 230-400 mesh (20-25% EA/PE) to afford methyl 3-[4-[4-[(tert-butoxycarbonylamino)methyl]-3-methyl-phenyl]pyrrolo[2,1-f][1,2,4]triazin-6-yl]oxycyclobutanecarboxylate (1 g, 1.71 mmol, 40.52% yield) as a yellow liquid. LC-MS(ES$^+$): m/z 467.38 [M+H]$^+$.

Step-2:

To a stirred solution of methyl 3-[4-[4-[(tert-butoxycarbonylamino)methyl]-3-methyl-phenyl]pyrrolo[2,1-f][1,2,4]triazin-6-yl]oxycyclobutanecarboxylate (1 g, 2.14 mmol) in THE (40 mL) was added LAH in THF (2.4 M, 1.79 mL) slowly at −78° C. and was stirred for about 1 hr. The reaction progress was monitored by TLC and LCMS. Upon completion, the reaction mixture was quenched with cold water (50 mL) and the aqueous layer was extracted with EtOAc (3×40 mL), dried over sodium sulfate, filtered and concentrated under reduced vacuum to afford product tert-butyl N-[[4-[6-[3-(hydroxymethyl)cyclobutoxy]pyrrolo[2,1-f][1,2,4]triazin-4-yl]-2-methyl-phenyl]methyl]carbamate (0.8 g, 1.53 mmol, 71.49% yield) as a yellow liquid. LC-MS(ES$^+$): m/z439.35 [M+H]$^+$.

Step-3:

To a stirred solution of tert-butyl N-[[4-[6-[3-(hydroxymethyl)cyclobutoxy]pyrrolo[2,1-f][1,2,4]triazin-4-yl]-2-methyl-phenyl]methyl]carbamate (1 g, 2.28 mmol) in DCM (50 mL) was added Dess-Martin periodinane (1.45 g, 3.42 mmol) at 0° C. and stirred the reaction mixture at 0° C. for 2 hr. The reaction progress was monitored by TLC. Upon completion, the reaction mixture was diluted with DCM (100 ml) and washed with sat. solution of $NaHCO_3$ (2×50 ml). The combined organic layers was dried over sodium sulfate and concentrated under a high vacuum to afford crude product tert-butyl N-[[4-[6-(3-formylcyclobutoxy)pyrrolo[2,1-f][1,2,4]triazin-4-yl]-2-methyl-phenyl]methyl]carbamate (900 mg, 742.26 μmol, 32.55% yield) as a yellow oil. The crude product was used for the next step without further purification. LC-MS(ES$^+$): m/z 437.69 [M+H]$^+$.

Synthesis of tert-butyl (8-(6-(4-bromobutyl)pyrrolo[2,1-f][1,2,4]triazin-4-yl)-2,3,4,5-tetrahydrobenzo[b]oxepin-5-yl)carbamate

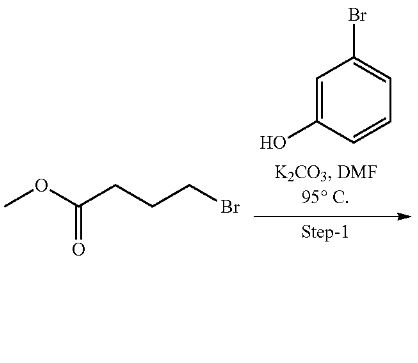

-continued

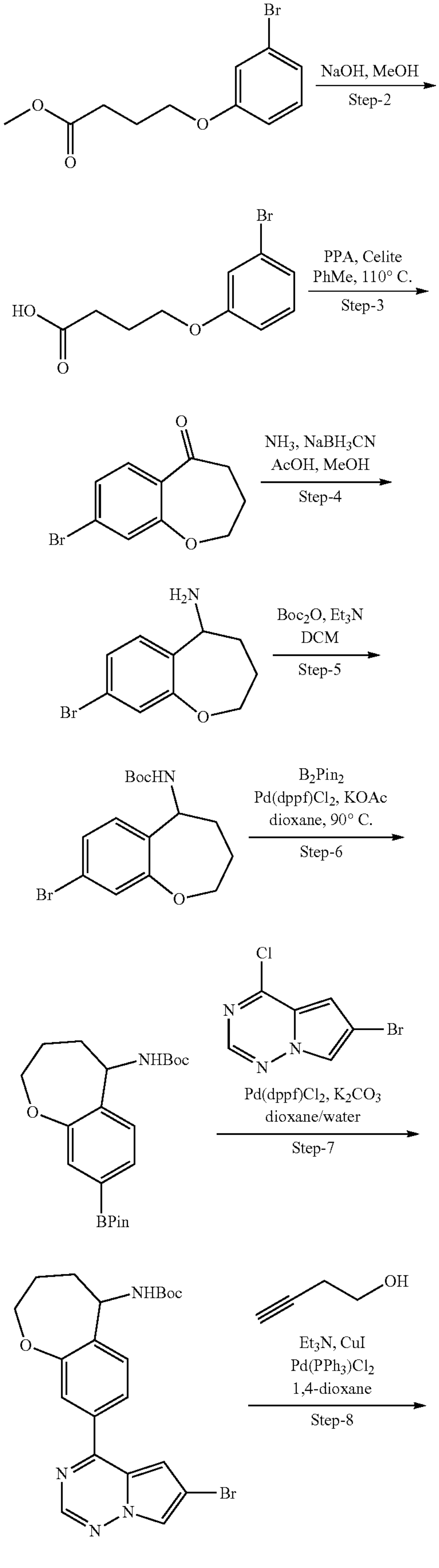

-continued

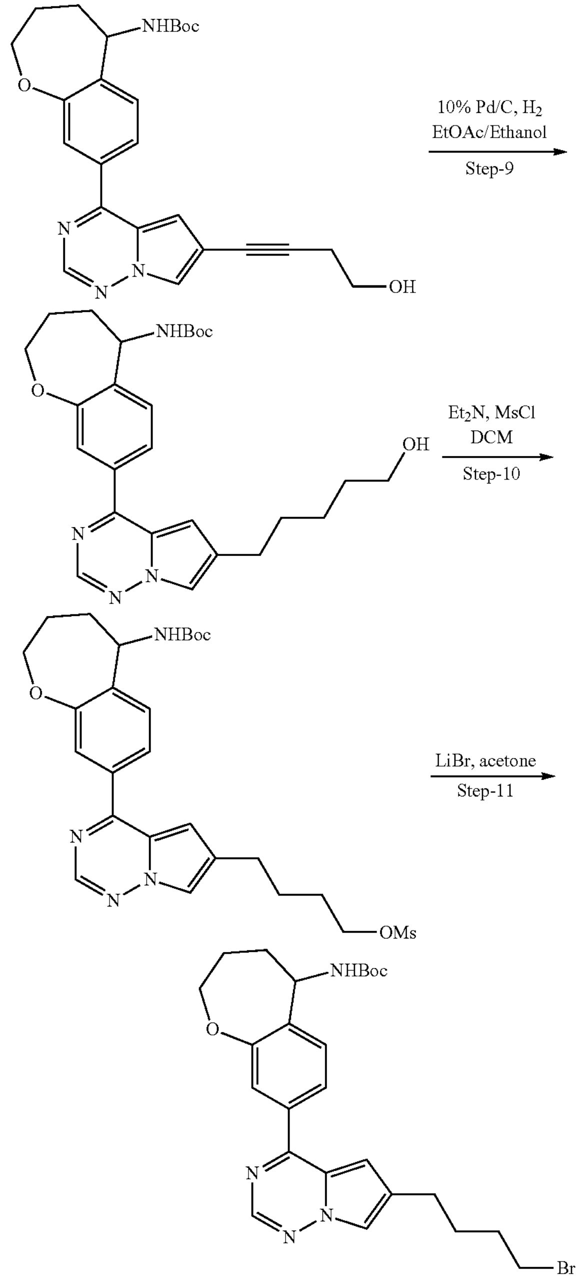

Step-1:

To a stirred solution of 3-bromophenol (20 g, 115.60 mmol) and methyl 4-bromobutanoate (25.20 g, 139.21 mmol) in DMF (100 mL) was added $K_2CO_3$ (31.95 g, 231.20 mmol) at room temperature and stirred for 30 min. Then the reaction mixture was stirred at 95° C. for 1.5 hr. The reaction progress was monitored by TLC. After completing the reaction, the reaction mixture was diluted with water (200 mL) and extracted with ethyl acetate (2×400 mL). The organic layer was washed with brine (200 mL), then dried over $Na_2SO_4$ and concentrated under reduced pressure to get the crude product to afford methyl 4-(3-bromophenoxy)butanoate (23.8 g, 80.16 mmol, 69.34% yield) as a brown colored liquid. LC-MS($ES^+$): m/z 272.10 $[M+H]^+$.

Step-2:

To a stirred solution of methyl 4-(3-bromophenoxy)butanoate (18 g, 65.90 mmol) in methanol (100 mL) was added 3 N NaOH aqueous solution (70 mL) at room temperature and stirred for 2 hrs. The reaction progress was monitored by TLC. After completing the reaction, MeOH was removed by concentration and diluted with water (100 mL). The reaction mass acidified to pH=2 with conc. HCl (20 mL) and extracted with ethyl acetate (2×500 mL). The organic layer was dried over $Na_2SO_4$ and concentrated under reduced pressure to get the 4-(3-bromophenoxy)butanoic acid (15 g, 54.53 mmol, 82.74% yield) as a brown colored semi-solid. LC-MS($ES^+$): m/z 257.25 $[M+H]^+$.

Step-3:

To a stirred solution of polyphosphoric acid (20 g) and celite (15 g) in toluene (50 mL) was added 4-(3-bromophenoxy)butanoic acid (5 g, 19.30 mmol) at room temperature. Then the reaction mixture was stirred for 3 hrs at 110° C. The reaction progress was monitored by TLC. After the completion, the reaction mixture was filtered through the celite bed, and the bed was washed with ethyl acetate (300 mL). The organic layer was washed with water (200 mL), then dried over $Na_2SO_4$ and concentrated completely. The crude was purified by column chromatography using 230-400 silica eluted with 0 to 10% Ethyl acetate in pet ether to afford the product 8-bromo-3,4-dihydro-2H-1-benzoxepin-5-one (2.5 g, 9.20 mmol, 47.66% yield) as a pale yellow liquid. LC-MS($ES^+$): m/z 241.08 $[M+H]^+$.

Step-4:

To a stirred solution of 8-bromo-3,4-dihydro-2H-1-benzoxepin-5-one (3.9 g, 16.18 mmol) in methanol (65 mL) was added acetic acid (1.13 g, 18.87 mmol, 1.08 mL), 7 M ammonia in MeOH (16.18 mmol, 67 mL) and sodium cyanoborohydride (2.21 g, 35.17 mmol). This reaction mixture was heated at 75° C. for 12 hrs in a steel bomb. Upon completion, the reaction mixture was concentrated in vacuo, and the product was extracted with DCM (2×50 mL), washed with water (1×25 mL), and brine solution (1×25 mL), and then dried over $Na_2SO_4$. The organic layer was concentrated under vacuum to give a residue, purified by column chromatography with 80-100% EtOA/PE as eluent to afford 8-bromo-2,3,4,5-tetrahydro-1-benzoxepin-5-amine (1.8 g, 6.69 mmol, 41.36% yield) as a brown gummy solid. $^1H$ NMR (400 MHz, DMSO-$d_6$) δ 7.45 (d, 1H, J=8.4 Hz), 7.27 (dd, J=8.4, 8.4 Hz, 1H), 7.14-7.096 (m, 2H), 4.67 (t, J=18, 1H), 4.23 (d, J=12 Hz, 1H), 3.61 (t, J=9.6 Hz, 1H), 1.94-1.84 (m, 3H), 1.62 (t, J=9.6 Hz, 2H).

Step-5:

To the stirred solution of 8-bromo-2,3,4,5-tetrahydro-1-benzoxepin-5-amine (2.7 g, 11.15 mmol) in dry DCM (33.19 mL) was added dropwise triethylamine (2.26 g, 22.30 mmol, 3.11 mL) at 0° C. under $N_2$ atm. The reaction mixture was stirred at the same temperature for 30 minutes and added dropwise $(Boc)_2O$ (2.68 g, 12.27 mmol, 2.82 mL) for 1 h. The reaction mixture was warmed to room temperature and stirred at the ambient temperature for 12 h. The reaction mixture was quenched with ice-cold water (50 ml), and the organic layer was partitioned. The organic layer was further washed with water (3×50 ml), brine (1×50 ml), dried over $Na_2SO_4$, filtered, and concentrated under vacuum to give the crude compound, which was purified by column chromatography using silica gel (100/200 mesh) and 40-50% ethyl acetate in hexane to afford tert-butyl N-(8-bromo-2,3,4,5-tetrahydro-1-benzoxepin-5-yl)carbamate (1.65 g, 4.34 mmol, 38.91% yield) as colorless solid. $^1H$ NMR (400 MHz, DMSO-$d_6$) δ 7.45 (d, 1H, J=8.4 Hz), 7.27 (dd, J=8.4, 8.4 Hz, 1H), 7.14-7.096 (m, 2H), 4.67 (t, J=18, 1H), 4.23 (d, J=12 Hz, 1H), 3.61 (t, J=9.6 Hz, 1H), 1.94-1.84 (m, 3H), 1.62 (t, J=9.6 Hz, 2H), 1.46-1.37 (m, 12H).

Step-6:

To a stirred solution of tert-butyl N-(8-bromo-2,3,4,5-tetrahydro-1-benzoxepin-5-yl)carbamate (2 g, 5.84 mmol) in 1,4-dioxane (30 mL) were added $B_2pin_2$ (1.56 g, 7.01 mmol) and potassium acetate (1.43 g, 14.61 mmol, 913.30 μL), the whole reaction mixture was degassed for 10 min before adding $PdCl_2(dppf)$ (42.76 mg, 58.44 μmol) and the reaction mixture stirred at 90-95° C. for 16 h. After completion of the reaction, the reaction mixture was filtered through celite and concentrated under high vacuum. The residue was diluted with water (200 mL) and extracted by ethyl acetate (3×200 mL). The combined organic layers were concentrated and purified by column chromatography to afford tert-butyl N-[8-(4,4,5,5-tetramethyl-1,3,2-dioxaborolan-2-yl)-2,3,4,5-tetrahydro-1-benzoxepin-5-yl]carbamate (1.7 g, 4.15 mmol, 70.99% yield). $^1H$ NMR (400 MHz, DMSO-$d_6$) δ 7.42 (d, 1H, J=8.4 Hz), 7.36 (d, J=7.6 Hz, 1H), 7.20 (t, J=6.4 Hz, 2H), 4.73 (t, J=9.2 Hz, 1H), 4.21 (t, J=11.6 Hz, 1H), 3.55 (t, J=10.0 Hz, 1H), 1.988-1.844 (m, 4H), 1.60 (d, J=10.0 Hz, 1H), 1.41 (d, J=16.0 Hz, 9H), 1.27 (s, 14H), 1.16 (s, 3H).

Step-7:

To the stirred solution of 6-bromo-4-chloro-pyrrolo[2,1-f][1,2,4]triazine (1.48 g, 6.37 mmol) and tert-butyl N-[8-(4,4,5,5-tetramethyl-1,3,2-dioxaborolan-2-yl)-2,3,4,5-tetrahydro-1-benzoxepin-5-yl]carbamate (1.98 g, 5.09 mmol) in water (15 mL) and 1,4-dioxane (60 mL) was added $K_2CO_3$ (2.20 g, 15.92 mmol) at room temperature under argon. The reaction mixture was degassed with argon for 10 min and added $PdCl_2(dppf)$ (0.117 g, 159.16 μmol) in one portion. The reaction mixture was again degassed with argon for another 15 minutes and then heated the reaction to 60° C. for 12 h. The reaction mixture was filtered off through a celite bed and washed with ethyl acetate (100 ml). The filtrate was concentrated to get the crude compound, which is purified by column chromatography over silica gel (100/200 mesh). The product was eluted at 20-30% ethyl acetate in hexane to afford tert-butyl N-[8-(6-bromopyrrolo[2,1-f][1,2,4]triazin-4-yl)-2,3,4,5-tetrahydro-1-benzoxepin-5-yl]carbamate (2 g, 2.98 mmol, 46.76% yield) as yellow solid. LC-MS($ES^+$): m/z 459.54 $[M+H]^+$.

Step-8:

To a solution of tert-butyl (8-(6-bromopyrrolo[2,1-f][1,2,4]triazin-4-yl)-2,3,4,5-tetrahydrobenzo[b]oxepin-5-yl)carbamate (500 mg, 1.09 mmol) in 1,4-dioxane (15.21 mL) was added triethylamine (330.44 mg, 3.27 mmol, 455.16 μL), but-3-yn-1-ol (76.29 mg, 1.09 mmol, 82.30 μL) and CuI (20.73 mg, 108.85 μmol) at room temperature under purging. The reaction mixture was purged with argon gas for 10 minutes, followed by the addition of $Pd(dppf)Cl_2$ (38.20 mg, 54.43 μmol). The reaction mixture was purged with argon for additional 5 min, and it was stirred at 90° C. for 4 h. Upon completion of reaction, the reaction mixture was filtered through celite and concentrated in vacuo to get the crude product, which was purified by flash chromatography using 230-400 mesh silica and 60-70% ethyl acetate in petroleum ether as eluent to afford tert-butyl (8-(6-(4-hydroxybut-1-yn-1-yl)pyrrolo[2,1-f][1,2,4]triazin-4-yl)-2,3,4,5-tetrahydrobenzo[b]oxepin-5-yl)carbamate (350 mg, 758.82 μmol, 69.71% yield) (2.5 g, 4.25 mmol, 45.39% yield) as a yellow gummy. LC-MS($ES^+$): m/z 449.66 $[M+H]^+$.

Step-9:

To a stirred solution of tert-butyl (8-(6-(4-hydroxybut-1-yn-1-yl)pyrrolo[2,1-f][1,2,4]triazin-4-yl)-2,3,4,5-tetrahydrobenzo[b]oxepin-5-yl)carbamate (800 mg, 1.78 mmol) in ethyl acetate (15 mL) and ethanol (5 mL) was added 10% Pd/C on 50% wet basis (800 mg, 1.78 mmol). The resultant reaction mixture was stirred at room temperature under $H_2$ for 4 h. Upon completion of reaction, the reaction mixture was filtered through celite. The filtrate was concentrated to get a crude mass tert-butyl (8-(6-(4-hydroxybutyl)pyrrolo[2,1-f][1,2,4]triazin-4-yl)-2,3,4,5-tetrahydrobenzo[b]oxepin-5-yl)carbamate (400 mg, 617.31 μmol, 34.61% yield). LC-MS ($ES^+$): m/z 453.61 $[M+H]^+$.

Step-10:

To a stirred solution of tert-butyl (8-(6-(4-hydroxybutyl)pyrrolo[2,1-f][1,2,4]triazin-4-yl)-2,3,4,5-tetrahydrobenzo[b]oxepin-5-yl)carbamate (300 mg, 662.92 μmol) in DCM (15 mL) was added TEA (67.08 mg, 662.92 μmol, 92.40 μL) followed by the addition of MsCl (75.94 mg, 662.92 μmol, 51.41 μL) at 0° C. The resultant reaction mixture was stirred at room temperature under inert atmosphere. Upon completion, the reaction was quenched in water (100 mL) and extracted with DCM (2×30 mL) then washed with brine (1×30 mL). The combined organic layer was dried over $Na_2SO_4$ and concentrated under vacuum to afford 4-(4-(5-((tert-butoxycarbonyl)amino)-2,3,4,5-tetrahydrobenzo[b]oxepin-8-yl)pyrrolo[2,1-f][1,2,4]triazin-6-yl)butyl methanesulfonate (300 mg, 529.12 μmol, 79.82% yield). LC-MS ($ES^+$): m/z 531.65 $[M+H]^+$.

Step-11:

To a stirred solution of 4-(4-(5-((tert-butoxycarbonyl)amino)-2,3,4,5-tetrahydrobenzo[b]oxepin-8-yl)pyrrolo[2,1-f][1,2,4]triazin-6-yl)butyl methanesulfonate (300 mg, 565.36 μmol) in acetone (10 mL) was added LiBr (49.10 mg, 565.36 μmol, 14.19 μL). The resultant reaction mixture was stirred at 80° C. under inert atmosphere. The completion reaction was confirmed by LCMS. Upon completion, the reaction mass was concentrated to get a crude product which was quenched in water (15 mL) and extracted with DCM (2×10 mL), washed with brine (1×15 mL). The combined organic layer was dried over $Na_2SO_4$ and concentrated under vacuum to afford tert-butyl (8-(6-(4-bromobutyl)pyrrolo[2,1-f][1,2,4]triazin-4-yl)-2,3,4,5-tetrahydrobenzo[b]oxepin-5-yl)carbamate (200 mg, 299.74 μmol, 53.02% yield). LC-MS ($ES^+$): m/z 515.56 $[M+H]^+$.

III. Synthesis of DSM Precursors

Intermediate 3-((4-(piperidin-4-yl)phenyl)amino)piperidine-2,6-dione was Prepared According to the Method Described on Page 267 of WO2018237026A1

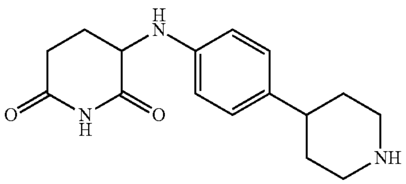 [SMILES: O=C1CCC(Nc2ccc(C3CCNCC3)cc2)C(=O)N1]

Intermediate 3-((4-(piperazin-1-yl)phenyl)amino)piperidine-2,6-dione was Prepared According to the Method Described on Page 268 of WO2018237026A1

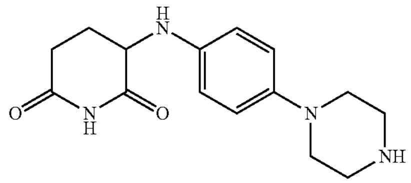 [SMILES: O=C1CCC(Nc2ccc(N3CCNCC3)cc2)C(=O)N1]

Intermediate 1-(4-(piperidin-4-yl)benzyl)dihydropyrimidine-2,4(1H,3H)-dione was Prepared According to the Method Described on Page 353 WO2020132561A1

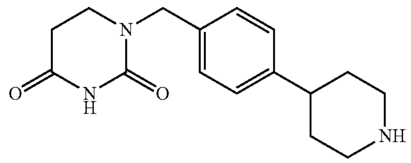 [SMILES: O=C1CCN(Cc2ccc(C3CCNCC3)cc2)C(=O)N1]

Intermediate 3-(2-oxo-6-(piperidin-4-yl)benzo[cd]indol-1(2H)-yl)piperidine-2,6-dione was Prepared According to the Method Described on Page 203 WO2021127586 A1

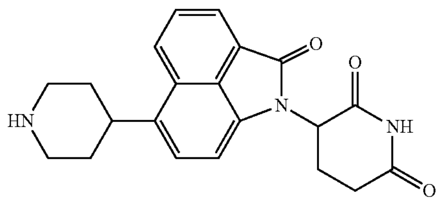 [SMILES: O=C1CCC(N2C(=O)c3cccc4c(C5CCNCC5)ccc2c34)C(=O)N1]

Intermediate 3-(1-methyl-6-(piperidin-4-yl)-1H-indazol-3-yl)piperidine-2,6-dione was Prepared According to the Method Described on Page 197 WO2021127586 A1

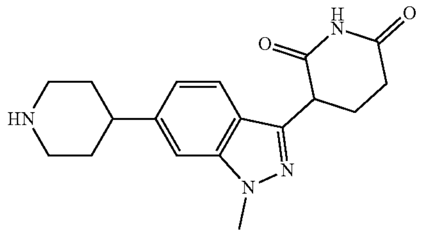 [SMILES: Cn1nc(C2CCC(=O)NC2=O)c2ccc(C3CCNCC3)cc21]

Synthesis of 3-[4-(2,2-dimethyl-4-piperidyl) anilino]piperidine-2,6-dione

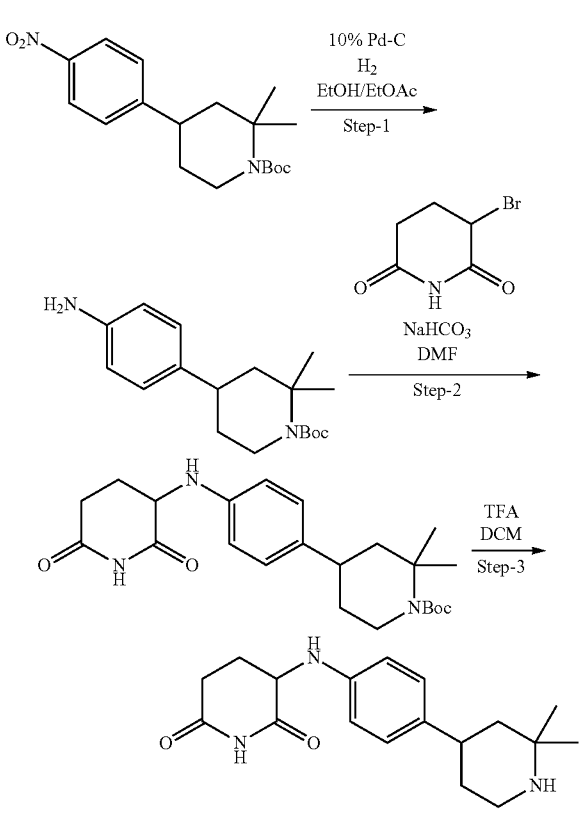

Step-1:

A solution of tert-butyl 6,6-dimethyl-4-(4-nitrophenyl)-2,5-dihydropyridine-1-carboxylate (2.3 g, 6.92 mmol) and 10 wt. % palladium on carbon (736.43 mg, 6.92 mmol) in ethanol (15 mL) and ethyl acetate (15 mL) was stirred under hydrogen pressure at room temperature for 16 hours. The reaction was filtered through a celite bed and washed with ethyl acetate. The filtrate was concentrated under reduced pressure, and the residue was purified by column chromatography (silica gel 230-400 mesh, 0-100% ethyl acetate in pet-ether) to afford tert-butyl 4-(4-aminophenyl)-2,2-dimethyl-piperidine-1-carboxylate (1.5 g, 4.68 mmol, 67.64% yield) as a white solid. LC-MS ($ES^+$): m/z 305.43 $[M+H]^+$.

Step-2:

A solution of tert-butyl 4-(4-aminophenyl)-2,2-dimethyl-piperidine-1-carboxylate (0.2 g, 656.97 μmol), 3-bromopiperidine-2,6-dione (378.44 mg, 1.97 mmol) and sodium bicarbonate (551.90 mg, 6.57 mmol) in DMF (3 mL) was purged with argon for 15 minutes. The resulting mixture was stirred at 70° C. for 16 hours. The reaction mixture was quenched with water and washed with ethyl acetate (50 mL×2). The filtrate was washed with water (50 mL) and brine solution (50 mL). The combined organic layers were dried over anhydrous sodium sulfate, filtered, and concentrated under reduced pressure. The crude was purified by column chromatography (silica gel 230-400 mesh, 0-100% ethyl acetate c in pet ether) to afford tert-butyl 4-[4-[(2,6-dioxo-3-piperidyl)amino]phenyl]-2,2-dimethyl-piperidine-1-carboxylate (0.18 g, 412.74 μmol, 62.82% yield). LC-MS ($ES^+$): m/z 416.36 $[M+H]^+$.

Step-3:

To stirred solution of tert-butyl 4-[4-[(2,6-dioxo-3-piperidyl)amino]phenyl]-2,2-dimethyl-piperidine-1-carboxylate (1 g, 2.41 mmol) in DCM (15 mL) at 0° C., trifluoroacetic acid, 99% (7.40 g, 64.90 mmol, 5 mL) was added dropwise. The reaction was stirred at 27° C. for 3 hours. The reaction mixture was concentrated under reduced pressure to give the crude product, which was triturated with diethyl ether to afford the final product 3-[4-(2,2-dimethyl-4-piperidyl)anilino]piperidine-2,6-dione TFA salt (1 g, 2.22 mmol, 92.21% yield) as a grey solid. LC-MS ($ES^+$): m/z 316.39 $[M+H]^+$.

Intermediate 3-[4-(8-azabicyclo[3.2.1]octan-3-yl) anilino]piperidine-2,6-dione was Prepared Following the Synthesis of 3-[4-(2,2-dimethyl-4-piperidyl) anilino]piperidine-2,6-dione

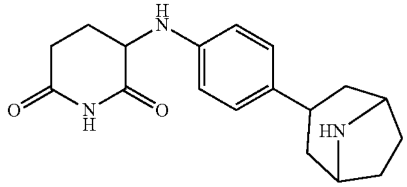 [SMILES: O=C1CCC(Nc2ccc(C3CC4CCC(C3)N4)cc2)C(=O)N1]

LC-MS ($ES^+$): m/z 314.36 $[M+H]^+$.

Intermediate 3-((4-(piperidin-3-yl)phenyl)amino) piperidine-2,6-dione was Prepared Following the Synthesis of 3-[4-(2,2-dimethyl-4-piperidyl)anilino] piperidine-2,6-dione

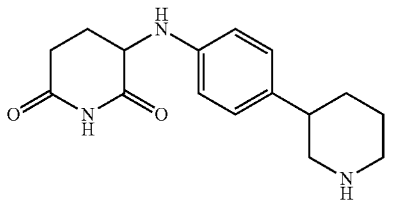 [SMILES: O=C1CCC(Nc2ccc(C3CCCNC3)cc2)C(=O)N1]

LC-MS ($ES^+$): m/z 288.36 $[M+H]^+$.

Intermediate 3-((4-(piperidin-4-yl)-3-(trifluoromethyl)phenyl)amino)piperidine-2,6-dione was Prepared Following the Synthesis of 3-[4-(2,2-dimethyl-4-piperidyl)anilino]piperidine-2,6-dione

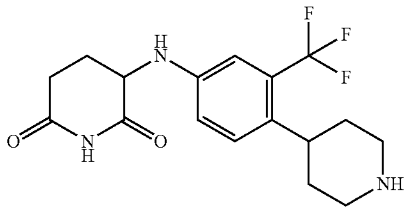

LC-MS ($ES^+$): m/z 245.10 $[M+H]^+$.

Synthesis of 3-[4-(3,3-difluoro-4-piperidyl)anilino] piperidine-2,6-dione

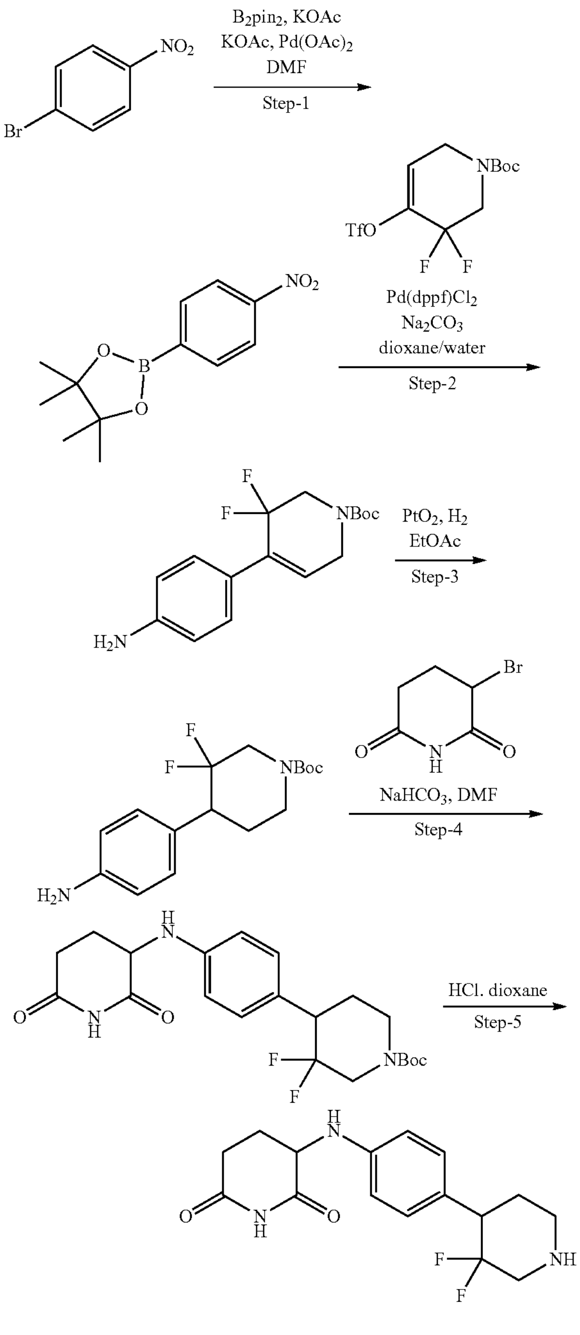

Step-1:

To a stirred a solution of 1-bromo-4-nitro-benzene (5 g, 24.75 mmol, 2.56 mL) in DMF (40 mL) was added 4,4,5,5-tetramethyl-2-(4,4,5,5-tetramethyl-1,3,2-dioxaborolan-2-yl)-1,3,2-dioxaborolane (6.91 g, 27.23 mmol) and potassium acetate (6.07 g, 61.88 mmol). The resulting mixture was purged with argon gas for 30 minutes before palladium acetate (166.71 mg, 742.55 μmol) was added, and the reaction was refluxed at 60° C. for 6 hours. After completion of the reaction as indicated by TLC, the mixture was poured into cold water (100 mL), and the resulting solid was filtered and dried under a high vacuum to afford 4,4,5,5-tetramethyl-2-(4-nitrophenyl)-1,3,2-dioxaborolane (3.5 g, 9.84 mmol, 40% yield) as a brown-black solid. $^1H$ NMR (400 MHz, $CDCl_3$) δ 8.19 (d, J=8.8 Hz, 2H), 7.96 (d, J=8.8 Hz, 2H), 1.37 (s, 12H).

Step-2:

In a sealed tube, a solution of tert-butyl 3,3-difluoro-4-(trifluoromethylsulfonyloxy)-2,6-dihydropyridine-1-carboxylate (8.0 g, 21.78 mmol) and 4,4,5,5-tetramethyl-2-(4-nitrophenyl)-1,3,2-dioxaborolane (7.05 g, 28.32 mmol) in 1,4-dioxane (80 mL) were added sodium carbonate (4.62 g, 43.56 mmol) and $Pd(dppf)Cl_2$ (1.59 g, 2.18 mmol) under argon atmosphere. The resulting mixture was stirred at 55° C. for 3 hours, and the progress of the reaction was monitored by TLC and LC-MS. After the completion of the reaction, it was washed with water and extracted with ethyl acetate (3×250 mL). The combined organic layer was dried over anhydrous sodium sulfate and concentrated under reduced pressure. The crude product was purified by column chromatography (silica gel 230-400 mesh, EtOAc in pet ether) to afford tert-butyl 3,3-difluoro-4-(4-nitrophenyl)-2,6-dihydropyridine-1-carboxylate (4.4 g, 11.64 mmol, 53% yield) as a gummy solid. $^1H$ NMR (400 MHz, $CDCl_3$) δ 8.27 (d, J=8.8 Hz, 2H), 7.74 (d, J=8.8 Hz, 2H), 6.83 (bs, 1H), 4.22 (bs, 2H), 3.97 (t, J=6.8 Hz, 2H), 1.44 (s, 9H).

Step-3:

To a stirred solution of tert-butyl 3,3-difluoro-4-(4-nitrophenyl)-2,6-dihydropyridine-1-carboxylate (9.0 g, 26.45 mmol) in ethyl acetate (100 mL) were added platinum (IV) oxide (6.01 g, 26.45 mmol). The reaction flask was evacuated and back filled with hydrogen gas using a hydrogen bladder, and the reaction was stirred under a hydrogen atmosphere at room temperature for 16 hours. After completion of the reaction, as shown by TLC, the reaction mixture was filtered through a celite bed. The filtrate was concentrated and purified by column chromatography (silica gel, ethyl acetate/pet ether) to afford tert-butyl 4-(4-aminophenyl)-3,3-difluoro-piperidine-1-carboxylate (5.4 g, 14.63 mmol, 55% yield) as a white solid. LC-MS ($ES^+$): m/z 257.2 $[M-tBu+H]^+$.

Step-4:

To a stirred solution of tert-butyl 4-(4-aminophenyl)-3,3-difluoro-piperidine-1-carboxylate (5.0 g, 16.01 mmol) and 3-bromopiperidine-2,6-dione (9.22 g, 48.02 mmol) in DMF (50 mL) was added sodium bicarbonate (8.07 g, 96.04 mmol) at room temperature. The reaction mixture was stirred at 80° C. for 16 hours. Progress of the reaction was monitored by TLC and LC-MS. After completion, the reaction was quenched with water (100 mL) and extracted with EtOAc (3×100 mL). The combined organic layer was dried over anhydrous $Na_2SO_4$ and concentrated in vacuo. The crude compound was purified by column chromatography (silica gel 100-200 mesh, 15% EtOAc in pet ether) to afford tert-butyl 4-[4-[(2,6-dioxo-3-piperidyl)amino]phenyl]-3,3-difluoro-piperidine-1-carboxylate (5.17 g, 11.77 mmol, 74% yield). LC-MS ($ES^+$): m/z 422.24 $[M-H]^-$.

Step-5:

To a stirred solution of tert-butyl 4-[4-[(2,6-dioxo-3-piperidyl)amino]phenyl]-3,3-difluoro-piperidine-1-carboxylate (0.5 g, 1.18 mmol) in dioxane (2 mL) was added HCl (4 M, 5 mL) under nitrogen atmosphere. The reaction was stirred at 0-28° C. for 2 hours and monitored by TLC and LC-MS. After completion of the reaction, the reaction mixture was concentrated to dryness and washed with diethyl ether (10 mL×2) to afford 3-[4-(3,3-difluoro-4-piperidyl)anilino]piperidine-2,6-dione hydrochloride (0.4 g, 1.06 mmol, 89% yield) as a solid. LC-MS ($ES^+$): m/z 324.09 $[M+H]^+$.

Synthesis of (3S)-3-[3-fluoro-4-(4-piperidyl)anilino]piperidine-2,6-dione and (3R)-3-[3-fluoro-4-(4-piperidyl)anilino]piperidine-2,6-dione

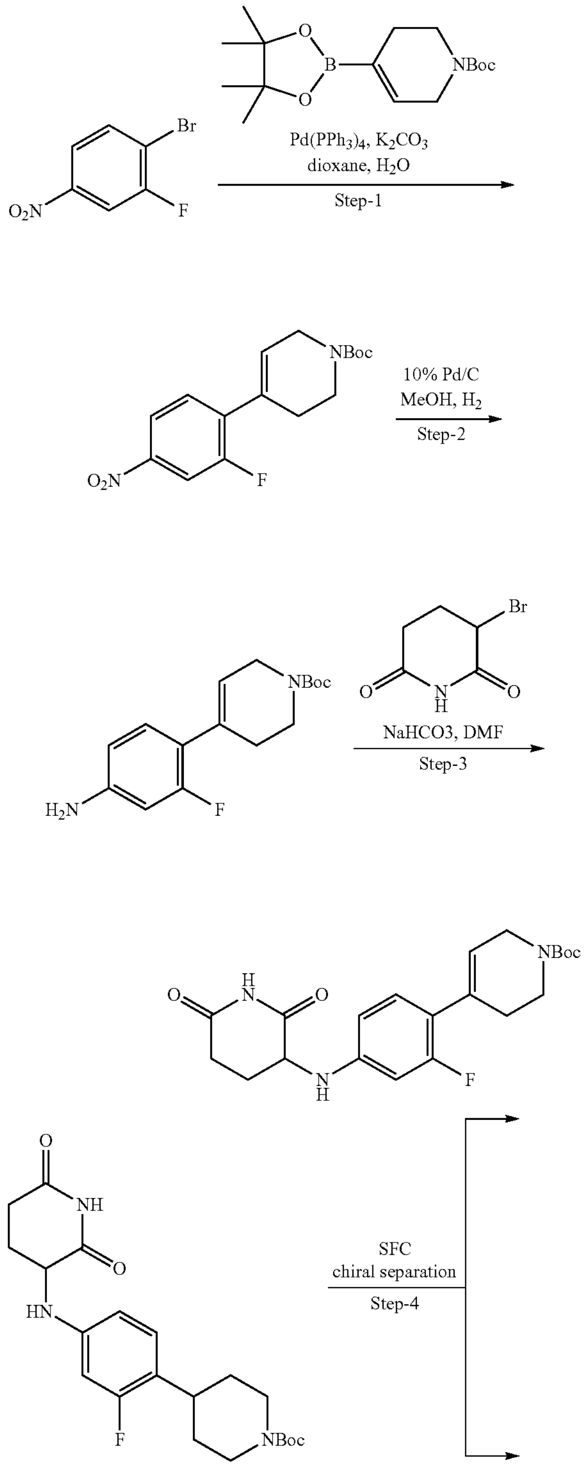

-continued

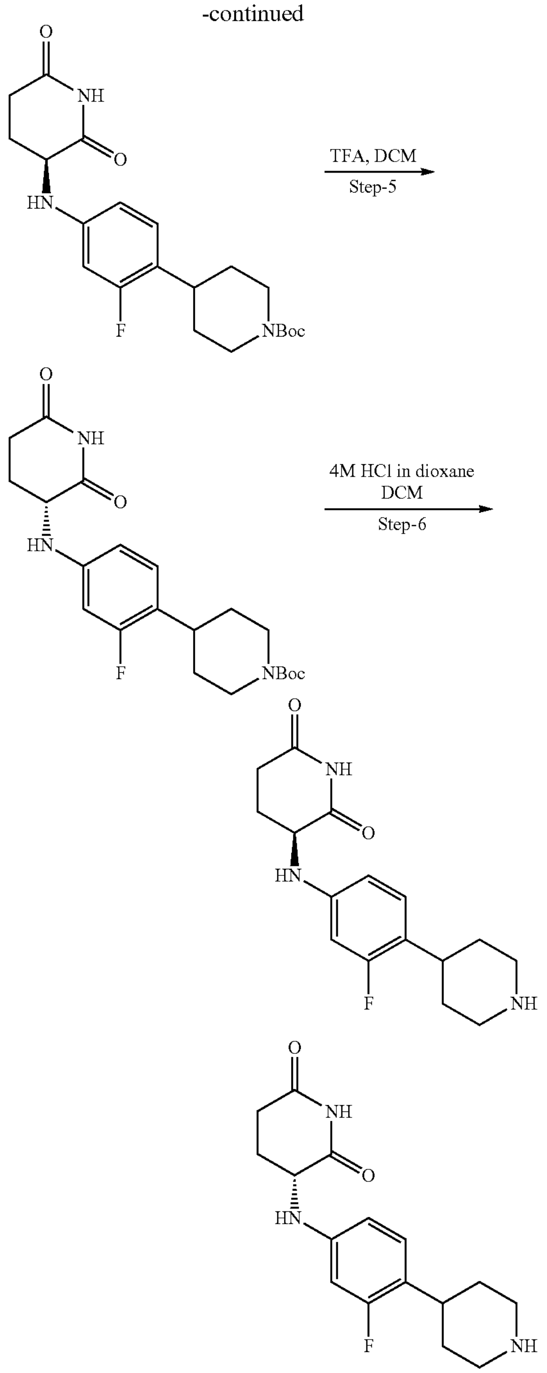

Step-1:

A solution of 1-bromo-2-fluoro-4-nitro-benzene (6 g, 27.27 mmol) and tert-butyl 4-(4,4,5,5-tetramethyl-1,3,2-dioxaborolan-2-yl)-3,6-dihydro-2H-pyridine-1-carboxylate (8.43 g, 27.27 mmol) in dioxane (60 mL) and water (15 mL) in a round bottom flask was purged with argon gas for 10 minutes, followed by the addition of potassium carbonate, granular (11.31 g, 81.82 mmol). The solution was purged with argon gas for another 20 minutes before $Pd(PPh_3)_4$ (1.58 g, 1.36 mmol) was added, and the reaction was stirred at 90° C. for 16 hours. The progress of the reaction was monitored by TLC and LC-MS. After completion of the reaction, the reaction mixture was filtered through a celite bed and washed with ethyl acetate. The filtrate was concentrated under reduced pressure, and the crude product was diluted with water and extracted with ethyl acetate (2×150 ml). The combined organic layer was concentrated in vacuo and purified by normal phase column chromatography (Devisil silica, 5% ethyl acetate in pet ether) to obtain tert-butyl 4-(2-fluoro-4-nitro-phenyl)-3,6-dihydro-2H-pyridine-1-carboxylate (5.95 g, 18.27 mmol, 67.01% yield) as a light yellow solid. LC-MS ($ES^+$): m/z 267.15 $[M-tBu+H]^+$.

Step-2:

To a stirred solution of tert-butyl 4-(2-fluoro-4-nitro-phenyl)-3,6-dihydro-2H-pyridine-1-carboxylate (3 g, 9.31 mmol) in methanol (70 mL) was added palladium, 10% on carbon, type 487, dry (3 g, 28.19 mmol) at room temperature. The reaction mixture was stirred for 6 hours at this temperature under a hydrogen atmosphere, and the reaction progress was monitored by LC-MS. After completion of the reaction, the reaction mixture was filtered through celite. The filtrate was concentrated under reduced pressure to afford compound tert-butyl 4-(4-amino-2-fluoro-phenyl)piperidine-1-carboxylate (2.5 g, 5.95 mmol, 63.88% yield) as purple solid, which was taken to the next step without purification. LC-MS ($ES^+$): m/z 239.30 $[M-tBu+H]^+$.

Step-3:

In a sealed tube, a solution of tert-butyl 4-(4-amino-2-fluoro-phenyl)piperidine-1-carboxylate (2.5 g, 8.49 mmol) and 3-bromopiperidine-2,6-dione (4.08 g, 21.23 mmol) in DMF (40 mL) was stirred for 10 minutes before sodium bicarbonate (3.57 g, 42.46 mmol) was added and the reaction was heated at 60° C. for 16 hours. The progress of the reaction was monitored by LC-MS and TLC. After completion of the reaction, the reaction mixture was filtered and concentrated in vacuo. The crude product was purified by column chromatography (Devisil silica, 0-30% ethyl acetate in pet ether) to furnish tert-butyl 4-[4-[(2,6-dioxo-3-piperidyl)amino]-2-fluoro-phenyl]piperidine-1-carboxylate (1.8 g, 3.64 mmol, 42.86% yield) as a brown solid. LC-MS ($ES^+$): m/z 404.3 $[M-H]^-$.

Step-4:

The racemic compound tert-butyl 4-[4-[(2,6-dioxo-3-piperidyl)amino]-2-fluoro-phenyl]piperidine-1-carboxylate (800 mg, 1.97 mmol) was separated by chiral SFC column to afford Peak-1 (380 mg, 927.83 μmol, 47.02% yield) as an off-white solid and Peak-2 (360 mg, 879.00 μmol, 44.55% yield) as an off-white solid.

SFC conditions

YMC Cellulose-SC [250×30 mm, 5 micron]

Mobile phase: 40% IPA-CO2 flow rate: 120 mL/min cycle time: 7.6 min back pressure: 100 bar

UV: 210 nm

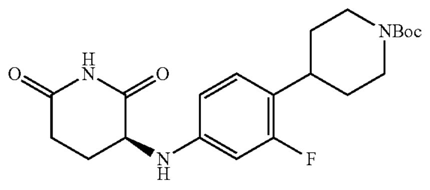 [SMILES: CC(C)(C)OC(=O)N1CCC(c2ccc(N[C@H]3CCC(=O)NC3=O)cc2F)CC1]

Peak-1: tert-butyl 4-[4-[[(3S)-2,6-dioxo-3-piperidyl]amino]-2-fluoro-phenyl]piperidine-1-carboxylate. >99.99% ee. LC-MS ($ES^-$): m/z 404.2 $[M-H]^-$.

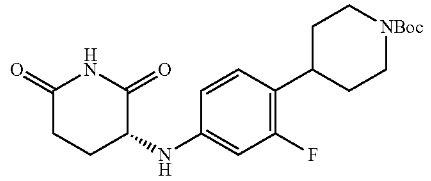 [SMILES: CC(C)(C)OC(=O)N1CCC(c2ccc(N[C@@H]3CCC(=O)NC3=O)cc2F)CC1]

Peak-2: tert-butyl 4-[4-[[(3R)-2,6-dioxo-3-piperidyl]amino]-2-fluoro-phenyl]piperidine-1-carboxylate. >99.99% ee. LC-MS ($ES^+$): m/z 406.1 $[M+H]^+$.

Step-5:

To a stirred solution of tert-butyl 4-[4-[[(3S)-2,6-dioxo-3-piperidyl]amino]-2-fluoro-phenyl]piperidine-1-carboxylate (0.1 g, 246.63 μmol) in DCM (15 mL) was added trifluoroacetic acid (740.00 mg, 6.49 mmol, 0.5 mL) dropwise at 0° C. The reaction was stirred at 27° C. for 3 hours. Upon completion of the reaction, the reaction mixture was concentrated under reduced pressure to give the crude product, which was triturated with diethyl ether to afford (3S)-3-[3-fluoro-4-(4-piperidyl)anilino]piperidine-2,6-dione TFA salt (0.100 g, 223.91 μmol, 90.79% yield) as a light blue solid. LC-MS ($ES^+$): m/z 306.35 $[M+H]^+$.

Step-6:

In a 50 mL single neck round bottom flask, a solution of tert-butyl 4-[4-[[(3R)-2,6-dioxo-3-piperidyl]amino]-2-fluoro-phenyl]piperidine-1-carboxylate (1.8 g, 4.44 mmol) in dry DCM (8 mL) was added 4 M hydrogen chloride solution in 1,4-dioxane (10 mL) at 0° C. The reaction mixture was stirred at room temperature for 2 hours while monitored by UPLC. After consumption of the starting material, the reaction mixture was concentrated under reduced pressure and triturated with diethyl ether (20 ml), and dried over reduced pressure to afford (3R)-3-[3-fluoro-4-(4-piperidyl)anilino]piperidine-2,6-dione HCl salt (1.5 g, 4.32 mmol, 97.26% yield) as an off-white solid. LC-MS ($ES^+$): m/z 306.2 $[M+H]^+$.

Synthesis of 3-[4-[3-(methylamino)propyl]anilino]piperidine-2,6-dione

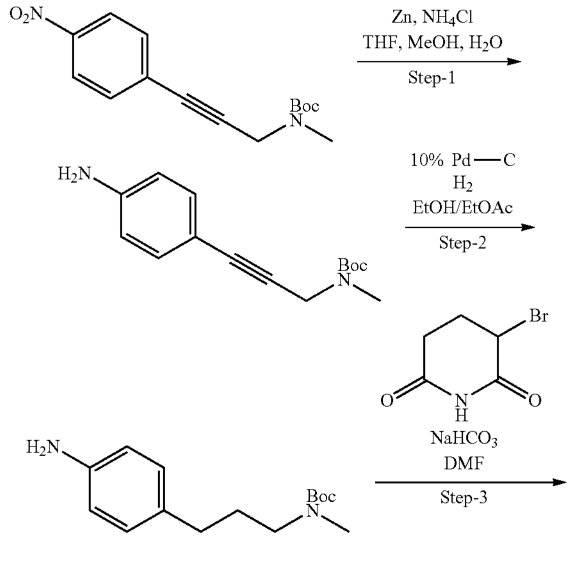

-continued

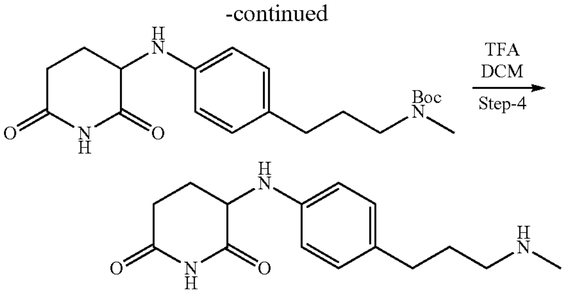

Step-1:

To a stirred solution of tert-butyl N-methyl-N-[3-(4-nitrophenyl)prop-2-ynyl]carbamate (9.2 g, 31.69 mmol) in THF (40 mL), methanol (40 mL) and water (20 mL) at 0° C. were added zinc (41.44 g, 633.80 mmol) and ammonia hydrochloride (33.90 g, 633.80 mmol) and the mixture was stirred at room temperature for 2 hours. Progress of the reaction was monitored by TLC and LC-MS. The reaction was filtered through a bed of celite and washed with MeOH. The filtrate was concentrated under reduced pressure to a residue. A saturated $NaHCO_3$ solution was added to the residue, and the mixture was extracted with ethyl acetate (40 mL×3). The combined organic layers were washed with brine solution, dried over anhydrous sodium sulfate, filtered, and concentrated under reduced pressure. The crude was purified by column chromatography (silica gel 100-200 mesh, 15% ethyl acetate in pet-ether) to afford tert-butyl N-[3-(4-aminophenyl)prop-2-ynyl]-N-methyl-carbamate (8.50 g, 29.39 mmol, 92.73% yield). LC-MS ($ES^+$): m/z 261.40 $[M+H]^+$.

Step-2:

To a stirred solution of tert-butyl N-[3-(4-aminophenyl)prop-2-ynyl]-N-methyl-carbamate (8 g, 30.73 mmol) in ethyl acetate (100 mL) and ethanol (100 mL) at room temperature, 10 wt. % palladium on carbon (10 g, 93.97 mmol) was added, and the reaction was stirred at this temperature under a hydrogen atmosphere. Upon completion, the reaction was filtered through a celite bed, filtered, and concentrated under reduced pressure. The crude product was purified by column chromatography (silica gel 100-200 mesh, 0-10% ethyl acetate in pet-ether) to afford tert-butyl N-[3-(4-aminophenyl)propyl]-N-methyl-carbamate (5.9 g, 20.68 mmol, 67.29% yield). LC-MS ($ES^+$): m/z 265.32 $[M+H]^+$.

Step-3:

An oven-dried sealed tube (50 mL) was charged with tert-butyl N-[3-(4-aminophenyl)propyl]-N-methyl-carbamate (600 mg, 2.27 mmol) and 3-bromopiperidine-2,6-dione (522.95 mg, 2.72 mmol) in DMF (5 mL). Sodium bicarbonate (571.99 mg, 6.81 mmol) was added at room temperature, and the mixture was stirred at 85° C. for 16 hours. The reaction mixture was cooled to room temperature, poured into ice (200 g), extracted with ethyl acetate (2×150 mL); the combined organics were then washed with brine (100 mL), dried over anhydrous sodium sulfate, filtered, and concentrated under reduced pressure. The crude compound was purified by column chromatography (100 g snap, 230×400 mesh silica, 80-90% ethyl acetate in petroleum ether) to afford tert-butyl N-[3-[4-[(2,6-dioxo-3-piperidyl)amino]phenyl]propyl]-N-methyl-carbamate (500 mg, 972.14 μmol, 42.83% yield) as a pale yellow liquid. LC-MS ($ES^+$): m/z 374.2$[M-H]^-$.

Step-4:

To a stirred solution of tert-butyl N-[3-[4-[(2,6-dioxo-3-piperidyl)amino]phenyl]propyl]-N-methyl-carbamate (0.5 g, 1.33 mmol) in DCM (10 mL) at 0° C. under argon atmosphere was added 2,2,2-trifluoroacetic acid (5.92 g, 51.92 mmol, 4 mL) and the reaction was stirred at room temperature for 2 hours. The reaction mixture was concentrated under reduced pressure to give the crude compound. The crude product was washed with ether to afford 3-[4-[3-(methylamino)propyl]anilino]piperidine-2,6-dione TFA salt (0.4 g, 886.36 μmol, 66.56% yield). LC-MS ($ES^+$): m/z 276.41 $[M+H]^+$.

Synthesis of 3-[4-(3-piperazin-1-ylpropyl)anilino]piperidine-2,6-dione

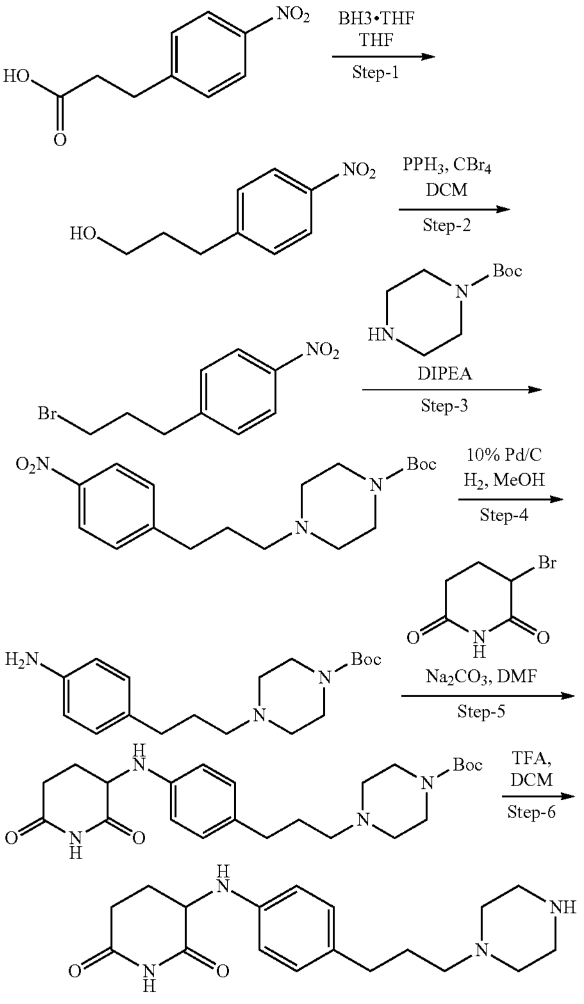

Step-1:

To a stirred solution of 3-(4-nitrophenyl)propanoic acid (10 g, 51.24 mmol) in THF (100 mL) was added borane in tetrahydrofuran solution (1 M, 10 mL) under nitrogen at 0° C. and stirred reaction for 3 hours at room temperature. The progress of the reaction was monitored by TLC and LCMS. Upon completion, the reaction mixture was diluted with ice-cold water and extracted with ethyl acetate. The combined organic layer was washed with brine, dried over sodium sulfate, and concentrated to give 3-(4-nitrophenyl)propan-1-ol (9 g, 47.19 mmol, 92.10% yield) as a crude product, which was used for the next step without any purification. LC-MS ($ES^+$): m/z 182.1 $[M+H]^+$.

Step-2:

Argon gas was purged through a solution of 3-(4-nitrophenyl)propan-1-ol (3 g, 16.56 mmol) and triphenyl phosphine (17.37 g, 66.24 mmol) in DCM (50 mL) for 15 minutes, followed by the addition of carbon tetrabromide (21.97 g, 66.24 mmol, 6.42 mL) to the reaction mixture at 0° C. The resulting mixture was stirred at 27° C. for 3 hours. The crude mixture was purified by column chromatography (silica gel 230-400 mesh, 0-50% ethyl acetate in pet ether) to afford 1-(3-bromopropyl)-4-nitro-benzene (3.5 g, 13.62 mmol, 82.26% yield). $^1H$ NMR (400 MHz, DMSO-$d^6$) δ 7.21 (d, J=8.6 Hz, 2H), 6.57 (d, J=8.6 Hz, 2H), 3.53 (t, J=6.8 Hz, 2H), 2.57 (t, J=6.8 Hz, 2H), 1.90 (t, J=7.6 Hz, 2H).

Step-3:

To a solution of tert-butyl piperazine-1-carboxylate (915.67 mg, 4.92 mmol) in acetonitrile (15 mL) placed in a 100 mL round bottom flask was added N-ethyl-N-isopropyl-propan-2-amine (1.59 g, 12.29 mmol, 2.14 mL) and 1-(3-bromopropyl)-4-nitro-benzene (1 g, 4.10 mmol). The reaction mixture was stirred at 70° C. for 16 hours. Then, the reaction mixture was cooled to room temperature, which was diluted with ethyl acetate, washed with water. The collected organic layer was dried over with anhydrous sodium sulfate, filtered, and concentrated under reduced pressure to afford the crude compound, which was purified by flash column chromatography (silica gel 100-230 mesh, 20-30% ethyl acetate in petroleum ether) to afford tert-butyl 4-[3-(4-nitrophenyl)propyl]piperazine-1-carboxylate (1.14 g, 3.01 mmol, 73.56% yield) as a solid. LC-MS ($ES^+$): m/z 350.3 $[M+H]^+$.

Step-4:

To a solution of tert-butyl 4-[3-(4-nitrophenyl)propyl] piperazine-1-carboxylate (1.00 g, 2.86 mmol) in methanol (15 mL) placed in a 100 mL round bottom flask was added Pd/C (143.21 mg, 2.86 mmol). The reaction mixture was stirred at 25° C. under a hydrogen bladder atmosphere for 16 hours. The progress of the reaction was monitored by LC-MS and TLC. The reaction mixture was filtered through a pad of celite and washed with ethyl acetate. The collected filtrate was concentrated under reduced pressure to afford the crude compound tert-butyl 4-[3-(4-aminophenyl)propyl] piperazine-1-carboxylate (0.9 g, 2.75 mmol, 96.03% yield), which was used next step without further purification. LC-MS ($ES^+$): m/z 320.3 $[M+H]^+$.

Step-5: z

To a solution of tert-butyl 4-[3-(4-aminophenyl)propyl] piperazine-1-carboxylate (0.9 g, 2.82 mmol) in DMF (15 mL) placed in a 50 mL round bottom flask was added sodium bicarbonate (591.71 mg, 7.04 mmol) and 3-bromopiperidine-2,6-dione (703.27 mg, 3.66 mmol). The reaction mixture was stirred at 70° C. for 16 hours. Then, the reaction mixture was cooled to room temperature and diluted with ethyl acetate and washed with water. The collected organic layer was dried over with anhydrous sodium sulfate, filtered, and concentrated under reduced pressure to afford the crude compound, which was purified by flash column chromatography (silica gel 100-230 mesh, 40-50% ethyl acetate in petroleum ether) to furnish tert-butyl 4-[3-[4-[(2,6-dioxo-3-piperidyl)amino]phenyl]propyl] piperazine-1-carboxylate (0.5 g, 865.78 μmol, 30.73% yield). LC-MS ($ES^+$): m/z 431.7 $[M+H]^+$.

Step-6:

To a solution of tert-butyl 4-[3-[4-[(2,6-dioxo-3-piperidyl)amino]phenyl]propyl]piperazine-1-carboxylate (80 mg, 185.81 μmol) in dioxane (1 mL) was added HCl (4 M in dioxane, 2 mL) under nitrogen at 0° C. and stirred for 2 hours at room temperature. Upon completion of the reaction, the reaction mixture was concentrate and triturated with diethyl ether (50 ml) to afford 3-[4-(3-piperazin-1-ylpropyl) anilino]piperidine-2,6-dione HCl salt (0.05 g, 88.58 μmol, 47.67% yield). LC-MS ($ES^+$): m/z 331.5 $[M+H]^+$.

Synthesis of 3-((4-((3S,4R)-3-hydroxypiperidin-4-yl)phenyl)amino)piperidine-2,6-dione

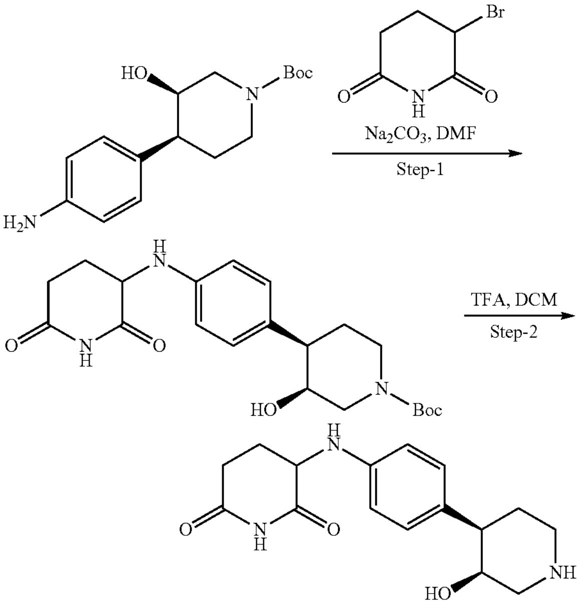

Step-1:

To a stirred solution of tert-butyl (3R,4S)-4-(4-aminophenyl)-3-hydroxy-piperidine-1-carboxylate (1.00 g, 3.42 mmol) in dry DMF (7 mL) was added 3-bromopiperidine-2,6-dione (1.97 g, 10.26 mmol) followed by the addition of sodium bicarbonate (2.87 g, 34.20 mmol). The reaction mixture was heated at 85° C. for 12 hr. After completing the reaction, the reaction mixture was quenched with ice-cold water (20 mL) and extracted with ethyl acetate (2×20 mL). The combined organic layer was washed with brine (1×20 mL), dried over anhydrous $Na_2SO_4$, filtered, and concentrated to afford the crude product. The crude was purified by column chromatography over 230-400 mess silica gel (0-70% ethyl acetate in pet ether as eluent) to afford product tert-butyl (3R,4S)-4-[4-[(2,6-dioxo-3-piperidyl)amino]phenyl]-3-hydroxy-piperidine-1-carboxylate (1.0 g, 2.13 mmol, 62.32% yield). LC-MS($ES^+$): m/z 402.44 $[M-H]^-$.

Step-2:

To a stirred solution of tert-butyl (3R,4S)-4-[4-[(2,6-dioxo-3-piperidyl)amino]phenyl]-3-hydroxy-piperidine-1-carboxylate (0.300 g, 743.55 μmol) in DCM (20 mL) was added 2,2,2-trifluoroacetic acid (38.94 mmol, 3.00 mL). Then, the reaction mixture was stirred at RT for 1 hr while monitoring by TLC and LCMS. After completion, the crude was concentrated under reduced pressure and triturated with diethylether (2×20 mL), then again dried to obtain 3-[4-[(3R,4S)-3-hydroxy-4-piperidyl]anilino]piperidine-2,6-dione (0.280 g, 637.31 μmol, 85.71% yield) as off white solid. LC-MS($ES^+$): m/z 304.15 $[M+H]^+$.

Synthesis of 3-[[1-[2-(methylamino)ethyl]pyrazol-3-yl]amino]piperidine-2,6-dione

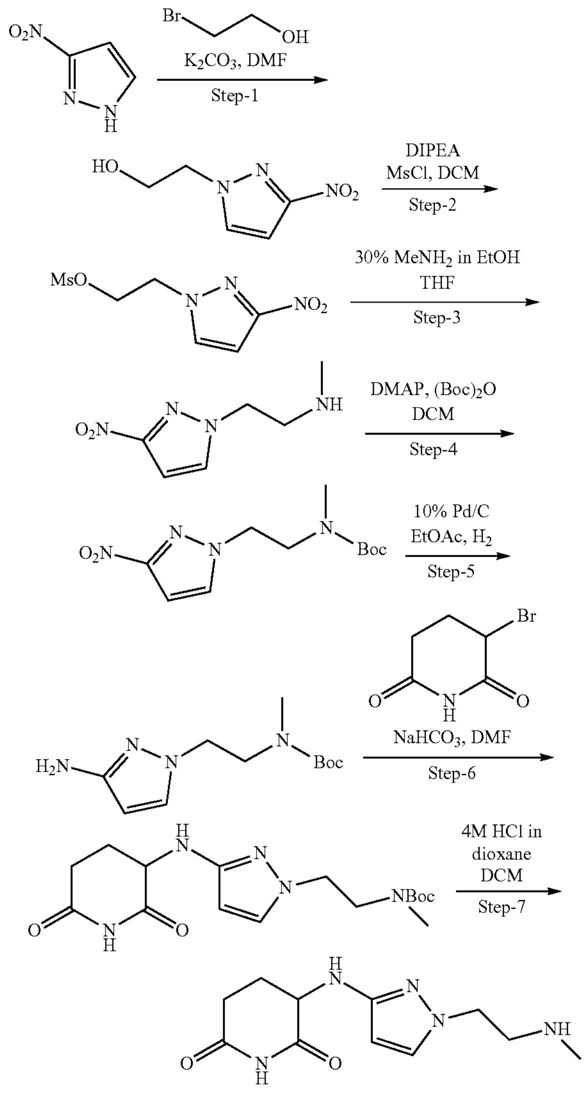

Step-1:

To a solution of 3-nitro-1H-pyrazole (10 g, 88.44 mmol) in THF (100 mL) was added 2-bromoethanol (16.58 g, 132.66 mmol, 9.42 mL) and potassium carbonate, anhydrous, 99% (30.56 g, 221.09 mmol) at room temperature under nitrogen atmosphere. The reaction mixture was heated at 70° C. and stirred for 12 hours. Then, the reaction mixture was concentrated to get the residual mass, which was dissolved in ethyl acetate (250 mL) and washed with water (1×100 mL), brine (1×100 mL), dried over anhydrous sodium sulfate, and concentrated in vacuo to get the crude product 2-(3-nitropyrazol-1-yl)ethanol (9 g, 51.55 mmol, 58.29% yield), which was used to the next step without further purification. LC-MS ($ES^+$): m/z 158.4 $[M+H]^+$.

Step-2:

To a solution of 2-(3-nitropyrazol-1-yl)ethanol (10 g, 63.64 mmol) in DCM (100 mL) was added N-ethyl-N-isopropyl-propan-2-amine (12.34 g, 95.46 mmol, 16.63 mL) at room temperature and the reaction mixture was cooled to 0° C. Then, methanesulfonyl chloride (10.94 g, 95.46 mmol, 7.39 mL) was added dropwise, and the reaction mixture was stirred at room temperature for 2 hours. Then, the reaction mixture was diluted with DCM (700 mL) and washed with saturated sodium bicarbonate solution (500 mL), and washed with aqueous brine solution (300 mL). The organic layer was dried over sodium sulfate and concentrated in vacuo to get the crude product 2-(3-nitropyrazol-1-yl)ethyl methanesulfonate (14 g, 47.62 mmol, 74.82% yield) as a brown color solid, which was used in the next step without any purification. LC-MS ($ES^+$): m/z 236.3 $[M+H]^+$.

Step-3:

In a sealed tube, methylamine, 33 wt % solution in absolute ethanol (29.76 mmol, 35 mL) was added to a stirred solution of 2-(3-nitropyrazol-1-yl)ethyl methanesulfonate (7 g, 29.76 mmol) in THF (10 mL) at 0° C. The reaction was heated at 70° C. for 16 h. After the completion, the reaction mixture was concentrated in vacuo to get the crude compound N-methyl-2-(3-nitropyrazol-1-yl)ethanamine (4.5 g, 10.31 mmol, 34.66% yield) as a brown color gum, which was used in the next step without any purification. LC-MS ($ES^+$): m/z 171.3 $[M+H]^+$.

Step-4:

To a solution of N-methyl-2-(3-nitropyrazol-1-yl)ethanamine (7 g, 41.14 mmol) in dry DCM (70 mL) was added N,N-dimethylpyridin-4-amine (5.03 g, 41.14 mmol) under $N_2$ atm. The reaction mixture was stirred at the same temperature for 5 minutes, and tert-butoxycarbonyl tert-butyl carbonate (13.47 g, 61.70 mmol, 14.16 mL) was added dropwise. The reaction mixture was stirred at RT for 16 h as monitored by TLC. Then, the reaction mixture was quenched with ice-cold water (200 ml) and the organic layer was partitioned. The organic layer was washed with water (3×100 ml), brine (1×100 ml), dried over anhydrous sodium sulfate, filtered, concentrated in vacuo to get the crude compound. The crude was purified by column chromatography (silica gel 100-200 mesh) to afford tert-butyl N-methyl-N-[2-(3-nitropyrazol-1-yl)ethyl]carbamate (6 g, 18.65 mmol, 45.33% yield) as a colorless liquid. LC-MS ($ES^+$): m/z 293.4 $[M+Na]^+$.

Step-5:

To a solution of tert-butyl N-methyl-N-[2-(3-nitropyrazol-1-yl)ethyl]carbamate (6 g, 22.20 mmol) in ethyl acetate (60 mL) was added palladium, 10% on carbon, type 487, dry (2.36 g, 22.20 mmol) at room temperature. The reaction mixture was stirred under balloon pressure hydrogen atmosphere for 32 h. Subsequently, it was filtered through a celite bed and washed with ethyl acetate (500 mL). The filtrate was concentrated under reduced pressure to afford tert-butyl N-[2-(3-aminopyrazol-1-yl)ethyl]-N-methyl-carbamate (5 g, 19.35 mmol, 87.17% yield) as a colorless gel, which was used for next step without further purification. LC-MS ($ES^+$): m/z 241.2 $[M+H]^+$.

Step-6:

To a solution of tert-butyl N-[2-(3-aminopyrazol-1-yl)ethyl]-N-methyl-carbamate (1.6 g, 6.66 mmol) and 3-bromopiperidine-2,6-dione (3.84 g, 19.97 mmol) in DMF (16 mL) was added Sodium bicarbonate (3.36 g, 39.95 mmol, 1.55 mL) in a sealed tube. The reaction mixture was stirred at 70° C. for 16 h. Upon the completion of the reaction, the reaction mixture was poured into ice-cooled water. The product was extracted using EtOAc, and the organic layer was washed with a cooled brine solution to get the crude product. It was purified by column chromatography (silica gel 230-400 mesh, 0-100% ethyl acetate in petroleum ether) to get tert-butyl N-[2-[3-[(2,6-dioxo-3-piperidyl)amino]

pyrazol-1-yl]ethyl]-N-methyl-carbamate (1.8 g, 4.00 mmol, 60.01% yield) as a green gum. LC-MS ($ES^+$): m/z 350.3 $[M-H]^-$.

Step-7:

To a solution of tert-butyl N-[2-[3-[(2,6-dioxo-3-piperidyl)amino]pyrazol-1-yl]ethyl]-N-methyl-carbamate (0.25 g, 711.44 μmol) in DCM (5 mL) was added 4 M hydrogen chloride solution in dioxane (2.5 mL) at 0° C. and the reaction mixture was stirred at room temperature for 2 h. Then, the reaction mixture was concentrated in vacuo to get the crude product, which was triturated with diethyl ether (50 mL) to afford 3-[[1-[2-(methylamino)ethyl]pyrazol-3-yl]amino]piperidine-2,6-dione (0.15 g, 459.64 μmol, 64.61% yield) as a light blue solid. LC-MS ($ES^+$): m/z 252.4 $[M+H]^+$.

Synthesis of 3-[[1-(4-piperidyl)pyrazol-3-yl]amino]piperidine-2,6-dione

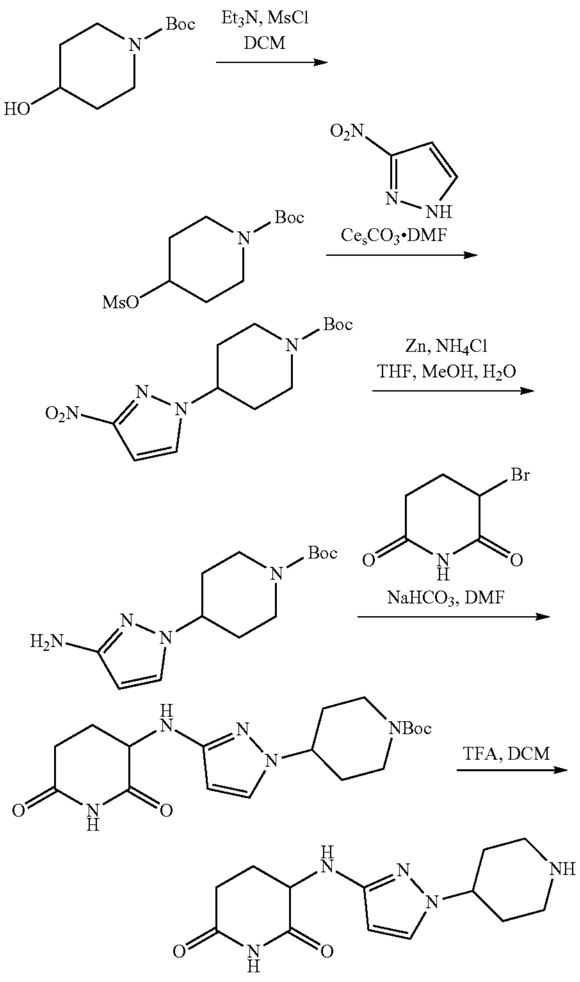

Step-1:

To a solution of tert-butyl 4-hydroxypiperidine-1-carboxylate (30 g, 149.06 mmol) in DCM (300 mL) was added triethyl amine (150.83 g, 1.49 mol, 207.76 mL) and stirred for 5 minutes. Mesyl chloride (25.61 g, 223.59 mmol, 17.31 mL) was added to the reaction mixture at 0° C., and the resulting mixture was stirred at 27° C. for 16 hours. The reaction mixture was quenched with water and extracted with DCM (100 mL×3). The organic layer was washed with water (100 mL) and brine solution (100 mL). The combined organic layers were dried over anhydrous sodium sulfate, filtered, and concentrated under reduced pressure. The crude product was purified by column chromatography (silica gel 230-400 mesh, 0-100% ethyl acetate in pet ether) to afford tert-butyl 4-methylsulfonyloxypiperidine-1-carboxylate (40 g, 136.03 mmol, 91.26% yield). $^1H$ NMR (400 MHz, DMSO-$d_6$) δ 7.21 (d, J=8.6 Hz, 2H), 6.57 (d, J=8.6 Hz, 2H), 3.53 (t, J=6.8 Hz, 2H), 2.57 (t, J=6.8 Hz, 2H), 1.90 (t, J=7.6 Hz, 2H).

Step-2:

To a solution of 3-nitro-1H-pyrazole (10 g, 88.44 mmol) and tert-butyl 4-methylsulfonyloxypiperidine-1-carboxylate (37.06 g, 132.66 mmol) in DMF (200 mL) was added cesium carbonate (86.44 g, 265.31 mmol) and the reaction was stirred for 16 hours at 65° C. Then, the reaction mixture was quenched by water and extracted with ethyl acetate. The organic layer was concentrated under reduced pressure, and the crude mixture was purified by column chromatography (30%-40% ethyl acetate in pet ether) to afford tert-butyl 4-(3-nitropyrazol-1-yl)piperidine-1-carboxylate (4 g, 11.88 mmol, 13.43% yield) as a white semi-liquid. LC-MS ($ES^+$): m/z 241.2 $[[M-C(CH_3)_3]+H]+H]^+$.

Step-3:

To a solution of tert-butyl 4-(3-nitropyrazol-1-yl)piperidine-1-carboxylate (4 g, 13.50 mmol) in THF (20 mL) and methanol (20 mL) was added $NH_4Cl$ (14.44 g, 269.98 mmol) in water (5 mL), followed by the addition of a suspension of zinc (8.83 g, 134.99 mmol). The reaction mixture was stirred at room temperature for 16 hours. Upon the completion of the reaction, the mixture was passed through a celite bed, and the filtrate was diluted with water (50 ml) and extracted with ethyl acetate (250 ml). The organic layer was separated and dried over anhydrous $Na_2SO_4$. The organic layer was evaporated under vacuum to get the crude compound, which was purified by column chromatography (Devisil silica, 0-100% ethyl acetate in hexane) to give tert-butyl 4-(3-aminopyrazol-1-yl)piperidine-1-carboxylate (2.5 g, 6.57 mmol, 48.68% yield) as a brown solid. LC-MS ($ES^+$): m/z 211.2 $[[M-C(CH_3)_3]+H]+H]^+$.

Step-4:

To a solution of tert-butyl 4-(3-aminopyrazol-1-yl)piperidine-1-carboxylate (2.0 g, 7.51 mmol) and 3-bromopiperidine-2,6-dione (4.33 g, 22.53 mmol) in DMF (10 mL) was added sodium bicarbonate (6.31 g, 75.09 mmol) in a sealed tube. The reaction mixture was stirred at 75° C. for 16 hours. Upon completion of the reaction, the mixture was poured into ice-cooled water and extracted using ethyl acetate. The organic layer was washed with a cooled brine solution to get the crude product. It was purified by reverse phase chromatography over celite using 10% formic acid in water to get tert-butyl 4-[3-[(2,6-dioxo-3-piperidyl)amino]pyrazol-1-yl]piperidine-1-carboxylate (1.1 g, 2.84 mmol, 37.83% yield) as alight ash color solid. LC-MS ($ES^+$): m/z 378.3 $[M+H]^+$.

Step-5:

To a solution of tert-butyl 4-[3-[(2,6-dioxo-3-piperidyl)amino]pyrazol-1-yl]piperidine-1-carboxylate (0.900 g, 2.38 mmol) in DCM (10 mL) was added 2,2,2-trifluoroacetic acid (271.89 mg, 2.38 mmol, 183.71 μL) at 0° C. and the reaction mixture was stirred at room temperature for 2 h. The reaction mixture was concentrated in vacuo and triturated with diethyl ether (100 mL) to afford 3-[[1-(4-piperidyl)pyrazol-3-yl]amino]piperidine-2,6-dione (0.900 g, 1.61 mmol, 67.51% yield) as a black solid. LC-MS ($ES^+$): m/z 278.5 $[M+H]^+$.

Synthesis of 3-((5-(piperidin-4-yl)pyridin-2-yl)amino)piperidine-2,6-dione

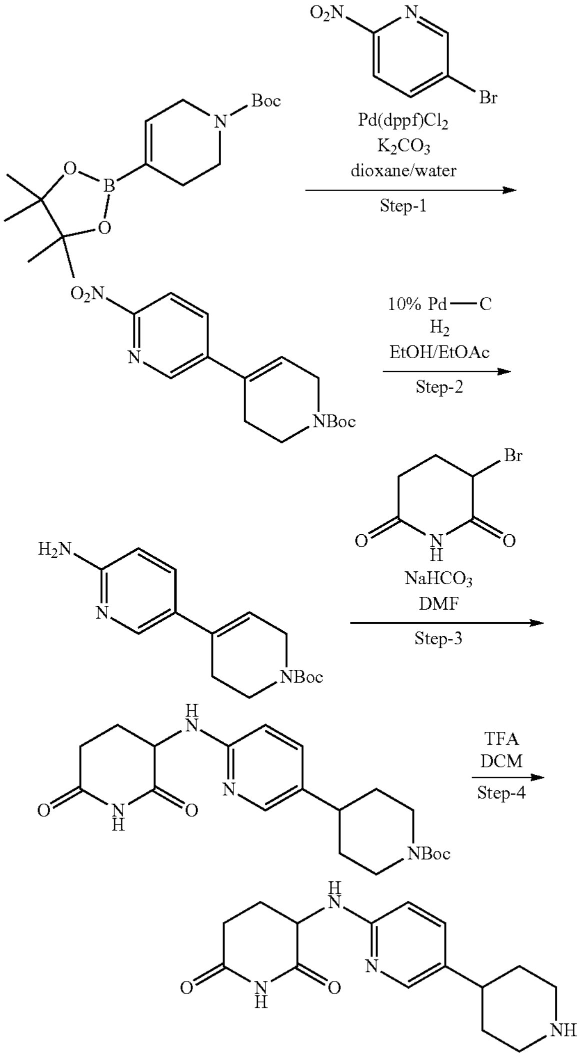

Step-1:

A solution of 5-bromo-2-nitro-pyridine (15 g, 73.89 mmol) in dioxane (150 mL) were added tert-butyl 4-(4,4,5,5-tetramethyl-1,3,2-dioxaborolan-2-yl)-3,6-dihydro-2H-pyridine-1-carboxylate (25.13 g, 81.28 mmol), potassium carbonate, anhydrous, 99% (30.64 g, 221.68 mmol) in water (30 mL). The mixture was purged with nitrogen gas for 20 minutes before Pd(dppf)$Cl_2$ (2.70 g, 3.69 mmol) was added, and the reaction refluxed at 80° C. for 4 hours. The reaction progress was monitored by TLC and LC-MS. After completion, the reaction was diluted with cold water and extracted with ethyl acetate. The organic layer was washed with brine solution and concentrated to dryness. The resulting crude product was purified by column chromatography (silica gel 100-200 mesh, 0-20% ethyl acetate in pet ether) to afford tert-butyl 4-(6-nitro-3-pyridyl)-3,6-dihydro-2H-pyridine-1-carboxylate (18 g, 57.18 mmol, 77.39% yield) as an off-white solid. LC-MS ($ES^+$): m/z 306.42[M+H]$^+$.

Step-2:

To a stirred solution of tert-butyl 4-(6-nitro-3-pyridyl)-3,6-dihydro-2H-pyridine-1-carboxylate (5 g, 16.38 mmol) in ethyl acetate (50 mL) was added palladium, 10% on carbon, type 487, dry (4.36 g, 40.94 mmol). The reaction was stirred under hydrogen gas for 16 hours. The reaction progress was monitored by TLC and LC-MS. After completion, the reaction was filtered through a celite bed and washed with ethyl acetate. The filtrate was concentrated in vacuo to afford tert-butyl 4-(6-amino-3-pyridyl)piperidine-1-carboxylate (4.4 g, 15.45 mmol, 94.35% yield) as a solid. LC-MS ($ES^+$): m/z 278.46 [M+H]$^+$.

Step-3:

To a stirred solution of tert-butyl 4-(6-amino-3-pyridyl)piperidine-1-carboxylate (2 g, 7.21 mmol) in DMF (20 mL) was added sodium bicarbonate (6.06 g, 72.11 mmol) followed by 3-bromopiperidine-2,6-dione (13.85 g, 72.11 mmol) under argon atmosphere in a sealed tube. The reaction mixture was stirred at 80° C. for 16 hours, and the reaction progress was monitored by TLC. The reaction mixture was poured into ice-cold water and stirred for 30 minutes. The solid product was separated by filtration and washed with water and pet ether. The product in the filtrate was extracted with ethyl acetate. The solid product was then dissolved in dichloromethane/methanol (5/1) and combined with the extracted product in ethyl acetate. It was dried over sodium sulfate and evaporated to dryness to obtain the crude product, which was purified by column chromatography (silica gel 230-400 mesh, 0-100% ethyl acetate in pet ether) to afford tert-butyl 4-[6-[(2,6-dioxo-3-piperidyl)amino]-3-pyridyl]piperidine-1-carboxylate (2.8 g, 4.61 mmol, 63.97% yield) as a light yellow solid. LC-MS ($ES^+$): m/z 389.25 [M+H]$^+$.

Step-4:

To a solution of tert-butyl 4-[6-[(2,6-dioxo-3-piperidyl)amino]-3-pyridyl]piperidine-1-carboxylate (1.1 g, 2.83 mmol) in dichloromethane (10 mL) was added trifluoroacetic acid (322.88 mg, 2.83 mmol, 218.16 μL) at 0° C. and the reaction was stirred at room temperature for 1 hour. The reaction mixture was then concentrated in vacuo to obtain the crude product, which was triturated with diethyl ether (50 mL) to afford 3-[[5-(4-piperidyl)-2-pyridyl]amino]piperidine-2,6-dione TFA salt (1.1 g, 2.05 mmol, 72.41% yield) as an off-white solid. LC-MS ($ES^+$): m/z 289.47 [M+H]$^+$.

Synthesis of 3-((6-(piperidin-4-yl)pyridin-3-yl)amino)piperidine-2,6-dione

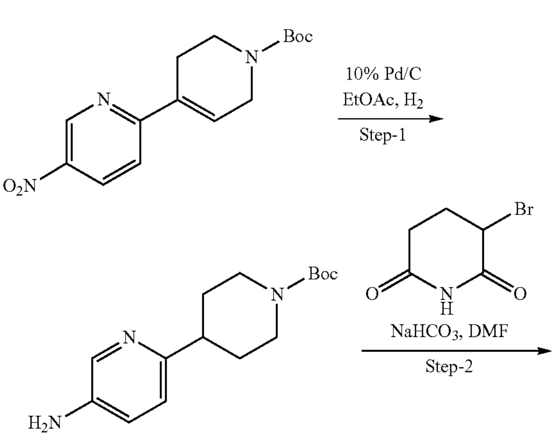

-continued

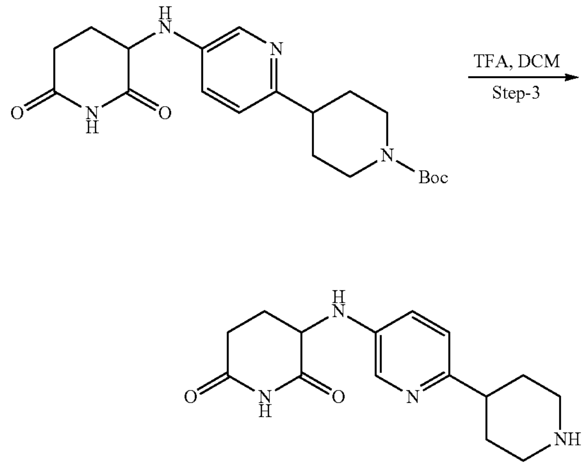

Step-1:

To a stirred solution of tert-butyl 4-(5-nitro-2-pyridyl)-3,6-dihydro-2H-pyridine-1-carboxylate (10 g, 32.75 mmol) in ethyl acetate (100 mL) was added 10 wt. % palladium on carbon, type 487, dry (3.49 g, 32.75 mmol) and the reaction was stirred under hydrogen atmosphere for 16 hours. The reaction progress was monitored by TLC and LC-MS. After completion, the reaction mixture was filtered through a pad of celite, and the filtrate was concentrated to dryness. The resulting crude product was purified by column chromatography (silica gel 60-120 mesh, 0-30% ethyl acetate in pet ether) to afford tert-butyl 4-(5-amino-2-pyridyl)piperidine-1-carboxylate (7 g, 23.47 mmol, 71.66% yield). LC-MS ($ES^+$): m/z 276.24 $[M-H]^-$.

Step-2:

To a stirred solution of tert-butyl 4-(5-amino-2-pyridyl) piperidine-1-carboxylate (6.5 g, 23.44 mmol) and 3-bromopiperidine-2,6-dione (13.50 g, 70.31 mmol) in DMF (40 mL) was added sodium bicarbonate (19.69 g, 234.35 mmol) in a sealed tube. The reaction mixture was stirred at 85° C. for 16 hours. The progress of the reaction was monitored by TLC and LC-MS. Upon completion of the reaction, the reaction mixture was poured into ice water, and the product was extracted with ethyl acetate. The organic layer was washed with cold brine solution, dried over anhydrous sodium sulfate, and concentrated to give the crude product, which was purified by column chromatography (silica gel 230-400 mesh, 0-100% ethyl acetate in pet ether) to afford tert-butyl 4-[5-[(2,6-dioxo-3-piperidyl)amino]-2-pyridyl]piperidine-1-carboxylate (2.84 g, 6.40 mmol, 27.32% yield) as a light green solid. LC-MS ($ES^+$): m/z 387.28 $[M-H]^-$.

Step-3:

To a stirred solution of tert-butyl 4-[5-[(2,6-dioxo-3-piperidyl)amino]-2-pyridyl]piperidine-1-carboxylate (1 g, 2.57 mmol) in DCM (10 mL) was added TFA (5.92 g, 51.92 mmol, 4 mL) at 0° C. The reaction mixture was stirred for 3 h, and the reaction progress was monitored by TLC and LC-MS. Upon completion of the reaction, the reaction mixture was evaporated to obtain the crude product, which was triturated with diethyl ether and concentrated in vacuo to afford 3-[[6-(4-piperidyl)-3-pyridyl]amino]piperidine-2,6-dione (700 mg, 2.03 mmol, 78.74% yield) as a green solid. LC-MS ($ES^+$): m/z 289.46 $[M+H]^+$.

Synthesis of 3-((5-fluoro-6-(piperidin-4-yl)pyridin-3-yl)amino)piperidine-2,6-dione

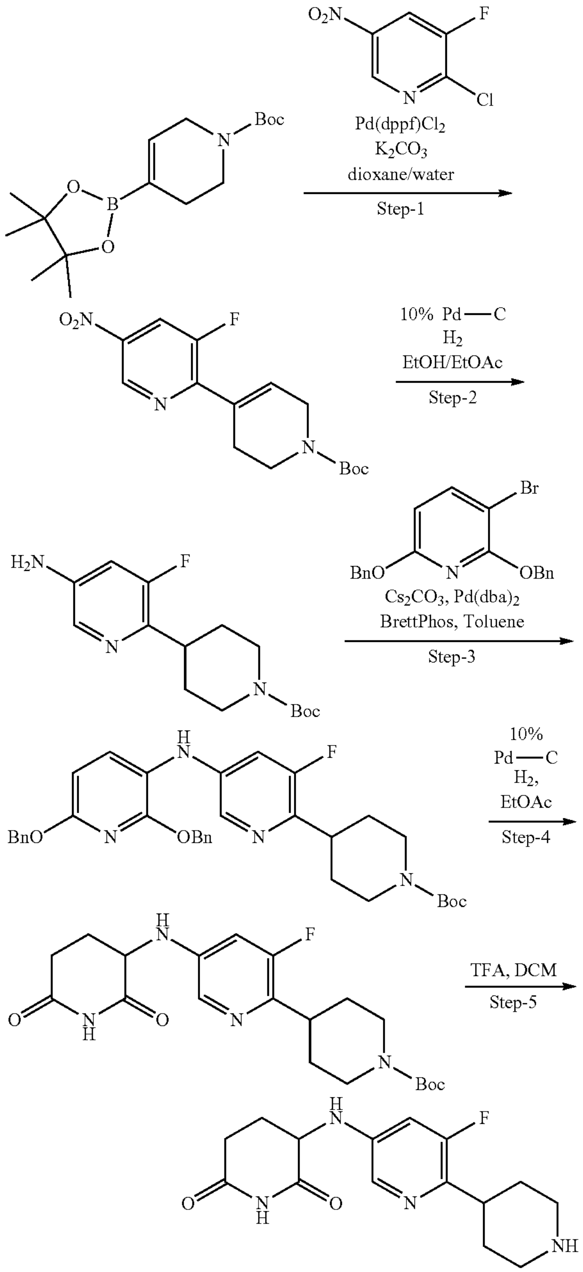

Step-1:

To a solution of benzyl 2-chloro-3-fluoro-5-nitro-pyridine (10 g, 56.65 mmol) and tert-butyl 4-(4,4,5,5-tetramethyl-1,3,2-dioxaborolan-2-yl)-3,6-dihydro-2H-pyridine-1-carboxylate (26.27 g, 84.97 mmol) in 1,4-dioxane (100 mL) and water (25 mL) was added potassium carbonate, anhydrous, 99% (23.49 g, 169.94 mmol) at room temperature. The reaction mixture was degassed with argon for 10 minutes, and $Pd(dppf)Cl_2$ (2.07 g, 2.83 mmol) was added. The reaction mixture was degassed with argon for an additional 5 minutes, and it was stirred at 80° C. for 16 hr. Subsequently, the reaction mixture was diluted with water and extracted with ethyl acetate. The combined organic layer was washed with brine solution, dried over sodium sulfate, filtered, and concentrated in vacuo to get the crude product, which was purified by column chromatography using 230-400 mesh silica gel and 0-10% ethyl acetate in pet ether as eluent to afford tert-butyl 4-(3-fluoro-5-nitro-2-pyridyl)-3,6-dihydro-2H-pyridine-1-carboxylate (18 g, 48.99 mmol, 86.49% yield) as an off white solid. LC-MS(ES$^+$): m/z 322.40 [M−H]$^-$.

Step-2:

A stirred solution of tert-butyl 4-(3-fluoro-5-nitro-2-pyridyl)-3,6-dihydro-2H-pyridine-1-carboxylate (5 g, 15.46 mmol) in ethanol (25 mL) and ethyl acetate (25 mL) was degassed with argon for 10 min. Palladium, 10% on carbon, Type 487, dry (5 g) was added to the room temperature, and it was stirred for 16 h at room temperature under $H_2$-balloon pressure. Upon completion of the reaction, it was filtered through celite bed, washed with EtOH and EtOAc. The filtrate was evaporated under reduced pressure to give the crude product, purified by using silica gel column chromatography and 0-100% EA-PE as eluent to afford tert-butyl 4-(5-amino-3-fluoro-2-pyridyl)piperidine-1-carboxylate (4 g, 12.60 mmol, 81.45% yield). LC-MS(ES$^+$): m/z 296.56 [M+H]$^+$ Step-3:

To a solution of 2,6-dibenzyloxy-3-bromo-pyridine (13 g, 35.11 mmol) and tert-butyl 4-(5-amino-3-fluoro-2-pyridyl)piperidine-1-carboxylate (8.30 g, 28.09 mmol) in Toulene (130 mL) was added Cesium carbonate (14.87 g, 45.65 mmol) at RT. The reaction mixture was degassed with nitrogen gas for 10 minutes, and $Pd(dba)_2$ (1.61 g, 1.76 mmol), BrettPhos (942.36 mg, 1.76 mmol) were added. The reaction mixture was degassed with nitrogen gas for additional 5 minutes, and it was stirred at 110° C. for 16 hr. The reaction mixture was filtered through a celite bed and washed with ethyl acetate (150 mL). The organic layer was washed with water (100 mL) and brine solution (100 mL), dried over sodium sulfate, filtered, and concentrated in vacuo to give the crude product, which was purified by using Davisil silica gel column chromatography (0-40% EA-PE as eluent) to get tert-butyl 4-[5-[(2,6-dibenzyloxy-3-pyridyl)amino]-3-fluoro-2-pyridyl]piperidine-1-carboxylate (9 g, 13.39 mmol, 38.14% yield) as a brown gum. LC-MS(ES$^+$): m/z 586.62 [M+H]$^+$ Step-4:

A stirred solution of tert-butyl 4-[5-[(2,6-dibenzyloxy-3-pyridyl)amino]-3-fluoro-2-pyridyl]piperidine-1-carboxylate (9 g, 15.39 mmol) in EtOAc (100 mL) was degassed with argon for 10 min. The 10% palladium on carbon, 60% wet basis (9 g) was added to the room temperature, and it was stirred for 16 hr at 25° C. under $H_2$-60 Psi pressure (Parr Shaker). Upon completion of the reaction, it was filtered through celite bed, washed with EtOAc. The filtrate was evaporated under reduced pressure to give the crude product, which was purified using silica gel (100-200 mesh) column chromatography and 0-100% EA-PE as eluent to afford tert-butyl 4-[5-[(2,6-dioxo-3-piperidyl)amino]-3-fluoro-2-pyridyl]piperidine-1-carboxylate (5.5 g, 13.29 mmol, 86.33% yield) as a light green solid. LC-MS(ES$^+$): m/z 407.09 [M+H]$^+$ Step-5:

To a stirred solution of tert-butyl 4-[5-[(2,6-dioxo-3-piperidyl)amino]-3-fluoro-2-pyridyl]piperidine-1-carboxylate (240 mg, 590.48 μmol) in DCM (5 mL) cooled to 0° C. was added trifluoroacetic acid (1 mL) dropwise under inert atmosphere. The reaction mixture was then allowed to stir at rt for 2 h. Upon completion of the reaction, the mixture was concentrated under reduced pressure, and the crude product was triturated with diethyl ether (3×5 mL) to afford TFA salt of 3-[[5-fluoro-6-(4-piperidyl)-3-pyridyl]amino]piperidine-2,6-dione (220 mg, 492.07 μmol, 83.33% yield) as a green solid. LC-MS(ES$^+$): m/z 307.11 [M+H]$^+$ Intermediate 3-((6-(piperidin-4-yl)pyridazin-3-yl)amino)piperidine-2,6-dione was Prepared Substantially Following the Synthesis of 3-[[6-(4-piperidyl)-3-pyridyl]amino]piperidine-2,6-dione

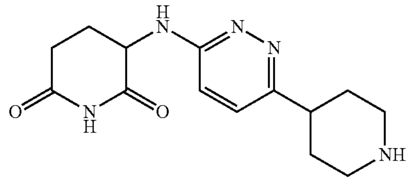 [SMILES: O=C1CCC(Nc2ccc(C3CCNCC3)nn2)C(=O)N1]

LC-MS (ES$^+$): m/z 290.2 [M+H]$^+$.

Synthesis of 3-[(6-piperazin-1-yl-3-pyridyl)amino]piperidine-2,6-dione

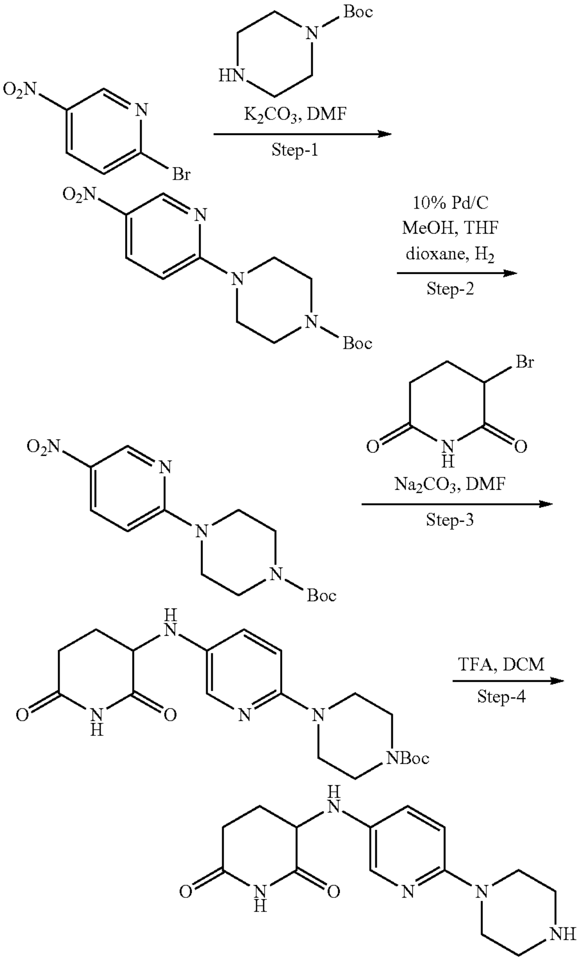

Step-1:

To a stirred solution of 2-bromo-5-nitropyridine (12 g, 59.12 mmol) in DMF (120 mL) was added tert-butyl piperazine-1-carboxylate (14.31 g, 76.85 mmol) followed by potassium carbonate (8.17 g, 59.12 mmol) at room temperature under nitrogen atmosphere. The reaction mixture was heated at 80° C. for 3 hours. The progress of the reaction was monitored by TLC. Upon completion, the reaction mixture was diluted with water (500 mL) and filtered. The residue obtained was washed with pentane (100 mL) and dried under vacuum to afford the compound tert-butyl 4-(5-nitropyridin-2-yl)piperazine-1-carboxylate (15 g, 46.22 mmol, 78.18% yield) as a yellow solid. LC-MS ($ES^+$): m/z 209.40 $[M-Boc+H]^+$.

The procedures from step-2 to step-4 are identical to the synthesis of intermediate 3-((6-(piperidin-4-yl)pyridin-3-yl)amino)piperidine-2,6-dione, and the product 3-[(6-piperazin-1-yl-3-pyridyl)amino]piperidine-2,6-dione was confirmed by LC-MS. LC-MS ($ES^+$): m/z 290.45 $[M+H]^+$.

Synthesis of 3-((5-fluoro-6-(piperazin-1-yl)pyridin-3-yl)amino)piperidine-2,6-dione

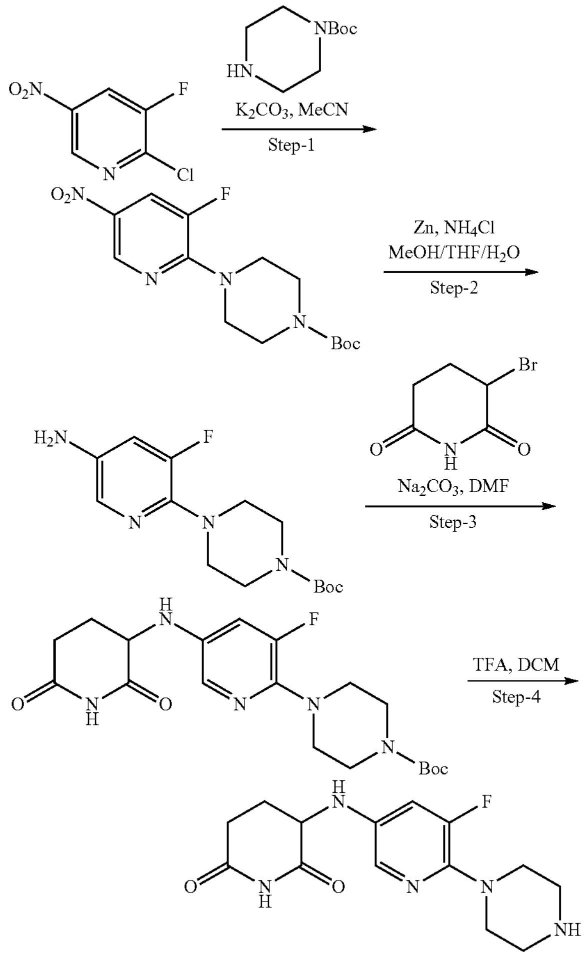

Step-1:

To a stirred solution of tert-butyl piperazine-1-carboxylate (26.38 g, 141.62 mmol) in MeCN (41.45 mL) were added potassium carbonate (19.57 g, 141.62 mmol, 8.55 mL) and 2-chloro-3-fluoro-5-nitro-pyridine (25 g, 141.62 mmol) under nitrogen at room temperature. The resulting mixture was heated at 70° C. for 6 hr. Upon completion of the reaction, the reaction was cooled to room temperature, diluted with ice-cold water, and dried under vacuum to give the crude product, which was purified by silica gel column chromatography (60/120 mesh) using 0-30% EA-PE as eluent to yield tert-butyl 4-(3-fluoro-5-nitro-2-pyridyl)piperazine-1-carboxylate (42 g, 115.84 mmol, 81.80% yield) as a yellow solid.

Step-2:

To a stirred solution of tert-butyl 4-(3-fluoro-5-nitro-2-pyridyl)piperazine-1-carboxylate (20 g, 61.29 mmol) in methanol (100 mL) and THF (100 mL) was added ammonium chloride (32.78 g, 612.89 mmol, 21.43 mL) followed by Zn (40.08 g, 612.89 mmol) in water (50 mL) mixture at 0° C. under argon atmosphere. The reaction mixture was allowed to stir at room temperature for 3 h. Subsequently, it was filtered through a celite bed and washed with MeOH (100 mL) and THF (100 mL). The filtrate was concentrated under reduced pressure to afford crude product. The crude was purified by silica gel column chromatography (100/200 mesh & 0-50% EA-PE as eluent) to afford tert-butyl 4-(5-amino-3-fluoro-2-pyridyl)piperazine-1-carboxylate (15 g, 40.49 mmol, 66.07% yield) as a brown solid. LC-MS ($ES^+$): m/z 297.61 $[M+H]^+$.

The procedures from step-3 to step-4 are identical to the synthesis of intermediate 3-((6-(piperidin-4-yl)pyridin-3-yl)amino)piperidine-2,6-dione, and the product 3-((5-fluoro-6-(piperazin-1-yl)pyridin-3-yl)amino)piperidine-2,6-dione was confirmed by LC-MS. LC-MS ($ES^+$): m/z 308.30 $[M+H]^+$.

Synthesis of 3-((5-(piperidin-4-yl)pyrazin-2-yl)amino)piperidine-2,6-dione

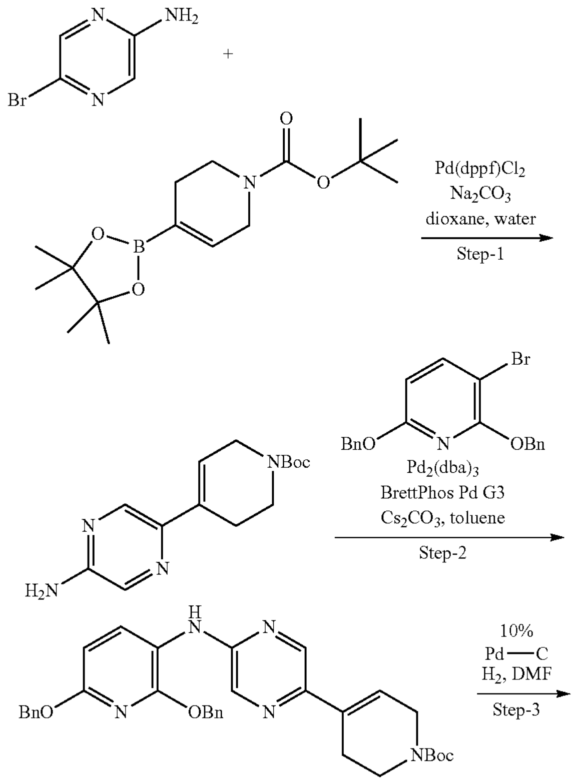

-continued

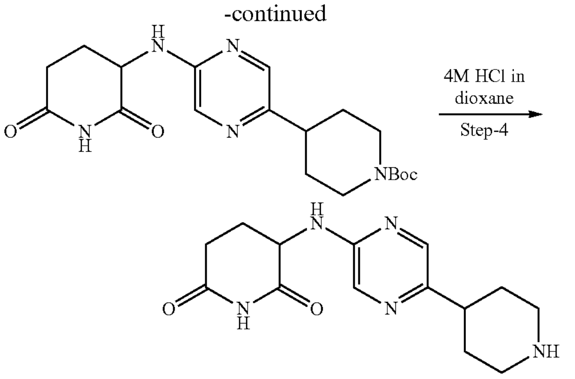

Step-1:

A mixture of 5-bromopyrazin-2-amine (3 g, 17.24 mmol), tert-butyl 4-(4,4,5,5-tetramethyl-1,3,2-dioxaborolan-2-yl)-5,6-dihydropyridine-1(2H)-carboxylate (5.86 g, 18.97 mmol), $Pd(dppf)Cl_2$ (1.41 g, 1.72 mmol) and sodium carbonate (5.48 g, 51.72 mmol) in dioxane (60 mL) and water (15 mL) was degassed and purged with $N_2$ three times. The mixture was stirred at 100° C. for 12 hours under an $N_2$ atmosphere. After LC-MS showed complete consumption of 5-bromopyrazin-2-amine, the reaction mixture was concentrated under reduced pressure to give the crude product tert-butyl 4-(5-aminopyrazin-2-yl)-5,6-dihydropyridine-1(2H)-carboxylate (4.6 g, 7.99 mmol, 46.34% yield) as a yellow solid. LC-MS ($ES^+$): m/z 277.4 $[M+H]^+$. The product was used directly for the next step without further purification.

Step-2:

A mixture of tert-butyl 4-(5-aminopyrazin-2-yl)-5,6-dihydropyridine-1(2H)-carboxylate (500 mg, 1.81 mmol), 2,6-bis(benzyloxy)-3-bromopyridine (669.91 mg, 1.81 mmol), cesium carbonate (1.47 g, 4.52 mmol), dicyclohexyl-[3,6-dimethoxy-2-[2,4,6-tri(propan-2-yl)phenyl]phenyl]phosphane (97.12 mg, 180.94 μmol) and (1E,4E)-1,5-diphenylpenta-1,4-dien-3-one; palladium (82.85 mg, 90.47 μmol) in toluene (1 mL) was degassed and purged with $N_2$ three times. The mixture was then stirred at 110° C. for 12 hours under $N_2$ atmosphere. After reaction was complete as shown by LC-MS, The reaction mixture was filtered and concentrated under reduced pressure to give a residue, which was purified by column chromatography (silica gel, petroleum ether/ethyl acetate=50/1 to 3/1) to afford compound tert-butyl 4-(5-((2,6-bis(benzyloxy)pyridin-3-yl)amino)pyrazin-2-yl)-5,6-dihydropyridine-1(2H)-carboxylate (1.1 g, 1.70 mmol, 94.04% yield) as a yellow solid. LC-MS ($ES^+$): m/z 566.2 $[M+H]^+$.

Step-3:

To a solution of tert-butyl 4-(5-((2,6-bis(benzyloxy)pyridin-3-yl)amino)pyrazin-2-yl)-5,6-dihydropyridine-1(2H)-carboxylate (1 g, 1.77 mmol) in DMF (50 mL) was added palladium (10% on carbon, wet, 500 mg) under nitrogen atmosphere. The suspension was degassed and purged with $H_2$ three times. The mixture was stirred under a hydrogen atmosphere (15 Psi) at 25° C. for 12 hours. The reaction was monitored by LC-MS. After completion, the reaction mixture was filtered and concentrated under reduced pressure to give a residue, which was purified by prep-TLC (silica gel, DCM:MeOH=10:1) to give the compound tert-butyl 4-(5-((2,6-dioxopiperidin-3-yl)amino)pyrazin-2-yl)piperidine-1-carboxylate (134 mg, 320.34 μmol, 18.12% yield) as a yellow solid. LC-MS ($ES^+$): m/z 334.2 $[M-tBu+H]^+$.

Step-4:

A solution of tert-butyl 4-(5-((2,6-dioxopiperidin-3-yl)amino)pyrazin-2-yl)piperidine-1-carboxylate (130 mg, 333.81 μmol) in dioxane (2 mL) was added 4 M hydrogen chloride solution in dioxane (2.55 mL). The mixture was stirred at 25° C. for 0.5 h. The reaction was monitored by LC-MS. Upon completion, the reaction mixture was concentrated under reduced pressure to give the crude product, which was used directly for the next step without further purification. Compound 3-((5-(piperidin-4-yl)pyrazin-2-yl)amino)piperidine-2,6-dione HCl salt (96 mg, 265.20 μmol, 79.45% yield) was obtained as a blue solid. LC-MS ($ES^+$): m/z 290.4 $[M+H]^+$.

Intermediate 3-[[5-(4-piperidyl)pyrimidin-2-yl]amino]piperidine-2,6-dione was Prepared Substantially Following the Synthesis of 3-((5-(piperidin-4-yl)pyrazin-2-yl)amino)piperidine-2,6-dione

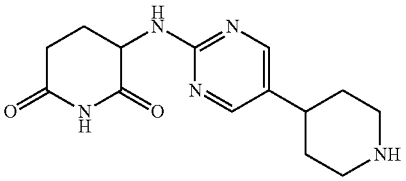 [SMILES: O=C1CCC(Nc2ncc(C3CCNCC3)cn2)C(=O)N1]

LC-MS ($ES^+$): m/z 290.4 $[M+H]^+$.

Synthesis of 3-[[2-(4-piperidyl)pyrimidin-5-yl]amino]piperidine-2,6-dione

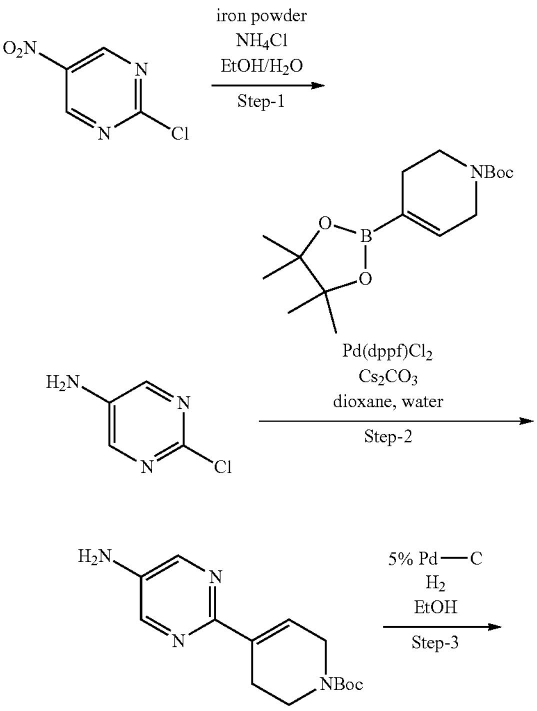

-continued

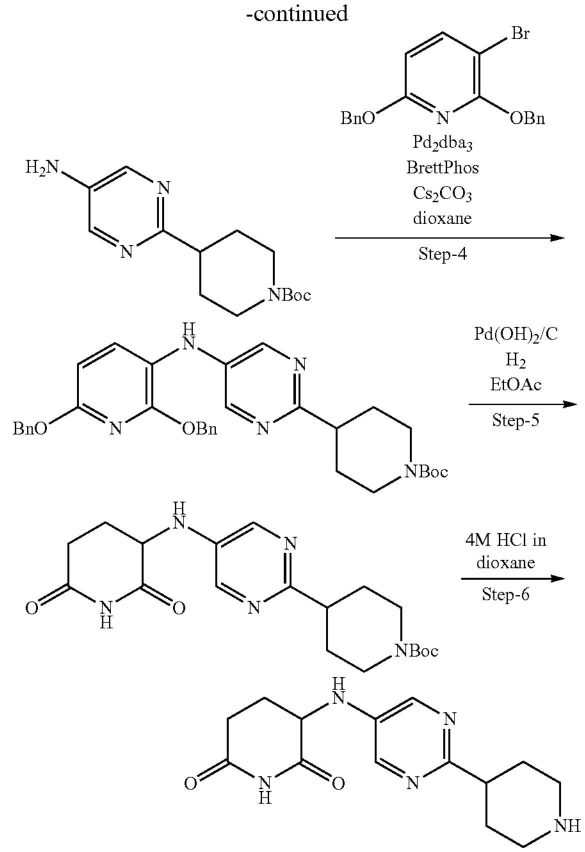

Step-1:

To a stirred solution of 2-chloro-5-nitro-pyrimidine (3.4 g, 21.31 mmol) in ethanol (29 mL) and water (7 mL) was added iron powder (5.95 g, 106.56 mmol) and ammonium chloride (2.28 g, 42.63 mmol). The reaction mixture was stirred at 70° C. for 6 hours. The reaction progress was monitored by TLC and LC-MS. After the reaction was complete, the mixture was filtered through a celite bed, and the filtrate was concentrated under reduced pressure. The solid obtained was diluted with water (100 mL) and extracted with ethyl acetate (2×100 mL). The combined organic layers were dried over sodium sulfate and concentrated under reduced pressure. The crude product was purified by column chromatography (30% ethyl acetate in pet ether) to give 2-chloropyrimidin-5-amine (1.5 g, 10.71 mmol, 50.24% yield) as a light-brown gummy compound. LC-MS ($ES^+$): m/*z* 130.1 $[M+H]^+$.

Step-2:

To the mixture of 2-chloropyrimidin-5-amine (3 g, 23.16 mmol) and tert-butyl 4-(4,4,5,5-tetramethyl-1,3,2-dioxaborolan-2-yl)-3,6-dihydro-2H-pyridine-1-carboxylate (8.59 g, 27.79 mmol) in dioxane (30 mL) and water (3 mL) was added Pd(dppf)$Cl_2$ (1.89 g, 2.32 mmol) and cesium carbonate (15.09 g, 46.32 mmol). The reaction was stirred at 100° C. for 12 hours. After the reaction was complete as shown by LC-MS, the reaction mixture was concentrated to give a residue, which was purified by flash column chromatography. (petroleum ether/ethyl acetate=1/1). The desired product tert-butyl 4-(5-aminopyrimidin-2-yl)-3,6-dihydro-2H-pyridine-1-carboxylate (5.42 g, 12.51 mmol, 54.04% yield) was obtained as a yellow solid. LC-MS ($ES^+$): m/*z* 276.9 $[M+H]^+$.

To a solution of tert-butyl 4-(5-aminopyrimidin-2-yl)-3,6-dihydro-2H-pyridine-1-carboxylate (5.42 g, 19.61 mmol) in ethanol (30 mL) was added palladium, 5% on activated carbon paste, (1.67 g, 15.69 mmol) under nitrogen atmosphere. The suspension was degassed and purged with hydrogen three times. The mixture was stirred under hydrogen (15 psi) at 25° C. for 4 h. After the completion of the reaction was confirmed by the LC-MS, the reaction mixture was filtered and concentrated to give a residue, which was purified by prep-TLC. (petroleum ether/ethyl acetate=1/1). The desired product tert-butyl 4-(5-aminopyrimidin-2-yl) piperidine-1-carboxylate (4.23 g, 11.96 mmol, 60.98% yield) was obtained as a yellow solid. LC-MS ($ES^+$): m/279.4 $[M+H]^+$.

Step-4: *z*

To the mixture of tert-butyl 4-(5-aminopyrimidin-2-yl) piperidine-1-carboxylate (3.5 g, 12.57 mmol) and 2,6-dibenzyloxy-3-bromo-pyridine (6.05 g, 16.35 mmol) in dioxane (20 mL) was added $Pd_2(dba)_3$ (1.15 g, 1.26 mmol), (5-diphenylphosphanyl-9,9-dimethyl-xanthen-4-yl)-diphenyl-phosphane (1.46 g, 2.51 mmol) and cesium carbonate (8.19 g, 25.15 mmol). The reaction was stirred at 100° C. for 12 hours, until LC-MS confirmed the completion of the reaction. The reaction mixture was then concentrated and purified by prep-TLC. (petroleum ether/ethyl acetate=2/1). The desired product tert-butyl 4-[5-[(2,6-dibenzyloxy-3-pyridyl) amino]pyrimidin-2-yl]piperidine-1-carboxylate (5.16 g, 3.35 mmol, 26.67% yield) was obtained as a yellow solid. LC-MS ($ES^+$): m/*z* 568.6 $[M+H]^+$.

Step-5:

To the solution of tert-butyl 4-[5-[(2,6-dibenzyloxy-3-pyridyl)amino]pyrimidin-2-yl]piperidine-1-carboxylate (50 mg, 88.08 μmol) in ethyl acetate (1.5 mL) was added 20 wt. % palladium hydroxide on carbon (24.74 mg, 176.16 μmol). The mixture was purged with hydrogen three times and stirred under a hydrogen atmosphere (15 psi) at 15° C. for 1 hour. After the reaction was complete, as shown by the LC-MS, the desired product tert-butyl 4-[5-[(2,6-dioxo-3-piperidyl)amino]pyrimidin-2-yl]piperidine-1-carboxylate (28 mg, 71.18 μmol, 80.81% yield) was obtained as a yellow solid, which was purified by prep-TLC (ethyl acetate). LC-MS ($ES^+$): m/*z* 334 $[M-55]^+$.

Step-6:

4 M Hydrogen chloride solution in dioxane (2 mL) was added to tert-butyl 4-[5-[(2,6-dioxo-3-piperidyl)amino]pyrimidin-2-yl]piperidine-1-carboxylate (150 mg, 385.16 μmol) at 10° C. The resulting mixture was warmed to room temperature and stirred for 16 hours. After completion of the reaction (as demonstrated by TLC and LC-MS), the reaction mixture was concentrated under reduced pressure, triturated with ether and lyophilized to afford 3-[[2-(4-piperidyl)pyrimidin-5-yl]amino]piperidine-2,6-dione HCl salt (90 mg, 256.28 μmol, 66.54% yield) as a yellow solid. $^1H$ NMR (400 MHz, DMSO-$d_6$) δ 10.87 (s, 1H), 9.03 (bs, 1H), 8.78 (bs, 1H), 8.27 (s, 2H), 4.50-4.46 (m, 1H), 3.31-3.29 (m, 2H), 3.05-2.97 (m, 3H), 2.72-2.68 (m, 1H), 2.62-2.58 (m, 1H), 2.07-1.88 (m, 6H). LC-MS ($ES^+$): m/*z* 290.1 $[M+H]^+$.

Synthesis of 3-[2-fluoro-4-(4-piperidyl)anilino]piperidine-2,6-dione

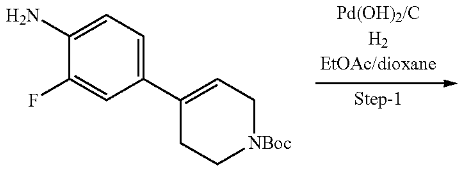

-continued

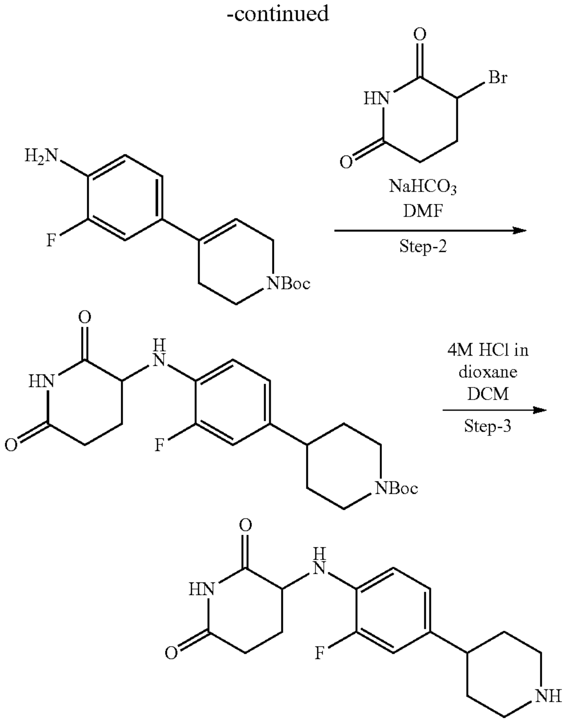

Step-1:

To a stirred solution of tert-butyl 4-(3-fluoro-4-nitro-phenyl)-3,6-dihydro-2H-pyridine-1-carboxylate (5.00 g, 15.51 mmol) in ethyl acetate (25 mL) and dioxane (25 mL), was added 20 wt. % palladium hydroxide on carbon (2.18 g, 15.51 mmol). Hydrogen gas was bubbled through the reaction for 10 minutes to saturate the solution, and the hydrogenation (1 atmosphere) was carried out at room temperature for 16 hours. Progress of the reaction was monitored by TLC and LC-MS. After completion, the reaction mixture was purged with nitrogen, and the catalyst was removed by filtration through a celite pad. The filtrate was concentrated under reduced pressure to afford crude tert-butyl 4-(4-amino-3-fluoro-phenyl)piperidine-1-carboxylate (4.2 g, 14.05 mmol, 90.60% yield) as a light brown liquid. LC-MS ($ES^+$): m/z 195.2 $[M+H-100]^+$.

Step-2:

In a seal tube, to a solution of tert-butyl 4-(4-amino-3-fluoro-phenyl)piperidine-1-carboxylate (1 g, 3.40 mmol) in DMF (10 mL) were added sodium bicarbonate (998.84 mg, 11.89 mmol) followed by 3-bromopiperidine-2,6-dione (1.63 g, 8.49 mmol) at room temperature under nitrogen atmosphere. The reaction mixture was stirred at 70° C. for 12 hours, and the reaction progress was monitored by TLC/LC-MS. After completion, the reaction mixture was diluted with water (20 mL) and extracted with ethyl acetate (3x30 mL). The organic layer was washed with brine solution (30 mL) and dried over sodium sulfate. The solution was then concentrated under reduced pressure to give the crude product, which was purified by column chromatography (silica gel, 60% ethyl acetate in pet ether) to afford tert-butyl 4-[4-[(2,6-dioxo-3-piperidyl)amino]-3-fluoro-phenyl]piperidine-1-carboxylate (0.6 g, 1.30 mmol, 38.31% yield) LC-MS ($ES^+$): m/z 306.2 $[M+H-100]^+$.

Step-3:

To a stirred solution of tert-butyl 4-[4-[(2,6-dioxo-3-piperidyl)amino]-3-fluoro-phenyl]piperidine-1-carboxylate (0.6 g, 1.48 mmol) in dioxane (4 mL) was added 4 M hydrogen chloride solution (369.95 L) at 5° C. under nitrogen atmosphere. The reaction mixture was stirred at room temperature for 6 hours, and the progress of the reaction was monitored by TLC and LC-MS. After completion of the reaction, the reaction mixture was concentrated under reduced pressure to afford 3-[2-fluoro-4-(4-piperidyl)anilino]piperidine-2,6-dione HCl salt (0.5 g, 1.45 mmol, 97.86% yield) as an off-white solid. LC-MS ($ES^+$): m/z 306.2 $[M+H]^+$.

Synthesis of 3-[3-chloro-4-(4-piperidyl)anilino]piperidine-2,6-dione

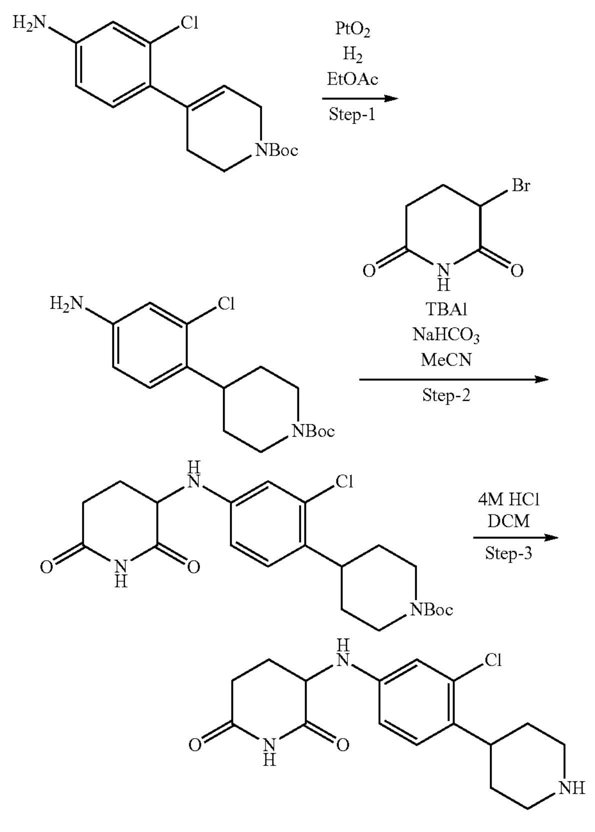

Step-1:

To a solution of tert-butyl 4-(4-amino-2-chloro-phenyl)-3,6-dihydro-2H-pyridine-1-carboxylate (1 g, 3.24 mmol) in ethyl acetate (30 mL) was added $PtO_2$ (303.70 mg, 1.34 mmol) and the system was purged with $N_2$ for three times. The mixture was stirred at 20° C. for 12 hours, and the reaction progress was monitored by LC-MS. After the reaction was complete, the reaction mixture was filtered, and the filtrate was concentrated in vacuo. Compound tert-butyl 4-(4-amino-2-chlorophenyl)piperidine-1-carboxylate (0.44 g, 1.38 mmol, 42.56% yield) was obtained as a black solid and was used for the next step without purification. LC-MS ($ES^+$): m/z 255.1 $[M-tBu+H]^+$.

Step-2:

To a solution of tert-butyl 4-(4-amino-2-chloro-phenyl) piperidine-1-carboxylate (2.1 g, 6.76 mmol) and 3-bromopiperidine-2,6-dione (1.95 g, 10.13 mmol) in acetonitrile (4 mL) was added tetrabutylammonium iodide (249.56 mg, 675.64 μmol) and sodium bicarbonate (1.70 g, 20.27 mmol). The mixture was stirred at 90° C. for 12 hours, and the reaction progress was monitored by LC-MS. After completion of the reaction, the reaction mixture was concentrated under reduced pressure to remove the solvent. The residue was purified by column chromatography (silica gel, petroleum ether/ethyl acetate=100/1 to 3/1) Compound tert-butyl 4-(2-chloro-4-((2,6-dioxopiperidin-3-yl)amino)phenyl)piperidine-1-carboxylate (0.8 g, 1.65 mmol, 34.18% yield) was obtained as blue solid. LC-MS ($ES^+$): m/z 366.0 $[M-tBu+H]^+$.

Step-3:

To a stirred solution of tert-butyl 4-[2-chloro-4-[(2,6-dioxo-3-piperidyl)amino]phenyl]piperidine-1-carboxylate (0.1 g, 237.01 μmol) in DCM (10 mL) at 0° C. was added 4 M HCl in dioxane (0.5 mL) dropwise. The reaction was stirred at 27° C. for 3 hours. The reaction was concentrated under reduced pressure to get crude. The crude was triturated with ether to give 3-[3-chloro-4-(4-piperidyl)anilino]piperidine-2,6-dione HCl salt (0.084 g, 231.70 μmol, 97.76% yield) as an off-white solid. LC-MS ($ES^+$): m/z 322.16 $[M+H]^+$.

Synthesis of 3-[4-(4-piperidyl)phenoxy]piperidine-2,6-dione

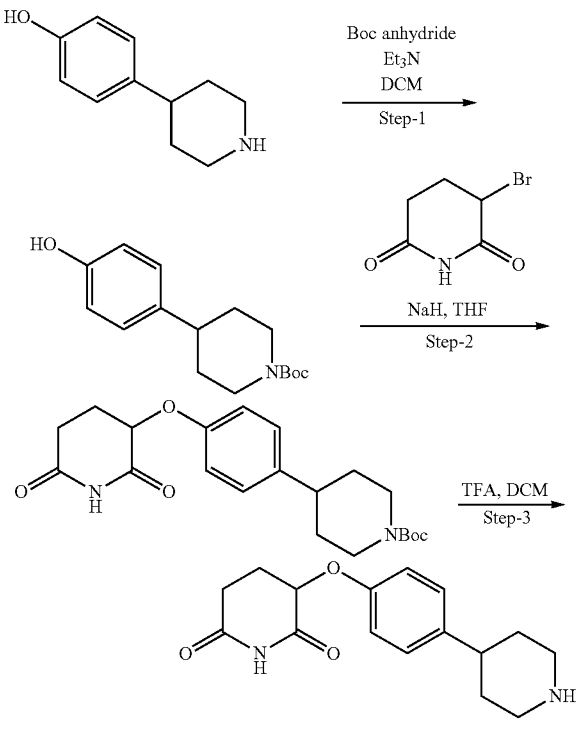

Step-1:

A solution of 4-(4-piperidyl)phenol HBr salt (2.00 g, 7.75 mmol) in DCM (20 mL) was added to a 100 mL round bottom flask. Tert-butoxycarbonyl tert-butyl carbonate (2.03 g, 9.30 mmol, 2.13 mL) and triethylamine (3.92 g, 38.74 mmol, 5.40 mL) were added, and the resulting mixture was stirred at room temperature for 2 hours. After completion of the reaction (confirmed by TLC), the reaction mixture was diluted with ethyl acetate (50 mL) and consecutively washed with water (20 mL) and brine (20 mL). The organic layer was dried over anhydrous sodium sulfate, filtered, and concentrated to obtain the crude product, which was purified by flash column chromatography (silica gel 230-400 mesh, 0-80% ethyl acetate in pet ether) to afford tert-butyl 4-(4-hydroxyphenyl)piperidine-1-carboxylate (1.8 g, 6.45 mmol, 83.22% yield) as a white solid. LC-MS ($ES^+$): m/z 178.2 $[M-Boc+H]^+$.

Step-2:

Sodium hydride (93.78 mg, 3.61 mmol) was added slowly to a stirred solution of tert-butyl 4-(4-hydroxyphenyl)piperidine-1-carboxylate (1.0 g, 3.61 mmol) in THF (10 mL) at 0° C. After addition, the reaction mixture was heated at 70° C. for 30 minutes. It was cooled to 0° C. again before 3-bromopiperidine-2,6-dione (553.83 mg, 2.88 mmol) was added very slowly, after which the reaction mixture was heated at 70° C. for 2 hours. Progress of the reaction was monitored by TLC. Upon completion, the reaction was quenched by ammonium chloride and extracted with ethyl acetate, concentrated under reduced pressure to give the crude product, which was purified by column chromatography (silica gel 230-400 mesh, 0-50% ethyl acetate in pet-ether) to afford tert-butyl 4-[4-[(2,6-dioxo-3-piperidyl)oxy]phenyl]piperidine-1-carboxylate (0.5 g, 1.05 mmol, 29.17% yield). LC-MS ($ES^+$): m/z 411.41 $[M+Na]^+$.

Step-3:

To a solution of tert-butyl 4-[4-[(2,6-dioxo-3-piperidyl)oxy]phenyl]piperidine-1-carboxylate (0.55 g, 1.42 mmol) in DCM (5 mL) was added. 2,2,2-trifluoroacetic acid (161.44 mg, 1.42 mmol, 109.08 μL) at 0° C. and the reaction mixture was stirred at room temperature for 1 h. The reaction mixture was then concentrated in vacuo to give the crude product, which was triturated with diethyl ether (20 mL) to afford 3-[4-(4-piperidyl)phenoxy]piperidine-2,6-dione TFA salt (0.5 g, 1.13 mmol, 80.02% yield) as a white solid. LC-MS ($ES^+$): m/z 289.28 $[M+H]^+$.

Synthesis of 3-(3-fluoro-4-(piperidin-4-yl)phenoxy)piperidine-2,6-dione

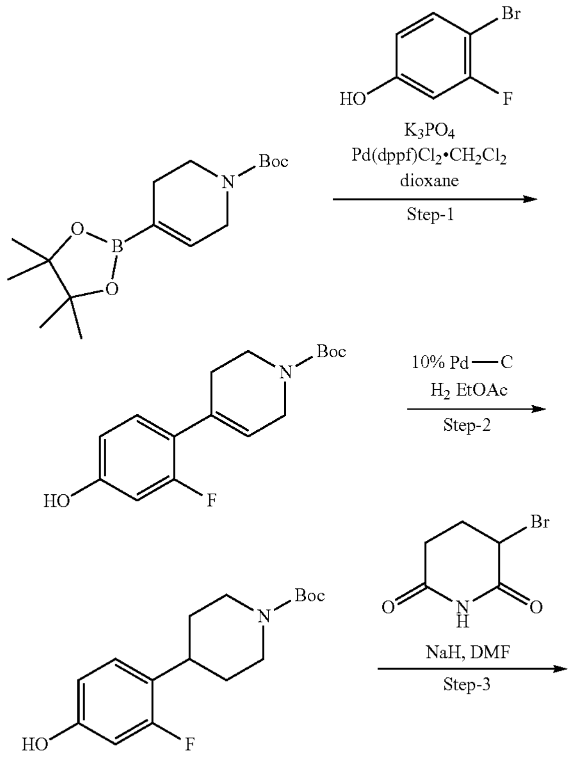

-continued

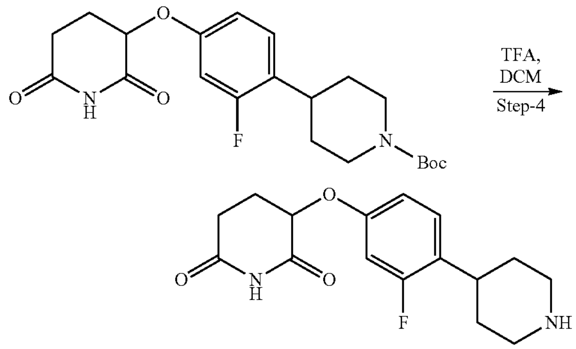

Step-1:

A solution of 4-bromo-3-fluoro-phenol (500 mg, 2.62 mmol), tert-butyl 4-(4,4,5,5-tetramethyl-1,3,2-dioxaborolan-2-yl)-3,6-dihydro-2H-pyridine-1-carboxylate (971.34 mg, 3.14 mmol) and potassium phosphate tribasic anhydrous (1.39 g, 6.54 mmol) in 1,4-dioxane (10 mL) was purged with nitrogen for 5 minutes and Pd(dppf)$Cl_2$—$CH_2Cl_2$ (213.78 mg, 261.78 μmol) was added. The resulting mixture was stirred for 3 hr at 100° C. It was then cooled to ambient temperature, diluted with ethyl acetate, filtered through celite, and washed with ethyl acetate. The solvent was evaporated completely under reduced pressure, and the crude product was purified by column chromatography (silica) with 0 to 20% ethyl acetate in pet ether as eluent to yield tert-butyl 4-(2-fluoro-4-hydroxy-phenyl)-3,6-dihydro-2H-pyridine-1-carboxylate (690 mg, 2.28 mmol, 87.16% yield) as an off white solid. LC-MS ($ES^+$): m/z 194.0 $[M-Boc+H]^+$.

Step-2:

To a stirred solution of tert-butyl 4-(2-fluoro-4-hydroxy-phenyl)-3,6-dihydro-2H-pyridine-1-carboxylate (690 mg, 2.35 mmol) in ethyl acetate (50 mL) was added palladium, 10% on carbon, Type 487, dry (100 mg, 939.67 μmol) under nitrogen pressure. The resulting mixture was stirred for 2 hr at 25° C. The resulting mixture was filtered through celite and washed with ethyl acetate (100 mL). The solvent was evaporated completely under reduced pressure to yield tert-butyl 4-(2-fluoro-4-hydroxy-phenyl)piperidine-1-carboxylate (650 mg, 2.15 mmol, 91.50% yield) as an off white solid. LC-MS ($ES^+$): m/z 196.2 $[M-Boc+H]^+$.

The procedures from step-3 to step-4 are identical to the synthesis of intermediate 3-[4-(4-piperidyl)phenoxy]piperidine-2,6-dione, and the product 3-(3-fluoro-4-(piperidin-4-yl)phenoxy)piperidine-2,6-dione was confirmed by LC-MS. LC-MS ($ES^+$): m/z 307.11 $[M+H]^+$.

Synthesis of 3-((6-(piperidin-4-yl)pyridin-3-yl)oxy)piperidine-2,6-dione

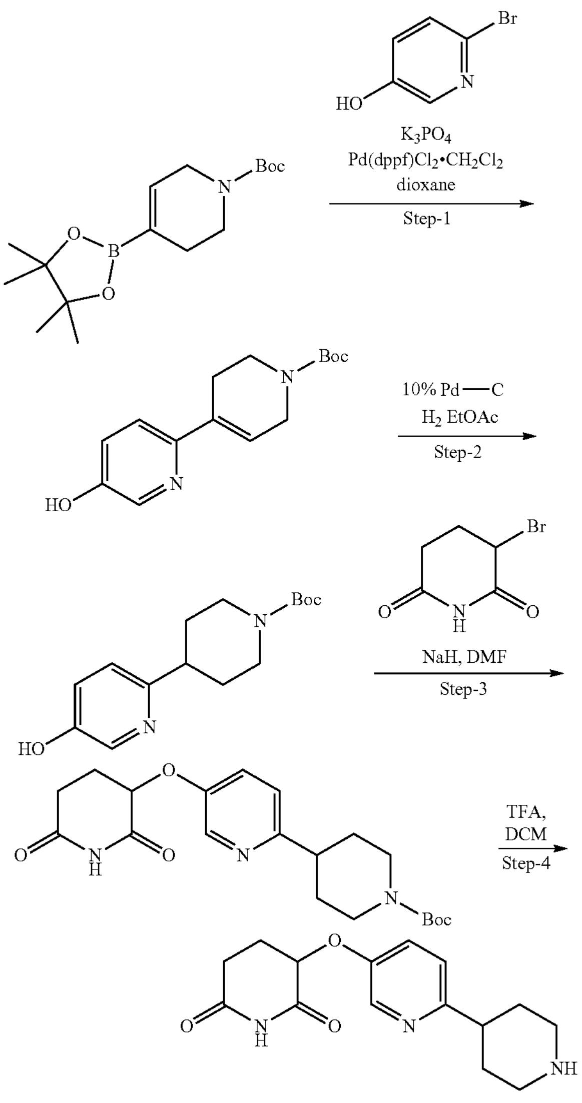

The procedures from step-1 to step-4 are identical to the synthesis of intermediate 3-[4-(4-piperidyl)phenoxy]piperidine-2,6-dione, and the product 3-((6-(piperidin-4-yl)pyridin-3-yl)oxy)piperidine-2,6-dione was confirmed by LC-MS. LC-MS ($ES^+$): m/z 290.55 $[M+H]^+$.

Synthesis of 3-[4-(4-piperidyl)phenyl]piperidine-2,6-dione

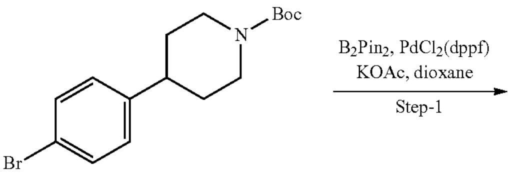

-continued

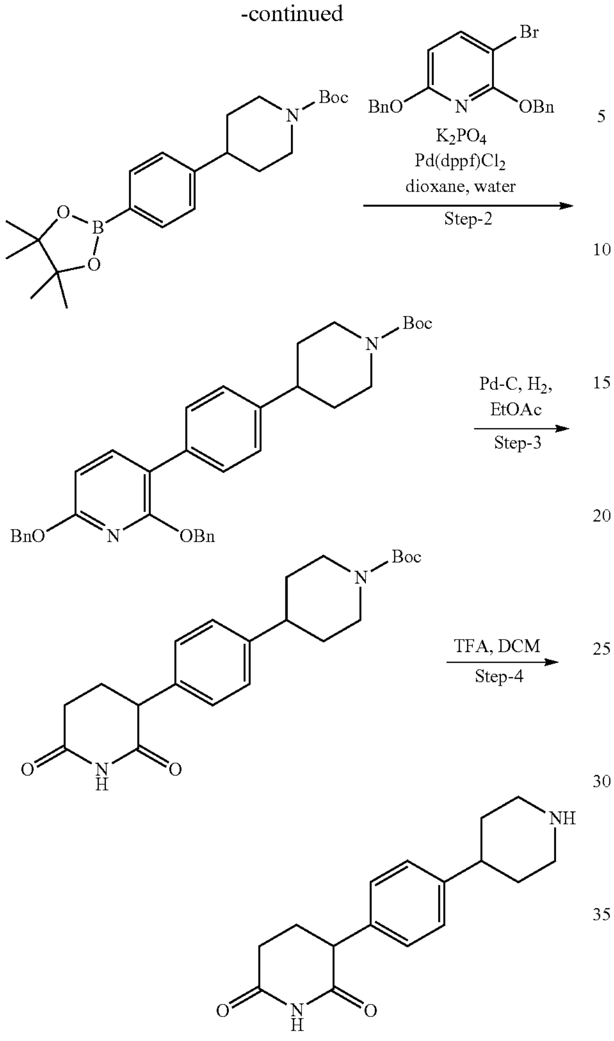

Step-1:

To a 500 mL round bottom flask was added a solution of tert-butyl 4-(4-bromophenyl)piperidine-1-carboxylate (10 g, 29.39 mmol) in 1,4-dioxane (100 mL) was added 4,4,5,5-tetramethyl-2-(4,4,5,5-tetramethyl-1,3,2-dioxaborolan-2-yl)-1,3,2-dioxaborolane (11.19 g, 44.08 mmol) followed by the addition of potassium acetate (8.65 g, 88.17 mmol) at room temperature under argon atmosphere. The reaction mixture was degassed with argon for 20 minutes, after which $Pd(dppf)Cl_2$ (2.40 g, 2.94 mmol) was added, and the reaction was heated at 100° C. for 6 hours while monitoring with TLC and LC-MS. After completion of the reaction, the volatiles was removed under reduced pressure, and the residue was extracted with ethyl acetate (200 mL×3) and water (200 mL). The combined organic layers were washed with brine solution (200 mL), dried over anhydrous sodium sulfate, filtered, and concentrated under reduced pressure. The crude product was purified by column chromatography (silica gel 100-200 mesh, 0-30% EtOAc in pet-ether) to afford tert-butyl 4-[4-(4,4,5,5-tetramethyl-1,3,2-dioxaborolan-2-yl)phenyl]piperidine-1-carboxylate (10 g, 24.27 mmol, 82.58% yield) as a pale yellow solid. LC-MS ($ES^+$): m/z 332.41 $[M-56+H]^+$.

Step-2:

To a 500 mL round bottom flask was added a solution of tert-butyl 4-[4-(4,4,5,5-tetramethyl-1,3,2-dioxaborolan-2-yl)phenyl]piperidine-1-carboxylate (10 g, 25.82 mmol) in 1,4 dioxane (120 mL) and water (30 mL), followed by the addition of 2,6-dibenzyloxy-3-bromo-pyridine (10.04 g, 27.11 mmol) and potassium phosphate tribasic anhydrous (16.44 g, 77.46 mmol) at room temperature under argon atmosphere. The reaction mixture was degassed with argon for 20 minutes, after which $Pd(dppf)Cl_2$ (1.89 g, 2.58 mmol) was added, and the reaction was heated at 110° C. for 16 hours while monitoring with TLC and LC-MS. Upon completion of the reaction, the catalyst was filtered off through a celite bed and washed with ethyl acetate (100 mL×3). The filtrate was washed with water (100 mL) and brine solution (100 mL). The combined organic layers were dried over anhydrous sodium sulfate, filtered, and concentrated under reduced pressure. The crude product was purified by column chromatography (silica gel 230-400 mesh, 0-40% ethyl acetate in pet-ether) to afford the desired product as a thick yellow liquid, which was triturated with pet ether to furnish pure tert-butyl 4-[4-(2,6-dibenzyloxy-3-pyridyl)phenyl]piperidine-1-carboxylate (7 g, 11.57 mmol, 44.80% yield) as a white color solid. LC-MS ($ES^+$): m/z 551.43 $[M+H]^+$.

Step-3:

A solution of tert-butyl 4-[4-(2,6-dibenzyloxy-3-pyridyl)phenyl]piperidine-1-carboxylate (14 g, 25.42 mmol) in ethyl acetate (420 mL) was added 10% wt. palladium on charcoal (14 g, 25.42 mmol), and the reaction was stirred under hydrogen pressure (70 psi) at room temperature for 16 hours. The reaction progress was monitored by TLC and LC-MS. After the reaction was complete, the catalyst was filtered off through celite and washed with ethyl acetate (200 mL). The filtrate was concentrated under reduced pressure, and the residue was triturated in pentane (100 mL) and diethyl ether (100 mL), dried and concentrated under reduced pressure to afford tert-butyl 4-[4-(2,6-dioxo-3-piperidyl)phenyl]piperidine-1-carboxylate (8.6 g, 23.05 mmol, 90.65% yield) as a white solid. LC-MS ($ES^+$): m/z 371.23 $[M-H]^-$.

Step-4:

To a stirred solution of tert-butyl 4-[4-(2,6-dioxo-3-piperidyl)phenyl]piperidine-1-carboxylate (250 mg, 671.22 μmol) in DCM (5 mL) was added TFA (5.92 g, 51.92 mmol, 4 mL) at 0° C. The reaction was stirred for 2 hours, and the reaction progress was monitored by LC-MS and TLC. Upon completion, the reaction mixture was concentrated in vacuo to yield the crude product, which was triturated with diethyl ether to obtain the desired product 3-[4-(4-piperidyl)phenyl]piperidine-2,6-dione TFA salt (250 mg, 404.22 μmol, 60.22% yield) as a brown liquid. LC-MS ($ES^+$): m/z 371.23 $[M-H]^-$.

Synthesis of 3-(3-fluoro-4-(piperidin-4-yl)phenyl)piperidine-2,6-dione

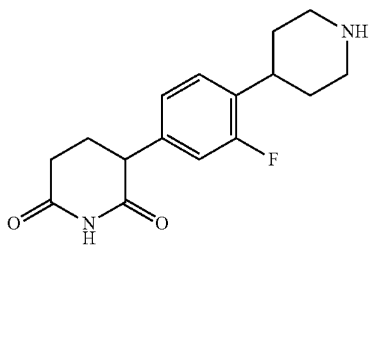 [SMILES: O=C1CCC(c2ccc(C3CCNCC3)c(F)c2)C(=O)N1]

The procedures were substantially similar to those of 3-[4-(4-piperidyl)phenyl]piperidine-2,6-dione, except the synthesis started with tert-butyl 4-(4-bromo-2-fluoro-phenyl)piperidine-1-carboxylate instead of tert-butyl 4-(4-bromophenyl)piperidine-1-carboxylate and palladium hydroxide was used instead of palladium for step-3. 3-(3-fluoro-4-(piperidin-4-yl)phenyl)piperidine-2,6-dione. LC-MS ($ES^+$): m/z 291.37 $[M+H]^+$ Synthesis of 3-(3,5-difluoro-4-(piperidin-4-yl)phenyl)piperidine-2,6-dione

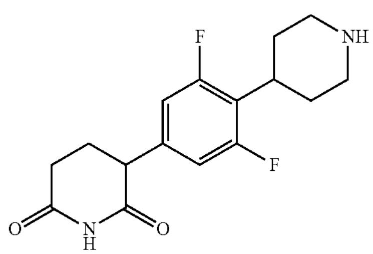 [SMILES: O=C1CCC(c2cc(F)c(C3CCNCC3)c(F)c2)C(=O)N1]

The procedures are substantially similar to those of 3-[4-(4-piperidyl)phenyl]piperidine-2,6-dione, except XPhos Pd G2 was used as catalyst instead of $Pd(dppf)Cl_2$ for step-2, and 4 M HCl in dioxane was used for the deprotection, instead of trifluoroacetic acid for step-4.

3-(3,5-difluoro-4-(piperidin-4-yl)phenyl)piperidine-2,6-dione. LC-MS ($ES^+$): m/z 309.1 $[M+H]^+$.

Synthesis of 3-[4-(3,3-difluoro-4-piperidyl)phenyl]piperidine-2,6-dione

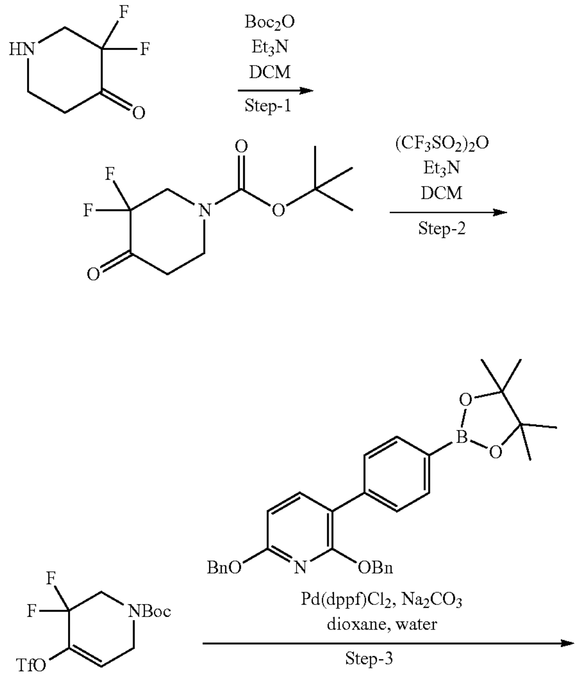

-continued

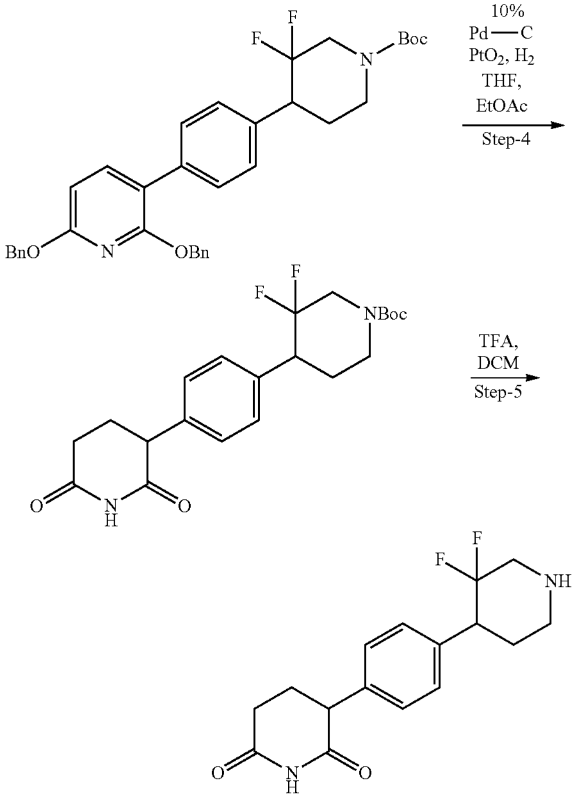

Step-1:

To a stirred solution of 3,3-difluoropiperidin-4-one (0.5 g, 3.70 mmol) in DCM (10 mL) was added triethylamine (561.70 mg, 5.55 mmol, 773.69 μL) and the reaction mixture was stirred for 10 minutes. Tert-butoxycarbonyl tert-butyl carbonate (969.18 mg, 4.44 mmol, 1.02 mL) was then added and stirred at room temperature for 16 hours. Progress of the reaction was monitored by TLC and LC-MS. Upon completion, the reaction was quenched by adding water (10 mL) and stirred for 5 min. The mixture was then extracted with DCM (2×10 mL). The organic layer was washed with 10 mL of brine, dried over anhydrous sodium sulfate, and concentrated under reduced pressure to obtain the crude product as a brown gummy solid. (700 mg, 48.25% yield). $^1H$ NMR (400 MHz, DMSO-$d_6$) δ 6.38 (s, 2H), 3.60 (t, J=11.6 Hz, 2H), 3.37 (bs, 2H), 1.68 (bs, 2H), 1.39 (s, 9H). The compound is in hydrate form.

Step-2:

To a stirred solution of tert-butyl 3,3-difluoro-4-oxo-piperidine-1-carboxylate (5 g, 21.26 mmol) in DCM (50 mL) was added triethylamine (6.45 g, 63.77 mmol, 8.89 mL) and the reaction was stirred for 1 hour at −30° C. This is followed by the addition of trifluoromethyl sulfonyl trifluoromethane sulfonate (9.00 g, 31.88 mmol, 5.36 mL), and the reaction was stirred at −30° C. for 16 hours and monitored by LC-MS and TLC. Upon completion, the reaction was quenched with water (3×50 ml) and extracted with DCM (3×50 ml). The organic layer was dried over sodium sulfate and concentrated under reduced pressure to yield a crude product, which was purified by column chromatography (Devisil-silica, 7% ethyl acetate/petroleum ether) to afford compound tert-butyl 3,3-difluoro-4-(trifluoromethylsulfonyloxy)-2,6-dihydropyridine-1-carboxylate (1.8 g, 4.42 mmol, 20.80% yield) as a yellow gummy liquid. LC-MS ($ES^+$): m/z 268.16 $[M-Boc+H]^+$.

Step-3:

To the stirred solution of tert-butyl 3,3-difluoro-4-(trifluoromethylsulfonyloxy)-2,6-dihydropyridine-1-carboxylate (3.5 g, 9.53 mmol) and 2,6-dibenzyloxy-3-[4-(4,4,5,5-tetramethyl-1,3,2-dioxaborolan-2-yl)phenyl]pyridine (5.64 g, 11.44 mmol) in dioxane (40 mL) water (10 mL) was added sodium carbonate (2.52 g, 23.82 mmol). The mixture was degassed with $N_2$ and Pd(dppf)$Cl_2$ (697.26 mg, 952.93 μmol) was added at room temperature. The reaction was stirred for 12 hours at 60° C., and the progress was monitored by TLC and LC-MS. After the reaction was complete, it was diluted with water (50 mL) and extracted with ethyl acetate (150 mL×3). The combined organic layers were dried over sodium sulfate and concentrated under reduced pressure to yield the crude product, which was purified by column chromatography (20-30% ethyl acetate in pet ether) to afford tert-butyl 4-[4-(2,6-dibenzyloxy-3-pyridyl)phenyl]-3,3-difluoro-2,6-dihydropyridine-1-carboxylate (2.0 g, 2.84 mmol, 29.80% yield) as a brown solid. LC-MS ($ES^+$): m/z 585.44 $[M+H]^+$.

Step-4:

To the stirred solution of tert-butyl 4-[4-(2,6-dibenzyloxy-3-pyridyl)phenyl]-3,3-difluoro-2,6-dihydropyridine-1-carboxylate (2 g, 3.42 mmol) in THF (40 mL) ethyl acetate (10 mL) was added 10 wt. % palladium on carbon wet (1.82 g, 17.10 mmol) and $PtO_2$ (932.15 mg, 4.11 mmol). The reaction was stirred for 12 hours at room temperature under a hydrogen atmosphere, and the reaction progress was monitored by the TLC and LC-MS. After completion, the reaction mixture was filtered through celite using ethyl acetate, and the filtrate was concentrated under reduced pressure to yield the crude product, which was triturated with diethyl ether. The diethyl ether layer was decanted, and desired product was dried under reduced pressure to afford tert-butyl 4-[4-(2,6-dioxo-3-piperidyl)phenyl]-3,3-difluoro-piperidine-1-carboxylate (995 mg, 2.22 mmol, 64.92% yield). LC-MS ($ES^+$): m/z 407.12 $[M-H]^-$.

Step-5:

To a stirred solution of tert-butyl 4-[4-(2,6-dioxo-3-piperidyl)phenyl]-3,3-difluoro-piperidine-1-carboxylate (0.1 g, 244.84 μmol) in DCM (2 mL) was added TFA (4.44 g, 38.94 mmol, 3 mL) under nitrogen and the reaction was stirred at 0-28° C. for 2 hours. The reaction progress was monitored by TLC and LC-MS. Upon completion, the reaction was evaporated to dryness and washed with diethyl ether (10 mL×2) to afford 3-[4-(3,3-difluoro-4-piperidyl)phenyl]piperidine-2,6-dione TFA salt (85 mg, 100.63 μmol, 41.10% yield) as a solid. LC-MS ($ES^+$): m/z 309.00 $[M+H]^+$.

Synthesis of 1-[4-(4-piperidyl)phenyl]hexahydropyrimidine-2,4-dione

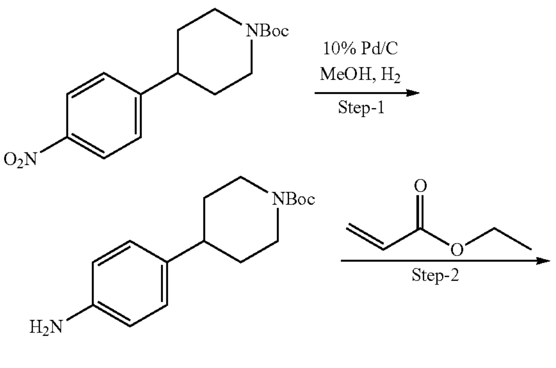

-continued

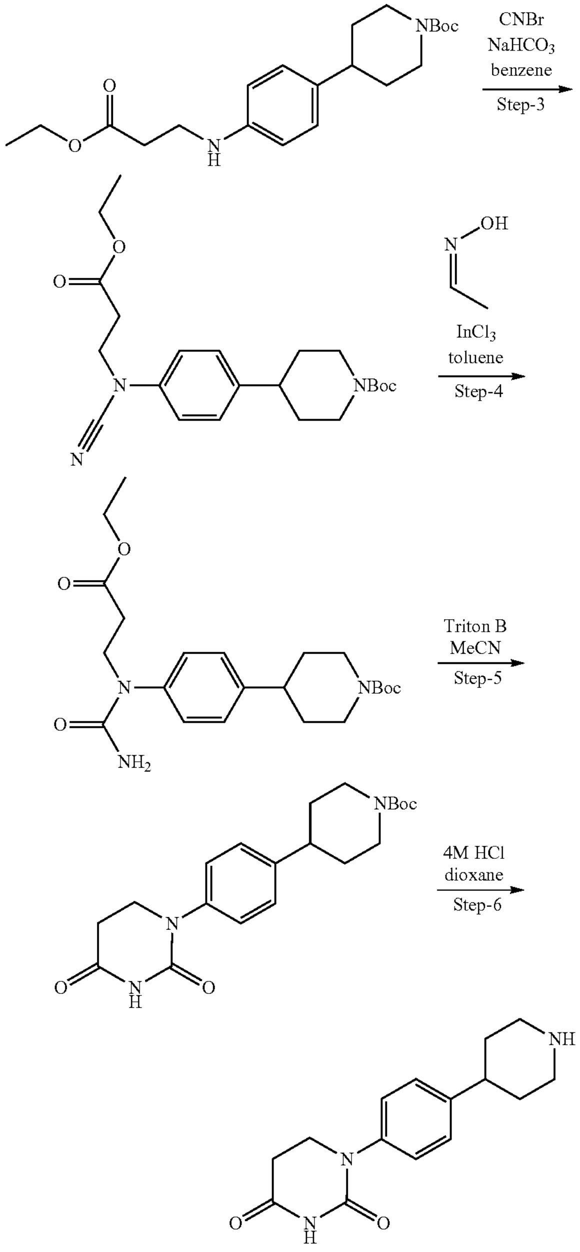

Step-1:

A solution of tert-butyl 4-(4-nitrophenyl)-3,6-dihydro-2H-pyridine-1-carboxylate (15.0 g, 49.29 mmol) in methanol (300 mL) was degassed argon gas for 10 minutes. To the reaction mixture was added 10 wt. % palladium on carbon (10.49 g, 98.57 mmol) at room temperature, and the hydrogenation was carried out at 70 psi using parr apparatus for 16 hours. The progress of the reaction was monitored by LC-MS. Upon completion, the reaction was filtered through a celite bed and washed with methanol (4×20 mL). The organic layer was concentrated under reduced pressure at 45° C. to afford the desired product tert-butyl 4-(4-aminophenyl)piperidine-1-carboxylate (11.8 g, 34.14 mmol, 69.26% yield) as an off-white solid, which was taken to the next step without any further purification. LC-MS ($ES^+$): m/z 177.17 $[M-100+H]^+$.

Step-2:

A mixture of tert-butyl 4-(4-aminophenyl)piperidine-1-carboxylate (16 g, 57.89 mmol), DBU lactic acid (ionic liquid) (10.28 g, 34.74 mmol) and ethyl acrylate (7.53 g, 75.26 mmol, 8.02 mL) was stirred at 90° C. for 3 hours. The progress of the reaction was monitored by TLC and LC-MS. Upon completion, the reaction was allowed cool to room temperature and diluted with ethyl acetate. The aqueous layer was separated, and the organic layer was dried over anhydrous sodium sulfate and concentrated to yield the crude product, which was purified by CombiFlash® using 5-10% ethyl acetate in hexane as eluent to afford tert-butyl 4-[4-[(3-ethoxy-3-oxo-propyl)amino]phenyl]piperidine-1-carboxylate (12.5 g, 31.54 mmol, 54.48% yield) as a gummy yellow liquid. LC-MS ($ES^+$): m/z 321.2 $[M-tBu+H]^+$.

Step-3:

To the stirred solution of tert-butyl 4-[4-[(3-ethoxy-3-oxo-propyl)amino]phenyl]piperidine-1-carboxylate (15 g, 39.84 mmol) in benzene (100 mL), cyanogen bromide (6.75 g, 63.75 mmol, 3.34 mL) and sodium bicarbonate (5.36 g, 63.75 mmol) were added simultaneously. The reaction was stirred for 24 hours at room temperature. After complete consumption of the starting material as monitored by TLC, the reaction mixture was diluted with ethyl acetate (20 ml). The organic phase was washed with water, separated, dried over sodium sulfate, and concentrated under vacuum to give a crude residue, which was purified by column chromatography to afford tert-butyl 4-[4-[cyano-(3-ethoxy-3-oxo-propyl)amino]phenyl]piperidine-1-carboxylate (12.5 g, 29.58 mmol, 74.24% yield). as a semi-solid. LC-MS ($ES^+$): m/z 402.2 $[M+H]^+$.

Step-4:

A stirred solution of tert-butyl 4-[4-[cyano-(3-ethoxy-3-oxo-propyl)amino]phenyl]piperidine-1-carboxylate (12.5 g, 31.13 mmol), trichloroindigane (2.07 g, 9.34 mmol) and (1Z)-acetaldehyde oxime (5.52 g, 93.40 mmol) in toluene (100 mL) was refluxed for 1 hour. After complete consumption of the starting material as monitored by TLC, the reaction mixture was concentrated in vacuo and washed with pentane to obtain tert-butyl 4-[4-[carbamoyl-(3-ethoxy-3-oxo-propyl)amino]phenyl]piperidine-1-carboxylate (12 g, 26.03 mmol, 83.61% yield) as a gummy liquid, which was used in the next step without further purification. LC-MS ($ES^+$): m/z 364.4 $[M-tBu+H]^+$.

Step-5:

A solution of tert-butyl 4-[4-[carbamoyl-(3-ethoxy-3-oxo-propyl)amino]phenyl]piperidine-1-carboxylate (12 g, 28.60 mmol) in acetonitrile (120 mL) was heated at 60° C. with stirring. Triton B (40% in methanol) (17.94 g, 42.91 mmol, 19.50 mL) was added to the mixture, and the reaction was stirred at the same temperature for 10 minutes. After complete consumption of the starting material (confirmed by TLC and LC-MS), the reaction mixture was concentrated in vacuo, and the crude residue was purified by column chromatography to afford tert-butyl 4-[4-(2,4-dioxohexahydropyrimidin-1-yl)phenyl]piperidine-1-carboxylate (8 g, 21.21 mmol, 74.14% yield) as a white solid. LC-MS ($ES^+$): m/z 318.1 $[M-tBu+H]^+$.

Step-6:

To a stirred suspension of tert-butyl 4-[4-(2,4-dioxohexahydropyrimidin-1-yl)phenyl]piperidine-1-carboxylate (13.50 g, 36.15 mmol) in dioxane (40 mL) was added 4 M HCl in dioxane (50 mL) at 0° C. and reaction mixture was stirred for 3 hours at room temperature. After completion of the reaction as evidenced from LC-MS, the volatiles are removed under vacuum to afford 1-[4-(4-piperidyl)phenyl]hexahydropyrimidine-2,4-dione HCl salt (11.1 g, 34.77 mmol, 96.18% yield) as a white solid. LC-MS ($ES^+$): m/z 274.4 $[M+H]^+$.

Synthesis of 3-[4-[2-(methylamino)ethyl]phenyl]piperidine-2,6-dione

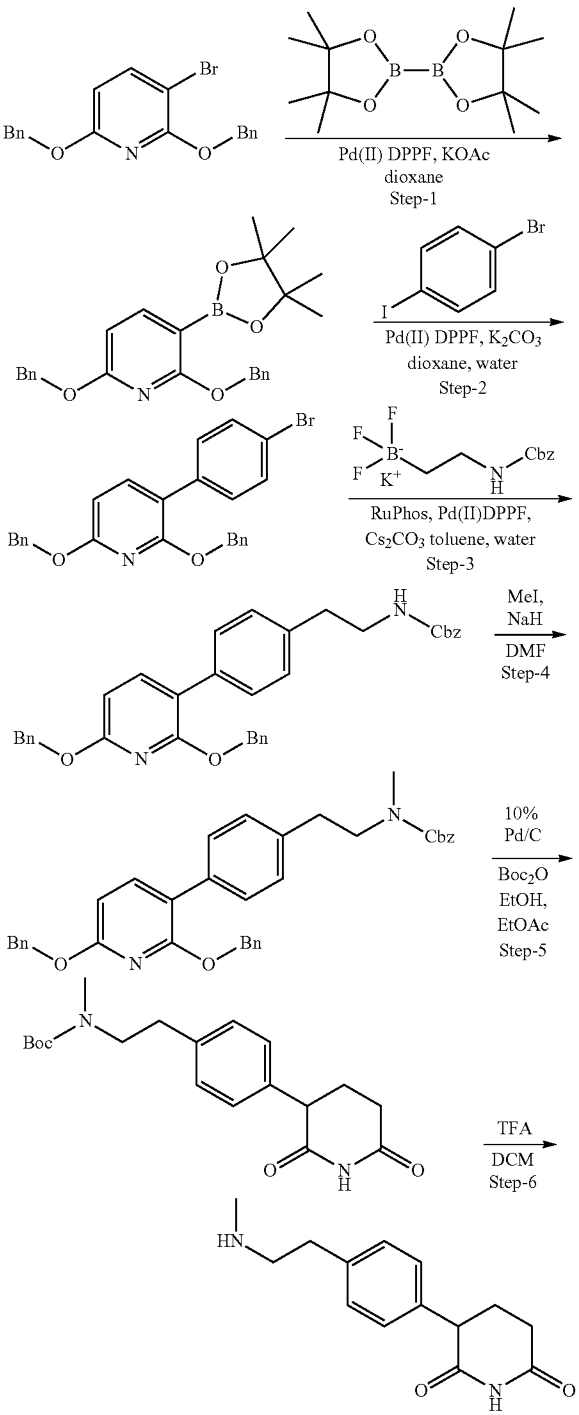

Step-1:

To a stirred solution of 2,6-dibenzyloxy-3-bromo-pyridine (25 g, 67.52 mmol) and 4,4,5,5-tetramethyl-2-(4,4,5,5-tetramethyl-1,3,2-dioxaborolan-2-yl)-1,3,2-dioxaborolane (25.72 g, 101.29 mmol) in 1,4-Dioxane (250 mL) was added potassium acetate (13.25 g, 135.05 mmol, 8.44 mL) at room temperature. Then the reaction mixture was degassed with argon gas for 10 min, and then Pd(dppf)$Cl_2$ (2.76 g, 3.38 mmol) was added. The reaction mixture was again degassed with argon gas for 2 min, and the reaction mixture was stirred at 100° C. for 16 hours. On completion of the reaction, the reaction mixture was concentrated under reduced pressure, and the residue obtained was dissolved in ethyl acetate (200 mL). The organic layer was washed with water (2×100 mL), dried over anhydrous sodium sulfate, and concentrated under reduced pressure. The residue obtained was purified by silica gel column chromatography using 5% ethyl acetate in pet ether as an eluent to afford 2,6-dibenzyloxy-3-(4,4,5,5-tetramethyl-1,3,2-dioxaborolan-2-yl) pyridine (15.2 g, 23.69 mmol, 35.09% yield) as white solid. LC-MS ($ES^+$): m/z 418.26 $[M+H]^+$.

Step-2:

To a stirred solution of (4-bromophenyl)boronic acid (18 g, 89.63 mmol) and 2,6-dibenzyloxy-3-iodo-pyridine (37.40 g, 89.63 mmol) in dioxane (240 mL) water (30 mL) was added $K_2CO_3$ (37.16 g, 268.89 mmol, 16.23 mL). The reaction mixture was degassed under nitrogen pressure, Pd(dppf)$Cl_2$ (6.56 g, 8.96 mmol) was added at room temperature, and the reaction was stirred for 12 hours at 70° C. The reaction mixture was diluted with water and extracted with ethyl acetate. The combined organic phase was collected and dried over sodium sulfate and concentrated under reduced pressure. The crude material was purified by column chromatography using 2-4% ethyl acetate in pet ether as an eluent to afford 2,6-dibenzyloxy-3-(4-bromophenyl) pyridine (12 g, 18.82 mmol, 21.00% yield) as a white solid. LC-MS ($ES^+$): m/z 446.15 $[M+H]^+$.

Step-3:

To a stirred solution of 2,6-dibenzyloxy-3-(4-bromophenyl)pyridine (1 g, 2.24 mmol) and potassium (2-{[(benzyloxy)carbonyl]amino}ethyl)(trifluoro)borate (958.14 mg, 3.36 mmol) in toluene (15 mL) was added an aqueous solution of cesium carbonate (2.19 g, 6.72 mmol) and purged with argon for 10 mins. Then 2-dicyclohexylphosphino-2',6'-diisopropoxybiphenyl (209.08 mg, 448.09 μmol) and Pd(dppf)$Cl_2$ (163.94 mg, 224.05 μmol) were added and degassed with argon. The reaction mixture was heated to 110° C. for 3 hours. After completion, the reaction mixture was diluted with ethyl acetate and filtered through celite, and the resulting filtrate was washed with a brine solution. The combined organic layer was dried over anhydrous sodium sulfate, concentrated under reduced pressure. The crude product was purified by silica gel column chromatography to give benzyl N-[2-[4-(2,6-dibenzyloxy-3-pyridyl)phenyl] ethyl]carbamate (1.2 g, 1.87 mmol, 83.59% yield) as an off-white solid. LC-MS ($ES^+$): m/z 545.33 $[M+H]^+$ Step-4:

Sodium hydride (60% dispersion in mineral oil) (113.97 mg, 4.96 mmol) was taken up in DMF (10 mL) under an inert atmosphere at 0° C. Benzyl N-[2-[4-(2,6-dibenzyloxy-3-pyridyl)phenyl]ethyl]carbamate (0.9 g, 1.65 mmol) in DMF was added dropwise and stirred for 30 mins. Then, methyl iodide (469.10 mg, 3.30 mmol, 205.75 μL) was added, and the reaction mixture was stirred at room temperature for 16 hours. After completion, the reaction mixture was quenched with ice-cold water and extracted with ethyl acetate. The combined organic layer was dried over $Na_2SO_4$, concentrated under reduced pressure. The crude material was purified by silica gel column chromatography (230-400) using 30% ethyl acetate/pet ether to give benzyl N-[2-[4-(2,6-dibenzyloxy-3-pyridyl)phenyl]ethyl]-N-methyl-carbamate (0.75 g, 1.17 mmol, 70.68% yield) as colorless oily liquid. LC-MS ($ES^-$): m/z 557.37 $[M-H]^-$ Step-5:

To a stirred solution of benzyl N-[2-[4-(2,6-dibenzyloxy-3-pyridyl)phenyl]ethyl]-N-methyl-carbamate (1 g, 1.79 mmol) in ethanol (10 mL) and ethyl acetate (10 mL) was added palladium, 10% on carbon, Type 487, dry (190.49 mg, 1.79 mmol) followed by Boc anhydride (390.66 mg, 1.79 mmol, 411.22 μL) under an inert atmosphere. The reaction mixture was stirred under bladder pressure hydrogen for 16 hours at 25° C. After completion, the reaction mixture was diluted with ethyl acetate and filtered through a celite bed. The reaction mixture was concentrated under reduced pressure, and the crude material was purified by normal phase column chromatography (Devisil silica, 30% ethyl acetate/pet ether) to obtain tert-butyl N-[2-[4-(2,6-dioxo-3-piperidyl)phenyl]ethyl]-N-methyl-carbamate (0.34 g, 902.95 μmol, 50.44% yield). LC-MS ($ES^-$): m/z 345.46 $[M-H]^-$.

Step-6:

To a stirred solution of tert-butyl N-[2-[4-(2,6-dioxo-3-piperidyl)phenyl]ethyl]-N-methyl-carbamate (0.34 g, 981.47 μmol) in DCM (2 mL) under an inert atmosphere was added trifluoroacetic acid (111.91 mg, 981.47 μmol, 75.61 μL) at 0° C. Then, the reaction mixture was stirred at room temperature for 2 hours. After completion, the reaction mixture was concentrated under reduced pressure and triturated with diethyl ether (2×50 mL). The obtained crude was purified by prep HPLC to give 3-[4-[2-(methylamino)ethyl] phenyl]piperidine-2,6-dione (23 mg, 91.34 μmol, 9.31% yield). LC-MS ($ES^+$): m/z 247.06 $[M+H]^+$ Synthesis of 3-methyl-3-[4-(4-piperidyl)phenyl] piperidine-2,6-dione

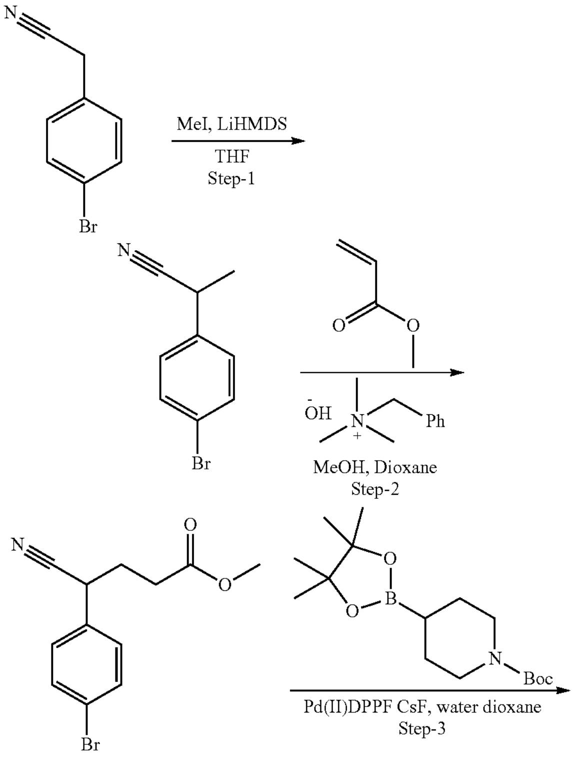

-continued

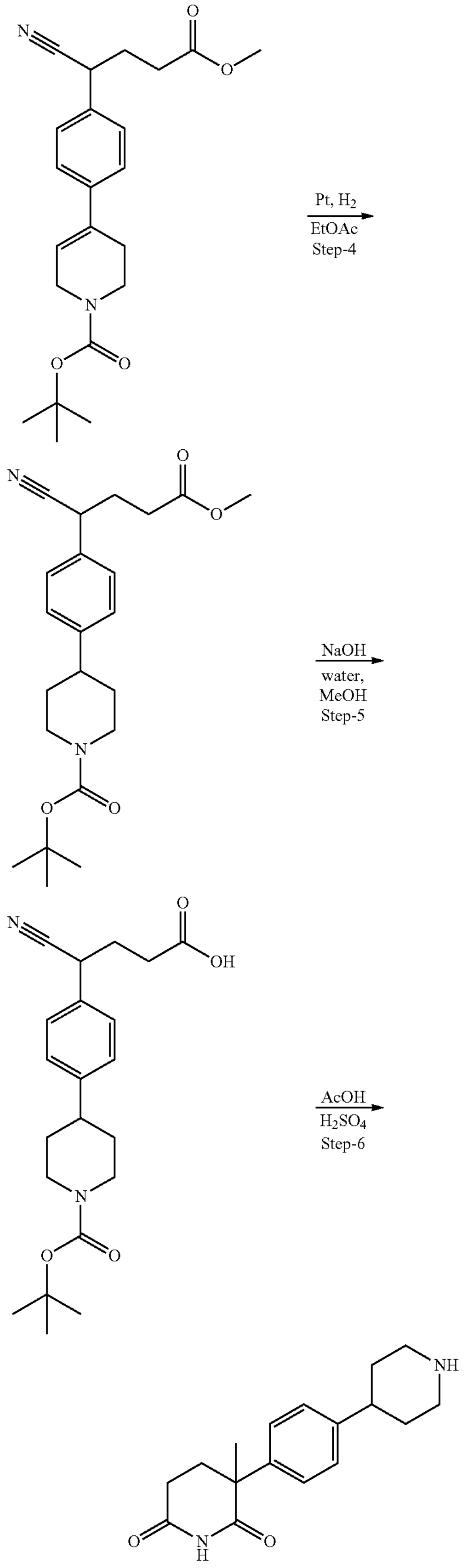

Step-1:

To a solution of 2-(4-bromophenyl)acetonitrile (2 g, 10.20 mmol, 1.34 mL) in THE (20 mL) was added lithium bis(trimethylsilyl)amide (1 M, 12.24 mL) at −78° C. under an atmosphere of argon. The mixture was stirred at −78° C. for 0.5 hour, then iodomethane (1.59 g, 11.22 mmol, 698.61 μL) was added, and the mixture was stirred at −78° C. for 2 hours. The reaction mixture was quenched by the addition of ammonium chloride (50 mL) and extracted with ethyl acetate (50 mL*2). The combined organic layers were washed with brine (50 mL), dried over $Na_2SO_4$, filtered, and concentrated under reduced pressure. The residue was purified by flash silica gel chromatography (10 g silica, 0-10% ethyl acetate/petroleum ether gradient at 70 mL/min) to give 2-(4-bromophenyl)propanenitrile (1.41 g, 6.64 mmol, 65.13% yield) as a yellow oil. 1H NMR (400 MHz, CDCl3) δ 7.54-7.52 (m, 2H), 7.27-7.24 (m, 2H), 3.88 (q, J=7.2 Hz, 1H), 1.65-1.63 (d, J=7.2 Hz, 3H).

Step-2:

To a solution of 2-(4-bromophenyl)propanenitrile (1 g, 4.76 mmol) in dioxane (10 mL) was added benzyltrimethylammonium hydroxide, 40% w/w in methanol (796.15 mg, 1.90 mmol) and 2-(4-bromophenyl)propanenitrile (1 g, 4.76 mmol) at 0° C. The mixture was stirred at 25° C. for 4 hours. The reaction mixture was quenched by adding ammonium chloride (20 mL) at 0° C. and extracted with ethyl acetate (50 mL×2). The combined organic layers were washed with brine (50 mL), dried over $Na_2SO_4$, filtered, and concentrated under reduced pressure to give methyl 4-(4-bromophenyl)-4-cyano-pentanoate (1.05 g, 3.51 mmol, 73.73% yield) as a yellow oil. $^1H$ NMR (400 MHz, $CDCl_3$) δ 7.47-7.45 (m, 2H), 7.26-7.24 (m, 2H), 3.56 (s, 3H), 2.42-2.14 (m, 4H), 1.66 (s, 3H).

Step-3:

A mixture of methyl 4-(4-bromophenyl)-4-cyano-pentanoate (1.05 g, 3.55 mmol), tert-butyl 4-(4,4,5,5-tetramethyl-1,3,2-dioxaborolan-2-yl)-3,6-dihydro-2H-pyridine-1-carboxylate (1.32 g, 4.25 mmol), Pd(dppf)$Cl_2$ (129.71 mg, 177.27 μmol) and CsF (1.62 g, 10.64 mmol, 392.15 μL) in water (2 mL) and dioxane (10 mL) was degassed and purged with nitrogen three times, and then the mixture was stirred at 90° C. for 12 hours under a nitrogen atmosphere. The reaction mixture was quenched by adding water (50 mL) and extracted with ethyl acetate (50 mL×2). The combined organic layers were washed with NaCl (50 mL), dried over $Na_2SO_4$, filtered, and concentrated under reduced pressure. The residue was purified by flash silica gel chromatography (10 g silica, 0-20% ethyl acetate in petroleum ether gradient at 60 mL/min) to give tert-butyl 4-[4-(1-cyano-4-methoxy-1-methyl-4-oxo-butyl)phenyl]-3,6-dihydro-2H-pyridine-1-carboxylate (1.3 g, 3.23 mmol, 91.09% yield) as a yellow oil. LC-MS ($ES^+$): m/z 299.1 $[M+H-Boc]^+$.

Step-4:

To a solution of tert-butyl 4-[4-(1-cyano-4-methoxy-1-methyl-4-oxo-butyl)phenyl]-3,6-dihydro-2H-pyridine-1-carboxylate (1.3 g, 3.26 mmol) in ethyl acetate (20 mL) was added palladium, 5% on activated carbon paste (347.17 mg, 3.26 mmol) under a nitrogen atmosphere. The suspension was degassed and purged with hydrogen three times. The mixture was stirred under hydrogen at 25° C. for 4 h. The reaction mixture was filtered and concentrated under reduced pressure. The product, tert-butyl 4-[4-(1-cyano-4-methoxy-1-methyl-4-oxo-butyl)phenyl]piperidine-1-carboxylate (1.3 g, 3.25 mmol, 99.50% yield) was used in the next step without further purification. LC-MS ($ES^+$): m/z 423.3 $[M+Na]^+$.

Step-5

To a solution of tert-butyl 4-[4-(1-cyano-4-methoxy-1-methyl-4-oxo-butyl)phenyl]piperidine-1-carboxylate (11.7 g, 29.21 mmol) in water (10 mL) and methanol (100 mL) was added sodium hydroxide, pearl (2.34 g, 58.43 mmol, 1.10 mL) and the mixture was stirred at 25° C. for 12 hours. The reaction mixture was concentrated under reduced pressure to remove MeOH, was diluted with $H_2O$ (50 mL), and extracted with ethyl acetate (100 mL×2). The water layer was adjusted pH with 1M HCl to 5, and extracted with DCM (100 mL×3), dried over $Na_2SO_4$, filtered and concentrated under reduced pressure to give 4-[4-(1-tert-butoxycarbonyl-4-piperidyl)phenyl]-4-cyano-pentanoic acid (9.5 g, 23.35 mmol, 79.94% yield) was as a white solid and was used in the next step without further purification. $^1$H NMR (400 MHz, DMSO-$d_6$) δ=12.57-12.04 (m, 1H), 7.46-7.38 (m, 2H), 7.32 (d, J=8.4 Hz, 2H), 4.15-4.00 (m, 2H), 2.94-2.65 (m, 3H), 2.33-2.13 (m, 3H), 2.11-1.97 (m, 1H), 1.75 (br d, J=12.5 Hz, 2H), 1.67 (s, 3H), 1.55-1.44 (m, 2H), 1.42 (s, 9H).

Step-6

A mixture of 4-[4-(1-tert-butoxycarbonyl-4-piperidyl)phenyl]-4-cyano-pentanoic acid (6.5 g, 16.82 mmol), acetic acid (52.50 g, 874.27 mmol, 50 mL) and sulfuric acid (1.65 g, 16.82 mmol, 10 mL) was stirred at 100° C. for 6 hours. The reaction mixture was concentrated under reduced pressure and the residue was purified by reversed phase flash chromatography (flow: 100 mL/min; gradient: from 100-50% water in acetonitrile (with HCl modifier) over 15 min; column: 330 g Flash Column Welch Ultimate XB_C18 20-40 μm; 120 A) to give 3-methyl-3-[4-(4-piperidyl)phenyl]piperidine-2,6-dione hydrochloride (4.40 g, 13.07 mmol, 77.73% yield) as a yellow solid. $^1$H NMR (400 MHz, DMSO-$d_6$) δ=10.94 (s, 1H), 9.10-8.74 (m, 2H), 7.28-7.21 (m, 4H), 3.36 (br s, 2H), 2.98 (br t, J=10.3 Hz, 2H), 2.88-2.78 (m, 1H), 2.49-2.41 (m, 1H), 2.40-2.32 (m, 1H), 2.14-2.02 (m, 2H), 1.93-1.82 (m, 4H), 1.42 (s, 3H).

Synthesis of 3-(6-piperazin-1-yl-3-pyridyl)piperidine-2,6-dione

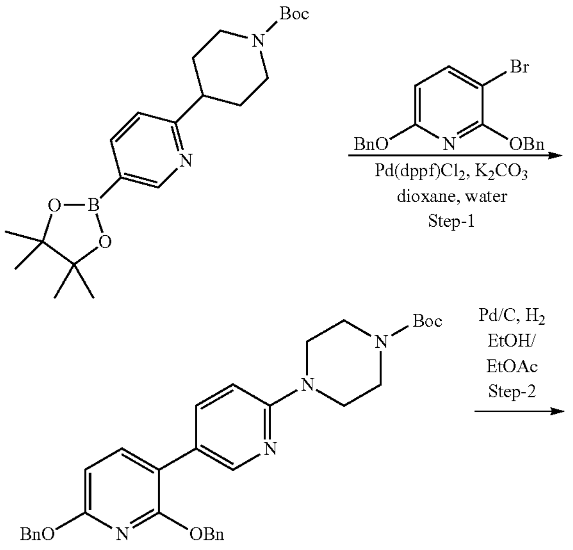

-continued

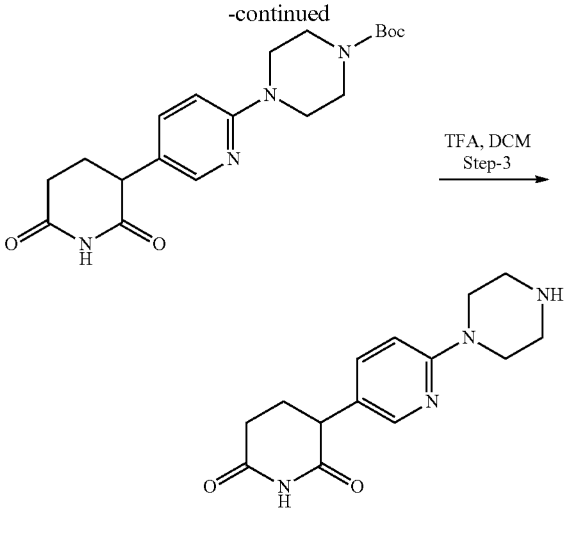

Step-1:

To a stirred solution of tert-butyl 4-[5-(4,4,5,5-tetramethyl-1,3,2-dioxaborolan-2-yl)-2-pyridyl]piperazine-1-carboxylate (5.3 g, 13.61 mmol) and 2,6-dibenzyloxy-3-bromo-pyridine (4.20 g, 11.35 mmol) in 1,4-dioxane (100 mL) and water (25 mL) was added $K_2CO_3$ (3.14 g, 22.69 mmol, 1.37 mL) and purged with nitrogen for 15 mins. Then Pd(dppf) $Cl_2{\cdot}CH_2Cl_2$ (415.07 mg, 567.26 μmol) was added and purged with nitrogen for 5 min. Then the reaction mixture was heated to 90° C. for 16 hours. After completion of the reaction, the reaction mixture was filtered through a celite bed and the filtrate was concentrated. The crude mater was purified by column chromatography (230-400 mesh silica gel, 15% ethyl acetate/pet ether as eluent) to give tert-butyl 4-[5-(2,6-dibenzyloxy-3-pyridyl)-2-pyridyl]piperazine-1-carboxylate (4.5 g, 6.92 mmol, 61.00% yield) as off white solid. LC-MS (ES$^+$): m/z 553.84 [M+H]$^+$. $^1$H NMR (400 MHz, $CDCl_3$) δ 8.37 (d, J=2.4 Hz, 1H), 7.75 (dd, J=8.8 Hz, J=2.4 Hz, 1H), 7.55 (d, J=8.4 Hz, 1H), 7.43-7.27 (m, 10H), 6.66 (d, J=8.8 Hz, 1H), 6.46 (d, J=8.4 Hz, 1H), 5.42 (s, 2H), 5.35 (s, 2H), 3.53 (bs, 8H), 1.49 (s, 9H).

Step-2:

To a stirred solution of tert-butyl 4-[5-(2,6-dibenzyloxy-3-pyridyl)-2-pyridyl]piperazine-1-carboxylate (4.5 g, 8.14 mmol) in ethyl acetate (100 mL) and ethanol (100 mL) was added palladium on carbon (4.50 g, 42.29 mmol). The reaction mixture was stirred under hydrogen gas at bladder pressure at room temperature for 12 hours. After completion of the reaction, the reaction mixture was filtered through a celite bed, concentrated, and purified by column chromatography using 230-400 mesh silica gel. The desired product was eluted at 95% ethyl acetate in pet ether to afford tert-butyl 4-[5-(2,6-dioxo-3-piperidyl)-2-pyridyl]piperazine-1-carboxylate (2.1 g, 5.33 mmol, 65.44% yield). LC-MS (ES$^+$): m/z 375.45 [M+H]$^+$ Step-3:

To a stirred solution of tert-butyl 4-[5-(2,6-dioxo-3-piperidyl)-2-pyridyl]piperazine-1-carboxylate (1.5 g, 4.01 mmol) in DCM (20 mL) under an inert atmosphere was added 2,2,2-trifluoroacetic acid (22.20 g, 194.70 mmol, 15 mL) at 0° C. Then, the reaction mixture was stirred at room temperature for 1 hr. After completion, the crude was concentrated under reduced pressure and triturated with diethyl ether (2×100 mL), then dried to obtain 3-(6-piperazin-1-yl-3-pyridyl)piperidine-2,6-dione TFA salt (1.5 g, 3.79 mmol, 94.49% yield) as an off-white solid. LC-MS ($ES^+$): m/z 275.45 $[M+H]^+$.

Synthesis of 1-[1-methyl-6-(4-piperidyl)indazol-3-yl]hexahydropyrimidine-2,4-dione

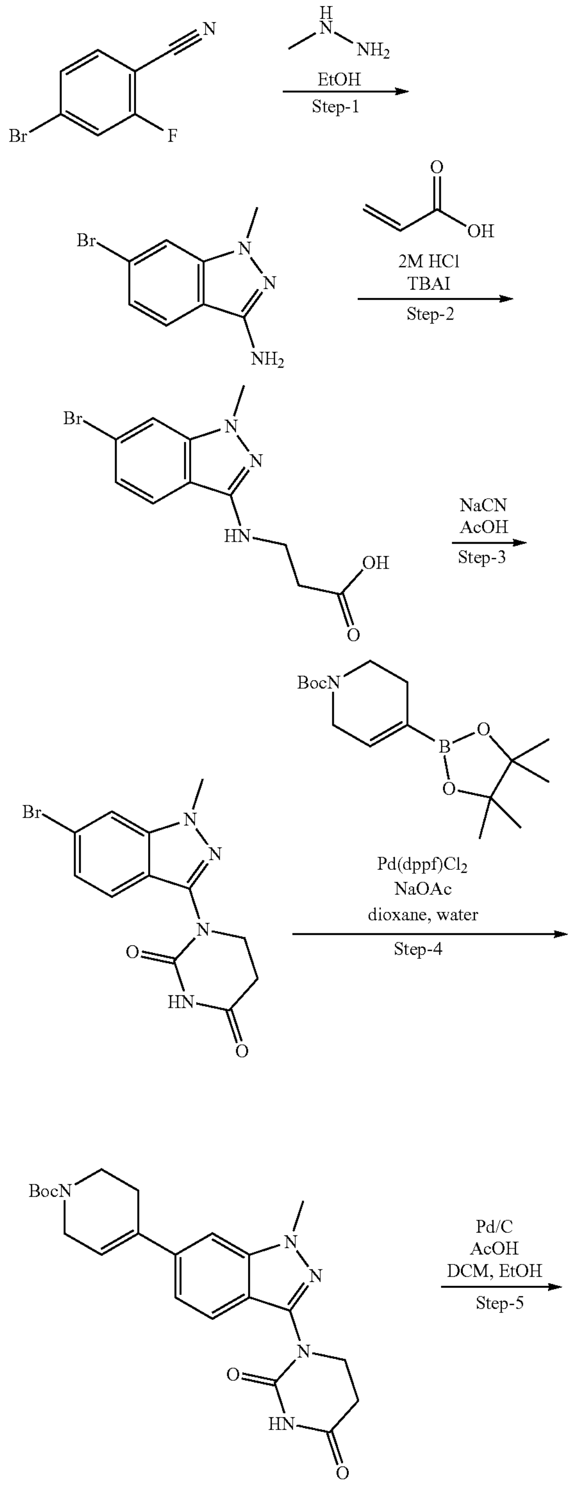

-continued

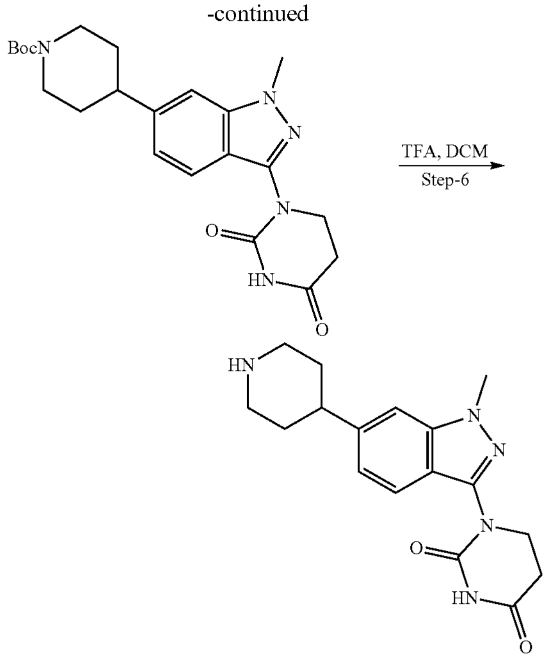

Step-1:

To a stirred solution of 4-bromo-2-fluorobenzonitrile (25 g, 125.00 mmol) in ethanol (500 mL) was added methyl hydrazine (85% aqueous solution) (51.83 g, 1.12 mol) at room temperature. The reaction mixture was heated at 125° C. in the autoclave (1000 ml) for 7 hours. The reaction mixture was cooled to room temperature, poured into ice cold water (2000 ml), and stirred for 30 minutes. The solidified mass was filtered-off, washed with water, and dried well to afford 6-bromo-1-methyl-1H-indazol-3-amine (25 g, 105.05 mmol, 84.05% yield) as an off-white solid. LC-MS ($ES^+$): m/z 291.37 $[M+H]^+$.

Step-2:

To the stirred solution of 6-bromo-1-methyl-indazol-3-amine (50 g, 221.17 mmol) in HCl (2 M aqueous solution) (500.00 mL) was added tetrabutylammonium bromide (7.13 g, 22.12 mmol) at room temperature. The reaction mixture was heated to 55° C. (internal temperature), and acrylic acid (23.91 g, 331.75 mmol, 22.77 mL) was added dropwise. The reaction was then heated to 100° C. (external) for 12 hours. After the reaction was complete, the reaction mixture was cooled to room temperature and diluted with ice-cold water (1000 ml). It was neutralized to pH 6.5 to 7 with 2 M $NaHCO_3$ solution (1000 ml) with good stirring. The solid precipitation was filtered-off, washed with excess ice-cold water, and dried well to afford 3-[(6-bromo-1-methyl-indazol-3-yl)amino]propanoic acid (54 g, 163.30 mmol, 73.84% yield) as an off-white solid. LC-MS ($ES^+$): m/z 298.28 $[M+H]^+$.

Step-3:

To a stirred solution of 3-[(6-bromo-1-methyl-indazol-3-yl)amino]propanoic acid (160 g, 536.67 mmol) in acetic acid (1.07 kg, 17.76 mol, 1.02 L) was added sodium cyanate, 95% (46.67 g, 717.88 mmol). The reaction mixture was heated at 100° C. for 12 hours, and the progress was monitored by TLC. Upon completion, the reaction was cooled to room temperature and filtered through a Buchner funnel, and washed with water (2×500 mL). The product was dried completely to yield 1-(6-bromo-1-methyl-indazol- 3-yl)hexahydropyrimidine-2,4-dione (175 g, 527.69 mmol, 98.33% yield) as an off-white solid. LC-MS ($ES^+$): m/z 323.27 $[M+H]^+$.

Step-4:

To a solution of 1-(6-bromo-1-methyl-indazol-3-yl)hexahydropyrimidine-2,4-dione (15 g, 46.42 mmol) and tert-butyl 4-(4,4,5,5-tetramethyl-1,3,2-dioxaborolan-2-yl)-3,6-dihydro-2H-pyridine-1-carboxylate (18.66 g, 60.34 mmol) in 1,4-dioxane (150 mL) and water (30 mL) was added sodium acetate, anhydrous (11.42 g, 139.26 mmol) at room temperature. The reaction mixture was degassed with argon gas for 10 minutes and 1,1'-bis(diphenylphosphino)ferrocene]palladium(II) dichloride (3.40 g, 4.64 mmol) was added. The reaction mixture was degassed with argon for an additional 5 minutes before it was stirred at 90° C. for 16 hours. Subsequently, the reaction mixture was concentrated in vacuo to yield the crude product, which was purified by column chromatography (silica gel 230-400 mesh, 70% ethyl acetate in pet ether) to afford tert-butyl 4-[3-(2,4-dioxohexahydropyrimidin-1-yl)-1-methyl-indazol-6-yl]-3,6-dihydro-2H-pyridine-1-carboxylate (18 g, 34.69 mmol, 74.73% yield) as a brown solid. LC-MS ($ES^+$): m/z 426.44 $[M+H]^+$.

Step-5:

A solution of tert-butyl 4-[3-(2,4-dioxohexahydropyrimidin-1-yl)-1-methyl-indazol-6-yl]-3,6-dihydro-2H-pyridine-1-carboxylate (3.6 g, 8.46 mmol) in ethanol (30 ml) and DCM (10 ml) and a catalytical amount of glacial acetic acid (508.09 mg, 8.46 mmol, 3 ml) was added to a Parr Shaker hydrogenator. Palladium on carbon, 10 wt. % (3.08 g, 25.38 mmol) was added to this mixture under an inert atmosphere, and the resulting reaction was stirred for 16 hours at room temperature. The reaction progress was monitored by TLC and LC-MS. Upon completion, the reaction was filtered through a celite bed and washed with 10% MeOH/DCM. The filtrate was concentrated under reduced pressure to afford tert-butyl 4-[3-(2,4-dioxohexahydropyrimidin-1-yl)-1-methyl-indazol-6-yl]piperidine-1-carboxylate (3.6 g, 8.17 mmol, 96.55% yield). LC-MS ($ES^+$): m/z 428.45 $[M+H]^+$.

Step-6:

To a stirred solution of tert-butyl 4-[3-(2,4-dioxohexahydropyrimidin-1-yl)-1-methyl-indazol-6-yl]piperidine-1-carboxylate (2.7 g, 6.32 mmol) in DCM (20 mL) was added TFA (22.20 g, 194.70 mmol, 15 mL) at 0° C. The reaction was stirred for 3 hours, and the reaction progress was monitored by TLC and LC-MS. Upon completion, the reaction mixture was evaporated to obtain the crude product, which was triturated with diethyl ether and concentrated in vacuo to afford 1-[1-methyl-6-(4-piperidyl)indazol-3-yl]hexahydropyrimidine-2,4-dione TFA salt (2.5 g, 4.92 mmol, 77.93% yield) as a brown solid. LC-MS ($ES^+$): m/z 328.48 $[M+H]^+$.

Synthesis of 1-(6-(3,3-difluoropiperidin-4-yl)-1-methyl-1H-indazol-yl)dihydropyrimidine-2,4(1H,3H)-dione

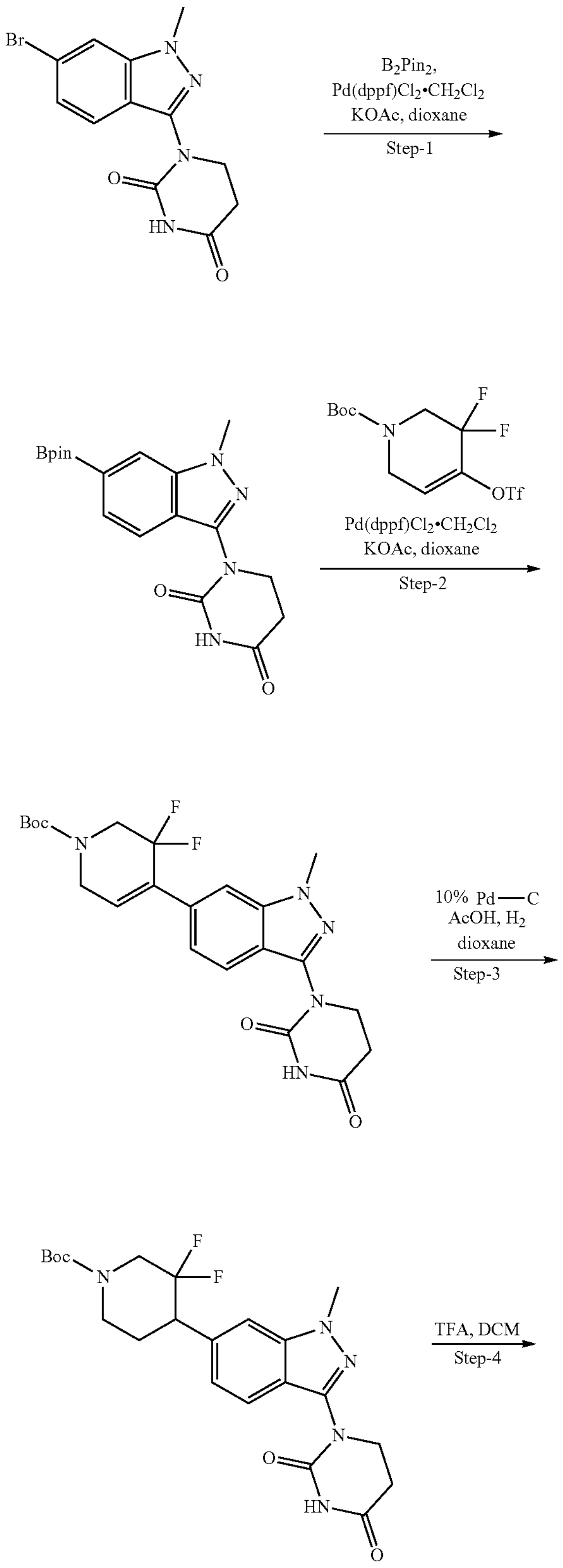

-continued

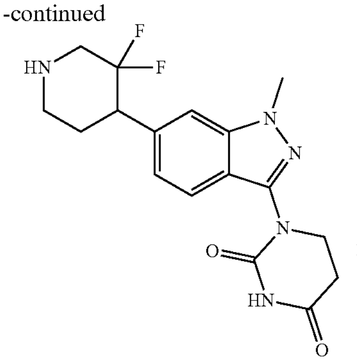

Step-1:

To a stirred solution of 1-(6-bromo-1-methyl-indazol-3-yl)hexahydropyrimidine-2,4-dione (5 g, 15.47 mmol) in 1,4-dioxane (50 mL) in a two necked 100 mL round bottle flask was added 4,4,5,5-tetramethyl-2-(4,4,5,5-tetramethyl-1,3,2-dioxaborolan-2-yl)-1,3,2-dioxaborolane (5.89 g, 23.21 mmol) and potassium acetate (3.80 g, 38.68 mmol, 2.42 mL). The reaction mixture was degassed with argon for 10 minutes. $Pd(dppf)Cl_2{\cdot}CH_2Cl_2$ (758.15 mg, 928.38 μmol) was added and the resulting mixture was stirred at 100° C. for 4 hr. Upon completion, the reaction was then cooled to room temperature and filtered through a short bed of celite. The filtrate was washed with ethyl acetate (200 mL) and concentrated under reduced pressure to give the crude product, which was purified by column chromatography (silica, gradient: 2-5% MeOH in DCM) to afford 1-[1-methyl-6-(4,4,5,5-tetramethyl-1,3,2-dioxaborolan-2-yl)indazol-3-yl]hexahydropyrimidine-2,4-dione (4.98 g, 10.29 mmol, 66.48% yield) as a pale brown solid. LC-MS ($ES^+$): m/z 371.36 $[M+H]^+$.

Step-2:

To a stirred solution of tert-butyl 3,3-difluoro-4-(trifluoromethylsulfonyloxy)-2,6-dihydropyridine-1-carboxylate (0.5 g, 1.36 mmol) in 1,4-dioxane (5 mL) were added 1-[1-methyl-6-(4,4,5,5-tetramethyl-1,3,2-dioxaborolan-2-yl)indazol-3-yl]hexahydropyrimidine-2,4-dione (453.58 mg, 1.23 mmol) and potassium acetate (334.00 mg, 3.40 mmol, 212.74 μL). The reaction mixture was degassed with argon for 10 minutes. $Pd(dppf)Cl_2{\cdot}CH_2Cl_2$ (66.70 mg, 81.68 mol) was added and the resulting mixture was stirred at 100° C. for 16 hr. Upon completion of the reaction, the reaction was then cooled to room temperature and filtered through a short bed of celite. The filtrate was diluted with ethyl acetate (2×50 mL), washed with water (50 mL), dried over anhydrous $Na_2SO_4$ and concentrated under reduced pressure to afford tert-butyl 4-[3-(2,4-dioxohexahydropyrimidin-1-yl)-1-methyl-indazol-6-yl]-3,3-difluoro-2,6-dihydropyridine-1-carboxylate (0.8 g, 1.09 mmol, 79.89% yield) as a black solid. LC-MS ($ES^+$): m/z 462.38 $[M+H]^+$.

Step-3:

To a stirred solution of tert-butyl 4-[3-(2,4-dioxohexahydropyrimidin-1-yl)-1-methyl-indazol-6-yl]-3,3-difluoro-2,6-dihydropyridine-1-carboxylate (0.2 g, 433.41 μmol) in 1,4-diaoxane (2 mL) and acetic acid (419.60 mg, 6.99 mmol, 400.00 μL) was added palladium, 10% on carbon, Type 487, dry (200.00 mg, 1.88 mmol) and it was stirred for 16 hr at 25° C. under $H_2$ pressure in bladder. Upon completion of the reaction, the reaction mixture was filtered through a celite bed, washed with 10% MeOH/DCM. The filtrate was evaporated under reduced pressure to give the crude compound, which was triturated with diethyl ether (50 ml), filtered, and dried well to afford tert-butyl 4-[3-(2,4-dioxohexahydropyrimidin-1-yl)-1-methyl-indazol-6-yl]-3,3-difluoro-piperidine-1-carboxylate (0.15 g, 275.00 μmol, 63.45% yield). LC-MS ($ES^+$): m/z 461.97 $[M-H]^-$.

Step-4:

To a stirred solution of tert-butyl 4-[3-(2,4-dioxohexahydropyrimidin-1-yl)-1-methyl-indazol-6-yl]-3,3-difluoro-piperidine-1-carboxylate (0.20 g, 431.52 μmol) in DCM (5 mL) was added trifluoroacetic acid (49.20 mg, 431.52 μmol, 33.24 μL) and stirred at room temperature for 3 hr. The reaction mixture was concentrated to give the crude product, which was triturated with diethyl ether to afford 1-[6-(3,3-difluoro-4-piperidyl)-1-methyl-indazol-3-yl]hexahydropyrimidine-2,4-dione (0.170 g, 289.23 μmol, 67.03% yield) as an off white solid. LC-MS ($ES^+$): m/z 364.13 $[M+H]^+$.

Synthesis of 1-(5-fluoro-1-methyl-6-(piperidin-4-yl)-1H-indazol-3-yl)dihydropyrimidine-2,4(1H,3H)-dione

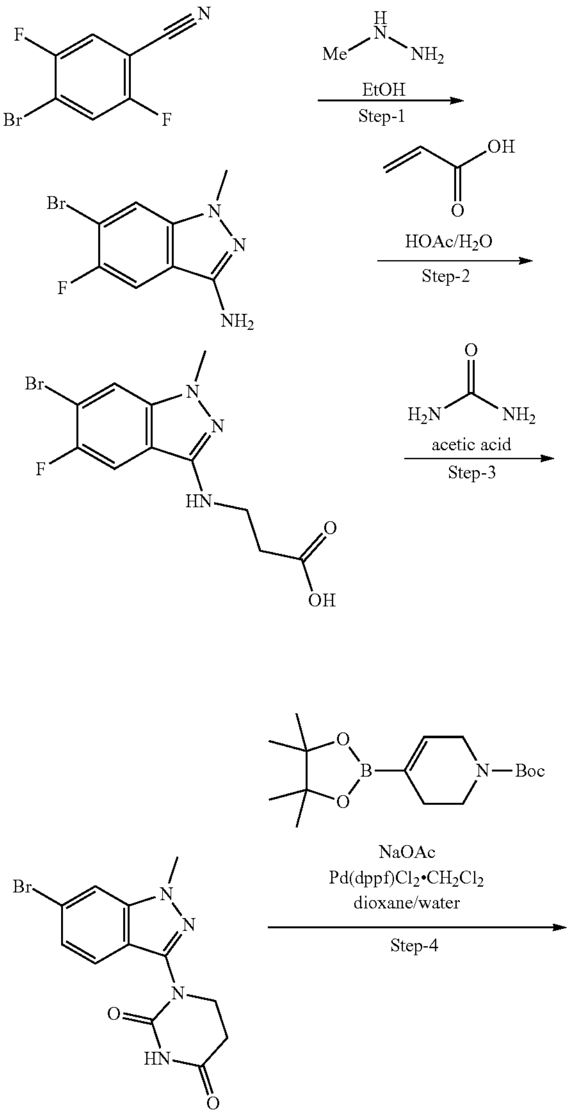

-continued

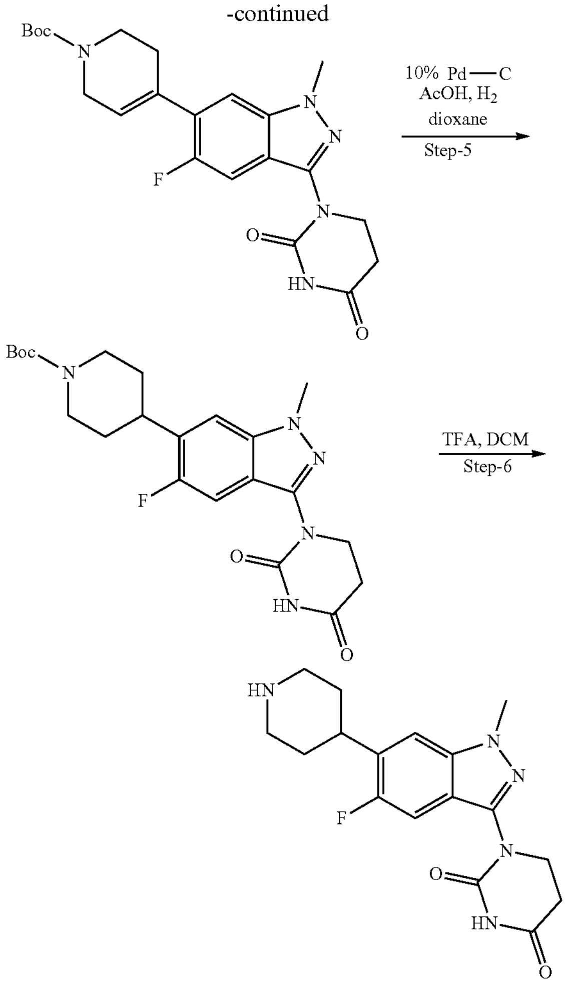

Step-1:

To a solution of 4-bromo-2,5-difluoro-benzonitrile (1 g, 4.59 mmol) in ethanol (10 mL), methyl hydrazine (253.60 mg, 5.50 mmol) was added at room temperature. The reaction mixture was heated at 100° C. for 16 hr in a microwave reactor. Upon completion of the reaction, the reaction mixture was concentrated and purified with chromatography ($Et_2O$-pentane=2:8) to get 6-bromo-5-fluoro-1-methyl-indazol-3-amine (700 mg, 2.60 mmol, 56.58% yield) as an off white solid. LC-MS ($ES^+$): m/z 244.94 $[M+H]^+$.

Step-2:

To a solution of 6-bromo-5-fluoro-1-methyl-indazol-3-amine (2.5 g, 10.24 mmol) in water (25 mL) within a sealed tube, acetic acid (492.09 mg, 8.19 mmol, 469.10 μL) and acrylic acid (885.78 mg, 12.29 mmol, 842.80 μL) were added at room temperature. The reaction mixture was heated to about 100° C. for 16 hr. Upon completion of the reaction, the reaction mixture was directly concentrated, and then 10 ml acetonitrile, and 100 ml diethyl ether were added to the crude product, resulting in a suspension. The suspension was stirred for 10 min, and the precipitate was collected and dried to get the crude 3-[(6-bromo-5-fluoro-1-methyl-indazol-3-yl)amino]propanoic acid (2.5 g, 4.78 mmol, 46.71% yield) as a light brown gummy solid directly taken for next step without further purification.

Step-3:

To a solution of 3-[(6-bromo-5-fluoro-1-methyl-indazol-3-yl)amino]propanoic acid (5 g, 15.82 mmol) in acetic acid (48.22 mL), urea (3.32 g, 55.36 mmol) was added at room temperature. The reaction mixture was heated at 120° C. for 16 hr and then cooled to room temperature. The reaction mixture was acidified to pH<1 using conc. HCl was then heated to about 120° C. for 30 minutes and cooled to room temperature. The reaction mixture was concentrated. The crude compound was purified by column chromatography using EtOAc—PE as eluent to give 1-(6-bromo-5-fluoro-1-methyl-indazol-3-yl)hexahydropyrimidine-2,4-dione (1.8 g, 4.68 mmol, 29.58% yield) as off white solid. LC-MS ($ES^+$): m/z 342.66 $[M+H]^+$.

Step-4:

To a stirred solution of 1-(6-bromo-5-fluoro-1-methyl-indazol-3-yl)hexahydropyrimidine-2,4-dione (1.5 g, 4.40 mmol), tert-butyl 4-(4,4,5,5-tetramethyl-1,3,2-dioxaborolan-2-yl)-3,6-dihydro-2H-pyridine-1-carboxylate (1.50 g, 4.84 mmol) in 1,4-dioxane (1.92 mL) and water (7.69 mL) was added sodium acetate (901.73 mg, 10.99 mmol, 590.14 μL). The mixture was degassed with nitrogen for 2 min. Pd(dppf)$Cl_2$·$CH_2Cl_2$ (359.08 mg, 439.71 μmol) was added to the mixture and stirred at 100° C. for 12 hours. The reaction mixture was diluted with EtOAc (30 mL), filtered through celite. The filtrate was washed with water (30 mL). The combined organic layer was concentrated under reduced pressure to give the crude product, which was purified by column chromatography (230-400 mesh silica, 90% of EtOAc in Pet-ether) to get tert-butyl 4-[3-(2,4-dioxohexahydropyrimidin-1-yl)-5-fluoro-1-methyl-indazol-6-yl]-3,6-dihydro-2H-pyridine-1-carboxylate (0.5 g, 1.00 mmol, 22.80% yield) as a brown solid. LC-MS ($ES^+$): m/z 444.35 $[M+H]^+$.

The procedures from step-5 to step-6 are identical to the synthesis of intermediate 1-(6-(3,3-difluoropiperidin-4-yl)-1-methyl-1H-indazol-3 yl)dihydropyrimidine-2,4(1H,3H)-dione, and the product 1-(5-fluoro-1-methyl-6-(piperidin-4-yl)-1H-indazol-3-yl)dihydropyrimidine-2,4(1H,3H)-dione was confirmed by LC-MS. LC-MS ($ES^+$): m/z 346.22 $[M+H]^+$.

Synthesis of 1-(7-fluoro-1-methyl-6-(piperidin-4-yl)-1H-indazol-3-yl)dihydropyrimidine-2,4(1H,3H)-dione

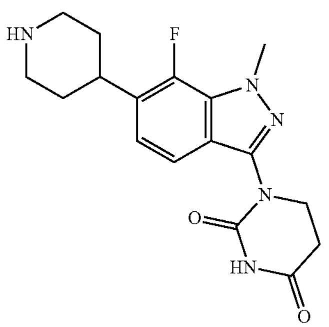 [SMILES: Cn1nc(N2CCC(=O)NC2=O)c2ccc(C3CCNCC3)c(F)c21]

The procedures are identical to the synthesis of intermediate 1-(5-fluoro-1-methyl-6-(piperidin-4-yl)-1H-indazol-3-yl)dihydropyrimidine-2,4(1H,3H)-dione. 4-bromo-2,3-difluorobenzonitrile was used as the starting material in Step-1. The product 1-(7-fluoro-1-methyl-6-(piperidin-4-yl)-1H-indazol-3-yl)dihydropyrimidine-2,4(1H,3H)-dione was confirmed by LC-MS. LC-MS ($ES^+$): m/z 346.31 $[M+H]^+$.

Synthesis of 1-(1-methyl-6-(piperidin-3-yl)-1H-indazol-3-yl)dihydropyrimidine-2,4(1H,3H)-dione

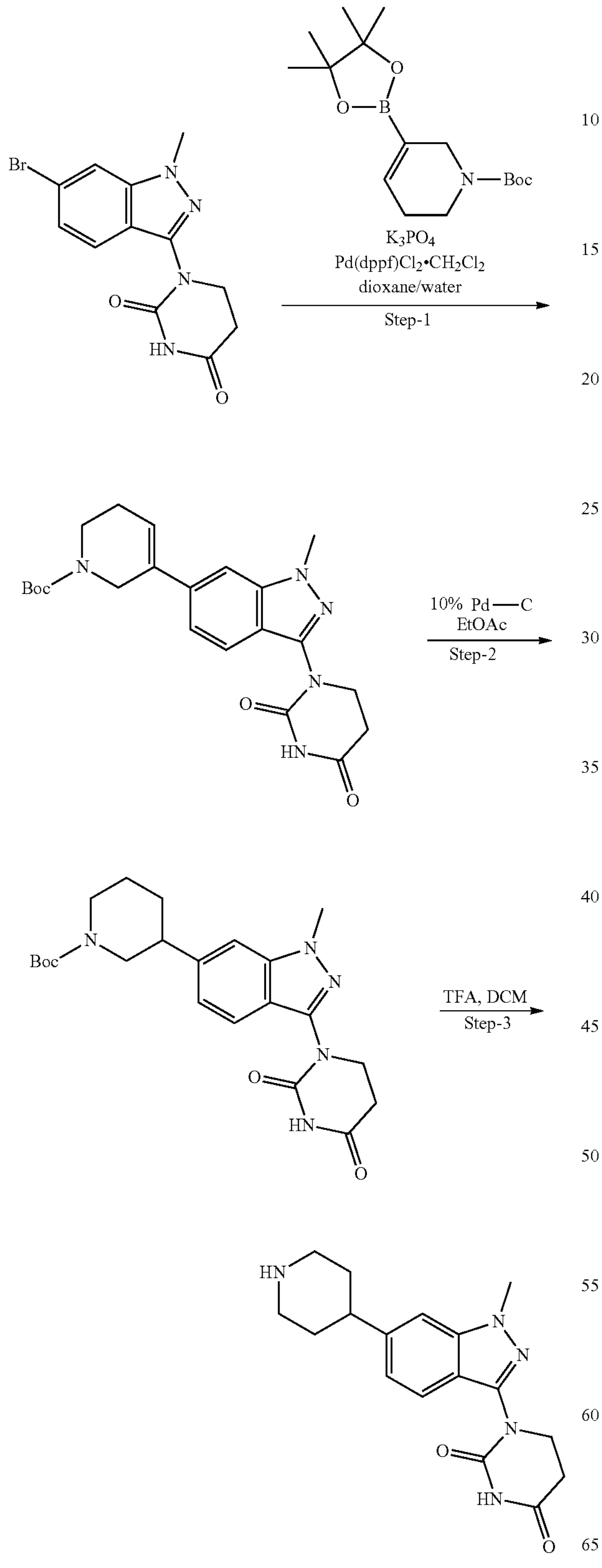

Step-1:

To a solution of 1-(6-bromo-1-methyl-indazol-3-yl)hexahydropyrimidine-2,4-dione (11 g, 34.04 mmol) and tert-butyl 5-(4,4,5,5-tetramethyl-1,3,2-dioxaborolan-2-yl)-3,6-dihydro-2H-pyridine-1-carboxylate (11.58 g, 37.44 mmol) in dioxane (150 mL) were added potassium phosphate tribasic (21.68 g, 102.12 mmol) at room temperature. The reaction mixture was degassed with nitrogen gas for 20 minutes, and Pd(dppf)$Cl_2 \cdot CH_2Cl_2$ (1.49 g, 2.04 mmol) was added. The resulted mixture was stirred at 100° C. for 12 h. Upon completion of the reaction, the reaction mixture was filtered through a celite bed and washed with Ethyl acetate (200 mL). The filtrate was concentrated under reduced pressure. The residue obtained was purified by column chromatography (Davisil silica) using 40% EtOAc in pet ether as an eluent to afford tert-butyl 5-[3-(2,4-dioxohexahydropyrimidin-1-yl)-1-methyl-indazol-6-yl]-3,6-dihydro-2H-pyridine-1-carboxylate (10.4 g, 23.85 mmol, 70.05% yield) as an off-white solid. LC-MS ($ES^+$): m/z 426.26 $[M+H]^+$.

Step-2:

A stirred solution of tert-butyl 5-[3-(2,4-dioxohexahydropyrimidin-1-yl)-1-methyl-indazol-6-yl]-3,6-dihydro-2H-pyridine-1-carboxylate (11.2 g, 26.32 mmol) in ethyl acetate (200 mL) and THF (200 mL) was degassed with nitrogen for 10 minutes. Palladium on carbon (8.96 g, 75.66 mmol) was added and stirred for 16 h at room temperature under an $H_2$ atmosphere (balloon pressure). Upon completion of the reaction, the reaction mixture was filtered through a celite bed and washed with THF (500 mL). The filtrate was concentrated under reduced pressure. The crude was triturated with diethyl ether (2×300 mL) to afford tert-butyl 3-[3-(2,4-dioxohexahydropyrimidin-1-yl)-1-methyl-indazol-6-yl]piperidine-1-carboxylate (10.44 g, 24.33 mmol, 92.42% yield) as an off-white solid. LC-MS ($ES^+$): m/z 426.38 $[M-H]^-$.

Step-3:

To a solution of tert-butyl 3-[3-(2,4-dioxohexahydropyrimidin-1-yl)-1-methyl-indazol-6-yl]piperidine-1-carboxylate (0.02 g, 46.78 μmol) in DCM (2 mL) was added TFA (53.34 mg, 467.84 μmol, 36.04 μL) at 0° C. The reaction mixture was stirred at room temperature for 2 h. Progress of the reaction was monitored by LCMS. Upon completion of the reaction, the reaction mixture was concentrated under reduced pressure. The residue obtained was triturated with diethyl ether and dried well to afford 1-[1-methyl-6-(3-piperidyl)indazol-3-yl]hexahydropyrimidine-2,4-dione (0.0147 g, 32.94 μmol, 70.40% yield) as an off-white solid. LC-MS ($ES^+$): m/z 328.43 $[M+H]^+$.

Synthesis of (R)-1-(1-methyl-6-(pyrrolidin-3-yl)-1H-indazol-3-yl)dihydropyrimidine-2,4(1H,3H)-dione and (S)-1-(1-methyl-6-(pyrrolidin-3-yl)-1H-indazol-3-yl)dihydropyrimidine-2,4(1H,3H)-dione

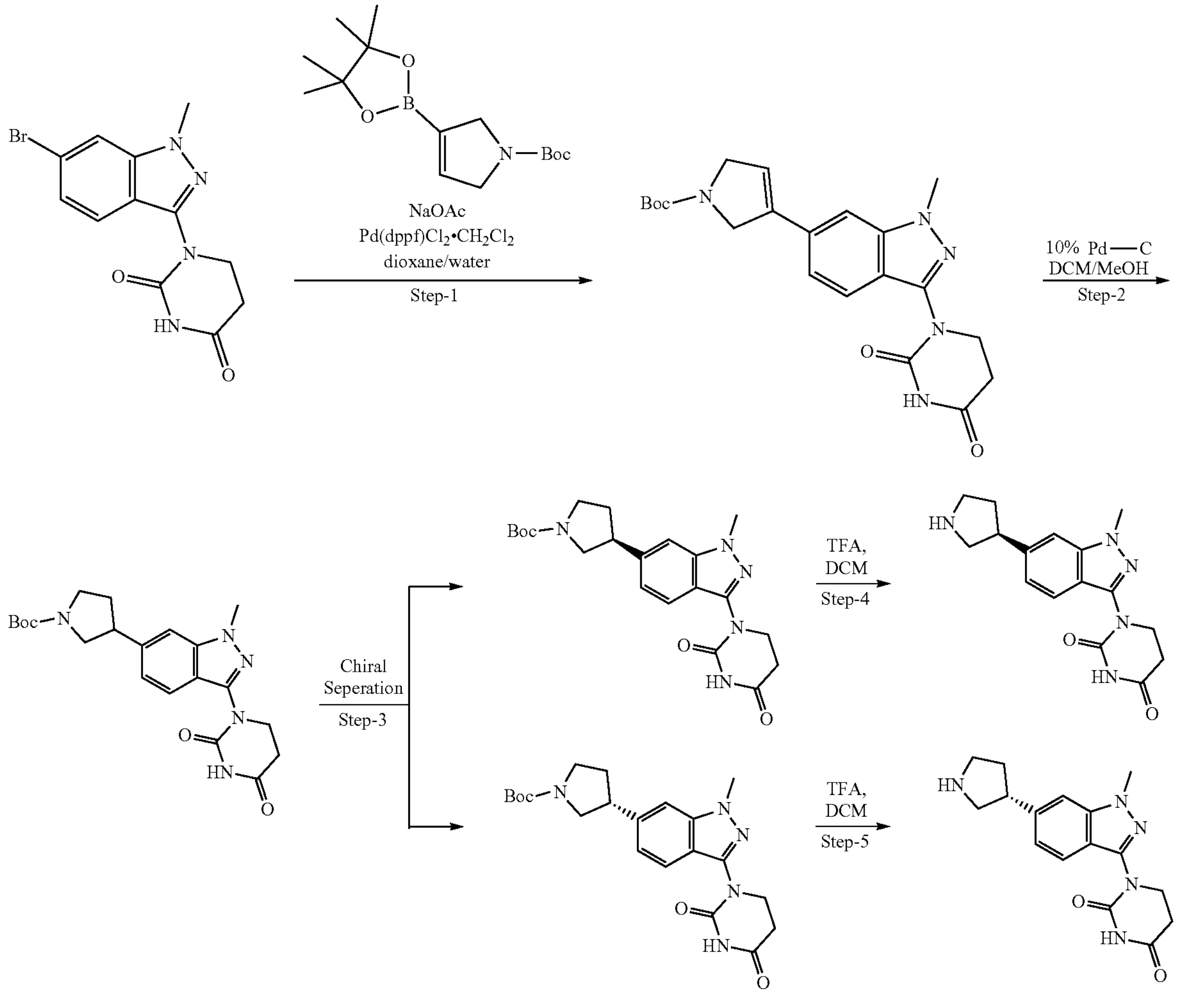

Step-1:

To a solution of benzyl 1-(6-bromo-1-methyl-indazol-3-yl)hexahydropyrimidine-2,4-dione (10 g, 30.95 mmol) and tert-butyl 3-(4,4,5,5-tetramethyl-1,3,2-dioxaborolan-2-yl)-2,5-dihydropyrrole-1-carboxylate (10.96 g, 37.14 mmol) in 1,4-dioxane (100 mL) and Water (30 mL) was added sodium acetate (7.62 g, 92.84 mmol) at room temperature. The reaction mixture was degassed with argon gas for 10 minutes, and Pd(dppf)$Cl_2$·$CH_2Cl_2$ (2.26 g, 3.09 mmol) was added. The reaction mixture was degassed with argon for additional 5 minutes, and it was stirred at 80° C. for 16 hr. Subsequently, the reaction mixture was diluted with water and extracted with ethyl acetate. The combined organic layer was washed with brine solution, dried over sodium sulfate, filtered, and concentrated to get the crude product, which was purified by column chromatography using 230-400 mesh silica and 0-80% ethyl acetate in pet ether as eluent to afford tert-butyl 3-[3-(2,4-dioxohexahydropyrimidin-1-yl)-1-methyl-indazol-6-yl]-2,5-dihydropyrrole-1-carboxylate (5 g, 10.45 mmol, 33.77% yield) as light brown solid. LC-MS ($ES^+$): m/z 412.61 $[M+H]^+$.

Step-2:

To a stirred solution of tert-butyl 3-[3-(2,4-dioxohexahydropyrimidin-1-yl)-1-methyl-indazol-6-yl]-2,5-dihydropyrrole-1-carboxylate (7 g, 17.01 mmol) in DCM (20 mL) and methanol (70 mL) was added 10% palladium on carbon, 60% wet basis (7 g) at 25° C. The reaction mixture was stirred in a steel bomb under a hydrogen atmosphere at 100 psi pressure for 16 hours. Subsequently, it was filtered through a celite bed and washed with MeOH (30 mL) and DCM (10 mL). The filtrate was concentrated under reduced pressure to afford crude product. The crude was triturate with diethyl ether (50 mL), and then filtrated to get tert-butyl 3-[3-(2,4-dioxohexahydropyrimidin-1-yl)-1-methyl-indazol-6-yl]pyrrolidine-1-carboxylate (2.5 g, 5.32 mmol, 31.28% yield) as light brown solid. LC-MS ($ES^+$): m/z 414.63 $[M+H]^+$.

Step-3:

The racemic tert-butyl 3-[3-(2,4-dioxohexahydropyrimidin-1-yl)-1-methyl-indazol-6-yl]pyrrolidine-1-carboxylate (2.5 g, 6.05 mmol) was further purified by SFC purification method to afford the product tert-butyl rac-(3S)-3-[3-(2,4-dioxohexahydropyrimidin-1-yl)-1-methyl-indazol-6-yl]pyrrolidine-1-carboxylate and tert-butyl rac-(3R)-3-[3-(2,4-dioxohexahydropyrimidin-1-yl)-1-methyl-indazol-6-yl]pyrrolidine-1-carboxylate in pure optical form.

Preparative SFC Conditions:
Column/dimensions: CHIRALCEL-OJ-H (30×250) mm, 5μ
% $CO_2$: 70%
% Co solvent: 30% (ACN)
Total Flow: 100 g/min
Back Pressure: 100 bar
Temperature: 30° C.
UV: 215 nm Step-4:

To the stirred solution of tert-butyl rac-(3S)-3-[3-(2,4-dioxohexahydropyrimidin-1-yl)-1-methyl-indazol-6-yl]pyrrolidine-1-carboxylate (0.18 g, 435.34 μmol) in DCM (5 mL) was added trifluoroacetic acid (1.33 g, 11.68 mmol, 0.9 mL) at 0° C. The reaction mixture was stirred at room temperature for 5 h. The reaction progress was monitored by TLC and LCMS. After completion, the reaction mixture was concentrated and the residual mass was triturated with diethyl ether (2×5 mL) to get pure 1-[1-methyl-6-[rac-(3S)-pyrrolidin-3-yl]indazol-3-yl]hexahydropyrimidine-2,4-dione (0.15 g, 347.47 μmol, 79.82% yield) as a brown gum. LC-MS ($ES^+$): m/z 314.40 $[M+H]^+$.

The procedure of Step-5 is identical to Step-4, tert-butyl rac-(3R)-3-[3-(2,4-dioxohexahydropyrimidin-1-yl)-1-methyl-indazol-6-yl]pyrrolidine-1-carboxylate is used as the starting material.

Synthesis of 5-(3-(2,4-dioxotetrahydropyrimidin-1(2H)-yl)-1-methyl-1H-indazol-6-yl) pentanal

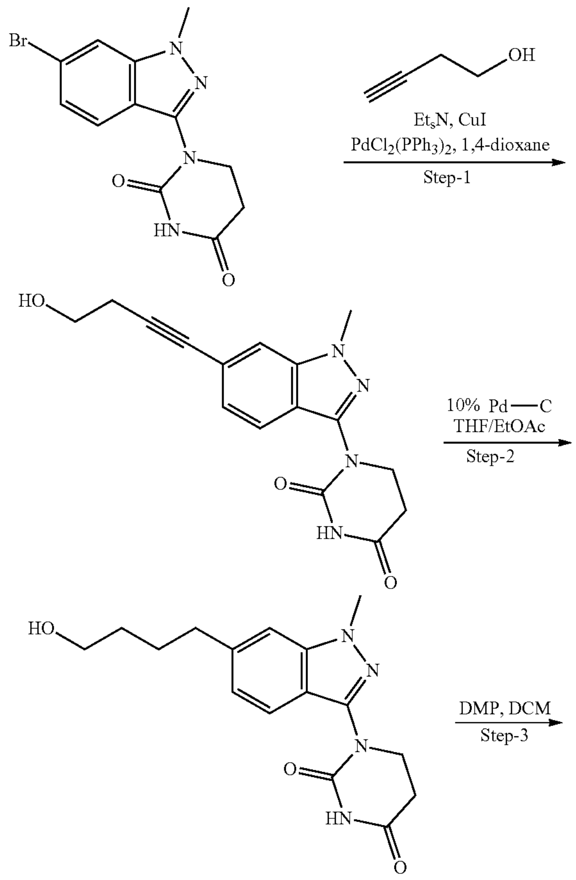

-continued

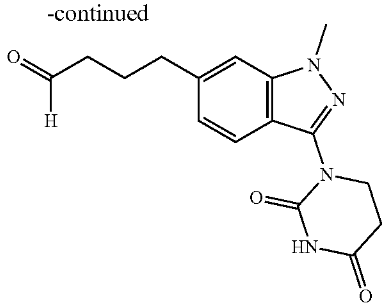

Step-1:

To a stirred solution mixture of 1-(6-bromo-1-methyl-indazol-3-yl)hexahydropyrimidine-2,4-dione (5 g, 15.47 mmol) and but-3-yn-1-ol (3.25 g, 46.41 mmol, 3.51 mL) was added triethyl amine (15.66 g, 154.73 mmol, 21.57 mL) and degassed the reaction mixture with argon for 10 minutes. CuI (1.56 g, 8.20 mmol) and $PdCl_2(PPh_3)_2$ (1.41 g, 2.32 mmol) were added to the reaction mixture, and the resulting mixture was heated at 120° C. for 6 hrs. After completion, the reaction mixture was diluted with water and extracted with ethyl acetate (3×100 mL). The combined extracts were dried over sodium sulfate, filtered, and concentrated under reduced vacuum to get crude which was purified by reverse-phase to afford 1-[6-(4-hydroxybut-1-ynyl)-1-methyl-indazol-3-yl]hexahydropyrimidine-2,4-dione (4.5 g, 6.96 mmol, 44.97% yield) as a solid. LC-MS ($ES^+$): m/z 313.53 $[M+H]^+$.

Step-2:

To a stirred solution of 1-[6-(4-hydroxybut-1-ynyl)-1-methyl-indazol-3-yl]hexahydropyrimidine-2,4-dione (3.6 g, 11.53 mmol) in THF (50 mL) was added 10% palladium on carbon wet (3.6 g, 33.83 mmol) and the resulting mixture was stirred under hydrogen gas atmosphere at room temperature for 30 h. The reaction was monitored by TLC and LCMS. Upon completion, the resulting mixture was filtered through a celite bed, and the resulting filtrate was concentrated under reduced vacuum to afford 1-[6-(4-hydroxybutyl)-1-methyl-indazol-3-yl] hexahydropyrimidine-2,4-dione (3.5 g, 5.89 mmol, 51.07% yield) as brown viscous material. LC-MS ($ES^+$): m/z 317.52 $[M+H]^+$.

Step-3:

To a stirred solution of 1-[6-(4-hydroxybutyl)-1-methyl-indazol-3-yl]hexahydropyrimidine-2,4-dione (150 mg, 474.15 μmol) in DCM (3 mL) was added Dess-Martin periodinane (603.32 mg, 1.42 mmol) at 0° C. and the resulting mixture was stirred at room temperature for 1 h. The reaction progress was monitored by TLC and LCMS. Upon completion, the resulting mixture was diluted with bicarbonate solution and extracted by ethyl acetate (3×50 mL). The combined organics were dried over sodium sulfate, filtered, and concentrated under reduced vacuum to afford 4-[3-(2,4-dioxohexahydropyrimidin-1-yl)-1-methyl-indazol-6-yl]butanal (130 mg, 266.92 μmol, 56.29% yield) as brown viscous material. LC-MS ($ES^+$): m/z 14.95 $[M+H]^+$.

Synthesis of 1-[1-methyl-6-[rac-(3R,4S)-3-methoxy-4-piperidyl]indazol-3-yl]hexahydropyrimidine-2,4-dione

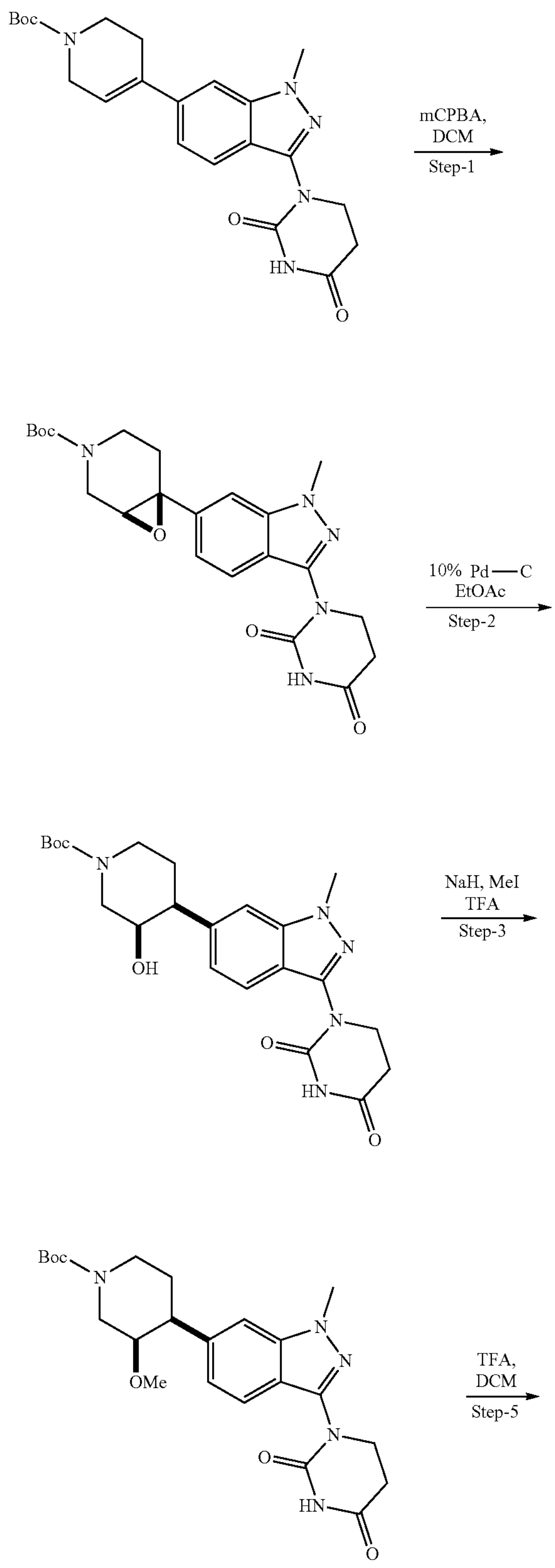

-continued

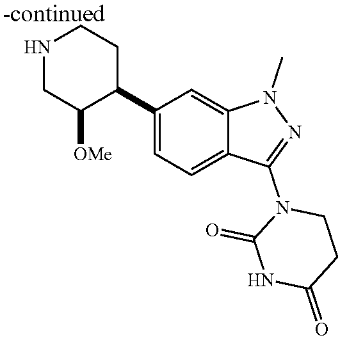

Step-1:

To a stirred solution of tert-butyl 4-(3-(2,4-dioxotetrahydropyrimidin-1(2H)-yl)-1-methyl-1H-indazol-6-yl)-3,6-dihydropyridine-1(2H)-carboxylate (9.5 g, 22.33 mmol) in DCM (150 mL) was added m-chloroperoxy benzoic acid (11.56 g, 66.98 mmol) at 0° C. under $N_2$ atmosphere. The reaction mixture was stirred at 0° C. for 4 h while monitoring the reaction by TLC and LC-MS. Upon completion, the reaction mixture was diluted with saturated $Na_2CO_3$ (100 mL×3) and extracted with DCM (2×100 mL). The combined organic layer was washed with brine solution (100 mL), dried over anhydrous sodium sulfate, and concentrated under reduced pressure to get the crude compound tert-butyl 6-(3-(2,4-dioxotetrahydropyrimidin-1(2H)-yl)-1-methyl-1H-indazol-6-yl)-7-oxa-3-azabicyclo[4.1.0]heptane-3-carboxylate (7 g, 10.04 mmol, 44.94% yield) as a pale brown gum. LC-MS ($ES^+$): m/z 442.36 $[M+H]^+$.

Step-2:

To a stirred solution of tert-butyl 6-[3-(2,4-dioxohexahydropyrimidin-1-yl)-1-methyl-indazol-6-yl]-7-oxa-3-azabicyclo[4.1.0]heptane-3-carboxylate (6 g, 13.59 mmol) in ethanol (200 mL) was added 10% palladium on carbon (50% w.t.) (6 g, 13.59 mmol) and it was stirred for 16 h at room temperature under $H_2$ pressure in the bladder, the reaction was monitored by TLC and LCMS. Upon completion, the reaction mixture was filtered through a celite bed, washed with 10% MeOH/DCM. The filtrate was evaporated under reduced pressure to get tert-butyl rac-(3S,4R)-4-[3-(2,4-dioxohexahydropyrimidin-1-yl)-1-methyl-indazol-6-yl]-3-hydroxy-piperidine-1-carboxylate (3.2 g, 5.47 mmol, 40.27% yield). LC-MS ($ES^+$): m/z 444.41 $[M+H]^+$.

Step-3:

To a stirred solution of tert-butyl rac-(3R,4S)-4-[3-(2,4-dioxohexahydropyrimidin-1-yl)-1-methyl-indazol-6-yl]-3-hydroxy-piperidine-1-carboxylate (300 mg, 676.45 μmol) in THE (5 mL), sodium hydride (in oil dispersion) 60% dispersion in mineral oil (81.17 mg, 2.03 mmol) was added, then the reaction was stirred for 1 h at room temperature and cooled to 0° C. Iodomethane (211.23 mg, 1.49 mmol, 92.65 μL) was added to the reaction mixture, and the reaction was continued for 4 h at room temperature. When starting material was consumed confirmed by TLC, then the reaction mixture was quenched with saturated ammonium chloride solution and extracted with ethyl acetate. The organic layer was washed further with brine solution, dried over sodium sulfate, and concentrated under reduced pressure to afford the crude compound. The crude mass was purified using column chromatography using 230-400 silica mesh (5-10% MeOH-DCM) to afford tert-butyl rac-(3R,4S)-4-[3-(2,4-dioxohexahydropyrimidin-1-yl)-1-methyl-indazol-6-yl]-3-methoxy-piperidine-1-carboxylate (40 mg, 76.94 μmol, 11.37% yield) as a colorless liquid. LC-MS ($ES^+$): m/z 480.55 $[M+Na]^+$.

Step-4:

To a stirred solution of tert-butyl rac-(3R,4S)-4-[3-(2,4-dioxohexahydropyrimidin-1-yl)-1-methyl-indazol-6-yl]-3-methoxy-piperidine-1-carboxylate (40 mg, 87.43 μmol) in DCM (3 mL) was added TFA (0.5 mL) at 0° C. and resulting suspension was stirred for 2 hr. The reaction progress was monitored by TLC and LCMS. Upon completion, the reaction mixture was concentrated under reduced pressure to get the crude product, which was triturated with diethyl ether (5 mL×2) to afford 1-[1-methyl-6-[rac-(3R,4S)-3-methoxy-4-piperidyl] indazol-3-yl]hexahydropyrimidine-2,4-dione (40 mg, 72.12 μmol, 82.49% yield) as a yellow liquid. LC-MS ($ES^+$): m/z 358.17 $[M+H]^+$.

Synthesis of 1-(7-(piperidin-4-yl)imidazo[1,2-a]pyridin-3-yl)dihydropyrimidine-2,4(1H,3H)-dione

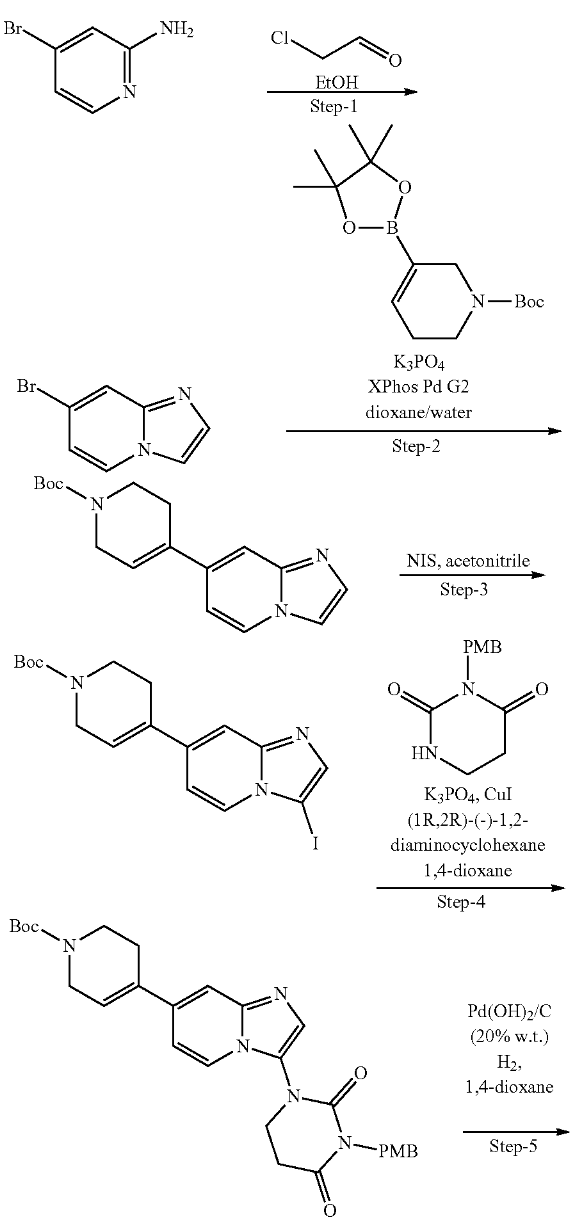

-continued

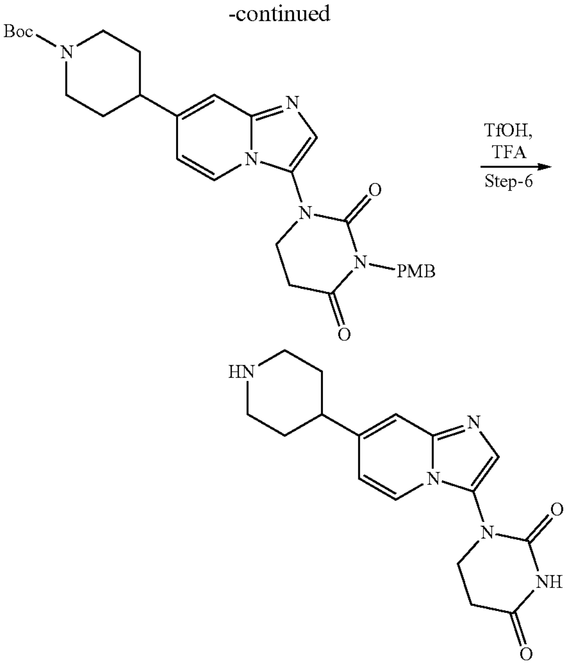

Step-1:

To a 250 mL three-necked-round bottomed flask containing 4-bromopyridin-2-amine (15 g, 86.70 mmol) in ethanol (80 mL), 2-chloroacetaldehyde (34.03 g, 433.50 mmol) was added to room temperature under nitrogen atmosphere. The resulting mixture was stirred at 100° C. for 4 h. The reaction mixture was allowed to room temperature and concentrated under reduced pressure to get the residue. The residue was dissolved in the ethyl acetate, followed by the addition of water. The mixture was extracted with ethyl acetate (3×60 mL). The combined organic layers were washed with 10% sodium bicarbonate solution, water (2×40 mL), brine, and dried over anhydrous sodium sulfate. The solvent was removed under reduced pressure, and the residue was purified by flash chromatography using silica gel (230-400 mesh) eluting with 70-80% ethyl acetate in petroleum ether to obtain 7-bromoimidazo[1,2-a]pyridine (15 g, 76.09 mmol, 87.76% yield) as a brown color solid. LC-MS ($ES^+$) m/z: 197.0 $[M+H]^+$.

Step-2:

To a 250 mL three-necked-round bottomed flask containing a solution of 7-bromoimidazo[1,2-a] pyridine (6 g, 30.44 mmol) and tert-butyl 4-(4,4,5,5-tetramethyl-1,3,2-dioxaborolan-2-yl)-3,6-dihydro-2H-pyridine-1-carboxylate (9.41 g, 30.44 mmol) in 1,4-dioxane (84 mL) and water (36 mL), $K_3PO_4$ (12.92 g, 60.87 mmol) was added. The reaction mixture was purged with nitrogen for 2 min, followed by adding XPhos Pd G2 (2.39 g, 3.04 mmol) and purged again with nitrogen for 2 min. The resulting mixture was stirred at 1000° C. for 2 h. Upon completion, the reaction mixture was cooled to room temperature and filtered through a celite bed; The filtration was concentrated under reduced pressure to get the residue. Ethyl acetate and water (10 mL) were added to dissolve the residue, followed by extraction with ethyl acetate (3×60 mL). The combined organic layers were collected, dried over anhydrous $Na_2SO_4$, filtered, and concentrated under reduced pressure to get the crude product. The obtained crude product was purified by flash chromatography using silica gel (230-400 mesh) eluting with 80-90% ethyl acetate in petroleum ether to get tert-butyl 4-imidazo[1,2-a]pyridin-7-yl-3,6-dihydro-2H-pyridine-1-carboxylate (6 g, 20.04 mmol, 65.85% yield) as a brown color solid. LC-MS ($ES^+$): m/z 1300.5 $[M+H]^+$.

Tert-butyl 4-imidazo[1,2-a] pyridin-7-yl-3,6-dihydro-2H-pyridine-1-carboxylate (6 g, 20.04 mmol) and acetonitrile (150 mL) was added into a 100 mL single neck round-bottomed flask, followed by the addition of N-Iodosuccinimide (4.51 g, 20.04 mmol) portion-wise under nitrogen atmosphere. The resulting mixture was stirred at room temperature for 30 minutes. The reaction mixture was filtered through the Buchner funnel, washed with acetonitrile, and dried to get tert-butyl 4-(3-iodoimidazo[1,2-a] pyridin-7-yl)-3,6-dihydro-2H-pyridine-1-carboxylate (6.5 g, 15.09 mmol, 75.30% yield) as a brown color solid. LC-MS ($ES^+$): m/z 426.5 $[M+H]^+$.

Step-4:

Tert-butyl 4-(3-iodoimidazo[1,2-a]pyridin-7-yl)-3,6-dihydro-2H-pyridine-1-carboxylate (3 g, 6.97 mmol), 3-[(4-methoxyphenyl)methyl]hexahydropyrimidine-2,4-dione (2.28 g, 9.75 mmol) and 1,4-dioxane (40 mL) was added into 40 mL screw-cap vial, followed by the addition of $K_3PO_4$ (2.96 g, 13.93 mmol). The reaction mixture was purged with nitrogen for 2 min. To this, (1R,2R)-(−)-1,2-diaminocyclohexane (159.08 mg, 1.39 mmol), copper (I) iodide (265.32 mg, 1.39 mmol, 47.21 μL) was added and purged with nitrogen for 2 min. The resulting mixture was stirred at 100° C. for 16 h. Upon completion, the reaction mixture was cooled to room temperature and concentrated under reduced pressure to get residue. Ethyl acetate and water (10 mL) were added to dissolve the residue, followed by extraction with ethyl acetate (3×60 mL). The organic layers were dried over anhydrous $Na_2SO_4$, filtered, and concentrated under reduced pressure to get the crude product. The obtained crude product was purified by flash chromatography using silica gel (230-400 mesh) eluting with 4-5% methanol in dichloromethane to get tert-butyl 4-[3-[3-[(4-methoxyphenyl)methyl]-2,4-dioxo-hexahydropyrimidin-1-yl]imidazo[1,2-a]pyridin-7-yl]-3,6-dihydro-2H-pyridine-1-carboxylate (2.5 g, 3.83 mmol, 55.04% yield) as a brown color solid. LC-MS ($ES^+$): m/z 532.8 $[M+H]^+$.

Step-5:

To a 250 mL single neck round bottomed flask containing tert-butyl 4-[3-[3-[(4-methoxyphenyl)methyl]-2,4-dioxo-hexahydropyrimidin-1-yl]imidazo[1,2-a]pyridin-7-yl]-3,6-dihydro-2H-pyridine-1-carboxylate (3 g, 4.60 mmol) in 1,4-dioxane (100 mL), palladium hydroxide on carbon (20% w.t.) (1.62 g, 11.50 mmol) was added at room temperature under nitrogen atmosphere. The resulting mixture was stirred under hydrogen bladder atmosphere at room temperature for 32 h. The reaction mixture was filtered on celite bed, washed with mixture of solvents 1,4-dioxane and ethyl acetate (500 mL) and filtrate was concentrated under reduced pressure to get tert-butyl 4-[3-[3-[(4-methoxyphenyl)methyl]-2,4-dioxo-hexahydropyrimidin-1-yl]imidazo[1,2-a]pyridin-7-yl]piperidine-1-carboxylate (3 g, 4.36 mmol, 94.75% yield) as a black color solid. LC-MS ($ES^+$): m/z 534.2 $[M+H]^+$.

Step-6:

To a 500 mL single neck round-bottomed flask containing tert-butyl 4-[3-[3-[(4-methoxyphenyl)methyl]-2,4-dioxo-hexahydropyrimidin-1-yl]imidazo[1,2-a]pyridin-7-yl]piperidine-1-carboxylate (3 g, 4.36 mmol) in trifluoroacetic acid (20 mL), trifluoromethanesulfonic acid (6.83 g, 45.52 mmol, 4 mL) was added at 0° C. under nitrogen atmosphere. The resulting mixture was stirred at 70° C. for 1 h. Upon completion of the reaction, the reaction mixture was allowed to warm up to room temperature, concentrated under reduced pressure, co-distilled with dichloromethane (2×15 mL), and dried to get 1-[7-(4-piperidyl)imidazo[1,2-a]pyridin-3-yl]hexahydropyrimidine-2,4-dione (3 g, 4.06 mmol, 93.15% yield) as a brown color oil. LC-MS ($ES^+$): m/z 314.3 $[M+H]^+$.

Synthesis of 1-(6-(piperidin-4-yl)pyrazolo[1,5-a]pyridin-3-yl)dihydropyrimidine-2,4(1H,3H)-dione

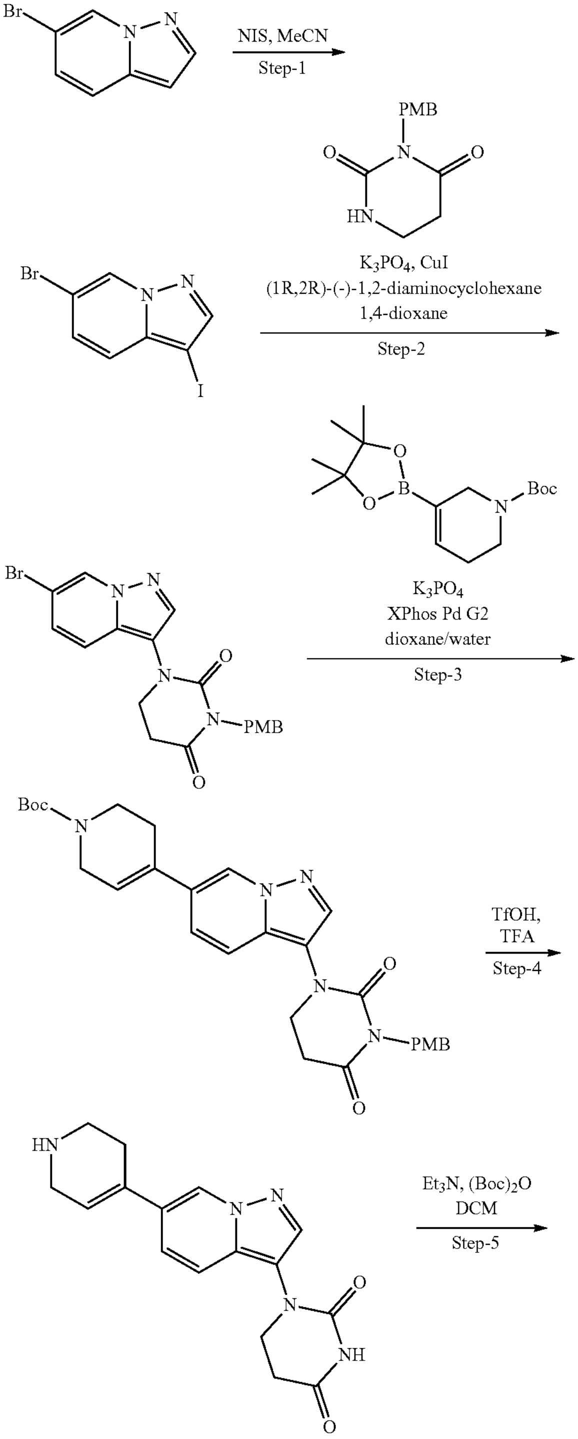

-continued

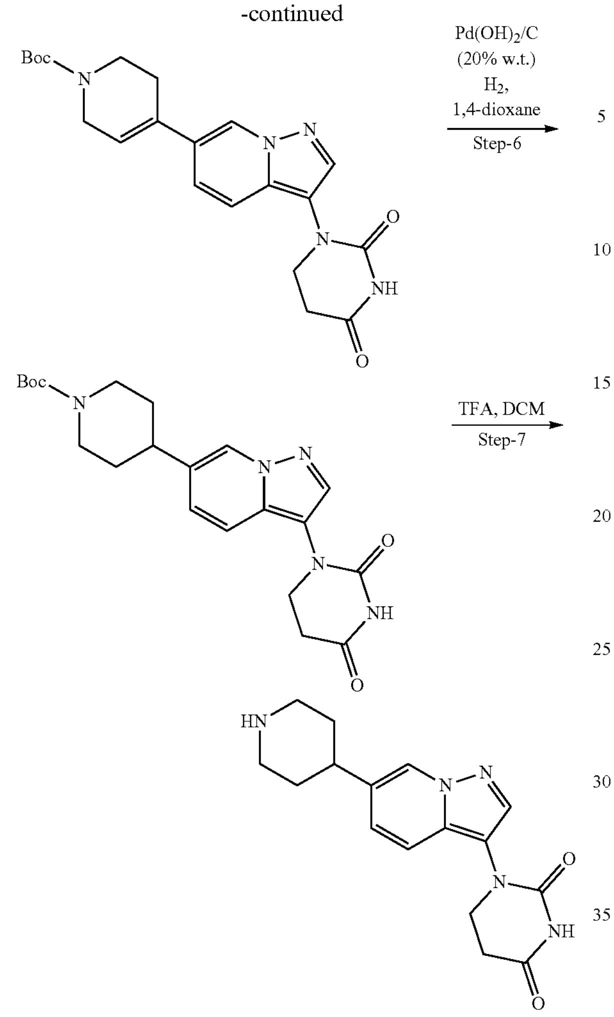

The procedures are identical to the synthesis of intermediate 1-(7-(piperidin-4-yl)imidazo[1,2-a]pyridin-3-yl)dihydropyrimidine-2,4(1H,3H)-dione, and the product 1-(6-(piperidin-4-yl)pyrazolo[1,5-a]pyridin-3-yl) dihydropyrimidine-2,4(1H,3H)-dione was confirmed by LC-MS. LC-MS (ES$^+$): m/z 314.40 [M+H]$^+$.

Synthesis of 1-(6-(piperidin-4-yl)benzo[d]isoxazol-3-yl)dihydropyrimidine-2,4(1H,3H)-dione

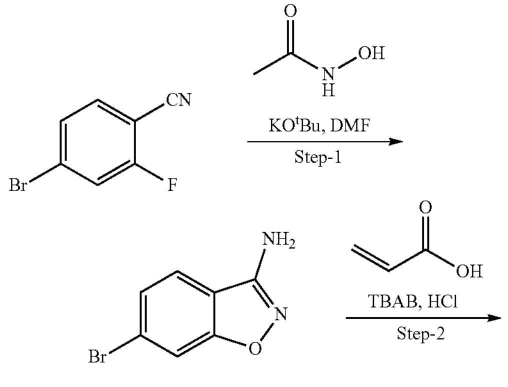

-continued

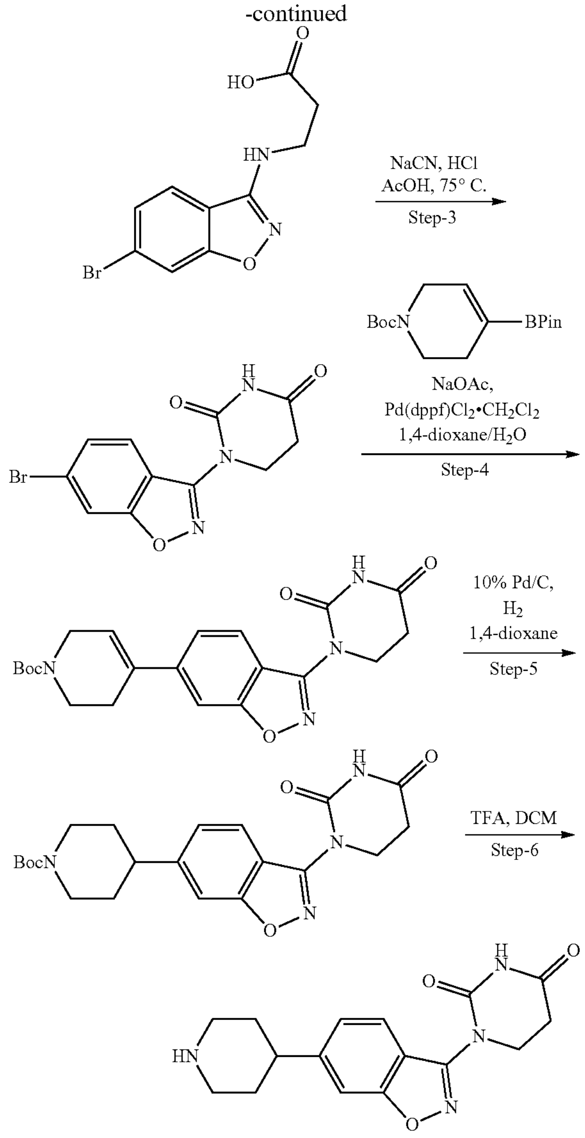

Step-1:

To a stirred solution of ethanehydroxamic acid (5 g, 66.61 mmol) in DMF (100 mL), potassium tert-butoxide (7.47 g, 66.61 mmol) was added at room temperature and stirred for 0.5 h. 4-Bromo-2-fluoro-benzonitrile (9.33 g, 46.63 mmol) was added to the reaction mixture and stirred for 4 h at room temperature. Subsequently, the reaction mixture was diluted with ice-cold water (300 mL) and extracted with EtOAc (2×300). The organic layer was separated, washed with brine, dried over $Na_2SO_4$, and concentrated under reduced pressure to afford the crude product. The crude compound was purified by column chromatography using silica (100-200 mesh size) and 30-50% EtOAc/PE as eluent to afford the product 6-bromo-1,2-benzoxazol-3-amine (5.2 g, 24.39 mmol, 36.61% yield) as a white solid. LC-MS (ES$^+$): m/z 212.58 [M+H]$^+$.

Step-2:

To the stirred solution of 6-bromo-1,2-benzoxazol-3-amine (20 g, 93.88 mmol) in tetrabutyl ammonium bromide (3.03 g, 9.39 mmol), 2M aq. HCl (200 mL) was added at room temperature. The reaction mixture was heated to 55° C. (internal temperature), and methyl prop-2-enoate (9.70 g, 112.66 mmol, 10.15 mL) was added dropwise at the same temperature. The reaction mixture was heated at 80° C. (external) for 12 h. After completion, the reaction mixture was cooled to room temperature and diluted with ice-cold water (200 mL), neutralized with aq. 2M $NaHCO_3$ solution (pH-6.5 to 7), stirred vigorously for 1 h. The solid precipitated out was filtered off and washed with an excess of ice-cold water (100 ml), vacuum dried for 12 h to afford 3-[(6-bromo-1,2-benzoxazol-3-yl)amino]propanoic acid (9.3 g, 23.92 mmol, 25.48% yield) as an off-white solid. LC-MS ($ES^+$): m/z 284.44 $[M+H]^+$.

Step-3:

To the stirred solution of 3-[(6-bromo-1,2-benzoxazol-3-yl)amino]propanoic acid (9 g, 31.57 mmol) in acetic acid (180 mL), sodium cyanate (20.52 g, 315.69 mmol) was added at room temperature. The reaction mixture was heated at 75° C. (external) for 12 h. Then added 4M aq. HCl (500 mL) solution to the reaction mixture at 75° C. (external) and continued the reaction at the same temperature for 4 h. The progress of the reaction was monitored by TLC and LC-MS. After completion, the reaction mixture was cooled to room temperature and stirred at room temperature for 3 h, and the solid precipitated out while stirring. The precipitated solid was filtered off, dried under vacuum to afford 1-(6-bromo-1,2-benzoxazol-3-yl)hexahydropyrimidine-2,4-dione (3.7 g, 11.82 mmol, 37.44% yield) as an off-white solid. LC-MS ($ES^+$): m/z 310.14 $[M+H]^+$.

Step-4:

To a stirred solution of 1-(6-bromo-1,2-benzoxazol-3-yl) hexahydropyrimidine-2,4-dione (100 mg, 322.47 μmol) in water (5 mL), tert-butyl 4-(4,4,5,5-tetramethyl-1,3,2-dioxaborolan-2-yl)-3,6-dihydro-2H-pyridine-1-carboxylate (129.62 mg, 419.22 μmol) was added, followed by sodium acetate (79.36 mg, 967.42 μmol) and the reaction mixture was purged with argon gas for 10 minutes. Pd(dppf) $Cl_2 \cdot CH_2Cl_2$ (13.2 mg, 16.12 μmol) into the reaction mixture, and then the mixture was heated to reflux at 90° C. for 16 hr. Upon completion, the reaction mixture was quenched with ice water and extracted with ethyl acetate (3×20 mL). The combined organic layers were dried over sodium sulfate, filtered, and concentrated under reduced pressure to give the crude product. The crude product was purified by column chromatography using (230-400 silica gel) 20-30% EtOAc/PE to afford tert-butyl 4-[3-(2,4-dioxohexahydropyrimidin-1-yl)-1,2-benzoxazol-6-yl]-3,6-dihydro-2H-pyridine-1-carboxylate (80 mg, 156.96 μmol, 48.67% yield) as an off white solid. LC-MS ($ES^+$): m/z 312.78 $[M-Boc+H]^+$.

Step-5:

To a stirred solution of tert-butyl 4-[3-(2,4-dioxohexahydropyrimidin-1-yl)-1,2-benzoxazol-6-yl]-3,6-dihydro-2H-pyridine-1-carboxylate (970 mg, 2.35 mmol) in 1,4-dioxane (50 mL) palladium on carbon (10% w.t.) (485 mg) was added at room temperature. The reaction mixture was stirred under the hydrogen atmosphere using a hydrogen bladder for 16 hr. Upon completion of the reaction, the reaction mixture was filtered through a celite bed and washed with 10% MeOH/DCM (250 mL). The filtrate was concentrated under reduced pressure to afford tert-butyl 4-[3-(2,4-dioxohexahydropyrimidin-1-yl)-1,2-benzoxazol-6-yl]piperidine-1-carboxylate (670 mg, 1.25 mmol, 53.22% yield) as a brown gummy liquid. LC-MS ($ES^-$): m/z 413.19 $[M-H]^-$.

Step-6:

Tert-butyl 4-[3-(2,4-dioxohexahydropyrimidin-1-yl)-1,2-benzoxazol-6-yl]piperidine-1-carboxylate (36 mg, 86.86 μmol) was dissolved in DCM (2 mL) and cooled to 0° C., followed by the addition of TFA (9.90 mg, 86.86 μmol, 6.69 μL) dropwise under inert atmosphere. The resulting reaction mixture was then allowed to stir at room temperature for 1 h. After completion of the reaction, the mixture was concentrated under reduced pressure. The crude product was triturated with diethyl ether (3×5 mL) to afford TFA salt of 1-[6-(4-piperidyl)-1,2-benzoxazol-3-yl]hexahydropyrimidine-2,4-dione (36 mg, 84.04 μmol) as brown solid. LC-MS ($ES^+$): m/z 315.3 $[M+H]^+$.

Synthesis of tert-butyl-7-(4-aminophenyl)-4-azaspiro[2.5]octane-4-carboxylate

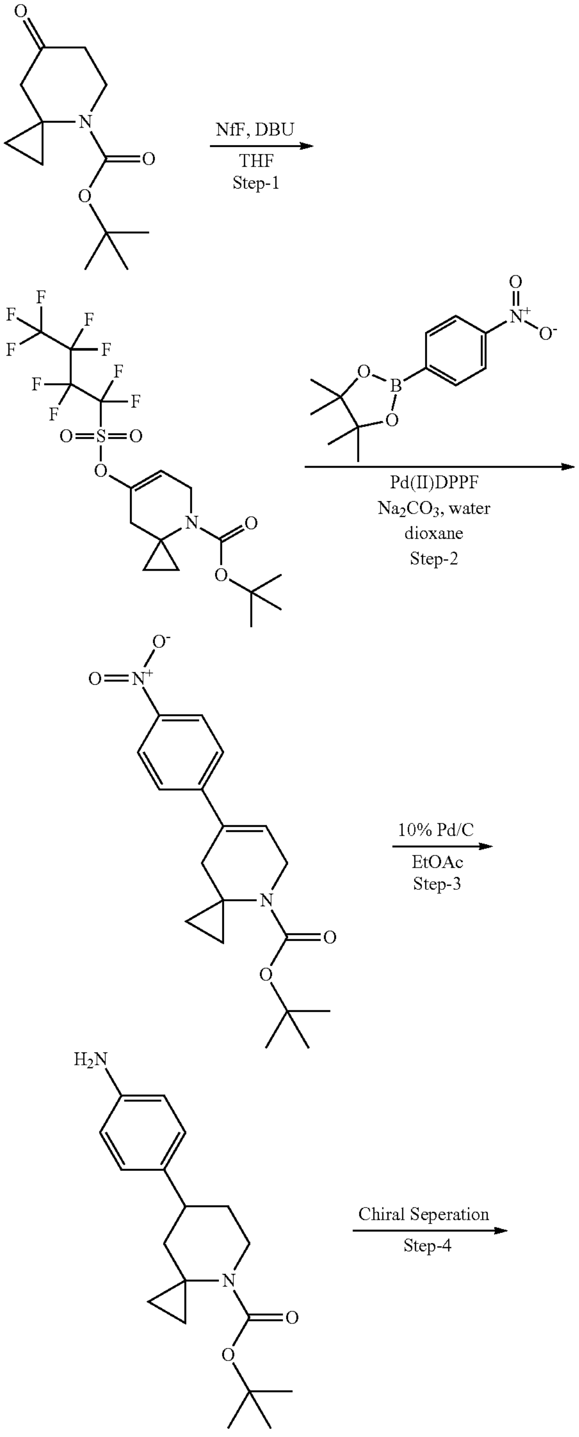

-continued

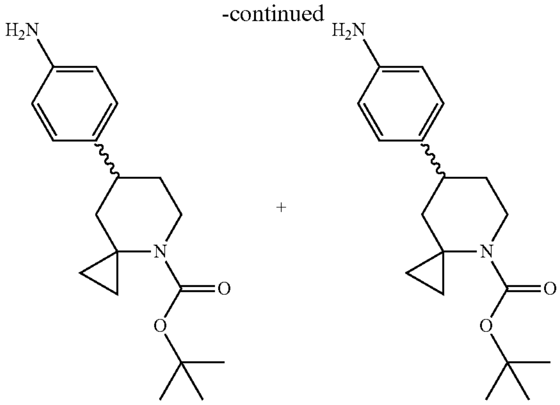

Isomer 1 Isomer 2

Step-1:

To THF (15 mL) solution of tert-butyl 7-oxo-4-azaspiro[2.5]octane-4-carboxylate (1 g, 4.44 mmol), 2,3,4,6,7,8,9,10-octahydropyrimido[1,2-a]azepine (3.38 g, 22.19 mmol, 3.31 mL) was added at −5° C.-0° C. After 10 minutes, 1,1,2,2,3,3,4,4,4-nonafluorobutane-1-sulfonyl fluoride (6.70 g, 22.19 mmol, 3.83 mL) was added to the reaction mixture and it was stirred for 2 hours at 0° C. After completing the reaction, cold water and ethyl acetate were added to the reaction mixture. The organic layer was separated, washed with brine, dried over sodium sulfate, and filtered. Then the filtrate was evaporated under reduced pressure, and the crude product was purified by column chromatography (silica gel 100-200 mesh) to afford tert-butyl 7-(1,1,2,2,3,3,4,4,4-nonafluorobutylsulfonyloxy)-4-azaspiro[2.5]oct-6-ene-4-carboxylate (2 g, 3.74 mmol, 84.36% yield). LC-MS ($ES^+$): m/z 451.9 $[M-tBu+H]^+$.

Step-2:

To a stirred solution of tert-butyl 7-(1,1,2,2,3,3,4,4,4-nonafluorobutylsulfonyloxy)-4-azaspiro[2.5]oct-6-ene-4-carboxylate (250 mg, 492.74 μmol) and 4,4,5,5-tetramethyl-2-(4-nitrophenyl)-1,3,2-dioxaborolane (147.27 mg, 591.29 μmol) in 1,4-dioxane (4 mL) and water (1 mL) was added sodium carbonate (156.67 mg, 1.48 mmol, 61.93 μL) and thoroughly purged with argon. $Pd(dppf)Cl_2$ (36.05 mg, 49.27 μmol) was added under an inert atmosphere, and the resulting mixture was heated at 55° C. for 2 hours. After completion (confirmed by TLC and LCMS), the reaction mixture was diluted with ethyl acetate, filtered through a short pad of celite, and washed with ethyl acetate. The combined organic layers were washed with water and brine, dried over anhydrous sodium sulfate, filtered, and concentrated under reduced pressure. The crude material was purified by column chromatography (15% ethyl acetate in hexane) to give tert-butyl 7-(4-nitrophenyl)-4-azaspiro[2.5]oct-6-ene-4-carboxylate (140 mg, 381.38 μmol, 77.40% yield). LC-MS ($ES^+$): m/z 331.04 $[M+H]^+$.

Step-3:

To a degassed solution of tert-butyl 7-(4-nitrophenyl)-4-azaspiro[2.5]oct-6-ene-4-carboxylate (4 g, 12.11 mmol) in ethyl acetate (60 mL) was added 10 wt. % palladium on carbon, wet, (1.29 g, 12.11 mmol) was added. The resulting mixture was stirred at room temperature under a balloon of hydrogen balloon for 16 h. After completion, the reaction mixture was filtered through a short pad of celite, washed with ethyl acetate, and concentrated under reduced pressure. The crude material was purified by reverse-phase prep-HPLC to give tert-butyl 7-(4-aminophenyl)-4-azaspiro[2.5]octane-4-carboxylate (2.5 g, 6.94 mmol, 57.36% yield). LC-MS ($ES^+$): m/z 303.60 $[M+H]^+$ Step-4:

Chiral separation of tert-butyl 7-(4-aminophenyl)-4-azaspiro[2.5]octane-4-carboxylate (4.4 g, 14.55 mmol) by normal phase prep HPLC afforded tert-butyl-7-(4-aminophenyl)-4-azaspiro[2.5]octane-4-carboxylate isomer 1 (1.2 g, 3.95 mmol, 27.13% yield) [eluent-2; 8.7 min-RT] and tert-butyl-7-(4-aminophenyl)-4-azaspiro[2.5]octane-4-carboxylate isomer 2 (1.6 g, 4.35 mmol, 29.90% yield) [eluent-1; 7.37 min-RT] after lyophilization.

Following method was used to separate the enantiomers by normal phase prep HPLC:

Column: Chiralcel OD-H (250×20 mm) 5u

Flow rate: 18 ml/min

Mobile phase—HEXANE/ETOH/IPAMINE: 90/10/20/0.1

Solubility: MEOH

Wave length: 238 nm

Run time: 20 min

Stack time: 8.3 min

Synthesis of 3-[4-[4-azaspiro[2.5]octan-7-yl]anilino]piperidine-2,6-dione isomer 1

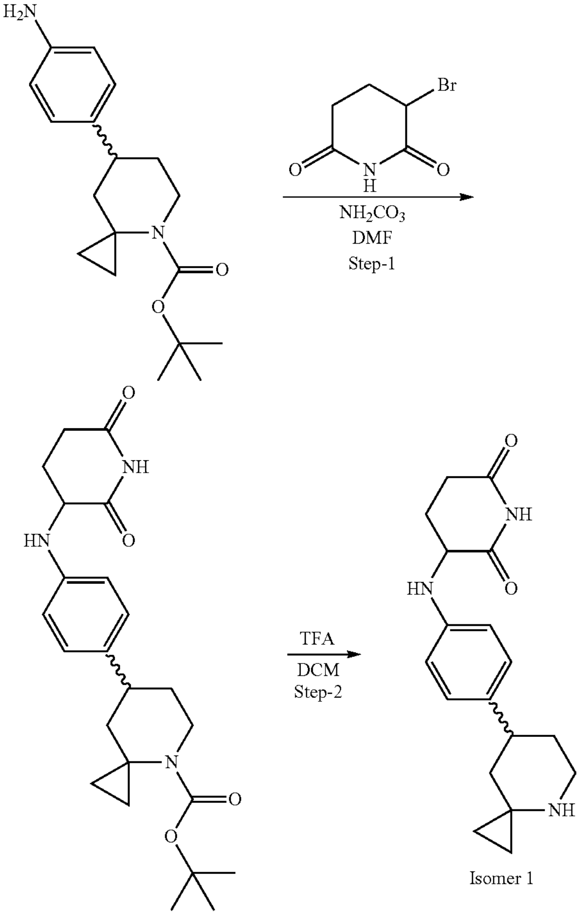

Isomer 1

Step-1:

To a stirred solution of tert-butyl-7-(4-aminophenyl)-4-azaspiro[2.5]octane-4-carboxylate isomer 1 (1.8 g, 5.95 mmol) and 3-bromopiperidine-2,6-dione (2.29 g, 11.90 mmol) in DMF (18 mL) was added sodium bicarbonate (2.00 g, 23.81 mmol) at room temperature in a sealed tube. The reaction mixture was heated to 70° C. and stirred for 16 hours. After completion, the reaction mixture was diluted with ethyl acetate (50 ml) and washed with water and brine. The organic layer was separated, dried over sodium sulfate, filtered, and concentrated under reduced pressure. The crude material was purified by silica gel column chromatography (35-40% ethyl acetate-hexane) to give tert-butyl-7-[4-[(2,6-dioxo-3-piperidyl)amino]phenyl]-4-azaspiro[2.5]octane-4-carboxylate isomer 1 (1.4 g, 3.39 mmol, 56.88% yield). LC-MS ($ES^+$): m/z 414.49 $[M+H]^+$.

Step-2:

To a DCM (28 mL) solution of tert-butyl (7R)-7-[4-[(2,6-dioxo-3-piperidyl)amino]phenyl]-4-azaspiro[2.5]octane-4-carboxylate (1.4 g, 3.39 mmol), trifluoroacetic acid (10.73 g, 94.07 mmol, 7.25 mL) was added at 0° C. Then the reaction mixture was stirred at room temperature for 4 hours. After the completion of the reaction, DCM was evaporated under reduced pressure, co-distilled with DCM and n-pentane, lyophilization afforded 3-[4-[4-azaspiro[2.5]octan-7-yl]anilino]piperidine-2,6-dione isomer 1 as a TFA salt (1.24 g, 2.75 mmol, 81.26% yield), which is a deep greenish solid. $^1H$ NMR (400 MHz, DMSO-$d_6$) δ 10.77 (s, 1H), 9.04 (bs, 1H), 8.34 (d, J=6.3 Hz, 1H), 6.96 (d, J=8.3 Hz, 2H), 6.63 (d, J=8.4 Hz, 2H), 4.29-4.25 (m, 2H), 4.20 (bs, 1H), 3.40 (d, J=11.5 Hz, 1H), 3.06 (d, J=11.0 Hz, 1H), 2.81-2.69 (m, 2H), 2.60-2.53 (m, 1H), 2.20-2.07 (m, 2H), 1.97-1.68 (m, 2H), 1.33 (d, J=13.8 Hz, 1H), 0.97 (q, J=9.8 Hz, 2H), 0.79 (s, 2H).

Synthesis of 3-[4-[4-azaspiro[2.5]octan-7-yl]anilino]piperidine-2,6-dione isomer 2

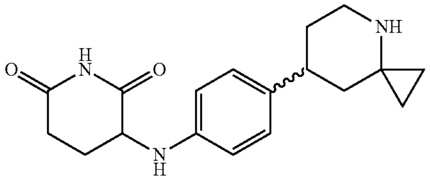

Isomer 2

Isomer 2 was synthesis in an analogous manner, except starting with the other enantiomer to give 3-[4-[4-azaspiro[2.5]octan-7-yl]anilino]piperidine-2,6-dione isomer 2 as a TFA salt (1.35 g, 3.09 mmol, 85.18% yield), which is a greenish solid. $^1H$ NMR (400 MHz, DMSO-$d_6$) δ 10.77 (s, 1H), 9.07 (bs, 1H), 8.37 (d, J=11.2 Hz, 1H), 6.96 (d, J=8.4 Hz, 2H), 6.63 (d, J=8.3 Hz, 2H), 4.90 (bs, 1H), 4.30-4.26 (m, 1H), 3.40 (d, J=11.6 Hz, 1H), 3.05 (d, J=10.6 Hz, 1H), 2.79-2.69 (m, 2H), 2.60-2.53 (m, 1H), 2.20-2.07 (m, 2H), 1.97-1.84 (m, 2H), 1.72 (d, J=12.9 Hz, 1H), 1.33 (d, J=14.4 Hz, 1H), 1.01-0.88 (m, 2H), 0.78 (s, 2H).

Synthesis of tert-butyl 4-[(4-aminophenyl)methyl]piperazine-1-carboxylate

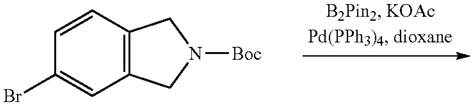

-continued

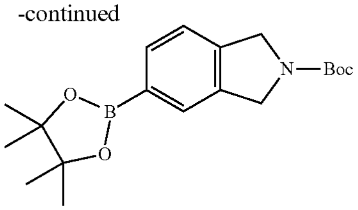

A solution of tert-butyl 5-bromoisoindoline-2-carboxylate (4.0 g, 13.41 mmol) and 4,4,5,5-tetramethyl-2-(4,4,5,5-tetramethyl-1,3,2-dioxaborolan-2-yl)-1,3,2-dioxaborolane (4.09 g, 16.10 mmol) in dioxane (40 mL) was stirred under argon atmosphere. Potassium acetate (5.27 g, 53.66 mmol) and tetrakis(triphenylphosphine)palladium(0) (141.59 mg, 134.15 μmol) were then added. The resulting mixture was stirred at 80° C. for 16 hours, and the progress of the reaction was monitored by TLC and LC-MS. After completion of the reaction, the reaction mixture was washed with ethyl acetate and filtered through celite, and the filtrate was extracted with ethyl acetate (3×100 mL). The combined organic layers were dried over anhydrous sodium sulfate and concentrated under reduced pressure to yield the crude product, which was purified by column chromatography (silica gel 230-400 mesh, 0-10% ethyl acetate) to afford tert-butyl 4-[(4-aminophenyl)methyl]piperazine-1-carboxylate (5.9 g, 19.23 mmol, 79.23% yield) as a white solid. LC-MS ($ES^+$): m/z 290.08 $[M-56+H]^+$.

Synthesis of tert-butyl 7-(4,4,5,5-tetramethyl-1,3,2-dioxaborolan-2-yl)-3,4-dihydro-1H-isoquinoline-2-carboxylate

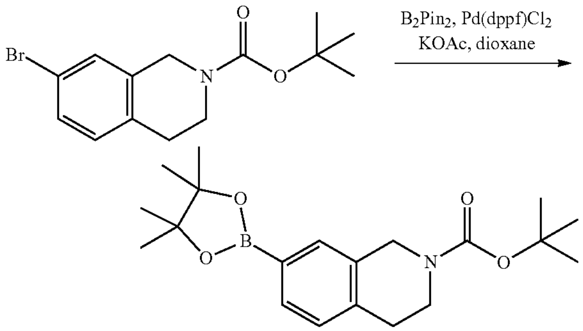

To a stirred solution of tert-butyl 7-bromo-3,4-dihydro-1H-isoquinoline-2-carboxylate (5 g, 16.02 mmol) in dioxane (30 mL) were added bis(pinacolato)diboron (4.47 g, 17.62 mmol) and potassium acetate (4.72 g, 48.05 mmol, 3.00 mL). The reaction mixture was purged with argon gas for 20 minutes before Pd(dppf)$Cl_2$ (1.17 g, 1.60 mmol) was added. The reaction was heated at 100° C. for 4 hours, and the reaction progress was monitored by TLC and LC-MS. Upon completion, the reaction was filtered through a celite bed and washed with ethyl acetate, and the filtrate was washed with brine solution. The organic layer was concentrated to dryness to yield the crude product, which was purified by Biotage (0-20% ethyl acetate in pet ether) to afford tert-butyl 7-(4,4,5,5-tetramethyl-1,3,2-dioxaborolan-2-yl)-3,4-dihydro-1H-isoquinoline-2-carboxylate (4.9 g, 13.50 mmol, 84.31% yield) as a semi-solid. LC-MS ($ES^+$): m/z 304.25 $[M-56+H]^+$.

Synthesis of 3-[4-(tert-butoxycarbonylamino)phenyl]propyl methanesulfonate

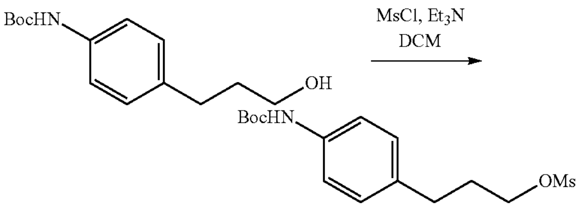

To a solution of tert-butyl N-[4-(3-hydroxypropyl)phenyl] carbamate (2 g, 7.96 mmol) in DCM was added triethylamine (2.42 g, 23.87 mmol, 3.33 mL) at room temperature and the reaction mixture was cooled to 0° C. Methanesulfonyl chloride, 98% (1.09 g, 9.55 mmol, 739.13 μL) was added dropwise, and the reaction was stirred at room temperature for 2 hours. The reaction mixture was diluted with DCM (30 mL) and washed with saturated $NaHCO_3$ solution (50 mL) and brine solution (50 mL). The organic layer was dried over sodium sulfate and concentrated in vacuo to yield the product 3-[4-(tert-butoxycarbonylamino)phenyl]propyl methanesulfonate (2.3 g, 5.93 mmol, 74.58% yield), which was used in the next step without any purification. LC-MS ($ES^+$): m/z 330.47 $[M+H]^+$.

Synthesis of 4-((tert-butoxycarbonyl)amino)phenethyl methanesulfonate

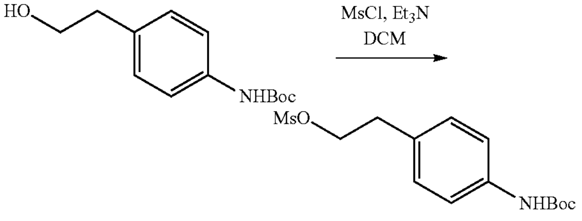

To a stirred solution of tert-butyl (4-(2-hydroxyethyl) phenyl)carbamate (5 g, 21.07 mmol,) in DCM (10 mL) was added triethylamine (21.32 g, 210.71 mmol, 29.37 mL). Subsequently, methanesulfonyl chloride (3.62 g, 31.61 mmol, 2.45 mL) was added, and the reaction was stirred at room temperature for 12 hours. After the reaction was complete, it was quenched with sodium bicarbonate solution and washed with ethyl acetate (100 mL). The organic layer was partitioned from the filtrate and concentrated in vacuo. The resultant crude product was purified by column chromatography (0-100% ethyl acetate in pet ether) to afford 4-((tert-butoxycarbonyl)amino)phenethyl methanesulfonate (5 g, 13.16 mmol, 62.45% yield) as a yellow gummy. LC-MS ($ES^+$): m/z 338.44 $[M+Na]^+$.

Synthesis of 2,2-difluorobut-3-ynoxymethylbenzene

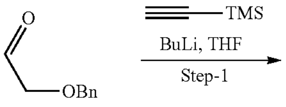

-continued

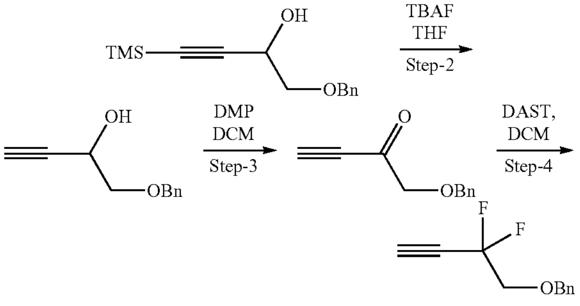

Step-1:

To a solution of ethynyl(trimethyl)silane (13.08 g, 133.18 mmol, 18.82 mL) in THE (450 mL) was slowly added butyllithium (13.65 g, 213.09 mmol, 66 mL) at −78° C. under nitrogen gas atmosphere. The resulting mixture was stirred at −78° C. for 30 minutes. To the reaction mixture, a solution of 2-benzyloxyacetaldehyde (10 g, 66.59 mmol) in THF (450 mL) was slowly added over 30 minutes, and the resulting mixture was stirred at −78° C. for additional 30 minutes and warmed up to room temperature for 2 h. After completion of the reaction, the mixture was quenched with saturated $NH_4Cl$ solution, diluted with water, and extracted with ethyl acetate (100 mlx3). The organic layers were combined and dried over anhydrous $Na_2SO_4$ and concentrated under reduced pressure to get crude 1-benzyloxy-4-trimethylsilyl-but-3-yn-2-ol (15 g, 51.33 mmol, 77.08% yield) as a light brown color liquid which was directly used for next step reaction without further purification.

1H NMR (400 MHz, CDCl3) δ 7.36-7.35 (m, 5H), 4.65 (s, 2H), 4.62-4.54 (m, 1H), 3.67-3.64 (m, 1H), 3.58-3.54 (m, 1H), 2.45 (d, J=4.4 Hz, 1H), 0.17 (s, 9H).

Step-2:

To a solution of 1-benzyloxy-4-trimethylsilyl-but-3-yn-2-ol (15 g, 60.39 mmol) in THF (300 mL) was added TBAF (67.72 g, 259.02 mmol, 75 mL) (1M in THF) at 0° C. and it was stirred for 2 h at rt under $N_2$. Upon completion of the reaction, the reaction mixture was quenched with sat-.$NaHCO_3$ (200 mL) and extracted with ethyl acetate (3×100 mL). The combined organic layer was washed with brine solution (50 mL), dried over anhydrous sodium sulfate, and concentrated under reduced pressure to get the crude product. The crude mixture was purified by column chromatography (silica gel 230-400 mesh, 5% ethyl acetate in petroleum ether) to afford 1-benzyloxybut-3-yn-2-ol (4.3 g, 21.96 mmol, 36.37% yield). $^1H$ NMR (400 MHz, $CDCl_3$) δ 7.38-7.28 (m, 5H), 4.69-4.54 (m, 3H), 3.68-3.64 (m, 1H), 3.61-3.56 (m, 1H), 2.59 (bs, 1H), 2.46 (d, J=2.4 Hz, 1H).

Step-3:

To a stirred solution of 1-benzyloxybut-3-yn-2-ol (16.5 g, 93.64 mmol) in DCM (500 mL) were added 1,1,1-Tris (acetyloxy)-1,1-dihydro-1,2-benziodoxol-3-(1H)-one (39.72 g, 93.64 mmol) at RT under $N_2$ atmosphere. The reaction mixture was stirred at room temperature for 16 h. Upon completion, the reaction mixture was diluted with water (100 mL) and filtered through a celite bed, and extracted with ethyl acetate (3×100 mL). The combined organic layer was washed with brine solution (100 mL), dried over anhydrous $Na_2SO_4$, and concentrated under reduced pressure to get the crude product which was purified by column chromatography (230-400 mesh silica) using 4% ethyl acetate in petroleum ether as eluent to afford 1-benzyloxybut-3-yn-2-one (7 g, 38.98 mmol, 41.63% yield). $^1$H NMR (400 MHz, $CDCl_3$) δ 7.38-7.32 (m, 5H), 4.65 (s, 2H), 4.25 (s, 2H), 3.32 (s, 1H).

Step-4:

To a solution of 1-benzyloxybut-3-yn-2-one (7 g, 40.18 mmol) in DCM (150 mL) was added diethylaminosulfur trifluoride (12.95 g, 80.37 mmol, 10.62 mL) at RT under $N_2$ atmosphere. The reaction mixture was heated at 55° C. for 16 h. Upon completion, the reaction mixture was diluted with water (100 mL) and extracted with ethyl acetate (3×50 mL). The combined organic layer was washed with brine solution (50 mL), dried over anhydrous sodium sulfate, and concentrated under reduced pressure to get the crude product which was purified by column chromatography (230-400 mesh silica) using 4% ethyl acetate in petroleum ether as eluent to afford 2,2-difluorobut-3-ynoxymethylbenzene (6 g, 28.14 mmol, 70.02% yield). $^1$H NMR (400 MHz, $CDCl_3$) δ 7.37-7.36 (m, 5H), 4.71 (s, 2H), 3.79 (t, J=12.1 Hz, 2H), 2.82 (t, J=5.1 Hz, 1H).

Intermediate Synthesis

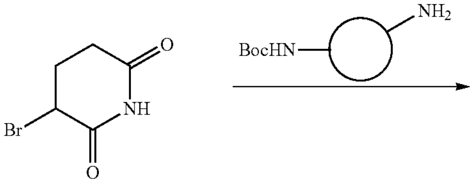

-continued

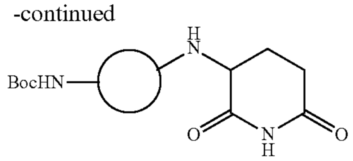

A solution of 3-bromopiperidine-2,6-dione (1 equiv.), the respective amine building block (1 equiv.), and DIPEA (3 equiv.) in 1,4-dioxane was stirred at 100° C. for 24 h under inert atmosphere. A second portion of 3-bromopiperidine-2,6-dione (1 equiv.) was added, and the reaction mixture was stirred for another 24 h at 100° C. The reacting mixture was evaporated, and the residue was subjected to prep HPLC. ((Waters SunFire C18 19*100 5 mkm column; gradient mixture H2O-MeCN as a mobile phase)) to afford the desired intermediates.

IV. Synthesis of Amine Precursors of Representative Compounds

Synthesis of 3-((4-(1-(4-(4-(4-(aminomethyl)-3-methylphenyl)pyrrolo[2,1-f][1,2,4]triazin-6-yl)benzyl)piperidin-4-yl)phenyl)amino)piperidine-2,6-dione

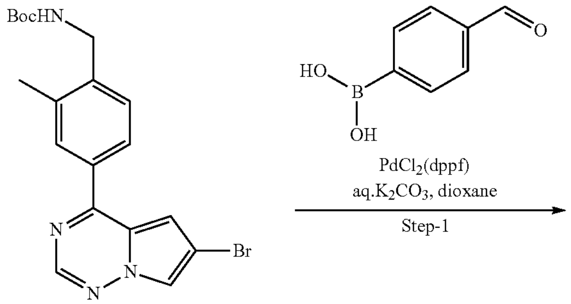

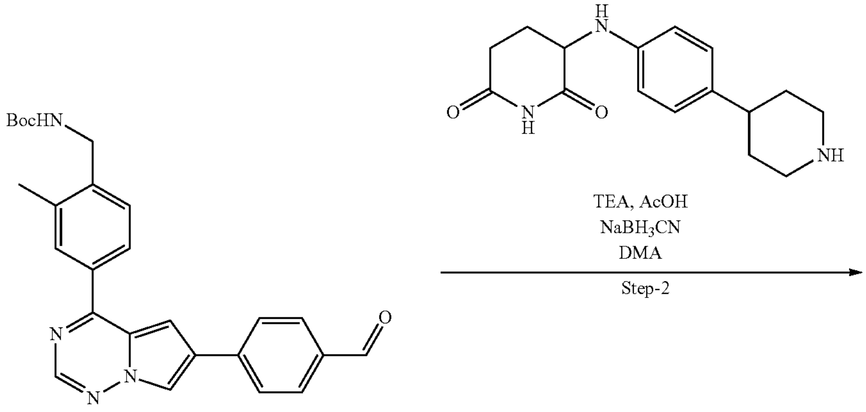

-continued

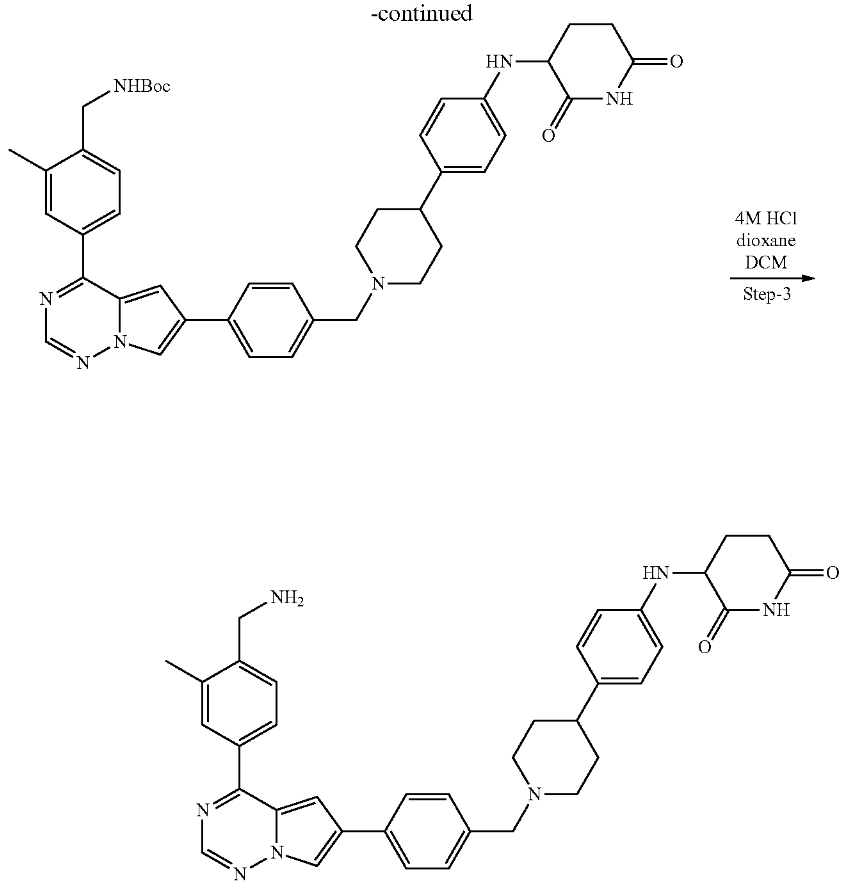

Step-1:

A mixture of tert-butyl 4-(6-bromopyrrolo[2,1-f][1,2,4]triazin-4-yl)-2-methylbenzylcarbamate (810 mg, 1.94 mmol), (4-formylphenyl)boronic acid (378.35 mg, 2.52 mmol), potassium carbonate (804.80 mg, 5.82 mmol) and Pd(dppf)$Cl_2$ (142.03 mg, 194.11 mol) in 1,4-dioxane (10 mL) and water (2.5 mL) was degassed and purged with nitrogen gas three times. Then the mixture was stirred at 100° C. for 2 hours under $N_2$ atmosphere. The progress of the reaction was monitored by LC-MS. Upon completion, the reaction mixture was filtered and concentrated under reduced pressure to give a residue. The residue was purified by flash column chromatography (silica gel, petroleum ether/ethyl acetate=10/1 to 2/1). The product tert-butyl 4-(6-(4-formylphenyl)pyrrolo[2,1-f][1,2,4]triazin-4-yl)-2-methylbenzylcarbamate (820 mg, 1.67 mmol, 85.92% yield) was obtained as a yellow solid. $^1$H NMR (400 MHz, DMSO-$d_6$) δ=10.03 (s, 1H), 8.87 (d, J=1.6 Hz, 1H), 8.64 (s, 1H), 8.21 (d, J=8.0 Hz, 2H), 8.07 (br d, J=8.0 Hz, 1H), 8.03-7.93 (m, 3H), 7.79 (d, J=1.6 Hz, 1H), 7.54-7.32 (m, 2H), 4.24 (br d, J=6.0 Hz, 2H), 2.42 (s, 3H), 1.43 (s, 9H).

Step-2:

To a mixture of 3-((4-(piperidin-4-yl)phenyl)amino)piperidine-2,6-dione HCl salt (3.51 g, 10.84 mmol) and DMA (120 mL) was added triethylamine (4.99 g, 49.26 mmol, 6.87 mL), and the mixture was stirred at 25° C. for 0.5 h. Then acetic acid (1.78 g, 29.56 mmol, 1.69 mL) and tert-butyl 4-(6-(4-formylphenyl)pyrrolo[2,1-f][1,2,4]triazin-4-yl)-2-methylbenzylcarbamate (4.36 g, 9.85 mmol) were added, and the reaction mixture was stirred at 25° C. for another hour. Sodium cyanoborohydride (1.24 g, 19.71 mmol) was then added, and the reaction was further stirred at this temperature for 12 hours. The progress of the reaction was monitored by LC-MS. After completion, the reaction mixture was poured into water (100 mL) and extracted with ethyl acetate (100 mL×2). The combined organic layers were washed with brine (100 mL), dried over anhydrous sodium sulfate, filtered, and concentrated under reduced pressure to give a residue. The residue was purified by column chromatography (silica gel, petroleum ether/ethyl acetate=10/1 to 0/1) to give tert-butyl 4-(6-(4-((4-(4-((2,6-dioxopiperidin-3-yl)amino)phenyl)piperidin-1-yl)methyl)phenyl)pyrrolo[2,1-f][1,2,4]triazin-4-yl)-2-methylbenzylcarbamate (5.6 g, 7.37 mmol, 74.76% yield) as a yellow solid. LC-MS ($ES^+$): m/z 714.4 $[M+H]^+$.

Step-3:

A mixture of tert-butyl 4-(6-(4-((4-(4-((2,6-dioxopiperidin-3-yl)amino)phenyl)piperidin-1-yl)methyl)phenyl)pyrrolo[2,1-f][1,2,4]triazin-4-yl)-2-methylbenzylcarbamate (1.01 g, 1.41 mmol) and 4 M hydrogen chloride solution in dioxane (5 mL) was stirred at 25° C. for 1 hour. The progress of the reaction was monitored by LC-MS. The reaction mixture was concentrated under reduced pressure to give the crude product, which was used directly for the next step without further purification. Compound 3-((4-(1-(4-(4-(4-(aminomethyl)-3-methylphenyl)pyrrolo[2,1-f][1,2,4]triazin-6-yl)benzyl)piperidin-4-yl)phenyl)amino)piperidine-2,6-dione HCl salt (1.22 g, 1.31 mmol, 92.83% yield) was obtained as a yellow solid. LC-MS ($ES^+$): m/z 614.4 $[M+H]^+$.

Synthesis of 3-[[6-[1-[[4-[4-[4-(aminomethyl)-3-fluoro-phenyl]pyrrolo[2,1-f][1,2,4]triazin-6-yl]phenyl]methyl]-4-piperidyl]-3-pyridyl]amino]piperidine-2,6-dione

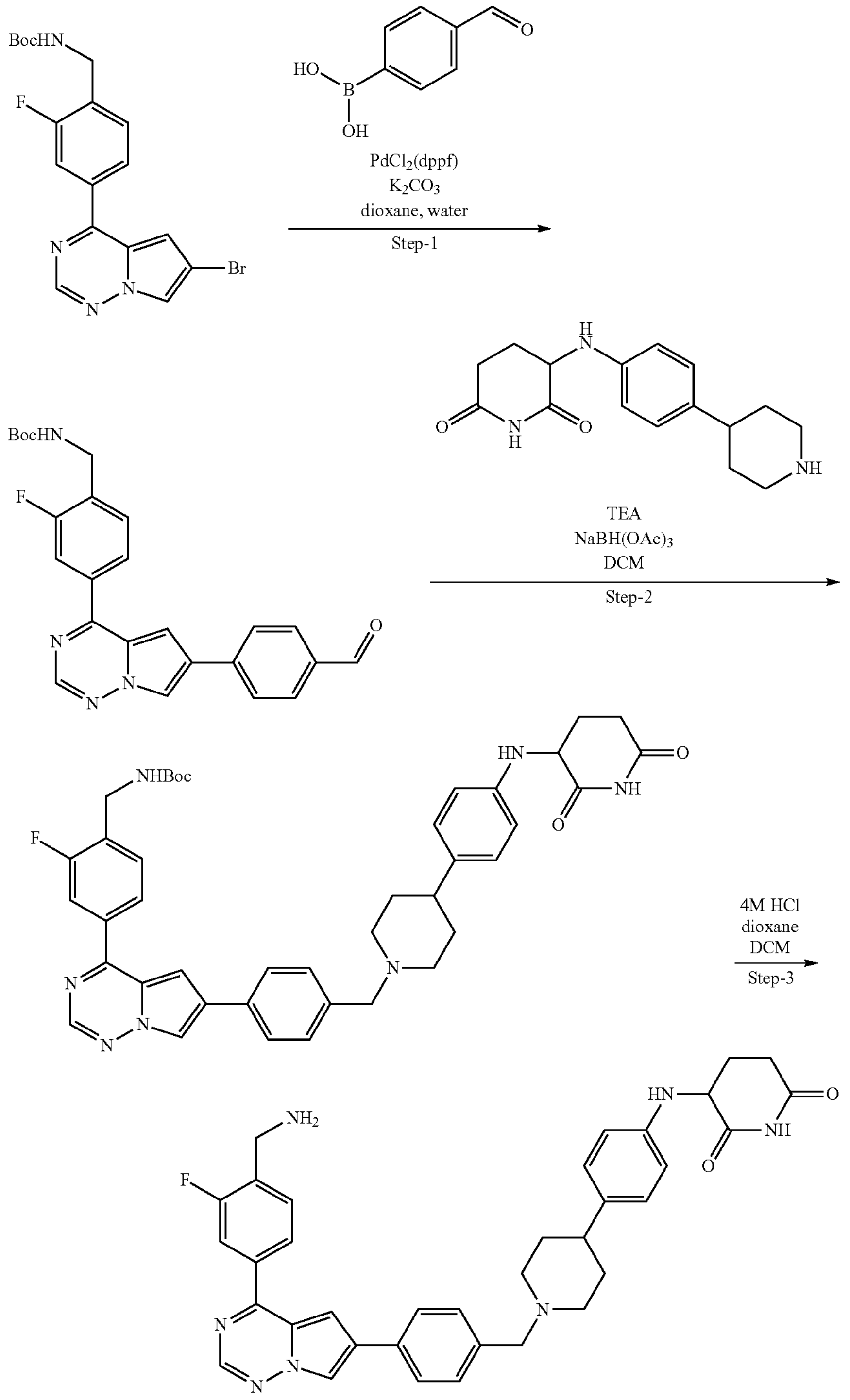

Step-1:

To a stirred solution of tert-butyl (4-(6-bromopyrrolo[2,1-f][1,2,4]triazin-4-yl)-2-fluorobenzyl)carbamate (6 g, 14.24 mmol) in 1,4-dioxane (40 mL) in a round bottom flask was added (4-formylphenyl)boronic acid (3.20 g, 21.36 mmol) at room temperature followed by an aqueous solution (10 mL) of potassium carbonate, anhydrous, 99% (5.91 g, 42.73 mmol) under argon atmosphere. The reaction mixture was degassed with argon gas repeatedly, and $Pd(dppf)Cl_2$ (1.04 g, 1.42 mmol) was added to the reaction mixture in one portion. The reaction mixture was again degassed with argon and then heated at 80° C. for 16 hours. The resultant crude product was purified by column chromatography (0-100% ethyl acetate/pet ether) to afford tert-butyl N-[[2-fluoro-4--

[6-(4-formylphenyl)pyrrolo[2,1-f][1,2,4]triazin-4-yl]phenyl]methyl]carbamate (6.2 g, 11.80 mmol, 82.87% yield) as a yellow solid. LC-MS ($ES^+$): m/z 447.23 $[M+H]^+$.

Step-2:

To a stirred solution of 3-[4-(4-piperidyl)anilino]piperidine-2,6-dione TFA salt (702.12 mg, 1.75 mmol) in DCM (10 mL) was added triethylamine (1.65 g, 16.29 mmol, 2.27 mL). Then, tert-butyl N-[[2-fluoro-4-[6-(4-formylphenyl)pyrrolo[2,1-f][1,2,4]triazin-4-yl]phenyl]methyl]carbamate (0.8 g, 1.79 mmol) was added and the reaction allowed to stir at room temperature for 1 hour. It was cooled to 0° C. before sodium triacetoxyborohydride (1.38 g, 6.52 mmol) was added, and the reaction was allowed to stir at room temperature for another 16 hours. The reaction was monitored by LC-MS. After 16 hours, the reaction was filtered through a celite bed, and the filtrate was concentrated in vacuo. The crude product was purified by prep-HPLC to afford tert-butyl N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-fluoro-phenyl]methyl]carbamate (1 g, 1.30 mmol, 79.54% yield) as a brown solid. LC-MS ($ES^+$): m/z 719.01 $[M+H]^+$.

Step-3:

To a stirred solution of tert-butyl N-[[4-[6-[4-[[4-[5-[(2,6-dioxo-3-piperidyl)amino]-2-pyridyl]-1-piperidyl]methyl]phenyl]pyrrolo[2,1-f][1,2,4]triazin-4-yl]-2-fluoro-phenyl]methyl]carbamate (1 g, 1.39 mmol) in dioxane (3 mL) was added 4 M hydrogen chloride solution in 1,4-dioxane (5 mL) under nitrogen and stirred at 0-28° C. for 2 hours. The reaction progress was monitored by TLC and LC-MS. After completion, reaction mass was concentrated under reduced pressure. The resulting crude was washed with diethyl ether (10 mL×2) to afford 3-[[6-[1-[[4-[4-[4-(aminomethyl)-3-fluoro-phenyl]pyrrolo[2,1-f][1,2,4]triazin-6-yl]phenyl]methyl]-4-piperidyl]-3-pyridyl]amino]piperidine-2,6-dione HCl salt (0.8 g, 1.04 mmol, 74.61% yield) as a solid compound. LC-MS ($ES^+$): m/z 619.43 $[M+H]^+$.

Synthesis of 3-[[6-[1-[[4-[4-[4-(aminomethyl)-3-fluoro-phenyl]pyrrolo[2,1-f][1,2,4]triazin-6-yl]phenyl]methyl]-4-piperidyl]-3-pyridyl]amino]piperidine-2,6-dione

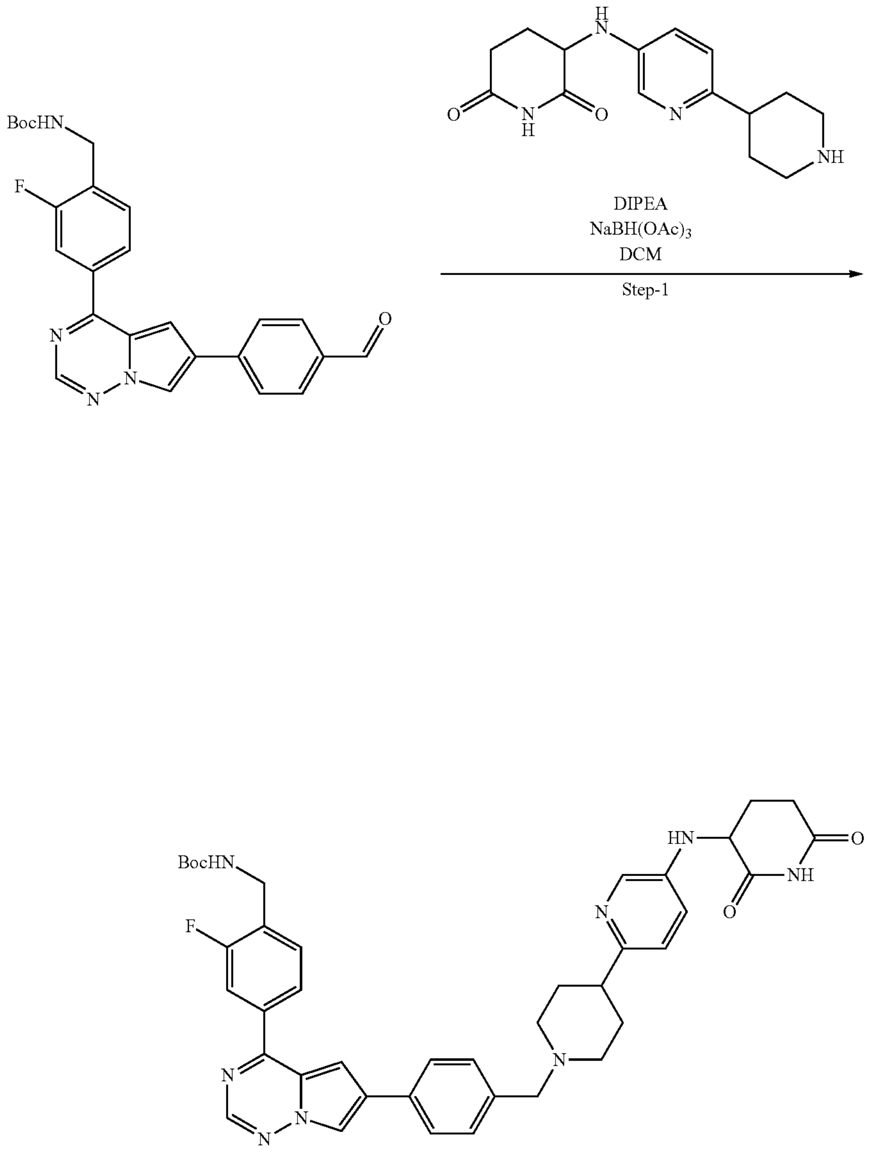

-continued

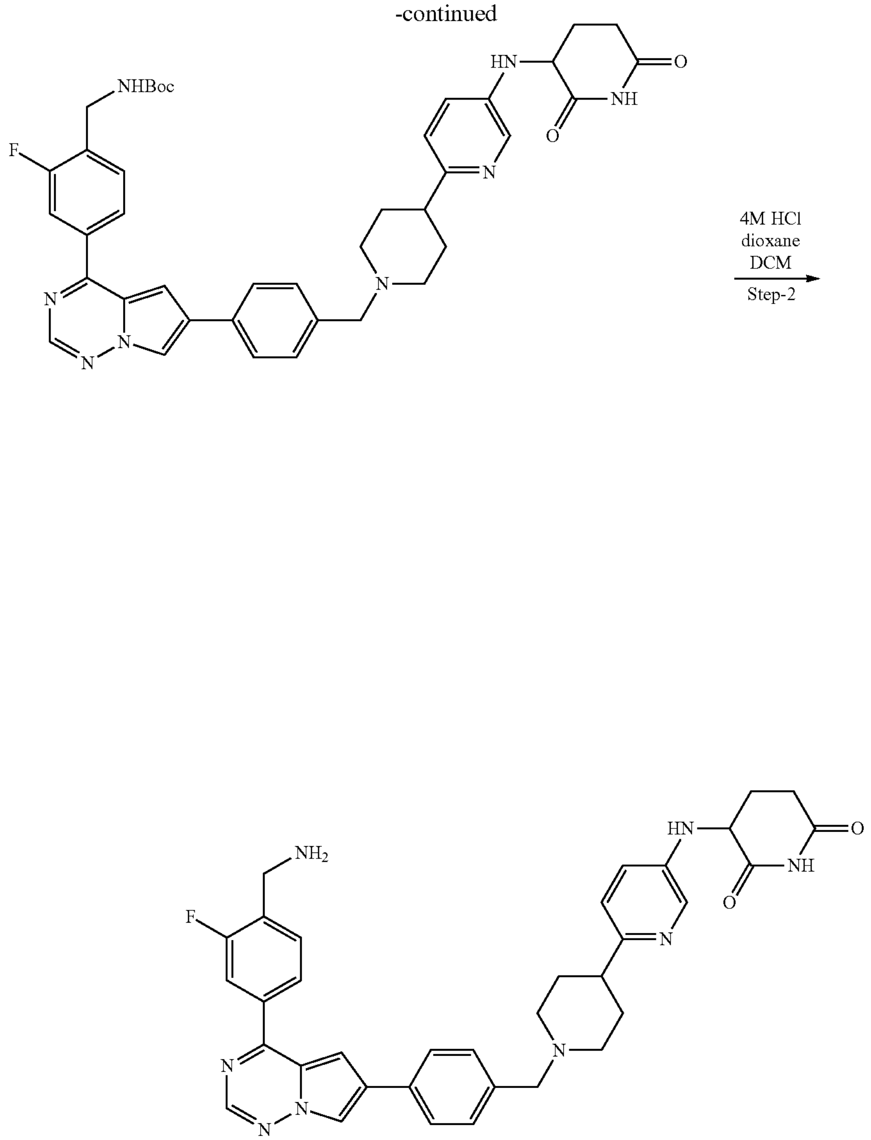

Step-1:

To a stirred solution of 3-[[6-(4-piperidyl)-3-pyridyl]amino]piperidine-2,6-dione HCl salt (545.62 mg, 1.68 mmol) in MeCN (3 mL) was added DIPEA (2.17 g, 16.80 mmol, 2.93 mL) and stirred for 10 minutes (basic pH). Tert-butyl N-[[2-fluoro-4-[6-(4-formylphenyl)pyrrolo[2,1-f][1,2,4]triazin-4-yl]phenyl]methyl]carbamate (0.75 g, 1.68 mmol) was added to the reaction and it was stirred for 1 hour at room temperature. The reaction was then cooled to 0° C., sodium triacetoxyborohydride (1.07 g, 5.04 mmol) was added, and the reaction stirred at room temperature for another 16 hours. The reaction progress was monitored by TLC and LC-MS. After completion, the reaction mixture was concentrated to dryness and purified by column chromatography (silica gel, 0-10% MeOH in DCM) to afford product tert-butyl (4-(6-(4-((4-(5-((2,6-dioxopiperidin-3-yl)amino)pyridin-2-yl)piperidin-1-yl)methyl)phenyl)pyrrolo[2,1-f][1,2,4]triazin-4-yl)-2-fluorobenzyl)carbamate (1 g, 1.36 mmol, 81.16% yield). LC-MS ($ES^+$): m/z 719.47 $[M+H]^+$.

Step-2:

To a stirred solution of tert-butyl N-[[4-[6-[4-[[4-[5-[(2,6-dioxo-3-piperidyl)amino]-2-pyridyl]-1-piperidyl]methyl]phenyl]pyrrolo[2,1-f][1,2,4]triazin-4-yl]-2-fluoro-phenyl]methyl]carbamate (1 g, 1.39 mmol) in 1,4-dioxane (3 mL) was added 4 M hydrogen chloride solution in 1,4-dioxane (5 mL) under nitrogen and stirred at 0-28° C. for 2 hours. The reaction progress was monitored by TLC and LC-MS. After the reaction was complete, the reaction mixture was concentrated at reduced pressure. The resulting crude was washed with diethyl ether (10 mL×2) to afford 3-[[6-[1-[[4-[4-[4-(aminomethyl)-3-fluoro-phenyl]pyrrolo[2,1-f][1,2,4]triazin-6-yl]phenyl]methyl]-4-piperidyl]-3-pyridyl]amino]piperidine-2,6-dione HCl salt (0.8 g, 1.04 mmol, 74.61% yield) as a solid compound. LC-MS ($ES^+$): m/z 619.43 $[M+H]^+$.

V. Synthesis of Representative Compounds

Example 1. Synthesis of 5-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-1,2,4-oxadiazole-3-carboxamide

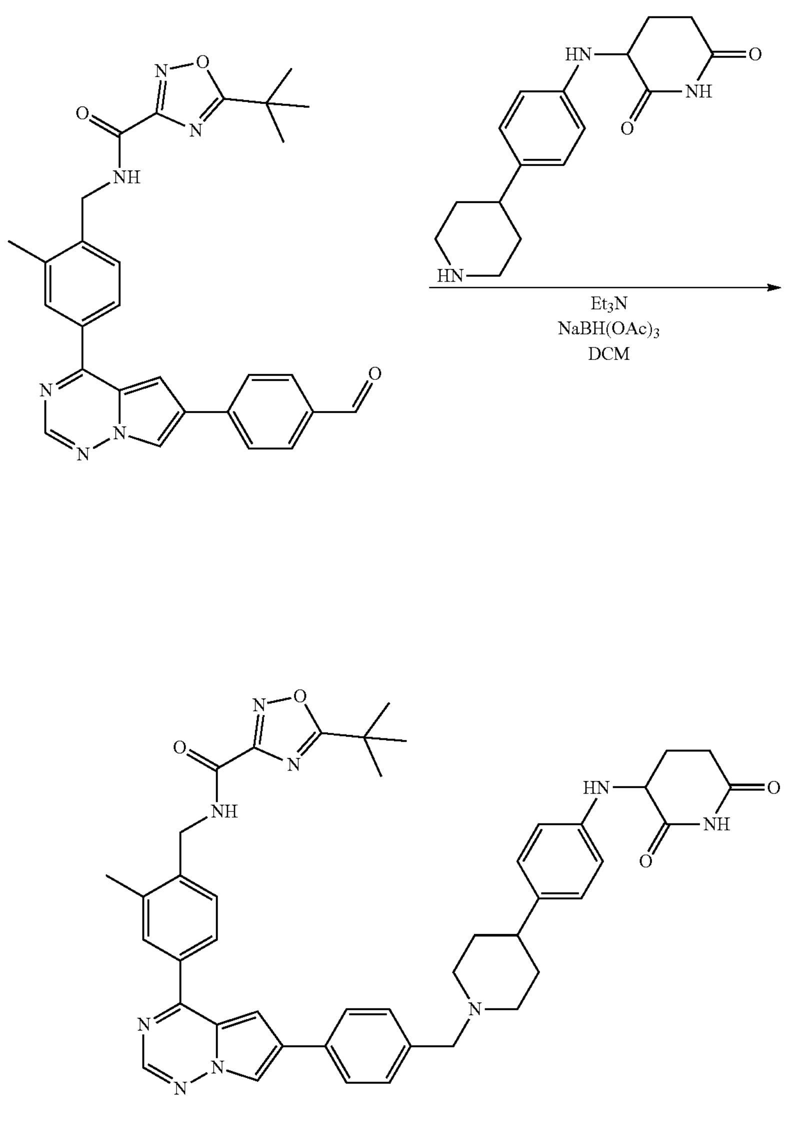

To a stirred solution of 3-[4-(4-piperidyl)anilino]piperidine-2,6-dione TFA salt (811.62 mg, 2.02 mmol) in DCM (10 mL) was added triethylamine (818.45 mg, 8.09 mmol, 1.13 mL). The reaction mixture was stirred for 10 minutes before 5-tert-butyl-N-[[4-[6-(4-formylphenyl)pyrrolo[2,1-f][1,2,4]triazin-4-yl]-2-methyl-phenyl]methyl]-1,2,4-oxadiazole-3-carboxamide (0.4 g, 808.83 μmol) was added. It was stirred at room temperature for an additional 30 minutes, followed by the addition of sodium triacetoxyborohydride (685.69 mg, 3.24 mmol). The reaction was stirred at this temperature for 16 hours, while the reaction progress was monitored by TLC and LC-MS. Upon completion, the reaction was filtered through celite bed and quenched with bicarbonate. The solid precipitate was filtered, washed with water (50 mL×3) and dissolved in ethyl acetate (50 mL). The organic layer was dried over anhydrous sodium sulfate and concentrated under reduced pressure to obtain the crude compound. The crude product was purified by normal phase column chromatography (silica gel 100-200 mesh, 0-100% ethyl acetate in pet-ether) to afford tert-butyl N-[[4-[6-(2-formylcyclopropyl)pyrrolo[2,1-f][1,2,4]triazin-4-yl]-2-methyl-phenyl]methyl]carbamate. The product was further purified by reverse phase column chromatography (0.1% formic acid in water with ACN) to obtain 5-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-1,2,4-oxadiazole-3-carboxamide (0.3 g, 384.53 μmol, 47.54% yield). $^1$H NMR (400 MHz, DMSO-$d_6$) δ 10.76 (s, 1H), 9.54 (t, J=5.9 Hz, 1H), 8.70 (s, 1H), 8.61 (s, 1H), 8.06-8.01 (m, 2H), 7.89 (d, J=8.0 Hz, 2H), 7.61 (s, 1H), 7.48 (d, J=8.0 Hz, 1H), 7.38 (d, J=8.0 Hz, 2H), 6.96 (d, J=8.3 Hz, 2H), 6.60 (d, J=8.4 Hz, 2H), 5.63 (d, J=7.5 Hz, 1H), 4.57 (d, J=5.9 Hz, 2H), 4.28-4.22 (m, 1H), 3.51 (s, 2H), 2.92 (d, J=10.8 Hz, 2H), 2.76-2.59 (m, 1H), 2.59-2.53 (m, 1H), 2.50 (bs, 3H), 2.36-2.30 (m, 1H), 2.11-2.00 (m, 3H), 1.87-1.82 (m, 1H), 1.69-1.57 (m, 4H), 1.44 (s, 9H). LC-MS ($ES^-$): m/z 764.25 $[M-H]^-$.

Example 2 and Example 3
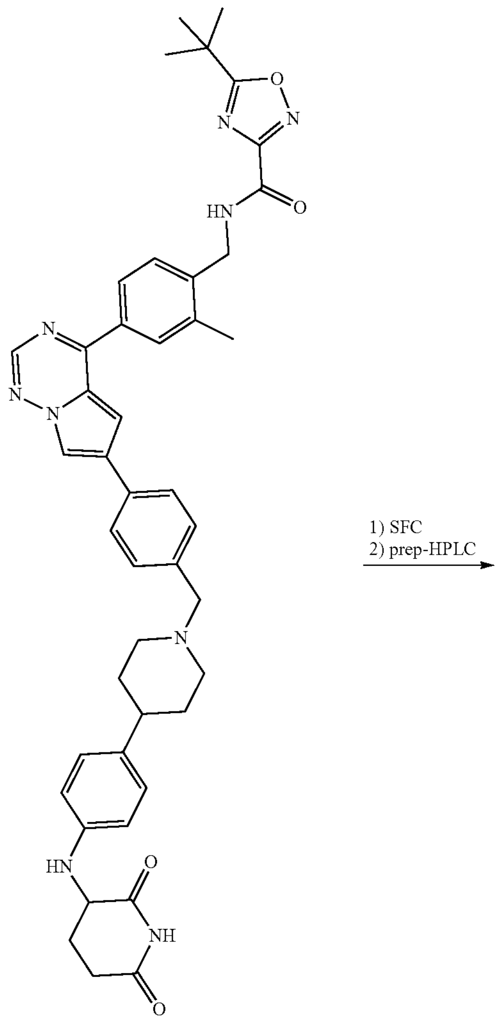
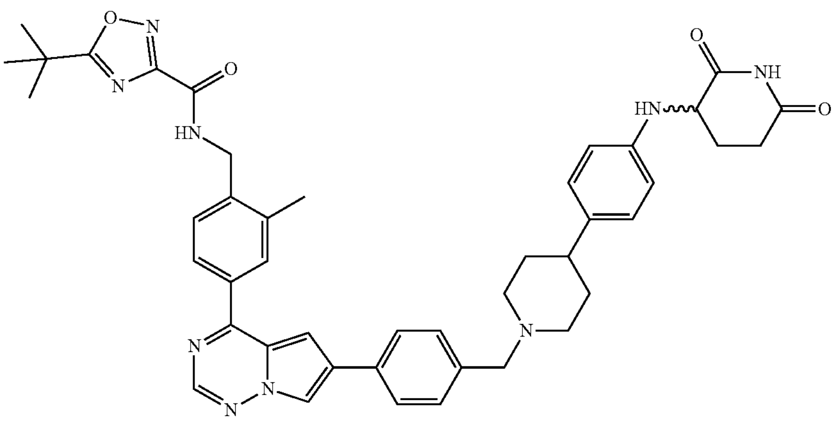
Isomer 1

-continued

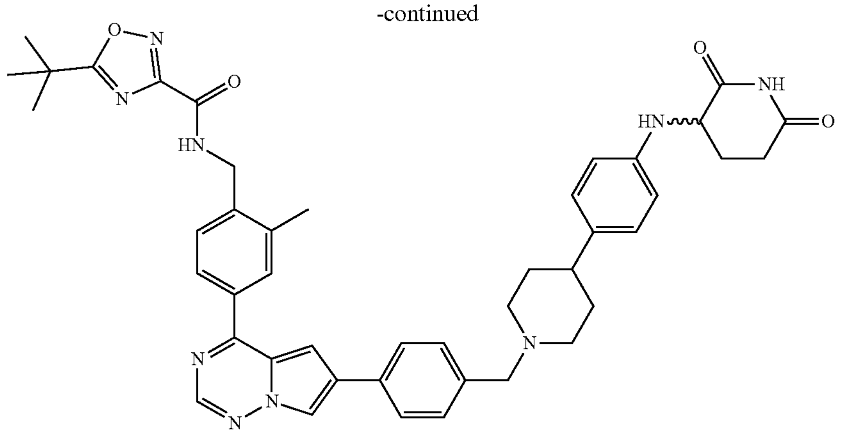

Isomer 2

0.1 g of Example 1 racemic was separated by SFC to obtain a single enantiomer.

During SFC separation, fractions of Peak-1 (Example 1) and Peak-2 (Example 1) were collected in TFA buffer; as during SFC separation method involved the use of the basic additive. Hence the obtained fractions of Peak-1 (Example 1) and Peak-2 (Example 1) were submitted again for prep-HPLC purification to remove the salt.

[Absolute configuration of both isomers was not determined, absolute stereochemistry was arbitrarily assigned, and the first eluted peak during SFC separation was assigned as Peak-1 (Example 1), and the second eluted peak was assigned as Peak-2 (Example 1)]

Preparative SFC Conditions

Column/dimensions: CHIRALPAK AS-H (30×250)mm, 5μ

% $CO_2$: 50%

% Co-solvent: 50% [0.2% 7M Methanolic Ammonia in ACN:MeOH (1:1)]

Total Flow: 100 g/min

Back Pressure: 100 bar

Temperature: 30° C.

UV: 215 nm

Solubility: ACN

No of injections: 10

Total purification time: 2:00 Hrs

Instrument details: Make/Model: SFC-150-II

Chiral HPLC RT for Peak-1 (Example 1): 6.491

Chiral HPLC RT for Peak-2 (Example 2): 9.476

Example 2

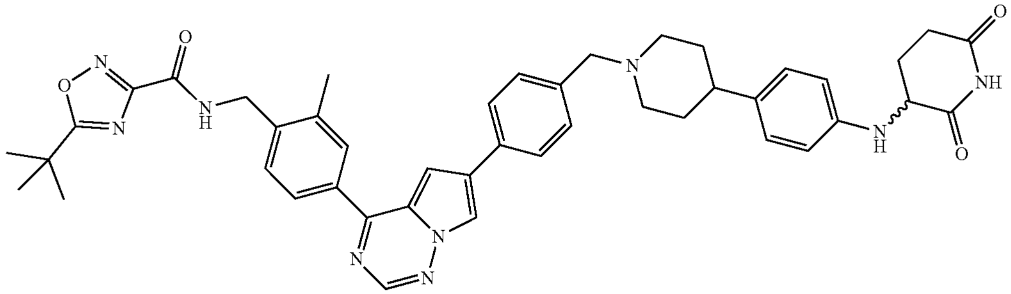

Isomer 1

5-tert-butyl-N-[[4-[6-[4-[[4-[4-[(2,6-dioxo-3-piperidyl) amino]phenyl]-1-piperidyl]methyl]phenyl] pyrrolo[2,1-f][1,2,4]triazin-4-yl]-2-methyl-phenyl]methyl]-1,2,4-oxadiazole-3-carboxamide isomer 1. $^1H$ NMR (400 MHz, DMSO-$d_6$) δ 10.76 (s, 1H), 9.54 (t, J=6.0 Hz, 1H), 8.71 (s, 1H), 8.61 (s, 1H), 8.13-8.01 (m, 2H), 7.91-7.89 (d, J=7.2 Hz, 2H), 7.62 (s, 1H), 7.48-7.46 (m, 1H), 7.40-7.38 (m, 2H), 6.96 (d, J=8.4 Hz, 2H), 6.60 (d, J=8.4 Hz, 2H), 5.64 (d, J=7.2 Hz, 1H), 4.57 (d, J=6.0 Hz, 2H), 4.28-4.22 (m, 1H), 3.53-3.49 (m, 2H), 2.95-2.88 (m, 2H), 2.74-2.67 (m, 2H), 2.58-2.50 (m, 4H), 2.11-2.07 (m, 3H), 1.90-1.81 (m, 1H), 1.79-1.60 (m, 4H), 1.44 (s, 9H). LC-MS ($ES^+$): m/z 766.13 $[M+H]^+$.

Example 3

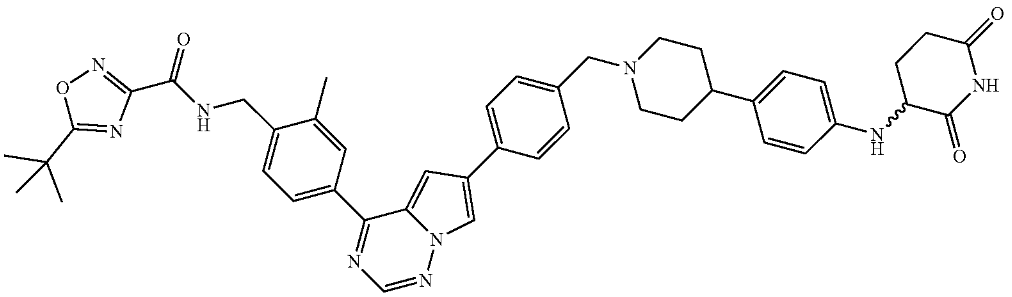

Isomer 2

5-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-1,2,4-oxadiazole-3-carboxamide isomer 2. $^{1}$H NMR (400 MHz, DMSO-$d_6$) δ 10.76 (s, 1H), 9.53-9.51 (m, 1H), 8.70 (s, 1H), 8.60 (s, 1H), 8.06-8.01 (m, 2H), 7.88 (d, J=8.0 Hz, 2H), 7.61 (s, 1H), 7.47 (d, J=7.6 Hz, 1H), 7.37 (d, J=8.0 Hz, 2H), 6.95 (d, J=8.4 Hz, 2H), 6.60 (d, J=8.0 Hz, 2H), 5.63 (d, J=7.2 Hz, 1H), 4.56 (d, J=6.0 Hz, 2H), 4.28-4.18 (m, 1H), 3.51 (s, 2H), 2.91 (d, J=10.8 Hz, 2H), 2.77-2.67 (m, 1H), 2.59-2.58 (m, 1H), 2.50 (s, 3H), 2.36-2.32 (m, 1H), 2.11-1.98 (m, 3H), 1.90-1.80 (m, 1H), 1.70-1.52 (m, 4H), 1.44 (s, 9H). LC-MS ($ES^+$): m/z 766.09 $[M+H]^+$.

Example 4

Example 4 was prepared following the synthesis of Example 1

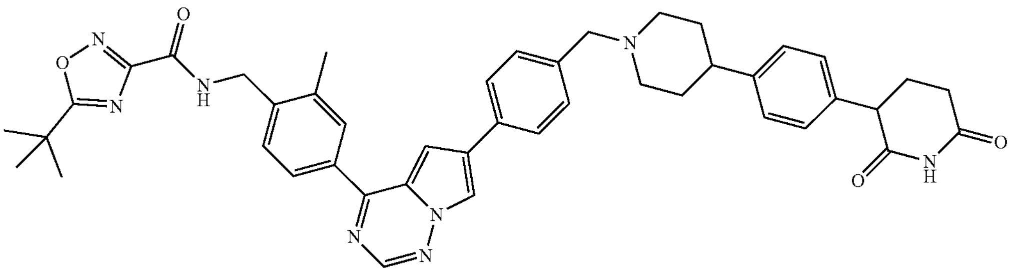 [SMILES: Cc1cc(-c2ncnn3cc(-c4ccc(CN5CCC(c6ccc(C7CCC(=O)NC7=O)cc6)CC5)cc4)cc23)ccc1CNC(=O)c1noc(C(C)(C)C)n1]

5-tert-butyl-N-[[4-[6-[4-[[4-[4-(2,6-dioxo-3-piperidyl)phenyl]-1-piperidyl]methyl]phenyl]pyrrolo[2,1-f][1,2,4]triazin-4-yl]-2-methyl-phenyl]methyl]-1,2,4-oxadiazole-3-carboxamide. $^{1}$H NMR (400 MHz, DMSO-$d_6$) δ 10.81 (s, 1H), 9.54 (t, J=5.9 Hz, 1H), 8.71 (s, 1H), 8.61 (s, 1H), 8.05 (d, J=8.0 Hz, 1H), 8.02 (s, 1H), 7.89 (d, J=8.0 Hz, 2H), 7.62 (s, 1H), 7.47 (d, J=8.0 Hz, 1H), 7.38 (d, J=8.0 Hz, 2H), 7.21 (d, J=8.0 Hz, 2H), 7.13 (d, J=8.0 Hz, 2H), 4.57 (d, J=5.9 Hz, 2H), 3.82-3.81 (m, 1H), 3.53 (s, 2H), 2.95 (m, 2H), 2.65 (m, 1H), 2.51-2.48 (m, 5H), 2.33-1.90 (m, 4H), 1.65-1.62 (m, 4H), 1.44 (s, 9H). LC-MS ($ES^-$): m/z 749.19 $[M-H]^-$.

Example 5

Example 5 was prepared following the synthesis of Example 1

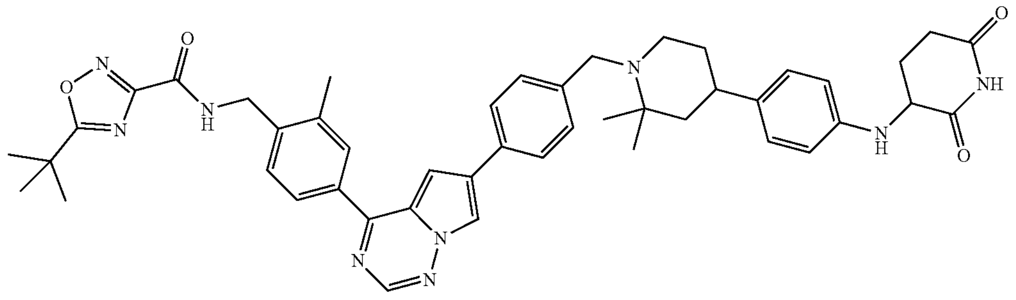 [SMILES: Cc1cc(-c2ncnn3cc(-c4ccc(CN5CCC(c6ccc(NC7CCC(=O)NC7=O)cc6)CC5(C)C)cc4)cc23)ccc1CNC(=O)c1noc(C(C)(C)C)n1]

5-tert-butyl-N-[[4-[6-[4-[[4-[4-[(2,6-dioxo-3-piperidyl) amino]phenyl]-2,2-dimethyl-1-piperidyl]methyl]phenyl] pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.76 (s, 1H), 9.56 (t, J=5.4 Hz, 1H), 8.81 (s, 2H), 8.64 (s, 1H), 8.10-8.01 (m, 4H), 7.70 (s, 1H), 7.60 (d, J=7.9 Hz, 2H), 7.48 (d, J=8.0 Hz, 1H), 7.21-6.93 (m, 3H), 6.62 (d, J=8.2 Hz, 2H), 4.71-4.68 (m, 1H), 4.58-4.56 (m, 2H), 4.28-4.25 (m, 1H), 3.98-3.95 (m, 1H), 3.25-3.23 (m, 2H), 2.93-2.90 (m, 1H), 2.73-2.67 (m, 1H), 2.50 (s, 3H), 2.10-2.05 (m, 1H), 1.99-1.87 (m, 4H), 1.63-1.61 (m, 4H), 1.51 (s, 3H), 1.44 (s, 9H), 1.25-1.21 (m, 1H). LC-MS ($ES^-$): m/z 794.19 $[M-H]^-$.

Example 6

Example 6 was prepared following the synthesis of Example 1

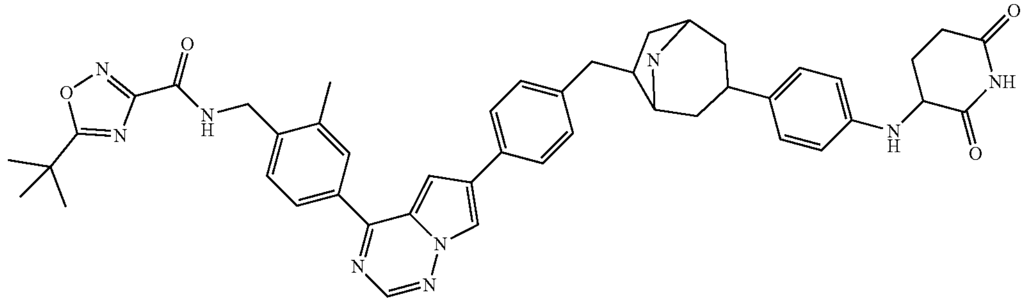 [SMILES: Cc1cc(-c2ncnn3cc(-c4ccc(CC5CC6CC(c7ccc(NC8CCC(=O)NC8=O)cc7)CC5N6)cc4)cc23)ccc1CNC(=O)c1noc(C(C)(C)C)n1]

5-tert-butyl-N-[[4-[6-[4-[[3-[4-[(2,6-dioxo-3-piperidyl) amino]phenyl]-8-azabicyclo[3.2.1]octan-8-yl]methyl]phenyl]pyrrolo[2,1-f][1,2,4]triazin-4-yl]-2-methyl-phenyl] methyl]-1,2,4-oxadiazole-3-carboxamide. $^1$H NMR (400 MHz, DMSO-$d_6$) δ 10.77 (s, 1H), 9.56 (t, J=5.8 Hz, 1H), 9.35-9.28 (m, 1H), 8.80 (s, 1H), 8.64 (s, 1H), 8.08-8.02 (m, 4H), 7.70-7.64 (m, 3H), 7.48 (d, J=6.4 Hz, 1H), 7.22 (d, J=10.5 Hz, 1H), 7.02 (d, J=8.4 Hz, 1H), 6.67-6.61 (m, 1H), 4.57 (d, J=5.8 Hz, 2H), 4.23-4.15 (m, 3H), 3.93-3.83 (m, 2H), 2.67-2.60 (m, 1H), 2.58 (s, 3H), 2.43-2.33 (m, 4H), 2.13-2.07 (m, 3H), 1.86-1.81 (m, 2H), 1.75-1.68 (m, 1H), 1.55-153 (m, 2H), 1.45 (s, 9H). LC-MS ($ES^+$): m/z 792.13 $[M+H]^+$.

Example 7

Example 7 was prepared following the synthesis of Example 1

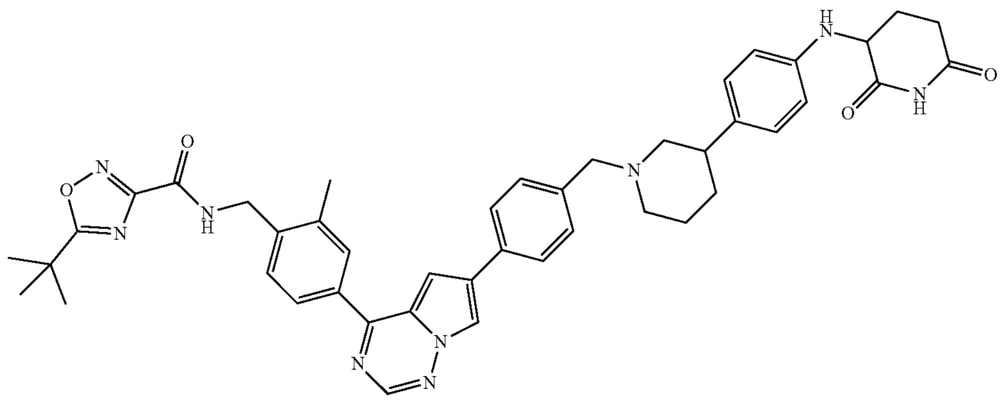 [SMILES: Cc1cc(-c2ncnn3cc(-c4ccc(CN5CCCC(c6ccc(NC7CCC(=O)NC7=O)cc6)C5)cc4)cc23)ccc1CNC(=O)c1noc(C(C)(C)C)n1]

5-tert-butyl-N-[[4-[6-[4-[[3-[4-[(2,6-dioxo-3-piperidyl) amino]phenyl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.77 (s, 1H), 9.55 (t, J=6.0 Hz, 1H), 9.51 (bs, 1H), 8.77 (d, J=1.1 Hz, 1H), 8.63 (s, 1H), 8.06-8.01 (m, 4H), 7.68 (s, 1H), 7.57 (d, J=8.0 Hz, 2H), 7.47 (d, J=8.0 Hz, 1H), 6.96 (d, J=8.0 Hz, 2H), 6.64 (d, J=8.5 Hz, 2H), 4.56-4.53 (m, 2H), 4.31-4.28 (m, 3H), 3.47 (m, 2H), 3.05-2.93 (m, 2H), 2.86-2.83 (m, 1H), 2.73-2.71 (m, 1H), 2.73-2.69 (m, 1H), 2.50 (s, 3H), 2.09-2.05 (m, 1H), 1.97-1.75 (m, 4H), 1.62-1.60 (m, 1H), 1.45 (s, 9H). LC-MS (ES$^+$): m/z 766.04 [M+H]$^+$.

Example 8

Example 8 was prepared following the synthesis of Example 1

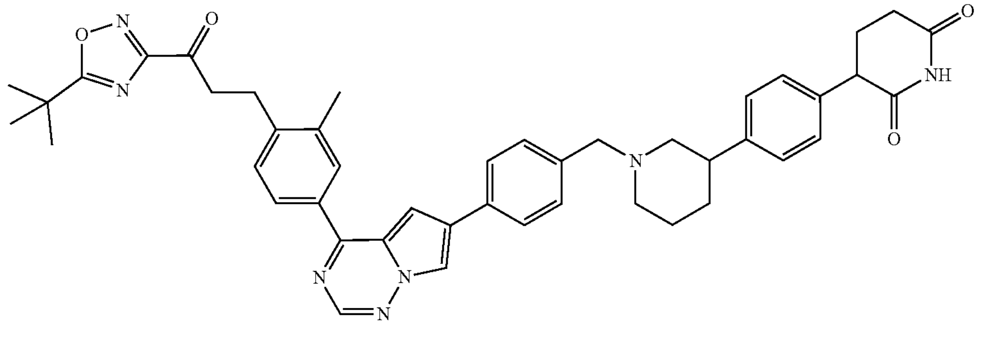 [SMILES: Cc1cc(-c2ncnn3cc(-c4ccc(CN5CCCC(c6ccc(C7CCC(=O)NC7=O)cc6)C5)cc4)cc23)ccc1CCC(=O)c1noc(C(C)(C)C)n1]

5-tert-butyl-N-[[4-[6-[4-[[3-[4-(2,6-dioxo-3-piperidyl) phenyl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (401 MHz, DMSO-$d_6$) δ 10.83 (s, 1H), 9.58 (s, 1H), 9.53 (t, J=5.8 Hz, 1H), 8.78 (s, 1H), 8.63 (s, 1H), 8.06-8.01 (m, 4H), 7.69 (s, 1H), 7.58 (d, J=8.1 Hz, 2H), 7.48 (d, J=8.0 Hz, 1H), 7.28-7.20 (m, 4H), 4.57 (d, J=5.8 Hz, 1H), 4.36-3.34 (m, 2H), 3.84-3.82 (m, 1H), 3.56-3.40 (m, 2H), 3.12-2.97 (m, 3H), 2.70-2.62 (m, 1H), 2.46 (s, 4H), 2.19-2.16 (m, 1H), 2.03-1.97 (m, 2H), 1.91-1.67 (m, 3H), 1.45 (s, 9H). LC-MS (ES$^+$): m/z 751.51 [M+H]$^+$.

Example 9

Example 9 was prepared following the synthesis of Example 1

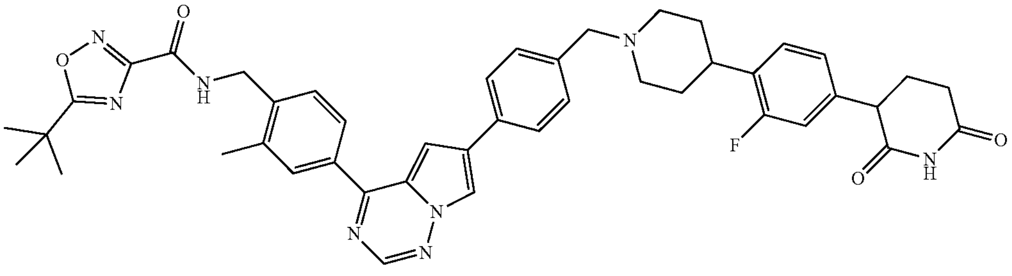 [SMILES: Cc1cc(-c2ncnn3cc(-c4ccc(CN5CCC(c6ccc(C7CCC(=O)NC7=O)cc6F)CC5)cc4)cc23)ccc1CNC(=O)c1noc(C(C)(C)C)n1]

5-tert-butyl-N-[[4-[6-[4-[[4-[4-(2,6-dioxo-3-piperidyl)-2-fluoro-phenyl]-1-piperidyl]methyl]phenyl]pyrrolo[2,1-f][1,2,4]triazin-4-yl]-2-methyl-phenyl]methyl]-1,2,4-oxadiazole-3-carboxamide. 1'H NMR (400 MHz, DMSO-$d_6$) δ 10.84 (s, 1H), 9.54 (t, J=6.1 Hz, 1H), 8.70 (d, J=1.2 Hz, 1H), 8.60 (s, 1H), 8.28 (s, 1H), 8.05 (d, J=8.1 Hz, 1H), 8.02 (s, 1H), 7.89 (d, J=8.1 Hz, 2H), 7.61 (d, J=1.2 Hz, 1H), 7.48 (d, J=7.9 Hz, 1H), 7.39 (d, J=8.1 Hz, 2H), 7.30 (t, J=8.2 Hz, 1H), 7.05-6.99 (m, 2H), 4.57 (d, J=6.1 Hz, 2H), 3.85 (dd, J=4.8, 11.9 Hz, 1H), 3.53 (s, 2H), 2.95 (br d, J=11.4 Hz, 2H), 2.76 (br d, J=6.7 Hz, 1H), 2.72-2.59 (m, 1H), 2.48 (br s, 3H), 2.28-2.15 (m, 1H), 2.13-1.96 (m, 3H), 1.72 (br s, 4H), 1.44 (s, 9H). LC-MS ($ES^+$): m/z 769.3 $[M+H]^+$.

Example 10

Example 10 was prepared following the synthesis of Example 1

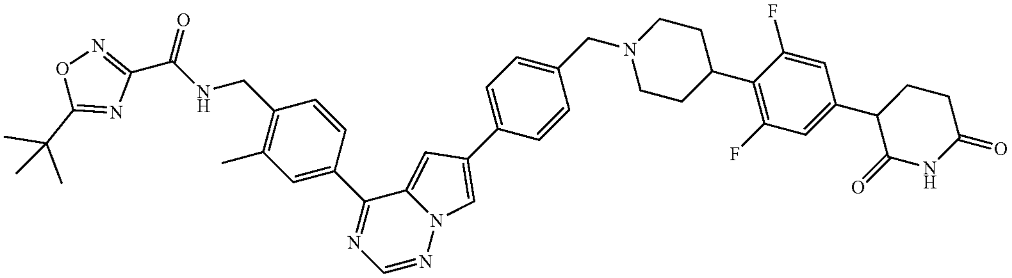 [SMILES: Cc1cc(-c2ncnn3cc(-c4ccc(CN5CCC(c6c(F)cc(C7CCC(=O)NC7=O)cc6F)CC5)cc4)cc23)ccc1CNC(=O)c1noc(C(C)(C)C)n1]

5-tert-butyl-N-[[4-[6-[4-[[4-[4-(2,6-dioxo-3-piperidyl)-2,6-difluoro-phenyl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.88 (s, 1H), 9.56 (t, J=6.0 Hz, 1H), 8.70 (d, J=1.6 Hz, 1H), 8.60 (s, 1H), 8.05 (d, J=8.0 Hz, 1H), 8.01 (s, 1H), 7.90 (d, J=8.4 Hz, 2H), 7.61 (d, J=1.6 Hz, 1H), 7.47 (d, J=8.0 Hz, 1H), 7.38 (d, J=8.4 Hz, 2H), 6.97 (d, J=9.6 Hz, 2H), 4.57 (d, J=6.0 Hz, 2H), 3.88 (dd, J=4.8, 12.4 Hz, 1H), 3.52 (s, 2H), 3.03-2.82 (m, 4H), 2.71-2.60 (m, 2H), 2.38-2.18 (m, 2H), 2.10-1.93 (m, 6H), 1.70-1.59 (m, 2H), 1.44 (s, 9H). LC-MS ($ES^+$): m/z 787.2 $[M+H]^+$.

Example 11

Example 11 was prepared following the synthesis of Example 1

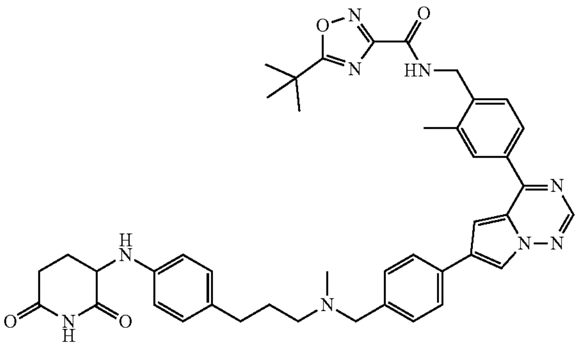 [SMILES: Cc1cc(-c2ncnn3cc(-c4ccc(CN(C)CCCc5ccc(NC6CCC(=O)NC6=O)cc5)cc4)cc23)ccc1CNC(=O)c1noc(C(C)(C)C)n1]

5-tert-butyl-N-[[4-[6-[4-[[3-[4-[(2,6-dioxo-3-piperidyl)amino]phenyl]propyl-methyl-amino]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.76 (s, 1H), 9.54 (t, J=6.0 Hz, 1H), 8.70 (d, J=1.6 Hz, 1H), 8.60 (s, 1H), 8.32 (brs, 2H), 8.05 (d, J=8.0 Hz, 1H), 8.01 (s, 1H), 7.89 (d, J=8.0 Hz, 2H), 7.62 (d, J=1.6 Hz, 1H), 7.48 (d, J=8.0 Hz, 1H), 7.35 (d, J=8.0 Hz, 2H), 6.90 (d, J=8.4 Hz, 2H), 6.58 (d, J=8.4 Hz, 2H), 5.60 (d, J=7.5 Hz, 1H), 4.57 (d, J=5.9 Hz, 2H), 4.24-4.21 (m, 1H), 3.47 (s, 2H), 2.71-2.67 (m, 1H), 2.58-2.51 (m, 1H), 2.49-2.44 (m, 5H), 2.34 (q, J=4.6 Hz, 2H), 2.13 (s, 3H), 1.85-1.80 (m, 1H), 1.70 (t, J=7.0 Hz, 2H), 1.44 (s, 9H). LC-MS ($ES^+$): m/z 754.20 $[M+H]^+$.

Example 12

Example 12 was prepared following the synthesis of Example 1

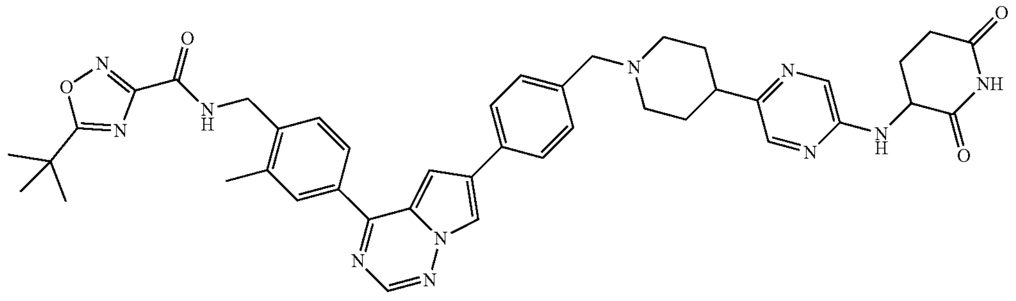 [SMILES: Cc1cc(-c2ncnn3cc(-c4ccc(CN5CCC(c6cnc(NC7CCC(=O)NC7=O)cn6)CC5)cc4)cc23)ccc1CNC(=O)c1noc(C(C)(C)C)n1]

5-tert-butyl-N-[[4-[6-[4-[[4-[5-[(2,6-dioxo-3-piperidyl) amino]pyrazin-2-yl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ=11.04-10.63 (m, 1H), 9.56 (t, J=6.0 Hz, 1H), 8.71 (d, J=1.6 Hz, 1H), 8.60 (s, 1H), 8.41-8.30 (m, 1H), 8.05 (br d, J=8.0 Hz, 1H), 8.01 (s, 1H), 7.98 (d, J=1.2 Hz, 1H), 7.89 (d, J=8.0 Hz, 2H), 7.84 (s, 1H), 7.62 (d, J=1.6 Hz, 1H), 7.47 (d, J=7.6 Hz, 1H), 7.38 (d, J=8.0 Hz, 2H), 7.27-7.15 (m, 1H), 4.79-4.64 (m, 1H), 4.57 (br d, J=6.0 Hz, 2H), 3.52 (br s, 2H), 2.92 (m, 2H), 2.84-2.59 (m, 3H), 2.48 (br s, 3H), 2.13-1.96 (m, 4H), 1.79-1.62 (m, 4H), 1.44 (s, 9H). LC-MS (ES$^+$): m/z 768.2 [M+H]$^+$.

Example 13

Example 13 was prepared following the synthesis of Example 1

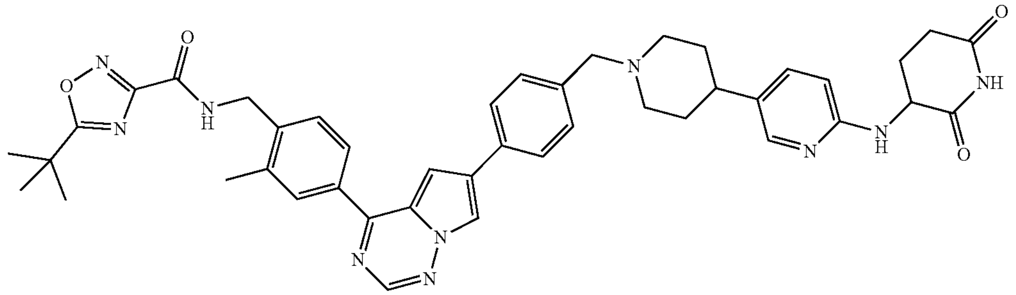 [SMILES: Cc1cc(-c2ncnn3cc(-c4ccc(CN5CCC(c6ccc(NC7CCC(=O)NC7=O)nc6)CC5)cc4)cc23)ccc1CNC(=O)c1noc(C(C)(C)C)n1]

5-tert-butyl-N-[[4-[6-[4-[[4-[6-[(2,6-dioxo-3-piperidyl) amino]-3-pyridyl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.74 (s, 1H), 9.54 (t, J=6.0 Hz, 1H), 8.70 (s, 1H), 8.61 (s, 1H), 8.35 (s, 1H), 8.10-7.97 (m, 2H), 7.89 (d, J=8.0 Hz, 2H), 7.82 (s, 1H), 7.61 (s, 1H), 7.48 (d, J=7.8 Hz, 1H), 7.42-7.28 (m, 3H), 6.65 (d, J=7.4 Hz, 1H), 6.53 (d, J=8.6 Hz, 1H), 4.78-4.66 (m, 1H), 4.57 (d, J=6.0 Hz, 2H), 3.51 (s, 2H), 2.92 (d, J=10.8 Hz, 2H), 2.84-2.69 (m, 1H), 2.57-2.52 (m, 2H), 2.45-2.30 (m, 3H), 2.11-1.95 (m, 4H), 1.72-1.54 (m, 4H), 1.44 (s, 9H). LC-MS (ES$^+$): m/z 767.4 [M+H]$^+$.

Example 14

Example 14 was prepared following the synthesis of Example 1

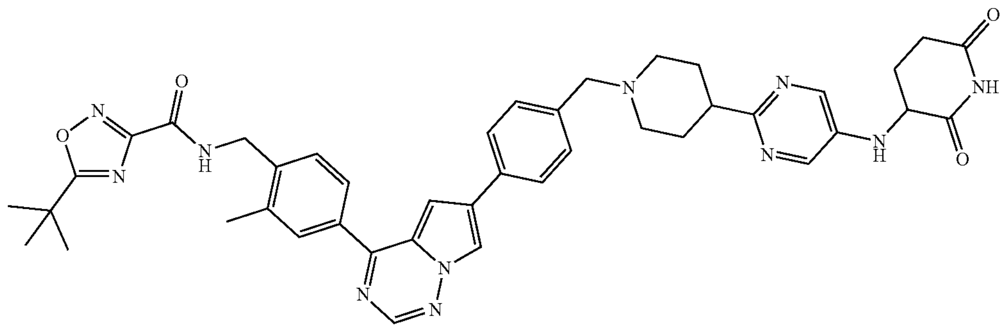 [SMILES: Cc1cc(-c2ncnn3cc(-c4ccc(CN5CCC(c6ncc(NC7CCC(=O)NC7=O)cn6)CC5)cc4)cc23)ccc1CNC(=O)c1noc(C(C)(C)C)n1]

5-tert-butyl-N-[[4-[6-[4-[[4-[5-[(2,6-dioxo-3-piperidyl)amino]pyrimidin-2-yl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ=10.84 (s, 1H), 9.54 (t, J=6.4 Hz, 1H), 8.71 (s, 1H), 8.60 (s, 1H), 8.31 (s, 1H), 8.16 (s, 2H), 8.06 (d, J=8.4 Hz, 1H), 8.02 (s, 1H), 7.89 (d, J=8.2 Hz, 2H), 7.62 (s, 1H), 7.48 (d, J=7.8 Hz, 1H), 7.38 (d, J=8.1 Hz, 2H), 6.23-6.11 (m, 1H), 4.57 (d, J=5.6 Hz, 2H), 4.42 (br s, 1H), 3.51 (s, 2H), 2.90 (d, J=11.8 Hz, 2H), 2.78-2.65 (m, 2H), 2.62 (d, J=11.0 Hz, 1H), 2.58-2.53 (m, 2H), 2.33 (s, 1H), 2.13-2.02 (m, 3H), 1.93 (d, J=7.4 Hz, 1H), 1.83 (br s, 2H), 1.76 (t, J=10.8 Hz, 2H), 1.44 (s, 9H). LC-MS ($ES^+$): m/z 768.3 $[M+H]^+$.

Example 15

Example 15 was prepared following the synthesis of Example 1

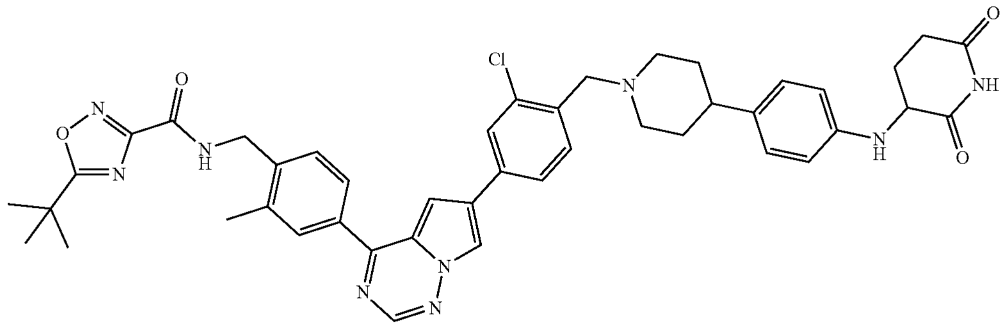 [SMILES: Cc1cc(-c2ncnn3cc(-c4ccc(CN5CCC(c6ccc(NC7CCC(=O)NC7=O)cc6)CC5)c(Cl)c4)cc23)ccc1CNC(=O)c1noc(C(C)(C)C)n1]

5-tert-butyl-N-[[4-[6-[3-chloro-4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.76 (br s, 1H), 9.54 (t, J=5.6 Hz, 1H), 8.78 (s, 1H), 8.62 (s, 1H), 8.48 (s, 1H), 8.10-8.04 (m, 2H), 8.02 (s, 1H), 7.91 (d, J=7.6 Hz, 1H), 7.71 (s, 1H), 7.55 (d, J=7.6 Hz, 1H), 7.48 (d, J=8.0 Hz, 1H), 6.97 (d, J=7.6 Hz, 2H), 6.64-6.58 (m, 2H), 5.64 (d, J=7.2 Hz, 1H), 4.57 (d, J=6.0 Hz, 2H), 4.33-4.18 (m, 1H), 3.60 (s, 2H), 3.01-2.89 (m, 2H), 2.80-2.66 (m, 2H), 2.59 (d, J=4.0 Hz, 1H), 2.43-2.29 (m, 2H), 2.20-2.04 (m, 3H), 1.94-1.76 (m, 2H), 1.74-1.54 (m, 5H), 1.44 (s, 9H). LC-MS ($ES^+$): m/z 800.5 $[M+H]^+$.

Example 16

Example 16 was prepared following the synthesis of Example 1

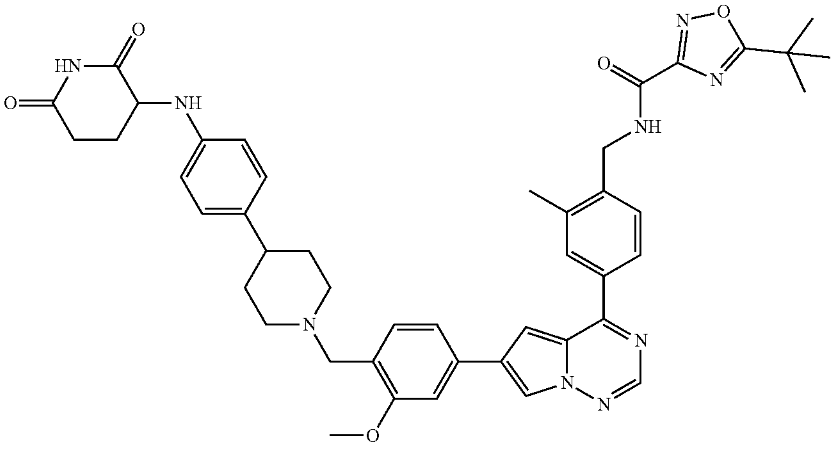 [SMILES: COc1cc(-c2cc3c(-c4ccc(CNC(=O)c5noc(C(C)(C)C)n5)c(C)c4)ncnn3c2)ccc1CN1CCC(c2ccc(NC3CCC(=O)NC3=O)cc2)CC1]

5-tert-butyl-N-[[4-[6-[4-[[4-[4-[(2,6-dioxo-3-piperidyl)amino]phenyl]-1-piperidyl]methyl]-3-methoxy-phenyl]pyrrolo[2,1-f][1,2,4]triazin-4-yl]-2-methyl-phenyl]methyl]-1,2,4-oxadiazole-3-carboxamide. $^{1}H$ NMR (400 MHz, DMSO-$d_6$) δ 10.77 (s, 1H), 9.62-9.51 (m, 1H), 8.77 (s, 1H), 8.62 (s, 1H), 8.32-8.24 (m, 1H), 8.11-7.98 (m, 2H), 7.65 (s, 1H), 7.55-7.45 (m, 3H), 7.39 (d, J=8.4 Hz, 1H), 7.04-6.91 (m, 3H), 6.73-6.57 (m, 3H), 5.64 (d, J=7.9 Hz, 1H), 4.64-4.55 (m, 2H), 4.32-4.22 (m, 1H), 3.91 (s, 2H), 3.52 (br s, 3H), 3.00-2.92 (m, 2H), 2.75-2.75 (m, 1H), 2.83-2.66 (m, 3H), 2.34 (br s, 2H), 2.09-2.08 (m, 1H), 2.08 (br s, 2H), 1.95-1.78 (m, 2H), 1.71-1.58 (m, 5H), 1.45 (s, 9H). LC-MS ($ES^+$): m/z 796.6 $[M+H]^+$.

Example 17

Example 17 was prepared following the synthesis of Example 1

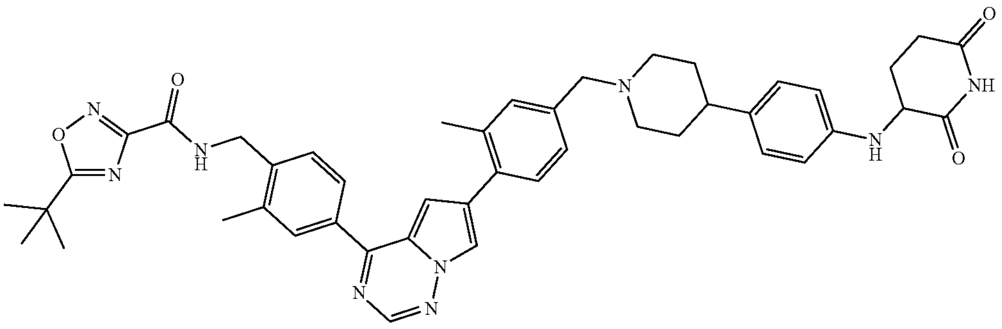 [SMILES: Cc1cc(-c2ncnn3cc(-c4ccc(CN5CCC(c6ccc(NC7CCC(=O)NC7=O)cc6)CC5)cc4C)cc23)ccc1CNC(=O)c1noc(C(C)(C)C)n1]

5-tert-butyl-N-[[4-[6-[4-[[4-[4-[(2,6-dioxo-3-piperidyl)amino]phenyl]-1-piperidyl]methyl]-2-methyl-phenyl]pyrrolo[2,1-f][1,2,4]triazin-4-yl]-2-methyl-phenyl]methyl]-1,2,4-oxadiazole-3-carboxamide. $^{1}H$ NMR (400 MHz, DMSO-$d_6$) δ 10.76 (s, 1H), 9.52 (t, J=6.0 Hz, 1H), 8.63 (s, 1H), 8.42 (d, J=1.2 Hz, 1H), 8.25 (s, 1H), 8.05-7.99 (m, 2H), 7.48 (dd, J=8.0, 15.2 Hz, 2H), 7.36 (d, J=1.2 Hz, 1H), 7.26 (s, 1H), 7.22 (d, J=8.0 Hz, 1H), 6.96 (d, J=8.4 Hz, 2H), 6.60 (d, J=8.4 Hz, 2H), 5.64 (d, J=7.6 Hz, 1H), 4.55 (d, J=6.0 Hz, 2H), 4.26 (ddd, J=4.8, 7.2, 11.6 Hz, 1H), 3.48 (s, 2H), 2.92 (d, J=10.8 Hz, 2H), 2.79-2.66 (m, 2H), 2.46 (s, 6H), 2.38-2.30 (m, 1H), 2.14-1.98 (m, 4H), 1.92-1.79 (m, 1H), 1.74-1.54 (m, 5H), 1.43 (s, 9H). LC-MS ($ES^+$): m/z 780.7 $[M+H]^+$.

Example 18

Example 18 was prepared following the synthesis of Example 1

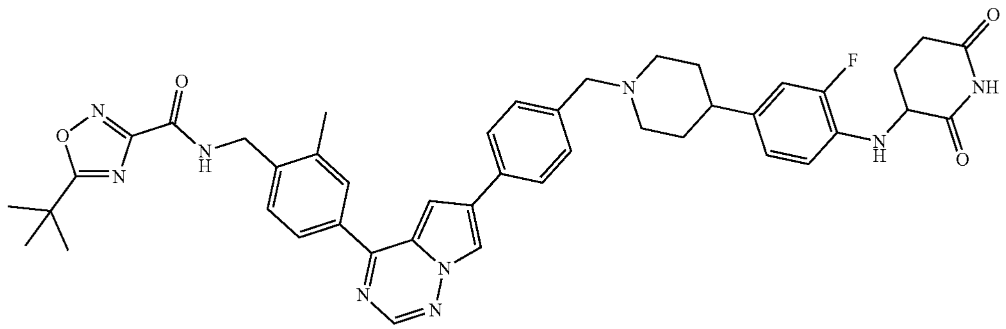 [SMILES: Cc1cc(-c2ncnn3cc(-c4ccc(CN5CCC(c6ccc(NC7CCC(=O)NC7=O)c(F)c6)CC5)cc4)cc23)ccc1CNC(=O)c1noc(C(C)(C)C)n1]

5-tert-butyl-N-[[4-[6-[4-[[4-[4-[(2,6-dioxo-3-piperidyl) amino]-3-fluoro-phenyl]-1-piperidyl]methyl]phenyl]pyrrolo[2,1-f][1,2,4]triazin-4-yl]-2-methyl-phenyl]methyl]-1,2,4-oxadiazole-3-carboxamide. $^{1}$H NMR (400 MHz, DMSO-$d_6$) δ 10.81 (s, 1H), 9.55 (t, J=5.9 Hz, 1H), 9.40 (s, 1H), 8.80 (s, 1H), 8.64 (s, 1H), 8.09-8.01 (m, 4H), 7.70 (s, 1H), 7.59 (d, J=7.9 Hz, 2H), 7.48 (d, J=8.0 Hz, 1H), 6.97-6.77 (m, 3H), 4.57 (d, J=5.8 Hz, 2H), 4.37 (d, J=3.6 Hz, 3H), 3.48 (d, J=11.4 Hz, 2H), 3.10-3.00 (m, 2H), 2.76-2.67 (m, 2H), 2.60-2.58 (m, 1H), 2.50 (s, 3H), 2.10-1.97 (m, 4H), 1.82-1.73 (m, 2H), 1.45 (s, 9H). LC-MS ($ES^-$): m/z 782.26 $[M-H]^-$.

Example 19

Example 19 was prepared following the synthesis of Example 1

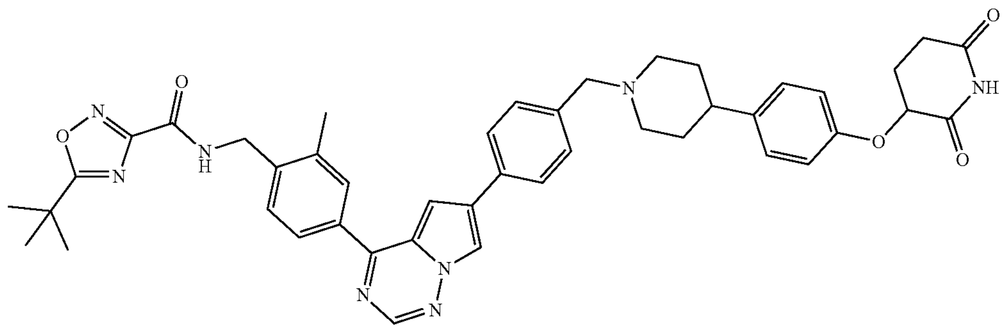 [SMILES: Cc1cc(-c2ncnn3cc(-c4ccc(CN5CCC(c6ccc(OC7CCC(=O)NC7=O)cc6)CC5)cc4)cc23)ccc1CNC(=O)c1noc(C(C)(C)C)n1]

5-tert-butyl-N-[[4-[6-[4-[[4-[4-[(2,6-dioxo-3-piperidyl) oxy]phenyl]-1-piperidyl]methyl]phenyl]pyrrolo[2,1-f][1,2,4]triazin-4-yl]-2-methyl-phenyl]methyl]-1,2,4-oxadiazole-3-carboxamide. 1H NMR (400 MHz, DMSO-$d_6$) δ 10.92 (s, 1H), 9.55 (t, J=5.8 Hz, 1H), 8.80 (s, 1H), 8.64 (s, 1H), 8.09-8.02 (m, 4H), 7.70 (s, 1H), 7.60 (d, J=8.0 Hz, 2H), 7.48 (d, J=8.0 Hz, 1H), 7.13 (d, J=8.4 Hz, 2H), 6.97 (d, J=8.5 Hz, 2H), 5.17-5.13 (m, 1H), 4.57 (d, J=5.8 Hz, 1H), 4.37 (d, J=3.3 Hz, 2H), 3.05 (m, 2H), 3.12-3.10 (m, 2H), 2.80-2.78 (m, 1H), 2.56 (m, 5H), 2.22-2.14 (m, 2H), 2.02-1.99 (m, 2H), 1.84-1.72 (m, 2H), 1.45 (s, 9H). LC-MS ($ES^-$): m/z 765.38 $[M-H]^-$.

Example 20

Example 20 was prepared following the synthesis of Example 1

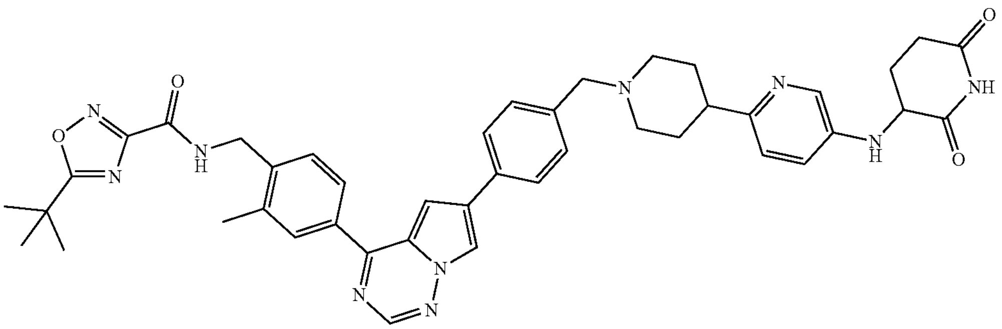 [SMILES: Cc1cc(-c2ncnn3cc(-c4ccc(CN5CCC(c6ccc(NC7CCC(=O)NC7=O)cn6)CC5)cc4)cc23)ccc1CNC(=O)c1noc(C(C)(C)C)n1]

5-tert-butyl-N-[[4-[6-[4-[[4-[5-[(2,6-dioxo-3-piperidyl)amino]-2-pyridyl]-1-piperidyl]methyl]phenyl]pyrrolo[2,1-f][1,2,4]triazin-4-yl]-2-methyl-phenyl]methyl]-1,2,4-oxadiazole-3-carboxamide. $^1H$ NMR (400 MHz, DMSO-$d_6$) δ 10.80 (br s, 1H), 9.56 (t, J=6.0 Hz, 1H), 8.71 (d, J=1.4 Hz, 1H), 8.61 (s, 1H), 8.31 (br s, 1H), 8.06 (d, J=7.8 Hz, 1H), 8.02 (s, 1H), 7.96 (s, 1H), 7.89 (d, J=8.4 Hz, 2H), 7.62 (d, J=1.2 Hz, 1H), 7.47 (d, J=8.2 Hz, 1H), 7.38 (d, J=8.2 Hz, 2H), 6.97 (s, 2H), 5.93 (d, J=7.8 Hz, 1H), 4.57 (d, J=6.0 Hz, 2H), 4.40-4.27 (m, 1H), 3.51 (s, 2H), 2.92 (d, J=11.6 Hz, 2H), 2.81-2.68 (m, 1H), 2.59 (d, J=4.0 Hz, 4H), 2.13-1.99 (m, 3H), 1.89 (dt, J=7.8, 12.0 Hz, 1H), 1.79-1.63 (m, 4H), 1.44 (s, 9H). LC-MS ($ES^+$): m/z 767.5 $[M+H]^+$.

Example 21

Example 21 was prepared following the synthesis of Example 1

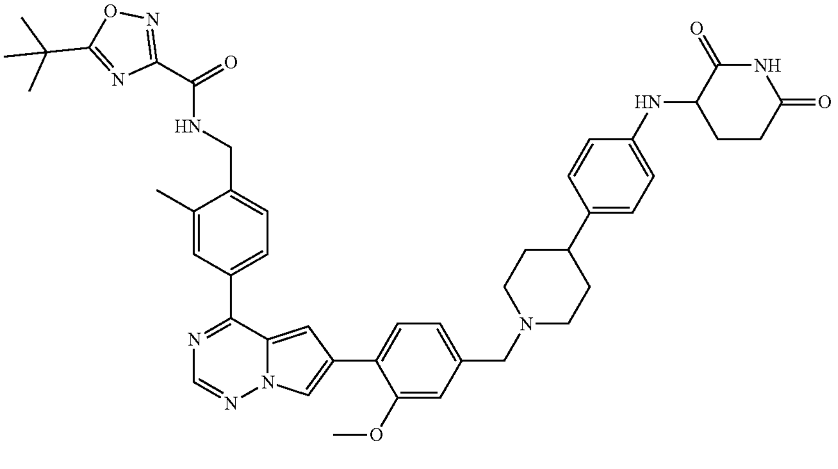 [SMILES: COc1cc(CN2CCC(c3ccc(NC4CCC(=O)NC4=O)cc3)CC2)ccc1-c1cc2c(-c3ccc(CNC(=O)c4noc(C(C)(C)C)n4)c(C)c3)ncnn2c1]

5-tert-butyl-N-[[4-[6-[4-[[4-[4-[(2,6-dioxo-3-piperidyl)amino]phenyl]-1-piperidyl]methyl]-2-methoxy-phenyl]pyrrolo[2,1-f][1,2,4]triazin-4-yl]-2-methyl-phenyl]methyl]-1,2,4-oxadiazole-3-carboxamide. $^1H$ NMR (400 MHz, DMSO-$d_6$) δ 10.79 (s, 1H), 9.56 (t, J=6.1 Hz, 1H), 8.60 (s, 1H), 8.56 (d, J=1.3 Hz, 1H), 8.08-7.97 (m, 2H), 7.85 (d, J=7.8 Hz, 1H), 7.59 (d, J=1.3 Hz, 1H), 7.48 (d, J=8.1 Hz, 1H), 7.09 (s, 1H), 7.04-6.92 (m, 3H), 6.61 (d, J=8.6 Hz, 2H), 5.66 (d, J=7.5 Hz, 1H), 4.57 (d, J=6.0 Hz, 2H), 4.27 (dd, J=4.8, 6.9, 11.3 Hz, 1H), 3.93 (s, 3H), 3.54 (s, 2H), 2.95 (d, J=11.0 Hz, 2H), 2.79-2.68 (m, 1H), 2.61-2.55 (m, 1H), 2.48 (s, 3H), 2.40-2.30 (m, 1H), 2.15-1.99 (m, 3H), 1.86 (d, J=4.6, 12.0 Hz, 1H), 1.72-1.56 (m, 4H), 1.45 (s, 9H). LC-MS ($ES^+$): m/z 796.7 $[M+H]^+$.

Example 22

Example 22 was prepared following the synthesis of Example 1

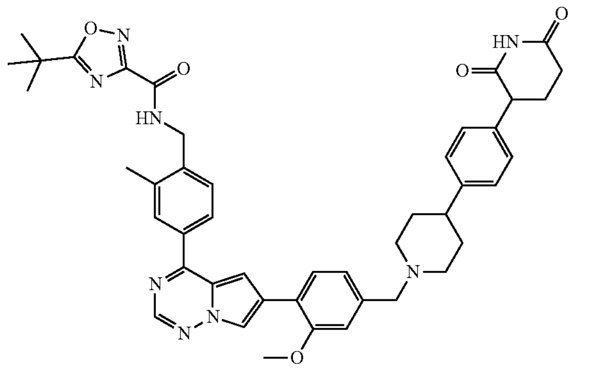 [SMILES: COc1cc(CN2CCC(c3ccc(C4CCC(=O)NC4=O)cc3)CC2)ccc1-c1cc2c(-c3ccc(CNC(=O)c4noc(C(C)(C)C)n4)c(C)c3)ncnn2c1]

5-tert-butyl-N-[[4-[6-[4-[[4-[4-(2,6-dioxo-3-piperidyl)phenyl]-1-piperidyl]methyl]-2-methoxy-phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.82 (s, 1H), 9.54 (t, J=6.0 Hz, 1H), 8.60 (s, 1H), 8.56 (d, J=1.4 Hz, 1H), 8.08-7.97 (m, 2H), 7.85 (d, J=7.9 Hz, 1H), 7.59 (d, J=1.4 Hz, 1H), 7.48 (d, J=7.9 Hz, 1H), 7.26-7.20 (m, 2H), 7.17-7.09 (m, 3H), 7.02 (d, J=7.8 Hz, 1H), 4.57 (d, J=5.9 Hz, 2H), 3.94 (s, 3H), 3.86-3.79 (m, 1H), 3.55 (s, 2H), 2.97 (d, J=11.0 Hz, 2H), 2.70-2.60 (m, 2H), 2.48 (s, 4H), 2.19-2.00 (m, 4H), 1.79-1.64 (m, 4H), 1.45 (s, 9H). LC-MS ($ES^+$): m/z 781.6 $[M+H]^+$.

Example 23

Example 23 was prepared following the synthesis of Example 1

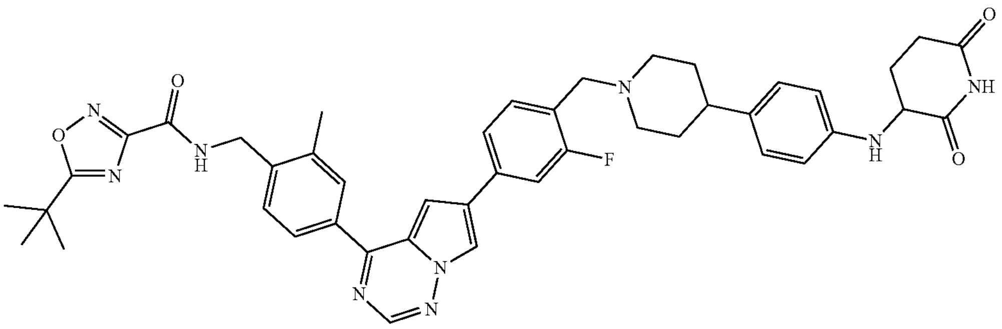 [SMILES: Cc1cc(-c2ncnn3cc(-c4ccc(CN5CCC(c6ccc(NC7CCC(=O)NC7=O)cc6)CC5)c(F)c4)cc23)ccc1CNC(=O)c1noc(C(C)(C)C)n1]

5-tert-butyl-N-[[4-[6-[4-[[4-[4-[(2,6-dioxo-3-piperidyl)amino]phenyl]-1-piperidyl]methyl]-3-fluoro-phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ=10.77 (s, 1H), 9.55 (t, J=5.9 Hz, 1H), 8.78 (d, J=1.5 Hz, 1H), 8.63 (s, 1H), 8.14-7.96 (m, 2H), 7.89-7.74 (m, 2H), 7.70 (d, J=1.3 Hz, 1H), 7.57-7.38 (m, 2H), 7.02-6.90 (m, 2H), 6.66-6.57 (m, 2H), 5.64 (d, J=7.5 Hz, 1H), 4.58 (d, J=6.0 Hz, 2H), 4.26 (dd, J=4.8, 6.7, 11.5 Hz, 1H), 3.57 (s, 2H), 2.94 (d, J=11.1 Hz, 2H), 2.79-2.68 (m, 1H), 2.59 (d, J=4.2 Hz, 1H), 2.58-2.52 (m, 3H), 2.36-2.29 (m, 1H), 2.16-2.03 (m, 3H), 1.91-1.80 (m, 1H), 1.71-1.55 (m, 4H), 1.45 (s, 9H). LC-MS ($ES^+$): m/z 784.6 $[M+H]^+$.

Example 24

Example 24 was prepared following the synthesis of Example 1

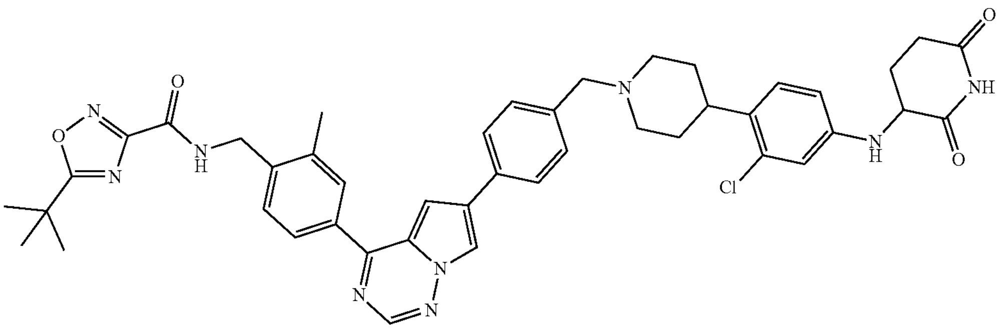 [SMILES: Cc1cc(-c2ncnn3cc(-c4ccc(CN5CCC(c6ccc(NC7CCC(=O)NC7=O)cc6Cl)CC5)cc4)cc23)ccc1CNC(=O)c1noc(C(C)(C)C)n1]

5-tert-butyl-N-[[4-[6-[4-[[4-[2-chloro-4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-1,2,4-oxadiazole-3-carboxamide. $^1H$ NMR (400 MHz, DMSO-$d_6$) δ 10.78 (s, 1H), 9.55 (t, J=5.8 Hz, 1H), 9.45 (s, 1H), 8.80 (s, 1H), 8.64 (s, 1H), 8.09-8.02 (m, 4H), 7.70 (s, 1H), 7.59 (d, J=7.8 Hz, 2H), 7.48 (d, J=7.9 Hz, 1H), 6.98 (d, J=8.8 Hz, 1H), 6.74 (s, 1H), 6.64 (d, J=8.1 Hz, 1H), 4.57 (d, J=5.8 Hz, 2H), 4.36-4.32 (m, 3H), 3.48 (d, J=11.2 Hz, 2H), 3.17-3.14 (m, 3H), 2.70-2.67 (m, 1H), 2.59-2.51 (m, 4H), 2.07-2.04 (m, 1H), 1.88-1.78 (m, 5H), 1.45 (s, 9H). LC-MS ($ES^+$): m/z 800.19 $[M+H]^+$.

Example 25

Example 25 was prepared following the synthesis of Example 1

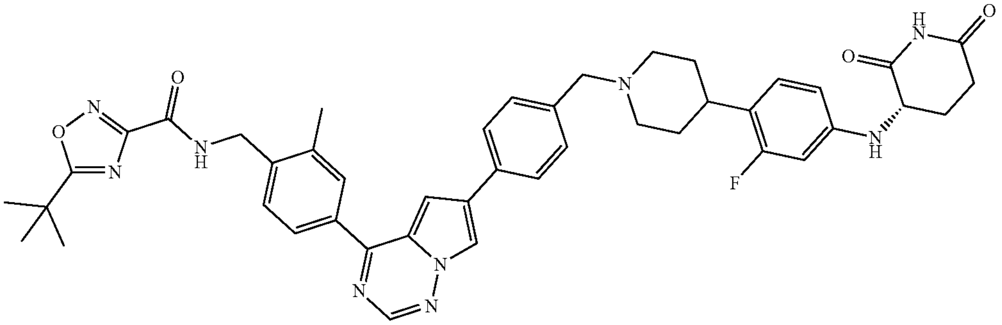 [SMILES: Cc1cc(-c2ncnn3cc(-c4ccc(CN5CCC(c6ccc(N[C@H]7CCC(=O)NC7=O)cc6F)CC5)cc4)cc23)ccc1CNC(=O)c1noc(C(C)(C)C)n1]

(S)-5-(tert-butyl)-N-(4-(6-(4-((4-(4-((2,6-dioxopiperidin-3-yl)amino)-2-fluorophenyl)piperidin-1-yl)methyl)phenyl)pyrrolo[2,1-f][1,2,4]triazin-4-yl)-2-methylbenzyl)-1,2,4-oxadiazole-3-carboxamide. $^1H$ NMR (400 MHz, DMSO-$d_6$) δ 10.79 (s, 1H), 9.55 (t, J=6.0 Hz, 1H), 9.41 (s, 1H), 8.80 (s, 1H), 8.64 (s, 1H), 8.09-8.01 (m, 4H), 7.70 (s, 1H), 7.58 (d, J=8.0 Hz, 2H), 7.49 (d, J=8.0 Hz, 1H), 6.95-6.90 (m, 1H), 6.46 (t, J=7.0 Hz, 2H), 4.57 (d, J=6.0 Hz, 2H), 4.32-4.28 (m, 3H), 3.48-3.42 (m, 2H), 3.13-3.09 (m, 2H), 2.91-2.84 (m, 1H), 2.73-2.67 (m, 1H), 2.58-252 (m, 1H), 2.50 (s, 3H), 2.08-2.04 (m, 1H), 1.88-1.70 (m, 5H), 1.44 (s, 9H). LC-MS ($ES^+$): m/z 784.15 $[M+H]^+$.

Example 26

Example 26 was prepared following the synthesis of Example 1

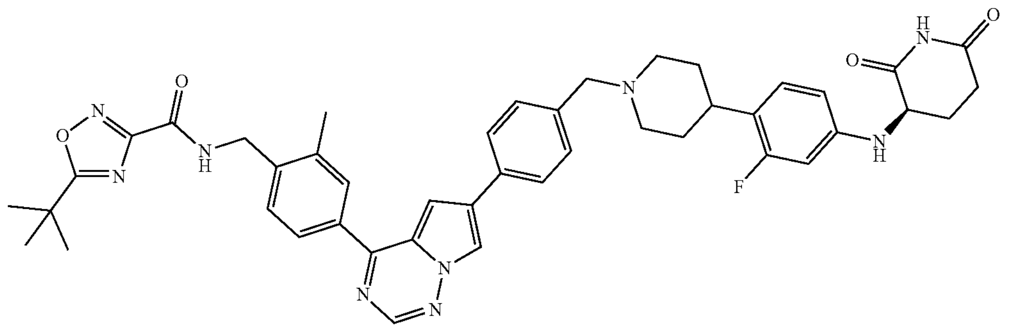 [SMILES: Cc1cc(-c2ncnn3cc(-c4ccc(CN5CCC(c6ccc(N[C@@H]7CCC(=O)NC7=O)cc6F)CC5)cc4)cc23)ccc1CNC(=O)c1noc(C(C)(C)C)n1]

(R)-5-(tert-butyl)-N-(4-(6-(4-((4-(4-((2,6-dioxopiperidin-3-yl)amino)-2-fluorophenyl)piperidin-1-yl)methyl)phenyl)pyrrolo[2,1-f][1,2,4]triazin-4-yl)-2-methylbenzyl)-1,2,4-oxadiazole-3-carboxamide. $^1$H NMR (400 MHz, DMSO-d6) δ 10.80 (s, 1H), 9.55 (t, J=6.0 Hz, 1H), 9.41 (bs, 1H), 8.80 (s, 1H), 8.64 (s, 2H), 8.09-8.02 (m, 4H), 7.70 (s, 1H), 7.58 (d, J=8.0 Hz, 2H), 7.48 (d, J=8.0 Hz, 2H), 7.21-6.90 (m, 1H), 6.48-6.45 (m, 2H), 4.57 (d, J=5.6 Hz, 2H), 4.36-4.29 (m, 1H), 3.40 (s, 2H), 3.12-3.10 (m, 2H) 2.91-2.89 (m, 1H), 2.72-2.67 (m, 1H), 2.59-2.57 (m, 1H), 2.49 (s, 3H), 2.07-2.05 (m, 1H), 1.89-1.85 (m, 5H), 1.44 (s, 9H). LC-MS ($ES^-$): m/z 782.26 $[M-H]^-$.

Example 27

Example 27 was prepared following the synthesis of Example 1

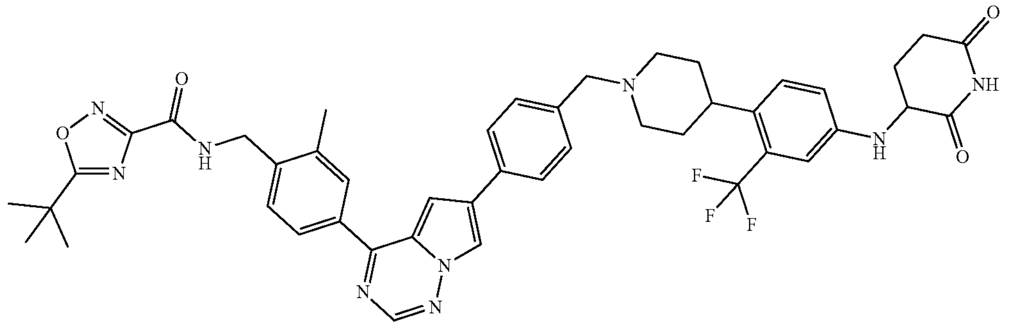 [SMILES: Cc1cc(-c2ncnn3cc(-c4ccc(CN5CCC(c6ccc(NC7CCC(=O)NC7=O)cc6C(F)(F)F)CC5)cc4)cc23)ccc1CNC(=O)c1noc(C(C)(C)C)n1]

5-tert-butyl-N-[[4-[6-[4-[[4-[4-[(2,6-dioxo-3-piperidyl)amino]-2-(trifluoromethyl)phenyl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.79 (s, 1H), 9.56 (t, J=6.1 Hz, 1H), 9.44 (s, 1H), 8.80 (d, J=1.2 Hz, 1H), 8.64 (s, 1H), 8.08-8.02 (m, 4H), 7.70 (s, 1H), 7.58 (d, J=8.2 Hz, 2H), 7.48 (d, J=8.2 Hz, 1H), 7.16 (d, J=8.6 Hz, 1H), 6.97 (s, 1H), 6.92 (d, J=8.6 Hz, 1H), 4.57 (d, J=5.9 Hz, 2H), 4.43-4.36 (m, 3H), 3.57-3.46 (m, 2H), 3.18-3.15 (m, 2H), 3.01-2.95 (m, 1H), 2.74-2.60 (m, 1H), 2.59-2.51 (m, 4H), 2.07-2.05 (m, 1H), 1.95-1.84 (m, 5H), 1.45 9s, 9H). LC-MS ($ES^+$): m/z 834.09 $[M+H]^+$.

Example 28

Example 28 was prepared following the synthesis of Example 1

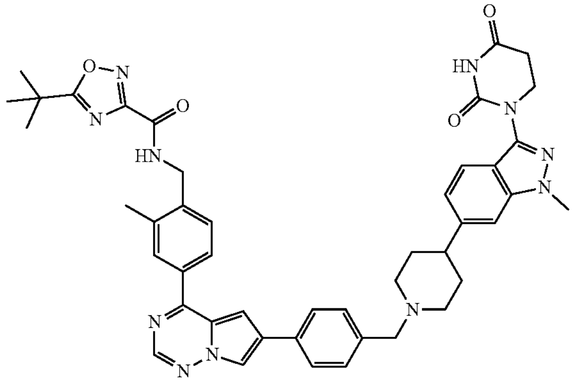 [SMILES: Cc1cc(-c2ncnn3cc(-c4ccc(CN5CCC(c6ccc7c(N8CCC(=O)NC8=O)nn(C)c7c6)CC5)cc4)cc23)ccc1CNC(=O)c1noc(C(C)(C)C)n1]

5-tert-butyl-N-[[4-[6-[4-[[4-[3-(2,4-dioxohexahydropyrimidin-1-yl)-1-methyl-indazol-6-yl]-1-piperidyl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.55 (s, 1H), 9.55-9.54 (m, 2H), 8.81 (s, 1H), 8.64 (s, 1H), 8.11-8.02 (m, 3H), 7.70 (s, 1H), 7.66-7.60 (m, 3H), 7.48 (d, J=8.0 Hz, 1H), 7.39 (s, 1H), 7.02 (d, J=8.4 Hz, 1H), 4.57 (d, J=5.6 Hz, 2H), 4.42 (s, 2H), 4.03-3.88 (m, 5H), 3.56-3.53 (m, 2H), 3.16-2.98 (m, 3H), 2.76-2.67 (m, 2H), 2.50-2.49 (s, 3H), 2.10-1.95 (m, 4H), 1.45 (s, 9H). LC-MS ($ES^+$): m/z 806.12 $[M+H]^+$.

Example 29

Example 29 was prepared following the synthesis of Example 1

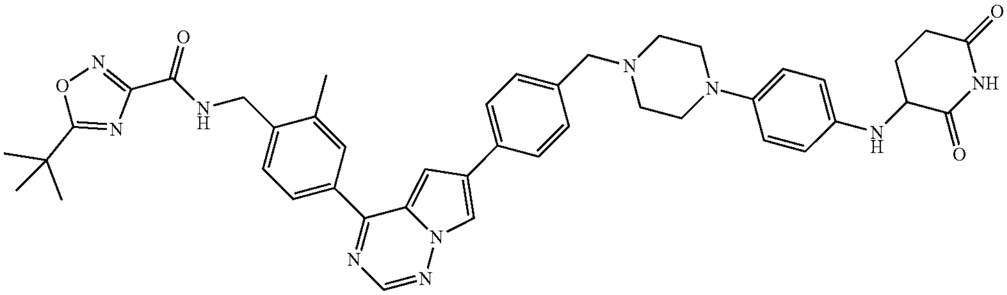 [SMILES: Cc1cc(-c2ncnn3cc(-c4ccc(CN5CCN(c6ccc(NC7CCC(=O)NC7=O)cc6)CC5)cc4)cc23)ccc1CNC(=O)c1noc(C(C)(C)C)n1]

5-tert-butyl-N-[[4-[6-[4-[[4-[4-[(2,6-dioxo-3-piperidyl)amino]phenyl]piperazin-1-yl]methyl]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.75 (s, 1H), 9.54 (t, J=5.9 Hz, 1H), 8.71 (s, 1H), 8.61 (s, 1H), 8.22 (s, 1H), 8.04 (t, J=10.0 Hz, 2H), 7.90 (d, J=8.0 Hz, 2H), 7.62 (s, 1H), 7.48 (d, J=8.0 Hz, 1H), 7.39 (d, J=8.0 Hz, 2H), 6.75 (d, J=8.8 Hz, 2H), 6.60 (d, J=8.8 Hz, 2H), 5.37 (d, J=6.8 Hz, 1H), 4.57 (d, J=6.0 Hz, 2H), 4.18-4.15 (m, 1H), 3.55 (s, 2H), 2.95 (s, 4H), 2.73-2.70 (m, 1H), 2.60-2.58 (m, 5H), 2.50 (s, 3H), 2.10-2.04 (m, 1H), 1.84-1.79 (m, 1H), 1.44 (s, 9H). LC-MS ($ES^+$): m/z 767.09 $[M+H]^+$.

Example 30

Example 30 was prepared following the synthesis of Example 1

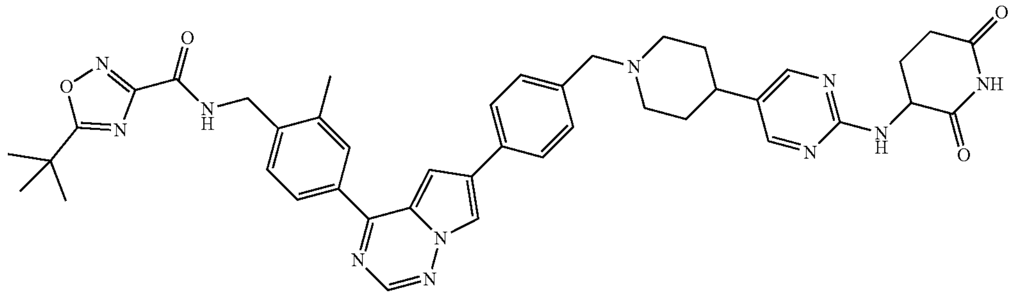 [SMILES: Cc1cc(-c2ncnn3cc(-c4ccc(CN5CCC(c6cnc(NC7CCC(=O)NC7=O)nc6)CC5)cc4)cc23)ccc1CNC(=O)c1noc(C(C)(C)C)n1]

5-tert-butyl-N-[[4-[6-[4-[[4-[2-[(2,6-dioxo-3-piperidyl) amino]pyrimidin-5-yl]-1-piperidyl]methyl]phenyl]pyrrolo [2,1-f][1,2,4]triazin-4-yl]-2-methyl-phenyl]methyl]-1,2,4-oxadiazole-3-carboxamide. $^1$H NMR (400 MHz, DMSO-$d_6$) δ=10.77 (s, 1H), 9.57 (t, J=5.9 Hz, 1H), 8.72 (d, J=1.4 Hz, 1H), 8.61 (s, 1H), 8.22 (s, 2H), 8.10-7.99 (m, 2H), 7.90 (d, J=8.1 Hz, 2H), 7.62 (d, J=1.4 Hz, 1H), 7.48 (d, J=8.0 Hz, 1H), 7.38 (d, J=8.1 Hz, 2H), 7.19 (d, J=8.5 Hz, 1H), 4.77-4.66 (m, 1H), 4.57 (d, J=6.0 Hz, 2H), 3.52 (s, 3H), 2.93 (d, J=10.6 Hz, 2H), 2.85-2.71 (m, 1H), 2.43-2.28 (m, 2H), 2.22-1.90 (m, 5H), 1.78-1.54 (m, 5H), 1.45 (s, 9H). LC-MS ($ES^+$): m/z 768.7 $[M-55]^+$.

Example 31

Example 31 was prepared following the synthesis of Example 1

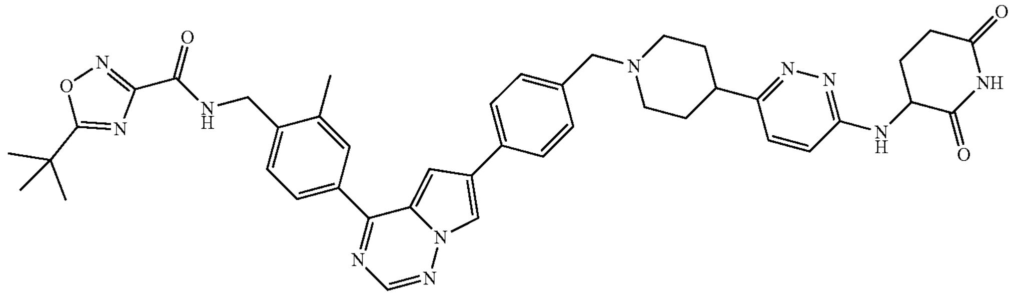 [SMILES: Cc1cc(-c2ncnn3cc(-c4ccc(CN5CCC(c6ccc(NC7CCC(=O)NC7=O)nn6)CC5)cc4)cc23)ccc1CNC(=O)c1noc(C(C)(C)C)n1]

5-tert-butyl-N-[[4-[6-[4-[[4-[6-[(2,6-dioxo-3-piperidyl) amino]pyridazin-3-yl]-1-piperidyl]methyl]phenyl]pyrrolo [2,1-f][1,2,4]triazin-4-yl]-2-methyl-phenyl]methyl]-1,2,4-oxadiazole-3-carboxamide. $^1$H NMR (400 MHz, DMSO-$d_6$) δ=10.84 (s, 1H), 9.57 (t, J=6.0 Hz, 1H), 8.72 (d, J=1.3 Hz, 1H), 8.61 (s, 1H), 8.11-7.99 (m, 2H), 7.90 (d, J=8.2 Hz, 2H), 7.63 (d, J=1.5 Hz, 1H), 7.48 (d, J=7.9 Hz, 1H), 7.39 (d, J=8.1 Hz, 2H), 7.26 (d, J=9.3 Hz, 1H), 7.03 (d, J=7.5 Hz, 1H), 6.90 (d, J=9.2 Hz, 1H), 4.89-4.77 (m, 1H), 4.57 (d, J=5.9 Hz, 2H), 3.54 (s, 2H), 2.94 (d, J=10.5 Hz, 2H), 2.84-2.73 (m, 1H), 2.71-2.63 (m, 1H), 2.57 (d, J=2.6 Hz, 1H), 2.49 (s, 3H), 2.18-2.04 (m, 4H), 1.82-1.68 (m, 4H), 1.45 (s, 9H). LC-MS ($ES^+$): m/z 768.3 $[M+H]^+$.

Example 32

Example 32 was prepared following the synthesis of Example 1

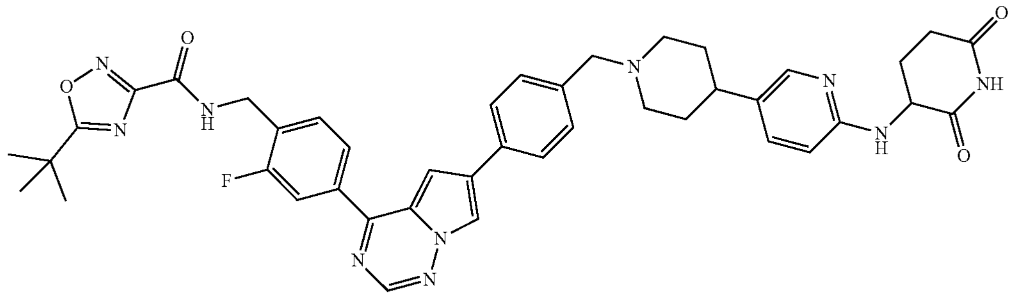

5-tert-butyl-N-[[4-[6-[4-[[4-[6-[(2,6-dioxo-3-piperidyl) amino]-3-pyridyl]-1-piperidyl]methyl]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.93 (s, 1H), 9.58 (t, J=6.0 Hz, 1H), 8.85 (s, 1H), 8.68 (s, 1H), 8.11-8.08 (m, 3H), 7.95 (d, J=11.2 Hz, 1H), 7.80 (d, J=6.8 Hz, 2H), 7.66-7.59 (m, 4H), 7.21-6.84 (m, 2H), 4.70 (s, 1H), 4.63 (d, J=6.0 Hz, 2H), 4.37 (s, 2H), 3.23-3.05 (m, 4H), 2.74-2.70 (m, 2H), 2.61-2.55 (m, 1H), 2.08-2.01 (m, 4H), 1.85-1.74 (m, 2H), 1.44 (s, 9H). LC-MS (ES$^+$): m/z 771.17 [M+H]$^+$.

Example 33

Example 33 was prepared following the synthesis of Example 1

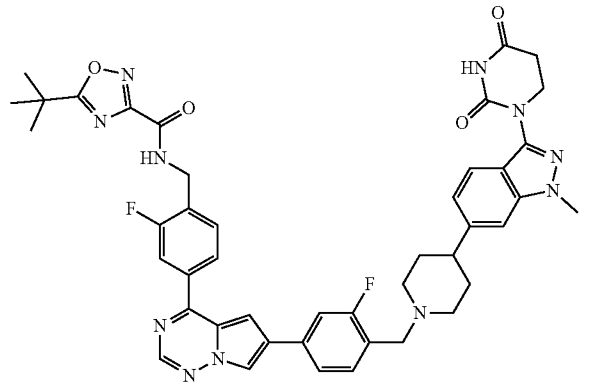 [SMILES: Cn1nc(N2CCC(=O)NC2=O)c2ccc(C3CCN(Cc4ccc(-c5cc6c(-c7ccc(CNC(=O)c8noc(C(C)(C)C)n8)c(F)c7)ncnn6c5)cc4F)CC3)cc21]

5-tert-butyl-N-[[4-[6-[4-[[4-[3-(2,4-dioxohexahydropyrimidin-1-yl)-1-methyl-indazol-6-yl]-1-piperidyl]methyl]-3-fluoro-phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.55 (s, 1H), 9.60 (t, J=5.9 Hz, 1H), 9.51 (bs, 1H), 8.93 (d, J=1.2 Hz, 1H), 8.69 (s, 1H), 8.11-8.08 (m, 2H), 8.00 (d, J=9.4 Hz, 2H), 7.88 (s, 1H), 7.70 (t, J=7.9 Hz, 1H), 7.38 (s, 1H), 7.01 (d, J=8.5 Hz, 2H), 4.64 (d, J=5.9 Hz, 2H), 4.47 (s, 2H), 3.97 (s, 3H), 3.90 (t, J=6.7 Hz, 2H), 3.60-3.57 (m, 2H), 3.29-3.22 (m, 2H), 3.03-2.97 (m, 1H), 2.75 (t, J=6.7 Hz, 2H), 2.11-1.97 (m, 4H), 1.44 (s, 9H). LC-MS (ES$^+$): m/z 828.16 [M+H]$^+$.

Example 34

Example 34 was prepared following the synthesis of Example 1

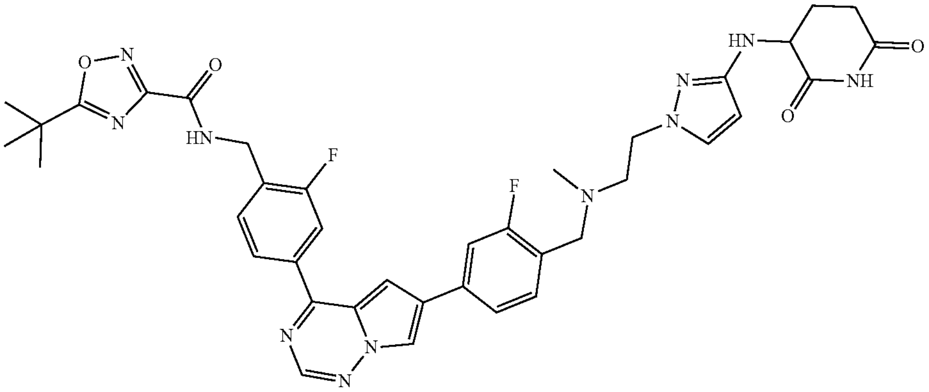 [SMILES: CN(CCn1ccc(NC2CCC(=O)NC2=O)n1)Cc1ccc(-c2cc3c(-c4ccc(CNC(=O)c5noc(C(C)(C)C)n5)c(F)c4)ncnn3c2)cc1F]

5-tert-butyl-N-[[4-[6-[4-[[2-[3-[(2,6-dioxo-3-piperidyl) amino]pyrazol-1-yl]ethyl-methyl-amino]methyl]-3-fluoro-phenyl]pyrrolo[2,1-f][1,2,4]triazin-4-yl]-2-fluoro-phenyl] methyl]-1,2,4-oxadiazole-3-carboxamide. $^1$H NMR (400 MHz, DMSO-$d_6$) δ 10.77 (s, 1H), 9.62 (t, J=5.8 Hz, 1H), 8.90 (d, J=1.2 Hz, 1H), 8.69 (s, 1H), 8.10-7.94 (m, 4H), 7.86 (s, 1H), 7.66-7.59 (m, 2H), 7.49 (s, 1H), 5.61 (d, J=2.4 Hz, 2H), 4.64 (d, J=5.6 Hz, 2H), 4.42-4.33 (m, 4H), 4.18-4.14 (m, 1H), 3.85 (s, 2H), 2.77 (s, 3H), 2.61-2.54 (m, 2H), 2.19-2.10 (m, 1H), 1.93-1.89 (m, 1H), 1.44 (s, 9H). LC-MS ($ES^+$): m/z 752.19 $[M+H]^+$.

Example 35

Example 35 was prepared following the synthesis of Example 1

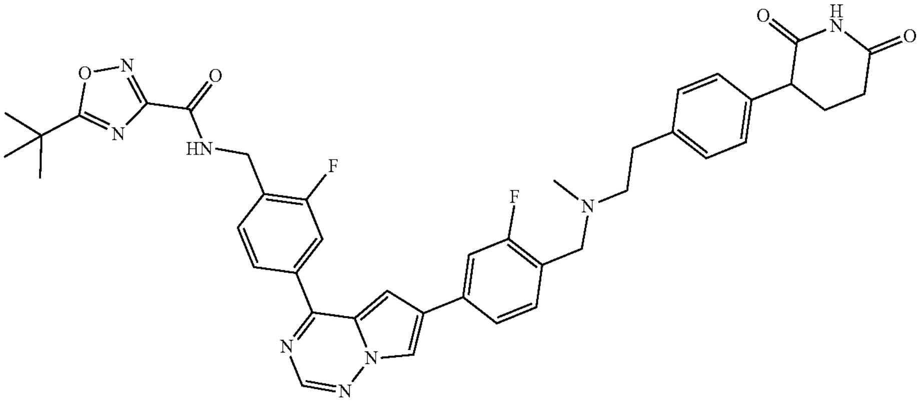 [SMILES: CN(CCc1ccc(C2CCC(=O)NC2=O)cc1)Cc1ccc(-c2cc3c(-c4ccc(CNC(=O)c5noc(C(C)(C)C)n5)c(F)c4)ncnn3c2)cc1F]

5-tert-butyl-N-[[4-[6-[4-[[2-[3-[(2,6-dioxo-3-piperidyl) amino]pyrazol-1-yl]ethyl-methyl-amino]methyl]-3-fluoro-phenyl]pyrrolo[2,1-f][1,2,4]triazin-4-yl]-2-fluoro-phenyl] methyl]-1,2,4-oxadiazole-3-carboxamide. $^1$H NMR (400 MHz, DMSO-$d_6$) δ 10.81 (s, 1H), 9.62 (t, J=5.8 Hz, 1H), 8.81 (s, 1H), 8.65 (s, 1H), 8.40 (s, 1H), 8.11 (d, J=8.2 Hz, 1H), 7.99 (d, J=10.9 Hz, 1H), 7.84 (d, J=10.9 Hz, 1H), 7.79-7.75 (m, 2H), 7.61 (t, J=7.8 Hz, 1H), 7.39 (t, J=7.8 Hz, 1H), 7.19-7.11 (m, 4H), 4.63 (d, J=5.8 Hz, 2H), 3.83-3.79 (m, 1H), 3.62 (s, 2H), 2.79-2.76 (m, 2H), 2.68-2.59 (m, 3H), 2.48-2.44 (m, 1H), 2.24 (s, 3H), 2.21-2.14 (m, 1H), 2.05-2.01 (m, 1H), 1.44 (s, 9H). LC-MS ($ES^-$): m/z 745.35 $[M-H]^-$.

Example 36

Example 36 was prepared following the synthesis of Example 1

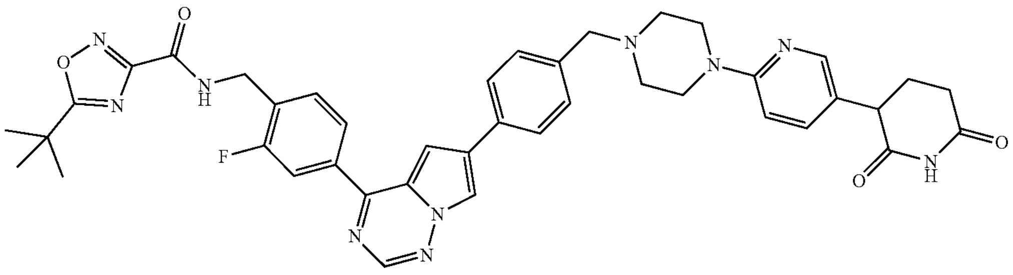 [SMILES: CC(C)(C)c1nc(C(=O)NCc2ccc(-c3ncnn4cc(-c5ccc(CN6CCN(c7ccc(C8CCC(=O)NC8=O)cn7)CC6)cc5)cc34)cc2F)no1]

5-tert-butyl-N-[[4-[6-[4-[[4-[5-(2,6-dioxo-3-piperidyl)-2-pyridyl]piperazin-1-yl]methyl]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.80 (s, 1H), 9.61 (t, J=5.9 Hz, 1H), 8.76 (d, J=1.2 Hz, 1H), 8.64 (s, 1H), 8.50 (s, 1H), 8.11-8.09 (m, 1H), 8.00-7.92 (m, 4H), 7.71 (d, J=1.2 Hz, 1H), 7.61 (t, J=7.9 Hz, 1H), 7.42-7.38 (m, 3H), 6.79 (d, J=8.9 Hz, 1H), 4.63 (d, J=5.9 Hz, 2H), 3.74-3.71 (m, 1H), 3.56 (s, 2H), 3.48 (bs, 4H), 2.70-2.63 (m, 1H), 2.48-2.40 (m, 5H), 2.23-2.13 (m, 1H), 2.01-1.98 (m, 1H), 1.44 (s, 9H). LC-MS ($ES^+$): m/z 757.47 $[M+H]^+$.

Example 37

Example 37 was prepared following the synthesis of Example 1

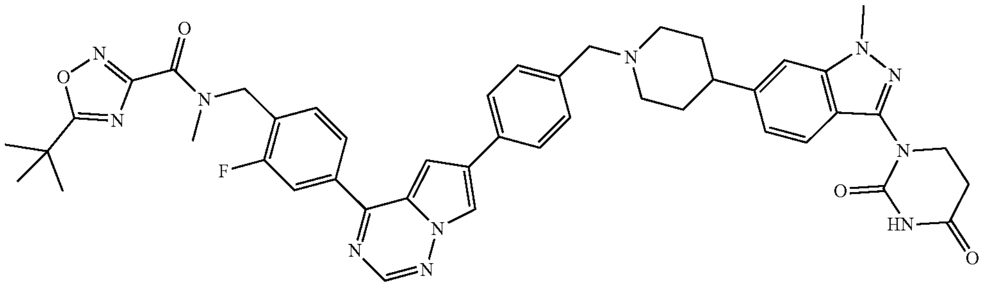 [SMILES: CN(Cc1ccc(-c2ncnn3cc(-c4ccc(CN5CCC(c6ccc7c(N8CCC(=O)NC8=O)nn(C)c7c6)CC5)cc4)cc23)cc1F)C(=O)c1noc(C(C)(C)C)n1]

5-tert-butyl-N-[[4-[6-[4-[[4-[3-(2,4-dioxohexahydropyrimidin-1-yl)-1-methyl-indazol-6-yl]-1-piperidyl]methyl]phenyl]pyrrolo[2,1-f][1,2,4]triazin-4-yl]-2-fluoro-phenyl]methyl]-N-methyl-1,2,4-oxadiazole-3-carboxamide. $^1$H NMR (400 MHz, DMSO-$d_6$) δ 10.55 (s, 1H), 9.52 (bs, 1H), 8.87 (s, 1H), 8.69 (d, J=2.8 Hz, 1H), 8.17-8.11 (m, 3H), 8.04-7.99 (m, 1H), 7.84-7.81 (m, 1H), 7.64-7.59 (m, 4H), 7.39 (s, 1H), 7.11 (d, J=8.4 Hz, 1H), 4.90-4.84 (m, 2H), 4.42 (d, J=3.2 Hz, 2H), 3.97 (s, 3H), 3.93 (t, J=6.8 Hz, 2H), 3.56-3.53 (m, 2H), 3.17-3.07 (m, 5H), 2.99-2.96 (m, 1H), 2.76 (t, J=6.8 Hz, 2H), 2.11-1.97 (m, 4H), 1.42 (s, 9H). LC-MS ($ES^-$): m/z 822.27 $[M-H]^-$.

Example 38

Example 38 was prepared following the synthesis of Example 1

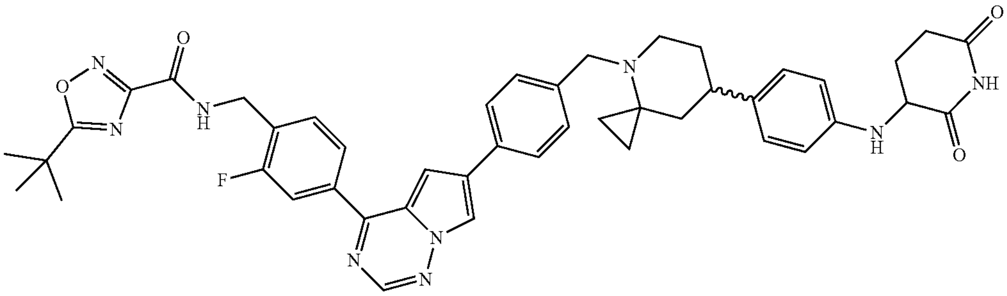

Isomer 1

5-tert-butyl-N-[[4-[6-[4-[[(7R)-7-[4-[(2,6-dioxo-3-piperidyl)amino]phenyl]-4-azaspiro[2.5]octan-4-yl]methyl]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.77 (s, 1H), 9.61 (t, J=6.0 Hz, 1H), 8.74 (d, J=1.6 Hz, 1H), 8.64 (s, 1H), 8.11-8.02 (m, 1H), 7.99-7.97 (m, 1H), 7.88 (d, J=8.1 Hz, 2H), 7.67 (d, J=1.6 Hz, 1H), 7.61 (t, J=8.0 Hz, 1H), 7.36 (d, J=8.0 Hz, 2H), 7.03 (d, J=8.5 Hz, 2H), 6.63 (d, J=8.5 Hz, 2H), 5.65 (d, J=7.5 Hz, 1H), 4.63 (d, J=6.0 Hz, 2H), 4.04-4.00 (m, 1H), 3.74 (d, J=13.6 Hz, 1H), 3.47 (d, J=13.5 Hz, 1H), 2.78-2.51 (m, 5H), 2.31-2.22 (m, 1H), 2.10-2.09 (m, 1H), 1.90-1.85 (m, 2H), 1.44 (s, 10H), 0.88-0.85 (m, 1H), 0.63-0.61 (m, 2H), 0.46 (bs, 2H). LC-MS ($ES^-$): m/z 794.36 $[M-H]^-$.

Example 39

Example 39 was prepared following the synthesis of Example 1

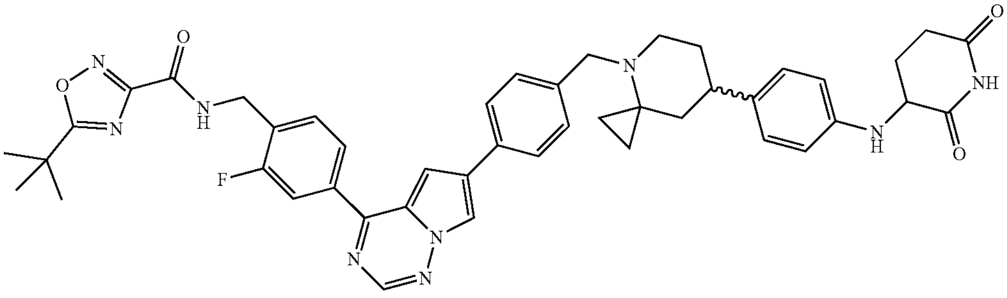

Isomer 2

5-tert-butyl-N-[[4-[6-[4-[[(7S)-7-[4-[(2,6-dioxo-3-piperidyl)amino]phenyl]-4-azaspiro[2.5]octan-4-yl]methyl]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.78 (s, 1H), 9.62 (t, J=6.0 Hz, 1H), 9.08 (bs, 1H), 8.86 (d, J=1.1 Hz, 1H), 8.67 (s, 1H), 8.09 (d, J=8.1 Hz, 3H), 7.98 (d, J=2.2 Hz, 1H), 7.78 (s, 1H), 7.67-7.58 (m, 3H), 7.18 (d, J=8.8 Hz, 2H), 6.67 (d, J=8.8 Hz, 2H), 5.76 (s, 1H), 4.89-4.79 (m, 1H), 4.63 (d, J=6.0 Hz, 3H), 4.33-4.31 (m, 1H), 3.23-3.21 (m, 2H), 2.87-2.51 (m, 3H), 2.33-2.32 (m, 1H), 2.12-2.07 (m, 1H), 1.89-1.86 (m, 2H), 1.44 (s, 9H), 1.26-1.24 (m, 3H), 1.03-1.00 (m, 1H), 0.89-0.86 (m, 2H).

LC-MS ($ES^+$): m/z 796.35 $[M+H]^+$.

Mobile phase-A: 0.1% FA in H2O

Mobile phase-B: ACN

Column: X Bridge BEH C18 2.5 μm, 2.1×50 mm

Flow: 0.5 mL/min, Temp: 40° C.

Time (min) and % B: 0-5; 0.5-5; 6.0-95; 8.5-95; 9.2-5; 10.2-5.

Example 40

Example 40 was prepared following the synthesis of Example 1

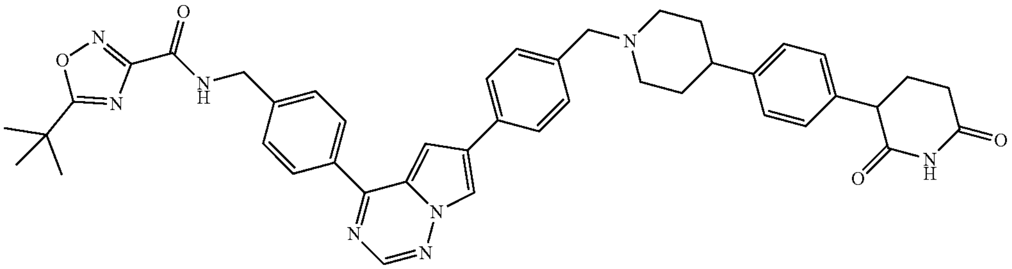 [SMILES: CC(C)(C)c1nc(C(=O)NCc2ccc(-c3ncnn4cc(-c5ccc(CN6CCC(c7ccc(C8CCC(=O)NC8=O)cc7)CC6)cc5)cc34)cc2)no1]

5-tert-butyl-N-[[4-[6-[4-[[4-[4-(2,6-dioxo-3-piperidyl) phenyl]-1-piperidyl]methyl]phenyl]pyrrolo[2,1-f][1,2,4]triazin-4-yl]phenyl]methyl]-1,2,4-oxadiazole-3-carboxamide. $^1$H NMR (400 MHz, DMSO-$d_6$) δ 10.81 (s, 1H), 9.62 (t, J=6.1 Hz, 1H), 8.75 (s, 1H), 8.63 (s, 1H), 8.22 (d, J=8.0 Hz, 2H), 7.96 (bs, 2H), 7.67 (bs, 1H), 7.57 (d, J=8.0 Hz, 2H), 7.46 (bs, 2H), 7.22-7.14 (m, 4H), 4.60 (d, J=6.1 Hz, 2H), 3.83-3.79 (m, 3H), 3.08-3.6 (m, 2H), 2.73-2.57 (m, 6H), 2.16-2.11 (m, 1H), 2.04-1.98 (m, 1H), 1.82-1.75 (m, 4H), 1.44 (s, 9H). LC-MS (ES$^+$): m/z 737.14 [M+H]$^+$.

Example 41

Example 41 was prepared following the synthesis of Example 1

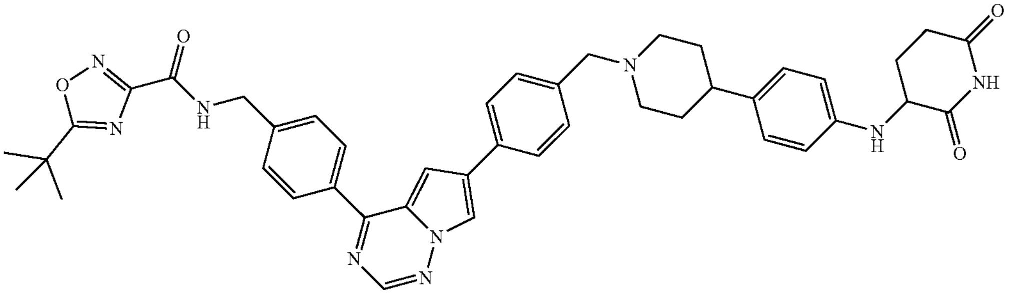

5-tert-butyl-N-[[4-[6-[4-[[4-[4-[(2,6-dioxo-3-piperidyl) amino]phenyl]-1-piperidyl]methyl]phenyl]pyrrolo[2,1-f][1,2,4]triazin-4-yl]phenyl]methyl]-1,2,4-oxadiazole-3-carboxamide. $^1$H NMR (400 MHz, DMSO-$d_6$) δ 10.75 (s, 1H), 9.61 (t, J=6.0 Hz, 1H), 8.72 (s, 1H), 8.62 (s, 1H), 8.22 (d, J=8.0 Hz, 2H), 7.91 (d, J=7.6 Hz, 2H), 7.64 (s, 1H), 7.57 (d, J=8.0 Hz, 2H), 7.40 (d, J=7.6 Hz, 2H), 6.96 (d, J=8.4 Hz, 2H), 6.60 (d, J=8.0 Hz, 2H), 5.64 (d, J=7.6 Hz, 1H), 4.60 (d, J=6.0 Hz, 2H), 4.28-4.22 (m, 1H), 3.58 (bs, 2H), 2.97-2.95 (m, 2H), 2.77-2.66 (m, 2H), 2.36-2.33 (m, 1H), 2.11-2.07 (m, 3H), 1.90-1.86 (m, 1H), 1.70-1.60 (m, 4H), 1.44 (s, 9H). LC-MS (ES$^+$): m/z 752.14 [M+H]$^+$.

Example 42

Example 42 was prepared following the synthesis of Example 1

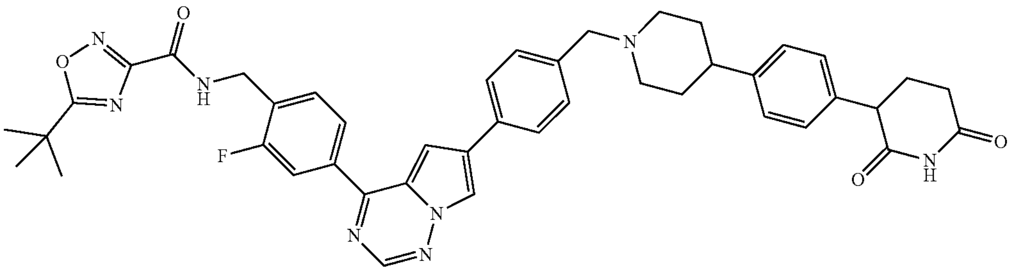 [SMILES: CC(C)(C)c1nc(C(=O)NCc2ccc(-c3ncnn4cc(-c5ccc(CN6CCC(c7ccc(C8CCC(=O)NC8=O)cc7)CC6)cc5)cc34)cc2F)no1]

5-tert-butyl-N-[[4-[6-[4-[[4-[4-(2,6-dioxo-3-piperidyl) phenyl]-1-piperidyl]methyl]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.82 (s, 1H), 9.62 (t, J=5.9 Hz, 1H), 8.85 (s, 1H), 8.67 (s, 1H), 8.12-8.07 (m, 3H), 7.99 (d, J=10.7 Hz, 1H), 7.79 (s, 1H), 7.66-7.58 (m, 3H), 7.19 (s, 4H), 4.64 (d, J=5.8 Hz, 2H), 4.38 (d, J=3.6 Hz, 2H), 3.84-3.80 (m, 1H), 3.52-3.48 (m, 2H), 3.14-3.07 (m, 2H), 2.85-2.79 (m, 1H), 2.69-2.62 (m, 2H), 2.18-2.15 (m, 1H), 2.07-2.01 (m, 3H), 1.91-1.84 (m, 2H), 1.44 (s, 9H). LC-MS (ES$^+$): m/z 755.12 [M+H]$^+$.

Example 43

Example 43 was prepared following the synthesis of Example 1

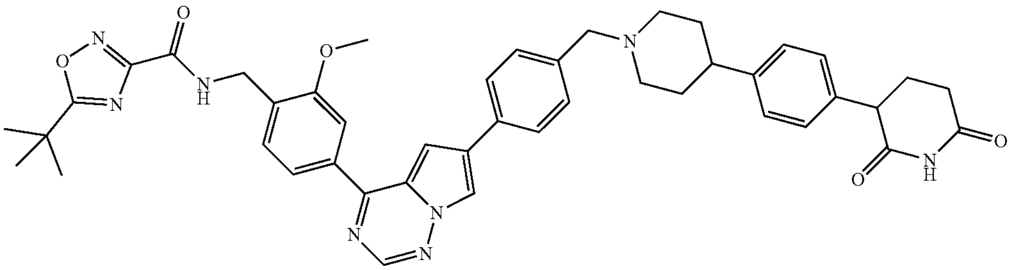 [SMILES: COc1cc(-c2ncnn3cc(-c4ccc(CN5CCC(c6ccc(C7CCC(=O)NC7=O)cc6)CC5)cc4)cc23)ccc1CNC(=O)c1noc(C(C)(C)C)n1]

5-tert-butyl-N-[[4-[6-[4-[[4-[4-(2,6-dioxo-3-piperidyl) phenyl]-1-piperidyl]methyl]phenyl]pyrrolo[2,1-f][1,2,4]triazin-4-yl]-2-methoxy-phenyl]methyl]-1,2,4-oxadiazole-3-carboxamide. $^1$H NMR (401 MHz, DMSO-$d_6$) δ 10.82 (s, 1H), 9.45 (t, J=5.9 Hz, 1H), 8.82 (s, 1H), 8.66 (s, 1H), 8.09 (d, J=8.1 Hz, 2H), 7.85 (d, J=7.9 Hz, 1H), 7.73 (s, 2H), 7.60 (d, J=8.1 Hz, 2H), 7.41 (d, J=7.8 Hz, 1H), 7.19 (s, 4H), 4.55 (d, J=5.6 Hz, 2H), 4.38 (d, J=3.6 Hz, 2H), 3.98 (s, 3H), 3.83-3.80 (m, 1H), 3.51 (d, J=11.7 Hz, 2H), 3.12-3.08 (m, 2H), 2.81-2.78 (m, 1H), 2.66-2.60 (m, 1H), 2.49 (s, 1H), 2.18 (q, J=6.8 Hz, 1H), 2.07-2.00 (m, 3H), 1.86 (q, J=12.0 Hz, 2H), 1.45 (s, 9H). LC-MS (ES$^+$): m/z 767.60 [M+H]$^+$.

Example 44

Example 44 was prepared following the synthesis of Example 1

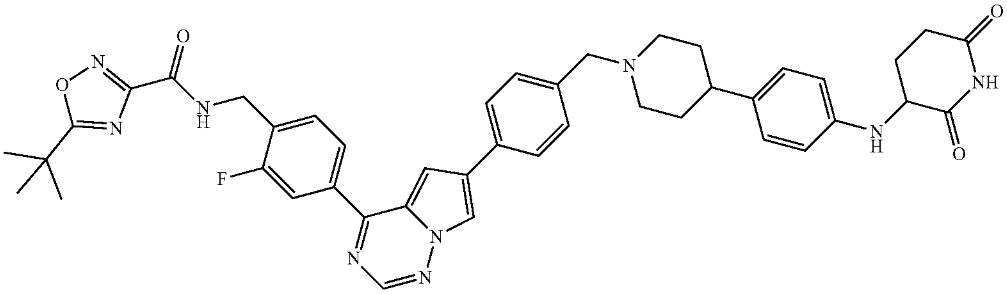 [SMILES: CC(C)(C)c1nc(C(=O)NCc2ccc(-c3ncnn4cc(-c5ccc(CN6CCC(c7ccc(NC8CCC(=O)NC8=O)cc7)CC6)cc5)cc34)cc2F)no1]

5-tert-butyl-N-[[4-[6-[4-[[4-[4-[(2,6-dioxo-3-piperidyl) amino]phenyl]-1-piperidyl]methyl]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.79 (s, 1H), 9.61 (s, 1H), 8.76 (s, 1H), 8.64 (s, 1H), 8.10 (d, J=8.0 Hz, 1H), 7.99-7.90 (m, 3H), 7.70 (s, 1H), 7.61 (t, J=7.9 Hz, 1H), 7.38 (d, J=8.1 Hz, 2H), 6.96 (d, J=8.4 Hz, 2H), 6.60 (d, J=8.5 Hz, 2H), 5.63 (d, J=7.3 Hz, 1H), 4.63 (s, 2H), 4.22 (s, 1H), 3.51 (s, 2H), 2.92 (d, J=10.8 Hz, 2H), 2.73-2.70 (m, 1H), 2.57-2.56 (m, 1H), 2.33-2.32 (bs, 1H), 2.08-2.00 (m, 3H), 1.84-1.81 (m, 1H), 1.69-1.60 (m, 4H), 1.44 (s, 9H). LC-MS ($ES^+$): m/z 770.21 $[M+H]^+$.

Example 45

Example 45 was prepared following the synthesis of Example 1

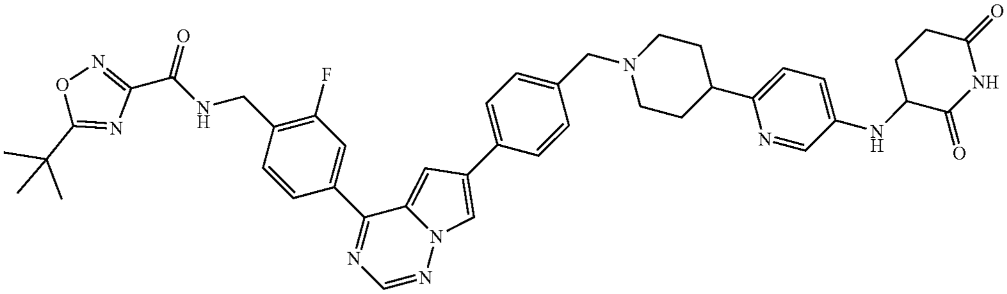 [SMILES: CC(C)(C)c1nc(C(=O)NCc2ccc(-c3ncnn4cc(-c5ccc(CN6CCC(c7ccc(NC8CCC(=O)NC8=O)cn7)CC6)cc5)cc34)cc2F)no1]

5-tert-butyl-N-[[4-[6-[4-[[4-[5-[(2,6-dioxo-3-piperidyl) amino]-2-pyridyl]-1-piperidyl]methyl]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.87 (s, 1H), 9.60 (t, J=6.0 Hz, 2H), 8.85 (d, J=1.2 Hz, 1H)), 8.67 (s, 1H), 8.11-8.08 (m, 3H), 8.03-7.97 (m, 2H), 7.78 (s, 1H), 7.63-7.59 (m, 3H), 7.52-6.50 (m, 2H), 4.63 (d, J=6.0 Hz, 2H), 4.52-4.46 (m, 1H), 4.38 (brs, 2H), 3.52-3.50 (m, 2H), 3.20-3.00 (m, 3H), 2.72-2.63 (m, 2H), 2.11-1.80 (m, 6H), 1.47 (s, 9H). LC-MS ($ES^+$): m/z 771.17 (4.16, $[M+H]^+$.

Example 46

Example 46 was prepared following the synthesis of Example 1

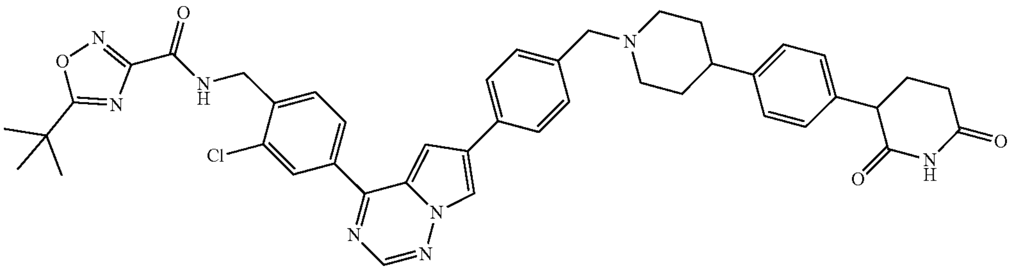 [SMILES: CC(C)(C)c1nc(C(=O)NCc2ccc(-c3ncnn4cc(-c5ccc(CN6CCC(c7ccc(C8CCC(=O)NC8=O)cc7)CC6)cc5)cc34)cc2Cl)no1]

5-tert-butyl-N-[[2-chloro-4-[6-[4-[[4-[4-(2,6-dioxo-3-piperidyl)phenyl]-1-piperidyl]methyl]phenyl]pyrrolo[2,1-f][1,2,4]triazin-4-yl]phenyl]methyl]-1,2,4-oxadiazole-3-carboxamide. $^{1}H$ NMR (400 MHz, DMSO-$d_6$) δ 10.82 (s, 1H), 9.65 (t, J=5.9 Hz, 1H), 8.86 (s, 1H), 8.68 (s, 1H), 8.23 (d, J=10.0 Hz, 2H), 8.10 (d, J=8.0 Hz, 2H), 7.75 (s, 1H), 7.60 (q, J=4.1 Hz, 3H), 7.19 (s, 4H), 4.66 (d, J=6.0 Hz, 2H), 4.38 (d, J=3.6 Hz, 2H), 3.82-3.80 (m, 1H), 3.52-3.49 (m, 2H), 3.14-3.06 (m, 2H), 2.81-2.78 (m, 1H), 2.65-2.60 (m, 1H), 2.50 (s, 1H), 2.20-2.10 (m, 1H), 2.07-1.98 (m, 3H), 1.90-1.80 (m, 2H), 1.45 (s, 9H). LC-MS ($ES^+$): m/z 771.08 $[M+H]^+$.

Example 47

Example 47 was prepared following the synthesis of Example 1

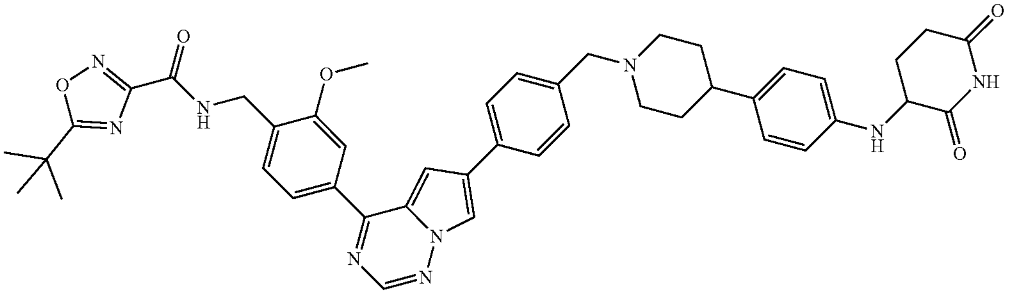 [SMILES: COc1cc(-c2ncnn3cc(-c4ccc(CN5CCC(c6ccc(NC7CCC(=O)NC7=O)cc6)CC5)cc4)cc23)ccc1CNC(=O)c1noc(C(C)(C)C)n1]

5-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methoxy-phenyl]methyl]-1,2,4-oxadiazole-3-carboxamide. $^{1}H$ NMR (400 MHz, DMSO-$d_6$) δ 10.77 (s, 1H), 9.46-9.45 (m, 2H), 8.82 (s, 1H), 8.66 (s, 1H), 8.08 (d, J=8.0 Hz, 2H), 7.84 (d, J=7.6 Hz, 1H), 7.73 (s, 2H), 7.59 (d, J=8.0 Hz, 2H), 7.41 (d, J=8.0 Hz, 1H), 6.93 (d, J=8.4 Hz, 2H), 6.63 (d, J=8.4 Hz, 2H), 4.55 (d, J=6.0 Hz, 2H), 4.36-4.24 (m, 3H), 3.98 (s, 3H), 3.51 (m, 2H), 3.16-3.02 (m, 2H), 2.75-2.58 (m, 3H), 2.10-1.80 (m, 6H), 1.45 (s, 9H). LC-MS ($ES^+$): m/z 782.13 $[M+H]^+$.

Example 48

Example 48 was prepared following the synthesis of Example 1

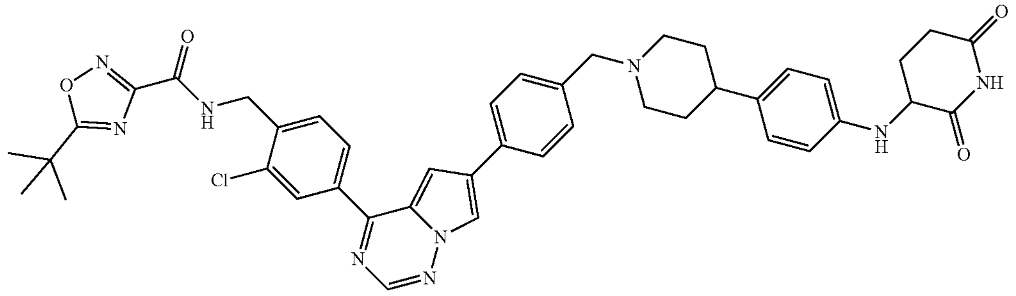

5-tert-butyl-N-[[2-chloro-4-[6-[4-[[4-[4-[(2,6-dioxo-3-piperidyl)amino]phenyl]-1-piperidyl]methyl]phenyl]pyrrolo[2,1-f][1,2,4]triazin-4-yl]phenyl]methyl]-1,2,4-oxadiazole-3-carboxamide. $^{1}$H NMR (400 MHz, DMSO-$d_6$) δ 10.76 (s, 1H), 9.64 (t, J=6.0 Hz, 1H), 8.76 (s, 1H), 8.64 (s, 1H), 8.25-81 (m, 2H), 7.90 (d, J=8.0 Hz, 2H), 7.67 (s, 1H), 7.59 (d, J=8.0 Hz, 1H), 7.38 (d, J=8.0 Hz, 2H), 6.96 (d, J=8.3 Hz, 2H), 6.60 (d, J=8.4 Hz, 2H), 5.63 (d, J=7.4 Hz, 1H), 4.66 (d, J=5.8 Hz, 2H), 4.28-4.22 (m, 1H), 3.51 (s, 2H), 2.92 (d, J=10.7 Hz, 2H), 2.73-2.67 (m, 1H), 2.59-2.54 (m, 1H), 2.32 (bs, 1H), 2.08-2.00 (m, 3H), 1.89 (bs, 1H), 1.83-1.69 (m, 4H), 1.45 (s, 9H). LC-MS (ES$^+$): m/z 786.12 [M+H]$^+$.

Example 49

Example 49 was prepared following the synthesis of Example 1

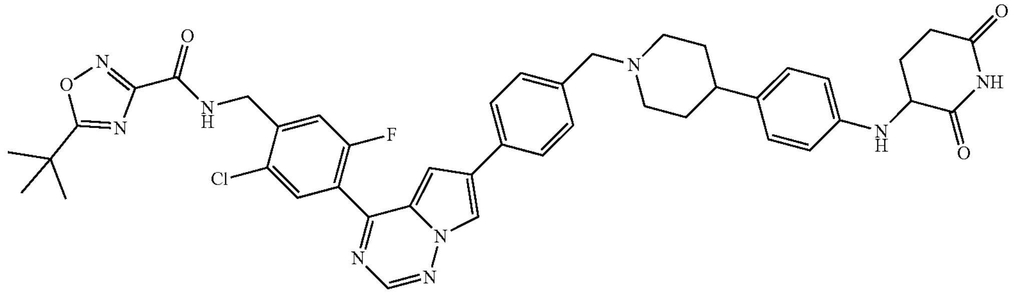 [SMILES: CC(C)(C)c1nc(C(=O)NCc2cc(F)c(-c3ncnn4cc(-c5ccc(CN6CCC(c7ccc(NC8CCC(=O)NC8=O)cc7)CC6)cc5)cc34)cc2Cl)no1]

5-tert-butyl-N-[[2-chloro-4-[6-[4-[[4-[4-[(2,6-dioxo-3-piperidyl)amino]phenyl]-1-piperidyl]methyl]phenyl]pyrrolo[2,1-f][1,2,4]triazin-4-yl]-5-fluoro-phenyl]methyl]-1,2,4-oxadiazole-3-carboxamide. $^{1}$H NMR (400 MHz, DMSO-$d_6$) δ 10.76 (s, 1H), 9.62 (t, J=5.9 Hz, 1H), 8.79 (s, 1H), 8.67 (s, 1H), 7.94 (d, J=6.4 Hz, 1H), 7.85 (d, J=8.0 Hz, 2H), 7.46 (d, J=10.4 Hz, 1H), 7.37-7.32 (m, 3H), 6.96 (d, J=8.3 Hz, 2H), 6.60 (d, J=8.3 Hz, 2H), 5.63 (d, J=7.4 Hz, 1H), 4.63 (d, J=6.0 Hz, 2H), 4.28-4.22 (m, 1H), 3.50 (s, 2H), 2.91 (d, J=10.9 Hz, 2H), 2.74-2.58 (m, 1H), 2.54-2.50 (s, 1H), 2.33 (t, J=11.7 Hz, 1H), 2.11-1.99 (m, 3H), 1.85 (s, 1H), 1.68-1.57 (m, 4H), 1.45 (s, 9H). LC-MS (ES$^+$): m/z 804.44 [M+H]$^+$.

Example 50. Synthesis of 5-tert-butyl-N-[[4-[6-[3-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-1,2,4-oxadiazole-3-carboxamide
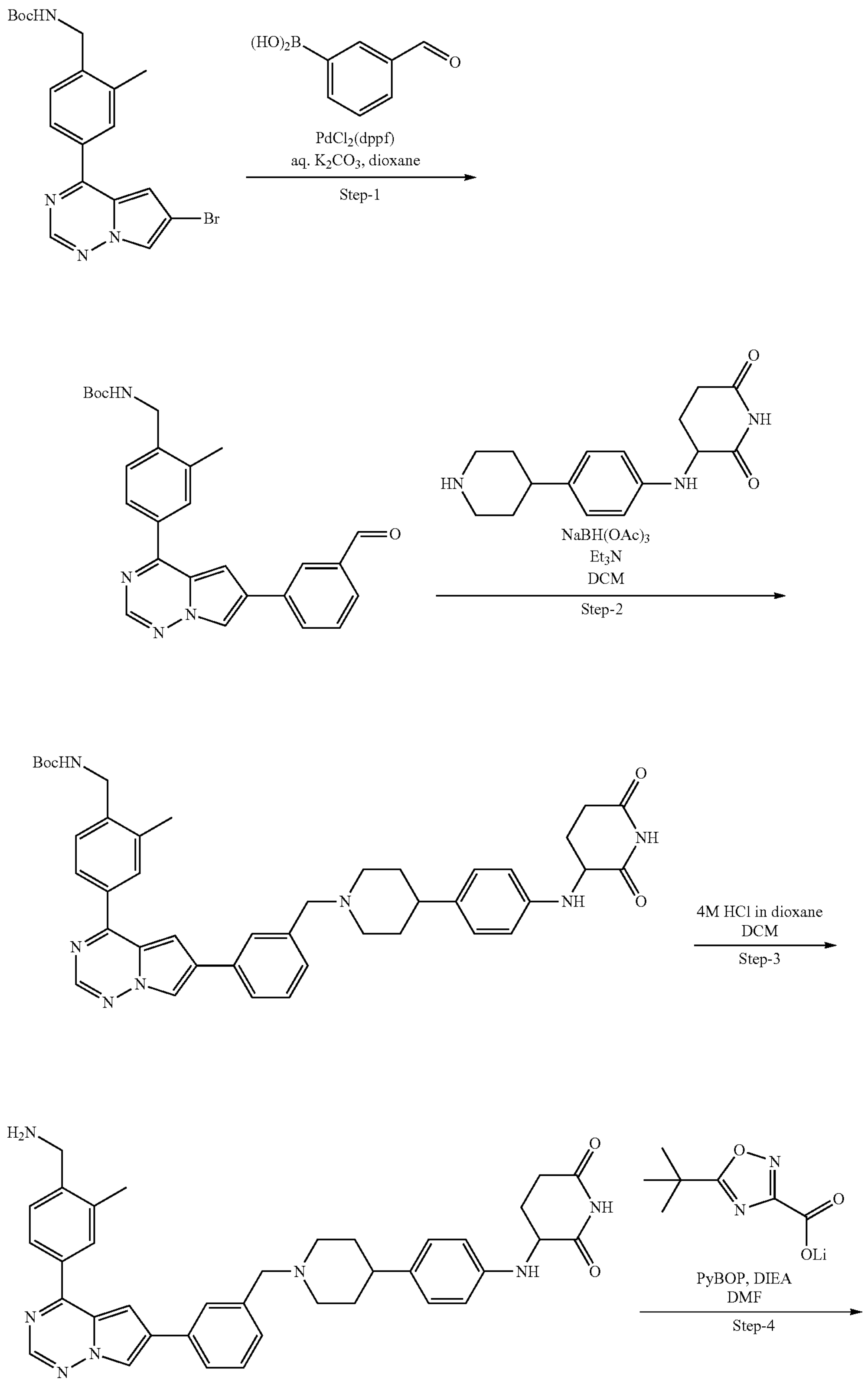

-continued

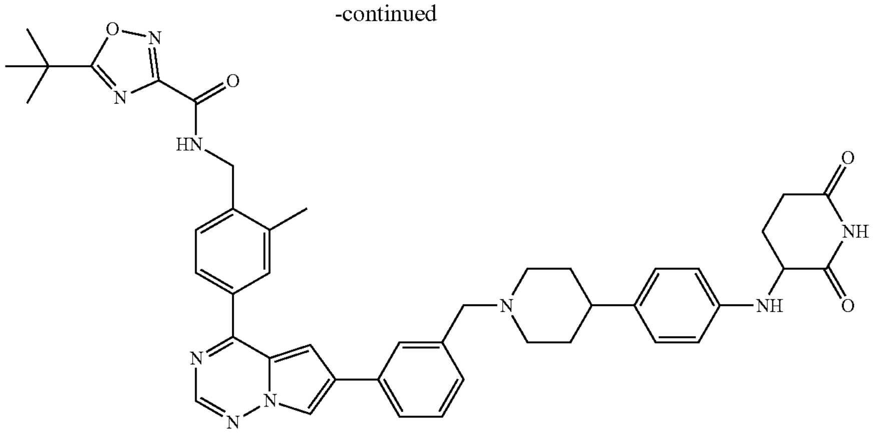

Step-1:

To a stirred solution of tert-butyl (4-(6-bromopyrrolo[2,1-f][1,2,4]triazin-4-yl)-2-methylbenzyl)carbamate (1 g, 2.40 mmol) in dioxane (10 mL) in a sealed tube was added 3-formylphenylboronic acid (718.62 mg, 4.79 mmol) at room temperature followed by an aqueous solution (5 mL) of potassium carbonate (993.58 mg, 7.19 mmol) under argon atmosphere. The reaction mixture was degassed with argon repeatedly and Pd(dppf)$Cl_2$ (175.34 mg, 239.64 μmol) was added to the reaction mixture in one portion. The reaction mixture was degassed again with argon and heated at 70° C. for 16 hours. The crude product was purified by flash column chromatography (0-100% ethyl acetate/pet ether) to afford tert-butyl (4-(6-(3-formylphenyl)pyrrolo[2,1-f][1,2,4]triazin-4-yl)-2-methylbenzyl)carbamate (0.5 g, 858.74 μmol, 35.84% yield) as a yellow solid. LC-MS ($ES^+$): m/z 443.28 $[M+H]^+$.

Step-2:

To the stirred solution of tert-butyl N-[[4-[6-(3-formylphenyl)pyrrolo[2,1-f][1,2,4]triazin-4-yl]-2-methyl-phenyl]methyl]carbamate (0.250 g, 564.96 μmol) and 3-[4-(4-piperidyl)anilino]piperidine-2,6-dione TFA salt (408.17 mg, 1.02 mmol) in DCM (5 mL) was added triethylamine (571.68 mg, 5.65 mmol, 787.44 μL) and reaction mixture was stirred for 30 minutes at room temperature. The reaction was cooled to 0° C. and sodium triacetoxyborohydride (478.95 mg, 2.26 mmol) was added before the reaction was stirred at room temperature for 12 hours. Progress of the reaction was monitored by TLC and LC-MS. After completion, the reaction mixture was concentrated under reduced pressure and the crude product was purified by column chromatography (silica 100-200, 0-10% methanol in DCM). to get the final product tert-butyl N-[[4-[6-[3-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]carbamate (0.150 g, 147.09 μmol, 26.03% yield) as a green solid. LC-MS ($ES^+$): m/z 714.21 $[M+H]^+$.

Step-3:

To stirred solution of tert-butyl N-[[4-[6-[3-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]carbamate (0.150 g, 210.12 μmol) in DCM (2 mL) at 0° C. under argon atmosphere, 4 M hydrogen chloride solution in dioxane (1.5 mL) was added and the reaction was stirred at room temperature for 2 hours. The progress of the reaction was monitored by LC-MS. Upon completion, the reaction was concentrated under reduced pressure to give the crude product, which was washed by ether to furnish the final product (0.0.150 g, 155.56 μmol, 74.03% yield). LC-MS ($ES^+$): m/z 614.19 $[M+H]^+$.

Step-4:

To a stirred solution of 3-[4-[1-[[3-[4-[4-(aminomethyl)-3-methyl-phenyl]pyrrolo[2,1-f][1,2,4]triazin-6-yl]phenyl]methyl]-4-piperidyl]anilino]piperidine-2,6-dione (0.150 g, 230.69 μmol, HCl salt) and (5-tert-butyl-1,2,4-oxadiazole-3-carbonyl)oxylithium (81.25 mg, 461.39 μmol) in DMF (2 mL) at 0° C. under argon atmosphere, N-ethyl-N-isopropyl-propan-2-amine (298.16 mg, 2.31 mmol, 401.83 μL) and benzotriazol-1-yloxy(tripyrrolidin-1-yl)phosphonium; hexafluorophosphate (240.10 mg, 461.39 μmol) was added, and the reaction mixture was stirred at 25° C. for 5 hours. Reaction progress was monitored by LC-MS. Upon completion, the reaction was concentrated in vacuo to furnish the crude product, which was purified by prep-HPLC to afford the final product 5-tert-butyl-N-[[4-[6-[3-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-1,2,4-oxadiazole-3-carboxamide TFA salt (96 mg, 103.25 μmol, 44.76% yield) as a brown solid. $^1H$ NMR (400 MHz, DMSO-$d_6$) δ 10.77 (s, 1H), 9.57 (t, J=5.9 Hz, 1H), 9.38 (s, 1H), 8.73 (d, J=8.0 Hz, 1H), 8.65 (s, 1H), 8.11-7.99 (m, 4H), 7.61-7.55 (m, 2H), 7.48 (d, J=8.0 Hz, 2H), 7.21-6.91 (m, 2H), 6.62 (d, J=8.4 Hz, 2H), 4.58-4.56 (d, J=5.8 Hz, 2H), 4.38-4.24 (m, 3H), 3.51-3.48 (m, 2H), 3.10-3.07 (m, 2H), 2.72-2.62 (m, 1H), 2.52-2.50 (m, 5H), 2.10-2.05 (m, 1H), 1.96-1.80 (m, 5H), 1.44 (s, 9H). LC-MS ($ES^-$): m/z 766.17 $[M-H]^-$.

Example 51. Synthesis of 5-tert-butyl-N-[[4-[6-[4-[2-[4-[4-(2,6-dioxo-3-piperidyl)phenyl]-3,3-difluoro-1-piperidyl]ethyl]phenyl]pyrrolo[2,1-f][1,2,4]triazin-4-yl]-2-methyl-phenyl]methyl]-1,2,4-oxadiazole-3-carboxamide
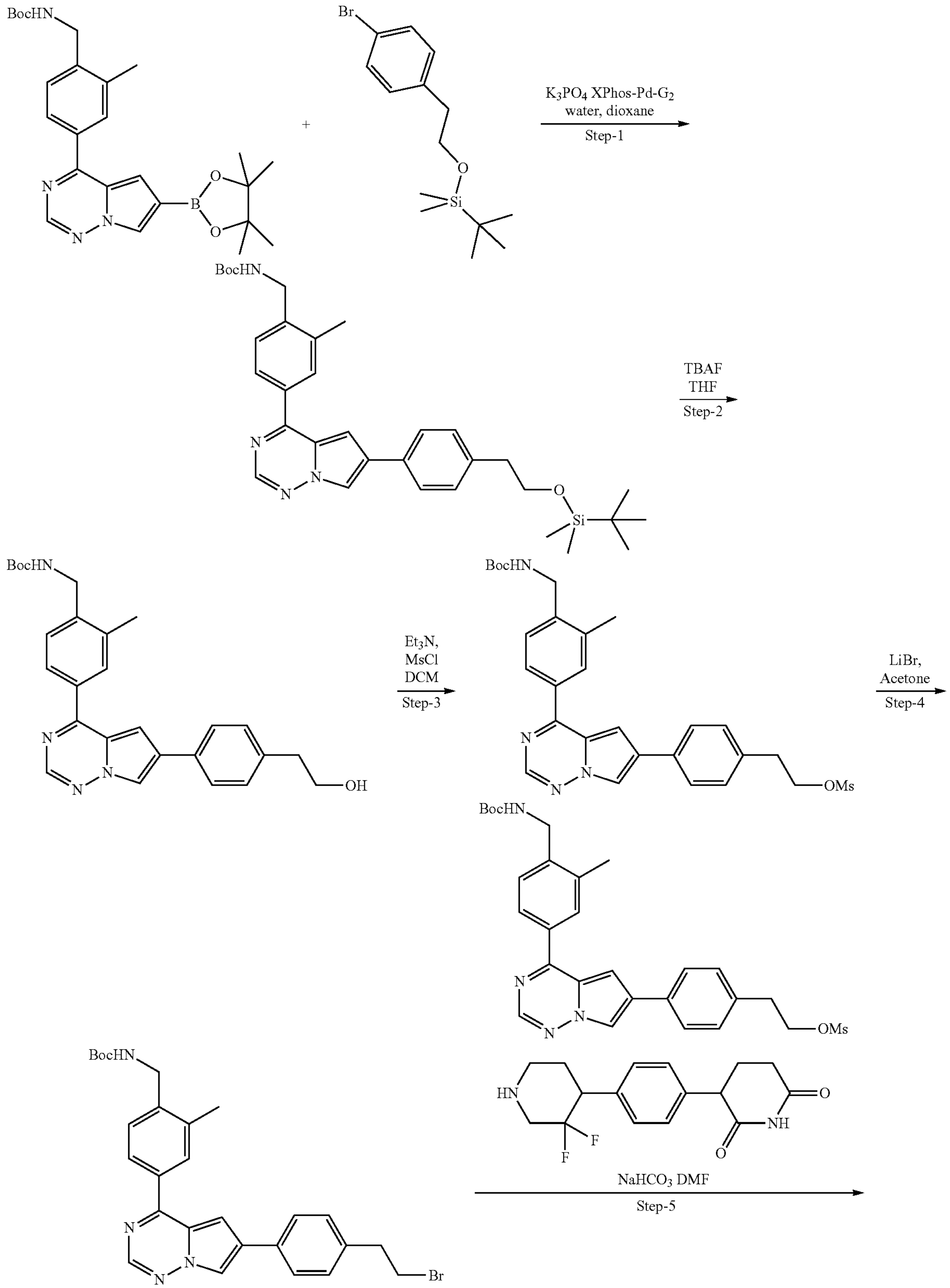

-continued

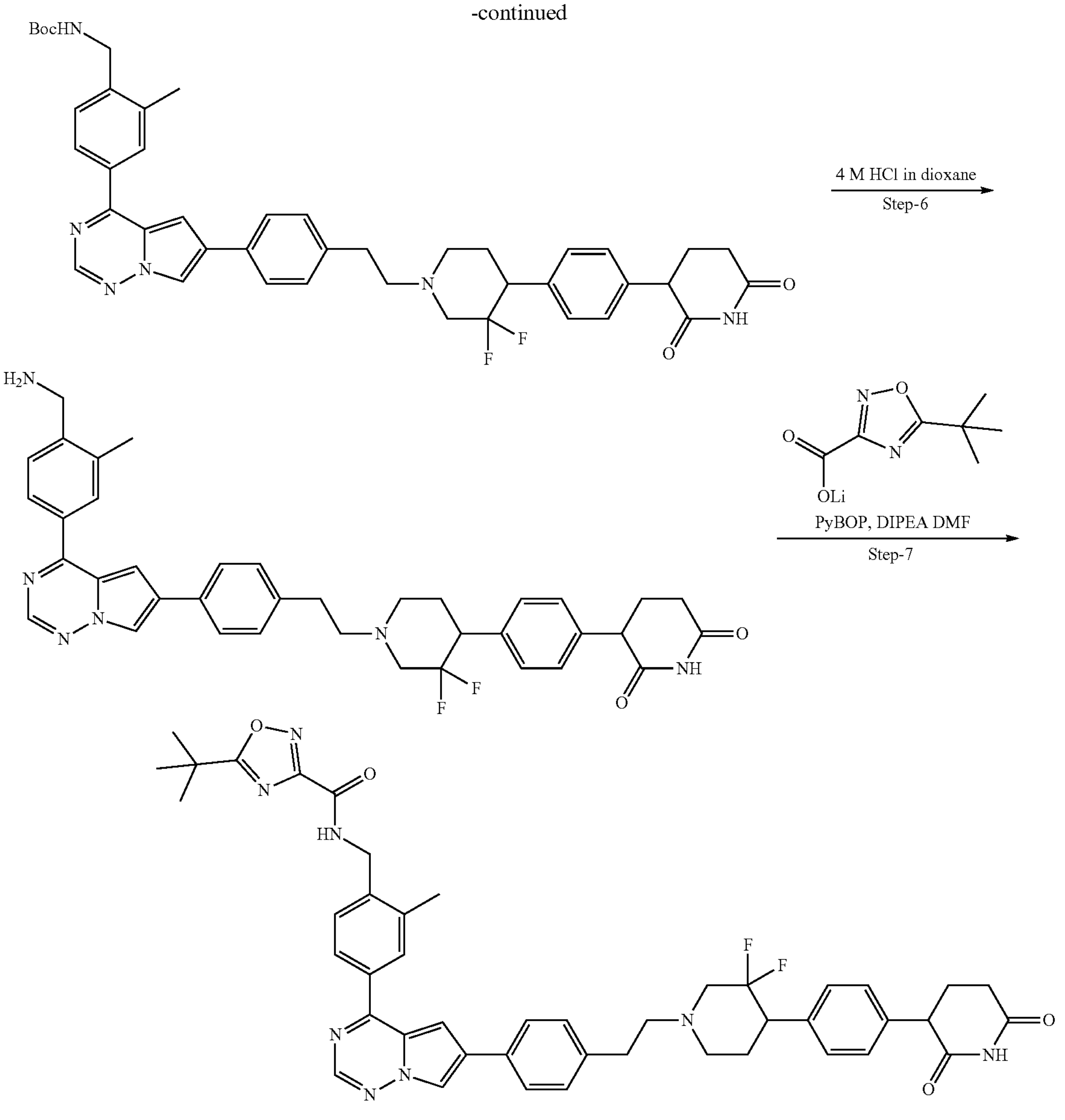

Step-1:

To a stirred solution of 2-(4-bromophenyl)ethoxy-tert-butyl-dimethyl-silane (0.025 g, 79.28 μmol) in dioxane (0.8 mL) and water (0.2 mL) purged with argon gas, tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (55.23 mg, 118.93 μmol), tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (55.23 mg, 118.93 μmol) and potassium phosphate (50.49 mg, 237.85 μmol) were added at room temperature and the reaction was stirred at this temperature for 10 minutes. XPhos-Pd-G2 (6.24 mg, 7.93 μmol) was then added and the reaction mixture was stirred at 90° C. for 16 hours. The reaction progress was monitored by TLC and LC-MS analysis. After the reaction was complete, it was quenched with water (60 mL) and extracted with ethyl acetate (50 mL×3). The combined organic layers were washed with brine solution (100 mL), dried over anhydrous sodium sulfate, filtered, and concentrated under reduced pressure. The crude compound was purified by flash column chromatography (silica gel 230-400 mesh, 0-100% ethyl acetate in pet-ether) to afford tert-butyl N-[[4-[6-[4-[2-[tert-butyl(dimethyl)silyl]oxyethyl]phenyl]pyrrolo[2,1-f][1,2,4]triazin-4-yl]-2-methyl-phenyl]methyl]carbamate (0.03 g, 40.55 μmol, 51.15% yield). LC-MS ($ES^+$): m/z 573.48 $[M+H]^+$.

Step-2:

To a stirred solution of tert-butyl N-[[4-[6-[4-[2-[tert-butyl(dimethyl)silyl]oxyethyl]phenyl]pyrrolo[2,1-f][1,2,4]triazin-4-yl]-2-methyl-phenyl]methyl]carbamate (0.1 g, 174.58 μmol) in THF (1 mL) at 0° C. under argon atmosphere, tetrabutylammonium fluoride (45.65 mg, 174.58 μmol) was added and the reaction mixture was stirred at room temperature for 2 hours. The reaction progress was monitored by TLC and LC-MS. Upon completion, the reaction was quenched with water (60 mL) and extracted with ethyl acetate (50 mL×3). The combined organic layers were washed with brine solution (100 mL), dried over anhydrous sodium sulfate, filtered, and concentrated under reduced pressure. The crude product was then purified by flash column chromatography (silica gel 100-200 mesh, 0-50% ethyl acetate in hexane) to afford tert-butyl N-[[4-[6-[4-(2-hydroxyethyl)phenyl]pyrrolo[2,1-f][1,2,4]triazin-4-yl]-2-methyl-phenyl]methyl]carbamate (0.03 g, 53.62 μmol, 30.71% yield). LC-MS ($ES^+$): m/z 459.45 $[M+H]^+$.

Step-3:

To a stirred tert-butyl N-[[4-[6-[4-(2-hydroxyethyl)phenyl]pyrrolo[2,1-f][1,2,4]triazin-4-yl]-2-methyl-phenyl] methyl]carbamate (0.03 g, 65.42 μmol) in DCM (1 mL) under argon atmosphere, Triethylamine (26.48 mg, 261.69 μmol, 36.47 μL) was added and the reaction mixture was stirred at 0° C. for 5 minutes. Then methanesulfonyl chloride (7.49 mg, 65.42 μmol, 5.06 μL) was added to the reaction mixture, and it was stirred at 0° C. for 2 hours. For the reaction workup, saturated sodium bicarbonate solution was added, and the mixture was extracted with ethyl acetate (40 mL×3). The combined organic layers were washed with water, brine solution, dried over anhydrous sodium sulfate, filtered, and concentrated under reduced pressure.

The crude product was washed with ether to afford the final product 4-(4-(4-(((tert-butoxycarbonyl)amino)methyl)-3-methylphenyl)pyrrolo[2,1-f][1,2,4]triazin-6-yl)phenethyl methanesulfonate (0.03 g, 45.82 μmol, 70.04% yield). LC-MS ($ES^+$): m/z 537.36 $[M+H]^+$.

Step-4:

In a 25 ml single neck round bottom flask, 4-(4-(4-(((tert-butoxycarbonyl)amino)methyl)-3-methylphenyl)pyrrolo[2,1-f][1,2,4]triazin-6-yl)phenethyl methanesulfonate (0.1 g, 186.34 μmol) was dissolved in acetone (5 mL) followed by the addition of lithium bromide (161.83 mg, 1.86 mmol). The reaction mixture was refluxed for 2 hours at 55-57° C. under a stream of nitrogen gas. Progress of the reaction was monitored with TLC and LC-MS. After completion of the reaction, the mixture was passed through a celite bed, and the filtrate was concentrated under reduced pressure to give the crude compound. The crude product was washed several times with diethyl ether to afford compound tert-butyl (4-(6-(4-(2-bromoethyl)phenyl)pyrrolo[2,1-f][1,2,4]triazin-4-yl)-2-methylbenzyl)carbamate (0.070 g, 113.09 μmol, 60.69% yield) as a yellowish solid, which was used for next step without further purification. LC-MS ($ES^+$): m/z 521.20 $[M+H]^+$.

Step-5:

In a 10 ml single neck round bottom flask, 3-(4-(3,3-difluoropiperidin-4-yl)phenyl)piperidine-2,6-dione TFA salt (354.77 mg, 840.00 μmol) was dissolved in DMF (5 mL) and basified with sodium bicarbonate (483.33 mg, 5.75 mmol). The formed reaction mixture was stirred at room temperature for 5-10 minutes under a stream of nitrogen gas. Tert-butyl N-[[4-[6-[4-(2-bromoethyl)phenyl]pyrrolo[2,1-f][1,2,4]triazin-4-yl]-2-methyl-phenyl]methyl]carbamate (0.3 g, 575.32 μmol) was added (in three separate portions) and reaction mixture was transferred to an oil bath and heated at 60° C. overnight. Progress of the reaction was monitored with TLC and LC-MS. After completion of the reaction, the mixture was poured into ice-cold water. The obtained precipitate was filtered through the vacuum, dried to obtain the compound tert-butyl (4-(6-(4-(2-(4-(4-(2,6-dioxopiperidin-3-yl)phenyl)-3,3-difluoropiperidin-1-yl)ethyl)phenyl)pyrrolo[2,1-f][1,2,4]triazin-4-yl)-2-methylbenzyl)carbamate (0.25 g, 292.24 μmol, 50.80% yield) as a yellowish solid. LC-MS ($ES^+$): m/z 749.29 $[M+H]^+$.

Step-6:

To the stirred solution of tert-butyl N-[[4-[6-[4-[2-[4-[4-(2,6-dioxo-3-piperidyl)phenyl]-3,3-difluoro-1-piperidyl] ethyl]phenyl]pyrrolo[2,1-f][1,2,4]triazin-4-yl]-2-methyl-phenyl]methyl]carbamate (0.200 g, 267.07 μmol) in DCM (5 mL) was added 4 M hydrogen chloride solution in 1,4-dioxane (2 mL) at room temperature and the reaction was stirred for 1 hour at this temperature. The reaction progress was monitored by the TLC and LC-MS. After completion, the reaction mixture was concentrated under reduced pressure and stirred in diethyl ether for 20 minutes. The diethyl ether layer was decanted, and the crude product 3-[4-[1-[2-[4-[4-[4-(aminomethyl)-3-methyl-phenyl]pyrrolo[2,1-f][1,2,4]triazin-6-yl]phenyl]ethyl]-3,3-difluoro-4-piperidyl]phenyl]piperidine-2,6-dione HCl salt (0.180 g, 179.66 μmol, 67.27% yield) was used as such for the next step. LC-MS ($ES^+$): m/z 649.30 $[M+H]^+$.

Step-7:

To a stirred 3-[4-[1-[2-[4-[4-[4-(aminomethyl)-3-methyl-phenyl]pyrrolo[2,1-f][1,2,4]triazin-6-yl]phenyl]ethyl]-3,3-difluoro-4-piperidyl]phenyl]piperidine-2,6-dione HCl salt (0.2 g, 291.88 μmol) in DMF (1 mL) under argon atmosphere, N-ethyl-N-isopropyl-propan-2-amine (398.44 mg, 3.08 mmol, 536.98 μL) and (5-tert-butyl-1,2,4-oxadiazole-3-carbonyl)oxylithium (108.58 mg, 616.58 μmol) were added at 0° C. After stirring for 10 minutes, benzotriazol-1-yloxy(tripyrrolidin-1-yl)phosphonium; hexafluorophosphate (320.86 mg, 616.58 μmol) was added and reaction was warmed up to room temperature and stirred for 5 hours. Upon completion, the reaction was concentrated in vacuo to get the crude product, which was purified by prep-HPLC to afford 5-tert-butyl-N-[[4-[6-[4-[2-[4-[4-(2,6-dioxo-3-piperidyl)phenyl]-3,3-difluoro-1-piperidyl]ethyl]phenyl]pyrrolo[2,1-f][1,2,4]triazin-4-yl]-2-methyl-phenyl]methyl]-1,2,4-oxadiazole-3-carboxamide (77.7 mg, 95.28 μmol, 32.64% yield) as a yellow solid. $^1H$ NMR (400 MHz, DMSO-$d_6$) δ 10.84 (s, 1H), 9.54 (t, J=6.0 Hz, 1H), 8.71 (s, 1H), 8.61 (s, 1H), 8.06 (d, J=8.0 Hz, 1H), 8.02 (s, 1H), 7.88 (d, J=4.6 Hz, 2H), 7.62 (s, 1H), 7.48 (d, J=8.0 Hz, 1H), 7.35-7.21 (m, 6H), 4.57 (d, J=5.9 Hz, 2H), 3.86-3.81 (m, 2H), 3.11 (bs, 2H), 2.72-2.64 (m, 8H), 2.47 (s, 3H), 2.33-2.14 (m, 2H), 2.07-2.02 (m, 1H), 1.87 (bs, 1H), 1.45 (s, 9H). LC-MS ($ES^+$): m/z 801.12 $[M+H]^+$.

Example 52

Example 52 was prepared following the synthesis of Example 51

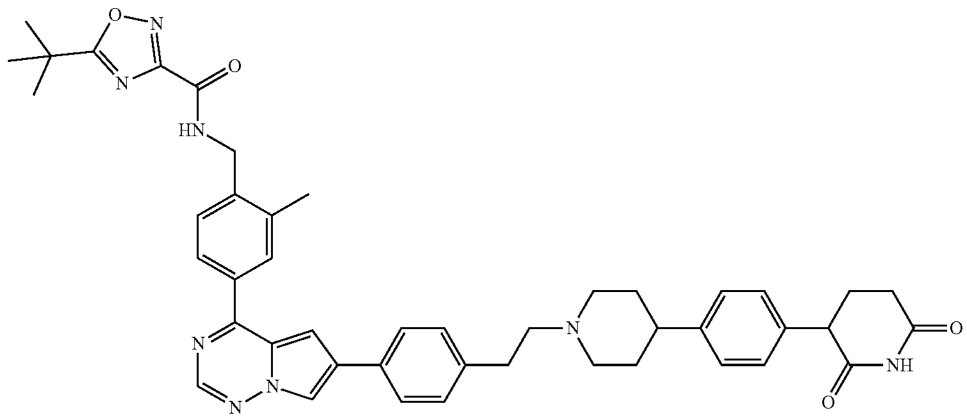 [SMILES: Cc1cc(-c2ncnn3cc(-c4ccc(CCN5CCC(c6ccc(C7CCC(=O)NC7=O)cc6)CC5)cc4)cc23)ccc1CNC(=O)c1noc(C(C)(C)C)n1]

5-tert-butyl-N-[[4-[6-[4-[2-[4-[4-(2,6-dioxo-3-piperidyl)phenyl]-1-piperidyl]ethyl]phenyl]pyrrolo[2,1-f][1,2,4]triazin-4-yl]-2-methyl-phenyl]methyl]-1,2,4-oxadiazole-3-carboxamide. $^1H$ NMR (400 MHz, DMSO-$d_6$) δ 10.84 (s, 1H), 9.55 (t, J=5.9 Hz, 1H), 9.32 (bs, 1H), 8.74 (s, 1H), 8.62 (s, 1H), 8.06 (d, J=8.0 Hz, 1H), 8.02 (s, 1H), 7.95 (d, J=7.8 Hz, 2H), 7.64 (s, 1H), 7.48 (d, J=8.0 Hz, 1H), 7.39 (d, J=7.8 Hz, 2H), 7.24-7.19 (m, 4H), 4.57 (d, J=5.8 Hz, 2H), 3.86-3.82 (m, 1H), 3.72-3.68 (m, 1H), 3.32-3.19 (m, 2H), 3.17-3.05 (m, 4H), 2.86-2.80 (m, 1H), 2.72-2.63 (m, 2H), 2.48 (s, 3H), 2.22-2.02 (m, 4H), 2.07-1.85 (m, 2H), 1.45 (s, 9H). LC-MS ($ES^+$): m/z 765.19 $[M+H]^+$.

Example 53

Example 53 was prepared following the synthesis of Example 51

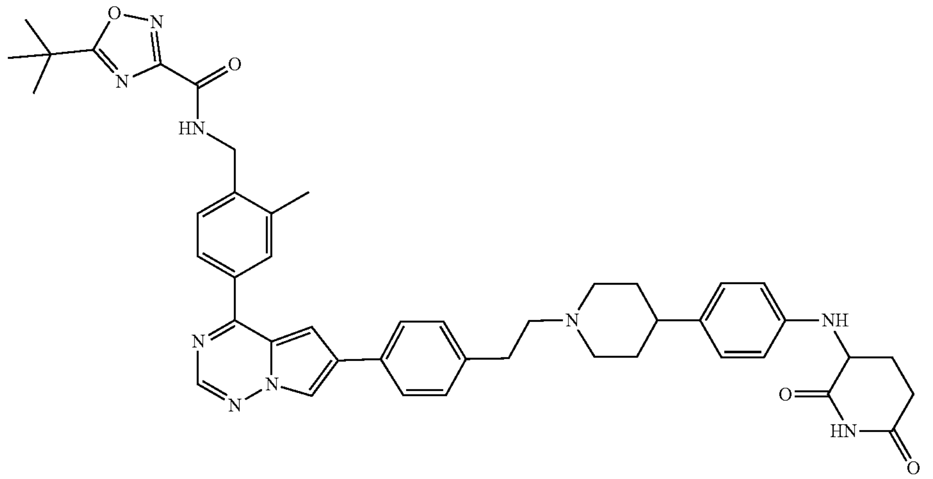 [SMILES: Cc1cc(-c2ncnn3cc(-c4ccc(CCN5CCC(c6ccc(NC7CCC(=O)NC7=O)cc6)CC5)cc4)cc23)ccc1CNC(=O)c1noc(C(C)(C)C)n1]

5-tert-butyl-N-[[4-[6-[4-[2-[4-[4-[(2,6-dioxo-3-piperidyl)amino]phenyl]-1-piperidyl]ethyl]phenyl]pyrrolo[2,1-f][1,2,4]triazin-4-yl]-2-methyl-phenyl]methyl]-1,2,4-oxadiazole-3-carboxamide. $^1H$ NMR (400 MHz, DMSO-$d_6$) δ 10.78 (s, 1H), 9.55 (t, J=5.8 Hz, 1H), 9.24 (s, 1H), 8.74 (s, 1H), 8.62 (s, 1H), 8.06-8.01 (m, 2H), 7.65 (d, J=8.0 Hz, 2H), 7.63 (s, 1H), 7.48 (d, J=8.0 Hz, 1H), 7.38 (d, J=8.0 Hz, 2H), 6.98 (d, J=8.4 Hz, 2H), 6.65 (d, J=8.0 Hz, 2H), 4.57 (d, J=6.0 Hz, 2H), 4.30-4.26 (m, 1H), 3.55 (s, 2H), 3.42-3.40 (m, 2H), 3.20-3.00 (m, 4H), 2.80-2.65 (m, 2H), 2.61-2.56 (m, 1H), 2.50 (s, 3H), 2.15-1.98 (m, 3H), 1.90-1.78 (m, 3H), 1.45 (s, 9H). LC-MS ($ES^+$): m/z 780.20 $[M+H]^+$.

Example 54
Synthesis of 5-tert-butyl-N-[[4-[6-[3-[2-[4-[4-[(2,6-dioxo-3-piperidyl)amino]phenyl]-1-piperidyl]ethyl]phenyl]pyrrolo[2,1-f][1,2,4]triazin-4-yl]-2-methyl-phenyl]methyl]-1,2,4-oxadiazole-3-carboxamide
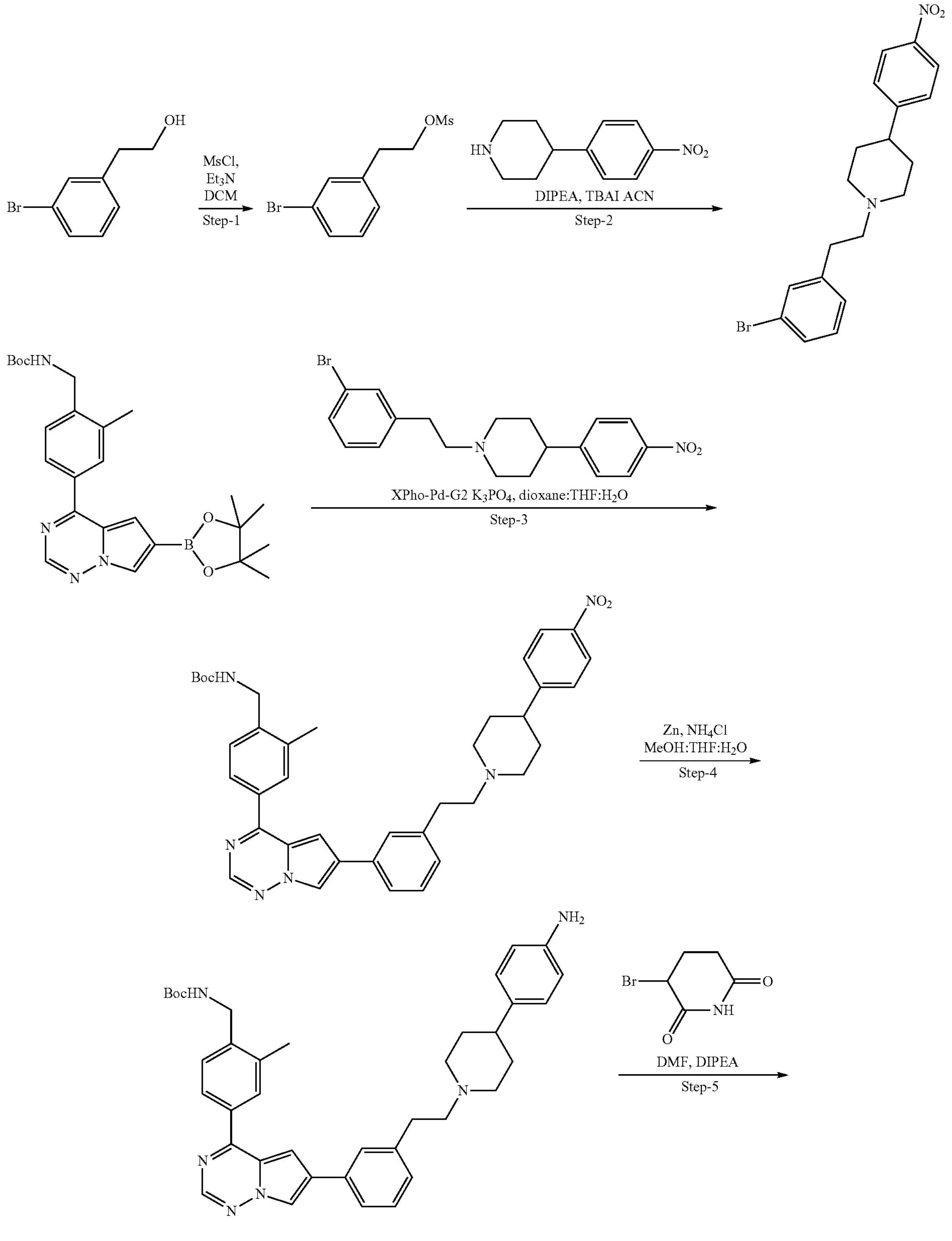

-continued

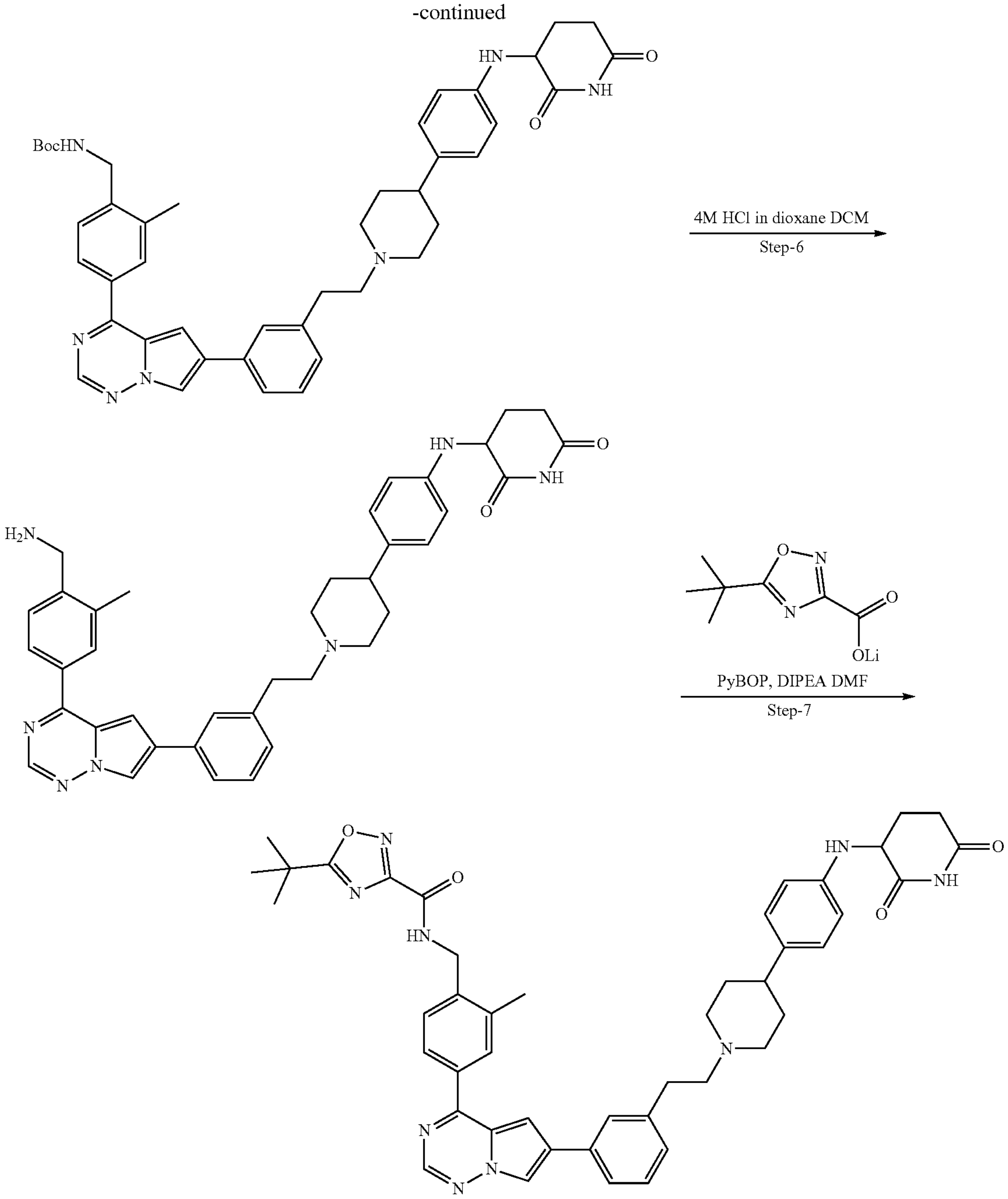

Step-1:

To a stirred solution of 2-(3-bromophenyl)ethanol (5 g, 24.87 mmol) in DCM (100 mL) was added triethylamine (3.77 g, 37.30 mmol, 5.20 mL) and methanesulfonyl chloride (3.70 g, 32.33 mmol, 2.50 mL) at 0° C. The reaction mixture was stirred at room temperature for 2 hours, and the progress of the reaction was monitored by TLC. After the reaction was complete, the reaction mixture was poured into water and extracted with DCM. The organic layer was dried and concentrated under reduced pressure to afford compound 2-(3-bromophenyl)ethyl methanesulfonate (7.1 g, 24.16 mmol, 97.16% yield), which was used in the next step without further purification. LC-MS ($ES^+$): m/z 183.36 $[M-MeSO_3^-]^+$.

Step-2:

To the stirred solution of 2-(3-bromophenyl)ethyl methanesulfonate (0.5 g, 1.79 mmol) and 4-(4-nitrophenyl)piperidine (738.81 mg, 3.58 mmol) in acetonitrile (10 mL) was added N-ethyl-N-isopropyl-propan-2-amine (2.31 g, 17.91 mmol, 3.12 mL) at room temperature. The reaction mixture was stirred for 20 minutes before tetrabutylammonium iodide (661.59 mg, 1.79 mmol) was added, and the reaction was heated at 70° C. for 12 hours. The reaction progress was monitored by TLC and LC-MS. The reaction mixture was diluted with sodium bicarbonate solution filtered, and dried under reduced pressure to give a residue, which was purified by column chromatography (silica gel 100-200 mesh, 15-20% ethyl acetate in pet ether) to obtain product 1-[2-

(3-bromophenyl)ethyl]-4-(4-nitrophenyl)piperidine (0.650 g, 1.55 mmol, 86.70% yield) as a yellow solid. LC-MS ($ES^+$): m/z 389.12 $[M+H]^+$.

Step-3:

To the stirred solution of tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (0.650 g, 1.40 mmol) and 1-[2-(3-bromophenyl)ethyl]-4-(4-nitrophenyl)piperidine (454.09 mg, 1.17 mmol) in THE (4 mL), dioxane (4 mL), water (2 mL) was added potassium phosphate (742.81 mg, 3.50 mmol). The reaction mixture was degassed with nitrogen gas, and XPhos Pd G2 (91.78 mg, 116.65 μmol) was added at room temperature, and the reaction was stirred for 16 hours at 90° C. The reaction progress was monitored by the TLC and LC-MS. The reaction mixture was diluted with water (50 mL) and extracted with ethyl acetate (200 mL×3). The combined organic layers were collected and dried over anhydrous sodium sulfate and concentrated under reduced pressure. The crude sample was purified by flash column chromatography (20-30% ethyl acetate in pet ether) to afford tert-butyl N-[[2-methyl-4-[6-[3-[2-[4-(4-nitrophenyl)-1-piperidyl]ethyl]phenyl]pyrrolo[2,1-f][1,2,4]triazin-4-yl]phenyl]methyl]carbamate (0.470 g, 668.55 μmol, 57.31% yield) as a brown solid. LC-MS ($ES^+$): m/z 647.21 $[M+H]^+$.

Step-4:

To a stirred solution of tert-butyl N-[[2-methyl-4-[6-[3-[2-[4-(4-nitrophenyl)-1-piperidyl]ethyl]phenyl]pyrrolo[2,1-f][1,2,4]triazin-4-yl]phenyl]methyl]carbamate (0.800 g, 1.24 mmol) in THF (4 mL), methanol (4 mL) and water (2 mL) was added zinc (80.88 mg, 1.24 mmol) and ammonia hydrochloride (66.16 mg, 1.24 mmol). The reaction was stirred for 2 hours at room temperature, and the reaction progress was monitored by TLC and LC-MS. After the reaction was complete, the reaction mixture was filtered through celite using ethyl acetate, and the filtrate was concentrated under reduced pressure to give the crude product, which was purified by column chromatography (silica gel 100-200 mesh, 0-10% methanol in DCM) to afford the final product tert-butyl N-[[4-[6-[3-[2-[4-(4-aminophenyl)-1-piperidyl]ethyl]phenyl]pyrrolo[2,1-f][1,2,4]triazin-4-yl]-2-methyl-phenyl]methyl]carbamate (0.470 g, 624.84 μmol, 50.52% yield) as a white solid. LC-MS ($ES^+$): m/z 617.30 $[M+H]^+$.

Step-5:

To the stirred solution of tert-butyl N-[[4-[6-[3-[2-[4-(4-aminophenyl)-1-piperidyl]ethyl]phenyl]pyrrolo[2,1-f][1,2,4]triazin-4-yl]-2-methyl-phenyl]methyl]carbamate (0.05 g, 81.06 μmol) and 3-bromopiperidine-2,6-dione (46.70 mg, 243.19 μmol) in DMF (5 mL) was added DIPEA (62.86 mg, 486.39 μmol, 84.72 μL) at room temperature and the reaction mixture was stirred at 70° C. for 12 hours. The reaction progress was monitor by TLC and LCMS. After the reaction was complete, the reaction mixture was diluted with sodium bicarbonate solution, filtered, and dried under reduced pressure. The crude product was purified by column chromatography (silica gel 100-200 mesh, 15-20% ethyl acetate in pet ether) to give tert-butyl N-[[4-[6-[3-[2-[4-[4-[(2,6-dioxo-3-piperidyl)amino]phenyl]-1-piperidyl]ethyl]phenyl]pyrrolo[2,1-f][1,2,4]triazin-4-yl]-2-methyl-phenyl]methyl]carbamate (0.04 g, 41.76 μmol, 51.52% yield) as a yellow solid. LC-MS ($ES^+$): m/z 728.63 $[M+H]^+$.

Step-6:

To the stirred solution of tert-butyl N-[[4-[6-[3-[2-[4-[4-[(2,6-dioxo-3-piperidyl)amino]phenyl]-1-piperidyl]ethyl]phenyl]pyrrolo[2,1-f][1,2,4]triazin-4-yl]-2-methyl-phenyl]methyl]carbamate (0.400 g, 549.53 μmol) in DCM (10 mL) was added 4 M hydrogen chloride solution in dioxane (4 mL) at room temperature and the reaction was stirred for 1 hour at this temperature. The reaction progress was monitored by TLC and LC-MS. After the reaction was complete, the reaction mixture was concentrated under reduced pressure and stirred in diethyl ether for 20 minutes. The diethyl layer was decanted, and the crude material 3-[4-[1-[2-[3-[4-[4-(aminomethyl)-3-methyl-phenyl]pyrrolo[2,1-f][1,2,4]triazin-6-yl]phenyl]ethyl]-4-piperidyl]anilino]piperidine-2,6-dione HCl salt (0.400 g, 313.14 μmol, 56.98% yield) was used directly in the next step. LC-MS ($ES^+$): m/z 628.62 $[M+H]^+$.

Step-7:

To a stirred solution of 3-[4-[1-[2-[3-[4-[4-(aminomethyl)-3-methyl-phenyl]pyrrolo[2,1-f][1,2,4]triazin-6-yl]phenyl]ethyl]-4-piperidyl]anilino]piperidine-2,6-dione HCl salt (0.400 g, 602.19 μmol) and (5-tert-butyl-1,2,4-oxadiazole-3-carbonyl)oxylithium (318.14 mg, 1.81 mmol) in DMF (5 mL) was added N-ethyl-N-isopropyl-propan-2-amine (778.28 mg, 6.02 mmol, 1.05 mL). The reaction mixture was cooled 0° C. before benzotriazol-1-yloxy(tripyrrolidin-1-yl)phosphonium; hexafluorophosphate (940.13 mg, 1.81 mmol) was added, and the reaction mixture was stirred at room temperature for 2 hours. Progress of the reaction was monitored by TLC and LC-MS. Upon completion, the reaction was diluted with sodium bicarbonate solution to obtain a solid. The crude sample was purified by prep HPLC using following method to furnish the final product 5-tert-butyl-N-[[4-[6-[3-[2-[4-[4-[(2,6-dioxo-3-piperidyl)amino]phenyl]-1-piperidyl]ethyl]phenyl]pyrrolo[2,1-f][1,2,4]triazin-4-yl]-2-methyl-phenyl]methyl]-1,2,4-oxadiazole-3-carboxamide TFA salt (55.70 mg, 60.61 μmol, 10.07% yield). $^1H$ NMR (400 MHz, DMSO-$d_6$) δ 10.78 (s, 1H), 9.56 (t, J=5.5 Hz, 1H), 9.34 (s, 1H), 8.73 (s, 1H), 8.63 (s, 1H), 8.04-8.00 (m, 2H), 7.86 (brs, 2H), 7.60 (s, 1H), 7.46-7.40 (m, 2H), 7.27 (d, J=7.2 Hz, 1H), 6.97 (d, J=8.0 Hz, 2H), 6.65 (d, J=8.0 Hz, 2H), 4.57 (d, J=5.6 Hz, 2H), 4.29 (q, J=5.2 Hz, 1H), 3.42 (brs, 4H), 3.10 (d, J=10.0 Hz, 4H), 2.74-2.71 (m, 3H), 2.50 (s, 3H), 2.10-1.98 (m, 3H)) 1.96-1.77 (m, 3H), 1.44 (s, 9H). LC-MS ($ES^-$): m/z 778.29 $[M-H]^-$.

Example 55. Synthesis of 5-tert-butyl-N-[[4-[6-[2-[2-[4-[(2,6-dioxo-3-piperidyl)amino]phenyl]ethyl]isoindolin-5-yl]pyrrolo[2,1-f][1,2,4]triazin-4-yl]-2-methyl-phenyl]methyl]-1,2,4-oxadiazole-3-carboxamide
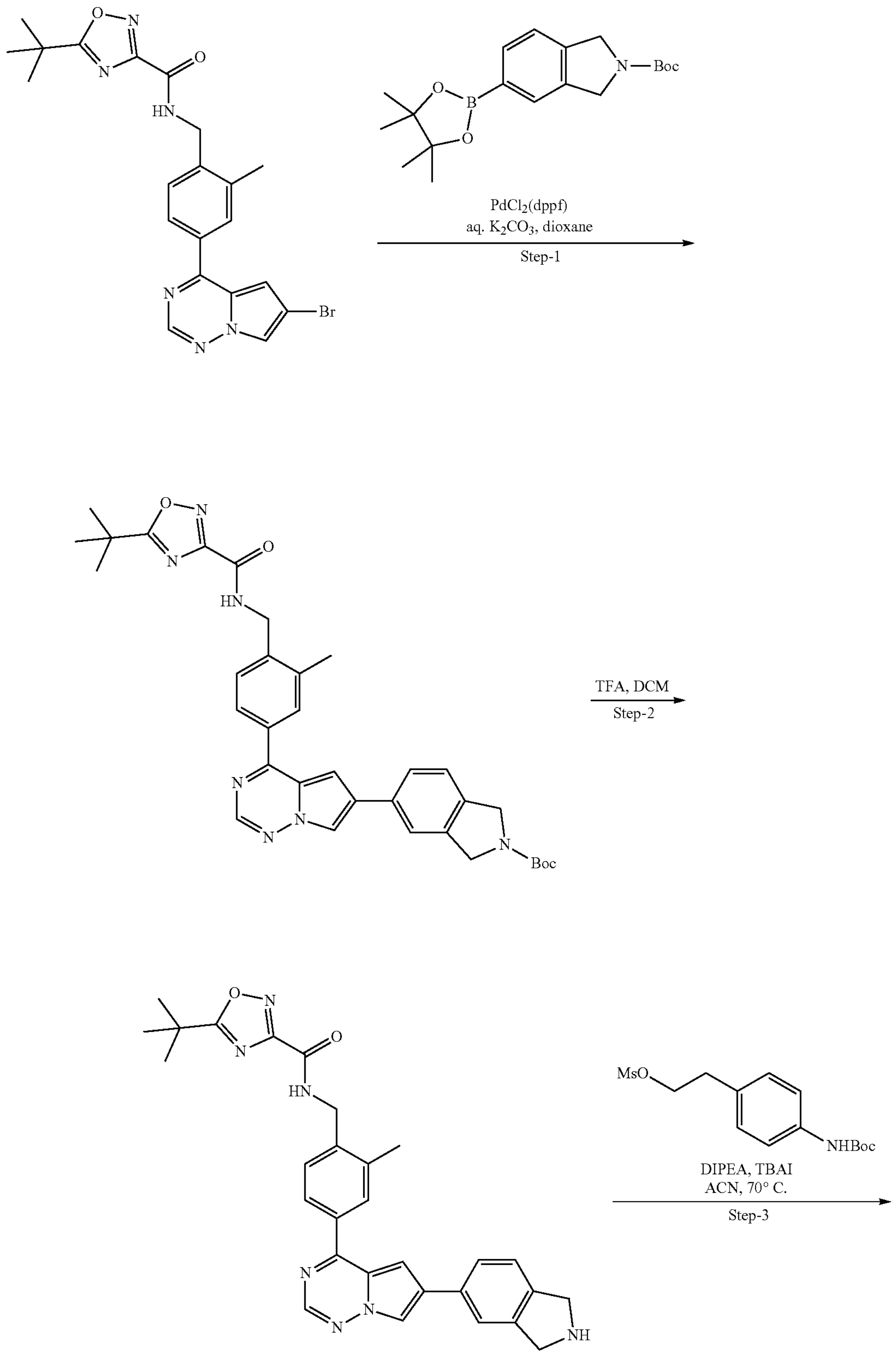

-continued
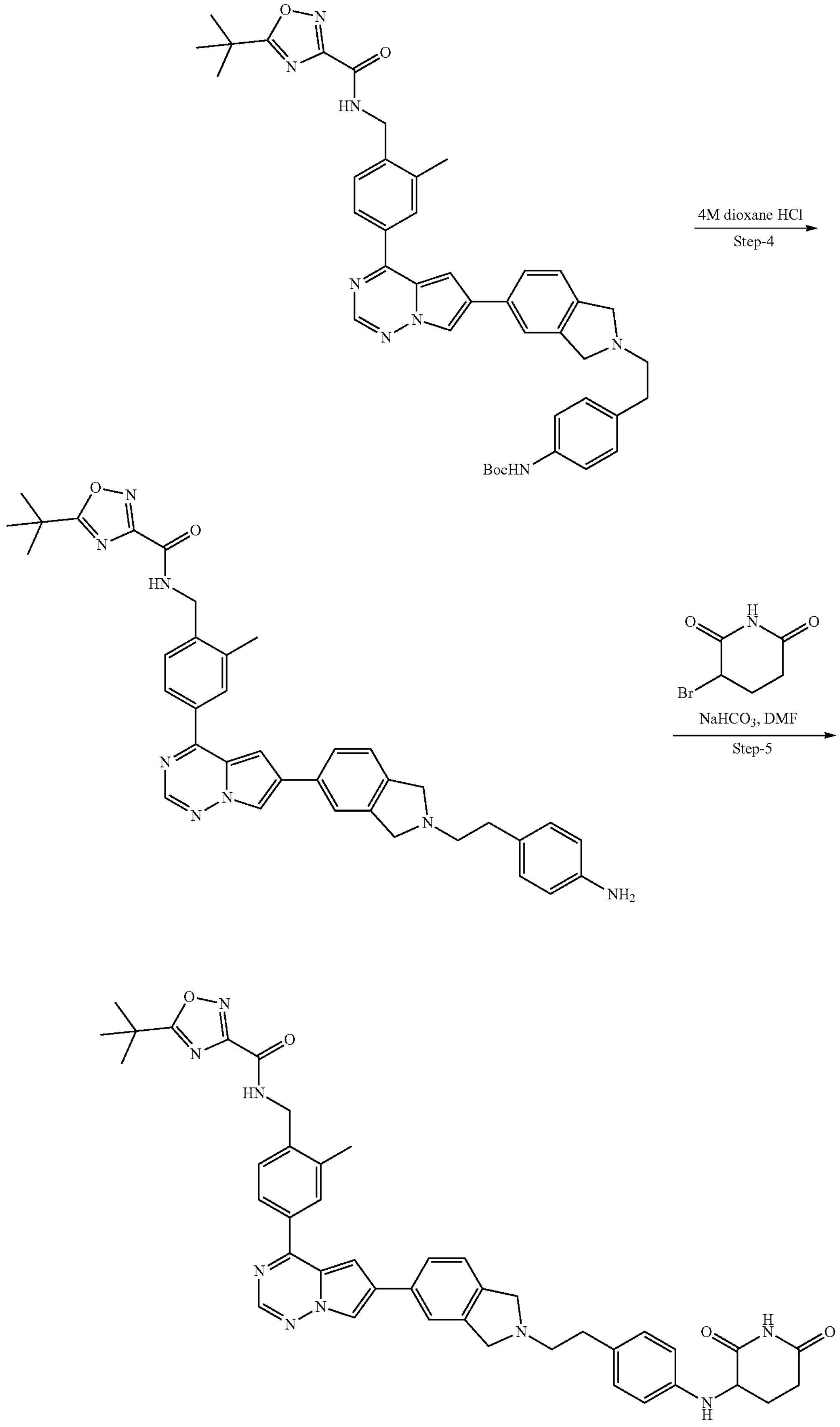

Step-1:

To a stirred solution of N-[[4-(6-bromopyrrolo[2,1-f][1,2,4]triazin-4-yl)-2-methyl-phenyl]methyl]-5-tert-butyl-1,2,4-oxadiazole-3-carboxamide (0.85 g, 1.81 mmol) and tert-butyl 5-(4,4,5,5-tetramethyl-1,3,2-dioxaborolan-2-yl) isoindoline-2-carboxylate (625.26 mg, 1.81 mmol) in 1,4-dioxane (12 mL) under argon atmosphere, Pd(dppf) $Cl_2 \cdot CH_2Cl_2$ (132.52 mg, 181.11 mol) and potassium carbonate (750.91 mg, 5.43 mmol) were added. The resulting mixture was stirred at 80° C. for 16 hours, and progress of the reaction was monitored by TLC and LC-MS.

After completion, the reaction was washed with water and extracted with ethyl acetate (3×100 mL). The combined organic layer was dried over anhydrous sodium sulfate and concentrated under reduced pressure to give the crude product. The crude product was purified by flash column chromatography (20% pet ether in ethyl acetate) to afford tert-butyl 5-[4-[4-[[(5-tert-butyl-1,2,4-oxadiazole-3-carbonyl)amino]methyl]-3-methyl-phenyl]pyrrolo[2,1-f][1,2,4]triazin-6-yl]isoindoline-2-carboxylate (0.65 g, 917.83 μmol, 50.68% yield) as a white solid. LC-MS ($ES^+$): m/z 608.42 $[M+H]^+$.

Step-2:

To a stirred solution of tert-butyl 5-[4-[4-[[(5-tert-butyl-1,2,4-oxadiazole-3-carbonyl)amino]methyl]-3-methyl-phenyl]pyrrolo[2,1-f][1,2,4]triazin-6-yl]isoindoline-2-carboxylate (0.9 g, 1.48 mmol) in DCM (10 mL) was added trifluoroacetic acid (3.38 g, 29.62 mmol, 2.28 mL) at 0° C., and allowed to stir at room temperature for 2 hours. The reaction was monitored by TLC and LC-MS. After reaction was complete, the reaction mixture was concentrated under reduced pressure, co-distilled with acetonitrile (5 mL) and triturated with diethyl ether (30 ml×2) to obtain 5-tert-butyl-N-[[4-(6-isoindolin-5-ylpyrrolo[2,1-f][1,2,4]triazin-4-yl)-2-methyl-phenyl]methyl]-1,2,4-oxadiazole-3-carboxamide TFA salt (0.9 g, 1.39 mmol, 93.90% yield) as a light green solid. LC-MS ($ES^+$): m/z 508.88 $[M+H]^+$.

Step-3:

To a stirred solution of 5-tert-butyl-N-[[4-(6-isoindolin-5-ylpyrrolo[2,1-f][1,2,4]triazin-4-yl)-2-methyl-phenyl]methyl]-1,2,4-oxadiazole-3-carboxamide TFA salt (0.4 g, 643.49 μmol) in acetonitrile (10 mL) was added DIPEA (831.65 mg, 6.43 mmol, 1.12 mL). This was followed by the addition of TBAI (237.68 mg, 643.49 μmol) and the reaction was allowed to stir at room temperature for 10 minutes. Then 2-[4-(tert-butoxycarbonylamino)phenyl]ethyl methanesulfonate (304.42 mg, 965.24 μmol) dissolved in acetonitrile (1 mL) was added to the reaction and it was heated at 70° C. for 16 hours. Reaction progress was monitored by TLC and LC-MS. After completion, the reaction mixture was concentrated under reduced pressure and purified by normal phase column chromatography (Devisil silica, 50-60% ethyl acetate/pet ether) using Biotage to obtain tert-butyl N-[4-[2-[5-[4-[4-[[(5-tert-butyl-1,2,4-oxadiazole-3-carbonyl)amino]methyl]-3-methyl-phenyl]pyrrolo[2,1-f][1,2,4]triazin-6-yl]isoindolin-2-yl]ethyl]phenyl]carbamate (0.2 g, 233.30 μmol, 36.26% yield). LC-MS ($ES^+$): m/z 727.60 $[M+H]^+$.

Step-4:

To a stirred solution of tert-butyl N-[4-[2-[5-[4-[4-[[(5-tert-butyl-1,2,4-oxadiazole-3-carbonyl)amino]methyl]-3-methyl-phenyl]pyrrolo[2,1-f][1,2,4]triazin-6-yl]isoindolin-2-yl]ethyl]phenyl]carbamate (0.2 g, 275.15 μmol) in dioxane (2 mL) was added 4 M hydrogen chloride solution (2 mL) under nitrogen and the reaction was stirred at 0 to 28° C. for 2 hours. The reaction progress was monitored by TLC and LC-MS. After completion, the reaction mixture was concentrated to dryness and washed with diethyl ether (10 mL×2) to afford N-[[4-[6-[2-[2-(4-aminophenyl)ethyl]isoindolin-5-yl]pyrrolo[2,1-f][1,2,4]triazin-4-yl]-2-methyl-phenyl]methyl]-5-tert-butyl-1,2,4-oxadiazole-3-carboxamide HCl salt (0.17 g, 205.06 μmol, 74.53% yield) as a solid. LC-MS ($ES^+$): m/z 627.54 $[M+H]^+$.

Step-5:

To a stirred solution of N-[[4-[6-[2-[2-(4-aminophenyl)ethyl]isoindolin-5-yl]pyrrolo[2,1-f][1,2,4]triazin-4-yl]-2-methyl-phenyl]methyl]-5-tert-butyl-1,2,4-oxadiazole-3-carboxamide HCl salt (0.15 g, 226.17 μmol) in DMF (3 mL) was added sodium bicarbonate (190.00 mg, 2.26 mmol) and stirred at room temperature for 10 minutes. The 3-bromopiperidine-2,6-dione (130.28 mg, 678.52 μmol) was added and the reaction was refluxed at 80° C. for 16 hours. The reaction progress was monitored by TLC and LC-MS. After completion, the reaction was diluted with ethyl acetate, filtered through celite bed, and washed with ethyl acetate. The filtrate was concentrated to dryness and purified by prep-HPLC to afford 5-tert-butyl-N-[[4-[6-[2-[2-[4-[(2,6-dioxo-3-piperidyl)amino]phenyl]ethyl]isoindolin-5-yl]pyrrolo[2,1-f][1,2,4]triazin-4-yl]-2-methyl-phenyl]methyl]-1,2,4-oxadiazole-3-carboxamide TFA salt (11.2 mg, 12.67 μmol, 5.60% yield). $^1H$ NMR (400 MHz, DMSO-$d_6$) δ 10.79 (s, 1H), 9.55 (t, J=6.0 Hz, 1H), 8.76 (s, 1H), 8.64 (s, 1H), 8.06-7.98 (m, 4H), 7.60 (s, 2H), 7.50-7.46 (m, 2H), 7.21-7.04 (m, 2H), 6.67 (d, J=8.4 Hz, 2H), 4.87-4.83 (m, 2H), 4.63-4.57 (m, 4H), 4.31 (t, J=4.6 Hz, 1H), 3.51-3.00 (m, 2H), 2.91-2.87 (m, 2H), 2.79-2.70 (m, 2H), 2.50 (s, 3H), 2.12-2.10 (m, 1H), 1.89-1.86 (m, 1H), 1.44 (s, 9H). LC-MS ($ES^+$): m/z 738.15 $[M+H]^+$.

Example 56

Example 56 was prepared following the synthesis of Example 55

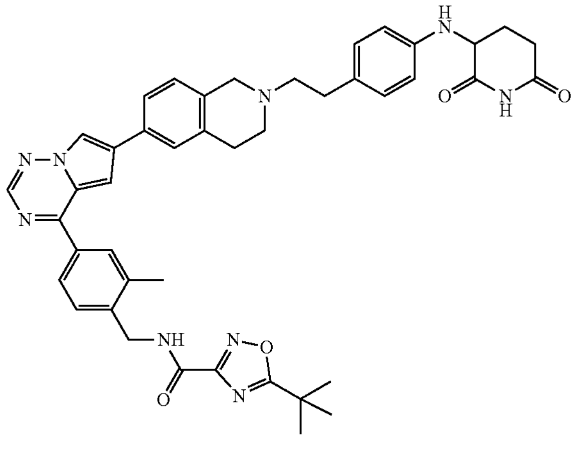 [SMILES: Cc1cc(-c2ncnn3cc(-c4ccc5c(c4)CCN(CCc4ccc(NC6CCC(=O)NC6=O)cc4)C5)cc23)ccc1CNC(=O)c1noc(C(C)(C)C)n1]

5-tert-butyl-N-[[4-[6-[2-[2-[4-[(2,6-dioxo-3-piperidyl)amino]phenyl]ethyl]-3,4-dihydro-1H-isoquinolin-6-yl]pyrrolo[2,1-f][1,2,4]triazin-4-yl]-2-methyl-phenyl]methyl]-1,2,4-oxadiazole-3-carboxamide. $^1H$ NMR (400 MHz, DMSO-$d_6$) δ 10.78 (s, 1H), 9.55 (t, J=8.0 Hz, 1H), 8.74 (s, 1H), 8.62 (s, 1H), 8.06-8.01 (m, 2H), 7.87 (d, J=12.0 Hz, 2H), 7.65 (s, 1H), 7.48 (d, J=8.0 Hz, 1H), 7.29 (d, J=8.0 Hz, 1H), 7.22-6.97 (m, 2H), 6.67 (d, J=8.2 Hz, 2H), 4.68-4.56 (m, 3H), 4.42-4.30 (m, 2H), 3.85-3.81 (m, 1H), 3.16-2.92 (m, 7H), 2.79-2.70 (m, 1H), 2.67-2.51 (m, 4H), 2.12-2.09 (m, 1H), 1.89-1.85 (m, 1H), 1.44 (s, 9H), 1.25 (m, 1H). LC-MS ($ES^+$): m/z 752.36 $[M+H]^+$.

Example 57

Example 57 was prepared following the synthesis of Example 55

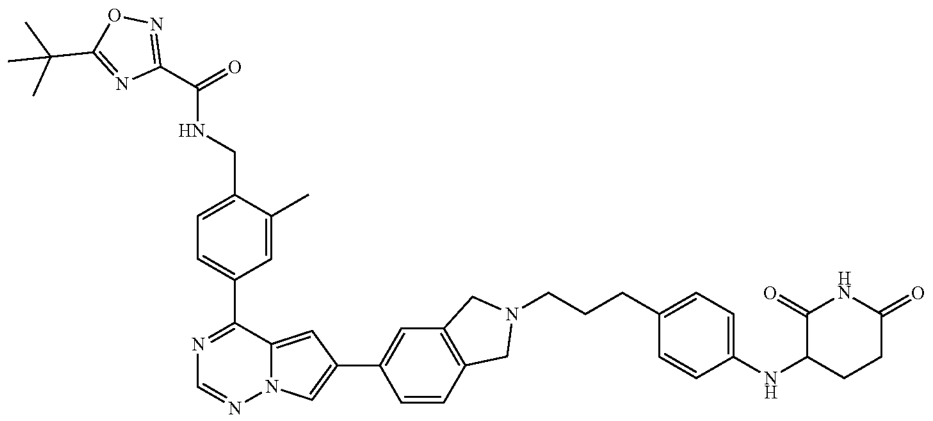 [SMILES: Cc1cc(-c2ncnn3cc(-c4ccc5c(c4)CN(CCCc4ccc(NC6CCC(=O)NC6=O)cc4)C5)cc23)ccc1CNC(=O)c1noc(C(C)(C)C)n1]

5-tert-butyl-N-[[4-[6-[2-[3-[4-[(2,6-dioxo-3-piperidyl) amino]phenyl]propyl]isoindolin-5-yl]pyrrolo[2,1-f][1,2,4] triazin-4-yl]-2-methyl-phenyl]methyl]-1,2,4-oxadiazole-3-carboxamide. $^1$H NMR (400 MHz, DMSO-$d_6$) δ 10.78 (s, 1H), 10.56 (s, 1H), 9.55 (t, J=6.0 Hz, 1H), 8.75 (d, J=1.3 Hz, 1H), 8.63 (s, 1H), 8.06-7.98 (m, 4H), 7.65 (s, 1H), 7.48 (d, J=7.8 Hz, 1H), 7.97 (d, J=8.4 Hz, 2H), 6.64 (d, J=8.4 Hz, 2H), 4.85 (d, J=6.0 Hz, 2H), 4.58-4.54 (m, 4H), 4.30-4.26 (m, 1H), 3.13-3.05 (m, 3H), 2.73-2.70 (m, 1H), 2.61-2.66 (m, 6H), 2.13-2.07 (m, 1H), 1.96-1.88 (m, 3H), 1.45 (s, 9H). LC-MS (ES$^+$): m/z 752.18 [M+H]$^+$.

Example 58

Example 58 was prepared following the synthesis of Example 55

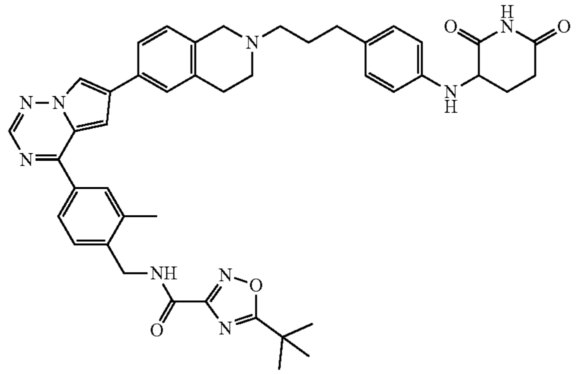 [SMILES: Cc1cc(-c2ncnn3cc(-c4ccc5c(c4)CCN(CCCc4ccc(NC6CCC(=O)NC6=O)cc4)C5)cc23)ccc1CNC(=O)c1noc(C(C)(C)C)n1]

5-tert-butyl-N-[[4-[6-[2-[3-[4-[(2,6-dioxo-3-piperidyl) amino]phenyl]propyl]-3,4-dihydro-1H-isoquinolin-6-yl] pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.78 (s, 1H), 9.76 (s, 1H), 9.55 (t, J=5.9 Hz, 1H), 8.74 (d, J=1.2 Hz, 1H), 8.62 (s, 1H), 8.03-7.99 (m, 2H), 7.84-7.82 (m, 1H), 7.61 (s, 1H), 7.48 (d, J=8.0 Hz, 1H), 7.31 (d, J=8.4 Hz, 1H), 7.01 (d, J=8.4 Hz, 2H), 6.64 (d, J=8.4 Hz, 2H), 4.57-4.55 (m, 3H), 4.35-4.24 (m, 2H), 3.78 (bs, 1H), 3.23-3.13 (m, 6H), 2.81-2.76 (m, 2H), 2.46 (s, 3H), 2.11-1.99 (m, 3H), 1.89-1.85 (m, 1H), 1.45 (s, 10H). LC-MS (ES$^+$): m/z 766.35 [M+H]$^+$.

Example 59

Example 59 was prepared following the synthesis of Example 55

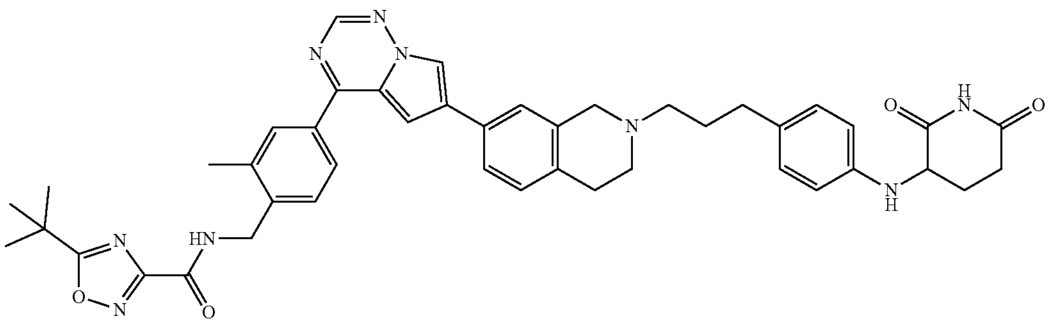 [SMILES: Cc1cc(-c2ncnn3cc(-c4ccc5c(c4)CN(CCCc4ccc(NC6CCC(=O)NC6=O)cc4)CC5)cc23)ccc1CNC(=O)c1noc(C(C)(C)C)n1]

5-tert-butyl-N-[[4-[6-[2-[3-[4-[(2,6-dioxo-3-piperidyl) amino]phenyl]propyl]-3,4-dihydro-1H-isoquinolin-7-yl] pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.78 (s, 1H), 9.77 (s, 1H), 9.55 (t, J=5.8 Hz, 1H), 8.69 (s, 1H), 8.62 (s, 1H), 8.04-7.98 (m, 2H), 7.89 (d, J=7.2 Hz, 1H), 7.80 (s, 1H), 7.59 (s, 1H), 7.48 (d, J=8.1 Hz, 1H), 7.33 (d, J=7.2 Hz, 1H), 6.98 (d, J=8.4 Hz, 2H), 6.64 (d, J=8.4 Hz, 2H), 5.73 (d, J=6.8 Hz, 1H), 4.59 (bs, 1H), 4.57 (d, J=5.8 Hz, 2H), 4.37-4.27 (m, 2H), 3.75 (bs, 1H), 3.27-3.10 (m, 5H), 2.74-2.70 (m, 1H), 2.61-2.55 (m, 3H), 2.48 (s, 3H), 2.12-2.01 (m, 3H), 1.89-1.86 (m, 1H), 1.46 (s, 9H). LC-MS ($ES^+$): m/z 766.35 $[M+H]^+$.

Example 60

Example 60 was prepared following the synthesis of Example 55

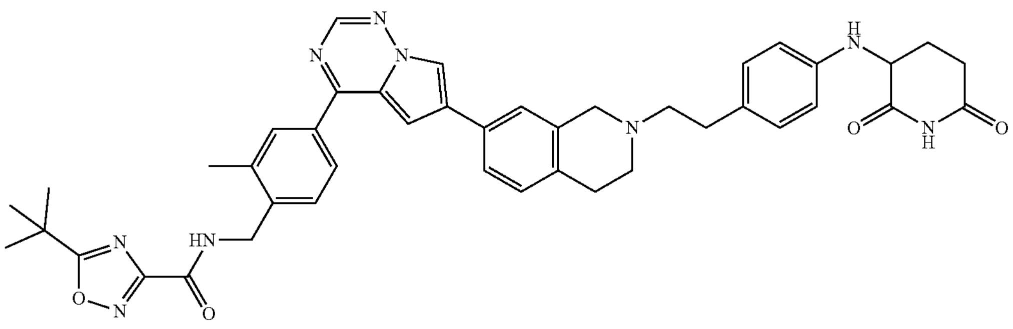

5-tert-butyl-N-[[4-[6-[2-[2-[4-[(2,6-dioxo-3-piperidyl) amino]phenyl]ethyl]-3,4-dihydro-1H-isoquinolin-7-yl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.77 (s, 1H), 9.54 (t, J=5.9 Hz, 1H), 8.66 (s, 1H), 8.59 (s, 1H), 8.16 (s, 1H), 8.06-8.00 (m, 2H), 7.68 (t, J=7.0 Hz, 2H), 7.58 (s, 1H), 7.48 (d, J=8.0 Hz, 1H), 7.16 (d, J=7.6 Hz, 1H), 6.99 (d, J=8.4 Hz, 2H), 6.61 (d, J=8.4 Hz, 2H), 4.57 (d, J=6.0 Hz, 2H), 4.27-4.25 (m, 1H), 3.69 (s, 2H), 2.84-2.60 (m, 10H), 2.50 (s, 3H), 2.11-2.08 (m, 1H), 1.87-1.84 (m, 1H), 1.44 (s, 9H). LC-MS ($ES^-$): m/z 750.25 $[M-H]^-$.

Example 61. Synthesis of 4-(difluoromethyl)-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]benzamide

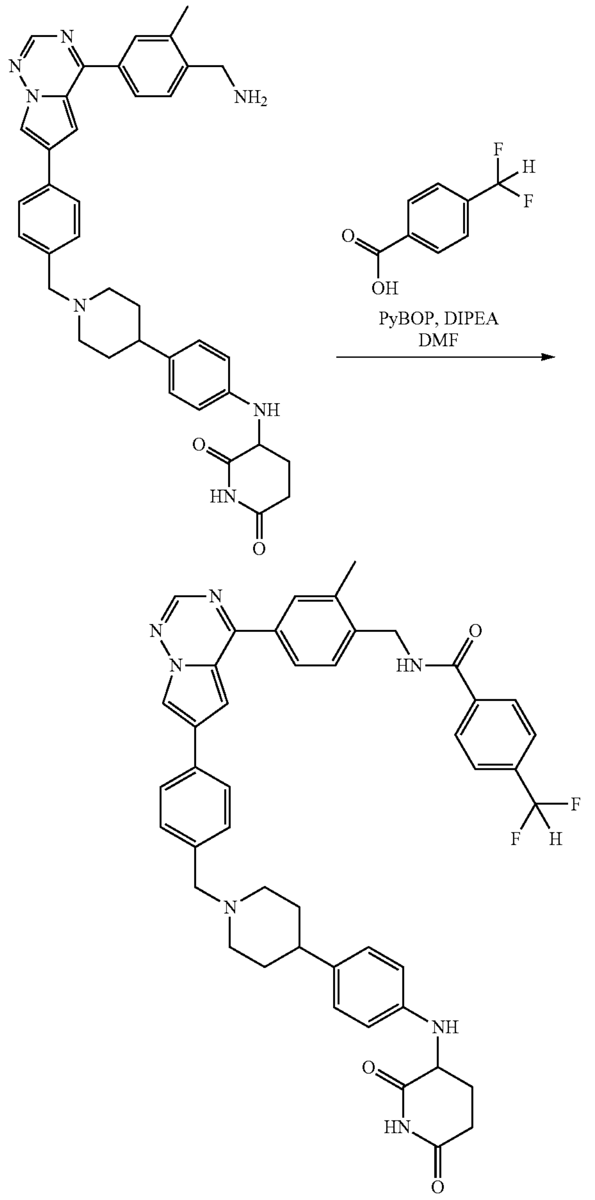

To the mixture of 3-[4-[1-[[4-[4-[4-(aminomethyl)-3-methyl-phenyl]pyrrolo[2,1-f][1,2,4]triazin-6-yl]phenyl] methyl]-4-piperidyl]anilino]piperidine-2,6-dione HCl salt (100 mg, 153.80 μmol) and 4-(difluoromethyl)benzoic acid (26.47 mg, 153.80 μmol) in DMF (1.5 mL) was added N-ethyl-N-isopropyl-propan-2-amine (59.63 mg, 461.39 μmol, 80.37 μL) and N,N,N',N'-tetramethyl-1-(3-oxido-2,3-dihydrotriazolo[4,5-b]pyridin-3-ium-1-yl)methanediamine; hexafluorophosphate (88.18 mg, 230.69 μmol), stirred at 25° C. for 2 hours. The progress of the reaction was monitored by LC-MS. The residue was purified by prep-HPLC. (water, 0.05% HCl and ACN). The desired product 4-(difluoromethyl)-N-[[4-[6-[4-[[4-[4-[(2,6-dioxo-3-piperidyl)amino] phenyl]-1-piperidyl]methyl]phenyl]pyrrolo[2,1-f][1,2,4]triazin-4-yl]-2-methyl-phenyl]methyl]benzamide HCl salt (46.11 mg, 53.60 μmol, 34.85% yield) was obtained as black gum. $^1$H NMR (400 MHz, DMSO-$d_6$) δ=10.77 (s, 1H), 10.14-9.99 (m, 1H), 9.27 (s, 1H), 8.79 (d, J=1.6 Hz, 1H), 8.63 (s, 1H), 8.06 (q, J=8.0 Hz, 6H), 7.75-7.69 (m, 3H), 7.65 (d, J=8.0 Hz, 2H), 7.51 (d, J=8.0 Hz, 1H), 6.95 (d, J=8.4 Hz, 2H), 6.70-6.61 (m, 2H), 4.61 (d, J=5.6 Hz, 2H), 4.34 (d, J=4.0 Hz, 2H), 4.30-4.25 (m, 1H), 3.30-3.27 (m, 4H), 3.13-2.96 (m, 3H), 2.80-2.57 (m, 5H), 2.61-2.56 (m, 2H), 2.13-2.03 (m, 1H), 1.95-1.89 (m, 3H), 1.87-1.83 (m, 1H). LC-MS (ES$^+$): m/z 768 [M+H]$^+$.

Example 62

Example 62 was prepared following the synthesis of Example 61

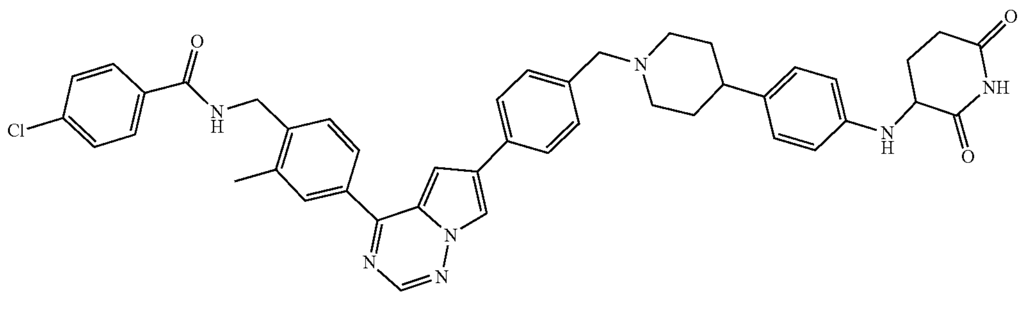 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(Cl)cc1]

4-chloro-N-[[4-[6-[4-[[4-[4-[(2,6-dioxo-3-piperidyl) amino]phenyl]-1-piperidyl]methyl]phenyl]pyrrolo[2,1-f][1,2,4]triazin-4-yl]-2-methyl-phenyl]methyl]benzamide. $^1$H NMR (400 MHz, DMSO-$d_6$) δ=10.91-10.58 (m, 1H), 9.16 (t, J=5.6 Hz, 1H), 8.69 (d, J=1.6 Hz, 1H), 8.60 (s, 1H), 8.10-8.00 (m, 2H), 8.00-7.94 (m, 2H), 7.88 (d, J=8.0 Hz, 2H), 7.64-7.56 (m, 3H), 7.48 (d, J=8.0 Hz, 1H), 7.37 (d, J=8.0 Hz, 2H), 6.95 (d, J=8.4 Hz, 2H), 6.60 (d, J=8.4 Hz, 2H), 5.63 (d, J=7.6 Hz, 1H), 4.58 (d, J=5.6 Hz, 2H), 4.31-4.20 (m, 1H), 3.50 (s, 2H), 2.91 (br d, J=11.2 Hz, 2H), 2.80-2.65 (m, 1H), 2.64-2.51 (m, 4H), 2.38-2.25 (m, 1H), 2.16-1.97 (m, 3H), 1.85 (dq, J=4.5, 12.2 Hz, 1H), 1.74-1.48 (m, 4H). LC-MS (ES$^+$): m/z 752.3 [M+H]$^+$.

Example 63

Example 62 was prepared following the synthesis of Example 61

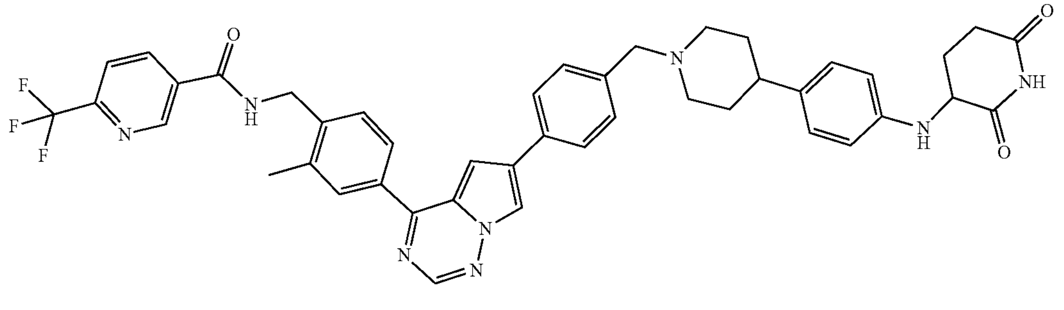 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(F)(F)F)nc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-6-(trifluoromethyl)pyridine-3-carboxamide. 11H NMR (400 MHz, DMSO-$d_6$) δ 1.84-2.17 (m, 7H), 2.55-2.78 (m, 4H), 2.94-3.08 (m, 2H), 3.42 (d, J=10.8 Hz, 2H), 4.64 (d, J=5.6 Hz, 2H), 6.68 (d, J=8.4 Hz, 2H), 6.97 (d, J=8.4 Hz, 2H), 7.54 (d, J=8.0 Hz, 1H), 7.65-7.76 (m, 3H), 8.00-8.13 (m, 5H), 8.58 (dd, J=8.0, 1.6 Hz, 1H), 8.64 (s, 1H), 8.81 (d, J=1.2 Hz, 1H), 9.27 (d, J=1.6 Hz, 1H), 9.57 (t, J=5.6 Hz, 1H), 10.58 (br s, 1H), 10.81 (s, 1H). LC-MS (ES$^+$): m/z 787.3 [M+H]$^+$.

Example 64

Example 64 was prepared following the synthesis of Example 61

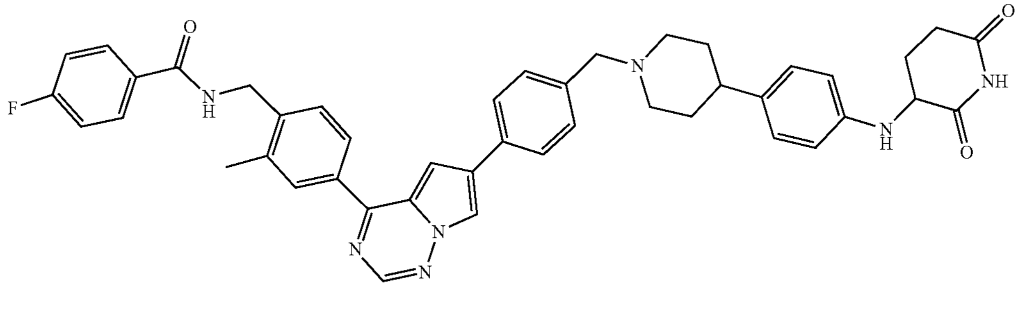 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(F)cc1]

-

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-4-fluoro-benzamide. $^1$H NMR (400 MHz, DMSO-$d_6$) δ 1.81-2.13 (m, 6H), 2.51-2.78 (m, 5H), 2.94-3.09 (m, 2H), 3.41 (d, J=11.2 Hz, 2H), 4.27-4.37 (m, 3H), 4.58 (d, J=5.6 Hz, 2H), 6.70 (d, J=8.4 Hz, 2H), 6.97 (d, J=8.4 Hz, 2H), 7.31-7.39 (m, 2H), 7.49 (d, J=8.0 Hz, 1H), 7.66-7.77 (m, 3H), 7.99-8.10 (m, 6H), 8.63 (s, 1H), 8.82 (d, J=1.2 Hz, 1H), 9.19 (t, J=5.6 Hz, 1H), 10.74 (d, J=2.0 Hz, 1H), 10.83 (s, 1H). LC-MS (ES$^+$): m/z 736.3 [M+H]$^+$.

Example 65

Example 65 was prepared following the synthesis of Example 64

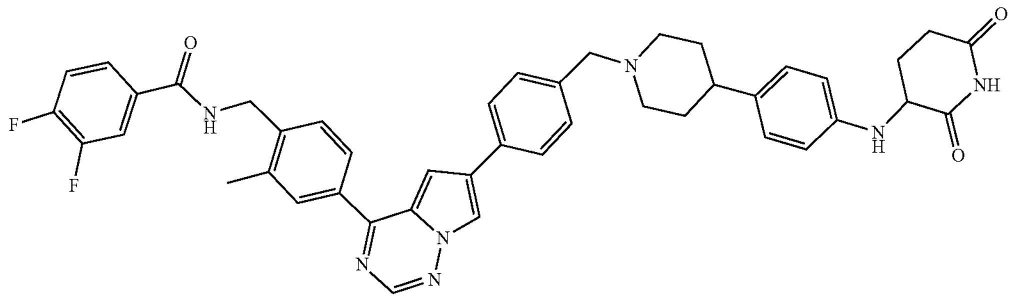 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(F)c(F)c1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-3,4-difluoro-benzamide. $^1$H NMR (400 MHz, DMSO-$d_6$) δ 1.81-2.19 (m, 6H), 2.53-2.83 (m, 6H), 2.95-3.09 (m, 2H), 3.38-3.48 (m, 2H), 4.17-4.46 (m, 1H), 4.25-4.42 (m, 2H), 4.58 (d, J=5.6 Hz, 2H), 6.61-6.77 (m, 2H), 6.91-7.03 (m, 2H), 7.49 (d, J=8.0 Hz, 1H), 7.55-7.77 (m, 4H), 7.87 (dt, J=4.0, 2.0 Hz, 1H), 7.99-8.14 (m, 5H), 8.63 (s, 1H), 8.80 (d, J=1.2 Hz, 1H), 9.24 (d, J=5.2 Hz, 1H), 10.79 (d, J=4.4 Hz, 1H). LC-MS (ES$^+$): m/z 754.3 $[M+H]^+$.

Example 66

Example 66 was prepared following the synthesis of Example 64

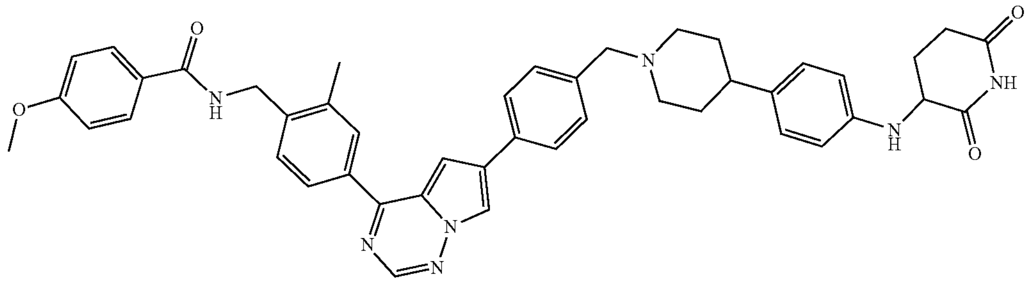 [SMILES: COc1ccc(C(=O)NCc2ccc(-c3ncnn4cc(-c5ccc(CN6CCC(c7ccc(NC8CCC(=O)NC8=O)cc7)CC6)cc5)cc34)cc2C)cc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-4-methoxy-benzamide. $^1$H NMR (400 MHz, DMSO-$d_6$) δ 1.83-1.93 (m, 3H), 2.00-2.12 (m, 3H), 2.51-2.78 (m, 6H), 2.94-3.10 (m, 2H), 3.33-3.47 (m, 2H), 3.82 (s, 3H), 4.32 (d, J=3.6 Hz, 3H), 4.53-4.59 (m, 2H), 6.69-6.77 (m, 2H), 6.96-7.06 (m, 4H), 7.45-7.52 (m, 1H), 7.68-7.75 (m, 3H), 7.95 (d, J=8.8 Hz, 2H), 8.00-8.09 (m, 3H), 8.03-8.04 (m, 1H), 8.05-8.06 (m, 1H), 8.61-8.67 (m, 1H), 8.78-8.85 (m, 1H), 8.95-9.04 (m, 1H), 10.81-10.87 (m, 1H), 10.87-11.02 (m, 1H). LC-MS (ES$^+$): m/z 748.4 $[M+H]^+$.

Example 67

Example 67 was prepared following the synthesis of Example 61

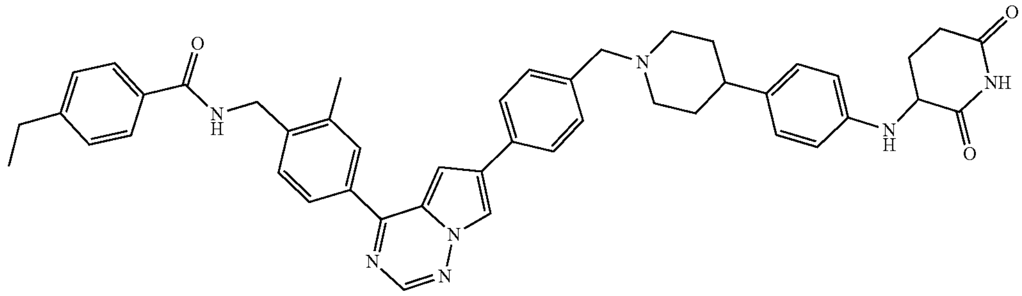 [SMILES: CCc1ccc(C(=O)NCc2ccc(-c3ncnn4cc(-c5ccc(CN6CCC(c7ccc(NC8CCC(=O)NC8=O)cc7)CC6)cc5)cc34)cc2C)cc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-4-ethyl-benzamide. $^1$H NMR (400 MHz, DMSO-$d_6$) δ 1.17-1.23 (m, 3H), 1.81-2.12 (m, 6H), 2.51-2.77 (m, 7H), 2.95-3.08 (m, 2H), 3.41 (d, J=11.2 Hz, 2H), 4.24-4.40 (m, 4H), 4.57 (d, J=5.6 Hz, 2H), 6.65-6.75 (m, 2H), 6.92-7.01 (m, 2H), 7.29-7.37 (m, 2H), 7.46-7.51 (m, 1H), 7.66-7.76 (m, 3H), 7.89 (d, J=8.4 Hz, 2H), 8.00-8.11 (m, 4H), 8.63 (s, 1H), 8.79-8.85 (m, 1H), 9.04-9.12 (m, 1H), 10.68-10.88 (m, 2H). LC-MS (ES$^+$): m/z 746.4 [M+H]$^+$.

Example 68

Example 68 was prepared following the synthesis of Example 61

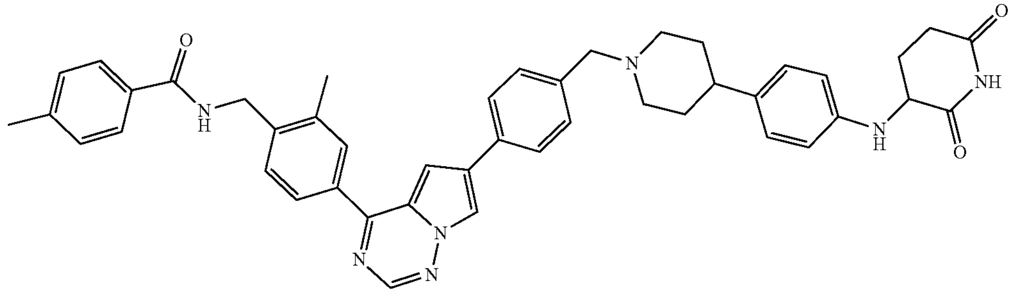 [SMILES: Cc1ccc(C(=O)NCc2ccc(-c3ncnn4cc(-c5ccc(CN6CCC(c7ccc(NC8CCC(=O)NC8=O)cc7)CC6)cc5)cc34)cc2C)cc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-4-methyl-benzamide. $^1$H NMR (400 MHz, DMSO-$d_6$) δ=10.87-10.73 (m, 1H), 10.54-10.39 (m, 1H), 9.05 (t, J=5.6 Hz, 1H), 8.80 (s, 1H), 8.63 (d, J=1.3 Hz, 1H), 8.13-7.99 (m, 4H), 7.87 (d, J=7.9 Hz, 2H), 7.76-7.63 (m, 3H), 7.49 (d, J=7.9 Hz, 1H), 7.32 (d, J=7.8 Hz, 2H), 6.96 (d, J=8.2 Hz, 2H), 6.74-6.59 (m, 2H), 4.58 (d, J=5.5 Hz, 2H), 4.38-4.26 (m, 3H), 3.09-2.99 (m, 2H), 2.81-2.67 (m, 3H), 2.65-2.54 (m, 4H), 2.38 (s, 4H), 2.09 (dd, J=4.5, 11.4 Hz, 2H), 2.02-1.82 (m, 5H). LC-MS (ES$^+$): m/z 732.4 [M+H]$^+$.

Example 69

Example 69 was prepared following the synthesis of Example 61

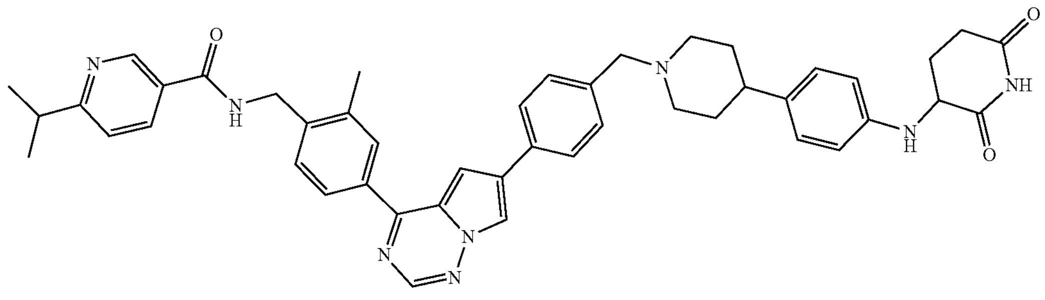 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(C)C)nc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-6-isopropyl-pyridine-3-carboxamide. $^1$H NMR (400 MHz, DMSO-$d_6$) δ=11.25-10.36 (m, 1H), 9.26-9.15 (m, 1H), 9.08-8.97 (m, 1H), 8.74-8.67 (m, 1H), 8.61 (s, 1H), 8.27-8.17 (m, 1H), 8.08-8.01 (m, 2H), 7.92-7.86 (m, 2H), 7.61 (s, 1H), 7.53-7.47 (m, 1H), 7.44 (s, 1H), 7.38 (d, J=8.0 Hz, 2H), 7.04-6.88 (m, 2H), 6.69-6.49 (m, 2H), 5.72-5.57 (m, 1H), 4.70-4.52 (m, 2H), 4.38-4.17 (m, 2H), 3.14-3.08 (m, 2H), 2.98-2.85 (m, 5H), 2.78 (s, 4H), 2.66-2.60 (m, 3H), 2.38-2.30 (m, 2H), 2.08-1.98 (m, 3H), 1.92-1.84 (m, 1H), 1.72-1.64 (m, 3H), 1.63-1.54 (m, 2H), 1.27 (d, J=6.9 Hz, 7H). LC-MS ($ES^+$): m/z 761.3 $[M+H]^+$.

Example 70

Example 70 was prepared following the synthesis of Example 61

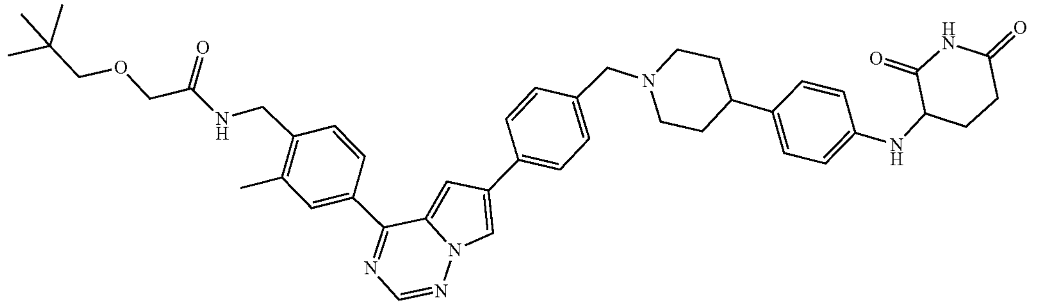 [SMILES: Cc1cc(-c2ncnn3cc(-c4ccc(CN5CCC(c6ccc(NC7CCC(=O)NC7=O)cc6)CC5)cc4)cc23)ccc1CNC(=O)COCC(C)(C)C]

2-(2,2-dimethylpropoxy)-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]acetamide. 1H NMR (400 MHz, DMSO-$d_6$) δ=10.83-10.76 (m, 1H), 8.80 (d, J=1.4 Hz, 1H), 8.66-8.59 (m, 1H), 8.15 (t, J=6.0 Hz, 1H), 8.09-8.03 (m, 3H), 8.00 (s, 1H), 7.78-7.64 (m, 3H), 7.43 (d, J=8.0 Hz, 1H), 6.95 (d, J=8.4 Hz, 2H), 6.73-6.62 (m, 2H), 4.43 (d, J=5.9 Hz, 2H), 4.33 (d, J=3.0 Hz, 2H), 4.30-4.24 (m, 1H), 3.98 (s, 3H), 3.48-3.38 (m, 2H), 3.18 (s, 2H), 3.09-2.94 (m, 2H), 2.78-2.68 (m, 1H), 2.68-2.63 (m, 1H), 2.59 (t, J=4.4 Hz, 1H), 2.45 (s, 3H), 2.11-2.02 (m, 1H), 2.00-1.80 (m, 4H), 0.92 (s, 9H). LC-MS ($ES^+$): m/z 742.4 $[M+H]^+$.

Example 71

Example 71 was prepared following the synthesis of Example 61

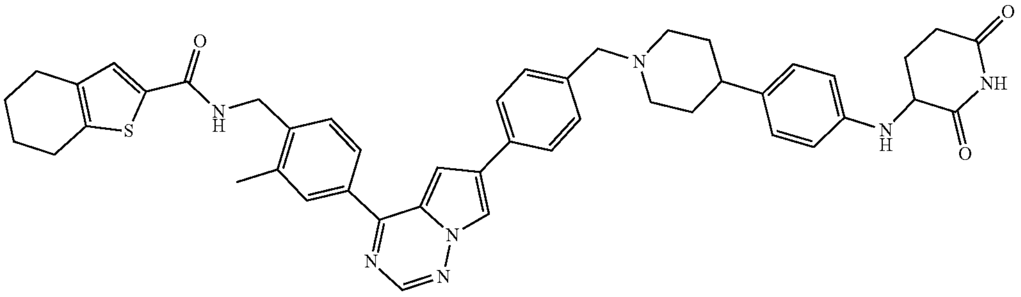 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1cc2c(s1)CCCC2]

N— [[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-4,5,6,7-tetrahydrobenzothiophene-2-carboxamide. $^{1}$H NMR (400 MHz, DMSO-$d_6$) δ=10.82-10.78 (m, 1H), 10.52-10.34 (m, 1H), 8.94 (t, J=5.9 Hz, 1H), 8.80 (d, J=1.6 Hz, 1H), 8.65-8.62 (m, 1H), 8.08-8.07 (m, 1H), 8.07 (d, J=8.4 Hz, 3H), 8.02 (s, 1H), 7.73-7.65 (m, 3H), 7.58 (s, 1H), 7.47 (d, J=8.0 Hz, 1H), 6.96 (d, J=8.8 Hz, 2H), 6.65 (d, J=8.4 Hz, 2H), 4.52 (d, J=5.6 Hz, 2H), 4.34 (d, J=4.4 Hz, 2H), 4.29 (dd, J=4.8, 11.6 Hz, 1H), 3.09-2.98 (m, 3H), 2.79-2.71 (m, 3H), 2.70-2.67 (m, 1H), 2.64 (d, J=4.0 Hz, 1H), 2.62-2.56 (m, 4H), 2.55 (d, J=4.4 Hz, 1H), 2.48 (s, 3H), 2.14-2.05 (m, 1H), 2.00-1.84 (m, 5H), 1.83-1.71 (m, 5H). LC-MS ($ES^+$): m/z 778.7 $[M+H]^+$.

Example 72

Example 72 was prepared following the synthesis of Example 61

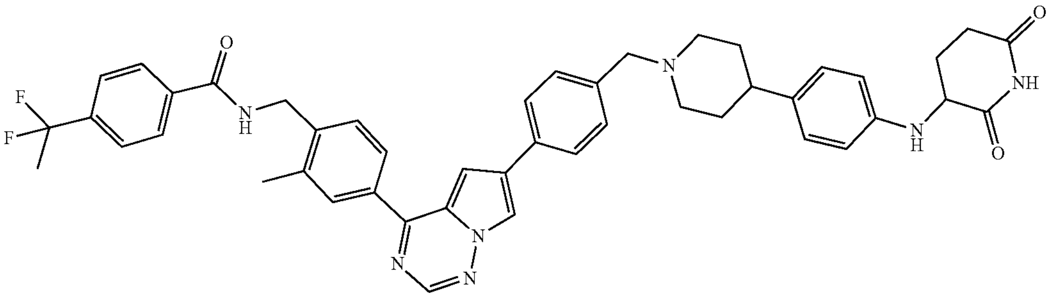 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(C)(F)F)cc1]

4-(1,1-difluoroethyl)-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]benzamide. $^{1}$H NMR (400 MHz, DMSO-$d_6$) δ=10.77 (s, 1H), 9.33-9.19 (m, 1H), 8.79 (d, J=1.5 Hz, 1H), 8.63 (s, 1H), 8.14-7.98 (m, 6H), 7.75-7.64 (m, 5H), 7.49 (d, J=7.9 Hz, 1H), 6.94 (d, J=8.6 Hz, 2H), 6.72-6.58 (m, 2H), 4.60 (d, J=5.6 Hz, 2H), 4.37-4.23 (m, 3H), 3.29-3.12 (m, 1H), 3.11-2.95 (m, 2H), 2.77-2.65 (m, 2H), 2.65-2.56 (m, 2H), 2.57-2.53 (m, 1H), 2.12-1.78 (m, 9H). LC-MS ($ES^+$): m/z 782.3 $[M+H]^+$.

Example 73

Example 73 was prepared following the synthesis of Example 61

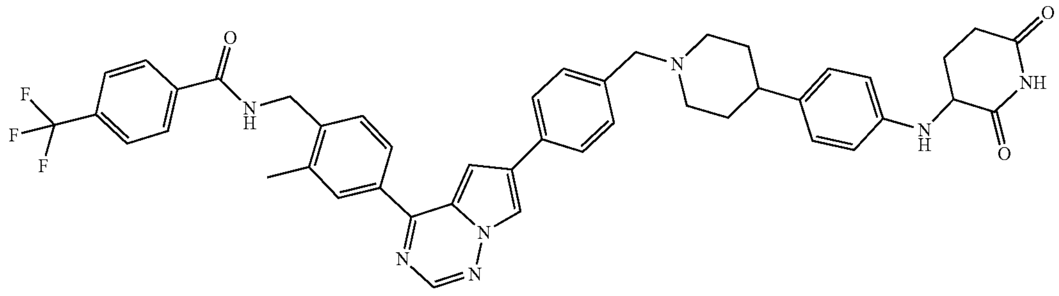 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(F)(F)F)cc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-4-(trifluoromethyl)benzamide. $^1$H NMR (400 MHz, DMSO-$d_6$) δ=10.84-10.75 (m, 1H), 9.43-9.30 (m, 1H), 8.79 (d, J=1.2 Hz, 1H), 8.65-8.59 (m, 1H), 8.15 (d, J=8.2 Hz, 2H), 8.10-8.00 (m, 4H), 7.89 (d, J=8.4 Hz, 2H), 7.77-7.63 (m, 3H), 7.50 (d, J=8.0 Hz, 1H), 6.94 (d, J=8.4 Hz, 2H), 6.65-6.64 (m, 1H), 6.75-6.56 (m, 1H), 4.60 (d, J=5.6 Hz, 2H), 4.32 (d, J=3.0 Hz, 2H), 4.30-4.23 (m, 1H), 3.45-3.37 (m, 3H), 3.08-2.94 (m, 2H), 2.77-2.63 (m, 2H), 2.58 (t, J=4.4 Hz, 1H), 2.54 (br s, 2H), 2.09-2.04 (m, 1H), 2.01-1.79 (m, 5H). LC-MS (ES$^+$): m/z 786.4 $[M+H]^+$.

Example 74

Example 74 was prepared following the synthesis of Example 61

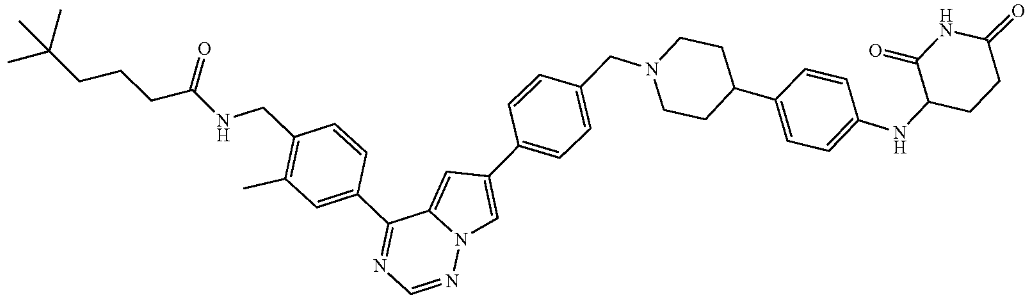 [SMILES: Cc1cc(-c2ncnn3cc(-c4ccc(CN5CCC(c6ccc(NC7CCC(=O)NC7=O)cc6)CC5)cc4)cc23)ccc1CNC(=O)CCCC(C)(C)C]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-5,5-dimethyl-hexanamide. $^1$H NMR (400 MHz, DMSO-$d_6$) δ=10.79 (s, 1H), 10.75-10.56 (m, 1H), 8.80 (d, J=1.6 Hz, 1H), 8.62 (s, 1H), 8.36 (t, J=5.6 Hz, 1H), 8.07-8.01 (m, 3H), 7.99 (s, 1H), 7.73-7.62 (m, 3H), 7.43 (d, J=8.0 Hz, 1H), 6.95 (d, J=8.0 Hz, 2H), 6.73-6.62 (m, 2H), 4.40-4.25 (m, 5H), 3.41 (d, J=11.0 Hz, 3H), 3.08-2.95 (m, 2H), 2.76-2.62 (m, 2H), 2.61-2.56 (m, 1H), 2.42 (s, 3H), 2.16 (t, J=7.4 Hz, 2H), 2.10-2.08 (m, 1H), 2.07-1.93 (m, 3H), 1.92-1.81 (m, 3H), 1.58-1.46 (m, 2H), 1.21-1.09 (m, 2H), 0.86 (s, 9H). LC-MS (ES$^+$): m/z 740.5 $[M+H]^+$.

Example 75

Example 75 was prepared following the synthesis of Example 61

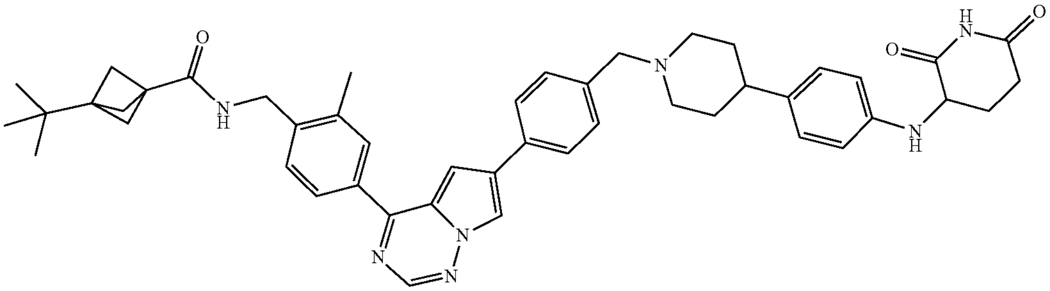 [SMILES: Cc1cc(-c2ncnn3cc(-c4ccc(CN5CCC(c6ccc(NC7CCC(=O)NC7=O)cc6)CC5)cc4)cc23)ccc1CNC(=O)C12CC(C(C)(C)C)(C1)C2]

3-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]bicyclo[1.1.1]pentane-1-carboxamide. $^1$H NMR (400 MHz, DMSO-$d_6$) δ=10.82-10.75 (m, 1H), 10.16-10.04 (m, 1H), 8.80 (d, J=1.4 Hz, 1H), 8.64 (s, 1H), 8.29 (t, J=6.0 Hz, 1H), 8.12-8.03 (m, 3H), 8.00 (s, 1H), 7.76-7.62 (m, 3H), 7.39 (d, J=8.0 Hz, 1H), 6.95 (d, J=8.5 Hz, 2H), 6.64 (d, J=8.7 Hz, 2H), 4.35 (d, J=5.6 Hz, 4H), 4.28 (d, J=4.8, 11.3 Hz, 1H), 3.17 (s, 1H), 3.10-2.99 (m, 2H), 2.77-2.66 (m, 2H), 2.60 (d, J=4.4 Hz, 2H), 2.43 (s, 3H), 2.39-2.22 (m, 2H), 2.19-2.04 (m, 2H), 1.99-1.82 (m, 5H), 1.43-1.03 (m, 1H), 0.85 (s, 9H). LC-MS (ES$^+$): m/z 764.4 [M+H]$^+$.

Example 76

Example 76 was prepared following the synthesis of Example 61

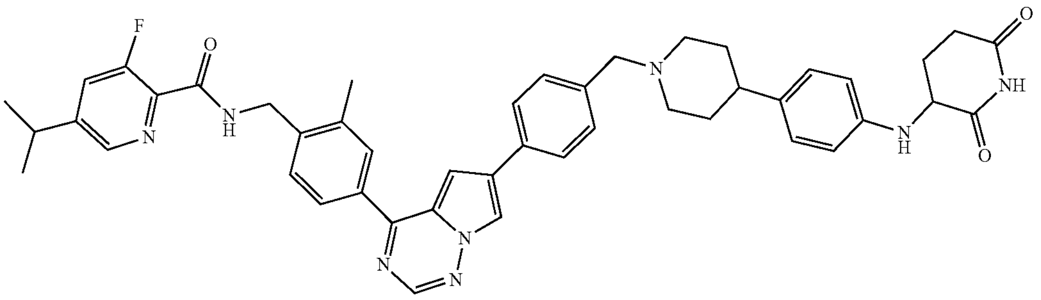 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ncc(C(C)C)cc1F]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-3-fluoro-5-isopropyl-pyridine-2-carboxamide. $^1$H NMR (400 MHz, DMSO-$d_6$) δ=10.94-10.79 (m, 1H), 9.25 (t, J=6.1 Hz, 1H), 8.91-8.79 (m, 1H), 8.64 (s, 1H), 8.45 (s, 1H), 8.17-7.97 (m, 4H), 7.80 (dd, J=1.4, 12.0 Hz, 1H), 7.75-7.62 (m, 3H), 7.51 (d, J=8.0 Hz, 1H), 7.12-6.97 (m, 2H), 6.86-6.66 (m, 2H), 4.77-4.47 (m, 2H), 4.44-4.23 (m, 3H), 3.42 (br d, J=11.2 Hz, 2H), 3.21-2.96 (m, 3H), 2.79-2.65 (m, 2H), 2.64-2.54 (m, 2H), 2.14-1.96 (m, 3H), 1.90 (br d, J=12.3 Hz, 3H), 1.27 (d, J=6.9 Hz, 6H). LC-MS (ES$^+$): m/z 779.4 [M+H]$^+$.

Example 77

Example 77 was prepared following the synthesis of Example 61

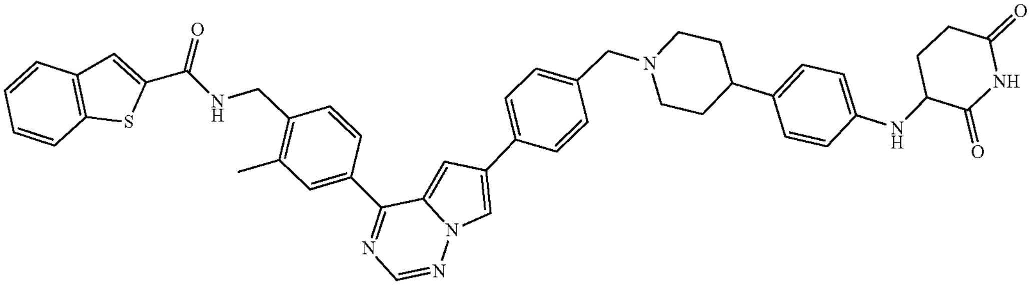 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1cc2ccccc2s1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]benzothiophene-2-carboxamide. $^1$H NMR (400 MHz, DMSO-$d_6$) δ=11.18-10.36 (m, 1H), 9.48-9.27 (m, 1H), 8.71 (d, J=1.3 Hz, 1H), 8.61 (s, 1H), 8.23 (s, 1H), 8.12-8.01 (m, 3H), 8.00-7.86 (m, 3H), 7.63 (d, J=1.4 Hz, 1H), 7.55 (d, J=8.0 Hz, 1H), 7.51-7.43 (m, 2H), 7.38 (d, J=8.0 Hz, 2H), 6.96 (d, J=8.4 Hz, 2H), 6.61 (d, J=8.7 Hz, 2H), 5.64 (d, J=7.3 Hz, 1H), 4.62 (d, J=5.6 Hz, 2H), 4.30-4.20 (m, 1H), 3.51 (s, 2H), 2.97-2.88 (m, 2H), 2.77-2.71 (m, 1H), 2.68 (br s, 1H), 2.59 (d, J=4.5 Hz, 7H), 2.33 (d, J=1.8 Hz, 1H), 2.14-1.98 (m, 3H), 1.73-1.54 (m, 4H). LC-MS ($ES^+$): m/z 774.5 $[M+H]^+$.

Example 78

Example 78 was prepared following the synthesis of Example 61

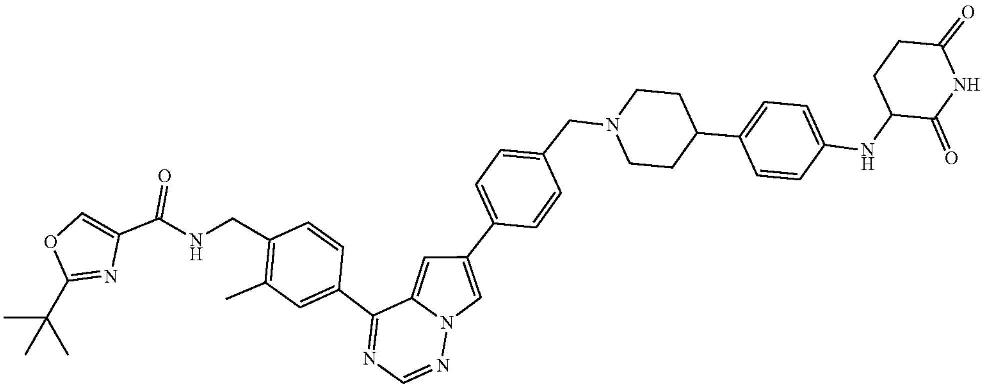 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1coc(C(C)(C)C)n1]

2-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]oxazole-4-carboxamide. $^1$H NMR (400 MHz, DMSO-$d_6$) δ=10.83 (br s, 1H), 8.82 (s, 1H), 8.72 (t, J=6.2 Hz, 1H), 8.64 (s, 1H), 8.58 (s, 1H), 8.06 (d, J=8.2 Hz, 3H), 8.01 (s, 1H), 7.78-7.68 (m, 3H), 7.46 (d, J=8.0 Hz, 1H), 6.99 (d, J=8.2 Hz, 2H), 6.80-6.68 (m, 2H), 4.54 (d, J=6.0 Hz, 6H), 3.42 (d, J=11.0 Hz, 2H), 3.09-2.95 (m, 2H), 2.79-2.63 (m, 2H), 2.61-2.54 (m, 1H), 2.48 (s, 3H), 2.13-2.01 (m, 3H), 1.89 (d, J=12.3 Hz, 3H), 1.38 (s, 9H). LC-MS ($ES^+$): m/z 765.3 $[M+H]^+$.

Example 79

Example 79 was prepared following the synthesis of Example 61

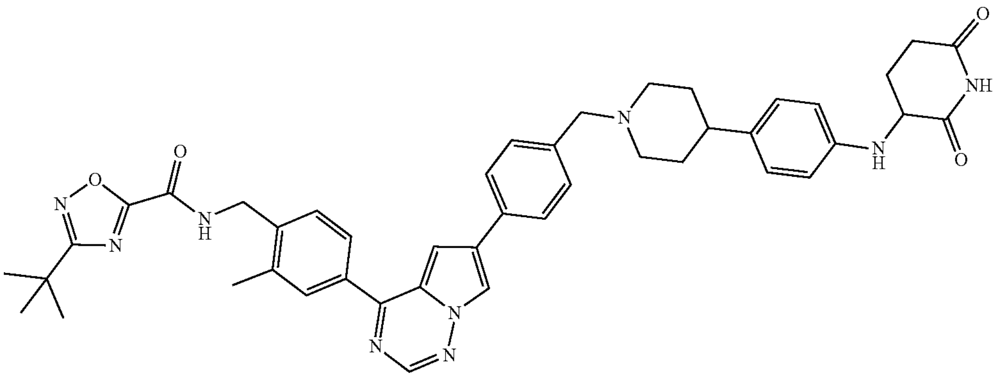 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1nc(C(C)(C)C)no1]

3-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-1,2,4-oxadiazole-5-carboxamide. $^1$H NMR (400 MHz, DMSO-$d_6$) δ=10.77 (s, 1H), 9.94 (t, J=6.0 Hz, 1H), 8.70 (s, 1H), 8.61 (s, 1H), 8.28 (s, 1H), 8.09-7.98 (m, 2H), 7.89 (d, J=8.0 Hz, 2H), 7.61 (s, 1H), 7.51 (d, J=8.0 Hz, 1H), 7.38 (d, J=8.0 Hz, 2H), 6.96 (d, J=8.4 Hz, 2H), 6.60 (d, J=8.4 Hz, 2H), 5.64 (d, J=7.6 Hz, 1H), 4.58 (d, J=6.0 Hz, 2H), 4.32-4.19 (m, 1H), 3.51 (br s, 3H), 2.91 (d, J=10.8 Hz, 2H), 2.81-2.63 (m, 2H), 2.39-2.25 (m, 2H), 2.15-1.77 (m, 5H), 1.72-1.54 (m, 4H), 1.38 (s, 9H). LC-MS ($ES^+$): m/z 766.3 $[M+H]^+$.

Example 80

Example 80 was prepared following the synthesis of Example 61

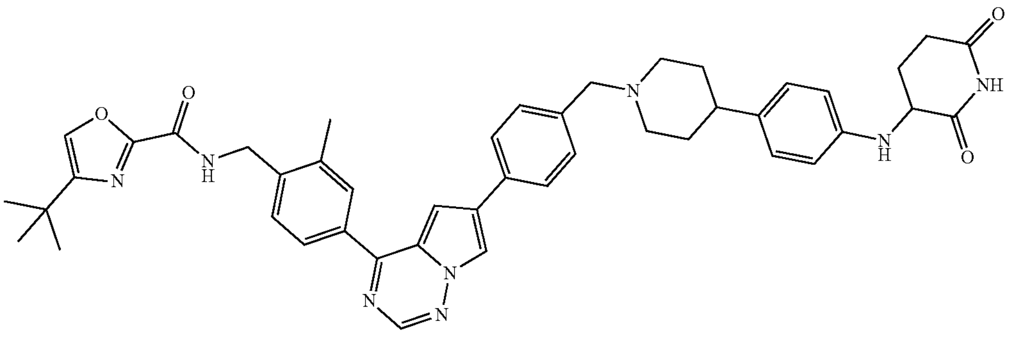 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1nc(C(C)(C)C)co1]

4-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]oxazole-2-carboxamide. $^1$H NMR (400 MHz, DMSO-$d_6$) δ=10.82-10.74 (m, 1H), 9.41 (t, J=6.0 Hz, 1H), 8.71 (d, J=1.2 Hz, 1H), 8.61 (s, 1H), 8.09-8.03 (m, 2H), 8.01 (s, 1H), 7.89 (d, J=8.2 Hz, 2H), 7.62 (d, J=1.2 Hz, 1H), 7.47 (d, J=8.0 Hz, 1H), 7.38 (d, J=8.0 Hz, 2H), 6.96 (d, J=8.4 Hz, 2H), 6.60 (d, J=8.6 Hz, 2H), 5.65 (d, J=7.2 Hz, 1H), 4.54 (d, J=6.0 Hz, 2H), 4.31-4.21 (m, 1H), 3.51 (s, 2H), 2.92 (d, J=10.8 Hz, 2H), 2.79-2.69 (m, 1H), 2.62-2.57 (m, 1H), 2.48 (s, 3H), 2.39-2.28 (m, 2H), 2.14-1.98 (m, 3H), 1.92-1.80 (m, 1H), 1.75-1.54 (m, 4H), 1.28 (s, 9H). LC-MS ($ES^+$): m/z 780.2 $[M+H]^+$.

Example 81

Example 81 was prepared following the synthesis of Example 61

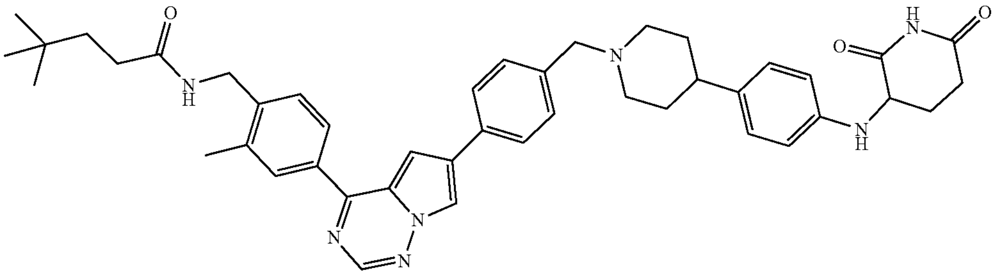 [SMILES: Cc1cc(-c2ncnn3cc(-c4ccc(CN5CCC(c6ccc(NC7CCC(=O)NC7=O)cc6)CC5)cc4)cc23)ccc1CNC(=O)CCC(C)(C)C]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-4,4-dimethyl-pentanamide. $^{1}H$ NMR (400 MHz, DMSO-$d_6$) δ=10.83-10.70 (m, 1H), 8.70 (d, J=1.6 Hz, 1H), 8.60 (s, 1H), 8.33 (t, J=5.6 Hz, 1H), 8.06-8.01 (m, 1H), 8.00 (s, 1H), 7.89 (d, J=8.4 Hz, 2H), 7.60 (d, J=1.6 Hz, 1H), 7.43 (d, J=8.0 Hz, 1H), 7.38 (d, J=8.0 Hz, 2H), 6.96 (d, J=8.6 Hz, 2H), 6.60 (d, J=8.8 Hz, 2H), 5.63 (d, J=7.2 Hz, 1H), 4.38-4.32 (m, 2H), 4.29-4.21 (m, 1H), 3.51 (s, 2H), 2.96-2.87 (m, 2H), 2.78-2.64 (m, 2H), 2.61-2.57 (m, 1H), 2.42 (s, 3H), 2.36-2.30 (m, 1H), 2.21-2.13 (m, 2H), 2.13-1.98 (m, 3H), 1.63-1.62 (m, 1H), 1.73-1.53 (m, 4H), 1.53-1.44 (m, 2H), 0.88 (s, 9H). LC-MS ($ES^+$): m/z 726.3 $[M+H]^+$.

Example 82

Example 82 was prepared following the synthesis of Example 61

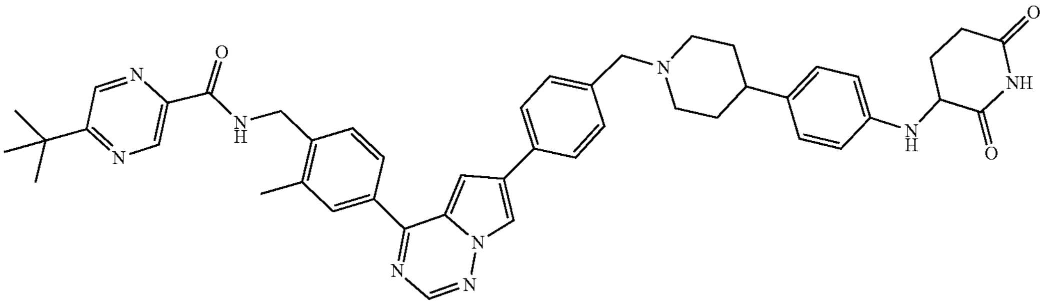 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1cnc(C(C)(C)C)cn1]

5-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]pyrazine-2-carboxamide. $^{1}H$ NMR (400 MHz, DMSO-$d_6$) δ=10.78 (s, 1H), 9.48 (t, J=6.2 Hz, 1H), 9.15 (d, J=1.5 Hz, 1H), 8.86 (d, J=1.5 Hz, 1H), 8.70 (d, J=1.3 Hz, 1H), 8.60 (s, 1H), 8.10-7.99 (m, 2H), 7.89 (d, J=8.2 Hz, 2H), 7.61 (d, J=1.5 Hz, 1H), 7.47 (d, J=7.7 Hz, 1H), 7.38 (d, J=8.3 Hz, 2H), 6.96 (d, J=8.3 Hz, 2H), 6.60 (d, J=8.6 Hz, 2H), 5.65 (d, J=7.5 Hz, 1H), 4.62 (d, J=6.0 Hz, 2H), 4.35-4.15 (m, 1H), 3.51 (s, 2H), 2.92 (d, J=11.0 Hz, 2H), 2.78-2.54 (m, 3H), 2.42-2.24 (m, 3H), 2.15-1.97 (m, 3H), 1.93-1.79 (m, 1H), 1.72-1.56 (m, 4H), 1.41 (s, 9H). LC-MS ($ES^+$): m/z 776.3 $[M+H]^+$.

Example 83

Example 83 was prepared following the synthesis of Example 61

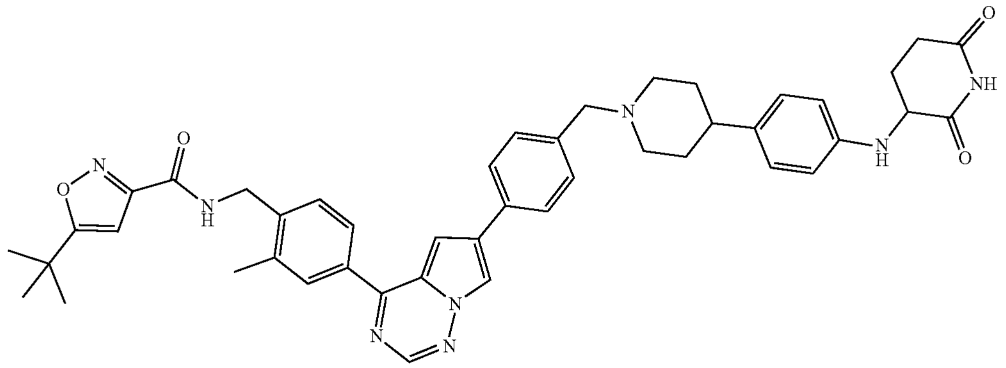 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1cc(C(C)(C)C)on1]

-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]isoxazole-3-carboxamide. $^1$H NMR (400 MHz, DMSO-$d_6$) δ=9.32 (t, J=6.0 Hz, 1H), 8.70 (d, J=1.2 Hz, 1H), 8.61 (s, 1H), 8.06 (d, J=8.0 Hz, 1H), 8.02 (s, 1H), 7.89 (d, J=8.0 Hz, 2H), 7.61 (d, J=1.6 Hz, 1H), 7.47 (d, J=8.0 Hz, 1H), 7.38 (d, J=8.0 Hz, 2H), 6.96 (d, J=8.4 Hz, 2H), 6.65-6.57 (m, 3H), 5.64 (d, J=7.6 Hz, 1H), 4.55 (d, J=6.0 Hz, 2H), 4.25 (ddd, J=5.2, 6.8, 11.6 Hz, 1H), 3.51 (s, 2H), 2.92 (br d, J=11.2 Hz, 2H), 2.79-2.65 (m, 1H), 2.62-2.57 (m, 1H), 2.48 (s, 3H), 2.41-2.29 (m, 2H), 2.15-1.98 (m, 3H), 1.93-1.79 (m, 1H), 1.73-1.51 (m, 4H), 1.35 (s, 9H). LC-MS ($ES^+$): m/z 765.1 $[M+H]^+$.

Example 84

Example 84 was prepared following the synthesis of Example 61

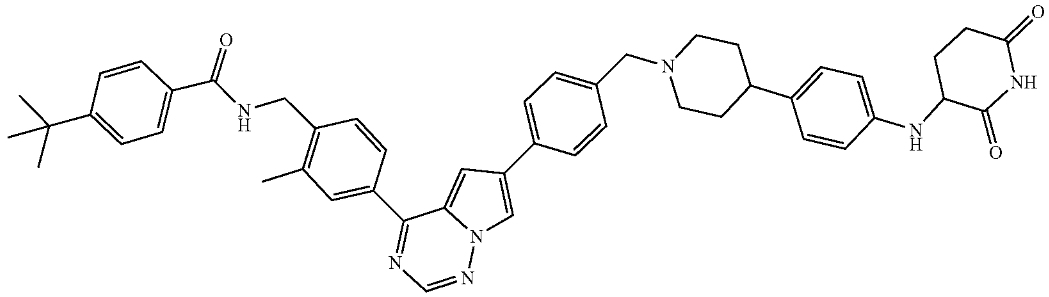 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(C)(C)C)cc1]

4-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]benzamide. $^1$HNMR (400 MHz, DMSO-$d_6$) δ=10.80-10.76 (m, 1H), 10.30-10.22 (m, 1H), 9.05 (t, J=5.6 Hz, 1H), 8.79 (d, J=1.2 Hz, 1H), 8.63 (s, 1H), 8.06-8.05 (m, 1H), 8.06 (d, J=8.4 Hz, 3H), 8.02 (s, 1H), 7.90 (d, J=8.4 Hz, 2H), 7.70 (d, J=1.2 Hz, 1H), 7.66 (d, J=8.4 Hz, 2H), 7.52 (d, J=8.4 Hz, 2H), 7.47 (d, J=8.0 Hz, 1H), 6.94 (d, J=8.8 Hz, 2H), 6.63 (d, J=8.8 Hz, 2H), 4.58 (d, J=5.6 Hz, 2H), 4.36-4.30 (m, 2H), 4.27 (dd, J=4.8, 11.2 Hz, 1H), 3.09-2.97 (m, 2H), 2.78-2.57 (m, 3H), 2.13-2.04 (m, 1H), 1.99-1.81 (m, 5H), 1.31 (s, 9H). LC-MS ($ES^+$): m/z 774.4 $[M+H]^+$.

Example 85

Example 85 was prepared following the synthesis of Example 61

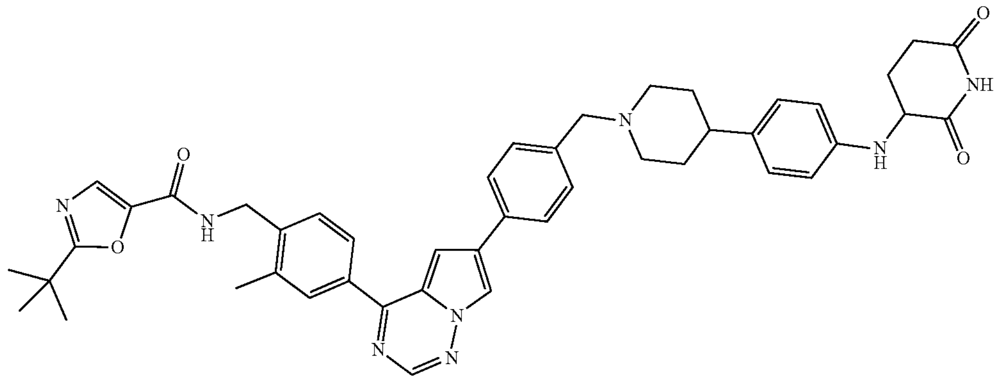 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1cnc(C(C)(C)C)o1]

2-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]oxazole-5-carboxamide. $^1$HNMR (400 MHz, DMSO-$d_6$) δ=10.75 (s, 1H), 9.06 (t, J=5.6 Hz, 1H), 8.70 (d, J=1.3 Hz, 1H), 8.60 (s, 1H), 8.16 (s, 1H), 8.07 (d, J=8.4 Hz, 1H), 8.02 (s, 1H), 7.89 (d, J=8.0 Hz, 2H), 7.71 (s, 1H), 7.61 (s, 1H), 7.48 (d, J=8.0 Hz, 1H), 7.39 (d, J=8.0 Hz, 2H), 6.96 (d, J=8.4 Hz, 2H), 6.60 (d, J=8.4 Hz, 2H), 5.63 (d, J=7.2 Hz, 1H), 4.55 (d, J=5.6 Hz, 2H), 4.30-4.21 (m, 1H), 3.56 (s, 2H), 2.94 (d, J=10.8 Hz, 2H), 2.79-2.66 (m, 1H), 2.59 (d, J=4.0 Hz, 1H), 2.48 (s, 3H), 2.42-2.30 (m, 1H), 2.15-2.02 (m, 3H), 1.92-1.79 (m, 1H), 1.75-1.51 (m, 4H), 1.37 (s, 9H). LC-MS ($ES^+$): m/z 765.6 $[M+H]^+$.

Example 86

Example 86 was prepared following the synthesis of Example 61

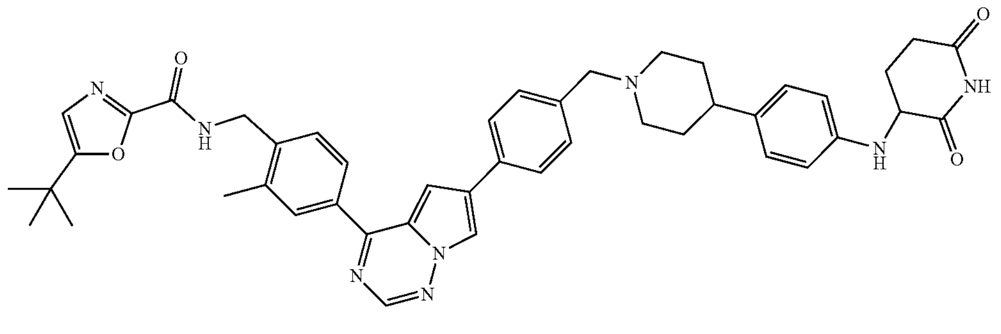 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ncc(C(C)(C)C)o1]

5-tert-butyl-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]oxazole-2-carboxamide. $^1$H NMR (400 MHz, DMSO-$d_6$) δ=10.77 (s, 1H), 9.45 (t, J=6.1 Hz, 1H), 8.73 (s, 1H), 8.61 (s, 1H), 8.06 (d, J=8.2 Hz, 1H), 8.01 (s, 1H), 7.93 (br s, 2H), 7.64 (s, 1H), 7.47 (d, J=8.0 Hz, 2H), 7.14 (s, 1H), 6.96 (d, J=8.2 Hz, 2H), 6.62 (d, J=8.5 Hz, 2H), 5.67 (d, J=7.0 Hz, 1H), 4.54 (d, J=6.0 Hz, 2H), 4.31-4.22 (m, 1H), 2.79-2.66 (m, 1H), 2.63-2.54 (m, 1H), 2.49 (br s, 3H), 2.14-2.07 (m, 2H), 1.86 (td, J=12.2, 16.7 Hz, 2H), 1.73 (d, J=1.8 Hz, 4H), 1.43-1.34 (m, 1H), 1.32 (s, 10H), 1.27-1.22 (m, 2H), 1.20-1.11 (m, 1H), 0.95-0.78 (m, 1H). LC-MS ($ES^+$): m/z 765.2 $[M+H]^+$.

Example 87

Example 87 was prepared following the synthesis of Example 61

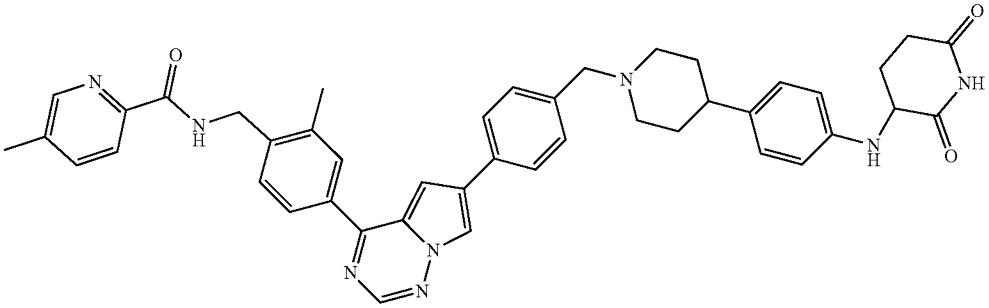 [SMILES: Cc1ccc(C(=O)NCc2ccc(-c3ncnn4cc(-c5ccc(CN6CCC(c7ccc(NC8CCC(=O)NC8=O)cc7)CC6)cc5)cc34)cc2C)nc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-5-methyl-pyridine-2-carboxamide. $^{1}$H NMR (400 MHz, DMSO-$d_6$) δ=10.76 (s, 1H), 9.33 (t, J=6.0 Hz, 1H), 8.69 (d, J=0.8 Hz, 1H), 8.59 (s, 1H), 8.53 (s, 1H), 8.25 (s, 1H), 8.07-7.96 (m, 3H), 7.88 (d, J=8.4 Hz, 2H), 7.83 (d, J=8.8 Hz, 1H), 7.61 (d, J=1.2 Hz, 1H), 7.46 (d, J=7.8 Hz, 1H), 7.37 (d, J=8.4 Hz, 2H), 6.96 (d, J=8.4 Hz, 2H), 6.60 (d, J=8.4 Hz, 2H), 5.63 (d, J=7.6 Hz, 1H), 4.60 (d, J=6.4 Hz, 2H), 4.31-4.21 (m, 1H), 3.51 (s, 3H), 2.96-2.87 (m, 2H), 2.80-2.65 (m, 2H), 2.59 (t, J=4.0 Hz, 1H), 2.41 (s, 3H), 2.35-2.30 (m, 1H), 2.14-1.98 (m, 4H), 1.92-1.78 (m, 1H), 1.73-1.52 (m, 4H). LC-MS (ES$^+$): m/z 733.2 [M+H]$^+$.

Example 88

Example 88 was prepared following the synthesis of Example 61

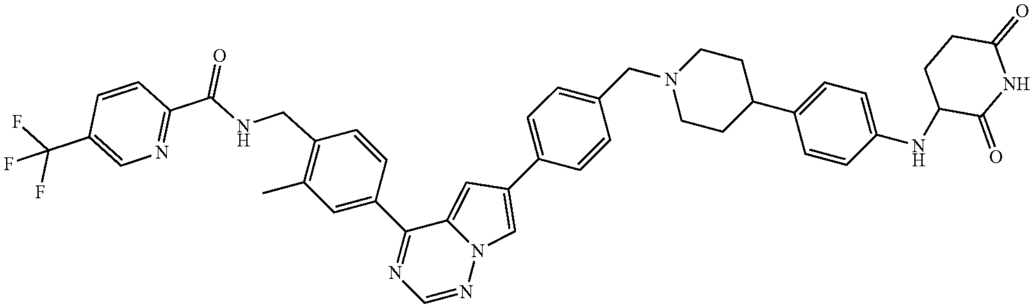 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(F)(F)F)cn1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-5-(trifluoromethyl)pyridine-2-carboxamide. $^{1}$H NMR (400 MHz, DMSO-$d_6$) δ=10.77 (s, 1H), 9.63 (t, J=6.4 Hz, 1H), 9.10 (d, J=0.8 Hz, 1H), 8.70 (d, J=1.6 Hz, 1H), 8.60 (s, 1H), 8.47 (dd, J=2.0, 8.4 Hz, 1H), 8.32 (s, 1H), 8.28 (d, J=8.4 Hz, 1H), 8.06-8.00 (m, 2H), 7.88 (d, J=8.4 Hz, 2H), 7.61 (d, J=1.6 Hz, 1H), 7.47 (d, J=8.0 Hz, 1H), 7.37 (d, J=8.4 Hz, 2H), 6.95 (d, J=8.4 Hz, 2H), 6.60 (d, J=8.8 Hz, 2H), 5.64 (d, J=7.6 Hz, 1H), 4.63 (d, J=6.0 Hz, 2H), 4.30-4.22 (m, 1H), 3.52-3.47 (m, 3H), 2.91 (d, J=11.0 Hz, 2H), 2.79-2.65 (m, 1H), 2.61-2.57 (m, 1H), 2.55-2.52 (m, 2H), 2.38-2.28 (m, 2H), 2.14-1.97 (m, 3H), 1.91-1.79 (m, 1H), 1.71-1.53 (m, 4H). LC-MS (ES$^+$): m/z 787.1 [M+H]$^+$.

Example 89

Example 89 was prepared following the synthesis of Example 61

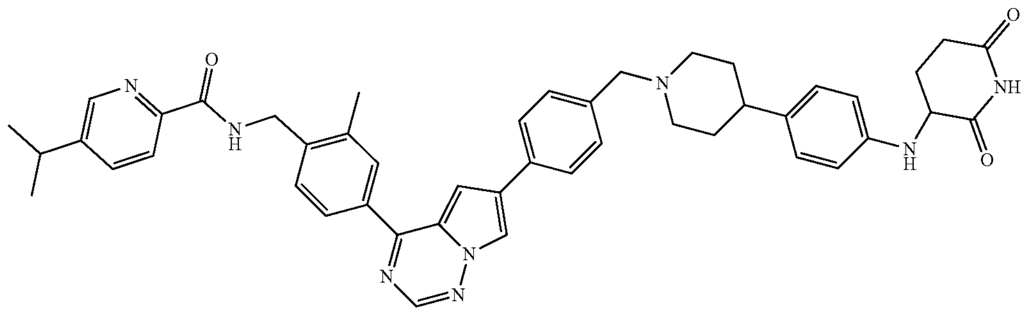 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(C)C)cn1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-5-isopropyl-pyridine-2-carboxamide. $^1$H NMR (400 MHz, DMSO-$d_6$) δ=10.77 (s, 1H), 9.39-9.29 (m, 1H), 8.70 (d, J=1.6 Hz, 1H), 8.61-8.55 (m, 2H), 8.31 (s, 1H), 8.06-7.98 (m, 3H), 7.93-7.85 (m, 3H), 7.61 (d, J=1.2 Hz, 1H), 7.45 (d, J=8.0 Hz, 1H), 7.37 (d, J=8.4 Hz, 2H), 6.95 (d, J=8.4 Hz, 2H), 6.60 (d, J=8.8 Hz, 2H), 5.64 (d, J=7.6 Hz, 1H), 4.60 (d, J=6.4 Hz, 2H), 4.31-4.21 (m, 1H), 3.50 (s, 2H), 3.12-3.01 (m, 1H), 2.91 (d, J=10.8 Hz, 2H), 2.82-2.64 (m, 2H), 2.61-2.56 (m, 1H), 2.39-2.27 (m, 2H), 2.16-1.95 (m, 3H), 1.91-1.77 (m, 1H), 1.72-1.50 (m, 4H), 1.27 (d, J=7.2 Hz, 6H). LC-MS (ES$^+$): m/z 761.2 [M+H]$^+$.

Example 90

Example 90 was prepared following the synthesis of Example 61

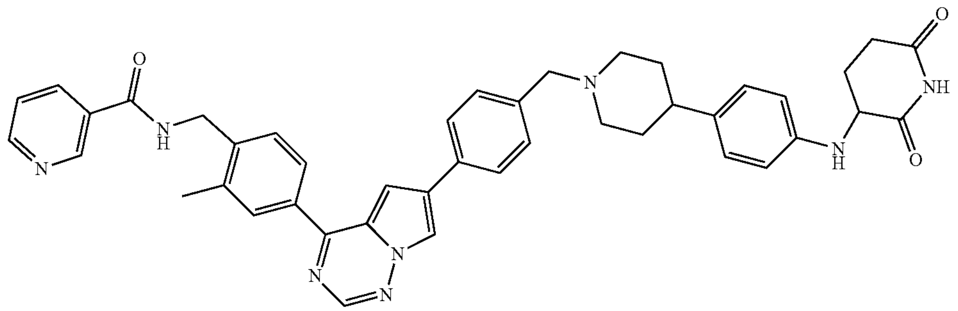 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1cccnc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]pyridine-3-carboxamide. $^1$H NMR (400 MHz, DMSO-$d_6$) δ=10.77 (s, 1H), 9.30 (t, J=5.6 Hz, 1H), 9.12 (d, J=1.6 Hz, 1H), 8.77-8.73 (m, 1H), 8.71 (d, J=1.1 Hz, 1H), 8.61 (s, 1H), 8.33-8.28 (m, 2H), 8.09-8.02 (m, 2H), 7.89 (d, J=8.1 Hz, 2H), 7.62 (d, J=1.1 Hz, 1H), 7.55-7.52 (m, 1H), 7.38 (d, J=8.1 Hz, 2H), 6.96 (d, J=8.2 Hz, 2H), 6.61 (d, J=8.4 Hz, 2H), 5.64 (d, J=7.3 Hz, 1H), 4.62 (d, J=5.5 Hz, 2H), 4.29-4.23 (m, 1H), 2.92 (d, J=11.0 Hz, 2H), 2.77-2.69 (m, 1H), 2.61-2.55 (m, 1H), 2.40-2.29 (m, 2H), 2.14-1.98 (m, 4H), 1.90-1.82 (m, 1H), 1.73-1.55 (m, 5H). LC-MS (ES$^+$): m/z 719.6 [M+H]$^+$.

Example 91

Example 91 was prepared following the synthesis of Example 61

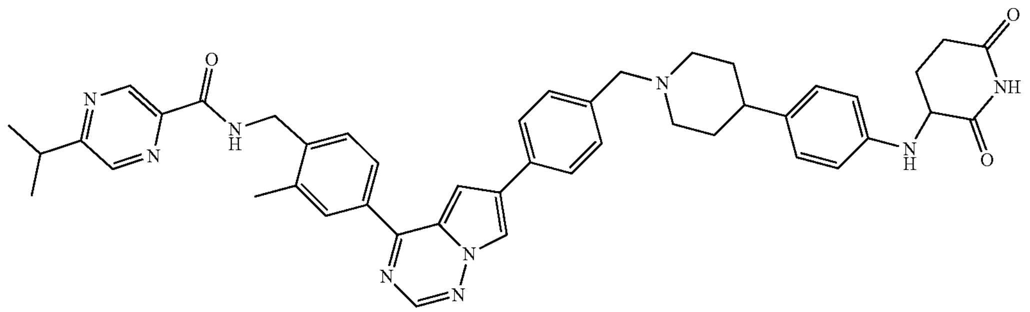 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1cnc(C(C)C)cn1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-5-isopropyl-pyrazine-2-carboxamide. $^1$H NMR (400 MHz, DMSO-$d_6$) δ=10.85-10.68 (m, 1H), 9.48 (t, J=6.2 Hz, 1H), 9.15 (d, J=1.1 Hz, 1H), 8.70 (dd, J=1.1, 9.7 Hz, 2H), 8.60 (s, 1H), 8.09-7.98 (m, 2H), 7.88 (d, J=8.1 Hz, 2H), 7.60 (d, J=1.1 Hz, 1H), 7.47 (d, J=7.9 Hz, 1H), 7.38 (d, J=8.1 Hz, 2H), 6.96 (d, J=8.4 Hz, 2H), 6.61 (d, J=8.4 Hz, 2H), 5.64 (d, J=7.3 Hz, 1H), 4.62 (d, J=6.1 Hz, 2H), 4.20 (s, 1H), 3.51 (s, 2H), 3.29-3.23 (m, 1H), 2.92 (d, J=10.8 Hz, 2H), 2.80-2.69 (m, 1H), 2.58 (td, J=4.2, 17.6 Hz, 1H), 2.50-2.48 (m, 3H), 2.34 (t, J=11.6 Hz, 1H), 2.14-1.99 (m, 3H), 1.87 (t, J=4.5, 12.0 Hz, 1H), 1.71-1.55 (m, 4H), 1.32 (d, J=7.0 Hz, 6H). LC-MS ($ES^+$): m/z 762.4 $[M+H]^+$.

Example 92

Example 92 was prepared following the synthesis of Example 61

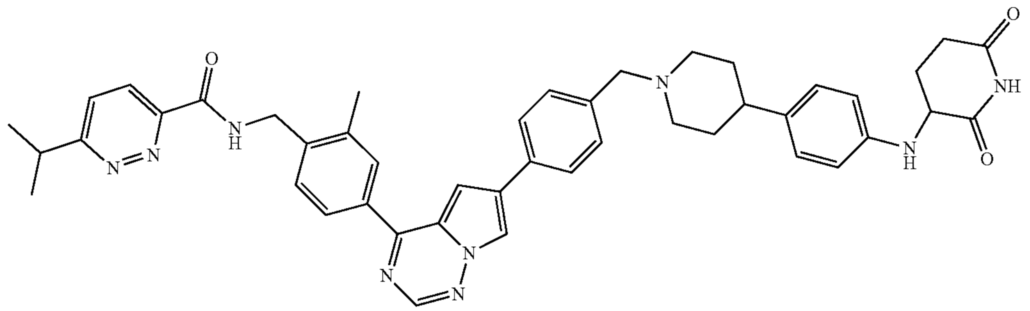 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(C)C)nn1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-6-isopropyl-pyridazine-3-carboxamide. $^1$H NMR (400 MHz, DMSO-$d_6$) δ=10.78 (s, 1H), 9.84 (t, J=6.2 Hz, 1H), 8.71 (d, J=1.4 Hz, 1H), 8.60 (s, 1H), 8.40 (s, 1H), 8.17 (d, J=8.6 Hz, 1H), 8.07-7.99 (m, 2H), 7.92-7.84 (m, 3H), 7.61 (d, J=1.4 Hz, 1H), 7.50 (d, J=7.8 Hz, 1H), 7.37 (d, J=8.2 Hz, 2H), 6.96 (d, J=8.4 Hz, 2H), 6.60 (d, J=8.4 Hz, 2H), 5.65 (d, J=7.4 Hz, 1H), 4.65 (d, J=6.2 Hz, 2H), 4.30-4.20 (m, 1H), 3.51 (s, 2H), 2.91 (d, J=10.0 Hz, 2H), 2.81-2.58 (m, 1H), 2.81-2.58 (m, 1H), 2.54-2.52 (m, 2H), 2.33 (br s, 1H), 2.14-1.95 (m, 4H), 1.85 (dt, J=7.6, 12.2 Hz, 1H), 1.73-1.56 (m, 4H), 1.36 (d, J=7.0 Hz, 6H). LC-MS ($ES^+$): m/z 762.6 $[M+H]^+$.

Example 93

Example 93 was prepared following the synthesis of Example 61

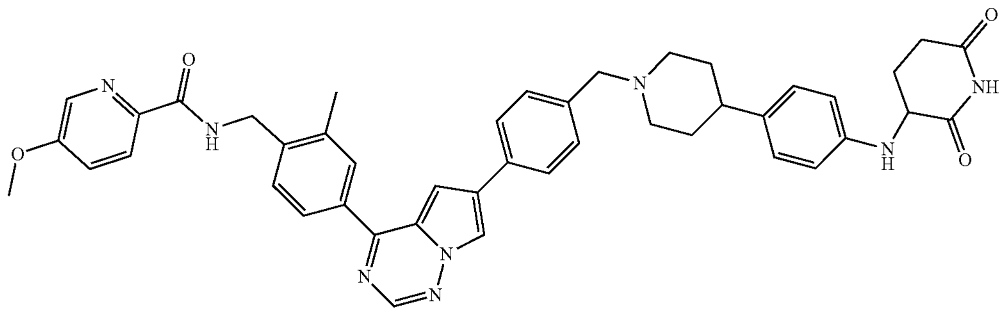 [SMILES: COc1ccc(C(=O)NCc2ccc(-c3ncnn4cc(-c5ccc(CN6CCC(c7ccc(NC8CCC(=O)NC8=O)cc7)CC6)cc5)cc34)cc2C)nc1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-5-methoxy-pyridine-2-carboxamide. $^1$H NMR (400 MHz, DMSO-$d_6$) δ=10.76 (s, 1H), 9.20 (t, J=6.0 Hz, 1H), 8.69 (s, 1H), 8.59 (s, 1H), 8.36 (d, J=2.8 Hz, 1H), 8.32 (s, 1H), 8.08-7.98 (m, 3H), 7.88 (d, J=8.0 Hz, 2H), 7.61 (s, 1H), 7.58 (dd, J=2.8, 8.8 Hz, 1H), 7.45 (d, J=8.0 Hz, 1H), 7.37 (d, J=8.0 Hz, 2H), 6.96 (d, J=8.4 Hz, 2H), 6.60 (d, J=8.4 Hz, 2H), 5.63 (d, J=7.2 Hz, 1H), 4.59 (d, J=6.4 Hz, 2H), 4.30-4.21 (m, 1H), 3.92 (s, 3H), 3.51 (s, 2H), 2.91 (d, J=11.2 Hz, 2H), 2.80-2.64 (m, 1H), 2.61-2.52 (m, 3H), 2.39-2.29 (m, 2H), 2.14-1.97 (m, 3H), 1.91-1.78 (m, 1H), 1.72-1.53 (m, 4H). LC-MS ($ES^+$): m/z 749.6 $[M+H]^+$.

Example 94

Example 94 was prepared following the synthesis of Example 61

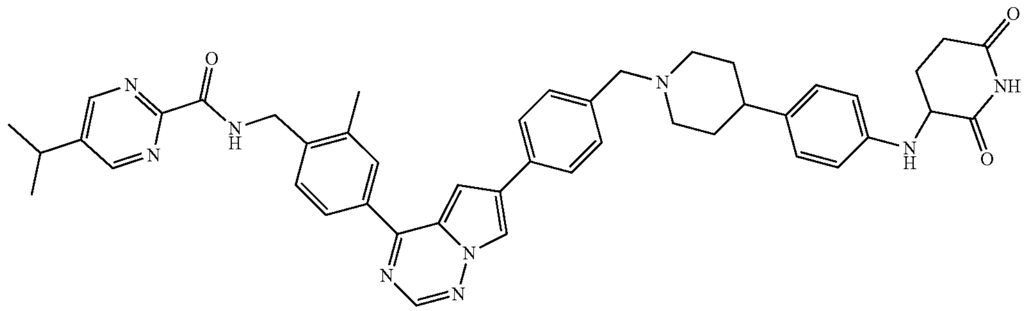 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ncc(C(C)C)cn1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-5-isopropyl-pyrimidine-2-carboxamide. $^1$H NMR (400 MHz, DMSO-$d_6$) δ=10.78 (s, 1H), 9.46 (t, J=6.4 Hz, 1H), 8.92 (s, 2H), 8.71 (s, 1H), 8.61 (s, 1H), 8.37 (s, 1H), 8.07-7.98 (m, 2H), 7.89 (d, J=8.0 Hz, 2H), 7.62 (s, 1H), 7.49 (d, J=7.8 Hz, 1H), 7.38 (d, J=8.1 Hz, 2H), 6.97 (d, J=8.4 Hz, 2H), 6.61 (d, J=8.4 Hz, 2H), 5.65 (d, J=7.4 Hz, 1H), 4.61 (d, J=6.0 Hz, 2H), 4.32-4.21 (m, 1H), 3.95-3.83 (m, 1H), 3.52 (br s, 4H), 3.09 (td, J=6.8, 13.7 Hz, 2H), 2.96-2.89 (m, 2H), 2.81-2.63 (m, 2H), 2.34 (d, J=1.8 Hz, 2H), 2.16-2.05 (m, 2H), 1.71-1.65 (m, 2H), 1.49-1.42 (m, 2H), 1.32 (d, J=7.0 Hz, 6H). LC-MS ($ES^+$): m/z 762.7 $[M+H]^+$.

Example 95

Example 95 was prepared following the synthesis of Example 61

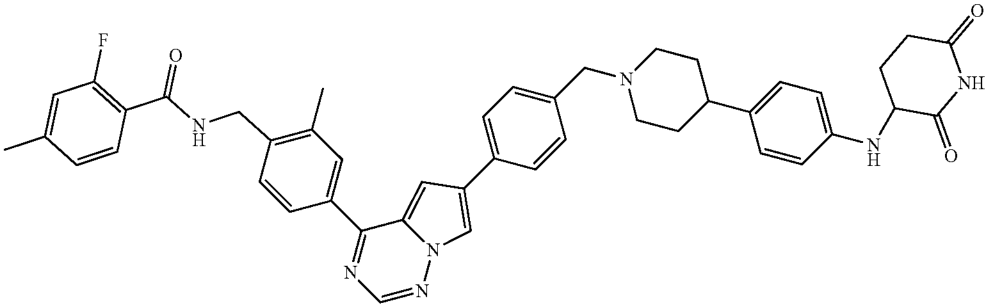 [SMILES: Cc1ccc(C(=O)NCc2ccc(-c3ncnn4cc(-c5ccc(CN6CCC(c7ccc(NC8CCC(=O)NC8=O)cc7)CC6)cc5)cc34)cc2C)c(F)c1]

N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]-2-fluoro-4-methyl-benzamide. $^1$H NMR (400 MHz, DMSO-$d_6$) δ=10.84-10.71 (m, 1H), 8.85-8.77 (m, 1H), 8.70 (s, 1H), 8.61 (s, 1H), 8.07 (d, J=8.8 Hz, 1H), 8.02 (s, 1H), 7.89 (d, J=8.2 Hz, 2H), 7.64-7.58 (m, 2H), 7.52 (d, J=7.8 Hz, 1H), 7.38 (d, J=8.2 Hz, 2H), 7.18-7.11 (m, 2H), 6.96 (d, J=8.3 Hz, 2H), 6.60 (d, J=8.2 Hz, 2H), 5.63 (d, J=7.6 Hz, 1H), 4.56 (d, J=5.7 Hz, 2H), 4.29-4.21 (m, 1H), 3.51 (s, 2H), 3.39 (s, 2H), 2.95-2.87 (m, 2H), 2.64-2.54 (m, 2H), 2.37 (s, 3H), 2.12-1.98 (m, 3H), 1.91-1.80 (m, 1H), 1.73-1.57 (m, 4H). LC-MS (ES$^+$): m/z 750.3 [M+H]$^+$.

Example 96

Example 96 was prepared following the synthesis of Example 61

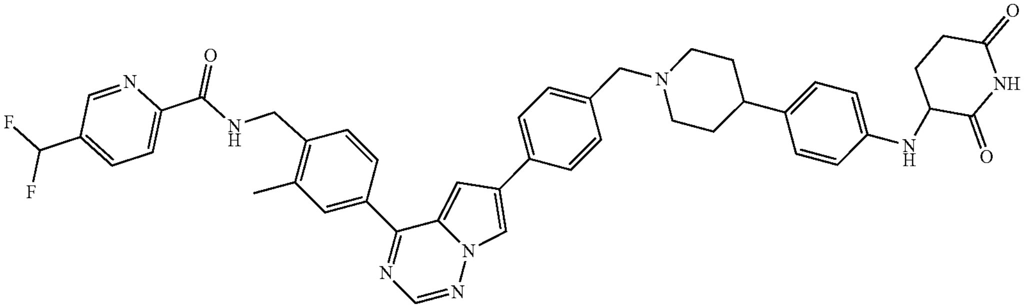 [SMILES: Cc1cc(-c2ncnn3cc(-c4ccc(CN5CCC(c6ccc(NC7CCC(=O)NC7=O)cc6)CC5)cc4)cc23)ccc1CNC(=O)c1ccc(C(F)F)cn1]

5-(difluoromethyl)-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]pyridine-2-carboxamide. $^1$H NMR (400 MHz, DMSO-$d_6$) δ=10.78 (s, 1H), 9.57 (t, J=6.0 Hz, 1H), 8.91 (s, 1H), 8.70 (d, J=1.2 Hz, 1H), 8.60 (s, 1H), 8.27 (s, 1H), 8.25-8.20 (m, 2H), 8.07-7.99 (m, 2H), 7.88 (d, J=8.0 Hz, 2H), 7.61 (d, J=1.2 Hz, 1H), 7.47 (d, J=8.4 Hz, 1H), 7.37 (d, J=8.4 Hz, 2H), 6.95 (d, J=8.8 Hz, 2H), 6.60 (d, J=8.8 Hz, 2H), 5.65 (d, J=7.2 Hz, 1H), 4.62 (d, J=6.0 Hz, 2H), 4.31-4.21 (m, 1H), 3.50 (s, 2H), 2.91 (d, J=10.4 Hz, 2H), 2.78-2.64 (m, 1H), 2.49-2.49 (m, 3H), 2.38-2.29 (m, 2H), 2.13-1.97 (m, 3H), 1.91-1.82 (m, 1H), 1.73-1.53 (m, 4H). LC-MS (ES$^+$): m/z 769.6 [M+H]$^+$.

Example 97. Synthesis of 3-tert-butoxy-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]azetidine-1-carboxamide

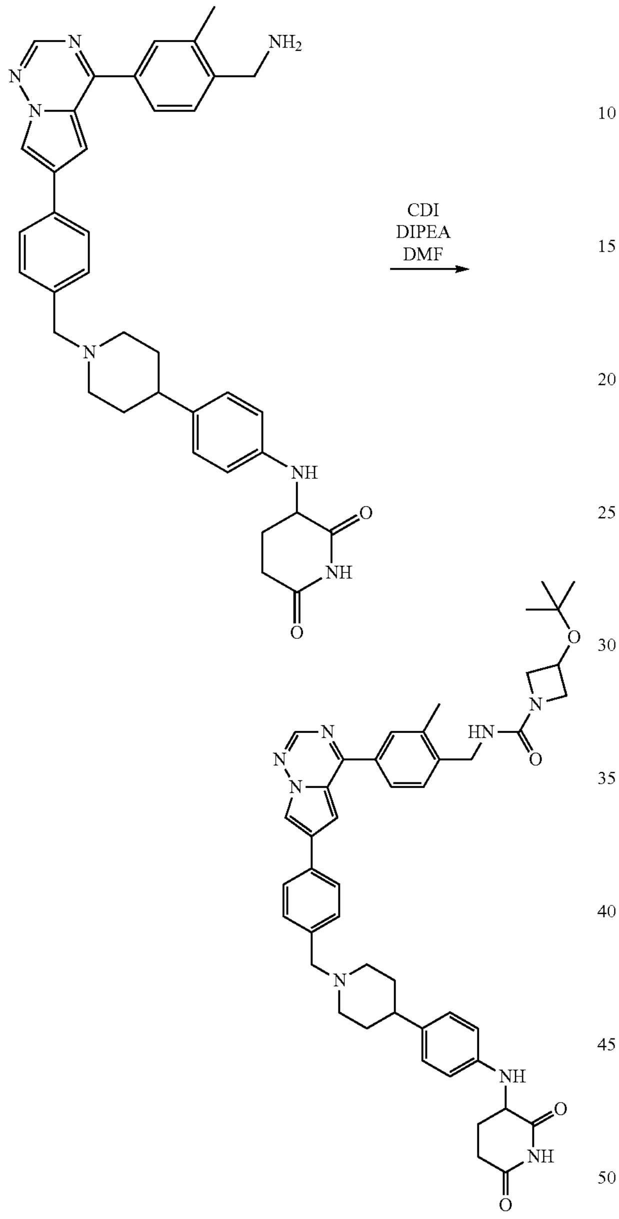

To a solution of 3-((4-(1-(4-(4-(4-(aminomethyl)-3-methylphenyl)pyrrolo[2,1-f][1,2,4]triazin-6-yl)benzyl)piperidin-4-yl)phenyl)amino)piperidine-2,6-dione (80 mg, 130.35 μmol) in DMF (0.8 mL) was added di(imidazol-1-yl)methanone (31.70 mg, 195.52 μmol) and DIPEA (50.54 mg, 391.04 μmol, 68.11 μL). The mixture was stirred at 25° C. for 0.5 hour. Then 3-(tert-butoxy)azetidine (18.52 mg, 143.38 μmol) was added to the reaction, and stirred for 11.5 hours. The progress of the reaction was monitored by LC-MS. The product was purified by prep-HPLC. Compound 3-(tert-butoxy)-N-(4-(6-(4-((4-(4-((2,6-dioxopiperidin-3-yl)amino)phenyl)piperidin-1-yl)methyl)phenyl)pyrrolo[2,1-f][1,2,4]triazin-4-yl)-2-methylbenzyl)azetidine-1-carboxamide (17.81 mg, 22.35 μmol, 17.15% yield) was obtained as a yellow solid. $^1$H NMR (400 MHz, DMSO-$d_6$) δ ppm 1.13 (s, 9H) 1.56-1.72 (m, 4H) 1.85 (br dd, J=12.4, 4.63 Hz, 1H) 1.99-2.07 (m, 2H) 2.42 (s, 3H) 2.54-2.62 (m, 2H) 2.66-2.80 (m, 1H) 2.92 (br d, J=11.2 Hz, 2H) 3.51 (s, 2H) 3.63 (dd, J=8.8, 5.2 Hz, 2H) 4.01-4.10 (m, 2H) 4.28 (br d, J=5.6 Hz, 2H) 4.44-4.54 (m, 1H) 5.63 (d, J=7.6 Hz, 1H) 6.60 (d, J=8.4 Hz, 2H) 6.91 (s, 1H) 6.96 (d, J=8.4 Hz, 2H) 7.38 (d, J=8.0 Hz, 2H) 7.45 (d, J=8.0 Hz, 1H) 7.61 (d, J=1.2 Hz, 1H) 7.89 (d, J=8.0 Hz, 2H) 7.97 (s, 1H) 8.02-8.11 (m, 1H) 8.60 (s, 1H) 8.69 (d, J=1.2 Hz, 1H) 10.76 (br s, 1H). LC-MS (ES$^+$): m/z 769.4 [M+H]$^+$.

Example 98

Example 98 was prepared following the synthesis of Example 97

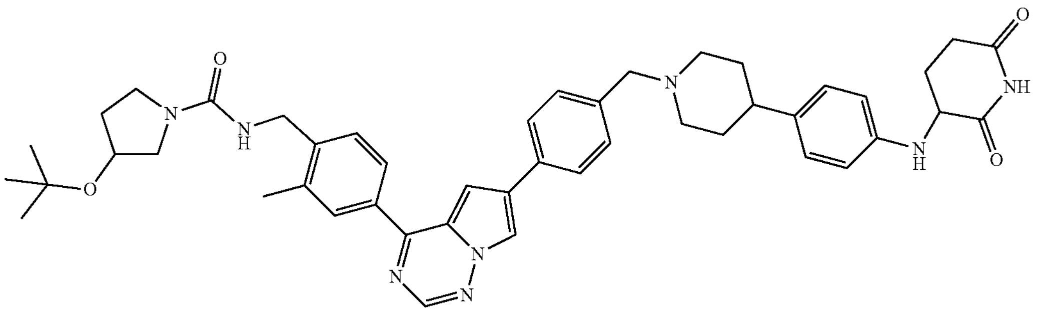 [SMILES: Cc1cc(-c2ncnn3cc(-c4ccc(CN5CCC(c6ccc(NC7CCC(=O)NC7=O)cc6)CC5)cc4)cc23)ccc1CNC(=O)N1CCC(OC(C)(C)C)C1]

3-tert-butoxy-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-methyl-phenyl]methyl]pyrrolidine-1-carboxamide. $^{1}$H NMR (400 MHz, DMSO-$d_6$) δ ppm 1.16 (s, 10H) 1.52-1.65 (m, 1H) 1.54-1.75 (m, 4H) 1.85 (br dd, J=12.0, 4.4 Hz, 1H) 1.96-2.15 (m, 4H) 2.43 (s, 4H) 2.52-2.81 (m, 4H) 2.55-2.55 (m, 1H) 2.92 (br d, J=11.2 Hz, 2H) 3.06 (dd, J=10.4, 4.4 Hz, 1H) 3.51 (s, 3H) 4.31 (br d, J=5.6 Hz, 4H) 5.63 (d, J=7.6 Hz, 1H) 6.60 (d, J=8.4 Hz, 2H) 6.71 (s, 1H) 6.96 (d, J=8.4 Hz, 2H) 7.38 (d, J=8.0 Hz, 2H) 7.48 (s, 1H) 7.61 (d, J=1.6 Hz, 1H) 7.89 (d, J=8.19 Hz, 2H) 7.97 (s, 1H) 8.05 (d, J=8.0 Hz, 1H) 8.60 (s, 1H) 8.69 (d, J=1.6 Hz, 1H) 10.76 (s, 1H). LC-MS ($ES^+$): m/z 783.7 $[M+H]^+$.

Example 99

Example 99 was prepared following the synthesis of Example 97

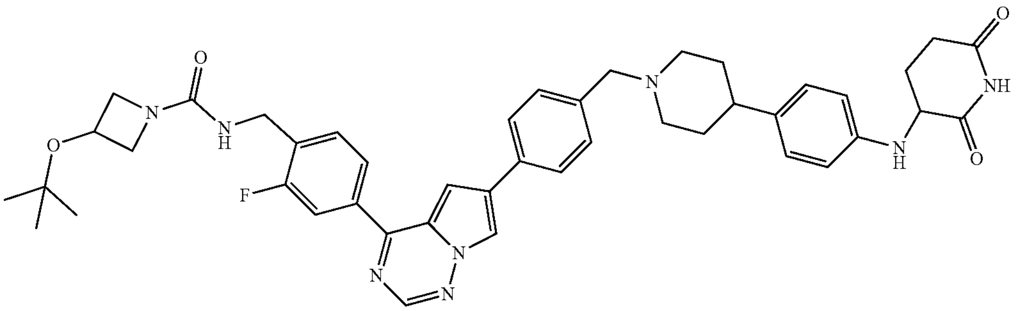 [SMILES: CC(C)(C)OC1CN(C(=O)NCc2ccc(-c3ncnn4cc(-c5ccc(CN6CCC(c7ccc(NC8CCC(=O)NC8=O)cc7)CC6)cc5)cc34)cc2F)C1]

3-tert-butoxy-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-fluoro-phenyl]methyl]azetidine-1-carboxamide. $^{1}$H NMR (400 MHz, DMSO-$d_6$) δ 10.80 (s, 1H), 9.36 (brs, 1H), 8.84 (d, J=1.6 Hz, 1H), 8.12 (s, 1H), 8.10-8.08 (m, 3H), 7.92 (d, J=1.2 Hz, 1H), 7.78 (brs, 1H), 7.61-7.55 (m, 3H), 7.21-6.92 (m, 3H), 6.30 (d, J=8.8 Hz, 2H), 4.50-4.49 (m, 1H), 4.36 (t, J=6.0 Hz, 5H), 4.05 (t, J=15.6 Hz, 2H), 3.50-3.40 (m, 2H), 3.10-3.00 (m, 2H), 2.67-2.50 (m, 3H), 2.49-2.40 (m, 2H), 2.10-2.07 (m, 1H), 2.06-1.75 (m, 5H), 1.13 (s, 9H). LC-MS ($ES^+$): m/z 773.54 $[M+H]^+$.

Example 100

Example 100 was prepared following the synthesis of Example 97

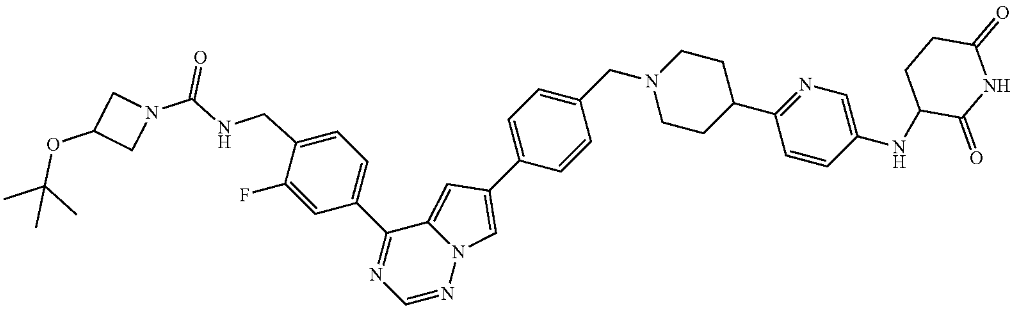 [SMILES: CC(C)(C)OC1CN(C(=O)NCc2ccc(-c3ncnn4cc(-c5ccc(CN6CCC(c7ccc(NC8CCC(=O)NC8=O)cn7)CC6)cc5)cc34)cc2F)C1]

3-tert-butoxy-N-[[4-[6-[4-[[4-[5-[(2,6-dioxo-3-piperidyl)amino]-2-pyridyl]-1-piperidyl]methyl]phenyl]pyrrolo[2,1-f][1,2,4]triazin-4-yl]-2-fluoro-phenyl]methyl]azetidine-1-carboxamide. $^1$H NMR (400 MHz, DMSO-$d_6$) δ 10.85 (s, 1H), 9.50 (bs, 1H), 8.85 (d, J=1.3 Hz, 1H), 8.67 (s, 1H), 8.12-8.05 (m, 3H), 8.01 (s, 1H), 7.94 (d, J=6.1 Hz, 1H), 7.79 (s, 1H), 7.63-7.55 (m, 3H), 7.40-6.95 (m, 3H), 4.47-4.34 (m, 6H), 4.05 (t, J=7.7 Hz, 2H), 3.64-3.58 (m, 4H), 3.24-3.08 (m, 2H), 2.90-2.71 (m, 1H), 2.75-2.67 (m, 1H), 2.69-2.62 (m, 1H), 2.08-2.04 (m, 3H), 1.96-1.89 (m, 3H), 1.13 (s, 9H). LC-MS (ES$^-$): m/z 772.26 [M−H]$^-$.

Example 101. Synthesis of 4-(difluoromethyl)-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-fluoro-phenyl]methyl]benzamide

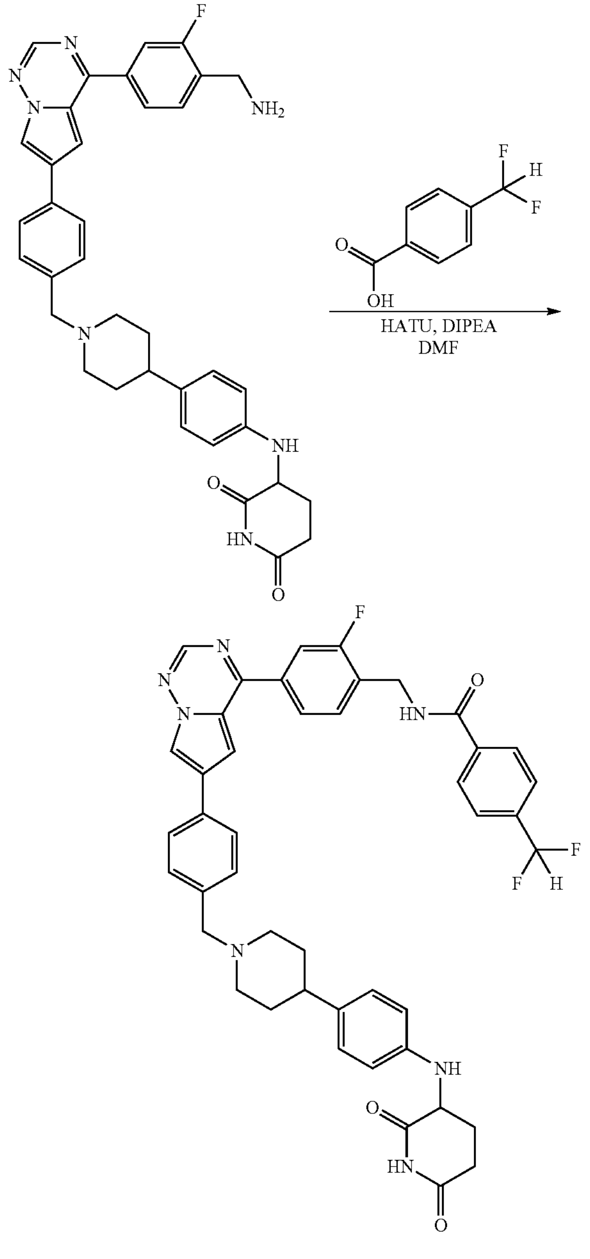

To a stirred solution of 3-[4-[1-[[4-[4-[4-(aminomethyl)-3-fluoro-phenyl]pyrrolo[2,1-f][1,2,4]triazin-6-yl]phenyl]methyl]-4-piperidyl]anilino]piperidine-2,6-dione HCl salt (0.1 g, 152.86 μmol) in DMF (2 mL) was added DIPEA (118.54 mg, 917.19 μmol, 159.75 μL) and the reaction was stirred for 5 minutes. This is followed by the addition of 4-(difluoromethyl)benzoic acid (39.47 mg, 229.30 μmol). Finally, HATU (145.31 mg, 382.16 μmol) was added, and the reaction was stirred at room temperature for 2 hours. The reaction was monitored by TLC and LC-MS. After completion, reaction mixture was poured onto ice cold water and the crude product was purified by prep-HPLC to afford 4-(difluoromethyl)-N-[[4-[6-[4-[[4-[4-[(2,6-dioxo-3-piperidyl)amino]phenyl]-1-piperidyl]methyl]phenyl]pyrrolo[2,1-f][1,2,4]triazin-4-yl]-2-fluoro-phenyl]methyl]benzamide formic acid salt (18.9 mg, 22.94 μmol, 15.01% yield) as a light green solid. $^1$H NMR (400 MHz, DMSO-$d_6$) δ 10.88 (s, 1H), 9.56 (t, J=5.8 Hz, 1H), 8.75 (s, 1H), 8.64 (s, 1H), 8.37 (bs, 1H), 8.11-8.06 (m, 3H), 7.98 (d, J=12.0 Hz, 1H), 7.91 (d, J=5.8 Hz, 2H), 7.72-7.65 (m, 3H), 7.62 (t, J=8.0 Hz, 1H), 7.38 (d, J=8.0 Hz, 2H), 7.26-6.95 (m, 3H), 6.60 (d, J=8.0 Hz, 2H), 5.63-5.60 (m, 1H), 4.67-4.56 (m, 2H), 4.25-4.23 (m, 1H), 3.51 (s, 2H), 2.93-2.90 (m, 2H), 2.80-2.70 (m, 1H), 2.60-2.59 (m, 1H), 2.60-2.58 (m, 1H), 2.39-2.35 (m, 1H), 2.10-2.00 (m, 3H), 1.90-1.80 (m, 1H), 1.69-1.57 (m, 4H). LC-MS (ES$^-$): m/z 772.16 [M−H]$^-$.

Example 102. Synthesis of 4-(difluoromethyl)-N-[[4-[6-[4-[[4-[5-[(2,6-dioxo-3-piperidyl)amino]-2-pyridyl]-1-piperidyl]methyl]phenyl]pyrrolo[2,1-f][1,2,4]triazin-4-yl]-2-fluoro-phenyl]methyl]benzamide

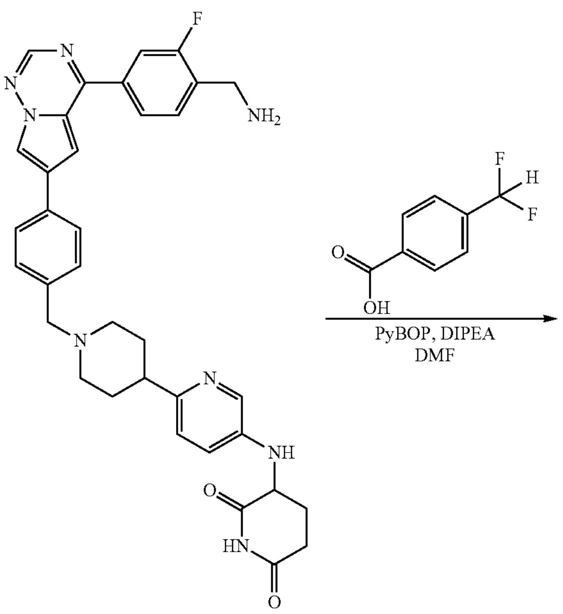

-continued

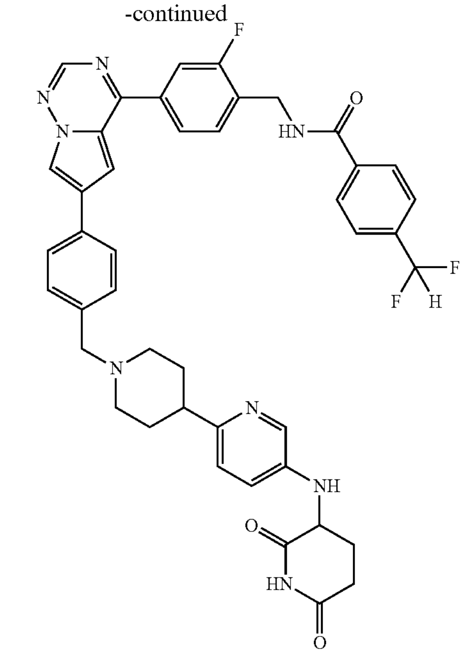

To a stirred solution of 3-[[6-[1-[[4-[4-[4-(aminomethyl)-3-fluoro-phenyl]pyrrolo[2,1-f][1,2,4]triazin-6-yl]phenyl]methyl]-4-piperidyl]-3-pyridyl]amino]piperidine-2,6-dione HCl salt (0.1 g, 152.63 μmol) and 4-(difluoromethyl)benzoic acid (39.41 mg, 228.95 μmol-) in DMF (3 mL), N-ethyl-N-isopropyl-propan-2-amine (118.36 mg, 915.80 μmol, 159.52 μL) was added and stirred for 5 minutes at 0° C. N,N,N',N'-tetramethyl-1-(3-oxido-2,3-dihydrotriazolo[4,5-b]pyridin-3-ium-1-yl)methanediamine; hexafluorophosphate (116.69 mg, 305.27 mol) was added and the reaction mixture was stirred at room temperature for 16 hours. The reaction was monitored by TLC and LC-MS. Upon completion of the reaction, the reaction mixture was concentrated under reduced pressure and the gummy crude product was purified by prep-HPLC using TFA buffer to afford 4-(difluoromethyl)-N-[[4-[6-[4-[[4-[5-[(2,6-dioxo-3-piperidyl)amino]-2-pyridyl]-1-piperidyl]methyl]phenyl]pyrrolo[2,1-f][1,2,4]triazin-4-yl]-2-fluoro-phenyl]methyl]benzamide TFA salt (21.5 mg, 23.90 μmol, 15.66% yield) as a yellow solid. $^1$H NMR (400 MHz, DMSO-$d_6$) δ 10.86 (s, 1H), 9.35 (t, J=5.8 Hz, 1H), 8.85 (d, J=1.3 Hz, 1H), 8.67 (s, 1H), 8.11-8.06 (m, 5H), 8.01-7.97 (m, 2H), 7.79 (d, J=1.3 Hz, 1H), 7.72 (d, J=8.2 Hz, 2H), 7.65-7.61 (m, 3H), 7.24 (d, J=14.9 Hz, 1H), 7.11 (s, 1H), 6.98 (d, J=5.7 Hz, 1H), 4.67 (d, J=5.7 Hz, 2H), 4.44 (bs, 1H), 4.37 (bs, 2H), 3.60-3.49 (m, 2H), 3.21-2.96 (m, 3H), 2.78-2.67 (m, 1H), 2.63-2.58 (m, 1H), 2.09-2.06 (m, 6H). LC-MS (ES$^+$): m/z 771.12 [M−H]$^-$.

Example 103. Synthesis of 3-[4-[1-[[4-[4-[4-[[4-(2,2-dimethylpropyl)-2-oxo-piperazin-1-yl]methyl]-3-methyl-phenyl]pyrrolo[2,1-f][1,2,4]triazin-6-yl]phenyl]methyl]-4-piperidyl]anilino]piperidine-2,6-dione

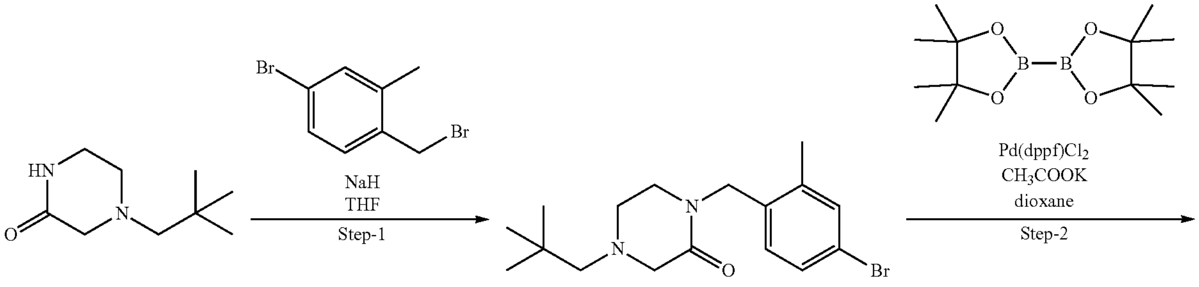

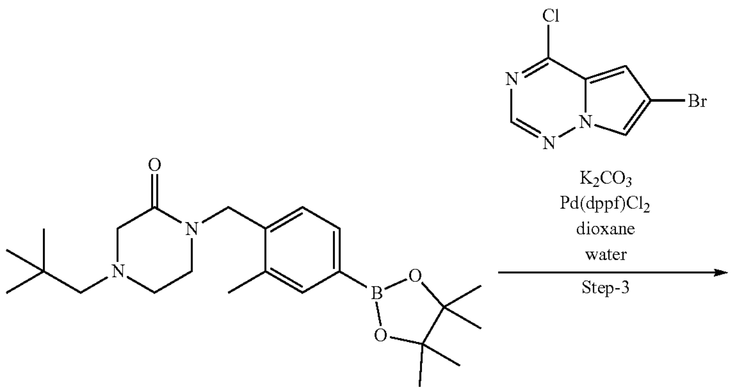

-continued

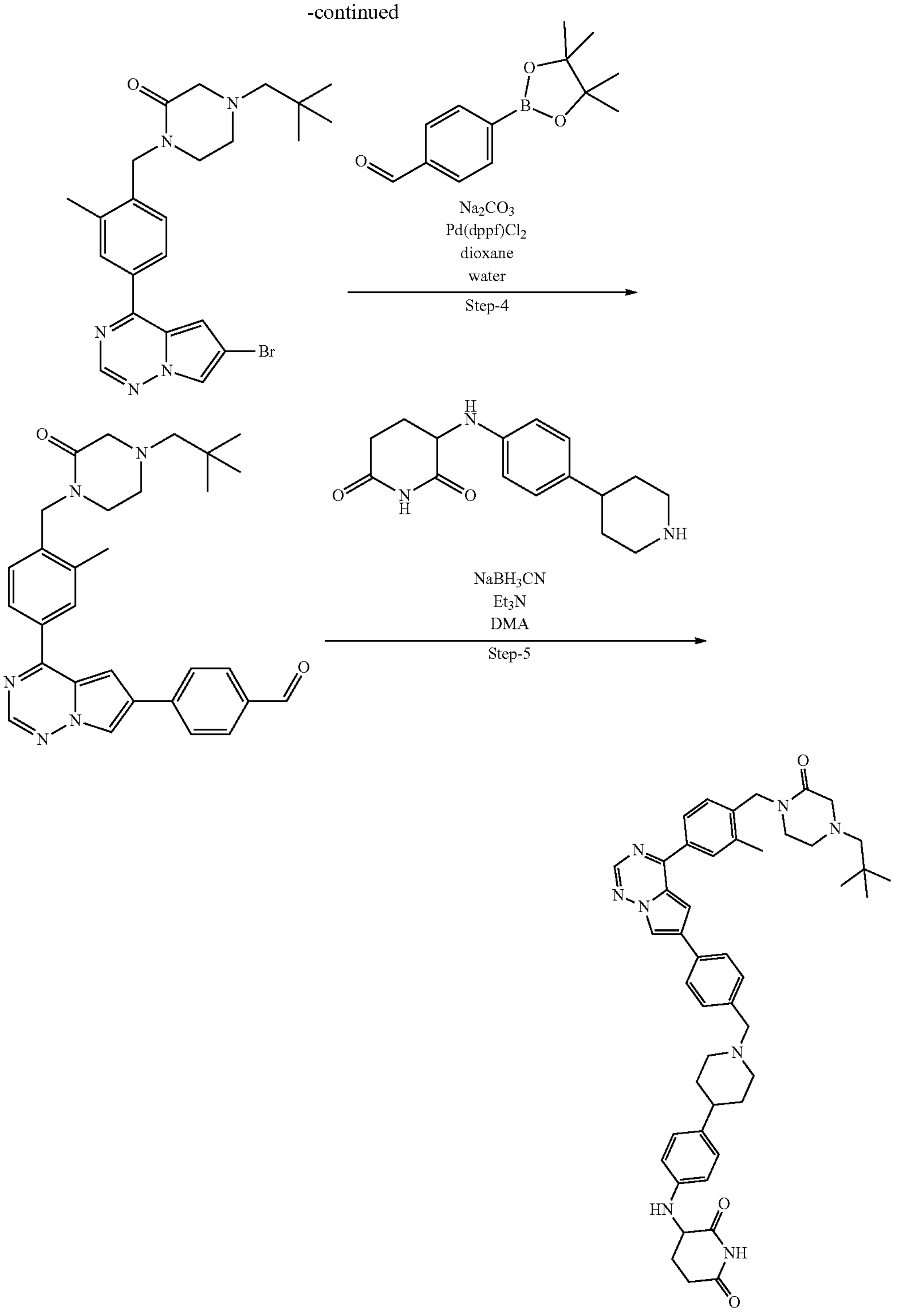

To a solution of 4-bromo-1-(bromomethyl)-2-methyl-benzene (744.19 mg, 2.82 mmol) in THF (12 mL) was added sodium hydride (60% dispersion in mineral oil, 84.57 mg, 3.52 mmol) and the reaction was stirred at 0° C. for 30 minutes. 4-(2,2-dimethylpropyl)piperazin-2-one (400 mg, 2.35 mmol) was added to the mixture, and it was stirred at 25° C. for 2 hours. The progress of the reaction was monitored by TLC. The reaction mixture was concentrated under reduced pressure to remove dioxane. The residue was diluted with water (60 mL) and extracted with ethyl acetate (50 mL×3). The combined organic layers were washed with brine (100 mL×3), dried over anhydrous sodium sulfate, filtered, and concentrated under reduced pressure. Compound 1-[(4-bromo-2-methyl-phenyl)methyl]-4-(2,2-dimethylpropyl)piperazin-2-one (478 mg, 1.35 mmol, 57.59% yield) was obtained as a white solid. $^1H$ NMR (400 MHz, DMSO-$d_6$) δ=7.46-7.33 (m, 2H), 7.03 (d, J=8.2 Hz, 1H), 4.49 (s, 2H), 3.19 (s, 2H), 3.11 (t, J=5.4 Hz, 2H), 2.76-2.66 (m, 2H), 2.23 (s, 3H), 2.13 (s, 2H), 0.85 (s, 9H).

Step-2:

To a solution of 1-(4-bromo-2-methylbenzyl)-4-neopentylpiperazin-2-one (450 mg, 1.27 mmol) and 4,4,4',4',5,5,5',5'-octamethyl-2,2'-bi(1,3,2-dioxaborolane) (388.13 mg, 1.53 mmol) in dioxane (10 mL) was added potassium acetate (375.02 mg, 3.82 mmol) and $Pd(dppf)Cl_2{\cdot}CH_2Cl_2$ (27.96 mg, 38.21 μmol). The mixture was stirred at 100° C. for 12 hours. The reaction was monitored by LC-MS. The reaction mixture was concentrated under reduced pressure to remove dioxane. The residue was diluted with $H_2O$ (60 mL) and extracted with ethyl acetate (50 mL×3). The combined organic layers were washed with brine (100 mL×3), dried over anhydrous sodium sulfate, filtered, and concentrated under reduced pressure. The residue was purified by column chromatography (silica gel, petroleum ether/ethyl acetate=50/1 to 20/1). Compound 1-(2-methyl-4-(4,4,5,5-tetramethyl-1,3,2-dioxaborolan-2-yl)benzyl)-4-neopentylpiperazin-2-one (448 mg, 87.85% yield) was obtained as a yellow oil. LC-MS ($ES^+$): z 401.3 $[M+H]^+$.

Step-3:

A solution of 1-(2-methyl-4-(4,4,5,5-tetramethyl-1,3,2-dioxaborolan-2-yl)benzyl)-4-neopentylpiperazin-2-one (448 mg, 1.12 mmol), 6-bromo-4-chloropyrrolo[2,1-f][1,2,4]triazine (260.13 mg, 1.12 mmol) in dioxane (10 mL) and water (2.5 mL) was added $Pd(dppf)Cl_2{\cdot}CH_2Cl_2$ (81.88 mg, 111.90 μmol), potassium carbonate, anhydrous (309.30 mg, 2.24 mmol), and the mixture was stirred at 80° C. for 4 hours under $N_2$ atmosphere. The reaction was monitored by LC-MS. The reaction mixture was concentrated under reduced pressure to remove dioxane, poured into saturated $NH_4Cl$ aqueous solution (20 mL) and extracted with ethyl acetate (10 mL×3). The combined organic layers were washed with brine (50 mL), dried over anhydrous sodium sulfate, filtered and concentrated. The residue was purified by column chromatography (silica gel, petroleum ether/ethyl acetate=3:1) Compound 1-(4-(6-bromopyrrolo[2,1-f][1,2,4]triazin-4-yl)-2-methylbenzyl)-4-neopentylpiperazin-2-one (382 mg, 812.07 μmol, 72.57% yield) was obtained as a white solid. $^1H$ NMR (400 MHz, $CDCl_3$) δ=8.52 (s, 1H), 7.91-7.86 (m, 3H), 7.33 (d, J=8.1 Hz, 1H), 7.12 (d, J=1.6 Hz, 1H), 4.88 (br d, J=7.9 Hz, 1H), 4.75 (s, 2H), 3.42 (br s, 2H), 3.23 (br s, 2H), 2.81 (br s, 2H), 2.44 (s, 3H), 2.23 (br d, J=15.4 Hz, 2H), 1.26 (s, 3H), 0.94 (br s, 9H). LC-MS ($ES^+$): m/z 472 $[M+H]^+$.

Step-4:

A solution of 1-(4-(6-bromopyrrolo[2,1-f][1,2,4]triazin-4-yl)-2-methylbenzyl)-4-neopentylpiperazin-2-one (300 mg, 637.75 μmol), 4-(4,4,5,5-tetramethyl-1,3,2-dioxaborolan-2-yl)benzaldehyde (162.81 mg, 701.52 μmol) in dioxane (10 mL) and $H_2O$ (2.5 mL) was added $Pd(dppf)Cl_2{\cdot}CH_2Cl_2$ (23.33 mg, 31.89 μmol), sodium carbonate (67.59 mg, 637.75 mol) and the mixture was stirred at 100° C. for 12 hours under $N_2$ atmosphere. The reaction was monitored by LC-MS. The reaction mixture was concentrated under reduced pressure to remove dioxane. poured into saturated $NH_4Cl$ aqueous solution (10 mL), and extracted with ethyl acetate (10 mL×3). The combined organic layer were washed with brine (30 mL), dried over anhydrous sodium sulfate, filtered, and concentrated. The residue was purified by column chromatography (silica gel, petroleum ether/ethyl acetate=3:1). Compound 4-(4-(3-methyl-4-((4-neopentyl-2-oxopiperazin-1-yl)methyl)phenyl)pyrrolo[2,1-f][1,2,4]triazin-6-yl)benzaldehyde (228 mg, 460.04 μmol, 72.13% yield) was obtained as a white solid. $^1H$ NMR (400 MHz, $CDCl_3$) δ=10.06 (s, 1H), 8.56 (s, 1H), 8.27 (d, J=1.6 Hz, 1H), 7.96 (d, J=7.6 Hz, 3H), 7.88 (d, J=8.2 Hz, 2H), 7.39-7.34 (m, 2H), 7.28 (s, 1H), 4.77 (s, 2H), 3.42 (s, 2H), 3.28-3.23 (m, 2H), 2.81 (t, J=5.3 Hz, 2H), 2.47 (s, 3H), 2.21-2.18 (m, 2H), 0.93 (s, 9H). LC-MS ($ES^+$): m/z 496.2 $[M+H]^+$.

Step-5:

To a solution of 4-(4-(3-methyl-4-((4-neopentyl-2-oxopiperazin-1-yl)methyl)phenyl)pyrrolo[2,1-f][1,2,4]triazin-6-yl)benzaldehyde (60 mg, 121.06 μmol) was added 3-((4-(piperidin-4-yl)phenyl)amino)piperidine-2,6-dione (41.75 mg, 145.27 μmol), and the mixture stirred at 25° C. for 1 hour. Then sodium cyanoborohydride (76.08 mg, 1.21 mmol) was added and heated at 100° C. for 12 hours under $N_2$ atmosphere. The reaction was monitored by LC-MS. The residue was purified by reverse phase prep-HPLC (C18, 0.05% HCl in water/MeCN). Compound 3-((4-(1-(4-(4-(3-methyl-4-((4-neopentyl-2-oxopiperazin-1-yl)methyl)phenyl)pyrrolo[2,1-f][1,2,4]triazin-6-yl)benzyl)piperidin-4-yl)phenyl)amino)piperidine-2,6-dione 2HCl salt (24.88 mg, 29.38 μmol, 24.27% yield) was obtained as a green gum. $^1H$ NMR (400 MHz, DMSO-$d_6$) δ=10.81 (s, 1H), 8.83 (d, J=1.5 Hz, 1H), 8.65 (s, 1H), 8.08-8.00 (m, 4H), 7.77-7.66 (m, 3H), 7.58 (d, J=7.9 Hz, 1H), 6.98 (d, J=8.6 Hz, 2H), 6.69 (d, J=8.6 Hz, 2H), 4.72 (br d, J=9.4 Hz, 2H), 4.37-4.26 (m, 3H), 4.04 (br s, 2H), 3.74 (br dd, J=1.7, 3.7 Hz, 2H), 3.42 (br d, J=11.1 Hz, 4H), 3.15 (br s, 2H), 3.09-2.96 (m, 2H), 2.78-2.62 (m, 2H), 2.60 (br s, 1H), 2.46 (s, 3H), 2.14-1.99 (m, 3H), 1.95-1.81 (m, 3H), 1.12 (s, 9H). LC-MS ($ES^+$): z 767.1 $[M+H]^+$.

Example 104. Synthesis of 5-tert-butyl-N-[[4-[6-[4-[2-[4-[4-(2,6-dioxo-3-piperidyl)phenyl]-1-piperidyl]ethoxy]phenyl]pyrrolo[2,1-f][1,2,4]triazin-4-yl]-2-methyl-phenyl]methyl]-1,2,4-oxadiazole-3-carboxamide

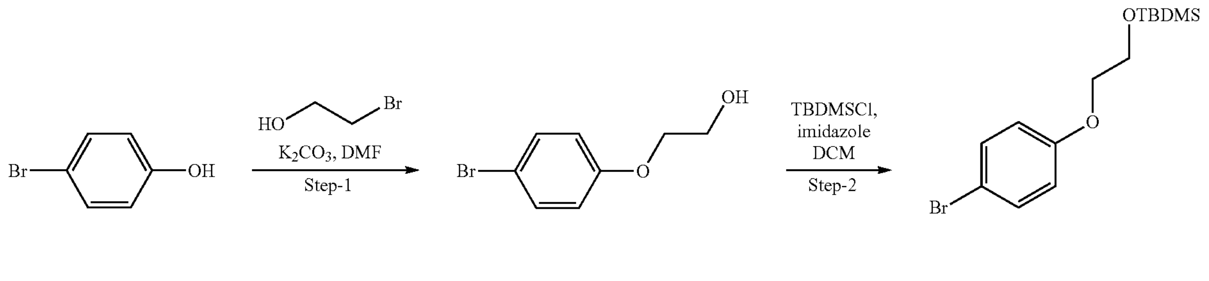

-continued
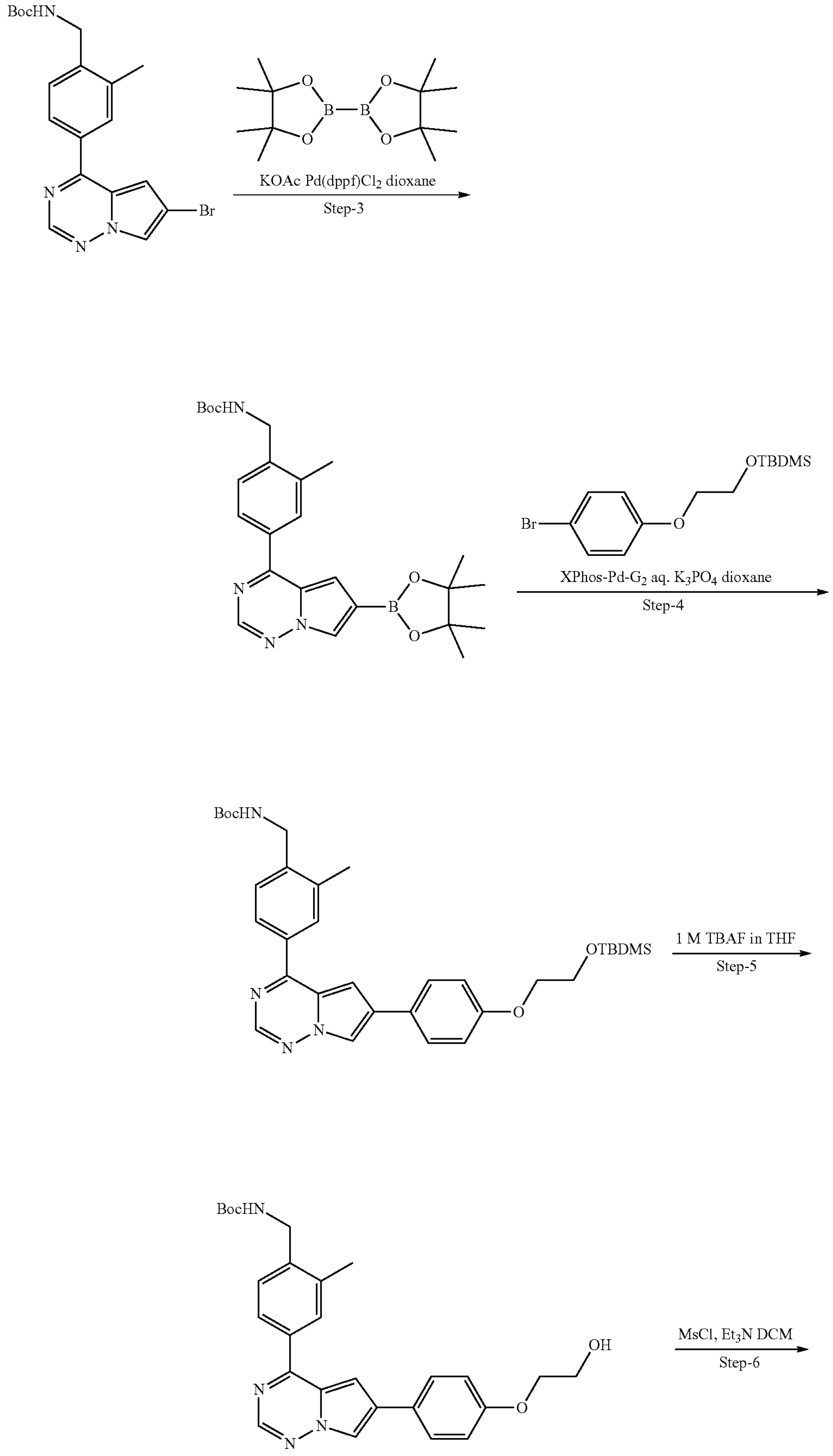

-continued
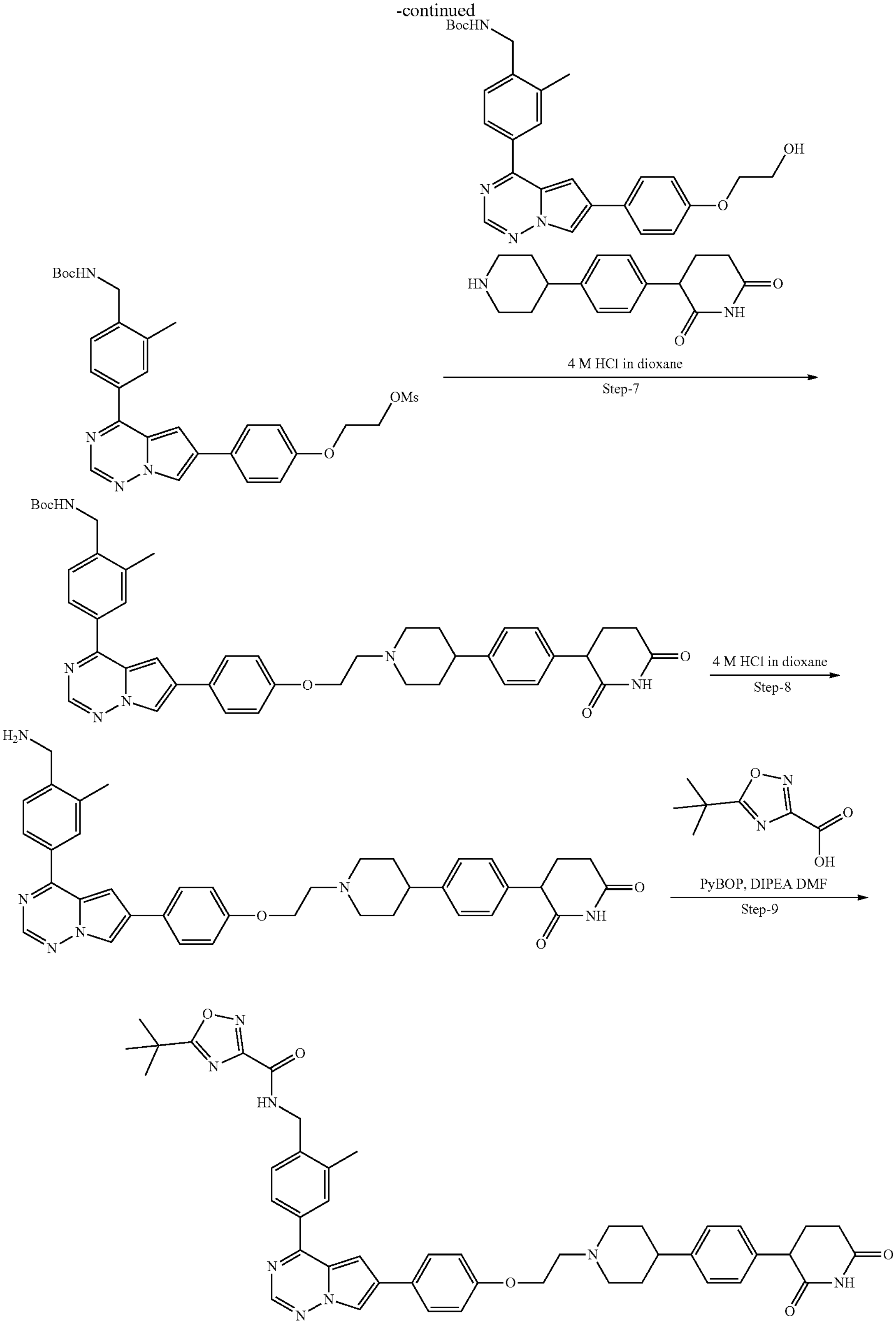

Step-1:

Potassium carbonate, anhydrous, 99% (23.97 g, 173.40 mmol) was added to a solution of 4-bromophenol (15 g, 86.70 mmol) and 2-bromoethanol (21.67 g, 173.40 mmol) in DMF (100 mL) at 27° C. under argon atmosphere. The reaction mixture was stirred at 70° C. for 48 hours. The reaction mixture was quenched with ice water and washed with ethyl acetate (100 mL×2). The organic layer was concentrated under reduced pressure to obtain the crude compound, which was purified by column chromatography (silica gel 230-400 mesh, 0-100% ethyl acetate in pet-ether) to afford 2-(4-bromophenoxy)ethanol (10 g, 45.96 mmol, 53.00% yield). LC-MS ($ES^+$): m/z 217.29 $[M+H]^+$.

Step-2:

To a stirred solution of 2-(4-bromophenoxy)ethanol (9 g, 41.46 mmol) in DCM (100 mL) at 0° C. under argon atmosphere, imidazole (8.47 g, 124.39 mmol) and tert-butyl-chloro-dimethyl-silane (6.25 g, 41.46 mmol, 7.72 mL) were added, and the reaction was stirred at 0° C. for 5 hours. Reaction progress was monitored by TLC and LC-MS. A saturated $NaHCO_3$ solution was added, and the mixture was extracted with ethyl acetate (50 ml×3). The combined organic layers were washed with water, brine solution, dried over anhydrous sodium sulfate, filtered, and concentrated under reduced pressure. The crude product was purified by column chromatography (silica gel 100-200 mesh 0-10% ethyl acetate in pet ether) to afford 2-(4-bromophenoxy) ethoxy-tert-butyl-dimethyl-silane (6.5 g, 19.45 mmol, 46.91% yield). $^1H$ NMR (400 MHz, DMSO-$d_6$) δ 7.39-736 (m, 2H), 6.85-6.83 (m, 2H), 3.96-3.94 (m, 2H), 3.85-3.83 (m, 2H), 0.80 (s, 9H), 0.09 (s, 6H).

Step-3:

To a stirred solution of tert-butyl N-[[4-(6-bromopyrrolo[2,1-f][1,2,4]triazin-4-yl)-2-methyl-phenyl]methyl]carbamate (5 g, 11.98 mmol) in dioxane (50 mL) purged with argon, potassium acetate (3.53 g, 35.95 mmol) and 4,4,5,5-tetramethyl-2-(4,4,5,5-tetramethyl-1,3,2-dioxaborolan-2-yl)-1,3,2-dioxaborolane (3.65 g, 14.38 mmol) were added at room temperature. The reaction mixture was stirred at this temperature for 10 minutes, after which $Pd(dppf)Cl_2 \cdot CH_2Cl_2$ (876.72 mg, 1.20 mmol) was added and the reaction mixture was heated at 90° C. for 16 hours. The reaction was monitored by TLC and LC-MS. The residue was quenched with water (60 mL) and extracted with ethyl acetate (50 mL×3). The combined organic layers were washed with brine solution (100 mL), dried over anhydrous sodium sulfate, filtered, and concentrated under reduced pressure. The crude was purified by column chromatography (silica gel 100-200 mesh, 0-30% ethyl acetate in hexane) to afford tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (5.0 g, 8.61 mmol, 71.89% yield). LC-MS ($ES^+$): m/z 465.39 $[M+H]^+$.

Step-4:

To a stirred solution of 2-(4-bromophenoxy)ethoxy-tert-butyl-dimethyl-silane (1.5 g, 4.53 mmol) in dioxane (16 mL) and water (4 mL) purged with argon, tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (2.31 g, 4.98 mmol) and potassium phosphate (961.00 mg, 4.53 mmol) were added at room temperature. The reaction mixture was stirred at room temperature for 10 minutes, after which XPhos-Pd-G2 (785.79 g, 4.53 mmol) was added, and the reaction stirred at 90° C. for 16 hours. The reaction was monitored by TLC and LC-MS. The residue was quenched with water (60 mL) and extracted with ethyl acetate (50 mL×3). The combined organic layers were washed with brine solution (100 mL), dried over anhydrous sodium sulfate, filtered, and concentrated under reduced pressure. The crude compound was purified by column chromatography (silica gel 230-400 mesh, 0-100% ethyl acetate in pet-ether) to afford tert-butyl N-[[4-[6-[4-[2-[tert-butyl(dimethyl)silyl]oxyethoxy]phenyl]pyrrolo[2,1-f][1,2,4]triazin-4-yl]-2-methyl-phenyl]methyl]carbamate (2.2 g, 3.02 mmol, 66.62% yield). LC-MS ($ES^+$): m/z 589.45 $[M+H]^+$.

Step-5:

To a stirred solution of tert-butyl N-[[4-[6-[4-[2-[tert-butyl(dimethyl)silyl]oxyethoxy]phenyl]pyrrolo[2,1-f][1,2,4]triazin-4-yl]-2-methyl-phenyl]methyl]carbamate (2.2 g, 3.74 mmol) in THF (10 mL) at 0° C. under argon atmosphere, tetrabutylammonium fluoride (976.91 mg, 3.74 mmol) was added and the reaction mixture was stirred at room temperature for 2 hours. The reaction was monitored by TLC and LC-MS. The residue was quenched with water (50 mL) and extracted with ethyl acetate (30 mL×3). The combined organic layers were washed with brine solution (100 mL), dried over anhydrous sodium sulfate, filtered, and concentrated under reduced pressure. The crude was purified by column chromatography (silica gel 100-200 mesh, 0-50% ethyl acetate in hexane) to afford tert-butyl N-[[4-[6-[4-(2-hydroxyethoxy)phenyl]pyrrolo[2,1-f][1,2,4]triazin-4-yl]-2-methyl-phenyl]methyl]carbamate (1.2 g, 2.29 mmol, 61.38% yield). LC-MS ($ES^+$): m/z 475.45 $[M+H]^+$.

Step-6:

To a stirred solution of tert-butyl N-[[4-[6-[4-(2-hydroxyethoxy)phenyl]pyrrolo[2,1-f][1,2,4]triazin-4-yl]-2-methyl-phenyl]methyl]carbamate (1.21 g, 2.55 mmol) in DCM (20 mL) at 0° C. under argon atmosphere, Triethylamine (1.03 g, 10.19 mmol, 1.42 mL) and methanesulfonyl chloride (291.82 mg, 2.55 mmol, 197.18 μL) were added and the reaction mixture was stirred at room temperature for 2 hours. The reaction was monitored by TLC and LC-MS. The residue was quenched with water (50 mL) and extracted with ethyl acetate (30 mL×3). The combined organic layers were washed with brine solution (100 mL), dried over anhydrous sodium sulfate, filtered, and concentrated under reduced pressure. The crude product was purified by column chromatography (silica gel 100-200 mesh 0-50% ethyl acetate in hexane) to afford 2-[4-[4-[4-[(tert-butoxycarbonylamino)methyl]-3-methyl-phenyl]pyrrolo[2,1-f][1,2,4]triazin-6-yl]phenoxy]ethyl methanesulfonate (1.2 g, 1.96 mmol, 77.12% yield). LC-MS ($ES^+$): m/z 553.36 $[M+H]^+$.

Step-7:

To the stirred solution of 2-[4-[4-[4-[(tert-butoxycarbonylamino)methyl]-3-methyl-phenyl]pyrrolo[2,1-f][1,2,4]triazin-6-yl]phenoxy]ethyl methanesulfonate (0.300 g, 542.85 μmol) and 3-[4-(4-piperidyl)phenyl]piperidine-2,6-dione TFA salt (419.47 mg, 1.09 mmol) in MeCN (10 mL) was added DIPEA (701.58 mg, 5.43 mmol, 945.52 μL) at room temperature. The reaction mixture was stirred for 20 minutes before tetrabutylammonium iodide (200.51 mg, 542.85 μmol) was added and the reaction mixture heated at 70° C. for 12 hours. The progress of the reaction was monitored by TLC and LC-MS. The reaction mixture was diluted with sodium bicarbonate solution, filtered and the residue was dried under reduced pressure. The residue was purified by column chromatography (silica 100-200 mesh, 15-20% ethyl acetate in pet ether) to give the product tert-butyl N-[[4-[6-[4-[2-[4-[4-(2,6-dioxo-3-piperidyl)phenyl]-1-piperidyl]ethoxy]phenyl]pyrrolo[2,1-f][1,2,4]triazin-4-yl]-2-methyl-phenyl]methyl]carbamate (0.350 g, 460.17 μmol, 84.77% yield) as a yellow solid. LC-MS ($ES^+$): m/z 729.62 $[M+H]^+$.

Step-8:

To a stirred solution of tert-butyl N-[[4-[6-[4-[2-[4-[4-(2,6-dioxo-3-piperidyl)phenyl]-1-piperidyl]ethoxy]phenyl]

pyrrolo[2,1-f][1,2,4]triazin-4-yl]-2-methyl-phenyl]methyl] carbamate (0.150 g, 205.80 μmol) in DCM (2 mL) at 0° C. under argon atmosphere. 4 M hydrogen chloride solution in dioxane (1.5 mL) was added and the reaction was stirred at room temperature for 2 hours. The progress of the reaction was monitored by TLC and LC-MS. Upon completion, the reaction was concentrated under reduced pressure to give the crude compound, which was washed by ether to afford the final product 3-(4-(1-(2-(4-(4-(4-(aminomethyl)-3-methylphenyl)pyrrolo[2,1-f][1,2,4]triazin-6-yl)phenoxy)ethyl) piperidin-4-yl)phenyl)piperidine-2,6-dione (0.150 g, 87.46% yield). LC-MS ($ES^+$): m/z 629.35 $[M+H]^+$.

Step-9:

To a stirred solution of 3-[4-[1-[2-[4-[4-[4-(aminomethyl)-3-methyl-phenyl]pyrrolo[2,1-f][1,2,4]triazin-6-yl] phenoxy]ethyl]-4-piperidyl]phenyl]piperidine-2,6-dione HCl salt (0.150 g, 225.49 μmol) in DMF (2 mL) was added (5-tert-butyl-1,2,4-oxadiazole-3-carbonyl)oxylithium (99.27 mg, 563.72 μmol=) and the mixture was cooled to 0° C. Then. N-ethyl-N-isopropyl-propan-2-amine (291.43 mg, 2.25 mmol, 392.76 L) and benzotriazol-1-yloxy(tripyrrolidin-1-yl)phosphonium; hexafluorophosphate (234.69 mg, 450.98 μmol) were added, and the mixture was stirred at room temperature for 2 hours. The reaction was monitored by TLC and LC-MS After completion, the reaction was diluted with sodium bicarbonate solution to give the crude product as a solid. The crude product was purified by prep-HPLC to give the final product 5-tert-butyl-N-[[4-[6-[4-[2-[4-[4-(2,6-dioxo-3-piperidyl)phenyl]-1-piperidyl] ethoxy]phenyl]pyrrolo[2,1-f][1,2,4]triazin-4-yl]-2-methyl-phenyl]methyl]-1,2,4-oxadiazole-3-carboxamide TFA salt (30 mg, 33.09 μmol, 14.67% yield). $^1$H NMR (400 MHz, DMSO-$d_6$) δ 10.83 (s, 1H), 9.54 (t, J=5.9 Hz, 1H), 8.68 (s, 1H), 8.60 (s, 1H), 8.06-8.02 (m, 2H), 7.94 (d, J=8.6 Hz, 2H), 7.58 (s, 1H), 7.47 (d, J=8.0 Hz, 1H), 7.21 (s, 4H), 7.10 (d, J=8.6 Hz, 2H), 4.57 (d, J=5.9 Hz, 2H), 4.49 (bs, 2H), 3.86-3.82 (m, 1H), 3.72-3.49 (m, 4H), 3.20-3.12 (m, 2H), 2.84-2.81 (m, 1H), 2.70-2.64 (m, 1H), 2.61-2.58 (m, 1H), 2.47 (s, 3H), 2.20-2.16 (m, 1H), 2.00-1.92 (m, 5H), 1.44 (s, 9H). LC-MS ($ES^+$): m/z 781.23 $[M+H]^+$.

Example 105

Example 105 was prepared following the synthesis of Example 104

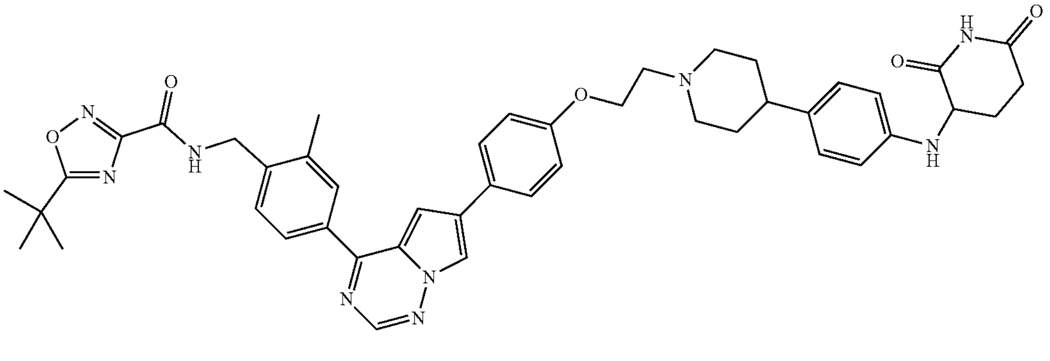 [SMILES: Cc1cc(-c2ncnn3cc(-c4ccc(OCCN5CCC(c6ccc(NC7CCC(=O)NC7=O)cc6)CC5)cc4)cc23)ccc1CNC(=O)c1noc(C(C)(C)C)n1]

5-tert-butyl-N-[[4-[6-[4-[2-[4-[4-[(2,6-dioxo-3-piperidyl) amino]phenyl]-1-piperidyl]ethoxy]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.78 (s, 1H), 9.54 (t, J=6.0 Hz, 1H) 9.42 (bs, 1H), 8.69 (s, 1H), 8.60 (s, 1H), 8.05-8.01 (m, 2H), 7.93 (d, J=8.6 Hz, 2H), 7.58 (s, 1H), 7.47 (d, J=8.0 Hz, 1H), 7.21-6.95 (m, 4H), 6.65 (d, J=8.4 Hz, 2H), 4.57 (d, J=5.9 Hz, 2H), 4.43 (bs, 2H), 4.29-4.26 (m, 1H), 3.58 (bs, 4H), 3.19-3.14 (m, 2H), 2.73-2.64 (m, 2H), 2.60-2.50 (m, 1H), 2.40-2.50 (m, 3H), 2.25-1.65 (m, 6H), 1.44 (s, 9H). LC-MS ($ES^+$): m/z 796.04 $[M+H]^+$.

Example 106

Example 106 was prepared following the synthesis of Example 104

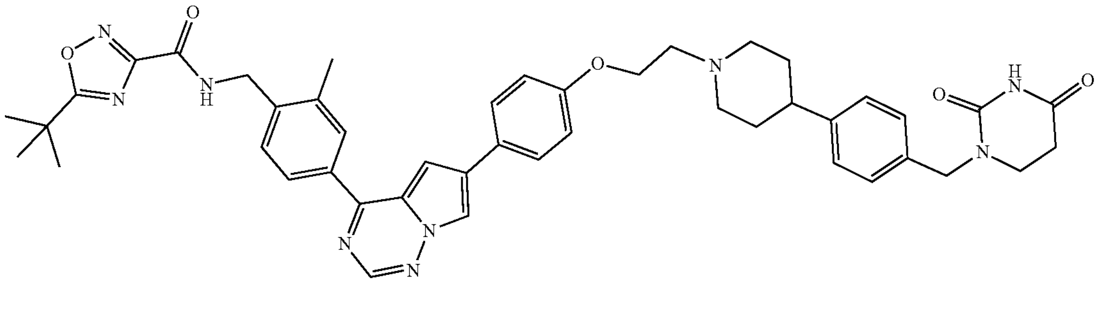 [SMILES: Cc1cc(-c2ncnn3cc(-c4ccc(OCCN5CCC(c6ccc(CN7CCC(=O)NC7=O)cc6)CC5)cc4)cc23)ccc1CNC(=O)c1noc(C(C)(C)C)n1]

5-tert-butyl-N-[[4-[6-[4-[2-[4-[4-[(2,4-dioxohexahydropyrimidin-1-yl)methyl]phenyl]-1-piperidyl]ethoxy]phenyl] pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.20 (s, 1H), 9.54 (t, J=6.0 Hz, 1H), 8.68 (d, J=1.2 Hz, 1H), 8.60 (s, 1H), 8.06-8.01 (m, 2H), 7.94 (d, J=8.7 Hz, 2H), 7.58 (d, J=1.0 Hz, 1H), 7.47 (d, J=8.0 Hz, 1H), 7.28-7.21 (m, 4H), 7.09-7.08 (m, 2H), 4.57 (d, J=6.0 Hz, 2H), 4.49 (s, 2H), 4.43 (bs, 2H), 3.70-3.69 (m, 2H), 3.60-3.57 (m, 2H), 3.29 (t, J=6.8 Hz, 2H), 3.25-3.19 (m, 2H), 2.87-2.81 (m, 1H), 2.56-2.54 (m, 2H), 2.48 (s, 3H), 2.03-1.91 (m, 4H), 1.44 (s, 9H). LC-MS ($ES^+$): m/z 796.12 $[M+H]^+$.

Example 107

Example 107 was prepared following the synthesis of Example 104

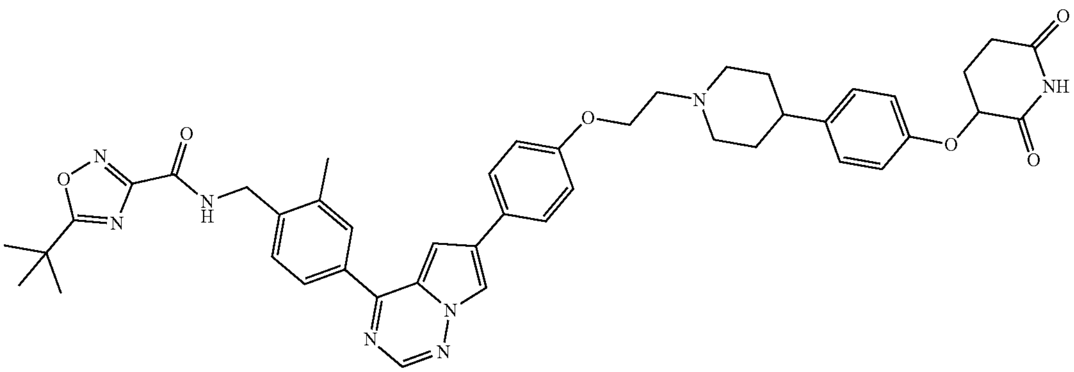 [SMILES: Cc1cc(-c2ncnn3cc(-c4ccc(OCCN5CCC(c6ccc(OC7CCC(=O)NC7=O)cc6)CC5)cc4)cc23)ccc1CNC(=O)c1noc(C(C)(C)C)n1]

5-tert-butyl-N-[[4-[6-[4-[2-[4-[4-[(2,6-dioxo-3-piperidyl)oxy]phenyl]-1-piperidyl]ethoxy]phenyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.92 (s, 1H), 9.54 (t, J=5.9 Hz, 1H), 9.42 (bs, 1H), 8.69 (d, J=1.4 Hz, 1H), 8.60 (s, 1H), 8.04 (d, J=8.4 Hz, 1H), 8.01 (s, 1H), 7.94 (d, J=8.8 Hz, 2H), 7.58 (d, J=1.4 Hz, 1H), 7.47 (d, J=8.0 Hz, 1H), 7.16 (d, J=8.8 Hz, 2H), 7.10 (d, J=8.0 Hz, 2H), 6.99 (d, J=8.8 Hz, 2H), 5.17-5.15 (m, 1H), 4.57 (d, J=6.0 Hz, 2H), 4.43 (bs, 2H), 3.71-3.67 (m, 2H), 3.58 (bs, 2H), 3.24-3.16 (m, 2H), 2.78-2.63 (m, 2H), 2.60-2.51 (m, 4H), 2.19-2.13 (m, 2H), 2.10-2.01 (m, 2H), 1.94-188 (m, 2H), 1.45 (s, 9H). LC-MS ($ES^+$): m/z 797.13 $[M+H]^+$.

Example 108

Example 108 was prepared substantially following the synthesis of Example 104

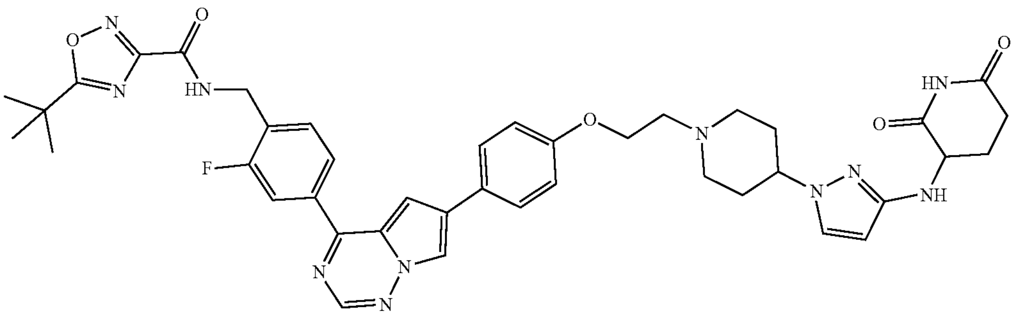 [SMILES: CC(C)(C)c1nc(C(=O)NCc2ccc(-c3ncnn4cc(-c5ccc(OCCN6CCC(n7ccc(NC8CCC(=O)NC8=O)n7)CC6)cc5)cc34)cc2F)no1]

The synthesis started with tert-butyl (4-(6-bromopyrrolo[2,1-f][1,2,4]triazin-4-yl)-2-fluorobenzyl)carbamate on step-3.

5-tert-butyl-N-[[4-[6-[4-[2-[4-[3-[(2,6-dioxo-3-piperidyl)amino]pyrazol-1-yl]-1-piperidyl]ethoxy]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.77 (s, 1H), 9.61 (t, J=6.0 Hz, 1H), 9.55 (bs, 1H), 8.74 (d, J=1.6 Hz, 1H), 8.63 (s, 1H), 8.09 (d, J=1.6 Hz, 1H), 8.08-7.95 (m, 3H), 7.66 (s, 1H), 7.61 (t, J=8.0 Hz, 1H), 7.55 (d, J=2.0 Hz, 1H), 7.09 (d, J=8.4 Hz, 3H), 5.70 (d, J=2.4 Hz, 1H), 4.63 (d, J=6.0 Hz, 2H), 4.42 (bs, 2H), 4.25-4.10 (m, 2H), 3.75-3.65 (m, 2H), 3.30-3.20 (m, 4H), 2.70-2.55 (m, 1H), 2.45-2.40 (m, 1H), 2.35-2.10 (m, 5H), 2.0-1.90 (m, 1H), 1.44 (s, 9H). LC-MS ($ES^-$): m/z 788.18 $[M-H]^-$.

Example 109

Example 109 was prepared substantially following the synthesis of Example 104

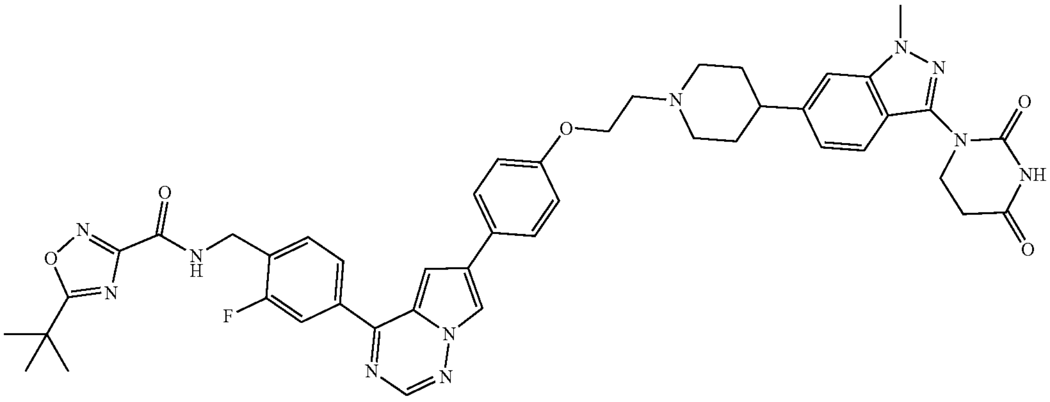 [SMILES: Cn1nc(N2CCC(=O)NC2=O)c2ccc(C3CCN(CCOc4ccc(-c5cc6c(-c7ccc(CNC(=O)c8noc(C(C)(C)C)n8)c(F)c7)ncnn6c5)cc4)CC3)cc21]

The synthesis started with tert-butyl (4-(6-bromopyrrolo[2,1-f][1,2,4]triazin-4-yl)-2-fluorobenzyl)carbamate on step-3. $^1$H NMR (400 MHz, DMSO-$d_6$) δ 10.56 (s, 1H), 9.61 (t, J=6.0 Hz, 1H), 9.49 (bs, 1H), 8.74 (d, J=1.2 Hz, 1H), 8.63 (s, 1H), 8.09 (d, J=8.0 Hz, 1H), 7.99-7.95 (m, 3H), 7.70-7.60 (m, 3H), 7.42 (s, 1H), 7.15-7.05 (m, 3H), 4.63 (d, J=6.0 Hz, 2H), 4.46 (bs, 2H), 3.99-3.90 (m, 7H), 3.52-3.48 (m, 2H), 3.30-3.20 (m, 2H), 3.10-3.00 (m, 1H), 2.76 (t, J=6.8 Hz, 2H), 2.15-2.00 (m, 4H), 1.44 (s, 9H). LC-MS (ES$^-$): m/z 838.19 [M−H]$^-$.

Example 110

Example 110 was prepared substantially following the synthesis of Example 104, except the synthesis started with tert-butyl (4-(6-bromopyrrolo[2,1-f][1,2,4]triazin-4-yl)-2-fluorobenzyl)carbamate on step-3.

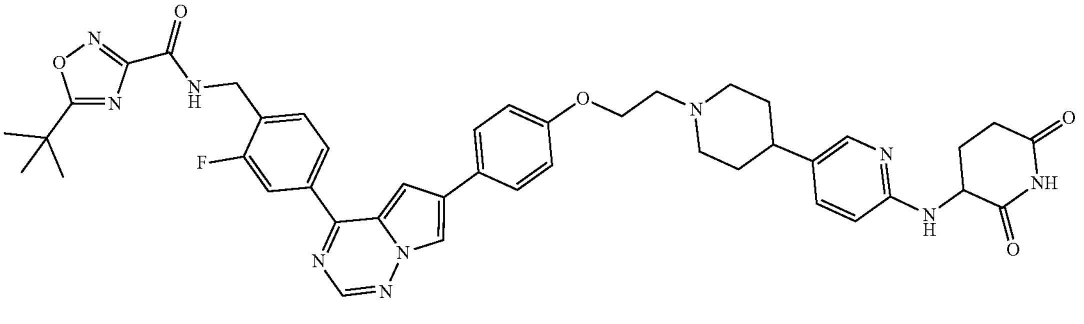 [SMILES: CC(C)(C)c1nc(C(=O)NCc2ccc(-c3ncnn4cc(-c5ccc(OCCN6CCC(c7ccc(NC8CCC(=O)NC8=O)nc7)CC6)cc5)cc34)cc2F)no1]

5-tert-butyl-N-[[4-[6-[4-[2-[4-[6-[(2,6-dioxo-3-piperidyl)amino]-3-pyridyl]-1-piperidyl]ethoxy]phenyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.82 (s, 1H), 9.61 (t, J=6.0 Hz, 1H), 9.46 (bs, 1H), 8.74 (d, J=1.2 Hz, 1H), 8.63 (s, 1H), 8.08 (d, J=8.0 Hz, 1H), 7.99-7.95 (m, 3H), 7.84 (d, J=1.6 Hz, 1H), 7.66 (d, J=1.2 Hz, 1H), 7.61 (t, J=8.0 Hz, 1H), 7.40 (bs, 1H), 7.10 (d, J=3.6 Hz, 2H), 6.68 (bs, 1H), 4.80-4.74 (m, 1H), 4.70 (d, J=6.0 Hz, 2H), 4.43-4.40 (m, 2H), 3.75-3.55 (m, 4H), 3.25-3.15 (m, 3H), 2.80-2.55 (m, 2H), 2.10-1.85 (m, 6H), 1.44 (s, 9H). LC-MS (ES$^-$): m/z 799.20 [M−H]$^-$.

Example 111

Example 111 was prepared substantially following the synthesis of Example 104

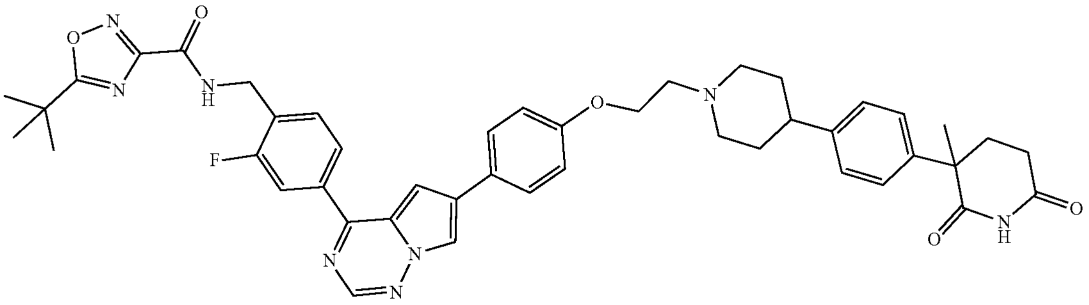 [SMILES: CC(C)(C)c1nc(C(=O)NCc2ccc(-c3ncnn4cc(-c5ccc(OCCN6CCC(c7ccc(C8(C)CCC(=O)NC8=O)cc7)CC6)cc5)cc34)cc2F)no1]

The synthesis started with tert-butyl (4-(6-bromopyrrolo [2,1-f][1,2,4]triazin-4-yl)-2-fluorobenzyl)carbamate on step-3.

5-tert-butyl-N-[[2-fluoro-4-[6-[4-[2-[4-[4-(3-methyl-2,6-dioxo-3-piperidyl)phenyl]-1-piperidyl]ethoxy]phenyl]pyrrolo[2,1-f][1,2,4]triazin-4-yl]phenyl]methyl]-1,2,4-oxadiazole-3-carboxamide. $^1$H NMR (400 MHz, DMSO-$d_6$) δ 10.92 (s, 1H), 9.61 (t, J=6.0 Hz, 1H), 8.73 (d, J=1.2 Hz, 1H), 8.63 (s, 1H), 8.08 (d, J=8.0 Hz, 1H), 7.99-7.94 (m, 3H), 7.66 (s, 1H), 7.61 (t, J=8.0 Hz, 1H), 7.26 (s, 4H), 7.10 (d, J=8.8 Hz, 2H), 4.63 (d, J=5.6 Hz, 2H), 4.43 (s, 2H), 3.70 (d, J=12.4 Hz, 2H), 3.59 (s, 2H), 3.24-3.16 (m, 2H), 2.83 (t, J=11.8 Hz, 1H), 2.49-2.32 (m, 2H), 2.13-2.02 (m, 4H), 1.96-1.90 (m, 2H), 1.44 (s, 3H), 1.42 (s, 9H). LC-MS (ES$^-$): m/z 797.15 [M−H]$^-$.

Example 112. Synthesis of 3-tert-butyl-N-[[4-[6-[4-[4-[4-[4-[(2,6-dioxo-3-piperidyl)amino]phenyl]-1-piperidyl]butoxy]phenyl]pyrrolo[2,1-f][1,2,4]triazin-4-yl]-2-methyl-phenyl]methyl]-1,2,4-thiadiazole-5-carboxamide

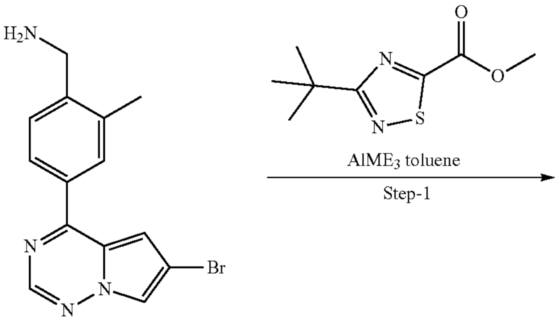

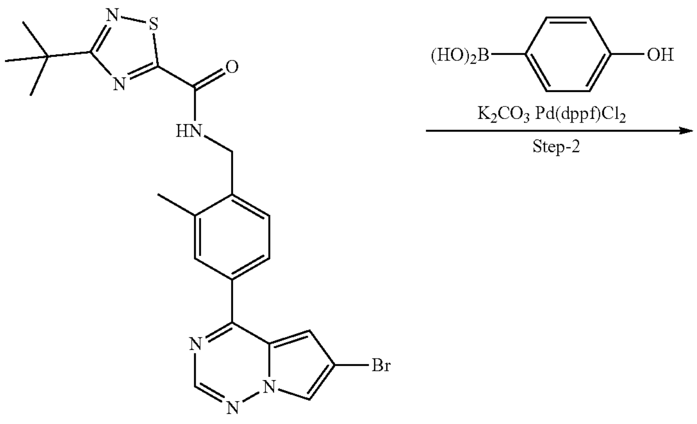

-continued

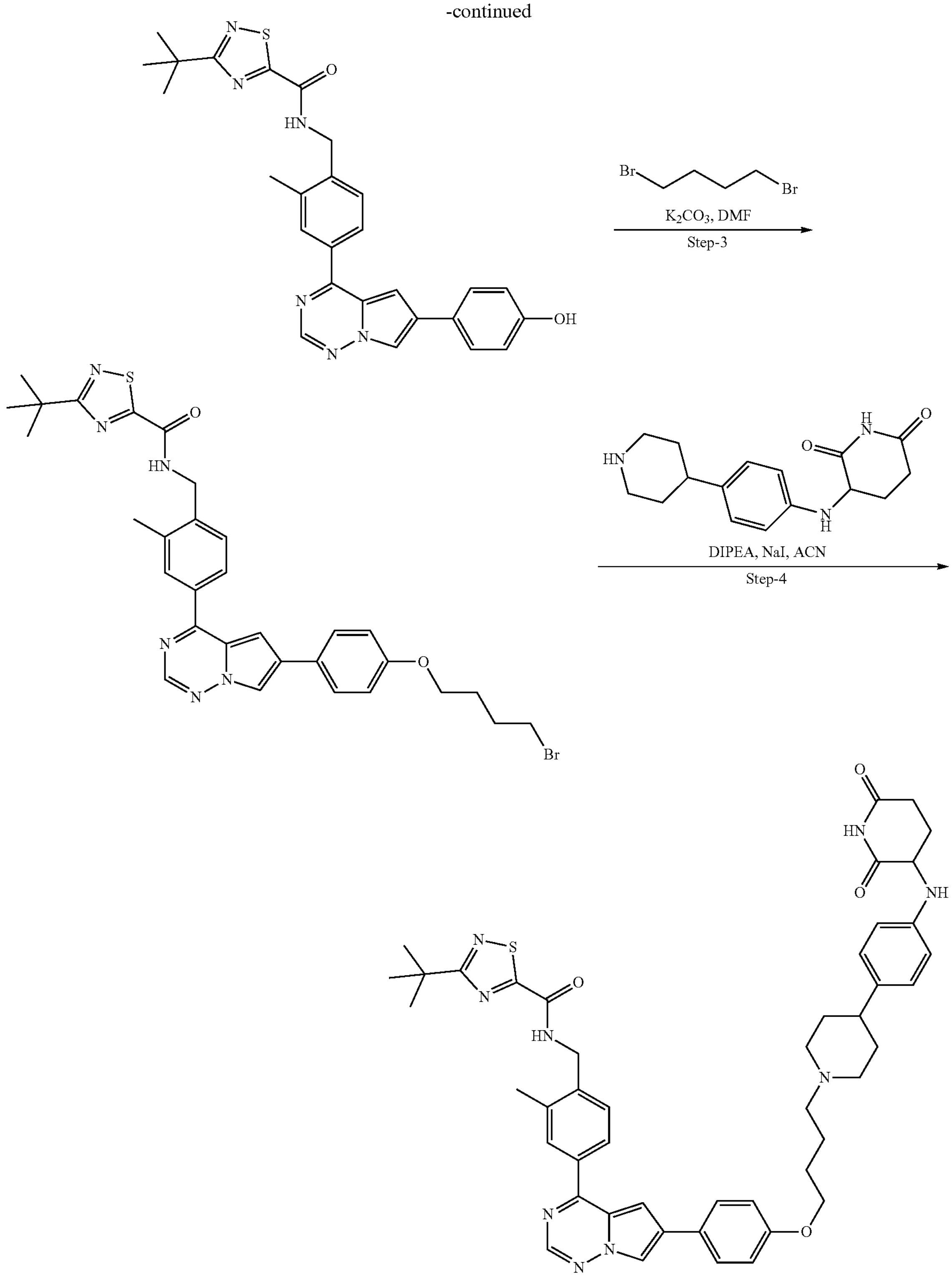

Step-1:

A solution of [4-(6-bromopyrrolo[2,1-f][1,2,4]triazin-4-yl)-2-methyl-phenyl]methanamine (1.5 g, 4.73 mmol) in toluene (15 mL) was added to a sealed tube at 0° C. with stirring. Trimethylaluminum (681.80 mg, 9.46 mmol) was added dropwise, and the reaction mixture was stirred at room temperature for 30 minutes. Following the addition of methyl 3-tert-butyl-1,2,4-thiadiazole-5-carboxylate (1.14 g, 5.67 mmol) in toluene, the reaction mixture was heated at 120° C. for 2 hours, and the reaction progress was monitored by TLC. Upon completion, the reaction was quenched with water (400 mL) and extracted with ethyl acetate (300 mL×3). The combined organic layers were washed with water (200 mL), brine solution (200 mL), dried over anhydrous sodium sulfate, filtered, and concentrated under reduced pressure to give the crude product, which was purified by column chromatography (silica gel 230-400 mesh, 0-10% ethyl acetate in pet-ether) to afford N-[[4-(6-bromopyrrolo[2,1-f][1,2,4]triazin-4-yl)-2-methyl-phenyl]methyl]-3-tert-butyl-1,2,4-thiadiazole-5-carboxamide (1.5 g, 3.00 mmol, 63.38% yield) as a pale yellow solid. LC-MS ($ES^+$): m/z 485.17 $[M+H]^+$.

Step-2:

A solution of N-[[4-(6-bromopyrrolo[2,1-f][1,2,4]triazin-4-yl)-2-methyl-phenyl]methyl]-3-tert-butyl-1,2,4-thiadiazole-5-carboxamide (1 g, 2.06 mmol) and (4-hydroxyphenyl) boronic acid (426.23 mg, 3.09 mmol) in dioxane (8 mL), water (2 mL) and potassium carbonate, granular (854.18 mg, 6.18 mmol) was added to a sealed tube with stirring. The reaction mixture was purged for 2 minutes under argon atmosphere and $Pd(dppf)Cl_2$ (150.60 mg, 206.02 μmol) was added. The reaction was purged again with argon gas for 5 minutes it was heated at 100° C. for 16 hours. Water (800 mL) was added to the reaction mixture and it was extracted with ethyl acetate (700 mL×3). The combined organic layers were washed with water (500 mL), brine solution (500 mL), dried over anhydrous sodium sulfate, filtered, and concentrated under reduced pressure to yield the crude product, which was purified by column chromatography (silica gel 230-400 mesh, 0-100% ethyl acetate in pet ether) to afford 3-tert-butyl-N-[[4-[6-(4-hydroxyphenyl)pyrrolo[2,1-f][1,2,4]triazin-4-yl]-2-methyl-phenyl]methyl]-1,2,4-thiadiazole-5-carboxamide (0.9 g, 1.46 mmol, 70.97% yield) as a pale yellow solid. LC-MS ($ES^+$): m/z 499.84 $[M+H]^+$.

Step-3:

To a stirred solution of 3-tert-butyl-N-[[4-[6-(4-hydroxyphenyl)pyrrolo[2,1-f][1,2,4]triazin-4-yl]-2-methyl-phenyl]methyl]-1,2,4-thiadiazole-5-carboxamide (180 mg, 361.01 mol) and 1,4-dibromobutane (77.95 mg, 361.01 μmol, 42.83 μL) in DMF (5 mL), potassium carbonate granular (49.89 mg, 361.01 μmol) was added and stirred at 70° C. for 16 hours. Water (100 mL) was added to the reaction mixture, and extraction was carried out using ethyl acetate (50 mL×3). The combined organic layers were washed with water (50 mL), brine solution (50 mL), dried over anhydrous sodium sulfate, filtered, and concentrated under reduced pressure to get the crude product. The crude was purified by column chromatography (silica gel 230-400 mesh, 0-100% ethyl acetate in pet ether) to afford N-[[4-[6-[4-(4-bromobutoxy)phenyl]pyrrolo[2,1-f][1,2,4]triazin-4-yl]-2-methyl-phenyl]methyl]-3-tert-butyl-1,2,4-thiadiazole-5-carboxamide (60 mg, 91.86 μmol, 25.44% yield) as a pale yellow liquid. LC-MS ($ES^+$): m/z 634.73 $[M+H]^+$.

Step-4:

To a stirred solution of N-[[4-[6-[4-(4-bromobutoxy)phenyl]pyrrolo[2,1-f][1,2,4]triazin-4-yl]-2-methyl-phenyl]methyl]-3-tert-butyl-1,2,4-thiadiazole-5-carboxamide (60 mg, 94.70 μmol) in ACN (3 mL) was added N-ethyl-N-isopropyl-propan-2-amine (122.39 mg, 946.97 mol, 164.94 μL). Sodium iodide (7.10 mg, 47.35 μmol) and 3-[4-(4-piperidyl)anilino]piperidine-2,6-dione TFA salt (49.41 mg, 123.11 μmol) were added to this solution and stirred at 80° C. for 16 hours. The reaction was monitored by LC-MS. The reaction mixture was concentrated in vacuo to get the crude compound, which was purified by prep-HPLC to afford 3-tert-butyl-N-[[4-[6-[4-[4-[4-[4-[(2,6-dioxo-3-piperidyl)amino]phenyl]-1-piperidyl]butoxy]phenyl]pyrrolo[2,1-f][1,2,4]triazin-4-yl]-2-methyl-phenyl]methyl]-1,2,4-thiadiazole-5-carboxamide TFA salt (31 mg, 31.30 μmol, 33.05% yield) as a yellow solid. LC-MS ($ES^+$): m/z 840.44 $[M+H]^+$.

Example 113

Example 113 was prepared substantially following the synthesis of Example 112

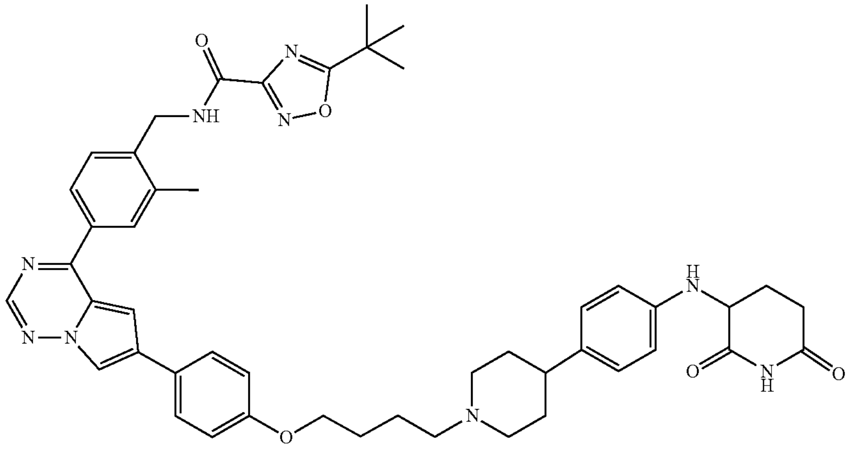 [SMILES: Cc1cc(-c2ncnn3cc(-c4ccc(OCCCCN5CCC(c6ccc(NC7CCC(=O)NC7=O)cc6)CC5)cc4)cc23)ccc1CNC(=O)c1noc(C(C)(C)C)n1]

For step-2, N-(4-(6-bromopyrrolo[2,1-f][1,2,4]triazin-4-yl)-2-methylbenzyl)-5-(tert-butyl)-1,2,4-oxadiazole-3-carboxamide was used instead of N-[[4-(6-bromopyrrolo[2,1-f][1,2,4]triazin-4-yl)-2-methyl-phenyl]methyl]-3-tert-butyl-1,2,4-thiadiazole-5-carboxamide.

-tert-butyl-N-[[4-[6-[4-[4-[4-[4-[(2,6-dioxo-3-piperidyl)amino]phenyl]-1-piperidyl]butoxy]phenyl]pyrrolo[2,1-f][1,2,4]triazin-4-yl]-2-methyl-phenyl]methyl]-1,2,4-oxadiazole-3-carboxamide. $^1H$ NMR (400 MHz, DMSO-$d_6$) δ 10.78 (s, 1H), 9.54 (t, J=6.0 Hz, 1H), 9.03 (bs, 1H), 8.66 (s, 1H), 8.59 (s, 1H), 8.04-8.01 (m, 2H), 7.89 (d, J=8.6 Hz, 2H), 7.56 (s, 1H), 7.47 (d, J=8.0 Hz, 1H), 7.07 (q, J=6.8 Hz, 2H), 6.95 (d, J=8.4 Hz, 2H), 6.64 (d, J=8.5 Hz, 2H), 4.57 (d, J=6.0 Hz, 2H), 4.29-4.25 (m, 1H), 4.09-4.08 (m, 2H), 3.57 (bs, 2H), 3.17 (bs, 2H), 3.07-2.99 (m, 2H), 2.73-2.54 (m, 3H), 2.50 (s, 3H), 2.11-2.07 (m, 1H), 1.97-1.76 (m, 9H), 1.45 (s, 9H). LC-MS ($ES^+$): m/z 824.44 $[M+H]^+$.

Example 114

Example 114 was prepared substantially following the synthesis of Example 112

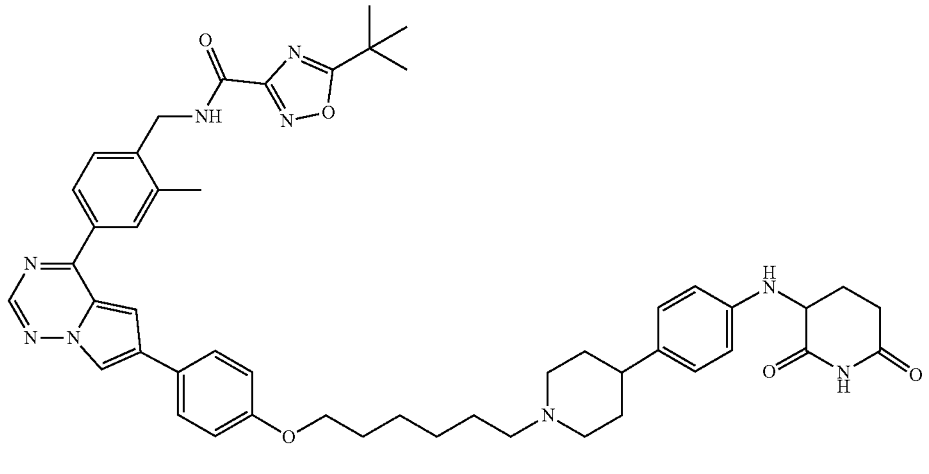 [SMILES: Cc1cc(-c2ncnn3cc(-c4ccc(OCCCCCCN5CCC(c6ccc(NC7CCC(=O)NC7=O)cc6)CC5)cc4)cc23)ccc1CNC(=O)c1noc(C(C)(C)C)n1]

In step-2, N-(4-(6-bromopyrrolo[2,1-f][1,2,4]triazin-4-yl)-2-methylbenzyl)-5-(tert-butyl)-1,2,4-oxadiazole-3-carboxamide was used instead of N-[[4-(6-bromopyrrolo[2,1-f][1,2,4]triazin-4-yl)-2-methyl-phenyl]methyl]-3-tert-butyl-1,2,4-thiadiazole-5-carboxamide. In step-3, 1,6-dibromohexane was used instead of 1,4-dibromobutane.

5-tert-butyl-N-[[4-[6-[4-[6-[4-[4-[(2,6-dioxo-3-piperidyl)amino]phenyl]-1-piperidyl]hexoxy]phenyl]pyrrolo[2,1-f][1,2,4]triazin-4-yl]-2-methyl-phenyl]methyl]-1,2,4-oxadiazole-3-carboxamide. $^1$H NMR (401 MHz, DMSO-$d_6$) δ 10.78 (s, 1H), 9.54 (t, J=6.0 Hz, 1H), 8.63 (d, J=13.5 Hz, 1H), 8.58 (s, 1H), 8.04 (d, J=8.6 Hz, 1H), 8.58 (s, 1H), 7.87 (d, J=8.6 Hz, 2H), 7.55 (s, 1H), 7.47 (d, J=8.0 Hz, 1H), 7.08-6.93 (m, 4H), 6.64 (d, J=8.5 Hz, 1H), 4.56 (d, J=5.9 Hz, 2H), 4.29-4.25 (m, 1H), 4.05-4.02 (m, 2H), 3.25-3.21 (m, 2H), 3.10-2.99 (m, 4H), 2.75-2.55 (m, 3H), 2.64 (s, 3H), 2.07-2.06 (m, 1H), 2.01-1.60 (m, 9H), 1.44 (m, 13H). LC-MS (ES$^+$): m/z 852.03 $[M+H]^+$.

Example 115

Example 115 was prepared substantially following the synthesis of Example 112

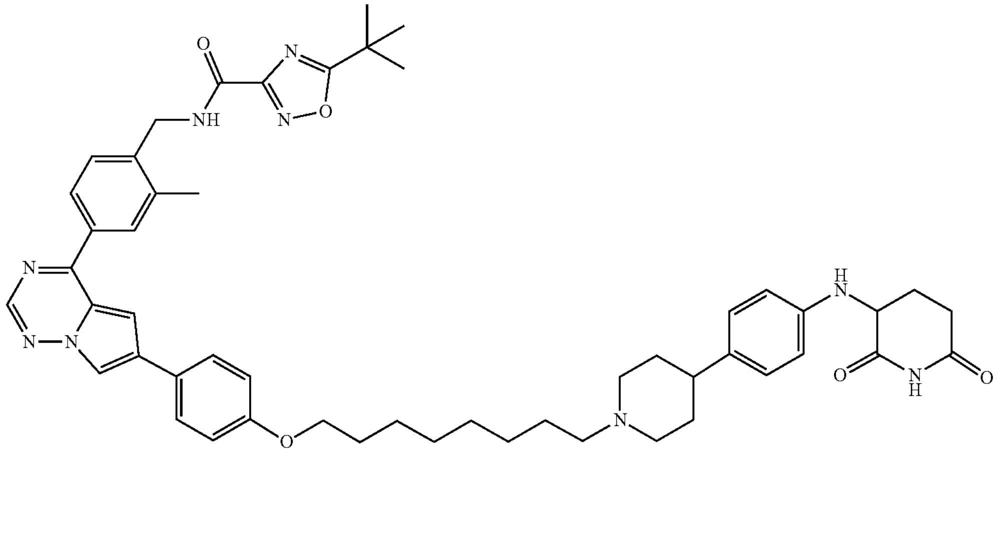 [SMILES: Cc1cc(-c2ncnn3cc(-c4ccc(OCCCCCCCCN5CCC(c6ccc(NC7CCC(=O)NC7=O)cc6)CC5)cc4)cc23)ccc1CNC(=O)c1noc(C(C)(C)C)n1]

In step-2, N-(4-(6-bromopyrrolo[2,1-f][1,2,4]triazin-4-yl)-2-methylbenzyl)-5-(tert-butyl)-1,2,4-oxadiazole-3-carboxamide was used instead of N-[[4-(6-bromopyrrolo[2,1-f][1,2,4]triazin-4-yl)-2-methyl-phenyl]methyl]-3-tert-butyl-1,2,4-thiadiazole-5-carboxamide. In step-3: 1,8-dibromooctane was used instead of 1,4-dibromobutane.

-tert-butyl-N-[[4-[6-[4-[8-[4-[4-[(2,6-dioxo-3-piperidyl)amino]phenyl]-1-piperidyl]octoxy]phenyl]pyrrolo[2,1-f][1,2,4]triazin-4-yl]-2-methyl-phenyl]methyl]-1,2,4-oxadiazole-3-carboxamide. $^1$H NMR (401 MHz, DMSO-$d_6$) δ 10.78 (s, 1H), 9.54 (t, J=5.9 Hz, 1H), 9.01 (bs, 1H), 8.62 (s, 1H), 8.57 (s, 1H), 8.05-8.01 (m, 2H), 7.86 (d, J=8.7 Hz, 2H), 7.55 (s, 1H), 7.47 (d, J=8.0 Hz, 1H), 7.06-6.92 (m, 4H), 6.63 (d, J=8.7 Hz, 2H), 4.57 (d, J=5.9 Hz, 2H), 4.29-4.25 (m, 1H), 4.02 (t, J=6.3 Hz, 2H), 3.54 (d, J=11.4 Hz, 2H), 3.05-2.94 (m, 4H), 2.67-2.60 (m, 3H), 2.48 (s, 3H), 2.11-2.07 (m, 1H), 1.95-1.71 (m, 9H), 1.51-1.31 (m, 8H), 1.44 (s, 9H). LC-MS (ES$^+$): m/z 880.00 (2.58, [M+H]$^+$.

Synthesis of 2-[4-[4-[(tert-butoxycarbonylamino)methyl]-3-methyl-phenyl]pyrrolo[2,1-f][1,2,4]triazin-6-yl]ethyl methanesulfonate

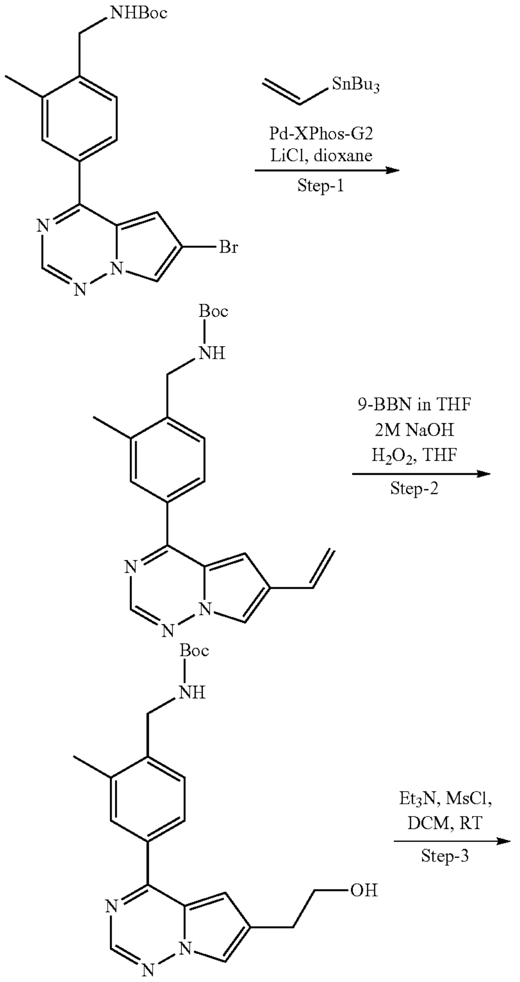

-continued

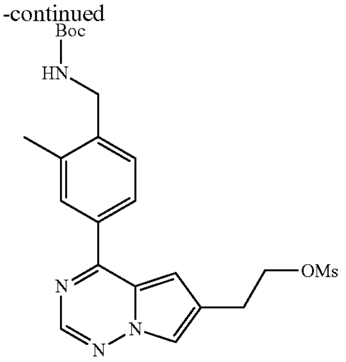

Step-1:

To a stirred solution of tert-butyl N-[[4-(6-bromopyrrolo[2,1-f][1,2,4]triazin-4-yl)-2-methyl-phenyl]methyl]carbamate (5.0 g, 11.98 mmol) in 1,4-dioxane (25 mL) and THF (25 mL), tributyl(vinyl)stannane (27.80 g, 47.93 mmol), anhydrous lithium chloride, (1.52 g, 35.95 mmol) and Pd-XPhos-G2 (941.77 mg, 1.20 mmol) was added. The reaction was stirred at 100° C. for 16 hours and the progress of the reaction was monitored by TLC and LC-MS. After completion, the reaction mixture was washed with water, extracted with ethyl acetate (250 mL×3), and concentrated under reduced pressure to get the crude product. The crude product was purified by column chromatography (silica 230-400 mesh, 0-40% ethyl acetate in pet ether) to afford tert-butyl N-[[2-methyl-4-(6-vinylpyrrolo[2,1-f][1,2,4]triazin-4-yl)phenyl]methyl]carbamate (4.4 g, 11.86 mmol, 98.95% yield) as a yellow solid. LC-MS (ES$^+$): m/z 365.92 [M+H]$^+$.

Step-2:

To a stirred solution of tert-butyl N-[[2-methyl-4-(6-vinylpyrrolo[2,1-f][1,2,4]triazin-4-yl)phenyl]methyl]carbamate (1 g, 2.74 mmol) in THF (10 mL) was added 9-borabicyclo[3.3.1]nonane solution (0.5 M in THF, 5.49 mmol) under inert atmosphere at 0° C. The reaction mixture was stirred for 16 hours at room temperature while monitoring by TLC and LC-MS. Upon reaction completion, the mixture was quenched with 2 M NaOH solution (2.74 mmol), followed by hydrogen peroxide solution, and stirred for 5 hours. The resulting solution was then diluted with water and extracted with ethyl acetate. The organic layer was dried over anhydrous sodium sulfate and concentrated to dryness. The crude product was purified via flash column chromatography (silica gel, 0-50% ethyl acetate in pet ether) to afford tert-butyl N-[[4-[6-(2-hydroxyethyl)pyrrolo[2,1-f][1,2,4]triazin-4-yl]-2-methyl-phenyl]methyl]carbamate (0.7 g, 1.67 mmol, 60.70% yield) as a yellow gum. LC-MS (ES$^+$): m/z 383.24 [M+H]$^+$.

Step-3:

To a stirred solution of tert-butyl N-[[4-[6-(2-hydroxyethyl)pyrrolo[2,1-f][1,2,4]triazin-4-yl]-2-methyl-phenyl]methyl]carbamate (0.9 g, 2.35 mmol) in DCM (20 mL) cooled to 0° C. was added triethylamine (595.31 mg, 5.88 mmol, 819.98 μL) at 0° C. Methanesulfonyl chloride (404.35 mg, 3.53 mmol, 273.21 μL) was added, and the reaction was stirred at 30° C. for 2 hours. The reaction was monitored by LC-MS and TLC. Upon reaction completion, the reaction mixture was diluted with cold water (50 mL) and extracted with ethyl acetate (2×50 mL). The combined organic layers were dried over $Na_2SO_4$ and concentrated under reduced pressure to give the crude product, which was purified via flash column chromatography (pet ether/ethyl acetate) to afford the product 2-[4-[4-[(tert-butoxycarbonylamino)methyl]-3-methyl-phenyl]pyrrolo[2,1-f][1,2,4]triazin-6-yl]ethyl methanesulfonate (0.85 g, 1.76 mmol, 74.74% yield) as a yellow gummy solid. LC-MS ($ES^+$): m/z 461.38 $[M+H]^+$.

Synthesis of 2-[4-[4-[(tert-butoxycarbonylamino)methyl]-3-fluoro-phenyl]pyrrolo[2,1-f][1,2,4]triazin-6-yl]ethyl methanesulfonate

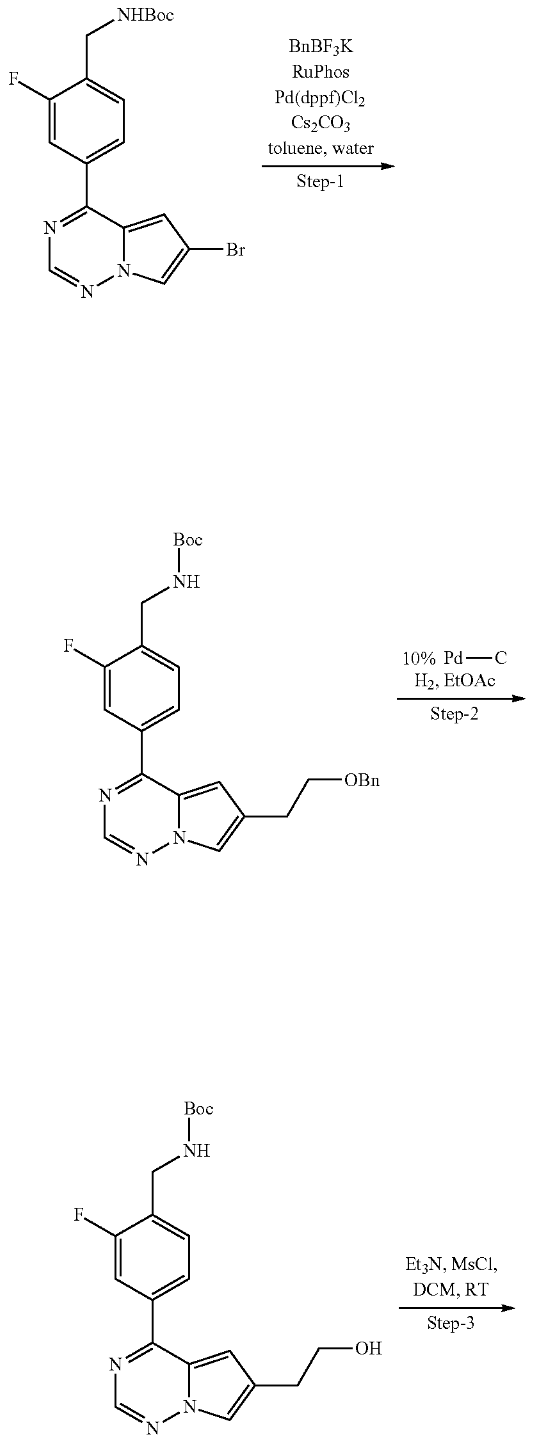

-continued

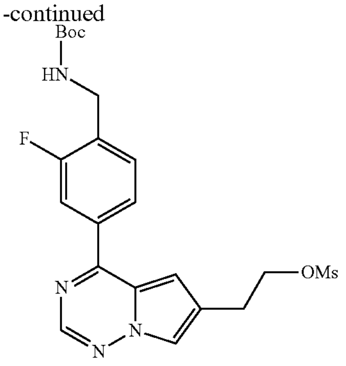

Step-1:

To a stirred solution of tert-butyl N-[[4-(6-bromopyrrolo[2,1-f][1,2,4]triazin-4-yl)-2-fluoro-phenyl]methyl]carbamate (5 g, 11.87 mmol) and potassium (2-benzyloxyethyl) trifluoroborate (4.32 g, 17.80 mmol) in toluene (50 mL) was added cesium carbonate (9.67 g, 29.67 mmol) in water (30 mL). The mixture was purged with nitrogen gas for 10 minutes, followed by the addition of RuPhos (1.11 g, 2.37 mmol) and $Pd(dppf)Cl_2 \cdot CH_2Cl_2$ (694.77 mg, 949.53 μmol). The reaction mixture was degassed (with nitrogen gas) and then heated to 110° C. for 16 hours while monitoring by TLC and LC-MS. Upon reaction completion, it was quenched with water and extracted with ethyl acetate. The organic layer was concentrated under reduced pressure, and the resulting residue was purified by flash column chromatography (0-30% ethyl acetate in pet ether) to afford tert-butyl N-[[4-[6-(2-benzyloxyethyl)pyrrolo[2,1-f][1,2,4]triazin-4-yl]-2-fluoro-phenyl]methyl]carbamate (4 g, 6.55 mmol, 55.16% yield). LC-MS ($ES^+$): m/z 477.51 $[M+H]^+$.

Step-2:

To a stirred solution of tert-butyl N-[[4-[6-(2-benzyloxyethyl)pyrrolo[2,1-f][1,2,4]triazin-4-yl]-2-fluoro-phenyl]methyl]carbamate (1.8 g, 3.78 mmol) under inert atmosphere was added 10 wt. % palladium on carbon, type 487, dry (4.02 g, 37.77 mmol). The reaction mixture was stirred under hydrogen atmosphere for 16 hours at room temperature while monitoring by TLC and LC-MS. Upon reaction completion, the reaction mixture was filtered through celite and washed with ethyl acetate. The resulting filtrate was concentrated under reduced pressure to give the crude product, which was purified via flash column chromatography (silica gel, 0-50% ethyl acetate in pet ether to afford tert-butyl N-[[2-fluoro-4-[6-(2-hydroxyethyl)pyrrolo[2,1-f][1,2,4]triazin-4-yl]phenyl]methyl]carbamate (0.98 g, 2.28 mmol, 60.43% yield). LC-MS ($ES^+$): m/z 387.44 $[M+H]^+$.

Step-3:

To a stirred solution of tert-butyl N-[[2-fluoro-4-[6-(2-hydroxyethyl)pyrrolo[2,1-f][1,2,4]triazin-4-yl]phenyl]methyl]carbamate (1.3 g, 3.36 mmol) in DCM (15 mL) was added triethylamine (1.02 g, 10.09 mmol, 1.41 mL) followed by methanesulfonyl chloride (462.45 mg, 4.04 mmol, 312.47 μL) at 0° C. under inert atmosphere. The reaction mixture was stirred for 2 hours while warmed up to room temperature. The progress of the reaction was monitored by TLC and LC-MS. Upon reaction completion, the reaction mixture was quenched with $NaHCO_3$ solution and extracted with DCM. The organic layer was dried over $Na_2SO_4$ and concentrated under reduced pressure. The crude product was purified via flash column chromatography (silica gel 40-63 mesh, 50% ethyl acetate in pet ether) to afford 2-[4-[4-[(tert-butoxycarbonylamino)methyl]-3-fluoro-phenyl]pyrrolo[2,1-f][1,2,4]triazin-6-yl]ethyl methanesulfonate (1.4 g, 2.98 mmol, 88.69% yield) as a yellow amorphous solid. LC-MS ($ES^+$): m/z 466.12 $[M+H]^+$.

Example 116. Synthesis of 5-tert-butyl-N-[[4-[6-[2-[4-[4-(2,6-dioxo-3-piperidyl)phenyl]-1-piperidyl]ethyl]pyrrolo[2,1-f][1,2,4]triazin-4-yl]-2-methyl-phenyl]methyl]-1,2,4-oxadiazole-3-carboxamide

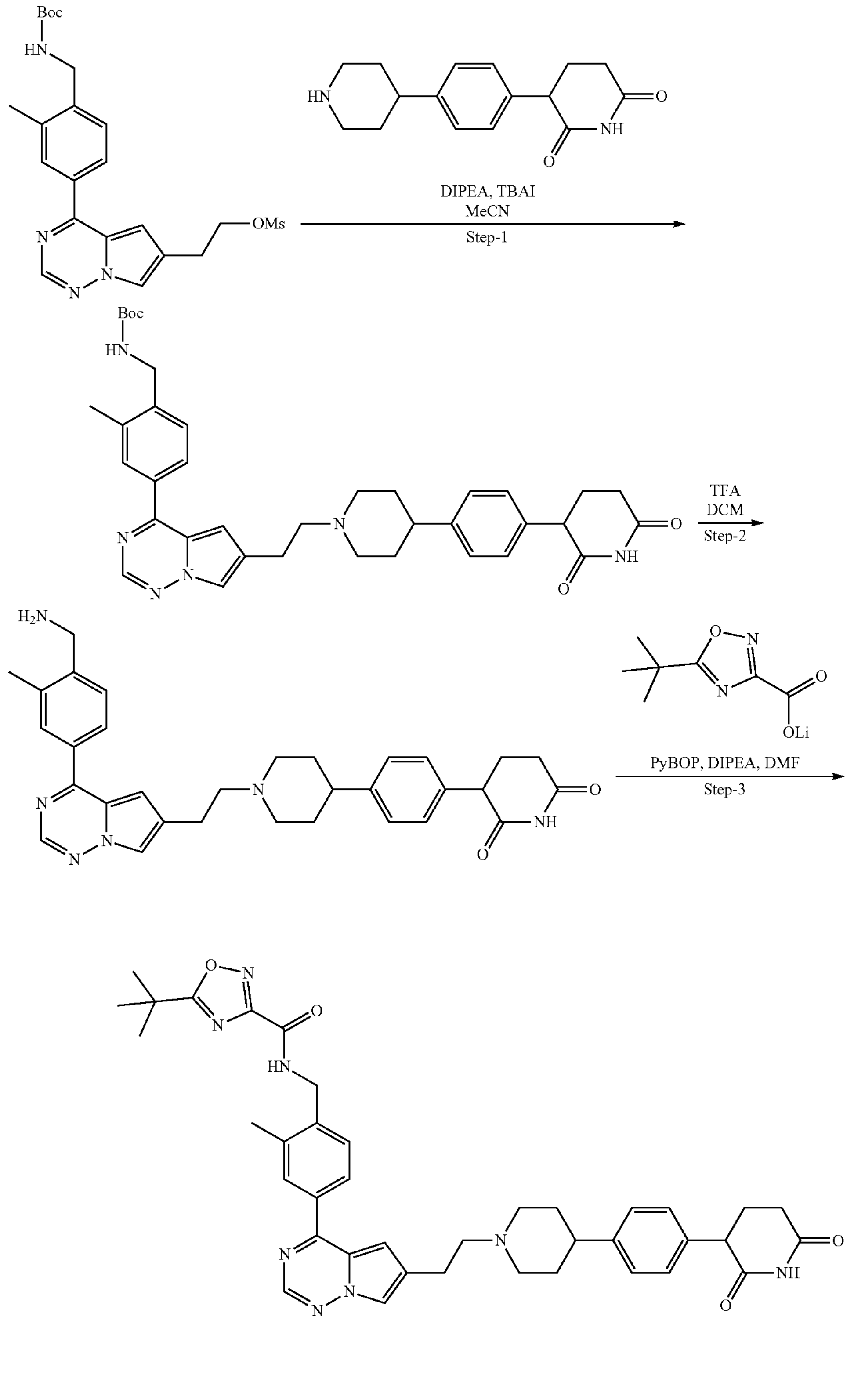

Step-1:

To a stirred solution of 3-[4-(4-piperidyl)phenyl]piperidine-2,6-dione (47.31 mg, 173.71 mol) in acetonitrile (5 mL) was added tetrabutylammonium iodide (80.20 mg, 217.13 mol) followed by N,N-diisopropylethylamine (84.19 mg, 651.40 μmol, 113.46 μL) under inert atmosphere. Then, 2-[4-[4-[(tert-butoxycarbonylamino)methyl]-3-methyl-phenyl]pyrrolo[2,1-f][1,2,4]triazin-6-yl]ethyl methanesulfonate (0.1 g, 217.13 μmol) was added portionwise. The reaction mixture was heated at 60° C. for 16 hours while monitoring by TLC and LC-MS. Upon reaction completion, it was quenched with water and extracted with DCM. The organic layer was washed with brine solution and concentrated to dryness under reduced pressure. The crude product was purified by Biotage (0-5% MeOH in DCM) to afford tert-butyl N-[[4-[6-[2-[4-[4-(2,6-dioxo-3-piperidyl)phenyl]-1-piperidyl]ethyl]pyrrolo[2,1-f][1,2,4]triazin-4-yl]-2-methyl-phenyl]methyl]carbamate (0.1 g, 155.47 μmol, 71.60% yield) as a brown sticky liquid. LC-MS ($ES^+$): m/z 637.25 $[M+H]^+$.

Step-2:

To a stirred solution of tert-butyl N-[[4-[6-[2-[4-[4-(2,6-dioxo-3-piperidyl)phenyl]-1-piperidyl]ethyl]pyrrolo[2,1-f][1,2,4]triazin-4-yl]-2-methyl-phenyl]methyl]carbamate (0.1 g, 157.04 μmol) in DCM (2 mL) was added trifluoroacetic acid (1.48 g, 12.98 mmol, 1 mL) under inert atmosphere. The reaction mixture was stirred for 3 hours at 2° C. while monitoring by TLC and LC-MS. Upon reaction completion, it was concentrated under reduced pressure and the resulting residue was washed with diethyl ether to afford 3-[4-[1-[2-[4-[4-(aminomethyl)-3-methyl-phenyl]pyrrolo[2,1-f][1,2,4]triazin-6-yl]ethyl]-4-piperidyl]phenyl]piperidine-2,6-dione TFA salt (0.1 g, 147.54 μmol, 93.95% yield) as a brown sticky liquid. It was used directly in the next step without purification. LC-MS ($ES^+$): m/z 537.29 $[M+H]^+$.

Step-3:

To a stirred solution of 3-[4-[1-[2-[4-[4-(aminomethyl)-3-methyl-phenyl]pyrrolo[2,1-f][1,2,4]triazin-6-yl]ethyl]-4-piperidyl]phenyl]piperidine-2,6-dione TFA salt (0.09 g, 138.31 μmol) and (5-tert-butyl-1,2,4-oxadiazole-3-carbonyl)oxylithium (24.36 mg, 138.31 mol) in DMF (4 mL) was added N,N-diisopropylethylamine (53.63 mg, 414.94 μmol, 72.28 L) followed by PyBOP (107.97 mg, 207.47 μmol). The reaction mixture was stirred for 16 hours at 28° C. while monitoring by TLC and LC-MS analysis. Upon reaction completion, the reaction mixture was concentrated under reduced pressure and the resulting product was purified by prep-HPLC to afford 5-tert-butyl-N-[[4-[6-[2-[4-[4-(2,6-dioxo-3-piperidyl)phenyl]-1-piperidyl]ethyl]pyrrolo[2,1-f][1,2,4]triazin-4-yl]-2-methyl-phenyl]methyl]-1,2,4-oxadiazole-3-carboxamide TFA salt (17.4 mg, 21.40 μmol, 15.47% yield) as a pale yellow solid. $^1H$ NMR (400 MHz, DMSO-$d_6$) δ 10.83 (s, 1H), 10.77 (s, 1H), 9.54 (t, J=6.0 Hz, 1H), 8.60 (s, 1H)), 8.19 (d, J=7.6 Hz, 1H), 7.94 (d, J=7.6 Hz, 2H), 7.46 (d, J=8.0 Hz, 1H), 7.33-6.97 (m, 4H), 4.55 (d, J=5.6 Hz, 2H), 3.82 (q, J=5.4 Hz, 1H), 3.66-3.62 (m, 2H), 3.21-3.09 (m, 6H), 2.86-2.83 (m, 1H), 2.69 (s, 2H), 2.50 (s, 3H), 2.18-2.13 (m, 1H), 2.07-2.00 (m, 3H), 1.92-1.86 (m, 2H), 1.44 (s, 9H). LC-MS ($ES^+$): m/z 689.21 $[M+H]^+$.

Example 117

Example 117 was prepared following the synthesis of Example 116

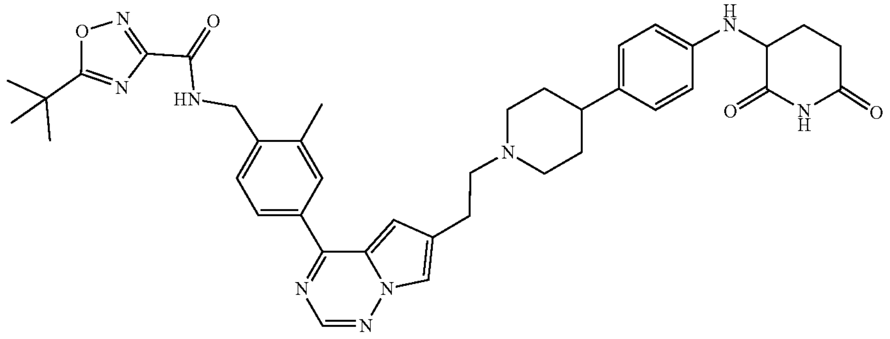 [SMILES: Cc1cc(-c2ncnn3cc(CCN4CCC(c5ccc(NC6CCC(=O)NC6=O)cc5)CC4)cc23)ccc1CNC(=O)c1noc(C(C)(C)C)n1]

5-tert-butyl-N-[[4-[6-[2-[4-[4-[(2,6-dioxo-3-piperidyl)amino]phenyl]-1-piperidyl]ethyl]pyrrolo[2,1-f][1,2,4]triazin-4-yl]-2-methyl-phenyl]methyl]-1,2,4-oxadiazole-3-carboxamide. $^1H$ NMR (400 MHz, DMSO-$d_6$) δ 10.78 (s, 1H), 9.54 (t, J=6.0 Hz, 1H), 9.25 (s, 1H), 8.61 (s, 1H), 8.18 (s, 1H), 7.95-7.93 (m, 2H), 7.46 (t, J=8.0 Hz, 1H), 7.24-6.94 (m, 3H), 6.64 (d, J=8.4 Hz, 2H), 4.56 (d, J=5.6 Hz, 2H), 4.29-4.25 (m, 1H), 3.50-3.42 (m, 4H), 3.20-3.05 (m, 4H), 2.73-2.60 (m, 3H), 2.47 (s, 3H), 2.11-2.10 (m, 1H), 2.08-1.75 (m, 5H), 1.44 (s, 9H). LC-MS ($ES^+$): m/z 704.70 $[M+H]^+$.

Example 118

Example 118 was prepared following the synthesis of Example 116

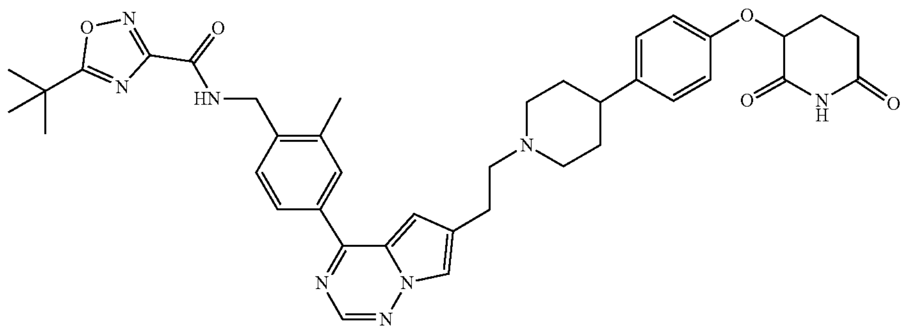 [SMILES: Cc1cc(-c2ncnn3cc(CCN4CCC(c5ccc(OC6CCC(=O)NC6=O)cc5)CC4)cc23)ccc1CNC(=O)c1noc(C(C)(C)C)n1]

5-tert-butyl-N-[[4-[6-[2-[4-[4-[(2,6-dioxo-3-piperidyl)oxy]phenyl]-1-piperidyl]ethyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ=10.91 (br s, 1H), 9.52 (t, J=5.8 Hz, 1H), 8.54 (s, 1H), 8.33 (s, 1H), 8.09 (s, 1H), 7.97-7.90 (m, 2H), 7.45 (d, J=8.6 Hz, 1H), 7.21-7.09 (m, 3H), 6.93 (d, J=8.6 Hz, 2H), 5.14 (dd, J=5.0, 10.5 Hz, 1H), 4.55 (d, J=6.0 Hz, 2H), 3.06 (br d, J=11.2 Hz, 2H), 2.90 (br t, J=7.4 Hz, 2H), 2.76-2.59 (m, 4H), 2.56 (br d, J=4.8 Hz, 1H), 2.46 (s, 4H), 2.22-2.15 (m, 1H), 2.08 (br d, J=10.4 Hz, 2H), 1.78-1.69 (m, 2H), 1.67-1.55 (m, 2H), 1.43 (s, 9H). LC-MS (ES$^+$): m/z 705.4 [M+H]$^+$.

Example 119

Example 119 was prepared following the synthesis of Example 116

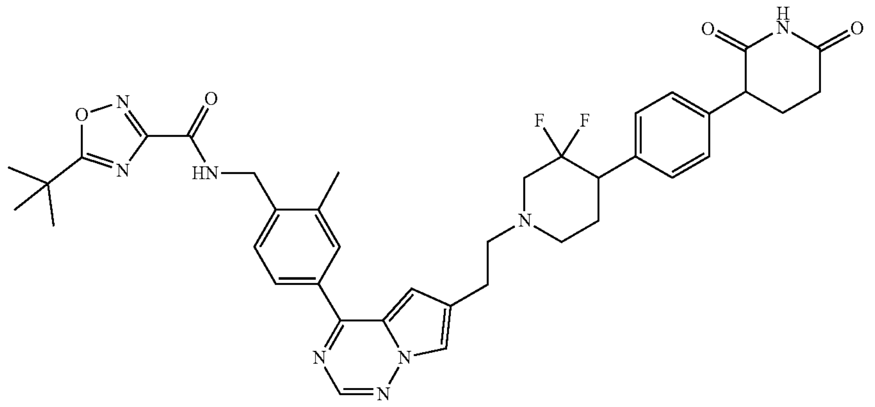 [SMILES: Cc1cc(-c2ncnn3cc(CCN4CCC(c5ccc(C6CCC(=O)NC6=O)cc5)C(F)(F)C4)cc23)ccc1CNC(=O)c1noc(C(C)(C)C)n1]

5-tert-butyl-N-[[4-[6-[2-[4-[4-(2,6-dioxo-3-piperidyl)phenyl]-3,3-difluoro-1-piperidyl]ethyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.83 (s, 1H), 9.51 (t, J=6.0 Hz, 1H), 8.55 (s, 1H), 8.32 (s, 1H), 8.10 (s, 1H), 7.96-7.94 (m, 2H), 7.45 (d, J=8.5 Hz, 1H), 7.28 (d, J=8.1 Hz, 2H), 7.20-7.16 (m, 3H), 4.55 (d, J=6.0 Hz, 2H), 3.87-3.83 (m, 1H), 3.07-2.00 (m, 3H), 2.91-2.91 (m, 2H), 2.80-2.78 (m, 2H), 2.67-2.63 (m, 1H), 2.46 (s, 5H), 2.41-2.17 (m, 2H), 2.11-2.03 (m, 2H), 1.83-178 (m, 1H), 1.44 (s, 9H). LC-MS (ES$^+$): m/z 725.17 [M+H]$^+$.

Example 120

Example 120 was prepared following the synthesis of Example 116

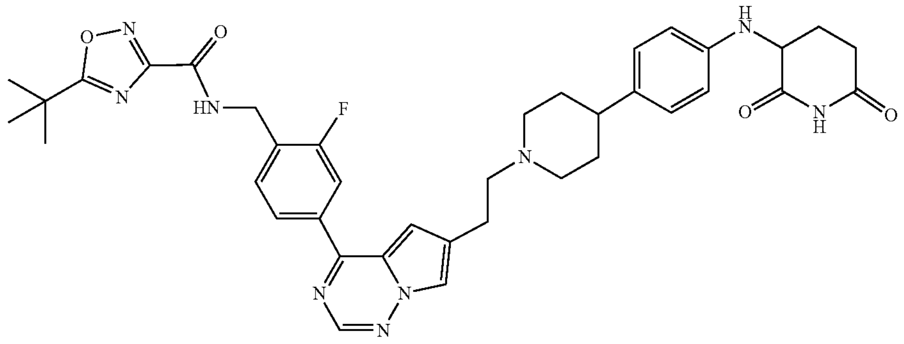 [SMILES: CC(C)(C)c1nc(C(=O)NCc2ccc(-c3ncnn4cc(CCN5CCC(c6ccc(NC7CCC(=O)NC7=O)cc6)CC5)cc34)cc2F)no1]

5-tert-butyl-N-[[4-[6-[2-[4-[4-[(2,6-dioxo-3-piperidyl) amino]phenyl]-1-piperidyl]ethyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.78 (s, 1H), 9.61 (t, J=6.0 Hz, 1H), 9.20 (bs, 1H), 8.65 (s, 1H), 8.23 (s, 1H), 7.98-7.97 (m, 1H), 7.91-7.87 (m, 1H), 7.61 (t, J=7.8 Hz, 1H), 7.26 (s, 1H), 6.96 (d, J=8.5 Hz, 2H), 6.64 (d, J=8.5 Hz, 2H), 4.62 (d, J=5.9 Hz, 2H), 4.30-4.26 (m, 1H), 3.52-3.49 (m, 3H), 3.37-3.06 (m, 4H), 2.74-2.67 (m, 1H), 2.60-2.55 (m, 3H), 2.11-2.04 (m, 1H), 1.99-1.94 (m, 2H), 1.81-1.75 (m, 3H), 1.44 (s, 9H). LC-MS ($ES^+$): m/z 708.24 $[M+H]^+$.

Example 121. Synthesis of 5-tert-butyl-N-[[2-fluoro-4-[6-[2-[4-[4-(3-methyl-2,6-dioxo-3-piperidyl)phenyl]-1-piperidyl]ethyl]pyrrolo[2,1-f][1,2,4]triazin-4-yl]phenyl]methyl]-1,2,4-oxadiazole-3-carboxamide

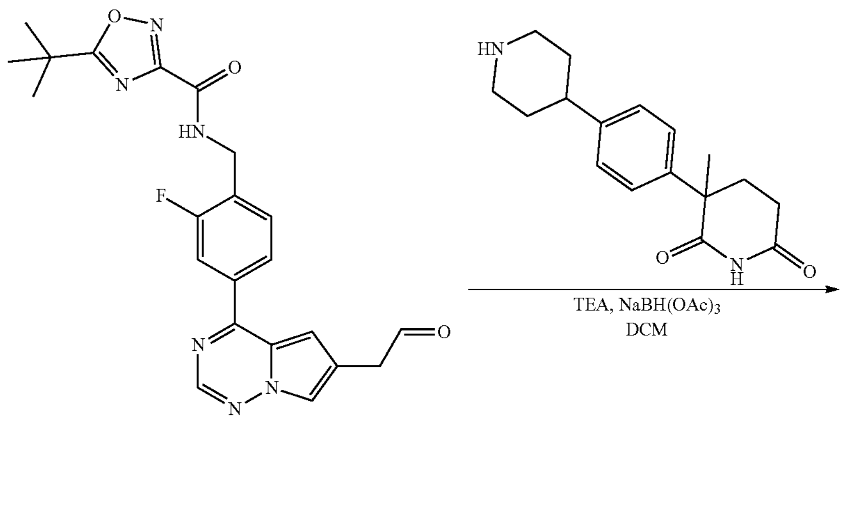

-continued

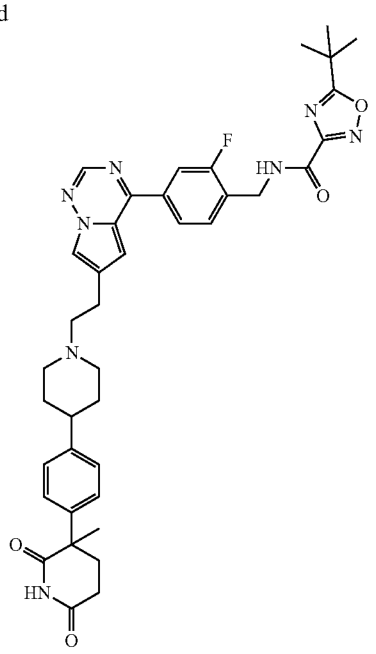

A stirred solution of 3-methyl-3-[4-(4-piperidyl)phenyl]piperidine-2,6-dione hydrochloride (98.42 mg, 304.87 μmol) in DCM (5 mL) was basified with triethylamine (347.78 mg, 3.44 mmol, 479.04 μL) and stirred for 5 minutes before the addition of 5-tert-butyl-N-[[2-fluoro-4-[6-(2-oxo-ethyl)pyrrolo[2,1-f][1,2,4]triazin-4-yl]phenyl]methyl]-1,2,4-oxadiazole-3-carboxamide (0.15 g, 343.69 μmol) and the reaction mixture was stirred for 2 hours at room temperature. The reaction mixture was cooled to 0° C., sodium triacetoxyborohydride (217.56 mg, 1.03 mmol) was added and the reaction mixture was stirred at room temperature for 16 hours. After completion of the reaction, solvent was concentrated under reduced pressure and purification by prep-HPLC using TFA as a buffer to afford 5-tert-butyl-N-[[2-fluoro-4-[6-[2-[4-[4-(3-methyl-2,6-dioxo-3-piperidyl)phenyl]-1-piperidyl]ethyl]pyrrolo[2,1-f][1,2,4]triazin-4-yl]phenyl]methyl]-1,2,4-oxadiazole-3-carboxamide trifluoroacetic acid salt (49.3 mg, 59.26 mol, 17.24% yield) as yellow solid. $^1$H NMR (400 MHz, DMSO-$d_6$) δ 10.92 (s, 1H), 9.61 (t, J=6.0 Hz, 1H), 8.64 (s, 1H), 8.23 (s, 1H), 7.98 (d, J=8.0 Hz, 1H), 7.91-7.88 (m, 1H), 7.60 (t, J=8.0 Hz, 1H), 7.20-7.26 (m, 5H), 4.62 (d, J=5.6 Hz, 2H), 3.55-3.45 (m, 4H), 3.21-3.08 (m, 4H), 2.86-2.80 (m, 1H), 2.49-2.40 (m, 2H), 2.10-1.89 (m, 4H), 1.86-1.80 (m, 2H), 1.43 (s, 12H). LC-MS (ES$^-$): m/z 705.45 [M−H]$^-$.

Example 122

Example 122 was prepared following the synthesis of Example 121

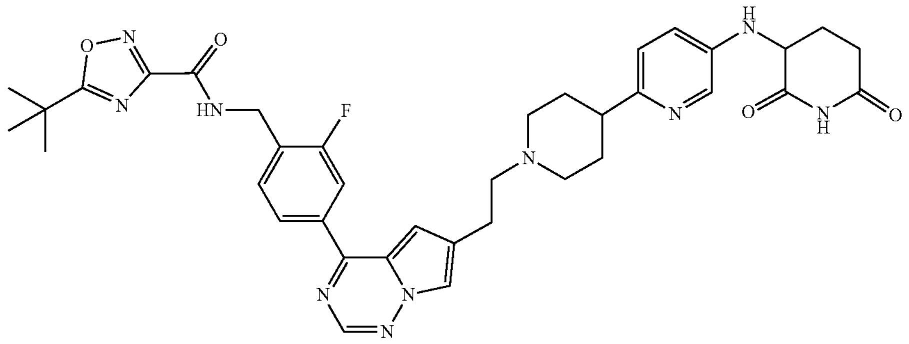 [SMILES: CC(C)(C)c1nc(C(=O)NCc2ccc(-c3ncnn4cc(CCN5CCC(c6ccc(NC7CCC(=O)NC7=O)cn6)CC5)cc34)cc2F)no1]

5-tert-butyl-N-[[4-[6-[2-[4-[5-[(2,6-dioxo-3-piperidyl)amino]-2-pyridyl]-1-piperidyl]ethyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.79 (s, 1H), 9.58 (t, J=6.0 Hz, 1H), 8.58 (s, 1H), 8.21 (brs, 2H), 8.13 (s, 1H), 7.98-7.87 (m, 2H), 7.89 (d, J=1.2 Hz, 1H), 7.59 (t, J=7.9 Hz, 1H), 7.18 (s, 1H), 6.98 (s, 2H), 4.61 (d, J=5.9 Hz, 2H), 4.34-4.30 (m, 1H), 3.05 (d, J=11.1 Hz, 2H), 2.91 (t, J=7.5 Hz, 2H), 2.80-2.67 (m, 5H), 2.11-2.05 (m, 3H), 1.91-1.88 (m, 1H), 1.80-1.60 (m, 4H), 1.43 (s, 9H). LC-MS (ES$^+$): m/z 709.25 [M+H]$^+$.

Example 123. Synthesis of 5-tert-butyl-N-[[4-[6-[2-[4-[3-[(2,6-dioxo-3-piperidyl)amino]pyrazol-1-yl]-1-piperidyl]ethyl]pyrrolo[2,1-f][1,2,4]triazin-4-yl]-2-fluoro-phenyl]methyl]-1,2,4-oxadiazole-3-carboxamide

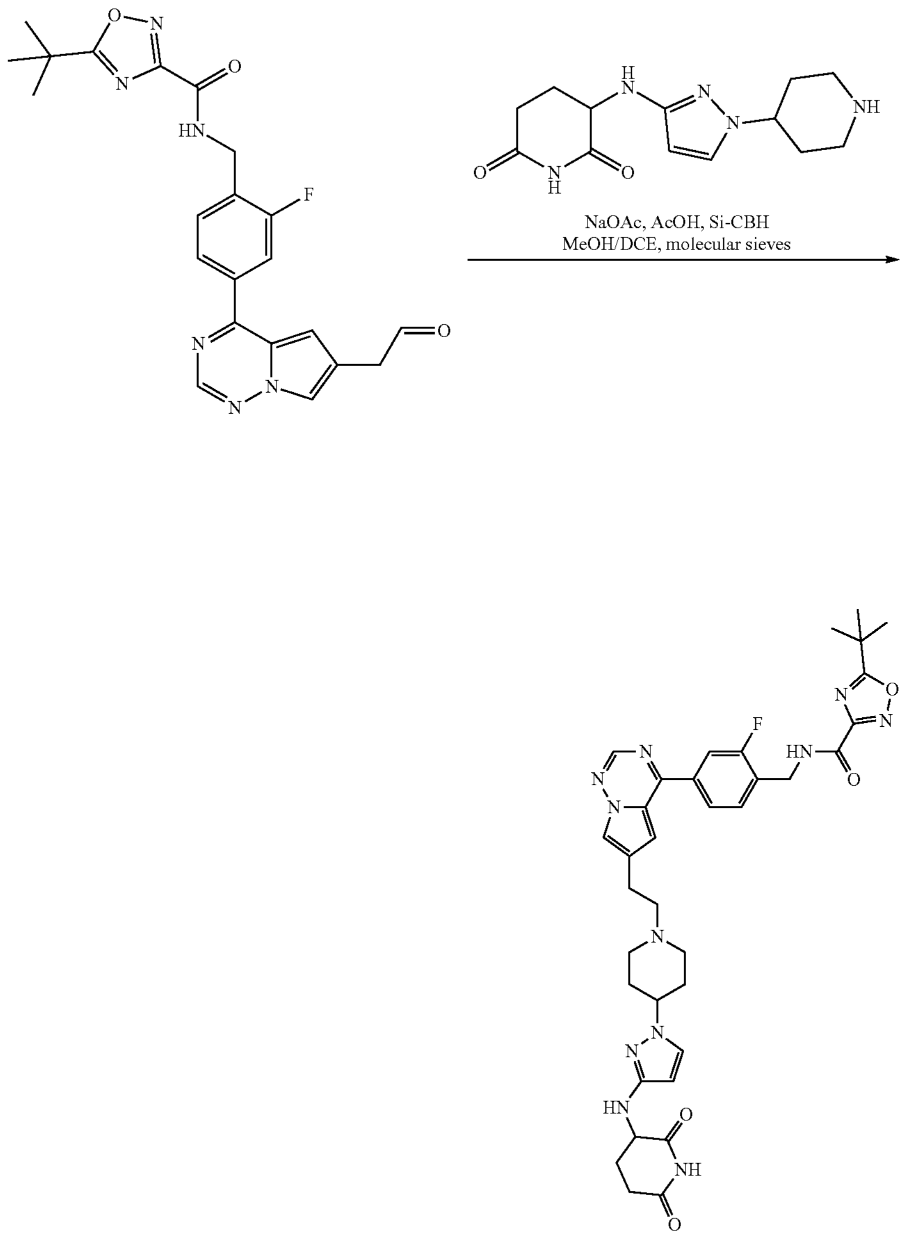 [SMILES: CC(C)(C)c1nc(C(=O)NCc2ccc(-c3ncnn4cc(CC=O)cc34)cc2F)no1 ; O=C1CCC(Nc2ccn(C3CCNCC3)n2)C(=O)N1 ; CC(C)(C)c1nc(C(=O)NCc2ccc(-c3ncnn4cc(CCN5CCC(n6ccc(NC7CCC(=O)NC7=O)n6)CC5)cc34)cc2F)no1]

To a stirred solution of 3-[[1-(4-piperidyl)pyrazol-3-yl]amino]piperidine-2,6-dione TFA salt (107.60 mg, 274.95 μmol) in DCE (3 mL) and methanol (3 mL) was added sodium acetate, anhydrous (56.39 mg, 687.38 μmol), acetic acid (13.76 mg, 229.13 μmol, 13.10 μL) and molecular sieves (0.1 g) under inert atmosphere. The reaction mixture was stirred for 10-15 minutes before adding 5-tert-butyl-N-[[2-fluoro-4-[6-(2-oxoethyl)pyrrolo[2,1-f][1,2,4]triazin-4-yl]phenyl]methyl]-1,2,4-oxadiazole-3-carboxamide (0.1 g, 229.13 μmol) and the reaction was refluxed at 70° C. for 4 hours. The reaction mixture was then cooled to 0° C. and Si—CBH (66.40 mg, 1.15 mmol) was added and stirred at room temperature for an additional 16 hours while monitoring by LC-MS. After completion of the reaction, the reaction mixture was filtered through celite and concentrated in vacuo to give the crude product, which was purified by prep-HPLC to afford 5-tert-butyl-N-[[4-[6-[2-[4-[3-[(2,6-dioxo-3-piperidyl)amino]pyrazol-1-yl]-1-piperidyl]ethyl]pyrrolo[2,1-f][1,2,4]triazin-4-yl]-2-fluoro-phenyl]methyl]-1,2,4-oxadiazole-3-carboxamide TFA salt (32 mg, 39.13 μmol, 17.08% yield) as a yellow solid. $^1$H NMR (400 MHz, DMSO-$d_6$) δ 10.78 (s, 1H), 9.60 (t, J=5.9 Hz, 1H), 9.30 (bs, 1H), 8.64 (d, J=2.1 Hz, 1H), 8.22 (s, 1H), 7.99-7.97 (m, 1H), 7.91-7.88 (m, 1H), 7.61 (t, J=7.9 Hz, 1H), 7.53 (d, J=2.2 Hz, 1H), 7.42 (d, J=2.1 Hz, 1H), 7.27-7.21 (m, 1H), 5.57 (d, J=2.3 Hz, 1H), 4.62 (d, J=5.9 Hz, 2H), 4.24-4.12 (m, 2H), 3.82-3.48 (m, 4H), 3.23-3.11 (m, 4H), 2.67-2.62 (m, 1H), 2.57-2.54 (m, 1H), 2.24-2.07 (m, 4H), 2.01-1.93 (m, 1H), 1.44 (s, 9H). LC-MS (ES$^+$): m/z 698.68 [M+H]$^+$.

Example 124

Example 124 was prepared following the synthesis of Example 123

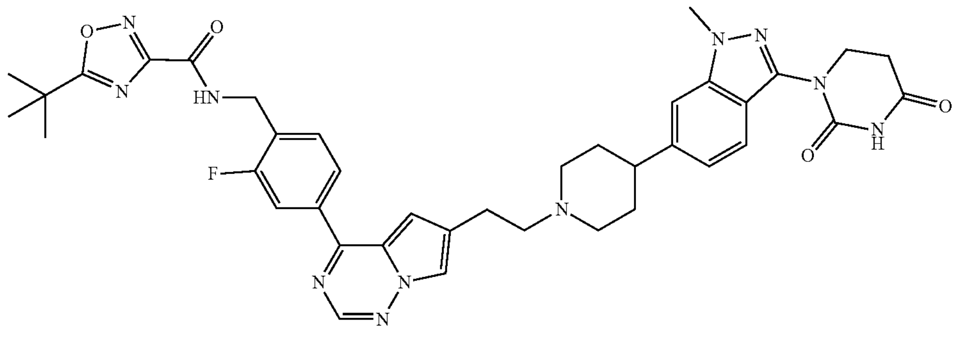 [SMILES: Cn1nc(N2CCC(=O)NC2=O)c2ccc(C3CCN(CCc4cc5c(-c6ccc(CNC(=O)c7noc(C(C)(C)C)n7)c(F)c6)ncnn5c4)CC3)cc21]

5-tert-butyl-N-[[4-[6-[2-[4-[3-(2,4-dioxohexahydropyrimidin-1-yl)-1-methyl-indazol-6-yl]-1-piperidyl]ethyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.55 (s, 1H), 9.61 (t, J=5.9 Hz, 1H), 9.25 (s, 1H), 8.65 (s, 1H), 8.25 (s, 1H), 8.00-7.98 (m, 1H), 7.91-7.89 (m, 1H), 7.63-7.60 (m, 2H), 7.41 (s, 1H), 7.32 (s, 1H), 7.05-7.03 (m, 1H), 4.62 (d, J=5.9 Hz, 2H), 3.98 (s, 3H), 3.91 (t, J=6.7 Hz, 2H), 3.58-3.49 (m, 4H), 3.24-3.12 (m, 4H), 3.04-2.98 (m, 1H), 2.76 (t, J=6.7 Hz, 2H), 2.14-2.11 (m, 2H), 2.01-1.92 (m, 2H), 1.44 (s, 9H). LC-MS ($ES^+$): m/z 748.15 $[M+H]^+$.

Example 125. Synthesis of 5-tert-butyl-N-[[4-[6-[[2-[4-[4-(2,6-dioxo-3-piperidyl)phenyl]-1-piperidyl]ethyl-methyl-amino]methyl]pyrrolo[2,1-f][1,2,4]triazin-4-yl]-2-methyl-phenyl]methyl]-1,2,4-oxadiazole-3-carboxamide

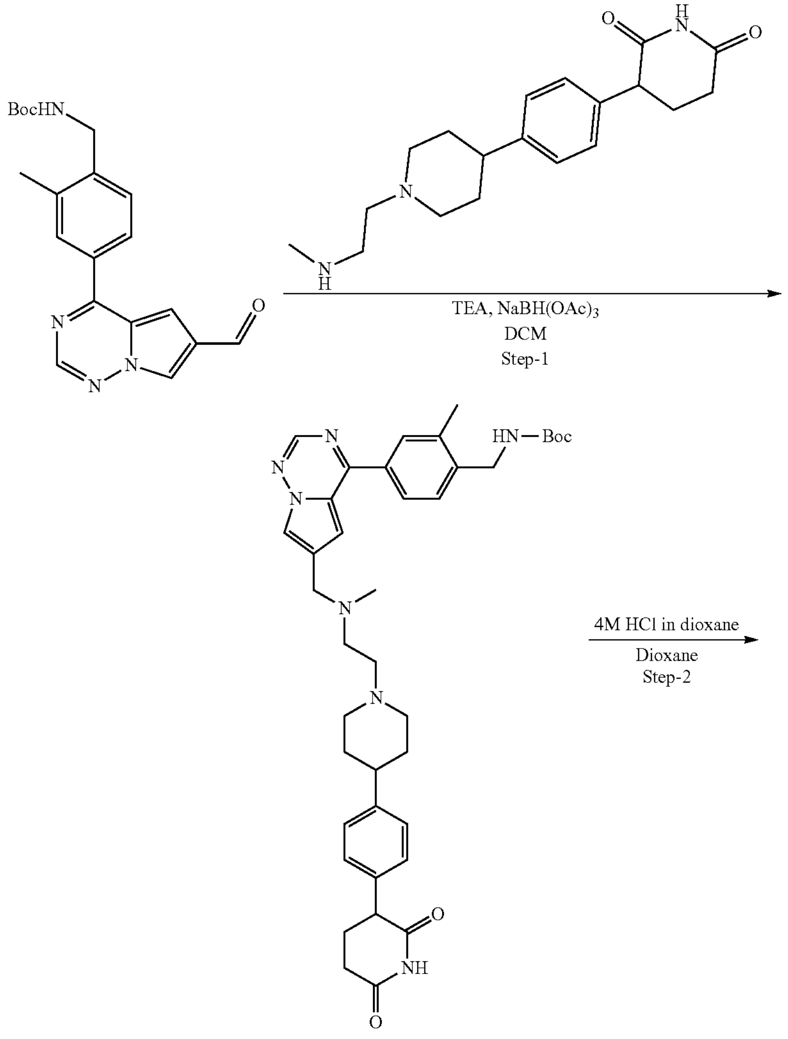

-continued

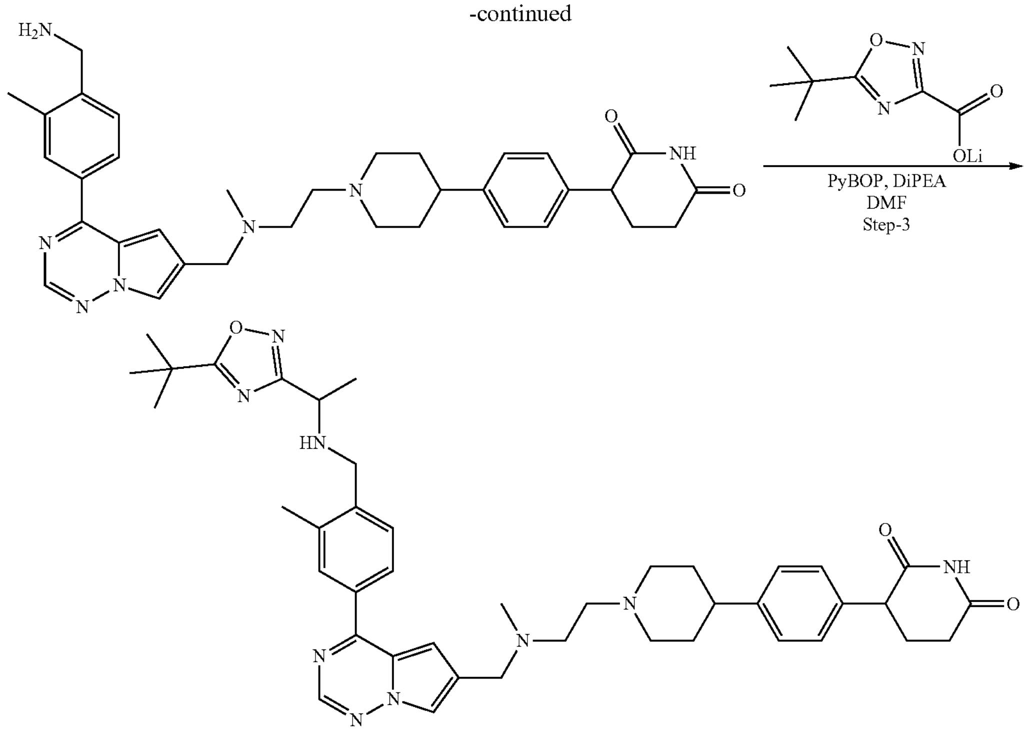

Step-1:

To a stirred solution of tert-butyl N-[[4-(6-formylpyrrolo[2,1-f][1,2,4]triazin-4-yl)-2-methyl-phenyl]methyl]carbamate (0.500 g, 1.36 mmol) in acetonitrile (4.43 mL) and DCM (4.43 mL) were added 3-[4-[1-[2-(methylamino)ethyl]-4-piperidyl]phenyl]piperidine-2,6-dione TFA salt (1.09 g, 2.46 mmol) and Triethylamine (1.38 g, 13.65 mmol, 1.90 mL) in a dropwise manner at room temperature. The reaction mixture was stirred for 5 hours. Subsequently, the reaction mixture was cooled to 0° C., and sodium triacetoxyborohydride (1.74 g, 8.19 mmol) was added portionwise. The reaction mixture was warmed to room temperature and stirred for 16 hours. The reaction mixture was quenched with water (50 mL) and extracted with ethyl acetate (3×150 mL). The combined organic layer was washed with a brine solution (50 mL), dried over anhydrous sodium sulfate, and concentrated under reduced pressure to give the crude product, which was purified by reverse phase chromatography (0.1% formic acid in water/acetonitrile) to afford tert-butyl N-[[4-[6-[[2-[4-[4-(2,6-dioxo-3-piperidyl)phenyl]-1-piperidyl]ethyl-methyl-amino]methyl]pyrrolo[2,1-f][1,2,4]triazin-4-yl]-2-methyl-phenyl]methyl]carbamate (500 mg, 640.36 μmol, 46.93% yield) as a pale yellow oil. LC-MS ($ES^+$): m/z 680.51 $[M+H]^+$ Step-2:

To a solution of tert-butyl N-[[4-[6-[[2-[4-[4-(2,6-dioxo-3-piperidyl)phenyl]-1-piperidyl]ethyl-methyl-amino]methyl]pyrrolo[2,1-f][1,2,4]triazin-4-yl]-2-methyl-phenyl]methyl]carbamate (0.200 g, 294.18 μmol) in DCM (6 mL) was added 4 M hydrogen chloride solution in 1,4-dioxane (2 mL) at 0° C. and the reaction mixture was stirred at room temperature for 2 hours. The reaction mixture was concentrated under reduced pressure to give the crude product, which was triturated with diethyl ether (150 mL) to afford 3-[4-[1-[2-[[4-[4-(aminomethyl)-3-methyl-phenyl]pyrrolo[2,1-f][1,2,4]triazin-6-yl]methyl-methyl-amino]ethyl]-4-piperidyl]phenyl]piperidine-2,6-dione HCl salt (0.200 g, 142.81 μmol, 48.55% yield) as an off-white solid. LC-MS ($ES^+$): m/z 580.26 $[M+H]^+$.

Step-3:

To a stirred solution of 3-[4-[1-[2-[[4-[4-(aminomethyl)-3-methyl-phenyl]pyrrolo[2,1-f][1,2,4]triazin-6-yl]methyl-methyl-amino]ethyl]-4-piperidyl]phenyl]piperidine-2,6-dione hydrochloride (0.200 g, 324.57 μmol) and (5-tert-butyl-1,2,4-oxadiazole-3-carbonyl)oxylithium (114.31 mg, 649.15 μmol) in DMF (4 mL) The reaction mixture was cooled 0° C., then N-ethyl-N-isopropyl-propan-2-amine (419.48 mg, 3.25 mmol, 565.33 μL) and PyBOP (337.81 mg, 649.15 μmol) were added, the reaction mixture was then stirred at room temperature for 2 hours. The reaction mixture was diluted with sodium bicarbonate, the solid filtered and the crude sample was purified by prep-HPLC Method to afford 5-tert-butyl-N-[[4-[6-[[2-[4-[4-(2,6-dioxo-3-piperidyl)phenyl]-1-piperidyl]ethyl-methyl-amino]methyl]pyrrolo[2,1-f][1,2,4]triazin-4-yl]-2-methyl-phenyl]methyl]-1,2,4-oxadiazole-3-carboxamide formic acid salt (39 mg, 49.37 μmol, 15.21% yield). $^1H$ NMR (400 MHz, DMSO-$d_6$) δ 10.81 (s, 1H), 9.50 (t, J=5.9 Hz, 1H), 8.58 (s, 1H), 8.16 (s, 1H), 8.10 (d, J=0.8 Hz, 1H), 7.95-7.93 (m, 2H), 7.46 (d, J=7.8 Hz, 1H), 7.19-7.12 (m, 5H), 4.54 (d, J=5.9 Hz, 2H), 3.82-3.78 (m, 1H), 3.71 (s, 2H), 3.01-2.97 (m, 2H), 2.68-2.51 (m, 1H), 2.51-2.44 (m, 5H), 2.43 (s, 3H), 2.22 (s, 3H), 2.18-2.09 (m, 4H), 1.72-1.60 (m, 4H), 1.43 (s, 9H). LC-MS ($ES^-$): m/z 730.31 $[M-H]^-$.

Example 126

Example 126 was prepared following the synthesis of Example 125

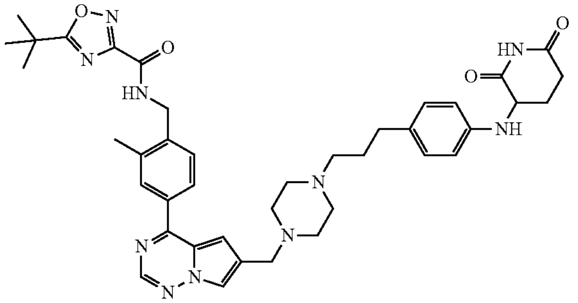 [SMILES: Cc1cc(-c2ncnn3cc(CN4CCN(CCCc5ccc(NC6CCC(=O)NC6=O)cc5)CC4)cc23)ccc1CNC(=O)c1noc(C(C)(C)C)n1]

5-tert-butyl-N-[[4-[6-[[4-[3-[4-[(2,6-dioxo-3-piperidyl)amino]phenyl]propyl]piperazin-1-yl]methyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.77 (s, 1H), 9.54 (t, J=5.9 Hz, 1H), 8.63 (s, 1H), 8.17 (s, 1H), 7.95-7.93 (m, 2H), 7.46 (d, J=7.9 Hz, 1H), 7.19 (s, 1H), 6.92 (d, J=8.4 Hz, 2H), 6.61 (d, J=8.4 Hz, 2H), 5.53 (bs, 1H), 4.55 (d, J=5.9 Hz, 2H), 4.28-4.24 (m, 1H), 3.51-3.45 (m, 6H), 3.11-3.01 (m, 6H), 2.73-2.61 (m, 1H), 2.60-2.59 (m, 1H), 2.46-2.43 (m, 2H), 2.38 (s, 3H), 2.09-2.08 (m, 1H), 1.86-1.82 (m, 3H), 1.44 (s, 9H). LC-MS (ES$^+$): m/z 733.23 [M+H]$^+$.

Example 127. Synthesis of 5-tert-butyl-N-[[4-[6-[3-[4-[4-[(2,6-dioxo-3-piperidyl)amino]phenyl]-1-piperidyl]propyl]pyrrolo[2,1-f][1,2,4]triazin-4-yl]-2-methyl-phenyl]methyl]-1,2,4-oxadiazole-3-carboxamide

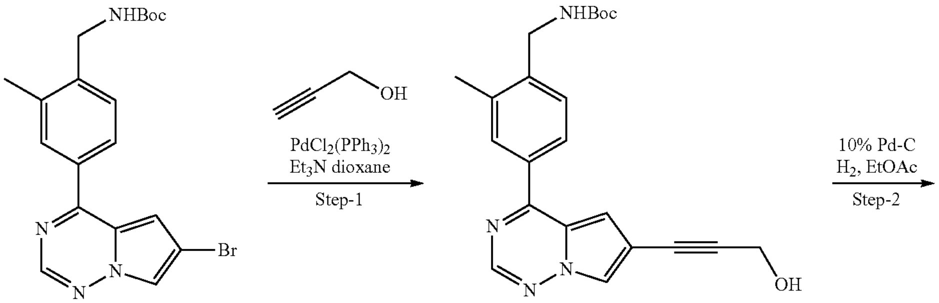

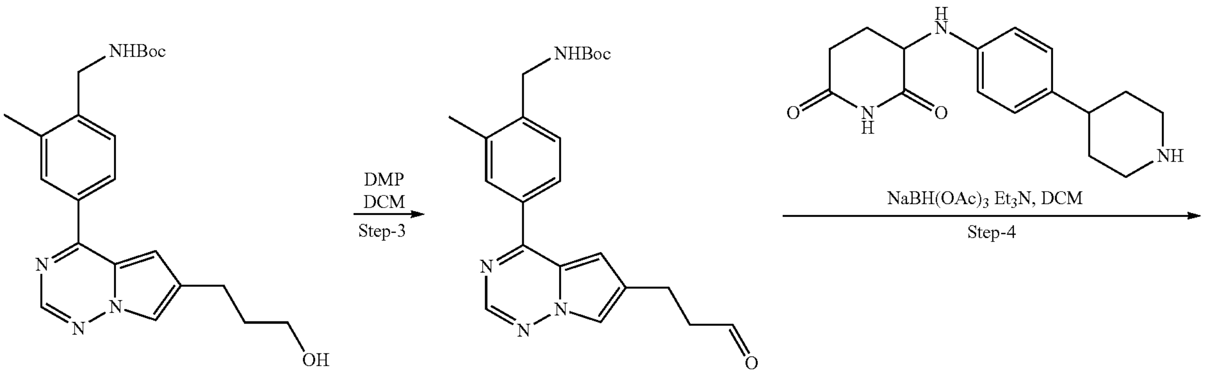

-continued

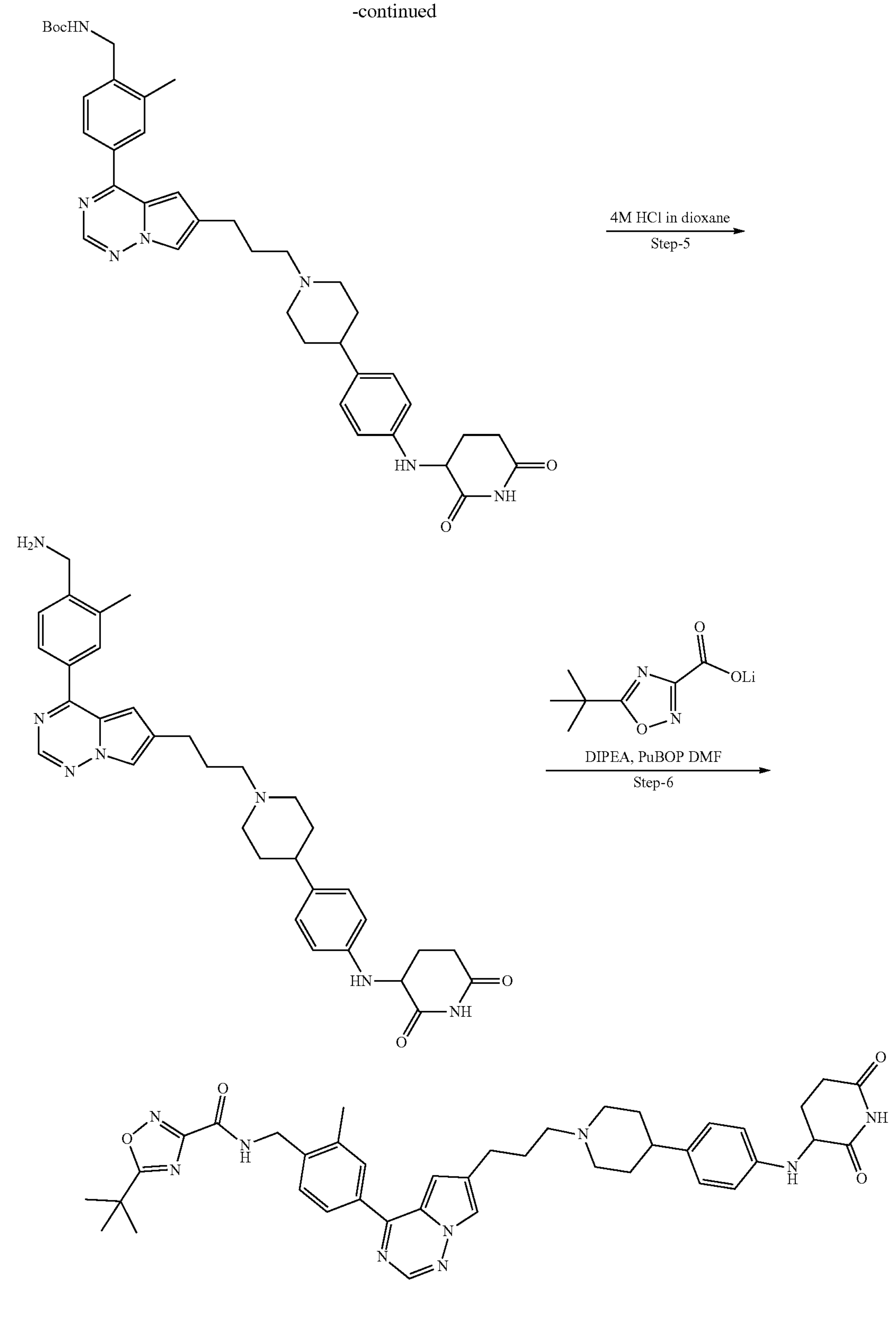

Step-1:

To a stirred solution of tert-butyl N-[[4-(6-bromopyrrolo [2,1-f][1,2,4]triazin-4-yl)-2-methyl-phenyl]methyl]carbamate (3.0 g, 7.19 mmol) in dioxane (15 mL) and Triethylamine (15 mL) was added prop-2-yn-1-ol (604.56 mg, 10.78 mmol, 637.05 μL) followed by CuI (273.83 mg, 1.44 mmol). The reaction mixture was degassed with argon for 30 minutes, and $Pd(PPh_3)_2Cl_2$ (504.60 mg, 718.91 μmol) was added and heated at 90° C. for 24 hours. After the reaction was complete, the reaction mixture was filtered through a celite pad and washed with ethyl acetate. The filtrate was diluted with water and extracted with ethyl acetate. The combined organic layers were dried over sodium sulfate and concentrated in vacuo to give the crude product, which was purified via column chromatography (silica gel) to afford tert-butyl N-[[4-[6-(3-hydroxyprop-1-ynyl)pyrrolo[2,1-f][1,2,4]triazin-4-yl]-2-methyl-phenyl]methyl]carbamate (1.5 g, 2.87 mmol, 39.87% yield) as a yellow oil. LC-MS ($ES^+$): m/z 393.18 $[M+H]^+$.

Step-2:

A solution of tert-butyl N-[[4-[6-(3-hydroxyprop-1-ynyl)pyrrolo[2,1-f][1,2,4]triazin-4-yl]-2-methyl-phenyl]methyl]carbamate (1.5 g, 3.82 mmol) in ethyl acetate (15 mL), 10 wt. % palladium on carbon, type 487, dry (406.75 mg, 3.82 mmol) was added, and the mixture was stirred under a hydrogen atmosphere (60 psi) at room temperature for 16 hours. After the reaction was completed, the reaction mixture was filtered through a celite pad and washed with ethyl acetate. The combined organic layer was concentrated in vacuo to give the crude product, which was purified via column chromatography (silica gel) to afford tert-butyl N-[[4-[6-(3-hydroxypropyl)pyrrolo[2,1-f][1,2,4]triazin-4-yl]-2-methyl-phenyl]methyl]carbamate (1.0 g, 1.89 mmol, 49.49% yield) as a yellow oil. LC-MS ($ES^+$): m/z 397.28 $[M+H]^+$.

Step-3:

To a stirred solution of tert-butyl N-[[4-[6-(3-hydroxypropyl)pyrrolo[2,1-f][1,2,4]triazin-4-yl]-2-methyl-phenyl]methyl]carbamate (1.0 g, 2.52 mmol) in DCM (10 mL) was added Dess-Martin periodinane (1.60 g, 3.78 mmol) at 0° C. and stirred at room temperature for 1 hour. After the reaction was completed, the reaction mixture was diluted with water and extracted with DCM. The combined organic layer was dried over sodium sulfate and concentrated in vacuo to get crude product. The resulting compound was purified over silica gel to afforded tert-butyl N-[[2-methyl-4-[6-(3-oxopropyl)pyrrolo[2,1-f][1,2,4]triazin-4-yl]phenyl]methyl]carbamate (0.7 g, 1.42 mmol, 56.29% yield) as a yellow oil. LC-MS ($ES^+$): m/z 395.43 $[M+H]^+$.

Step-4:

To a stirred solution of 3-[4-(4-piperidyl)anilino]piperidine-2,6-dione TFA salt (1.27 g, 3.17 mmol) in DCM (5 mL) was added Triethylamine (1.28 g, 12.68 mmol, 1.77 mL) at 0° C. This was followed by the addition of tert-butyl N-[[2-methyl-4-[6-(3-oxopropyl)pyrrolo[2,1-f][1,2,4]triazin-4-yl]phenyl]methyl]carbamate (0.50 g, 1.27 mmol) and the reaction was stirred at room temperature for 1 hour. Sodium triacetoxyborohydride (805.93 mg, 3.80 mmol) was added, and the reaction was stirred for 16 hours at room temperature. After completion of the reaction, the mixture was concentrated in vacuo, diluted with water, and extracted with ethyl acetate. The combined organic layers were dried over sodium sulfate and concentrated in vacuo to give the crude product, which was purified by column chromatography (silica gel) to afford tert-butyl N-[[4-[6-[3-[4-[4-[(2,6-dioxo-3-piperidyl)amino]phenyl]-1-piperidyl]propyl]pyrrolo[2,1-f][1,2,4]triazin-4-yl]-2-methyl-phenyl]methyl]carbamate (0.50 g, 638.31 μmol, 50.36% yield) as a light green solid. LC-MS ($ES^+$): m/z 666.49 $[M+H]^+$.

Step-5:

To a stirred solution of tert-butyl N-[[4-[6-[3-[4-[4-[(2,6-dioxo-3-piperidyl)amino]phenyl]-1-piperidyl]propyl]pyrrolo[2,1-f][1,2,4]triazin-4-yl]-2-methyl-phenyl]methyl]carbamate (0.15 g, 225.29 μmol) in DCM (2 mL) was added 4 M hydrogen chloride solution in dioxane (1.5 mL) at 0° C. The reaction was stirred at room temperature for 1 hour, and was concentrated in vacuo and triturated with diethyl ether. The resulting crude product was dried under high vacuum to afford 3-[4-[1-[3-[4-[4-(aminomethyl)-3-methyl-phenyl]pyrrolo[2,1-f][1,2,4]triazin-6-yl]propyl]-4-piperidyl]anilino]piperidine-2,6-dione HCl salt (0.15 g, 201.77 μmol, 89.56% yield) as a yellow solid. LC-MS ($ES^+$): m/z 566.48 $[M+H]^+$.

Step-6:

To a stirred solution of 3-[4-[1-[3-[4-[4-(aminomethyl)-3-methyl-phenyl]pyrrolo[2,1-f][1,2,4]triazin-6-yl]propyl]-4-piperidyl]anilino]piperidine-2,6-dione HCl salt (0.15 g, 265.15 mol) in DMF (2 mL) was added (5-tert-butyl-1,2,4-oxadiazole-3-carbonyl)oxylithium (97.07 mg, 530.31 μmol) and N-ethyl-N-isopropyl-propan-2-amine (342.69 mg, 2.65 mmol, 461.84 μL) at 0° C. and the reaction was stirred at room temperature for 10 minutes. Then benzotriazol-1-yloxy(tripyrrolidin-1-yl)phosphonium; hexafluorophosphate (275.97 mg, 530.31 μmol) was added and stirred for 1 hour at this temperature. After completion, the reaction was concentrated under high vacuum to give the crude product, which was purified by prep-HPLC to afford 5-tert-butyl-N-[[4-[6-[3-[4-[4-4[(2,6-dioxo-3-piperidyl)amino]phenyl]-1-piperidyl]propyl]pyrrolo[2,1-f][1,2,4]triazin-4-yl]-2-methyl-phenyl]methyl]-1,2,4-oxadiazole-3-carboxamide (29.2 mg, 40.09 μmol, 15.12% yield) as a yellow solid. $^1H$ NMR (400 MHz, DMSO-$d_6$) δ 10.77 (s, 1H), 9.53 (t, J=5.8 Hz, 1H), 8.57 (s, 1H), 8.12 (s, 1H), 7.95 (d, J=7.4 Hz, 2H), 7.46 (d, J=8.0 Hz, 1H), 7.13 (s, 1H), 6.94 (d, J=7.9 Hz, 2H), 6.63 (d, J=8.3 Hz, 2H), 5.74 (d, J=7.2 Hz, 1H), 4.55 (d, J=5.9 Hz, 2H), 4.30-4.24 (m, 1H), 3.51 (bs, 2H), 3.19-2.67 (m, 7H), 2.60-2.55 (m, 2H), 2.33 (s, 3H), 2.11-2.07 (m, 3H), 1.92-1.72 (m, 5H), 1.44 (s, 9H). LC-MS ($ES^+$): m/z 718.24 $[M+H]^+$.

Example 128. Synthesis of 5-tert-butyl-N-[[4-[6-[4-[4-[4-(2,6-dioxo-3-piperidyl)phenyl]-1-piperidyl]butyl]pyrrolo[2,1-f][1,2,4]triazin-4-yl]-2-methyl-phenyl]methyl]-1,2,4-oxadiazole-3-carboxamide

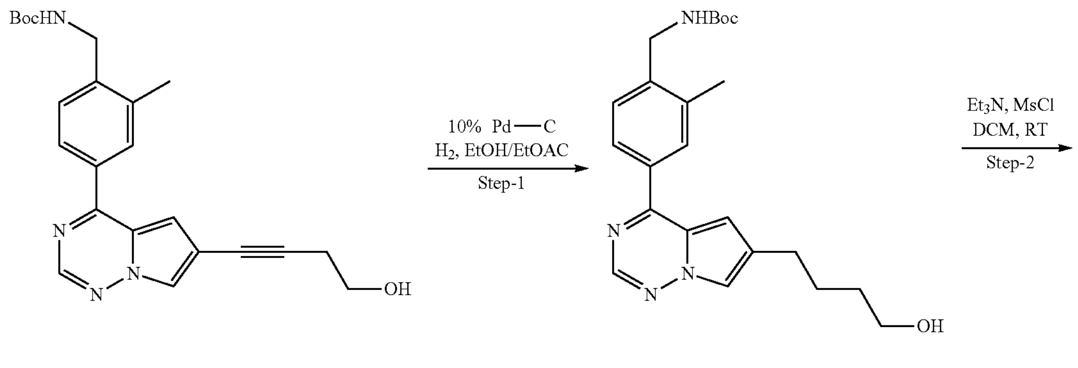

-continued
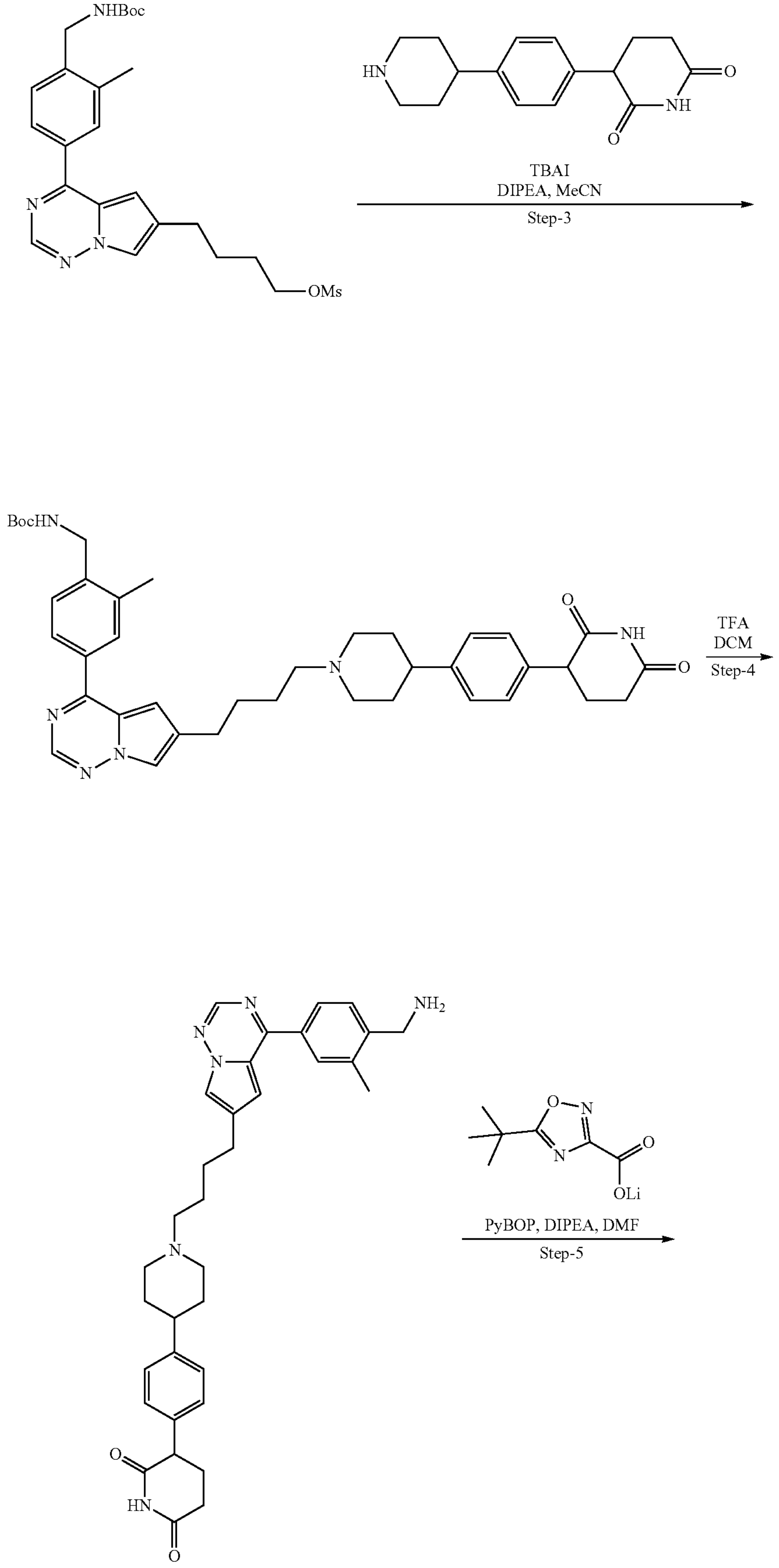

-continued

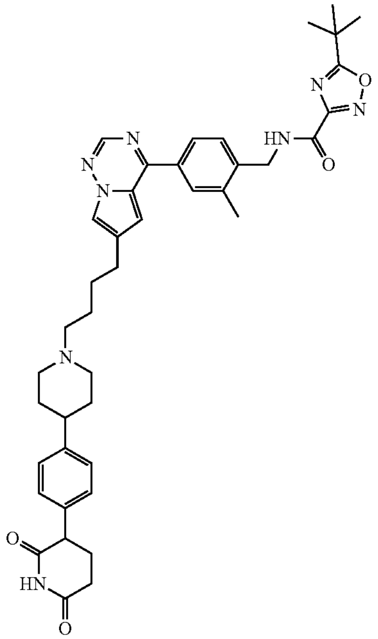 [SMILES: Cc1cc(-c2ncnn3cc(CCCCN4CCC(c5ccc(C6CCC(=O)NC6=O)cc5)CC4)cc23)ccc1CNC(=O)c1noc(C(C)(C)C)n1]

Step-1:

Palladium on carbon, 10 wt. % (3 g, 28.19 mmol) was added to a solution of tert-butyl N-[[4-[6-(4-hydroxybut-1-ynyl)pyrrolo[2,1-f][1,2,4]triazin-4-yl]-2-methyl-phenyl] methyl]carbamate (2.7 g, 6.64 mmol) in ethyl acetate (50 mL) at 27° C. under hydrogen atmosphere. The reaction mixture was stirred at 27° C. for 16 hours. The reaction mixture was filtered through a celite bed and washed with ethyl acetate (100 mL×2). The organic layer was concentrated under reduced pressure to obtain the crude product, which was purified by flash column chromatography (silica gel 230-400 mesh, 0-100% ethyl acetate in pet-ether) to afford tert-butyl N-[[4-[6-(4-hydroxybutyl)pyrrolo[2,1-f][1,2,4]triazin-4-yl]-2-methyl-phenyl]methyl]carbamate (2.5 g, 5.89 mmol, 88.64% yield) as a white solid. LC-MS ($ES^+$): m/z 411.48 $[M+H]^+$.

Step-2:

In a 25 ml single neck round bottom flask, tert-butyl N-[[4-[6-(4-hydroxybutyl)pyrrolo[2,1-f][1,2,4]triazin-4-yl]-2-methyl-phenyl]methyl]carbamate (0.9 g, 2.19 mmol) was dissolved in DCM (30 mL) and cooled to 0° C. Triethylamine (221.85 mg, 2.19 mmol, 305.58 μL) was added, followed by the addition of methanesulfonyl chloride (251.14 mg, 2.19 mmol, 169.69 μL). The reaction mixture was warmed up to room temperature and stirred for 1 hour. Progress of the reaction was monitored with TLC and LC-MS. After completion of the reaction, the reaction mixture was concentrated under reduced pressure, washed several times with a saturated sodium bicarbonate solution, and extracted with ethyl acetate. The organic layer was concentrated under reduced pressure to give the crude product, which was triturated with diethyl ether to afford compound 4-[4-[4-[(tert-butoxycarbonylamino)methyl]-3-methyl-phenyl]pyrrolo[2,1-f][1,2,4]triazin-6-yl]butyl methanesulfonate (0.90 g, 1.77 mmol, 80.77% yield) as a yellowish semi-solid. LC-MS ($ES^+$): m/z 489.24 $[M+H]^+$.

Step-3:

To a stirred solution of 3-[4-(4-piperidyl)phenyl]piperidine-2,6-dione TFA salt (125.41 mg, 324.60 μmol) in acetonitrile (6 mL) was added tetrabutylammonium iodide (188.99 mg, 511.67 μmol) followed by N,N-diisopropylethylamine (198.39 mg, 1.54 mmol, 267.37 μL) under inert atmosphere. Then, 4-[4-[4-[(tert-butoxycarbonylamino) methyl]-3-methyl-phenyl]pyrrolo[2,1-f][1,2,4]triazin-6-yl] butyl methanesulfonate (0.25 g, 511.67 μmol) was added portionwise, and the reaction mixture was heated at 55° C. for 16 hours. The reaction progress was monitored by TLC and LC-MS. Upon completion, the reaction was quenched with water and extracted with DCM. The organic layer was washed with brine solution and concentrated to dryness under reduced pressure. The crude product was purified by Biotage using 0-5% MeOH in DCM to afford tert-butyl N-[[4-[6-[4-[4-[4-(2,6-dioxo-3-piperidyl)phenyl]-1-piperidyl]butyl]pyrrolo[2,1-f][1,2,4]triazin-4-yl]-2-methyl-phenyl]methyl]carbamate (0.1 g, 130.86 μmol, 25.58% yield) as a brown sticky liquid. LC-MS ($ES^+$): m/z 665.27 $[M+H]^+$.

Step-4:

To a stirred solution of tert-butyl N-[[4-[6-[4-[4-[4-(2,6-dioxo-3-piperidyl)phenyl]-1-piperidyl]butyl]pyrrolo[2,1-f] [1,2,4]triazin-4-yl]-2-methyl-phenyl]methyl]carbamate (0.06 g, 90.25 μmol) in DCM (2 mL) was added trifluoroacetic acid (102.90 mg, 902.48 μmol, 69.53 μL) under inert atmosphere. The reaction mixture was stirred for 3 hours at 0° C. while monitoring by TLC and LC-MS. After completion of the reaction, the reaction mixture was concentrated under reduced pressure and the resulting residue was washed with diethyl ether to afford 3-[4-[1-[4-[4-[4-(aminomethyl)-3-methyl-phenyl]pyrrolo[2,1-f][1,2,4]triazin-6-yl]butyl]-4-piperidyl]phenyl]piperidine-2,6-dione TFA salt (0.05 g, 63.35 μmol, 70.20% yield) as a brown sticky liquid. The product was taken into the next step without purification. LC-MS ($ES^+$): m/z 565.33 $[M+H]^+$.

Step-5:

To a stirred solution of 3-[4-[1-[4-[4-[4-(aminomethyl)-3-methyl-phenyl]pyrrolo[2,1-f][1,2,4]triazin-6-yl]butyl]-4-piperidyl]phenyl]piperidine-2,6-dione TFA salt (0.09 g, 132.60 μmol) and (5-tert-butyl-1,2,4-oxadiazole-3-carbonyl)oxylithium (28.02 mg, 159.12 mol) in DMF (3 mL) was added PyBOP (103.50 mg, 198.90 μmol) followed by N,N-diisopropylethylamine (68.55 mg, 530.39 μmol, 92.38 L). The reaction mixture was stirred for 16 hours at 28° C. while monitoring by TLC and LC-MS. After completion of the reaction, the reaction mixture was concentrated under reduced pressure and resulting crude product was purified by prep-HPLC to afford 5-tert-butyl-N-[[4-[6-[4-[4-[4-(2,6-dioxo-3-piperidyl)phenyl]-1-piperidyl]butyl]pyrrolo[2,1-f][1,2,4]triazin-4-yl]-2-methyl-phenyl]methyl]-1,2,4-oxadiazole-3-carboxamide formic acid salt (14.6 mg, 18.94 μmol, 14.29% yield) as a pale yellow solid. $^1$H NMR (400 MHz, DMSO-$d_6$) δ 10.80 (s, 1H), 9.50 (t, J=6.0 Hz, 1H), 8.54 (s, 1H), 8.21 (s, 1H), 8.06 (s, 1H), 7.96-7.94 (m, 2H), 7.44 (d, J=8.0 Hz, 1H), 7.19-7.07 (m, 5H), 4.54 (d, J=5.6 Hz, 2H), 3.82-3.78 (m, 1H), 2.97-2.94 (m, 2H), 2.75-2.60 (m, 3H), 2.45 (s, 3H), 2.40-2.30 (m, 2H), 2.17-1.96 (m, 5H), 1.73-1.49 (m, 9H), 1.43 (s, 9H). LC-MS (ES$^+$): m/z 717.19 [M+H]$^+$.

Example 129

Example 129 was prepared following the synthesis of Example 128

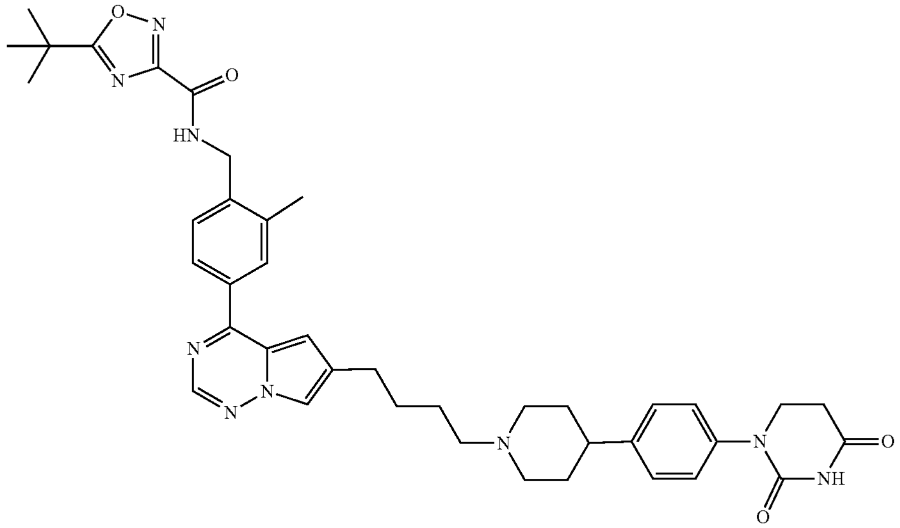 [SMILES: Cc1cc(-c2ncnn3cc(CCCCN4CCC(c5ccc(N6CCC(=O)NC6=O)cc5)CC4)cc23)ccc1CNC(=O)c1noc(C(C)(C)C)n1]

5-tert-butyl-N-[[4-[6-[4-[4-[4-(2,4-dioxohexahydropyrimidin-1-yl)phenyl]-1-piperidyl]butyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.36 (s, 1H), 9.54 (d, J=6.0 Hz, 1H), 8.99 (bs, 1H), 8.56 (s, 1H), 8.10 (s, 1H), 7.95-7.94 (m, 2H), 7.45 (d, J=8.4 Hz, 1H), 7.35-7.22 (m, 3H), 7.11 (s, 1H), 4.55 (d, J=5.2 Hz, 2H), 3.76 (t, J=6.4 Hz, 2H), 3.05 (m, 2H), 3.11-2.98 (m, 4H), 2.79-2.68 (m, 5H), 2.49-2.46 (m, 3H), 2.02-1.71 (m, 8H), 1.44 (s, 9H). LC-MS (ES$^+$): m/z 718.20 [M+H]$^+$.

Example 130

Example 130 was prepared following the synthesis of Example 128

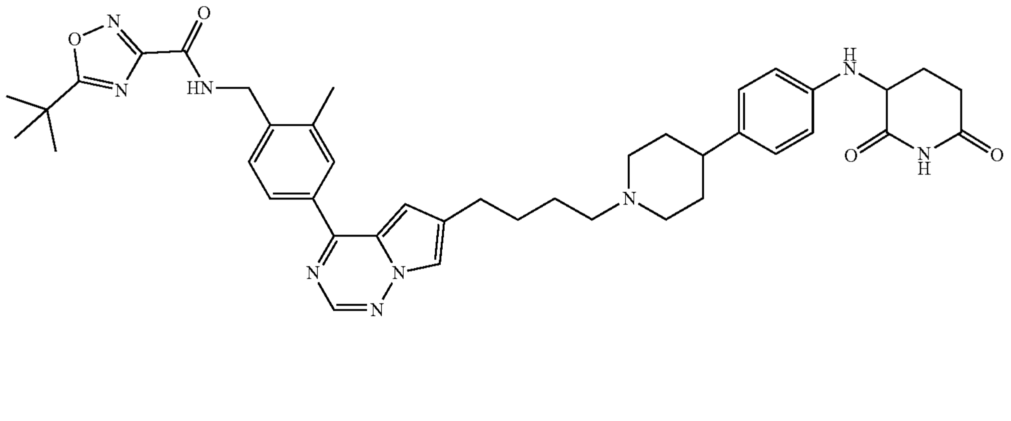 [SMILES: Cc1cc(-c2ncnn3cc(CCCCN4CCC(c5ccc(NC6CCC(=O)NC6=O)cc5)CC4)cc23)ccc1CNC(=O)c1noc(C(C)(C)C)n1]

5-tert-butyl-N-[[4-[6-[4-[4-[4-[(2,6-dioxo-3-piperidyl) amino]phenyl]-1-piperidyl]butyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.76 (s, 1H), 9.51 (d, J=4.8 Hz 1H), 8.54 (s, 1H), 8.06 (s, 1H), 7.96-7.94 (m, 2H), 7.45 (d, J=7.6 Hz, 1H), 7.08 (s, 1H), 6.94 (d, J=8.0 Hz, 2H), 6.60 (d, J=7.6 Hz, 2H), 5.63 (d, J=7.0 Hz, 1H), 4.55 (d, J=4.8 Hz, 2H), 4.25 (bs, 1H), 2.92 (d, J=9.6 Hz, 2H), 2.80-2.55 (m, 4H), 2.46 (s, 3H), 2.30 (bs, 3H), 2.20-1.9 (m, 4H), 1.70-1-50 (m, 8H), 1.44 (s, 9H). LC-MS (ES$^+$): m/z 730.22 [M−H]$^-$.

Example 131

Example 131 was prepared following the synthesis of Example 128

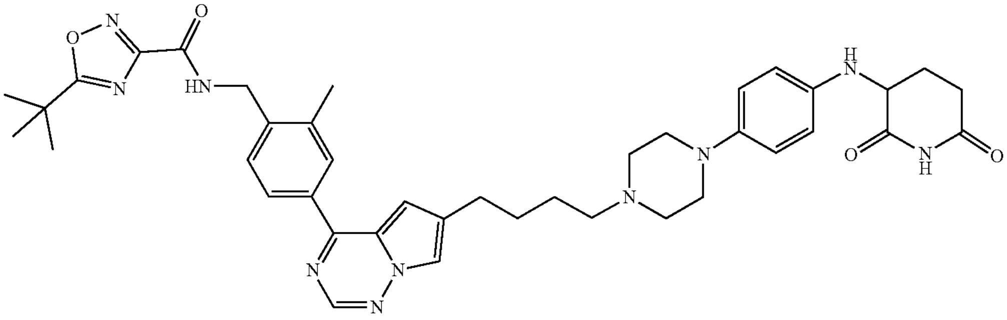 [SMILES: Cc1cc(-c2ncnn3cc(CCCCN4CCN(c5ccc(NC6CCC(=O)NC6=O)cc5)CC4)cc23)ccc1CNC(=O)c1noc(C(C)(C)C)n1]

5-tert-butyl-N-[[4-[6-[4-[4-[4-[(2,6-dioxo-3-piperidyl) amino]phenyl]piperazin-1-yl]butyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.77 (s, 1H), 9.53 (t, J=5.8 Hz, 1H), 9.23 (s, 1H), 8.56 (s, 1H), 8.10 (s, 1H), 7.95 (m, 2H), 7.45 (d, J=8.0 Hz, 1H), 7.21 (s, 1H), 6.80 (d, J=8.8 Hz, 2H), 6.65 (d, J=8.8 Hz, 2H), 4.55 (d, J=5.6 Hz, 2H), 4.24-4.20 (m, 1H), 3.54-3.51 (m, 4H), 3.16-3.10 (m, 4H), 2.83-2.72 (m, 5H), 2.60-2.59 (m, 1H), 2.46 (s, 3H), 2.07-2.00 (m, 1H), 1.90-1.70 (m, 5H), 1.44 (s, 9H). LC-MS (ES$^+$): m/z 733.19 [M+H]$^+$.

Example 132

Example 132 was prepared following the synthesis of Example 128

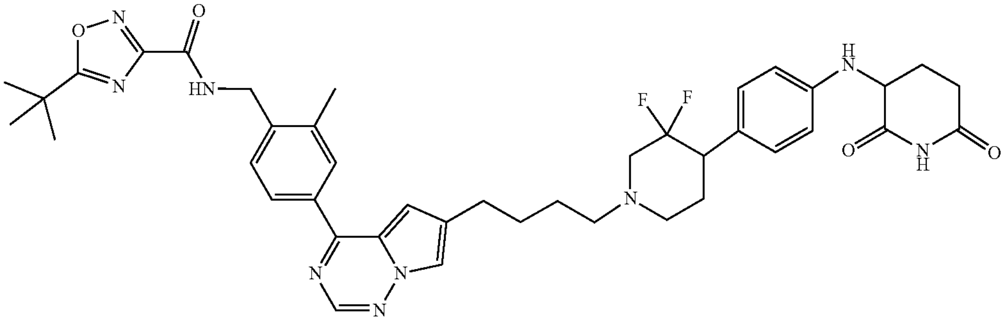 [SMILES: Cc1cc(-c2ncnn3cc(CCCCN4CCC(c5ccc(NC6CCC(=O)NC6=O)cc5)C(F)(F)C4)cc23)ccc1CNC(=O)c1noc(C(C)(C)C)n1]

5-tert-butyl-N-[[4-[6-[4-[4-[4-[(2,6-dioxo-3-piperidyl)amino]phenyl]-3,3-difluoro-1-piperidyl]butyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.79 (s, 1H), 10.12 (bs, 1H), 9.53 (t, J=5.9 Hz, 1H), 8.56 (s, 1H), 8.10 (s, 1H), 7.95 (d, J=7.2 Hz, 2H), 7.45 (d, J=8.3 Hz, 1H), 7.10 (d, J=6.9 Hz, 1H), 6.98 (d, J=8.4 Hz, 2H), 6.66 (d, J=8.4 Hz, 2H), 4.55 (d, J=6.0 Hz, 2H), 4.31-4.27 (m, 1H), 4.42-3.39 (m, 2H), 3.33-3.00 (m, 4H), 2.78-2.70 (m, 3H), 2.67-2.15 (m, 1H), 2.46 (s, 3H), 2.18-2.07 (m, 3H), 1.93-1.84 (m, 1H), 1.71 (bs, 4H), 1.44 (s, 9H). LC-MS (ES$^+$): m/z 768.47 [M+H]$^+$.

Example 133

Example 133 was prepared following the synthesis of Example 128

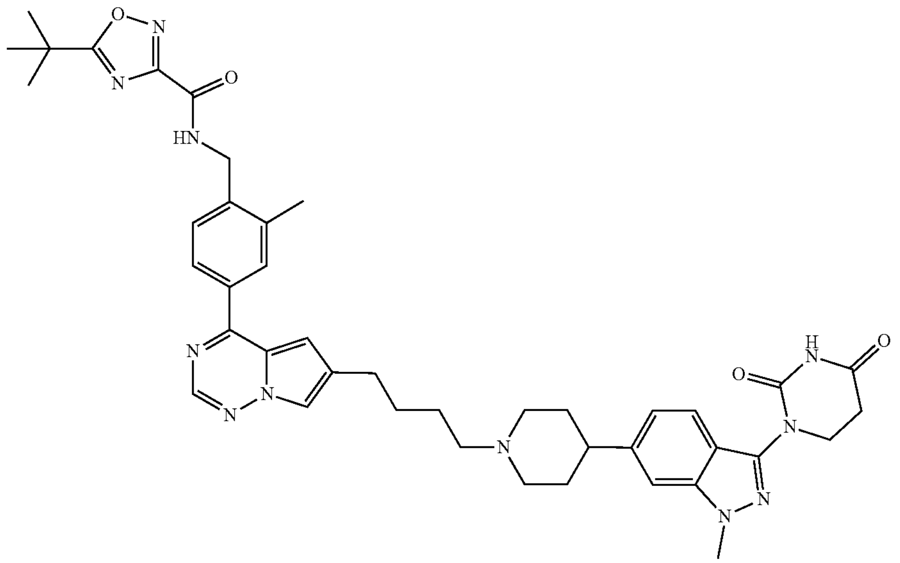 [SMILES: Cc1cc(-c2ncnn3cc(CCCCN4CCC(c5ccc6c(N7CCC(=O)NC7=O)nn(C)c6c5)CC4)cc23)ccc1CNC(=O)c1noc(C(C)(C)C)n1]

5-tert-butyl-N-[[4-[6-[4-[4-[3-(2,4-dioxohexahydropyrimidin-1-yl)-1-methyl-indazol-6-yl]-1-piperidyl]butyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.53 (s, 1H), 9.50 (t, J=6.0 Hz, 1H), 8.54 (s, 1H), 8.22 (bs, 1H), 8.07 (s, 1H), 7.96-7.94 (m, 2H), 7.54 (d, J=8.4 Hz, 1H), 7.45-7.42 (m, 2H), 7.08 (s, 1H), 7.02 (d, J=8.4 Hz, 111), 4.54 (d, J=6.0 Hz, 2H), 3.95 (s, 3H), 3.91-3.88 (m, 2H), 3.00-2.98 (m, 2H), 2.74-2.64 (m, 5H), 2.46 (s, 3H), 2.38-2.32 (m, 2H), 2.07-1.90 (m, 2H), 1.80-1.50 (m, 9H), 1.43 (s, 9H). LC-MS (ES$^+$): m/z 772.83 [M+H]$^+$.

Example 134. Synthesis of 5-tert-butyl-N-[[4-[6-[4-[4-[5-[(2,6-dioxo-3-piperidyl)amino]-2-pyridyl]-1-piperidyl]butyl]pyrrolo[2,1-f][1,2,4]triazin-4-yl]-2-fluoro-phenyl]methyl]-1,2,4-oxadiazole-3-carboxamide

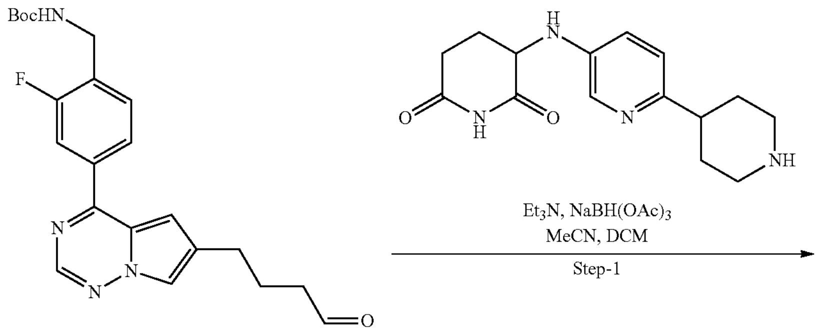

-continued

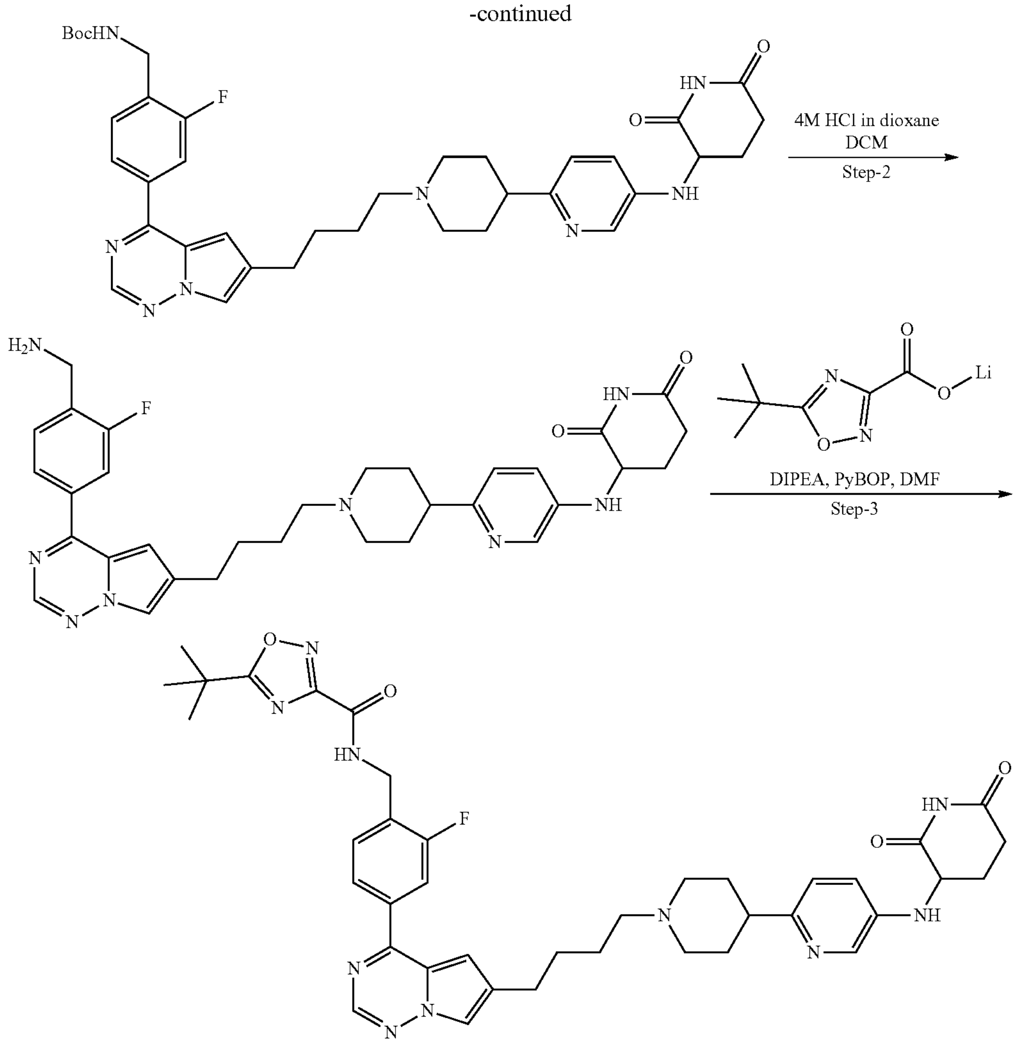

Step-1:

To a stirred solution of 3-[[6-(4-piperidyl)-3-pyridyl]amino]piperidine-2,6-dione HCl salt (236.25 mg, 727.35 µmol) in DCM (5 mL) and acetonitrile (2 mL) was added Triethylamine (368.00 mg, 3.64 mmol, 506.89 µL) at 0° C. followed by tert-butyl N-[[2-fluoro-4-[6-(4-oxobutyl)pyrrolo[2,1-f][1,2,4]triazin-4-yl]phenyl]methyl]carbamate (0.15 g, 363.67 µmol). The reaction mixture was stirred at room temperature for 1 hour. Then sodium triacetoxyborohydride (231.23 mg, 1.09 mmol) was added and the reaction mixture stirred at room temperature for 16 hours. After completion of the reaction, the reaction mixture was diluted with water and extracted with DCM. The combined organic layers were dried over sodium sulfate and concentrated under high vacuum to give the crude product, which was purified by column chromatography (silica gel) to afford tert-butyl N-[[4-[6-[4-[4-[5-[(2,6-dioxo-3-piperidyl)amino]-2-pyridyl]-1-piperidyl]butyl]pyrrolo[2,1-f][1,2,4]triazin-4-yl]-2-fluoro-phenyl]methyl]carbamate (0.15 g, 170.85 µmol, 46.98% yield) as yellow solid. LC-MS ($ES^-$): m/z 683.39 $[M-H]^-$.

Step-2:

To a stirred solution of tert-butyl N-[[4-[6-[4-[4-[5-[(2,6-dioxo-3-piperidyl)amino]-2-pyridyl]-1-piperidyl]butyl]pyrrolo[2,1-f][1,2,4]triazin-4-yl]-2-fluoro-phenyl]methyl]carbamate (0.15 g, 219.04 µmol) in DCM (2 mL) was added 4 M hydrogen chloride solution in dioxane (1.5 mL) at 0° C. and the reaction mixture was stirred at room temperature for 2 hours. After completion of the reaction, the reaction mixture was concentrated in vacuo to give the crude product, which was triturated with diethyl ether to furnish a solid product. The solid was dried under high vacuum to afford 3-[[6-[1-[4-[4-[4-(aminomethyl)-3-fluoro-phenyl]pyrrolo[2,1-f][1,2,4]triazin-6-yl]butyl]-4-piperidyl]-3-pyridyl]amino]piperidine-2,6-dione HCl salt (0.12 g, 162.28 µmol, 74.09% yield) as a yellow solid. LC-MS ($ES^-$): m/z 583.39 $[M-H]^-$.

Step-3:

To a stirred solution of 3-[[6-[1-[4-[4-[4-(aminomethyl)-3-fluoro-phenyl]pyrrolo[2,1-f][1,2,4]triazin-6-yl]butyl]-4-piperidyl]-3-pyridyl]amino]piperidine-2,6-dione HCl salt (0.1 g, 160.99 µmol) in DMF (0.5 mL) was added (5-tert-butyl-1,2,4-oxadiazole-3-carbonyl)oxylithium (58.94 mg, 321.99 µmol) followed by DIPEA (208.07 mg, 1.61 mmol, 280.42 µL) at 28° C. Then PyBOP (167.56 mg, 321.99 µmol) was added and the reaction mixture was stirred at room temperature for 1 hour. After completion of the reaction, the reaction mixture was diluted with water and the resulting precipitate was filtered through sintered funnel, washed with water, and dried under high vacuum to give the crude product. The resulting crude was purified by prep-HPLC to afford 5-tert-butyl-N-[[4-[6-[4-[4-[5-[(2,6-dioxo-3-piperidyl)amino]-2-pyridyl]-1-piperidyl]butyl]pyrrolo[2,1-f][1,2,4]triazin-4-yl]-2-fluoro-phenyl]methyl]-1,2,4-oxadiazole-3-carboxamide TFA salt (55 mg, 63.40 μmol, 39.38% yield) as a yellow solid. $^1$H NMR (400 MHz, DMSO-$d_6$) δ 10.89 (s, 1H), 9.60 (t, J=6.0 Hz, 1H), 9.08 (bs, 1H), 8.60 (s, 1H), 8.15 (s, 1H), 8.03-7.99 (m, 2H), 7.98-7.97 (m, 1H), 7.59 (t, J=8.0 Hz, 1H), 7.48-7.34 (m, 2H), 7.15 (s, 1H), 4.61 (d, J=6.0 Hz, 2H), 4.47 (m, 1H), 3.59-3.57 (m, 2H), 3.11-2.97 (m, 5H), 2.79-2.63 (m, 4H), 2.09-1.96 (m, 6H), 1.72 (s, 3H), 1.43 (s, 9H). LC-MS (ES$^+$): m/z 737.60 [M+H]$^+$.

Example 135

Example 135 was prepared following the synthesis of Example 134

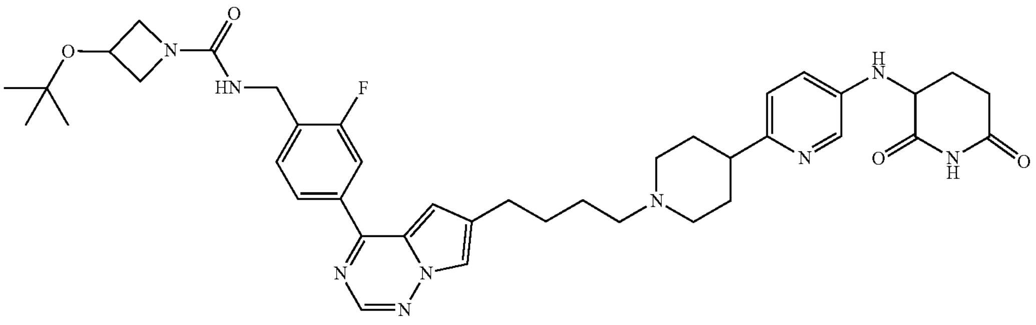 [SMILES: CC(C)(C)OC1CN(C(=O)NCc2ccc(-c3ncnn4cc(CCCCN5CCC(c6ccc(NC7CCC(=O)NC7=O)cn6)CC5)cc34)cc2F)C1]

3-tert-butoxy-N-[[4-[6-[4-[4-[5-[(2,6-dioxo-3-piperidyl)amino]-2-pyridyl]-1-piperidyl]butyl]pyrrolo[2,1-f][1,2,4]triazin-4-yl]-2-fluoro-phenyl]methyl]azetidine-1-carboxamide. $^1$H NMR (400 MHz, DMSO-$d_6$) δ 10.87 (s, 1H), 9.02 (d, J=5.9 Hz, 1H), 8.60 (s, 1H), 8.01-7.97 (m, 2H), 7.86-7.83 (m, 1H), 7.64 (t, J=7.9 Hz, 1H), 7.16-6.94 (m, 4H), 4.49-4.46 (m, 2H), 4.32 (d, J=5.9 Hz, 2H), 4.04-4.02 (m, 2H), 3.29-3.00 (m, 9H), 2.78-2.63 (m, 4H), 2.08-1.85 (m, 6H), 1.72 (bs, 4H), 1.13 (s, 9H). LC-MS (ES$^+$): m/z 740.21 [M+H]$^+$.

Example 136

Example 136 was prepared following the synthesis of Example 134

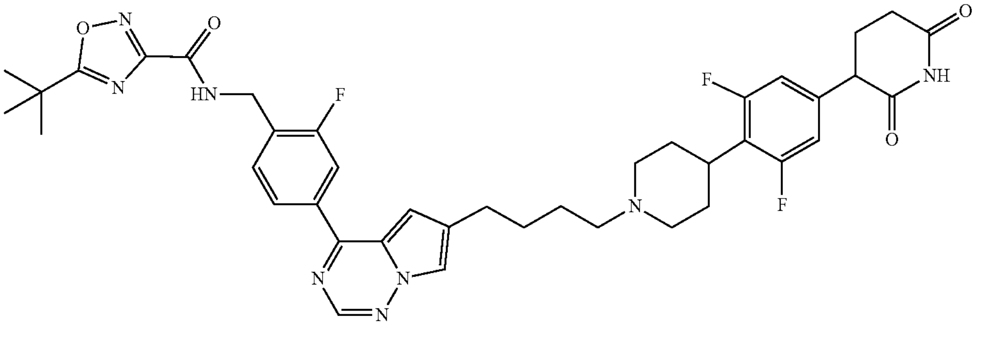 [SMILES: CC(C)(C)c1nc(C(=O)NCc2ccc(-c3ncnn4cc(CCCCN5CCC(c6c(F)cc(C7CCC(=O)NC7=O)cc6F)CC5)cc34)cc2F)no1]

5-tert-butyl-N-[[4-[6-[4-[4-[4-(2,6-dioxo-3-piperidyl)-2,6-difluoro-phenyl]-1-piperidyl]butyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.89 (s, 1H), 9.60 (t, J=6.0 Hz, 1H), 9.07 (bs, 1H), 8.60 (s, 1H), 8.15 (s, 1H), 7.99 (d, J=8.0 Hz, 1H), 7.89 (d, J=8.0 Hz, 1H), 7.59 (t, J=8.0 Hz, 1H), 7.16 (s, 1H), 7.02 (d, J=10.0 Hz, 1H), 4.61 (d, J=6.0 Hz, 2H), 3.92-3.88 (m, 1H), 3.40-3.20 (m, 3H), 3.15-3.00 (m, 4H), 2.80-2.55 (m, 4H), 2.30-2.15 (m, 3H), 2.05-1.85 (m, 2H), 1.80-1.65 (m, 5H), 1.43 (s, 9H). LC-MS ($ES^-$): m/z 755.19 $[M-H]^-$.

Example 137

Example 137 was prepared following the synthesis of Example 134

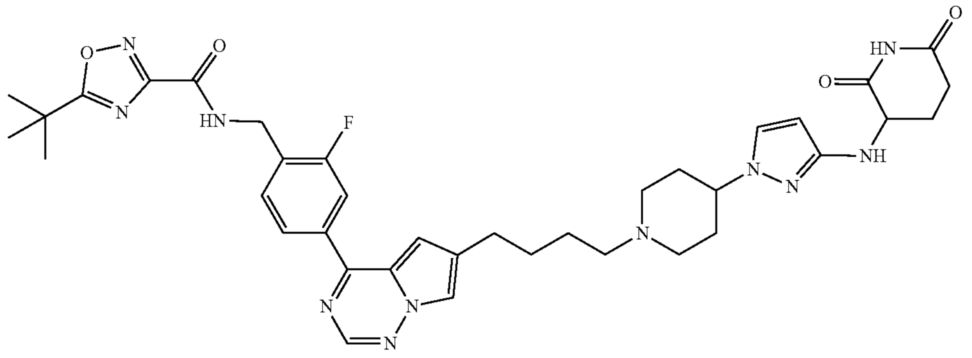 [SMILES: CC(C)(C)c1nc(C(=O)NCc2ccc(-c3ncnn4cc(CCCCN5CCC(n6ccc(NC7CCC(=O)NC7=O)n6)CC5)cc34)cc2F)no1]

5-tert-butyl-N-[[4-[6-[4-[4-[3-[(2,6-dioxo-3-piperidyl)amino]pyrazol-1-yl]-1-piperidyl]butyl]pyrrolo[2,1-f][1,2,4]triazin-4-yl]-2-fluoro-phenyl]methyl]-1,2,4-oxadiazole-3-carboxamide. $^1$H NMR (400 MHz, DMSO-$d_6$) δ 10.77 (s, 1H), 9.60 (t, J=6.0 Hz, 1H), 9.10 (bs, 1H), 8.60 (s, 1H), 8.14 (s, 1H), 7.98 (d, J=8.0 Hz, 1H), 7.90-7.87 (m, 1H), 7.60 (t, J=8.0 Hz, 1H), 7.40 (d, J=2.4 Hz, 1H), 7.15 (s, 1H), 5.55 (s, 1H), 4.61 (d, J=6.0 Hz, 2H), 4.20-4.14 (m, 2H), 3.40-3.60 (m, 6H), 2.78 (t, J=6.8 Hz, 2H), 2.70-2.60 (m, 2H), 2.30-2.00 (m, 6H), 1.85-1.60 (m, 4H), 1.43 (s, 9H). LC-MS ($ES^+$): m/z 726.77 $[M+H]^+$.

Example 138

Example 138 was prepared following the synthesis of Example 134

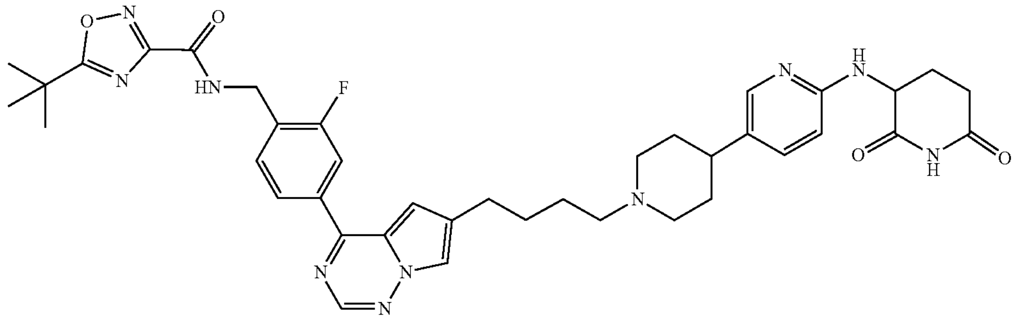 [SMILES: CC(C)(C)c1nc(C(=O)NCc2ccc(-c3ncnn4cc(CCCCN5CCC(c6ccc(NC7CCC(=O)NC7=O)nc6)CC5)cc34)cc2F)no1]

5-tert-butyl-N-[[4-[6-[4-[4-[6-[(2,6-dioxo-3-piperidyl)amino]-3-pyridyl]-1-piperidyl]butyl]pyrrolo[2,1-f][1,2,4]triazin-4-yl]-2-fluoro-phenyl]methyl]-1,2,4-oxadiazole-3-carboxamide. $^{1}$H NMR (400 MHz, DMSO-$d_6$) δ 10.92 (s, 1H), 9.60 (t, J=6.0 Hz, 1H), 9.03 (bs, 1H), 8.60 (s, 1H), 8.15 (s, 1H), 7.99 (d, J=1.6 Hz, 1H), 7.97 (d, J=1.6 Hz, 1H), 7.81 (s, 1H), 7.59 (t, J=8.0 Hz, 2H), 7.16 (s, 2H), 4.75-4.70 (m, 1H), 4.61 (d, J=6.0 Hz, 2H), 3.55-3.50 (m, 2H), 3.30-3.28 (m, 1H), 3.15-2.95 (m, 4H), 2.80-2.60 (m, 4H), 2.15-1.90 (m, 4H), 1.80-1.65 (m, 6H), 1.43 (s, 9H). LC-MS ($ES^+$): m/z 737.26 $[M+H]^+$.

Example 139

Example 139 was prepared following the synthesis of Example 134

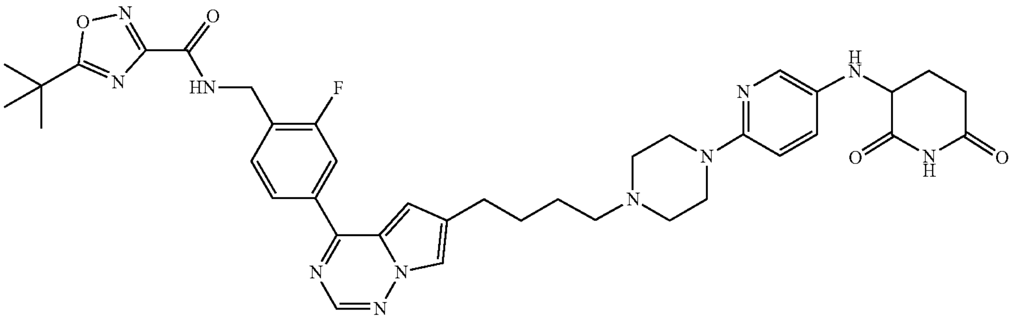 [SMILES: CC(C)(C)c1nc(C(=O)NCc2ccc(-c3ncnn4cc(CCCCN5CCN(c6ccc(NC7CCC(=O)NC7=O)cn6)CC5)cc34)cc2F)no1]

5-tert-butyl-N-[[4-[6-[4-[4-[5-[(2,6-dioxo-3-piperidyl)amino]-2-pyridyl]piperazin-1-yl]butyl]pyrrolo[2,1-f][1,2,4]triazin-4-yl]-2-fluoro-phenyl]methyl]-1,2,4-oxadiazole-3-carboxamide. $^{1}$H NMR (400 MHz, DMSO-$d_6$) δ 10.78 (s, 1H), 9.60 (t, J=6.0 Hz, 1H), 9.29 (bs, 1H), 8.60 (s, 1H), 8.15 (d, J=1.2 Hz, 1H), 7.99 (d, J=1.6 Hz, 1H), 7.89 (d, J=1.6 Hz, 1H), 7.69 (d, J=2.4 Hz, 1H), 7.59 (t, J=8.0 Hz, 1H), 7.16 (s, 2H), 6.85 (d, J=8.8 Hz, 1H), 4.61 (d, J=6.0 Hz, 2H), 4.30-4.20 (m, 1H), 4.15-4.05 (m, 2H), 3.54 (d, J=11.2 Hz, 2H), 3.20-2.90 (m, 6H), 2.80-2.55 (m, 4H), 2.15-2.05 (m, 1H), 1.95-1.80 (m, 1H), 1.75-1.60 (m, 4H), 1.43 (s, 9H). LC-MS ($ES^+$): m/z 738.24 $[M+H]^+$.

Example 140

Example 140 was prepared following the synthesis of Example 134

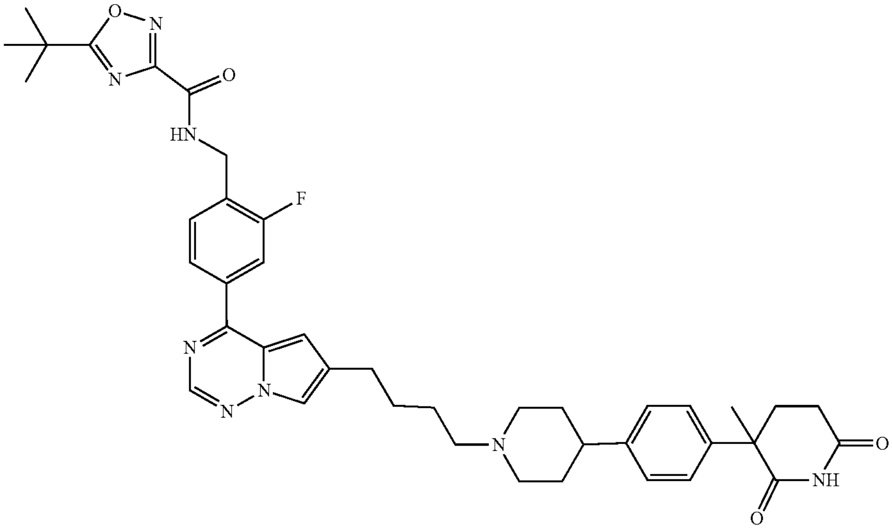 [SMILES: CC(C)(C)c1nc(C(=O)NCc2ccc(-c3ncnn4cc(CCCCN5CCC(c6ccc(C7(C)CCC(=O)NC7=O)cc6)CC5)cc34)cc2F)no1]

5-tert-butyl-N-[[2-fluoro-4-[6-[4-[4-[4-(3-methyl-2,6-dioxo-3-piperidyl)phenyl]-1-piperidyl]butyl]pyrrolo[2,1-f][1,2,4]triazin-4-yl]phenyl]methyl]-1,2,4-oxadiazole-3-carboxamide. $^1$H NMR (400 MHz, DMSO-$d_6$) δ 10.91 (s, 1H), 9.60 (t, J=6.0 Hz, 1H), 8.99 (bs, 1H), 8.60 (s, 1H), 8.15 (s, 1H), 7.98 (d, J=8.0 Hz, 1H), 7.89 (d, J=10.8 Hz, 1H), 7.59 (t, J=8.0 Hz, 1H), 7.30-7.15 (m, 4H), 4.61 (d, J=6.0 Hz, 2H), 3.56 (d, J=12.0 Hz, 2H), 3.15-2.95 (m, 4H), 2.85-2.75 (m, 3H), 2.45-2.35 (m, 2H), 2.15-1.95 (m, 4H), 1.85-1.65 (m, 6H), 1.43 (s, 9H), 1.42 (s, 3H). LC-MS (ES$^+$): m/z 735.32 $[M+H]^+$.

Example 141 and Example 142. Synthesis of 5-tert-butyl-N-[[2-fluoro-4-[6-[4-[4-[4-(3-methyl-2,6-dioxo-3-piperidyl)phenyl]-1-piperidyl]butyl]pyrrolo[2,1-f][1,2,4]triazin-4-yl]phenyl]methyl]-1,2,4-oxadiazole-3-carboxamide isomer 1 (Example 141) and 5-tert-butyl-N-[[2-fluoro-4-[6-[4-[4-[4-(3-methyl-2,6-dioxo-3-piperidyl)phenyl]-1-piperidyl]butyl]pyrrolo[2,1-f][1,2,4]triazin-4-yl]phenyl]methyl]-1,2,4-oxadiazole-3-carboxamide isomer 2 (Example 142)

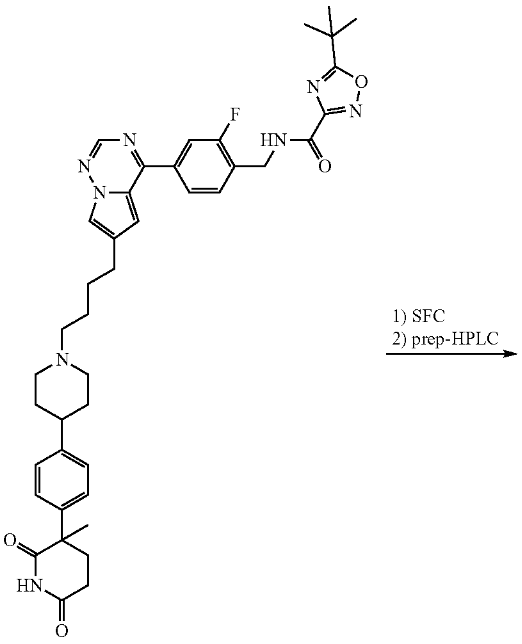

C

-continued

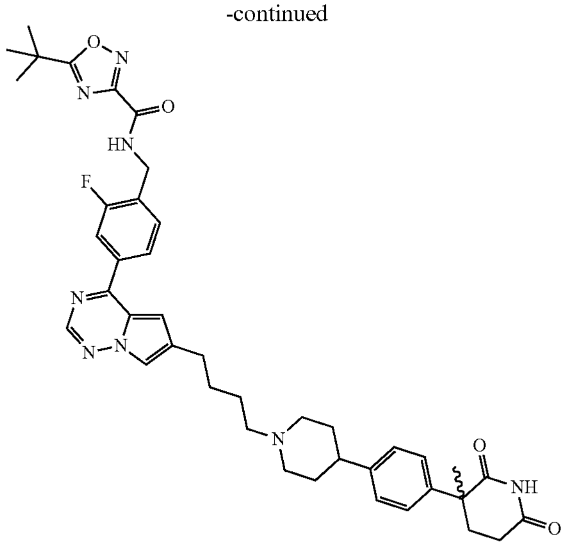

Isomer 1

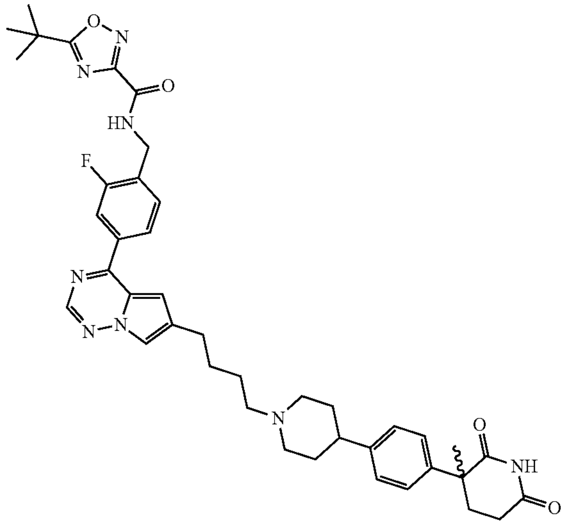

Isomer 2

0.15 g of the compound of Example 140 was separated by chiral SFC to obtain enantiomers.

During SFC separation, the fraction of isomer 1 (example 141) and isomer 2 (example 142) were collected in TFA buffer to avoid piperidine-2,6-dione ring-opening, as the SFC separation method involved the use of the additive. Hence the obtained fraction of isomer 1 and isomer 2 was submitted again for prep HPLC purification to remove the excess salt.

Preparative SFC Conditions:

Instrument details: Make/Model: SFC-150-II

Column/dimensions: CHIRALPAK AS-3 (4.6×150)mm, 3μ

% $CO_2$: 50%

% Co solvent: 50% (0.2% Methanolic ammonia in ACN: MEOH (1:1))

Total Flow: 110 g/min

Back Pressure: 100 bar

Temperature: 30 C

UV: 215 nm

Solubility: ACN

No. of injections: 15

Total purification time: 2:00 hours

Run time: 3.5 minutes

Prep. HPLC Condition for Isomer 1:

Mobile Phase (A): 0.03% TFA in $H_2O$

Mobile Phase (B): 100% Acetonitrile

Flow Rate: 16 ml/min

Column: SUNFIRE C18, 5 μm (19×150 mm)

Gradient Time % B: 0/10, 5/10, 10/50, 13/50, 13.10/100, 17/100, 17.10/10, 19/10 Solubility: THF+ACN+WATER Prep. HPLC Condition for Isomer 2:

Mobile Phase (A): 0.03% TFA in $H_2O$

Mobile Phase (B): 100% Acetonitrile

Flow Rate: 16 ml/min

Column: SUNFIRE C18, 5 μm (19×150 mm)

Gradient Time % B: 0/10, 5/10, 10/50, 13/50, 13.10/100, 17/100, 17.10/10, 19/10 Solubility: THF+ACN+WATER Note: Absolute configurations of both isomers were not determined, absolute stereochemistry was arbitrarily assigned, the first eluted peak during SFC separation was assigned as isomer 1, and the second eluted peak was assigned as isomer 2.

Isomer 1=+21.6600

Isomer 2=−27.3800

Isomer 1: 3.37 min

Isomer 2: 6.40 min

Example 141 Isomer 1

Isomer 1

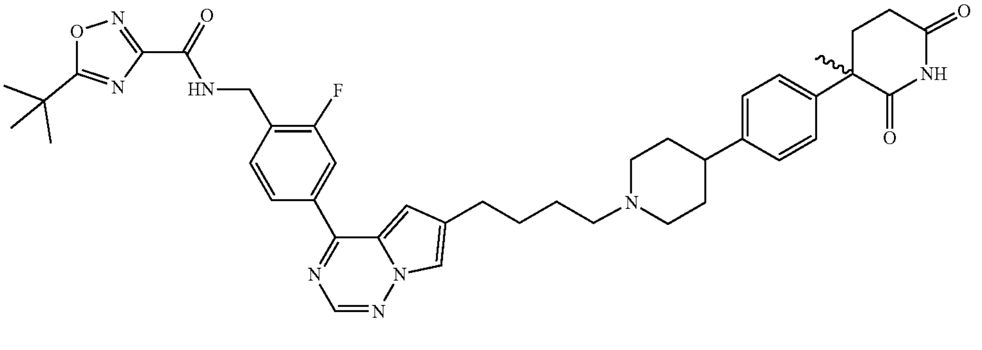

5-tert-butyl-N-[[2-fluoro-4-[6-[4-[4-[4-(3-methyl-2,6-dioxo-3-piperidyl)phenyl]-1-piperidyl]butyl]pyrrolo[2,1-f][1,2,4]triazin-4-yl]phenyl]methyl]-1,2,4-oxadiazole-3-carboxamide isomer 1. $^1$H NMR (400 MHz, DMSO-$d_6$) δ 10.91 (s, 1H), 9.60 (t, J=6.0 Hz, 1H), 8.60 (s, 1H), 8.15 (s, 1H), 7.97 (d, J=1.6 Hz, 1H), 7.89 (d, J=1.6 Hz, 1H), 7.59 (t, J=8.0 Hz, 1H), 7.27-7.08 (m, 5H), 4.61 (d, J=6.0 Hz, 2H), 3.56 (d, J=11.6 Hz, 2H), 3.10-2.99 (m, 4H), 2.79-2.77 (m, 3H), 2.49-2.44 (m, 2H), 2.09-1.97 (m, 4H), 1.81-1.71 (m, 6H), 1.43 (s, 3H), 1.42 (s, 9H). LC-MS ($ES^-$): m/z 733.19 $[M-H]^-$.

Example 142 Isomer 2

Isomer 2

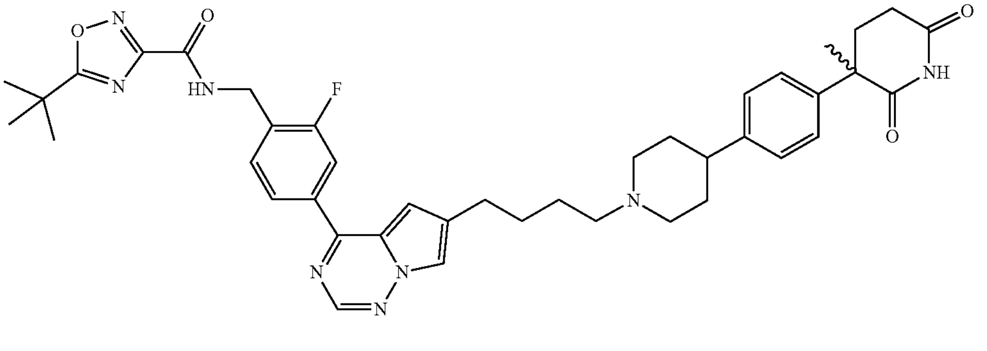

5-tert-butyl-N-[[2-fluoro-4-[6-[4-[4-[4-(3-methyl-2,6-dioxo-3-piperidyl)phenyl]-1-piperidyl]butyl]pyrrolo[2,1-f][1,2,4]triazin-4-yl]phenyl]methyl]-1,2,4-oxadiazole-3-carboxamide isomer 2. $^1H$ NMR (400 MHz, DMSO-$d_6$) δ 10.91 (s, 1H), 9.60 (t, J=6.0 Hz, 1H), 8.60 (s, 1H), 8.14 (s, 1H), 7.97 (d, J=1.2 Hz, 1H), 7.89 (d, J=1.6 Hz, 1H), 7.59 (t, J=8.0 Hz, 1H), 7.27-7.08 (m, 5H), 4.61 (d, J=5.6 Hz, 2H), 3.56 (d, J=11.6 Hz, 2H), 3.10-2.99 (m, 4H), 2.79-2.77 (m, 3H), 2.49-2.44 (m, 2H), 2.09-1.97 (m, 4H), 1.81-1.71 (m, 6H), 1.43 (s, 3H), 1.42 (s, 9H). LC-MS ($ES^-$): m/z 733.19 $[M-H]^-$.

Example 143. Synthesis of 5-tert-butyl-N-[[4-[6-[2-[4-[4-[(2,6-dioxo-3-piperidyl)amino]phenyl]-1-piperidyl]ethoxymethyl]pyrrolo[2,1-f][1,2,4]triazin-4-yl]-2-methyl-phenyl]methyl]-1,2,4-oxadiazole-3-carboxamide

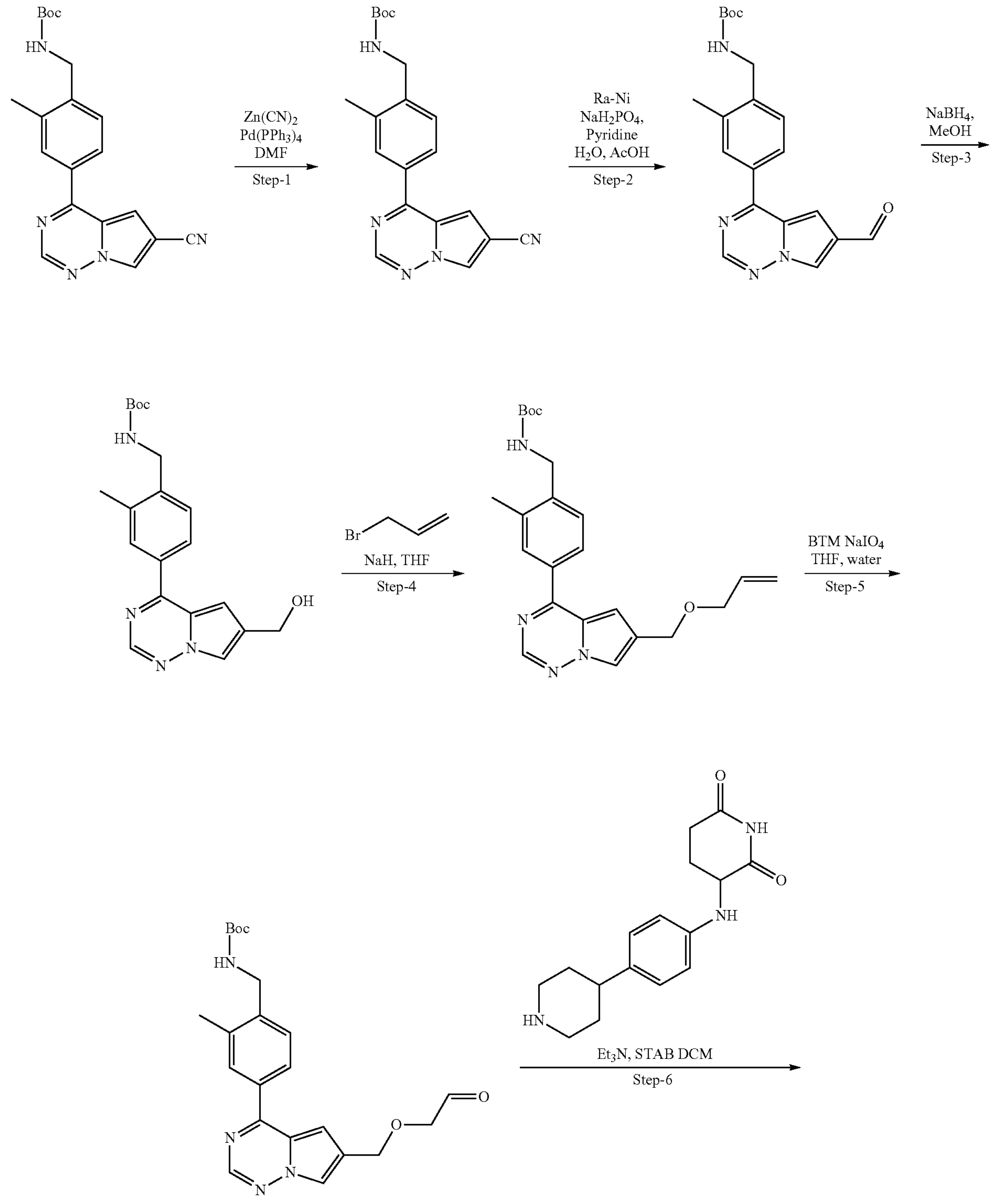

-continued

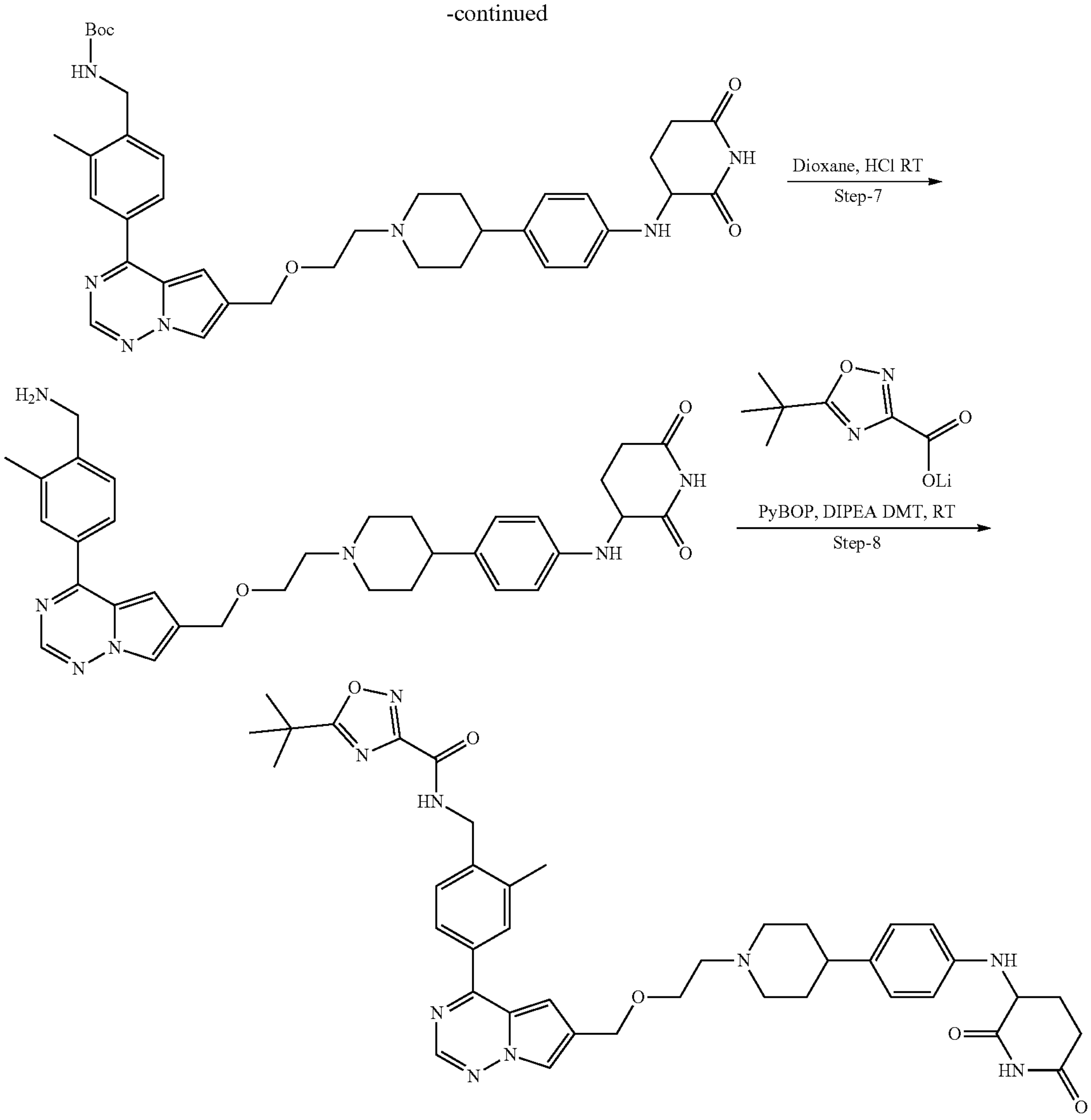

Step-1:

To a solution tert-butyl N-[[4-(6-bromopyrrolo[2,1-f][1,2,4]triazin-4-yl)-2-methyl-phenyl]methyl]carbamate (5 g, 11.98 mmol) and zinc cyanide (2.81 g, 23.96 mmol) in DMF (50 mL) at room temperature was added palladium-tetrakis (triphenylphosphine) (1.38 g, 1.20 mmol). The reaction mixture was stirred at 120° C. for 40 minutes. Upon completion of the reaction, saturated $NaHCO_3$ solution was added to the reaction mixture, and it was extracted with Ethyl acetate (50 mL×3). The combined organic layers were washed with water, and brine solution, dried over anhydrous sodium sulfate, filtered, and concentrated under reduced pressure to give the crude product. The crude product was purified by flash column chromatography (silica gel mesh 230-400 mesh, 0-30% ethyl acetate in pet ether) to afford tert-butyl N-[[4-(6-cyanopyrrolo[2,1-f][1,2,4]triazin-4-yl)-2-methyl-phenyl]methyl]carbamate (3.8 g, 10.20 mmol, 85.13% yield). LC-MS ($ES^+$): m/z 364.42 $[M+H]^+$.

Step-2:

To a stirred solution of tert-butyl N-[[4-(6-cyanopyrrolo[2,1-f][1,2,4]triazin-4-yl)-2-methyl-phenyl]methyl]carbamate (3.4 g, 9.36 mmol) in water (8 mL), pyridine (16 mL), and AcOH (8 mL) at 0° C., monosodium phosphate (8.27 g, 79.52 mmol) was added and the reaction mixture was stirred at 0° C. for 30 minutes. Raney nickel (3.4 g, 57.93 mmol) was added portionwise, and the reaction was heated at 65° C. for 2 hours. The reaction mixture was filtered through a celite bed to remove the catalyst and then washed with ethyl acetate. The filtrate was concentrated under reduced pressure to a residue, which was quenched with water (60 mL) and extracted using Ethyl acetate (50 mL×3). The combined organic layers were washed with brine solution (100 mL), dried over anhydrous sodium sulfate, filtered, and concentrated under reduced pressure to give the crude product. The crude product was purified by flash column chromatography (silica gel mesh 230-400, 0-10% ethyl acetate in pet-ether) to afford tert-butyl N-[[4-(6-formylpyrrolo[2,1-f][1,2,4]triazin-4-yl)-2-methyl-phenyl]methyl]carbamate (1.2 g, 3.05 mmol, 32.56% yield). LC-MS ($ES^+$): m/z 367.24 $[M+H]^+$.

Step-3:

To a stirred solution of tert-butyl N-[[4-(6-formylpyrrolo[2,1-f][1,2,4]triazin-4-yl)-2-methyl-phenyl]methyl]carbamate (0.4 g, 1.09 mmol) in MeOH (5 mL) was added sodium borohydride (49.56 mg, 1.31 mmol) at 0° C. and stirred at room temperature for 1 hour. After completion of the reaction, the reaction mixture was diluted with water and extracted with ethyl acetate. The combined organic layers were dried over anhydrous sodium sulfate and concentrated in vacuo to afford tert-butyl N-[[4-[6-(hydroxymethyl)pyrrolo[2,1-f][1,2,4]triazin-4-yl]-2-methyl-phenyl]methyl]carbamate (0.30 g, 724.70 μmol, 66.38% yield). LC-MS ($ES^+$): m/z 369.20 $[M+H]^+$.

Step-4:

To a stirred solution of sodium hydride (60% dispersion in mineral oil, 46.80 mg, 2.04 mmol) in THF (3 mL) was added tert-butyl N-[[4-[6-(hydroxymethyl)pyrrolo[2,1-f][1,2,4]triazin-4-yl]-2-methyl-phenyl]methyl]carbamate (0.30 g, 814.27 μmol), followed by 3-bromoprop-1-ene (118.21 mg, 977.12 μmol) at 0° C. The reaction was warmed up to room temperature slowly over 12 hours. After completion of the reaction, the reaction mixture was diluted with water and extracted with ethyl acetate. The combined organic layers were dried over anhydrous sodium sulfate and concentrated in vacuo to get the crude product. The resulting crude product was purified via flash column chromatography (silica gel mesh 100-200) to afford tert-butyl N-[[4-[6-(allyloxymethyl)pyrrolo[2,1-f][1,2,4]triazin-4-yl]-2-methyl-phenyl]methyl]carbamate (0.10 g, 239.91 μmol, 29.46% yield) as a yellow solid. LC-MS ($ES^+$): m/z 409.31 $[M+H]^+$.

Step-5:

To a stirred solution of tert-butyl N-[[4-[6-(allyloxymethyl)pyrrolo[2,1-f][1,2,4]triazin-4-yl]-2-methyl-phenyl]methyl]carbamate (0.15 g, 367.20 μmol) in water (1 mL) and THF (1 mL) was added 2-[bis(2-hydroxyethyl)amino]-2-(hydroxymethyl)propane-1,3-diol (3.84 mg, 18.36 μmol) followed by sodium periodate (392.71 mg, 1.84 mmol). The reaction mixture was stirred at room temperature for 1 hour. After completion of the reaction, the reaction mixture was diluted with water and extracted with DCM. The combined organic layers were dried over anhydrous sodium sulfate and concentrated in vacuo to afford tert-butyl N-[[2-methyl-4-[6-(2-oxoethoxymethyl)pyrrolo[2,1-f][1,2,4]triazin-4-yl]phenyl]methyl]carbamate (0.15 g, 105.98 mol, 28.86% yield) as a black sticky oil. The resulting crude product was used as such without further purification. LC-MS ($ES^+$): m/z 7411.44 $[M+H]^+$.

Step-6:

To a stirred solution of 3-[4-(4-piperidyl)anilino]piperidine-2,6-dione TFA salt (176.02 mg, 438.53 μmol) in DCM (2 mL) was added Triethylamine (369.79 mg, 3.65 mmol, 509.35 μL) at 0° C. followed by tert-butyl N-[[2-methyl-4-[6-(2-oxoethoxymethyl)pyrrolo[2,1-f][1,2,4]triazin-4-yl]phenyl]methyl]carbamate (0.15 g, 365.44 μmol). The reaction was stirred at room temperature for 1 hour. Then sodium triacetoxyborohydride (232.35 mg, 1.10 mmol) was added at 0° C., and the reaction mixture was stirred at rt for 16 hours. After completion of the reaction, the reaction mixture was diluted with water and extracted with ethyl acetate. The combined organic layers were dried over anhydrous sodium sulfate and concentrated in vacuo to give the crude product. The resulting crude product was purified via flash column chromatography (silica gel mesh 100-200) to afford tert-butyl N-[[4-[6-[2-[4-[4-[(2,6-dioxo-3-piperidyl)amino]phenyl]-1-piperidyl]ethoxymethyl]pyrrolo[2,1-f][1,2,4]triazin-4-yl]-2-methyl-phenyl]methyl]carbamate (0.06 g, 79.20 μmol, 21.67% yield) as a yellow solid. LC-MS ($ES^+$): m/z 682.62 $[M+H]^+$.

Step-7

To a stirred solution of tert-butyl N-[[4-[6-[2-[4-[4-[(2,6-dioxo-3-piperidyl)amino]phenyl]-1-piperidyl]ethoxymethyl]pyrrolo[2,1-f][1,2,4]triazin-4-yl]-2-methyl-phenyl]methyl]carbamate (0.06 g, 88.00 μmol) in DCM (1 mL) was added 4 M hydrogen chloride solution in dioxane (0.6 mL) at 0° C. and the reaction mixture was stirred at room temperature for 2 hours. After completion of the reaction, the reaction mixture was concentrated in vacuo, and the resulting crude product was triturated with diethyl ether to afford 3-[4-[1-[2-[[4-[4-(aminomethyl)-3-methyl-phenyl]pyrrolo[2,1-f][1,2,4]triazin-6-yl]methoxy]ethyl]-4-piperidyl]anilino]piperidine-2,6-dione HCl salt (0.06 g, 80.56 μmol, 91.55% yield) as a yellow solid. LC-MS ($ES^+$): m/z 582.22 $[M+H]^+$.

Step-8:

To a stirred solution of 3-[4-[1-[2-[[4-[4-(aminomethyl)-3-methyl-phenyl]pyrrolo[2,1-f][1,2,4]triazin-6-yl]methoxy]ethyl]-4-piperidyl]anilino]piperidine-2,6-dione HCl salt (0.06 g, 97.06 μmol) in DMF (2 mL) was added (5-tert-butyl-1,2,4-oxadiazole-3-carbonyl)oxylithium (35.53 mg, 194.12 μmol) followed by N-ethyl-N-isopropyl-propan-2-amine (125.44 mg, 970.61 μmol, 169.06 μL) at 0° C. The reaction mixture was stirred for 10 minutes before benzotriazol-1-yloxy(tripyrrolidin-1-yl)phosphonium; hexafluorophosphate (101.02 mg, 194.12 μmol) was added and the reaction stirred for an additional hour at room temperature. After the reaction was complete, the reaction mixture was concentrated in vacuo to furnish the crude product, which was purified by prep-HPLC to afford 5-tert-butyl-N-[[4-[6-[2-[4-[4-[(2,6-dioxo-3-piperidyl)amino]phenyl]-1-piperidyl]ethoxymethyl]pyrrolo[2,1-f][1,2,4]triazin-4-yl]-2-methyl-phenyl]methyl]-1,2,4-oxadiazole-3-carboxamide (6.6 mg, 8.31 μmol, 8.57% yield) as light orange solid. $^1$H NMR (400 MHz, DMSO-$d_6$) δ 10.77 (s, 1H), 9.52 (t, J=5.8 Hz, 1H), 8.61 (s, 1H), 8.21 (s, 1H), 7.96-7.93 (m, 2H), 7.46 (d, J=8.5 Hz, 1H), 7.22 (s, 1H), 6.93 (d, J=7.7 Hz, 2H), 6.62 (d, J=8.3 Hz, 2H), 5.71 (d, J=7.3 Hz, 1H), 4.72 (s, 2H), 4.55 (d, J=5.9 Hz, 2H), 4.30-4.26 (m, 1H), 3.73 (bs, 2H), 3.31-3.01 (bm, 5H), 2.74-2.67 (m, 1H), 2.60-2.57 (m, 3H), 2.45 (s, 3H), 2.09-2.07 (m, 1H), 1.91-1.81 (m, 5H), 1.44 (s, 9H). LC-MS ($ES^+$): m/z 734.16 $[M+H]^+$.

Example 144

Example 144 was prepared following the synthesis of Example 143

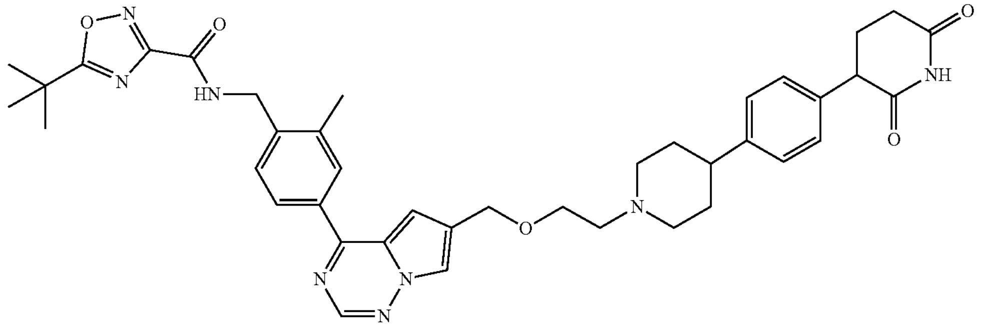 [SMILES: Cc1cc(-c2ncnn3cc(COCCN4CCC(c5ccc(C6CCC(=O)NC6=O)cc5)CC4)cc23)ccc1CNC(=O)c1noc(C(C)(C)C)n1]

5-tert-butyl-N-[[4-[6-[2-[4-[4-(2,6-dioxo-3-piperidyl)phenyl]-1-piperidyl]ethoxymethyl]pyrrolo[2,1-f][1,2,4]triazin-4-yl]-2-methyl-phenyl]methyl]-1,2,4-oxadiazole-3-carboxamide. $^1$H NMR (400 MHz, DMSO-$d_6$) δ 10.76 (s, 1H), 9.62 (t, J=6.1 Hz, 1H), 8.59 (s, 1H), 8.16 (s, 1H), 7.96-7.92 (m, 2H), 7.49-7.39 (m, 1H), 7.31-7.11 (m, 5H), 4.60 (s, 2H), 4.56 (d, J=6.1 Hz, 2H), 3.82-3.71 (m, 1H), 3.61-3.57 (m, 2H), 2.98-2.94 (m, 2H), 2.67-2.65 (m, 2H), 2.54-2.51 (m, 2H), 2.45 (s, 3H), 2.40-2.37 (m, 1H), 2.22-2.03 (m, 4H), 1.71-1.59.03 (m, 4H), 1.44 (s, 9H).

LC-MS (ES$^+$): m/z 719.45 [M+H]$^+$.

Example 145. Synthesis of 5-tert-butyl-N-[[4-[6-[2-[[4-[4-[(2,6-dioxo-3-piperidyl)amino]phenyl]-1-piperidyl]methyl]cyclopropyl]pyrrolo[2,1-f][1,2,4]triazin-4-yl]-2-methyl-phenyl]methyl]-1,2,4-oxadiazole-3-carboxamide

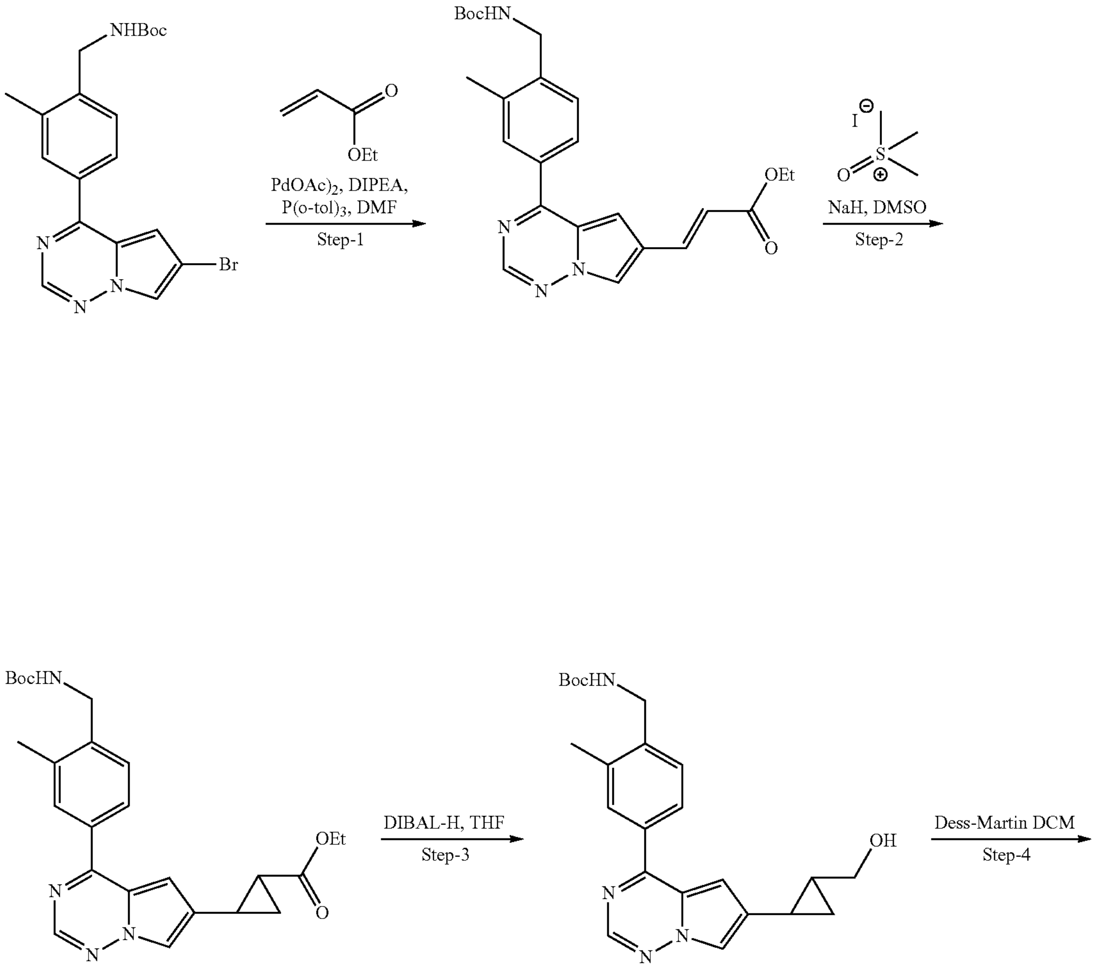

-continued
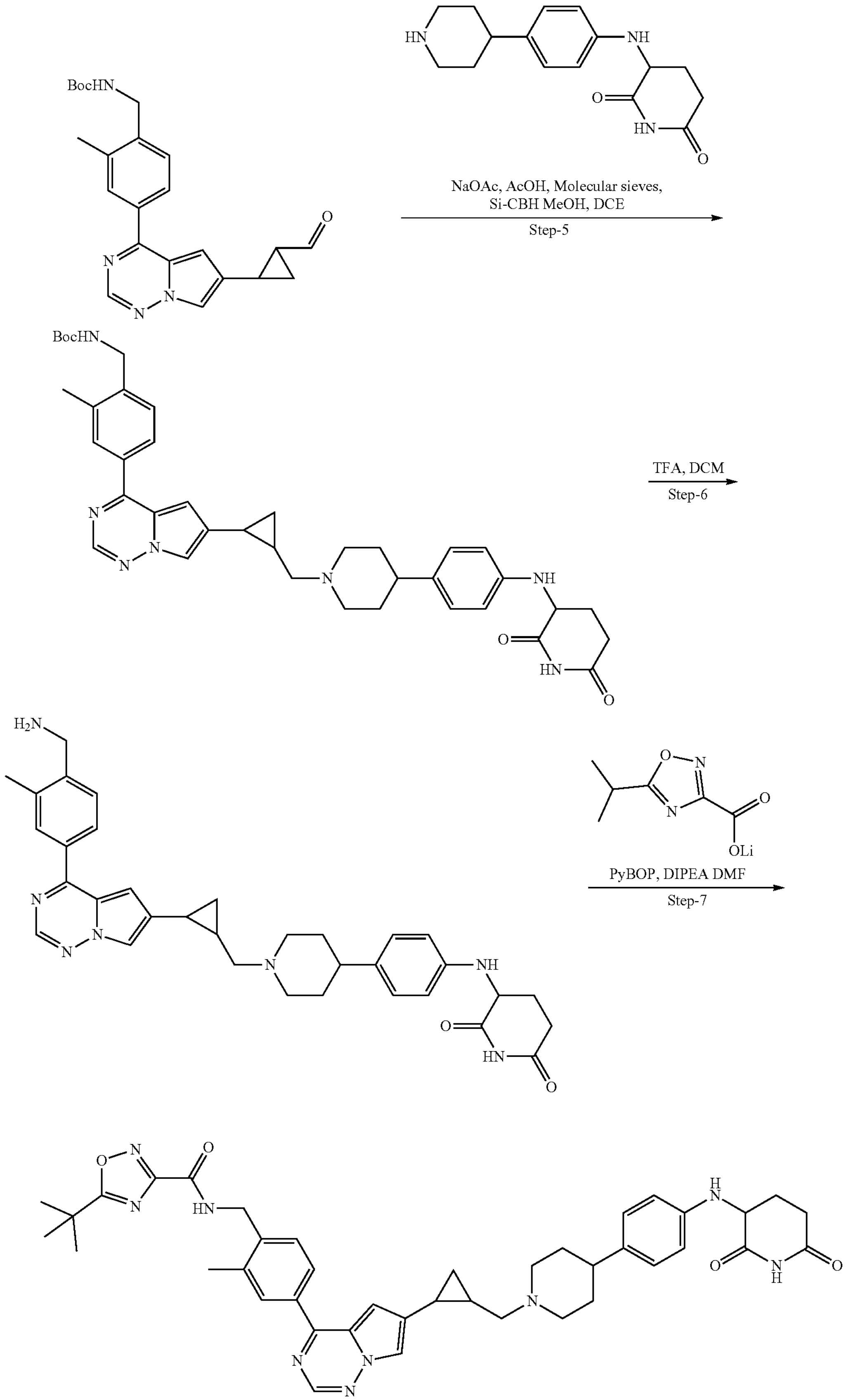

Step-1:

A solution of tert-butyl N-[[4-(6-bromopyrrolo[2,1-f][1,2,4]triazin-4-yl)-2-methyl-phenyl]methyl]carbamate (7 g, 16.77 mmol), ethyl prop-2-enoate (5.04 g, 50.32 mmol, 5.45 mL) and DIPEA (21.68 g, 167.75 mmol, 29.22 mL) in DMF (70 mL) was purged with argon gas for 15 minutes. This was followed by the addition of palladium acetate (37.66 mg, 167.75 μmol), and the resulting mixture was stirred at 110° C. for 16 hours. After the reaction was complete, the reaction mixture was filtered through celite and washed with ethyl acetate (100 mL×3). The filtrate was washed with water (100 mL) and brine solution (100 mL). The combined organic layers were dried over anhydrous sodium sulfate, filtered, and concentrated under reduced pressure. The crude product was purified by column chromatography (silica gel 230-400 mesh, 0-100% ethyl acetate in pet ether) to afford ethyl (E)-3-[4-[4-[(tert-butoxycarbonylamino)methyl]-3-methyl-phenyl]pyrrolo[2,1-f][1,2,4]triazin-6-yl]prop-2-enoate (4.6 g, 10.18 mmol, 60.67% yield). LC-MS ($ES^+$): m/z 437.29 $[M+H]^+$.

Step-2:

A solution of trimethylsulfoxonium iodide (4.54 g, 20.61 mmol) in THF (20 mL) was purged with argon gas. Sodium hydride (60% dispersion in mineral oil) (412.16 mg, 17.18 mmol) was added to the solution at 20° C., and the resulting mixture was stirred at 27° C. for 40 minutes. This was followed by the dropwise addition of ethyl (E)-3-[4-[4-[(tert-butoxycarbonylamino)methyl]-3-methyl-phenyl]pyrrolo[2,1-f][1,2,4]triazin-6-yl]prop-2-enoate (3 g, 6.87 mmol) in DMSO (50 mL) and THF (20 mL), and the reaction mixture was further stirred at 27° C. for 16 hours. Upon completion, the reaction was quenched with ice-cold water and extracted with ethyl acetate (100 mL×2). The filtrate was washed with ice water (100 ml) and brine solution (100 ml). Then the organic layer was dried over sodium sulfate and concentrated under reduced pressure to yield the crude compound, which was purified by reverse phase column chromatography (0.1% formic acid in acetonitrile/water) to afford ethyl 2-[4-[4-[(tert-butoxycarbonylamino)methyl]-3-methyl-phenyl]pyrrolo[2,1-f][1,2,4]triazin-6-yl]cyclopropanecarboxylate (1.8 g, 3.84 mmol, 55.91% yield) as a yellow solid. LC-MS ($ES^+$): m/z 451.28 $[M+H]^+$.

Step-3:

DIBAL-H (25% in toluene) (1.66 g, 11.66 mmol) was added to a solution of ethyl 2-[4-[4-[(tert-butoxycarbonylamino)methyl]-3-methyl-phenyl]pyrrolo[2,1-f][1,2,4]triazin-6-yl]cyclopropanecarboxylate (1.5 g, 3.33 mmol) in THE (20 mL) at 0° C. under argon atmosphere. The reaction mixture was stirred at room temperature for 2 hours and was then quenched with saturated ammonium chloride solution and extracted with ethyl acetate (100 mL×2). The filtrate was concentrated under reduced pressure to afford tert-butyl N-[[4-[6-[2-(hydroxymethyl)cyclopropyl]pyrrolo[2,1-f][1,2,4]triazin-4-yl]-2-methyl-phenyl]methyl]carbamate (1 g, 2.25 mmol, 67.69% yield) as a yellow solid. LC-MS ($ES^+$): m/z 409.26 $[M+H]^+$.

Step-4:

Dess-Martin periodinane (3.64 g, 8.58 mmol) was added to a solution of tert-butyl N-[[4-[6-[2-(hydroxymethyl)cyclopropyl]pyrrolo[2,1-f][1,2,4]triazin-4-yl]-2-methyl-phenyl]methyl]carbamate (1 g, 2.45 mmol) in DCM (20 mL), at 0° C. The reaction mixture was stirred at room temperature for 3 hours and monitored by LC-MS. After completion, the reaction was filtered through celite and quenched with 1:1 bicarbonate and sodium sulfate solution. The mixture was then extracted with ethyl acetate (100 mL×2), and washed with water (50 mL) and brine solution (50 mL). The combined organic layers were dried over sodium sulfate and concentrated in vacuo to yield the crude compound, which was purified by column chromatography (silica gel 100-200 mesh, 0-100% ethyl acetate in pet ether) to afford tert-butyl N-[[4-[6-(2-formylcyclopropyl)pyrrolo[2,1-f][1,2,4]triazin-4-yl]-2-methyl-phenyl]methyl]carbamate (0.9 g, 1.76 mmol, 71.85% yield) as a light yellow solid. LC-MS ($ES^+$): m/z 407.27 $[M+H]^+$.

Step-5.

To a stirred solution of 3-[4-(4-piperidyl)anilino]piperidine-2,6-dione TFA salt (276.49 mg, 688.85 μmol) in methanol (5 mL) and 1,2-dichloroethane (5 mL) were added sodium acetate (84.76 mg, 1.03 mmol), acetic acid (62.05 mg, 1.03 mmol, 59.10 μL) and molecular sieves (0.15 g, 344.42 μmol). The reaction mixture was stirred for 10 minutes before tert-butyl N-[[4-[6-(2-formylcyclopropyl)pyrrolo[2,1-f][1,2,4]triazin-4-yl]-2-methyl-phenyl]methyl]carbamate (0.14 g, 344.42 μmol) was added and the reaction heated at 70° C. for 5 hours. The reaction was cooled to room temperature, followed by the addition of Si—CBH (0.15 g, 2.59 mmol). The reaction was stirred at room temperature for 4 hours, while progress of the reaction was monitored by TLC and LC-MS. Upon completion, the reaction was filtered through celite and concentrated under reduced pressure to yield the crude product, which was purified by column chromatography (silica gel 100-200 mesh, 0-10% MeOH in DCM) to afford tert-butyl N-[[4-[6-[2-[[4-[4-[(2,6-dioxo-3-piperidyl)amino]phenyl]-1-piperidyl]methyl]cyclopropyl]pyrrolo[2,1-f][1,2,4]triazin-4-yl]-2-methyl-phenyl]methyl]carbamate (0.1 g, 141.61 μmol, 41.12% yield) as a light yellow solid. LC-MS ($ES^+$): m/z 678.42 $[M+H]^+$.

Step-6:

To a stirred solution of tert-butyl N-[[4-[6-[2-[[4-[4-[(2,6-dioxo-3-piperidyl)amino]phenyl]-1-piperidyl]methyl]cyclopropyl]pyrrolo[2,1-f][1,2,4]triazin-4-yl]-2-methyl-phenyl]methyl]carbamate (0.1 g, 147.53 μmol) in DCM (5 mL), 4 M HCl in dioxane (1 mL) was added dropwise at 0° C. The reaction was then stirred at 27° C. for 3 hours. Upon completion, the reaction was concentrated under reduced pressure to yield the crude product, which was triturated with diethyl ether to afford solid 3-[4-[1-[[2-[4-[4-(aminomethyl)-3-methyl-phenyl]pyrrolo[2,1-f][1,2,4]triazin-6-yl]cyclopropyl]methyl]-4-piperidyl]anilino]piperidine-2,6-dione HCl salt (0.090 g, 142.54 μmol, 96.62% yield) as an off-white solid. LC-MS ($ES^+$): m/z 578.23 $[M+H]^+$.

Step-7:

To a solution of 3-[4-[1-[[2-[4-[4-(aminomethyl)-3-methyl-phenyl]pyrrolo[2,1-f][1,2,4]triazin-6-yl]cyclopropyl]methyl]-4-piperidyl]anilino]piperidine-2,6-dione (0.09 g, 146.54 μmol, HCl salt) and (5-tert-butyl-1,2,4-oxadiazole-3-carbonyl)oxylithium (51.91 mg, 293.08 μmol) in DMF (5 mL), DIPEA (113.64 mg, 879.24 μmol, 153.15 μL) was added at 0° C. and the resulting mixture was stirred for 5 minutes. This was followed by the addition of PyBOP (152.52 mg, 293.08 μmol) and the reaction mixture was stirred at room temperature for 2 hours. Progress of the reaction was monitored by LCMS. After the reaction was complete, the crude product was purified by prep HPLC to afford 5-tert-butyl-N-[[4-[6-[2-[[4-[4-[(2,6-dioxo-3-piperidyl)amino]phenyl]-1-piperidyl]methyl]cyclopropyl]pyrrolo[2,1-f][1,2,4]triazin-4-yl]-2-methyl-phenyl]methyl]-1,2,4-oxadiazole-3-carboxamide formic acid salt (25 mg, 31.50 μmol, 21.50% yield). $^1H$ NMR (400 MHz, DMSO-$d_6$) δ 10.76 (s, 1H), 9.51 (t, J=6.0 Hz, 1H), 8.52 (s, 1H), 8.06 (s, 1H), 7.95-7.93 (m, 2H), 7.44 (d, J=7.6 Hz, 1H), 6.97-6.93 (m, 3H), 6.60 (d, J=8.4 Hz, 2H), 5.64 (d, J=7.6 Hz, 1H), 4.54 (d, J=6.0 Hz, 2H), 4.30-4.20 (m, 1H), 3.20-3.10 (m, 2H), 2.80-2.55 (m, 4H), 2.45 (s, 3H), 2.40-2.15 (m, 3H), 2.10-2.00 (m, 1H), 1.90-1.80 (m, 2H), 1.75-1.55 (m, 5H), 1.44 (s, 9H), 1.06-1.04 (m, 1H), 0.93-0.90 (m, 1H). LC-MS ($ES^+$): m/z 730.21 $[M+H]^+$.
Example 146. Synthesis of 5-tert-butyl-N-[[4-[6-[4-[4-[4-(2,6-dioxo-3-piperidyl)phenyl]-1-piperidyl]phenyl]pyrrolo[2,1-f][1,2,4]triazin-4-yl]-2-methyl-phenyl]methyl]-1,2,4-oxadiazole-3-carboxamide
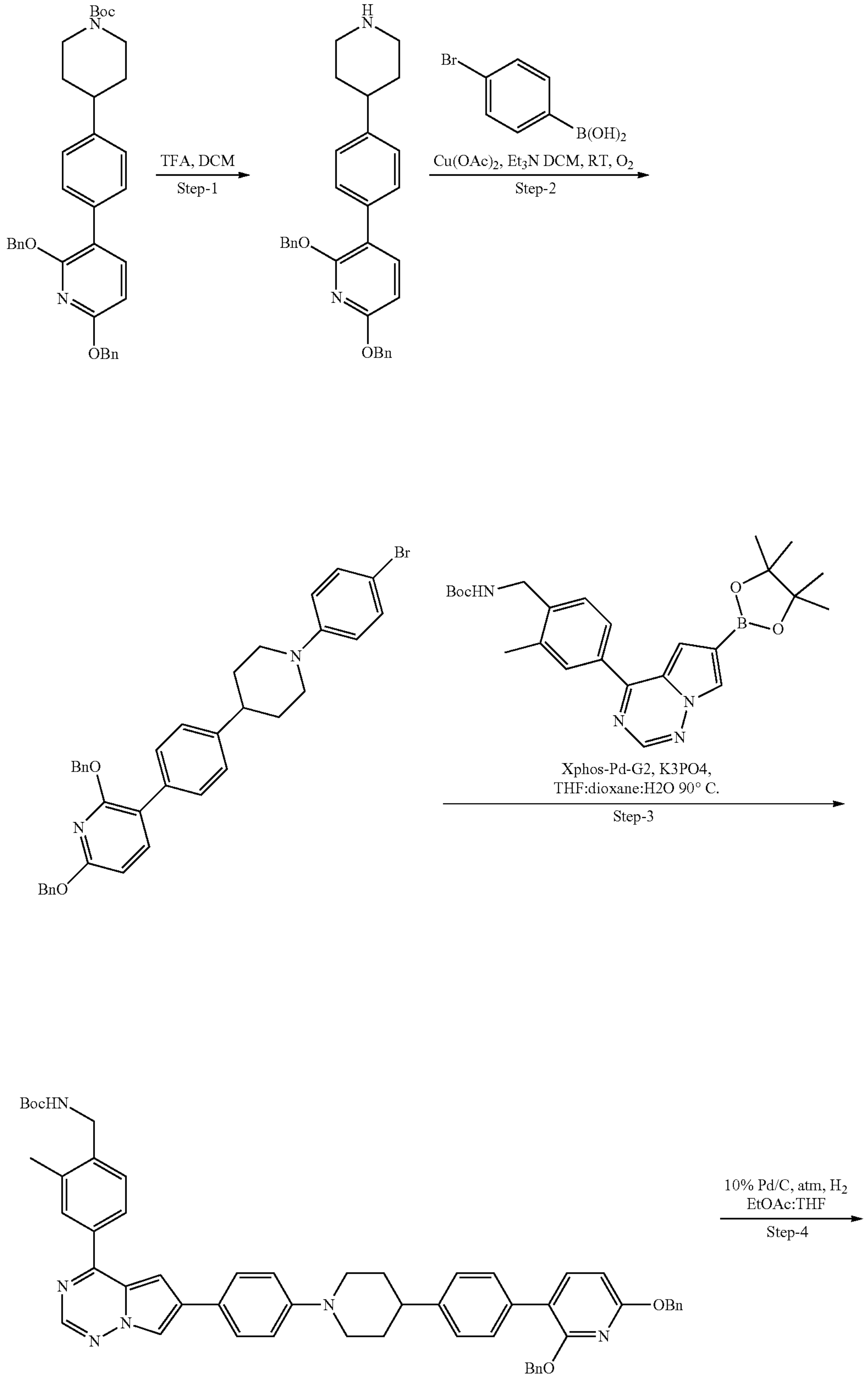

-continued

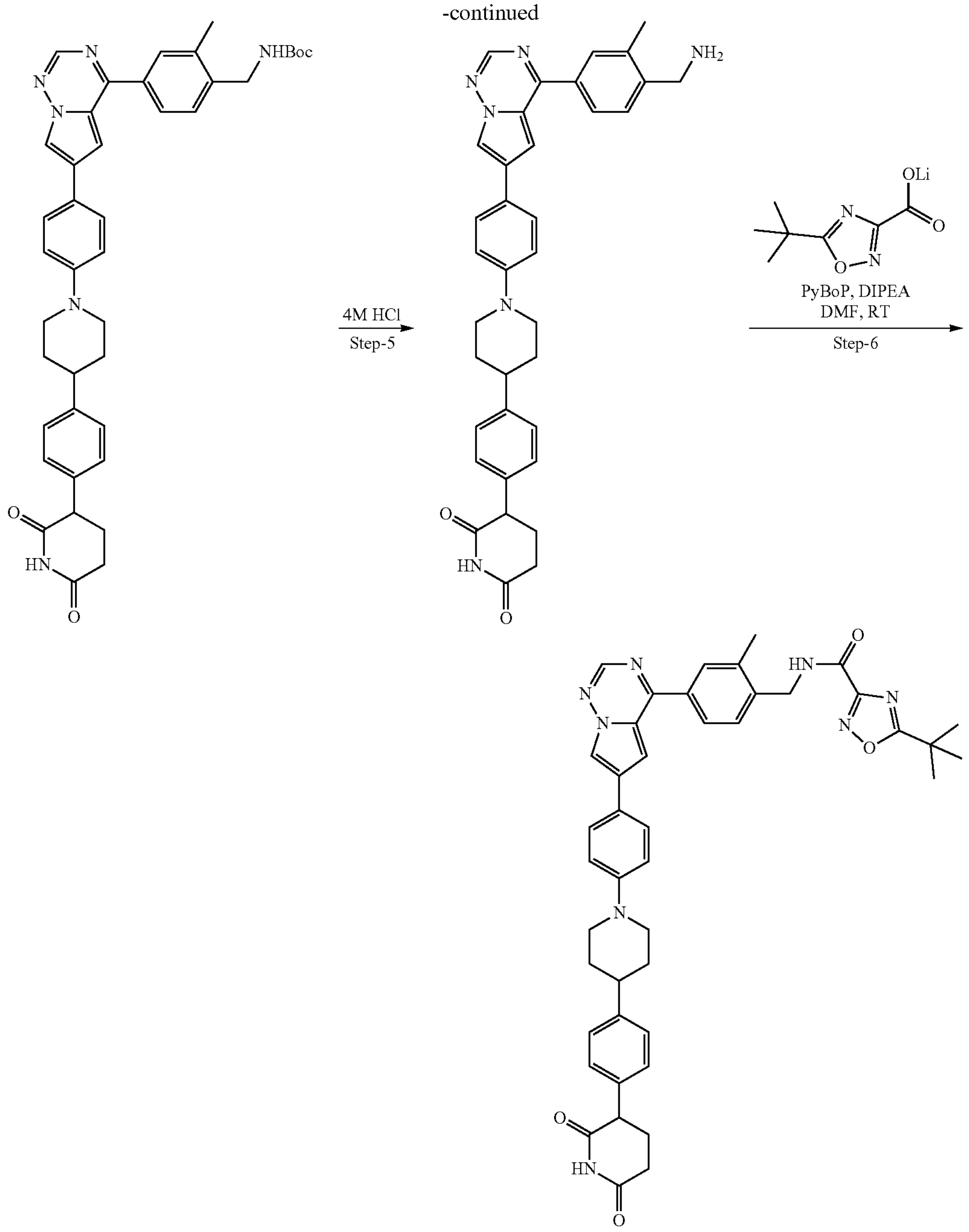

Step-1:

To a stirred solution of tert-butyl 4-[4-(2,6-dibenzyloxy-3-pyridyl)phenyl]piperidine-1-carboxylate (1 g, 1.82 mmol) in DCM (20 mL) at 0° C. under an argon atm. was added 2,2,2-trifluoroacetic acid (7.40 g, 64.90 mmol, 5 mL). The reaction was stirred at −78° C. for 3 hours. The reaction was concentrated under reduced pressure; the residue was triturated with ether to give 2,6-dibenzyloxy-3-[4-(4-piperidyl)phenyl]pyridine (1 g, 95.9% yield). LC-MS ($ES^+$): m/z 451.26 $[M+H]^+$ Step-2:

To a stirred solution of tert-butyl 4-[4-(2,6-dibenzyloxy-3-pyridyl)phenyl]piperidine-1-carboxylate (1 g, 1.82 mmol) and triethylamine (1.84 g, 18.16 mmol, 2.53 mL) in DCM (20 mL) at room temperature was purged with oxygen. (4-Bromophenyl)boronic acid (729.36 mg, 3.63 mmol) was added. The reaction mixture was stirred at room temperature for 15 minutes, then copper diacetate (659.66 mg, 3.63 mmol) was added, and the reaction mixture was stirred at room temperature for 16 hr. Water was added, and extraction was carried out using EtOAc (30 mL×3). The combined organic layers were washed with water, and brine solution, dried over anhydrous sodium sulfate, filtered, and concentrated under reduced pressure to give 2,6-dibenzyloxy-3-[4-[1-(4-bromophenyl)-4-piperidyl]phenyl]pyridine (1 g, 68.3% yield). LC-MS ($ES^+$): m/z 607.05 $[M+H]^+$ Step-3

A stirred solution of 2,6-dibenzyloxy-3-[4-[1-(4-bromophenyl)-4-piperidyl]phenyl]pyridine (0.450, 743.11 μmol) in dioxane (8 mL) and water (2 mL) at room temperature was purged with argon for 10 min. Tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (690.15 mg, 1.49 mmol) and tripotassium phosphate (473.21 mg, 2.23 mmol) was added and the reaction mixture was stirred at room temperature for 10 mins. XPhos Pd G2 (58.47 mg, 74.31 μmol) was added and the reaction mixture was stirred at 90° C. for 16 hr. The residue was quenched with water (60 mL) and extraction was carried out using EtOAc (50 mL×3). The combined organic layers were washed with brine solution (100 mL), dried over anhydrous sodium sulfate, filtered, and concentrated under reduced pressure. The crude material was purified by column chromatography (silica gel 100-200 mesh, 0-50% ethyl acetate in pet ether) to afford tert-butyl N-[[4-[6-[4-[4-[4-(2,6-dibenzyloxy-3-pyridyl)phenyl]-1-piperidyl]phenyl]pyrrolo[2,1-f][1,2,4]triazin-4-yl]-2-methyl-phenyl]methyl]carbamate (0.3 g, 278.08 μmol, 37.42% yield). LC-MS (ES$^+$): m/z 863.46 [M+H]$^+$ $^1$H NMR (400 MHz, DMSO-d$_6$) δ 8.61 (s, 1H), 8.56 (s, 1H), 8.05 (d, J=8.0 Hz, 1H), 7.95 (bs, 1H), 7.80 (d, J=8.2 Hz, 2H), 7.73 (d, J=8.2 Hz, 1H), 7.52-7.21 (m, 18H), 7.05 (d, J=8.6 Hz, 1H), 6.55 (d, J=8.0 Hz, 1H), 5.41 (s, 2H), 5.37 (s, 2H), 4.23 (d, J=6.1 Hz, 2H), 3.90-3.93 (m, 1H), 2.86-2.67 (m, 2H), 2.42 (s, 3H), 1.92-1.78 (m, 2H), 1.43 (s, 13H).

Step-4

To a stirred tert-butyl N-[[4-[6-[4-[4-[4-(2,6-dibenzyloxy-3-pyridyl)phenyl]-1-piperidyl]phenyl]pyrrolo[2,1-f][1,2,4]triazin-4-yl]-2-methyl-phenyl]methyl]carbamate (0.280 g, 324.43 μmol) in ethyl acetate (5 mL) and THE (5 mL) at room temperature was added palladium on carbon (0.280 g, 2.63 mmol) and the reaction was stirred at room temperature under an atmosphere of hydrogen atm for 16 hr. The reaction mixture was filtered through celite and washed with EtOAc. The filtrate was concentrated under reduced pressure to give tert-butyl N-[[4-[6-[4-[4-[4-(2,6-dioxo-3-piperidyl)phenyl]-1-piperidyl]phenyl]pyrrolo[2,1-f][1,2,4]triazin-4-yl]-2-methyl-phenyl]methyl]carbamate (60 mg, 14.5% yield). LC-MS (ES$^+$): m/z 685.22 [M+H]$^+$.

Step-5:

To stirred solution of tert-butyl N-[[4-[6-[4-[4-[4-(2,6-dioxo-3-piperidyl)phenyl]-1-piperidyl]phenyl]pyrrolo[2,1-f][1,2,4]triazin-4-yl]-2-methyl-phenyl]methyl]carbamate (0.06 g, 87.61 μmol) was in DCM (2 mL) at 0° C. under argon atm was added 4 M hydrogen chloride solution in 1,4-dioxane, (1 mL) and the reaction mixture was stirred at room temperature for 2 hours. Evaporation followed by trituration with ether gave 3-[4-[1-[4-[4-[4-(aminomethyl)-3-methyl-phenyl]pyrrolo[2,1-f][1,2,4]triazin-6-yl]phenyl]-4-piperidyl]phenyl]piperidine-2,6-dione hydrochloride (50 mg, 53.5% yield). LC-MS (ES$^+$): m/z 585.41 [M+H]$^+$.

Step-6:

To a stirred solution of 3-[4-[1-[4-[4-[4-(aminomethyl)-3-methyl-phenyl]pyrrolo[2,1-f][1,2,4]triazin-6-yl]phenyl]-4-piperidyl]phenyl]piperidine-2,6-dione (0.06 g, 102.62 μmol) and (5-tert-butyl-1,2,4-oxadiazole-3-carbonyl)oxylithium (36.14 mg, 205.23 μmol) in DMF (2 mL) at 0° C. under argon atm was added N-ethyl-N-isopropyl-propan-2-amine (132.62 mg, 1.03 mmol, 178.74 μL). Benzotriazol-1-yloxy(tripyrrolidin-1-yl)phosphonium; hexafluorophosphate (106.80 mg, 205.23 μmol) was added to the reaction mixture and stirred at room temperature for 5 hours. The reaction was concentrated in vacuo to get crude. The crude compound was purified by prep-HPLC to afford 5-tert-butyl-N-[[4-[6-[4-[4-[4-(2,6-dioxo-3-piperidyl)phenyl]-1-piperidyl]phenyl]pyrrolo[2,1-f][1,2,4]triazin-4-yl]-2-methyl-phenyl]methyl]-1,2,4-oxadiazole-3-carboxamide TFA salt (20.5 mg, 24% yield) as a brown solid. $^1$H NMR (400 MHz, DMSO-d$_6$) δ 10.82 (s, 1H), 9.54 (t, J=5.9 Hz, 1H), 8.64 (s, 1H), 8.04 (d, J=8.0 Hz, 1H), 8.01 (s, 1H), 7.85 (d, J=8.0 Hz, 2H), 7.55 (s, 1H), 7.48 (d, J=8.0 Hz, 1H), 7.27-7.16 (m, 6H), 4.57 (d, J=5.9 Hz, 2H), 3.91-3.81 (m, 4H), 2.97 (bs, 2H), 2.76-2.62 (m, 2H), 2.47 (s, 3H), 2.20-2.16 (m, 1H), 2.06-2.01 (m, 1H), 1.93-1.81 (m, 4H), 1.44 (s, 9H). LC-MS (ES$^+$): m/z 737.14 [M+H]$^+$.

Example 147. Synthesis of 5-tert-butyl-N-[[4-[6-[4-[3-[4-[(2,6-dioxo-3-piperidyl)amino]phenyl]propoxymethyl]phenyl]pyrrolo[2,1-f][1,2,4]triazin-4-yl]-2-methyl-phenyl]methyl]-1,2,4-oxadiazole-3-carboxamide

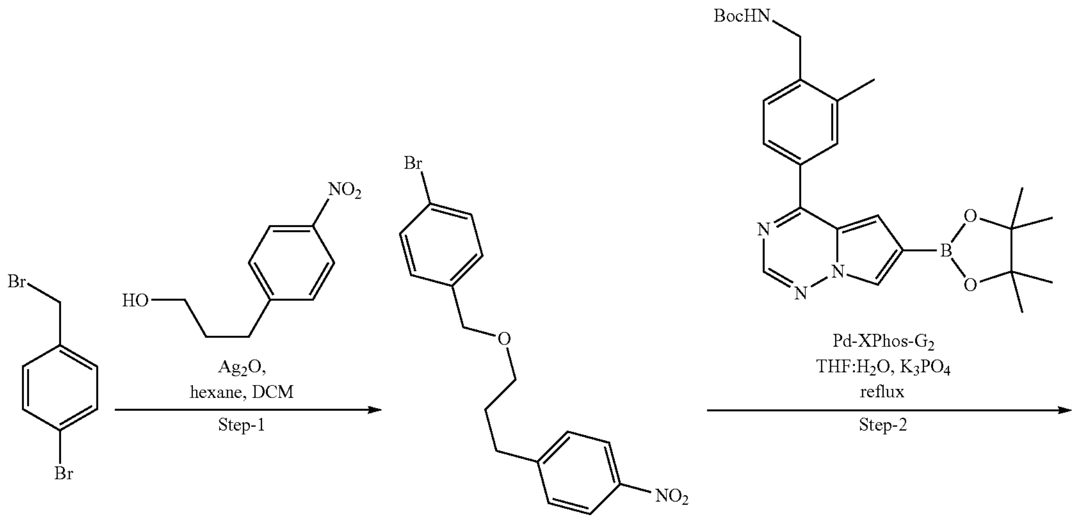

-continued
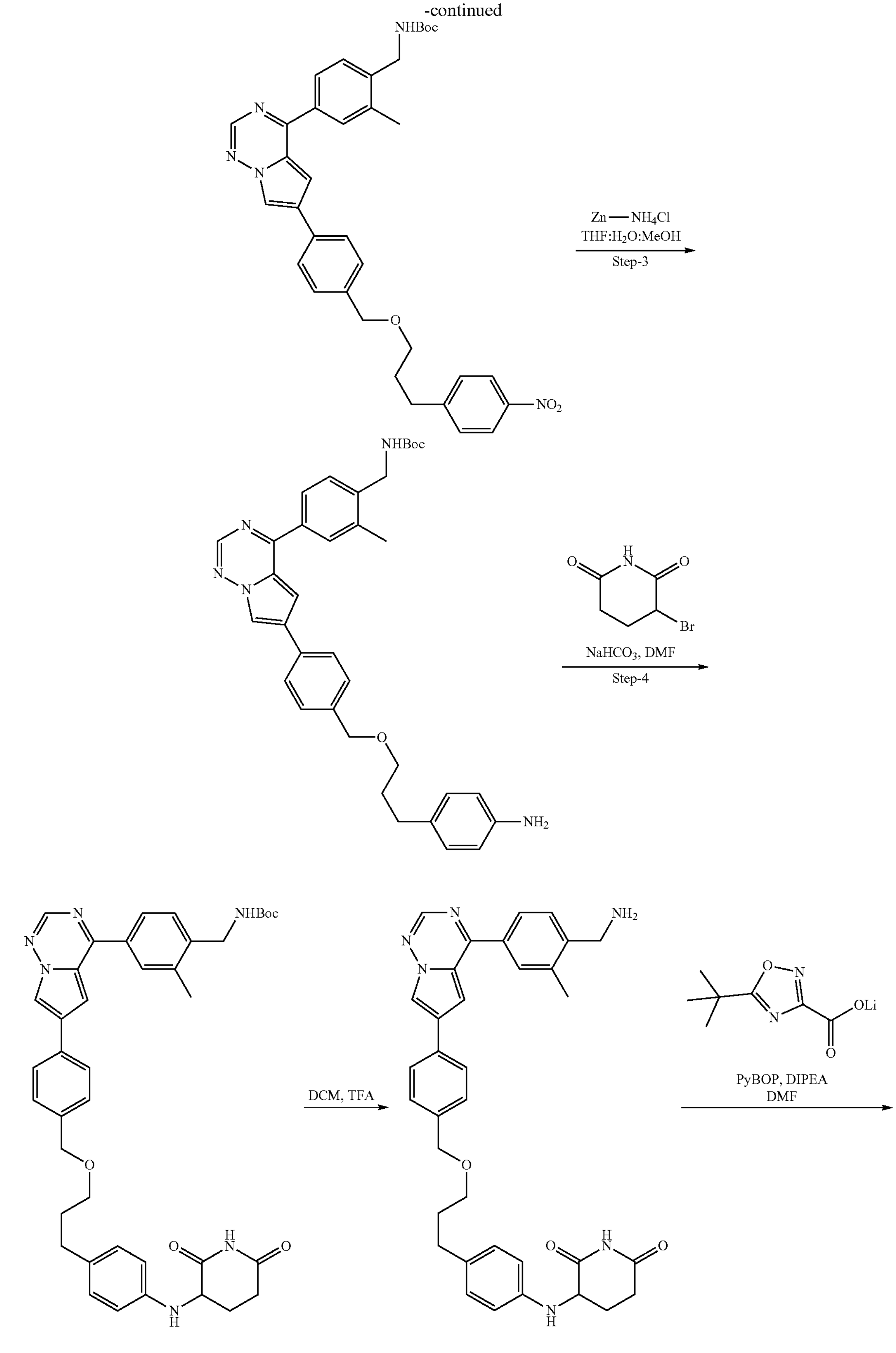

-continued

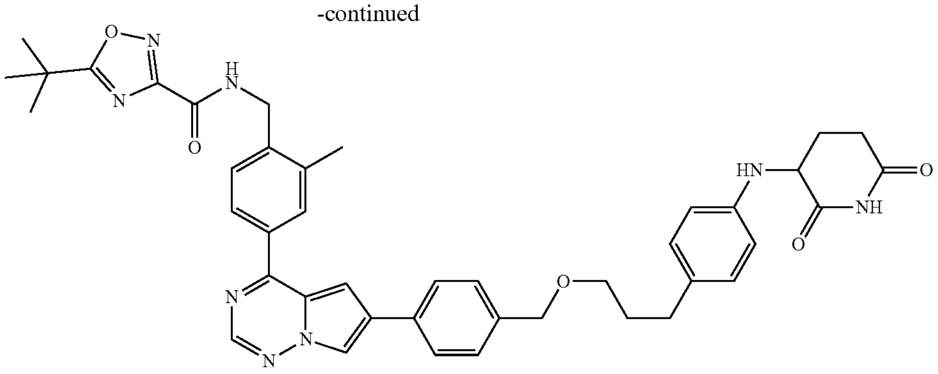

Step-1

In 30 ml vial containing 3-(4-nitrophenyl)propan-1-ol (1 g, 5.52 mmol) and 1-bromo-4-(bromomethyl)benzene (2.07 g, 8.28 mmol) in DCM (5 mL) and hexane (5 mL) was added silver oxide (2.05 g, 16.56 mmol) under inert atmosphere. Molecular sieves (1 g, 5.52 mmol) were added and degassed, followed by heating the vial at 60° C. for 16 hours in the dark. The reaction mixture was filtered through celite and washed with DCM, and the resulting filtrate was concentrated. The crude product was purified by column chromatography (silica gel 100-200 mesh) to give 1-[3-[(4-bromophenyl)methoxy]propyl]-4-nitro-benzene (1.1 g, 2.80 mmol, 50.65% yield) as a colorless liquid. LC-MS ($ES^+$): m/z 350.32 $[M+H]^+$.

Step-2:

In a 10 mL round bottom flask containing a solution of tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (0.2 g, 430.70 μmol) and 1-[3-[(4-bromophenyl)methoxy]propyl]-4-nitro-benzene (181.00 mg, 516.84 μmol) in dioxane (2.50 mL) was added potassium phosphate tribasic anhydrous (228.56 mg, 1.08 mmol) in water (2.50 mL) and was purged with argon for 10 mins. Then Xphos Pd G2 (36.46 mg, 46.33 μmol) was added and degassed. The reaction mixture was then heated to 90° C. and maintained at this temp for 6 hr. After completion, the reaction mixture was quenched with water and extracted with ethyl acetate. The organic layer was concentrated under reduced pressure. The crude product was purified by column chromatography (silica gel, 0-30% ethyl acetate in petroleum ether) to afford tert-butyl N-[[2-methyl-4-[6-[4-[3-(4-nitrophenyl)propoxymethyl]phenyl]pyrrolo[2,1-f][1,2,4]triazin-4-yl]phenyl]methyl]carbamate (0.2 g, 302.78 μmol, 70.30% yield). LC-MS ($ES^+$): m/z 608.22 $[M+H]^+$.

Step-3:

To a stirred solution of tert-butyl N-[[2-methyl-4-[6-[4-[3-(4-nitrophenyl)propoxymethyl]phenyl]pyrrolo[2,1-f][1,2,4]triazin-4-yl]phenyl]methyl]carbamate (0.250 g, 411.39 μmol) in water (2 mL) was added ammonium chloride (176.04 mg, 3.29 mmol, 115.06 μL) and zinc dust (3.29 mmol) then stirred at room temperature for 12 hours. The reaction mixture was filtered through a pad of celite and washed with DCM. The filtrate was concentrated and the crude material was purified by column chromatography (silica gel 100-200 mesh, 15% ethyl acetate in pet ether) to afford tert-butyl N-[[4-[6-[4-[3-(4-aminophenyl)propoxymethyl]phenyl]pyrrolo[2,1-f][1,2,4]triazin-4-yl]-2-methyl-phenyl]methyl]carbamate (0.12 g, 145.40 μmol, 35.34% yield). LC-MS ($ES^+$): m/z 578.50 $[M+H]^+$.

Step-4:

To a stirred solution of tert-butyl N-[[4-[6-[4-[3-(4-aminophenyl)propoxymethyl]phenyl]pyrrolo[2,1 f][1,2,4]triazin-4-yl]-2-methyl-phenyl]methyl]carbamate (150 mg, 259.64 μmol) in DMF (3 mL) was added sodium bicarbonate (174.49 mg, 2.08 mmol) and stirred for 5 minutes. 3-bromopiperidine-2,6-dione (199.42 mg, 1.04 mmol) was added to the reaction mixture and heated at 80° C. in a sealed tube for 16 hours. The reaction mixture was diluted with water and extracted with ethyl acetate. The organic layer was concentrate to dryness and the residue was purified by column chromatography (silica gel, 0-70% ethyl acetate in pet ether) to afford tert-butyl N-[[4-[6-[4-[3-[4-[(2,6-dioxo-3-piperidyl)amino]phenyl]propoxymethyl]phenyl]pyrrolo[2,1-f][1,2,4]triazin-4-yl]-2-methyl-phenyl]methyl]carbamate (0.1 g, 139.37 μmol, 53.68% yield). LC-MS ($ES^+$): m/z 689.42 $[M+H]^+$.

Step-5:

To a stirred solution of tert-butyl N-[[4-[6-[4-[3-[4-[(2,6-dioxo-3-piperidyl)amino]phenyl]propoxymethyl]phenyl]pyrrolo[2,1-f][1,2,4]triazin-4-yl]-2-methyl-phenyl]methyl]carbamate (0.075 g, 108.88 μmol) in DCM (2 mL) was added trifluoroacetic acid (248.30 mg, 2.18 mmol, 167.77 μL) under an inert atmosphere. The reaction mixture was then stirred at room temperature for 3 hours. After completion, the reaction mixture was concentrated under reduced pressure and the resulting residue was triturated with diethyl ether to afford 3-[4-[3-[[4-[4-[4-(aminomethyl)-3-methyl-phenyl]pyrrolo[2,1-f][1,2,4]triazin-6-yl]phenyl]methoxy]propyl]anilino]piperidine-2,6-dione trifluoroacetic acid salt (0.070 g, 93.64 mol, 86.00% yield). LC-MS ($ES^+$): m/z 589.41 $[M+H]^+$.

Step-6:

To a stirred solution of (5-tert-butyl-1,2,4-oxadiazole-3-carbonyl)oxylithium (24.43 mg, 138.75 μmol) in DMF (4 mL) was added DIPEA (71.73 mg, 554.99 μmol, 96.67 μL) followed by pyBOP (96.27 mg, 185.00 μmol) then added 3-[4-[3-[[4-[4-[4-(aminomethyl)-3-methyl-phenyl]pyrrolo[2,1-f][1,2,4]triazin-6-yl]phenyl]methoxy]propyl]anilino]piperidine-2,6-dione (0.065 g, 92.50 μmol, TFA salt). The reaction mixture was stirred for 4 hours. After completion, it was concentrated under reduced pressure and the resulting residue was purified by prep-HPLC to give 5-tert-butyl-N-[[4-[6-[4-[3-[4-[(2,6-dioxo-3-piperidyl)amino]phenyl]propoxymethyl]phenyl]pyrrolo[2,1-f][1,2,4]triazin-4-yl]-2-methyl-phenyl]methyl]-1,2,4-oxadiazole-3-carboxamide trifluoroacetic acid salt (17.6 mg, 19.88 μmol, 21.49% yield) as a greenish-yellow semi-solid. $^1H$ NMR (400 MHz, DMSO-$d_6$) δ 10.76 (s, 1H), 9.54 (t, J=5.9 Hz, 1H), 8.72 (s, 1H), 8.61 (s, 1H), 8.07-8.02 (m, 2H), 7.93 (d, J=8.0 Hz, 2H), 7.63 (s, 1H), 7.47 (d, J=7.6 Hz, 1H), 7.39 (d, J=8.0 Hz, 2H), 6.90 (d, J=8.0 Hz, 2H), 6.59 (d, J=8.0 Hz, 2H), 5.62 (bs, 1H), 4.57 (d, J=6.0 Hz, 2H), 4.48 (s, 2H), 4.26-4.22 (m, 1H), 3.44-3.41 (m, 2H), 2.73-2.67 (m, 1H), 2.58-2.52 (m, 1H), 2.50 (s, 5H), 2.11-2.07 (m, 1H), 1.86-1.70 (m, 3H), 1.44 (s, 9H). LC-MS ($ES^+$): m/z 741.13 $[M+H]^+$.
Example 148. Synthesis of 5-tert-butyl-N-[[4-[6-[4-[3-[4-[(2,6-dioxo-3-piperidyl)amino]phenyl]azetidin-1-yl]butyl]pyrrolo[2,1-f][1,2,4]triazin-4-yl]-2-methyl-phenyl]methyl]-1,2,4-oxadiazole-3-carboxamide
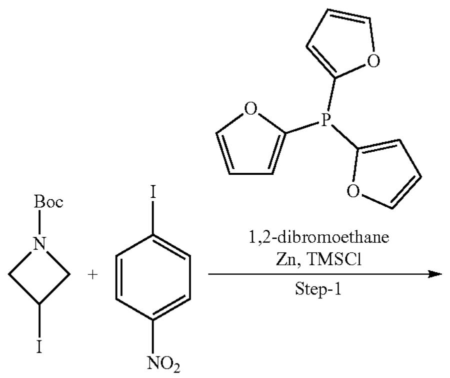
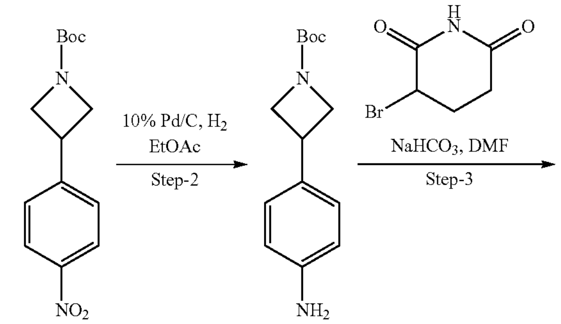
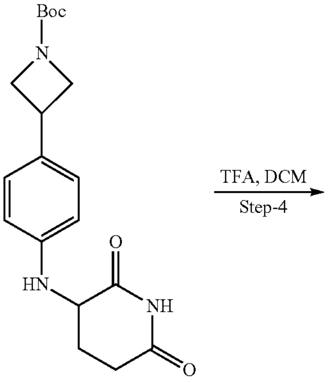
-continued
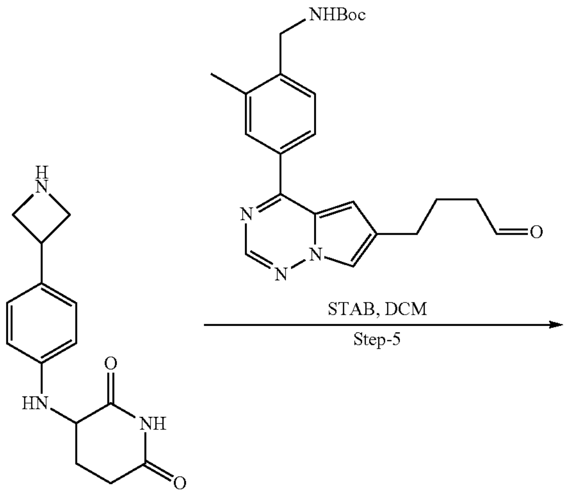
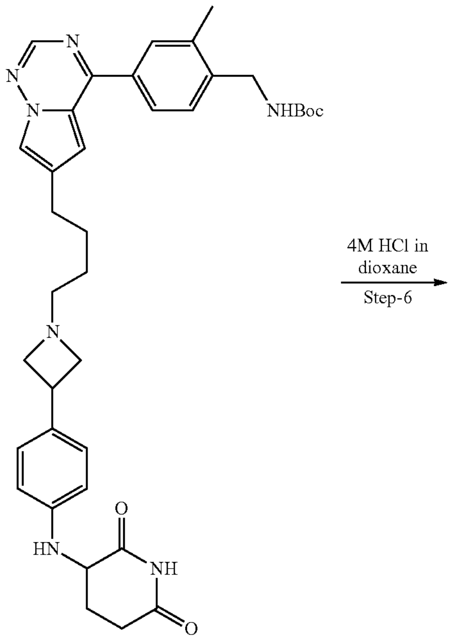

-continued

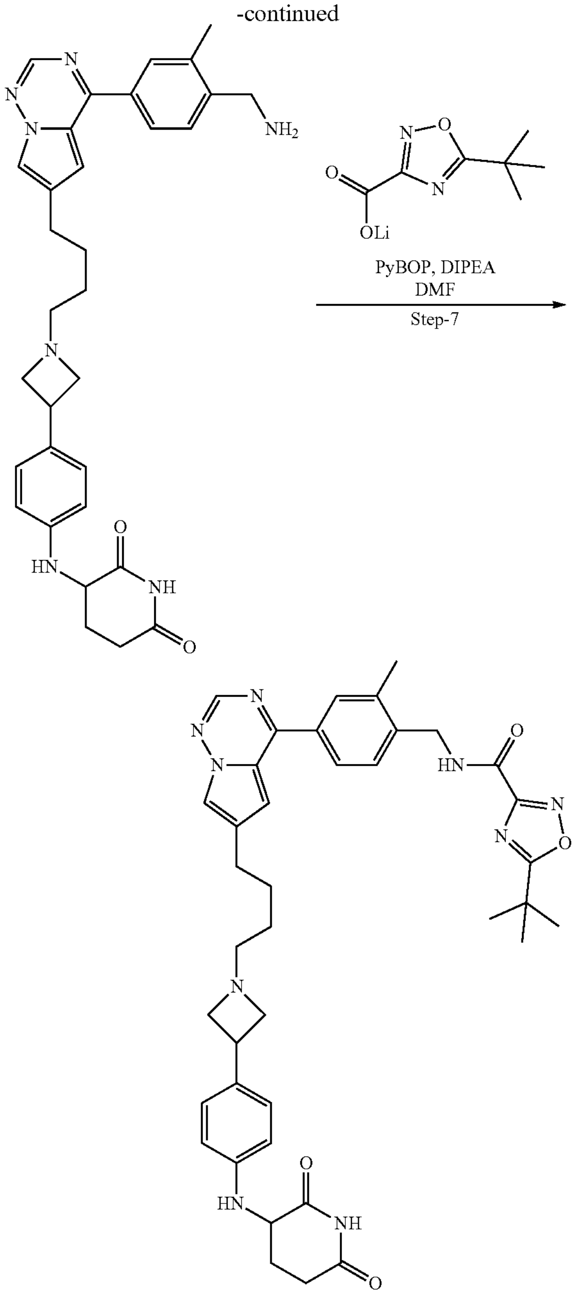

Step-1:

1,2-dibromoethane (318.28 mg, 1.69 mmol, 0.146 mL) was added to a vigorously stirred suspension of zinc dust in THF (3.5 ml) under a nitrogen atmosphere, and the resulting suspension was heated at 55° C. for 10 minutes. Chloro (trimethyl)silane (172.91 mg, 1.59 mmol, 0.202 mL) in THF (1.75 ml) was added at room temperature, and after stirring for 4 minutes, a solution of tert-butyl 3-iodoazetidine-1-carboxylate (3 g, 10.60 mmol) in THF (3.5 ml) was added dropwise over a period of 15 minutes. The resulting mixture was stirred at room temperature for 2 hours, then (1E,4E)-1,5-diphenylpenta-1,4-dien-3-one; palladium (0.155 g, 169.27 μmol) and tris(2-furyl)phosphane (0.143 g, 615.92 μmol) were added followed by 1-iodo-4-nitro-benzene (2.9 g, 11.65 mmol) in THF (18 ml). The resulting mixture was heated at 55° C. for 16 hr. A saturated sodium bicarbonate solution was added, and extraction was carried out using ethyl acetate (50 mL×3). The combined organic layers were washed with water, and brine solution, dried over anhydrous sodium sulfate, filtered, and concentrated under reduced pressure. The crude material was purified by column chromatography (silica gel 100-200 mesh, 10% ethyl acetate in pet ether) to afford tert-butyl 3-(4-nitrophenyl)azetidine-1-carboxylate (1.8 g, 5.81 mmol, 49.88% yield). LC-MS ($ES^+$): m/z 264.11 $[M+H]^+$ Step-2:

To a stirred solution of tert-butyl 3-(4-nitrophenyl)azetidine-1-carboxylate (0.5 g, 1.80 mmol) in ethyl acetate (5 mL) at room temperature was added palladium (0.3 g, 2.82 mmol) and the reaction was stirred at room temperature under hydrogen atm. The reaction was monitored by TLC and LCMS. The reaction mixture was then filtered through celite and washed with ethyl acetate. The filtrate was concentrated under reduced pressure to give tert-butyl 3-(4-aminophenyl)azetidine-1-carboxylate (0.45 g, 79.5% yield). LC-MS ($ES^+$): m/z 249.26 $[M+H]^+$.

Step-3:

To a stirred solution of tert-butyl 3-(4-aminophenyl)azetidine-1-carboxylate (450 mg, 1.81 mmol) and 3-bromopiperidine-2,6-dione (1.04 g, 5.44 mmol) in DMF (5 mL) at room temperature under an argon atm. was added sodium hydrogen carbonate (913.41 mg, 10.87 mmol, 422.87 μL), and the reaction mixture was stirred at 70° C. for 16 hours. The reaction mixture was poured into cold water 100 ml, and a solid precipitate was formed and filtered. This precipitate was dried under reduced pressure to give tert-butyl 3-[4-[(2,6-dioxo-3-piperidyl)amino]phenyl]azetidine-1-carboxylate (520 mg, 1.27 mmol, 70.26% yield) as a green solid. LC-MS ($ES^-$): m/z358.25 $[M-H]^-$ Step-4:

To stirred solution of tert-butyl 3-[4-[(2,6-dioxo-3-piperidyl)amino]phenyl]azetidine-1-carboxylate (520 mg, 1.45 mmol) in DCM (5 mL) at 0° C. was added trifluoroacetic acid (222.00 mg, 1.95 mmol, 0.15 mL) dropwise. The reaction was stirred at room temperature for 2 hours. The reaction mixture was evaporated under reduced pressure to give the crude compound. The crude material was triturated with Et2O to afford 3-[4-(azetidin-3-yl)anilino]piperidine-2,6-dione trifluoroacetic acid salt (500 mg, 1.30 mmol, 90.03% yield) as a black-brown solid. LC-MS ($ES^+$): m/z 260.48 $[M+H]^+$.

Step-5:

To a stirred solution of 3-[4-(azetidin-3-yl)anilino]piperidine-2,6-dione trifluoroacetate acid salt (0.15 g, 401.79 μmol) in DCM (10 mL) was added to Triethylamine (40.66 mg, 401.79 μmol, 56.00 μL) and the reaction mixture was stirred at room temperature for 5 minute, tert-butyl N-[[2-methyl-4-[6-(4-oxobutyl)pyrrolo[2,1-f][1,2,4]triazin-4-yl]phenyl]methyl]carbamate (164.13 mg, 401.79 μmol) was then added, and the reaction mixture was stirred at room temperature for 1 hour. The reaction mixture was cooled to 0° C. sodium triacetoxyborohydride (85.16 mg, 401.79 μmol) was added and the reaction mixture was stirred at room temperature for 16 hours. The reaction was filtered through celite and washed with DCM. The filtrate was concentrated under reduced pressure to give tert-butyl N-[[4-[6-[4-[3-[4-[(2,6-dioxo-3-piperidyl)amino]phenyl]azetidin-1-yl]butyl]pyrrolo[2,1-f][1,2,4]triazin-4-yl]-2-methyl-phenyl]methyl]carbamate (0.3 g, 90.8% yield). LC-MS ($ES^-$): m/z 650.49 $[M-H]^-$.

Step-6:

To stirred solution of tert-butyl N-[[4-[6-[4-[3-[4-[(2,6-dioxo-3-piperidyl)amino]phenyl]azetidin-1-yl]butyl]pyrrolo[2,1-f][1,2,4]triazin-4-yl]-2-methyl-phenyl]methyl]carbamate (0.150 g, 230.13 μmol) in DCM (1 mL) at 0° C. under an argon atm was added 4.0 M hydrogen chloride in dioxane (800.00 mg, 21.94 mmol, 1 mL) and the reaction mixture was stirred at room temperature for 2 h. The reaction was concentrated under reduced pressure and washed with ether to give 3-[4-[1-[4-[4-[4-(aminomethyl)-3-methyl-phenyl]pyrrolo[2,1-f][1,2,4]triazin-6-yl]butyl]azetidin-3-yl]anilino]piperidine-2,6-dione (0.1 g, 70.7% yield). LC-MS ($ES^-$): m/z 5550.55 $[M-H]^-$.

Step-7:

To a stirred solution of 3-[4-[1-[4-[4-[4-(aminomethyl)-3-methyl-phenyl]pyrrolo[2,1-f][1,2,4]triazin-6-yl]butyl]azetidin-3-yl]anilino]piperidine-2,6-dione hydrochloride (0.150 g, 255.04 μmol) and (5-tert-butyl-1,2,4-oxadiazole-3-carbonyl)oxylithium (95.76 mg, 543.79 μmol) in DMF (1 mL) at 0° C. under an argon atm was added N-ethyl-N-isopropyl-propan-2-amine (35.14 mg, 271.90 μmol, 47.36 μL) and benzotriazol-1-yloxy(tripyrrolidin-1-yl)phosphonium; hexafluorophosphate (141.49 mg, 271.90 μmol) to the reaction mixture at same temperature and then stirred at 25° C. for 5 hr. The reaction mixture was concentrated in vacuo and the crude material was purified by prep-HPLC to give 5-tert-butyl-N-[[4-[6-[4-[3-[4-[(2,6-dioxo-3-piperidyl)amino]phenyl]azetidin-1-yl]butyl]pyrrolo[2,1-f][1,2,4]triazin-4-yl]-2-methyl-phenyl]methyl]-1,2,4-oxadiazole-3-carboxamide (0.022 g, 30.44 μmol, 11.20% yield) as a yellow solid. $^1H$ NMR (400 MHz, DMSO-$d_6$) δ 10.78 (s, 1H), 9.65 (bs, 1H), 9.52 (t, J=5.9 Hz, 1H), 8.56 (s, 1H), 8.09 (s, 1H), 7.95-7.93 (m, 1H), 7.45 (d, J=8.0 Hz, 1H), 7.12 (d, J=8.0 Hz, 2H), 7.09 (bs, 1H), 6.70-6.66 (m, 2H), 4.55 (d, J=5.9 Hz, 2H), 4.34-4.32 (m, 2H), 4.24-4.12 (m, 1H), 4.01-3.97 (m, 2H), 3.26-3.21 (m, 2H), 2.76-2.60 (m, 5H), 2.46 (s, 3H), 2.32-2.26 (m, 1H), 2.01-1.89 (m, 1H), 1.81-1.68 (m, 2H), 1.55-1.49 (m, 2H), 1.44 (s, 9H). LC-MS ($ES^-$): m/z 702.34 $[M-H]^-$.

Example 149. Synthesis of 5-tert-butyl-N-[[4-[6-[4-[4-[4-[(2,6-dioxo-3-piperidyl)amino]phenyl]butyl]phenyl]pyrrolo[2,1-f][1,2,4]triazin-4-yl]-2-methyl-phenyl]methyl]-1,2,4-oxadiazole-3-carboxamide

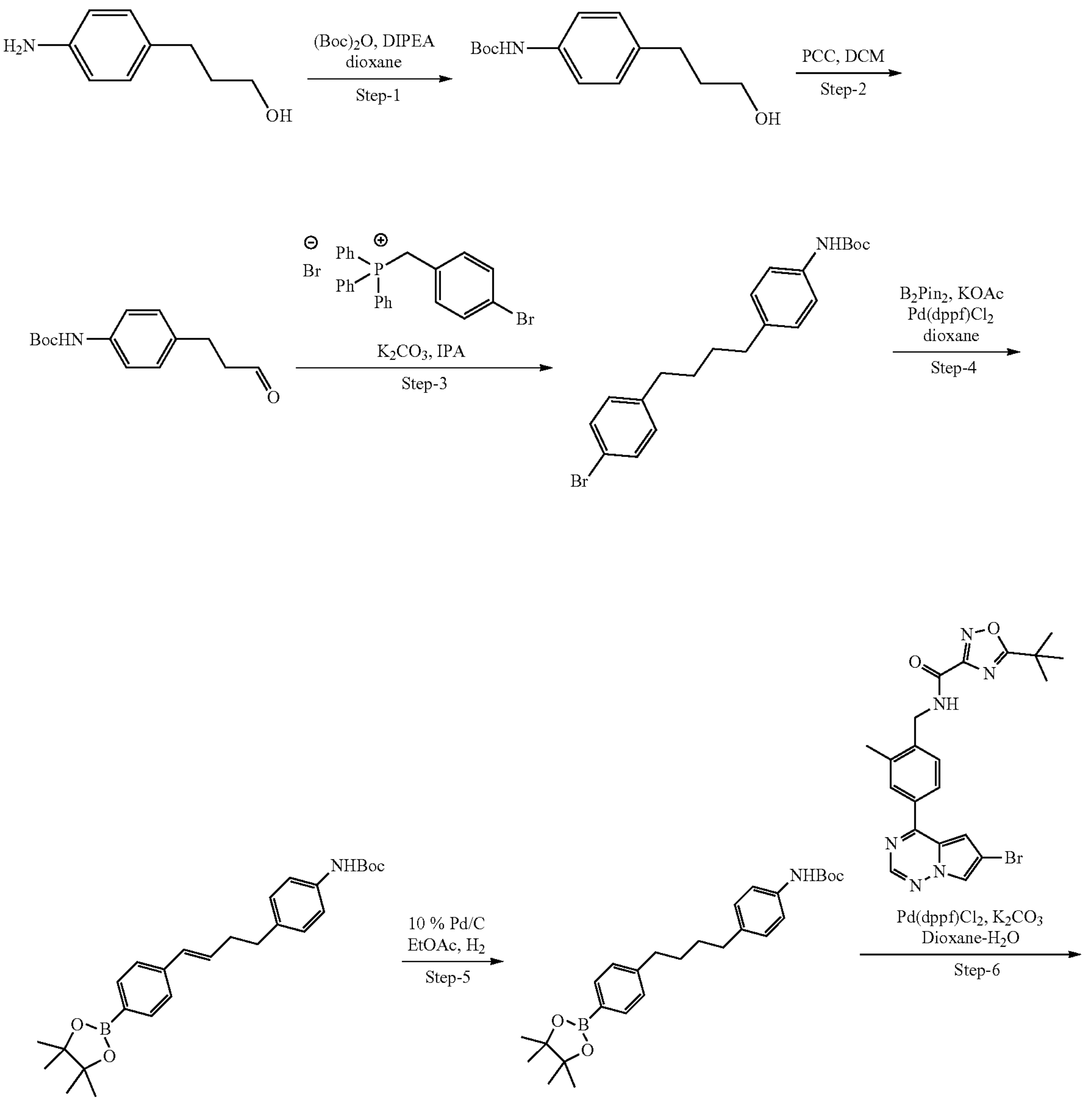

-continued

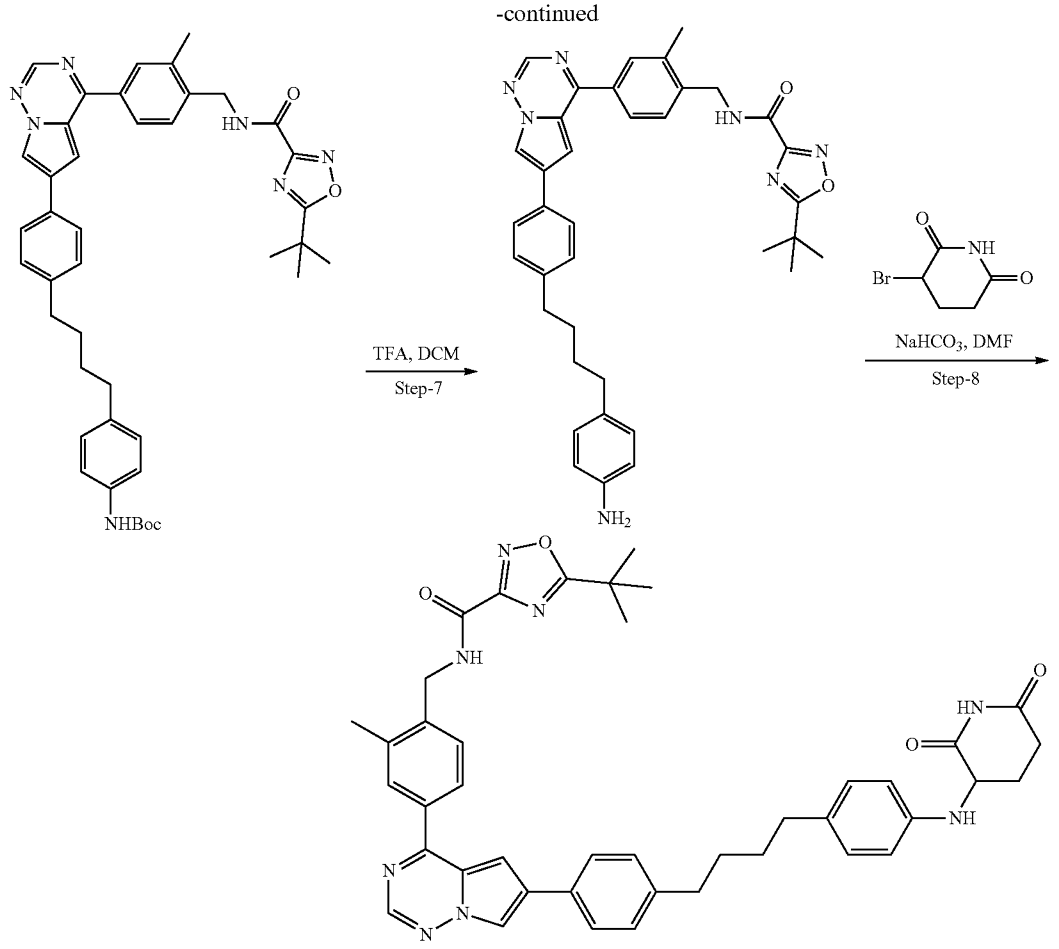

Step-1:

To a stirred solution of 3-(4-aminophenyl)propan-1-ol (1.2 g, 7.94 mmol) in 1-4 dioxane (15 mL) was added DIPEA (6.15 g, 47.62 mmol, 8.29 mL), tert-butoxycarbonyl tert-butyl carbonate (2.60 g, 11.90 mmol, 2.73 mL) under nitrogen atmosphere at 0° C. The reaction mixture was stirred at 25° C. for 16 hours, while the progress of the reaction was monitored by TLC and LCMS. Upon completion, the reaction was diluted with cold water and extracted with ethyl acetate. The organic layer was washed with brine solution, dried over sodium sulfate, filtered, and concentrated in vacuo to give the crude product, which was purified by column chromatography (silica gel, 0-100% ethyl acetate in pet ether) to afford tert-butyl N-[4-(3-hydroxypropyl) phenyl]carbamate (1.8 g, 6.45 mmol, 81.22% yield) as a liquid. $^1$H NMR (400 MHz, DMSO-d$_6$) δ 9.19 (s, 1H), 7.33 (d, J=8.4 Hz, 2H), 7.05 (d, J=8.4 Hz, 2H), 4.42 (t, J=5.2 Hz, 1 Hz), 3.40-3.31 (m, 2H), 2.53-2.49 (m, 2H), 1.69-1.62 (m, 2H), 1.46 (s, 9H).

Step-2:

To a stirred solution of tert-butyl N-[4-(3-hydroxypropyl) phenyl]carbamate (1.2 g, 4.77 mmol) in DCM (15 mL) were added celite (1.2 g, 4.77 mmol) followed by pyridinium chlorochromate, 98% (2.06 g, 9.55 mmol) under nitrogen atmosphere at 0° C. The reaction mixture was then stirred at 50° C. for 1 hour while the reaction progress was monitored by TLC. After the reaction was complete, it was cooled to room temperature, filtered through a pad of celite, and washed with DCM (200 mL). The filtrate was evaporated to dryness to afford tert-butyl N-[4-(3-oxopropyl)phenyl]carbamate (0.6 g, 2.05 mmol, 42.84% yield) as a gummy compound. $^1$H NMR (400 MHz, DMSO-d$_6$) δ 9.69 (s, 1H), 9.21 (s, 1H), 7.33 (d, J=8.4 Hz, 2H), 7.08 (d, J=8.4 Hz, 2H), 2.78-2.71 (m, 4H), 1.46 (s, 9H).

Step-3:

To a stirred solution of tert-butyl N-[4-(3-oxopropyl) phenyl]carbamate (0.9 g, 3.61 mmol) in isopropyl alcohol (10 mL) were added potassium carbonate, anhydrous, 99% (1.50 g, 10.83 mmol) followed by (4-bromobenzyl)triphenylphosphonium bromide (1.85 g, 3.61 mmol) under nitrogen atmosphere. The reaction was refluxed at 80° C. for 16 hours and monitored by TLC and LCMS. After completion, the reaction mixture was evaporated to dryness, and the resulting crude product was purified by column chromatography (silica gel 100-200 mesh, 0-5% ethyl acetate in pet ether) to afford tert-butyl N-[4-[(E)-4-(4-bromophenyl)but-3-enyl]phenyl]carbamate (0.9 g, 1.90 mmol, 52.67% yield) as a white solid. LC-MS (ES$^+$): m/z 346.29 [M−56+H]$^+$.

Step-4:

To a stirred solution of tert-butyl N-[4-[(E)-4-(4-bromophenyl)but-3-enyl]phenyl]carbamate (0.25 g, 621.39 μmol) in dioxane (5 mL) were added 4,4,5,5-tetramethyl-2-(4,4,5,5-tetramethyl-1,3,2-dioxaborolan-2-yl)-1,3,2-dioxaborolane (236.69 mg, 932.08 μmol), potassium acetate (182.95 mg, 1.86 mmol). The reaction mixture was degassed with argon for 15 minutes. Then Pd(dppf)Cl$_2$ (45.47 mg, 62.14 μmol)

was added, and the reaction was refluxed at 100° C. for 16 hours. The progress of the reaction was monitored by TLC and LC-MS. After completion of the reaction, the mixture was diluted with ethyl acetate and filtered through a pad of celite. The filtrate was then washed with brine solution, and the organic layer was concentrated in vacuo to give the crude product, which was purified by Biotage® Isolera (0-20% ethyl acetate in pet ether) to afford tert-butyl N-[4-[(E)-4-[4-(4,4,5,5-tetramethyl-1,3,2-dioxaborolan-2-yl)phenyl]but-3-enyl]phenyl]carbamate (0.25 g, 534.06 µmol, 85.95% yield). LC-MS ($ES^-$): m/z 448.58 $[M-H]^-$.

Step-5:

To a stirred solution of tert-butyl N-[4-[(E)-4-[4-(4,4,5,5-tetramethyl-1,3,2-dioxaborolan-2-yl)phenyl]but-3-enyl]phenyl]carbamate (0.250 g, 556.31 µmol) in ethyl acetate (5 mL) was added 10 wt. % palladium on carbon, type 487, dry (59.20 mg, 556.31 µmol). The reaction was stirred under a hydrogen atmosphere for 4 hours while monitoring by TLC and LC-MS. Upon completion, the reaction was filtered through celite and washed with ethyl acetate. The filtrate was concentrated in vacuo to give the crude product, which was purified by Biotage® Isolera to afford tert-butyl N-[4-[4-[4-(4,4,5,5-tetramethyl-1,3,2-dioxaborolan-2-yl)phenyl]butyl]phenyl]carbamate (0.2 g, 332.30 µmol, 59.73% yield). LC-MS ($ES^+$): m/z 352.51 $[M-100+H]^+$.

Step-6:

To a stirred solution of N-[[4-(6-bromopyrrolo[2,1-f][1,2,4]triazin-4-yl)-2-methyl-phenyl]methyl]-5-tert-butyl-1,2,4-oxadiazole-3-carboxamide (0.05 g, 106.53 µmol) and tert-butyl N-[4-[4-[4-(4,4,5,5-tetramethyl-1,3,2-dioxaborolan-2-yl)phenyl]butyl]phenyl]carbamate (72.13 mg, 159.80 µmol) in dioxane (5 mL) was added potassium carbonate, anhydrous, 99% (29.45 mg, 213.07 µmol) in water (2 mL). This is followed by the addition of $Pd(dppf)Cl_2 \cdot CH_2Cl_2$ (7.80 mg, 10.65 µmol) and the mixture was purged with argon for 10-15 minutes. It was then heated at 80° C. for 8 hours while monitoring by TLC and LC-MS. After completion of the reaction, it was concentrated under reduced pressure and the resulting residue was purified by column chromatography (silica gel, 0-40% ethyl acetate in pet ether) to afford tert-butyl N-[4-[4-[4-[4-[4-[[(5-tert-butyl-1,2,4-oxadiazole-3-carbonyl)amino]methyl]-3-methyl-phenyl]pyrrolo[2,1-f][1,2,4]triazin-6-yl]phenyl]butyl]phenyl]carbamate (0.05 g, 39.22 µmol, 36.82% yield). LC-MS ($ES^-$): m/z 712.14 $[M-H]^-$.

Step-7:

To a stirred solution of tert-butyl N-[4-[4-[4-[4-[4-[[(5-tert-butyl-1,2,4-oxadiazole-3-carbonyl)amino]methyl]-3-methyl-phenyl]pyrrolo[2,1-f][1,2,4]triazin-6-yl]phenyl]butyl]phenyl]carbamate (0.300 g, 420.25 µmol) in DCM (5 mL) was added TFA (479.18 mg, 4.20 mmol, 323.77 µL), and the reaction mixture was stirred for 5 hours at 40° C. The progress of the reaction was monitored by TLC and LC-MS. Upon completion of the reaction, the reaction mixture was concentrated under reduced pressure and resulting residue was triturated with toluene and diethyl ether to afford N-[[4-[6-[4-[4-(4-aminophenyl)butyl]phenyl]pyrrolo[2,1-f][1,2,4]triazin-4-yl]-2-methyl-phenyl]methyl]-5-tert-butyl-1,2,4-oxadiazole-3-carboxamide TFA salt (0.27 g, 293.09 µmol, 69.74% yield) as a brown liquid. LC-MS ($ES^+$): m/z 614.73 $[M+H]^+$.

Step-8:

In a 25 mL round bottom flask, a solution of N-[[4-[6-[4-[4-(4-aminophenyl)butyl]phenyl]pyrrolo[2,1-f][1,2,4]triazin-4-yl]-2-methyl-phenyl]methyl]-5-tert-butyl-1,2,4-oxadiazole-3-carboxamide TFA salt (0.150 g, 206.11 µmol) in DMF (4 mL) was added sodium bicarbonate (138.52 mg, 1.65 mmol). The mixture was purged with nitrogen gas for 10 minutes before 3-bromopiperidine-2,6-dione (118.72 mg, 618.32 µmol) was added and the reaction heated at 80° C. for 16 hours while monitoring by TLC and LC-MS. Upon completion, the reaction was filtered through celite and the filtrate was washed with brine solution and concentrated in vacuo to give the crude product, which was purified by prep-HPLC to afford 5-tert-butyl-N-[[4-[6-[4-[4-[4-[(2,6-dioxo-3-piperidyl)amino]phenyl]butyl]phenyl]pyrrolo[2,1-f][1,2,4]triazin-4-yl]-2-methyl-phenyl]methyl]-1,2,4-oxadiazole-3-carboxamide formic acid salt (12 mg, 15.40 µmol, 7.47% yield) as a pale yellow solid. $^1H$ NMR (400 MHz, DMSO-$d_6$) δ 10.76 (s, 1H), 9.54 (t, J=5.9 Hz, 1H), 8.67 (s, 1H), 8.59 (s, 1H), 8.06-8.01 (m, 2H), 7.83 (d, J=7.6 Hz, 2H), 7.58 (s, 1H), 7.47 (d, J=7.6 Hz, 1H), 7.24 (d, J=7.6 Hz, 2H), 6.89 (d, J=8.0 Hz, 2H), 6.58 (d, J=8.0 Hz, 2H), 5.61 (d, J=7.2 Hz, 1H), 4.57 (d, J=5.6 Hz, 2H), 4.24 (s, 1H), 2.73-2.52 (m, 4H), 2.50 (s, 5H), 2.08-2.07 (m, 1H), 1.85-1.82 (m, 1H), 1.59-1.54 (m, 4H), 1.44 (s, 9H). LC-MS ($ES^+$): m/z 725.21 $[M+H]^+$.

Example 150. Synthesis of 5-tert-butyl-N-[[4-[6-[4-[[[3-[4-[(2,6-dioxo-3-piperidyl)amino]phenyl]-2,2-difluoro-propyl]-methyl-amino]methyl]phenyl]pyrrolo[2,1-f][1,2,4]triazin-4-yl]-2-methyl-phenyl]methyl]-1,2,4-oxadiazole-3-carboxamide

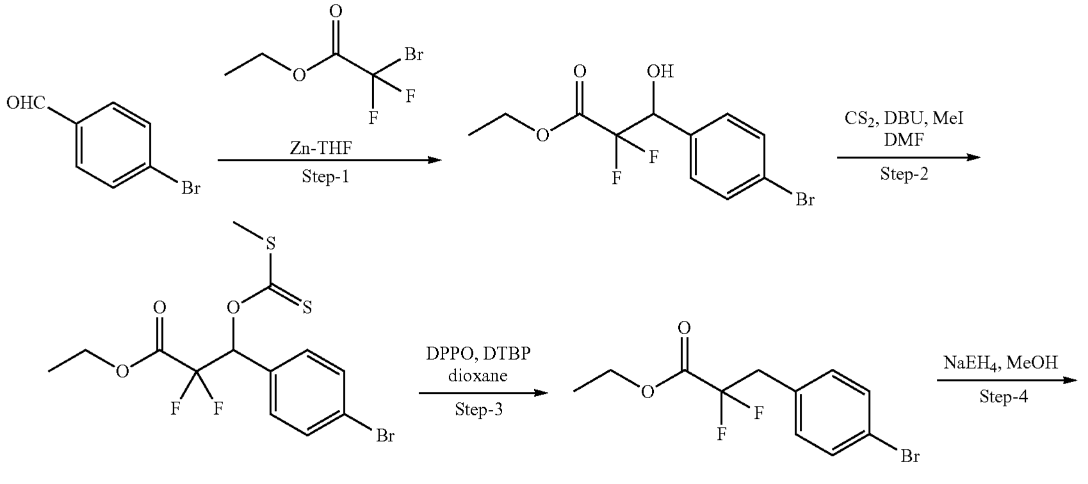

-continued

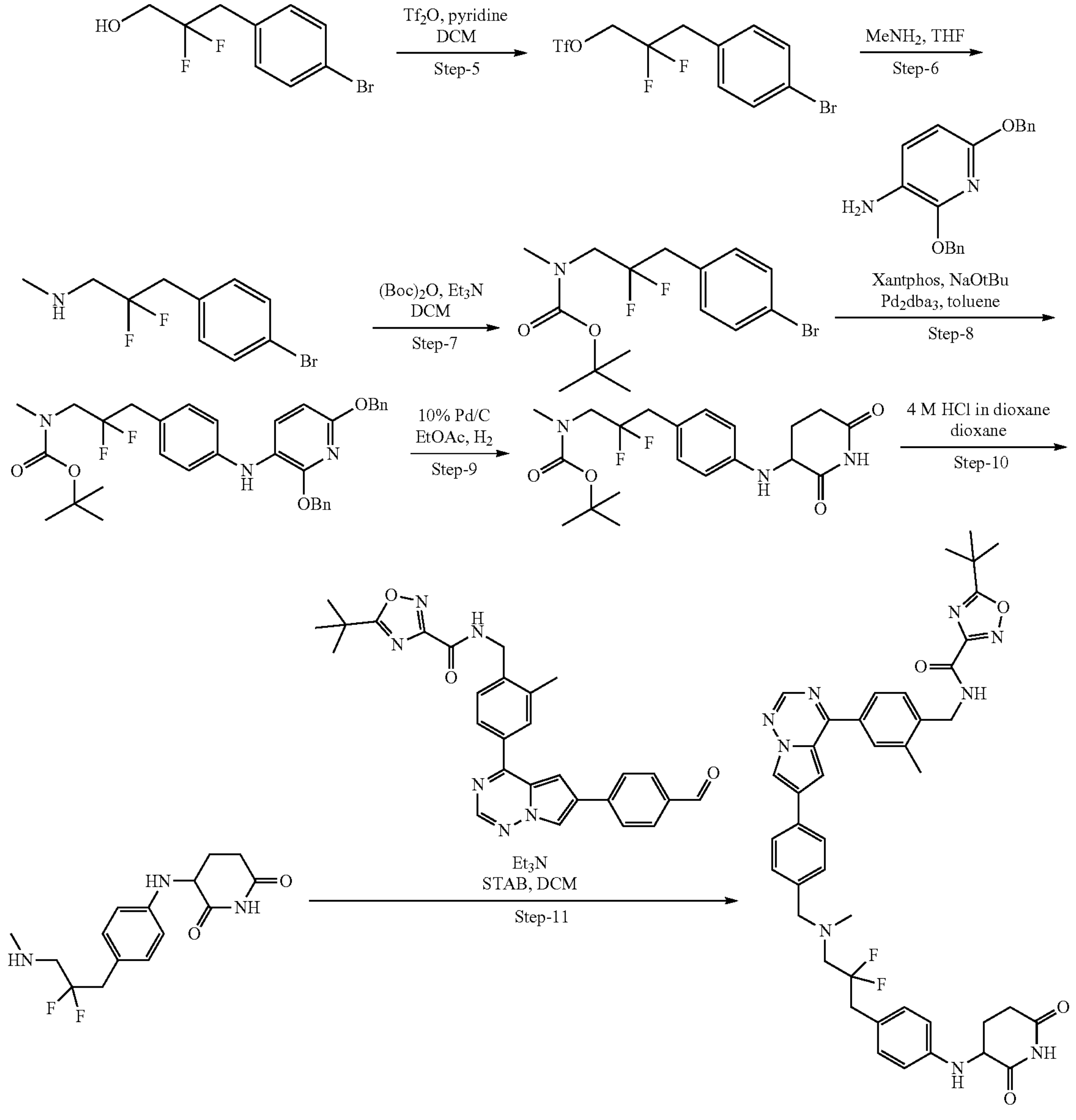

Step-1:

To a stirred solution of zinc (21.21 g, 324.29 mmol) in THF (300 mL) was added ethyl 2-bromo-2,2-difluoro-acetate (59.24 g, 291.86 mmol, 37.50 mL) dropwise at 0° C. and the mixture was refluxed for 1.5 hours. 4-Bromobenzaldehyde (30.0 g, 162.15 mmol) in THF (30 mL) was then added dropwise at room temperature, and the reaction was heated at 55° C. for 3 hours while the progress was monitored by TLC. Upon completion of the reaction, the solution was cooled to 25° C., diluted with ethyl acetate (50 mL), washed with 1 M $KHSO_4$ solution (2×50 mL), and brine (50 mL). It was then dried over anhydrous sodium sulfate and concentrated in vacuo to yield the crude product, which was purified by flash chromatography (silica gel 100-200 mesh, 35% ethyl acetate in pet-ether) to afford ethyl 3-(4-bromophenyl)-2,2-difluoro-3-hydroxy-propanoate (20.0 g, 58.23 mmol, 35.91% yield) as a yellow oil. $^1H$ NMR (400 MHz, DMSO-d6) δ 7.46 (d, J=8.0 Hz, 2H), 7.26-7.19 (m, 2H), 5.11-5.06 (m, 1H), 4.27-4.22 (m, 2H), 2.75-2.69 (m, 1H), 1.26-1.22 (m, 3H).

Step-2:

To a stirred solution of ethyl 3-(4-bromophenyl)-2,2-difluoro-3-hydroxy-propanoate (10 g, 32.35 mmol) in DMF (100 mL) were added 2,3,4,6,7,8,9,10-octahydropyrimido[1,2-a]azepine (29.55 g, 194.11 mmol, 28.97 mL) and methanedithione (24.63 g, 323.52 mmol) sequentially. The reaction mixture was stirred for 1.5 hours at room temperature before iodomethane (41.33 g, 291.16 mmol, 18.13 mL) was added, and the mixture was stirred for a further 1.5 hours at this temperature. The reaction mixture was then partitioned between ethyl acetate and water. The organic layer was separated, washed with brine, and dried over anhydrous sodium sulfate to afford the crude product, which was purified by column chromatography (silica 100-200 mesh, 0-100% ethyl acetate in pet ether) to afford ethyl 3-(4-bromophenyl)-2,2-difluoro-3-methylsulfanylcarbothioyloxy-propanoate (9 g, 15.78 mmol, 48.77% yield) as a yellow liquid. $^1H$ NMR (400 MHz, DMSO-$d_6$) δ 7.53 (d, J=8.4 Hz, 2H), 7.32-7.29 (m, 2H), 6.94-6.88 (m, 1H), 4.37-4.30 (m, 2H), 2.57 (s, 3H), 1.31 (t, J=6.8 Hz, 3H).

Step-3:

A solution of ethyl 3-(4-bromophenyl)-2,2-difluoro-3-methylsulfanylcarbothioyloxy-propanoate (2 g, 5.01 mmol), phenylphosphonoylbenzene (2.53 g, 12.52 mmol) and 2-tert-butylperoxy-2-methyl-propane (732.47 mg, 5.01 mmol) in 1,4 dioxane (20 mL) was stirred for 16 hours at 100° C., while the progress of the reaction was monitored by TLC. After the reaction was complete, cold water was added to the reaction mixture, and it was extracted with ethyl acetate. The combined organic layers were washed with water, and brine, and dried over anhydrous $Na_2SO_4$. It was then filtered and concentrated under reduced pressure to give the crude compound, which was purified by column chromatography (silica gel 100-200 mesh) to afford ethyl 3-(4-bromophenyl)-2,2-difluoro-propanoate (1.2 g, 4.09 mmol, 81.73% yield). LC-MS ($ES^+$): m/z 265.31 $[M-C_2H_5+H]^+$.

Step-4:

A solution of ethyl 3-(4-bromophenyl)-2,2-difluoro-propanoate (1.5 g, 5.12 mmol), sodium borohydride (1.94 g, 51.18 mmol) in methanol (15 mL) was stirred for 16 hours at 45° C. TLC was used to monitor the progress of the reaction. After the reaction was complete, it was concentrated in vacuo, diluted with cold water, and extracted with ethyl acetate. The combined organic layers were washed with water, brine, dried over anhydrous sodium sulfate, filtered, and concentrated under reduced pressure to yield the crude compound, which was purified by column chromatography (silica gel 100-200 mesh) to afford 3-(4-bromophenyl)-2,2-difluoro-propan-1-ol (1.050 g, 4.18 mmol, 81.72% yield). LC-MS ($ES^+$): m/z 251.00 $[M+H]^+$.

Step-5:

To a stirred solution of 3-(4-bromophenyl)-2,2-difluoro-propan-1-ol (0.37 g, 1.47 mmol) in DCM (8 mL) were added pyridine (582.85 mg, 7.37 mmol, 595.96 L) and trifluoromethanesulfonic anhydride (1.04 g, 3.68 mmol, 618.73 μL) at 0° C. The resulting reaction mixture was warmed to room temperature and stirred for 3 hours. The reaction mixture was then quenched by saturated sodium bicarbonate solution and partitioned between water and DCM. The organic layer was separated, washed with brine, dried over anhydrous sodium sulfate, and concentrated in vacuo to yield the crude product, which was purified by column chromatography (silica gel 60-120 mesh, 0-10% ethyl acetate in pet ether) to afford [3-(4-bromophenyl)-2,2-difluoro-propyl] trifluoromethanesulfonate (0.32 g, 810.17 μmol, 54.98% yield) as a colorless oil. $^1H$ NMR (400 MHz, DMSO-$d_6$) δ 7.51-7.49 (m, 2H), 7.15 (d, J=8.4 Hz, 2H), 4.41 (t, J=11.2 Hz, 2H), 3.25 (t, J=16.0 Hz, 2H).

Step-6:

A solution of [3-(4-bromophenyl)-2,2-difluoro-propyl] trifluoromethanesulfonate (0.450 g, 1.17 mmol), methylamine (291.82 mg, 9.40 mmol, 324.61 μL) in THF (10 mL) was stirred for 5 hours at 45° C. The progress of the reaction was monitored by LCMS. The reaction mixture was then diluted with cold water and extracted with ethyl acetate. The combined organic layers were washed with water, brine, dried over anhydrous sodium sulfate, filtered, and concentrated under reduced pressure to give the crude product 3-(4-bromophenyl)-2,2-difluoro-N-methyl-propan-1-amine (0.300 g, 1.02 mmol, 87.04% yield) as a yellow oil. LC-MS ($ES^+$): m/z 264.08 $[M+H]^+$.

Step-7:

A solution of 3-(4-bromophenyl)-2,2-difluoro-N-methyl-propan-1-amine (0.200 g, 757.26 μmol), Triethylamine (153.25 mg, 1.51 mmol, 211.09 μL) and tert-butoxycarbonyl tert-butyl carbonate (198.32 mg, 908.71 μmol, 208.54 μL) in DCM (4 mL) was stirred for 12 hours at 0-25° C. The progress of the reaction was monitored by TLC and LCMS. The reaction mixture was then diluted with cold water and extracted with DCM. The combined organic layer was washed with water, brine, dried over anhydrous sodium sulfate, filtered, and concentrated under reduced pressure to give the crude compound, which was purified by column chromatography (silica gel 60-120 mesh) to afford tert-butyl N-[3-(4-bromophenyl)-2,2-difluoro-propyl]-N-methyl-carbamate (0.270 g, 726.47 μmol, 95.93% yield). LC-MS ($ES^+$): m/z 264.12 $[M-100+H]^+$.

Step-8:

A solution of tert-butyl N-[3-(4-bromophenyl)-2,2-difluoro-propyl]-N-methyl-carbamate (0.250 g, 686.39 μmol), tert-butyl N-[3-(4-bromophenyl)-2,2-difluoro-propyl]-N-methyl-carbamate (0.250 g, 686.39 μmol), sodium; 2-methylpropan-2-olate (197.89 mg, 2.06 mmol), Xantphos (79.43 mg, 137.28 μmol) and (1E,4E)-1,5-diphenylpenta-1,4-dien-3-one; palladium (62.85 mg, 68.64 μmol) in toluene (5 mL) was purged with argon gas for 10 minutes. The reaction mixture was then stirred for 16 hours at 100° C., while the progress of the reaction was monitored by TLC and LCMS. Upon completion of the reaction, the mixture was diluted with cold water and extracted with ethyl acetate. The combined organic layers were washed with water, brine, dried over anhydrous sodium sulfate, filtered, and concentrated under reduced pressure to yield the crude compound tert-butyl N-[3-[4-[(2,6-dibenzyloxy-3-pyridyl)amino]phenyl]-2,2-difluoro-propyl]-N-methyl-carbamate (0.325 g, 424.39 μmol, 61.83% yield). LC-MS ($ES^-$): m/z 588.45 $[M-H]^-$.

Step-9:

To a stirred solution of tert-butyl N-[3-[4-[(2,6-dibenzyloxy-3-pyridyl)amino]phenyl]-2,2-difluoro-propyl]-N-methyl-carbamate (0.100 g, 169.59 μmol) in ethyl acetate (5 mL) was added 10 wt. % palladium on carbon (type 487, 50 mg). The reaction mixture was then stirred under a hydrogen atmosphere (1 atm. pressure) at room temperature for 16 hours. The progress of the reaction was monitored by TLC and LCMS. After the reaction was complete, the reaction mixture was filtered through a pad of celite, which was washed with methanol. The organics were concentrated under reduced pressure to give the crude product tert-butyl N-[3-[4-[(2,6-dioxo-3-piperidyl)amino]phenyl]-2,2-difluoro-propyl]-N-methyl-carbamate (0.050 g, 76.56 μmol, 45.15% yield). LC-MS ($ES^-$): m/z 410.40 $[M-H]^-$.

Step-10:

To a stirred solution of tert-butyl N-[3-[4-[(2,6-dioxo-3-piperidyl)amino]phenyl]-2,2-difluoro-propyl]-N-methyl-carbamate (0.200 g, 486.10 μmol) was in 4 M hydrogen chloride solution in dioxane (4 mL) stirred for 2 hours at 0-25° C. The progress of the reaction was monitored by TLC and LC-MS. The reaction mass was concentrated under reduced pressure to give the crude compound, which was washed with diethyl ether to afford 3-[4-[2,2-difluoro-3-(methylamino)propyl]anilino]piperidine-2,6-dione (0.150 g, 404.72 μmol, 83.26% yield). LC-MS ($ES^+$): m/z 312.42 $[M+H]^+$.

Step-11:

To a stirred solution of 3-[4-[2,2-difluoro-3-(methylamino)propyl]anilino]piperidine-2,6-dione HCl salt (0.06 g, 172.52 μmol) in DCE (6 mL) and methanol (2 mL) were added sodium acetate (113.22 mg, 1.38 mmol), acetic acid (82.88 mg, 1.38 mmol, 78.93 μL) and molecular sieve (80 mg). The reaction mixture was stirred for 10 minutes before 5-tert-butyl-N-[[4-[6-(4-formylphenyl)pyrrolo[2,1-f][1,2,4]triazin-4-yl]-2-methyl-phenyl]methyl]-1,2,4-oxadiazole-3-carboxamide (93.85 mg, 189.77 μmol) was added and the reaction heated at 60° C. for 4 hours. The reaction mixture was then cooled to room temperature, followed by the addition of Si—CBH (50.00 mg, 862.60 μmol). The reaction mixture was stirred at room temperature for an additional 12 hours, while the reaction progress was monitored by TLC and LCMS. Upon completion of the reaction, the reaction mixture was filtered through a pad of celite and washed with methanol and DCE. The filtrate was concentrated in vacuo to give the crude product, which was purified by prep-HPLC to afford 5-tert-butyl-N-[[4-[6-[4-[[[3-[4-[(2,6-dioxo-3-piperidyl)amino]phenyl]-2,2-difluoro-propyl]-methyl-amino] methyl]phenyl]pyrrolo[2,1-f][1,2,4]triazin-4-yl]-2-methyl-phenyl]methyl]-1,2,4-oxadiazole-3-carboxamide TFA salt (27.9 mg, 29.72 μmol, 17.23% yield) as a yellow solid. $^1$H NMR (400 MHz, DMSO-$d_6$) δ 10.77 (s, 1H), 9.54 (t, J=5.9 Hz, 1H), 8.75 (bs, 1H), 8.62 (s, 1H), 8.07-7.99 (m, 4H), 7.66 (bs, 1H), 7.48 (d, J=8.0 Hz, 2H), 7.45 (bs, 1H), 6.97 (d, J=8.4 Hz, 2H), 6.62 (d, J=8.4 Hz, 2H), 4.57 (d, J=5.9 Hz, 2H), 4.29-4.25 (m, 1H), 3.99-3.82 (m, 2H), 3.42-3.10 (m, 5H), 2.75-2.68 (m, 3H), 2.61-2.55 (m, 1H), 2.46 (s, 3H), 2.09-2.03 (m, 1H), 1.88-1.75 (m, 1H), 1.44 (s, 9H). LC-MS ($ES^+$): m/z 790.16 $[M+H]^+$.

Example 151. Synthesis of 5-tert-butyl-N-[[4-[6-[4-[4-[4-(2,6-dioxo-3-piperidyl)phenyl]phenyl]butyl] pyrrolo[2,1-f][1,2,4]triazin-4-yl]-2-methyl-phenyl] methyl]-1,2,4-oxadiazole-3-carboxamide

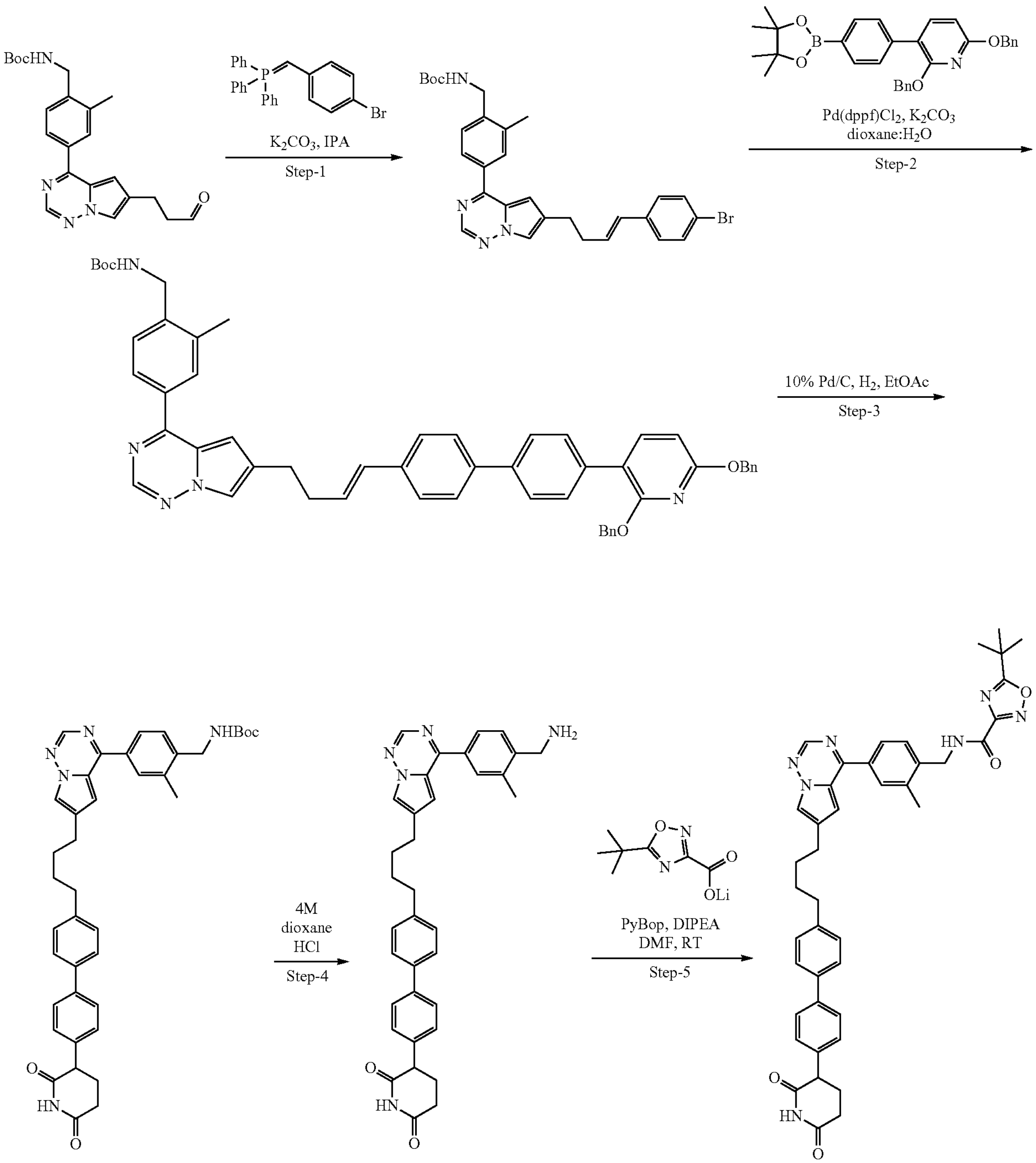

Step-1:

To a stirred solution of tert-butyl N-[[2-methyl-4-[6-(3-oxopropyl)pyrrolo[2,1-f][1,2,4]triazin-4-yl]phenyl]methyl] carbamate (0.60 g, 1.52 mmol) in propan-2-ol (6 mL) was added potassium carbonate (420.43 mg, 3.04 mmol) followed by (4-bromobenzylidene)triphenyl-V-phosphane (656.03 mg, 1.52 mmol) and the resulting reaction mixture was heated at 80° C. for 4 hours. Upon completion, the reaction was cooled, diluted with water, and extracted with ethyl acetate. The combined organic layer was dried over sodium sulfate and concentrated under a high vacuum to yield the crude product, which was purified by column chromatography (silica gel 100-200 mesh) to afford tert-butyl N-[[4-[6-[(E)-4-(4-bromophenyl)but-3-enyl]pyrrolo[2,1-f][1,2,4]triazin-4-yl]-2-methyl-phenyl]methyl]carbamate (0.50 g, 849.34 μmol, 55.84% yield) as a yellow oil. LC-MS ($ES^+$): m/z 547.18 $[M+H]^+$.

Step-2:

To a stirred solution of tert-butyl N-[[4-[6-[(E)-4-(4-bromophenyl)but-3-enyl]pyrrolo[2,1-f][1,2,4]triazin-4-yl]-2-methyl-phenyl]methyl]carbamate (0.40 g, 730.61 mol) in dioxane (5 mL) and water (1 mL) were added 2,6-dibenzyloxy-3-[4-(4,4,5,5-tetramethyl-1,3,2-dioxaborolan-2-yl) phenyl]pyridine (432.58 mg, 876.74 μmol) followed by sodium carbonate (154.87 mg, 1.46 mmol). The reaction mixture was degassed with argon for 10 minutes before $Pd(dppf)Cl_2{\cdot}CH_2Cl_2$ (53.46 mg, 73.06 μmol) was added and the reaction heated at 90° C. for 16 hours. After completion of the reaction, the reaction mixture was cooled, filtered through celite pad, and washed with ethyl acetate. The organic layer was concentrated under high vacuum to yield the crude product, which was purified by column chromatography (silica gel) to afford tert-butyl N-[[4-[6-[(E)-4-[4-[4-(2,6-dibenzyloxy-3-pyridyl)phenyl]phenyl]but-3-enyl] pyrrolo[2,1-f][1,2,4]triazin-4-yl]-2-methyl-phenyl]methyl] carbamate (0.30 g, 323.74 μmol, 44.31% yield) as a yellow solid. LC-MS ($ES^+$): m/z 834.65 $[M+H]^+$.

Step-3:

To a stirred solution of tert-butyl N-[[4-[6-[(E)-4-[4-[4-(2,6-dibenzyloxy-3-pyridyl)phenyl]phenyl]but-3-enyl]pyrrolo[2,1-f][1,2,4]triazin-4-yl]-2-methyl-phenyl]methyl]carbamate (0.30 g, 359.71 μmol) in ethyl acetate (5 mL) was added 10 wt. % palladium on carbon, type 487, dry (306.24 mg, 2.88 mmol). The reaction mixture was stirred at room temperature under a hydrogen atmosphere. Upon completion of the reaction, the reaction mixture was filtered through celite pad, and washed with ethyl acetate. The organic layer was concentrated under high vacuum to give the crude product, which was purified by column chromatography (silica gel) to afford tert-butyl N-[[4-[6-[4-[4-[4-(2,6-dioxo-3-piperidyl)phenyl]phenyl]butyl]pyrrolo[2,1-f][1,2,4]triazin-4-yl]-2-methyl-phenyl]methyl]carbamate (0.15 g, 212.07 μmol, 58.96% yield) as a yellow solid. LC-MS ($ES^-$): m/z 656.56 $[M-H]^-$.

Step-4

To a stirred solution of tert-butyl N-[[4-[6-[4-[4-[4-(2,6-dioxo-3-piperidyl)phenyl]phenyl]butyl]pyrrolo[2,1-f][1,2,4]triazin-4-yl]-2-methyl-phenyl]methyl]carbamate (0.05 g, 76.01 μmol) in DCM (1 mL) was added 4 M hydrogen chloride solution in 1,4-dioxane (0.5 mL) at 0° C. The reaction mixture was stirred at room temperature for 2 hours. After completion of the reaction, the reaction mixture was concentrated under high vacuum to give the crude product, which was triturated with diethyl ether to afford 3-[4-[4-[4-[4-[4-(aminomethyl)-3-methyl-phenyl]pyrrolo[2,1-f][1,2,4] triazin-6-yl]butyl]phenyl]phenyl]piperidine-2,6-dione HCl salt (0.05 g, 75.74 μmol, 99.64% yield) as a yellow solid. LC-MS ($ES^-$): m/z 556.53 $[M-H]^-$.

Step-5:

To a stirred solution of 3-[4-[4-[4-[4-[4-(aminomethyl)-3-methyl-phenyl]pyrrolo[2,1-f][1,2,4]triazin-6-yl]butyl] phenyl]phenyl]piperidine-2,6-dione HCl salt (0.10 g, 168.31 mol) in DMF (2 mL) were added (5-tert-butyl-1,2,4-oxadiazole-3-carbonyl)oxylithium (61.61 mg, 349.89 μmol) and N-ethyl-N-isopropyl-propan-2-amine (217.53 mg, 1.68 mmol, 293.16 μL) at 30° C. Benzotriazol-1-yloxy(tripyrrolidin-1-yl)phosphonium; hexafluorophosphate (175.17 mg, 336.62 μmol) was then added and the reaction mixture stirred at room temperature for 1 hour.

After completion of the reaction, the reaction mixture was diluted with ice water, and the resulting solid was filtered using a sintered funnel, washed with water and dried under high vacuum to yield the crude product, which was purified by prep-HPLC to afford 5-tert-butyl-N-[[4-[6-[4-[4-[4-(2,6-dioxo-3-piperidyl)phenyl]phenyl]butyl]pyrrolo[2,1-f][1,2,4]triazin-4-yl]-2-methyl-phenyl]methyl]-1,2,4-oxadiazole-3-carboxamide (24 mg, 33.22 μmol, 19.73% yield) as a yellow solid. $^1H$ NMR (400 MHz, DMSO-$d_6$) δ 10.85 (s, 1H), 9.50 (t, J=5.9 Hz, 1H), 8.53 (s, 1H), 8.05 (s, 1H), 7.95-7.93 (m, 2H), 7.60-7.54 (m, 4H), 7.44 (d, J=8.0 Hz, 1H), 7.30-7.27 (m, 4H), 7.08 (s, 1H), 4.54 (d, J=5.9 Hz, 2H), 3.92-3.88 (m, 1H), 2.78-2.61 (m, 6H), 2.46 (s, 3H), 2.29-2.18 (m, 1H), 2.09-2.05 (m, 1H), 1.72-1.66 (m, 4H), 1.43 (s, 9H). LC-MS ($ES^+$): m/z 710.22 $[M+H]^+$.

Example 152. Synthesis of N-(3-(6-(4-((4-(4-((2,6-dioxopiperidin-3-yl)amino)phenyl)piperidin-1-yl) methyl)phenyl)pyrrolo[2,1-f][1,2,4]triazin-4-yl)-5-fluoro-2-methylphenyl)-4,5,6,7-tetrahydrobenzo[b] thiophene-2-carboxamide

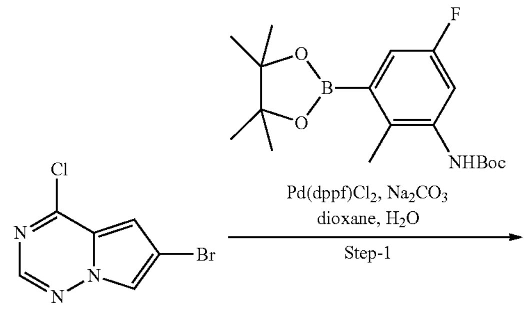

-continued
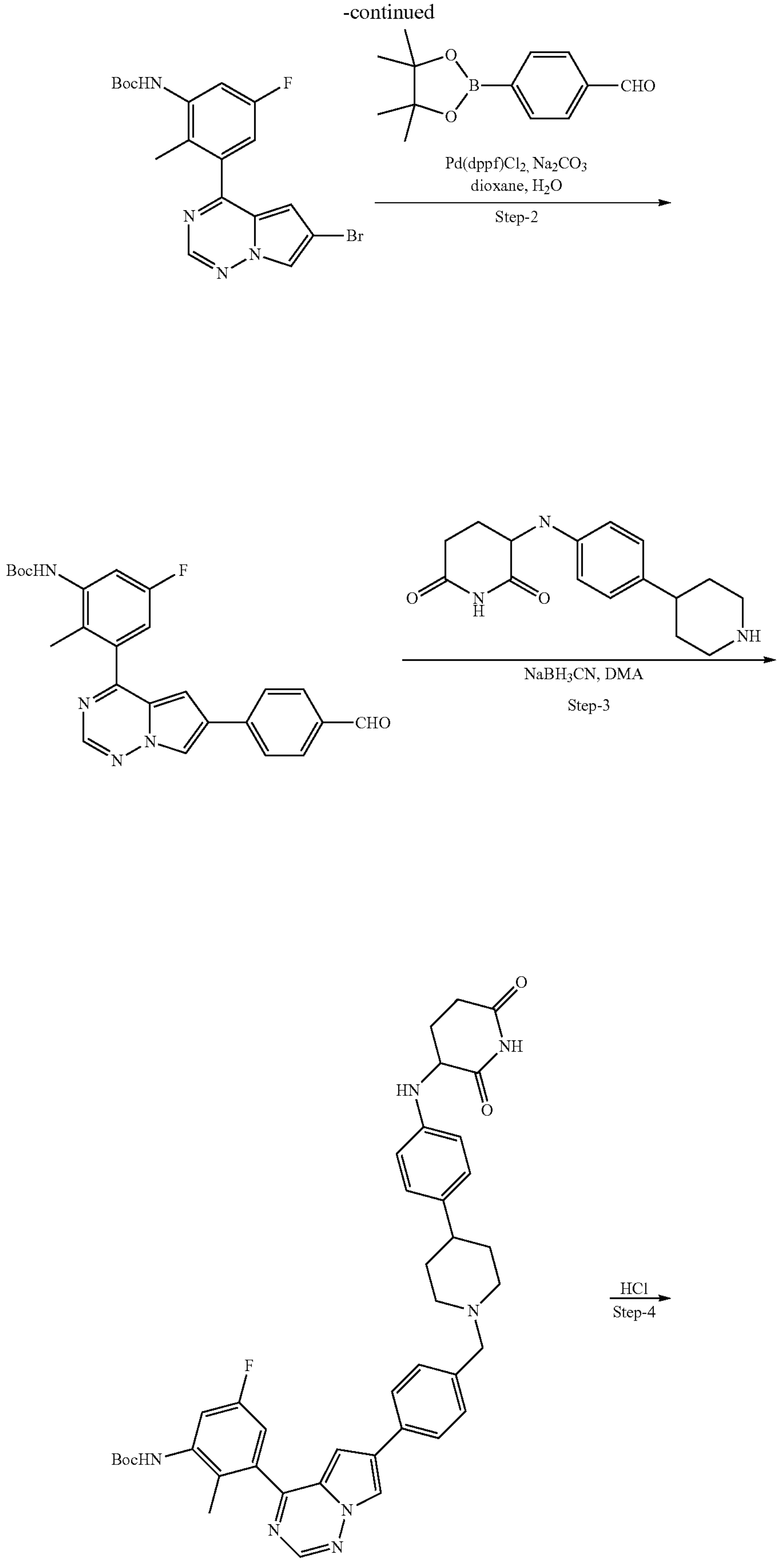

-continued

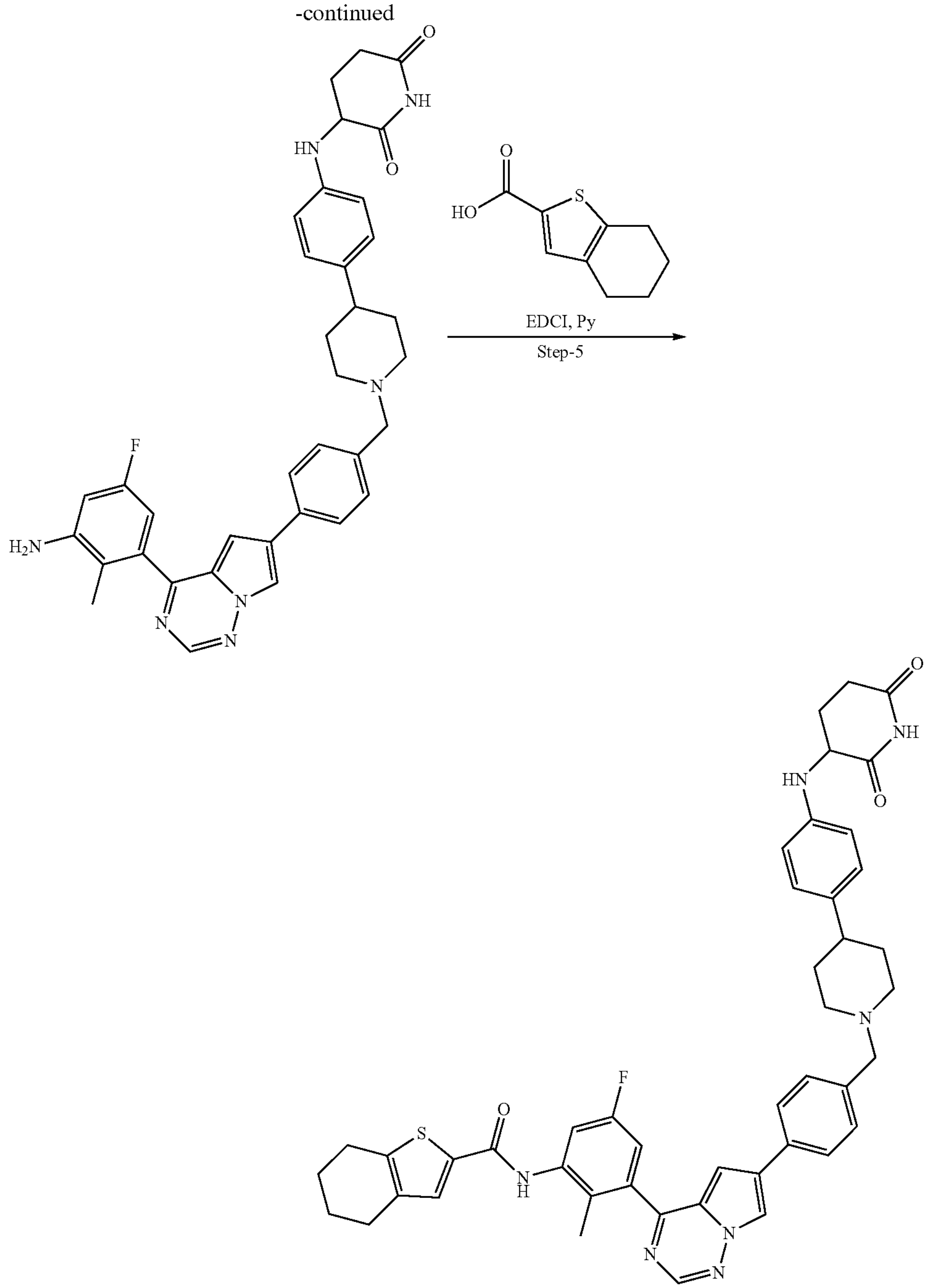

Step-1:

A mixture of 6-bromo-4-chloropyrrolo[2,1-f][1,2,4]triazine (600 mg, 2.58 mmol), tert-butyl (5-fluoro-2-methyl-3-(4,4,5,5-tetramethyl-1,3,2-dioxaborolan-2-yl)phenyl)carbamate (WO2016079669) (906.51 mg, 2.58 mmol), $Pd(dppf)Cl_2$ (210.78 mg, 258.10 μmol) and potassium carbonate (1.07 g, 7.74 mmol) in 1,4-dioxane (16 mL) and water (4 mL) was degassed and purged with nitrogen gas three times, and then the mixture was stirred at 60° C. for 1 hour under a nitrogen atmosphere. The reaction mixture was poured into water (20 mL) and extracted with ethyl acetate (10 mL×3). The combined organic layer was dried over anhydrous sodium sulfate, filtered, and concentrated under reduced pressure to give a residue, which was purified by column chromatography (silica gel, pet ether/ethyl acetate=100/1 to 5/1) to give tert-butyl (3-(6-bromopyrrolo[2,1-f][1,2,4]triazin-4-yl)-5-fluoro-2-methylphenyl)carbamate (670 mg, 1.41 mmol, 54.47% yield) as a yellow solid. LC-MS ($ES^+$): m/z 421.0 $[M+H]^+$.

Step-2:

A mixture of tert-butyl (3-(6-bromopyrrolo[2,1-f][1,2,4]triazin-4-yl)-5-fluoro-2-methylphenyl)carbamate (670 mg, 1.59 mmol), (4-formylphenyl)boronic acid (310.01 mg, 2.07 mmol), cyclopentyl(diphenyl)phosphane; dichloromethane; dichloropalladium; iron (129.88 mg, 159.05 μmol) and potassium carbonate (659.43 mg, 4.77 mmol) in dioxane (10 mL) was degassed and purged with nitrogen gas three times, and then the mixture was stirred at 100° C. for 1 hour under a nitrogen atmosphere. The reaction mixture was poured into water (20 mL) and extracted with ethyl acetate (20 mL×3). The combined organic layer was dried over anhydrous sodium sulfate, filtered, and concentrated under reduced pressure to give a residue. The residue was purified by column chromatography (silica gel, pet ether/ethyl acetate=100/1 to 3/1) to give tert-butyl (5-fluoro-3-(6-(4-formylphenyl)pyrrolo[2,1-f][1,2,4]triazin-4-yl)-2-methylphenyl)carbamate (603 mg, 1.26 mmol, 79.48% yield) as a yellow solid. LC-MS ($ES^+$): m/z 447.1 $[M+H]^+$.

Step-3:

To a solution of tert-butyl (5-fluoro-3-(6-(4-formylphenyl)pyrrolo[2,1-f][1,2,4]triazin-4-yl)-2-methylphenyl)carbamate (315 mg, 705.53 μmol) and 3-((4-(piperidin-4-yl)phenyl)amino)piperidine-2,6-dione (608.22 mg, 2.12 mmol) in DMA (3 mL) was added DIPEA (455.92 mg, 3.53 mmol, 614.45 μL) and sodium cyanoborohydride (443.37 mg, 7.06 mmol). The mixture was stirred at 25° C. for 12 hours. The reaction mixture was poured into water (20 mL) and extracted with ethyl acetate (20 mL×3). The combined organic layer was dried over anhydrous sodium sulfate, filtered, and concentrated under reduced pressure to give a residue, which was purified by column chromatography (silica gel, pet ether/ethyl acetate=100/1 to 1/2) to give tert-butyl (3-(6-(4-((4-(4-((2,6-dioxopiperidin-3-yl)amino)phenyl)piperidin-1-yl)methyl)phenyl)pyrrolo[2,1-f][1,2,4]triazin-4-yl)-5-fluoro-2-methylphenyl)carbamate (456 mg, 517.09 μmol, 73.29% yield) as a yellow solid. LC-MS ($ES^+$): m/z 718.2 $[M+H]^+$.

benzyl)piperidin-4-yl)phenyl)amino)piperidine-2,6-dione HCl salt (310 mg, 462.03 μmol, 53.93% yield) as a yellow solid. LC-MS ($ES^+$): m/z 618.2 $[M+H]^+$.

Step-5:

To a solution of 3-((4-(1-(4-(4-(3-amino-5-fluoro-2-methylphenyl)pyrrolo[2,1-f][1,2,4]triazin-6-yl)benzyl)piperidin-4-yl)phenyl)amino)piperidine-2,6-dione (60 mg, 97.13 μmol) and 4,5,6,7-tetrahydrobenzo[b]thiophene-2-carboxylic acid (17.70 mg, 97.13 μmol) in pyridine (1 mL) was added 3-(ethyliminomethyleneamino)-N,N-dimethyl-propan-1-amine; hydrochloride (37.24 mg, 194.26 μmol). The mixture was stirred at 25° C. for 4 hours. The reaction mixture was diluted with water (1 mL) and extracted with ethyl acetate (1 mL×3). The combined organic layers were concentrated under reduced pressure. A solution of the crude product in DMF (2 mL) was purified by prep-HPLC. (column: Phenomenex Synergi C18 150×25 mm×10 um, mobile phase: [water (0.225% formic acid)-ACN]; B %: 23%-53%, 10 min)] to give N-(3-(6-(4-((4-(4-((2,6-dioxopiperidin-3-yl)amino)phenyl)piperidin-1-yl)methyl)phenyl)pyrrolo[2,1-f][1,2,4]triazin-4-yl)-5-fluoro-2-methylphenyl)-4,5,6,7-tetrahydrobenzo[b]thiophene-2-carboxamide trifluoroacetic acid salt (22.61 mg, 26.30 μmol, 27.07% yield) as a green solid. $^1H$ NMR (400 MHz, DMSO-$d_6$) δ ppm 1.56-1.71 (m, 4H) 1.71-1.87 (m, 6H) 2.02 (br t, J=10.4 Hz, 2H) 2.14 (s, 3H) 2.58-2.65 (m, 5H) 2.74-2.81 (m, 3H) 2.90 (br d, J=11.2 Hz, 3H) 4.21-4.33 (m, 1H) 5.63 (br d, J=7.2 Hz, 1H) 6.60 (d, J=8.8 Hz, 2H) 6.95 (d, J=8.4 Hz, 2H) 7.09 (d, J=1.6 Hz, 1H) 7.35 (br d, J=8.0 Hz, 3H) 7.47-7.55 (m, 1H) 7.71 (s, 1H) 7.82 (s, 2H) 8.34 (s, 1H) 8.66 (s, 1H) 8.76 (d, J=1.6 Hz, 1H) 9.93 (s, 1H) 10.76 (s, 1H). LC-MS ($ES^+$): m/z 782.4 $[M+H]^+$.

Example 153

Example 153 was prepared following the synthesis of Example 152.

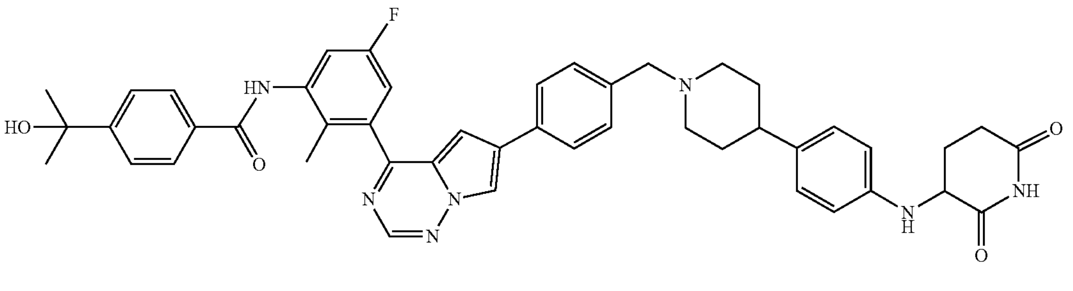 [SMILES: Cc1c(NC(=O)c2ccc(C(C)(C)O)cc2)cc(F)cc1-c1ncnn2cc(-c3ccc(CN4CCC(c5ccc(NC6CCC(=O)NC6=O)cc5)CC4)cc3)cc12]

Step-4:

A solution of tert-butyl (3-(6-(4-((4-(4-((2,6-dioxopiperidin-3-yl)amino)phenyl)piperidin-1-yl)methyl)phenyl)pyrrolo[2,1-f][1,2,4]triazin-4-yl)-5-fluoro-2-methylphenyl)carbamate (615 mg, 856.75 μmol) in 1,4-dioxane (6 mL) was added 4 M hydrogen chloride solution in dioxane (16 equiv.). The mixture was stirred at 25° C. for 0.5 hour. The reaction mixture was concentrated under reduced pressure to give 610 mg of crude product, 500 mg of which was purified by reverse-HPLC (column: 3_Phenomenex Luna C18 75*30 mm*3 um, mobile phase: [water (0.05% HCl v/v)-ACN]; B %: 21%-41%, 6.5 min) to give 3-((4-(1-(4-(4-(3-amino-5-fluoro-2-methylphenyl)pyrrolo[2,1-f][1,2,4]triazin-6-yl)

N-[3-[6-[4-[[4-[4-[(2,6-dioxo-3-piperidyl)amino]phenyl]-1-piperidyl]methyl]phenyl]pyrrolo[2,1-f][1,2,4]triazin-4-yl]-5-fluoro-2-methyl-phenyl]-4-(1-hydroxy-1-methyl-ethyl)benzamide.

$^1H$ NMR (400 MHz, DMSO-$d_6$) δ=10.76 (s, 1H), 10.03 (s, 1H), 8.76 (s, 1H), 8.67 (s, 1H), 8.29 (s, 1H), 7.95 (d, J=8.4 Hz, 2H), 7.83 (d, J=8.0 Hz, 2H), 7.62 (d, J=8.0 Hz, 2H), 7.57 (dd, J=2.4, 9.6 Hz, 1H), 7.44-7.30 (m, 3H), 7.10 (s, 1H), 6.95 (d, J=8.4 Hz, 2H), 6.60 (d, J=8.4 Hz, 2H), 5.63 (d, J=7.6 Hz, 1H), 4.31-4.19 (m, 1H), 2.90 (m, 2H), 2.77-2.57 (m, 2H), 2.33 (br s, 2H), 2.17 (s, 3H), 2.02 (br s, 4H), 1.91-1.52 (m, 6H), 1.46 (s, 6H).

LC-MS ($ES^+$): m/z 780.32 $[M+H]^+$.

Example 154. Synthesis of 5-tert-butyl-N-[[4-[6-[4-[[4-[4-[(2,6-dioxo-3-piperidyl)amino]phenyl]-1-piperidyl]methyl]phenyl]pyrrolo[1,2-b]pyridazin-4-yl]-2-methyl-phenyl]methyl]-1,2,4-oxadiazole-3-carboxamide
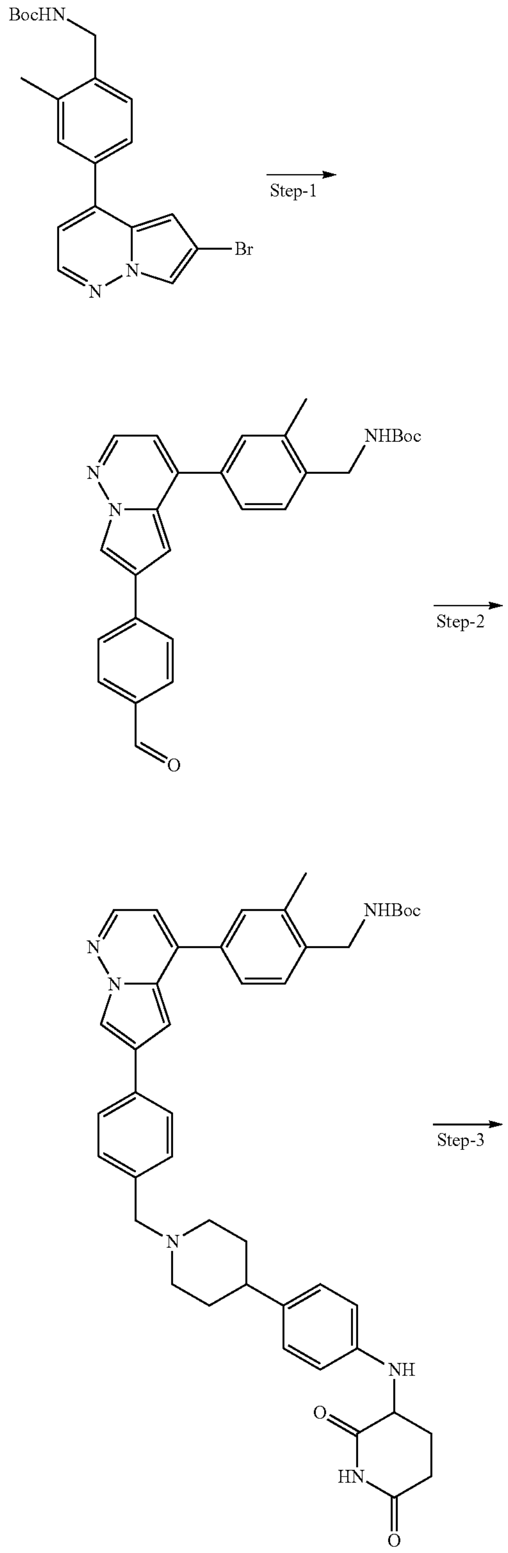
-continued
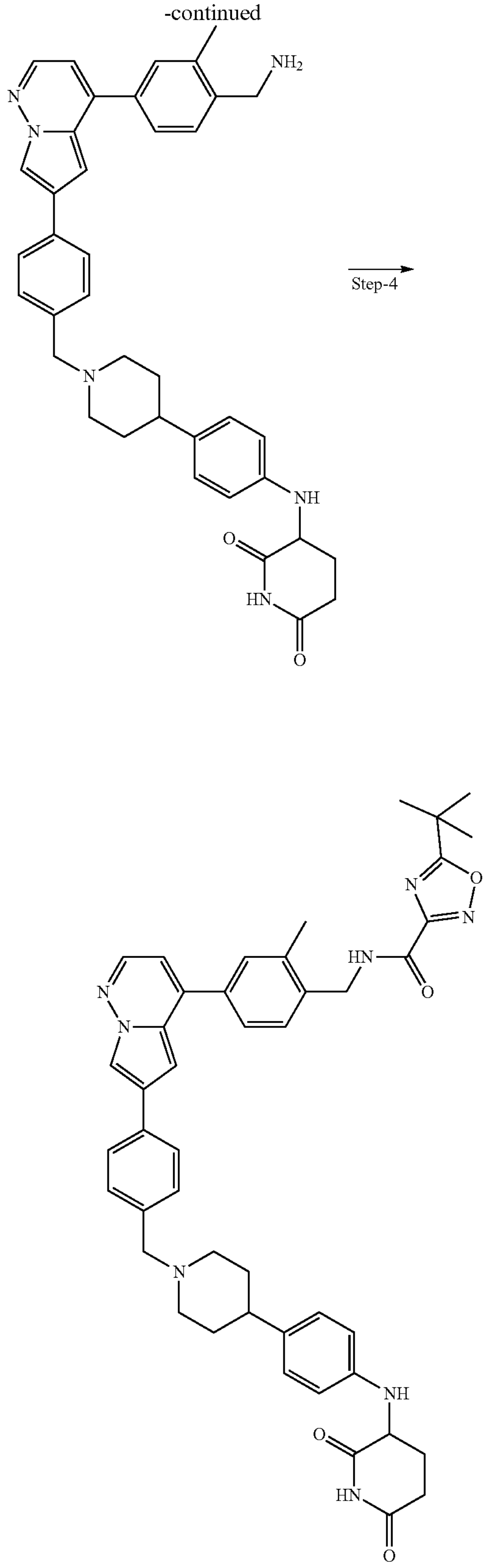
Reaction steps and conditions are identical (using different building blocks) to the representative compound of Example 61 shown below.

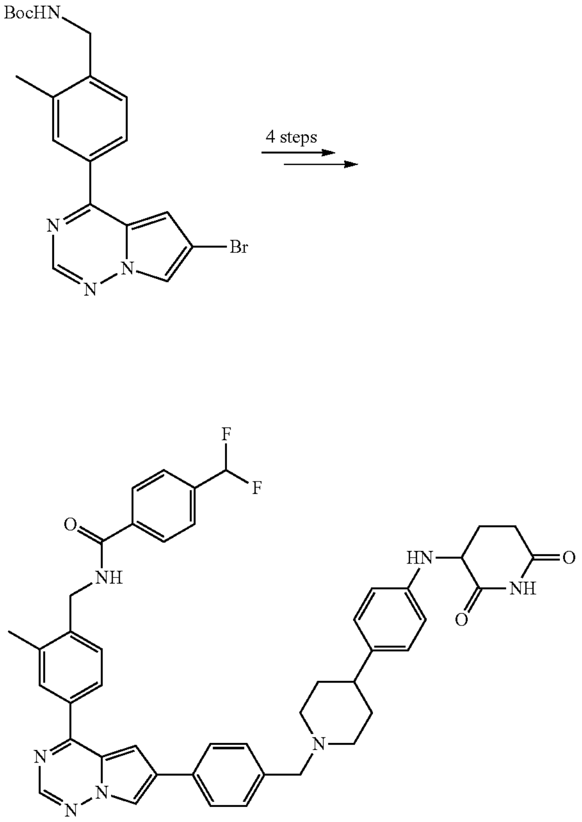

Step-1:

tert-butyl N-[[4-[6-(4-formylphenyl)pyrrolo[1,2-b]pyridazin-4-yl]-2-methyl-phenyl]methyl]carbamate (0.15 g, 224.06 μmol, 38.87% yield). LC-MS ($ES^+$): m/z 442.3 $[M+H]^+$.

Step-2:

tert-butyl N-[[4-[6-[4-[[4-[4-[(2,6-dioxo-3-piperidyl)amino]phenyl]-1-piperidyl]methyl]phenyl]pyrrolo[1,2-b]pyridazin-4-yl]-2-methyl-phenyl]methyl]carbamate (0.12 g, 162.14 μmol, 59.66% yield). LC-MS ($ES^+$): m/z 713.6 $[M+H]^+$.

Step-3:

3-[4-[1-[[4-[4-[4-(aminomethyl)-3-methyl-phenyl]pyrrolo[1,2-b]pyridazin-6-yl]phenyl]methyl]-4-piperidyl]anilino]piperidine-2,6-dione (0.1 g, 139.54 μmol, 82.89% yield). LC-MS ($ES^-$): m/z 611.3 $[M-H]^-$.

Step-4:

5-tert-butyl-N-[[4-[6-[4-[[4-[4-[(2,6-dioxo-3-piperidyl)amino]phenyl]-1-piperidyl]methyl]phenyl]pyrrolo[1,2-b]pyridazin-4-yl]-2-methyl-phenyl]methyl]-1,2,4-oxadiazole-3-carboxamide TFA salt (37.6 mg, 40.91 μmol, 26.56% yield). $^1H$ NMR (400 MHz, DMSO-$d_6$) δ 10.77 (s, 1H), 9.52 (t, J=6.0 Hz, 1H), 9.33 (s, 1H), 8.55 (d, J=1.2 Hz, 1H), 8.25 (d, J=4.8 Hz, 1H), 7.97 (d, J=8.0 Hz, 2H), 7.68-7.53 (m, 4H), 7.44 (d, J=8.0 Hz, 1H), 7.12 (d, J=1.2 Hz, 1H), 6.95-6.92 (m, 2H), 6.78 (d, J=4.8 Hz, 1H), 6.63 (d, J=8.8 Hz, 2H), 4.54 (d, J=6.0 Hz, 2H), 4.34-4.24 (m, 3H), 3.45-3.30 (m, 2H), 3.07-3.04 (m, 2H), 2.72-2.54 (m, 3H), 2.49-2.45 (m, 3H), 2.09-1.76 (m, 6H), 1.44 (s, 9H). LC-MS ($ES^+$): m/z 765.2 $[M+H]^+$.

Example 155. Synthesis of 5-tert-butyl-N-[[4-[6-[2-[4-[4-[(2,6-dioxo-3-piperidyl)amino]phenyl]-1-piperidyl]ethyl]pyrrolo[1,2-b]pyridazin-4-yl]-2-methyl-phenyl]methyl]-1,2,4-oxadiazole-3-carboxamide

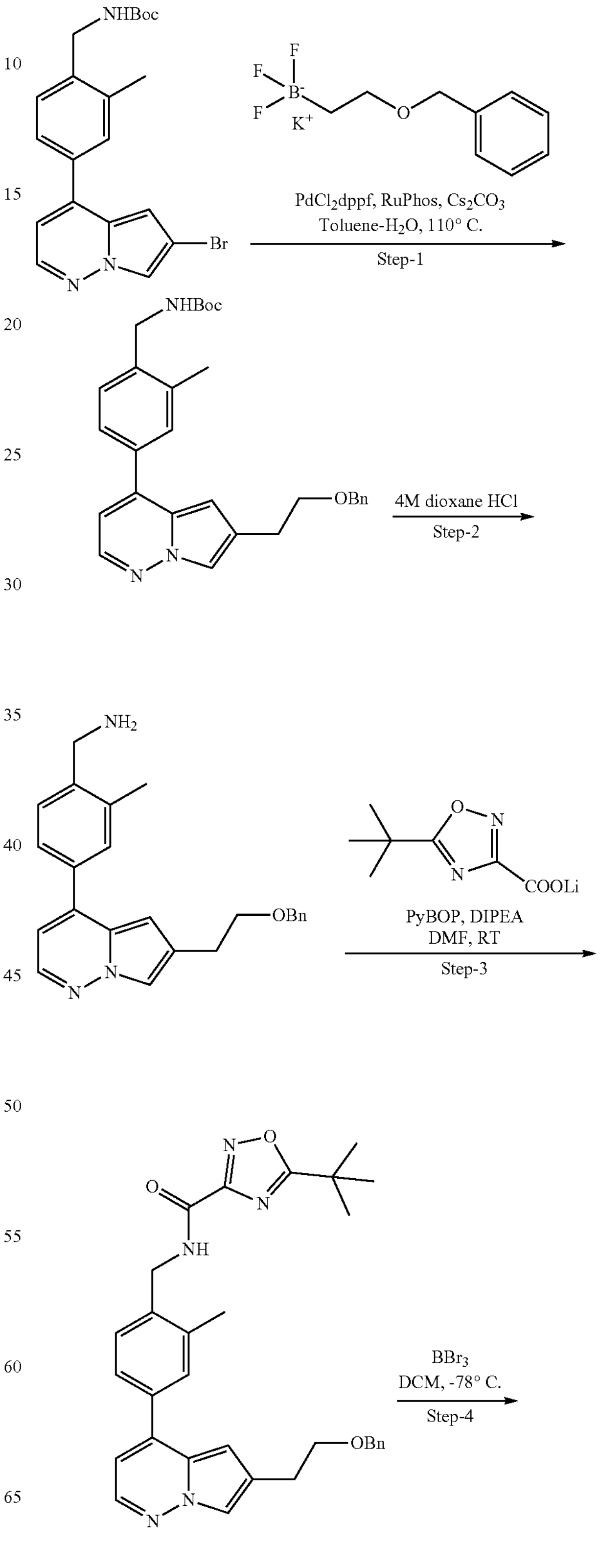

-continued

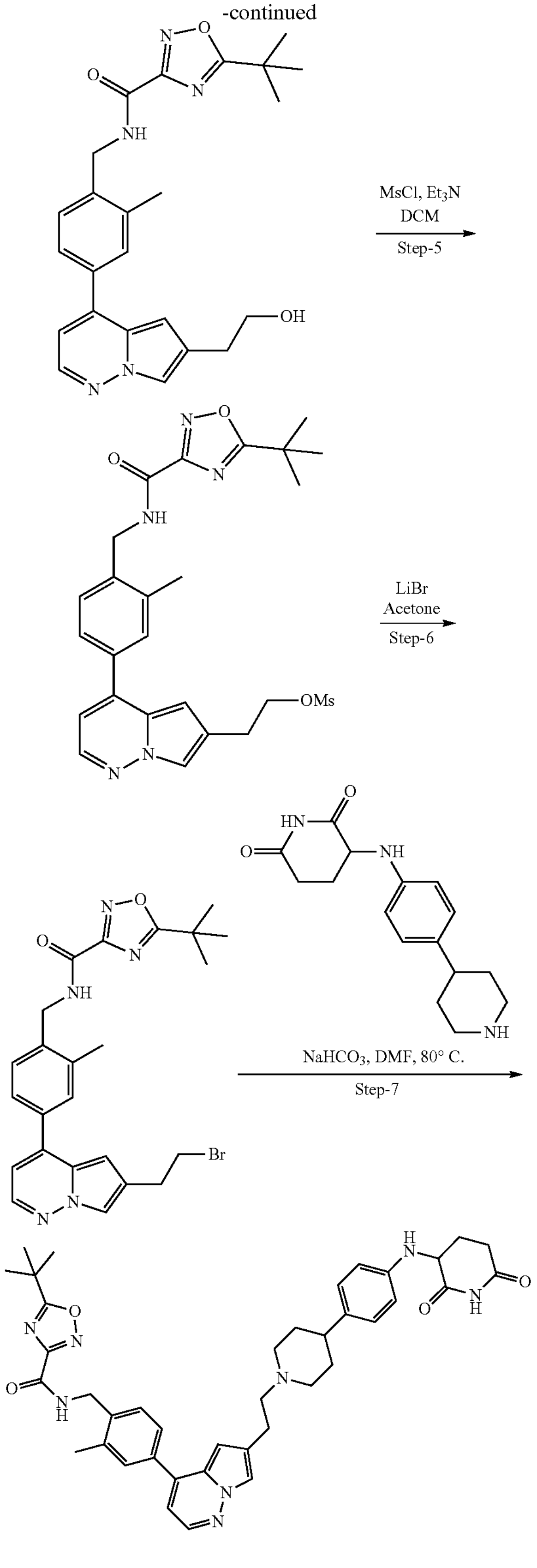

Step-1:

In 25 ml flask containing the solution of tert-butyl N-[[4-(6-bromopyrrolo[1,2-b]pyridazin-4-yl)-2-methyl-phenyl]methyl]carbamate (1 g, 2.40 mmol) and potassium (2-benzyloxyethyl)trifluoroborate (872.30 mg, 3.60 mmol) in toluene (20 mL) was added cesium carbonate (1.96 g, 6.01 mmol) in water (10 mL) and purged argon for 10 minutes. Then, to the mixture was added RuPhos (112.08 mg, 240.21 μmol) and Pd(dppf)$Cl_2$·$CH_2Cl_2$ (131.82 mg, 180.15 μmol) sequentially. The reaction mixture was heated to 110° C. for 16 hours while monitoring by TLC and LC-MS. After completion, the reaction mixture was quenched with water and extracted with ethyl acetate. The organic layer was concentrated under reduced pressure. The crude product was purified by Biotage® Isolera (0-30% ethyl acetate in petroleum ether) to afford tert-butyl N-[[4-[6-(2-benzyloxyethyl)pyrrolo[1,2-b]pyridazin-4-yl]-2-methyl-phenyl]methyl]carbamate (0.8 g, 1.58 mmol, 65.68% yield) as a pale green sticky liquid. LC-MS ($ES^+$): m/z 472.29 $[M+H]^+$.

Step-2:

To a stirred solution of tert-butyl N-[[4-[6-(2-benzyloxyethyl)pyrrolo[1,2-b]pyridazin-4-yl]-2-methyl-phenyl]methyl]carbamate (0.7 g, 1.48 mmol) in dioxane (10 mL) was added 4 M dioxane HCl (4 M, 3 mL) and the reaction was allowed to stirred for 30 minutes under inert atmosphere. The reaction was monitored by TLC and LCMS. After completion, the reaction mixture was concentrated under reduced pressure and the resulting solid was washed with diethyl ether to afford [4-[6-(2-benzyloxyethyl)pyrrolo[1,2-b]pyridazin-4-yl]-2-methyl-phenyl]methanamine HCl salt (0.61 g, 1.42 mmol, 95.70% yield) as pale brown solid. LC-MS ($ES^+$): m/z 372.4 $[M+H]^+$.

Step-3:

To a stirred solution of (5-tert-butyl-1,2,4-oxadiazole-3-carbonyl)oxylithium (420.89 mg, 2.39 mmol) in DMF (10 mL) under inert atmosphere was added DIPEA (1.24 g, 9.56 mmol, 1.67 mL) followed by PyBOP (1.24 g, 2.39 mmol). Then, [4-[6-(2-benzyloxyethyl)pyrrolo[1,2-b]pyridazin-4-yl]-2-methyl-phenyl]methanamine HCl salt (0.65 g, 1.59 mmol) in DMF was added, and the reaction mixture was stirred for 4 hours at room temperature while monitoring by TLC and LC-MS. After completion, the reaction mixture was quenched with ice-cooled water and extracted with ethyl acetate. The organic layer was washed with brine solution and dried over anhydrous sodium sulfate, and concentrated to dryness under reduced pressure. The crude product was purified by column chromatography (silica gel, 0-40% ethyl acetate in petroleum ether) to afford N-[[4-[6-(2-benzyloxyethyl)pyrrolo[1,2-b]pyridazin-4-yl]-2-methyl-phenyl]methyl]-5-tert-butyl-1,2,4-oxadiazole-3-carboxamide (0.45 g, 782.05 μmol, 49.08% yield) as a yellow sticky liquid. LC-MS ($ES^+$): m/z 524.7 $[M+H]^+$.

Step-4:

To a stirred solution of N-[[4-[6-(2-benzyloxyethyl)pyrrolo[1,2-b]pyridazin-4-yl]-2-methyl-phenyl]methyl]-5-tert-butyl-1,2,4-oxadiazole-3-carboxamide (0.45 g, 859.40 μmol) in DCM (5 mL) was added boron tribromide (861.19 mg, 3.44 mmol) under inert atmosphere at −78° C. and maintained for 1 hour while monitoring by TLC and LC-MS. After completion, the reaction mixture was quenched with 10% $NaHCO_3$ solution and extracted with DCM, washed with brine solution, dried over anhydrous sodium sulfate, and concentrated under reduced pressure. The crude mixture was purified by column chromatography (0-70% ethyl acetate in pet ether) to afford 5-tert-butyl-N-[[4-[6-(2-hydroxyethyl)pyrrolo[1,2-b]pyridazin-4-yl]-2-methyl-phenyl]methyl]-1,2,4-oxadiazole-3-carboxamide (0.15 g, 301.04 μmol, 35.03% yield) as pale brown sticky liquid. LC-MS ($ES^+$): m/z 434.5 $[M+H]^+$.

Step-5:

In a 25 ml single neck RBF, 5-(tert-butyl)-N-(4-(6-(2-hydroxyethyl)pyrrolo[1,2-b]pyridazin-4-yl)-2-methylbenzyl)-1,2,4-oxadiazole-3-carboxamide (0.13 g, 299.88 μmol) was dissolved in DCM (5 mL) and cooled to 0° C. Triethylamine (91.04 mg, 899.65 μmol, 125.39 L) was added, followed by methanesulfonyl chloride (41.22 mg, 359.86 μmol, 27.85 L), and the reaction mixture was warmed up to room temperature and stirred for 1 hour. Progress of the reaction was monitored by TLC and LC-MS. After completion of the reaction, the reaction mixture was concentrated under reduced pressure and washed several times with a saturated solution of sodium bicarbonate, and extracted with the ethyl acetate. Separation of organic layer and concentration under reduced pressure gave the crude mass, which on trituration with diethyl ether afforded compound 2-(4-(4-((5-(tert-butyl)-1,2,4-oxadiazole-3-carboxamido)methyl)-3-methylphenyl)pyrrolo[1,2-b]pyridazin-6-yl)ethyl methanesulfonate (0.1 g, 146.60 μmol, 48.89% yield) as a yellowish semi-solid. LC-MS ($ES^+$): m/z 512.6 $[M+H]^+$.

Step-6:

To a stirred solution of 2-[4-[4-[[(5-tert-butyl-1,2,4-oxadiazole-3-carbonyl)amino]methyl]-3-methyl-phenyl]pyrrolo[1,2-b]pyridazin-6-yl]ethyl methanesulfonate (0.150 g, 293.20 μmol) in acetone (5 mL) was added lithium bromide (38.19 mg, 439.80 μmol) all at once under inert atmosphere. Then, the reaction mixture was heated the mixture to 65° C. for 4 hours while monitoring by TLC and LC-MS. After completion, the reaction mixture was cooled and filtered through a pad of celite, and the resulting filtrate was concentrated under reduced pressure. The crude product was taken into the next step without further purification. LC-MS ($ES^+$): m/z 496.3 $[M+H]^+$.

Step-7:

To a stirred solution of 3-((4-(piperidin-4-yl)phenyl)amino)piperidine-2,6-dione TFA salt (38.21 mg, 95.19 μmol) in DMF (5 mL) was added sodium bicarbonate (81.23 mg, 966.97 mol) under inert atmosphere. Then, N-[[4-[6-(2-bromoethyl)pyrrolo[1,2-b]pyridazin-4-yl]-2-methyl-phenyl]methyl]-5-tert-butyl-1,2,4-oxadiazole-3-carboxamide (60.00 mg, 120.87 μmol) in DMF was added and heated to 80° C. for 16 hours while monitoring by TLC and LC-MS. After completion, the reaction was quenched with water, the solid was filtered and washed with ice-water. The resulting solid was purified by prep-HPLC (water, 0.1% TFA and ACN) to afford 5-tert-butyl-N-[[4-[6-[2-[4-[4-[(2,6-dioxo-3-piperidyl)amino]phenyl]-1-piperidyl]ethyl]pyrrolo[1,2-b]pyridazin-4-yl]-2-methyl-phenyl]methyl]-1,2,4-oxadiazole-3-carboxamide TFA salt (20.7 mg, 24.88 μmol, 20.59% yield) as a pale yellow solid. $^1$H NMR (400 MHz, DMSO-$d_6$) δ 10.78 (s, 1H), 9.51 (t, J=5.7 Hz, 1H), 9.17 (s, 1H), 8.21 (d, J=4.7 Hz, 1H), 7.94 (s, 1H), 7.59 (brs, 2H), 7.42 (d, J=8.4 Hz, 1H), 7.08 (d, J=8.4 Hz, 2H), 6.74 (d, J=4.6 Hz, 1H), 6.64 (d, J=8.0 Hz, 3H), 4.53 (d, J=6.0 Hz, 2H), 4.28-4.25 (m, 1H), 3.51-3.50 (m, 4H), 3.08-3.00 (m, 4H), 2.73-2.60 (m, 3H), 2.44 (s, 3H), 1.96-1.94 (m, 6H), 1.44 (s, 9H). LC-MS ($ES^+$): m/z 703.2 $[M+H]^+$.

Example 156. Synthesis of 5-tert-butyl-N-[[4-[6-[4-[4-[4-[(2,6-dioxo-3-piperidyl)amino]phenyl]-1-piperidyl]butyl]pyrrolo[1,2-b]pyridazin-4-yl]-2-methyl-phenyl]methyl]-1,2,4-oxadiazole-3-carboxamide

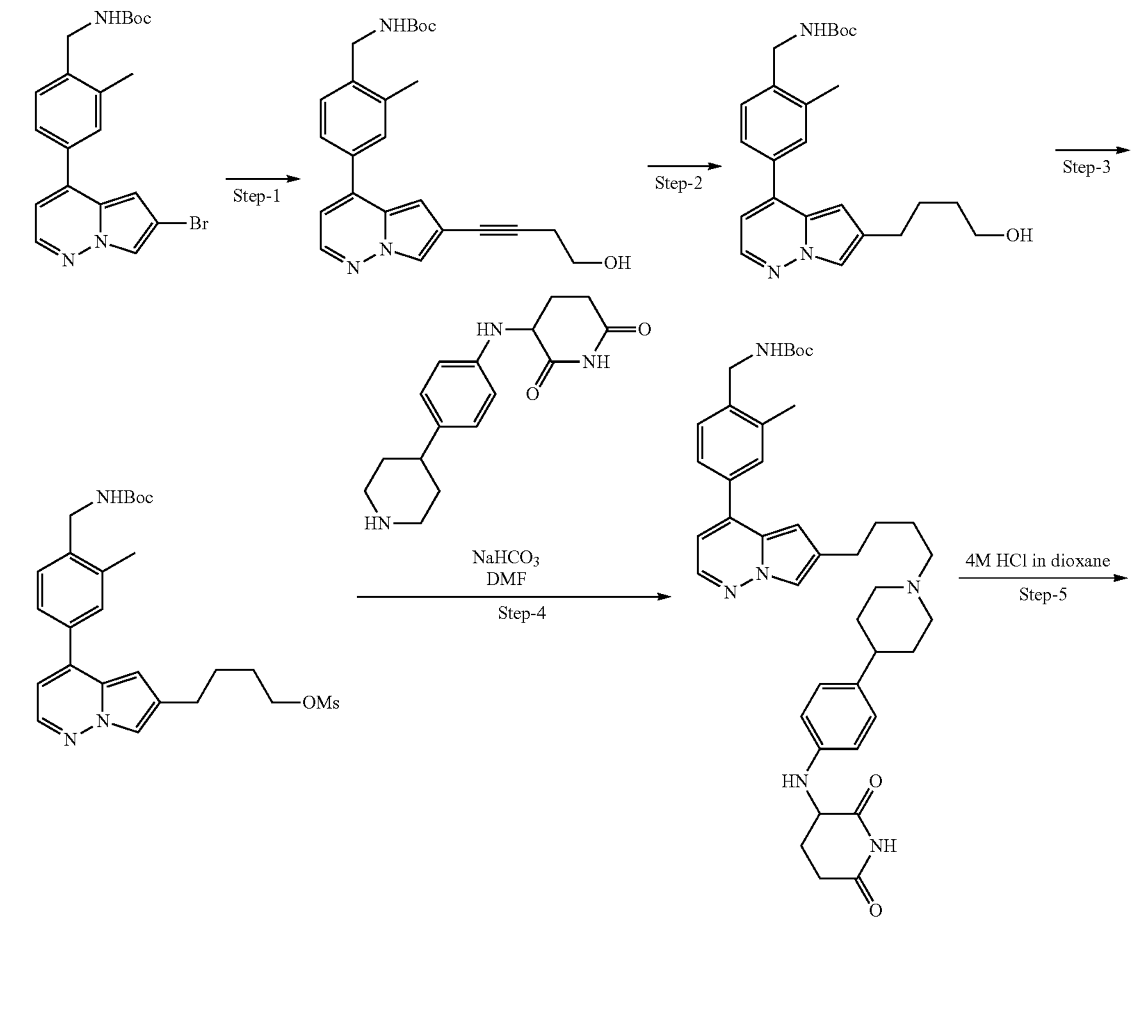

-continued
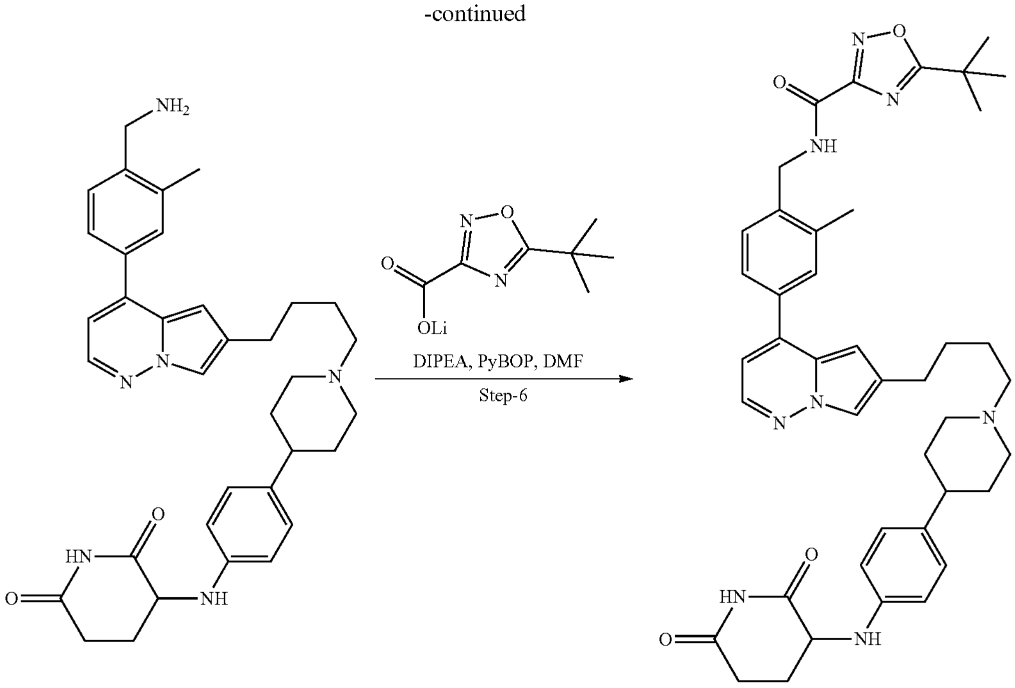
Unless otherwise noted, reaction steps and conditions are identical (using different building blocks) to the representative compound shown below.
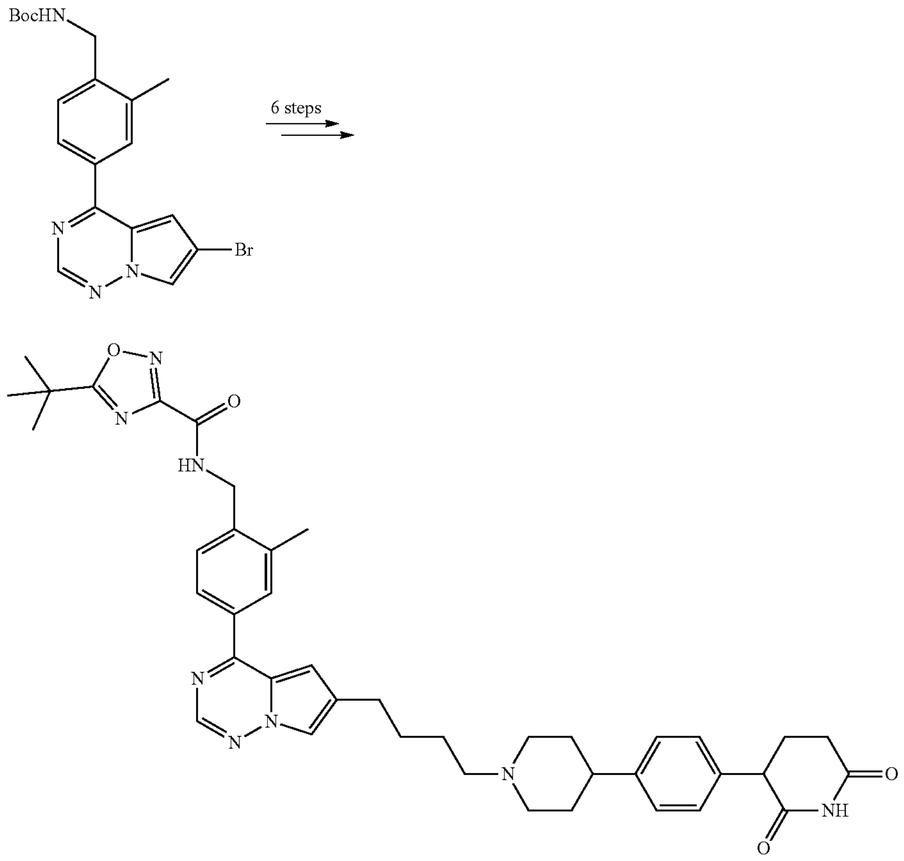 [SMILES: Cc1cc(-c2ncnn3cc(Br)cc23)ccc1CNC(=O)OC(C)(C)C ; Cc1cc(-c2ncnn3cc(CCCCN4CCC(c5ccc(C6CCC(=O)NC6=O)cc5)CC4)cc23)ccc1CNC(=O)c1noc(C(C)(C)C)n1]

Step-1:

tert-butyl N-[[4-[6-(4-hydroxybut-1-ynyl)pyrrolo[1,2-b]pyridazin-4-yl]-2-methyl-phenyl]methyl]carbamate (1.5 g, 3.13 mmol, 65.07% yield). LC-MS ($ES^+$): m/z 406.2 $[M+H]^+$.

Step-2:

tert-butyl N-[[4-[6-(4-hydroxybutyl)pyrrolo[1,2-b]pyridazin-4-yl]-2-methyl-phenyl]methyl]carbamate (0.35 g, 790.56 μmol, 45.79% yield). LC-MS ($ES^+$): m/z 410.2 $[M+H]^+$.

Step-3:

4-[4-[4-[(tert-butoxycarbonylamino)methyl]-3-methyl-phenyl]pyrrolo[1,2-b]pyridazin-6-yl]butyl methanesulfonate (0.015 g, 26.11 μmol, 53.46% yield). LC-MS ($ES^+$): m/z 488.4 $[M+H]^+$.

Step-4:

To a stirred solution of 4-[4-[4-[(tert-butoxycarbonylamino)methyl]-3-methyl-phenyl]pyrrolo[1,2-b]pyridazin-6-yl]butyl methanesulfonate (0.35 g, 717.79 μmol) in DMF (5 mL) were added sodium bicarbonate (361.81 mg, 4.31 mmol) and the reaction was stirred at 80° C. After 16 hours, the reaction was quenched with water (100 mL) and extracted with ethyl acetate (3×100 mL). The combined organic layer was dried over anhydrous sodium sulfate and concentrated in vacuo. The crude mixture was purified by column chromatography (silica gel 100-200 mesh, 15% ethyl acetate in petroleum ether) to afford tert-butyl N-[[4-[6-[4-[4-[4-[(2,6-dioxo-3-piperidyl)amino]phenyl]-1-piperidyl]butyl]pyrrolo[1,2-b]pyridazin-4-yl]-2-methyl-phenyl]methyl]carbamate (0.2 g, 233.16 μmol, 32.48% yield). LC-MS ($ES^+$): m/z 679.8 $[M+H]^+$.

Step-5:

To the stirred solution of tert-butyl N-[[4-[6-[4-[4-[4-[(2,6-dioxo-3-piperidyl)amino]phenyl]-1-piperidyl]butyl]pyrrolo[1,2-b]pyridazin-4-yl]-2-methyl-phenyl]methyl]carbamate (0.2 g, 294.61 μmol) in DCM (10 mL) was added hydrogen chloride solution, 4.0 M in dioxane (53.71 mg, 1.47 mmol, 2 mL) at 0° C. The reaction mixture was stirred at RT for 4 h. After the completion of the reaction, the reaction mixture was concentrated and the residual mass was triturated with diethyl ether (2×30 mL) and solid was extracted with DCM:Methanol (9:1) and water. The combined organic layer was dried over $Na_2SO_4$, concentrated under reduced pressure to give 3-[4-[1-[4-[4-[4-(aminomethyl)-3-methyl-phenyl]pyrrolo[1,2-b]pyridazin-6-yl]butyl]-4-piperidyl]anilino]piperidine-2,6-dione HCl salt (0.2 g, 292.45 μmol, 99.27% yield) as a yellow solid. LC-MS ($ES^-$): m/z 577.4 $[M-H]^-$.

Step-6:

5-tert-butyl-N-[[4-[6-[4-[4-[4-[(2,6-dioxo-3-piperidyl)amino]phenyl]-1-piperidyl]butyl]pyrrolo[1,2-b]pyridazin-4-yl]-2-methyl-phenyl]methyl]-1,2,4-oxadiazole-3-carboxamide TFA salt (34.3 mg, 40.27 μmol, 12.39% yield). $^1H$ NMR (400 MHz, DMSO-$d_6$) δ 10.77 (s, 1H), 9.50 (t, J=5.8 Hz, 1H), 8.91 (s, 1H), 8.16 (d, J=4.4 Hz, 1H), 7.84 (s, 1H), 7.58 (s, 2H), 7.41 (d, J=8.4 Hz, 3H), 6.72-6.55 (m, 4H), 4.52 (d, J=5.6 Hz, 2H), 4.27 (q, J=5.2 Hz, 1H), 3.16-2.96 (m, 5H), 2.72-2.52 (m, 6H), 2.50 (s, 3H), 2.09-2.07 (m, 1H), 1.93-1.64 (m, 9H), 1.43 (s, 9H). LC-MS ($ES^+$): m/z 731.22 $[M+H]^+$.

Example 157. Synthesis of 5-tert-butyl-N-[[4-[2-[4-[[4-[4-[(2,6-dioxo-3-piperidyl)amino]phenyl]-1-piperidyl]methyl]phenyl]thieno[2,3-b]pyridin-4-yl]-2-methyl-phenyl]methyl]-1,2,4-oxadiazole-3-carboxamide

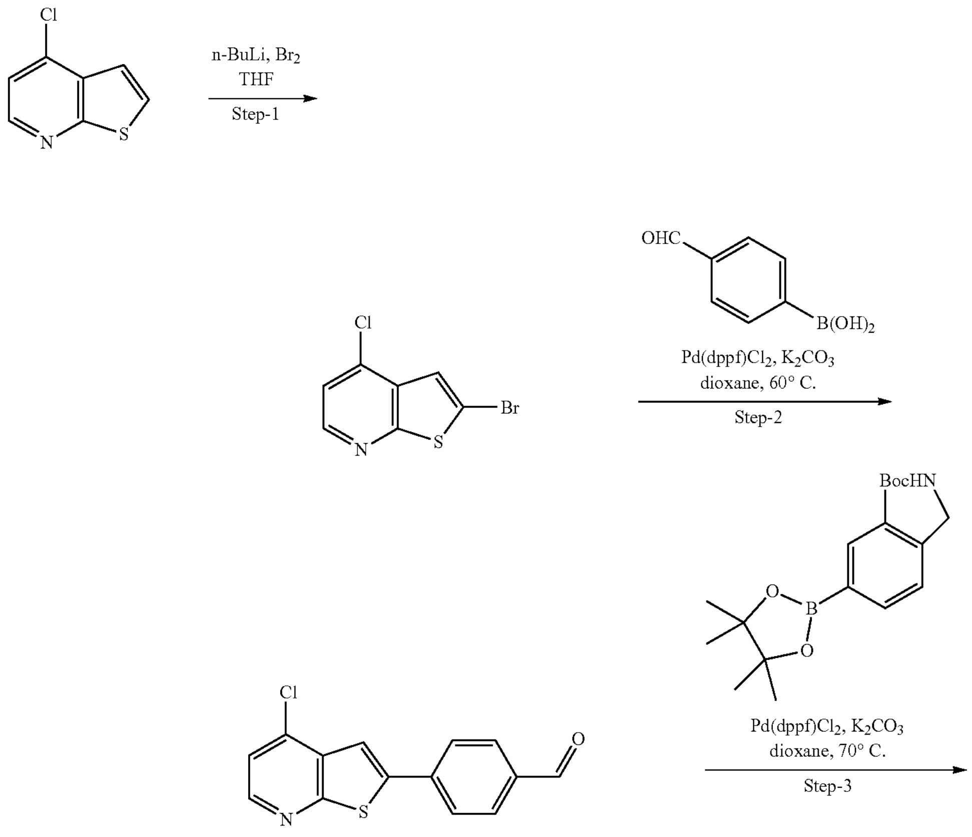

-continued
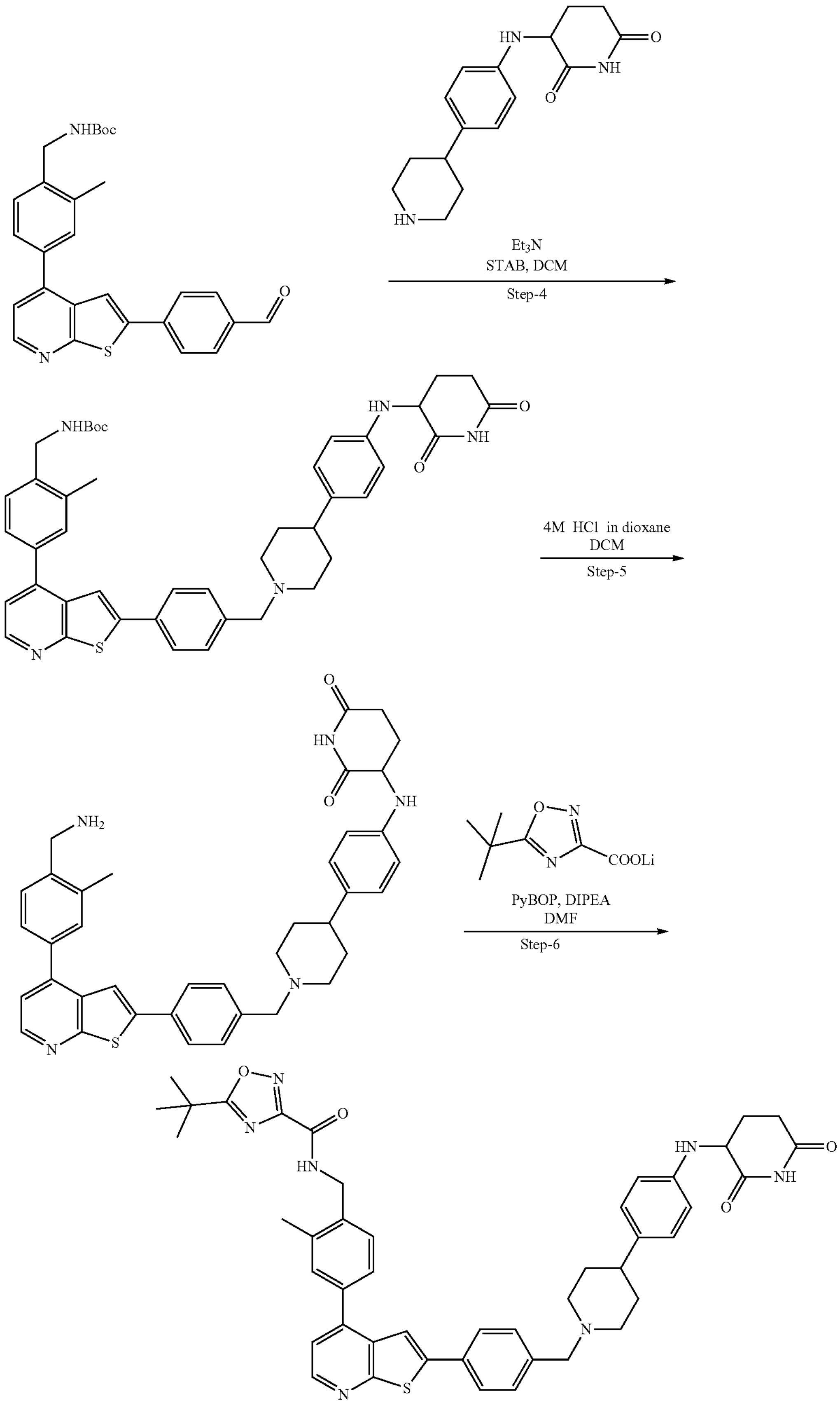

Step-1:

In a 100 ml two neck round bottom flask, 4-chlorothieno[2,3-b]pyridine (5 g, 29.48 mmol) was dissolved in THF (80 mL), and the formed reaction mixture was stirred at −78° C. under the stream of nitrogen for 10 mins. N-butyllithium (1.89 g, 29.48 mmol) was added dropwise over 10 mins, and the reaction was stirred at the same temp for 1 hr. Molecular bromine (4.71 g, 29.48 mmol) was added, and the reaction was warmed to room temp for 2 hours. Progress of the reaction was monitored with the help of TLC and LC-MS. After completion of the reaction, the mixture was quenched with a saturated solution of ammonium chloride and extracted with ethyl acetate. The organic layer was separated and concentrated under reduced pressure, and obtained crude compound was purified through column chromatography (silica gel 230-400 mesh, 0-10% ethyl acetate in pet-ether) to give the compound 2-bromo-4-chloro-thieno[2,3-b]pyridine (3.5 g, 11.95 mmol, 40.54% yield) as a white dull solid. LC-MS ($ES^+$): m/z 248.0 $[M+H]^+$.

Step-2:

In a 25 ml two neck round bottom flask, 2-bromo-4-chloro-thieno[2,3-b]pyridine (1 g, 4.02 mmol) was dissolved in a mixture of 1,4-Dioxane (16 mL) and Water (4 mL) and formed mixture was nitrogen purged for 5 mins. Potassium carbonate—granular (1.67 g, 12.07 mmol) was added, followed by the addition of (4-formylphenyl)boronic acid (482.65 mg, 3.22 mmol), and the reaction was purged for additional 10 minutes at room temperature. Pd(dppf)$Cl_2$·$CH_2Cl_2$ (164.30 mg, 201.19 μmol) was added to the mixture, and it was purged for 5 minutes and heated at 55-60° C. for 1 hour. Progress of the reaction was monitored with the help of TLC and LC-MS. After completion of the reaction, the mixture was cooled to room temperature and filtered through a celite bed, and the filtrate was concentrated under reduced pressure. Water was added to the obtained crude mass and extracted with ethyl acetate. Combined organic layers were dried over sodium sulfate and concentrated under reduced pressure. The crude mixture was purified by column chromatography (silica gel 230-400 mesh, 0-100% ethyl acetate in pet-ether) to afford compound 4-(4-chlorothieno[2,3-b]pyridin-2-yl)benzaldehyde (0.8 g, 1.96 mmol, 48.66% yield). LC-MS ($ES^+$): m/z 274.3 $[M+H]^+$.

Step-3:

In a 25 ml two neck round bottom flask, 4-(4-chlorothieno[2,3-b]pyridin-2-yl)benzaldehyde (0.3 g, 1.10 mmol) was dissolved in a mixture of 1,4-dioxane (8 mL) and water (2 mL) and the mixture was purged with nitrogen gas for 5 minutes. Potassium phosphate monobasic (149.15 mg, 1.10 mmol) was added followed by tert-butyl N-[[2-methyl-4-(4,4,5,5-tetramethyl-1,3,2-dioxaborolan-2-yl)phenyl]methyl]carbamate (456.69 mg, 1.32 mmol) and the reaction was purged for an additional 10 minutes at room temperature. Chloro(2-dicyclohexylphosphino-2',4',6'-triisopropyl-1,1'-biphenyl)[2-(2'-amino-1,1'-biphenyl)]palladium(II) (862.29 mg, 1.10 mmol) was added to the reaction mixture and the mixture was purged for 5 minutes and then heated at 80-90° C. for overnight. Progress of the reaction was monitored with the help of TLC and LC-MS. After completion of the reaction, the reaction was allowed to cool at room temperature and filtered through a celite bed, dried over sodium sulfate. The filtrate was concentrated under reduced pressure to give tert-butyl N-[[4-[2-(4-formylphenyl)thieno[2,3-b]pyridin-4-yl]-2-methyl-phenyl]methyl]carbamate (0.19 g, 368.75 μmol, 33.65% yield) as a brown semi-solid. LC-MS ($ES^+$): m/z 459.2 $[M+H]^+$.

Step-4:

In a 25 ml single neck round bottom flask, 3-[4-(4-piperidyl)anilino]piperidine-2,6-dione TFA salt (315.10 mg, 785.05 μmol) was dissolved in DCM (15 mL) and basified with Triethylamine (39.72 mg, 392.52 μmol, 54.71 μL) and formed reaction mixture was allowed to stir a cool at 0° C. under a stream of nitrogen. After 5 minutes, tert-butyl N-[[4-[2-(4-formylphenyl)thieno[2,3-b]pyridin-4-yl]-2-methyl-phenyl]methyl]carbamate (0.18 g, 392.52 μmol) was added and reaction mixture was allowed to warm at room temp for 2 hrs. Sodium triacetoxyborohydride (748.73 mg, 3.53 mmol) was added at 0° C., and the reaction was stirred at room temperature overnight. Progress of the reaction was monitored with the help of TLC and LC-MS. After completion of the reaction, the solvent was concentrated under reduced pressure, and the crude product was washed with a saturated sodium bicarbonate solution. The obtained precipitate was filtered and washed several times with diethyl ether to afford tert-butyl N-[[4-[2-[4-[[4-[4-[(2,6-dioxo-3-piperidyl)amino]phenyl]-1-piperidyl]methyl]phenyl]thieno[2,3-b]pyridin-4-yl]-2-methyl-phenyl]methyl]carbamate (0.23 g, 274.14 μmol, 69.84% yield) as a pale yellow solid. LC-MS ($ES^+$): m/z 730.4 $[M+H]^+$.

Step-5:

In a 25 ml single neck round bottom flask, tert-butyl N-[[4-[2-[4-[[4-[4-[(2,6-dioxo-3-piperidyl)amino]phenyl]-1-piperidyl]methyl]phenyl]thieno[2,3-b]pyridin-4-yl]-2-methyl-phenyl]methyl]carbamate (0.15 g, 205.50 μmol) was suspended in DCM (5 mL) and stirred at 0° C. for 15 minutes under a stream of nitrogen. 4 M HCl in dioxane (1.5 mL) was added dropwise over a period of 5 minutes, and the formed reaction mixture was allowed to stir at 0-15° C. for 1 hour. Progress of the reaction was monitored with TLC and LC-MS. After completion of the reaction, the reaction mixture was concentrated under reduced pressure, and the obtained solid mass was triturated several times with diethyl ether to afford compound 3-[4-[1-[[4-[4-[4-(aminomethyl)-3-methyl-phenyl]thieno[2,3-b]pyridin-2-yl]phenyl]methyl]-4-piperidyl]anilino]piperidine-2,6-dione HCl salt (0.15 g, 191.90 μmol, 93.38% yield) as a greenish solid. LC-MS ($ES^-$): m/z 628.3 $[M-H]^-$.

Step-6:

In a 50 ml single neck round bottom flask, 3-[4-[1-[[4-[4-[4-(aminomethyl)-3-methyl-phenyl]thieno[2,3-b]pyridin-2-yl]phenyl]methyl]-4-piperidyl]anilino]piperidine-2,6-dione HCl salt (0.15 g, 225.13 μmol) was dissolved in DMF (4 mL) and basified with N,N-diisopropylethylamine (290.97 mg, 2.25 mmol, 392.14 μL) followed by addition of (5-tert-butyl-1,2,4-oxadiazole-3-carbonyl)oxylithium (79.29 mg, 450.27 μmol). The formed reaction mixture was cooled to 0° C. and benzotriazol-1-yloxy(tripyrrolidin-1-yl)phosphonium; hexafluorophosphate (234.32 mg, 450.27 μmol) was added and the reaction was stirred at room temperature for 1.5 hour. Progress of the reaction was monitored with TLC and LC-MS. After completion of the reaction, solvent was concentrated under reduced pressure and the obtained crude compound was purified by prep-HPLC (water, 0.05% TFA and ACN) to afford compound 5-tert-butyl-N-[[4-[2-[4-[[4-[4-[(2,6-dioxo-3-piperidyl)amino]phenyl]-1-piperidyl]methyl]phenyl]thieno[2,3-b]pyridin-4-yl]-2-methyl-phenyl]methyl]-1,2,4-oxadiazole-3-carboxamide TFA salt (59 mg, 64.33 μmol, 28.57% yield) as a grey solid. $^1H$ NMR (400 MHz, DMSO-$d_6$) δ 10.77 (s, 1H), 9.52 (t, J=5.9 Hz, 1H), 9.38 (bs, 1H), 8.61 (d, J=4.8 Hz, 1H), 7.97 (d, J=8.0 Hz, 2H), 7.88 (s, 1H), 7.63 (d, J=8.0 Hz, 2H), 7.58-7.56 (m, 2H), 7.47-7.44 (m, 2H), 6.94 (d, J=8.4 Hz, 2H), 6.63 (d, J=8.4 Hz, 2H), 4.55 (d, J=5.9 Hz, 2H), 4.39 (bs, 2H), 4.29-4.25 (m, 1H), 3.48-3.45 (m, 2H), 3.08-3.03

(m 2H), 2.73-2.59 (m, 3H), 2.46 (s, 3H), 2.10-2.06 (m, 1H), 1.96-1.75 (m, 5H), 1.44 (s, 9H). LC-MS (ES+): m/z 782.13 [M+H]+.

Example 158. Synthesis of 5-tert-butyl-N-[[4-[2-[4-[4-[4-[(2,6-dioxo-3-piperidyl)amino]phenyl]-1-piperidyl]butyl]thieno[2,3-b]pyridin-4-yl]-2-methyl-phenyl]methyl]-1,2,4-oxadiazole-3-carboxamide

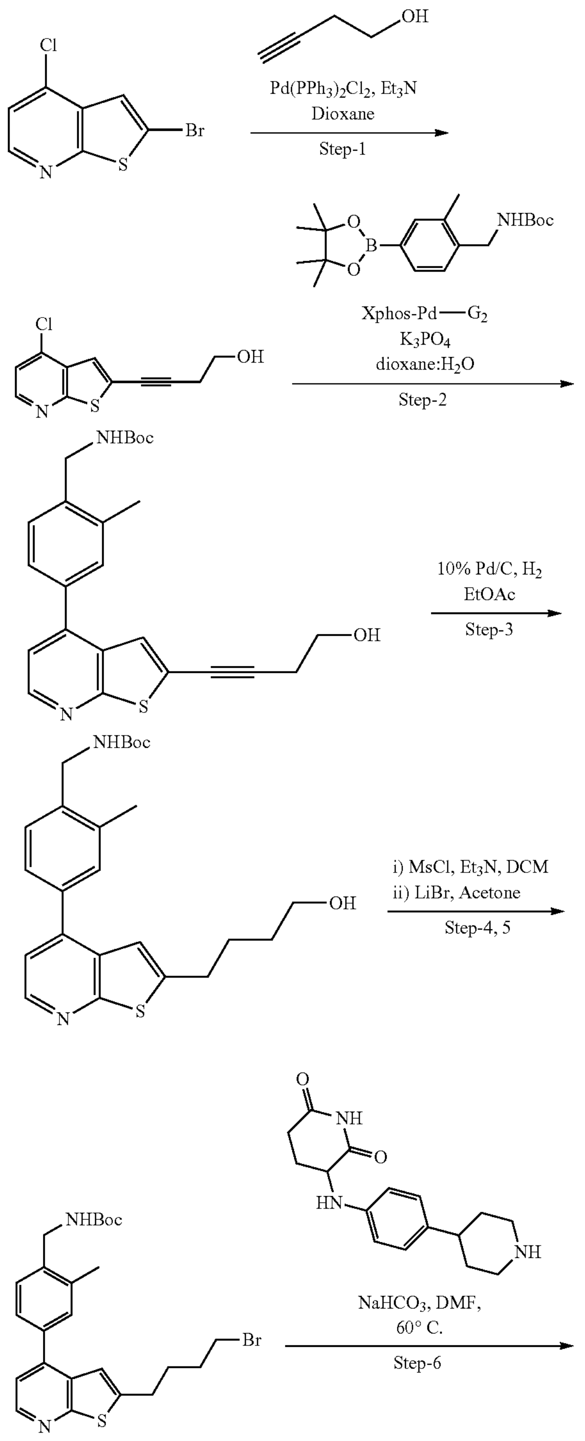

-continued

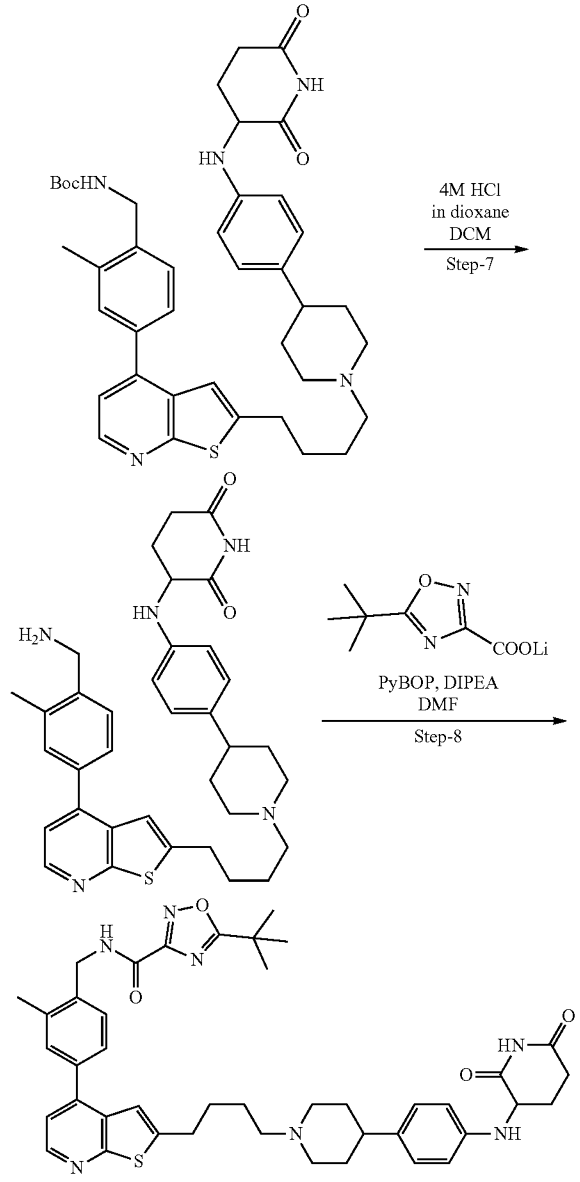

Step-1:

To a solution of 2-bromo-4-chloro-thieno[2,3-b]pyridine (2 g, 8.05 mmol) and but-3-yn-1-ol (564.04 mg, 8.05 mmol, 608.46 μL) in dioxane (20 mL) was added triethylamine (4.89 g, 48.28 mmol, 6.73 mL) at room temperature and the reaction was degassed with nitrogen. Then, CuI (306.53 mg, 1.61 mmol) and $Pd(PPh_3)Cl_2$ (564.84 mg, 804.74 μmol) were added sequentially, and the reaction mixture was stirred at 60° C. for 12 hours. Then, the reaction mixture was quenched by a saturated solution of $NH_4Cl$ and extracted with ethyl acetate. The combined organic layers were concentrated in vacuo, and the crude product was purified by column chromatography (30-40% ethyl acetate in petroleum ether) to afford 4-(4-chlorothieno[2,3-b]pyridin-2-yl)but-3-yn-1-ol (1.6 g, 5.72 mmol, 71.10% yield) as a brown liquid. LC-MS (ES+): z 238.0 [M+H]+.

Step-2:

To a solution of 4-(4-chlorothieno[2,3-b]pyridin-2-yl)but-3-yn-1-ol (1.4 g, 5.89 mmol) and tert-butyl N-[[2-methyl-4-(4,4,5,5-tetramethyl-1,3,2-dioxaborolan-2-yl)phenyl]

methyl]carbamate (2.66 g, 7.66 mmol) in dioxane (40 mL) and water (10 mL) was added potassium phosphate tribasic anhydrous (3.75 g, 17.67 mmol) and resulting mixture was purged with nitrogen gas for 20 minutes. Then, XPhos Pd G2 (926.80 mg, 1.18 mmol) was added, and the resulting mixture was heated to 95° C. for 16 hours. After the completion of the reaction, the resulting mixture was diluted with water (150 mL) and extracted by DCM (100 mL×3). The combined organic layer was dried under a high vacuum. The crude mixture was purified by normal phase column chromatography (35% ethyl acetate in petroleum ether) to afford tert-butyl N-[[4-[2-(4-hydroxybut-1-ynyl)thieno[2,3-b]pyridin-4-yl]-2-methyl-phenyl]methyl]carbamate (1.3 g, 2.74 mmol, 46.52% yield) as a white solid. LC-MS ($ES^+$): m/z 423.4 $[M+H]^+$.

Step-3:

To a solution of tert-butyl N-[[4-[2-(4-hydroxybut-1-ynyl)thieno[2,3-b]pyridin-4-yl]-2-methyl-phenyl]methyl]carbamate (1.4 g, 3.31 mmol) in ethyl acetate (140 mL) was added 10 wt. % palladium on carbon wet (1.4 g, 13.16 mmol) and the resulting mixture was stirred under hydrogen atmosphere at room temperature for 16 hours. Then, the resulting mixture was filtered through celite and the resulting filtrate was concentrated under high vacuum to afford tert-butyl N-[[4-[2-(4-hydroxybutyl)thieno[2,3-b]pyridin-4-yl]-2-methyl-phenyl]methyl]carbamate (1.3 g, 2.68 mmol, 80.80% yield) as a brown viscous material. LC-MS ($ES^+$): m/z 449.2 [M+Na].

Step-4:

To a solution of tert-butyl N-[[4-[2-(4-hydroxybutyl)thieno[2,3-b]pyridin-4-yl]-2-methyl-phenyl]methyl]carbamate (1.3 g, 3.05 mmol) in DCM (150 mL) was added triethylamine (308.38 mg, 3.05 mmol, 424.77 μL) followed by the addition of methanesulfonyl chloride (349.10 mg, 3.05 mmol, 235.88 μL) at 0° C. and resulting mixture was stirred at rt for 6 h. After the completion of reaction, the resulting crude mixture was diluted with bicarbonate solution (150 mL) and extracted by DCM (100 ml×3). The combined organic layer was concentrated under high vacuum to afford 4-[4-[4-[(tert-butoxycarbonylamino)methyl]-3-methyl-phenyl]thieno[2,3-b]pyridin-2-yl]butyl methanesulfonate (1.3 g, 2.30 mmol, 75.36% yield) as a brown viscous material. LC-MS ($ES^+$): m/z 505.8 $[M+H]^+$.

Step-5:

To a solution of 4-[4-[4-[(tert-butoxycarbonylamino)methyl]-3-methyl-phenyl]thieno[2,3-b]pyridin-2-yl]butyl methanesulfonate (0.3 g, 594.46 μmol) in acetone (16 mL) was added lithium bromide (51.63 mg, 594.46 μmol) and the resulting mixture was heated to 60° C. for 6 hours. The progress of reaction was monitored by TLC. After completion, the resulting crude was purified by column chromatography to give tert-butyl N-[[4-[2-(4-bromobutyl)thieno[2,3-b]pyridin-4-yl]-2-methyl-phenyl]methyl]carbamate (0.3 g, 414.02 μmol, 69.65% yield) as an off white solid. LC-MS ($ES^+$): m/z 489.4 $[M+H]^+$.

Step-6:

To a solution mixture of tert-butyl N-[[4-[2-(4-bromobutyl)thieno[2,3-b]pyridin-4-yl]-2-methyl-phenyl]methyl]carbamate (0.3 g, 612.91 μmol) in DMF (16 mL) was added 3-[4-(4-piperidyl)anilino]piperidine-2,6-dione TFA salt (615.02 mg, 1.53 mmol) followed by the addition of sodium bicarbonate (51.49 mg, 612.91 μmol) and the resulting mixture was heated to reflux at 70° C. for 12 hours. After completion of the reaction, the resulting crude was diluted with water and extracted using DCM. The organic layer was combined and dried under a high vacuum to give the crude product, which was purified by column chromatography (0-100% ethyl acetate in petroleum ether) to afford tert-butyl N-[[4-[2-[4-[4-[4-[(2,6-dioxo-3-piperidyl)amino]phenyl]-1-piperidyl]butyl]thieno[2,3-b]pyridin-4-yl]-2-methyl-phenyl]methyl]carbamate (0.18 g, 107.55 μmol, 17.55% yield) as an off white solid material. LC-MS ($ES^-$): m/z 694.2 $[M-H]^-$.

Step-7:

To the stirred solution of tert-butyl N-[[4-[2-[4-[4-[4-[(2,6-dioxo-3-piperidyl)amino]phenyl]-1-piperidyl]butyl]thieno[2,3-b]pyridin-4-yl]-2-methyl-phenyl]methyl]carbamate (0.200 g, 287.39 μmol) in DCM (5 mL) was added 4M hydrogen chloride in 1,4-dioxane, 99% (2 mL) at 0° C. and the reaction was stirred for 1 hour at room temperature. The reaction was monitored by the TLC & LC-MS. After the completion, the reaction mixture was concentrated under reduced pressure and triturated with diethyl ether to give 3-[4-[1-[4-[4-[4-(aminomethyl)-3-methyl-phenyl]thieno[2,3-b]pyridin-2-yl]butyl]-4-piperidyl]anilino]piperidine-2,6-dione (200 mg, 171.42 μmol, 59.65% yield). LC-MS ($ES^-$): m/z 594.4 $[M-H]^-$.

Step-8:

To a stirred solution of 3-[4-[1-[4-[4-[4-(aminomethyl)-3-methyl-phenyl]thieno[2,3-b]pyridin-2-yl]butyl]-4-piperidyl]anilino]piperidine-2,6-dione HCl salt (0.250 g, 395.41 μmol) and (5-tert-butyl-1,2,4-oxadiazole-3-carbonyl)oxylithium (139.26 mg, 790.82 μmol) in DMF (2 mL) at 0° C. were added N-ethyl-N-isopropyl-propan-2-amine (511.03 mg, 3.95 mmol, 688.72 μL) and PyBOP (411.53 mg, 790.82 μmol). The reaction mixture was stirred at room temperature for 2 hours and monitored by TLC and LCMS. After completion of the reaction, the solvent was concentrated under reduced pressure and obtained crude compound was purified by prep-HPLC (water, 0.1% TFA and ACN) to afford compound 5-tert-butyl-N-[[4-[2-[4-[4-[4-[(2,6-dioxo-3-piperidyl)amino]phenyl]-1-piperidyl]butyl]thieno[2,3-b]pyridin-4-yl]-2-methyl-phenyl]methyl]-1,2,4-oxadiazole-3-carboxamide (23 mg, 29.92 μmol, 7.57% yield). $^1H$ NMR (400 MHz, DMSO-$d_6$) δ 10.76 (s, 1H), 9.48 (t, J=5.9 Hz, 1H), 8.51 (d, J=4.8 Hz, 1H), 8.24 (s, 1H), 7.45-7.36 (m, 4H), 7.20 (s, 1H), 6.93 (d, J=8.4 Hz, 2H), 6.59 (d, J=8.4 Hz, 2H), 5.63 (d, J=7.5 Hz, 1H), 4.53 (d, J=5.9 Hz, 2H), 4.29-4.23 (m, 1H), 3.01-2.92 (m, 4H), 2.73-2.60 (m, 2H), 2.43 (s, 3H), 2.33-2.30 (m, 3H), 2.09-2.05 (m, 1H), 1.95-1.89 (m, 3H), 1.73-1.49 (m, 8H), 1.43 (s, 9H). LC-MS ($ES^+$): m/z 748.47 $[M+H]^+$.

Example 159. Synthesis of 5-tert-butyl-N-[[4-[2-[4-[[4-[4-[(2,6-dioxo-3-piperidyl)amino]phenyl]-1-piperidyl]methyl]phenyl]pyrazolo[3,4-b]pyridin-4-yl]-2-methyl-phenyl]methyl]-1,2,4-oxadiazole-3-carboxamide
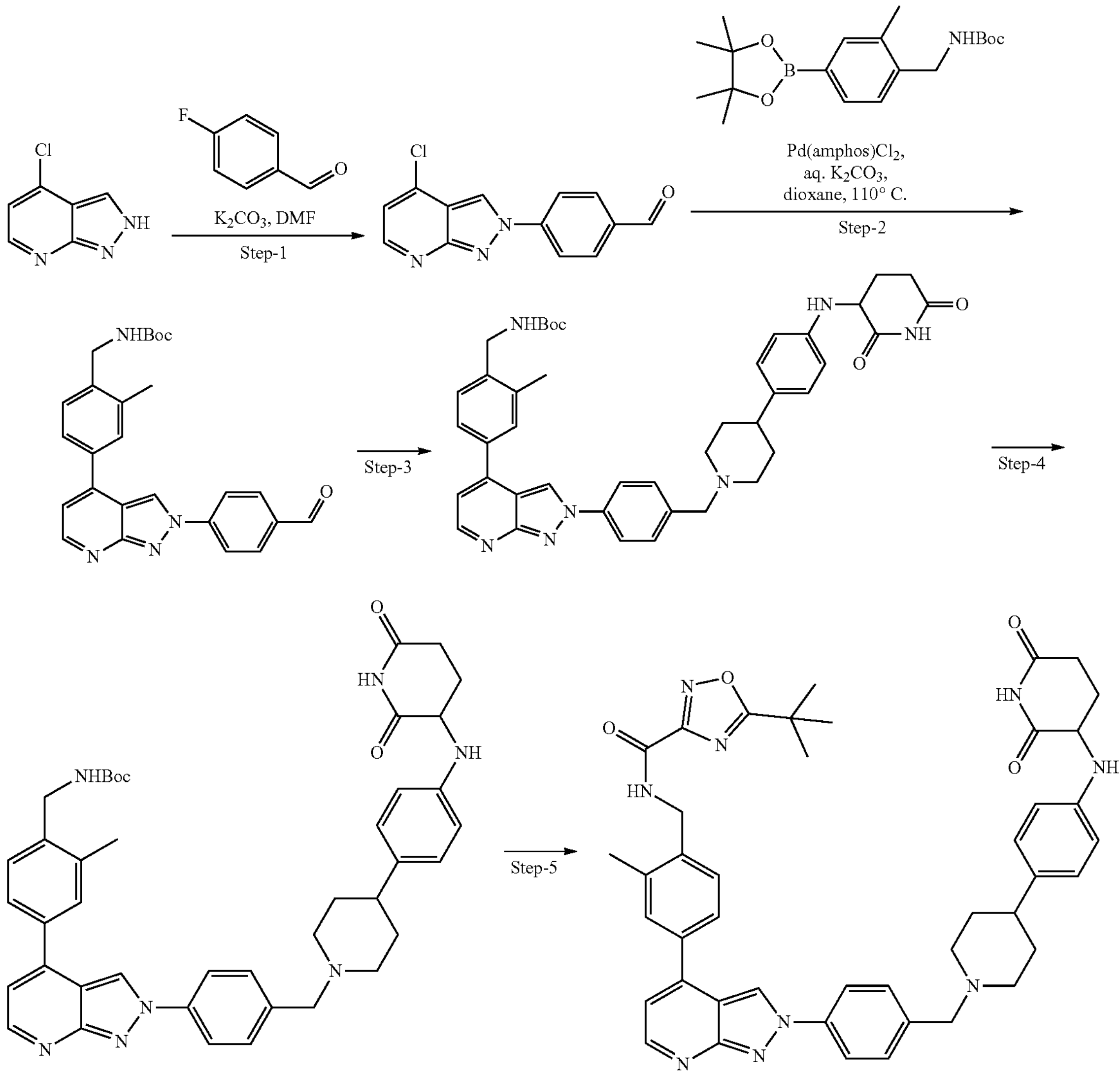
Reaction steps and conditions from step-3 to step-5 are identical (using different building blocks) to the representative compound Example 61 shown below.
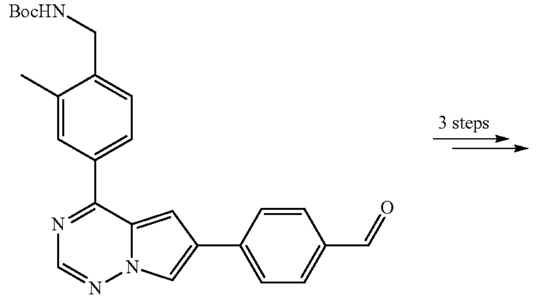
-continued
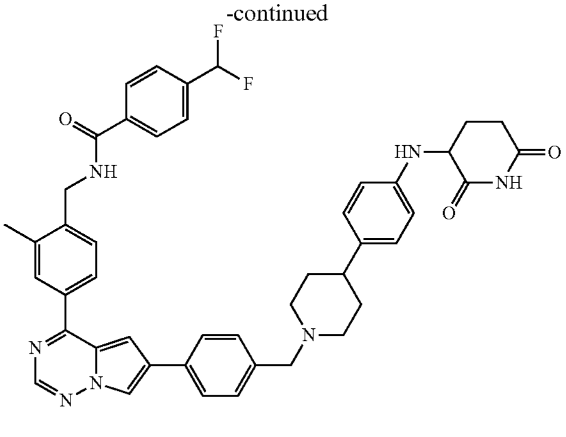

Step-1:

To a solution of 4-chloro-2H-pyrazolo[3,4-b]pyridine (1.5 g, 9.77 mmol) and 4-fluorobenzaldehyde (1.45 g, 11.72 mmol, 1.25 mL) in DMF (20 mL) at room temperature was added potassium carbonate (4.05 g, 29.30 mmol) and the reaction mixture was stirred at 110° C. for 12 h. Then, the reaction mixture was diluted with water (30 mL) and filtered. Collected solid residue was washed with acetonitrile (2×50 mL) and dried under reduced pressure to give a crude product of 4-(4-chloropyrazolo[3,4-b]pyridin-2-yl)benzaldehyde (1.2 g, 3.40 mmol, 34.81% yield). LC-MS (ES$^+$): m/z 258.3 [M+H]$^+$.

Step-2:

To a solution of 4-(4-chloropyrazolo[3,4-b]pyridin-2-yl) benzaldehyde (2.2 g, 8.54 mmol) and tert-butyl N-[[2-methyl-4-(4,4,5,5-tetramethyl-1,3,2-dioxaborolan-2-yl)phenyl]methyl]carbamate (3.56 g, 10.25 mmol) in dioxane (16 mL) and water (4 mL) was added tripotassium phosphate (5.44 g, 25.61 mmol). Then, the reaction mixture was degassed under $N_2$ pressure, and XPhos-Pd-G2 (671.76 mg, 853.79 μmol) was added at room temperature. Then, the reaction was stirred for 12 hours at 80° C. The reaction mixture was cooled to room temperature and diluted with water (100 mL), and extracted with ethyl acetate (100 mL×3). The combined organic phase was collected, dried over sodium sulfate, and concentrated under reduced pressure. The crude sample was purified by column chromatography (20-30% ethyl acetate in petroleum ether) to afford tert-butyl N-[[4-[2-(4-formylphenyl)pyrazolo[3,4-b]pyridin-4-yl]-2-methyl-phenyl]methyl]carbamate (700 mg, 873.20 μmol, 10.23% yield) as a yellow solid. LC-MS (ES$^+$): m/z 443.9 [M+H]$^+$.

Step-3:

tert-butyl N-[[4-[2-[4-[[4-[4-[(2,6-dioxo-3-piperidyl) amino]phenyl]-1-piperidyl]methyl]phenyl]pyrazolo[3,4-b] pyridin-4-yl]-2-methyl-phenyl]methyl]carbamate (0.700 g, 637.38 μmol, 56.41% yield). LC-MS (ES$^+$): m/z 712.4 [M+H]$^+$.

Step-4:

3-[4-[1-[[4-[4-[4-(aminomethyl)-3-methyl-phenyl]pyrazolo[3,4-b]pyridin-2-yl]phenyl]methyl]-4-piperidyl]anilino]piperidine-2,6-dione HCl salt (0.400 g, 375.26 μmol, 66.97% yield). LC-MS (ES$^+$): m/z 614.7 [M+H]$^+$.

Step-5:

5-tert-butyl-N-[[4-[2-[4-[[4-[4-[(2,6-dioxo-3-piperidyl) amino]phenyl]-1-piperidyl]methyl]phenyl]pyrazolo[3,4-b] pyridin-4-yl]-2-methyl-phenyl]methyl]-1,2,4-oxadiazole-3-carboxamide TFA salt (59.4 mg, 66.05 μmol, 10.74% yield). $^1H$ NMR (400 MHz, DMSO-$d_6$) δ 10.77 (s, 1H), 9.53 (t, J=5.9 Hz, 1H), 9.45 (bs, 1H), 9.38 (s, 1H), 8.75 (d, J=4.5 Hz, 1H), 8.36 (d, J=8.4 Hz, 2H), 7.78-7.76 (m, 4H), 7.46 (d, J=7.6 Hz, 1H), 7.35 (d, J=4.5 Hz, 1H), 6.94 (d, J=8.4 Hz, 2H), 6.63 (d, J=8.4 Hz, 2H), 5.78 (bs, 1H), 4.55 (d, J=5.9 Hz, 2H), 4.44 (d, J=4.1 Hz, 2H), 4.29-4.25 (m, 1H), 3.51-3.45 (m, 2H), 3.10-3.07 (m, 2H), 2.73-2.54 (m, 3H), 2.46 (s, 3H), 2.09-2.03 (m, 1H), 1.98-1.77 (m, 5H), 1.44 (s, 9H). LC-MS (ES$^+$): m/z 766.17 [M+H]$^+$.

Example 160. Synthesis of 5-tert-butyl-N-[[4-[2-[4-[4-[4-[(2,6-dioxo-3-piperidyl)amino]phenyl]-1-piperidyl]butyl]pyrazolo[3,4-b]pyridin-4-yl]-2-methyl-phenyl]methyl]-1,2,4-oxadiazole-3-carboxamide

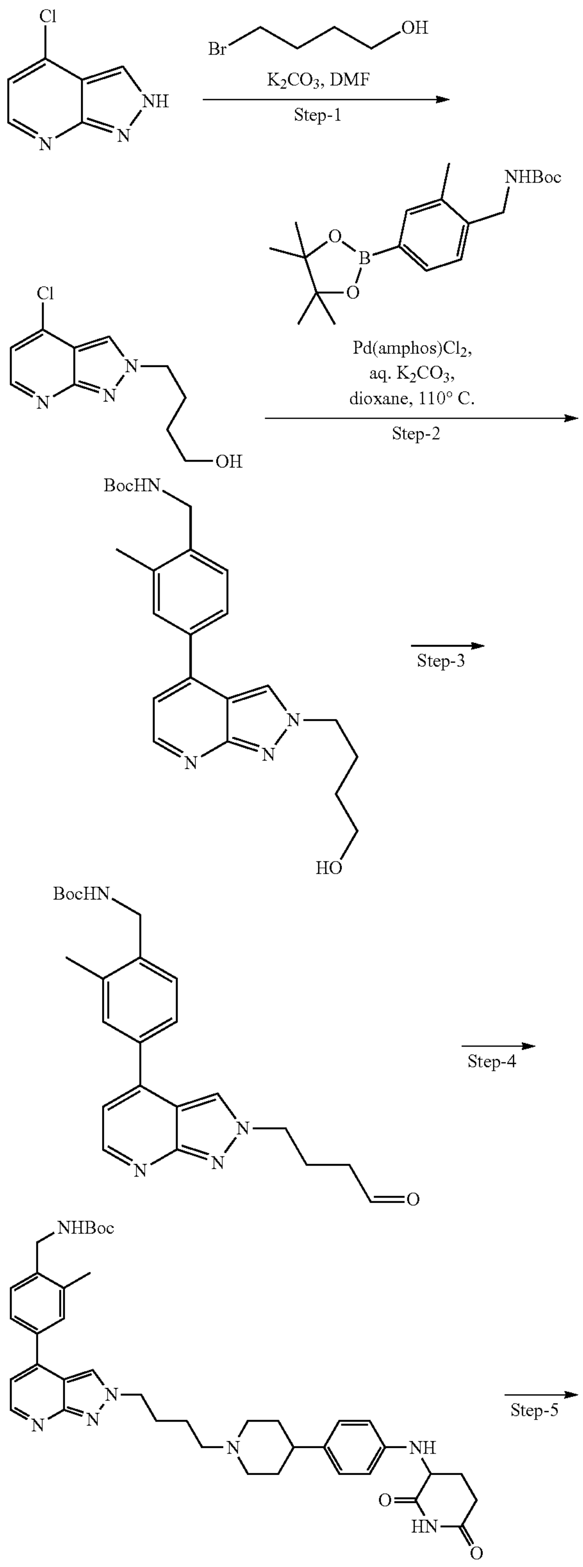

-continued
-continued
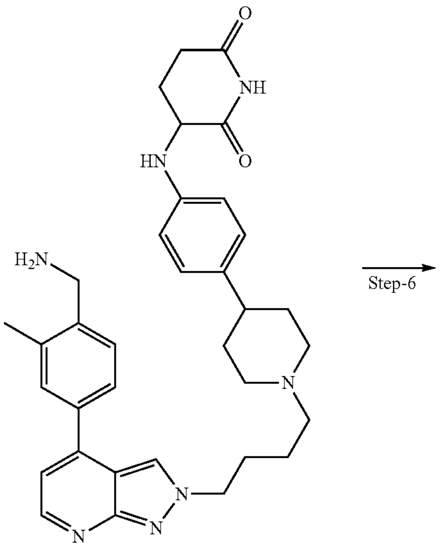
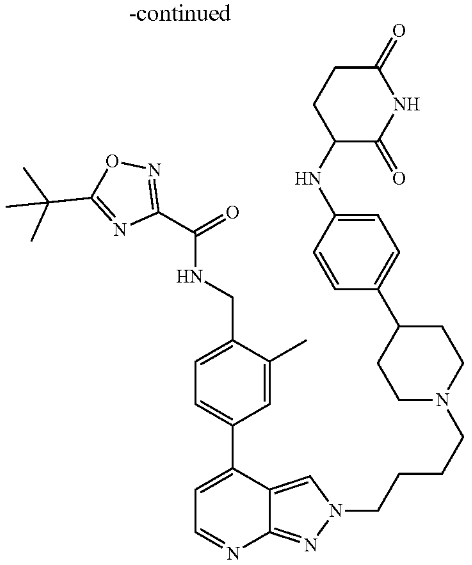
Reaction steps and conditions from step-3 to step-6 are identical to the representative compound Example 127 shown below.
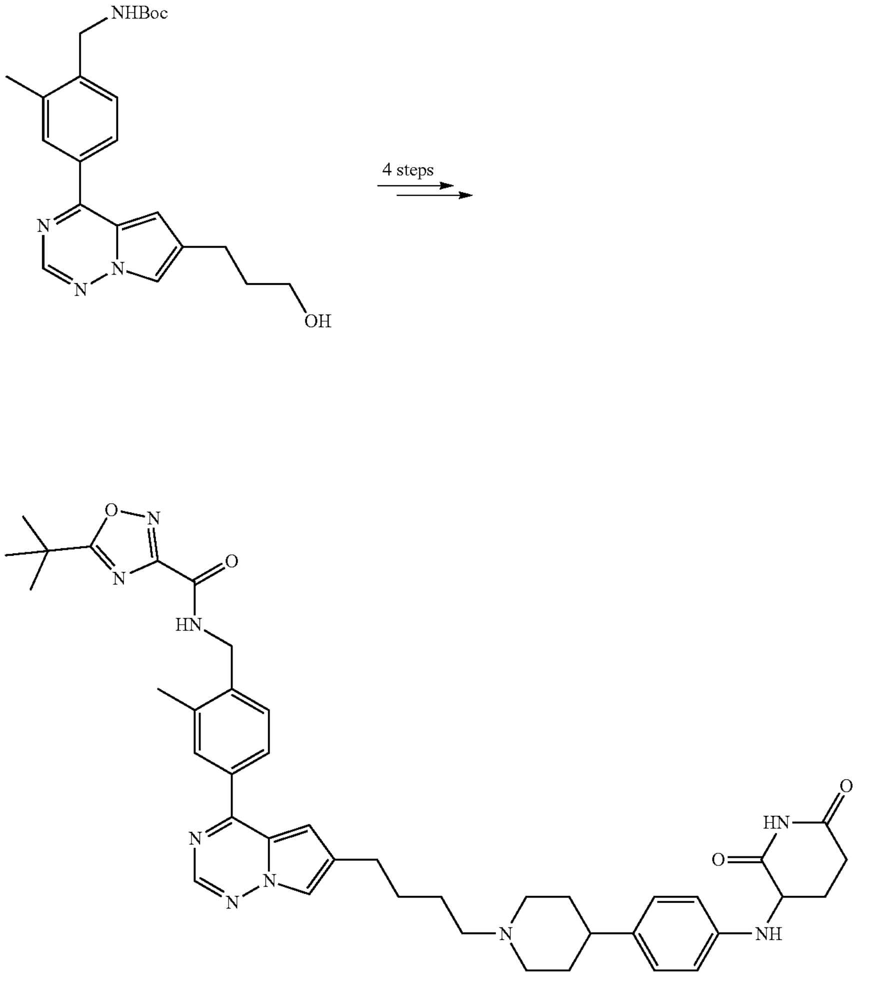

Step-1:

To a solution of 4-chloro-2H-pyrazolo[3,4-b]pyridine (5.0 g, 32.56 mmol) and 4-bromobutan-1-ol (4.98 g, 32.56 mmol) in DMF (50 mL) was added potassium carbonate (4.50 g, 32.56 mmol) and the reaction mixture was stirred at 70° C. for 16 hours. The reaction progress was monitored by TLC and LC-MS. After completion, the crude mixture was directly concentrated under reduced pressure and purified by reverse phase purification using 0.1% formic acid in $H_2O$/ACN to afford 4-(4-chloropyrazolo[3,4-b]pyridin-2-yl)butan-1-ol (0.7 g, 3.00 mmol, 9.23% yield) as a liquid. LC-MS ($ES^+$): m/z 226.4 $[M+H]^+$.

Step-2:

To a solution of 4-(4-chloropyrazolo[3,4-b]pyridin-2-yl)butan-1-ol (0.9 g, 3.99 mmol) and tert-butyl N-[[2-methyl-4-(4,4,5,5-tetramethyl-1,3,2-dioxaborolan-2-yl)phenyl]methyl]carbamate (1.66 g, 4.79 mmol) in dioxane (8 mL) and water (2 mL) was added potassium carbonate (1.69 g, 12.25 mmol) at room temperature. The reaction mixture was degassed with argon gas for 10 minutes and 4-ditert-butylphosphanyl-N,N-dimethyl-aniline; palladium(II); dichloride (271.13 mg, 398.80 µmol) was added. The reaction mixture was degassed with argon for an additional 5 minutes, and it was stirred at 80° C. for 16 hours. Subsequently, the reaction mixture was concentrated in vacuo to get the crude product, which was purified by column chromatography (Devisil silica, 2% methanol in DCM) to afford tert-butyl N-[[4-[2-(4-hydroxybutyl)pyrazolo[3,4-b]pyridin-4-yl]-2-methyl-phenyl]methyl]carbamate (0.3 g, 629.73 µmol, 15.79% yield) as a brown solid. LC-MS ($ES^+$): m/z 411.3 $[M+H]^+$.

Step-3:

tert-butyl N-[[2-methyl-4-[2-(4-oxobutyl)pyrazolo[3,4-b]pyridin-4-yl]phenyl]methyl]carbamate (0.25 g, 358.64 µmol, 58.89% yield). LC-MS ($ES^+$): m/z 409.5 $[M+H]^+$.

Step-4:

tert-butyl N-[[4-[2-[4-[4-[4-[(2,6-dioxo-3-piperidyl)amino]phenyl]-1-piperidyl]butyl]pyrazolo[3,4-b]pyridin-4-yl]-2-methyl-phenyl]methyl]carbamate (0.2 g, 162.59 mol, 22.14% yield). LC-MS ($ES^+$): m/z 680.3 $[M+H]^+$.

Step-5:

3-[4-[1-[4-[4-[4-(aminomethyl)-3-methyl-phenyl]pyrazolo[3,4-b]pyridin-2-yl]butyl]-4-piperidyl]anilino]piperidine-2,6-dione HCl salt (0.23 g, 170.09 µmol, 50.28% yield). LC-MS ($ES^-$): m/z 578.3 $[M-H]^-$.

Step-6

5-tert-butyl-N-[[4-[2-[4-[4-[4-[(2,6-dioxo-3-piperidyl)amino]phenyl]-1-piperidyl]butyl]pyrazolo[3,4-b]pyridin-4-yl]-2-methyl-phenyl]methyl]-1,2,4-oxadiazole-3-carboxamide TFA salt (36.3 mg, 38.85 µmol, 10.41% yield). $^1H$ NMR (400 MHz, DMSO-$d_6$) δ 10.77 (s, 1H), (t, J=6.0 Hz, 1H), 8.73 (s, 1H), 8.64 (d, J=4.4 Hz, 1H), 7.67 (d, J=6.0 Hz, 2H), 7.43 (d, J=8.4 Hz, 1H), 7.27 (d, J=4.4 Hz, 1H), 6.92 (d, J=8.0 Hz, 2H), 6.62 (d, J=8.4 Hz, 2H), 5.74 (d, J=7.2 Hz, 1H), 4.55-4.49 (m, 4H), 4.29-4.23 (m, 1H), 3.54-3.48 (m, 2H), 3.17-2.90 (m, 4H), 2.77-2.59 (m, 3H), 2.45 (s, 3H), 2.10-1.92 (m, 3H), 1.90-1.80 (m, 3H), 1.74-1.56 (m, 4H), 1.43 (s, 9H). LC-MS ($ES^+$): m/z 723.23 $[M+H]^+$.

Example 161. Synthesis of 5-tert-butyl-N-[[4-[2-[4-[[4-[4-[(2,6-dioxo-3-piperidyl)amino]phenyl]-1-piperidyl]methyl]phenyl]-1H-pyrrolo[2,3-b]pyridin-4-yl]-2-methyl-phenyl]methyl]-1,2,4-oxadiazole-3-carboxamide

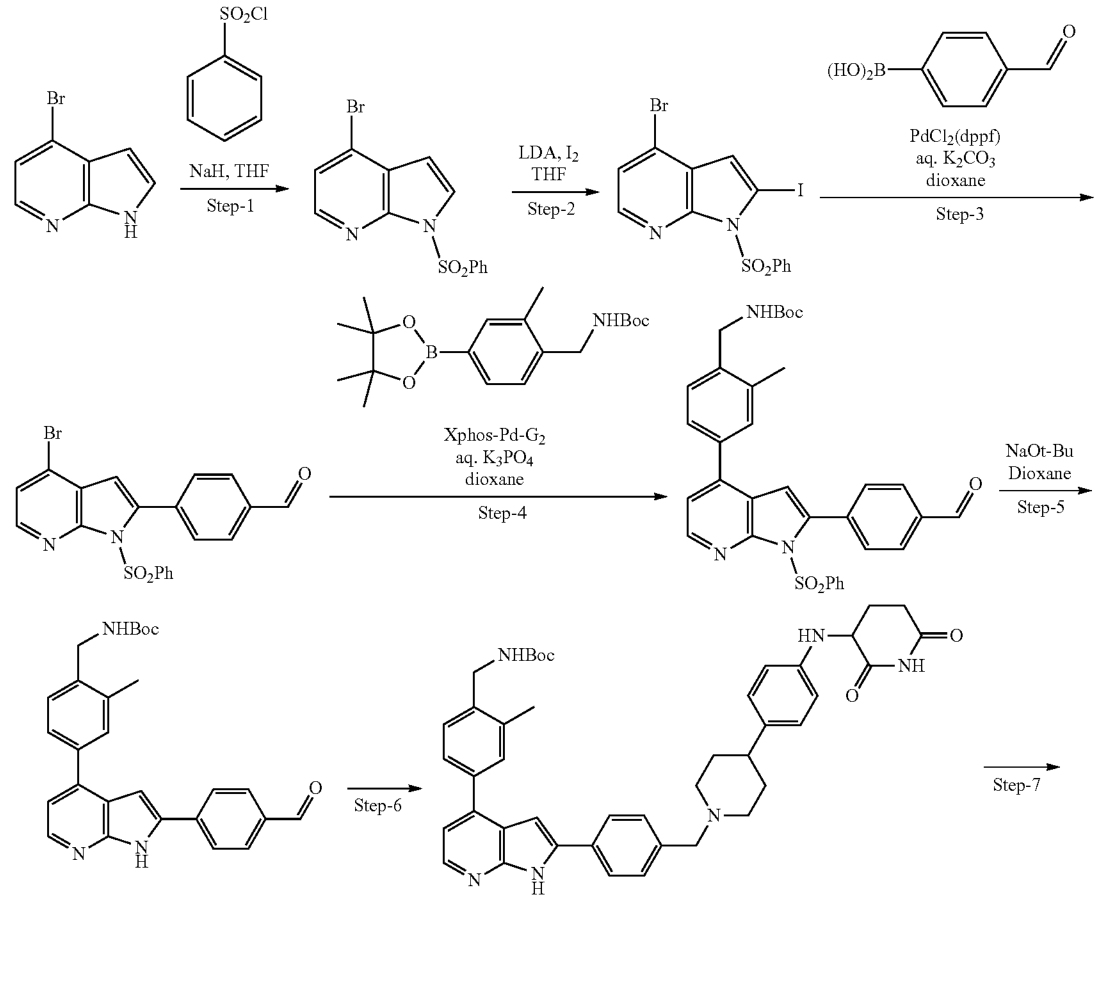

-continued

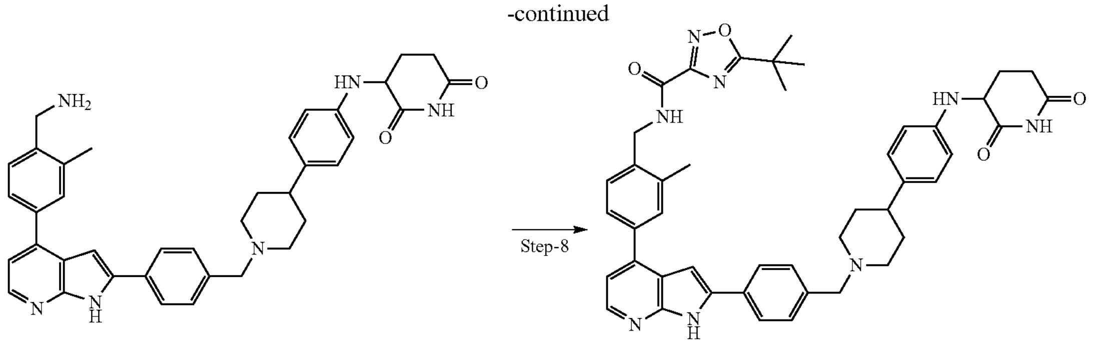

Reaction steps and conditions from step-6 to step-8 are identical (using different building blocks) to the representative compound Example 61 shown below.

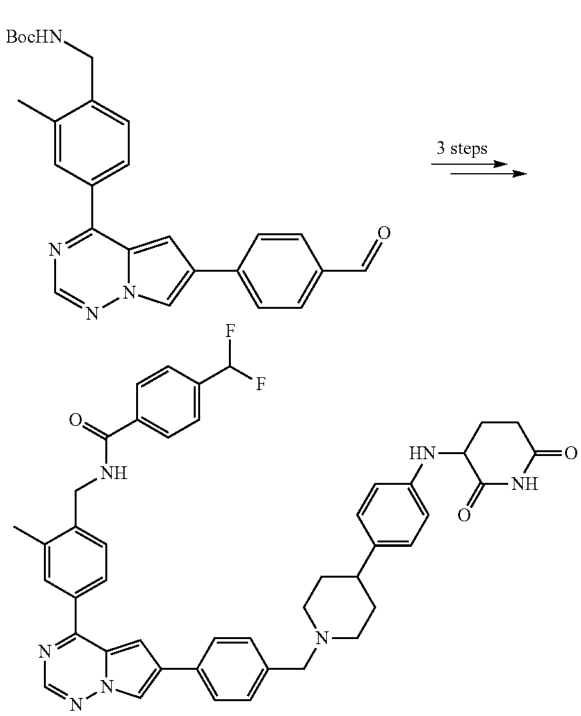

Step-1:

To a solution of 4-bromo-1H-pyrrolo[2,3-b]pyridine (15 g, 76.13 mmol) in THF (150 mL) was added sodium hydride, 60% dispersion in mineral oil (2.10 g, 91.36 mmol) at 0° C. and reaction mixture was stirred for 20 minutes at the same temperature, then benzenesulfonyl chloride (16.14 g, 91.36 mmol) was added and reaction mixture was stirred at room temperature for 12 hours. After completion of the reaction, the mixture was diluted with saturated ammonium chloride solution and extracted with ethyl acetate (200×2). The organic layer was dried under reduced pressure to afford 1-(benzenesulfonyl)-4-bromo-pyrrolo[2,3-b]pyridine (20 g, 55.16 mmol, 72.46% yield) as a yellow solid. LC-MS ($ES^+$): m/z 337.1 $[M+H]^+$.

Step-2:

A solution of 1-(benzenesulfonyl)-4-bromo-pyrrolo[2,3-b]pyridine (5 g, 14.83 mmol) in dry THF (80 mL) at −78° C. was treated dropwise with a freshly prepared solution of (diisopropylamino)lithium (3.18 g, 29.66 mmol) over 10 minutes. The resulting orange solution was stirred at −78° C. for 1 hour. Then, molecular iodine (4.89 g, 19.28 mmol) was added in portions at −78° C. and the resulting solution was stirred at −78° C. for 4 hours. The reaction mixture was quenched with aqueous sodium thiosulfate solution, diluted with DCM (100 mL) and the organic layer was separated. The aqueous layer was extracted with DCM and the combined organic layer was washed with brine, dried over anhydrous sodium sulfate, and evaporated under reduced pressure. The crude product was purified by flash column chromatography (silica gel 230-400 mesh, 5% ethyl acetate in pet ether) to afford 1-(benzenesulfonyl)-4-bromo-2-iodo-pyrrolo[2,3-b]pyridine (3 g, 5.83 mmol, 39.32% yield). LC-MS ($ES^+$): m/z 462.9 $[M+H]^+$.

Step-3:

Argon gas was purged through a solution of 1-(benzenesulfonyl)-4-bromo-2-iodo-pyrrolo[2,3-b]pyridine (8 g, 17.28 mmol), (4-formylphenyl)boronic acid (2.07 g, 13.82 mmol) and potassium carbonate, anhydrous, 99% (7.16 g, 51.83 mmol) in 1,4-dioxane (64 mL) and water (16 mL) for 15 minutes followed by the addition of [1,1'-Bis(diphenylphosphino)ferrocene]palladium(II) dichloride (1.26 g, 1.73 mmol). The resulting mixture was stirred at 60° C. for 10 hours. The reaction mixture was filtered through celite and washed with ethyl acetate (100 mL×3). The filtrate was washed with water (100 mL) and brine solution (100 mL) and combined organic layers were dried over anhydrous sodium sulfate, filtered, then concentrated under reduced pressure. The crude mixture was purified by column chromatography (silica gel 230-400 mesh, 0-100% ethyl acetate in pet ether) to afford 4-[1-(benzenesulfonyl)-4-bromo-pyrrolo[2,3-b]pyridin-2-yl]benzaldehyde (2.8 g, 4.65 mmol, 26.93% yield). LC-MS ($ES^+$): m/z 441.2 $[M+H]^+$.

Step-4:

Argon gas was purged through a solution of 4-[1-(benzenesulfonyl)-4-bromo-pyrrolo[2,3-b]pyridin-2-yl]benzaldehyde (2.8 g, 6.34 mmol), tert-butyl N-[[2-methyl-4-(4,4,5,5-tetramethyl-1,3,2-dioxaborolan-2-yl)phenyl]methyl] carbamate (2.20 g, 6.34 mmol) and potassium carbonate, anhydrous, 99% (2.63 g, 19.03 mmol) in 1,4-dioxane (32 mL) and water (8 mL) for 15 minutes followed by the addition of [1,1'-Bis(diphenylphosphino)ferrocene]palladium(II) dichloride (464.26 mg, 634.49 μmol). The resulting mixture was stirred at 80° C. for 16 hours. The reaction mixture was filtered through celite and washed with ethyl acetate (100 mL×3). The filtrate was washed with water (100 mL) and brine solution (100 mL). The combined organic layers were dried over anhydrous sodium sulfate, filtered, and concentrated under reduced pressure. The crude material was purified by column chromatography (silica gel 230-400 mesh, 0-100% ethyl acetate in pet ether) to afford tert-butyl N-[[4-[1-(benzenesulfonyl)-2-(4-formylphenyl) pyrrolo[2,3-b]pyridin-4-yl]-2-methyl-phenyl]methyl]carbamate (2.8 g, 4.04 mmol, 63.69% yield). LC-MS ($ES^+$): m/z 582.4 $[M+H]^+$.

Step-5:

A solution of tert-butyl N-[[4-[L-(benzenesulfonyl)-2-(4-formylphenyl)pyrrolo[2,3-b]pyridin-4-yl]-2-methyl-phenyl] methyl]carbamate (3.1 g, 5.33 mmol) in dioxane (50 mL) was purged with argon for 5 minutes before sodium tert-butoxide (768.26 mg, 7.99 mmol) was added, and the resulting mixture was stirred for 6 hours at 80° C. The reaction was monitored by TLC and LC-MS. The reaction mixture was then quenched with water (100 mL) and washed with ethyl acetate (100 mL×2). The filtrate was washed with water (100 mL) and brine solution (100 mL). The combined organic layers were dried over anhydrous sodium sulfate, filtered, and concentrated under reduced pressure. The crude mixture was purified by column chromatography (silica gel 100-200 mesh, 0-100% ethyl acetate in pet ether) to afford tert-butyl N-[[4-[2-(4-formylphenyl)-1H-pyrrolo[2,3-b]pyridin-4-yl]-2-methyl-phenyl]methyl] carbamate (1.1 g, 2.37 mmol, 44.41% yield). LC-MS ($ES^+$): m/z 442.4 $[M+H]^+$.

Step-6:

tert-butyl N-[[4-[2-[4-[[4-[4-[(2,6-dioxo-3-piperidyl) amino]phenyl]-1-piperidyl]methyl]phenyl]-1H-pyrrolo[2,3-b]pyridin-4-yl]-2-methyl-phenyl]methyl]carbamate (0.22 g, 163.28 μmol, 72.09% yield). LC-MS ($ES^+$): m/z 713.5 $[M+H]^+$.

Step-7:

3-[4-[1-[[4-[4-[4-(aminomethyl)-3-methyl-phenyl]-1H-pyrrolo[2,3-b]pyridin-2-yl]phenyl]methyl]-4-piperidyl]anilino]piperidine-2,6-dione HCl salt (0.182 g, 133.02 μmol, 47.41% yield). LC-MS ($ES^+$): m/z 613.5 $[M+H]^+$.

Step-8:

5-tert-butyl-N-[[4-[2-[4-[[4-[4-[(2,6-dioxo-3-piperidyl) amino]phenyl]-1-piperidyl]methyl]phenyl]-1H-pyrrolo[2,3-b]pyridin-4-yl]-2-methyl-phenyl]methyl]-1,2,4-oxadiazole-3-carboxamide TFA salt (29 mg, 31.95 μmol, 11.52% yield). $^1H$ NMR (400 MHz, DMSO-$d_6$) δ 12.38 (s, 1H), 10.77 (s, 1H), 9.56 (t, J=5.9 Hz, 1H) 9.45 (bs, 1H), 8.30 (d, J=5.0 Hz, 1H), 8.12 (d, J=8.2 Hz, 2H), 7.66-7.60 (m, 4H), 7.43 (d, J=7.7 Hz, 1H), 7.20 (d, J=5.0 Hz, 2H), 6.94 (d, J=7.7 Hz, 2H), 6.63 (d, J=8.5 Hz, 2H), 4.54 (d, J=5.9 Hz, 2H), 4.37-4.25 (m, 3H), 3.60-3.40 (m, 31H), 3.11-3.05 (m, 2H), 2.73-2.51 (m, 2H), 2.47 (s, 3H), 2.12-2.05 (m, 1H), 1.97-1.77 (m, 5H), 1.44 (s, 9H). LC-MS ($ES^+$): m/z 765.46 $[M+H]^+$.

Example 162. Synthesis of 5-tert-butyl-N-[[4-[2-[4-[[4-[4-[(2,6-dioxo-3-piperidyl)amino]phenyl]-1-piperidyl]methyl]phenyl]pyrazolo[1,5-a]pyrimidin-7-yl]-2-methyl-phenyl]methyl]-1,2,4-oxadiazole-3-carboxamide

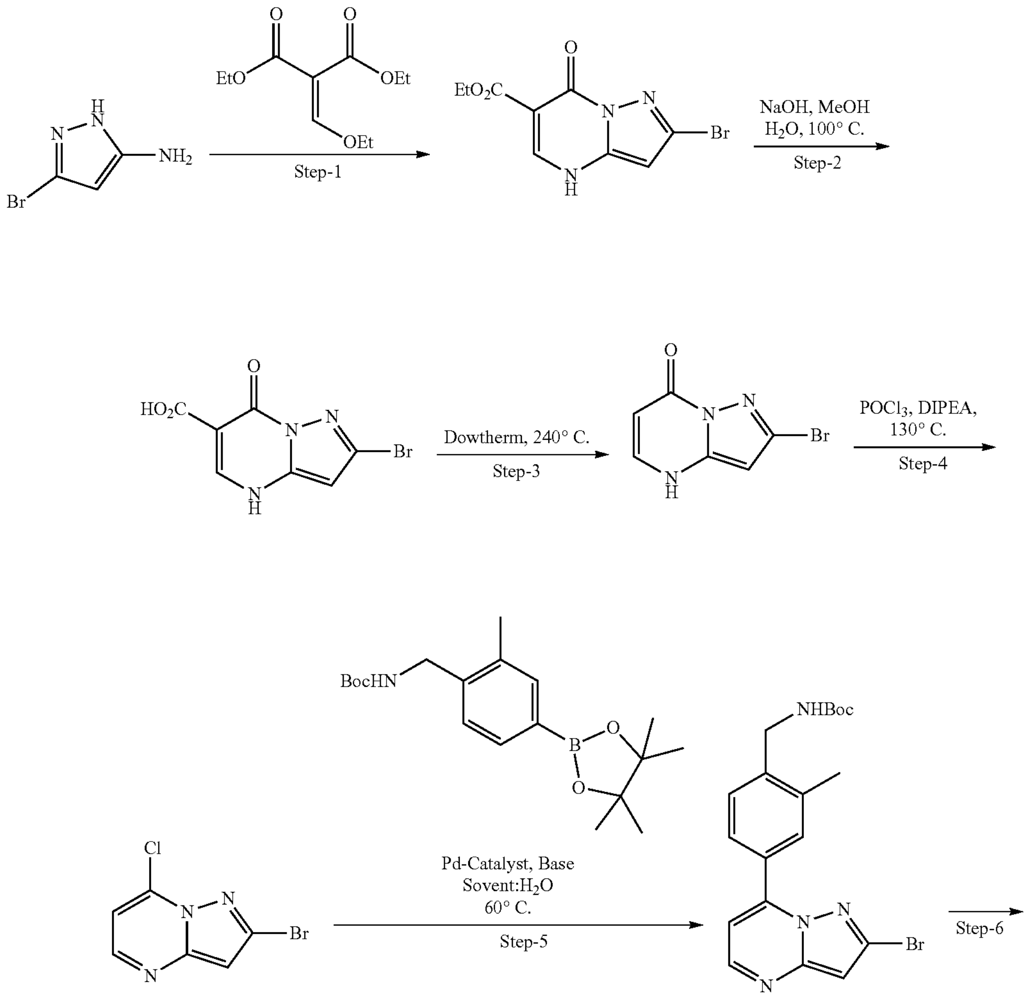

-continued

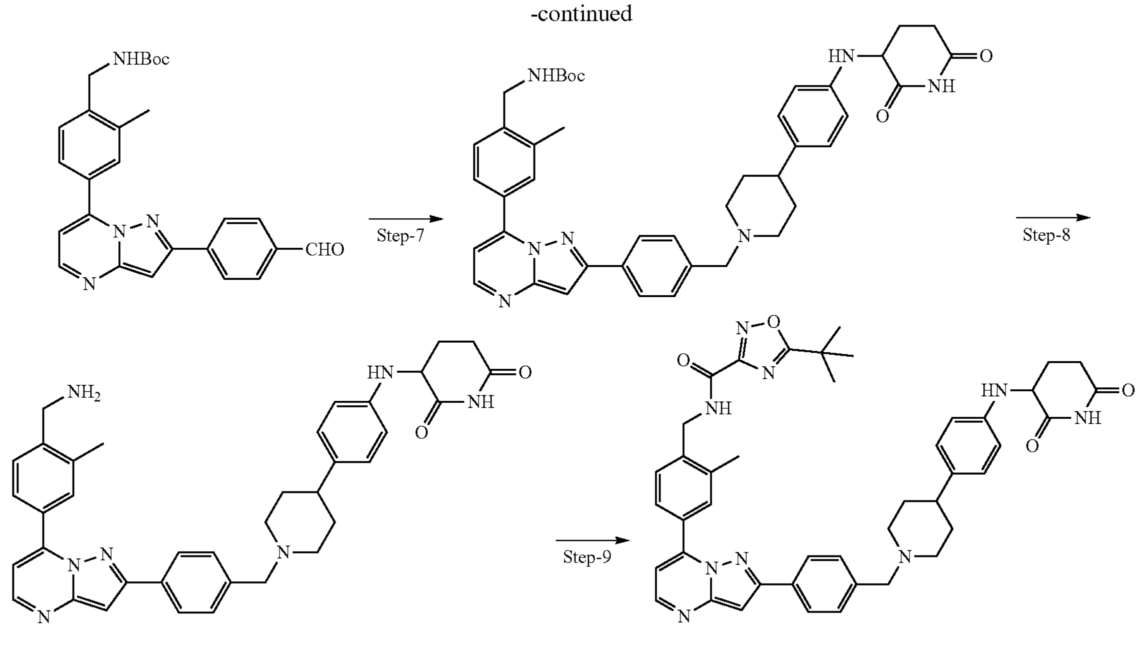

Reaction steps and conditions from step-6 to step-9 are identical (using different building blocks) to the representative compound Example 61 shown below.

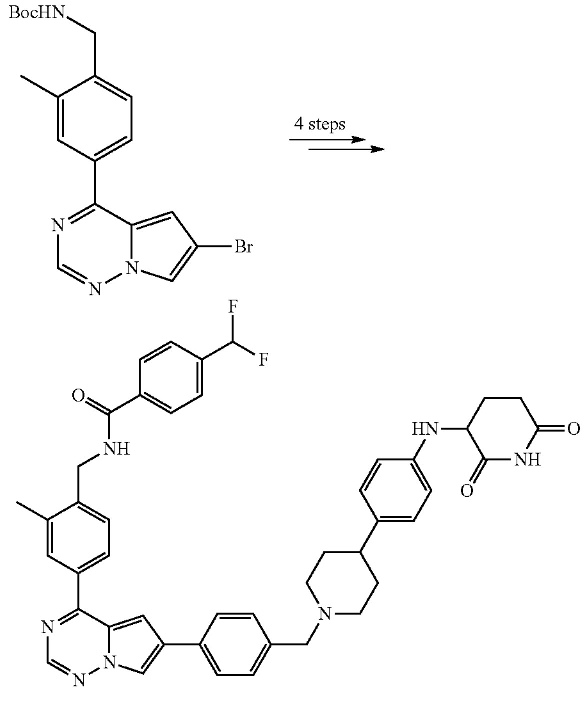

Step-1:

To a solution of 3-bromo-1H-pyrazol-5-amine (23 g, 141.99 mmol) in acetic acid (860 mL) was added diethyl 2-(ethoxymethylene)propanedioate (33.77 g, 156.18 mmol, 31.27 mL) at room temperature. The mixture was refluxed for 4 hours, cooled to room temperature, and the acetic acid was removed in vacuo. The crude solid was suspended in cold ethanol, then filtered and washed with cold ethanol to yield ethyl 2-bromo-7-oxo-4H-pyrazolo[1,5-a]pyrimidine-6-carboxylate (32 g, 106.26 mmol, 74.84% yield) as a white solid. LC-MS ($ES^+$): m/z 286.3 $[M+H]^+$.

Step-2:

To a stirred solution of ethyl 2-bromo-7-oxo-4H-pyrazolo[1,5-a]pyrimidine-6-carboxylate (32 g, 111.86 mmol) in ethanol (270 mL) was added 2.5 N NaOH solution. Then, the reaction mixture was heated to reflux and stirred for 12 hours at 100° C. Then, the reaction was cooled to 0° C. and saturated citric acid solution was added to adjust the pH and the mixture stirred for 45 minutes. The mixture was filtered and the wet solid was azeotroped with toluene (3×200 mL) to yield 2-bromo-7-oxo-4H-pyrazolo[1,5-a]pyrimidine-6-carboxylic acid (28 g, 103.09 mmol, 92.16% yield) as a white solid. LC-MS ($ES^+$): m/z 258.2 $[M+H]^+$.

Step-3:

A solution of 2-bromo-7-oxo-4H-pyrazolo[1,5-a]pyrimidine-6-carboxylic acid (2 g, 7.75 mmol) in Dowtherm oil (33 mL) was heat at 240° C. and stirred for 3 hours. Then, the reaction was cooled to room temperature and diluted with hexane (50 ml). The precipitate was filtered, and resuspended and stirred in hexanes (150 ml) to give 2-bromo-4H-pyrazolo[1,5-a]pyrimidin-7-one (1.70 g, 7.55 mmol, 97.35% yield) as an off white solid. $^1H$ NMR (400 MHz, DMSO-$d_6$) δ 7.85 (d, J=7.2 Hz, 1H), 6.33 (s, 1H), 5.70 (d, J=7.2 Hz, 1H).

Step-4:

To 2-bromopyrazolo[1,5-a]pyrimidin-7(4H)-one (1 g, 4.67 mmol) was added $POCl_3$ (35.82 g, 233.62 mmol) and DIPEA (1.33 g, 10.28 mmol, 1.79 mL) at 0° C. After that the reaction mixture was warmed to 100° C. and stirred for 16 hours. Upon the completion of the reaction, the reaction mixture was concentrated in vacuo, the residual mass was dissolved in ethyl acetate (50 ml) and then quenched by saturated solution of sodium bicarbonate. The reaction mixture was partitioned between water and ethyl acetate. The organic layer was separated, washed with brine dried over anhydrous sodium sulfate to afford the crude product which was then purified by column chromatography (silica gel 100-200 mesh, 15-20% ethyl acetate in pet ether) to afford 2-bromo-7-chloropyrazolo[1,5-a]pyrimidine (0.6 g, 2.58 mmol, 55.15% yield) as an off white solid. LC-MS ($ES^+$): m/z 232.0 $[M+H]^+$.

Step-5:

To a solution of 2-bromo-7-chloro-pyrazolo[1,5-a]pyrimidine (1.7 g, 7.31 mmol) and tert-butyl N-[[2-methyl-4-(4,4,5,5-tetramethyl-1,3,2-dioxaborolan-2-yl)phenyl]methyl]carbamate (2.03 g, 5.85 mmol) in dioxane (40 mL) was added potassium carbonate—granular (2.02 g, 14.63 mmol) in water (8 mL) and the mixture was purged with nitrogen gas for 15 minutes. Then, $Pd(dppf)Cl_2 \cdot CH_2Cl_2$ (267.55 mg, 365.65 μmol) was added, and the reaction mixture was purged with nitrogen gas for another 5 minutes. Then the reaction mixture was heated to 60° C. and stirred for 2 hours while monitoring by TLC and LCMS. After completion, the reaction mixture was filtered through a celite bed. The filtrate was concentrated to obtain the crude product, which was purified by normal phase column chromatography (Devisil silica, 20% ethyl acetate/petroleum ether) using Biotage® to obtain tert-butyl N-[[4-(2-bromopyrazolo[1,5-a]pyrimidin-7-yl)-2-methyl-phenyl]methyl]carbamate (1.4 g, 3.10 mmol, 42.34% yield). LC-MS ($ES^+$): m/z 5417.5 $[M+H]^+$.

Step-6:

tert-butyl N-[[4-[2-(4-formylphenyl)pyrazolo[1,5-a]pyrimidin-7-yl]-2-methyl-phenyl]methyl]carbamate (0.225 g, 401.69 μmol, 55.87% yield). LC-MS ($ES^+$): m/z 443.4 $[M+H]^+$.

Step-7:

tert-butyl N-[[4-[2-[4-[[4-[4-[(2,6-dioxo-3-piperidyl)amino]phenyl]-1-piperidyl]methyl]phenyl]pyrazolo[1,5-a]pyrimidin-7-yl]-2-methyl-phenyl]methyl]carbamate (0.14 g, 166.70 μmol, 36.88% yield). LC-MS ($ES^+$): m/z 714.6 $[M+H]^+$.

Step-8:

3-[4-[1-[[4-[7-[4-(aminomethyl)-3-methyl-phenyl]pyrazolo[1,5-a]pyrimidin-2-yl]phenyl]methyl]-4-piperidyl]anilino]piperidine-2,6-dione HCl salt (0.12 g, 129.19 μmol, 61.48% yield). LC-MS ($ES^+$): m/z 614.4 $[M+H]^+$.

Step-9:

5-tert-butyl-N-[[4-[2-[4-[[4-[4-[(2,6-dioxo-3-piperidyl)amino]phenyl]-1-piperidyl]methyl]phenyl]pyrazolo[1,5-a]pyrimidin-7-yl]-2-methyl-phenyl]methyl]-1,2,4-oxadiazole-3-carboxamide TFA salt (26 mg, 28.58 μmol, 16.02% yield). $^1H$ NMR (400 MHz, DMSO-$d_6$) δ 10.77 (s, 1H), 9.55 (bs, 2H), 8.62 (s, 1H), 8.14-8.02 (m, 4H), 7.65 (d, J=7.8 Hz, 2H), 7.48-7.39 (m, 2H), 7.26-6.92 (m, 3H), 6.63 (d, J=7.8 Hz, 2H), 4.57 (d, J=5.2 Hz, 2H), 4.39 (bs, 2H), 4.27-4.25 (m, 1H), 3.30-3.45 (m, 2H), 3.08-3.05 (m, 2H), 2.72-2.59 (m, 3H), 2.49 (s, 3H), 2.15-2.05 (m, 1H), 1.95-1.78 (m, 5H), 1.44 (s, 9H). LC-MS ($ES^+$): m/z 764.36 $[M+H]^+$.

Example 163. Synthesis of 5-tert-butyl-N-[[4-[2-[4-[4-[4-[(2,6-dioxo-3-piperidyl)amino]phenyl]-1-piperidyl]butyl]pyrazolo[1,5-a]pyrimidin-7-yl]-2-methyl-phenyl]methyl]-1,2,4-oxadiazole-3-carboxamide

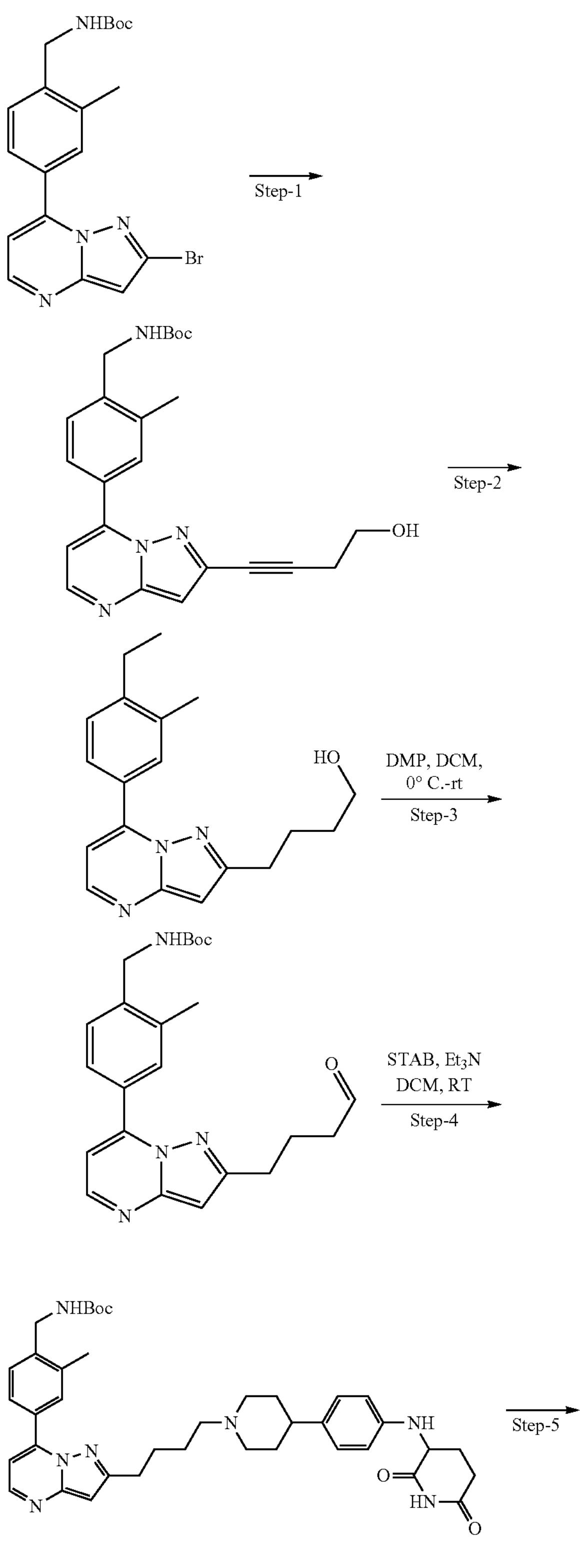

-continued

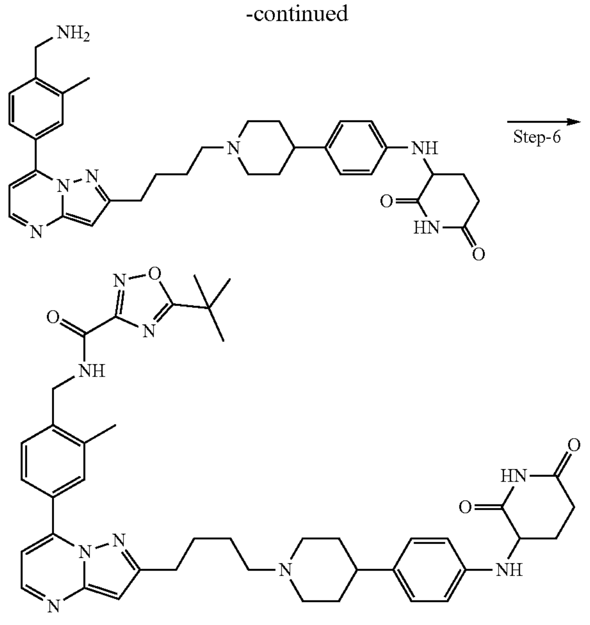

Unless otherwise noted, reaction steps and conditions are identical to the representative compound Example 130 shown below.

Step-1:

tert-butyl N-[[4-[2-(4-hydroxybut-1-ynyl)pyrazolo[1,5-a]pyrimidin-7-yl]-2-methyl-phenyl]methyl]carbamate (0.5 g, 1.06 mmol, 44.14% yield). LC-MS ($ES^+$): m/z 407.3 $[M+H]^+$.

Step-2:

tert-butyl N-[[4-[2-(4-hydroxybutyl)pyrazolo[1,5-a]pyrimidin-7-yl]-2-methyl-phenyl]methyl]carbamate (0.285 g, 624.84 μmol, 36.28% yield). LC-MS ($ES^+$): m/z 411.5 $[M+H]^+$.

Step-3:

To a solution of tert-butyl N-[[4-[2-(4-hydroxybutyl)pyrazolo[1,5-a]pyrimidin-7-yl]-2-methyl-phenyl]methyl]carbamate (0.466 g, 1.14 mmol) dissolved in DCM (5 mL) was added (1,1,1-triacetoxy)-1,1-dihydro-1,2-benziodoxol-3(1H)-one (481.48 mg, 1.14 mmol) and sodium; hydrogen carbonate (95.36 mg, 1.14 mmol) at 0° C. and then stirred for 3 hours at room temperature. After the completion, the mixture was partitioned between water and DCM. The organic layer was separated and washed further with a saturated solution of sodium thiosulfate and $NaHCO_3$ aqueous solution. The organic layer was washed with brine dried over $Na_2SO_4$ to afford crude product. The crude mixture was purified by column chromatography using silica (100-200 mesh size) and 0-100% EtOAc/Petroleum ether as eluent to afford the product tert-butyl N-[[2-methyl-4-[2-(4-oxobutyl)pyrazolo[1,5-a]pyrimidin-7-yl]phenyl]methyl]carbamate

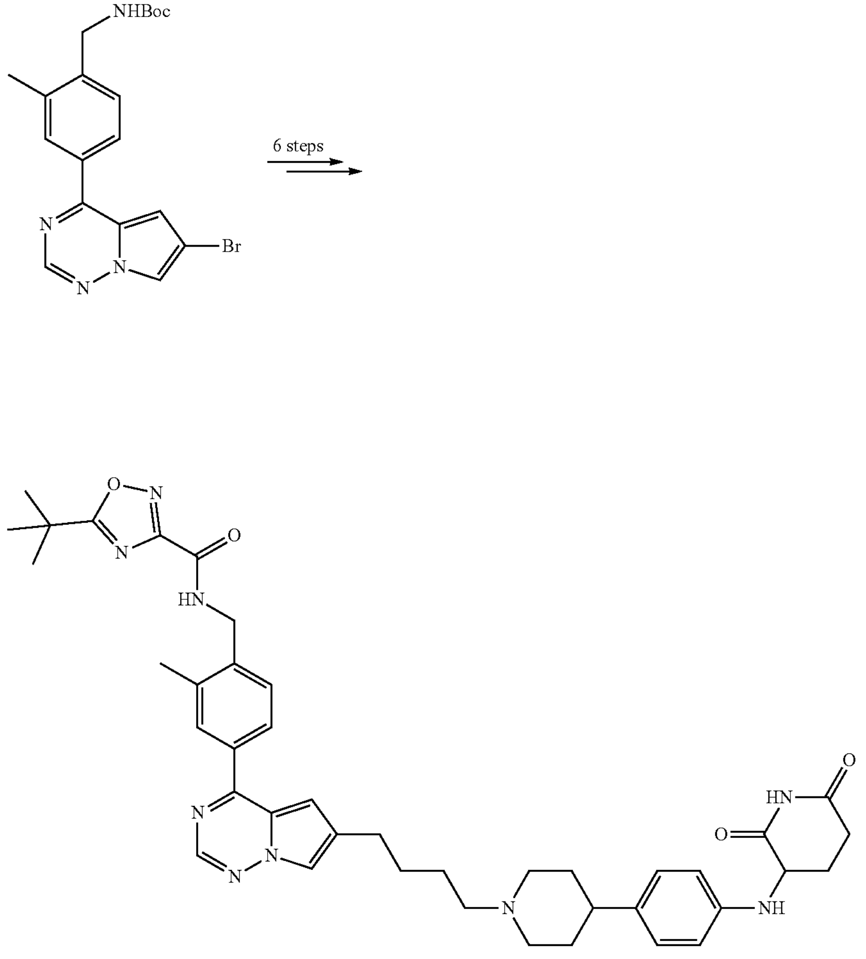

(0.170 g, 249.70 μmol, 22.00% yield) as a light yellow viscous oil. LC-MS ($ES^+$): m/z 409.4 $[M+H]^+$.

Step-4:

To a solution of 3-[4-(4-piperidyl)anilino]piperidine-2,6-dione TFA salt (483.43 mg, 1.20 mmol) dissolved in DCM (4 mL) was added triethylamine (487.50 mg, 4.82 mmol, 671.49 μL) and stirred for 30 minutes. Reactant tert-butyl N-[[2-methyl-4-[2-(4-oxobutyl)pyrazolo[1,5-a]pyrimidin-7-yl]phenyl]methyl]carbamate (0.164 g, 401.48 μmol) was added to the reaction mixture and stirred for 2 hours at room temperature. The reaction mixture was cooled to 0° C., and sodium triacetoxyborohydride was added (510.54 mg, 2.41 mmol) and then stirred for further 14 hours at room temperature. The reaction was monitored by TLC and LC-MS. Then, the reaction mixture was concentrated in vacuo and was diluted with a saturated solution of $NaHCO_3$. The reaction mixture was filtered through filter paper to afford the product which was purified by column chromatography using silica (100-200 mesh size) and 0-10% MeOH/DCM as eluent to afford the product tert-butyl N-[[4-[2-[4-[4-[4-[(2,6-dioxo-3-piperidyl)amino]phenyl]-1-piperidyl]butyl]pyrazolo[1,5-a]pyrimidin-7-yl]-2-methyl-phenyl]methyl]carbamate (0.05 g, 58.84 μmol, 14.66% yield) as a light blue solid. LC-MS ($ES^+$): m/z 680.4 $[M+H]^+$.

Step-5:

3-[4-[1-[4-[7-[4-(aminomethyl)-3-methyl-phenyl]pyrazolo[1,5-a]pyrimidin-2-yl]butyl]-4-piperidyl]anilino]piperidine-2,6-dione HCl salt (0.038 g, 39.47 μmol, 58.33% yield). LC-MS ($ES^+$): m/z 580.4 $[M+H]^+$.

Step-6:

5-tert-butyl-N-[[4-[2-[4-[4-[4-[(2,6-dioxo-3-piperidyl)amino]phenyl]-1-piperidyl]butyl]pyrazolo[1,5-a]pyrimidin-7-yl]-2-methyl-phenyl]methyl]-1,2,4-oxadiazole-3-carboxamide TFA salt (8.9 mg, 9.77 μmol, 17.20% yield).

$^1H$ NMR (400 MHz, DMSO-$d_6$) δ 10.77 (s, 1H), 9.53 (t, J=5.9 Hz, 1H), 8.91 (bs, 1H), 8.54 (d, J=4.4 Hz, 1H), 7.95 (d, J=7.9 Hz, 1H), 7.90 (s, 1H), 7.43 (d, J=7.9 Hz, 1H), 7.13 (d, J=4.4 Hz, 1H), 6.95-6.92 (m, 2H), 6.68 (s, 1H), 6.63 (d, J=8.4 Hz, 2H), 5.74 (bs, 1H), 4.54 (d, J=5.9 Hz, 2H), 4.28-4.26 (m, 1H), 3.53-3.50 (m, 2H), 3.11 (bs, 2H), 2.98-2.95 (m, 2H), 2.85-2.83 (m, 2H), 2.62-2.59 (m, 3H), 2.43 (s, 3H), 2.11-2.02 (m, 1H), 1.99-1.90 (m, 3H), 1.77-1.67 (m, 6H), 1.43 (s, 9H).

LC-MS ($ES^+$): m/z 732.2 $[M+H]^+$.

Mobile phase-A: 10 mM Ammonium Acetate in Water

Mobile phase-B: ACN

Column: X Bridge BEH C18 2.5 μm, 2.1×50 mm

Flow: 0.5 mL/min

Temp: 40° C.

Time (min) and % B: 0-10; 0.5-10; 6.0-90; 8.6-90; 9.0-10; 10.50-10

Example 164 and Example 165. Synthesis of 5-tert-butyl-N-[[4-[2-[4-[[4-[3-(2,4-dioxohexahydropyrimidin-1-yl)-1-methyl-indazol-6-yl]-1-piperidyl]methyl]phenyl]pyrazolo[1,5-a]pyrimidin-7-yl]-2-fluoro-phenyl]methyl]-1,2,4-oxadiazole-3-carboxamide (Example 164) and 3-tert-butoxy-N-[[4-[2-[4-[[4-[3-(2,4-dioxohexahydropyrimidin-1-yl)-1-methyl-indazol-6-yl]-1-piperidyl]methyl]phenyl]pyrazolo[1,5-a]pyrimidin-7-yl]-2-fluoro-phenyl]methyl]azetidine-1-carboxamide (Example 165)

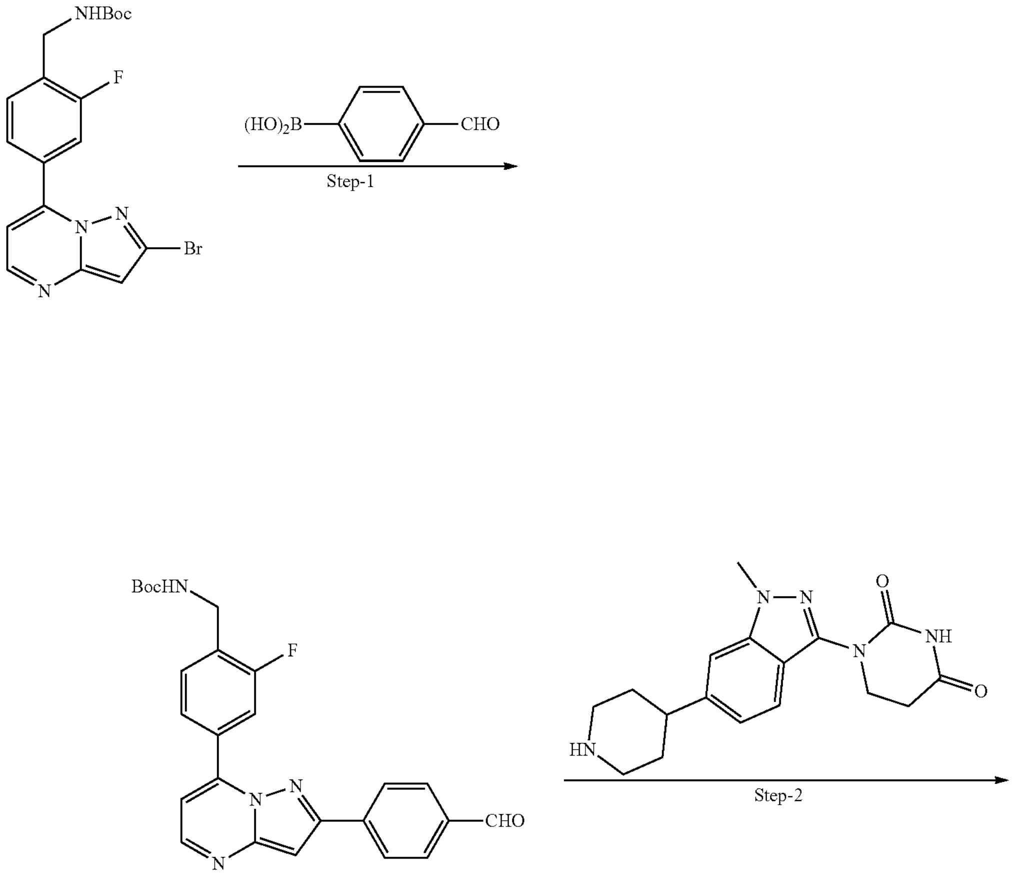

-continued
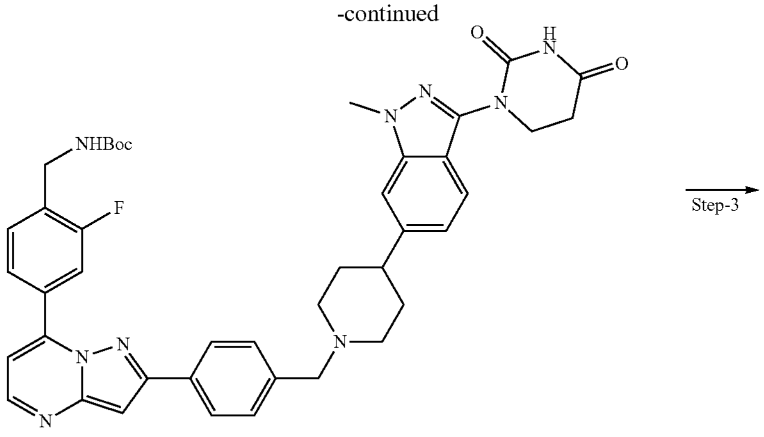
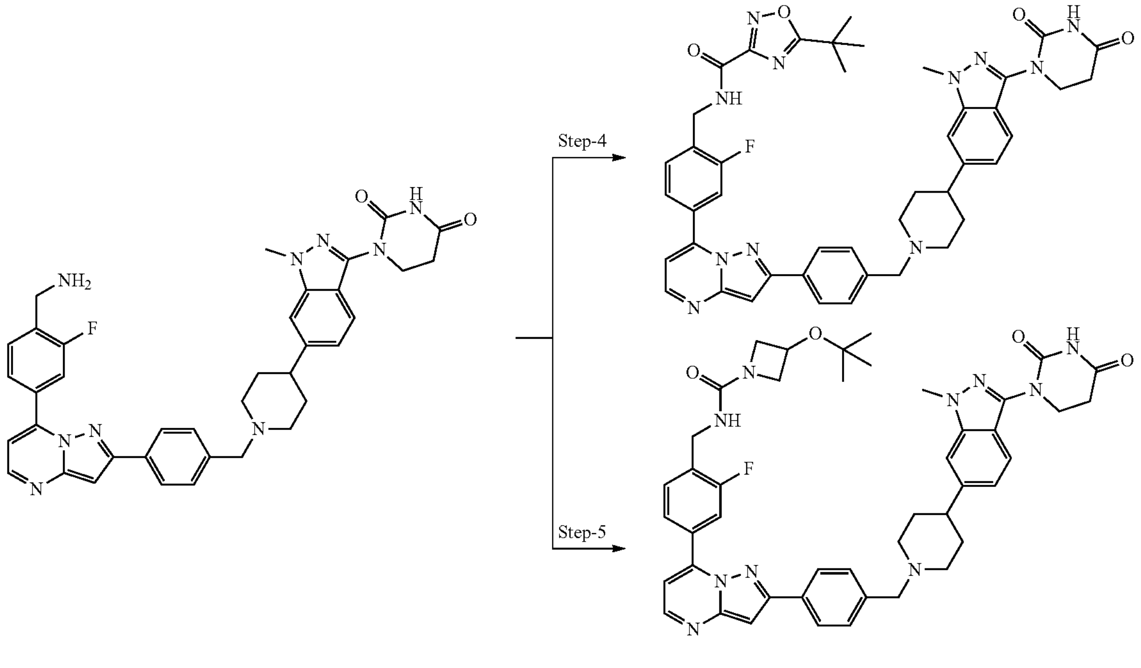
Reaction steps and conditions are identical (using different building blocks) to the representative compound Example 61 shown below.
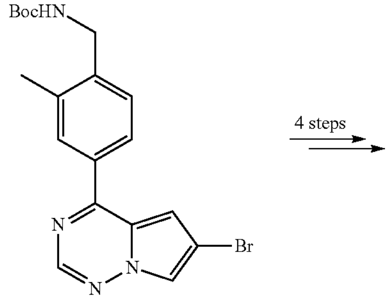
-continued
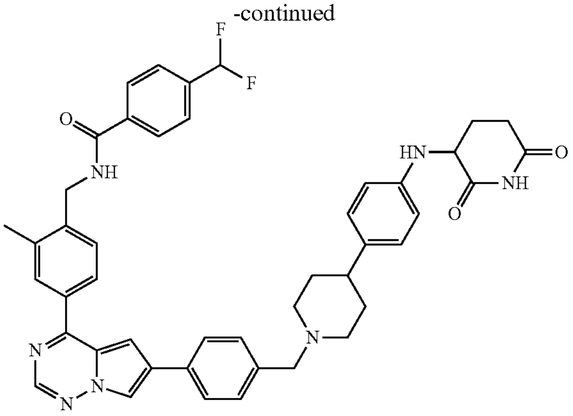

Step-1:

tert-butyl N-[[2-fluoro-4-[2-(4-formylphenyl)pyrazolo[1,5-a]pyrimidin-7-yl]phenyl]methyl]carbamate (0.45 g, 952.06 μmol, 61.70% yield). LC-MS ($ES^+$): m/z 447.4 $[M+H]^+$.

Step-2:

tert-butyl N-[[4-[2-[4-[[4-[3-(2,4-dioxohexahydropyrimidin-1-yl)-1-methyl-indazol-6-yl]-1-piperidyl]methyl]phenyl]pyrazolo[1,5-a]pyrimidin-7-yl]-2-fluoro-phenyl]methyl]carbamate (0.35 g, 420.27 μmol, 41.70% yield). LC-MS ($ES^+$): m/z 758.5 $[M+H]^+$.

Step-3:

1-[6-[1-[[4-[7-[4-(aminomethyl)-3-fluoro-phenyl]pyrazolo[1,5-a]pyrimidin-2-yl]phenyl]methyl]-4-piperidyl]-1-methyl-indazol-3-yl]hexahydropyrimidine-2,4-dione HCl salt (0.3 g, 384.96 μmol, 83.36% yield). LC-MS ($ES^+$): m/z 658.4 $[M+H]^+$.

Step-4:

5-tert-butyl-N-[[4-[2-[4-[[4-[3-(2,4-dioxohexahydropyrimidin-1-yl)-1-methyl-indazol-6-yl]-1-piperidyl]methyl]phenyl]pyrazolo[1,5-a]pyrimidin-7-yl]-2-fluoro-phenyl]methyl]-1,2,4-oxadiazole-3-carboxamide TFA salt (52 mg, 56.23 μmol, 32.53% yield). 1H NMR (400 MHz, DMSO-$d_6$) δ 10.55 (s, 1H), 9.61 (t, J=5.9 Hz, 1H), 8.58 (bs, 1H), 8.65 (d, J=4.4 Hz, 1H), 8.18-8.15 (m, 3H), 8.08-8.06 (m, 1H), 7.71-7.60 (m, 4H), 7.44 (s, 1H), 7.39 (s, 1H), 7.33 (d, J=4.4 Hz, 1H) 7.02 (d, J=8.8, 1H), 4.63 (d, J=5.9 Hz, 2H), 4.44 (d, J=4.1 Hz, 2H), 3.97 (s, 3H), 3.90 (t, J=6.8 Hz, 2H), 3.20-2.95 (m, 5H), 2.75 (t, J=6.8 Hz, 2H), 2.32-1.95 (m, 4H), 1.44 (s, 9H).

LC-MS ($ES^+$): m/z 810.6 $[M+H]^+$.

Mobile phase-A: 0.1% FA in H2O

Mobile phase-B: ACN

Column: X Bridge BEH C18 2.5 μm, 2.1×50 mm

Flow: 0.6 mL/min

Temp: 40° C.

Time (min) and % B: 0-5; 0.3-5; 2.5-95; 3.7-95; 4-5; 4.8-5

Step-5:

3-tert-butoxy-N-[[4-[2-[4-[[4-[3-(2,4-dioxohexahydropyrimidin-1-yl)-1-methyl-indazol-6-yl]-1-piperidyl]methyl]phenyl]pyrazolo[1,5-a]pyrimidin-7-yl]-2-fluoro-phenyl]methyl]azetidine-1-carboxamide TFA salt (54 mg, 57.50 μmol, 33.26% yield).

1H NMR (400 MHz, DMSO-$d_6$) δ 10.55 (s, 1H), 9.50 (s, 1H), 8.65 (d, J=4.4 Hz, 1H), 8.18-8.04 (m, 4H), 7.74 (d, J=8.4 Hz, 2H), 7.69-7.55 (m, 2H), 7.44 (s, 1H), 7.39 (d, J=4.4 Hz, 1H), 7.08-7.00 (m, 2H), 4.45-4.36 (m, 5H), 4.07-4.01 (m, 2H), 3.97 (s, 3H), 3.91 (t, J=6.1 Hz, 2H), 3.64-3.54 (m, 4H), 3.18-3.15 (m, 2H), 3.02-3.96 (m, 1H), 2.79 (t, J=6.1 Hz, 2H), 2.11-1.92 (m, 4H), 1.13 (s, 9H).

LC-MS ($ES^+$): m/z 811.3 $[M+H]^+$.

Mobile phase-A: 0.1% FA in H2O

Mobile phase-B: ACN

Column: X Bridge BEH C18 2.5 μm, 2.1×50 mm

Flow: 0.6 mL/min

Temp: 40° C.

Time (min) and % B: 0-5; 0.3-5; 2.5-95; 3.7-95; 4-5; 4.8-5

Example 166 and Example 167

Synthesis of 5-tert-butyl-N-[[4-[2-[4-[[4-[3-(2,4-dioxohexahydropyrimidin-1-yl)-1-methyl-indazol-6-yl]-1-piperidyl]methyl]-3-fluoro-phenyl]pyrazolo[1,5-a]pyrimidin-7-yl]-2-fluoro-phenyl]methyl]-1,2,4-oxadiazole-3-carboxamide (Example 166) and 3-tert-butoxy-N-[[4-[2-[4-[[4-[3-(2,4-dioxohexahydropyrimidin-1-yl)-1-methyl-indazol-6-yl]-1-piperidyl]methyl]-3-fluoro-phenyl]pyrazolo[1,5-a]pyrimidin-7-yl]-2-fluoro-phenyl]methyl]azetidine-1-carboxamide (Example 167)

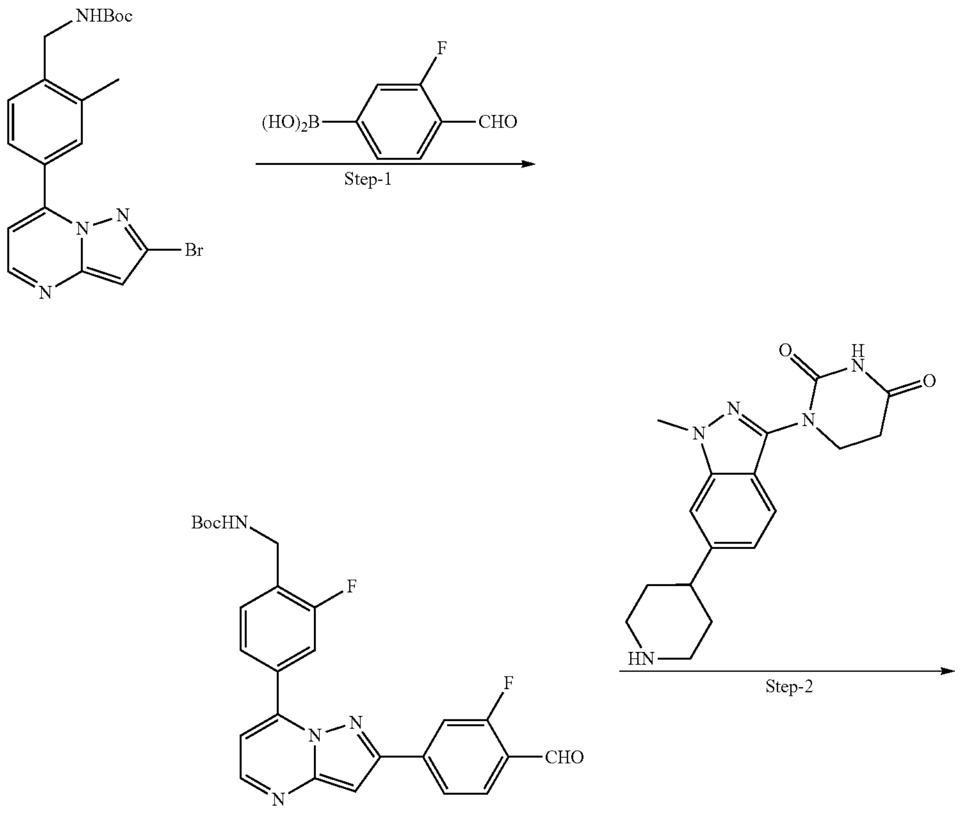

-continued

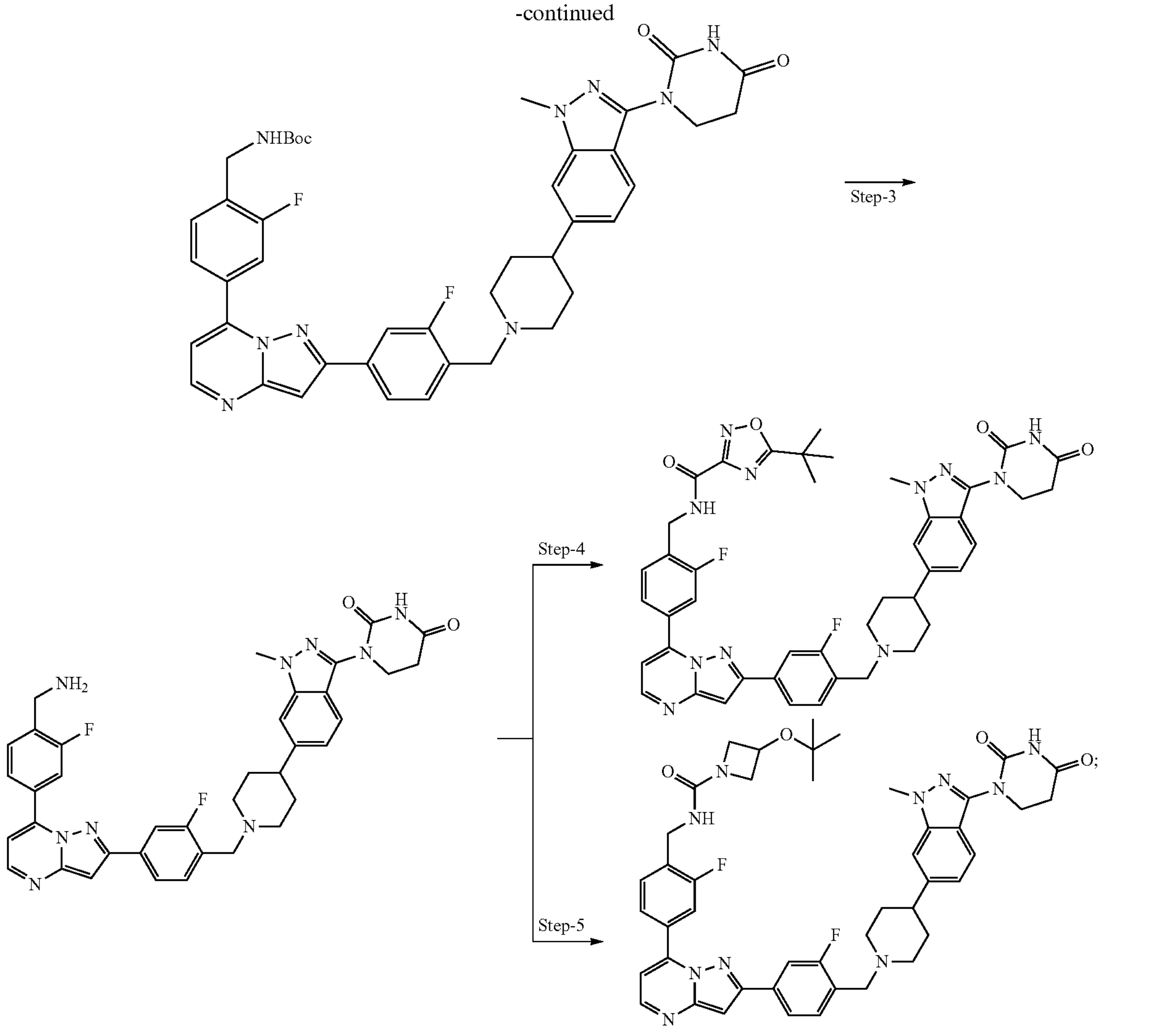

Step-1:

tert-butyl N-[[2-fluoro-4-[2-(3-fluoro-4-formyl-phenyl) pyrazolo[1,5-a]pyrimidin-7-yl]phenyl]methyl]carbamate (0.65 g, 1.34 mmol, 70.36% yield). LC-MS ($ES^+$): m/z 465.6 $[M+H]^+$.

Step-2:

tert-butyl N-[[4-[2-[4-[[4-[3-(2,4-dioxohexahydropyrimidin-1-yl)-1-methyl-indazol-6-yl]-1-piperidyl]methyl]-3-fluoro-phenyl]pyrazolo[1,5-a]pyrimidin-7-yl]-2-fluoro-phenyl]methyl]carbamate (0.32 g, 317.59 μmol, 36.88% yield). LC-MS ($ES^+$): m/z 776.2 $[M+H]^+$.

Step-3:

1-[6-[1-[[4-[7-[4-(aminomethyl)-3-fluoro-phenyl]pyrazolo[1,5-a]pyrimidin-2-yl]-2-fluoro-phenyl]methyl]-4-piperidyl]-1-methyl-indazol-3-yl]hexahydropyrimidine-2,4-dione HCl salt (0.32 g, 359.45 μmol, 87.15% yield). LC-MS ($ES^+$): m/z 676.4 $[M+H]^+$.

Step-4:

5-tert-butyl-N-[[4-[2-[4-[[4-[3-(2,4-dioxohexahydropyrimidin-1-yl)-1-methyl-indazol-6-yl]-1-piperidyl]methyl]-3-fluoro-phenyl]pyrazolo[1,5-a]pyrimidin-7-yl]-2-fluoro-phenyl]methyl]-1,2,4-oxadiazole-3-carboxamide TFA salt (45.2 mg, 47.07 μmol, 33.52% yield).

1H NMR (400 MHz, DMSO-$d_6$) δ 10.54 (s, 1H), 9.61 (t, J=5.9 Hz, 1H), 8.65 (d, J=4.4 Hz, 1H), 8.17-7.23 (m, 10H), 7.04 (bs, 1H), 4.64 (d, J=5.9 Hz, 2H), 3.97 (s, 3H), 3.90 (t, J=6.6 Hz, 2H), 3.63-3.41 (m, 3H), 3.27-3.11 (m, 2H), 2.98 (bs, 2H), 2.75 (t, J=6.6 Hz, 2H), 2.54-2.51 (m, 1H), 2.97-1.91 (m, 3H), 1.81 (bs, 2H), 2.07 (d, J=6.7 Hz, 1H), 1.44 (s, 9H).

LC-MS ($ES^+$): m/z 826.3 $[M+H]^+$.

Mobile phase-A: 0.1% FA in H2O

Mobile phase-B: ACN

Column: AQUITY UPLC BEH C18 1.7 μm, 2.1×50 mm

Flow: 0.6 mL/min

Temp: 40° C.

Time (min) and % B: 0-5; 0.3-5; 2.5-95; 3.7-95; 4-5; 4.8-5

Step-5:

3-tert-butoxy-N-[[4-[2-[4-[[4-[3-(2,4-dioxohexahydropyrimidin-1-yl)-1-methyl-indazol-6-yl]-1-piperidyl]methyl]-3-fluoro-phenyl]pyrazolo[1,5-a]pyrimidin-7-yl]-2-fluoro-phenyl]methyl]azetidine-1-carboxamide formic acid salt (28.4 mg, 31.61 μmol, 22.51% yield).

$^1H$ NMR (400 MHz, DMSO-$d_6$) δ 10.53 (s, 1H), 8.63 (d, J=4.4 Hz, 1H), 8.11-8.06 (m, 2H), 7.89-7.82 (m, 2H), 7.60-7.53 (m, 3H), 7.46 (s, 1H), 7.43 (s, 1H), 7.33 (d, J=4.4 Hz, 1H), 7.05-6.99 (m, 2H), 4.52-4.46 (m, 1H), 4.35 (d, J=5.7 Hz, 2H), 4.05 (t, J=7.7 Hz, 2H), 3.96 (s, 3H), 3.90 (t, J=6.7 Hz, 2H), 3.64-3.61 (m, 4H), 3.01-2.99 (m, 2H), 2.74

(t, J=6.7 Hz, 2H), 2.67-2.61 (m, 1H), 2.17-2.16 (m, 2H), 1.89-1.79 (m, 4H), 1.12 (s, 9H).

LC-MS (ES$^+$): m/z 831.9 [M+H]$^+$.

Mobile phase-A: 0.1% FA in H2O

Mobile phase-B: ACN

Column: X Bridge BEH C18 2.5 μm, 2.1×50 mm

Flow: 0.6 mL/min

Temp: 40° C.

Time (min) and % B: 0-5; 0.3-5; 2.5-95; 3.7-95; 4-5; 4.8-5

Example 168. Synthesis of 5-tert-butyl-N-[[4-[6-[4-[4-[4-(2,6-dioxo-3-piperidyl)phenyl]-1-piperidyl]-3,3-difluoro-butyl]pyrrolo[2,1-f][1,2,4]triazin-4-yl]-2-methyl-phenyl]methyl]-1,2,4-oxadiazole-3-carboxamide

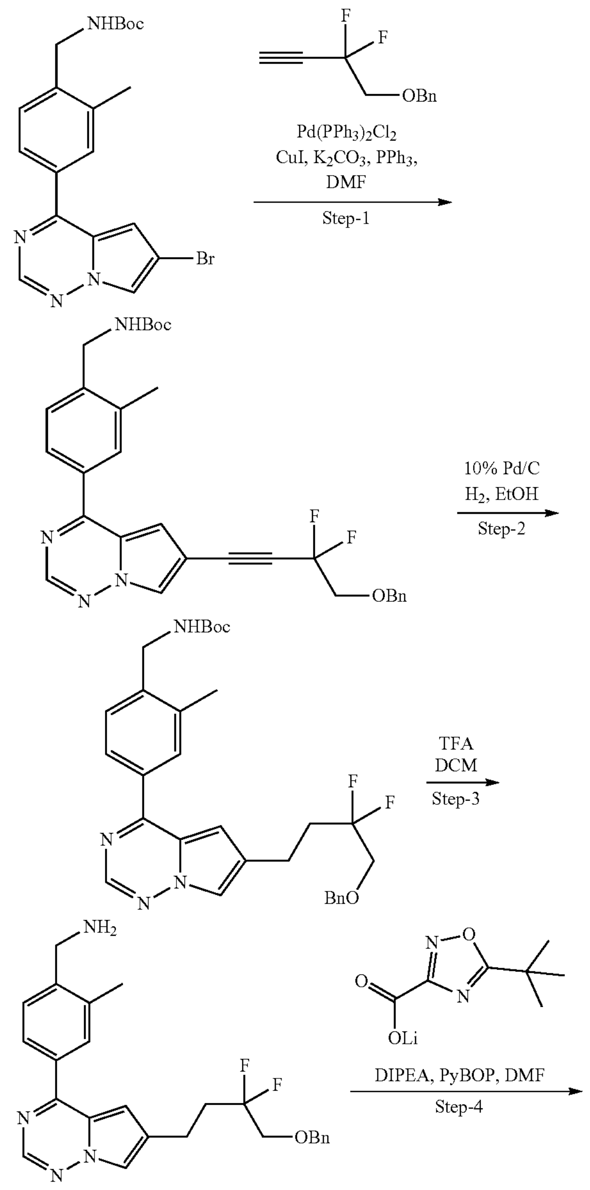

-continued

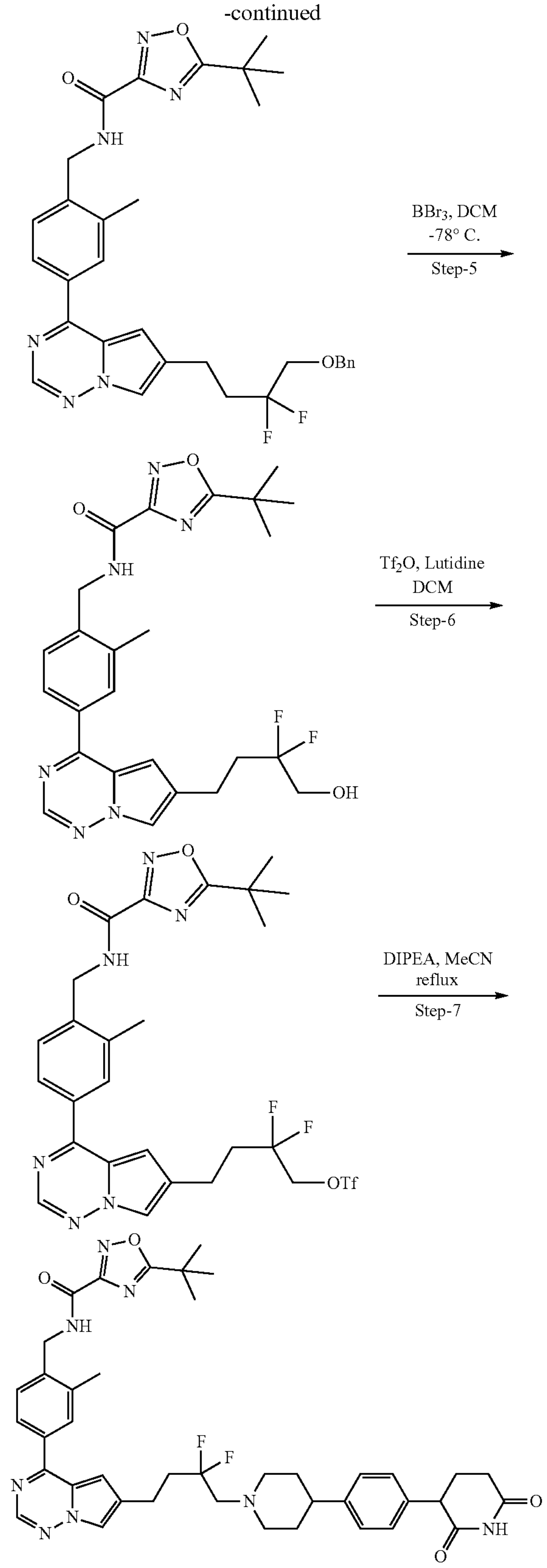

Step-1:

To a solution of tert-butyl N-[[4-(6-bromopyrrolo[2,1-f][1,2,4]triazin-4-yl)-2-methyl-phenyl]methyl]carbamate (1.5 g, 3.59 mmol) in DMF (10 mL) was added potassium carbonate, anhydrous, 99% (993.60 mg, 7.19 mmol), Copper (I) iodide (68.46 mg, 359.45 μmol), and triphenylphosphane (141.42 mg, 539.18 μmol) at room temperature. The reaction mixture was degassed with nitrogen for 20 minutes and 2,2-difluorobut-3-ynoxymethylbenzene (3.53 g, 17.97 mmol) was added and the mixture was degassed with nitrogen for an additional 5 minutes and stirred at 120° C. for 1.5 hour in microwave reactor. After completion, the reaction mixture was diluted with water and extracted with ethyl acetate, dried over sodium sulfate, and concentration in vacuo. The crude mixture was purified by column chromatography (silica gel 230-400 mesh) to afford tert-butyl N-[[4-[6-(4-benzyloxy-3,3-difluoro-but-1-ynyl)pyrrolo[2,1-f][1,2,4]triazin-4-yl]-2-methyl-phenyl]methyl]carbamate (0.5 g, 874.42 μmol, 24.33% yield). LC-MS ($ES^+$): m/z 533.6 $[M+H]^+$.

Step-2:

To a stirred solution of tert-butyl N-[[4-[6-(4-benzyloxy-3,3-difluoro-but-1-ynyl)pyrrolo[2,1-f][1,2,4]triazin-4-yl]-2-methyl-phenyl]methyl]carbamate (0.400 g, 751.06 μmol) in ethanol (20 mL) was added palladium (200.00 mg, 1.88 mmol) at room temperature. The reaction mixture was stirred under hydrogen balloon for 16 hours. Subsequently, it was filtered through celite bed and washed with ethyl acetate (20 mL). The filtrate was concentrated under reduced pressure to afford tert-butyl N-[[4-[6-(4-benzyloxy-3,3-difluoro-butyl)pyrrolo[2,1-f][1,2,4]triazin-4-yl]-2-methyl-phenyl]methyl]carbamate (0.400 g, 636.14 μmol, 84.70% yield). LC-MS ($ES^+$): m/z 537.3 $[M+H]^+$.

Step-3:

To a solution of tert-butyl N-[[4-[6-(4-benzyloxy-3,3-difluoro-butyl)pyrrolo[2,1-f][1,2,4]triazin-4-yl]-2-methyl-phenyl]methyl]carbamate (0.4 g, 745.42 μmol) in DCM (10 mL) was added 4 M hydrochloric acid in dioxane (2 mL) at 0° C. and the reaction mixture was stirred at RT for 2 h. The reaction mixture was concentrated in vacuo to get the crude product, which was triturated with diethyl ether (20 mL) to afford [4-[6-(4-benzyloxy-3,3-difluoro-butyl)pyrrolo[2,1-f][1,2,4]triazin-4-yl]-2-methyl-phenyl]methanamine HCl salt (0.35 g, 648.04 μmol, 86.94% yield) as an off-white solid. LC-MS ($ES^+$): m/z 437.8 $[M+H]^+$.

Step-4:

To a solution of [4-[6-(4-benzyloxy-3,3-difluoro-butyl)pyrrolo[2,1-f][1,2,4]triazin-4-yl]-2-methyl-phenyl]methanamine (0.3 g, 687.29 μmol) and (5-tert-butyl-1,2,4-oxadiazole-3-carbonyl)oxylithium (251.60 mg, 1.37 mmol) in DMF (10 mL) was added PyBOP (1.07 g, 2.06 mmol) followed by N-ethyl-N-isopropyl-propan-2-amine (444.13 mg, 3.44 mmol, 598.56 μL) at RT. The reaction mixture was stirred at room temperature for 16 hours. Subsequently, the reaction mixture was concentrated under reduced pressure to get the crude product, which was purified by column chromatography (silica gel 230-400 mesh) to afford N-[[4-[6-(4-benzyloxy-3,3-difluoro-butyl)pyrrolo[2,1-f][1,2,4]triazin-4-yl]-2-methyl-phenyl]methyl]-5-tert-butyl-1,2,4-oxadiazole-3-carboxamide (0.17 g, 230.03 μmol, 33.47% yield). LC-MS ($ES^+$): m/z 589.4 $[M+H]^+$.

Step-5:

A stirred solution of N-[[4-[6-(4-benzyloxy-3,3-difluoro-butyl)pyrrolo[2,1-f][1,2,4]triazin-4-yl]-2-methyl-phenyl]methyl]-5-tert-butyl-1,2,4-oxadiazole-3-carboxamide (0.16 g, 271.81 μmol) in DCM (8 mL) was added $BBr_3$ (408.57 mg, 1.63 mmol) at −78° C. under Nitrogen atmosphere, then the reaction was stirred for 2 hours at −78° C. Upon completion of reaction, the mixture was diluted with ice cold water at −78° C. and extracted with ethyl acetate. The combined organic layer was concentrated to obtain crude 5-tert-butyl-N-[[4-[6-(3,3-difluoro-4-hydroxy-butyl)pyrrolo[2,1-f][1,2,4]triazin-4-yl]-2-methyl-phenyl]methyl]-1,2,4-oxadiazole-3-carboxamide (0.12 g, 215.97 μmol, 79.45% yield) and used for the next step without further purification. LC-MS ($ES^+$): m/z 499.5 $[M+H]^+$.

Step-6:

To a solution of 5-tert-butyl-N-[[4-[6-(3,3-difluoro-4-hydroxy-butyl)pyrrolo[2,1-f][1,2,4]triazin-4-yl]-2-methyl-phenyl]methyl]-1,2,4-oxadiazole-3-carboxamide (0.16 g, 320.95 mol) in DCM (8 mL) was added triethylamine (324.77 mg, 3.21 mmol, 447.34 μL) at room temperature and the reaction mixture was cooled to −10° C. Trifluoromethylsulfonic anhydride (181.10 mg, 641.90 μmol, 107.80 μL) was added dropwise and the reaction mixture was stirred at −10° C. for 2 h. The reaction mixture was diluted with DCM (30 mL), and washed with saturated $NaHCO_3$ solution (30 mL) and brine solution (20 mL). The organic layer was dried over sodium sulfate, and concentrated in vacuo to get crude product [4-[4-[4-[[(5-tert-butyl-1,2,4-oxadiazole-3-carbonyl)amino]methyl]-3-methyl-phenyl]pyrrolo[2,1-f][1,2,4]triazin-6-yl]-2,2-difluoro-butyl] trifluoromethanesulfonate (0.18 g, 128.48 μmol, 40.03% yield) which was used in the next step without any purification. LC-MS ($ES^+$): m/z 631.4 $[M+H]^+$.

Step-7:

To a solution of 3-[4-(4-piperidyl)phenyl]piperidine-2,6-dione TFA salt (91.91 mg, 237.87 μmol) in ACN (10 mL) were added N-ethyl-N-isopropyl-propan-2-amine (204.95 mg, 1.59 mmol, 276.22 μL) and [4-[4-[4-[[(5-tert-butyl-1,2,4-oxadiazole-3-carbonyl)amino]methyl]-3-methyl-phenyl]pyrrolo[2,1-f][1,2,4]triazin-6-yl]-2,2-difluoro-butyl] trifluoromethanesulfonate (0.1 g, 158.58 μmol) at room temperature under nitrogen atmosphere. The reaction mixture was heated at 80° C. for 2 hours. Upon completion, the reaction mixture was dried under vacuum and the crude mixture was purified by Prep HPLC to Afford 5-tert-butyl-N-[[4-[6-[4-[4-[4-(2,6-dioxo-3-piperidyl)phenyl]-1-piperidyl]-3,3-difluoro-butyl]pyrrolo[2,1-f][1,2,4]triazin-4-yl]-2-methyl-phenyl]methyl]-1,2,4-oxadiazole-3-carboxamide (0.03 g, 38.26 μmol, 24.13% yield) as an off white solid. $^1H$ NMR (400 MHz, DMSO-$d_6$) δ 10.80 (s, 1H), 9.51 (t, J=5.7 Hz, 1H), 8.56 (s, 1H), 8.15 (s, 1H), 7.97-7.95 (m, 2H), 7.45 (d, J=7.8 Hz, 1H), 7.19-7.11 (m, 5H), 4.55 (d, J=5.7 Hz, 2H), 3.82-3.78 (m, 1H), 2.99-2.67 (m, 8H), 2.45 (s, 3H), 2.41-2.27 (m, 5H), 2.20-1.98 (m, 2H), 1.72-1.63 (m, 4H), 1.43 (s, 9H). LC-MS ($ES^+$): m/z 753.4 $[M+H]^+$.

Example 169. Synthesis of 5-tert-butyl-N-[[4-[6-[4-[4-[4-(2,6-dioxo-3-piperidyl)phenyl]-1-piperidyl]-3,3-difluoro-butyl]pyrrolo[2,1-f][1,2,4]triazin-4-yl]-2-fluoro-phenyl]methyl]-1,2,4-oxadiazole-3-carboxamide

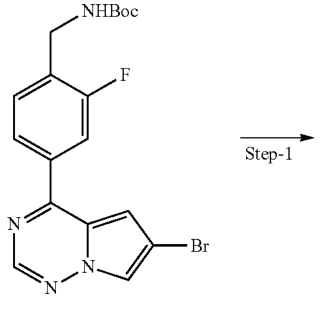

-continued
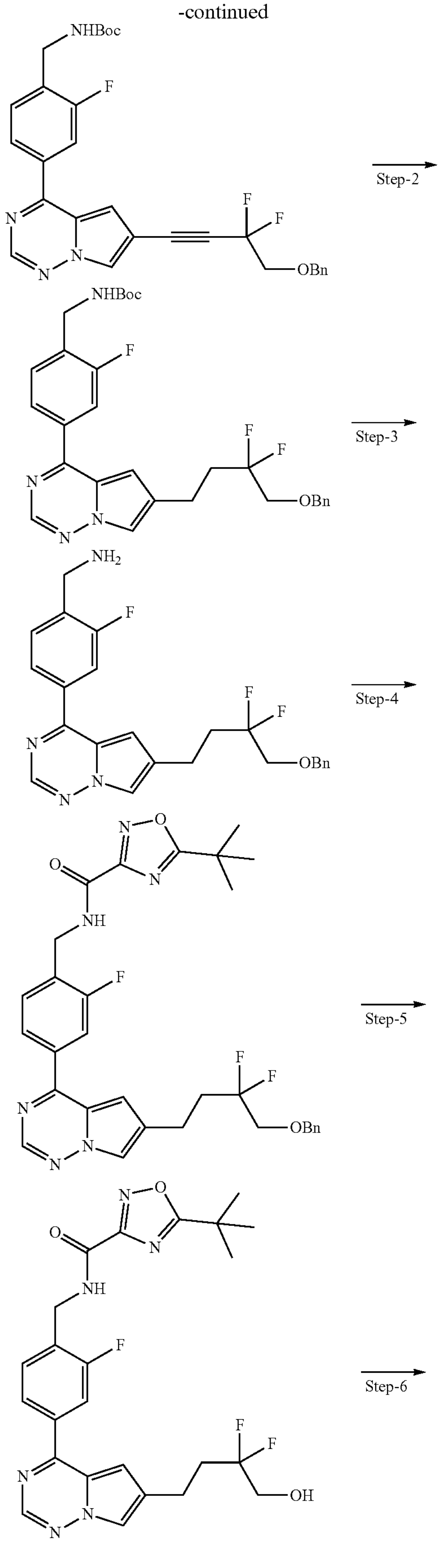
-continued
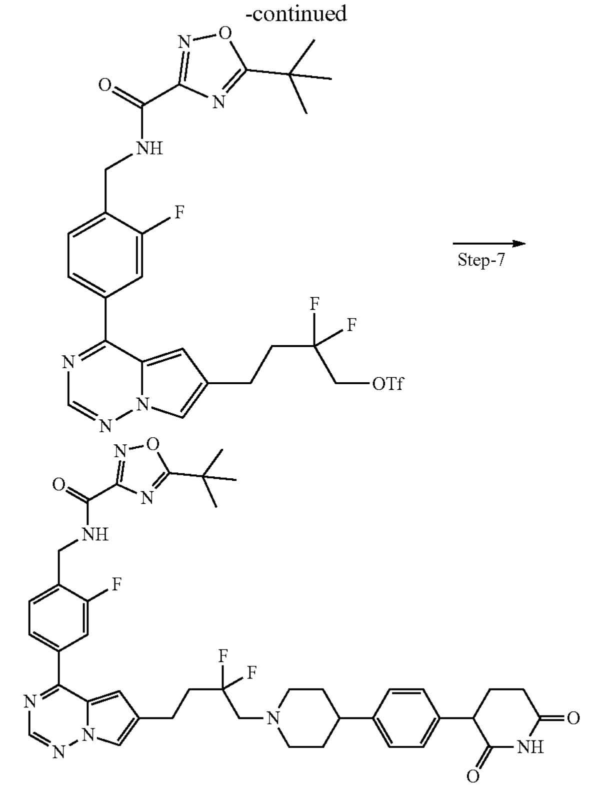
Reaction steps and conditions are identical (using different building blocks) to the representative compound Example 168 shown below.
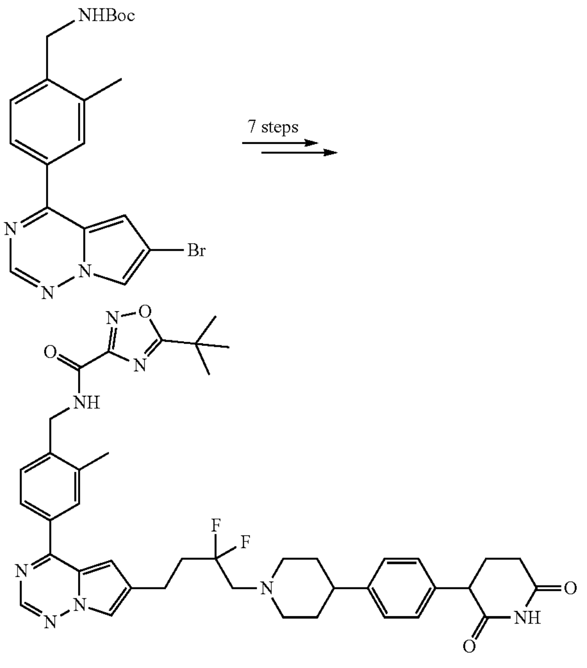
Step-1:
tert-butyl N-[[4-[6-(4-benzyloxy-3,3-difluoro-but-1-ynyl)pyrrolo[2,1-f][1,2,4]triazin-4-yl]-2-fluoro-phenyl]methyl]carbamate (1 g, 1.79 mmol, 50.37% yield).
LC-MS ($ES^+$): m/z 537.5 $[M+H]^+$.

Step-2:

tert-butyl N-[[4-[6-(4-benzyloxy-3,3-difluoro-butyl)pyrrolo[2,1-f][1,2,4]triazin-4-yl]-2-fluoro-phenyl]methyl]carbamate (0.495 g, 822.84 μmol, 88.30% yield).

LC-MS ($ES^+$): m/z 541.7 $[M+H]^+$.

Step-3:

[4-[6-(4-benzyloxy-3,3-difluoro-butyl)pyrrolo[2,1-f][1,2,4]triazin-4-yl]-2-fluoro-phenyl]methanamine TFA salt (0.520 g, 863.91 μmol, 77.83% yield).

LC-MS ($ES^+$): m/z 441.4 $[M+H]^+$.

Step-4:

N-[[4-[6-(4-benzyloxy-3,3-difluoro-butyl)pyrrolo[2,1-f][1,2,4]triazin-4-yl]-2-fluoro-phenyl]methyl]-5-tert-butyl-1,2,4-oxadiazole-3-carboxamide (0.150 g, 253.12 μmol, 49.55% yield). LC-MS ($ES^-$): m/z 591.4 $[M-H]^-$.

Step-5:

5-tert-butyl-N-[[4-[6-(3,3-difluoro-4-hydroxy-butyl)pyrrolo[2,1-f][1,2,4]triazin-4-yl]-2-fluoro-phenyl]methyl]-1,2,4-oxadiazole-3-carboxamide (0.125 g, 194.68 μmol, 76.91% yield).

LC-MS ($ES^+$): m/z 503.4 $[M+H]^+$.

Step-6:

[4-[4-[4-[[(5-tert-butyl-1,2,4-oxadiazole-3-carbonyl)amino]methyl]-3-fluoro-phenyl]pyrrolo[2,1-f][1,2,4]triazin-6-yl]-2,2-difluoro-butyl] trifluoromethanesulfonate (0.09 g, 9.45 μmol, 41.28% yield). LC-MS ($ES^+$): m/z 635.5 $[M+H]^+$.

Step-7:

5-tert-butyl-N-[[4-[6-[4-[4-[4-(2,6-dioxo-3-piperidyl)phenyl]-1-piperidyl]-3,3-difluoro-butyl]pyrrolo[2,1-f][1,2,4]triazin-4-yl]-2-fluoro-phenyl]methyl]-1,2,4-oxadiazole-3-carboxamide TFA salt (0.0335 g, 37.14 μmol, 26.18% yield). $^1$H NMR (400 MHz, DMSO-$d_6$) δ 10.81 (s, 1H), 9.59 (t, J=5.9 Hz, 1H), 8.60 (s, 1H), 8.20 (s, 1H), 8.00 (d, J=7.9 Hz, 1H), 7.92-7.89 (m, 1H), 7.59 (t, J=7.9 Hz, 1H), 7.24-7.08 (m, 5H), 4.61 (d, J=5.9 Hz, 2H), 3.92-3.64 (m, 3H), 3.01-2.61 (m, 7H), 2.45-2.01 (m, 8H), 1.71-1.61 (m, 2H), 1.43 (s, 9H). LC-MS ($ES^+$): m/z 757.39 $[M+H]^+$.

Example 170. Synthesis of 5-tert-butyl-N-[[4-[6-[4-[4-[4-[(2,6-dioxo-3-piperidyl)amino]phenyl]-1-piperidyl]-3-fluoro-butyl]pyrrolo[2,1-f][1,2,4]triazin-4-yl]-2-fluoro-phenyl]methyl]-1,2,4-oxadiazole-3-carboxamide

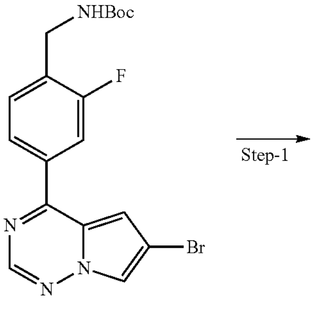

-continued

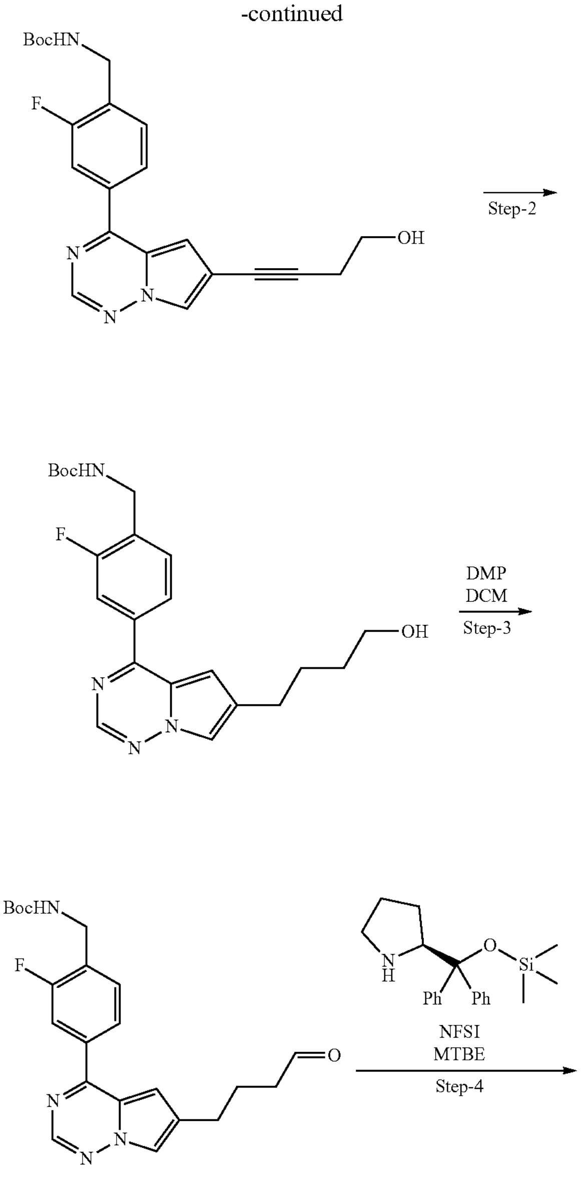

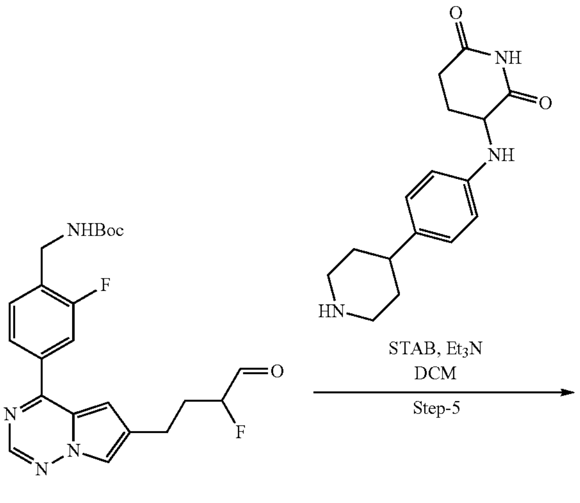

-continued
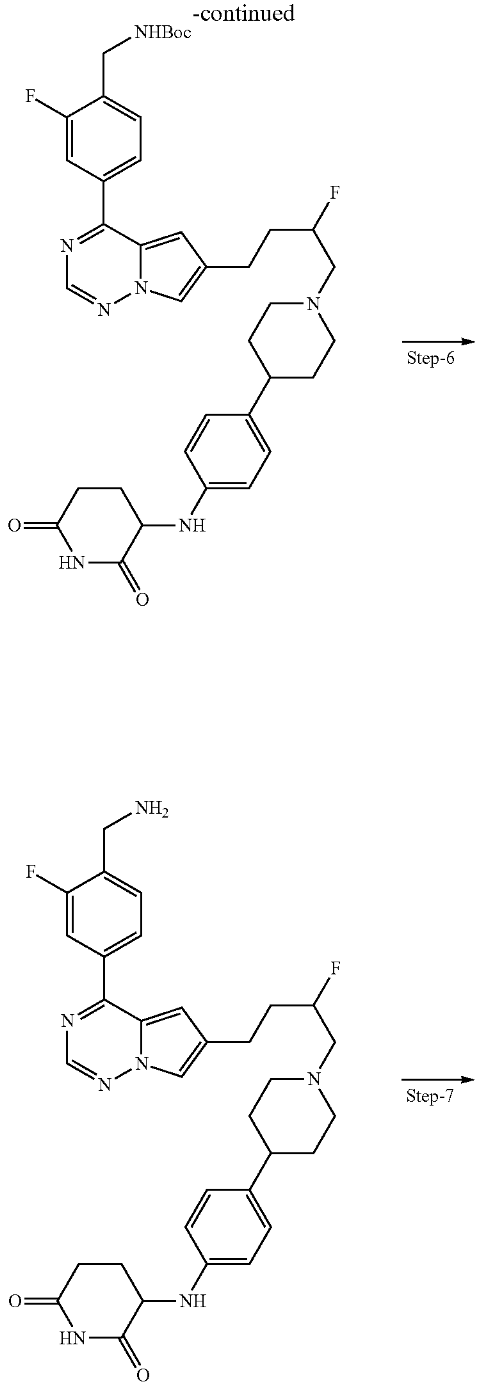
-continued
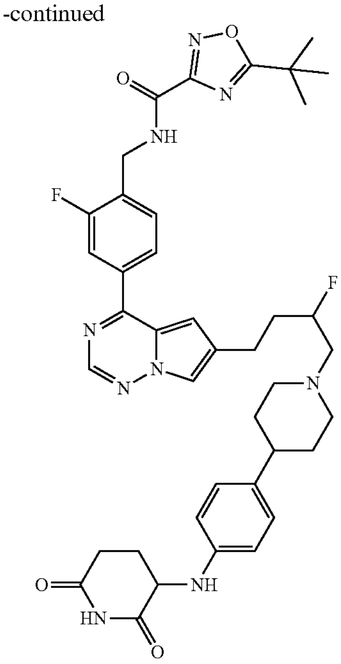
Unless otherwise noted, reaction steps and conditions for step-1, step-2, step-6, and step-7 are identical (using different building blocks) to the representative compound Example 128 shown below.
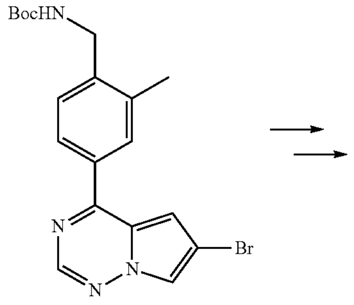

-continued

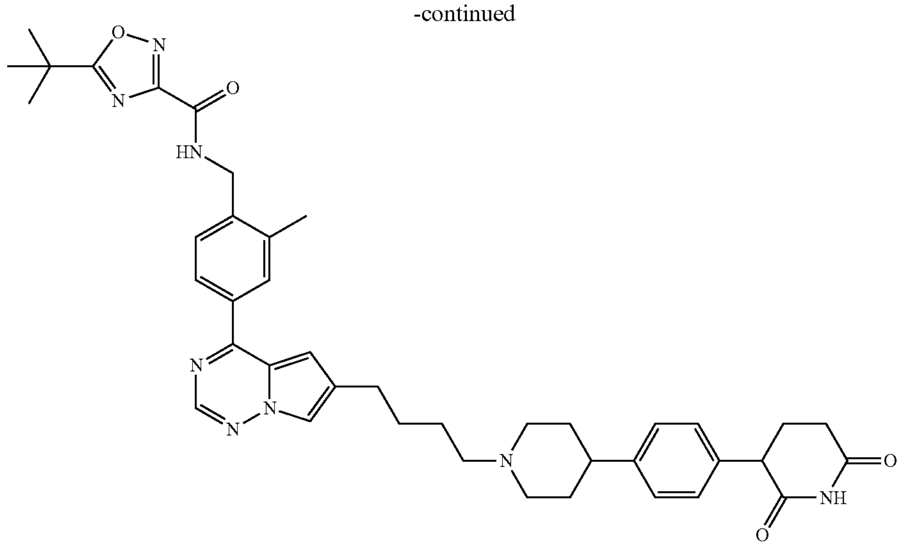

Step-1:

tert-butyl N-[[2-fluoro-4-[6-(4-hydroxybut-1-ynyl)pyrrolo[2,1-f][1,2,4]triazin-4-yl]phenyl]methyl]carbamate (5 g, 11.39 mmol, 95.96% yield). LC-MS ($ES^+$): m/z 411.3 $[M+H]^+$.

Step-2:

tert-butyl N-[[2-fluoro-4-[6-(4-hydroxybutyl)pyrrolo[2,1-f][1,2,4]triazin-4-yl]phenyl]methyl]carbamate (2.5 g, 5.49 mmol, 56.27% yield). LC-MS ($ES^+$): m/z 415.5 $[M+H]^+$.

Step-3:

To a solution of tert-butyl N-[[2-fluoro-4-[6-(4-hydroxybutyl)pyrrolo[2,1-f][1,2,4]triazin-4-yl]phenyl]methyl]carbamate (0.5 g, 1.21 mmol) was added Dess-Martin periodinane (769.82 mg, 1.81 mmol) at 0° C. and stirred for 30 min at 0° C. The reaction was monitored by TLC and LCMS. After completing the starting material. The reaction was diluted with DCM and filtered through a pad of celite. Further, the reaction mixture was washed with saturated $NaHCO_3$ solution (100 mL) and brine solution (100 mL). The organic layer was dried over sodium sulfate and concentrated in vacuo to get a crude product which was purified by column chromatography over silica gel (230-400 mesh) using 0-100% EtOAc in pet-ether as an eluent to afford tert-butyl N-[[2-fluoro-4-[6-(4-oxobutyl)pyrrolo[2,1-f][1,2,4]triazin-4-yl]phenyl]methyl]carbamate (0.5 g, 1.08 mmol, 89.30% yield). LC-MS ($ES^+$): m/z 413.5 $[M+H]^+$.

Step-4:

To a solution of (S)-(−)-α,α-diphenyl-2-pyrrolidinemethanol trimethylsilyl ether (30.24 mg, 72.74 μmol) and tert-butyl N-[[2-fluoro-4-[6-(4-oxobutyl)pyrrolo[2,1-f][1,2,4]triazin-4-yl]phenyl]methyl]carbamate (0.3 g, 727.35 μmol) in methyl-t-butyl ether (10 mL) was added N-fluorobenzenesulfonimide (573.41 mg, 1.82 mmol) at 0° C. and the reaction was stirred for 6 hours at room temperature to give the product tert-butyl N-[[2-fluoro-4-[6-(3-fluoro-4-oxo-butyl)pyrrolo[2,1-f][1,2,4]triazin-4-yl]phenyl]methyl]carbamate (36.41% yield). LC-MS ($ES^+$): m/z 431.44 $[M+H]^+$.

Step-5:

In a 25 ml single neck round bottom flask, 3-[4-(4-piperidyl)anilino]piperidine-2,6-dione (400.55 mg, 1.39 mmol) was dissolved in DCM (21 mL) and acetonitrile (9 mL), then triethyl amine (705.24 mg, 6.97 mmol, 971.41 μL) was added. After 5 minutes, tert-butyl N-[[2-fluoro-4-[6-(3-fluoro-4-oxo-butyl)pyrrolo[2,1-f][1,2,4]triazin-4-yl]phenyl]methyl]carbamate (0.3 g, 696.95 μmol) was added to the reaction mixture and allowed to stirred for 2 hours at room temperature. Next, Sodium triacetoxyborohydride, 95% (886.27 mg, 4.18 mmol) was added at 0° C., and the reaction was stirred at room temperature for 16 hours. After completion of the reaction, the solvent was concentrated under reduced pressure, and the crude mass was washed with a saturated sodium bicarbonate solution. The obtained precipitate was filtered and washed several times with diethyl ether. The solid crude mixture was further purified by prep-HPLC using ammonium acetate buffer to afford tert-butyl N-[[4-[6-[4-[4-[4-[(2,6-dioxo-3-piperidyl)amino]phenyl]-1-piperidyl]-3-fluoro-butyl]pyrrolo[2,1-f][1,2,4]triazin-4-yl]-2-fluoro-phenyl]methyl]carbamate (0.035 g, 45.61 μmol, 6.54% yield) as a light yellow solid. LC-MS ($ES^+$): m/z 702.8 $[M+H]^+$.

Step-6:

3-[4-[1-[4-[4-[4-(aminomethyl)-3-fluoro-phenyl]pyrrolo[2,1-f][1,2,4]triazin-6-yl]-2-fluoro-butyl]-4-piperidyl]anilino]piperidine-2,6-dione (0.031 g, 44.53 μmol, 89.30% yield). LC-MS ($ES^+$): m/z 602.3 $[M+H]^+$.

Step-7:

5-tert-butyl-N-[[4-[6-[4-[4-[4-[(2,6-dioxo-3-piperidyl)amino]phenyl]-1-piperidyl]-3-fluoro-butyl]pyrrolo[2,1-f][1,2,4]triazin-4-yl]-2-fluoro-phenyl]methyl]-1,2,4-oxadiazole-3-carboxamide (43 mg, 48.00 μmol, 98.81% yield). $^1H$ NMR (400 MHz, DMSO-$d_6$) δ 10.77 (s, 1H), 9.60 (t, J=6.0 Hz, 1H), 9.42 (bs, 1H), 8.61 (s, 1H), 8.17 (s, 1H), 7.99 (d, J=8.0 Hz, 1H), 7.91-7.88 (m, 1H), 7.60 (t, J=8.0 Hz, 1H), 7.20 (d, J=5.2 Hz, 2H), 6.94 (d, J=8.8 Hz, 2H), 6.63 (d, J=8.8 Hz, 1H), 5.20-5.10 (m, 1H), 4.61 (d, J=6.0 Hz, 2H), 4.30-4.20 (m, 1H), 3.40-3.30 (m, 2H), 3.20-2.85 (m, 5H), 2.80-2.55 (m, 3H), 2.15-1.80 (m, 9H), 1.43 (s, 9H). LC-MS ($ES^+$): m/z 752.4 $[M+H]^+$.

Example 171. Synthesis of 5-tert-butyl-N-[[4-[6-[(4S)-5-[4-[4-(2,6-dioxo-3-piperidyl)phenyl]-1-piperidyl]-4-fluoro-pentyl]pyrrolo[2,1-f][1,2,4]triazin-4-yl]-2-methyl-phenyl]methyl]-1,2,4-oxadiazole-3-carboxamide
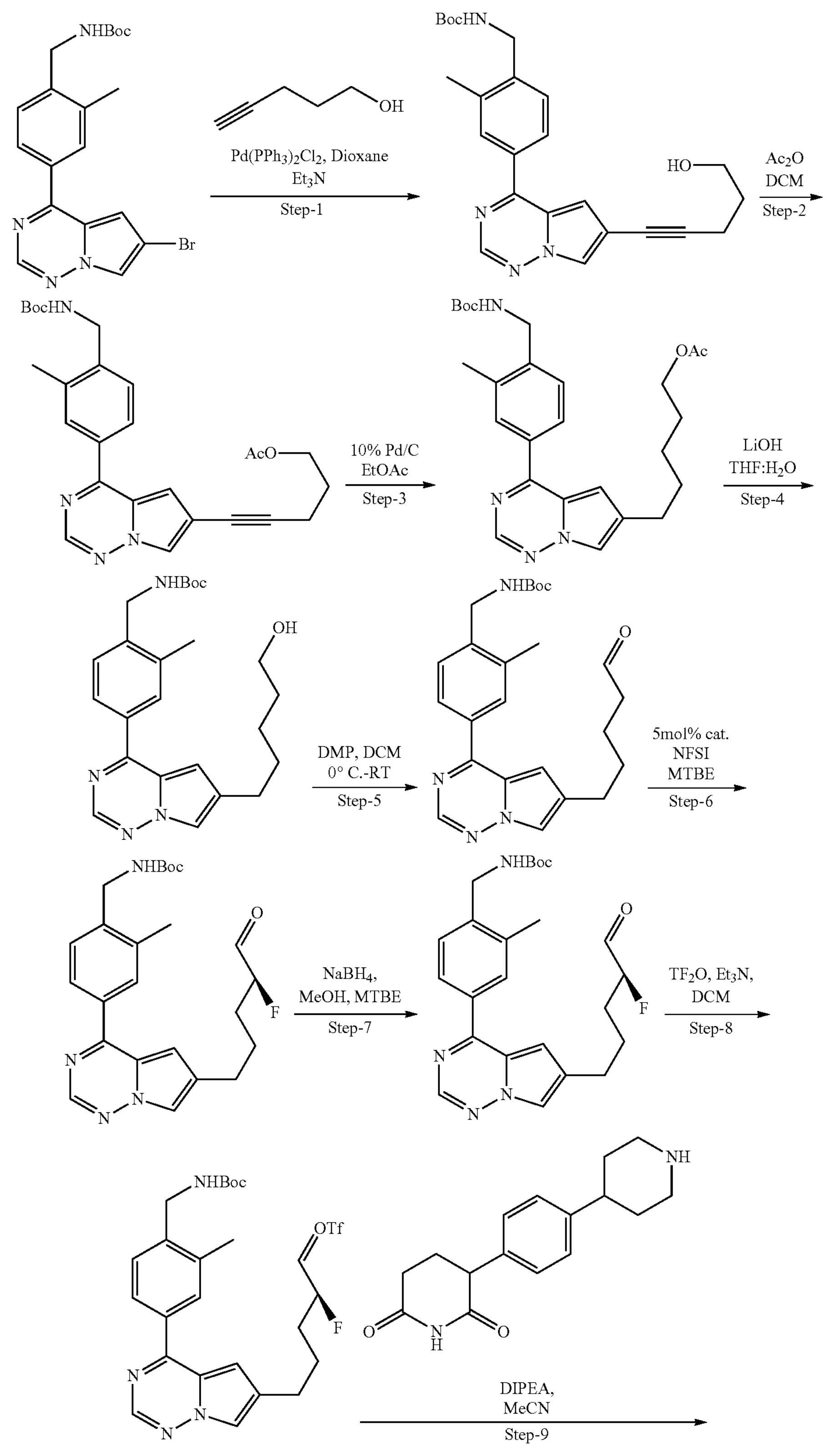

-continued

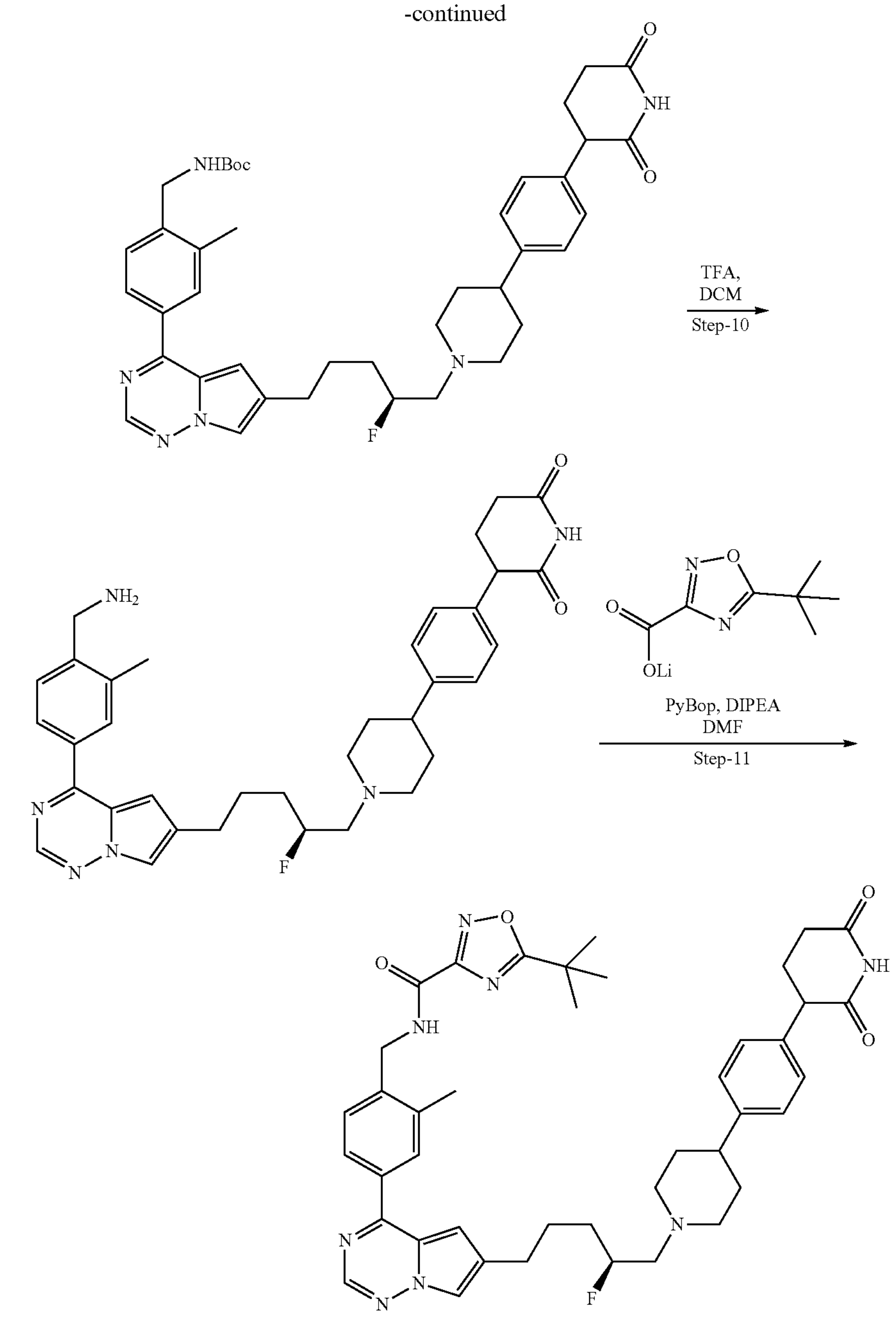

Step-1:

To a solution of tert-butyl N-[[4-(6-bromopyrrolo[2,1-f][1,2,4]triazin-4-yl)-2-methyl-phenyl]methyl]carbamate (5 g, 11.98 mmol) in 1,4-dioxane (50 mL) was added pent-4-yn-1-ol (5.04 g, 59.91 mmol), triethylamine (12.12 g, 119.82 mmol, 16.70 mL) and CuI (456.39 mg, 2.40 mmol) sequentially. Then, the mixture was degassed with argon for 20 minutes. Then, $Pd(PPh_3)Cl_2$ (1.68 g, 2.40 mmol) was added and heated the reaction mixture at 120° C. for 16 hr. After the completion, the reaction mixture was cooled, diluted with water, and extracted with ethyl acetate. The combined organic layer was dried over sodium sulfate and concentrated under a high vacuum to get the crude product. The resulting crude product was purified over silica gel to afforded tert-butyl N-[[4-[6-(5-hydroxypent-1-ynyl)pyrrolo[2,1-f][1,2,4]triazin-4-yl]-2-methyl-phenyl]methyl]carbamate (3.5 g, 7.66 mmol, 63.91% yield) as an off-white solid. LC-MS ($ES^+$): m/z 421.5 $[M+H]^+$.

Step-2:

To a solution of tert-butyl N-[[4-[6-(5-hydroxypent-1-ynyl)pyrrolo[2,1-f][1,2,4]triazin-4-yl]-2-methyl-phenyl]methyl]carbamate (3.5 g, 8.32 mmol) in DCM (40 mL) was added Triethylamine (842.24 mg, 8.32 mmol, 1.16 mL) followed by the addition of acetyl acetate (849.72 mg, 8.32 mmol, 786.78 µL) at 0° C. and stirred the reaction mixture at 28° C. for 16 hr. After the completion, the reaction mixture was diluted with water and extracted with DCM. The combined organic layer was dried over sodium sulfate and concentrated under a high vacuum to get the crude product. The resulting crude was purified over silica gel to afford 5-[4-[4-[(tert-butoxycarbonylamino)methyl]-3-methyl-phenyl]pyrrolo[2,1-f][1,2,4]triazin-6-yl]pent-4-ynyl acetate (3 g, 6.23 mmol, 74.81% yield) as a yellow solid. LC-MS ($ES^+$): m/z 463.5 $[M+H]^+$.

Step-3:

To a solution of 5-[4-[4-[(tert-butoxycarbonylamino) methyl]-3-methyl-phenyl]pyrrolo[2,1-f][1,2,4]triazin-6-yl] pent-4-ynyl acetate (3 g, 6.49 mmol) in ethyl acetate (30 mL) was added palladium, 10 wt. % on carbon, type 487, dry (2.76 g, 25.94 mmol) and stirred the reaction mixture at room temperature for 6 hours. After the completion, the reaction mixture was filtered through a celite pad and washed with ethyl acetate. The combined organic layer was concentrated under a high vacuum to obtain crude product. The resulting crude was purified by column chromatography (silica gel 100-200 mesh, 30% ethyl acetate in pet ether) to afford 5-[4-[4-[(tert-butoxycarbonylamino)methyl]-3-methyl-phenyl]pyrrolo[2,1-f][1,2,4]triazin-6-yl]pentyl acetate (3 g, 6.24 mmol, 96.16% yield) as a yellow oil. LC-MS ($ES^+$): m/z 468.0 $[M+H]^+$.

Step-4:

To a solution of 5-[4-[4-[(tert-butoxycarbonylamino) methyl]-3-methyl-phenyl]pyrrolo[2,1-f][1,2,4]triazin-6-yl] pentyl acetate (3.5 g, 7.50 mmol) in THF (30 mL) and water (6 mL) was added lithium hydroxide monohydrate, 98% (1.57 g, 37.51 mmol) at 0° C. and stirred for 4 hours. After the consumption of the starting material, the reaction was diluted with ethyl acetate (100 mL) and washed with water (100 mL) and brine solution (100 mL). The combined organic layer was dried over sodium sulfate and concentrated in vacuo to get the crude product. The crude was purified by column chromatography (silica gel 230-400 mesh, using 0-10% ethyl acetate in pet-ether) to afford tert-butyl N-[[4-[6-(5-hydroxypentyl)pyrrolo[2,1-f][1,2,4] triazin-4-yl]-2-methyl-phenyl]methyl]carbamate (2.5 g, 5.83 mmol, 77.72% yield). LC-MS ($ES^+$): m/z 426.1 $[M+H]^+$.

Step-5:

To a stirred solution of tert-butyl N-[[4-[6-(5-hydroxypentyl)pyrrolo[2,1-f][1,2,4]triazin-4-yl]-2-methyl-phenyl] methyl]carbamate (0.8 g, 1.88 mmol) in DCM (10 mL) was DMP (4.00 g, 9.42 mmol) at 0° C. and stirred the reaction mixture at room temperature for 1 hour. After the completion, the reaction mixture was diluted with water and extracted with DCM. The combined organic layer was dried over sodium sulfate and concentrated under a high vacuum to get the crude product. The resulting crude was purified over silica gel to afford tert-butyl N-[[2-methyl-4-[6-(5-oxopentyl)pyrrolo[2,1-f][1,2,4]triazin-4-yl]phenyl]methyl] carbamate (0.6 g, 1.32 mmol, 70.08% yield) as a yellow oil. LC-MS ($ES^+$): m/z 423.6 $[M+H]^+$.

Step-6:

To a solution of tert-butyl N-[[2-methyl-4-[6-(5-oxopentyl)pyrrolo[2,1-f][1,2,4]triazin-4-yl]phenyl]methyl]carbamate (0.6 g, 1.42 mmol) in MTBE (6 mL) was added (S)-α, α-bis[3,5-bis(trifluoromethyl)phenyl]-2-pyrrolidinemethanol trimethylsilyl ether (42.42 mg, 71.00 mol) at 0° C. and stirred the reaction mixture at same temperature for 30 minutes. Then, N-(benzenesulfonyl)-N-fluoro-benzenesulfonamide (447.80 mg, 1.42 mmol) was added and allowed to warm the reaction mixture from 0° C. to room temperature for 24 hours. After completion, the reaction was quenched with ice cold saturated solution of sodium bicarbonate at −40° C. Then the organic layer was separated, dried over sodium sulfate to obtained tert-butyl N-[[4-[6-[(4S)-4-fluoro-5-oxo-pentyl]pyrrolo[2,1-f][1,2,4] triazin-4-yl]-2-methyl-phenyl]methyl]carbamate (0.6 g, 340.51 μmol, 23.98% yield) as a yellow oil. LC-MS ($ES^+$): m/z 441.2 $[M+H]^+$.

Step-7:

To a solution of tert-butyl N-[[4-[6-[(4S)-4-fluoro-5-oxo-pentyl]pyrrolo[2,1-f][1,2,4]triazin-4-yl]-2-methyl-phenyl] methyl]carbamate (600.00 mg, 1.36 mmol) in MTBE (4 mL) was added a solution of sodium borohydride (51.53 mg, 1.36 mmol) in methanol (2 mL) at −10° C. and stirred at the same temperature for 1 hour. After the completion, the reaction mixture was diluted with water and extracted with ethyl acetate. The organic layer was dried over sodium sulfate and concentrated under high vacuum to obtain crude product. The resulting crude was purified by column chromatography (silica gel) to afford tert-butyl N-[[4-[6-[(4S)-4-fluoro-5-hydroxy-pentyl]pyrrolo[2,1-f][1,2,4]triazin-4-yl]-2-methyl-phenyl]methyl]carbamate (0.15 g, 291.51 μmol, 21.40% yield) as a yellow oil. LC-MS ($ES^+$): m/z 443.4 $[M+H]^+$.

Step-8:

To a solution of tert-butyl N-[[4-[6-[(4S)-4-fluoro-5-hydroxy-pentyl]pyrrolo[2,1-f][1,2,4]triazin-4-yl]-2-methyl-phenyl]methyl]carbamate (120.00 mg, 271.17 μmol) in DCM (3 mL) were added 2,6-dimethylpyridine (72.64 mg, 677.93 μmol, 78.70 μL) and $Tf_2O$ (114.76 mg, 406.76 μmol, 68.43 μL) at −10° C. and the reaction mixture was stirred at room temperature for 1 hour. After completion, the reaction mixture was diluted with water and extracted with DCM. The combined organic layer was dried over sodium sulfate and concentrated under high vacuum to afford [(2S)-5-[4-[4-[(tert-butoxycarbonylamino)methyl]-3-methyl-phenyl] pyrrolo[2,1-f][1,2,4]triazin-6-yl]-2-fluoro-pentyl] trifluoromethanesulfonate (0.14 g, 155.94 μmol, 57.51% yield) as a red oil. LC-MS ($ES^+$): m/z 575.8 $[M+H]^+$.

Step-9:

To a solution of 3-[4-(4-piperidyl)phenyl]piperidine-2,6-dione TFA salt (112.97 mg, 292.38 μmol) in ACN (5 mL) was added N-ethyl-N-isopropyl-propan-2-amine (314.90 mg, 2.44 mmol, 424.40 μL) was added [(2S)-5-[4-[4-[(tert-butoxycarbonylamino)methyl]-3-methyl-phenyl]pyrrolo[2,1-f][1,2,4]triazin-6-yl]-2-fluoro-pentyl] trifluoromethanesulfonate (140.00 mg, 243.65 μmol) and the reaction mixture was heated at 70° C. for 16 hours. After completion, the reaction mixture was cooled, diluted with water, and extracted with ethyl acetate. The combined organic layer was dried over sodium sulfate and concentrated under high vacuum to obtained crude product. The resulting crude product was purified by column chromatography (silica gel 100-200 mesh, 8% MeOH in DCM) to afford tert-butyl N-[[4-[6-[(4S)-5-[4-[4-(2,6-dioxo-3-piperidyl)phenyl]-1-piperidyl]-4-fluoro-pentyl]pyrrolo[2,1-f][1,2,4]triazin-4-yl]-2-methyl-phenyl]methyl]carbamate (0.16 g, 220.42 μmol, 90.46% yield) as a yellow solid. LC-MS ($ES^-$): m/z 695.2 $[M-H]^-$.

Step-10:

To a solution of tert-butyl N-[[4-[6-[(4S)-5-[4-[4-(2,6-dioxo-3-piperidyl)phenyl]-1-piperidyl]-4-fluoro-pentyl]pyrrolo[2,1-f][1,2,4]triazin-4-yl]-2-methyl-phenyl]methyl]carbamate (0.13 g, 186.55 μmol) in DCM (5 mL) was added trifluoroacetic acid (212.71 mg, 1.87 mmol, 143.73 μL) at 0° C. and stirred the reaction mixture at room temperature for 1 hour. After completion, the reaction mixture was concentrated and triturated with diethyl ether. The resulting solid was dried under a high vacuum to obtain the crude product. The resulting crude 3-[4-[1-[(2S)-5-[4-[4-(aminomethyl)-3-methyl-phenyl]pyrrolo[2,1-f][1,2,4]triazin-6-yl]-2-fluoro-pentyl]-4-piperidyl]phenyl]piperidine-2,6-dione (0.11 g, 1156.51 μmol, 62.45% yield) was used as such in next step without purification. LC-MS ($ES^-$): m/z 595.4 $[M-H]^-$.

Step-11:

To a solution of 3-[4-[1-[(2S)-5-[4-[4-(aminomethyl)-3-methyl-phenyl]pyrrolo[2,1-f][1,2,4]triazin-6-yl]-2-fluoro-pentyl]-4-piperidyl]phenyl]piperidine-2,6-dione TFA salt (0.15 g, 211.04 μmol) in DMF (2 mL) was added 3-[4-[1-[(2S)-5-[4-[4-(aminomethyl)-3-methyl-phenyl]pyrrolo[2,1-f][1,2,4]triazin-6-yl]-2-fluoro-pentyl]-4-piperidyl]phenyl]piperidine-2,6-dione TFA salt (0.15 g, 211.04 μmol) and N-ethyl-N-isopropyl-propan-2-amine (272.76 mg, 2.11 mmol, 367.60 μL) at 0° C. Then, benzotriazol-1-yloxy (tripyrrolidin-1-yl)phosphonium; hexafluorophosphate (219.65 mg, 422.08 μmol) was added and stirred the reaction mixture at room temperature for 2 hours. After completion, the reaction mixture the was dilute with ice cold water to obtained solid. The resulting solid was filtered and dried to obtained crude product. The resulting crude mixture was purified by prep-HPLC to afford 5-tert-butyl-N-[[4-[6-[(4S)-5-[4-[4-(2,6-dioxo-3-piperidyl)phenyl]-1-piperidyl]-4-fluoro-pentyl]pyrrolo[2,1-f][1,2,4]triazin-4-yl]-2-methyl-phenyl]methyl]-1,2,4-oxadiazole-3-carboxamide formic acid salt (29.4 mg, 36.84 μmol, 17.46% yield) as a yellow solid. $^1H$ NMR (400 MHz, DMSO-$d_6$) δ 10.81 (s, 1H), 9.50 (t, J=5.8 Hz, 1H), 8.54 (s, 1H), 8.23 (s, 1H), 8.08 (s, 1H), 7.96-7.94 (m, 2H), 7.45 (d, J=7.6 Hz, 1H), 7.19-7.09 (m, 5H), 4.73 (d, J=49.9 Hz, 1H), 4.54 (d, J=5.8 Hz, 2H), 3.82-3.78 (m, 1H), 2.95 (t, J=10.1 Hz, 2H), 2.77 (t, J=7.3 Hz, 2H), 2.70-2.51 (m, 3H), 2.45 (s, 3H), 2.43-2.38 (m, 2H), 2.18-2.01 (m, 4H), 1.83-1.58 (m, 8H), 1.44 (s, 9H). LC-MS ($ES^+$): m/z 749.4 $[M+H]^+$.

General Procedure (Piperazines)

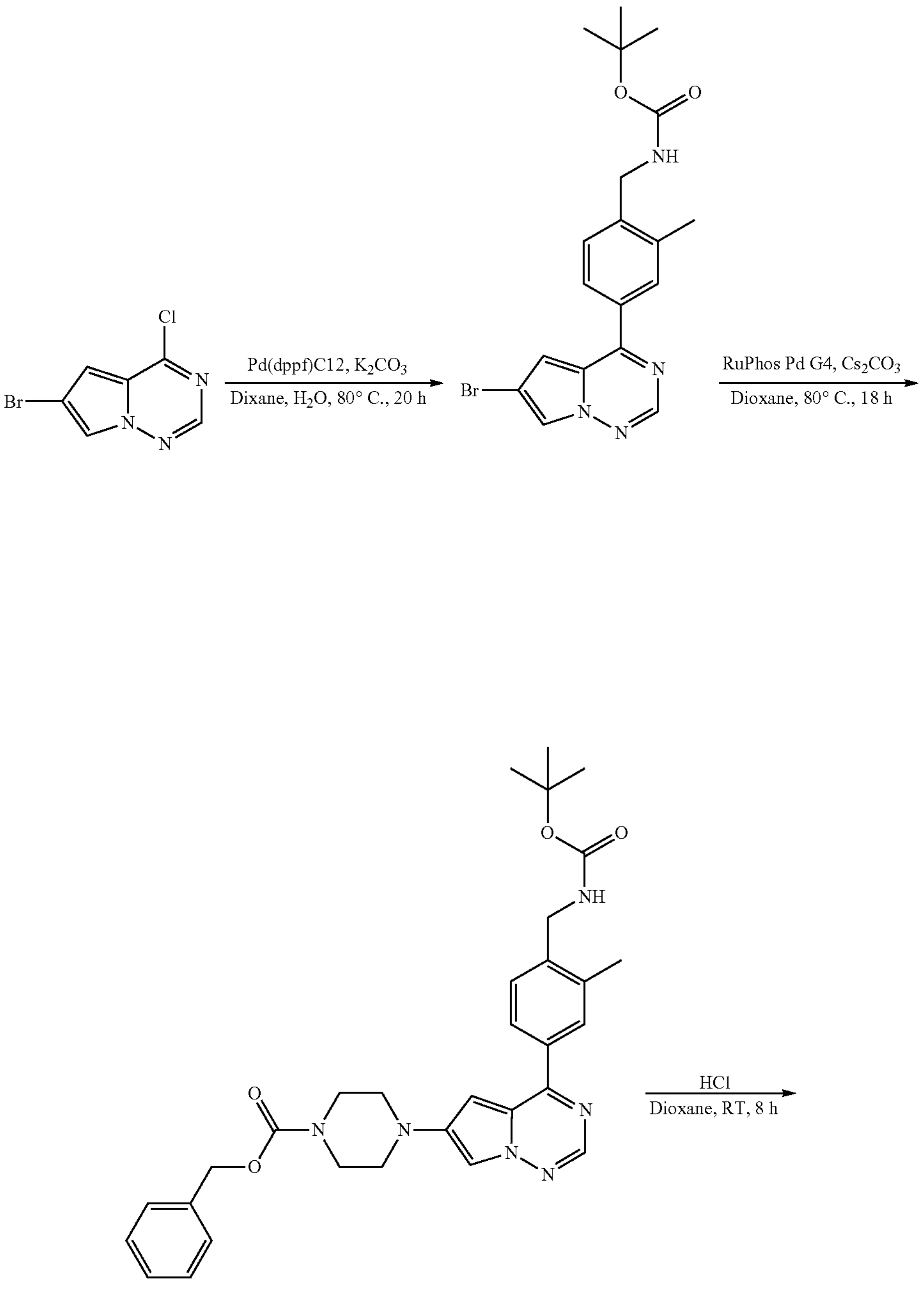

-continued

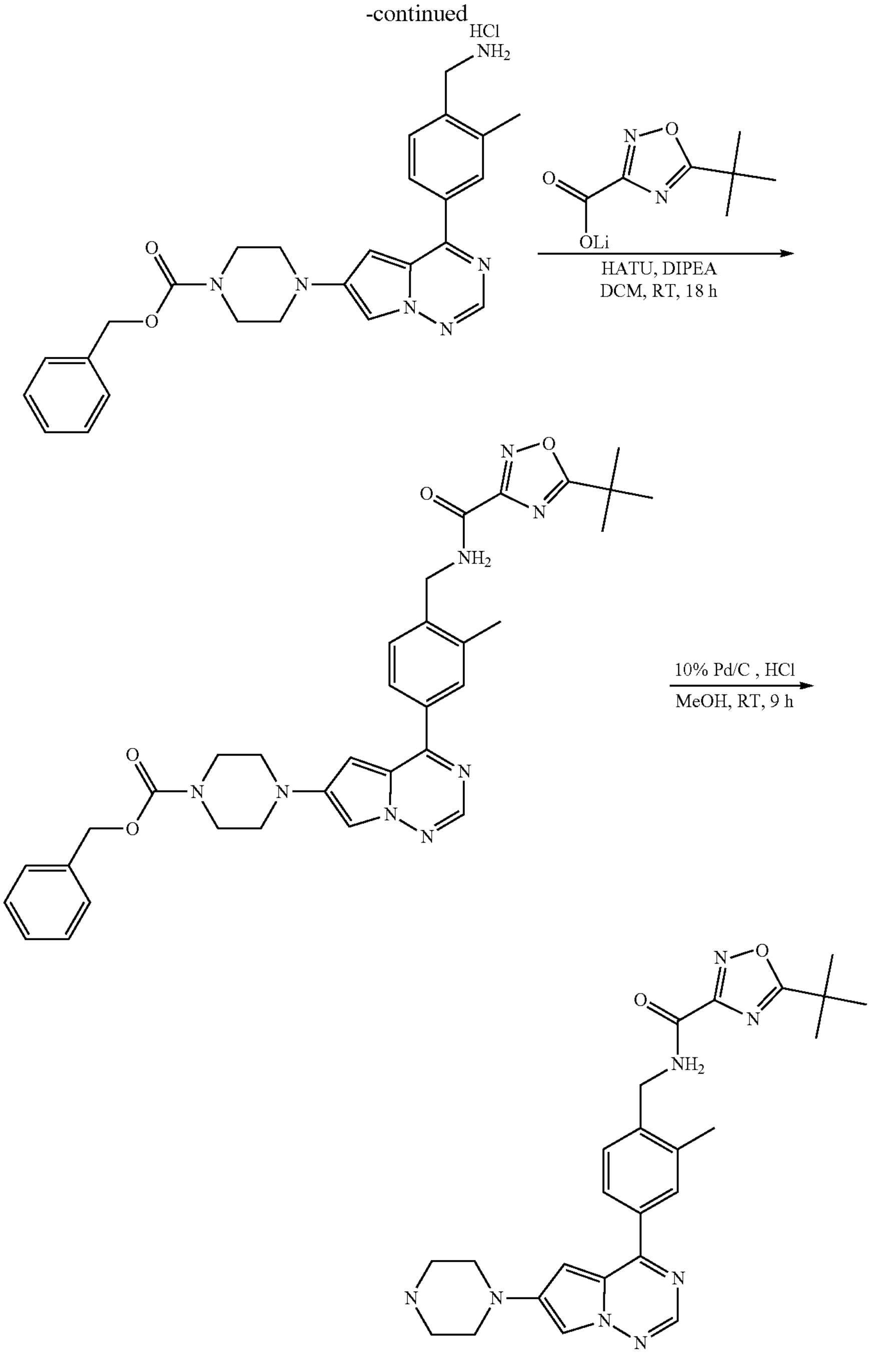

tert-butyl (4-(6-bromopyrrolo[2,1-f][1,2,4]triazin-4-yl)-2-methylbenzyl)carbamate A solution of tert-butyl N-[[2-methyl-4-(4,4,5,5-tetramethyl-1,3,2-dioxaborolan-2-yl)phenyl]methyl]carbamate (41.3 g, 118.93 mmol), 6-bromo-4-chloro-pyrrolo[2,1-f][1,2,4]triazine (27.65 g, 118.93 mmol), $K_2CO_3$ (49.31 g, 356.80 mmol) and Pd(dppf)$Cl_2$·$CH_2Cl_2$ (4.86 g, 5.95 mmol) in 1,4-Dioxane (450 mL) and $H_2O$ (90 mL) was stirred at 80° C. for 18 h under inert atmosphere. After cooling to rt, the mixture was diluted in water (400 mL) and extracted with Ethyl acetate (250 mL×3). The combined organic layers were washed with brine, dried and concentrated. The residue was purified by column chromatography (Companion combiflash; 720 g $SiO_2$; petroleum ether/EtOAc) to give tert-butyl (4-(6-bromopyrrolo[2,1-f][1,2,4]triazin-4-yl)-2-methylbenzyl)carbamate (30.1 g, 68.52 mmol, 58% yield). $^1$H NMR (500 MHz, CHLOROFORM-d) δ=8.49 (s, 1H), 7.85 (m, 3H), 7.42 (br d, J=8.2 Hz, 1H), 7.07 (s, 1H), 4.92 (br s, 1H), 4.40 (br s, 2H), 2.43 (s, 3H), 1.49 (s, 9H).

benzyl 4-(4-(4-(((tert-butoxycarbonyl)amino)methyl)-3-methylphenyl)pyrrolo[2,1-f][1,2,4]triazin-6-yl)piperazine-1-carboxylate tert-butyl N-[[4-(6-bromopyrrolo[2,1-f][1,2,4]triazin-4-yl)-2-methylphenyl]methyl]carbamate (29 g, 69.49 mmol), benzyl piperazine-1-carboxylate (45.92 g, 208.48 mmol, 40.21 mL), $Cs_2CO_3$ (67.93 g, 208.48 mmol) were dissolved in 1,4-dioxane (350 mL). The solution was degassed under reduced pressure followed by addition of RuPhos Pd G4 (3.54 g, 4.17 mmol). The reaction mixture was heated at 80° C. under argon atmosphere overnight. After cooling to rt, the mixture was diluted with $H_2O$ (300 mL) and extracted with Ethyl acetate (250 mL×3). The combined organic layers were washed with brine, dried and concentrated. The residue was purified by column chromatography (Companion combiflash; 720 g $SiO_2$; petroleum ether/EtOAc) to give benzyl 4-(4-(4-(((tert-butoxycarbonyl)amino)methyl)-3-methylphenyl)pyrrolo[2,1-f][1,2,4]triazin-6-yl)piperazine-1-carboxylate (22.1 g, 38.83 mmol, 56% yield) as a yellow oil. LC-MS($ES^+$): m/z=557.4 $[M+H]^+$.

benzyl 4-(4-(4-(aminomethyl)-3-methylphenyl)pyrrolo[2,1-f][1,2,4]triazin-6-yl)piperazine-1-carboxylate HCl To a solution of benzyl 4-[4-[4-[(2,2-dimethylpropanoylamino)methyl]-3-methylphenyl]pyrrolo[2,1-f][1,2,4]triazin-6-yl]piperazine-1-carboxylate (10.6 g, 19.61 mmol) in 1,4-dioxane (40 mL) was added 24.51 mL HCl in dioxane (4 M in dioxane, 24.51 mL) at room temperature and stirred for 7 h. The reaction mixture was evaporated in vacuo and triturated with MTBE (50 ml) and filtered to give benzyl 4-[4-[4-(aminomethyl)-3-methyl-phenyl]pyrrolo[2,1-f][1,2,4]triazin-6-yl]piperazine-1-carboxylate (8.95 g, 16.52 mmol, 84% yield, Hydrochloride) as a red solid. LC-MS ($ES^+$): m/z=457.0 $[M+H]^+$.

benzyl 4-(4-(4-((5-(tert-butyl)-1,2,4-oxadiazole-3-carboxamido)methyl)-3-methylphenyl)pyrrolo[2,1-f][1,2,4]triazin-6-yl)piperazine-1-carboxylate To a solution of benzyl 4-[4-[4-(aminomethyl)-3-methylphenyl]pyrrolo[2,1-f][1,2,4]triazin-6-yl]piperazine-1-carboxylate (19.05 g, 38.64 mmol, Hydrochloride) in DCM (500 mL) and DMF (50 mL) were added 5-tert-butyl-1,2,4-oxadiazole-3-carboxylate (10.21 g, 57.96 mmol, Lithium), HATU (22.10 g, 57.96 mmol) and DIPEA (14.98 g, 115.92 mmol, 20.19 mL). The mixture was stirred at 20° C. for overnight. The mixture was poured into water (250 mL), and extracted with DCM (100 mL×3). The combined organic layers were washed with brine (2×150 mL), dried and concentrated. The residue was purified by column chromatography (Companion combiflash; 240 g $SiO_2$, petroleum ether/MTBE with MTBE from 0-100%, flow rate=80 mL/min. Rv=50-130) to give benzyl 4-[4-[4-[[(5-tert-butyl-1,2,4-oxadiazole-3-carbonyl)amino]methyl]-3-methyl-phenyl]pyrrolo[2,1-f][1,2,4]triazin-6-yl]piperazine-1-carboxylate (7.2 g, 11.24 mmol, 29% yield) as a yellow solid. LC-MS($ES^+$): m/z=609.2 $[M+H]^+$.

5-(tert-butyl)-N-(2-methyl-4-(6-(piperazin-1-yl)pyrrolo[2,1-f][1,2,4]triazin-4-yl)benzyl)-1,2,4-oxadiazole-3-carboxamide A solution of benzyl 4-[4-[4-[[(5-tert-butyl-1,2,4-oxadiazole-3-carbonyl)amino]methyl]-3-methylphenyl]pyrrolo[2,1-f][1,2,4]triazin-6-yl]piperazine-1-carboxylate (2.05 g, 3.37 mmol) and 10 wt. % palladium on carbon (358.41 mg, 336.79 μmol) in methanol (120 mL) and HCl in water (1 M, 16.84 mL) was stirred for 14 h at room temperature under hydrogen atmosphere (1 atm). The solution was filtered and concentrated in vacuo. 1M potassium carbonate (1M in water) was added for neutralization and the solution was extracted with DCM (25 mL×3) and evaporated. The crude material was purified by chromatography (Companion combiflash; 40 g $SiO_2$, chloroform/methanol+TEA (2%) with methanol+TEA (2%) from 5~8% flow rate=40 mL/min, Rv=5-12 CV) to give 5-tert-butyl-N-[[2-methyl-4-(6-piperazin-1-ylpyrrolo[2,1-f][1,2,4]triazin-4-yl)phenyl]methyl]-1,2,4-oxadiazole-3-carboxamide (0.75 g, 1.45 mmol, 43% yield) as a yellow solid. LC-MS($ES^+$): m/z 475.2 $[M+H]^+$.

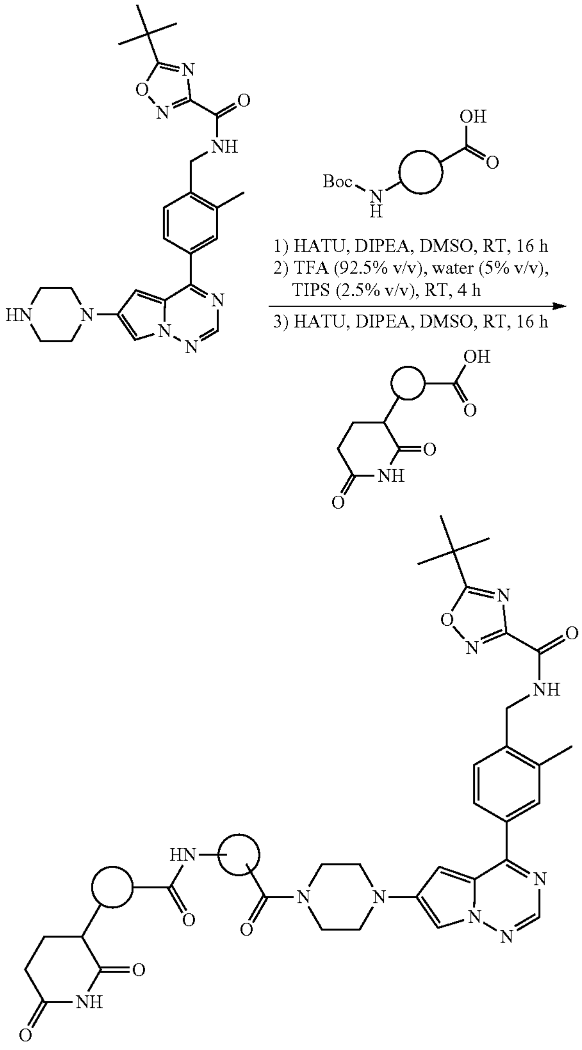

General procedure: All reactions were performed on 30-50 mg scale.

A solution of 5-(Tert-butyl)-N-(2-methyl-4-(6-(piperazin-1-yl)pyrrolo[2,1-f][1,2,4]triazin-4-yl)benzyl)-1,2,4-oxadiazole-3-carboxamide (1 equiv.), respective acid building block (1.1 equiv.), see Table 1, HATU (1.1 equiv.) and DIPEA (2.5 equiv.) in dry DMSO (0.7 mL) was stirred at room temperature for 16 hours. The reacting mixture was washed with water (3 mL), and the obtained solution was concentrated under reduced pressure. A solution of TFA (92.5% v/v), water (5% v/v) and TIPS (2.5% v/v) was then added in one portion and stirred at room temperature for 6 hours. The reacting mixture was concentrated under reduced pressure. The residue was dissolved in dry DMSO (0.7 mL)

followed by addition of 4-((2,6-dioxopiperidin-3-yl)oxy)benzoic acid or 2-(2,6-dioxopiperidin-3-yl)acetic acid (1.1 equiv.), DIPEA (5.2 equiv.), and HATU (1.1 equiv.) were stirred at room temperature for 16 hours. The mixture was concentrated under reduced pressure, and the residue was dissolved in DMSO (1 mL). The solution was filtered, analyzed by LCMS, and then subjected to prep. HPLC (Waters SunFire C18 19*100 5 mkm column; gradient mixture H2O-MeCN-0.1% TFA as a mobile phase) to afford the corresponding products.

TABLE 1

| Example | IUPAC name | | 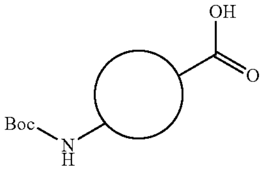 "respective acid building block" |
|---|---|---|---|
| 172 | 5-(tert-butyl)-N-(4-(6-(4-(1-(4-((2,6-dioxopiperidin-3-yl)oxy)benzoyl)pyrrolidine-3-carbonyl)piperazin-1-yl)pyrrolo[2,1-f][1,2,4]triazin-4-yl)-2-methylbenzyl)-1,2,4-oxadiazole-3-carboxamide | LCMS: m/z = 803.2 [M + H]+ | 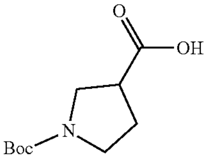 [SMILES: CC(C)(C)OC(=O)N1CCC(C(=O)O)C1] |
| | 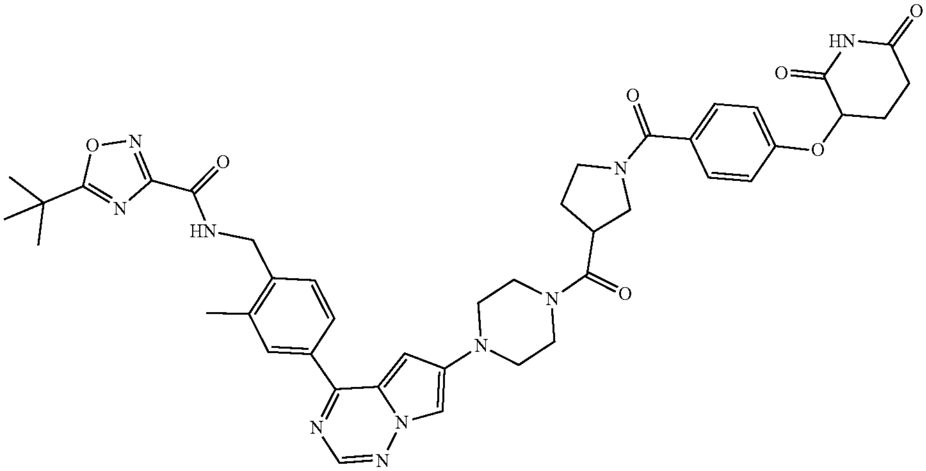 [SMILES: Cc1cc(-c2ncnn3cc(N4CCN(C(=O)C5CCN(C(=O)c6ccc(OC7CCC(=O)NC7=O)cc6)C5)CC4)cc23)ccc1CNC(=O)c1noc(C(C)(C)C)n1] | | |
| 173 | 5-(tert-butyl)-N-(4-(6-(4-(5-(4-((2,6-dioxopiperidin-3-yl)oxy)benzamido)pentanoyl)piperazin-1-yl)pyrrolo[2,1-f][1,2,4]triazin-4-yl)-2-methylbenzyl)-1,2,4-oxadiazole-3-carboxamide | LCMS: 805.4 [M + H]+ | 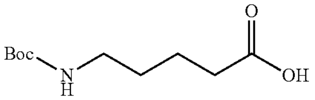 [SMILES: CC(C)(C)OC(=O)NCCCCC(=O)O] |
| | 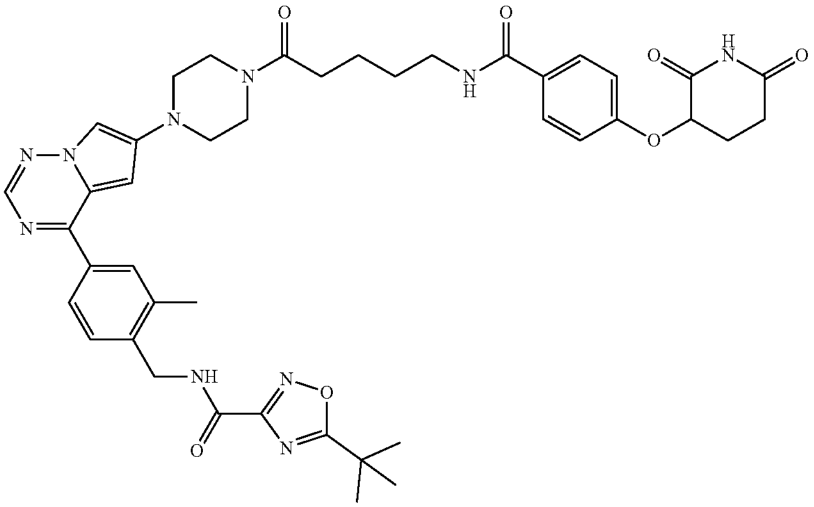 [SMILES: Cc1cc(-c2ncnn3cc(N4CCN(C(=O)CCCCNC(=O)c5ccc(OC6CCC(=O)NC6=O)cc5)CC4)cc23)ccc1CNC(=O)c1noc(C(C)(C)C)n1] | | |

TABLE 1-continued

| Example | IUPAC name | | 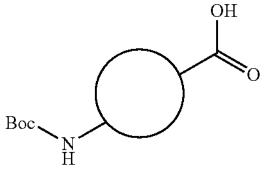 "respective acid building block" |
|---|---|---|---|
| 174 | 5-(tert-butyl)-N-(4-(6-(4-(1-((4-((2,6-dioxopiperidin-3-yl)oxy)benzamido)methyl)cyclopropane-1-carbonyl)piperazin-1-yl)pyrrolo[2,1-f][1,2,4]triazin-4-yl)-2-methylbenzyl)-1,2,4-oxadiazole-3-carboxamide | LCMS: m/z = 803.4 [M + H]$^+$ | 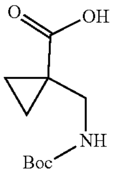 |
| | 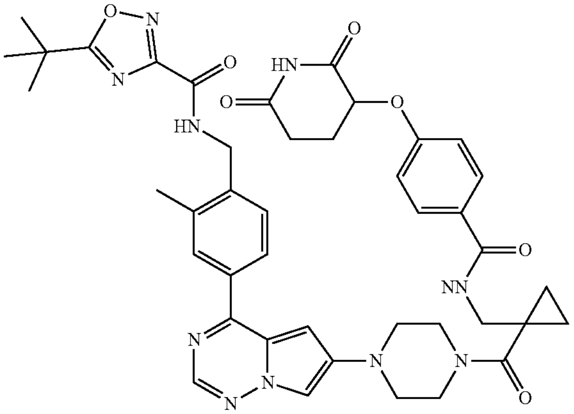 | | |
| 175 | 5-(tert-butyl)-N-(4-(6-(4-(2-(3-(4-((2,6-dioxopiperidin-3-yl)oxy)benzamido)cyclobutyl)acetyl)piperazin-1-yl)pyrrolo[2,1-f][1,2,4]triazin-4-yl)-2-methylbenzyl)-1,2,4-oxadiazole-3- | LCMS: m/z = 817.4 [M + H]$^+$ | 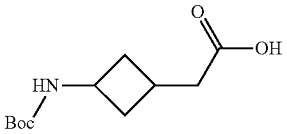 [SMILES: CC(C)(C)OC(=O)NC1CC(CC(=O)O)C1] |
| | 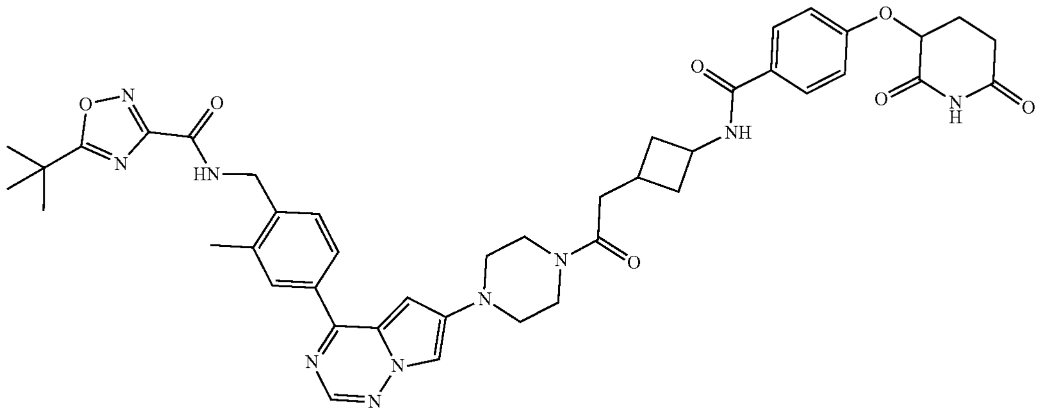 [SMILES: Cc1cc(-c2ncnn3cc(N4CCN(C(=O)CC5CC(NC(=O)c6ccc(OC7CCC(=O)NC7=O)cc6)C5)CC4)cc23)ccc1CNC(=O)c1noc(C(C)(C)C)n1] | | |
| 176 | 5-(tert-butyl)-N-(4-(6-(4-(2-(1-(4-((2,6-dioxopiperidin-3-yl)oxy)benzoyl)piperidin-2-yl)acetyl)piperazin-1-yl)pyrrolo[2,1-f][1,2,4]triazin-4-yl)-2-methylbenzyl)-1,2,4-oxadiazole-3-carboxamide | LCMS: m/z = 831.4 [M + H]$^+$ | 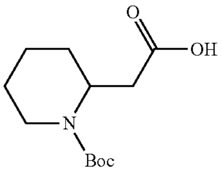 |

TABLE 1-continued

| Example | IUPAC name | | 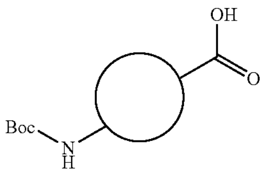 "respective acid building block" |
|---|---|---|---|
| | 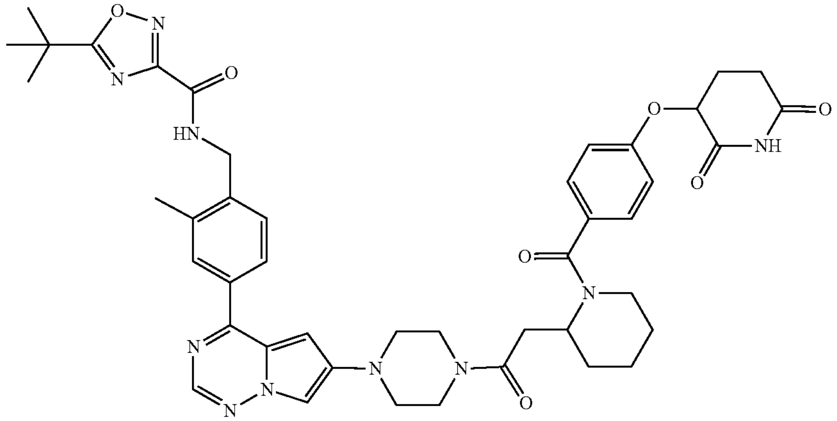 [SMILES: Cc1cc(-c2ncnn3cc(N4CCN(C(=O)CC5CCCCN5C(=O)c5ccc(OC6CCC(=O)NC6=O)cc5)CC4)cc23)ccc1CNC(=O)c1noc(C(C)(C)C)n1] | | |
| 177 | 5-(tert-butyl)-N-(4-(6-(4-(1-(2-(4-((2,6-dioxopiperidin-3-yl)oxy)benzamido)ethyl)-1H-1,2,3-triazole-4-carbonyl)piperazin-1-yl)pyrrolo[2,1-f][1,2,4]triazin-4-yl)-2-methylbenzyl)-1,2,4-oxadiazole-3-carboxamide | LCMS: m/z = 844.2 $[M + H]^+$ | 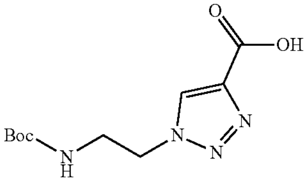 [SMILES: CC(C)(C)OC(=O)NCCn1cc(C(=O)O)nn1] |
| | 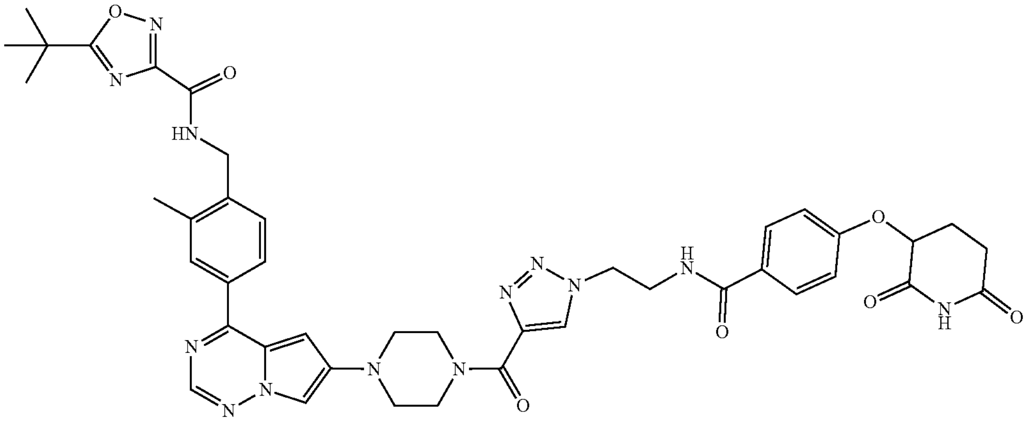 [SMILES: Cc1cc(-c2ncnn3cc(N4CCN(C(=O)c5cn(CCNC(=O)c6ccc(OC7CCC(=O)NC7=O)cc6)nn5)CC4)cc23)ccc1CNC(=O)c1noc(C(C)(C)C)n1] | | |
| 178 | 5-(tert-butyl)-N-(4-(6-(4-(6-(4-((2,6-dioxopiperidin-3-yl)oxy)benzoyl)-6-azaspiro[3.4]octane-2-carbonyl)piperazin-1-yl)pyrrolo[2,1-f][1,2,4]triazin-4-yl)-2-methylbenzyl)-1,2,4-oxadiazole-3-carboxamide | LCMS: m/z = 843.4 $[M + H]^+$ | 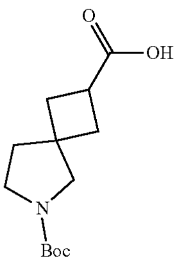 [SMILES: CC(C)(C)OC(=O)N1CCC2(CC(C(=O)O)C2)C1] |

TABLE 1-continued

| Example | IUPAC name | | 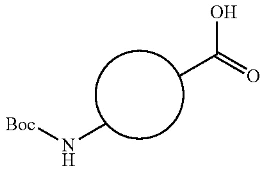<br>"respective acid building block" |
|---|---|---|---|
| | 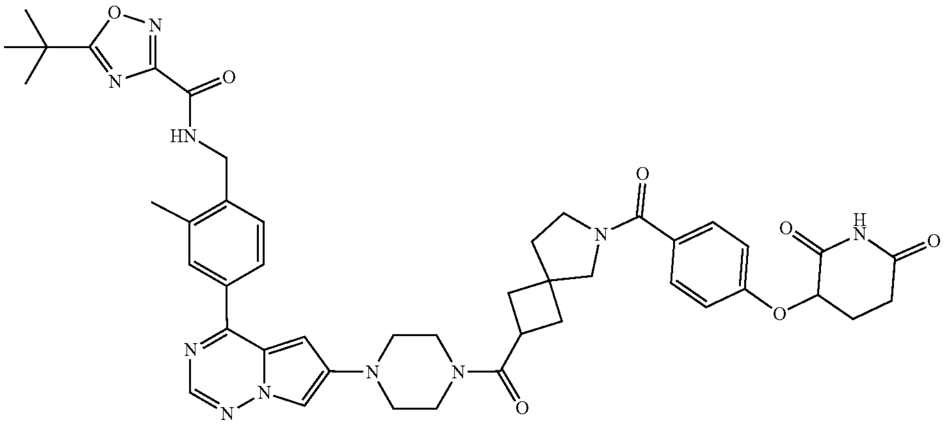 [SMILES: Cc1cc(-c2ncnn3cc(N4CCN(C(=O)C5CC6(CCN(C(=O)c7ccc(OC8CCC(=O)NC8=O)cc7)C6)C5)CC4)cc23)ccc1CNC(=O)c1noc(C(C)(C)C)n1] | | |
| 179 | 5-(tert-butyl)-N-(4-(6-(4-(6-((4-((2,6-dioxopiperidin-3-yl)oxy)benzamido)methyl)nicotinoyl)piperazin-1-yl)pyrrolo[2,1-f][1,2,4]triazin-4-y1)-2-methylbenzyl)-1,2,4-oxadiazole-3-carboxamide | LCMS: m/z = 840.2 $[M + H]^+$ | 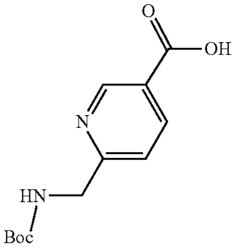 [SMILES: CC(C)(C)OC(=O)NCc1ccc(C(=O)O)cn1] |
| | 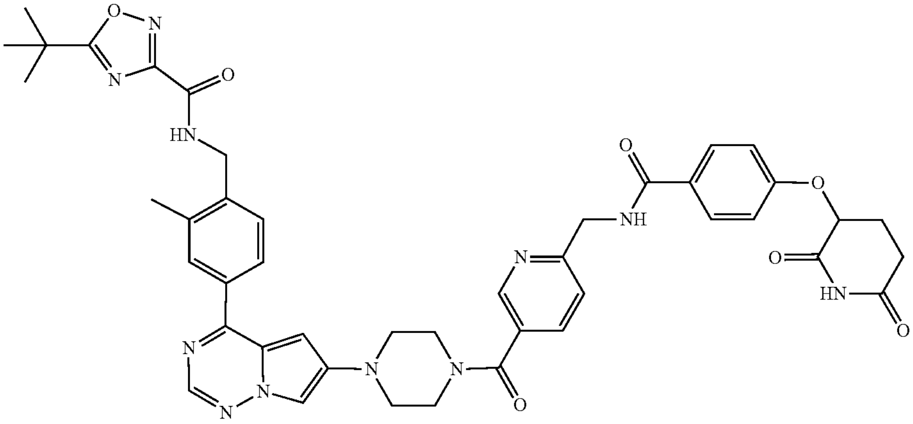 [SMILES: Cc1cc(-c2ncnn3cc(N4CCN(C(=O)c5ccc(CNC(=O)c6ccc(OC7CCC(=O)NC7=O)cc6)nc5)CC4)cc23)ccc1CNC(=O)c1noc(C(C)(C)C)n1] | | |
| 180 | 5-(tert-butyl)-N-(4-(6-(4-(9-(4-((2,6-dioxopiperidin-3-yl)oxy)benzamido)nonanoyl)piperazin-1-yl)pyrrolo[2,1-f][1,2,4]triazin-4-yl)-2-methylbenzyl)-1,2,4-oxadiazole-3-carboxamide | LCMS: m/z = 861.4 $[M + H]^+$ | 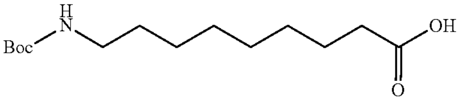 [SMILES: CC(C)(C)OC(=O)NCCCCCCCCC(=O)O] |

TABLE 1-continued

| Example | IUPAC name | | 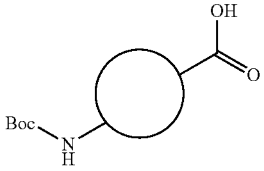<br>"respective acid building block" |
|---|---|---|---|
| | 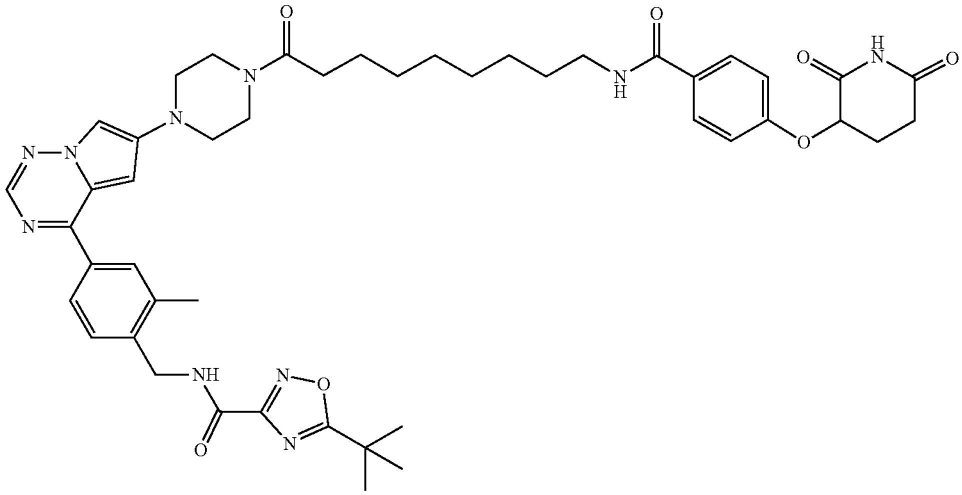 [SMILES: Cc1cc(-c2ncnn3cc(N4CCN(C(=O)CCCCCCCCNC(=O)c5ccc(OC6CCC(=O)NC6=O)cc5)CC4)cc23)ccc1CNC(=O)c1noc(C(C)(C)C)n1] | | |
| 181 | 5-(tert-butyl)-N-(4-(6-(4-(3-(1-(4-((2,6-dioxopiperidin-3-yl)oxy)benzoyl)pyrrolidin-2-yl)propanoyl)piperazin-1-yl)pyrrolo[2,1-f][1,2,4]triazin-4-yl)-2-methylbenzyl)-1,2,4-oxadiazole-3-carboxamide | LCMS: m/z = 831.6 $[M + H]^+$ | 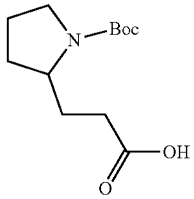 [SMILES: CC(C)(C)OC(=O)N1CCCC1CCC(=O)O] |
| | 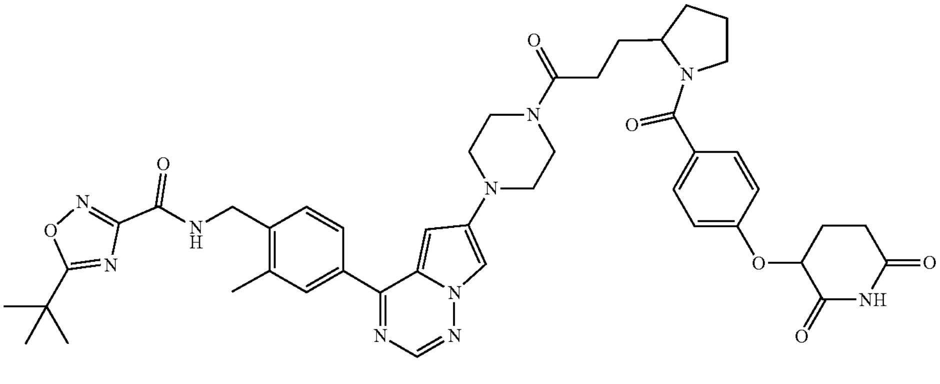 [SMILES: Cc1cc(-c2ncnn3cc(N4CCN(C(=O)CCC5CCCN5C(=O)c5ccc(OC6CCC(=O)NC6=O)cc5)CC4)cc23)ccc1CNC(=O)c1noc(C(C)(C)C)n1] | | |
| 182 | 5-(tert-butyl)-N-(4-(6-(4-(5-(1-(4-((2,6-dioxopiperidin-3-yl)oxy)benzoyl)piperidin-4-yl)pentanoyl)piperazin-1-yl)pyrrolo[2,1-f][1,2,4]triazin-4-yl)-2-methylbenzyl)-1,2,4-oxadiazole-3-carboxamide | LCMS: m/z = 873.6 $[M + H]^+$ | 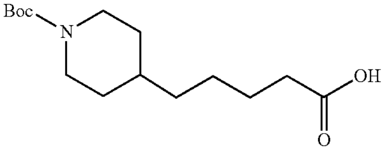 [SMILES: CC(C)(C)OC(=O)N1CCC(CCCCC(=O)O)CC1] |

TABLE 1-continued

| Example | IUPAC name | | 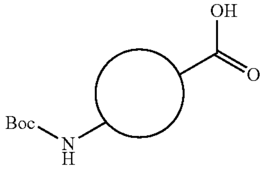 "respective acid building block" |
|---|---|---|---|
| | 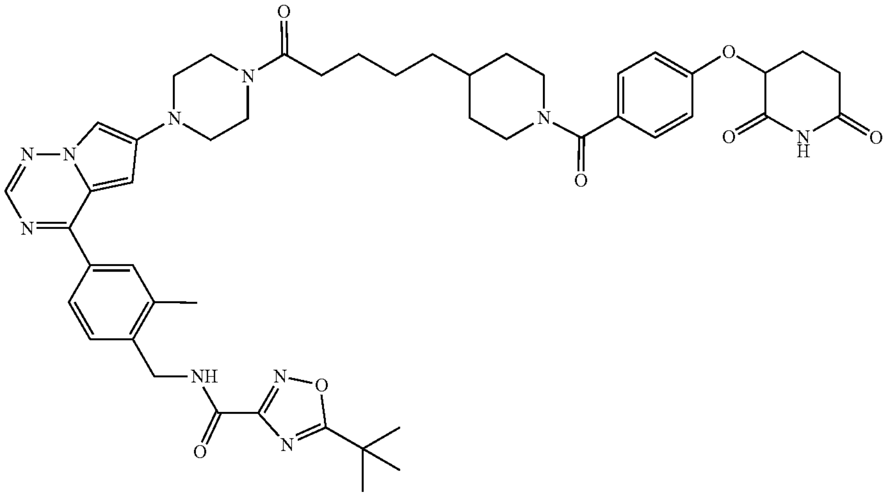 [SMILES: Cc1cc(-c2ncnn3cc(N4CCN(C(=O)CCCCC5CCN(C(=O)c6ccc(OC7CCC(=O)NC7=O)cc6)CC5)CC4)cc23)ccc1CNC(=O)c1noc(C(C)(C)C)n1] | | |
| 183 | 5-(tert-butyl)-N-(4-(6-(4-(3-(2-((4-((2,6-dioxopiperidin-3-yl)oxy)benzamido)methyl)phenyl)propanoy 1)piperazin-1-yl)pyrrolo[2,1-f][1,2,4]triazin-4-y1)-2-methylbenzyl)-1,2,4-oxadiazole-3-carboxamide | LCMS: m/z = 867.4 [M + H]$^+$ | 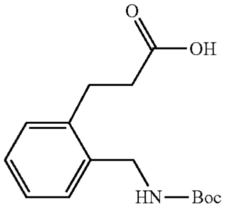 [SMILES: CC(C)(C)OC(=O)NCc1ccccc1CCC(=O)O] |
| | 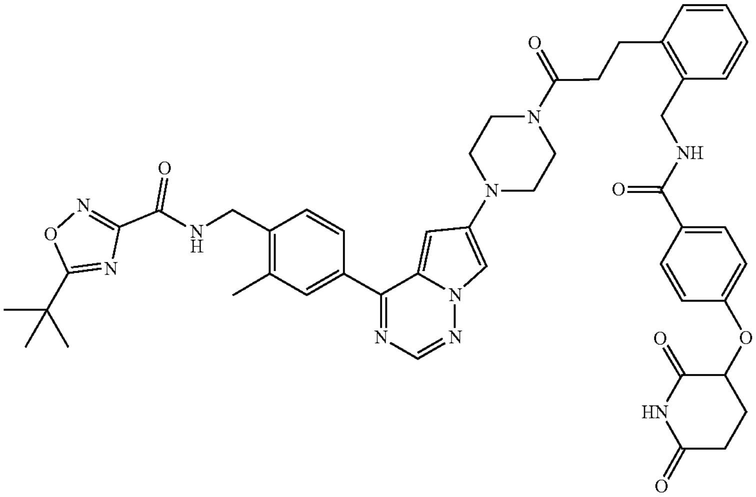 [SMILES: Cc1cc(-c2ncnn3cc(N4CCN(C(=O)CCc5ccccc5CNC(=O)c5ccc(OC6CCC(=O)NC6=O)cc5)CC4)cc23)ccc1CNC(=O)c1noc(C(C)(C)C)n1] | | |
| 184 | 5-(tert-butyl)-N-(4-(6-(4-(4-(1-(4-((2,6-dioxopiperidin-3-yl)oxy)benzoyl)azetidin-3-yl)butanoyl)piperazin-1-yl)pyrrolo[2,1-f][1,2,4]triazin-4-yl)-2-methylbenzyl)-1,2,4-oxadiazole-3-carboxamide | LCMS: m/z = 831.4 [M + H]+ | 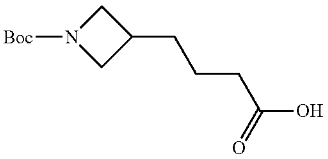 [SMILES: CC(C)(C)OC(=O)N1CC(CCCC(=O)O)C1] |

TABLE 1-continued

| Example | IUPAC name | | 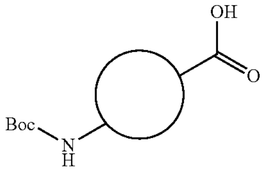 "respective acid building block" |
|---|---|---|---|
| | 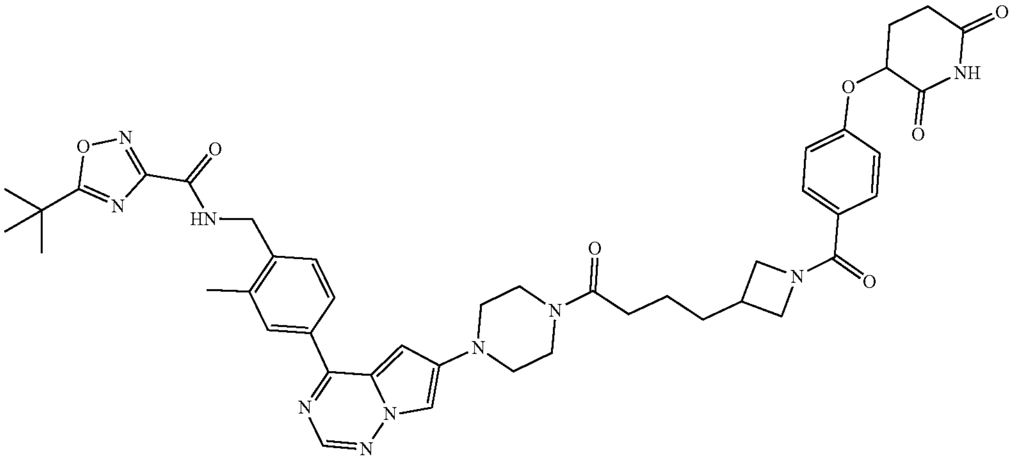 [SMILES: Cc1cc(-c2ncnn3cc(N4CCN(C(=O)CCCC5CN(C(=O)c6ccc(OC7CCC(=O)NC7=O)cc6)C5)CC4)cc23)ccc1CNC(=O)c1noc(C(C)(C)C)n1] | | |
| 185 | 5-(tert-butyl)-N-(4-(6-(4-(2-(2-(4-((2,6-dioxopiperidin-3-yl)oxy)benzoyl)-2-azaspiro[3.3]heptan-6-yl)acetyl)piperazin-1-yl)pyrrolo[2,1-f][1,2,4]triazin-4-yl)-2-methylbenzyl)-1,2,4-oxadiazole-3-carboxamide | LCMS: m/z = 844.4 [M + H]$^+$ | 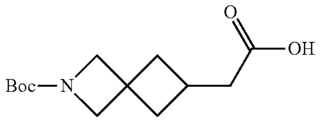 [SMILES: CC(C)(C)OC(=O)N1CC2(CC(CC(=O)O)C2)C1] |
| | 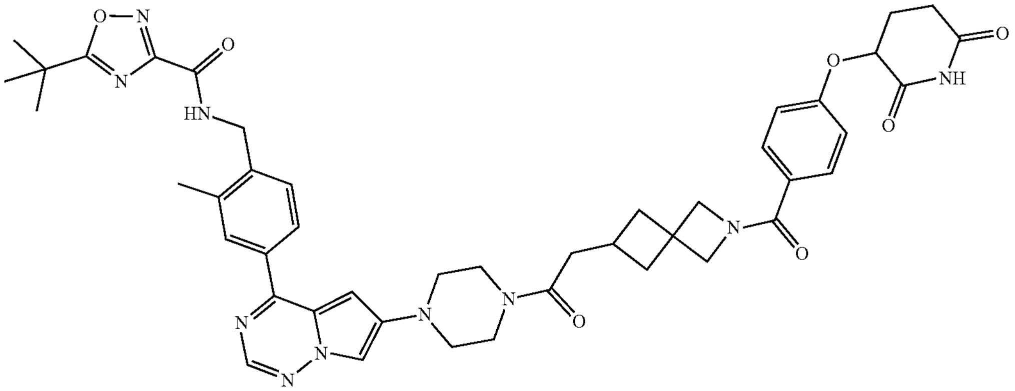 [SMILES: Cc1cc(-c2ncnn3cc(N4CCN(C(=O)CC5CC6(C5)CN(C(=O)c5ccc(OC7CCC(=O)NC7=O)cc5)C6)CC4)cc23)ccc1CNC(=O)c1noc(C(C)(C)C)n1] | | |
| 186 | 5-(tert-butyl)-N-(4-(6-(4-(5-(4-((2,6-dioxopiperidin-3-yl)oxy)benzoyl)-5-azaspiro[3.4]octane-2-carbonyl)piperazin-1-yl)pyrrolo[2,1-f][1,2,4]triazin-4-yl)-2-methylbenzyl)-1,2,4-oxadiazole-3-carboxamide | LCMS: m/z = 843.4 [M + H]+ | 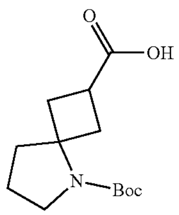 [SMILES: CC(C)(C)OC(=O)N1CCCC12CC(C(=O)O)C2] |

TABLE 1-continued

| Example | IUPAC name | | 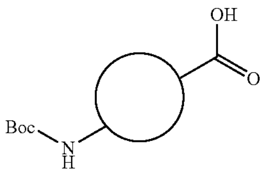 "respective acid building block" |
|---|---|---|---|
| | 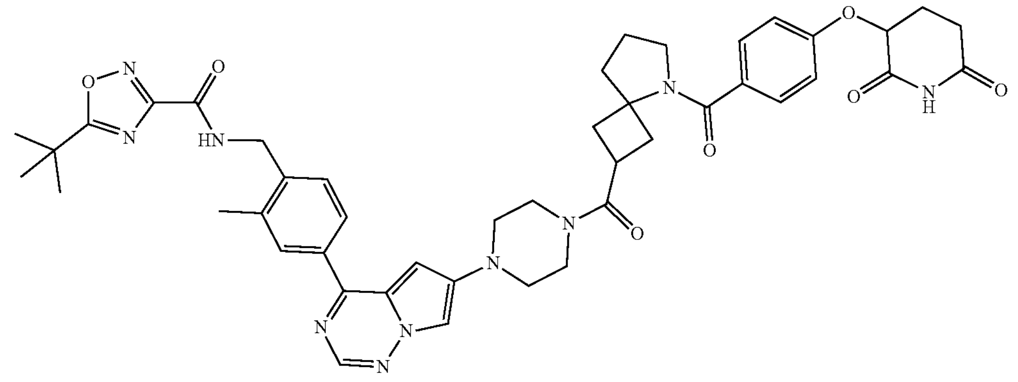 [SMILES: Cc1cc(-c2ncnn3cc(N4CCN(C(=O)C5CC6(CCCN6C(=O)c6ccc(OC7CCC(=O)NC7=O)cc6)C5)CC4)cc23)ccc1CNC(=O)c1noc(C(C)(C)C)n1] | | |
| 187 | 5-(tert-butyl)-N-(4-(6-(4-(2-((4-((2,6-dioxopiperidin-3-yl)oxy)benzamido)methyl)tetrahydrofuran-3-carbonyl)piperazin-1-yl)pyrrolo[2,1-f][1,2,4]triazin-4-yl)-2-methylbenzyl)-1,2,4-oxadiazole-3-carboxamide | LCMS: m/z = 833.4 [M + H]+ | 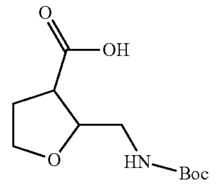 [SMILES: CC(C)(C)OC(=O)NCC1OCCC1C(=O)O] |
| | 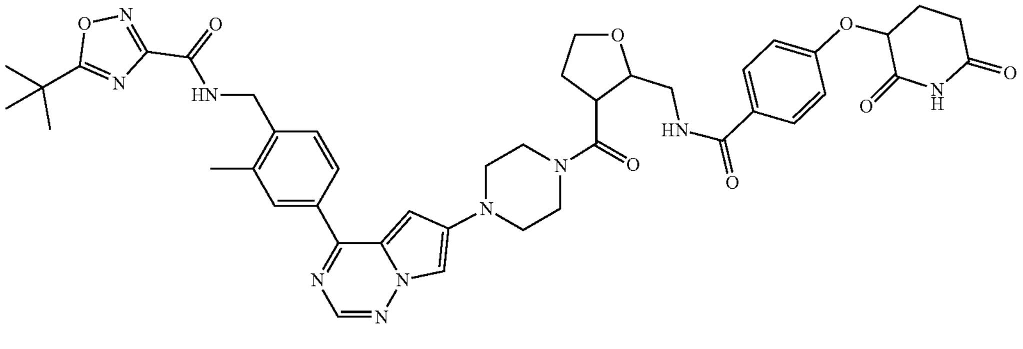 [SMILES: Cc1cc(-c2ncnn3cc(N4CCN(C(=O)C5CCOC5CNC(=O)c5ccc(OC6CCC(=O)NC6=O)cc5)CC4)cc23)ccc1CNC(=O)c1noc(C(C)(C)C)n1] | | |
| 188 | 5-(tert-butyl)-N-(4-(6-(4-((1R,3S)-3-(4-((2,6-dioxopiperidin-3-yl)oxy)benzamido)cyclohexane-1-carbonyl)piperazin-1-yl)pyrrolo[2,1-f][1,2,4]triazin-4-yl)-2-methylbenzyl)-1,2,4-oxadiazole-3-carboxamide | LCMS: m/z = 831.4 [M + H]+ | 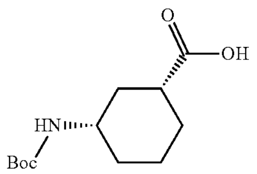 [SMILES: CC(C)(C)OC(=O)N[C@H]1CCC[C@@H](C(=O)O)C1] |

TABLE 1-continued

| Example | IUPAC name | | "respective acid building block" |
|---|---|---|---|
| | | | 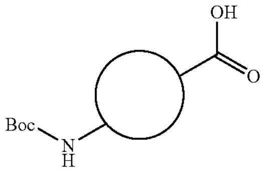 |
| | 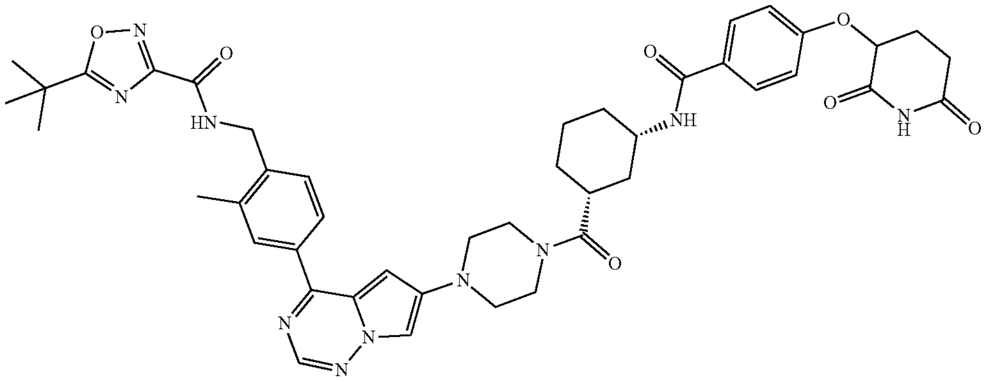 [SMILES: Cc1cc(-c2ncnn3cc(N4CCN(C(=O)[C@@H]5CCC[C@H](NC(=O)c6ccc(OC7CCC(=O)NC7=O)cc6)C5)CC4)cc23)ccc1CNC(=O)c1noc(C(C)(C)C)n1] | | |
| 189 | 5-(tert-butyl)-N-(4-(6-(4-(5-((4-((2,6-dioxopiperidin-3-yl)oxy)benzamido)methyl)oxazole-4-carbonyl)piperazin-1-yl)pyrrolo[2,1-f][1,2,4]triazin-4-yl)-2-methylbenzyl)-1,2,4-oxadiazole-3-carboxamide | LCMS: m/z = 830.0 [M + H]+ | |
| | 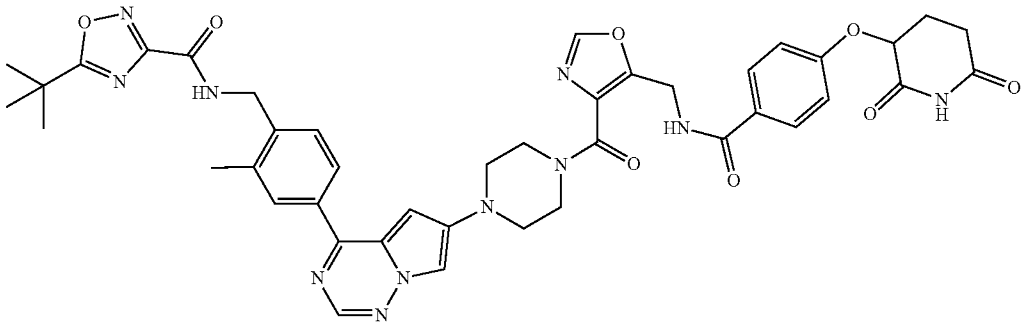 [SMILES: Cc1cc(-c2ncnn3cc(N4CCN(C(=O)c5ncoc5CNC(=O)c5ccc(OC6CCC(=O)NC6=O)cc5)CC4)cc23)ccc1CNC(=O)c1noc(C(C)(C)C)n1] | | |
| 190 | 5-(tert-butyl)-N-(4-(6-(4-(2-(2-(4-((2,6-dioxopiperidin-3-yl)oxy)benzoyl)-6-oxa-2-azaspiro[3.4]octan-7-yl)acetyl)piperazin-1-yl)pyrrolo[2,1-f][1,2,4]triazin-4-yl)-2-methylbenzyl)-1,2,4-oxadiazole-3-carboxamide | LCMS: m/z = 859.4 [M + H]+ | 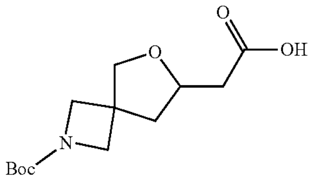 [SMILES: CC(C)(C)OC(=O)N1CC2(COC(CC(=O)O)C2)C1] |

TABLE 1-continued

| Example | IUPAC name | | 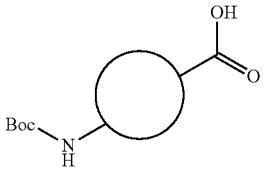 "respective acid building block" |
|---|---|---|---|
| | 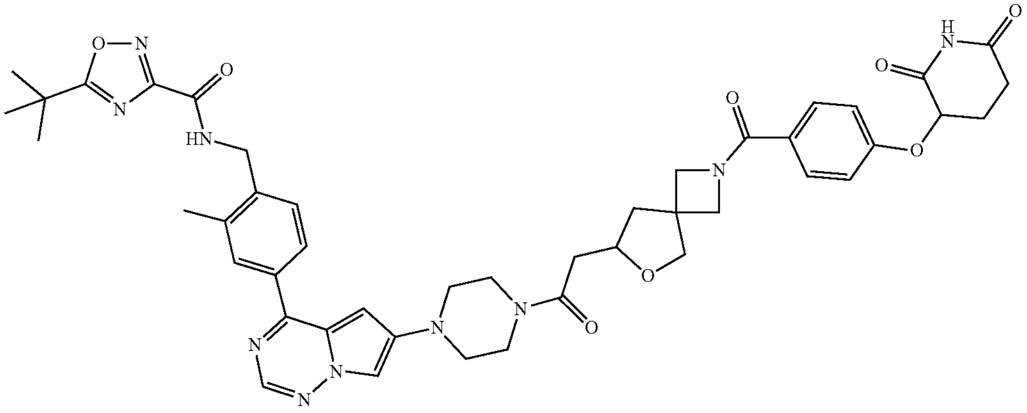 [SMILES: Cc1cc(-c2ncnn3cc(N4CCN(C(=O)CC5CC6(CO5)CN(C(=O)c5ccc(OC7CCC(=O)NC7=O)cc5)C6)CC4)cc23)ccc1CNC(=O)c1noc(C(C)(C)C)n1] | | |
| 191 | 5-(tert-butyl)-N-(4-(6-(4-(5-(4-((2,6-dioxopiperidin-3-yl)oxy)benzoyl)-5-azaspiro[3.4]octane-8-carbonyl)piperazin-1-yl)pyrrolo[2,1-f][1,2,4]triazin-4-yl)-2-methylbenzyl)-1,2,4-oxadiazole-3-carboxamide | LCMS: m/z = 843.4 [M + H]+ | 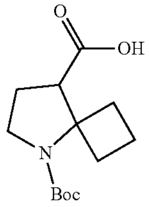 [SMILES: CC(C)(C)OC(=O)N1CCC(C(=O)O)C12CCC2] |
| | 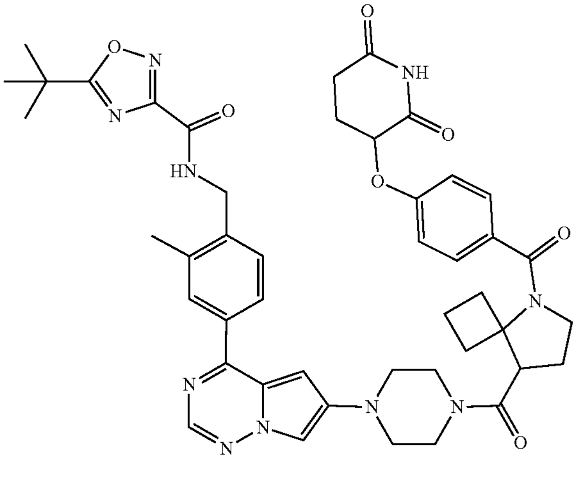 [SMILES: Cc1cc(-c2ncnn3cc(N4CCN(C(=O)C5CCN(C(=O)c6ccc(OC7CCC(=O)NC7=O)cc6)C56CCC6)CC4)cc23)ccc1CNC(=O)c1noc(C(C)(C)C)n1] | | |
| 192 | 5-(tert-butyl)-N-(4-(6-(4-(4-(4-((2,6-dioxopiperidin-3-yl)oxy)benzamido)-3,3-dimethylbutanoyl)piperazin-1-yl)pyrrolo[2,1-f][1,2,4]triazin-4-yl)-2-methylbenzyl)-1,2,4-oxadiazole-3-carboxamide | LCMS: m/z = 819.4 $[M + H]^+$ | 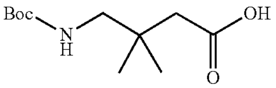 [SMILES: CC(C)(CNC(=O)OC(C)(C)C)CC(=O)O] |

TABLE 1-continued
| Example | IUPAC name | | 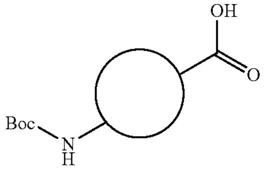 "respective acid building block" |
|---|---|---|---|
| | 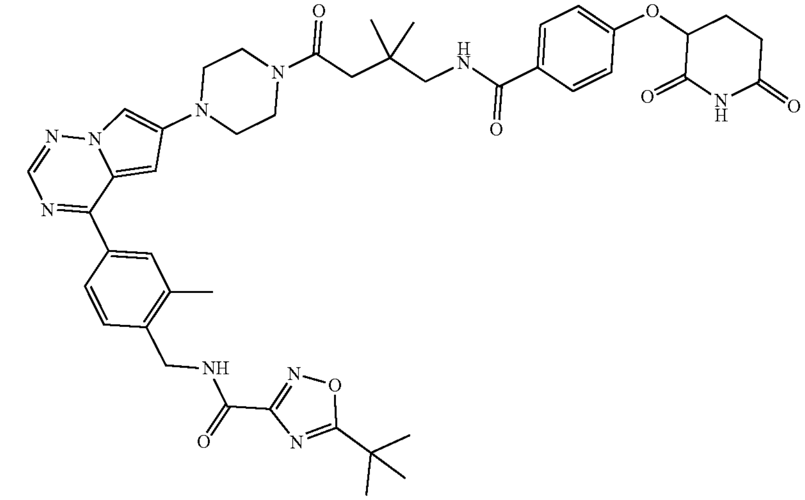 [SMILES: Cc1cc(-c2ncnn3cc(N4CCN(C(=O)CC(C)(C)CNC(=O)c5ccc(OC6CCC(=O)NC6=O)cc5)CC4)cc23)ccc1CNC(=O)c1noc(C(C)(C)C)n1] | | |
| 193 | 5-(tert-butyl)-N-(4-(6-(4-(2-((4-((2,6-dioxopiperidin-3-yl)oxy)benzamido)methyl)benzoyl)piperazin-1-yl)pyrrolo[2,1-f][1,2,4]triazin-4-yl)-2-methylbenzyl)-1,2,4-oxadiazole-3-carboxamide | LCMS: m/z = 839.2 [M + H]+ | 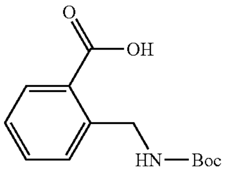 [SMILES: CC(C)(C)OC(=O)NCc1ccccc1C(=O)O] |
| | 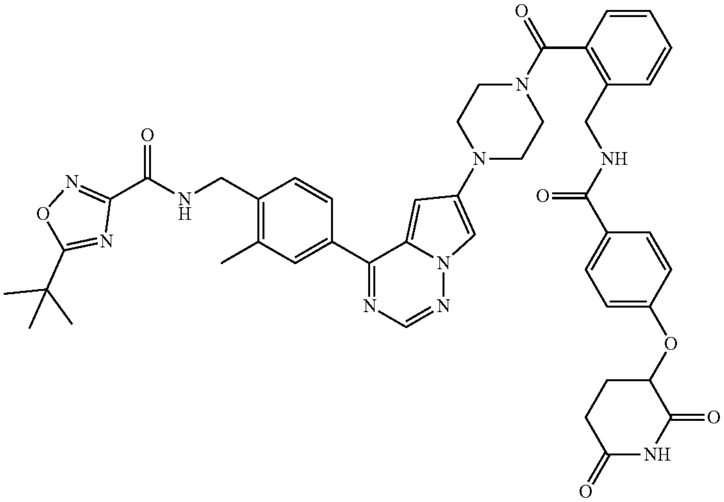 [SMILES: Cc1cc(-c2ncnn3cc(N4CCN(C(=O)c5ccccc5CNC(=O)c5ccc(OC6CCC(=O)NC6=O)cc5)CC4)cc23)ccc1CNC(=O)c1noc(C(C)(C)C)n1] | | |

General Procedures (Benzamides)

Intermediate Synthesis

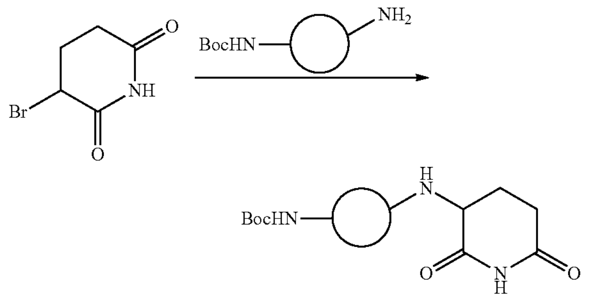

A solution of 3-bromopiperidine-2,6-dione (1 equiv.), the respective amine building block (1 equiv.), and DIPEA (3 equiv.) in 1,4-dioxane was stirred at 100° C. for 24 h under inert atmosphere. A second portion of 3-bromopiperidine-2,6-dione (1 equiv.) was added, and the reaction mixture was stirred for another 24 h at 100° C. The reacting mixture was evaporated, and the residue was subjected to prep-HPLC. ((Waters SunFire C18 19*100 5 mkm column; gradient mixture H2O-MeCN as a mobile phase)) to afford the desired intermediates.

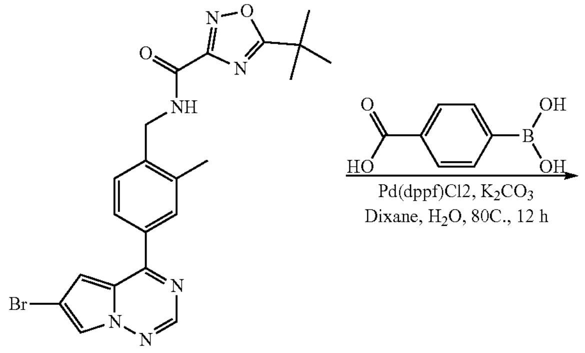

-continued

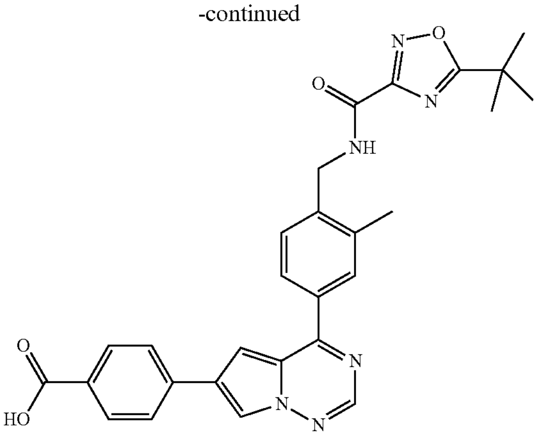

4-(4-(4-((5-(tert-butyl)-1,2,4-oxadiazole-3-carboxamido)methyl)-3-methylphenyl) pyrrolo[2,1-f][1,2,4]triazin-6-yl)benzoic acid A solution of N-[[4-(6-bromopyrrolo[2,1-f][1,2,4]triazin-4-yl)-2-methyl-phenyl]methyl]-5-tert-butyl-1,2,4-oxadiazole-3-carboxamide (4.01 g, 8.54 mmol), 4-(4,4,5,5-tetramethyl-1,3,2-dioxaborolan-2-yl)benzoic acid (2.33 g, 9.40 mmol), Pd(dppf)$Cl_2$·$CH_2Cl_2$ (697.74 mg, 854.40 μmol) and $K_2CO_3$ (3.54 g, 25.63 mmol) in 1,4-Dioxane (40 mL) and water (10 mL), was stirred at 90° C. for 12 h under inert atmosphere. After cooling to rt, the mixture was concentrated, then was diluted in water (250 ml) and filtered. The filtrates were acidified with 1M $NaHSO_4$ (pH 3-4) and filtered. The solid was dried, refluxed in $CH_3CN$ (40 ml) and filtered. The cake was washed with $CH_3CN$ (20 ml) and dried to provide 4-[4-[4-[[(5-tert-butyl-1,2,4-oxadiazole-3-carbonyl)amino]methyl]-3-methyl-phenyl]pyrrolo[2,1-f][1,2,4]triazin-6-yl]benzoic acid (3.7 g, 6.59 mmol, 77% yield) as a yellow solid. LC-MS($ES^+$): m/z=511.2 $[M+H]^+$.

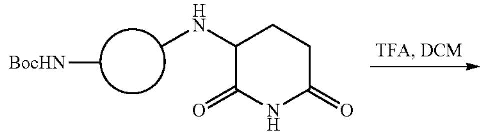

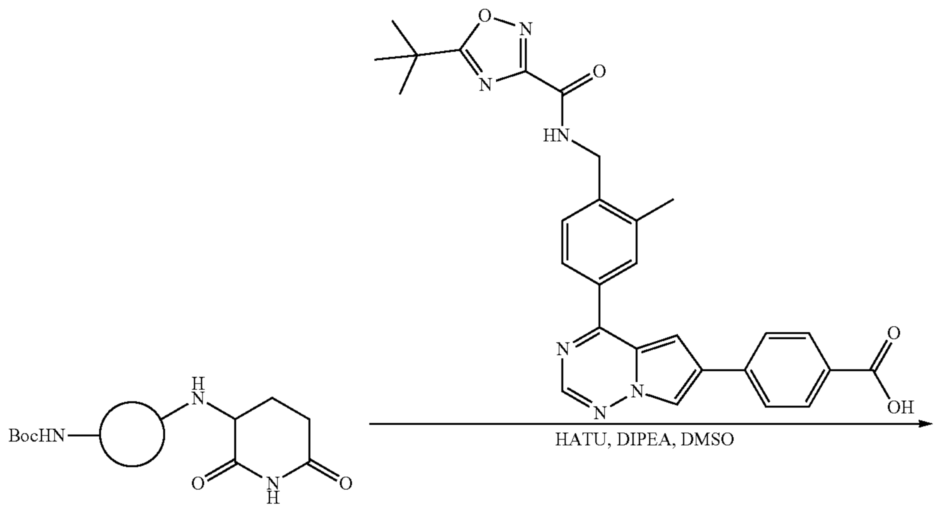

-continued

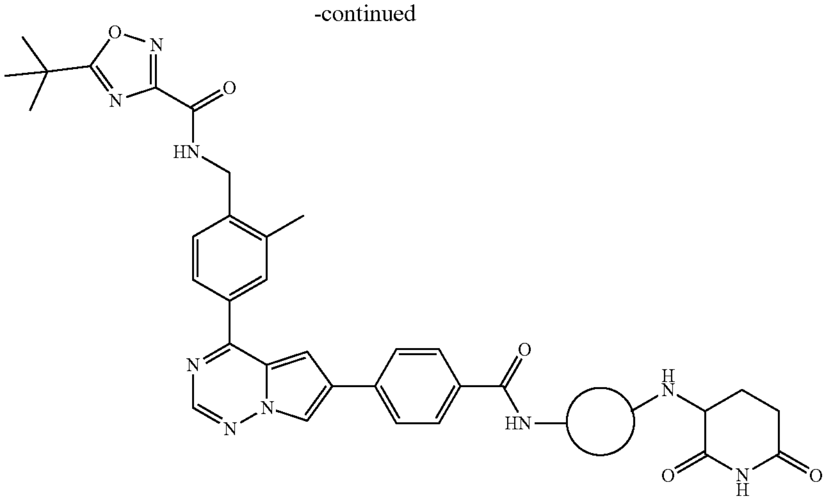

All the syntheses were performed on a ~40 mg-scale.

The Respective Intermediate building block (1.0 equiv.), see Table 2, was stirred in dry DCM (0.5 mL) and TFA (0.5 mL) at room temperature for 4 hours, then was concentrated under reduced pressure. The residue was dissolved in dry DMSO (0.3 mL) followed by addition of 4-(4-(4-((5-(tert-butyl)-1,2,4-oxadiazole-3-carboxamido)methyl)-3-methylphenyl)pyrrolo[2,1-f][1,2,4]triazin-6-yl)benzoic acid (1.0 equiv.), DIPEA (6.0 equiv.) and HATU (1.1 equiv.) and stirred for 16 hours at room temperature. The reacting mixture was concentrated under reduced pressure, and the residue was dissolved in DMSO (0.15 mL). The solution was filtered, analyzed by LCMS, and then subjected to prep-HPLC (Waters SunFire C18 19*100 5 mkm column; gradient mixture H2O-MeCN-0.1% TFA as a mobile phase) to afford the corresponding products.

TABLE 2

| Example | IUPAC name | | 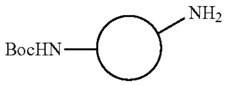 "Respective Intermediate building block" precursor |
|---|---|---|---|
| 194 | 5-(tert-butyl)-N-(4-(6-(4-((2-(2,6-dioxopiperidin-3-yl)-1,2,3,4-tetrahydroisoquinolin-5-yl)carbamoyl)phenyl)pyrrolo[2,1-f][1,2,4]triazin-4-yl)-2-methylbenzyl)-1,2,4-oxadiazole-3-carboxamide | LCMS: m/z = 752.4 $[M + H]^+$ | 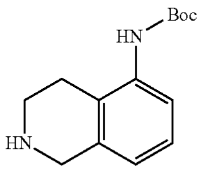 |
| | 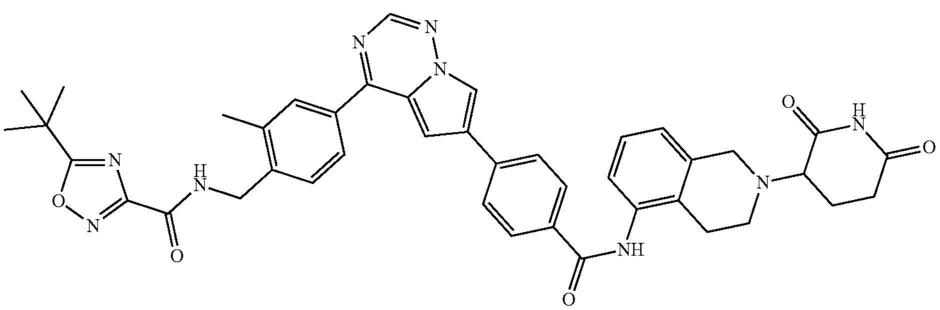 [SMILES: Cc1cc(-c2ncnn3cc(-c4ccc(C(=O)Nc5cccc6c5CCN(C5CCC(=O)NC5=O)C6)cc4)cc23)ccc1CNC(=O)c1noc(C(C)(C)C)n1] | | |
| 195 | 5-(tert-butyl)-N-(4-(6-(4-(6-((2,6-dioxopiperidin-3-yl)amino)-1,2,3,4-tetrahydroisoquinoline-1-carbonyl)phenyl)pyrrolo[2,1-f][1,2,4]triazin-4-yl)-2-methylbenzyl)-1,2,4-oxadiazole-3-carboxamide | LCMS: m/z = 752.2 $[M + H]^+$ | 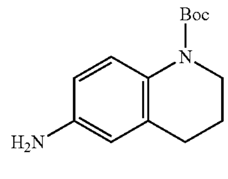 |

TABLE 2-continued

| Example | IUPAC name | | 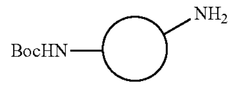<br>"Respective Intermediate building block" precursor |
|---|---|---|---|
| | 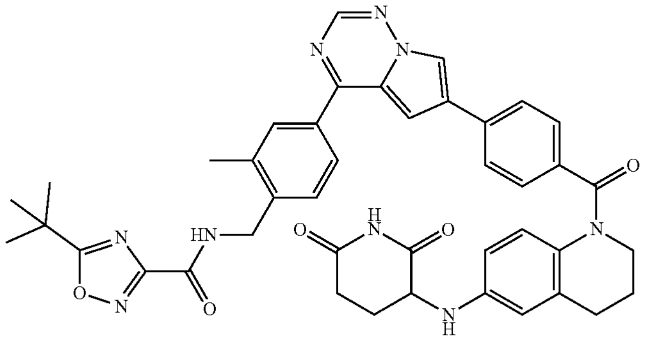 [SMILES: Cc1cc(-c2ncnn3cc(-c4ccc(C(=O)N5CCCc6cc(NC7CCC(=O)NC7=O)ccc65)cc4)cc23)ccc1CNC(=O)c1noc(C(C)(C)C)n1] | | |
| 196 | 5-(tert-butyl)-N-(4-(2-(4-((4-(3-(2,4-dioxotetrahydropyrimidin-1(2H)-yl)-1-methyl-1H-indazol-6-yl)piperidin-1-yl)methyl)-3-fluorophenyl)pyrazolo[1,5-a]pyrimidin-7-yl)-2-fluorobenzyl)-1,2,4-oxadiazole-3-carboxamide | LCMS: m/z = 740.3 [M + H]+ | 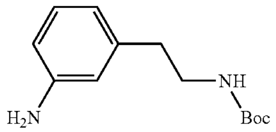 [SMILES: CC(C)(C)OC(=O)NCCc1cccc(N)c1] |
| | 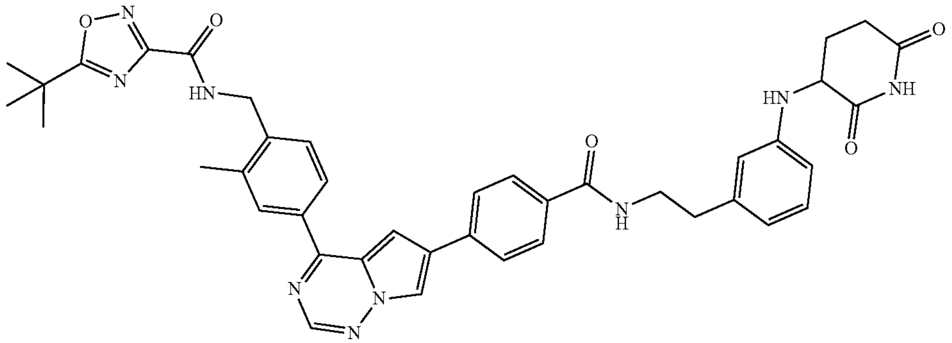 [SMILES: Cc1cc(-c2ncnn3cc(-c4ccc(C(=O)NCCc5cccc(NC6CCC(=O)NC6=O)c5)cc4)cc23)ccc1CNC(=O)c1noc(C(C)(C)C)n1] | | |
| 197 | 5-(tert-butyl)-N-(4-(6-(4-((6-((2,6-dioxopiperidin-3-yl)amino)-1,2,3,4-tetrahydronaphthalen-2-yl)carbamoyl)phenyl)pyrrolo[2,1-f][1,2,4]triazin-4-yl)-2-methylbenzyl)-1,2,4-oxadiazole-3-carboxamide | LCMS: m/z = 766.4 [M + H]+ | 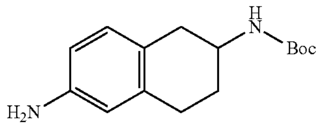 |
| | 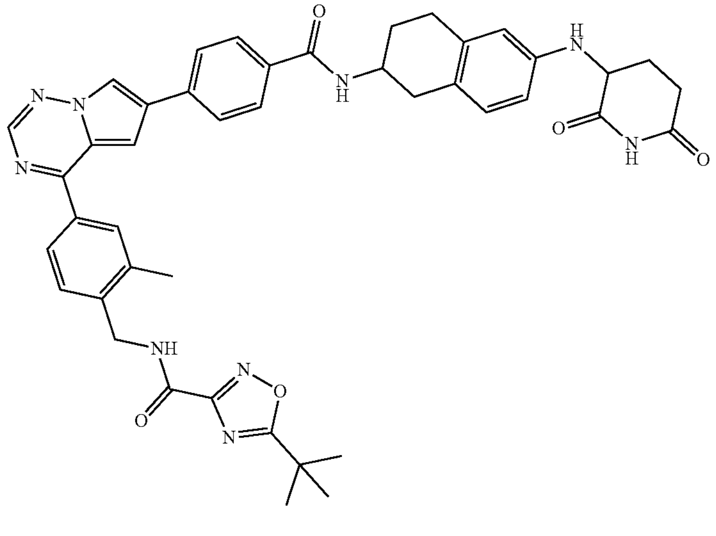 [SMILES: Cc1cc(-c2ncnn3cc(-c4ccc(C(=O)NC5CCc6cc(NC7CCC(=O)NC7=O)ccc6C5)cc4)cc23)ccc1CNC(=O)c1noc(C(C)(C)C)n1] | | |

TABLE 2-continued

| Example | IUPAC name | | 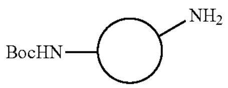<br>"Respective Intermediate building block" precursor |
|---|---|---|---|
| 198 | 5-(tert-butyl)-N-(4-(6-(4-((4-((2,6-dioxopiperidin-3-yl)amino)phenethyl)carbamoyl)phenyl)pyrrolo[2,1-f][1,2,4]triazin-4-yl)-2-methylbenzyl)-1,2,4-oxadiazole-3-carboxamide | LCMS: m/z = 740.2 $[M + H]^+$ | 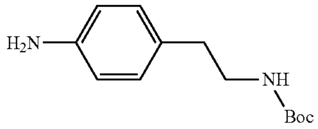 [SMILES: CC(C)(C)OC(=O)NCCc1ccc(N)cc1] |
| | 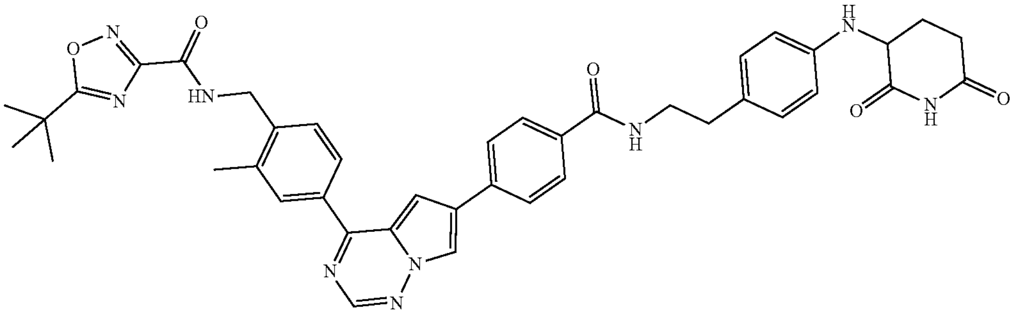 [SMILES: Cc1cc(-c2ncnn3cc(-c4ccc(C(=O)NCCc5ccc(NC6CCC(=O)NC6=O)cc5)cc4)cc23)ccc1CNC(=O)c1noc(C(C)(C)C)n1] | | |
| 199 | 5-(tert-butyl)-N-(4-(6-(4-(((1R)-1-(3-((2,6-dioxopiperidin-3-yl)amino)phenyl)ethyl)carbamoyl)phenyl)pyrrolo[2,1-f][1,2,4]triazin-4-yl)-2-methylbenzyl)-1,2,4-oxadiazole-3-carboxamide | LCMS: m/z = 738.4 $[M + H]^-$ | 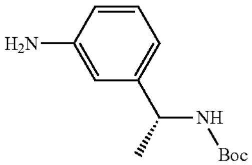 [SMILES: C[C@@H](NC(=O)OC(C)(C)C)c1cccc(N)c1] |
| | 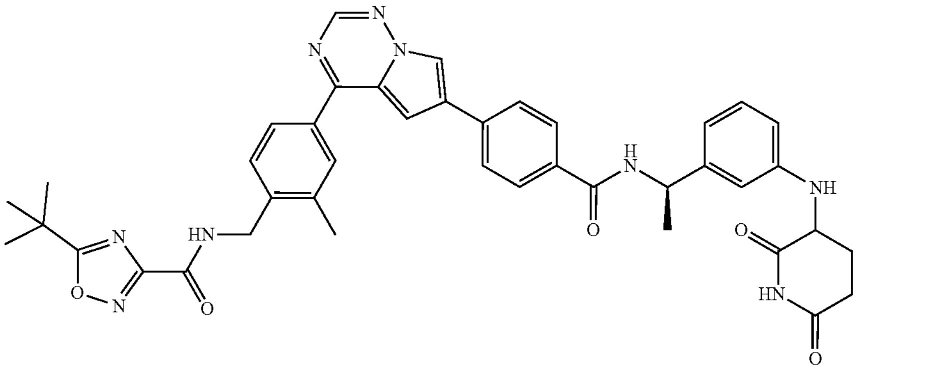 [SMILES: Cc1cc(-c2ncnn3cc(-c4ccc(C(=O)N[C@H](C)c5cccc(NC6CCC(=O)NC6=O)c5)cc4)cc23)ccc1CNC(=O)c1noc(C(C)(C)C)n1] | | |

General Procedure (Benzyl Linkers)

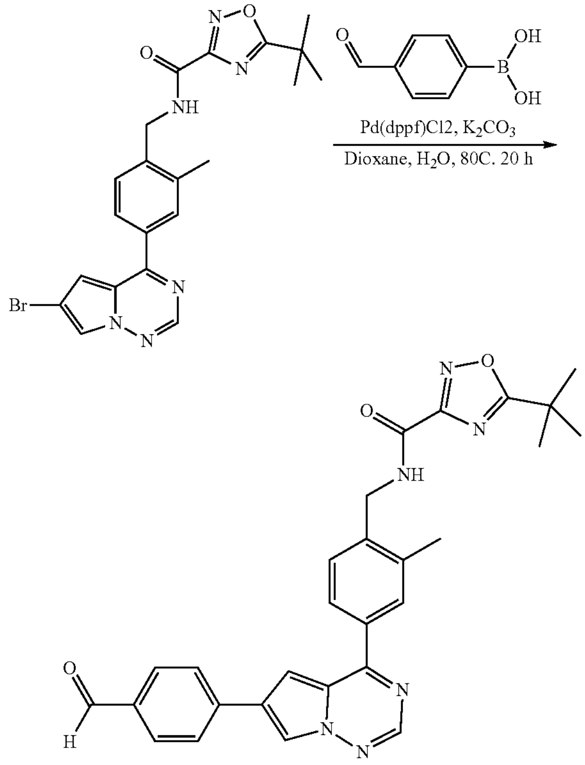

5-(tert-butyl)-N-(4-(6-(4-formylphenyl)pyrrolo[2,1-f][1,2,4]triazin-4-yl)-2-methylbenzyl)-1,2,4-oxadiazole-3-carboxamide To a solution of tert-butyl N-[[4-(6-bromopyrrolo[2,1-f][1,2,4]triazin-4-yl)-2-methyl-phenyl]methyl]carbamate (3.65 g, 8.75 mmol) in 1,4-dioxane (75 mL) and $H_2O$ (7.5 mL), (4-formylphenyl)boronic acid (1.44 g, 9.62 mmol), $K_2CO_3$ (3.63 g, 26.24 mmol) and $Pd(dppf)Cl_2CH_2Cl_2$ (357.15 mg, 437.34 μmol) were added under inert atmosphere. The mixture was stirred at 80° C. for 18 h. After cooling to rt, the mixture was diluted with water (200 mL) and extracted with ethyl acetate (150 mL×3). The combined organic layers were washed with brine, dried, filtered, and concentrated. The residue was purified by column chromatography (Companion combiflash; 120 g $SiO_2$; petroleum ether/EtOAc flow rate=75 ml/min, Rv=40-80 cv.) to give tert-butyl N-[[4-[6-(4-formylphenyl)pyrrolo[2,1-f][1,2,4]triazin-4-yl]-2-methyl-phenyl]methyl]carbamate (1.72 g, 3.69 mmol, 42% yield) as a yellow solid. LC-MS($ES^+$): m/z=495.1 $[M+H]^+$.

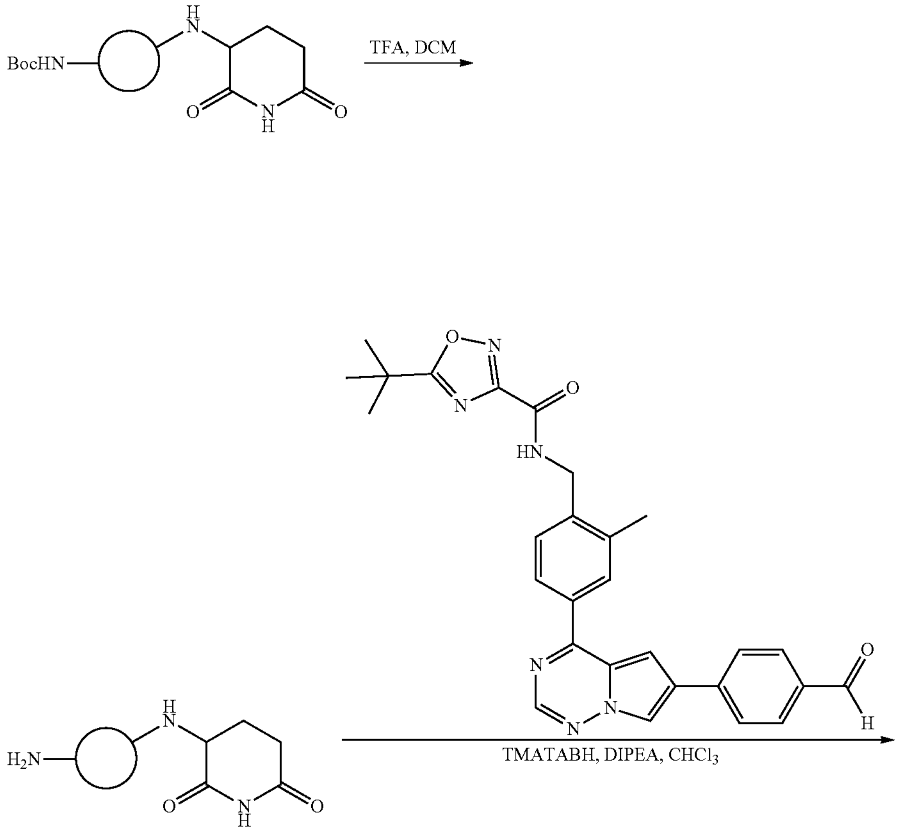

-continued

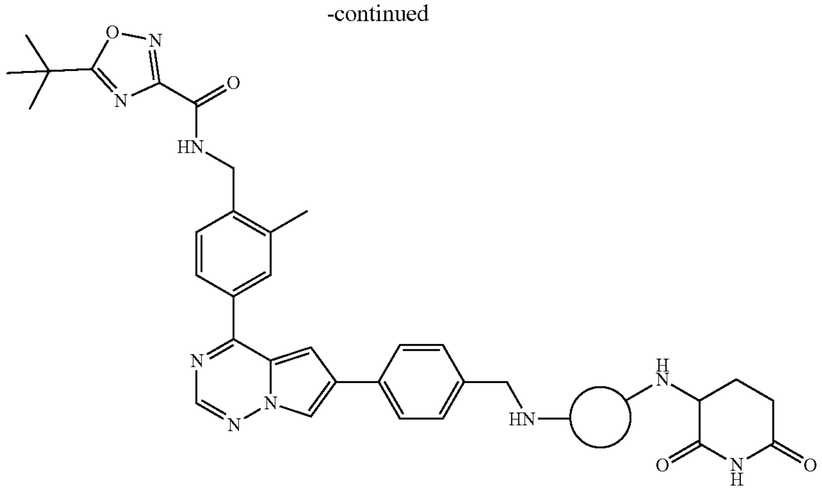

The Respective Intermediate building block (1.0 equiv.), see Table 3, was stirred in dry DCM (0.5 mL) and TFA (0.5 mL) at room temperature for 4 hours, then was concentrated under reduced pressure. The residue was diluted in dry chloroform (0.5 mL) followed by addition of 5-(tert-butyl)-N-(4-(6-(4-formylphenyl)pyrrolo[2,1-f][1,2,4]triazin-4-yl)-2-methylbenzyl)-1,2,4-oxadiazole-3-carboxamide (1 equiv.), DIPEA (7 equiv.) and Tetramethylammonium triacetoxyborohydride (TMATABH) (4.0 equiv.). The solution was stirred for 24 hours at room temperature, then was concentrated under reduced pressure. The residue was mixed with Ammonia methanol solution (0.5 mL of 5% solution) and was concentrated. The residue was dissolved in DMSO (0.15 mL), neutralized with acetic acid, filtered, analyzed by LCMS, and then subjected to prep. HPLC (Waters SunFire C18 19*100 5 mkm column; gradient mixture $H_2O$-MeCN-0.1% TFA as a mobile phase) to afford the desired products.

TABLE 3

| Example | IUPAC name | | 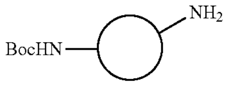 "Respective Intermediate building block" precursor |
|---|---|---|---|
| 200 | 5-(tert-butyl)-N-(4-(6-(4-((2-(4-((2,6-dioxopiperidin-3-yl)amino)phenyl)morpholino)methyl)phenyl)pyrrolo[2,1-f][1,2,4]triazin-4-yl)-2-methylbenzyl)-1,2,4-oxadiazole-3-carboxamide | LCMS: m/z = 768.4 [M + H]+ | 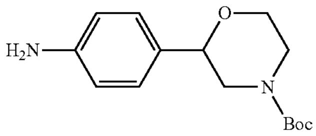 [SMILES: CC(C)(C)OC(=O)N1CCOC(c2ccc(N)cc2)C1] |
| | 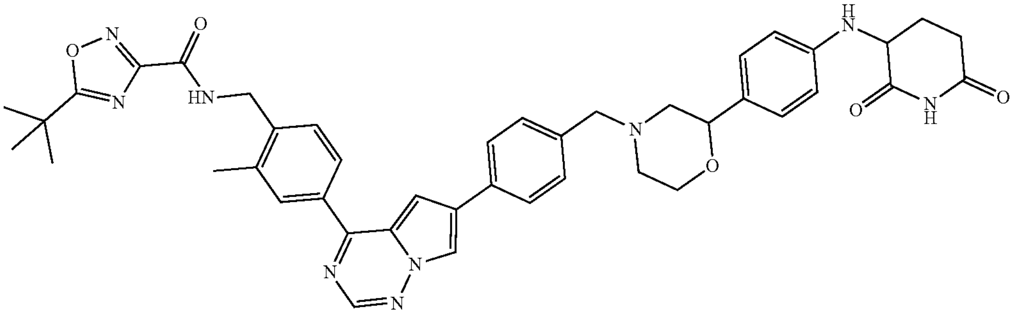 [SMILES: Cc1cc(-c2ncnn3cc(-c4ccc(CN5CCOC(c6ccc(NC7CCC(=O)NC7=O)cc6)C5)cc4)cc23)ccc1CNC(=O)c1noc(C(C)(C)C)n1] | | |
| 201 | 5-(tert-butyl)-N-(4-(6-(4-((4-(4-((2,6-dioxopiperidin-3-yl)amino)phenoxy)piperidin-1-yl)methyl)phenyl)pyrrolo[2,1-f][1,2,4]triazin-4-yl)-2-methylbenzyl)-1,2,4-oxadiazole-3-carboxamide | LCMS: m/z = 782.4 [M + H]+ | 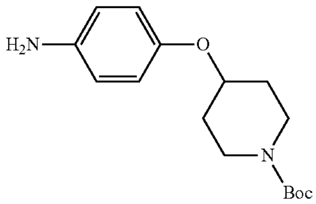 [SMILES: CC(C)(C)OC(=O)N1CCC(Oc2ccc(N)cc2)CC1] |

TABLE 3-continued

| Ex-ample | IUPAC name | | 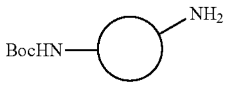 "Respective Intermediate building block" precursor |
|---|---|---|---|
| | 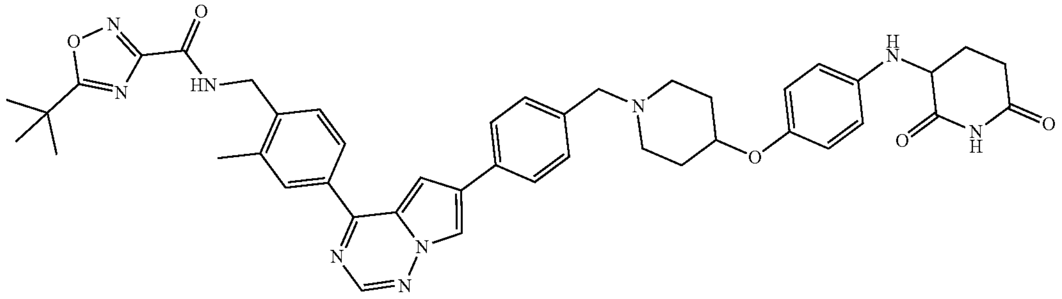 [SMILES: Cc1cc(-c2ncnn3cc(-c4ccc(CN5CCC(Oc6ccc(NC7CCC(=O)NC7=O)cc6)CC5)cc4)cc23)ccc1CNC(=O)c1noc(C(C)(C)C)n1] | | |
| 202 | 5-(tert-butyl)-N-(4-(6-(4-(((6-((2,6-dioxopiperidin-3-yl)amino)-1,2,3,4-tetrahydronaphthalen-2-yl)amino)methyl)phenyl)pyrrolo[2,1-f][1,2,4]triazin-4-yl)-2-methylbenzyl)-1,2,4-oxadiazole-3-carboxamide | LCMS: m/z = 752.4 $[M + H]^+$ | 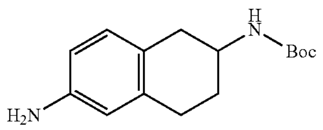 |
| | 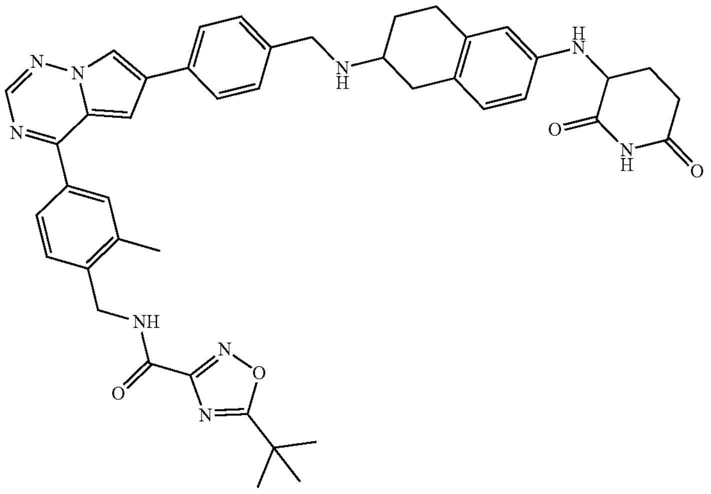 [SMILES: Cc1cc(-c2ncnn3cc(-c4ccc(CNC5CCc6cc(NC7CCC(=O)NC7=O)ccc6C5)cc4)cc23)ccc1CNC(=O)c1noc(C(C)(C)C)n1] | | |
| 203 | 5-(tert-butyl)-N-(4-(6-(4-((6-(4-((2,6-dioxopiperidin-3-yl)amino)-1H-pyrazol-1-yl)-1,4-oxazepan-4-yl)methyl)phenyl)pyrrolo[2,1-f][1,2,4]triazin-4-yl)-2-methylbenzyl)-1,2,4-oxadiazole-3-carboxamide | LCMS: m/z = 772.4 $[M + H]^+$ | 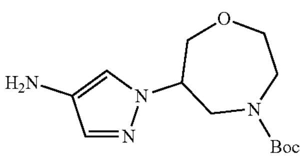 [SMILES: CC(C)(C)OC(=O)N1CCOCC(n2cc(N)cn2)C1] |

TABLE 3-continued

| Ex-ample | IUPAC name | 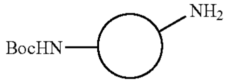 "Respective Intermediate building block" precursor |
|---|---|---|
| | 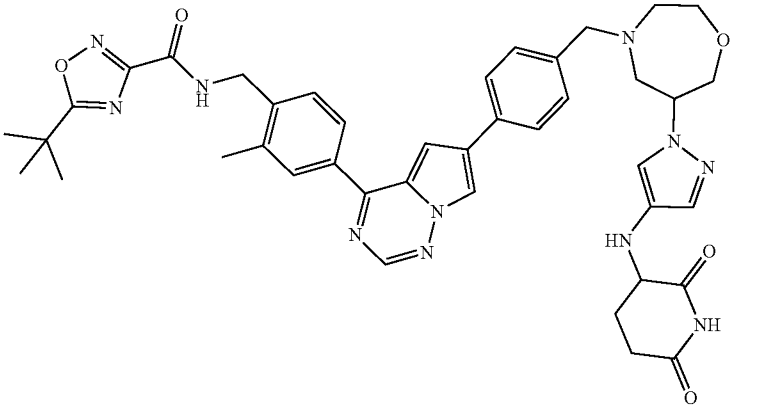 [SMILES: Cc1cc(-c2ncnn3cc(-c4ccc(CN5CCOCC(n6cc(NC7CCC(=O)NC7=O)cn6)C5)cc4)cc23)ccc1CNC(=O)c1noc(C(C)(C)C)n1] | |

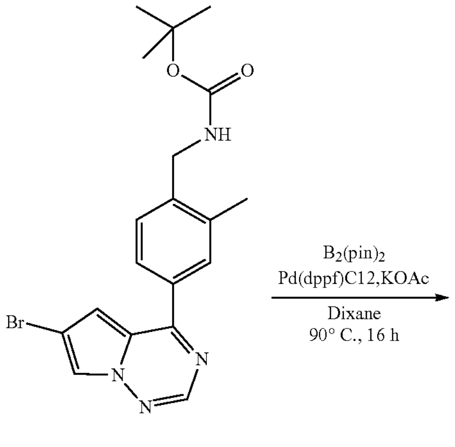

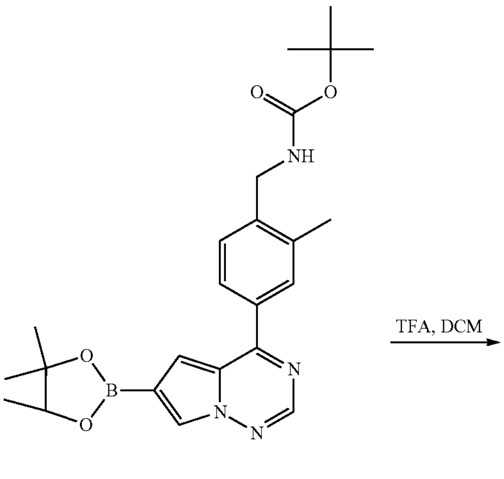

-continued

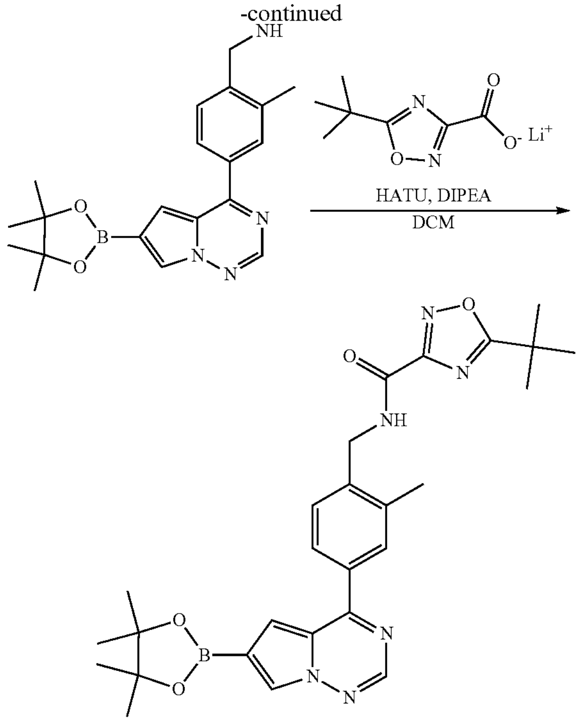

tert-butyl (2-methyl-4-(6-(4,4,5-trimethyl-1,3,2-dioxaborolan-2-yl)pyrrolo[2,1-f][1,2,4]triazin-4-yl)benzyl)carbamate A solution of tert-butyl N-[[4-(6-bromopyrrolo[2,1-f][1,2,4]triazin-4-yl)-2-methylphenyl]methyl]carbamate (10 g, 21.81 mmol) 4,4,5,5-tetramethyl-2-(4,4,5,5-tetramethyl-1,3,2-dioxaborolan-2-yl)-1,3,2-dioxaborolane (6.65 g, 26.17 mmol) and KOAc (6.42 g, 65.42 mmol) in 1,4-dioxane (150 mL) was degassed and then heated overnight at 80° C. under argon atmosphere. The reaction mixture was cooled to RT and concentrated. The residue was dissolved in EtOAc (200 ml), filtered and washed with brine (200 ml×2). The organic layer was dried over $Na_2SO_4$ filtered and concentrated in vacuo. The residue was purified by column chromatography (Companion; 120 g $SiO_2$; petroleum ether/MtBE with MtBE from 0 to 50%, flow rate=85 ml/min, Rv=8-9 cv.) to give tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (5 g, 9.69 mmol, 44% yield) as a yellow solid. $^1$H NMR (500 MHz, CHLOROFORM-d) δ=8.55-8.42 (m, 1H), 8.14 (m, 1H), 8.02-7.83 (m, 2H), 7.50-7.33 (m, 2H), 4.82 (br s, 1H), 4.40 (br s, 2H), 2.54-2.33 (m, 311), 1.48-1.27 (m, 21H)

5-(tert-butyl)-N-(2-methyl-4-(6-(4,4,5,5-tetramethyl-1,3,2-dioxaborolan-2-yl)pyrrolo[2,1-f][1,2,4]triazin-4-yl)benzyl)-1,2,4-oxadiazole-3-carboxamide To a solution of tert-butyl N-[[2-methyl-4-[6-(4,4,5,5-tetramethyl-1,3,2-dioxaborolan-2-yl)pyrrolo[2,1-f][1,2,4]triazin-4-yl]phenyl]methyl]carbamate (5 g, 10.77 mmol) in DCM (50 mL) was added TFA (33.09 g, 290.20 mmol, 22.22 mL) at room temperature. The solution was stirred for 48 h, then was concentrated to provide [2-methyl-4-[6-(4,4,5,5-tetramethyl-1,3,2-dioxaborolan-2-yl)pyrrolo[2,1-f][1,2,4]triazin-4-yl]phenyl]methanamine (5 g, 8.90 mmol, 83% yield Trifluoroacetate) as a dark yellow oil and used in the next step without purification. A solution of [2-methyl-4-[6-(4,4,5,5-tetramethyl-1,3,2-dioxaborolan-2-yl)pyrrolo[2,1-f][1,2,4]triazin-4-yl]phenyl]methanamine (2.4 g, 5.03 mmol, Trifluoroacetate), (5-tert-butyl-1,2,4-oxadiazole-3-carbonyl)oxylithium (1.33 g, 7.26 mmol, Lithium), HATU (2.88 g, 7.54 mmol) and DIPEA (1.95 g, 15.09 mmol, 2.63 mL) in DCM (50 ml) was stirred at room temperature overnight. The solution was washed with water, brine (50 ml×2), dried over $Na_2SO_4$, filtered and concentrated. The residue was crystalized from i-PrOH\Ether (2:1), to give 5-tert-butyl-N-[[2-methyl-4-[6-(4,4,5,5-tetramethyl-1,3,2-dioxaborolan-2-yl)pyrrolo[2,1-f][1,2,4]triazin-4-yl]phenyl]methyl]-1,2,4-oxadiazole-3-carboxamide (0.91 g, 1.59 mmol, 31.54% yield). LC-MS(ES$^+$): m/z=517.2 [M+H]$^+$.

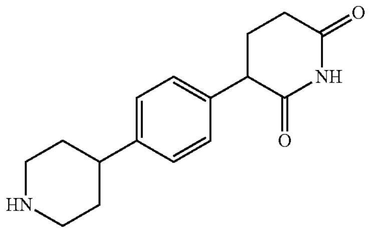

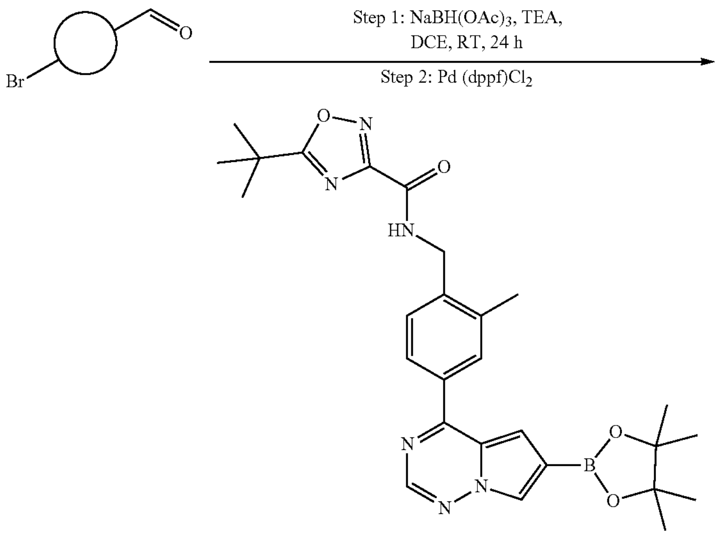

-continued

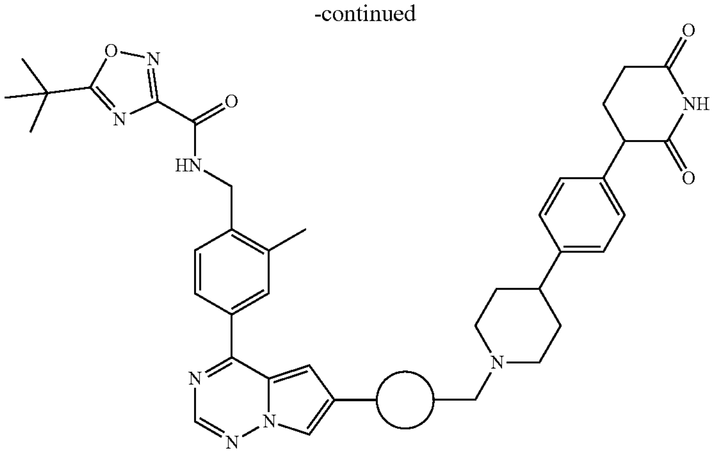

Step1. A solution of RCHO (1.0 equiv.), see Table 4, 3-(4-(piperidin-4-yl)phenyl)piperidine-2,6-dione hydrochloride (1.1 equiv.), sodium triacetoxyborohydride (NaBH$(OAc)_3$) (3.0 equiv.), and triethylamine (2.0 equiv.) in dry DCE (appr. 2.5 mL per 100 mg of product) was added and the resulting solution was stirred for 24 hours at ambient temperature. The reaction was quenched with 2 mL of 10% $NaHCO_3$ aq. sol., followed by extraction with DCM (2×2 mL). The combined organic layers were dried over sodium sulfate, filtered, and evaporated under reduced pressure. The product obtained was of sufficient purity and was used in further experiments without any additional purification.

Step 2. (Method A used for Examples 207 and 208)

A vial was charged with the material prepared in step 1 (1.0 equiv.), 5-(tert-butyl)-N-(2-methyl-4-(6-(4,4,5,5-tetramethyl-1,3,2-dioxaborolan-2-yl)pyrrolo[2,1-f][1,2,4]triazin-4-yl)benzyl)-1,2,4-oxadiazole-3-carboxamide (1.0 equiv.), $K_3PO_4$ (2.5 equiv.), and Pd(dppf)$Cl_2$DCM (10% mol.) and 1,4-dioxane (2 mL). The reaction mixture was sealed and heated with stirring for 24 h at 80-85° C. under an inert atmosphere. The resulting solution was cooled to room temperature, filtered, and the solvent was removed under reduced pressure. The residue was subjected to prep. HPLC (Waters SunFire C18 19*100 5 mkm column; gradient mixture $H_2O$-ACN-TFA 0.1%; flow 30 ml/min (loading pump 4 ml/min acetonitrile)) to afford the corresponding products.

Step 2. (Method B) A vial was charged with the material prepared in step 1 (1.0 equiv.), 5-(tert-butyl)-N-(2-methyl-4-(6-(4,4,5,5-tetramethyl-1,3,2-dioxaborolan-2-yl)pyrrolo[2,1-f][1,2,4]triazin-4-yl)benzyl)-1,2,4-oxadiazole-3-carboxamide (1.0 equiv.), $Na_2CO_3$ (2.5 equiv.), and Pd(dppf)$Cl_2$ DCM (10% mol.) and dioxane/$H_2O$ (20:1) (2 mL). The reaction mixture was sealed and heated with stirring for 24 h at 80-85° C. under an inert atmosphere. The resulting solution was cooled to room temperature, filtered, and the solvent was removed under reduced pressure. The residue was subjected to prep. HPLC (Waters SunFire C18 19*100 5 mkm column; gradient mixture $H_2O$-ACN-TFA 0.1%; flow 30 ml/min (loading pump 4 ml/min acetonitrile)) to afford the corresponding products.

TABLE 4

| Example | IUPAC name | | 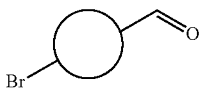 "RCHO" |
| --- | --- | --- | --- |
| 204 | 5-(tert-butyl)-N-(4-(6-(3-(2-(4-((4-(4-(2,6-dioxopiperidin-3-yl)phenyl)piperidin-1-yl)methyl)-2-methoxyphenyl)ethoxy)phenyl)pyrrolo[2,1-f][1,2,4]triazin-4-yl)-2-methylbenzyl)-1,2,4-oxadiazole-3-carboxamide | LCMS: m/z = 918.4 [M + H]+ | 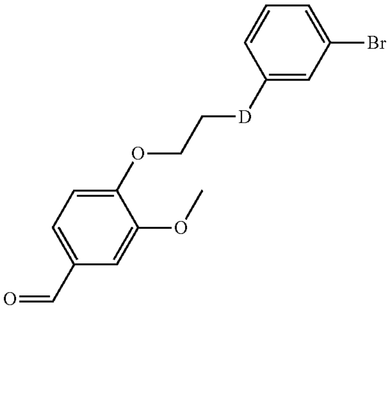 |

TABLE 4-continued

| Example | IUPAC name | | 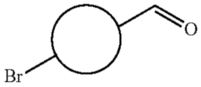<br>"RCHO" |
|---|---|---|---|
| | 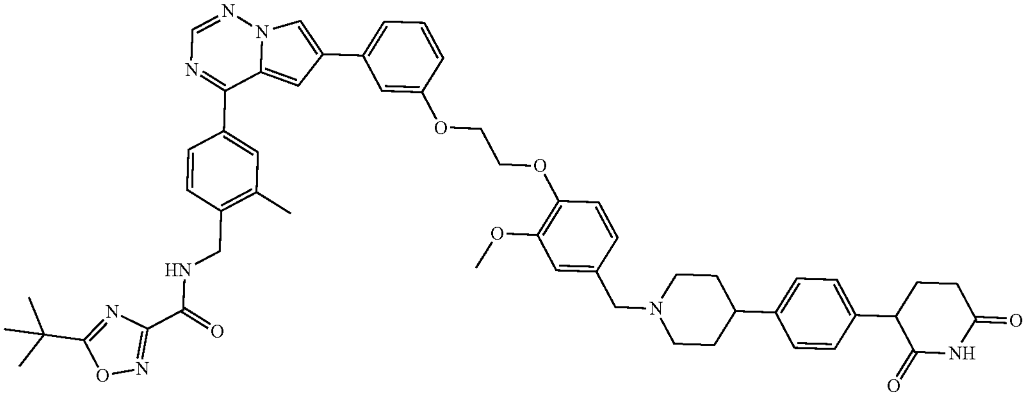 [SMILES: COc1cc(CN2CCC(c3ccc(C4CCC(=O)NC4=O)cc3)CC2)ccc1OCCOc1cccc(-c2cc3c(-c4ccc(CNC(=O)c5noc(C(C)(C)C)n5)c(C)c4)ncnn3c2)c1] | | |
| 205 | 5-(tert-butyl)-N-(4-(6-(3-(4-((4-(4-(2,6-dioxopiperidin-3-yl)phenyl)piperidin-1-yl)methyl)-3-methyl-1H-pyrazol-1-yl)phenyl)pyrrolo[2,1-f][1,2,4]triazin-4-yl)-2-methylbenzyl)-1,2,4-oxadiazole-3-carboxamide | LCMS: m/z = 831.2 [M + H]+ | 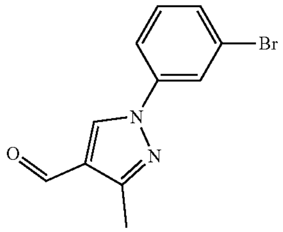 |
| | 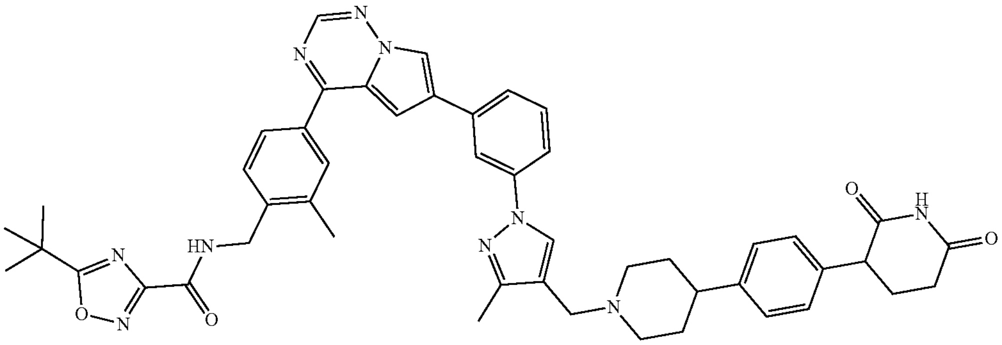 [SMILES: Cc1cc(-c2ncnn3cc(-c4cccc(-n5cc(CN6CCC(c7ccc(C8CCC(=O)NC8=O)cc7)CC6)c(C)n5)c4)cc23)ccc1CNC(=O)c1noc(C(C)(C)C)n1] | | |
| 206 | 5-(tert-butyl)-N-(4-(6-(2-(4-((4-(4-(2,6-dioxopiperidin-3-yl)phenyl)piperidin-1-yl)methyl)phenoxy)pyrimidin-5-yl)pyrrolo[2,1-f][1,2,4]triazin-4-yl)-2-methylbenzyl)-1,2,4-oxadiazole-3-carboxamide | LCMS: m/z = 845.6 [M + H]+ | 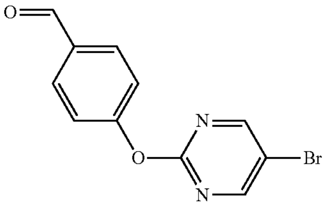 [SMILES: O=Cc1ccc(Oc2ncc(Br)cn2)cc1] |
| | 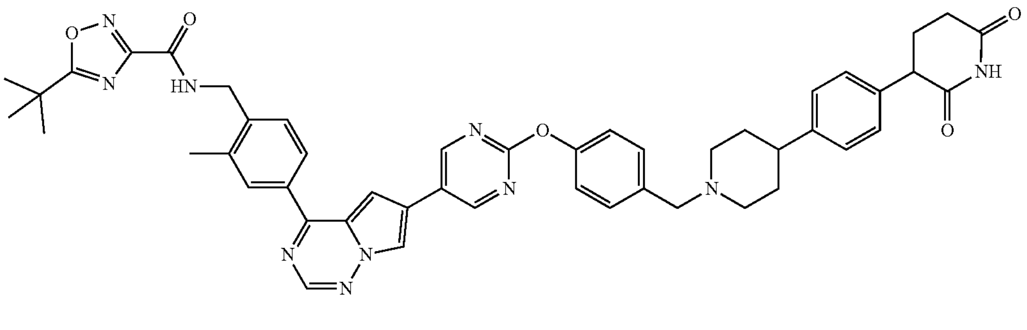 [SMILES: Cc1cc(-c2ncnn3cc(-c4cnc(Oc5ccc(CN6CCC(c7ccc(C8CCC(=O)NC8=O)cc7)CC6)cc5)nc4)cc23)ccc1CNC(=O)c1noc(C(C)(C)C)n1] | | |

TABLE 4-continued

| Example | IUPAC name | | 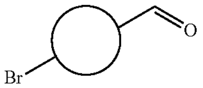<br>"RCHO" |
|---|---|---|---|
| 207 | 5-(tert-butyl)-N-(4-(6-(3-(1-(4-(4-(2,6-dioxopiperidin-3-yl)phenyl)piperidin-1-yl)propan-2-yl)phenyl)pyrrolo[2,1-f][1,2,4]triazin-4-yl)-2-methylbenzyl)-1,2,4-oxadiazole-3-carboxamide | LCMS: m/z = 779.4 [M + H]$^+$ | 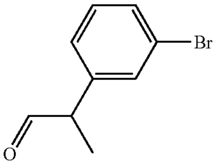 |
| | 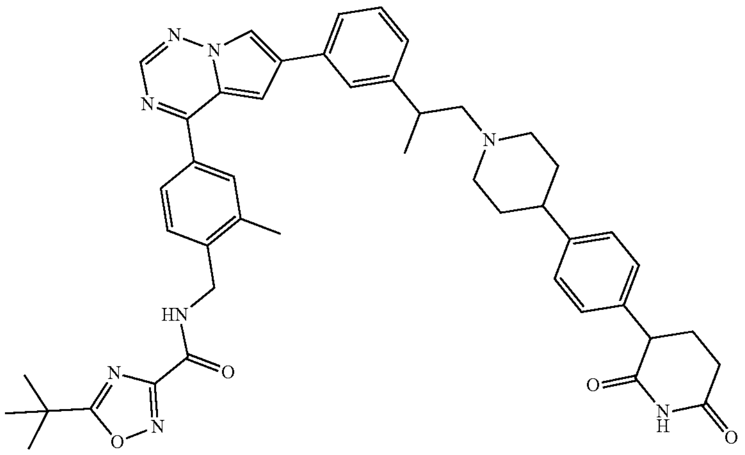 [SMILES: Cc1cc(-c2ncnn3cc(-c4cccc(C(C)CN5CCC(c6ccc(C7CCC(=O)NC7=O)cc6)CC5)c4)cc23)ccc1CNC(=O)c1noc(C(C)(C)C)n1] | | |
| 208 | 5-(tert-butyl)-N-(4-(6-(2-((4-(4-(2,6-dioxopiperidin-3-yl)phenyl)piperidin-1-yl)methyl)thiazol-4-yl)pyrrolo[2,1-f][1,2,4]triazin-4-yl)-2-methylbenzyl)-1,2,4-oxadiazole-3-carboxamide | LCMS: m/z = 758.2 [M + H]$^+$ | 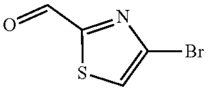 |
| | 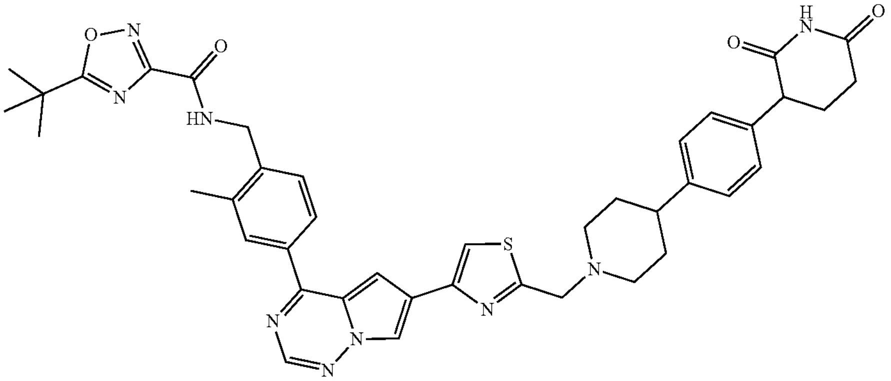 [SMILES: Cc1cc(-c2ncnn3cc(-c4csc(CN5CCC(c6ccc(C7CCC(=O)NC7=O)cc6)CC5)n4)cc23)ccc1CNC(=O)c1noc(C(C)(C)C)n1] | | |
| 209 | 5-(tert-butyl)-N-(4-(6-(2-((4-(4-(2,6-dioxopiperidin-3-yl)phenyl)piperidin-1-yl)methyl)-1-methyl-1H-imidazol-4-yl)pyrrolo[2,1-f][1,2,4]triazin-4-yl)-2-methylbenzyl)-1,2,4-oxadiazole-3-carboxamide | LCMS: m/z = 755.2 [M + H]$^+$ | 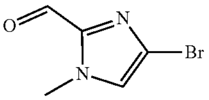 |

TABLE 4-continued
| Example | IUPAC name | | 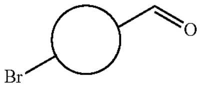 "RCHO" |
|---|---|---|---|
| | 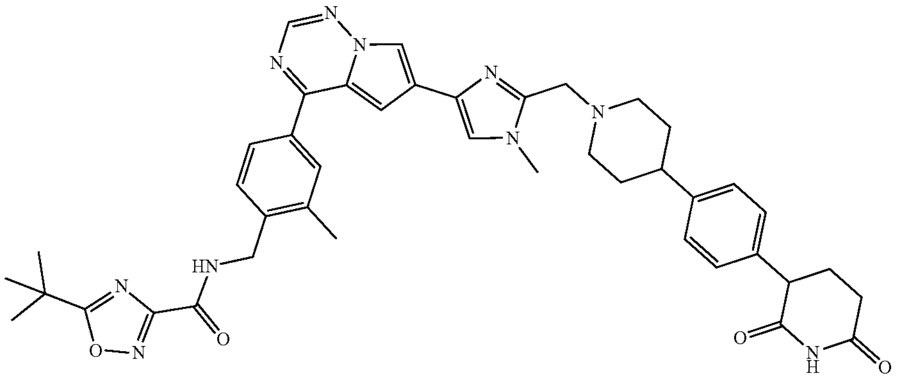 [SMILES: Cc1cc(-c2ncnn3cc(-c4cn(C)c(CN5CCC(c6ccc(C7CCC(=O)NC7=O)cc6)CC5)n4)cc23)ccc1CNC(=O)c1noc(C(C)(C)C)n1] | | |
| 210 | 5-(tert-butyl)-N-(4-(6-(5-((4-(4-(2,6-dioxopiperidin-3-yl) phenyl)piperidin-1-yl)methyl)imidazo[2,1-b]thiazol-2-yl) pyrrolo[2,1-f][1,2,4]triazin-4-yl)-2-methylbenzyl)-1,2,4-oxadiazole-3-carboxamide | LCMS: m/z = 797.2 $[M + H]^+$ | 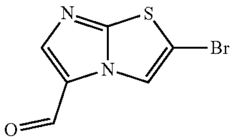 [SMILES: O=Cc1cnc2sc(Br)cn12] |
| | 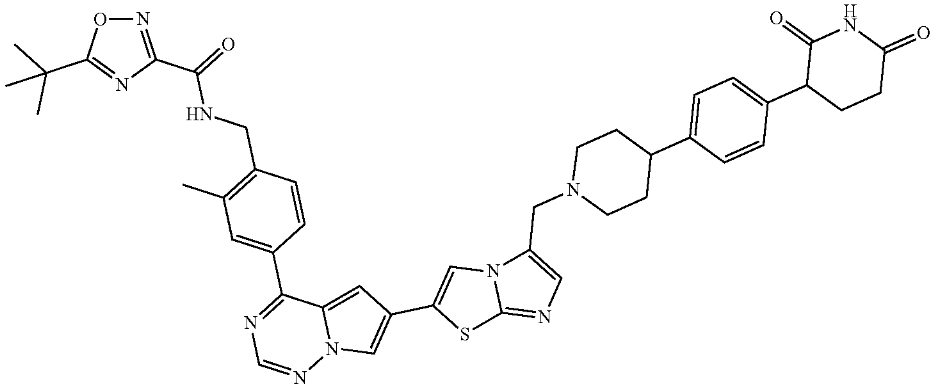 [SMILES: Cc1cc(-c2ncnn3cc(-c4cn5c(CN6CCC(c7ccc(C8CCC(=O)NC8=O)cc7)CC6)cnc5s4)cc23)ccc1CNC(=O)c1noc(C(C)(C)C)n1] | | |
| 211 | 5-(tert-butyl)-N-(4-(6-(2-((4-(4-(2,6-dioxopiperidin-3-yl)phenyl)piperidin-1-yl)methyl)imidazo[1,2-a]pyridin-7-yl)pyrrolo[2,1-f][1,2,4]triazin-4-yl)-2-methylbenzyl)-1,2,4-oxadiazole-3-carboxamide | LCMS: m/z = 791.4 $[M + H]^+$ | 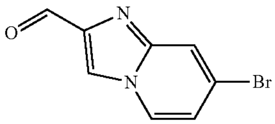 [SMILES: O=Cc1cn2ccc(Br)cc2n1] |
| | 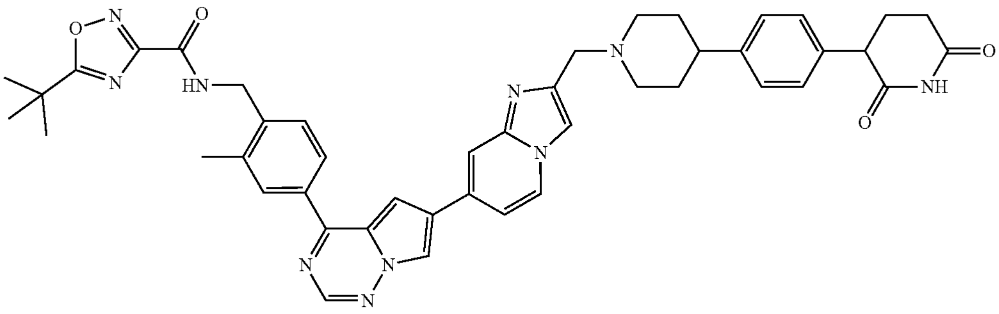 [SMILES: Cc1cc(-c2ncnn3cc(-c4ccn5cc(CN6CCC(c7ccc(C8CCC(=O)NC8=O)cc7)CC6)nc5c4)cc23)ccc1CNC(=O)c1noc(C(C)(C)C)n1] | | |

TABLE 4-continued

| Example | IUPAC name | | 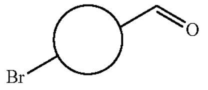 "RCHO" |
|---|---|---|---|
| 212 | 5-(tert-butyl)-N-(4-(6-(3-((4-(4-(2,6-dioxopiperidin-3-yl)phenyl)piperidin-1-yl)methyl)-2-methyl-2H-indazol-7-yl)pyrrolo[2,1-f][1,2,4]triazin-4-yl)-2-methylbenzyl)-1,2,4-oxadiazole-3-carboxamide | LCMS: m/z = 804.8 [M + H]+ | 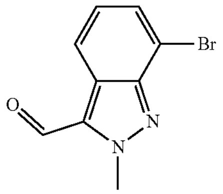 |
| | 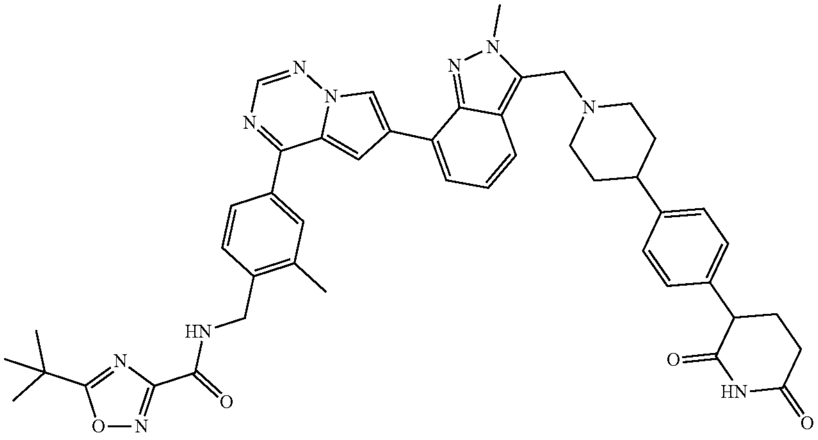 [SMILES: Cc1cc(-c2ncnn3cc(-c4cccc5c(CN6CCC(c7ccc(C8CCC(=O)NC8=O)cc7)CC6)n(C)nc45)cc23)ccc1CNC(=O)c1noc(C(C)(C)C)n1] | | |
| 213 | 5-(tert-butyl)-N-(4-(6-(5-((4-(4-(2,6-dioxopiperidin-3-yl)phenyl)piperidin-1-yl)methyl)-3-methylpyridin-2-yl)pyrrolo[2,1-f][1,2,4]triazin-4-yl)-2-methylbenzyl)-1,2,4-oxadiazole-3-carboxamide | LCMS: m/z = 766.2 [M + H]+ | 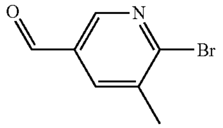 |
| | 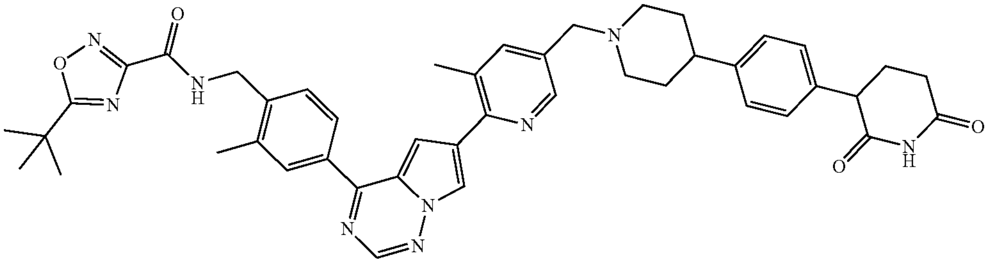 [SMILES: Cc1cc(-c2ncnn3cc(-c4ncc(CN5CCC(c6ccc(C7CCC(=O)NC7=O)cc6)CC5)cc4C)cc23)ccc1CNC(=O)c1noc(C(C)(C)C)n1] | | |
| 214 | 5-(tert-butyl)-N-(4-(6-(6-((4-(4-(2,6-dioxopiperidin-3-yl)phenyl)piperidin-1-yl)methyl)pyridin-2-yl)pyrrolo[2,1-f][1,2,4]triazin-4-yl)-2-methylbenzyl)-1,2,4-oxadiazole-3-carboxamide | LCMS: m/z = 752.4 [M + H]+ | 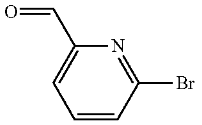 |

TABLE 4-continued

| Example | IUPAC name | | 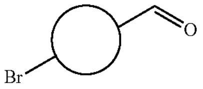<br>"RCHO" |
|---|---|---|---|
| | 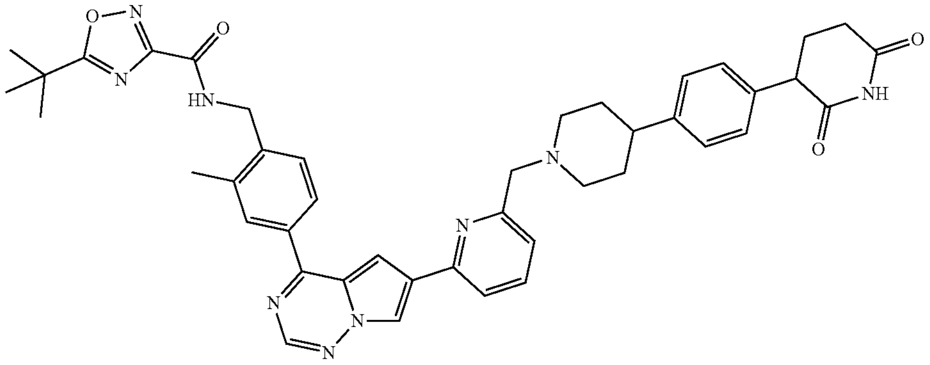 [SMILES: Cc1cc(-c2ncnn3cc(-c4cccc(CN5CCC(c6ccc(C7CCC(=O)NC7=O)cc6)CC5)n4)cc23)ccc1CNC(=O)c1noc(C(C)(C)C)n1] | | |
| 215 | 5-(tert-butyl)-N-(4-(6-(4-((4-(4-(2,6-dioxopiperidin-3-yl)phenyl)piperidin-1-yl)methyl)pyrimidin-2-yl)pyrrolo[2,1-f][1,2,4]triazin-4-yl)-2-methylbenzyl)-1,2,4-oxadiazole-3-carboxamide | LCMS: m/z = 753.4 [M + H]$^+$ | 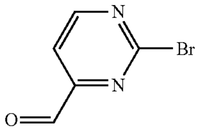 |
| | 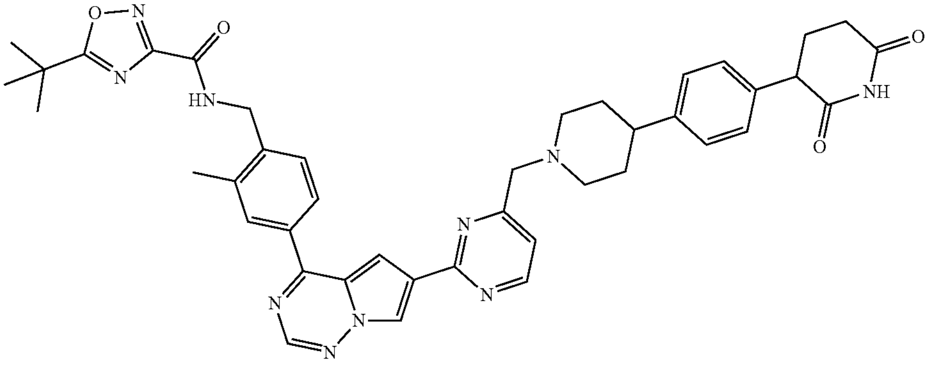 [SMILES: Cc1cc(-c2ncnn3cc(-c4nccc(CN5CCC(c6ccc(C7CCC(=O)NC7=O)cc6)CC5)n4)cc23)ccc1CNC(=O)c1noc(C(C)(C)C)n1] | | |
| 216 | 5-(tert-butyl)-N-(4-(6-(4-((4-(4-(2,6-dioxopiperidin-3-yl)phenyl)piperidin-1-yl)methyl)pyridin-2-yl)pyrrolo[2,1-f][1,2,4]triazin-4-yl)-2-methylbenzyl)-1,2,4-oxadiazole-3-carboxamide | LCMS: m/z = 753.4 [M + H]$^+$ | 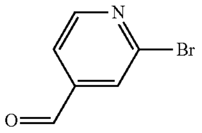 |
| | 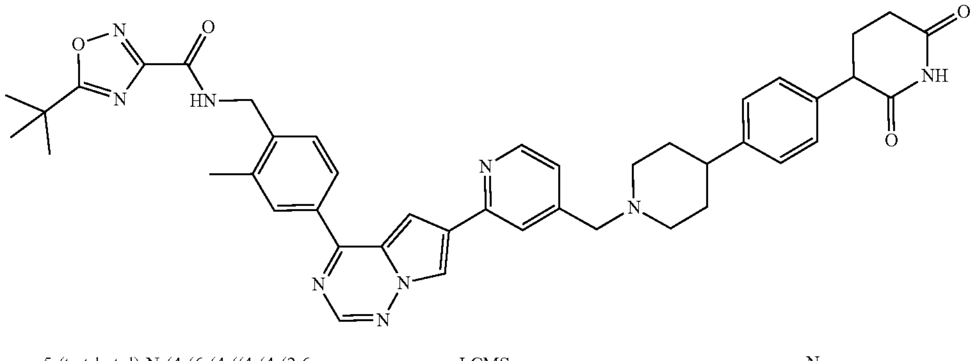 | | |
| 217 | 5-(tert-butyl)-N-(4-(6-(4-((4-(4-(2,6-dioxopiperidin-3-yl)phenyl)piperidin-1-yl)methyl)-3-fluoropyridin-2-yl)pyrrolo[2,1-f][1,2,4]triazin-4-yl)-2-methylbenzyl)-1,2,4-oxadiazole-3-carboxamide | LCMS: m/z = 770.2 [M + H]$^+$ | 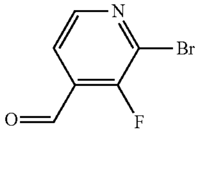 |

TABLE 4-continued

| Example | IUPAC name | | 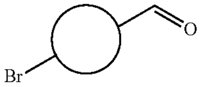<br>"RCHO" |
|---|---|---|---|
| | 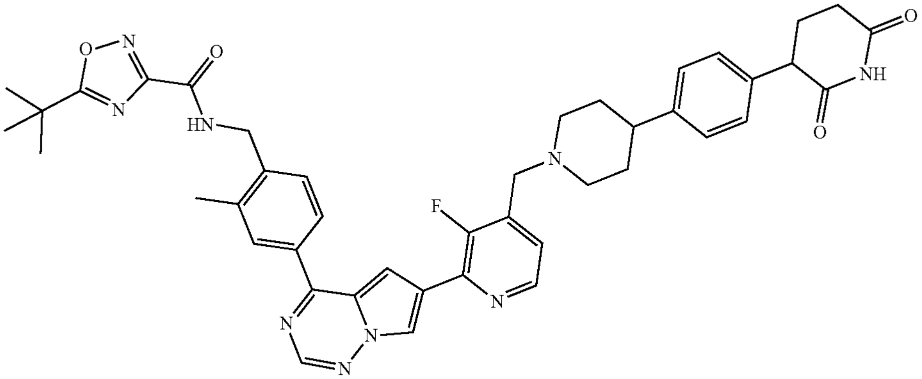 [SMILES: Cc1cc(-c2ncnn3cc(-c4nccc(CN5CCC(c6ccc(C7CCC(=O)NC7=O)cc6)CC5)c4F)cc23)ccc1CNC(=O)c1noc(C(C)(C)C)n1] | | |
| 218 | 5-(tert-butyl)-N-(4-(6-(2-((4-(4-(2,6-dioxopiperidin-3-yl)phenyl)piperidin-1-yl) methyl)thieno[3,2-b]pyridin-5-yl)pyrrolo[2,1-f] [1,2,4]triazin-4-yl)-2-methylbenzyl)-1,2,4-oxadiazole-3-carboxamide | LCMS: m/z = 808.4 $[M + H]^+$ | 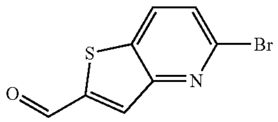 [SMILES: O=Cc1cc2nc(Br)ccc2s1] |
| | 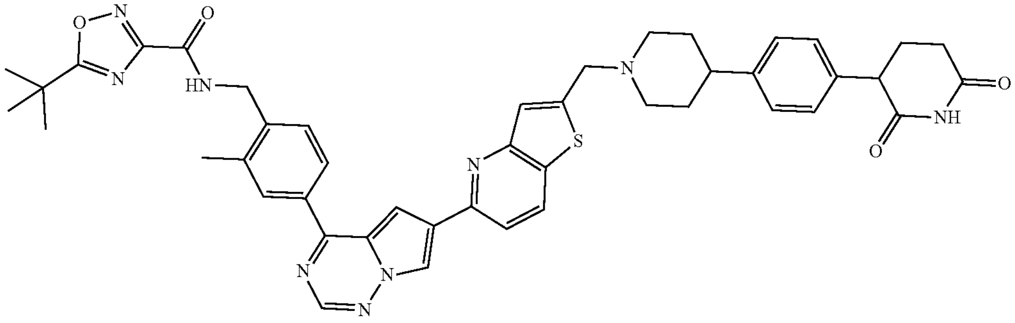 [SMILES: Cc1cc(-c2ncnn3cc(-c4ccc5sc(CN6CCC(c7ccc(C8CCC(=O)NC8=O)cc7)CC6)cc5n4)cc23)ccc1CNC(=O)c1noc(C(C)(C)C)n1] | | |
| 219 | 5-(tert-butyl)-N-(4-(6-(4-((4-(4-(2,6-dioxopiperidin-3-yl)phenyl)piperidin-1-yl)methyl)oxazol-2-yl)pyrrolo[2,1-f][1,2,4]triazin-4-yl)-2-methylbenzyl)-1,2,4-oxadiazole-3-carboxamide | LCMS: m/z = 742.0 $[M + H]^+$ | 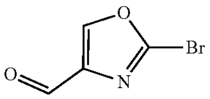 |
| | 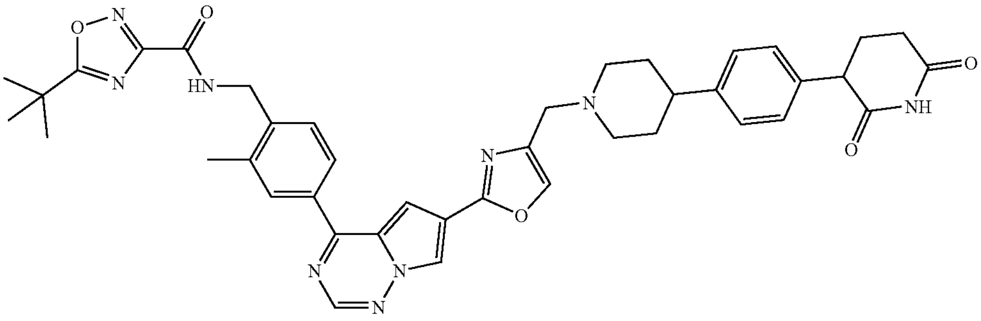 [SMILES: Cc1cc(-c2ncnn3cc(-c4nc(CN5CCC(c6ccc(C7CCC(=O)NC7=O)cc6)CC5)co4)cc23)ccc1CNC(=O)c1noc(C(C)(C)C)n1] | | |
| 220 | 5-(tert-butyl)-N-(4-(6-(5-(4-((4-(4-(2,6-dioxopiperidin-3-yl)phenyl)piperidin-1-yl) methyl)-1H-pyrazol-3-yl)thiophen-2-yl)pyrrolo [2,1-f][1,2,4]triazin-4-yl)-2-methylbenzyl)-1,2,4-oxadiazole-3-carboxamide | LCMS: m/z = 823.4 $[M + H]^+$ | 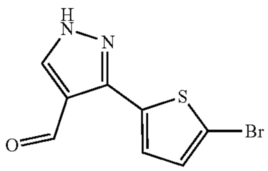 [SMILES: O=Cc1c[nH]nc1-c1ccc(Br)s1] |

TABLE 4-continued

| Example | IUPAC name | 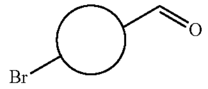 "RCHO" |
| --- | --- | --- |
| 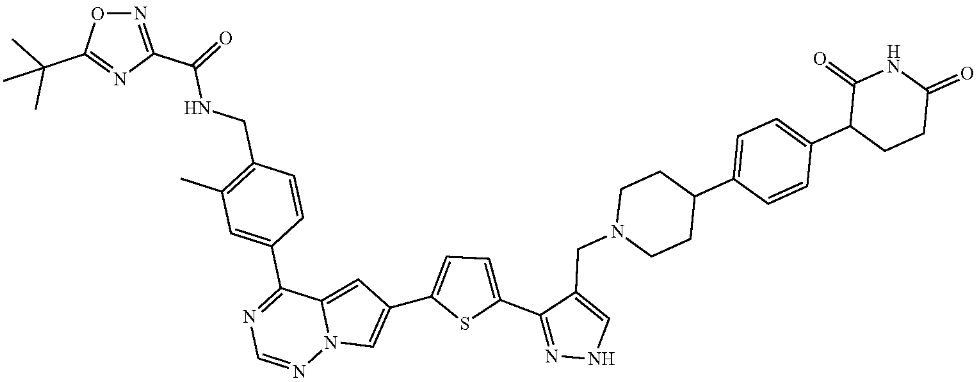 [SMILES: Cc1cc(-c2ncnn3cc(-c4ccc(-c5n[nH]cc5CN5CCC(c6ccc(C7CCC(=O)NC7=O)cc6)CC5)s4)cc23)ccc1CNC(=O)c1noc(C(C)(C)C)n1] | | |

Example 221

Example 221 was prepared following the synthesis of Example 97

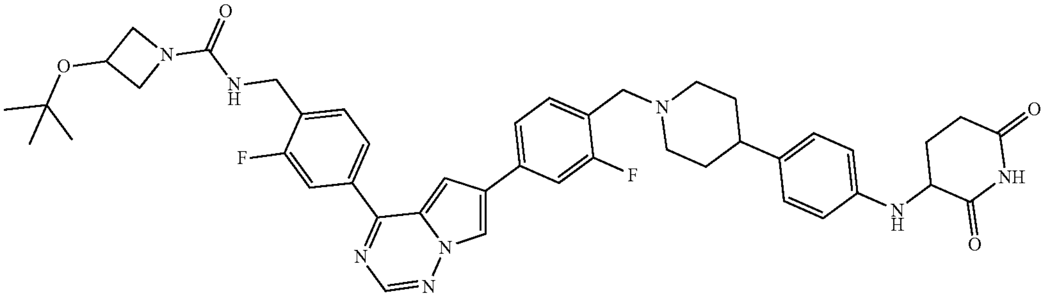 [SMILES: CC(C)(C)OC1CN(C(=O)NCc2ccc(-c3ncnn4cc(-c5ccc(CN6CCC(c7ccc(NC8CCC(=O)NC8=O)cc7)CC6)c(F)c5)cc34)cc2F)C1]

3-(tert-butoxy)-N-(4-(6-(4-((4-(4-((2,6-dioxopiperidin-3-yl)amino)phenyl)piperidin-1-yl)methyl)-3-fluorophenyl)pyrrolo[2,1-f][1,2,4]triazin-4-yl)-2-fluorobenzyl)azetidine-1-carboxamide $^1$H NMR (400 MHz, DMSO-$d_6$) δ 10.77 (s, 1H), 9.47 (s, 1H), 8.91 (d, J=1.2 Hz, 1H), 8.68 (s, 1H), 8.09 (d, J=6.4 Hz, 1H), 8.07 (s, 1H), 8.00-7.94 (m, 2H), 7.88 (s, 1H), 7.68 (t, J=7.8 Hz, 1H), 7.58 (t, J=7.8 Hz, 1H), 7.04 (t, J=6.4 Hz, 1H), 6.93 (d, J=8.8 Hz, 2H), 6.63 (d, J=8.8 Hz, 2H), 4.49-4.26 (m, 6H), 4.05 (t, J=7.7 Hz, 2H), 3.64-3.61 (m, 2H), 3.39-3.32 (m, 2H), 3.17-3.13 (m, 1H), 2.83-2.67 (m, 1H), 2.60-2.55 (m, 2H), 2.16-2.7 (m, 1H), 1.97-1.75 (m, 5H), 1.13 (s, 9H).

LCMS ($ES^-$): m/z 789.28[M−H]−

Mobile phase-A: 0.1% FA in H2O

Mobile phase-B: ACN

Column: X Bridge BEH C18 2.5 μm, 2.1×50 mm

Flow: 0.6 mL/min

Temp: 40° C.

Time (min) and % B: 0-5; 0.3-5; 2.5-95; 3.7-95; 4-5; 4.8-5

Example 222

Example 222 was prepared following the synthesis of Example 1

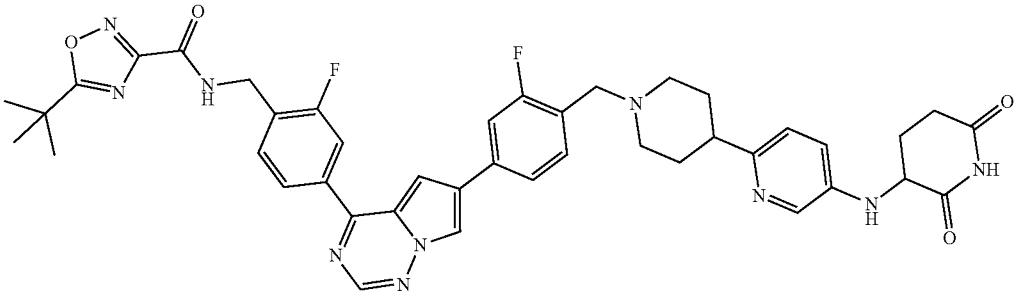 [SMILES: CC(C)(C)c1nc(C(=O)NCc2ccc(-c3ncnn4cc(-c5ccc(CN6CCC(c7ccc(NC8CCC(=O)NC8=O)cn7)CC6)c(F)c5)cc34)cc2F)no1]

5-(tert-butyl)-N-(4-(6-(4-((4-(5-((2,6-dioxopiperidin-3-yl)amino)pyridin-2-yl)piperidin-1-yl)methyl)-3-fluorophenyl)pyrrolo[2,1-f][1,2,4]triazin-4-yl)-2-fluorobenzyl)-1,2,4-oxadiazole-3-carboxamide $^1$H NMR (400 MHz, DMSO-$d_6$) δ 10.79 (s, 1H), 9.61 (t, J=5.8 Hz, 1H), 8.83 (s, 1H), 8.66 (s, 1H), 8.14 (s, 1H), 8.10 (d, J=7.6 Hz, 1H), 8.01 (s, 1H), 7.97 (d, J=6.4 Hz, 1H), 7.87-7.79 (m, 3H), 7.61 (t, J=7.8 Hz, 1H), 7.47 (t, J=7.8 Hz, 1H), 6.97 (bs, 2H), 5.91 (d, J=7.8 Hz, 1H), 4.63 (d, J=5.8 Hz, 1H), 4.36-4.30 (m, 1H), 3.32 (s, 2H), 2.95-2.92 (m, 2H), 2.81-2.73 (m, 1H), 2.60-2.55 (m, 2H), 2.13-2.07 (m, 3H), 1.91-1.87 (m, 1H), 1.77-1.66 (m, 4H), 1.44 (s, 9H).

LCMS (ES$^+$): m/z 789.20[M+H]$^+$

Mobile phase-A: 0.05% TFA in water.

Mobile phase-B: ACN

Column: Acquity UPLC BEH C18, 1.7 μm, 2.1×50 mm

Flow: 0.6 mL/min

Temp: 40° C.

Time (min) and % B: 0-5; 0.3-5:2.5-95; 3.7-95; 4.0-5; 4.6-5.

Gas flow 1.6 SLM

Neb temperature: 40° C.

Evaporator temperature: 40° C.

Example 223. Synthesis of 5-tert-butyl-N-[[4-[2-[4-[4-[4-[(2,6-dioxo-3-piperidyl)amino]phenyl]-1-piperidyl]butyl]pyrazolo[4,3-b]pyridin-7-yl]-2-methyl-phenyl]methyl]-1,2,4-oxadiazole-3-carboxamide

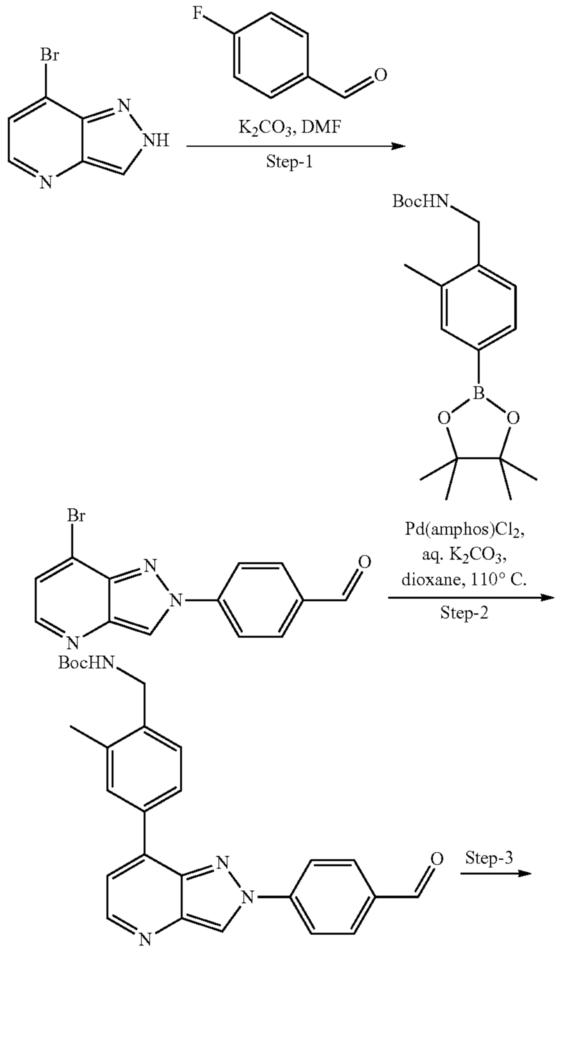

-continued

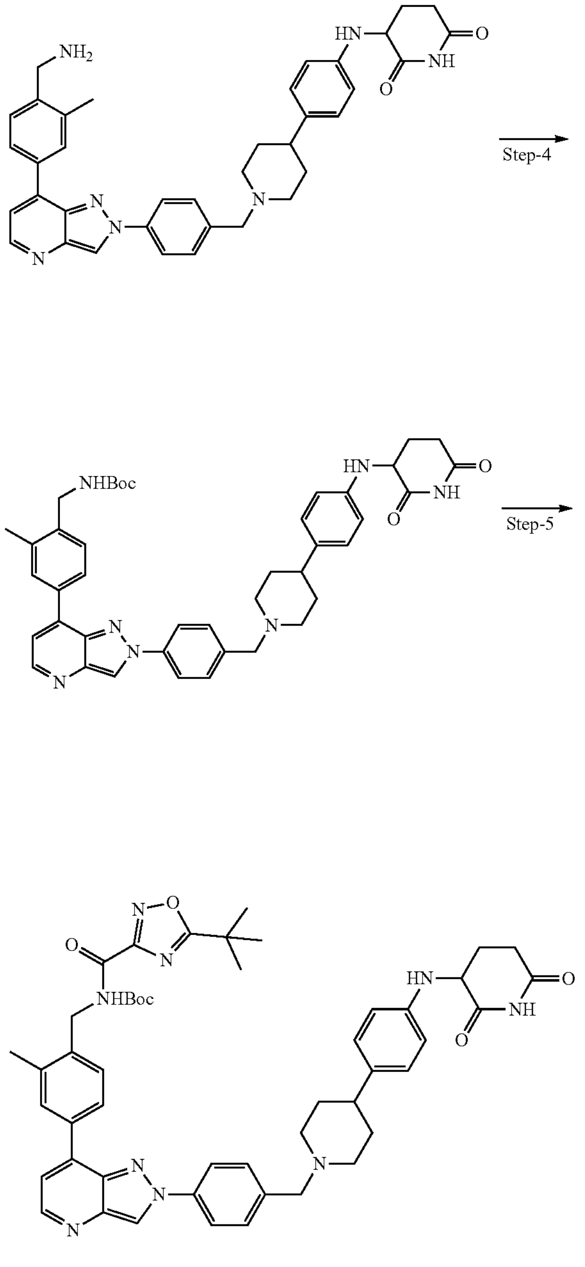

Reaction steps and conditions from step-3 to step-5 are identical (using different building blocks) to Example 61 shown below.

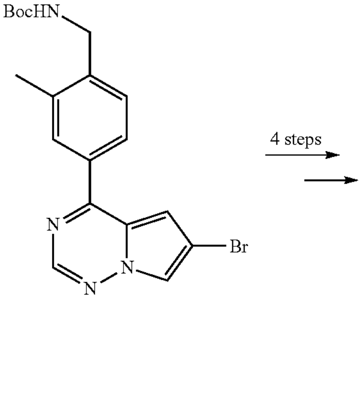

-continued

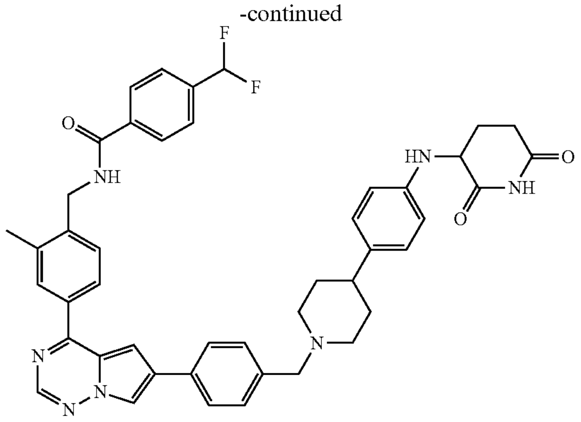

Step-1:

To a solution of 7-bromo-2H-pyrazolo[4,3-b]pyridine (2 g, 10.10 mmol) in DMF (30 mL) was added 4-fluorobenzaldehyde (1.50 g, 12.12 mmol, 1.30 mL) followed by the addition of potassium carbonate, granular (2.79 g, 20.20 mmol) and the resulting mixture was heated to reflux at 120° C. for up to 16 h. Upon the completion of the reaction, the resulting crude was diluted with water, and the resulting precipitate was filtered and triturated by ACN (20 mL) to afford 4-(7-bromopyrazolo[4,3-b]pyridin-2-yl)benzaldehyde (1.4 g, 3.66 mmol, 36.24% yield) as a grey solid. LC-MS ($ES^+$): m/z 302.3 $[M+H]^+$.

Step-2:

To a stirred a solution mixture of 4-(7-bromopyrazolo[4,3-b]pyridin-2-yl)benzaldehyde (1.4 g, 4.63 mmol) and tert-butyl N-[[2-methyl-4-(4,4,5,5-tetramethyl-1,3,2-dioxaborolan-2-yl)phenyl]methyl]carbamate (1.61 g, 4.63 mmol) in dioxane (64 mL) and water (16 mL) was added potassium carbonate—granular (1.92 g, 13.90 mmol) and the resulting mixture was purged with nitrogen gas for 20 minutes. Then, bis(di-tert-butyl(4-dimethylaminophenyl)phosphine)dichloropalladium(II) (328.11 mg, 463.38 μmol) was added and the resulting mixture was heated to reflux at 110° C. for 24 hours. After completion, the resulting mixture diluted with water (150 mL) and extracted by DCM (100 mL×3) combined organic dried to high vacuum to get crude which was purified by reverse phase (DP eluted at 65% ACN in water with formic acid) to afford tert-butyl N-[[4-[2-(4-formylphenyl)pyrazolo[4,3-b]pyridin-7-yl]-2-methyl-phenyl]methyl]carbamate (0.590 g, 1.12 mmol, 24.28% yield) as a white solid. LC-MS ($ES^+$): m/z 443.5 $[M+H]^+$.

Step-3:

tert-butyl N-[[4-[2-[4-[[4-[4-[(2,6-dioxo-3-piperidyl)amino]phenyl]-1-piperidyl]methyl]phenyl]pyrazolo[4,3-b]pyridin-7-yl]-2-methyl-phenyl]methyl]carbamate (0.220 g, 231.57 μmol, 34.16% yield). LC-MS ($ES^+$): m/z 714.4 $[M+H]^+$.

Step-4:

3-[4-[1-[[4-[7-[4-(aminomethyl)-3-methyl-phenyl]pyrazolo[4,3-b]pyridin-2-yl]phenyl]methyl]-4-piperidyl]anilino]piperidine-2,6-dione HCl salt (0.220 g, 259.31 μmol, 92.56% yield). LC-MS ($ES^+$): m/z 614.4 $[M+H]^+$.

Step-5:

5-tert-butyl-N-[[4-[2-[4-[[4-[4-[(2,6-dioxo-3-piperidyl)amino]phenyl]-1-piperidyl]methyl]phenyl]pyrazolo[4,3-b]pyridin-7-yl]-2-methyl-phenyl]methyl]-1,2,4-oxadiazole-3-carboxamide TFA salt (57 mg, 63.49 μmol, 20.64% yield).

$^1$H NMR (400 MHz, DMSO-$d_6$) δ 10.76 (s, 1H), 9.68 (s, 1H), 9.57 (t, J=5.8 Hz, 1H), 9.47 (s, 1H), 8.67 (d, J=4.4 Hz, 1H), 8.30 (d, J=8.5 Hz, 1H), 8.16 (d, J=8.0 Hz, 1H), 8.12 (s, 1H), 7.80 (d, J=8.4 Hz, 2H), 7.63 (d, J=4.4 Hz, 1H), 7.44 (d, J=8.0 Hz, 1H), 6.94 (d, J=8.4 Hz, 2H), 6.63 (d, J=8.4 Hz, 2H), 4.55 (d, J=5.8 Hz, 2H), 4.44 (d, J=4.0 Hz, 2H), 4.29-4.26 (m, 1H), 3.57-3.47 (m, 2H), 3.10-3.08 (m, 2H), 2.69-2.60 (m, 3H), 2.47 (s, 3H), 2.11-2.07 (m, 1H), 1.97-1.81 (m, 5H), 1.44 (s, 9H).

LC-MS ($ES^+$): m/z 764.3 $[M+H]^+$.

Mobile phase-A: 0.1% FA in H2O

Mobile phase-B: ACN

Column: AQUITY UPLC BEH C18 1.7 μm, 2.1×50 mm

Flow: 0.6 mL/min

Temp: 40° C.

Time (min) and % B: 0-5; 0.3-5; 2.5-95; 3.7-95; 4-5; 4.8-5

Example 224. Synthesis of 5-tert-butyl-N-[[4-[2-[4-[4-[4-[(2,6-dioxo-3-piperidyl)amino]phenyl]-1-piperidyl]butyl]pyrazolo[4,3-b]pyridin-7-yl]-2-methyl-phenyl]methyl]-1,2,4-oxadiazole-3-carboxamide

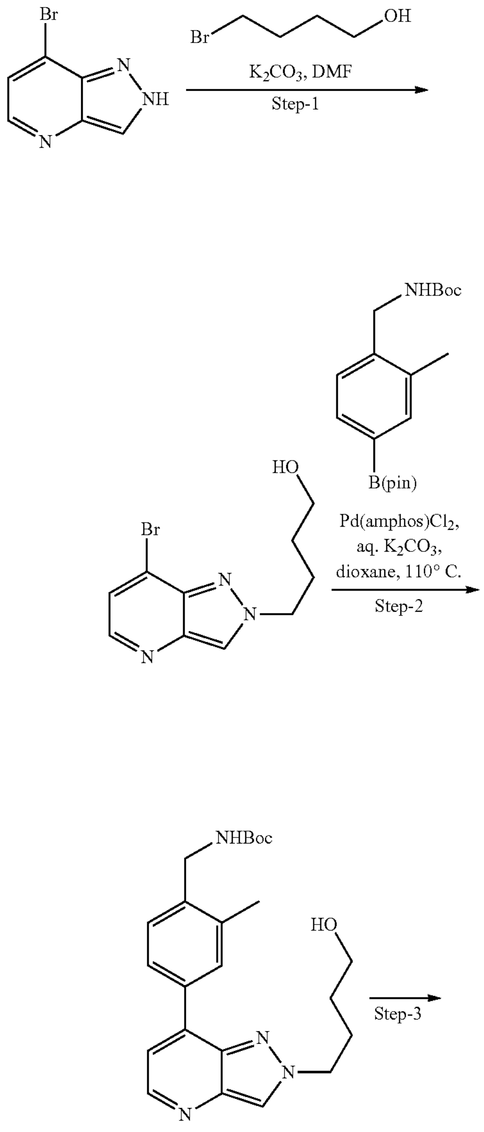

-continued
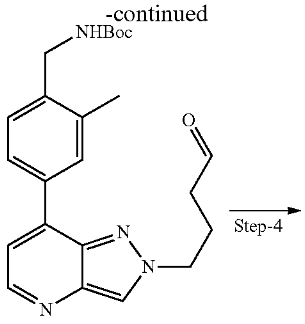
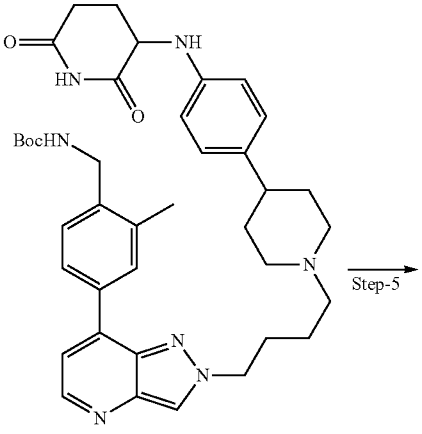
-continued
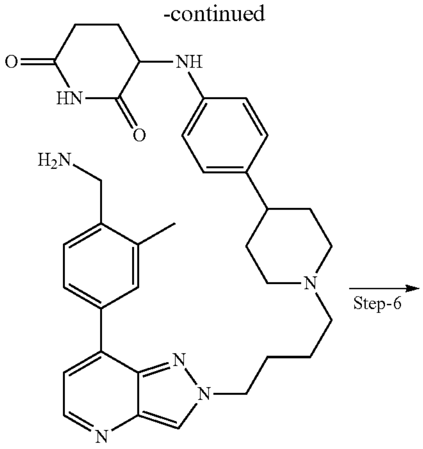
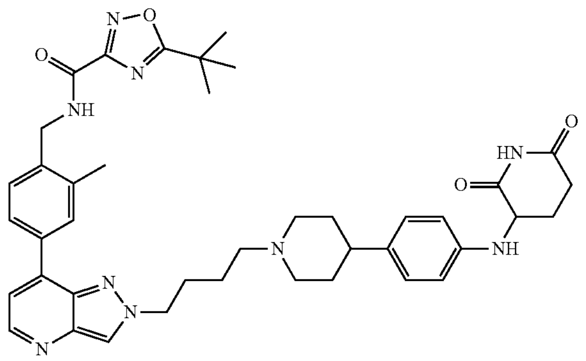
Reaction steps and conditions from step-3 to step-6 are identical to Example 127 shown below.
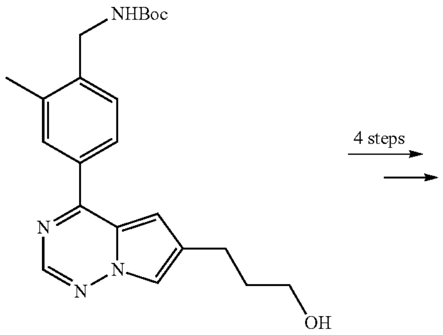

-continued

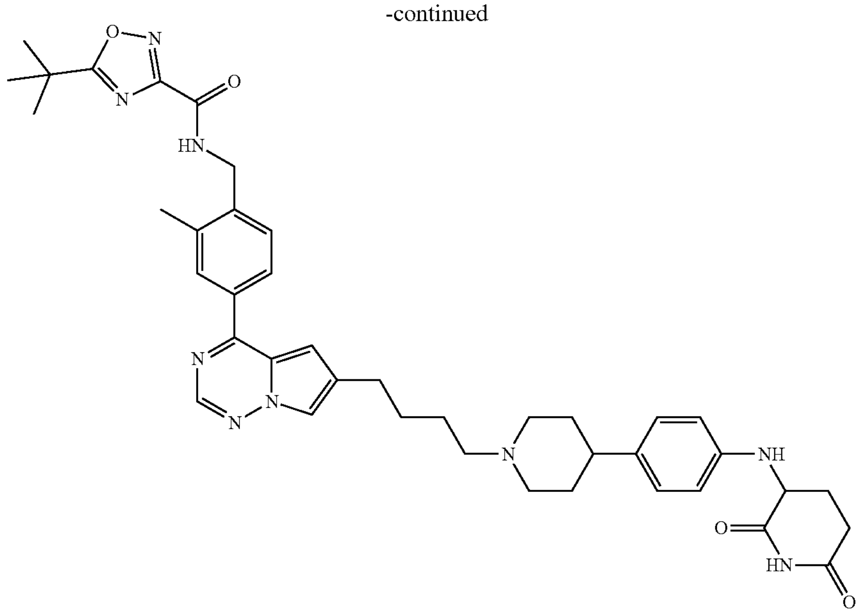

Step-1:

To a stirred solution of 7-bromo-2H-pyrazolo[4,3-b]pyridine (1.5 g, 7.57 mmol) and 4-bromobutan-1-ol (1.16 g, 7.57 mmol) in DMF (5 mL) was added potassium carbonate (3.14 g, 22.72 mmol) and stirred it for 10 minutes at room temperature. The reaction was monitored by LCMS and TLC. After completion, it was directly concentrated under reduced pressure to get the crude product, which was purified by reverse-phase purification using 0.1% formic acid in $H_2O$/ACN to afford 4-(7-bromopyrazolo[4,3-b]pyridin-2-yl)butan-1-ol (0.5 g, 1.39 mmol, 18.34% yield) as a liquid. LC-MS ($ES^+$): m/z 270.3 $[M+H]^+$.

Step-2:

To a solution of benzyl 4-(7-bromopyrazolo[4,3-b]pyridin-2-yl)butan-1-ol (0.5 g, 1.85 mmol) and tert-butyl N-[[2-methyl-4-(4,4,5,5-tetramethyl-1,3,2-dioxaborolan-2-yl)phenyl]methyl]carbamate (771.32 mg, 2.22 mmol) in dioxane (16 mL) and water (4 mL) was added potassium carbonate (767.48 mg, 5.55 mmol) at room temperature. The reaction mixture was degassed with argon for 10 minutes and $PdCl_2(Amphos)_2$ (185.10 μmol) was added. The reaction mixture was degassed with argon for additional 5 min and it was stirred at 80° C. for 16 hours. Subsequently, the reaction mixture was concentrated in vacuo to get the crude product, which was purified by column chromatography (devisil silica, 2% methanol in DCM) to afford tert-butyl N-[[4-[2-(4-hydroxybutyl)pyrazolo[4,3-b]pyridin-7-yl]-2-methyl-phenyl]methyl]carbamate (0.2 g, 455.63 μmol, 24.62% yield) as a brown solid. LC-MS ($ES^+$): m/z 411.4 $[M+H]^+$.

Step-3:

tert-butyl N-[[2-methyl-4-[2-(4-oxobutyl)pyrazolo[4,3-b]pyridin-7-yl]phenyl]methyl]carbamate (0.22 g, 234.55 μmol, 41.86% yield). LC-MS ($ES^+$): m/z 409.4 $[M+H]^+$.

Step-4:

tert-butyl N-[[4-[2-[4-[4-[4-[(2,6-dioxo-3-piperidyl)amino]phenyl]-1-piperidyl]butyl]pyrazolo[4,3-b]pyridin-7-yl]-2-methyl-phenyl]methyl]carbamate (0.2 g, 102.82 μmol, 19.09% yield). LC-MS ($ES^+$): m/z 680.5 $[M+H]^+$.

Step-5:

3-[4-[1-[4-[7-[4-(aminomethyl)-3-methyl-phenyl]pyrazolo[4,3-b]pyridin-2-yl]butyl]-4-piperidyl]anilino]piperidine-2,6-dione HCl salt (0.18 g, 90.03 μmol, 34.00% yield). LC-MS ($ES^+$): m/z 580.5 $[M+H]^+$.

Step-6:

5-tert-butyl-N-[[4-[2-[4-[4-[4-[(2,6-dioxo-3-piperidyl)amino]phenyl]-1 piperidyl]butyl]pyrazolo[4,3-b]pyridin-7-yl]-2-methyl-phenyl]methyl]-1,2,4-oxadiazole-3 carboxamide TFA salt (19 mg, 21.87 μmol, 6.74% yield).

$^1H$ NMR (400 MHz, DMSO-$d_6$) δ 10.78 (s, 1H), 9.48 (t, J=5.9 Hz, 1H), 8.93 (bs, 1H), 8.81 (s, 1H), 8.60 (d, J=4.5 Hz, 1H), 8.06 (d, J=8.0 Hz, 1H), 8.03 (s, 1H), 7.55 (d, J=4.5 Hz, 1H), 7.41 (d, J=8.0 Hz, 1H), 6.94 (d, J=8.4 Hz, 2H), 6.63 (d, J=8.4 Hz, 2H), 4.57 (t, J=6.8 Hz, 2H), 4.52 (d, J=5.9 Hz, 2H), 4.29-4.25 (m, 1H), 3.39-3.22 (m, 1H), 3.17-3.12 (m, 2H), 2.96-2.92 (m, 2H), 2.74-2.61 (m, 1H), 2.61-2.59 (m, 2H), 2.45 (s, 3H), 2.04-2.01 (m, 3H), 1.92-1.85 (m, 3H), 1.76-1.69 (m, 4H), 1.44 (s, 9H).

LC-MS ($ES^+$): m/z 732.2 $[M+H]^+$.

Mobile phase-A: 10 mM Ammonium Acetate in Water
Mobile phase-B: ACN
Column: X Bridge BEH C18 2.5 μm, 2.1×50 mm
Flow: 0.5 mL/min
Temp: 40° C.
Time (min) and % B: 0-5; 0.5-5; 2.5-95; 3.7-95; 4.0-5; 5-5

Example 225. Synthesis of 5-tert-butyl-N-[[4-[6-[4-[4-[4-(2,6-dioxo-3-piperidyl)phenyl]-1-piperidyl]-3,3-difluoro-but-1-ynyl]pyrrolo[2,1-f][1,2,4]triazin-4-yl]-2-fluoro-phenyl]methyl]-1,2,4-oxadiazole-3-carboxamide

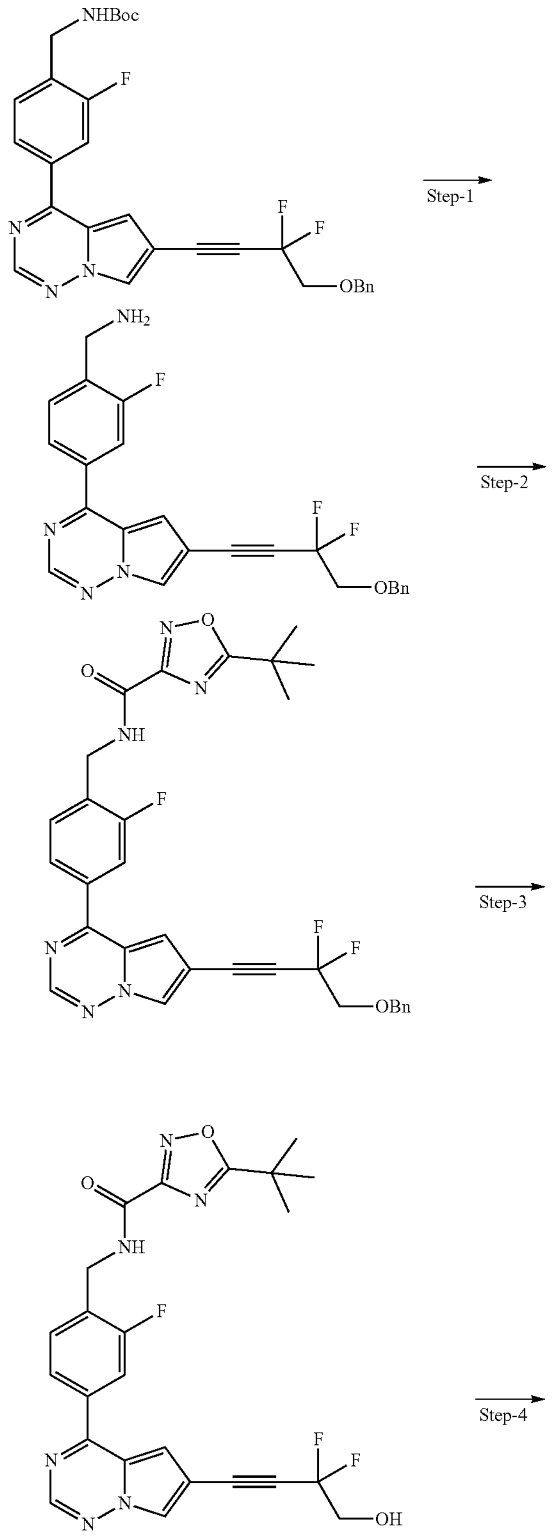

-continued

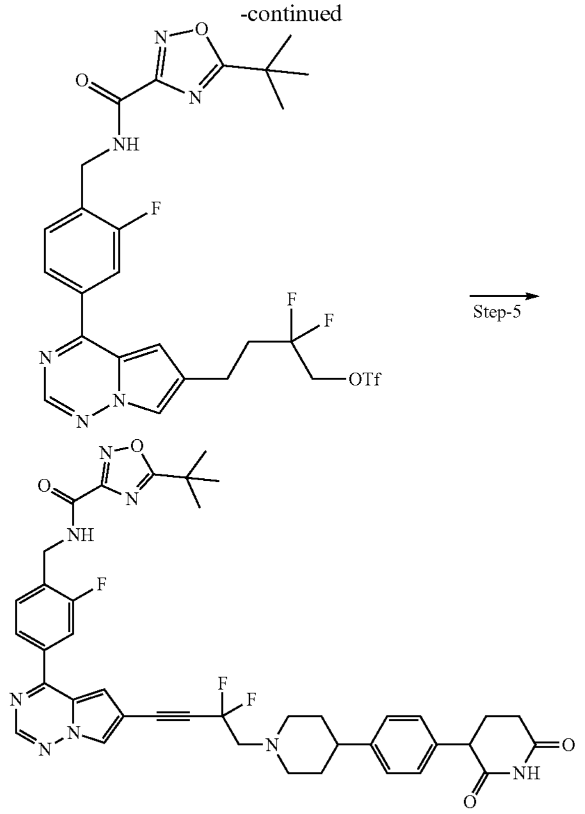

Reaction steps and conditions are identical to Example 169 shown below.

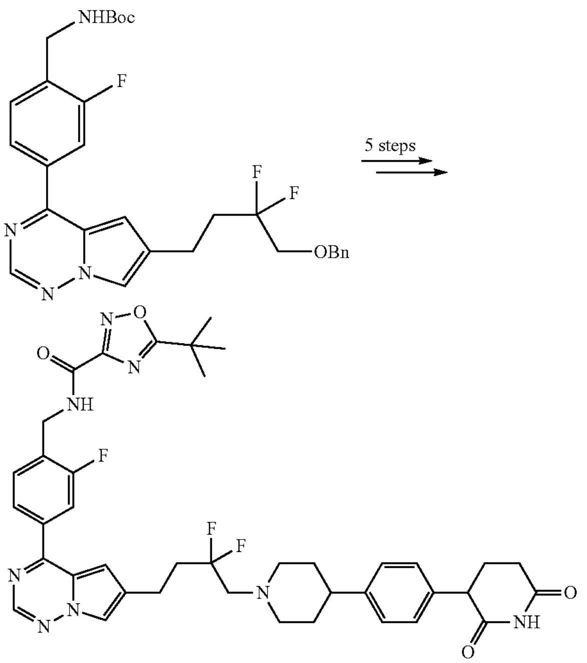

Step-1:

[4-[6-(4-benzyloxy-3,3-difluoro-but-1-ynyl)pyrrolo[2,1-f][1,2,4]triazin-4-yl]-2-fluoro-phenyl]methanamine HCl salt (0.4 g, 814.23 μmol, 91.01% yield). LC-MS ($ES^+$): m/z 437.4 $[M+H]^+$.

Step-2:

N-[[4-[6-(4-benzyloxy-3,3-difluoro-but-1-ynyl)pyrrolo[2,1-f][1,2,4]triazin-4-yl]-2-fluoro-phenyl]methyl]-5-tert-butyl-1,2,4-oxadiazole-3-carboxamide (0.45 g, 731.53 μmol, 79.81% yield). LC-MS ($ES^+$): m/z 589.9 $[M+H]^+$.

Step-3:

5-tert-butyl-N-[[4-[6-(3,3-difluoro-4-hydroxy-but-1-ynyl)pyrrolo[2,1-f][1,2,4]triazin-4-yl]-2-fluoro-phenyl]methyl]-1,2,4-oxadiazole-3-carboxamide (0.02 g, 28.93 μmol, 68.10% yield). LC-MS ($ES^+$): m/z 499.5 $[M+H]^+$.

Step-4:

[4-[4-[4-[[(5-tert-butyl-1,2,4-oxadiazole-3-carbonyl)amino]methyl]-3-fluoro-phenyl]pyrrolo[2,1-f][1,2,4]triazin-6-yl]-2,2-difluoro-butyl] trifluoromethanesulfonate (0.1 g, 104.20 μmol, 51.94% yield). LC-MS ($ES^+$): m/z 631.3 $[M+H]^+$.

Step-5:

tert-butyl-N-[[4-[6-[4-[4-[4-(2,6-dioxo-3-piperidyl)phenyl]-1-piperidyl]-3,3-difluoro-but-1-ynyl]pyrrolo[2,1-f][1,2,4]triazin-4-yl]-2-fluoro-phenyl]methyl]-1,2,4-oxadiazole-3-carboxamide TFA salt (0.105 g, 120.53 μmol, 63.33% yield).

$^1H$ NMR (400 MHz, DMSO-$d_6$) δ 10.83 (s, 1H), 9.63 (t, J=6.0 Hz, 1H), 8.92 (d, J=1.2 Hz, 1H), 8.87 (s, 1H), 8.08-8.06 (m, 1H), 8.00-7.97 (m, 1H), 7.79 (d, J=1.2 Hz, 1H), 7.64 (t, J=7.8 Hz, 1H), 7.44 (s, 1H), 7.29 (d, J=8.4 Hz, 2H), 7.21 (d, J=8.4 Hz, 2H), 5.04 (t, J=11.2 Hz, 2H), 4.63 (d, J=6.0 Hz, 2H), 4.04 (t, J=11.2 Hz, 2H), 3.84-3.82 (m, 1H), 3.75-3.72 (m, 2H), 3.09-3.02 (m, 1H), 2.70-2.63 (m, 1H), 2.33-2.01 (m, 6H), 1.43 (s, 9H).

LC-MS ($ES^+$): m/z 753.4 $[M+H]^+$.

Mobile Phase A: 10 mM Ammonium Acetate in water.

Mobile Phase B: ACN

Gradient % of B: 0/5, 0.3/5, 7/95, 8.2/95, 9.2/5, 12/5

Flow: 0.5 mL/min

Column: XBRIDGE C18 2.5 μm, 3.0×50 mm

General Procedures (Pyridine-Linked Compounds)

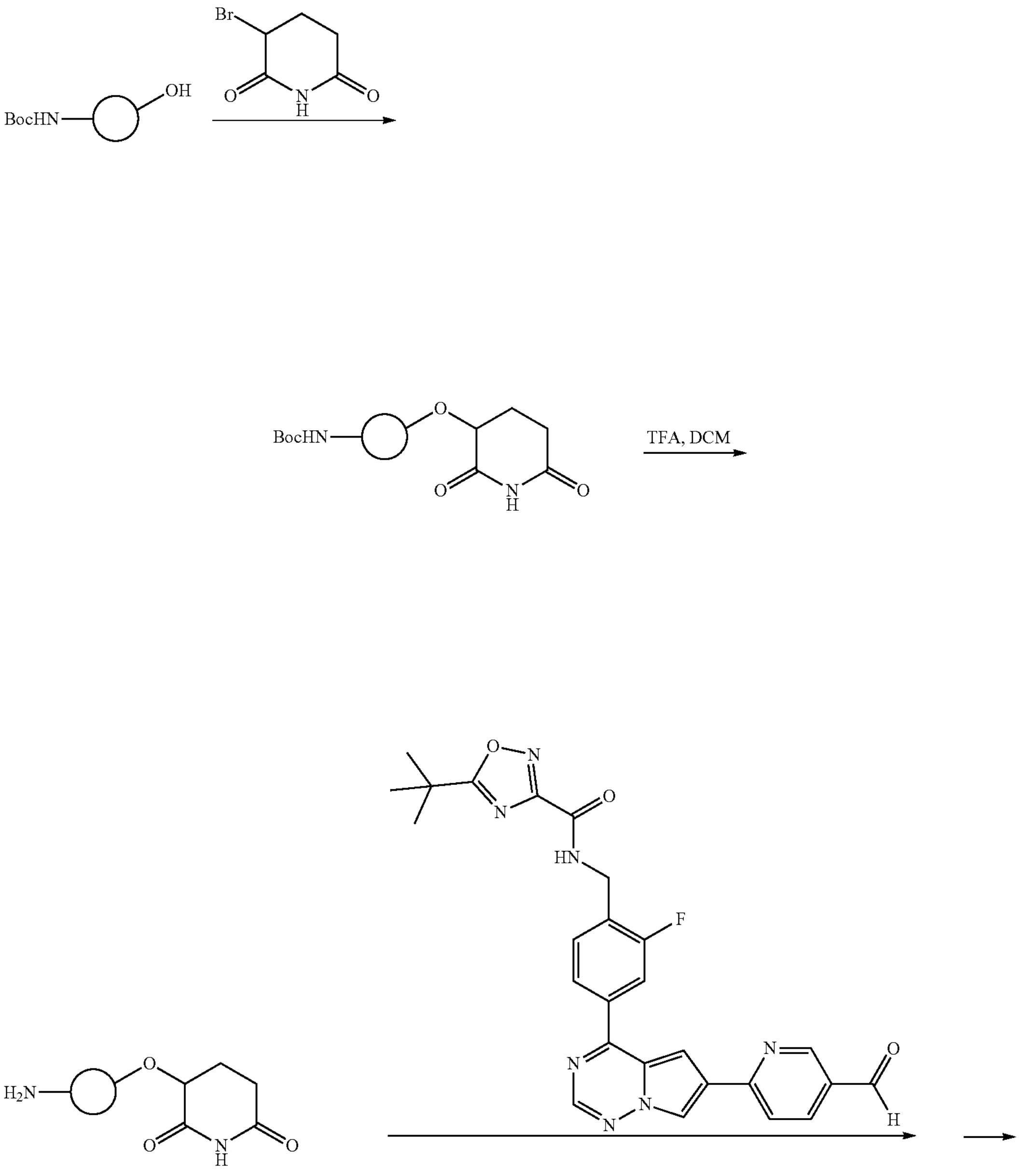

-continued

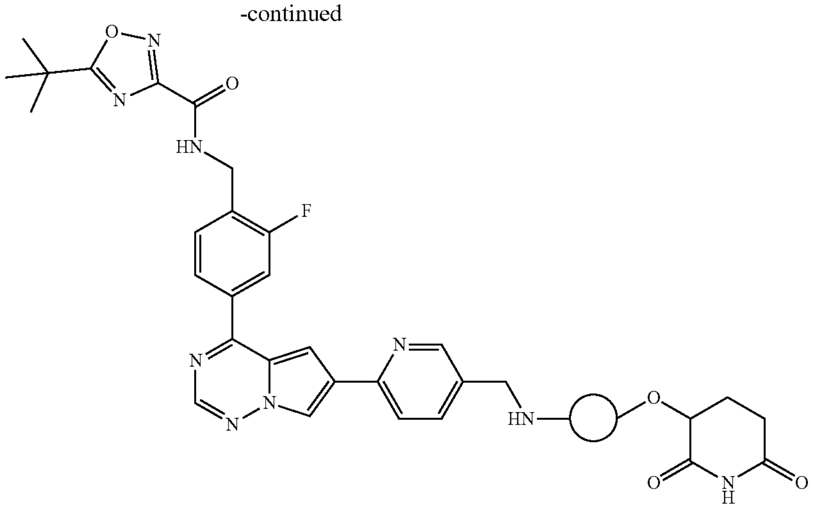

As illustrated in the synthetic scheme shown above, Examples 226-237 were prepared in substantially the same manner as Example 200 described above, except that a Boc-protected amino-phenol/alcohol was reacted with the 3-bromopiperidine-2,6-dione instead of a Boc-protected diamine.

TABLE 5

| Example | IUPAC name | 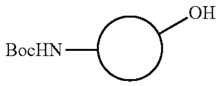 "Respective Intermediate building block" precursor |
|---|---|---|
| 226 | 5-(tert-butyl)-N-(4-(6-(5-((7-((2,6-dioxopiperidin-3-yl)oxy)-3,4-dihydroisoquinolin-2(1H)-yl)methyl) pyridin-2-yl)pyrrolo[2,1-f][1,2,4]triazin-4-yl)-2-fluorobenzyl)-1,2,4-oxadiazole-3-carboxamide | 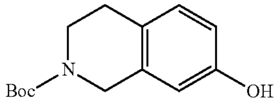 [SMILES: CC(C)(C)OC(=O)N1CCc2ccc(O)cc2C1] |
| | 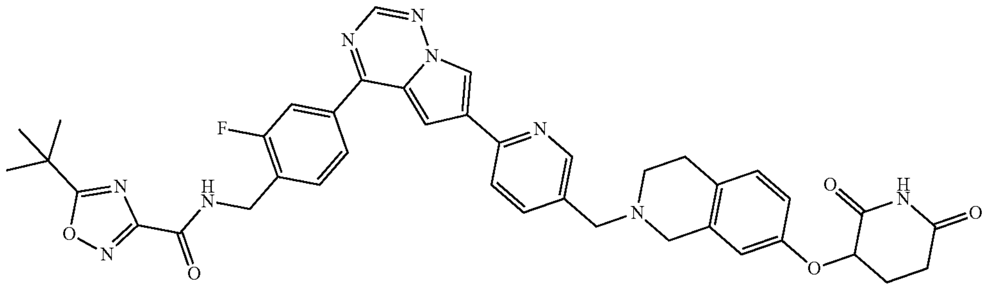 [SMILES: CC(C)(C)c1nc(C(=O)NCc2ccc(-c3ncnn4cc(-c5ccc(CN6CCc7ccc(OC8CCC(=O)NC8=O)cc7C6)cn5)cc34)cc2F)no1] | |
| 227 | 5-(tert-butyl)-N-(4-(6-(5-((3-(4-((2,6-dioxopiperidin-3-yl)oxy)benzyl)piperidin-1-yl)methyl)pyridin-2-yl) pyrrolo[2,1-f][1,2,4]triazin-4-yl)-2-fluorobenzyl)-1,2,4-oxadiazole-3-carboxamide | 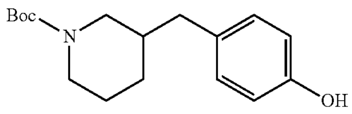 [SMILES: CC(C)(C)OC(=O)N1CCCC(Cc2ccc(O)cc2)C1] |
| | 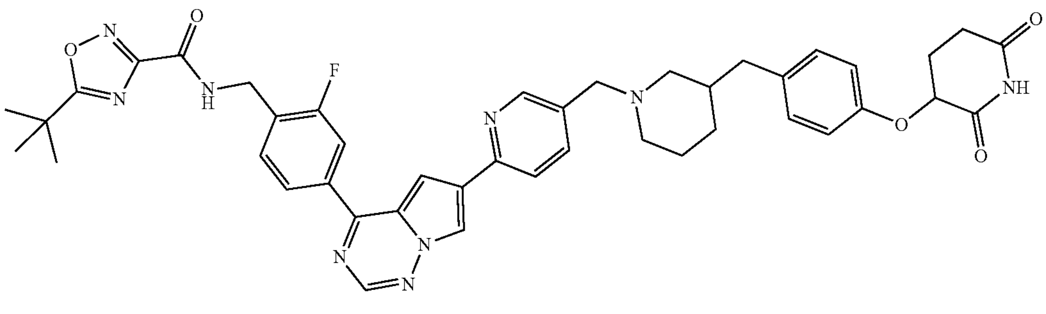 [SMILES: CC(C)(C)c1nc(C(=O)NCc2ccc(-c3ncnn4cc(-c5ccc(CN6CCCC(Cc7ccc(OC8CCC(=O)NC8=O)cc7)C6)cn5)cc34)cc2F)no1] | |

TABLE 5-continued

| Example | IUPAC name | 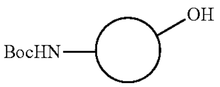 "Respective Intermediate building block" precursor |
|---|---|---|
| 228 | 5-(tert-butyl)-N-(4-(6-(5-((8-(2,6-dioxopiperidin-3-yl)oxy)-2,3-dihydrobenzo[f][1,4]oxazepin-4(5H)-yl)methyl)pyridin-2-yl)pyrrolo[2,1-f][1,2,4]triazin-4-yl)-2-fluorobenzyl)-1,2,4-oxadiazole-3-carboxamide | 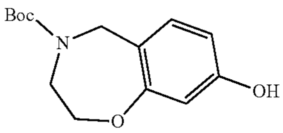 [SMILES: CC(C)(C)OC(=O)N1CCOc2cc(O)ccc2C1] |
| | 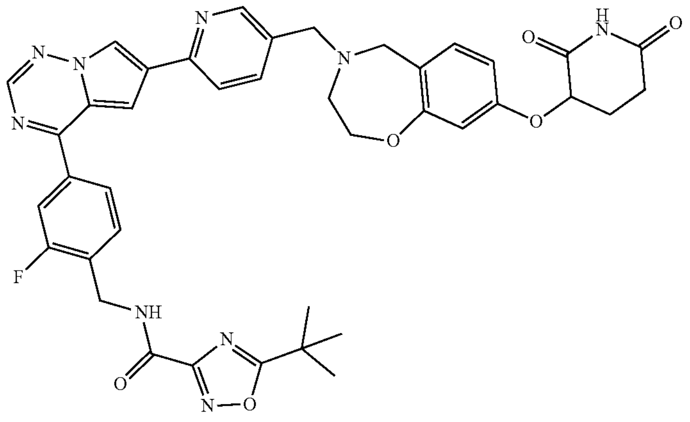 [SMILES: CC(C)(C)c1nc(C(=O)NCc2ccc(-c3ncnn4cc(-c5ccc(CN6CCOc7cc(OC8CCC(=O)NC8=O)ccc7C6)cn5)cc34)cc2F)no1] | |
| 229 | 5-(tert-butyl)-N-(4-(6-(5-(((2-(4-((2,6-dioxopiperidin-3-yl)oxy)phenoxy)ethyl)(methyl)amino)methyl) pyridin-2-yl)pyrrolo[2,1-f][1,2,4]triazin-4-yl)-2-fluorobenzyl)-1,2,4-oxadiazole-3-carboxamide | 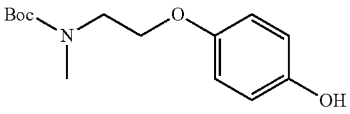 [SMILES: CN(CCOc1ccc(O)cc1)C(=O)OC(C)(C)C] |
| | 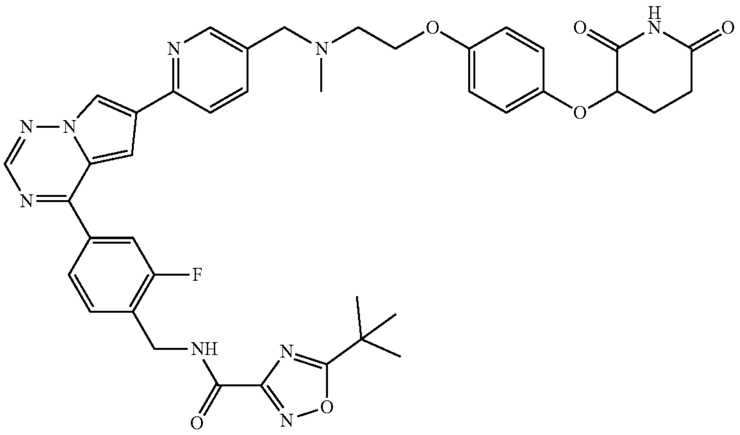 [SMILES: CN(CCOc1ccc(OC2CCC(=O)NC2=O)cc1)Cc1ccc(-c2cc3c(-c4ccc(CNC(=O)c5noc(C(C)(C)C)n5)c(F)c4)ncnn3c2)nc1] | |
| 230 | 5-(tert-butyl)-N-(4-(6-(5-((7-((2,6-dioxopiperidin-3-yl)oxy)-1,2,4,5-tetrahydro-3H-benzo[d]azepin-3-yl)methyl)pyridin-2-yl)pyrrolo [2,1-f][1,2,4]triazin-4-yl)-2-fluorobenzyl)-1,2,4-oxadiazole-3-carboxamide | 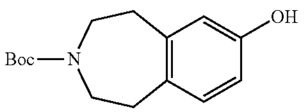 [SMILES: CC(C)(C)OC(=O)N1CCc2ccc(O)cc2CC1] |

TABLE 5-continued

| Example | IUPAC name | 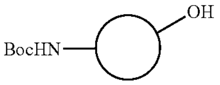 "Respective Intermediate building block" precursor |
|---|---|---|
| | 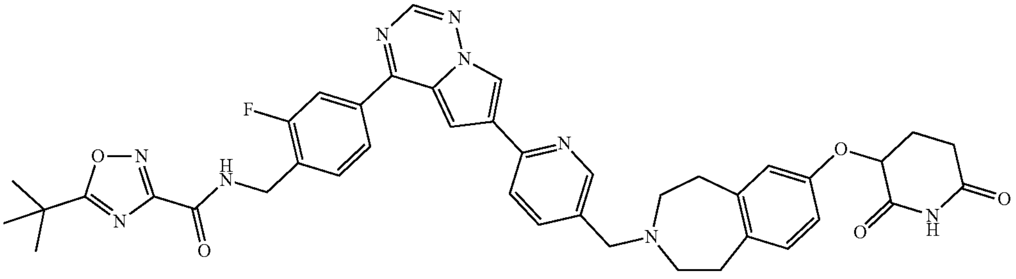 [SMILES: CC(C)(C)c1nc(C(=O)NCc2ccc(-c3ncnn4cc(-c5ccc(CN6CCc7ccc(OC8CCC(=O)NC8=O)cc7CC6)cn5)cc34)cc2F)no1] | |
| 231 | 5-(tert-butyl)-N-(4-(6-(5-((4-(3-((2,6-dioxopiperidin-3-yl)oxy)benzyl)piperidin-1-yl)methyl)pyridin-2-yl)pyrrolo[2,1-f][1,2,4]triazin-4-yl)-2-fluorobenzyl)-1,2,4-oxadiazole-3-carboxamide | 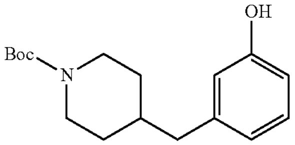 [SMILES: CC(C)(C)OC(=O)N1CCC(Cc2cccc(O)c2)CC1] |
| | 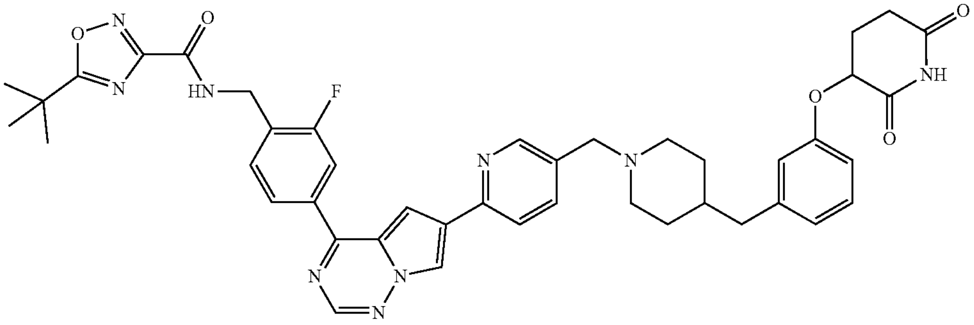 [SMILES: CC(C)(C)c1nc(C(=O)NCc2ccc(-c3ncnn4cc(-c5ccc(CN6CCC(Cc7cccc(OC8CCC(=O)NC8=O)c7)CC6)cn5)cc34)cc2F)no1] | |
| 232 | 5-(tert-butyl)-N-(4-(6-(5-((7-((2,6-dioxopiperidin-3-yl)oxy)-1-methyl-3,4-dihydroisoquinolin-2(1H)-yl)methyl)pyridin-2-yl)pyrrolo[2,1-f][1,2,4]triazin-4-yl)-2-fluorobenzyl)-1,2,4-oxadiazole-3-carboxamide | 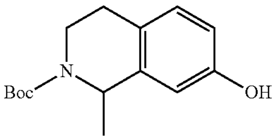 [SMILES: CC1c2cc(O)ccc2CCN1C(=O)OC(C)(C)C] |
| | 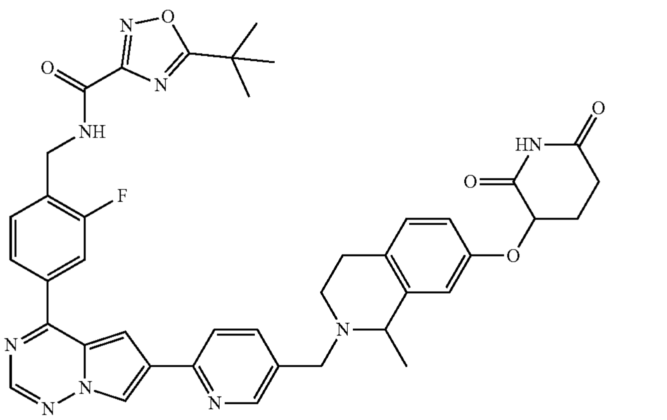 [SMILES: CC1c2cc(OC3CCC(=O)NC3=O)ccc2CCN1Cc1ccc(-c2cc3c(-c4ccc(CNC(=O)c5noc(C(C)(C)C)n5)c(F)c4)ncnn3c2)nc1] | |

TABLE 5-continued

| Example | IUPAC name | 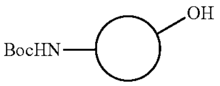 "Respective Intermediate building block" precursor |
| --- | --- | --- |
| 233 | 5-(tert-butyl)-N-(4-(6-(5-((2-(4-((2,6-dioxopiperidin-3-yl)oxy)benzyl)piperidin-1-yl)methyl)pyridin-2-yl)pyrrolo[2,1-f][1,2,4]triazin-4-yl)-2-fluorobenzyl)-1,2,4-oxadiazole-3-carboxamide | 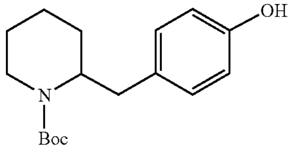 [SMILES: CC(C)(C)OC(=O)N1CCCCC1Cc1ccc(O)cc1] |
| | 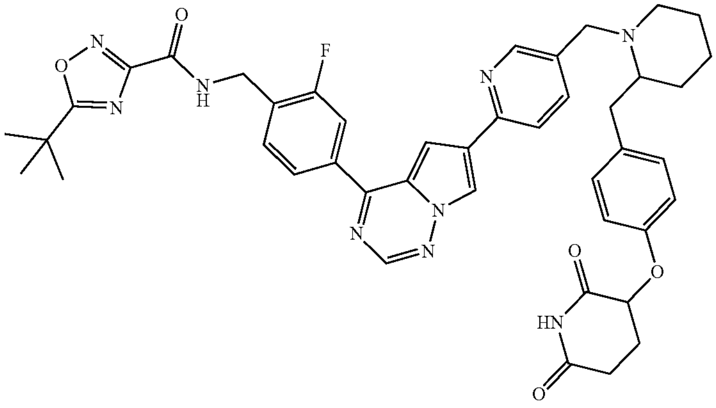 [SMILES: CC(C)(C)c1nc(C(=O)NCc2ccc(-c3ncnn4cc(-c5ccc(CN6CCCCC6Cc6ccc(OC7CCC(=O)NC7=O)cc6)cn5)cc34)cc2F)no1] | |
| 234 | 5-(tert-butyl)-N-(4-(6-(5-((4-(4-((2,6-dioxopiperidin-3-yl)oxy)benzyl)piperazin-1-yl)methyl)pyridin-2-yl)pyrrolo[2,1-f][1,2,4]triazin-4-yl)-2-fluorobenzyl)-1,2,4-oxadiazole-3-carboxamide | 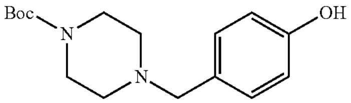 [SMILES: CC(C)(C)OC(=O)N1CCN(Cc2ccc(O)cc2)CC1] |
| | 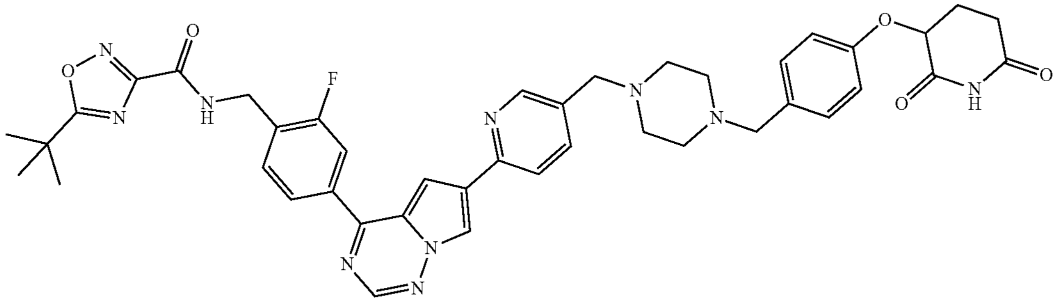 [SMILES: CC(C)(C)c1nc(C(=O)NCc2ccc(-c3ncnn4cc(-c5ccc(CN6CCN(Cc7ccc(OC8CCC(=O)NC8=O)cc7)CC6)cn5)cc34)cc2F)no1] | |
| 235 | 5-(tert-butyl)-N-(4-(6-(5-((4-(3-((2,6-dioxopiperidin-3-yl)oxy)benzyl)piperazin-1-yl)methyl)pyridin-2-yl)pyrrolo[2,1-f][1,2,4]triazin-4-yl)-2-fluorobenzyl)-1,2,4-oxadiazole-3-carboxamide | 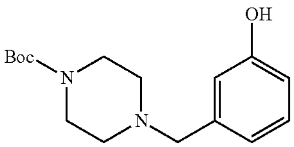 [SMILES: CC(C)(C)OC(=O)N1CCN(Cc2cccc(O)c2)CC1] |

TABLE 5-continued
| Example | IUPAC name | 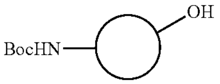 "Respective Intermediate building block" precursor |
|---|---|---|
| | 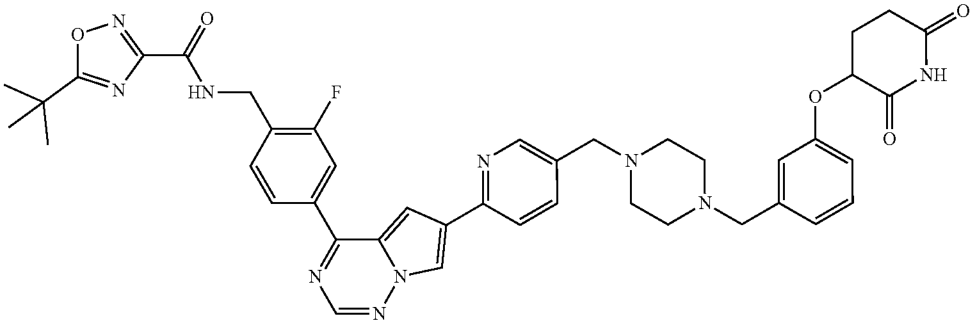 [SMILES: CC(C)(C)c1nc(C(=O)NCc2ccc(-c3ncnn4cc(-c5ccc(CN6CCN(Cc7cccc(OC8CCC(=O)NC8=O)c7)CC6)cn5)cc34)cc2F)no1] | |
| 236 | 5-(tert-butyl)-N-(4-(6-(5-((3-(4-((2,6-dioxopiperidin-3-yl)oxy)phenyl)piperidin-1-yl)methyl)pyridin-2-yl)pyrrolo[2,1-f][1,2,4]triazin-4-yl)-2-fluorobenzyl)-1,2,4-oxadiazole-3-carboxamide | 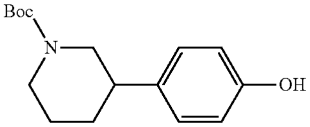 |
| | 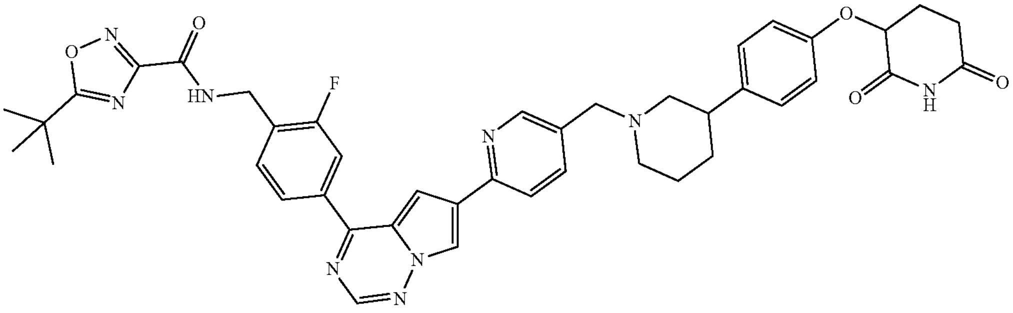 [SMILES: CC(C)(C)c1nc(C(=O)NCc2ccc(-c3ncnn4cc(-c5ccc(CN6CCCC(c7ccc(OC8CCC(=O)NC8=O)cc7)C6)cn5)cc34)cc2F)no1] | |
| 237 | 5-(tert-butyl)-N-(4-(6-(5-((3-(4-((2,6-dioxopiperidin-3-yl)oxy)benzyl)pyrrolidin-1-yl)methyl)pyridin-2-yl)pyrrolo[2,1-f][1,2,4]triazin-4-yl)-2-fluorobenzyl)-1,2,4-oxadiazole-3-carboxamide | 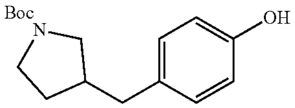 |
| | 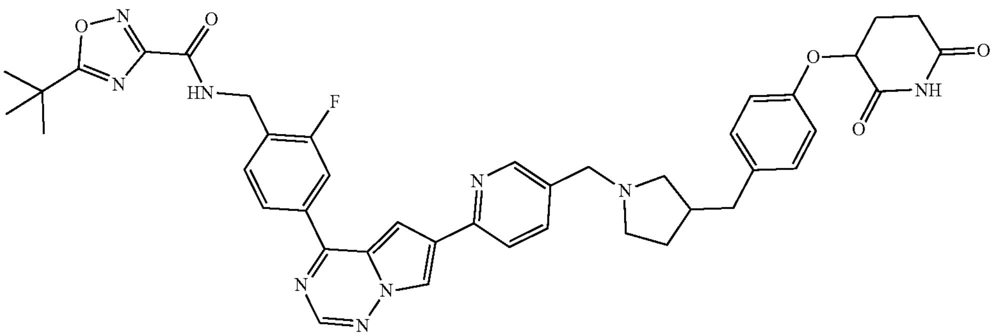 [SMILES: CC(C)(C)c1nc(C(=O)NCc2ccc(-c3ncnn4cc(-c5ccc(CN6CCC(Cc7ccc(OC8CCC(=O)NC8=O)cc7)C6)cn5)cc34)cc2F)no1] | |

TABLE 5-continued

| Example | IUPAC name | 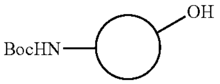<br>"Respective Intermediate building block" precursor |
|---|---|---|
| 238 | 5-(tert-butyl)-N-(4-(6-(5-((3-(4-((2,6-dioxopiperidin-3-yl)oxy)benzyl)morpholino)methyl)pyridin-2-yl)pyrrolo [2,1-f][1,2,4]triazin-4-yl)-2-fluorobenzyl)-1,2,4-oxadiazole-3-carboxamide | 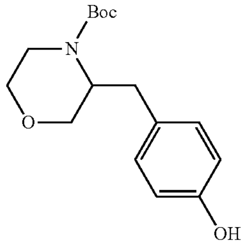 [SMILES: CC(C)(C)OC(=O)N1CCOCC1Cc1ccc(O)cc1] |
| | 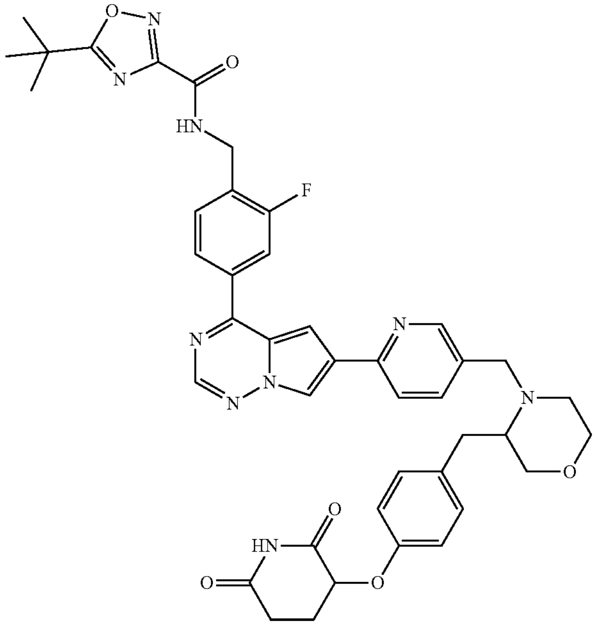 [SMILES: CC(C)(C)c1nc(C(=O)NCc2ccc(-c3ncnn4cc(-c5ccc(CN6CCOCC6Cc6ccc(OC7CCC(=O)NC7=O)cc6)cn5)cc34)cc2F)no1] | |
| 239 | 5-(tert-butyl)-N-(4-(6-(5-((4-(4-((2,6-dioxopiperidin-3-yl)oxy)phenethyl)piperidin-1-yl)methyl)pyridin-2-yl)pyrrolo [2,1-f][1,2,4]triazin-4-yl)-2-fluorobenzyl)-1,2,4-oxadiazole-3-carboxamide | 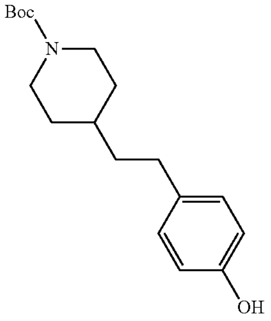 [SMILES: CC(C)(C)OC(=O)N1CCC(CCc2ccc(O)cc2)CC1] |

TABLE 5-continued

| Example | IUPAC name | 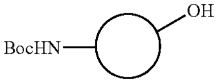 "Respective Intermediate building block" precursor |
| --- | --- | --- |
| | | 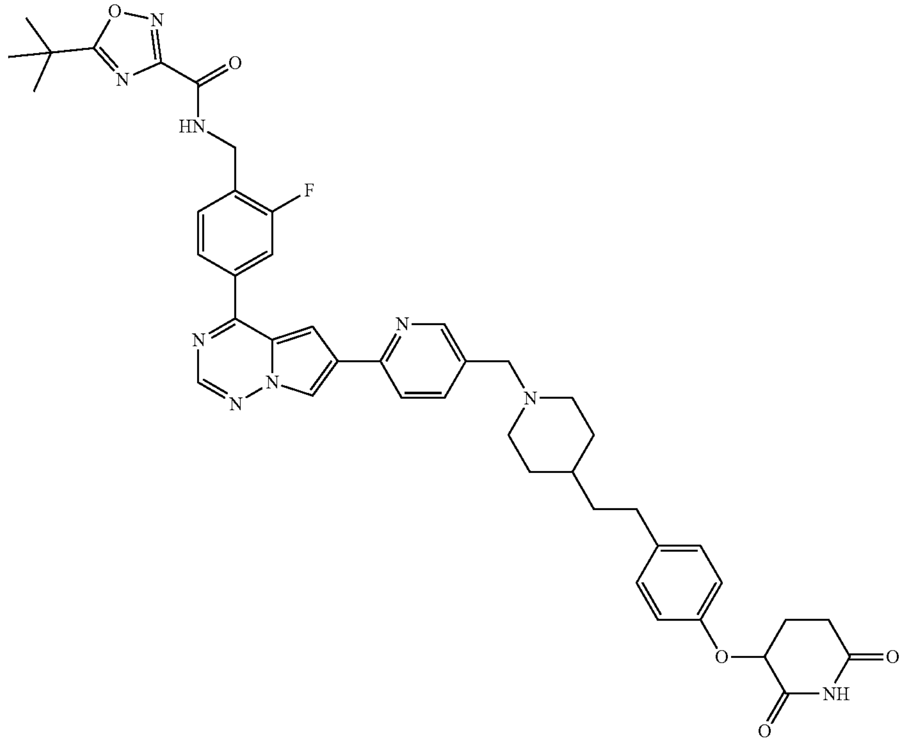 [SMILES: CC(C)(C)c1nc(C(=O)NCc2ccc(-c3ncnn4cc(-c5ccc(CN6CCC(CCc7ccc(OC8CCC(=O)NC8=O)cc7)CC6)cn5)cc34)cc2F)no1] |

Example 240

Example 240 was prepared following the synthesis of Example 1

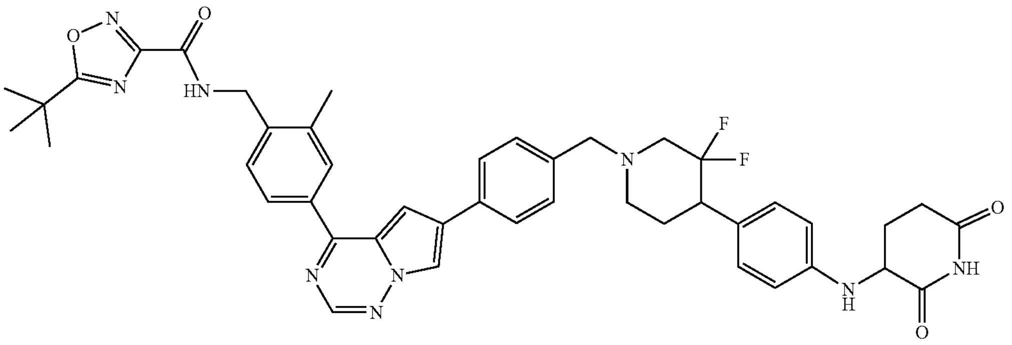 [SMILES: Cc1cc(-c2ncnn3cc(-c4ccc(CN5CCC(c6ccc(NC7CCC(=O)NC7=O)cc6)C(F)(F)C5)cc4)cc23)ccc1CNC(=O)c1noc(C(C)(C)C)n1]

5-(tert-butyl)-N-(4-(6-(4-((4-(4-((2,6-dioxopiperidin-3-yl)amino)phenyl)-3,3-difluoropiperidin-1-yl)methyl)phenyl)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.79 (s, 1H), 9.54 (t, J=6.0 Hz, 1H), 8.72 (s, 1H), 8.61 (s, 1H), 8.06 (d, J=8.4 Hz, 1H), 8.02 (s, 1H), 7.92 (d, J=8.0 Hz, 2H), 7.63 (s, 1H), 7.48 (d, J=8.0 Hz, 1H), 7.40 (d, J=8.0 Hz, 2H), 7.01 (d, J=8.4 Hz, 2H), 6.63 (d, J=8.4 Hz, 2H), 5.80 (d, J=7.2 Hz, 1H), 4.57 (d, J=6.0 Hz, 2H), 4.32-4.27 (m, 1H), 3.66 (q, J=12.5 Hz, 2H), 3.10 (br s, 1H), 2.97-2.59 (m, 5H), 2.47 (s, 3H), 2.41-2.18 (m, 2H), 2.12-1.71 (m, 4H), 1.44 (s, 9H). LC-MS ($ES^+$): m/z 802.48 $[M+H]^+$.

Example 241

Example 241 was prepared following the synthesis of Example 1

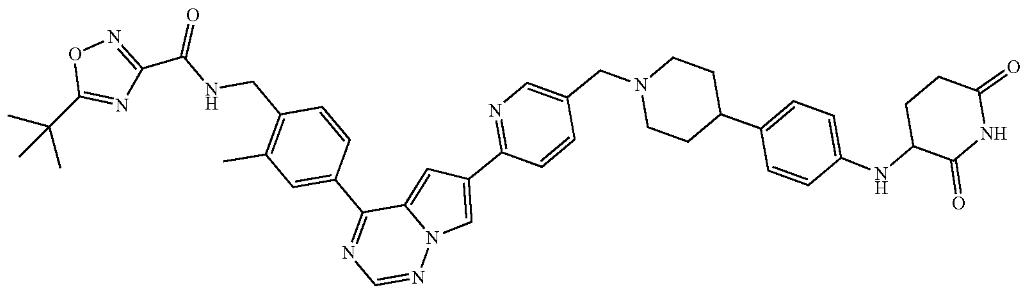 [SMILES: Cc1cc(-c2ncnn3cc(-c4ccc(CN5CCC(c6ccc(NC7CCC(=O)NC7=O)cc6)CC5)cn4)cc23)ccc1CNC(=O)c1noc(C(C)(C)C)n1]

5-(tert-butyl)-N-(4-(6-(5-((4-(4-((2,6-dioxopiperidin-3-yl)amino)phenyl)piperidin-1-yl)methyl)pyridin-2-yl)pyrrolo[2,1-f][1,2,4]triazin-4-yl)-2-methylbenzyl)-1,2,4-oxadiazole-3-carboxamide. $^1$H NMR (400 MHz, DMSO-$d_6$) δ=10.78 (s, 1H), 9.56 (t, J=6.0 Hz, 1H), 8.74 (d, J=1.5 Hz, 1H), 8.65 (s, 1H), 8.56 (d, J=1.5 Hz, 1H), 8.28 (s, 1H), 8.10-7.98 (m, 3H), 7.83-7.70 (m, 2H), 7.50 (d, J=7.9 Hz, 1H), 6.96 (d, J=8.6 Hz, 2H), 6.60 (d, J=8.6 Hz, 2H), 5.65 (d, J=7.6 Hz, 1H), 4.58 (d, J=6.2 Hz, 2H), 4.26 (ddd, J=4.6, 6.7, 11.4 Hz, 1H), 3.55 (s, 3H), 2.92 (br d, J=10.8 Hz, 2H), 2.80-2.64 (m, 2H), 2.63-2.55 (m, 1H), 2.39-2.28 (m, 2H), 2.13-2.02 (m, 3H), 1.85 (dt, J=7.3, 12.3 Hz, 1H), 1.72-1.56 (m, 4H), 1.45 (s, 9H). LC-MS (ES$^+$): m/z 767.4 [M+H]$^+$.

Example 242

Example 242 was prepared following the synthesis of Example 50

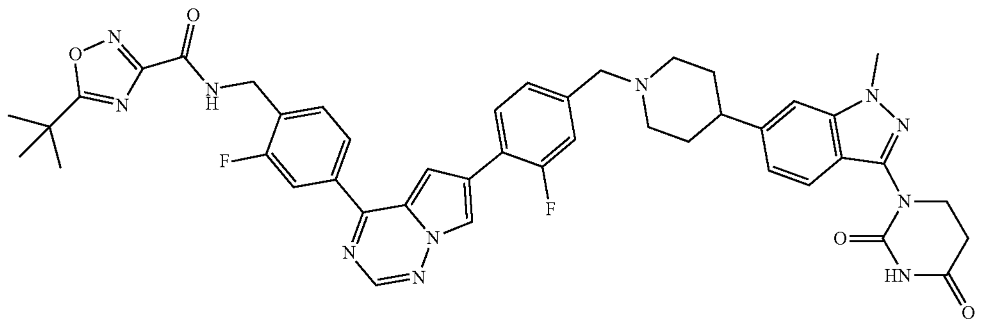 [SMILES: Cn1nc(N2CCC(=O)NC2=O)c2ccc(C3CCN(Cc4ccc(-c5cc6c(-c7ccc(CNC(=O)c8noc(C(C)(C)C)n8)c(F)c7)ncnn6c5)c(F)c4)CC3)cc21]

5-(tert-butyl)-N-(4-(6-(4-((4-(3-(2,4-dioxotetrahydropyrimidin-1(2H)-yl)-1-methyl-1H-indazol-6-yl)piperidin-1-yl)methyl)-2-fluorophenyl)pyrrolo[2,1-f][1,2,4]triazin-4-yl)-2-fluorobenzyl)-1,2,4-oxadiazole-3-carboxamide. $^1$H-NMR (400 MHz, DMSO-$d_6$) δ 10.89 (s, 1H), 9.60 (t, J=6.0 Hz, 1H), 9.50 (br s, 1H), 8.73-8.67 (m, 2H), 8.22 (t, J=8.0 Hz, 1H), 8.08-8.06 (m, 1H), 7.98 (d, J=10.8 Hz, 1H), 7.73 (s, 1H), 7.65-7.55 (m, 3H), 7.50 (d, J=7.6 Hz, 1H), 7.40 (s, 1H), 7.22-6.95 (m, 2H), 4.64 (d, J=5.6 Hz, 2H), 4.45 (d, J=4.0 Hz, 2H), 3.95-3.89 (m, 5H), 3.56 (d, J=12.0 Hz, 2H), 3.18-3.15 (m, 2H), 3.00-2.90 (m, 1H), 2.87-2.73 (m, 2H), 2.40-2.24 (m, 3H), 1.45 (s, 9H). LC-MS (ES$^-$): m/z 826.26 [M−H]$^-$.

Example 243

Example 243 was prepared following the synthesis of Example 50

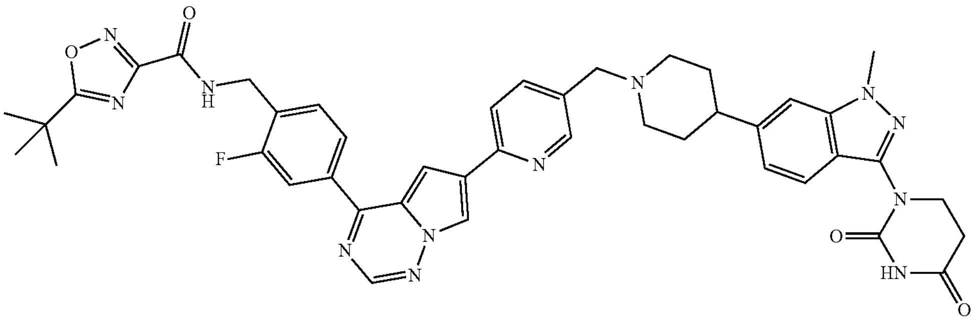 [SMILES: Cn1nc(N2CCC(=O)NC2=O)c2ccc(C3CCN(Cc4ccc(-c5cc6c(-c7ccc(CNC(=O)c8noc(C(C)(C)C)n8)c(F)c7)ncnn6c5)nc4)CC3)cc21]

5-(tert-butyl)-N-(4-(6-(5-((4-(3-(2,4-dioxotetrahydropyrimidin-1(2H)-yl)-1-methyl-1H-indazol-6-yl)piperidin-1-yl)methyl)pyridin-2-yl)pyrrolo[2,1-f][1,2,4]triazin-4-yl)-2-fluorobenzyl)-1,2,4-oxadiazole-3-carboxamide. $^1$H NMR (400 MHz, DMSO-$d_6$) δ 10.55 (s, 1H), 9.62 (t, J=6.0 Hz, 1H), 8.84 (s, 1H), 8.78 (s, 1H), 8.72 (s, 1H), 8.27 (d, J=8.0 Hz, 1H), 8.08-8.04 (m, 2H), 7.97 (d, J=12.0 Hz, 1H), 7.87 (s, 1H), 7.66-7.60 (m, 2H), 7.39 (s, 1H), 7.01 (d, J=8.4 Hz, 1H), 4.64 (d, J=6.0 Hz, 2H), 4.47 (s, 2H), 3.97 (s, 3H), 3.90 (t, J=6.8 Hz, 2H), 3.60-3.50 (m, 2H), 3.20-3.00 (m, 3H), 2.75 (t, J=6.8 Hz, 2H), 2.20-1.90 (m, 4H), 1.44 (s, 9H). LC-MS ($ES^-$): m/z 809.35 $[M-H]^-$.

Example 244

Example 244 was prepared following the synthesis of Example 50

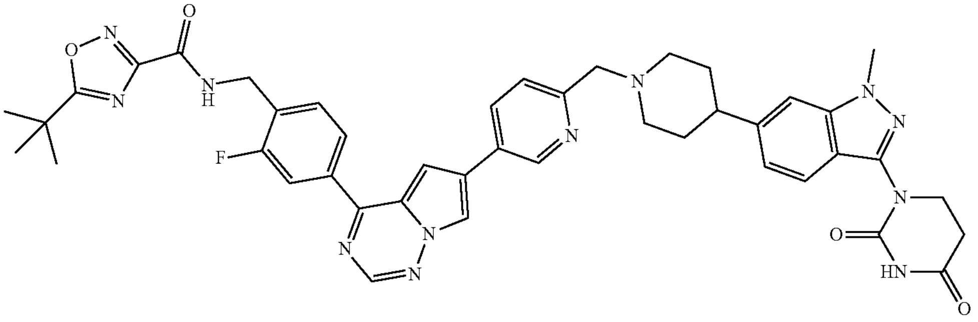 [SMILES: Cn1nc(N2CCC(=O)NC2=O)c2ccc(C3CCN(Cc4ccc(-c5cc6c(-c7ccc(CNC(=O)c8noc(C(C)(C)C)n8)c(F)c7)ncnn6c5)cn4)CC3)cc21]

5-(tert-butyl)-N-(4-(6-(6-((4-(3-(2,4-dioxotetrahydropyrimidin-1(2H)-yl)-1-methyl-1H-indazol-6-yl)piperidin-1-yl)methyl)pyridin-3-yl)pyrrolo[2,1-f][1,2,4]triazin-4-yl)-2-fluorobenzyl)-1,2,4-oxadiazole-3-carboxamide. $^1$H-NMR (400 MHz, DMSO-$d_6$) δ 10.56 (s, 1H), 9.61 (t, J=6.0 Hz, 1H), 9.11 (d, J=1.6 Hz, 1H), 8.87 (d, J=1.2 Hz, 1H), 8.67 (s, 1H), 8.34 (dd, J=2.0 & 8.0 Hz, 1H), 8.15 (s, 1H), 8.10 (d, J=8.0 Hz, 1H), 7.99 (d, J=10.8 Hz, 1H), 7.82 (s, 1H), 7.61 (t, J=8.0 Hz, 3H), 7.55 (d, J=8.4 Hz, 1H), 7.46 (s, 1H), 7.05 (d, J=8.4 Hz, 1H), 4.63 (d, J=6.0 Hz, 2H), 3.97 (s, 1H), 3.90 (t, J=6.8 Hz, 2H), 3.70 (s, 2H), 3.01 (d, J=10.8 Hz, 2H), 2.74 (t, J=6.8 Hz, 2H), 2.69 (br s, 1H), 2.21 (br s, 2H), 1.82 (br s, 4H), 1.44 (s, 9H). LC-MS ($ES^-$): m/z 809.27 $[M-H]^-$.

Example 245

Example 245 was prepared following the synthesis of Example 50

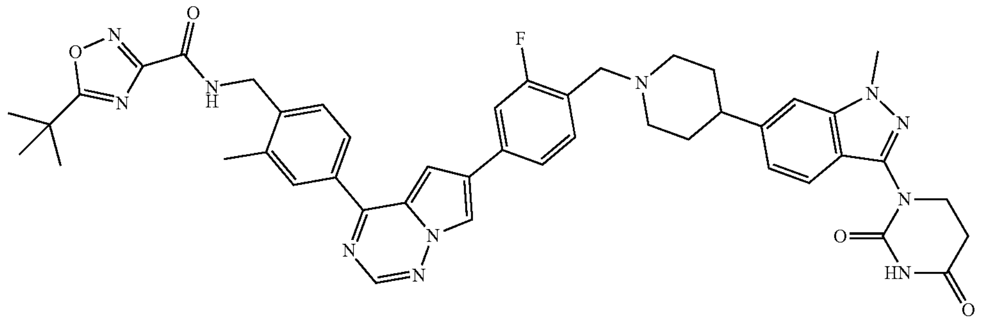 [SMILES: Cc1cc(-c2ncnn3cc(-c4ccc(CN5CCC(c6ccc7c(N8CCC(=O)NC8=O)nn(C)c7c6)CC5)c(F)c4)cc23)ccc1CNC(=O)c1noc(C(C)(C)C)n1]

5-(tert-butyl)-N-(4-(6-(4-((4-(3-(2,4-dioxotetrahydropyrimidin-1(2H)-yl)-1-methyl-1H-indazol-6-yl)piperidin-1-yl)methyl)-3-fluorophenyl)pyrrolo[2,1-f][1,2,4]triazin-4-yl)-2-methylbenzyl)-1,2,4-oxadiazole-3-carboxamide. $^{1}$H-NMR (400 MHz, DMSO-$d_6$) δ 10.58 (s, 1H), 9.56 (m, 1H), 8.08-8.05 (m, 1H), 8.02 (s, 2H), 7.98 (d, J=7.6 Hz, 1H), 7.79 (s, 1H), 7.70 (t, J=8.0 Hz, 2H), 7.61 (d, J=8.4 Hz, 1H), 7.48 (d, J=8.0 Hz, 1H), 7.38 (s, 3H), 7.01 (d, J=8.8 Hz, 1H), 4.57 (d, J=6.0 Hz, 2H), 4.46 (s, 2H), 4.02 (s, 3H), 3.90 (t, J=6.6 Hz, 2H), 3.48 (br s, 2H), 3.27-3.22 (m, 2H), 3.01-2.99 (m, 1H), 2.75 (t, J=6.8 Hz, 2H), 2.44 (br s, 3H), 2.11-1.98 (m, 4H), 1.45 (s, 9H). LC-MS ($ES^+$): m/z 824.40 $[M+H]^+$.

Example 246

Example 246 was prepared following the synthesis of Example 50

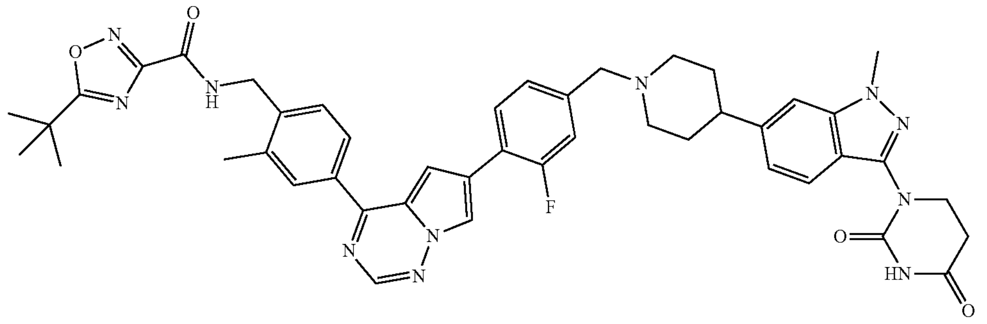 [SMILES: Cc1cc(-c2ncnn3cc(-c4ccc(CN5CCC(c6ccc7c(N8CCC(=O)NC8=O)nn(C)c7c6)CC5)cc4F)cc23)ccc1CNC(=O)c1noc(C(C)(C)C)n1]

5-(tert-butyl)-N-(4-(6-(4-((4-(3-(2,4-dioxotetrahydropyrimidin-1(2H)-yl)-1-methyl-1H-indazol-6-yl)piperidin-1-yl)methyl)-2-fluorophenyl)pyrrolo[2,1-f][1,2,4]triazin-4-yl)-2-methylbenzyl)-1,2,4-oxadiazole-3-carboxamide. $^{1}$H-NMR (400 MHz, DMSO-$d_6$) δ 10.54 (s, 1H), 9.54 (t, J=6.0 Hz, 1H), 8.68 (s, 1H), 8.63 (s, 1H), 8.20 (t, J=8.0 Hz, 1H), 8.02 (t, J=7.6 Hz, 2H), 7.66 (s, 1H), 7.60 (t, J=8.4 Hz, 2H), 7.49 (d, J=8.0 Hz, 2H), 7.39 (s, 1H), 7.08-7.00 (m, 1H), 4.57 (d, J=5.6 Hz, 2H), 4.43 (br s, 2H), 3.97 (s, 3H), 3.90 (t, J=6.4 Hz, 2H), 3.56-3.53 (m, 2H), 3.16-2.99 (m, 3H), 2.75 (t, J=6.4 Hz, 2H), 2.50 (s, 3H), 2.11-1.96 (m, 4H), 1.44 (s, 9H). LC-MS ($ES^+$): m/z 824.40 $[M+H]^+$.

Example 247

Example 247 was prepared following the synthesis of Example 50

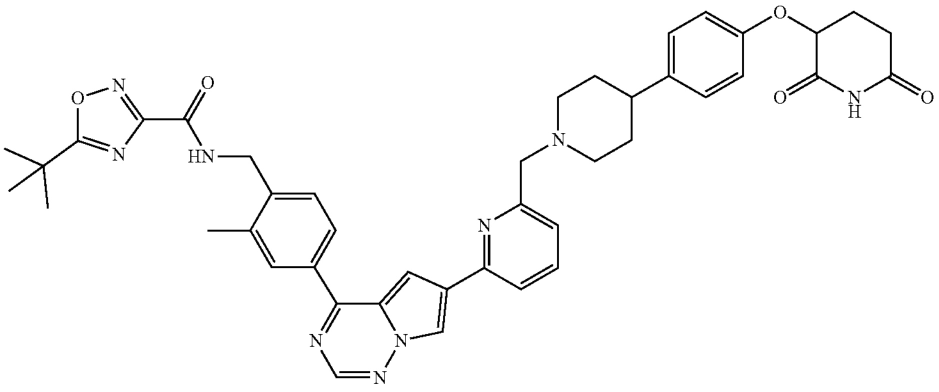 [SMILES: Cc1cc(-c2ncnn3cc(-c4cccc(CN5CCC(c6ccc(OC7CCC(=O)NC7=O)cc6)CC5)n4)cc23)ccc1CNC(=O)c1noc(C(C)(C)C)n1]

5-(tert-butyl)-N-(4-(6-(6-((4-(4-((2,6-dioxopiperidin-3-yl)oxy)phenyl)piperidin-1-yl)methyl)pyridin-2-yl)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.92 (s, 1H), 9.55 (t, J=5.6 Hz, 1H), 8.93 (s, 1H), 8.68 (s, 1H), 8.16 (d, J=8.0 Hz, 1H), 8.01 (t, J=13.0 Hz, 3H), 7.91 (s, 1H), 7.47 (t, J=8.8 Hz, 2H), 7.19 (d, J=11.6 Hz, 2H), 7.01 (d, J=8.4 Hz, 2H), 5.20-5.16 (m, 1H), 4.61 (s, 2H), 4.55 (d, J=5.2 Hz, 2H), 3.68 (s, 2H), 3.26 (s, 2H), 2.75-2.67 (m, 3H), 2.44 (s, 3H), 2.19-2.08 (m, 6H), 1.43 (s, 9H). LC-MS ($ES^-$): m/z 766.29 $[M-H]^-$.

Example 248

Example 248 was prepared following the synthesis of Example 50

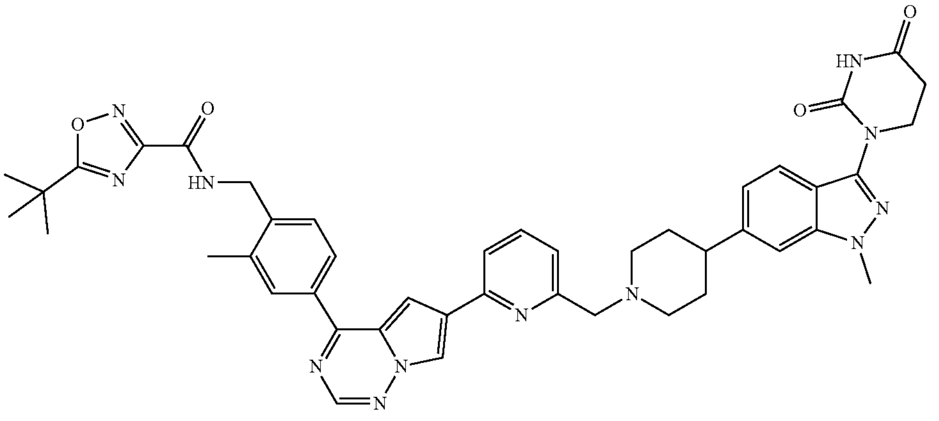 [SMILES: Cc1cc(-c2ncnn3cc(-c4cccc(CN5CCC(c6ccc7c(N8CCC(=O)NC8=O)nn(C)c7c6)CC5)n4)cc23)ccc1CNC(=O)c1noc(C(C)(C)C)n1]

5-(tert-butyl)-N-(4-(6-(6-((4-(3-(2,4-dioxotetrahydropyrimidin-1(2H)-yl)-1-methyl-1H-indazol-6-yl)piperidin-1-yl)methyl)pyridin-2-yl)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.53 (s, 1H), 9.51 (t, J=6.0 Hz, 1H), 8.65 (s, 1H), 8.13 (s, 1H), 8.02 (t, J=8.4 Hz, 3H), 7.89 (t, J=7.6 Hz, 1H), 7.76 (s, 1H), 7.56 (d, J=8.4 Hz, 1H), (m, 3H), 7.06 (d, J=8.4 Hz, 1H), 4.56 (d, J=5.6 Hz, 2H), 3.97 (s, 3H), 3.90 (t, J=6.8 Hz, 4H), 3.13 (s, 2H), 2.75 (t, J=6.4 Hz, 3H), 2.57-2.50 (m, 5H), 1.88 (s, 4H), 1.44 (s, 9H). LC-MS ($ES^+$): m/z 807.68 $[M+H]^+$.

Example 249. Synthesis of 5-tert-butyl-N-[[4-[6-[2-[4-[3-(2,4-dioxohexahydropyrimidin-1-yl)-1-methyl-indazol-6-yl]-1-piperidyl]ethyl]pyrrolo[2,1-f][1,2,4]triazin-4-yl]-2-methyl-phenyl]methyl]-1,2,4-oxadiazole-3-carboxamide
Step-1:
To a stirred solution of tert-butyl N-[[4-(6-bromopyrrolo[2,1-f][1,2,4]triazin-4-yl)-2-methyl-phenyl]methyl]carbamate (2 g, 4.79 mmol) and potassium vinyltrifluoroborate (1.41 g, 10.5 mmol) in water (6 mL) and dioxane (24 mL)
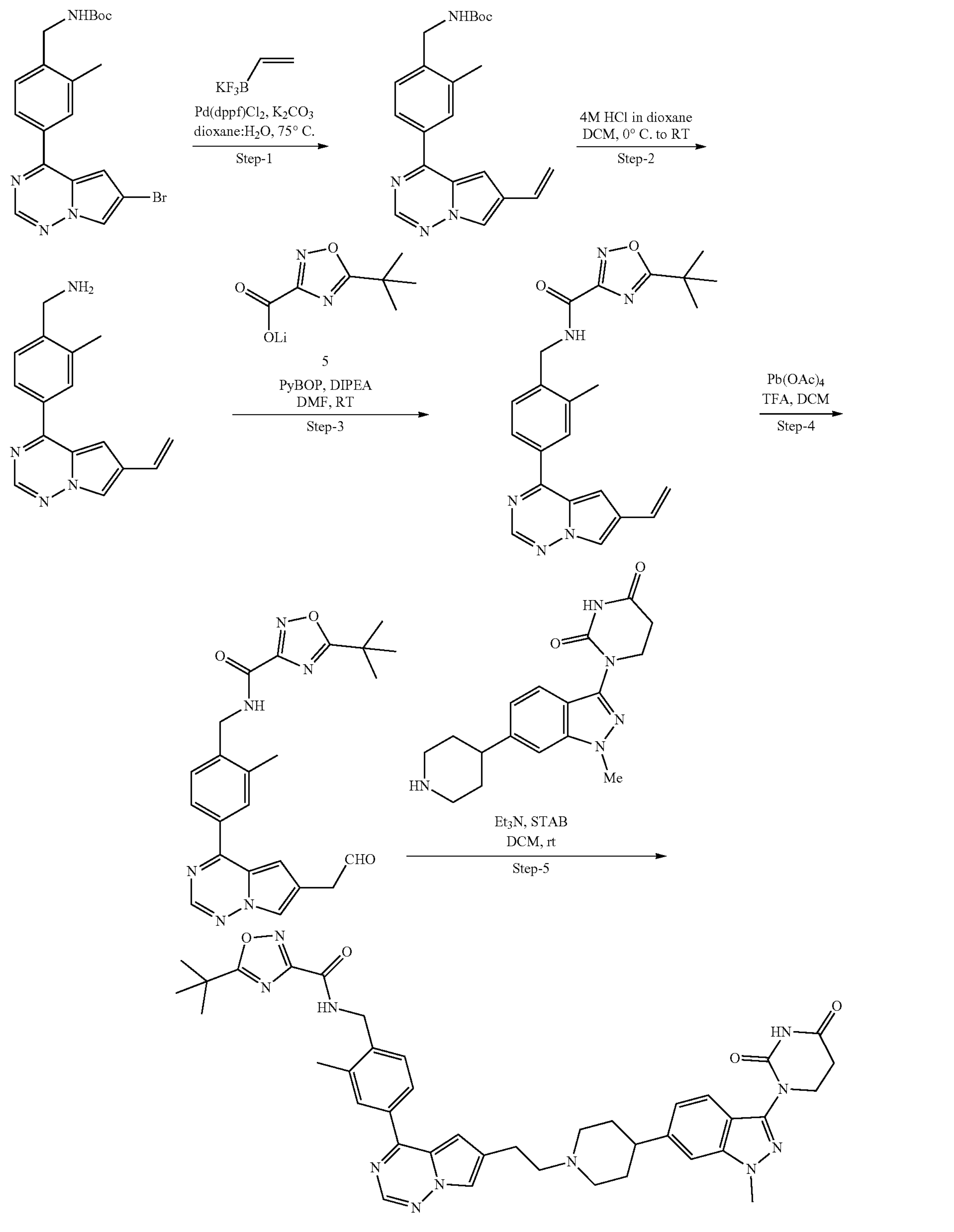

was added potassium carbonate (1.99 g, 14.4 mmol) at RT. The reaction mixture was purged with argon gas for 20 minutes, and Pd(dppf)$Cl_2$ (526 mg, 719 μmol) was added. The reaction mixture was purged with argon gas for additional 10 minutes, and it was stirred at 80° C. for 12 h. Subsequently, the reaction mixture was concentrated under reduced pressure, and the material was then partitioned between water and EtOAc. The organic layer was separated, washed with brine solution, dried over $Na_2SO_4$, and concentrated to afford crude product. The crude compound was purified by column chromatography using silica (100-200 mesh size) and 0-50% EtOAc/petroleum ether as eluent to afford the product tert-butyl N-[[2-methyl-4-(6-vinylpyrrolo[2,1-f][1,2,4]triazin-4-yl)phenyl]methyl]carbamate (1.5 g, 3.91 mmol, 81% yield) as an off white solid. Rf=0.3 (20%, EtOAc/petroleum ether). LC-MS ($ES^+$): m/z 365.38 $[M+H]^+$.

Step-2:

To a solution of tert-butyl N-[[2-methyl-4-(6-vinylpyrrolo[2,1-f][1,2,4]triazin-4-yl)phenyl]methyl]carbamate (1.5 g, 4.12 mmol) in DCM (6 mL) was added 4M HCl, in 1,4-dioxane (20.6 mL) at 0° C. The reaction mixture was slowly brought to RT and stirred for 1 h. The reaction mixture was concentrated in vacuo and the crude was triturated with n-pentane (2×10 mL) to afford the desired product [2-methyl-4-(6-vinylpyrrolo[2,1-f][1,2,4]triazin-4 yl)phenyl]methanamine (1.2 g, 3.91 mmol, 95% yield) as an pale yellow solid. LC-MS ($ES^+$): m/z 265.52 $[M+H]^+$.

Step-3:

To a stirred solution of [2-methyl-4-(6-vinylpyrrolo[2,1-f][1,2,4]triazin-4-yl)phenyl]methanamine (1.0 g, 3.32 mmol, HCl salt) and (5-tert-butyl-1,2,4-oxadiazole-3-carbonyl)oxylithium (878 mg, 4.99 mmol) in DMF (10 mL) was added DIPEA (579 μL, 3.32 mmol) followed by the addition of PyBOP (3.46 g, 6.65 mmol) at RT. The reaction mixture was stirred at RT for 1 h. Subsequently, the reaction mixture was diluted with ice-cold water (50 mL) and the obtained precipitate was filtered out and dried under vacuum to afford the crude product. The crude compound was purified by column chromatography using silica (100-200 mesh size) and 0-100% EtOAc/petroleum ether as eluent to afford the product 5-tert-butyl-N-[[2-methyl-4-(6-vinylpyrrolo[2,1-f][1,2,4]triazin-4-yl)phenyl]methyl]-1,2,4-oxadiazole-3-carboxamide (1.00 g, 2.28 mmol, 69% yield) as an pale yellow solid. LC-MS ($ES^+$): m/z 417.57 $[M+H]^+$.

Step-4:

To a solution of 5-tert-butyl-N-[[2-methyl-4-(6-vinylpyrrolo[2,1-f][1,2,4]triazin-4-yl)phenyl]methyl]-1,2,4-oxadiazole-3-carboxamide (0.2 g, 480 μmol) in DCM (3 mL) was added 2,2,2-trifluoroacetic acid (2.96 g, 26.0 mmol, 2.0 mL) at 0° C. The reaction mixture was stirred for five minutes, and then, lead (IV) acetate (213 mg, 480 μmol) was added to it. The reaction mixture was warmed slowly to room temperature and was stirred for 2 h. Subsequently, the reaction mixture was concentrated in vacuo to get the crude product, which was partitioned between water and DCM. The organic layer was separated, washed with a saturated solution of $NaHCO_3$, brine, and then dried over $Na_2SO_4$. The combined organic layer was concentrated to afford the desired product 5-tert-butyl-N-[[2-methyl-4-[6-(2-oxoethyl)pyrrolo[2,1-f][1,2,4]triazin-4-yl]phenyl]methyl]-1,2,4-oxadiazole-3-carboxamide (0.17 g, 279 μmol, 58% yield) as light red solid. The crude product was used for the next step without further purification. LC-MS ($ES^+$): m/z 433.57 $[M+H]^+$.

Step-5:

To a stirred solution of 1-[1-methyl-6-(4-piperidyl)indazol-3-yl]hexahydropyrimidine-2,4-dione (173.51 mg, 393.09 μmol, TFA salt) in DCM (4 mL) was added triethylamine (397.76 mg, 3.93 mmol, 547.89 μL) at 0° C. and stirred for 10 minutes before adding 5-tert-butyl-N-[[2-methyl-4-[6-(2-oxoethyl)pyrrolo[2,1-f][1,2,4]triazin-4-yl]phenyl]methyl]-1,2,4-oxadiazole-3-carboxamide (0.17 g, 393.09 μmol). The reaction mixture was warmed to room temperature and stirred for 5 h. After which, the reaction mixture was cooled to 0° C., and sodium triacetoxyborohydride (499.87 mg, 2.36 mmol) was added. The reaction mixture was warmed to room temperature and stirred for another 11 h. The reaction mixture was quenched with water (2 mL) and extracted with 10% MeOH-DCM solution (3×10 mL). The combined organic layer was washed with brine solution (5 mL), dried over anhydrous sodium sulfate, and concentrated under reduced pressure to get the crude product. The crude product was purified by reverse phase preparative HPLC to afford the product 5-tert-butyl-N-[[4-[6-[2-[4-[3-(2,4-dioxohexahydropyrimidin-1-yl)-1-methyl-indazol-6-yl]-1-piperidyl]ethyl]pyrrolo[2,1-f][1,2,4]triazin-4-yl]-2-methyl-phenyl]methyl]-1,2,4-oxadiazole-3-carboxamide (95.6 mg, 119.88 μmol, 30.50% yield) as yellow solid.

Prep-HPLC Method:

Column/dimensions: sunfire C18 (19*250*5μ)

Mobile phase A: 0.1% FA in water (aq)

Mobile phase B: Acetonitrile (ORG)

Gradient (Time/% B): 0/10, 3/10, 12/38, 13.5/38, 13.51/100, 17/100, 17.1/10, 20/10

Flow rate: 16 mL/min

Solubility: Acetonitrile+THF+water $^1$H-NMR (400 MHz, DMSO-$d_6$) δ 10.51 (s, 1H), 9.49 (t, J=5.8 Hz, 1H), 8.54 (s, 1H), 8.15 (s, 1H), 8.10 (s, 1H), 7.95 (d, J=6.4 Hz, 2H), 7.55 (d, J=8.4 Hz, 1H), 7.45 (d, J=8.4 Hz, 2H), 7.14 (s, 1H), 7.04 (d, J=8.8 Hz, 1H), 4.55 (d, J=5.6 Hz, 2H), 3.96 (s, 3H), 3.90 (t, J=6.8 Hz, 2H), 3.11 (d, J=10.8 Hz, 2H), 2.92-2.91 (m, 2H), 2.76-2.68 (m, 5H), 2.46 (s, 3H), 2.14 (t, J=10.4 Hz, 2H), 1.84-1.75 (m, 4H), 1.43 (s, 9H). LC-MS ($ES^+$): m/z 744.41 $[M+H]^+$.

Example 250

Example 250 was prepared following the synthesis of Example 249

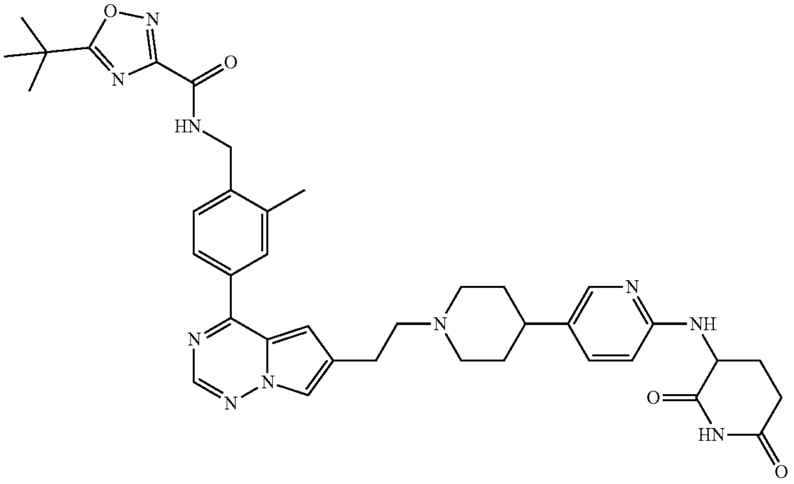 [SMILES: Cc1cc(-c2ncnn3cc(CCN4CCC(c5ccc(NC6CCC(=O)NC6=O)nc5)CC4)cc23)ccc1CNC(=O)c1noc(C(C)(C)C)n1]

5-(tert-butyl)-N-(4-(6-(2-(4-(6-((2,6-dioxopiperidin-3-yl)amino)pyridin-3-yl)piperidin-1-yl)ethyl)pyrrolo[2,1-f][1,2,4]triazin-4-yl)-2-methylbenzyl)-1,2,4-oxadiazole-3-carboxamide.

Prep. HPLC condition:

Column/dimensions: X-SELECT C18 (19*250, 5 um)

Mobile phase A: 0.1% TFA in water

Mobile phase B: 100% ACN

Gradient (Time/% B): 0/10, 2/10, 10/40, 12/40, 12.1/100.

Flow rate: 18 mL/min.

Solubility: water+THF+CAN $^1$H-NMR (400 MHz, DMSO-$d_6$) δ 10.96 (s, 1H), 9.54 (t, J=6.0 Hz, 1H), 9.32 (br s, 1H), 8.61 (s, 1H), 8.18 (d, J=6.0 Hz, 1H), 7.94 (d, J=7.6 Hz, 2H), 7.88-7.82 (m, 1H), 7.63 (br s, 1H), 7.46 (d, J=8.0 Hz, 1H), 7.20 (s, 1H), 7.09 (d, J=9.2 Hz, 1H), 4.71 (br s, 1H), 4.56 (d, J=6.0 Hz, 2H), 3.52-3.50 (m, 4H), 3.20-3.18 (m, 2H), 3.07 (d, J=11.6 Hz, 2H), 2.80-2.54 (m, 3H), 2.47 (s, 3H), 2.12-2.01 (m, 4H), 1.82 (t, J=12.2 Hz, 2H), 1.47 (s, 9H). LC-MS (ES$^+$): m/z 705.45 [M+H]$^+$.

Example 251

Example 251 was prepared following the synthesis of Example 249

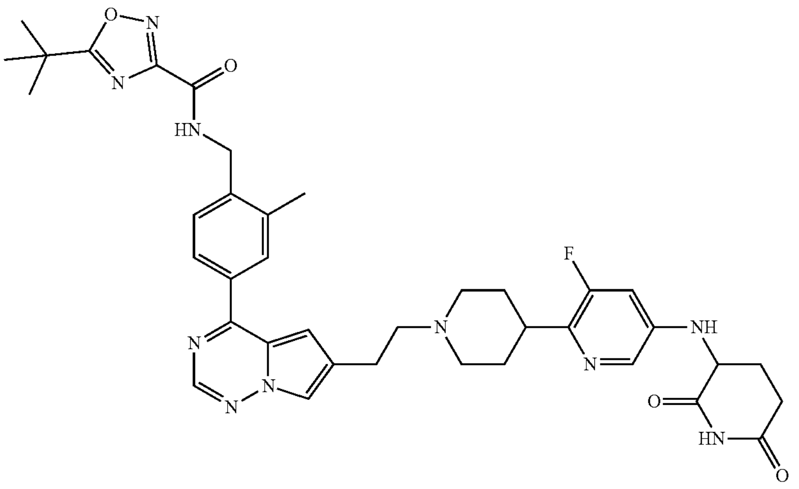 [SMILES: Cc1cc(-c2ncnn3cc(CCN4CCC(c5ncc(NC6CCC(=O)NC6=O)cc5F)CC4)cc23)ccc1CNC(=O)c1noc(C(C)(C)C)n1]

5-(tert-butyl)-N-(4-(6-(2-(4-(5-((2,6-dioxopiperidin-3-yl)amino)-3-fluoropyridin-2-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: X-select 18 C18(19*150, 5 um)
Mobile phase A: 0.1% TFA in water
Mobile phase B: 100% ACN
Gradient (Time/% B): 0/20, 2/10, 10/40 15/40 16/100 17/100 18/100
Flow rate: 16 mL/min
Solubility: $ACN+H_2O$ $^1$H-NMR (400 MHz, DMSO-$d_6$) δ 10.87 (s, 1H), 9.53 (t, J=6.0 Hz, 1H), 8.60 (s, 1H), 8.18 (s, 1H), 7.94 (d, J=7.6 Hz, 2H), 7.87 (s, 1H), 7.46 (d, J=8.0 Hz, 1H), 7.21 (d, J=9.2 Hz, 1H), 6.92 (dd, J=2.0, 12.8 Hz, 1H), 6.43 (br s, 1H), 4.54 (d, J=5.6 Hz, 2H), 4.39 (d, J=6.8 Hz, 1H), 3.67-3.64 (m, 2H), 3.55-3.47 (m, 2H), 3.22-3.12 (m, 5H), 2.72-2.68 (m, 1H), 2.57-2.50 (m, 1H), 2.47 (s, 3H), 2.08-1.90 (m, 6H), 1.43 (s, 9H). LC-MS ($ES^+$): m/z 723.27 $[M+H]^+$.

Example 252

Example 252 was prepared following the synthesis of Example 249

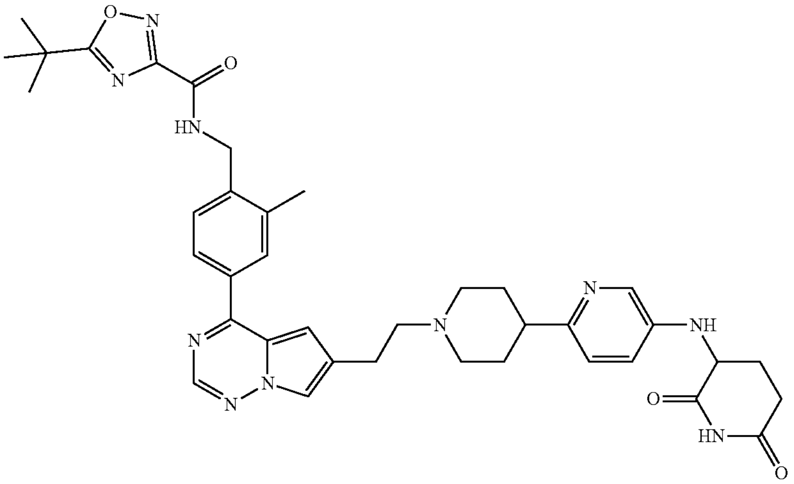 [SMILES: Cc1cc(-c2ncnn3cc(CCN4CCC(c5ccc(NC6CCC(=O)NC6=O)cn5)CC4)cc23)ccc1CNC(=O)c1noc(C(C)(C)C)n1]

5-(tert-butyl)-N-(4-(6-(2-(4-(5-((2,6-dioxopiperidin-3-yl)amino)pyridin-2-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Mobile Phase (A): 0.1% TFA IN WATER
Mobile Phase (B): ACN
Flow Rate: 17 mL/min
Column: X-SELECT C18 5 μm (19×150 mm)
Gradient Time % B: 0/15, 2/15, 10/35, 13/35 13.1/98, 15/98, 15.1/10, 17/10
Solubility: THF+ACN+water $^1$H-NMR (400 MHz, DMSO-$d_6$) δ 10.96 (s, 1H), 9.54 (t, J=6.0 Hz, 1H), 9.33 (br s, 1H), 8.61 (s, 1H), 8.18 (s, 1H), 8.03 (d, J=2.0 Hz, 1H), 7.94 (d, J=7.2 Hz, 2H), 7.46 (d, J=8.4, 2H), 7.36 (br s, 1H), 7.21 (d, J=7.6 Hz, 1H), 4.55 (d, J=6.0 Hz, 2H), 4.48-4.46 (m, 1H), 3.71-3.68 (m, 2H), 3.52-3.49 (m, 2H), 3.21-3.06 (m, 5H), 2.74-2.59 (m, 2H), 2.47 (s, 3H), 2.20-2.10 (m, 3H), 2.07-1.82 (m, 3H), 1.43 (s, 9H). LC-MS ($ES^+$): m/z 705.29 $[M+H]^+$.

Example 253

Example 253 was prepared following the synthesis of Example 249

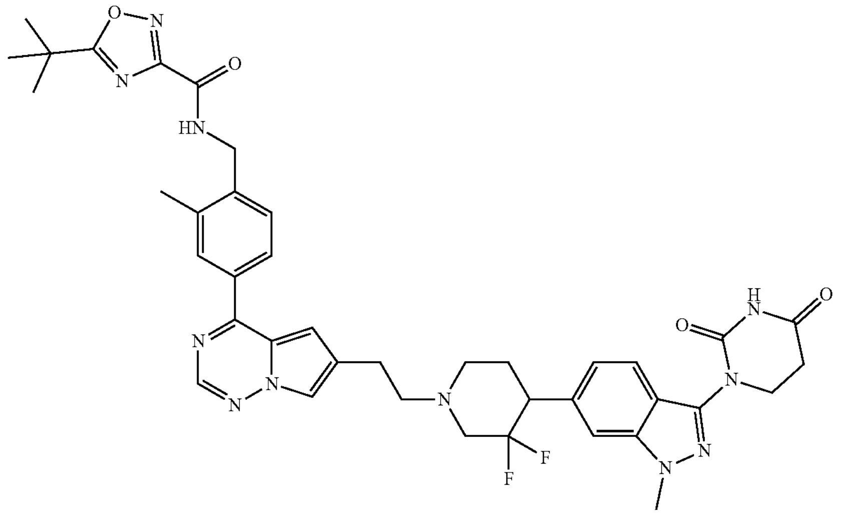 [SMILES: Cc1cc(-c2ncnn3cc(CCN4CCC(c5ccc6c(N7CCC(=O)NC7=O)nn(C)c6c5)C(F)(F)C4)cc23)ccc1CNC(=O)c1noc(C(C)(C)C)n1]

5-(tert-butyl)-N-(4-(6-(2-(4-(3-(2,4-dioxotetrahydropyrimidin-1(2H)-yl)-1-methyl-1H-indazol-6-yl)-3,3-difluoropiperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: kinetex C18 (19*250, 5 um)

Mobile phase A: 5 MM AMMONIUM ACETATE IN water

Mobile phase B: Acetonitrile

Gradient (Time/% B) 0/25, 2/25, 10/60, 16/60, 16.10/100, 19/100, 19.10/25, 22/25

Flow rate: 18 mL/min.

Solubility: THF+ACN+water $^1$H-NMR (400 MHz, DMSO-$d_6$) δ 10.55 (s, 111), 9.51 (t, J=5.8 Hz, 1H), 8.55 (s, 111), 8.11 (s, 1H), 7.96 (d, J=6.4 Hz, 2H), 7.60-7.55 (m, 2H), 7.45 (d, J=8.4 Hz, 1H), 7.17 (s, 1H), 7.08 (d, J=8.4 Hz, 1H), 4.54 (d, J=5.6 Hz, 2H), 3.98 (s, 3H), 3.92 (t, J=6.6 Hz, 2H), 3.31-3.12 (m, 3H), 3.01-2.92 (m, 2H), 2.82-2.74 (m, 4H), 2.54-2.50 (m, 1H), 2.46 (s, 3H), 2.32-2.23 (m, 2H), 1.87-1.85 (m, 1H), 1.43 (s, 9H). LC-MS ($ES^+$): m/z 780.35 $[M+H]^+$.

Example 254

Example 254 was prepared following the synthesis of Example 249

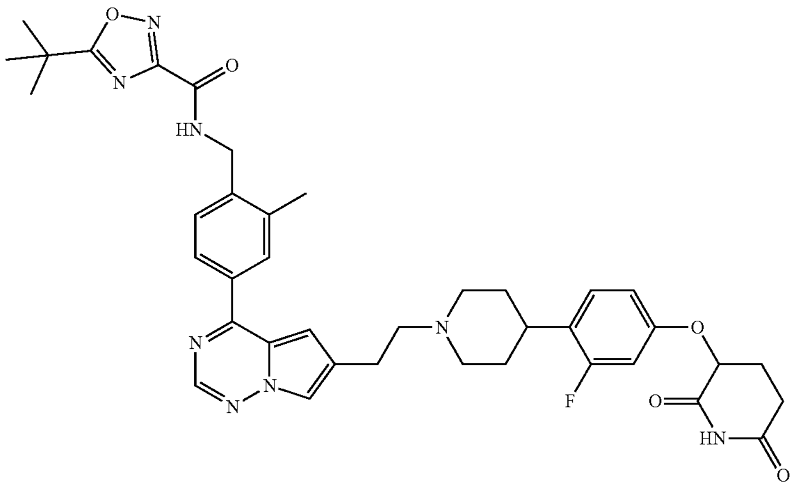 [SMILES: Cc1cc(-c2ncnn3cc(CCN4CCC(c5ccc(OC6CCC(=O)NC6=O)cc5F)CC4)cc23)ccc1CNC(=O)c1noc(C(C)(C)C)n1]

5-(tert-butyl)-N-(4-(6-(2-(4-(4-((2,6-dioxopiperidin-3-yl)oxy)-2-fluorophenyl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: X-Select C18 (19*250*5 um)

Mobile phase A: 0.05% TFA in water

Mobile phase B: ACN (org)

Gradient (Time/% B): 0/10, 2.50/15, 16.10/57, 16.20/98, 18.50/98, 18.60/10, 20.50/10

Flow rate: 17 mL/min

Solubility: ACN+THF $^1$H-NMR (400 MHz, DMSO-$d_6$) δ 10.92 (s, 1H), 9.54 (t, J=5.8 Hz, 1H), 8.60 (s, 1H), 8.19 (d, J=9.2 Hz, 1H), 7.98-7.93 (m, 2H), 7.46 (d, J=8.0 Hz, 1H), 7.42-7.15 (m, 2H), 6.95 (d, J=6.4 Hz, 1H), 6.86 (d, J=2.4 Hz, 1H), 5.23-5.22 (m, 1H), 4.54 (d, J=4.8 Hz, 2H), 3.65-3.51 (m, 2H), 3.49-3.48 (m, 2H), 3.20-3.13 (m, 5H), 2.70-2.62 (m, 2H), 2.47 (s, 3H), 2.20-2.11 (m, 2H), 2.07-1.90 (m, 4H), 1.43 (s, 9H). LC-MS (ES$^+$): m/z 780.35 [M+H]$^+$.

Example 255

Example 255 was prepared following the synthesis of Example 249

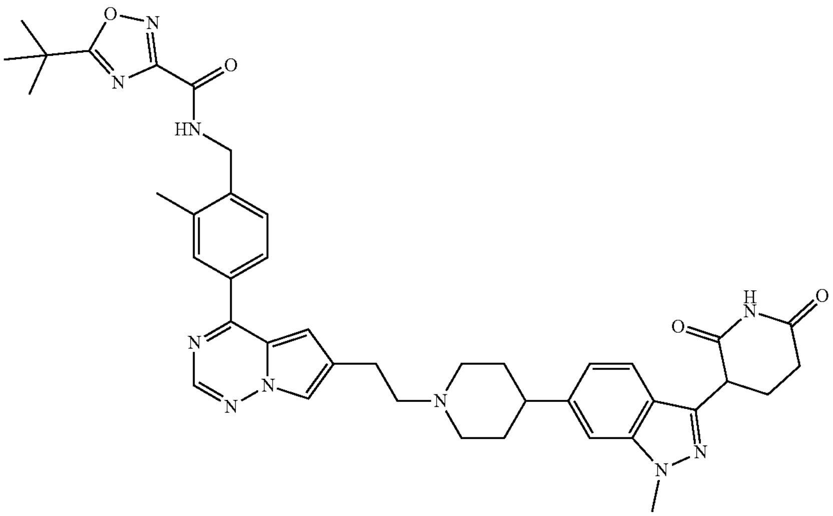 [SMILES: Cc1cc(-c2ncnn3cc(CCN4CCC(c5ccc6c(C7CCC(=O)NC7=O)nn(C)c6c5)CC4)cc23)ccc1CNC(=O)c1noc(C(C)(C)C)n1]

5-(tert-butyl)-N-(4-(6-(2-(4-(3-(2,6-dioxopiperidin-3-yl)-1-methyl-1H-indazol-6-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: Sunfire C18(19*150, 5 um)

Mobile phase A: 0.1% TFA in water

Mobile phase B: Acetonitrile

Gradient (Time/% B): 0/10, 3/10, 10/35, 18/35, 18.10/100, 22/100, 22.1/10, 24/20.

Flow rate: 18 mL/min

Solubility: THF+ACN+water $^1$H-NMR (400 MHz, DMSO-$d_6$) δ 10.84 (s, 1H), 9.50 (t, J=6.2 Hz, 1H), 8.55 (s, 1H), 8.11 (d, J=1.2 Hz, 1H), 7.95-7.97 (m, 2H), 7.60 (d, J=8.4 Hz, 1H), 7.45-7.47 (m, 2H), 7.14 (s, 1H), 7.04 (d, J=7.6 Hz, 1H), 4.44 (d, J=6.2 Hz, 2H), 4.33-4.31 (m, 1H), 3.96 (s, 3H), 3.12-3.32 (m, 2H), 2.91-2.94 (m, 2H), 2.50-2.68 (m, 5H), 2.42 (s, 3H), 2.32-2.31 (m, 1H), 1.75-1.81 (m, 3H), 1.43-1.43 (m, 4H), 1.45 (s, 9H). LC-MS (ES$^+$): m/z 743.22 [M+H]$^+$.

Example 256

Example 256 was prepared following the synthesis of Example 249

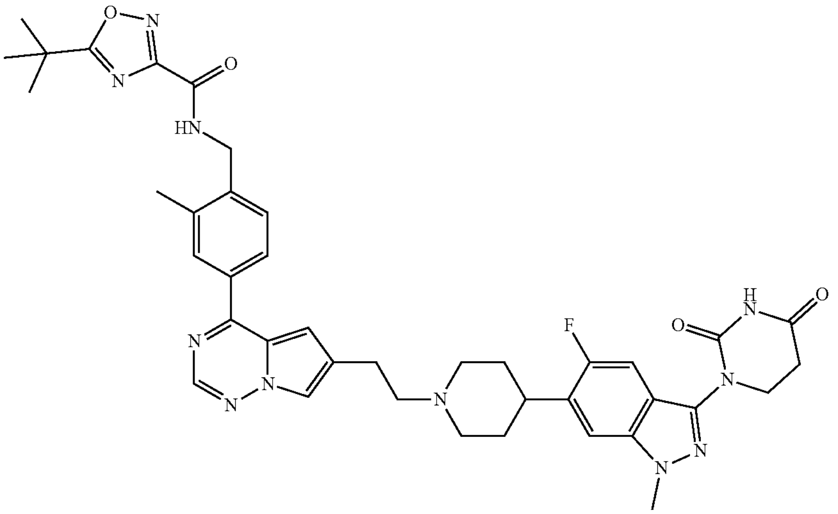 [SMILES: Cc1cc(-c2ncnn3cc(CCN4CCC(c5cc6c(cc5F)c(N5CCC(=O)NC5=O)nn6C)CC4)cc23)ccc1CNC(=O)c1noc(C(C)(C)C)n1]

5-(tert-butyl)-N-(4-(6-(2-(4-(3-(2,4-dioxotetrahydropyrimidin-1(2H)-yl)-5-fluoro-1-methyl-1H-indazol-6-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: Sunfire C18 (19*250*5μ)

Mobile phase A: 0.1% TFA in water

Mobile phase B: Acetonitrile

Gradient (Time/% B): 0/10, 2/10, 15/60, 16/100, 20/100, 20.1/10, 23/10

Flow rate: 16 mL/min

Solubility: Acetonitrile+water $^1$H-NMR (400 MHz, DMSO-$d_6$) δ 10.54 (s, 1H), 9.54 (t, J=6.0 Hz, 1H), 8.61 (s, 1H), 8.20 (d, J=9.6 Hz, 1H), 7.95 (d, J=7.6 Hz, 2H), 7.48-7.40 (m, 3H), 7.26-7.22 (m, 1H), 4.55 (d, J=6.0 Hz, 2H), 4.00 (s, 3H), 3.90 (t, J=6.6 Hz, 2H), 3.73-3.70 (m, 2H), 3.53-3.52 (m, 2H), 3.23-3.16 (m, 5H), 2.75 (t, J=6.8 Hz, 2H), 2.47 (s, 3H), 2.11-2.01 (m, 4H), 1.43 (s, 9H). LC-MS (ES$^+$): m/z 762.36 $[M+H]^+$.

Example 257

Example 257 was prepared following the synthesis of Example 249

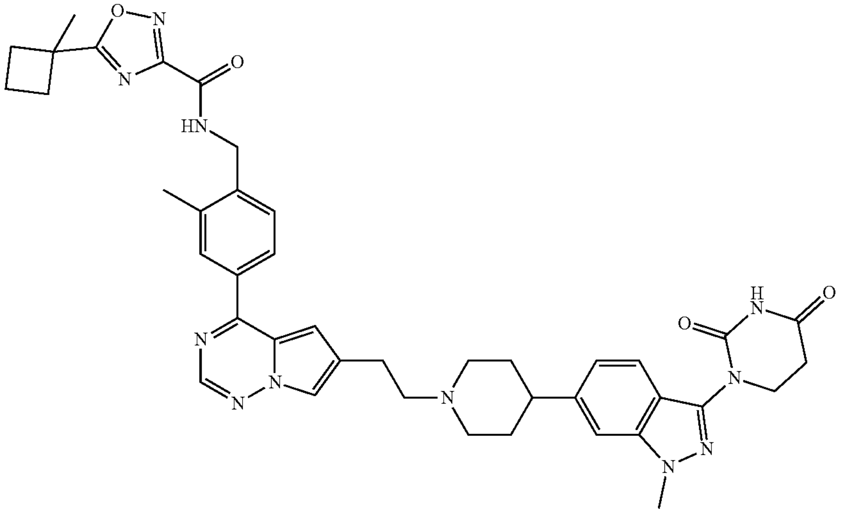 [SMILES: Cc1cc(-c2ncnn3cc(CCN4CCC(c5ccc6c(N7CCC(=O)NC7=O)nn(C)c6c5)CC4)cc23)ccc1CNC(=O)c1noc(C2(C)CCC2)n1]

N-(4-(6-(2-(4-(3-(2,4-dioxotetrahydropyrimidin-1(2H)-yl)-1-methyl-1H-indazol-6-yl)piperidin-1-yl)ethyl)pyrrolo[2,1-f][1,2,4]triazin-4-yl)-2-methylbenzyl)-5-(1-methylcyclobutyl)-1,2,4-oxadiazole-3-carboxamide.

Prep-HPLC Method:

Column/dimensions: X-Select C18 (19*250, 5 m)

Mobile phase A: 5 mM AA in water

Mobile phase B: 100% Acetonitrile

Gradient (Time/% B): 0/15, 2/15, 10/55, 19/55, 19.1/100.

Flow rate: 18 mL/min

Diluent: Acetonitrile+water+THF $^1$H-NMR (400 MHz, DMSO-$d_6$) δ 10.55 (s, 1H), 9.51 (t, J=6.0 Hz, 1H), 8.54 (s, 1H), 8.10 (s, 1H), 7.95 (d, J=6.8 Hz, 2H), 7.54 (d, J=8.4 Hz, 1H), 7.46 (d, J=8.4 Hz, 2H), 7.14 (s, 1H), 7.04 (dd, J=1.0, 8.6 Hz, 1H), 4.54 (d, J=5.6 Hz, 2H), 3.96 (s, 3H), 3.90 (t, J=6.6 Hz, 2H), 3.12-3.09 (m, 2H), 2.92-2.88 (m, 2H), 2.76-2.50 (m, 7H), 2.46 (s, 3H), 2.15-2.09 (m, 4H), 2.08-1.90 (m, 1H), 1.90 (s, 2H), 1.80-1.75 (m, 3H), 1.62 (s, 3H). LC-MS (ES$^-$): m/z 754.10 [M−H]$^-$ Example 258

Example 258 was prepared following the synthesis of Example 249

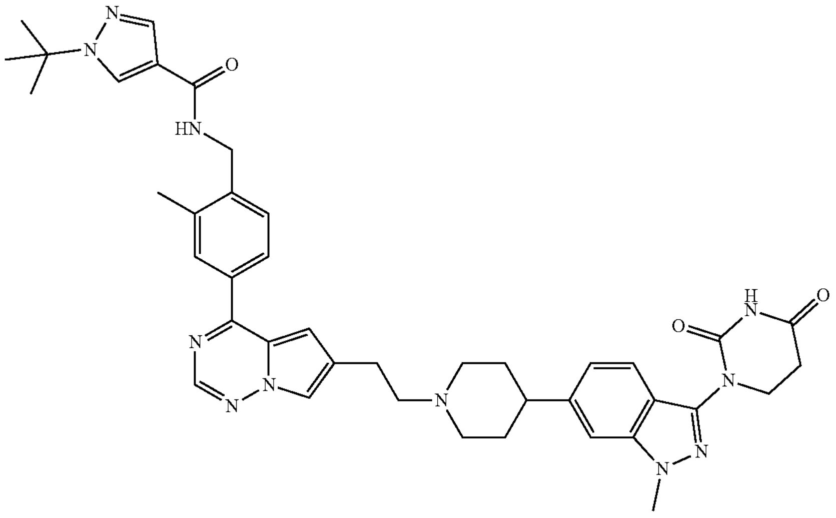

1-(tert-butyl)-N-(4-(6-(2-(4-(3-(2,4-dioxotetrahydropyrimidin-1(2H)-yl)-1-methyl-1H-indazol-6-yl)piperidin-1-yl)ethyl)pyrrolo[2,1-f][1,2,4]triazin-4-yl)-2-methylbenzyl)-1H-pyrazole-4-carboxamide.

Prep-HPLC Method:

Column/dimensions: XBridge—C18 (19*250*5 um)

Mobile phase A: 5 mM ABC in water

Mobile phase B: Acetonitrile

Gradient (Time/% B): 0/15, 2/15, 10/35, 20/40, 22/65, 22.1/100, 24/100, 24.1/15, 26/15

Flow rate: 17 mL/min

Solubility: Acetonitrile+water+THF $^1$H-NMR (400 MHz, DMSO-$d_6$) δ 10.54 (s, 1H), 8.54-8.52 (m, 2H), 8.33 (s, 1H), 8.10-8.09 (m, 1H), 7.96-7.93 (m, 3H), 7.54 (d, J=8.4 Hz, 1H), 7.44 (t, J=4.0 Hz, 2H), 7.13 (s, 1H), 7.04 (d, J=7.6 Hz, 1H), 4.49 (d, J=5.6 Hz, 2H), 3.96 (s, 3H), 3.90 (t, J=6.6 Hz, 2H), 3.13-3.09 (m, 2H), 2.94-2.90 (m, 2H), 2.74 (t, J=6.6 Hz, 2H), 2.69-2.65 (m, 3H), 2.44 (s, 3H), 2.14-2.09 (m, 2H), 1.83-1.72 (m, 4H), 1.53 (s, 9H). LC-MS (ES$^-$): m/z 740.12 [M−H]$^-$ Example 259

Example 259 was prepared following the synthesis of Example 249

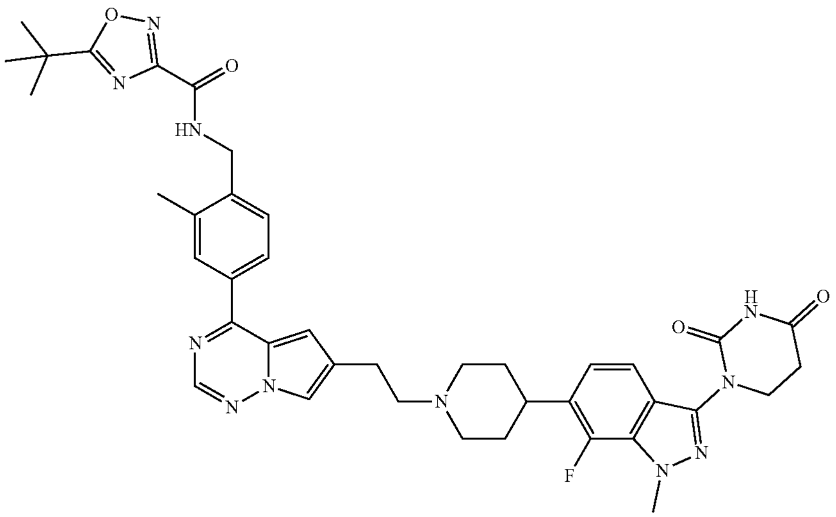 [SMILES: Cc1cc(-c2ncnn3cc(CCN4CCC(c5ccc6c(N7CCC(=O)NC7=O)nn(C)c6c5F)CC4)cc23)ccc1CNC(=O)c1noc(C(C)(C)C)n1]

5-(tert-butyl)-N-(4-(6-(2-(4-(3-(2,4-dioxotetrahydropyrimidin-1(2H)-yl)-7-fluoro-1-methyl-1H-indazol-6-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: X-Select C18 (19*250, 5 um)

Mobile phase A: 0.05% TFA in water

Mobile phase B: ACN

Gradient (Time/% B): 0/10, 2/10, 14.90/59.1, 15/98, 17/98, 17.10/10, 19/10

Flow rate: 17 mL/min.

Solubility: THF+ACN

LCMS ($ES^-$): m/z 760.05 $[M-H]^-$ $^1$H-NMR (400 MHz, DMSO-$d_6$) δ 10.64 (s, 1H), 9.54 (t, J=6.0 Hz, 1H), 9.24 (br s, 1H), 8.61 (s, 1H), 8.20 (s, 1H), 7.95 (d, J=8.4 Hz, 2H), 7.47-7.45 (m, 2H), 7.22 (s, 1H), 6.99-6.95 (m, 1H), 4.55 (d, J=6.0 Hz, 2H), 4.11 (s, 3H), 3.91 (t, J=6.6 Hz, 2H), 3.72-3.70 (m, 2H), 3.42-3.12 (m, 7H), 2.75 (t, J=6.6 Hz, 2H), 2.47 (s, 3H), 2.20-1.80 (m, 4H), 1.43 (s, 9H). LC-MS ($ES^-$): m/z 760.05 $[M-H]^-$

Example 260

Example 260 was prepared following the synthesis of Example 249

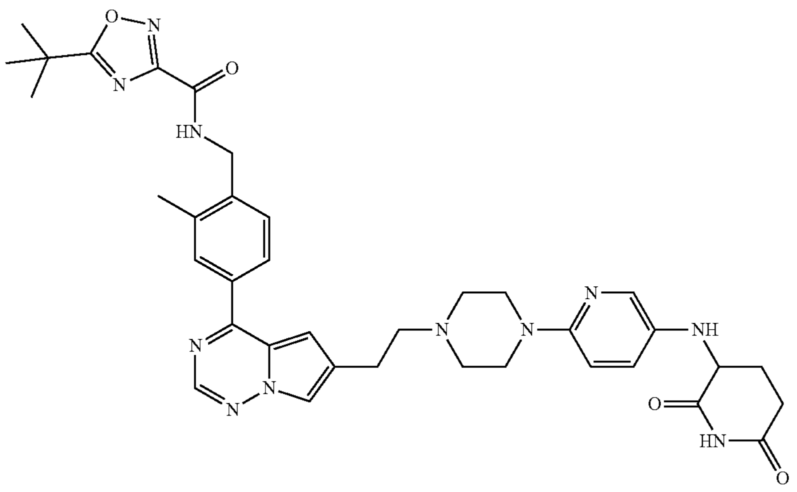 [SMILES: Cc1cc(-c2ncnn3cc(CCN4CCN(c5ccc(NC6CCC(=O)NC6=O)cn5)CC4)cc23)ccc1CNC(=O)c1noc(C(C)(C)C)n1]

5-(tert-butyl)-N-(4-(6-(2-(4-(5-((2,6-dioxopiperidin-3-yl)amino)pyridin-2-yl)piperazin-1-yl)ethyl)pyrrolo[2,1-f][1,2,4]triazin-4-yl)-2-methylbenzyl)-1,2,4-oxadiazole-3-carboxamide.

Prep-HPLC Method:
- Column/dimensions: Sunfire C18 (19*150, 5 um)
- Mobile phase A: 0.05% TFA in water
- Mobile phase B: 100% Acetonitrile
- Gradient (Time/% B): 0/10, 2/10, 10.4/50, 10.5/98, 12.5/98, 12.6/10, 14.6/10
- Flow rate: 17 mL/min.
- Solubility: ACN+water+THF $^1$H-NMR (400 MHz, DMSO-$d_6$) δ 10.84 (s, 1H), 9.56 (br s, 1H), 9.54 (t, J=6.0 Hz, 1H), 8.60 (s, 1H), 8.17 (s, 1H), 7.94 (d, J=7.2 Hz, 2H), 7.68 (d, J=2.4 Hz, 1H), 7.46 (d, J=8.0 Hz, 1H), 7.19 (s, 2H), 6.89 (d, J=8.8 Hz, 1H), 4.55 (d, J=6.0 Hz, 2H), 4.29-4.26 (m, 1H), 4.14-4.11 (m, 2H), 3.65-3.62 (m, 2H), 3.54-3.50 (m, 2H), 3.20-3.04 (m, 6H), 2.73-2.67 (m, 1H), 2.62-2.57 (m, 1H), 2.46 (s, 3H), 2.12-2.07 (m, 1H), 1.92-1.82 (m, 1H), 1.43 (s, 9H). LC-MS (ES$^-$): m/z 704.08 [M−H]$^-$

Example 261

Example 261 was prepared following the synthesis of Example 249

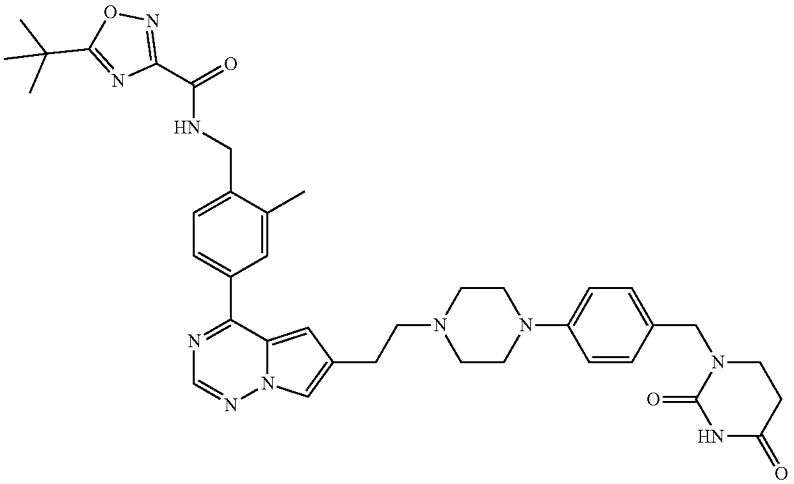 [SMILES: Cc1cc(-c2ncnn3cc(CCN4CCN(c5ccc(CN6CCC(=O)NC6=O)cc5)CC4)cc23)ccc1CNC(=O)c1noc(C(C)(C)C)n1]

5-(tert-butyl)-N-(4-(6-(2-(4-(4-((2,4-dioxotetrahydropyrimidin-1(2H)-yl)methyl)phenyl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:
- Column/dimensions: LUNA C 18(21*250*5 um)
- Mobile phase: 0.05% TFA in water
- Mobile phase B: ACN
- Gradient (Time/% B): 0/10, 2.5/25, 15.25/54, 15.35/98, 17.35/98, 17.45/10, 19.45/10
- Flow rate: 17 mL/min
- Solubility: ACN+water $^1$H-NMR (400 MHz, DMSO-$d_6$) δ 10.20 (s, 1H), 9.52 (t, J=6.0 Hz, 1H), 9.23 (br s, 1H), 8.61 (s, 1H), 8.18 (s, 1H), 7.94 (d, J=7.6 Hz, 2H), 7.46 (d, J=8.0 Hz, 1H), 7.33-7.21 (m, 5H), 4.55 (d, J=6.0 Hz, 2H), 4.48 (s, 2H), 3.68-3.65 (m, 2H), 3.57-3.47 (m, 2H), 3.27 (t, J=6.4 Hz, 2H), 3.20-3.06 (m, 4H), 2.86-2.80 (m, 1H), 2.51-2.49 (m, 2H), 2.47 (s, 3H), 2.15-2.04 (m, 2H), 1.86-1.78 (m, 2H), 1.43 (s, 9H). LC-MS (ES$^+$): m/z 704.45 [M+H]$^+$.

Example 262

Example 262 was prepared following the synthesis of Example 249

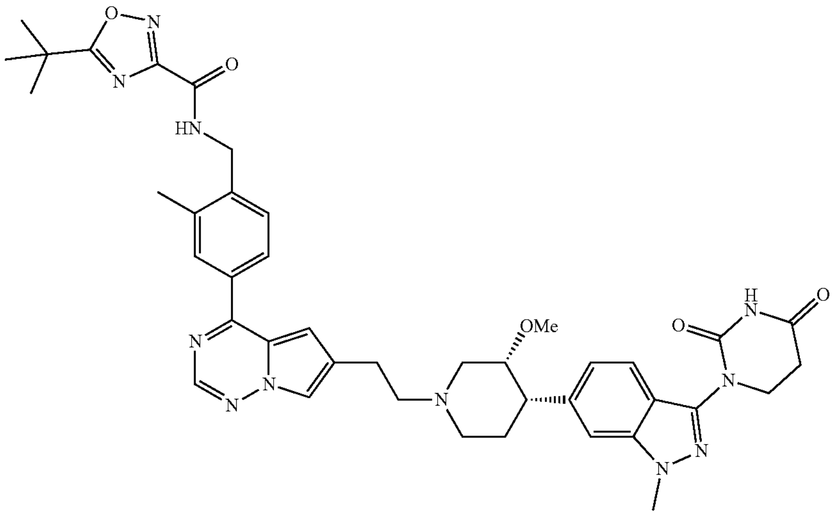 [SMILES: CO[C@H]1CN(CCc2cc3c(-c4ccc(CNC(=O)c5noc(C(C)(C)C)n5)c(C)c4)ncnn3c2)CC[C@H]1c1ccc2c(N3CCC(=O)NC3=O)nn(C)c2c1]

5-(tert-butyl)-N-(4-(6-(2-((3R,4S)-4-(3-(2,4-dioxotetrahydropyrimidin-1(2H)-yl)-1-methyl-1H-indazol-6-yl)-3-methoxypiperidin-1-yl)ethyl)pyrrolo[2,1-f][1,2,4]triazin-4-yl)-2-methylbenzyl)-1,2,4-oxadiazole-3-carboxamide. (Stereochemistry was arbitrarily assigned)

Prep-HPLC Method:
- Column/dimensions: KINETEX-C18 (19*250 um)
- Mobile phase A: 0.05% TFA in water
- Mobile phase B: 100% Acetonitrile
- Gradient (Time/% B): 0/10, 2/10, 16/63.10, 16.1/98, 18.1/98, 18.2/10, 20.20/10
- Flow rate: 17 mL/min
- Solubility: Acetonitrile+water $^1$H-NMR (400 MHz, DMSO-$d_6$) δ 10.52 (s, 1H), 9.54 (t, J=6.0 Hz, 1H), 9.25 (br s, 1H), 8.61 (s, 1H), 8.18 (s, 1H), 7.96 (s, 1H), 7.94 (s, 1H), 7.60 (d, J=8.4 Hz, 1H), 7.46 (d, J=8.0 Hz, 1H), 7.42 (s, 1H), 7.21 (s, 1H), 7.13 (d, J=7.6 Hz, 1H), 4.56 (d, J=5.6 Hz, 2H), 3.98 (s, 3H), 3.96-3.90 (m, 4H), 3.62-3.50 (m, 3H), 3.27-3.18 (m, 5H), 3.13 (s, 3H), 2.76 (t, J=6.8 Hz, 2H), 2.41 (s, 3H), 2.03-2.00 (m, 1H), 1.44 (s, 9H). LC-MS (ES$^+$): m/z 774.70 [M+H]$^+$.

Example 263

Example 263 was prepared following the synthesis of Example 249

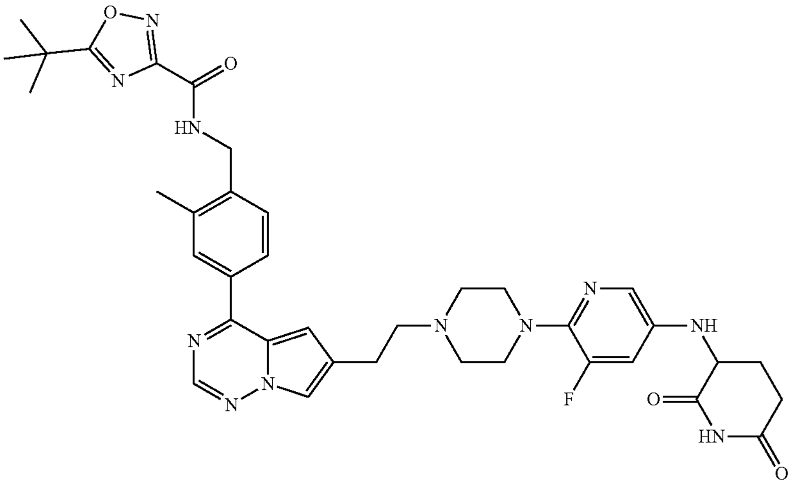 [SMILES: Cc1cc(-c2ncnn3cc(CCN4CCN(c5ncc(NC6CCC(=O)NC6=O)cc5F)CC4)cc23)ccc1CNC(=O)c1noc(C(C)(C)C)n1]

5-(tert-butyl)-N-(4-(6-(2-(4-(5-((2,6-dioxopiperidin-3-yl)amino)-3-fluoropyridin-2-yl)piperazin-1-yl)ethyl)pyrrolo[2,1-f][1,2,4]triazin-4-yl)-2-methylbenzyl)-1,2,4-oxadiazole-3-carboxamide.

Prep-HPLC Method:

Mobile Phase (A): 0.1% TFA in $H_2O$

Mobile Phase (B): 100% ACN

Flow Rate: 16 mL/min

Column: X-Select CSH C18 5 μm (19×250 mm)

Gradient Time % B: 0/30, 2/30, 12/90, 13/100.

$^1$H NMR (400 MHz, DMSO-$d_6$) δ 10.84 (s, 1H), 9.53 (t, J=6.0 Hz, 1H), 9.52 (brs, 1H), 8.60 (s, 1H), 8.18 (s, 1H), 7.94 (d, J=7.6 Hz, 2H), 7.60 (s, 1H), 7.46 (d, J=8.0 Hz, 1H), 7.19 (s, 1H), 7.03 (dd, J=2.2, 14.6 Hz, 1H), 6.10 (brs, 1H), 4.55 (d, J=6.0 Hz, 2H), 4.34-4.33 (m, 1H), 3.69-3.61 (m, 4H), 3.55 (brs, 2H), 3.19-3.15 (m, 4H), 3.08 (t, J=11.6 Hz, 2H), 2.71-2.68 (m, 1H), 2.60-2.59 (m, 1H), 2.47 (s, 3H), 2.11-2.08 (m, 1H), 1.88-1.78 (m, 1H), 1.43 (s, 9H). LC-MS ($ES^-$): m/z 722.03 $[M-H]^-$.

Example 264

Example 264 was prepared following the synthesis of Example 249

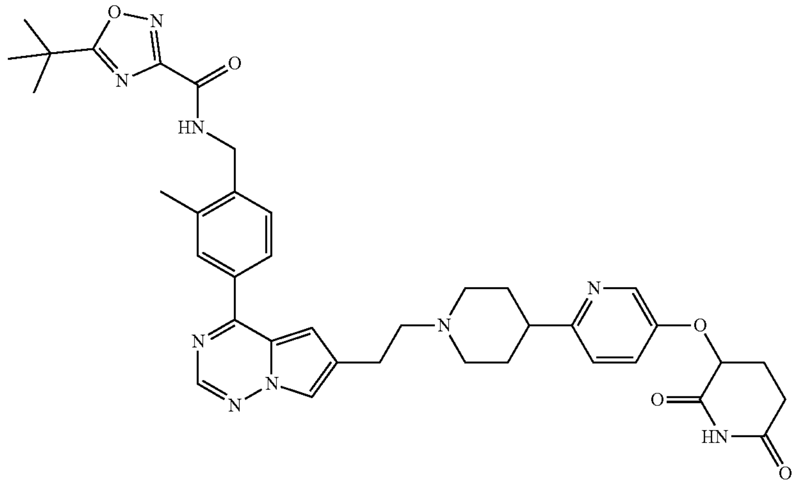 [SMILES: Cc1cc(-c2ncnn3cc(CCN4CCC(c5ccc(OC6CCC(=O)NC6=O)cn5)CC4)cc23)ccc1CNC(=O)c1noc(C(C)(C)C)n1]

5-(tert-butyl)-N-(4-(6-(2-(4-(5-((2,6-dioxopiperidin-3-yl)oxy)pyridin-2-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: XSelect C18(19*250, 5 μm)

Mobile phase A: 0.1% TFA in water

Mobile phase B: 100% Acetonitrile

Gradient (Time/% B): 0/10, 3/10, 10/35, 16/35, 16.1/100, 19/100, 19.1/10, 21/10, Flow rate: 16 mL/min.

Solubility: ACN+water+THF $^1$H-NMR (400 MHz, DMSO-$d_6$) δ 10.98 (s, 1H), 9.54 (t, J=6.0 Hz, 1H), 9.19 (br s, 1H), 8.61 (s, 1H), 8.29 (d, J=2.8 Hz, 1H), 8.18 (s, 1H), 7.95 (d, J=7.2 Hz, 1H, semi-covered), 7.94 (s, 1H), 7.48-7.43 (m, 2H), 7.26 (d, J=8.8 Hz, 1H), 7.21 (s, 1H), 5.31-5.27 (m, 1H), 4.56 (d, J=5.6 Hz, 2H), 3.69-3.67 (m, 2H), 3.49-3.47 (m, 2H), 3.21-3.09 (m, 4H), 2.96 (t, J=12.0 Hz, 1H), 2.71-2.60 (m, 2H), 2.47 (s, 3H), 2.23-2.19 (m, 2H), 2.18-1.94 (m, 4H), 1.44 (s, 9H) ppm. LC-MS ($ES^+$): m/z 706.39 $[M+H]^+$.

Example 265

Example 265 was prepared following the synthesis of Example 249

(S)-5-(tert-butyl)-N-(4-(6-(2-(3-(3-(2,4-dioxotetrahydropyrimidin-1(2H)-yl)-1-methyl-1H-indazol-6-yl)pyrrolidin-1-yl)ethyl)pyrrolo[2,1-f][1,2,4]triazin-4-yl)-2-methylbenzyl)-1,2,4-oxadiazole-3-carboxamide.

(Stereochemistry was arbitrarily assigned)

Prep HPLC Condition:

Column/dimensions: Sunfire-C18 (19*250*5 um)

Mobile phase A: 0.05% TFA in water

Mobile phase B: Acetonitrile

Gradient (Time/% B): 0/10, 2/10, 13.20/44.2, 13.30/98, 16/98, 16.10/10, 19/10

Flow rate: 17 mL/min

Solubility: Acetonitrile+THF $^{1}$H-NMR (400 MHz, DMSO-$d_6$) δ 10.56 (s, 1H), 9.72 (br s, 1H), 9.54 (t, J=6.0 Hz, 1H), 8.61 (s, 1H), 8.20 (s, 1H), 7.96 (s, 1H), 7.94 (s, 1H), 7.65 (d, J=8.8 Hz, 1H), 7.59 (s, 1H), 7.53 (s, 1H), 7.46 (d, J=8.0 Hz, 1H), 7.23 (s, 1H), 7.21-7.10 (m, 1H), 4.55 (d, J=6.0 Hz, 2H), 3.98 (s, 3H), 3.89 (t, J=10.0, 2H), 3.66-3.29 (m, 7H), 3.19-3.18 (m, 2H), 2.76 (t, J=6.6 Hz, 2H), 2.49 (s, 3H), 2.08-2.07 (m, 1H), 1.43 (s, 9H). LC-MS (ES$^-$): m/z 728.02 [M−H]$^-$.

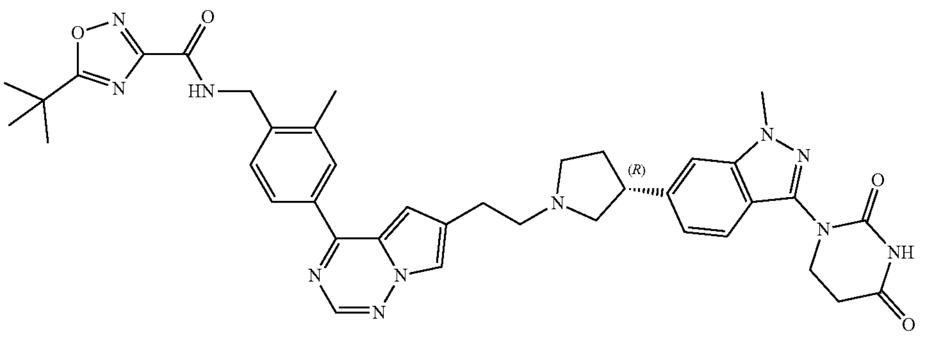

(R)-5-(tert-butyl)-N-(4-(6-(2-(3-(3-(2,4-dioxotetrahydropyrimidin-1(2H)-yl)-1-methyl-1H-indazol-6-yl)pyrrolidin-1-yl)ethyl)pyrrolo[2,1-f][1,2,4]triazin-4-yl)-2-methylbenzyl)-1,2,4-oxadiazole-3-carboxamide.

(Stereochemistry was arbitrarily assigned)

Prep-HPLC Method:

Column/dimensions: Sunfire-C18 (19*250*5 um)

Mobile phase A: 0.05% TFA in water

Mobile phase B: Acetonitrile

Gradient (Time/% B): 0/10, 2/10, 13.20/44.2, 13.30/98, 16/98, 16.10/10, 19/10

Flow rate: 17 mL/min

Solubility: Acetonitrile+THF $^{1}$H-NMR (400 MHz, DMSO-$d_6$) δ 10.56 (s, 1H), 9.72 (br s, 1H), 9.54 (t, J=6.0 Hz, 1H), 8.61 (s, 1H), 8.20 (s, 1H), 7.96 (s, 1H), 7.94 (s, 1H), 7.65 (d, J=8.8 Hz, 1H), 7.59 (s, 1H), 7.53 (s, 1H), 7.46 (d, J=8.0 Hz, 1H), 7.23 (s, 1H), 7.21-7.16 (m, 1H), 4.55 (d, J=6.0 Hz, 2H), 4.01 (s, 3H), 3.92 (t, J=6.0 Hz, 2H), 3.69-3.28 (m, 7H), 3.19-3.18 (m, 2H), 2.76 (t, J=6.6 Hz, 2H), 2.49 (s, 3H), 2.32-2.20 (m, 1H), 1.43 (s, 9H). LC-MS (ES$^-$): m/z 728.09 [M−H]$^-$.

Example 266

Example 266 was prepared following the synthesis of Example 249

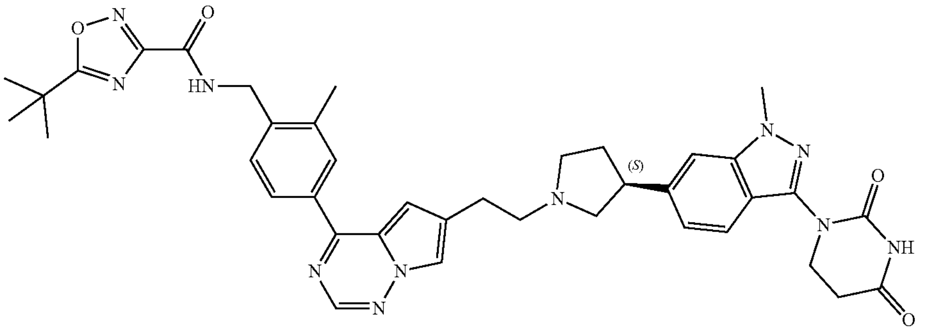

Example 267

Example 267 was prepared following the synthesis of Example 249

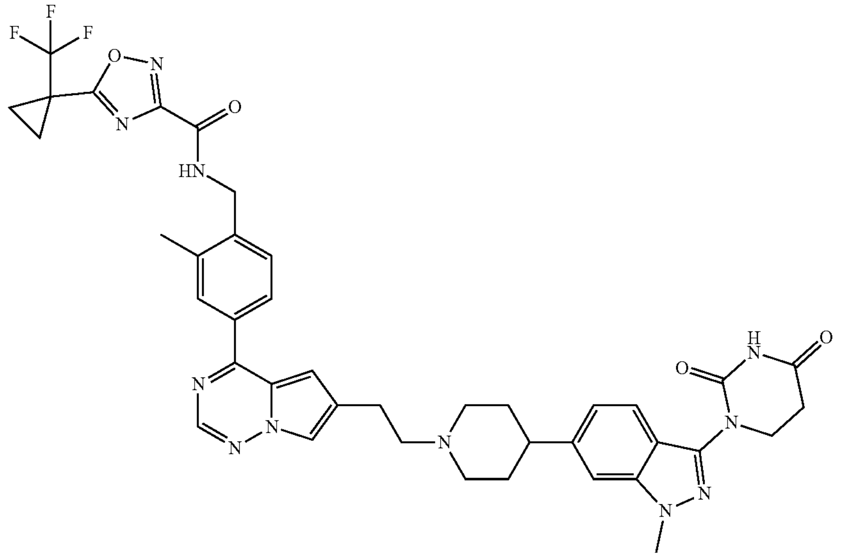 [SMILES: Cc1cc(-c2ncnn3cc(CCN4CCC(c5ccc6c(N7CCC(=O)NC7=O)nn(C)c6c5)CC4)cc23)ccc1CNC(=O)c1noc(C2(C(F)(F)F)CC2)n1]

N-(4-(6-(2-(4-(3-(2,6-dioxopiperidin-3-yl)-1-methyl-1H-indazol-6-yl)piperidin-1-yl)ethyl)pyrrolo[2,1-f][1,2,4]triazin-4-yl)-2-methylbenzyl)-5-(1-(trifluoromethyl)cyclopropyl)-1,2,4-oxadiazole-3-carboxamide.

Prep-HPLC Method:

Column/dimensions: X Select-C18 (19*250*5 um)

Mobile Phase (A): 0.1% FA in $H_2O$

Mobile phase B: ACN

Gradient (Time/% B): 0/35, 2/35, 12/40, 16/40, 16.10/98, 18.10/98, 18.20/35, 20.20/35

Flow rate: 17 mL/min.

Solubility: THF+water+ACN $^1$H-NMR (400 MHz, DMSO-$d_6$) δ 10.84 (s, 1H), 9.45 (t, J=6.0 Hz, 1H), 8.54 (s, 1H), 8.33 (br s, 3H), 8.10 (s, 1H), 7.95 (d, J=4.4 Hz, 2H), 7.60 (d, J=7.6 Hz, 1H), 7.46-7.44 (m, 2H), 7.14 (s, 1H), 7.04 (d, J=8.0 Hz, 1H), 4.40 (d, J=6.0 Hz, 2H), 4.33-4.30 (m, 1H), 3.96 (s, 3H), 3.16-3.12 (m, 2H), 2.92 (t, J=7.4 Hz, 2H), 2.70-2.61 (m, 5H), 2.46 (s, 3H), 2.33-2.32 (m, 1H), 2.18-2.07 (m, 3H), 1.86-1.75 (m, 8H). LC-MS ($ES^+$): m/z 795.77 $[M+H]^+$.

Example 268

Example 268 was prepared following the synthesis of Example 249

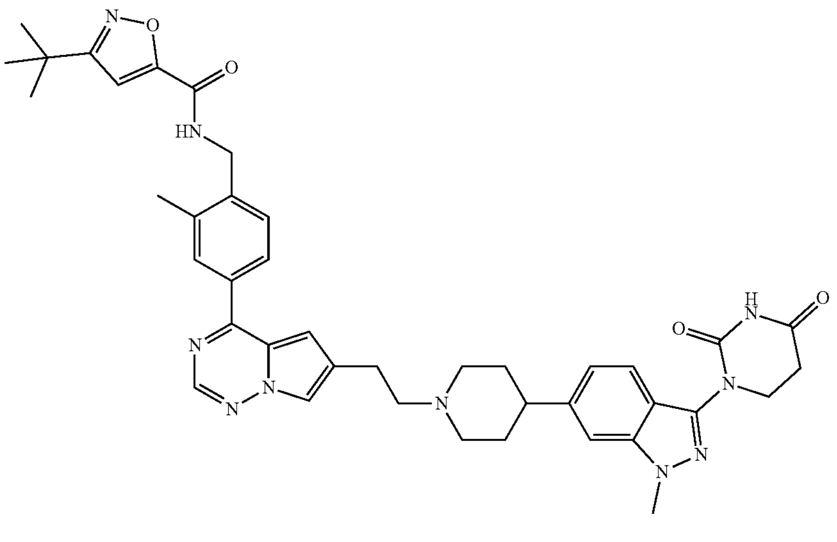 [SMILES: Cc1cc(-c2ncnn3cc(CCN4CCC(c5ccc6c(N7CCC(=O)NC7=O)nn(C)c6c5)CC4)cc23)ccc1CNC(=O)c1cc(C(C)(C)C)no1]

3-(tert-butyl)-N-(4-(6-(2-(4-(3-(2,6-dioxopiperidin-3-yl)-1-methyl-1H-indazol-6-yl)piperidin-1-yl)ethyl)pyrrolo[2,1-f][1,2,4]triazin-4-yl)-2-methylbenzyl)isoxazole-5-carboxamide.

Prep-HPLC Method:

Column/dimensions: X-Select C18 (19*250, 5 m)

Mobile phase A: 0.1% TFA in water

Mobile phase B: 100% Acetonitrile

Gradient (Time/% B): 0/20, 2/20, 10/40, 15/40, 15.1/100, 18/100, 18.1/20, 21/20.

Flow rate: 16 mL/min.

Solubility: ACN+water+THF $^1$H NMR (400 MHz, DMSO-d$_6$) δ 10.88 (s, 1H), 9.47 (t, J=6.0 Hz, 1H), 9.24 (br s, 1H), 8.61 (s, 1H), 8.20 (d, J=8.4 Hz, 1H), 7.96-7.94 (m, 2H), 7.67 (d, J=8.4 Hz, 1H), 7.46 (d, J=8.0 Hz, 1H), 7.40 (s, 1H), 7.21 (s, 1H), 7.18 (s, 1H), 7.07 (d, J=8.8 Hz, 1H), 4.54 (d, J=5.6 Hz, 2H), 4.36-4.32 (m, 1H), 3.98 (s, 3H), 3.65-3.53 (m, 4H), 3.22-3.13 (m, 4H), 3.08-3.00 (m, 1H), 2.67-2.60 (m, 2H), 2.47 (s, 3H), 2.34-2.32 (m, 1H), 2.17-2.13 (m, 3H), 1.98-1.95 (m, 2H), 1.31 (s, 9H). LC-MS (ES$^-$): m/z 740.12 [M−H]$^-$.

Example 269

Example 269 was prepared following the synthesis of Example 249

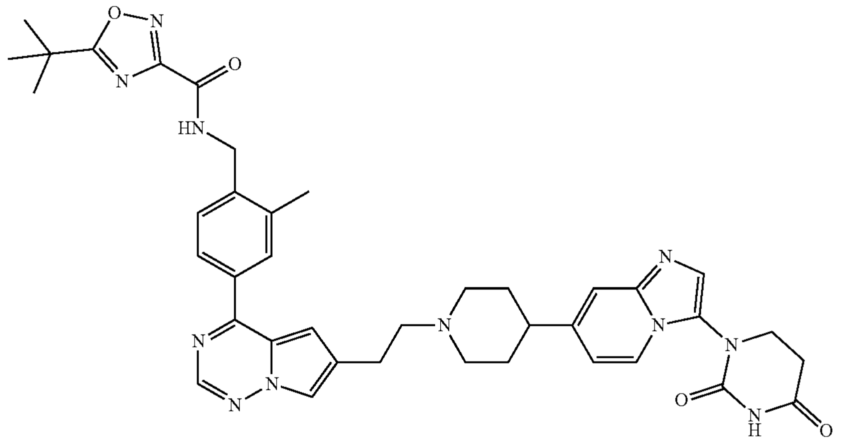 [SMILES: Cc1cc(-c2ncnn3cc(CCN4CCC(c5ccn6c(N7CCC(=O)NC7=O)cnc6c5)CC4)cc23)ccc1CNC(=O)c1noc(C(C)(C)C)n1]

5-(tert-butyl)-N-(4-(6-(2-(4-(3-(2,4-dioxotetrahydropyrimidin-1(2H)-yl)imidazo[1,2-a]pyridin-7-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: Sunfire C18 (19*150, 5 um)

Mobile phase A: 0.05% TFA in water

Mobile phase B: Acetonitrile

Gradient (Time/% B): 0/10, 3/10, 12/35, 13/35, 13.10/100

Flow rate: 16 mL/min.

Solubility: Acetonitrile+water $^1$H-NMR (400 MHz, DMSO-d$_6$) δ 10.84 (s, 1H), 9.54 (t, J=5.6 Hz, 1H), 9.38 (br s, 1H), 8.71 (s, 1H), 8.61 (s, 1H), 8.19 (s, 1H), 8.01 (s, 1H), 7.96-7.94 (m, 2H), 7.68 (s, 1H), 7.46 (d, J=8.0 Hz, 1H), 7.35 (br s, 1H), 7.22 (d, J=6.8 Hz, 1H), 4.54 (d, J=6.0 Hz, 2H), 3.86-3.83 (m, 2H), 3.72-3.66 (m, 2H), 3.53-3.50 (m, 2H), 3.21-3.09 (m, 5H), 2.85 (br s, 2H), 2.47 (s, 3H), 2.19-2.16 (m, 2H), 1.97-1.88 (m, 2H), 144 (s, 9H). LC-MS (ES$^+$): m/z 730.16 [M+H]$^+$.

Example 270

Example 270 was prepared following the synthesis of Example 249

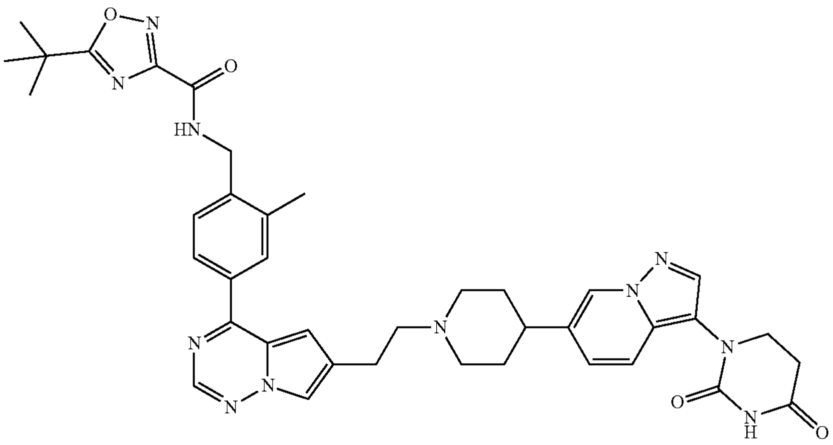 [SMILES: Cc1cc(-c2ncnn3cc(CCN4CCC(c5ccc6c(N7CCC(=O)NC7=O)cnn6c5)CC4)cc23)ccc1CNC(=O)c1noc(C(C)(C)C)n1]

5-(tert-butyl)-N-(4-(6-(2-(4-(3-(2,4-dioxotetrahydropyrimidin-1(2H)-yl)pyrazolo[1,5-a]pyridin-6-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: Sunfire-C18

Mobile phase A: 0.1% TFA in water

Mobile phase B: ACN

Gradient (Time/% B) 0/15, 2/15, 10/40, 12/40, 12.1/100, 16/100, 16.1/15, 18/15

Flow rate: 16 mL/min

Solubility: ACN+THF+water $^1$H-NMR (400 MHz, DMSO-$d_6$) δ 10.43 (s, 1H), 9.54 (t, J=6.0 Hz, 1H), 9.20 (br s, 1H), 8.60 (d, J=4.0 Hz, 1H), 8.49 (s, 1H), 8.19 (d, J=4.0 Hz, 1H), 8.01 (s, 1H), 7.96-7.94 (m, 2H), 7.59 (d, J=9.2 Hz, 1H), 7.46 (d, J=8.0 Hz, 1H), 7.23-7.18 (m, 2H), 4.54 (d, J=6.0 Hz, 2H), 3.76 (t, J=6.6 Hz, 4H), 3.54-3.51 (m, 2H), 3.22-3.08 (m, 4H), 2.95-2.92 (m, 1H), 2.77 (t, J=6.8 Hz, 2H), 2.47 (s, 3H), 2.16-2.13 (m, 2H), 1.94-1.89 (m, 2H), 1.43 (s, 9H). LC-MS (ES$^+$): m/z 730.48 $[M+H]^+$.

Example 271

Example 271 was prepared following the synthesis of Example 249

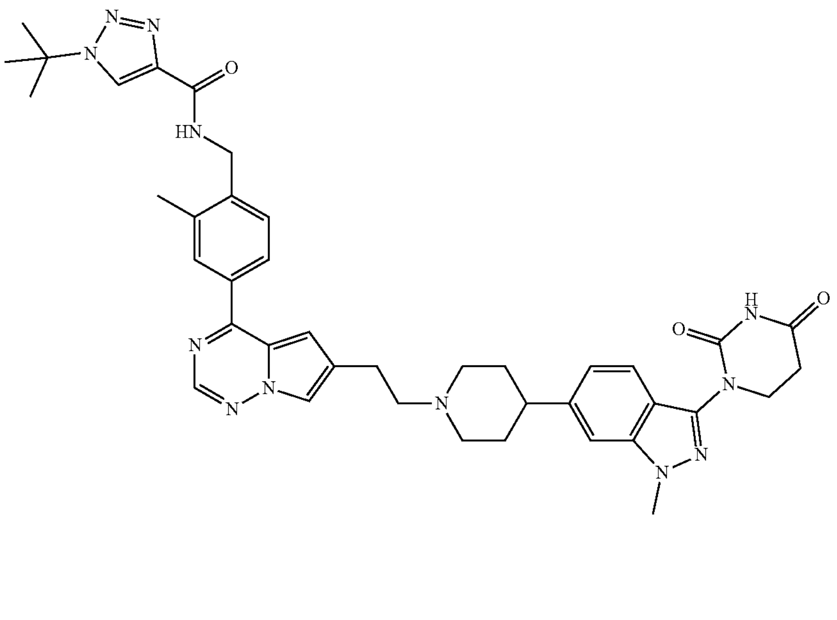 [SMILES: Cc1cc(-c2ncnn3cc(CCN4CCC(c5ccc6c(N7CCC(=O)NC7=O)nn(C)c6c5)CC4)cc23)ccc1CNC(=O)c1cn(C(C)(C)C)nn1]

Prep-HPLC Method:

Column/dimensions: X-Select C18 (25*250 mm) 5p
Mobile phase A: 0.1% TFA in water
Mobile phase B: Acetonitrile
Gradient (Time/% B): 0.01/10, 1/10, 8/30, 16.5/30, 16.6/100, 20/100, 20.1/10, 22/10
Flow rate: 18 mL/min.
Solubility: THF+ACN+water $^1$H-NMR (400 MHz, DMSO-$d_6$) δ 10.99 (s, 1H), 9.22 (br s, 1H), 9.09 (t, J=6.2 Hz, 1H), 8.72 (d, J=2.4 Hz, 1H), 8.61 (s, 1H), 8.20 (d, J=6.8 Hz, 1H), 7.94 (d, J=6.0 Hz, 2H), 7.67 (d, J=8.4 Hz, 1H), 7.46 (d, J=8.4 Hz, 1H), 7.40 (s, 1H), 7.22 (s, 1H), 7.03 (d, J=8.4 Hz, 1H), 4.55 (d, J=6.0 Hz, 2H), 4.32-4.36 (m, 1H), 3.98 (s, 3H), 3.73 (br s, 2H), 3.55 (br s, 2H), 3.22-2.99 (m, 5H), 2.61-2.69 (m, 2H), 2.50 (s, 3H), 2.32-2.37 (m, 1H), 2.13-2.19 (m, 3H), 1.95-1.98 (m, 2H), 1.64 (s, 9H). LC-MS ($ES^-$): m/z 740.45 $[M-H]^-$.

Example 272

Example 272 was prepared following the synthesis of Example 249

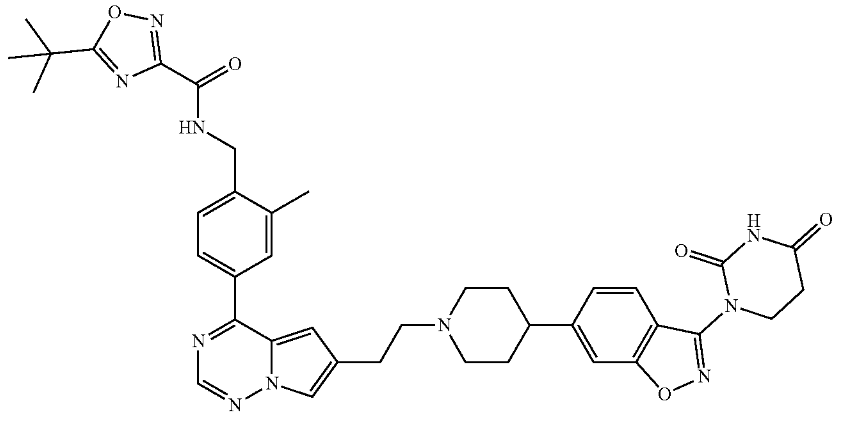 [SMILES: Cc1cc(-c2ncnn3cc(CCN4CCC(c5ccc6c(N7CCC(=O)NC7=O)noc6c5)CC4)cc23)ccc1CNC(=O)c1noc(C(C)(C)C)n1]

5-(tert-butyl)-N-(4-(6-(2-(4-(3-(2,4-dioxotetrahydropyrimidin-1(2H)-yl)benzo[d]isoxazol-6-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:

Column/dimensions: X-Bridge C18(19*250, 5 um)
Mobile phase A: 5 mM AA in water
Mobile phase B: 100% ACN
Gradient (Time/% B): 0/20, 2/20, 10/50, 15/50, 15/100, 20/100, 20.1/20, 23/20.
Flow rate: 18 mL/min.
Solubility: Water+THF+ACN $^1$H-NMR (400 MHz, DMSO-$d_6$) δ 10.84 (S, 1H), 9.50 (t, J=6.0 Hz, 1H), 8.55 (s, 1H), 8.10 (d, J=1.2 Hz, 1H), 7.97-7.95 (m, 2H), 7.75 (d, J=8.4 Hz, 1H), 7.58 (s, 1H), 7.45 (d, J=8.8 Hz, 1H), 7.33 (d, J=8.8 Hz, 1H), 7.14 (d, J=1.2 Hz, 1H), 4.55 (d, J=6.0 Hz, 2H), 4.04 (t, J=6.6 Hz, 2H), 3.10 (d, J=11.6 Hz, 2H), 2.90 (t, J=7.6 Hz, 2H), 2.71 (t, J=15.8 Hz, 2H), 2.66 (t, J=7.4 Hz, 3H), 2.49 (s, 3H), 2.09 (t, J=10.6 Hz, 2H), 1.81-1.72 (m, 4H), 1.44 (s, 9H). LC-MS ($ES^+$): m/z 731.21 $[M+H]^+$.

Example 273

Example 273 was prepared following the synthesis of Example 249

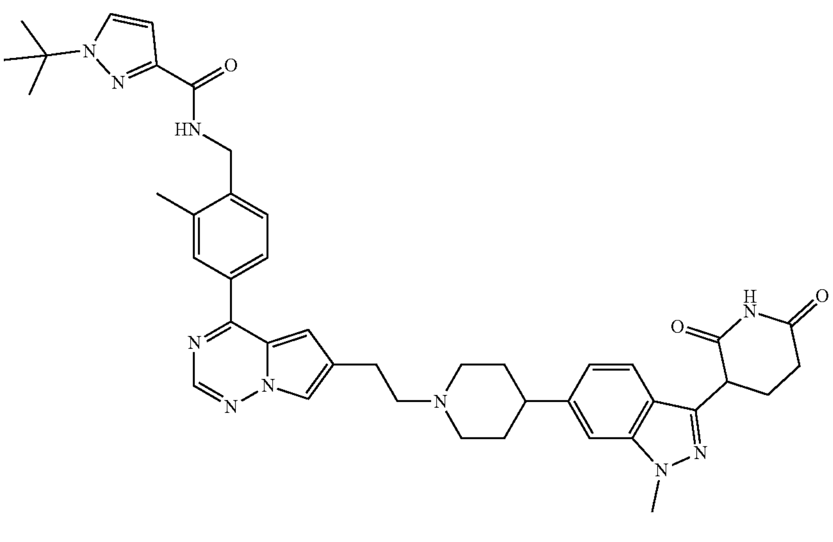 [SMILES: Cc1cc(-c2ncnn3cc(CCN4CCC(c5ccc6c(C7CCC(=O)NC7=O)nn(C)c6c5)CC4)cc23)ccc1CNC(=O)c1ccn(C(C)(C)C)n1]

1-(tert-butyl)-N-(4-(6-(2-(4-(3-(2,6-dioxopiperidin-3-yl)-1-methyl-1H-indazol-6-yl)piperidin-1-yl)ethyl)pyrrolo[2,1-f][1,2,4]triazin-4-yl)-2-methylbenzyl)-1H-pyrazole-3-carboxamide.

Prep-HPLC Method:

Column/dimensions: Symmetry C18 (19*300*7μ)

Mobile phase A: 0.05% TFA in water

Mobile phase B: Acetonitrile

Gradient (Time/% B) 0/10, 2/20, 14.5/52, 14.6/98, 17/98, 17.1/10, 20/10.

Flow rate: 17 mL/min

Solubility: ACN+THF $^1$H-NMR (400 MHz, DMSO-$d_6$) δ 10.99 (s, 1H), 9.15 (br s, 1H), 8.61-8.55 (m, 2H), 8.20 (d, J=7.2 Hz, 1H), 7.96-7.93 (m, 3H), 7.67 (d, J=8.4 Hz, 1H), 7.46 (d, J=8.0 Hz, 1H), 7.40 (s, 1H), 7.26-6.96 (m, 2H), 6.67 (d, J=2.4 Hz, 1H), 4.53 (d, J=6.4 Hz, 2H), 4.36-4.32 (m, 1H), 3.98 (s, 3H), 3.73-3.70 (m, 2H), 3.56-3.52 (m, 2H), 3.13-3.00 (m, 1H), 2.69-2.61 (m, 2H), 2.48 (s, 3H), 2.37-2.34 (m, 1H), 2.19-2.09 (m, 3H), 1.98-1.98 (m, 2H), 1.98 (s, 9H). LC-MS (ES$^+$): m/z 741.47 [M+H]$^+$.

Example 274

Example 274 was prepared following the synthesis of Example 249

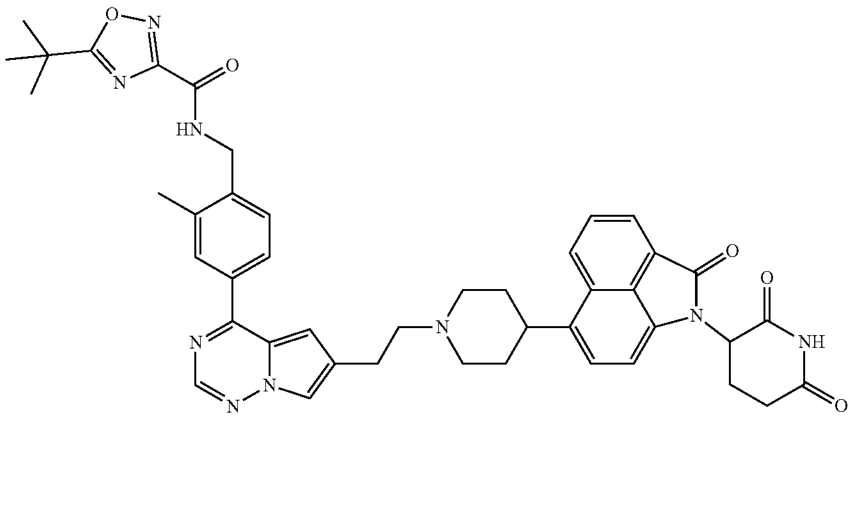 [SMILES: Cc1cc(-c2ncnn3cc(CCN4CCC(c5ccc6c7c(cccc57)C(=O)N6C5CCC(=O)NC5=O)CC4)cc23)ccc1CNC(=O)c1noc(C(C)(C)C)n1]

5-(tert-butyl)-N-(4-(6-(2-(4-(1-(2,6-dioxopiperidin-3-yl)-2-oxo-1,2-dihydrobenzo[cd]indol-6-yl)piperidin-1-yl)ethyl)pyrrolo[2,1-f][1,2,4]triazin-4-yl)-2-methylbenzyl)-1,2,4-oxadiazole-3-carboxamide.

Prep-HPLC Method:
- Column/dimensions: X-select C18 (19*250, 5 um)
- Mobile phase A: 0.1% TFA in water
- Mobile phase B: Acetonitrile
- Gradient (Time/% B): 0/15, 2/15, 12/45, 17/45, 17.10/98, 21.50/98, 21.60/1524.50/15
- Flow rate: 16 mL/min.
- Solubility: ACN+water+THF $^1$H-NMR (400 MHz, DMSO-$d_6$) 11.14 (s, 1H), 9.53 (t, J=6.0 Hz, 1H), 9.30 (s, 1H), 8.62 (s, 1H), 8.50 (s, 1H), 8.23 (s, 1H), 8.14 (d, J=6.8 Hz, 1H), 7.95-7.97 (m, 2H), 7.88-7.92 (m, 1H), 7.47 (d, J=8.0 Hz, 1H), 7.32 (d, J=7.6 Hz, 1H), 7.25-7.27 (m, 1H), 7.07 (d, J=7.6 Hz, 1H), 5.44-5.48 (m, 1H), 4.56 (d, J=6.0 Hz, 2H), 3.62-3.66 (m, 2H), 3.54-3.56 (m, 2H), 3.21-3.29 (m, 4H), 2.92-3.00 (m, 1H), 2.77-2.79 (m, 1H), 2.64-2.67 (m, 1H), 2.49-2.50 (m, 1H), 2.48 (s, 3H), 2.06-2.16 (m, 5H), 1.43 (s, 9H). LC-MS (ES$^+$): m/z 780.38 [M+H]$^+$.

Example 275

Example 275 was prepared following the synthesis of Example 249

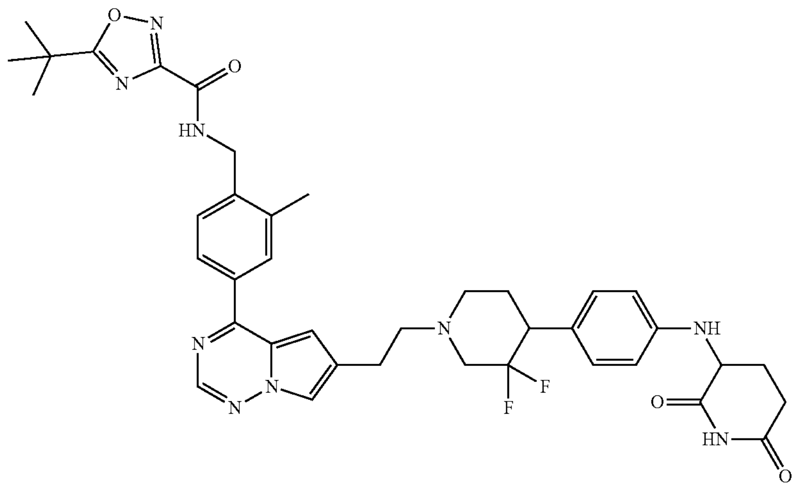 [SMILES: Cc1cc(-c2ncnn3cc(CCN4CCC(c5ccc(NC6CCC(=O)NC6=O)cc5)C(F)(F)C4)cc23)ccc1CNC(=O)c1noc(C(C)(C)C)n1]

5-(tert-butyl)-N-(4-(6-(2-(4-(4-((2,6-dioxopiperidin-3-yl)amino)phenyl)-3,3-difluoropiperidin-1-yl)ethyl)pyrrolo[2,1-f][1,2,4]triazin-4-yl)-2-methylbenzyl)-1,2,4-oxadiazole-3-carboxamide.

Prep. HPLC condition:
- Column/dimensions: XBRIDGE-C8(19*250*5 um)
- Mobile phase A: 0.1% TFA in water (aq)
- Mobile phase B: Acetonitrile
- Gradient (Time/% B): 0/10, 3/10, 10/45, 20/45, 20.1/100, 22/100, 22.1/10, 24/10
- Flow rate: 17 ml/min
- Solubility: Acetonitrile+THF $^1$H-NMR (400 MHz, DMSO-$d_6$) δ 10.78 (s, 1H), 9.52 (t, J=6.0 Hz, 1H), 8.55 (s, 1H), 8.10 (s, 1H), 7.95 (d, J=6.4 Hz, 1H), 7.95 (s, 1H), 7.46 (d, J=8.8 Hz, 1H), 7.16 (s, 1H), 7.01 (d, J=8.4 Hz, 2H), 6.63 (d, J=8.4 Hz, 2H), 5.80 (d, J=7.6 Hz, 1H), 4.55 (d, J=5.6 Hz, 2H), 4.31-4.29 (m, 1H), 3.23 (br s, 1H), 2.93-2.51 (m, 8H), 2.46 (s, 3H), 2.46-1.72 (m, 6H), 1.44 (s, 9H). LC-MS (ES$^+$): m/z 705.45 [M+H]$^+$.

Example 276

Example 276 was prepared substantially following the synthesis of Example 104

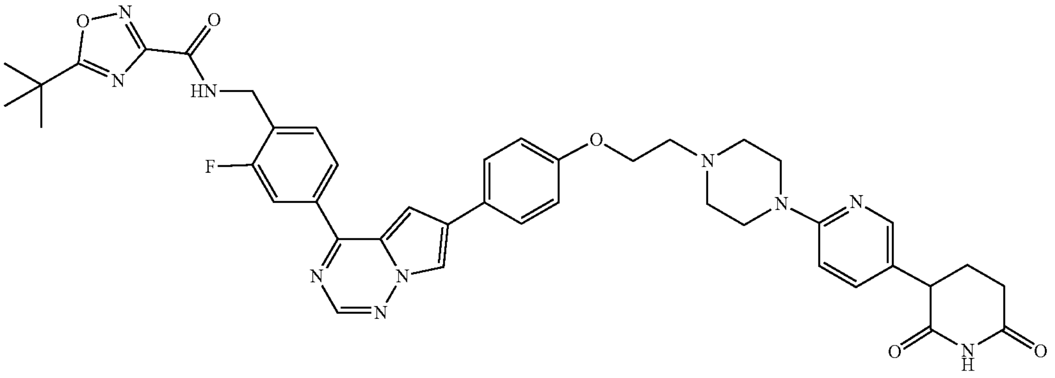 [SMILES: CC(C)(C)c1nc(C(=O)NCc2ccc(-c3ncnn4cc(-c5ccc(OCCN6CCN(c7ccc(C8CCC(=O)NC8=O)cn7)CC6)cc5)cc34)cc2F)no1]

5-(tert-butyl)-N-(4-(6-(4-(2-(4-(5-(2,6-dioxopiperidin-3-yl)pyridin-2-yl)piperazin-1-yl)ethoxy)phenyl)pyrrolo[2,1-f][1,2,4]triazin-4-yl)-2-fluorobenzyl)-1,2,4-oxadiazole-3-carboxamide. $^1$H-NMR (400 MHz, DMSO-$d_6$) δ 10.89 (s, 1H), 9.89 (s, 1H), 9.61 (s, 1H), 8.74 (d, J=1.2 Hz, 1H), 8.63 (s, 1H), 8.08 (t, J=4.6 Hz, 1H), 8.03 (d, J=2.4 Hz, 1H), 8.00-7.95 (m, 3H), 7.67 (d, J=1.2 Hz, 1H), 7.59 (t, J=7.8 Hz, 1H), 7.52 (dd, J=8.8, 2.0 Hz, 1H), 7.21 (s, 1H), 7.12-7.09 (m, 2H), 6.97 (d, J=8.4 Hz, 1H), 4.63 (d, J=6.0 Hz, 2H), 4.44-4.39 (m, 4H), 3.82-3.65 (m, 4H), 3.30-3.20 (m, 4H), 2.74-2.65 (m, 1H), 2.54 (s, 1H), 2.27-2.23 (m, 1H), 2.20-2.17 (m, 1H), 2.17 (s, 9H). LC-MS ($ES^-$): m/z 785.18 $[M-H]^-$.

Example 277

Example 277 was prepared following the synthesis of Example 128

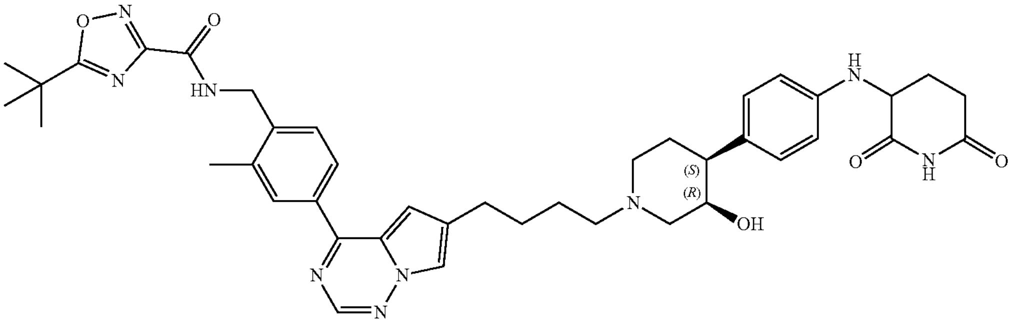

5-(tert-butyl)-N-(4-(6-(4-((3S,4R)-4-(4-((2,6-dioxopiperidin-3-yl)amino)phenyl)-3-hydroxypiperidin-1-yl)butyl)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.89 (s, 1H), 9.52 (t, J=6.0 Hz, 1H), 8.98 (br s, 1H), 8.56 (s, 1H), 8.09 (d, J=0.8 Hz, 1H), 7.95 (d, J=6.8 Hz, 2H), 7.45 (d, J=8.4 Hz, 1H), 7.21 (s, 1H), 7.09 (d, J=5.6 Hz, 1H), 6.96 (t, J=8.0 Hz, 1H), 6.62 (d, J=8.4 Hz, 2H), 6.61 (br s, 2H), 4.55 (d, J=6.0 Hz, 2H), 4.28-4.25 (m, 1H), 3.36 (s, 1H), 3.40-3.33 (m, 2H), 3.17-3.03 (m, 4H), 2.77-2.72 (m, 4H), 2.72-2.67 (m, 1H), 2.46 (s, 3H), 2.33-2.32 (m, 1H), 2.10-2.07 (m, 1H), 1.88-1.84 (m, 1H), 1.84-1.75 (m, 5H), 1.43 (s, 9H). LC-MS ($ES^-$): m/z 746.30 $[M-H]^-$.

Example 278

Example 278 was prepared following the synthesis of Example 128

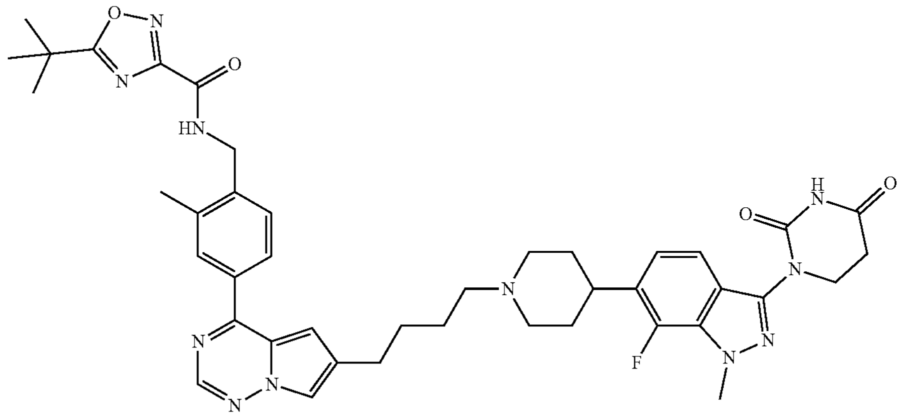 [SMILES: Cc1cc(-c2ncnn3cc(CCCCN4CCC(c5ccc6c(N7CCC(=O)NC7=O)nn(C)c6c5F)CC4)cc23)ccc1CNC(=O)c1noc(C(C)(C)C)n1]

5-(tert-butyl)-N-(4-(6-(4-(4-(3-(2,4-dioxotetrahydropyrimidin-1(2H)-yl)-7-fluoro-1-methyl-1H-indazol-6-yl)piperidin-1-yl)butyl)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.58 (s, 1H), 9.50 (s, 1H), 8.54 (s, 1H), 8.07 (s, 1H), 7.96-7.94 (m, 2H), 7.45 (d, J=7.6 Hz, 1H), 7.39 (d, J=8.4 Hz, 1H), 7.08-7.02 (m, 2H), 4.55 (d, J=6.0 Hz, 2H), 4.09 (s, 3H), 3.90 (t, J=6.4 Hz, 2H), 3.10-3.00 (m, 3H), 2.80-2.65 (m, 4H), 2.45 (s, 3H), 2.42-2.40 (m, 2H), 2.15-2.00 (m, 2H), 1.85-1.50 (m, 8H), 1.43 (s, 9H). LC-MS (ES$^+$): m/z 790.48 [M+H]$^+$.

Example 279

Example 279 was prepared following the synthesis of Example 128

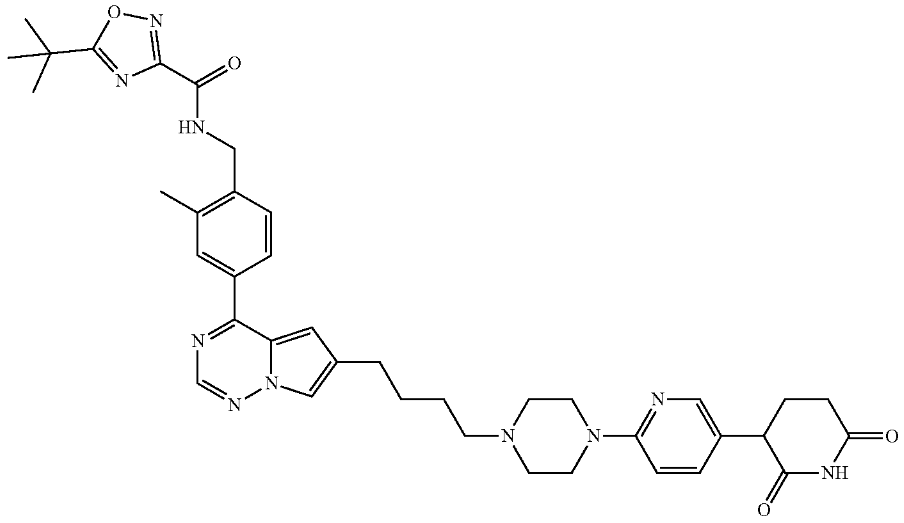 [SMILES: Cc1cc(-c2ncnn3cc(CCCCN4CCN(c5ccc(C6CCC(=O)NC6=O)cn5)CC4)cc23)ccc1CNC(=O)c1noc(C(C)(C)C)n1]

5-(tert-butyl)-N-(4-(6-(4-(4-(5-(2,6-dioxopiperidin-3-yl)pyridin-2-yl)piperazin-1-yl)butyl)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.79 (s, 1H), 9.49 (t, J=6.0 Hz, 1H), 8.53 (s, 1H), 8.06 (s, 1H), 7.95-7.93 (m, 3H), 7.45 (d, J=8.0 Hz, 1H), 7.39 (d, J=8.4 Hz, 1H), 7.08 (s, 1H), 6.78 (d, J=8.8 Hz, 1H), 4.54 (d, J=6.0 Hz, 2H), 3.75-3.71 (m, 1H), 3.50-3.40 (m, 4H), 2.80-2.55 (m, 5H), 2.45-2.35 (m, 8H), 2.25-1.95 (m, 2H), 1.70-1.50 (m, 4H), 1.43 (s, 9H). LC-MS (ES$^+$): m/z 719.38 [M+H]$^+$.

Example 280

Example 280 was prepared following the synthesis of Example 128

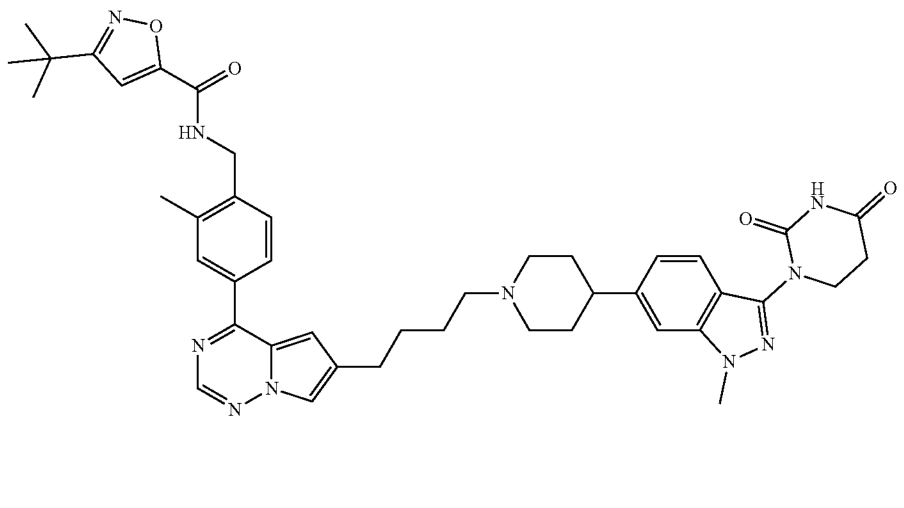 [SMILES: Cc1cc(-c2ncnn3cc(CCCCN4CCC(c5ccc6c(N7CCC(=O)NC7=O)nn(C)c6c5)CC4)cc23)ccc1CNC(=O)c1cc(C(C)(C)C)no1]

3-(tert-butyl)-N-(4-(6-(4-(4-(3-(2,4-dioxotetrahydropyrimidin-1(2H)-yl)-1-methyl-1H-indazol-6-yl)piperidin-1-yl)butyl)pyrrolo[2,1-f][1,2,4]triazin-4-yl)-2-methylbenzyl)isoxazole-5-carboxamide. $^1$H-NMR (400 MHz, DMSO-$d_6$) δ 10.52 (s, 1H), 9.42 (t, J=6.0 Hz, 1H), 8.54 (s, 1H), 8.06 (s, 1H), 7.96-7.94 (m, 2H), 7.54 (d, J=8.4 Hz, 1H), 7.45-7.42 (m, 2H), 7.18 (s, 1H), 7.08 (s, 1H), 7.02 (d, J=8.4 Hz, 1H), 4.53 (d, J=6.0 Hz, 2H), 3.95 (s, 3H), 3.90 (t, J=6.4 Hz, 2H), 3.00 (d, J=10.8 Hz, 2H), 2.80-2.55 (m, 5H), 2.45 (s, 3H), 2.40-2.30 (m, 2H), 1.90-1.50 (m, 10H), 1.30 (s, 9H). LC-MS ($ES^+$): m/z 771.56 $[M+H]^+$.

Example 281

Example 281 was prepared following the synthesis of Example 128

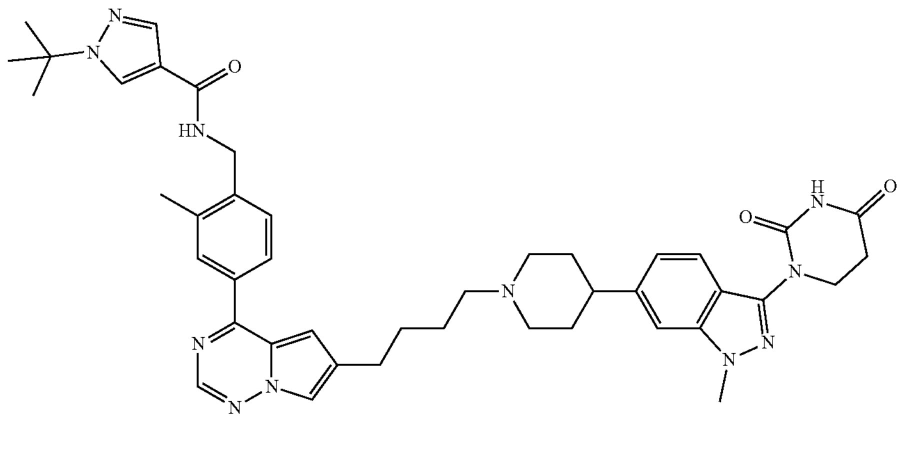 [SMILES: Cc1cc(-c2ncnn3cc(CCCCN4CCC(c5ccc6c(N7CCC(=O)NC7=O)nn(C)c6c5)CC4)cc23)ccc1CNC(=O)c1cnn(C(C)(C)C)c1]

1-(tert-butyl)-N-(4-(6-(4-(4-(3-(2,4-dioxotetrahydropyrimidin-1(2H)-yl)-1-methyl-1H-indazol-6-yl)piperidin-1-yl)butyl)pyrrolo[2,1-f][1,2,4]triazin-4-yl)-2-methylbenzyl)-1H-pyrazole-4-carboxamide. $^1$H-NMR (400 MHz, DMSO-$d_6$) δ 10.51 (s, 1H), 8.53 (br s, 1H), 8.51 (t, J=6.0 Hz, 1H), 8.33 (s, 1H), 8.96 (s, 1H), 8.05 (s, 1H), 7.96-7.93 (m, 3H), 7.53 (d, J=8.4 Hz, 1H), 7.46-7.42 (m, 2H), 7.07 (s, 1H), 7.02 (d, J=8.4 Hz, 1H), 4.49 (d, J=5.6 Hz, 2H), 3.95 (s, 3H), 3.89 (t, J=6.8 Hz, 4H), 3.31-3.00 (m, 2H), 2.72 (t, J=6.8 Hz, 5H), 2.49 (s, 3H), 2.44-2.35 (m, 2H), 2.07-2.02 (m, 2H), 1.77-1.70 (m, 6H), 1.45 (s, 9H). LC-MS ($ES^+$): m/z 768.08 $[M-H]^-$.

Example 282

Example 282 was prepared following the synthesis of Example 128

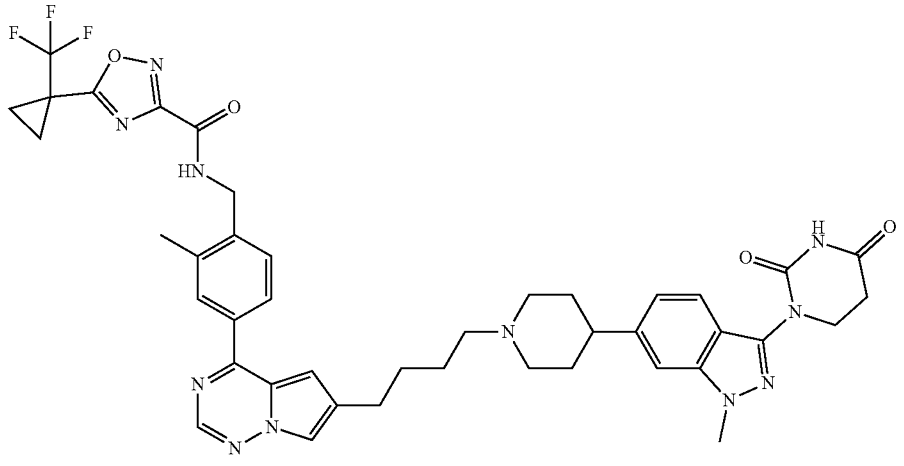 [SMILES: Cc1cc(-c2ncnn3cc(CCCCN4CCC(c5ccc6c(N7CCC(=O)NC7=O)nn(C)c6c5)CC4)cc23)ccc1CNC(=O)c1noc(C2(C(F)(F)F)CC2)n1]

N-(4-(6-(4-(4-(3-(2,4-dioxotetrahydropyrimidin-1(2H)-yl)-1-methyl-1H-indazol-6-yl)piperidin-1-yl)butyl)pyrrolo[2,1-f][1,2,4]triazin-4-yl)-2-methylbenzyl)-5-(1-(trifluoromethyl)cyclopropyl)-1,2,4-oxadiazole-3-carboxamide. $^1$H-NMR (400 MHz, DMSO-$d_6$) δ 10.54 (s, 1H), 9.59 (t, J=6.0 Hz, 1H), 8.54 (s, 1H), 8.17 (s, 1H), 7.95-7.94 (m, 2H), 7.54 (d, J=8.4 Hz, 1H), 7.50-7.40 (m, 2H), 7.08 (s, 1H), 7.02 (d, J=8.4 Hz, 1H), 4.55 (d, J=6.0 Hz, 2H), 3.95 (s, 3H), 3.90 (t, J=7.8 Hz, 2H), 3.10 (d, J=10.0 Hz, 2H), 2.80-2.55 (m, 5H), 2.45 (s, 3H), 2.44-2.40 (m, 2H), 2.10-2.00 (m, 2H), 1.85-1.50 (m, 12H). LC-MS ($ES^+$): m/z 824.60 $[M+H]^+$.

Example 283

Example 283 was prepared following the synthesis of Example 128

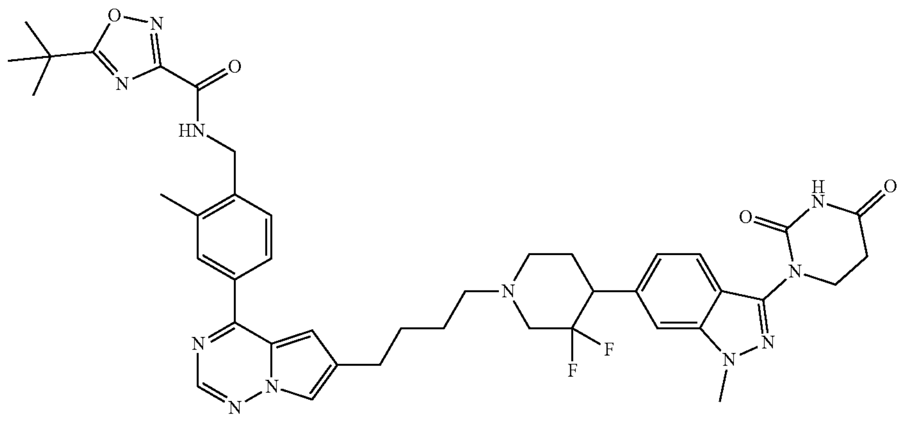 [SMILES: Cc1cc(-c2ncnn3cc(CCCCN4CCC(c5ccc6c(N7CCC(=O)NC7=O)nn(C)c6c5)C(F)(F)C4)cc23)ccc1CNC(=O)c1noc(C(C)(C)C)n1]

5-(tert-butyl)-N-(4-(6-(4-(4-(3-(2,4-dioxotetrahydropyrimidin-1(2H)-yl)-1-methyl-1H-indazol-6-yl)-3,3-difluoropiperidin-1-yl)butyl)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.57 (s, 1H), 9.55 (t, J=6.0 Hz, 1H), 8.57 (s, 1H), 8.11 (s, 1H), 8.00-7.94 (m, 2H), 7.65 (d, J=8.4 Hz, 1H), 7.50-7.40 (m, 2H), 7.11 (s, 1H), 7.10-7.00 (m, 1H), 4.55 (d, J=6.0 Hz, 2H), 4.10-4.04 (m, 1H), 4.08 (s, 3H), 3.92 (t, J=6.4 Hz, 2H), 3.70-3.30 (m, 5H), 2.80-2.50 (m, 5H), 2.49 (s, 3H), 2.40-2.20 (m, 3H), 1.80-1.70 (m, 4H), 1.43 (s, 9H). LC-MS ($ES^+$): m/z 808.32 $[M+H]^+$.

Example 284

Example 284 was prepared following the synthesis of Example 134

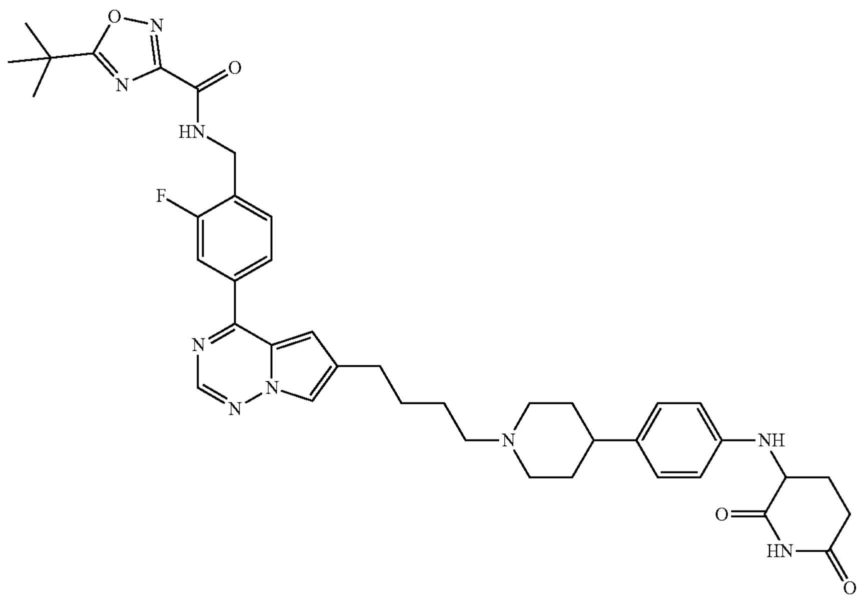 [SMILES: CC(C)(C)c1nc(C(=O)NCc2ccc(-c3ncnn4cc(CCCCN5CCC(c6ccc(NC7CCC(=O)NC7=O)cc6)CC5)cc34)cc2F)no1]

5-(tert-butyl)-N-(4-(6-(4-(4-(4-((2,6-dioxopiperidin-3-yl)amino)phenyl)piperidin-1-yl)butyl)pyrrolo[2,1-f][1,2,4]triazin-4-yl)-2-fluorobenzyl)-1,2,4-oxadiazole-3-carboxamide. H-NMR (400 MHz, DMSO-$d_6$) δ 10.77 (s, 1H), 9.58 (t, J=6.0 Hz, 1H), 8.58 (s, 1H), 8.17 (s, 1H), 8.11 (d, J=1.2 Hz, 1H), 7.99 (dd, J=8.2, 1.4 Hz, 1H), 7.89 (dd, J=11.2, 1.6 Hz, 1H), 7.59 (t, J=7.8 Hz, 1H), 7.13 (d, J=0.8 Hz, 1H), 6.93 (d, J=8.8 Hz, 2H), 6.60 (d, J=8.8 Hz, 2H), 4.60 (d, J=6.0 Hz, 2H), 4.21-4.28 (m, 1H), 2.97 (d, J=10.8 Hz, 2H), 2.76-2.49 (m, 4H), 2.41-2.33 (m, 3H), 2.08-2.00 (m, 3H), 1.71-1.66 (m, 1H), 1.60-1.51 (m, 8H), 1.43 (s, 9H). LC-MS ($ES^+$): m/z 736.27 $[M+H]^+$.

Example 285. Synthesis of 5-(tert-butyl)-N-(4-(6-((3S)-4-(4-(4-(2,6-dioxopiperidin-3-yl)phenyl)piperidin-1-yl)-3-fluorobutyl)pyrrolo[2,1-f][1,2,4]triazin-4-yl)-2-methylbenzyl)-1,2,4-oxadiazole-3-carboxamide (Stereochemistry was arbitrarily assigned)

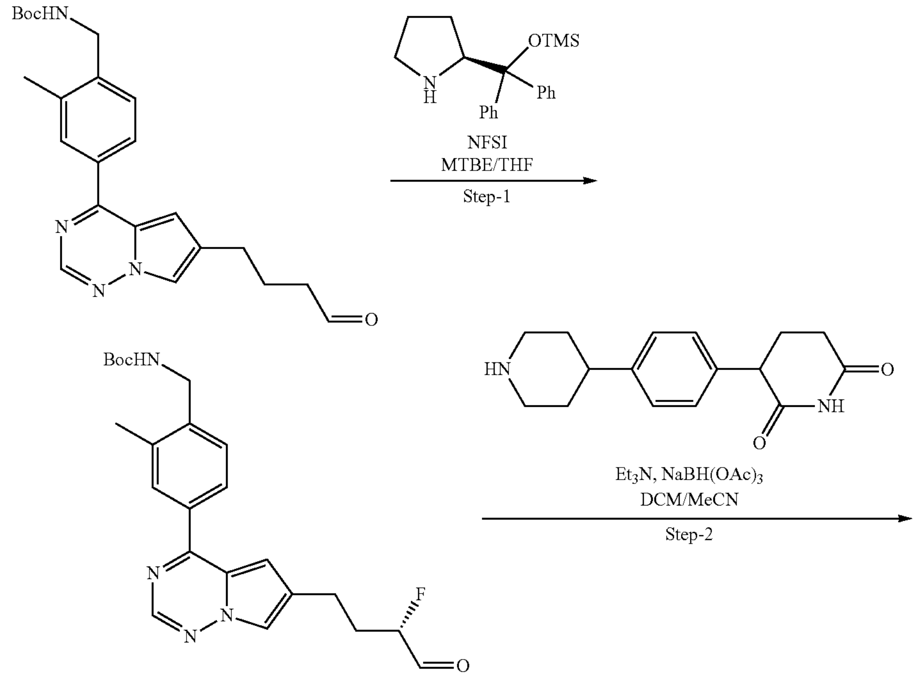

-continued

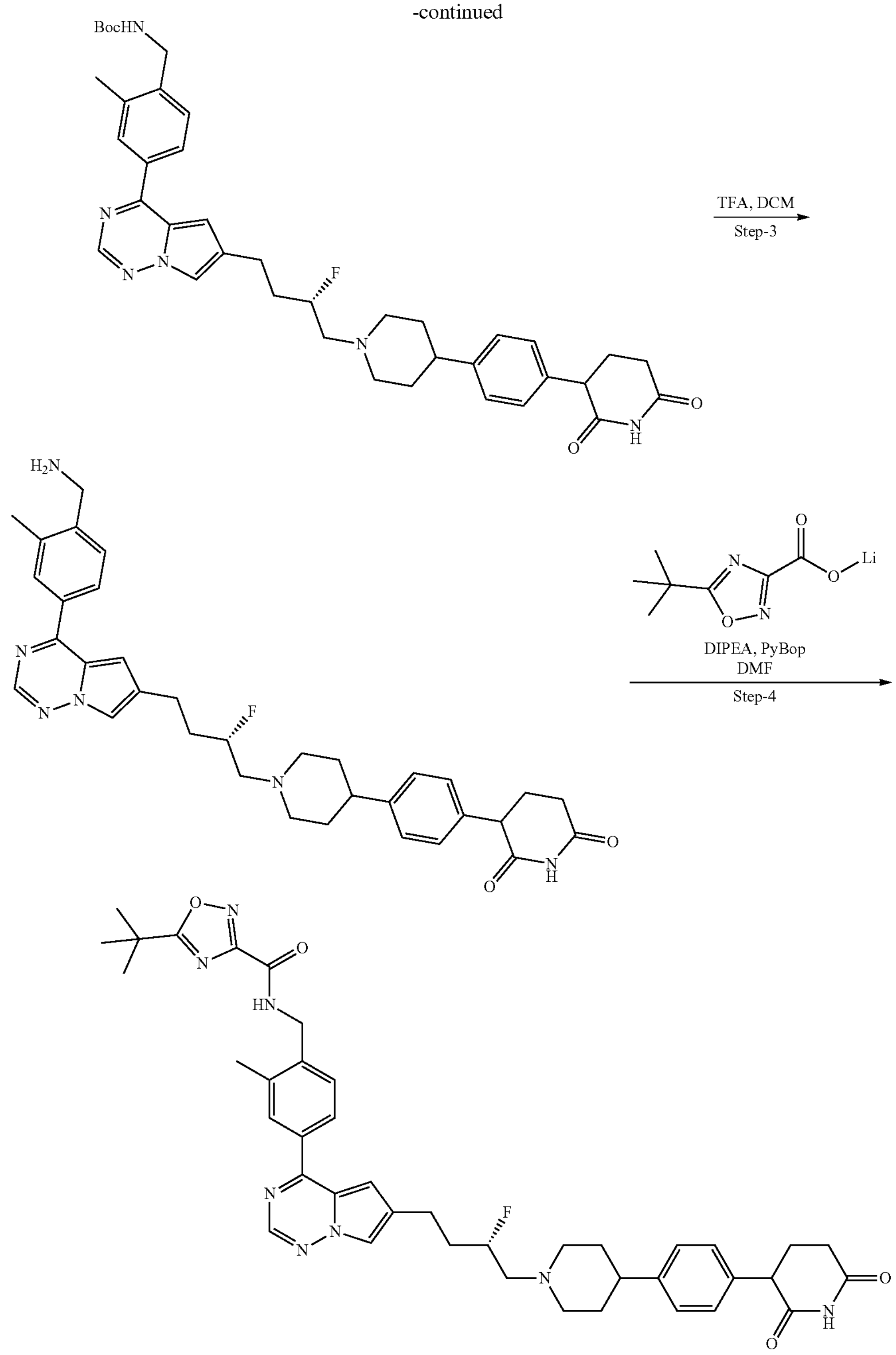

Step-1

To a solution of (S)-(−)-α,α-Diphenyl-2-pyrrolidinemethanol trimethylsilyl ether (20.35 mg, 48.96 μmol) and tert-butyl N-[[2-methyl-4-[6-(4-oxobutyl)pyrrolo[2,1-f][1,2,4]triazin-4-yl]phenyl]methyl]carbamate (0.4 g, 979.21 μmol) in MTBE (7.5 mL) and THF (2.5 mL) was added N-Fluorobenzenesulfonimide (277.91 mg, 881.29 μmol) at 0° C. and stirred for 16 hr at RT. The reaction mixture was quenched with sat. $NaHCO_3$ solution at 0° C. and extracted with MTBE (10 mL) and THF (10 mL). The combined organic layers were dried over anhydrous sodium sulfate, filtered and concentrated under reduced pressure to afford tert-butyl N-[[2-methyl-4-[6-[rac-(3S)-3-fluoro-4-oxo-butyl]pyrrolo[2,1-f][1,2,4]triazin-4-yl]phenyl]methyl]carbamate (0.4 g, 402.92 μmol, 41.15% yield) as the crude product directly used in the next step. LC-MS ($ES^+$): m/z 427.99 $[M+H]^+$.

Step-2:

In a 25 ml single neck RBF, 3-[4-(4-piperidyl)phenyl] piperidine-2,6-dione (543.56 mg, 1.41 mmol) was dissolved in DCM (21 mL) and acetonitrile (9 mL) followed by basified with triethyl amine (949.06 mg, 9.38 mmol, 1.31 mL). After 5 mins, tert-butyl N-[[2-methyl-4-[6-[rac-(3S)-3-fluoro-4-oxo-butyl]pyrrolo[2,1-f][1,2,4]triazin-4-yl]phenyl]methyl]carbamate (400.00 mg, 937.90 μmol) was added to the reaction mixture and allowed to stirred for 2 h at rt. Next, sodium triacetoxyborohydride (993.90 mg, 4.69 mmol) was added at 0° C., and the reaction was stirred at room temp for 16 hr. The reaction was monitored by TLC and LCMS. After completion of the reaction, the solvent was concentrated under reduced pressure, and crude mass was washed with sat. sodium bicarbonate solution. The obtained precipitate was filtered under vacuum and washed several times with diethyl ether. The solid crude was further purified by Prep. HPLC using ammonium acetate buffer to afford tert-butyl N-[[2-methyl-4-[6-[rac-(3S)-4-[4-[4-(2,6-dioxo-3-piperidyl)phenyl]-1-piperidyl]-3-fluoro-butyl]pyrrolo[2,1-f][1,2,4]triazin-4-yl]phenyl]methyl]carbamate (0.050 g, 71.85 μmol, 7.66% yield) as a light yellow solid. LC-MS ($ES^-$): m/z 681.28 $[M-H]^-$.

phenyl]piperidine-2,6-dione (0.047 g, 64.71 μmol, 94.02% yield). LC-MS ($ES^-$): m/z 581.36 $[M-H]^-$.

Step-4:

To a stirred solution of 3-[4-[1-[(2S)-4-[4-[4-(aminomethyl)-3-methyl-phenyl]pyrrolo[2,1-f][1,2,4]triazin-6-yl]-2-fluoro-butyl]-4-piperidyl]phenyl]piperidine-2,6-dione (45.00 mg, 72.68 μmol, HCl salt) and (5-tert-butyl-1,2,4-oxadiazole-3-carbonyl)oxylithium (15.36 mg, 87.22 μmol) in DMF (1 mL) was added DIPEA (93.93 mg, 726.80 μmol, 126.60 μL) and stirred it for 5 min at 0° C. PyBOP (75.64 mg, 145.36 μmol) was added next and reaction mixture was stirred at room temperature for 1 hr. The reaction was monitored by LCMS analysis. The reaction mixture was concentrated under reduced pressure to get the gummy crude. The crude material was purified by Prep. HPLC to afford 5-tert-butyl-N-[[4-[6-[(3S)-4-[4-[4-(2,6-dioxo-3-piperidyl)phenyl]-1-piperidyl]-3-fluoro-butyl]pyrrolo[2,1-f][1,2,4]triazin-4-yl]-2-methyl-phenyl]methyl]-1,2,4-oxadiazole-3-carboxamide (25 mg, 29.39 μmol, 40.44% yield). $^1$H-NMR (400 MHz, DMSO-$d_6$) δ 10.89 (s, 1H), 9.55-9.49 (m, 2H), 8.58 (s, 1H), 8.13 (s, 1H), 7.95 (d, J=7.2 Hz, 2H), 7.45 (d, J=8.4 Hz, 1H), 7.32-6.96 (m, 5H), 5.15-5.08 (m, 1H), 4.55 (d, J=8.0 Hz, 2H), 3.85-3.81 (m, 6H), 3.68-3.62 (m, 2H), 2.93-2.84 (m, 3H), 2.67-2.62 (m, 1H), 2.47 (s, 3H), 2.33-1.88 (m, 8H), 1.42 (s, 9H). LC-MS ($ES^+$): m/z 735.36 $[M+H]^+$.

Example 286

Example 286 was prepared following the synthesis of Example 285

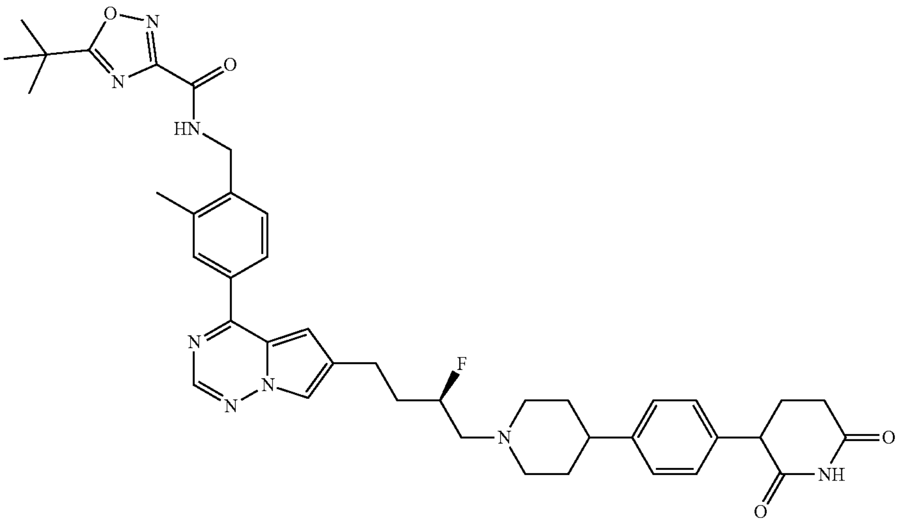 [SMILES: Cc1cc(-c2ncnn3cc(CC[C@@H](F)CN4CCC(c5ccc(C6CCC(=O)NC6=O)cc5)CC4)cc23)ccc1CNC(=O)c1noc(C(C)(C)C)n1]

Step-3:

To a stirred solution of tert-butyl N-[[4-[6-[(3S)-4-[4-[4-(2,6-dioxo-3-piperidyl)phenyl]-1-piperidyl]-3-fluoro-butyl]pyrrolo[2,1-f][1,2,4]triazin-4-yl]-2-methyl-phenyl]methyl] carbamate (0.047 g, 68.83 μmol) in DCM (10 mL) at 0° C., trifluoroacetic acid, 99% (592.00 mg, 5.19 mmol, 0.4 mL) was added dropwise. The reaction was stirred at 27° C. for 2 hr. The reaction was concentrated under reduced pressure to get crude. The crude was triturate with $Et_2O$ to get solid 3-[4-[1-[(2S)-4-[4-[4-(aminomethyl)-3-methyl-phenyl]pyrrolo[2,1-f][1,2,4]triazin-6-yl]-2-fluoro-butyl]-4-piperidyl]

5-(tert-butyl)-N-(4-(6-((3S)-4-(4-(4-(2,6-dioxopiperidin-3-yl)phenyl)piperidin-1-yl)-3-fluorobutyl)pyrrolo[2,1-f][1,2,4]triazin-4-yl)-2-methylbenzyl)-1,2,4-oxadiazole-3-carboxamide. (Stereochemistry was arbitrarily assigned) $^1$H-NMR (400 MHz, DMSO-$d_6$) δ 10.79 (s, 1H), 9.49 (t, J=6.0 Hz, 1H), 8.55 (s, 1H), 8.20-8.05 (m, 1H), 7.94 (d, J=8.0 Hz, 2H), 7.45 (d, J=8.0 Hz, 1H), 7.30-7.05 (m, 5H), 4.78 (d, J=5.0 Hz, 1H), 4.54 (d, J=5.6 Hz, 2H), 3.96-3.60 (m, 1H), 3.18-2.96 (m, 2H), 2.95-2.72 (m, 3H), 2.70-2.52 (m, 3H), 2.45 (s, 4H), 2.98-1.90 (m, 6H), 1.85-1.56 (m, 4H), 1.49 (s, 9H). LC-MS ($ES^+$): m/z 735.43 $[M+H]^+$.

Example 287

Example 287 was prepared following the synthesis of Example 285

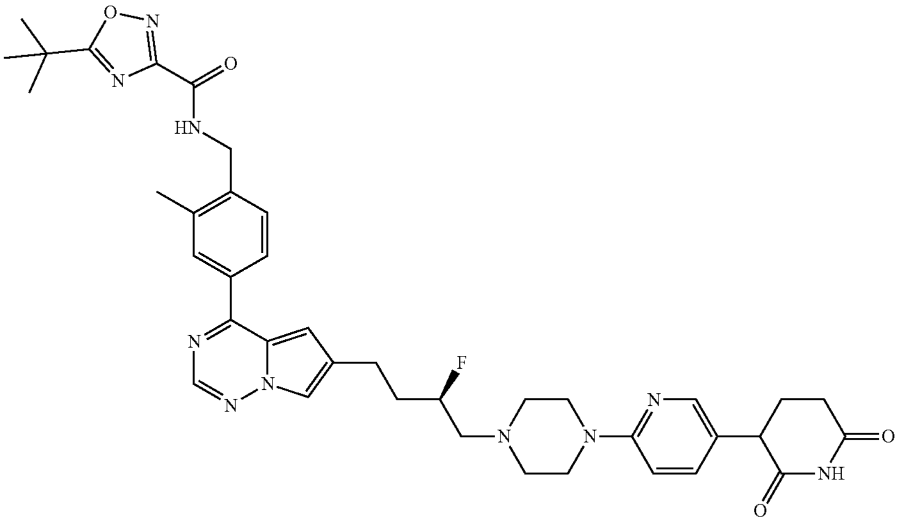 [SMILES: Cc1cc(-c2ncnn3cc(CC[C@@H](F)CN4CCN(c5ccc(C6CCC(=O)NC6=O)cn5)CC4)cc23)ccc1CNC(=O)c1noc(C(C)(C)C)n1]

5-(tert-butyl)-N-(4-(6-((3R)-4-(4-(5-(2,6-dioxopiperidin-3-yl)pyridin-2-yl)piperazin-1-yl)-3-fluorobutyl)pyrrolo[2,1-f][1,2,4]triazin-4-yl)-2-methylbenzyl)-1,2,4-oxadiazole-3-carboxamide. (Stereochemistry was arbitrarily assigned)

$^1$H-NMR (400 MHz, DMSO-$d_6$) δ 10.83 (s, 1H), 9.53 (t, J=6.0 Hz, 1H), 8.57 (s, 1H), 8.12 (s, 1H), 8.01 (d, J=2.0 Hz, 1H), 7.95 (d, J=7.2 Hz, 2H), 7.45 (d, J=8.4 Hz, 2H), 7.29-6.91 (m, 2H), 5.09 (d, J=54.4 Hz, 1H), 4.54 (d, J=6.0 Hz, 2H), 4.35 (br s, 2H), 3.40-2.70 (m, 13H), 2.46 (s, 3H), 2.25-1.98 (m, 4H), 1.45 (s, 9H). LC-MS ($ES^+$): m/z 737.27 $[M+H]^+$.

Example 288

The procedures of Step-1 to Step-3 in Example 288 were identical to those of Step-2 to Step-4 in Example 285.

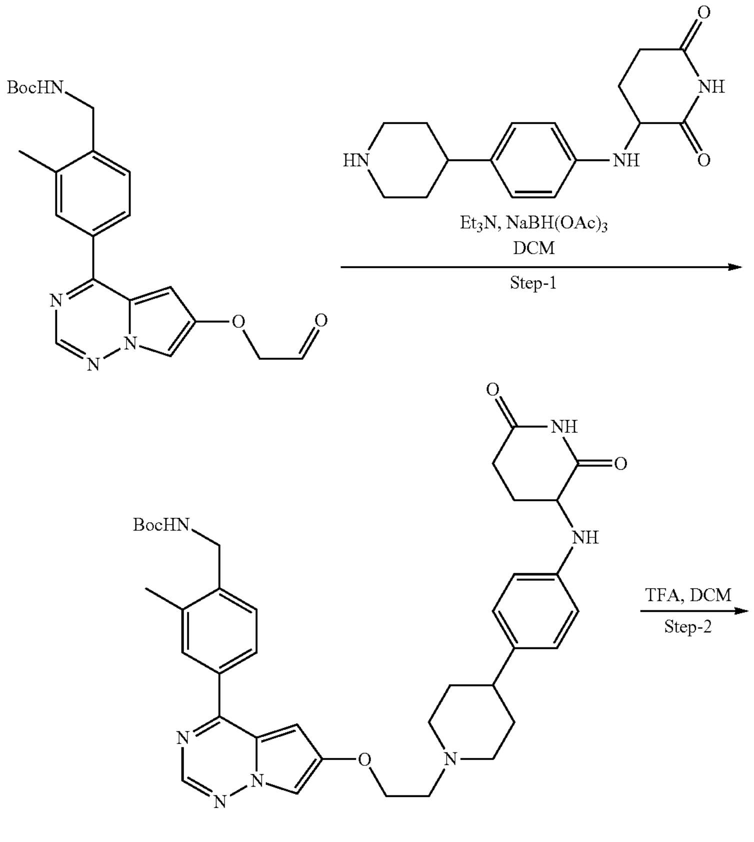

-continued

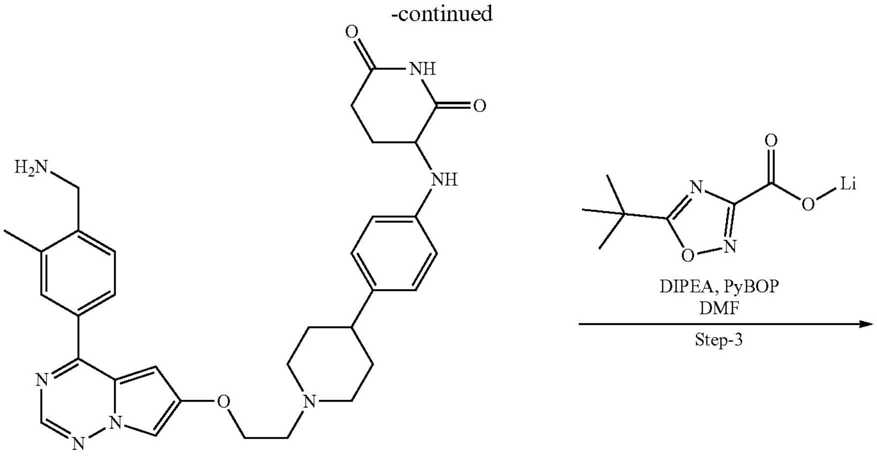

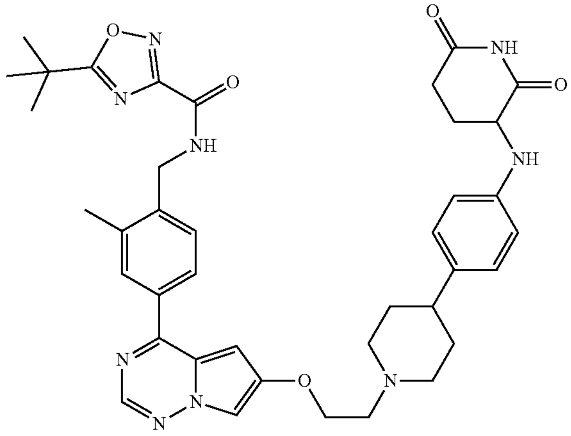

5-(tert-butyl)-N-(4-(6-(2-(4-(4-((2,6-dioxopiperidin-3-yl)amino)phenyl)piperidin-1-yl)ethoxy)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.78 (s, 1H), 9.53 (t, J=6.0 Hz, 2H), 8.62 (s, 1H), 8.13 (d, J=1.6 Hz, 1H), 7.93 (d, J=7.6 Hz, 1H), 7.93 (s, 1H), 7.45 (d, J=8.0 Hz, 1H), 6.96-6.93 (m, 3H), 6.64 (d, J=8.8 Hz, 2H), 5.55 (br s, 1H), 4.56-4.52 (m, 4H), 4.28 (dd, J=11.6, 4.8 Hz, 1H), 3.67 (d, J=11.6 Hz, 2H), 3.59 (br s, 2H), 3.17-3.14 (m, 2H), 2.74-2.60 (m, 3H), 2.46 (s, 3H), 2.11-2.07 (m, 1H), 1.98-1.89 (m, 5H), 1.44 (s, 9H). LC-MS ($ES^+$): $m/z$ 720.17 $[M+H]^+$.

Example 289

The procedures of Step-1 to Step-3 in Example 289 were identical to those of Step-2 to Step-4 in Example 285.

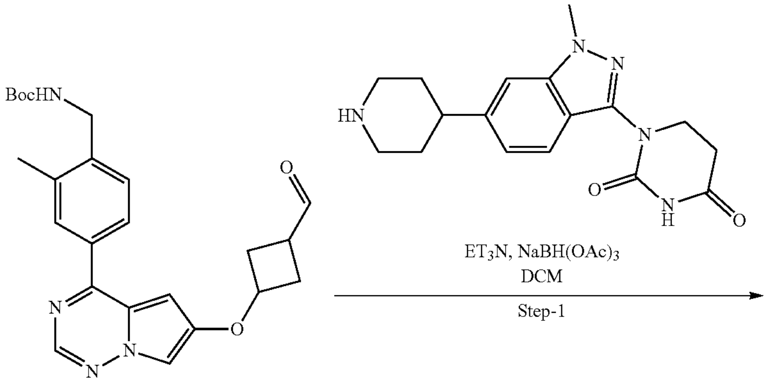

-continued
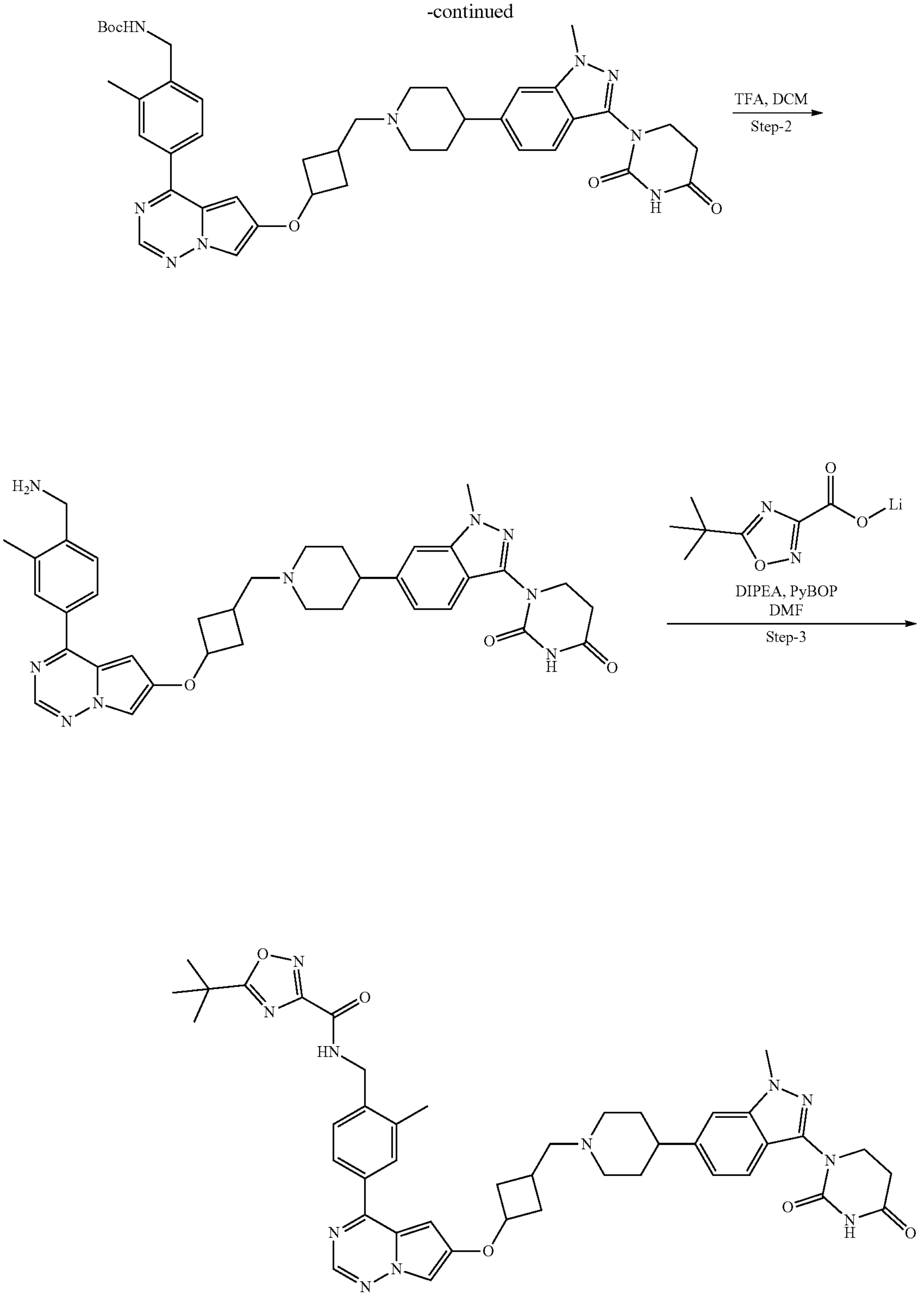
5-(tert-butyl)-N-(4-(6-(3-((4-(3-(2,4-dioxotetrahydropyrimidin-1(2H)-yl)-1-methyl-1H-indazol-6-yl)piperidin-1-yl)methyl)cyclobutoxy)pyrrolo[2,1-f][1,2,4]triazin-4-yl)-2-methylbenzyl)-1,2,4-oxadiazole-3-carboxamide. $^1$H NMR (400 MHz, DMSO-$d_6$) δ 10.50 (s, 1H), 9.40 (s, 1H), 8.57 (s, 1H), 7.96 (d, J=1.6 Hz, 1H), 7.93-7.91 (m, 2H), 7.54 (d, J=8.4 Hz, 1H), 7.45-7.43 (m, 2H), 7.03 (dd, J=8.6, 1.0 Hz, 1H), 6.71 (d, J=2.0 Hz, 1H), 4.92-4.90 (m, 1H), 4.55 (d, J=6.0 Hz, 2H), 3.96 (s, 3H), 3.92 (t, J=6.8 Hz, 2H), 2.98 (d, J=11.6 Hz, 2H), 2.76 (t, J=6.6 Hz, 2H), 2.67-2.54 (m, 4H), 2.49 (s, 3H), 2.33-2.22 (m, 4H), 2.08-2.03 (m, 2H), 1.78-1.74 (m, 4H), 1.43 (s, 9H). LC-MS (ES$^+$): $m/z$ 800.14 [M+H]$^+$.

Example 290. Synthesis of 5-(tert-butyl)-N-(8-(6-(4-(4-(3-(2,4-dioxotetrahydropyrimidin-1(2H)-yl)-1-methyl-1H-indazol-6-yl)piperidin-1-yl)butyl)pyrrolo[2,1-f][1,2,4]triazin-4-yl)-2,3,4,5-tetrahydrobenzo[b]oxepin-5-yl)-1,2,4-oxadiazole-3-carboxamide
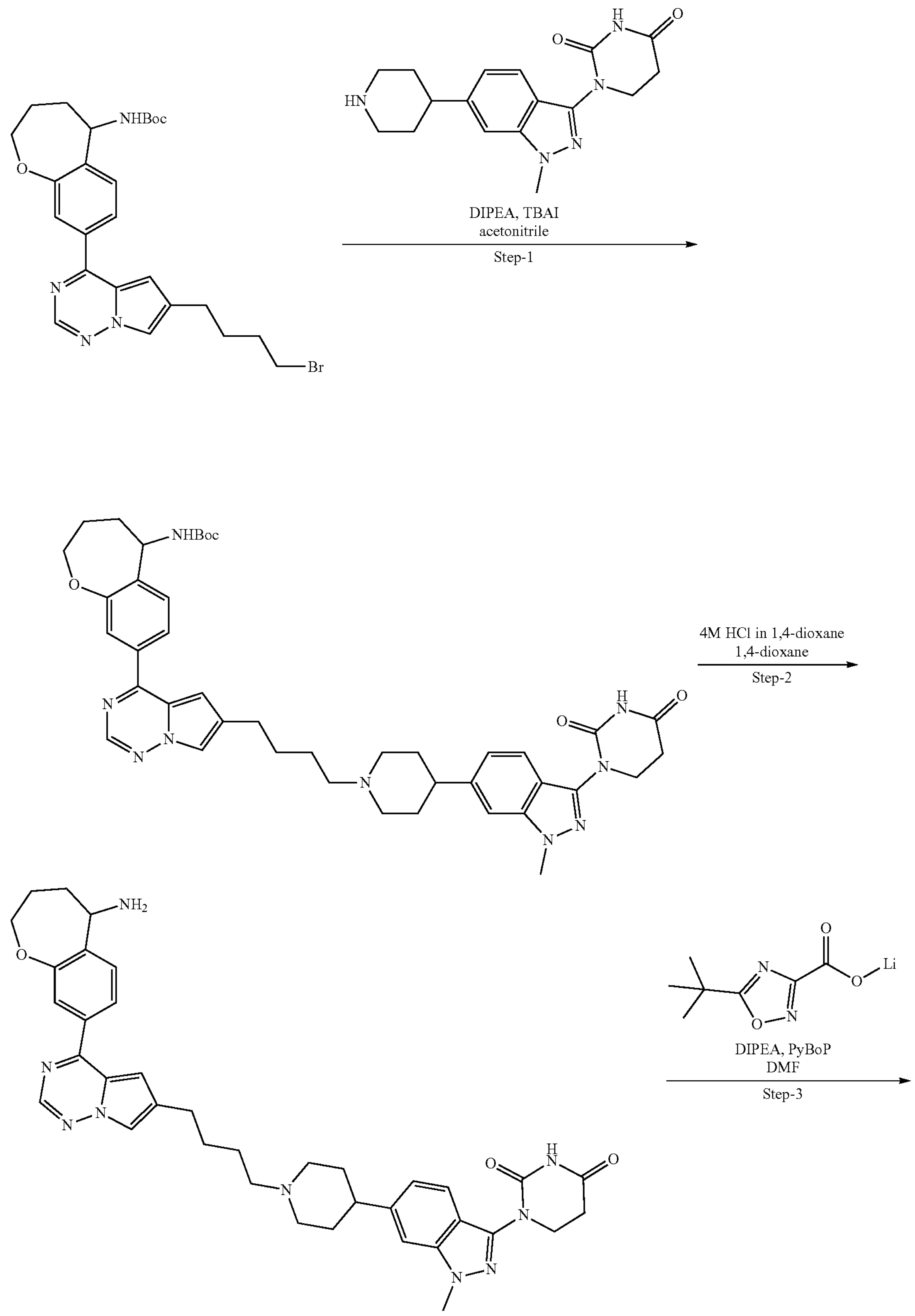

-continued

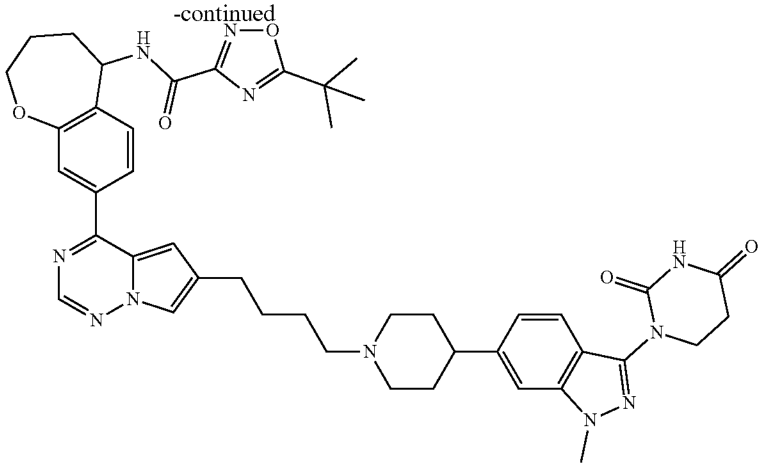

Step-1:

To a stirred solution of 1-(1-methyl-6-(piperidin-4-yl)-1H-indazol-3-yl)dihydropyrimidine-2,4-(1H,3H)-dione (70 mg, 158.59 μmol) in CAN (5 mL) was added DIPEA (102.48 mg, 792.93 μmol, 138.11 μL) followed by the addition of TBAI (5 mg, 1.07 mmol) and tert-butyl (8-(6-(4-bromobutyl)pyrrolo[2,1-f][1,2,4]triazin-4-yl)-2,3,4,5-tetrahydrobenzo[b]oxepin-5-yl)carbamate (119.79 mg, 232.40 μmol). The resulting reaction mixture was stirred at 80° C. for 4 h. The completion of reaction was monitored by LCMS. Upon completion, subsequently, the reaction mixture was concentrated under reduced pressure to get the crude product, which was triturated with diethyl ether to afford tert-butyl (8-(6-(4-(4-(3-(2,4-dioxotetrahydropyrimidin-1(2H)-yl)-1-methyl-1H-indazol-6-yl)piperidin-1-yl) butyl)pyrrolo[2,1-f][1,2,4]triazin-4-yl)-2,3,4,5-tetrahydrobenzo[b]oxepin-5-yl)carbamate (200 mg, 144.51 μmol). LC-MS ($ES^+$): m/z 762.69 $[M+H]^+$.

Step-2:

To a stirred solution of tert-butyl (8-(6-(4-(4-(3-(2,4-dioxotetrahydropyrimidin-1(2H)-yl)-1-methyl-1H-indazol-6-yl)piperidin-1-yl)butyl)pyrrolo[2,1-f][1,2,4]triazin-4-yl)-2,3,4,5-tetrahydrobenzo[b]oxepin-5-yl)carbamate (200 mg, 262.50 μmol) in 1,4-dioxane (5 mL) was added 4M 1,4-dioxane in HCl (262.50 μmol, 10 mL). The reaction mixture was stirred at RT for 3 h. The reaction progress was monitored by LCMS. Upon completion of reaction, the reaction mass was concentrated to get a crude mass, which was triturated to afford 1-(6-(1-(4-(4-(5-amino-2,3,4,5-tetrahydrobenzo[b]oxepin-8-yl)pyrrolo[2,1-f][1,2,4]triazin-6-yl)butyl)piperidin-4-yl)-1-methyl-1H-indazol-3-yl)dihydropyrimidine-2,4(1H,3H)-dione (180 mg, 243.76 μmol, 92.86% yield). LC-MS ($ES^+$): m/z 662.69 $[M+H]^+$.

Step-3:

To a solution of tert-butyl N-[8-[6-[4-[4-[3-(2,4-dioxohexahydropyrimidin-1-yl)-1-methyl-indazol-6-yl]-1-piperidyl]butyl]pyrrolo[2,1-f][1,2,4]triazin-4-yl]-2,3,4,5-tetrahydro-1-benzoxepin-5-yl]carbamate (140 mg, 175.36 μmol) in DMF (3 mL) was added DIPEA (226.64 mg, 1.75 mmol, 305.44 μL) and PyBOP (182.51 mg, 350.71 μmol) followed by (5-tert-butyl-1,2,4-oxadiazole-3-carbonyl)oxylithium (61.76 mg, 350.71 μmol) at room temperature. The reaction mixture was stirred under inert atmosphere at room temperature for 2 h. Upon mass conformation by LCMS, the reaction mixture was concentrated under reduced pressure to get the crude product, which was purified by reverse phase preparative HPLC to afford 5-(tert-butyl)-N-(8-(6-(4-(4-(3-(2,4-dioxotetrahydropyrimidin-1(2H)-yl)-1-methyl-1H-indazol-6-yl)piperidin-1-yl)butyl)pyrrolo[2,1-f][1,2,4]triazin-4-yl)-2,3,4,5-tetrahydrobenzo[b]oxepin-5-yl)-1,2,4-oxadiazole-3-carboxamide (0.0461 g, 49.58 μmol, 28.28% yield). $^1$H-NMR (400 MHz, DMSO-$d_6$) δ 10.55 (s, 1H), 9.54 (d, J=8.0 Hz, 1H), 9.00 (br s, 1H), 8.58 (s, 1H), 8.12 (s, 1H), 7.87 (dd, J=8.0, 8.4 Hz, 1H), 7.72 (d, J=1.6 Hz, 1H), 7.61 (d, J=8.8 Hz, 1H), 7.43 (d, J=8.0 Hz, 1H), 7.39 (s, 1H), 7.21 (s, 1H), 5.34 (t, J=8.2 Hz, 1H), 4.35 (d, J=12.0 Hz, 1H), 3.97 (s, 3H), 3.91 (t, J=6.6 Hz, 2H), 3.80-3.75 (m, 2H), 3.17 (br s, 2H), 3.04 (d, J=10.4 Hz, 4H), 2.80-2.79 (m, 2H), 2.75 (t, J=6.6 Hz, 2H), 2.09 (s, 2H), 2.08 (br s, 2H), 2.06 (br s, 2H), 2.12-1.99 (m, 2H), 1.96 (br s, 4H), 1.49 (s, 9H). LC-MS ($ES^+$): m/z 814.46 $[M+H]^+$.

$Na_2SO_4$ and concentrated to get crude. The crude was purified by Prep. HPLC to afforded 5-tert-butyl-N-[[4-[6-[4-[4-[4-(2,6-dioxo-3-piperidyl)phenyl]-1-piperidyl]but-1-ynyl]pyrrolo[2,1-f][1,2,4]triazin-4-yl]-2-methyl-phenyl]

Example 291. Synthesis of 5-(tert-butyl)-N-(4-(6-(4-(4-(4-(2,6-dioxopiperidin-3-yl)phenyl)piperidin-1-yl)but-1-yn-1-yl)pyrrolo[2,1-f][1,2,4]triazin-4-yl)-2-methylbenzyl)-1,2,4-oxadiazole-3-carboxamide

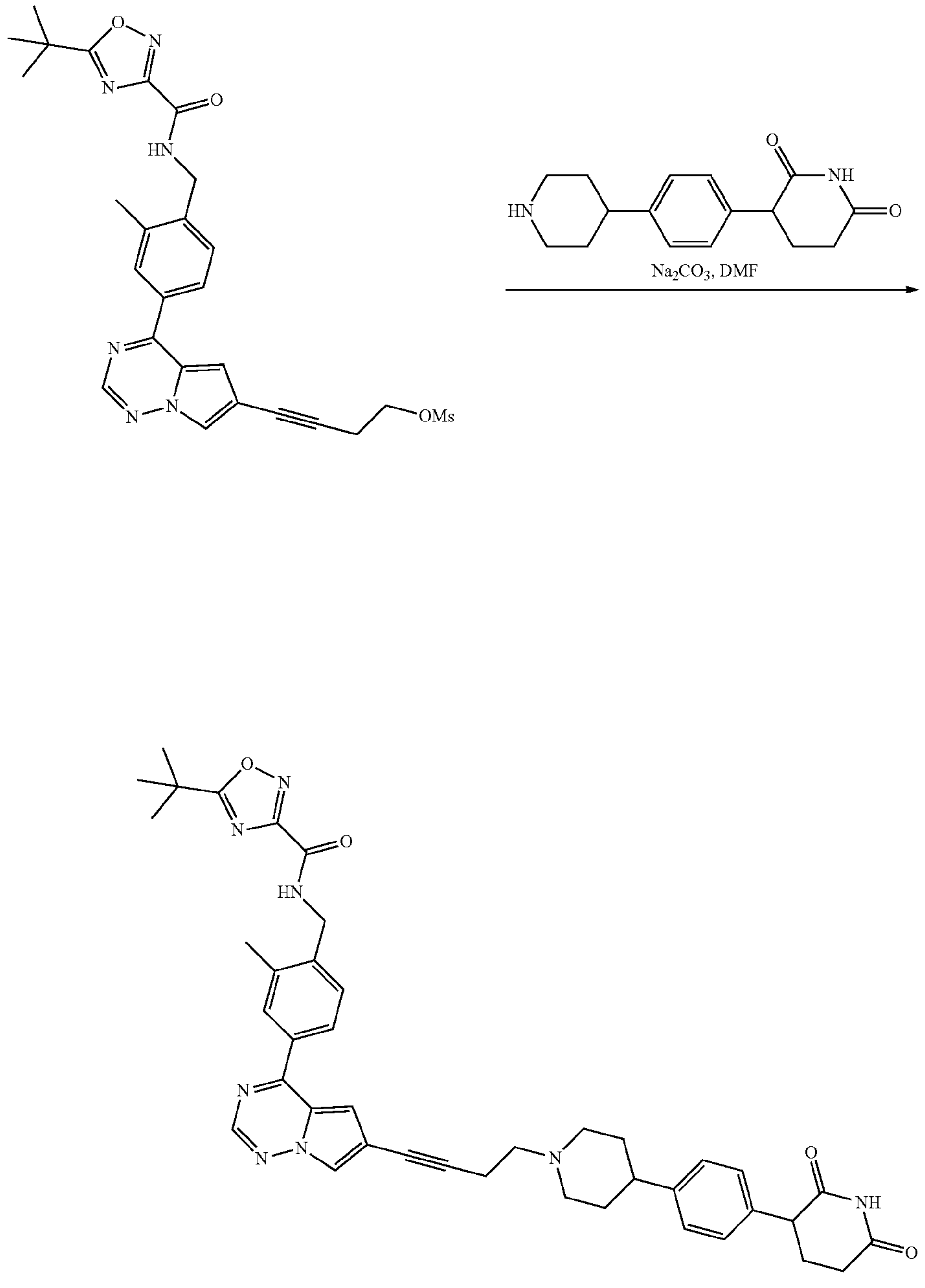

To a stirred solution of 3-[4-(4-piperidyl)phenyl]piperidine-2,6-dione (76.13 mg, 197.04 μmol) in DMF (2 mL) was added sodium bicarbonate (78.28 mg, 931.79 μmol, 36.24 μL) at 50° C. followed by solution of 3-[4-(4-piperidyl)phenyl]piperidine-2,6-dione (76.13 mg, 197.04 mol, TFA salt) in DMF (add in 2 lots). The reaction was stirred at same temperature for 16 h. The reaction was quenching with water and extracted was carried out using EtOAc. The organic layer was washed with water, brine solution, dried over methyl]-1,2,4-oxadiazole-3-carboxamide (27 mg, 32.24 μmol, 34.60% yield) as an pale yellow solid. $^1$H-NMR (400 MHz, DMSO-$d_6$) δ 10.83 (s, 1H), 9.53 (t, J=6.0 Hz, 1H), 9.43 (br s, 1H), 8.68 (s, 1H), 8.39 (s, 1H), 7.96 (d, J=6.4 Hz, 1H), 7.95 (s, 1H), 7.46 (d, J=8.4 Hz, 1H), 7.30 (s, 1H), 7.23-7.19 (m, 4H), 4.55 (d, J=6.0 Hz, 2H), 3.91-3.82 (m, 1H), 3.69 (d, J=11.6 Hz, 2H), 3.48-3.41 (m, 2H), 3.19-3.11 (m, 2H), 3.02 (t, J=7.4 Hz, 2H), 2.86-2.80 (m, 1H), 2.71-2.64 (m, 1H), 2.46 (s, 3H), 2.33-1.85 (m, 6H), 1.44 (s, 9H). LC-MS ($ES^+$): m/z 713.60 $[M+H]^+$.

Example 292. Synthesis of (S)-5-(tert-butyl)-N-(4-(6-(3-(3-(3-(2,4-dioxotetrahydropyrimidin-1(2H)-yl)-1-methyl-1H-indazol-6-yl)piperidin-1-yl)propoxy)pyrrolo[2,1-f][1,2,4]triazin-4-yl)-2-methylbenzyl)-1,2,4-oxadiazole-3-carboxamide (Stereochemistry was arbitrarily assigned)

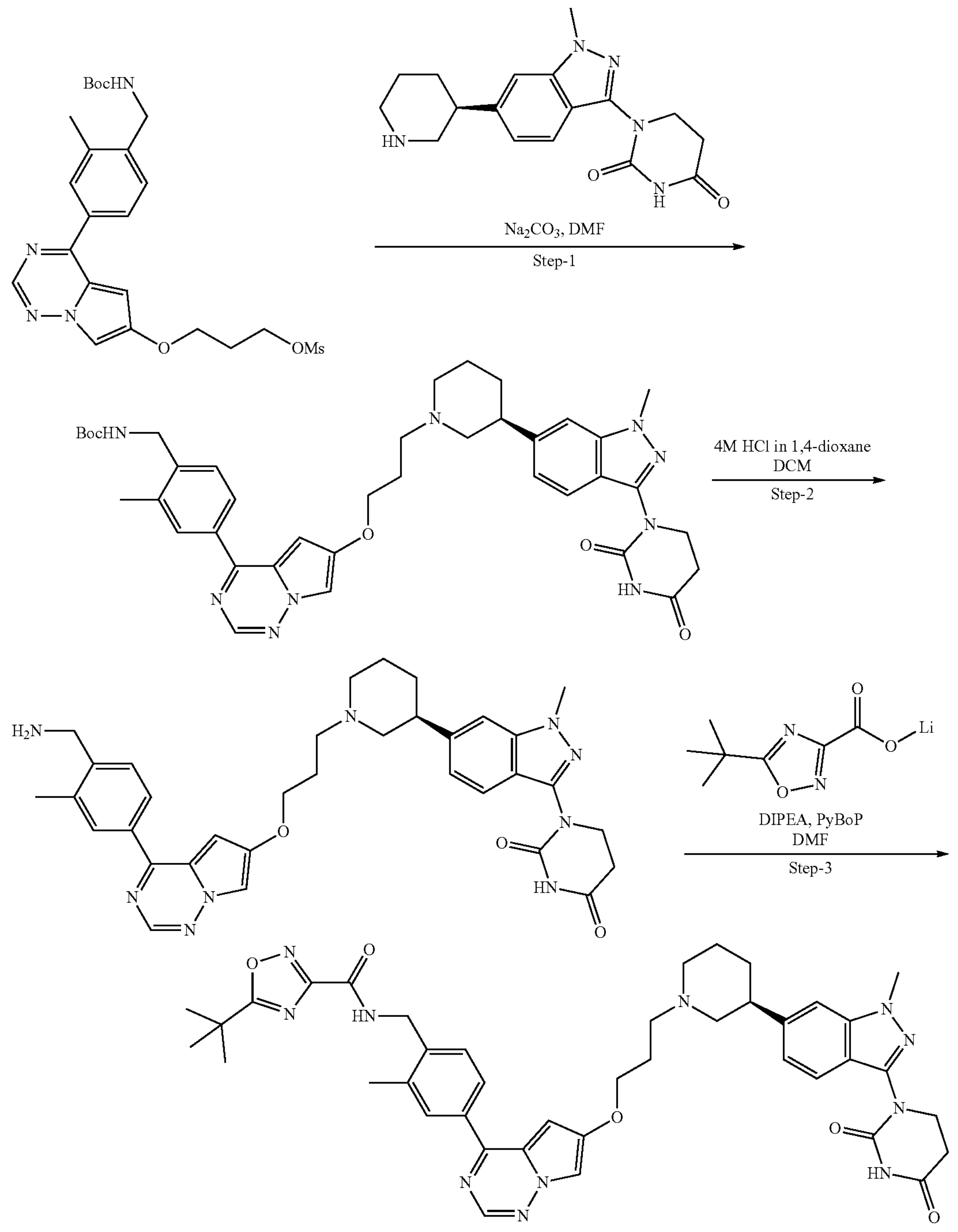

Step-1:

To a stirred solution of 1-[1-methyl-6-[rac-(3S)-3-piperidyl]indazol-3-yl]hexahydropyrimidine-2,4-dione (269.93 mg, 611.53 μmol) was added sodium bicarbonate (428.11 mg, 5.10 mmol, 198.29 μL) followed by the addition of 3-[4-[4-[(tert-butoxycarbonylamino)methyl]-3-methyl-phenyl]pyrrolo[2,1-f][1,2,4]triazin-6-yl]oxypropyl methanesulfonate (0.25 g, 509.61 μmol) and heated the reaction to 50° C. for 16 hr while monitoring by TLC and LCMS. After completion, the reaction was quenched with ice cold water to obtain solid. The solid was then filtered and triturated with diethyl ether to obtain tert-butyl N-[[4-[6-[3-[3-[3-(2,4-dioxohexahydropyrimidin-1-yl)-1-methyl-indazol-6-yl]-1-piperidyl]propoxy]pyrrolo[2,1-f][1,2,4]triazin-4-yl]-2-methyl-phenyl]methyl]carbamate (0.15 g, 139.23 μmol, 27.32% yield) as an yellow solid. LC-MS ($ES^+$): m/z 722.40 $[M+H]^+$.

Step-2:

To a stirred solution of tert-butyl N-[[4-[6-[3-[3-[3-(2,4-dioxohexahydropyrimidin-1-yl)-1-methyl-indazol-6-yl]-1-piperidyl]propoxy]pyrrolo[2,1-f][1,2,4]triazin-4-yl]-2-methyl-phenyl]methyl]carbamate (0.15 g, 207.80 μmol) in DCM (2 mL) at 0° C., 4M HCl in 1,4-dioxane (1.5 mL) was added dropwise. The reaction was stirred at 25° C. for 2 hr while monitoring by TLC and LCMS. After completion the reaction was concentrated under reduced pressure to get crude. The crude was triturate with $Et_2O$ and dried to afford 1-[6-[1-[3-[4-[4-(aminomethyl)-3-methyl-phenyl]pyrrolo[2,1-f][1,2,4]triazin-6-yl]oxypropyl]-3-piperidyl]-1-methyl-indazol-3-yl]hexahydropyrimidine-2,4-dione (0.15 g, 150.41 μmol, 72.38% yield) as an light yellow solid. LC-MS (ES$^+$): m/z 622.66 [M+H]$^+$.

Step-3:

To a stirred solution of 1-[1-methyl-6-[rac-(3S)-1-[3-[4-[4-(aminomethyl)-3-methyl-phenyl]pyrrolo[2,1-f][1,2,4]triazin-6-yl]oxypropyl]-3-piperidyl]indazol-3-yl]hexahydropyrimidine-2,4-dione (0.15 g, 227.90 μmol) in DMF (2 mL) was added DIPEA (294.53 mg, 2.28 mmol, 396.95 μL) and stirred for 5 mins followed by the addition of (5-tert-butyl-1,2,4-oxadiazole-3-carbonyl)oxylithium (80.26 mg, 455.79 μmol). Finally, PyBOP (177.89 mg, 341.85 μmol) was added to the RM and stirred at RT for 2 hrs. After completion, solvent was removed under reduced pressure and purified by prep HPLC to afford 5-tert-butyl-N-[[2-methyl-4-[6-[3-[rac-(3S)-3-[3-(2,4-dioxohexahydropyrimidin-1-yl)-1-methyl-indazol-6-yl]-1-piperidyl]propoxy]pyrrolo[2,1-f][1,2,4]triazin-4-yl]phenyl]methyl]-1,2,4-oxadiazole-3-carboxamide (16.1 mg, 17.53 μmol, 7.69% yield) as pale brown solid. $^1$H-NMR (400 MHz, DMSO-$d_6$) δ 10.52 (s, 1H), 9.51 (t, J=6.0 Hz, 1H), 8.57 (s, 1H), 8.13 (s, 1H), 8.04 (br s, 1H), 7.93 (s, 1H), 7.91 (s, 1H), 7.58 (d, J=8.0 Hz, 1H), 7.48 (s, 1H), 7.43 (d, J=8.0 Hz, 1H), 7.05 (d, J=8.4 Hz, 1H), 6.82 (s, 1H), 4.54 (d, J=5.6 Hz, 2H), 4.19 (br s, 1H), 3.97 (s, 3H), 3.91 (t, J=6.6 Hz, 2H), 3.30 (s, 2H), 3.35-2.87 (m, 3H), 2.75 (t, J=6.0 Hz, 4H), 2.40 (s, 3H), 2.08-2.07 (m, 2H), 1.92 (br s, 2H), 1.69 (br s, 2H), 1.43 (s, 9H). LC-MS (ES$^+$): m/z 774.61 [M+H]$^+$.

Example 293

Example 293 was prepared following the synthesis of Example 292

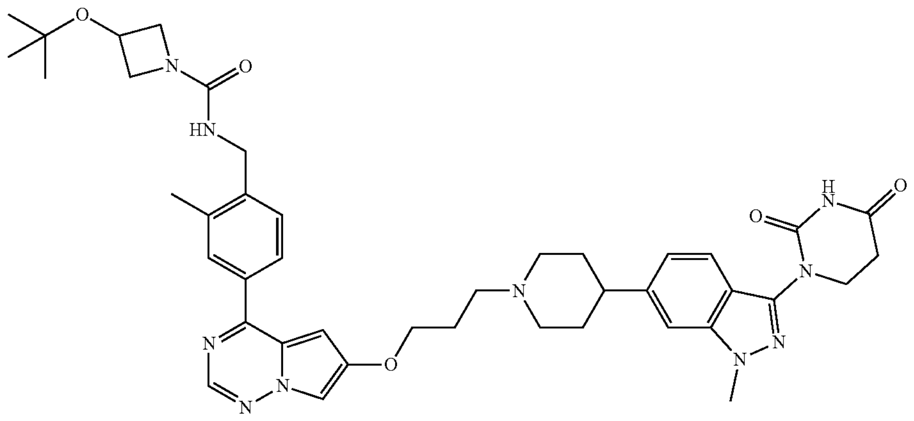 [SMILES: Cc1cc(-c2ncnn3cc(OCCCN4CCC(c5ccc6c(N7CCC(=O)NC7=O)nn(C)c6c5)CC4)cc23)ccc1CNC(=O)N1CC(OC(C)(C)C)C1]

3-(tert-butoxy)-N-(4-(6-(3-(4-(3-(2,4-dioxotetrahydropyrimidin-1(2H)-yl)-1-methyl-1H-indazol-6-yl)piperidin-1-yl)propoxy)pyrrolo[2,1-f][1,2,4]triazin-4-yl)-2-methylbenzyl)azetidine-1-carboxamide. $^1$H NMR (400 MHz, DMSO-$d_6$) δ 10.55 (s, 1H), 9.23 (br s, 1H), 8.59 (s, 1H), 8.07 (d, J=1.6 Hz, 1H), 7.93-7.88 (m, 2H), 7.61 (d, J=4.0 Hz, 1H), 7.45-7.40 (m, 2H), 7.03 (d, J=8.4 Hz, 1H), 6.90 (t, J=6.0 Hz, 1H), 6.85 (d, J=1.6 Hz, 1H), 4.46-4.45 (m, 1H), 4.26-4.23 (m, 4H), 4.06-4.02 (m, 2H), 3.98 (s, 3H), 3.91 (t, J=6.0 Hz, 2H), 3.70-3.59 (m, 4H), 3.31 (br s, 2H), 3.16-3.00 (m, 3H), 2.75 (t, J=6.8 Hz, 2H), 2.39 (s, 3H), 2.21-1.94 (m, 6H), 1.12 s, 9H). LC-MS (ES$^+$): m/z 777.46 [M+H]$^+$.

Example 294

Example 294 was prepared following the synthesis of Example 292

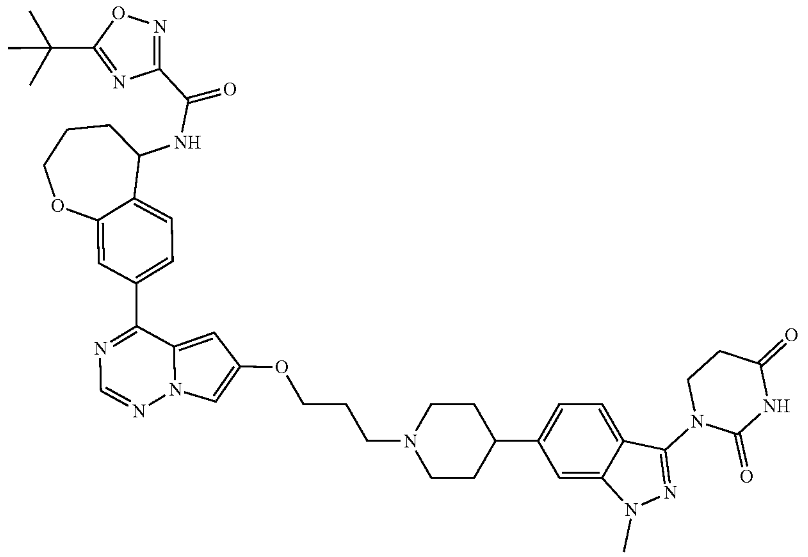 [SMILES: Cn1nc(N2CCC(=O)NC2=O)c2ccc(C3CCN(CCCOc4cc5c(-c6ccc7c(c6)OCCCC7NC(=O)c6noc(C(C)(C)C)n6)ncnn5c4)CC3)cc21]

5-(tert-butyl)-N-(8-(6-(3-(4-(3-(2,4-dioxotetrahydropyrimidin-1(2H)-yl)-1-methyl-1H-indazol-6-yl)piperidin-1-yl)propoxy)pyrrolo[2,1-f][1,2,4]triazin-4-yl)-2,3,4,5-tetrahydrobenzo[b]oxepin-5-yl)-1,2,4-oxadiazole-3-carboxamide. $^1$H-NMR (400 MHz, DMSO-d$^6$) 10.55 (s, 1H), 9.54 (d, J=8.4 Hz, 1H), 8.60 (s, 1H), 8.08 (d, J=1.6 Hz, 1H), 7.86 (dd, J=8.2, 1.4 Hz, 1H), 7.70 (d, J=1.6 Hz, 1H), 7.59 (d, J=8.4 Hz, 1H), 7.43 (s, 1H), 7.42 (d, J=8.0 Hz, 1H), 7.04 (d, J=8.4 Hz, 1H), 6.85 (d, J=1.2 Hz, 1H), 5.34 (t, J=8.2 Hz, 1H), 4.34 (d, J=12.0 Hz, 1H), 4.22 (br s, 2H), 3.97 (s, 3H), 3.91 (t, J=6.6 Hz, 2H), 3.78 (t, J=10.0 Hz, 1H), 3.32 (s, 2H), 3.15-2.74 (m, 6H), 2.46 (br s, 1H), 2.09-1.90 (m, 10H), 1.45 (s, 9H). LC-MS (ES$^+$): m/z 816.69 [M+H]$^+$.

Example 295. Synthesis of (S)-5-(tert-butyl)-N-(4-(6-(3-(4-(3-(2,4-dioxotetrahydropyrimidin-1(2H)-yl)-1-methyl-1H-indazol-6-yl)piperidin-1-yl)-2-fluoropropoxy)pyrrolo[2,1-f][1,2,4]triazin-4-yl)-2-methylbenzyl)-1,2,4-oxadiazole-3-carboxamide

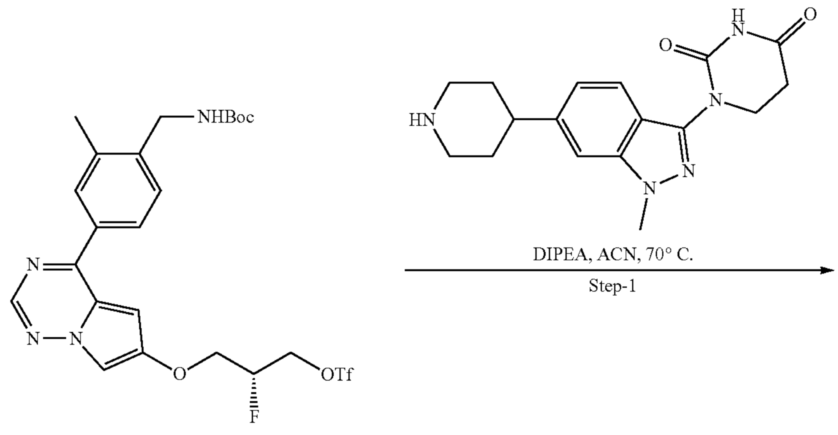

-continued
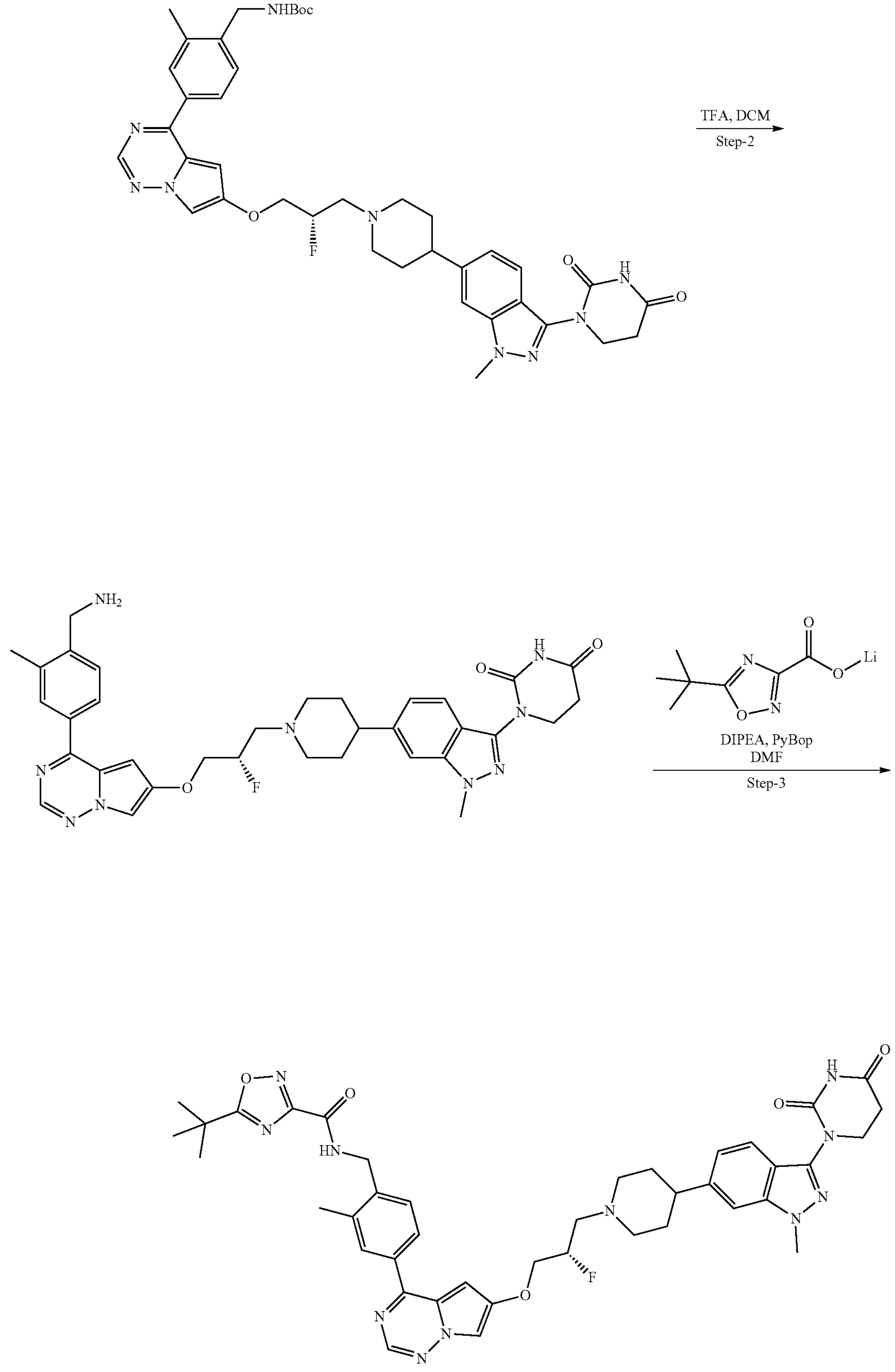

Step-1:

To a stirred solution of 1-[1-methyl-6-(4-piperidyl)indazol-3-yl]hexahydropyrimidine-2,4-dione (411.95 mg, 933.28 μmol) in acetonitrile (5 mL) was added DIPEA (804.13 mg, 6.22 mmol, 1.08 mL) followed by the addition of [rac-(2R)-3-[4-[4-[(tert-butoxycarbonylamino)methyl]-3-methyl-phenyl]pyrrolo[2,1-f][1,2,4]triazin-6-yl]oxy-2-fluoro-propyl] trifluoromethanesulfonate (0.35 g, 622.19 μmol) and stirred the reaction mixture to room temperature for 1 hr. After completion, the reaction mixture was diluted with water (100 mL) and extracted with 10% MeOH in DCM (50×3 ml). The combined organic layer was dried over sodium sulfate and concentrated under high vacuum to get crude product. The resulting crude was purified by column chromatography by using silica (230-400 mesh, 10% MeOH in DCM as mobile phase) to afforded tert-butyl N-[[2-methyl-4-[6-[rac-(2S)-3-[4-[3-(2,4-dioxohexahydropyrimidin-1-yl)-1-methyl-indazol-6-yl]-1-piperidyl]-2-fluoro-propoxy]pyrrolo[2,1-f][1,2,4]triazin-4-yl]phenyl]methyl] carbamate (0.14 g, 158.95 μmol, 25.55% yield) as a yellow solid. LC-MS ($ES^+$): m/z 740.29 $[M+H]^+$.

Step-2:

To a stirred solution of tert-butyl N-[[2-methyl-4-[6-[rac-(2S)-3-[4-[3-(2,4-dioxohexahydropyrimidin-1-yl)-1-methyl-indazol-6-yl]-1-piperidyl]-2-fluoro-propoxy]pyrrolo[2,1-f][1,2,4]triazin-4-yl]phenyl]methyl]carbamate (0.14 g, 189.23 mol) in DCM (3 mL) was added trifluoroacetic acid (1 mL) at 0° C. and stirred the reaction mixture at room temperature for 1 hr. After completion, the reaction mixture was concentrated under high vacuum to get crude product. The resulting crude was triturated with diethyl ether to afforded 1-[1-methyl-6-[1-[rac-(2S)-3-[4-[4-(aminomethyl)-3-methyl-phenyl]pyrrolo[2,1-f][1,2,4]triazin-6-yl]oxy-2-fluoro-propyl]-4-piperidyl]indazol-3-yl]hexahydropyrimidine-2,4-dione (0.14 g, 148.59 μmol, 78.52% yield) as a yellow solid.

Step-3:

To a stirred solution of 1-[1-methyl-6-[1-[rac-(2S)-3-[4-[4-(aminomethyl)-3-methyl-phenyl]pyrrolo[2,1-f][1,2,4]triazin-6-yl]oxy-2-fluoro-propyl]-4-piperidyl]indazol-3-yl] hexahydropyrimidine-2,4-dione (0.14 g, 204.16 μmol) in DMF (3 mL) was added DIPEA (263.86 mg, 2.04 mmol, 355.60 μL) followed by the addition of (5-tert-butyl-1,2,4-oxadiazole-3-carbonyl)oxylithium (53.93 mg, 306.24 μmol) at 0° C. and stirred at room temperature for 1 h. After completion, the reaction mixture was concentrated under high vacuum to get crude product. The resulting crude was purified by prep. HPLC to afforded 5-tert-butyl-N-[[2-methyl-4-[6-[rac-(2S)-3-[4-[3-(2,4-dioxohexahydropyrimidin-1-yl)-1-methyl-indazol-6-yl]-1-piperidyl]-2-fluoro-propoxy]pyrrolo[2,1-f][1,2,4]triazin-4-yl]phenyl]methyl]-1,2,4-oxadiazole-3-carboxamide (20.2 mg, 23.71 μmol, 11.61% yield) as an pale yellow solid. $^1$H-NMR (400 MHz, DMSO-$d_6$) δ 10.54 (s, 1H), 9.50, (s, 1H), 8.59 (s, 1H), 8.16 (s, 1H), 8.10 (d, J=1.2 Hz, 1H), 8.02-7.89 (m, 2H), 7.54 (d, J=8.4 Hz, 1H), 7.49-7.38 (m, 2H), 7.03 (d, J=8.8 Hz, 1H), 6.89 (d, J=1.6 Hz, 1H), 5.07 (d, J=50.4 Hz, 1H), 4.53 (d, J=6.0 Hz, 2H), 4.42-4.28 (m, 2H), 3.96 (s, 3H), 3.90 (t, J=6.8 Hz, 2H), 3.15-3.0 (m, 2H), 2.74 (t, J=6.8 Hz, 2H), 2.70-2.60 (m, 3H), 2.45 (s, 3H), 2.32-2.21 (m, 2H), 1.79 (s, 4H), 1.43 (s, 9H). LC-MS ($ES^+$): m/z 792.25 $[M+H]^+$.

Example 296

Example 296 was prepared following the synthesis of Example 295

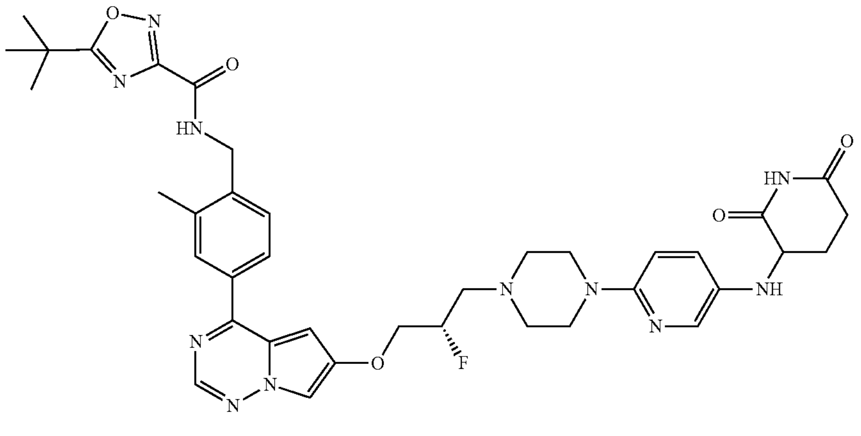 [SMILES: Cc1cc(-c2ncnn3cc(OC[C@@H](F)CN4CCN(c5ccc(NC6CCC(=O)NC6=O)cn5)CC4)cc23)ccc1CNC(=O)c1noc(C(C)(C)C)n1]

5-(tert-butyl)-N-(4-(6-((2S)-3-(4-(5-((2,6-dioxopiperidin-3-yl)amino)pyridin-2-yl)piperazin-1-yl)-2-fluoropropoxy) pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.48 (s, 1H), 9.50 (t, J=6.0 Hz, 1H), 8.58 (s, 1H), 8.18-8.02 (m, 1H), 8.04-7.55 (m, 2H), 7.43 (d, J=8.6 Hz, 1H), 7.80-7.62 (m, 1H), 7.18-6.98 (m, 1H), 6.96-6.80 (m, 1H), 6.68 (d, J=9.2 Hz, 1H), 5.41 (d, J=7.6 Hz, 1H), 5.10 (d, J=8.8 Hz, 1H), 4.53 (d, J=6.0 Hz, 2H), 4.45-4.15 (m, 3H), 3.26 (br s, 4H), 2.80-2.68 (m, 3H), 2.65-2.55 (m, 5H), 2.45 (s, 3H), 2.12-2.07 (m, 1H), 1.98-1.72 (m, 1H), 1.43 (s, 9H). LC-MS ($ES^+$): m/z 754.59 $[M+H]^+$.

Example 297. Synthesis of 5-(tert-butyl)-N-(4-(6-(4-(4-(3-(2,4-dioxotetrahydropyrimidin-1(2H)-yl)-1-methyl-1H-indazol-6-yl)butyl)piperazin-1-yl)pyrrolo[2,1-f][1,2,4]triazin-4-yl)-2-methylbenzyl)-1,2,4-oxadiazole-3-carboxamide

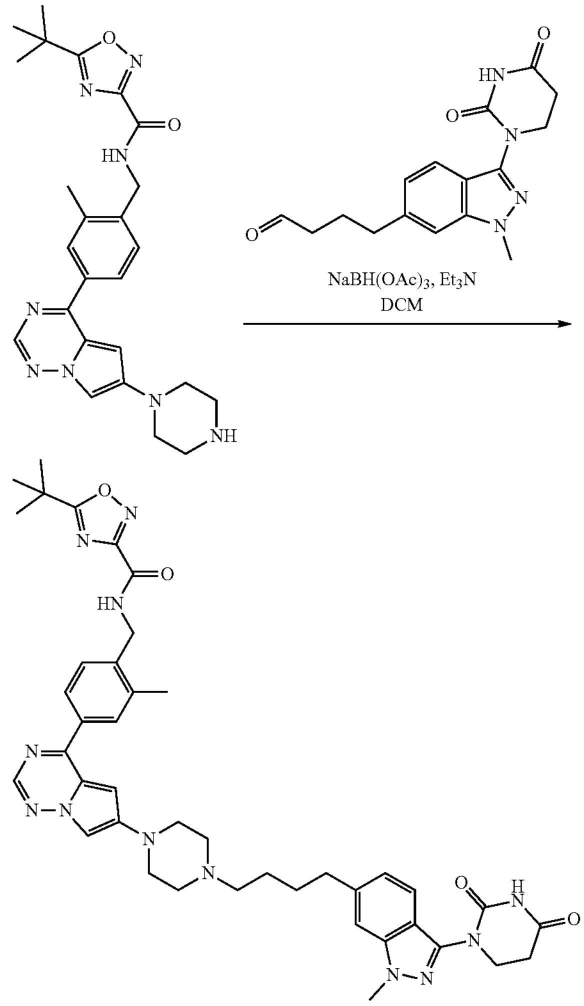

To a stirred solution of 5-tert-butyl-N-[[2-methyl-4-(6-piperazin-1-ylpyrrolo[2,1-f][1,2,4]triazin-4-yl)phenyl]methyl]-1,2,4-oxadiazole-3-carboxamide (70 mg, 118.93 mol) in dichloroethane (10 mL) at 0° C. under argon atmosphere was added triethyl amine (120.35 mg, 1.19 mmol, 165.77 μL) (pH should be basic) and sodium triacetoxyborohydride (126.03 mg, 594.65 μmol), the reaction mixture was stirred at rt for 18 hr. Upon completion, solvent was evaporated to dryness to obtained crude mass. Crude compound was purified by prep HPLC and lyophilized to yield desired product 5-tert-butyl-N-[[4-[6-[4-[4-[3-(2,4-dioxohexahydropyrimidin-1-yl)-1-methyl-indazol-6-yl]butyl]piperazin-1-yl]pyrrolo[2,1-f][1,2,4]triazin-4-yl]-2-methyl-phenyl]methyl]-1,2,4-oxadiazole-3-carboxamide (55.2 mg, 61.43 mol, 51.65% yield) as a yellow solid. $^1$H NMR (400 MHz, DMSO-$d_6$) δ 10.54 (s, 1H), 9.53 (br s, 2H), 8.51 (s, 1H), 8.06 (s, 1H), 7.94-7.91 (m, 2H), 7.57 (d, J=8.4 Hz, 1H), 7.43-7.42 (m, 2H), 7.01 (d, J=8.4 Hz, 1H), 6.81 (s, 2H), 4.54 (d, J=6.0 Hz, 1H), 3.96 (s, 3H), 3.92-3.89 (m, 4H), 3.57-3.54 (m, 2H), 3.10-3.18 (m, 4H), 3.07-3.01 (m, 2H), 2.78-2.73 (m, 4H), 2.50 (s, 3H), 1.69 (br s, 4H), 1.43 (s, 9H). LC-MS (ES$^+$): m/z 773.47 [M+H]$^+$.

Example 298. Synthesis of 5-(tert-butyl)-N-(4-(6-(1-(2-(4-(5-(2,6-dioxopiperidin-3-yl)pyridin-2-yl)piperazin-1-yl)ethyl)-1H-pyrazol-4-yl)pyrrolo[2,1-f][1,2,4]triazin-4-yl)-2-methylbenzyl)-1,2,4-oxadiazole-3-carboxamide

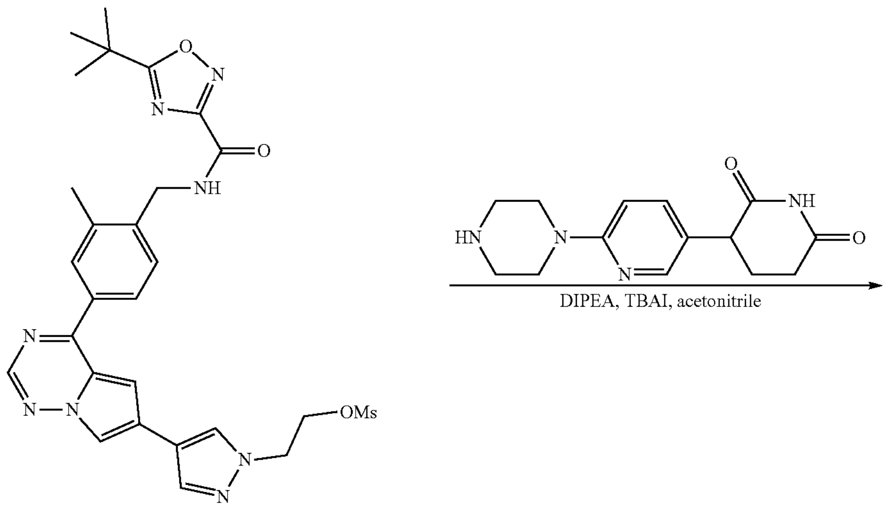

-continued

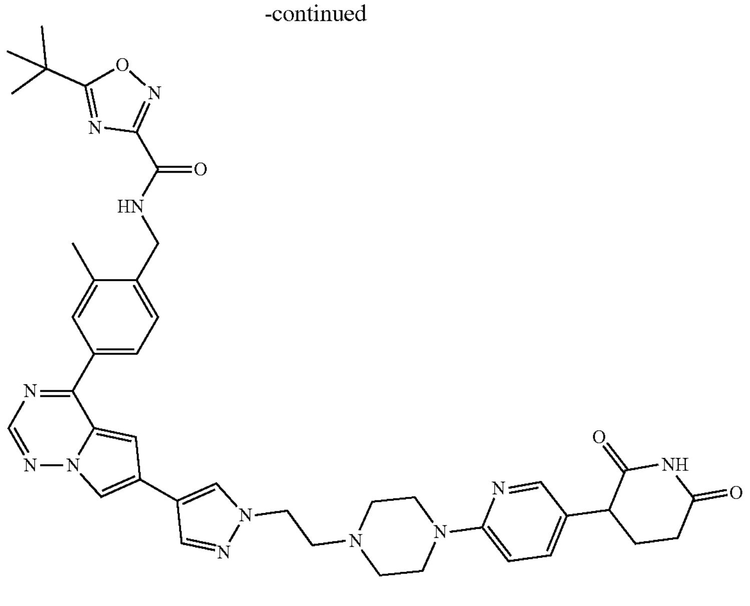

518.46 µmol) in acetonitrile (5 mL) at rt under argon. DIPEA (335.03 mg, 2.59 mmol, 451.52 L), 2-[4-[4-[4-[1 [(5-tert-butyl-1,2,4-oxadiazole-3-carbonyl)amino]methyl]-3-methyl-phenyl]pyrrolo[2,1-f][1,2,4]triazin-6-yl]pyrazol-1-yl]ethyl methanesulfonate (0.25 g, 432.05 mol) and tetrabutylammonium iodide (31.92 mg, 86.41 µmol) were added into the solution and the solution was stirred at 80° C. for 16 hr. The progress of the reaction was monitored by LCMS. The reaction mixture was concentrated under reduced pressure to get the crude product. The crude was washed with sodium bicarbonate solution and extracted with EtOAc (3x20 mL), The combined organic layer was dried over sodium sulfate and concentrated under reduced pressure to get crude. crude purified by prep-HPLC using 0.05% TFA as buffer to afforded 5-tert-butyl-N-[[4-[6-[1-[2-[4-[5-(2,6-dioxo-3-piperidyl)-2-pyridyl]piperazin-1-yl]ethyl] pyrazol-4-yl]pyrrolo[2,1-f][1,2,4]triazin-4-yl]-2-methyl-phenyl]methyl]-1,2,4-oxadiazole-3-carboxamide (74.56 mg, 83.95 µmol, 19.43% yield) as a yellow solid. $^1$H-NMR (400 MHz, DMSO-$d_6$) δ 10.55 (s, 1H), 9.53 (d, J=6.0 Hz, 1H), 8.58 (s, 1H), 8.50 (d, J=1.6 Hz, 1H), 8.33 (s, 1H), 8.12 (s, 1H), 8.02-7.97 (m, 3H), 7.53-7.42 (m, 3H), 6.96 (s, 1H), 4.60 (t, J=6.4 Hz, 2H), 4.56 (d, J=6.0 Hz, 2H), 4.36 (br s, 1H), 3.81-3.77 (m, 6H), 3.18-3.16 (m, 4H), 2.73-2.64 (m, 1H), 2.54-2.53 (m, 1H), 2.48 (s, 3H), 2.22-2.19 (m, 1H), 1.98-1.94 (m, 1H), 1.44 (s, 9H). LC-MS (ES$^+$): m/z 757.33 [M+H]$^+$.

Example 299

Example 299 was prepared following the synthesis of Example 298

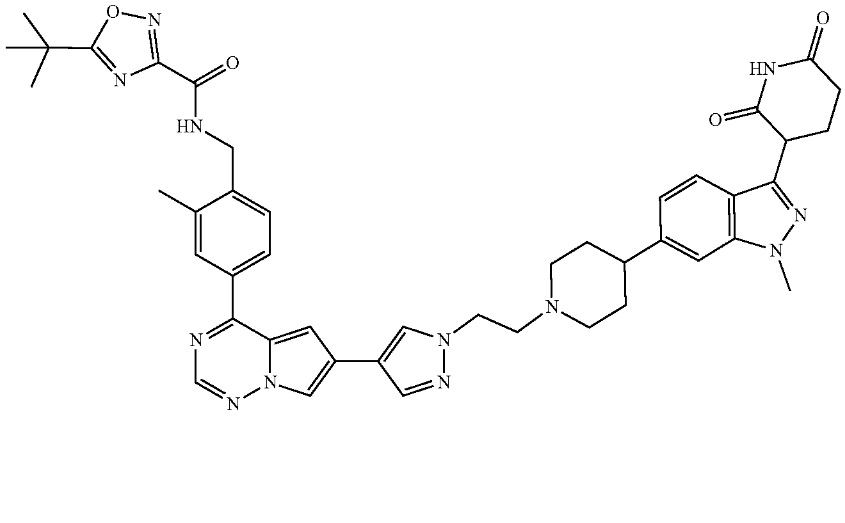 [SMILES: Cc1cc(-c2ncnn3cc(-c4cnn(CCN5CCC(c6ccc7c(C8CCC(=O)NC8=O)nn(C)c7c6)CC5)c4)cc23)ccc1CNC(=O)c1noc(C(C)(C)C)n1]

5-(tert-butyl)-N-(4-(6-(1-(2-(4-(3-(2,6-dioxopiperidin-3-yl)-1-methyl-1H-indazol-6-yl)piperidin-1-yl)ethyl)-1H-pyrazol-4-yl)pyrrolo[2,1-f][1,2,4]triazin-4-yl)-2-methylbenzyl)-1,2,4-oxadiazole-3-carboxamide. $^1$H-NMR (400 MHz, DMSO-$d_6$) δ 10.88 (s, 1H), 9.54 (t, J=6.4 Hz, 1H), 9.43 (s, 1H), 8.58 (s, 1H), 8.51 (d, J=1.2 Hz, 1H), 8.36 (s, 1H), 8.13 (s, 1H), 8.00-7.97 (m, 2H), 7.66 (d, J=8.4 Hz, 1H), 7.54-7.40 (m, 2H), 7.21-6.96 (m, 1H), 4.65-4.55 (m, 4H), 4.35-4.32 (m, 1H), 3.98 (s, 3H), 3.73-3.56 (m, 4H), 3.24-3.18 (m, 2H), 3.12-2.96 (m, 2H), 2.72-2.62 (m, 2H), 2.48 (s, 3H), 2.37-2.32 (m, 1H), 2.18-1.95 (m, 5H), 1.43 (s, 9H). LC-MS (ES$^+$): m/z 809.42 [M+H]$^+$.

Example 300

Example 300 was prepared following the synthesis of Example 163

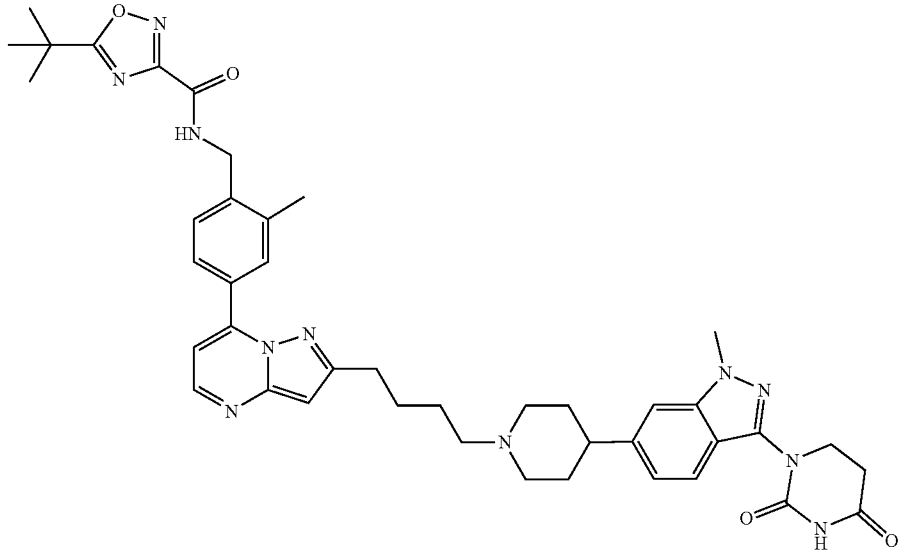 [SMILES: Cc1cc(-c2ccnc3cc(CCCCN4CCC(c5ccc6c(N7CCC(=O)NC7=O)nn(C)c6c5)CC4)nn23)ccc1CNC(=O)c1noc(C(C)(C)C)n1]

5-(tert-butyl)-N-(4-(2-(4-(4-(3-(2,4-dioxotetrahydropyrimidin-1(2H)-yl)-1-methyl-1H-indazol-6-yl)piperidin-1-yl)butyl)pyrazolo[1,5-a]pyrimidin-7-yl)-2-methylbenzyl)-1,2,4-oxadiazole-3-carboxamide. $^1$H-NMR (400 MHz, DMSO-$d_6$) δ 10.55 (s, 1H), 9.55-9.50 (m, 1H), 8.54 (d, J=4.4 Hz, 1H), 7.96-7.90 (m, 2H), 7.61 (d, J=8.4 Hz, 1H), 7.44-7.38 (m, 2H), 7.12 (d, J=4.4 Hz, 1H), 7.01 (d, J=8.8 Hz, 1H), 6.69 (s, 1H), 4.53 (d, J=6.0 Hz, 2H), 3.97 (s, 3H), 3.90 (t, J=6.6 Hz, 2H), 3.62-3.60 (m, 2H), 3.16-3.10 (m, 2H), 3.09-2.98 (m, 3H), 2.86-2.80 (m, 2H), 2.75 (t, J=6.6 Hz, 2H), 2.43 (s, 3H), 2.07-2.00 (m, 2H), 1.95-1.89 (m, 2H), 1.76 (s, 4H), 1.42 (s, 9H). LC-MS (ES$^+$): m/z 770.55 [M−H]$^-$.

VI. Compound Testing and Data

Selected compounds were tested in a BTK degradation assay using the HiBiT Method. $DC_{50}$ values at each protein are given in Table 6.

Materials

Park Memorial Institute (RPM1) 1640 Medium with phenol red, L-Glutamine, Sodium Pyruvate, and fetal bovine serum (FBS) were purchased from Gibco (Grand Island, NY, USA). Nano-Glo® HiBiT Lytic Assay System was purchased from Promega (Madison, WI, USA). GM01501 cells were obtained from the NIGMS Human Genetic Cell Repository at the Coriell Institute for Medical Research. The GM01501.3 cell line endogenously expresses BTK with a HiBiT fusion tag via CRISPR knock-in at its C-terminal region. It was engineered by electroporation with the Neon Transfection System (Themo Fisher Scientific), according to manufacturer indications. Electroporation conditions: 1 pulse of 1,350 V for 30 ms for 0.5x10_6 cells. Cell culture flasks and 384-well microplates were acquired from VWR (Radnor, PA, USA).

BTK Degradation Analysis

BTK degradation was evaluated by quantification of luminescent signal using Nano-Glo® HiBiT Lytic Assay kit. Test compounds were added to the 384-well plate from a top concentration of 10 μM with 11 points, half log titration in duplicates. GM01501.3 cells were added into 384-well plates at a cell density of 10,000 cells per well in a total volume of 30 μl. The plates were kept at 37° C. with 5% $CO_2$ for 6 hours. Negative control wells included cells treated with DMSO only and positive control wells included only growing media, without Nano-Glo® HiBiT Lytic reagent. After a 6-hour incubation, Nano-Glo® HiBiT Lytic Assay reagent was added to the cells following manufacturer indications. Luminescence was acquired on EnVision™ Multilabel Reader (PerkinElmer, Santa Clara, CA, USA). Table 6 shows the activity of selected compounds of this invention in the in vitro Btk kinase assay, wherein each compound number corresponds to the compound numbering set forth in Examples 1-300 described herein. "++++" represents a $DC_{50}$ value of less than 100 nM. "+++" represents a $DC_{50}$ value of 100 nM-500 nM. "++" represents a $DC_{50}$ value of 500 nM-1000 nM. "+" represents a $DC_{50}$ value of greater than 1000 nM.

TABLE 6

| Example | $DC_{50}$ (nM) |
|---|---|
| 1 | ++++ |
| 2 | ++++ |
| 3 | ++++ |
| 4 | ++++ |
| 5 | ++++ |

TABLE 6-continued

| Example | $DC_{50}$ (nM) |
|---|---|
| 6 | ++++ |
| 7 | ++++ |
| 8 | +++ |
| 9 | ++++ |
| 10 | ++++ |
| 11 | ++++ |
| 12 | ++++ |
| 13 | ++++ |
| 14 | ++++ |
| 15 | ++++ |
| 16 | ++++ |
| 17 | ++++ |
| 18 | ++++ |
| 19 | ++++ |
| 20 | ++++ |
| 21 | ++++ |
| 22 | ++++ |
| 23 | ++++ |
| 24 | ++++ |
| 25 | ++++ |
| 26 | ++++ |
| 27 | ++++ |
| 28 | ++++ |
| 29 | ++++ |
| 30 | ++++ |
| 31 | ++++ |
| 32 | ++++ |
| 33 | ++++ |
| 34 | ++++ |
| 35 | ++++ |
| 36 | ++++ |
| 37 | +++ |
| 38 | ++++ |
| 39 | +++ |
| 40 | ++++ |
| 41 | ++++ |
| 42 | ++++ |
| 43 | ++++ |
| 44 | ++++ |
| 45 | ++++ |
| 46 | ++++ |
| 47 | ++++ |
| 48 | ++++ |
| 49 | ++++ |
| 50 | ++++ |
| 51 | ++++ |
| 52 | ++++ |
| 53 | ++++ |
| 54 | ++++ |
| 55 | ++++ |
| 56 | ++++ |
| 57 | ++++ |
| 58 | ++++ |
| 59 | ++++ |
| 60 | ++++ |
| 61 | ++++ |
| 62 | ++++ |
| 63 | ++++ |
| 64 | ++++ |
| 65 | ++++ |
| 66 | ++++ |
| 67 | ++++ |
| 68 | ++++ |
| 69 | ++++ |
| 70 | ++++ |
| 71 | ++++ |
| 72 | ++++ |
| 73 | ++++ |
| 74 | ++++ |
| 75 | ++++ |
| 76 | ++++ |
| 77 | ++++ |
| 78 | ++++ |
| 79 | ++++ |
| 80 | ++++ |
| 81 | ++++ |
| 82 | ++++ |
| 83 | ++++ |

TABLE 6-continued

| Example | $DC_{50}$ (nM) |
|---|---|
| 84 | ++++ |
| 85 | ++++ |
| 86 | ++++ |
| 87 | ++++ |
| 88 | ++++ |
| 89 | ++++ |
| 90 | ++++ |
| 91 | ++++ |
| 92 | ++++ |
| 93 | ++++ |
| 94 | ++++ |
| 95 | ++++ |
| 96 | ++++ |
| 97 | ++++ |
| 98 | ++++ |
| 99 | ++++ |
| 100 | ++++ |
| 101 | ++++ |
| 102 | ++++ |
| 103 | ++++ |
| 104 | ++++ |
| 105 | ++++ |
| 106 | ++++ |
| 107 | ++++ |
| 108 | ++++ |
| 109 | ++++ |
| 110 | ++++ |
| 111 | ++++ |
| 112 | ++++ |
| 113 | ++++ |
| 114 | ++++ |
| 115 | ++++ |
| 116 | ++++ |
| 117 | ++++ |
| 118 | ++++ |
| 119 | ++++ |
| 120 | ++++ |
| 121 | +++ |
| 122 | ++++ |
| 123 | +++ |
| 124 | ++++ |
| 125 | ++++ |
| 126 | +++ |
| 127 | ++++ |
| 128 | ++++ |
| 129 | ++++ |
| 130 | ++++ |
| 131 | ++++ |
| 132 | ++++ |
| 133 | ++++ |
| 134 | ++++ |
| 135 | ++++ |
| 136 | ++++ |
| 137 | ++++ |
| 138 | ++++ |
| 139 | ++++ |
| 140 | ++++ |
| 141 | ++++ |
| 143 | ++++ |
| 144 | ++++ |
| 145 | ++++ |
| 146 | +++ |
| 147 | +++ |
| 148 | +++ |
| 149 | +++ |
| 150 | +++ |
| 151 | +++ |
| 152 | ++++ |
| 153 | ++++ |
| 154 | ++++ |
| 155 | ++++ |
| 156 | ++++ |
| 157 | +++ |
| 158 | +++ |
| 159 | +++ |
| 160 | + |
| 161 | ++++ |
| 162 | ++++ |

TABLE 6-continued

| Example | $DC_{50}$ (nM) |
|---|---|
| 163 | ++++ |
| 164 | ++++ |
| 165 | ++++ |
| 166 | ++++ |
| 167 | ++++ |
| 168 | ++++ |
| 169 | +++ |
| 170 | ++++ |
| 171 | ++++ |
| 172 | +++ |
| 173 | +++ |
| 174 | ++++ |
| 175 | +++ |
| 176 | +++ |
| 177 | + |
| 178 | ++++ |
| 179 | +++ |
| 180 | ++++ |
| 181 | ++++ |
| 182 | ++++ |
| 183 | ++++ |
| 184 | ++++ |
| 185 | ++++ |
| 186 | ++++ |
| 187 | ++++ |
| 188 | ++++ |
| 189 | ++++ |
| 190 | ++++ |
| 191 | ++++ |
| 192 | ++++ |
| 193 | ++++ |
| 194 | ++++ |
| 195 | ++++ |
| 196 | ++++ |
| 197 | ++++ |
| 198 | ++++ |
| 199 | ++++ |
| 200 | ++++ |
| 201 | ++++ |
| 202 | ++++ |
| 203 | ++++ |
| 204 | +++ |
| 205 | ++++ |
| 206 | ++++ |
| 207 | ++++ |
| 208 | ++++ |
| 209 | ++++ |
| 210 | +++ |
| 211 | ++++ |
| 212 | +++ |
| 213 | ++++ |
| 214 | ++++ |
| 215 | ++++ |
| 216 | ++++ |
| 217 | ++++ |
| 218 | +++ |
| 219 | ++++ |
| 220 | ++++ |
| 221 | ++++ |
| 222 | ++++ |
| 223 | ++++ |
| 224 | ++++ |
| 225 | + |
| 226 | ++++ |
| 227 | +++ |
| 228 | +++ |
| 229 | ++++ |
| 230 | ++++ |
| 231 | +++ |
| 232 | +++ |
| 233 | ++++ |
| 234 | ++++ |
| 235 | ++++ |
| 236 | ++++ |
| 237 | ++++ |
| 238 | ++++ |
| 239 | ++++ |
| 240 | ++++ |

TABLE 6-continued

| Example | $DC_{50}$ (nM) |
|---|---|
| 241 | ++++ |
| 242 | ++++ |
| 243 | ++++ |
| 244 | ++++ |
| 245 | ++++ |
| 246 | ++++ |
| 247 | ++++ |
| 248 | ++++ |
| 250 | ++++ |
| 251 | ++++ |
| 252 | ++++ |
| 253 | ++++ |
| 254 | ++++ |
| 255 | ++++ |
| 256 | ++++ |
| 257 | ++++ |
| 258 | ++++ |
| 259 | ++++ |
| 260 | ++++ |
| 261 | ++++ |
| 262 | ++++ |
| 263 | ++++ |
| 264 | ++++ |
| 265 | ++++ |
| 266 | ++++ |
| 267 | ++++ |
| 268 | ++++ |
| 269 | ++++ |
| 270 | ++++ |
| 271 | ++++ |
| 272 | + |
| 273 | ++++ |
| 274 | ++++ |
| 275 | ++++ |
| 278 | ++++ |
| 279 | ++++ |
| 280 | ++++ |
| 281 | ++++ |
| 282 | ++++ |
| 283 | ++++ |
| 286 | ++++ |
| 287 | ++++ |
| 288 | ++++ |
| 289 | ++++ |
| 290 | ++++ |
| 291 | +++ |
| 292 | ++++ |
| 293 | ++++ |
| 294 | ++++ |
| 295 | ++++ |
| 296 | ++++ |
| 297 | ++++ |
| 298 | ++++ |
| 299 | ++++ |
| 300 | ++++ |

* DC50 for HiBiT Degradation on GM01501.3 BTK @ 6 hours (nM)

OTHER EMBODIMENTS

All of the features disclosed in this specification may be combined in any combination. Each feature disclosed in this specification may be replaced by an alternative feature serving the same, equivalent or similar purpose. Thus, unless expressly stated otherwise, each feature disclosed is only an example of a series of equivalent or similar features.

From the above description, one skilled in the art can easily ascertain the essential characteristics of the present invention, and without departing from the spirit and scope thereof, can make various changes and modifications of the invention to adapt it to various usage and conditions. Thus, other embodiments are also within the scope of the following claims.

What is claimed is:

1. A compound, wherein the compound is represented by formula (A-Ia-1):

(A-1a-1)

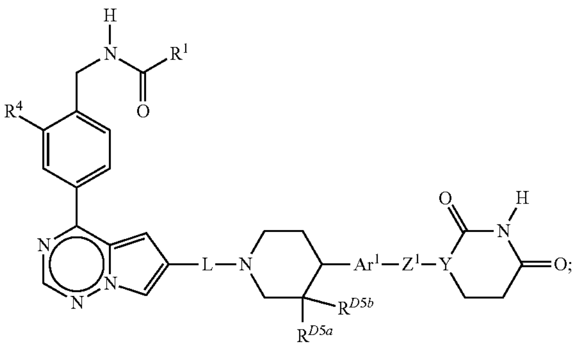

or a pharmaceutically acceptable salt thereof, wherein:

$R^1$ is phenyl, 1,2,4-oxadiazolyl, pyrazolyl, triazolyl, or azetidinyl, each of which is optionally substituted with 1 to 3 $R^{10}$;

$R^{10}$ is $C_{1-4}$ alkyl, $C_{1-4}$ haloalkyl or $C_{3-6}$ cycloalkyl optionally substituted with 1 to 3 halogen;

$R^4$ is selected from H, $C_{1-4}$ alkyl, halogen and —$OR^{4a}$, $R^{4a}$ is $C_{1-4}$ alkyl;

$Ar^1$ is phenyl, pyrazoyl, pyrazolo-pyridinyl, pyridinyl, pyrimidinyl, pyridazinyl, benzoisoxazolyl, benzo[cd]indol-2 (1H)-onyl, imidazo-pyridinyl or indazolyl, each or which is optionally substituted with 1 or 2 halogen;

$Z^1$ is a bond, $CH_2$, NH or O;

$R^{D5a}$ and $R^{D5b}$ are each independently H, OH, F or —$OCH_3$;

Y is CH, $C(CH_3)$ or —N—; and

L is represented by the following formula:

(L-2A)

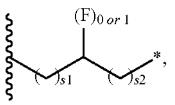

wherein:

*— represents a bond to the piperidine ring;

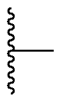

represents a bond to the pyrrolo[2,1-f][1,2,4]triazine ring;

s1 is 0 or an integer from 1 to 4; and s2 is 0 or an integer from 1 to 4.

2. The compound of claim 1, or a pharmaceutically acceptable salt thereof, wherein:

$R^1$ is represented by the following formula:

(C4)

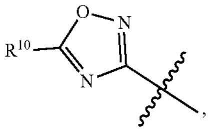

(C23)

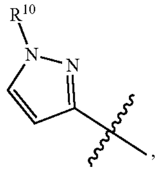

(C24)

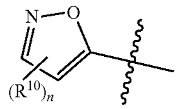

(C25)

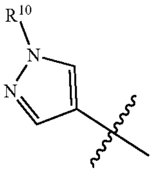

or (C26)

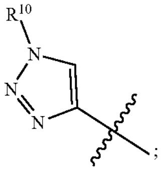

$Ar^1$ is

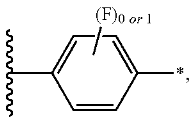

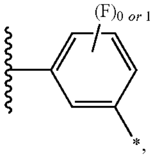

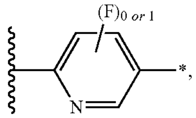

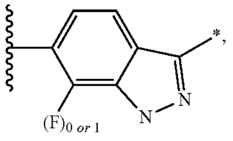

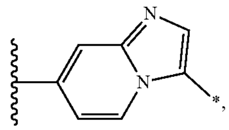

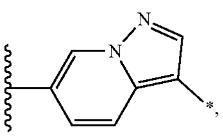

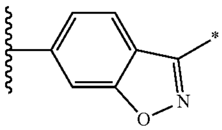

or

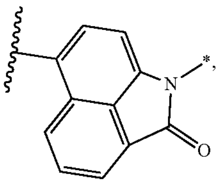

wherein *— represents a bond to $Z^1$.

3. The compound of claim 1, wherein the compound is represented by the following formula:

(A-V)

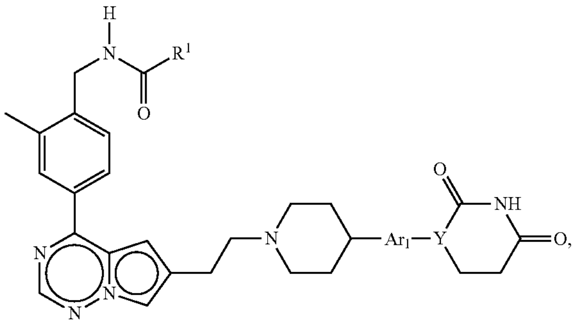

or a pharmaceutically acceptable salt thereof, wherein:

$R^1$ is 1,2,4-oxadiazolyl or triazolyl, each of which is substituted with $R^{10}$, wherein $R^{10}$ is $C_{1-4}$alkyl;

Y is N or CH; and $Ar_1$ is indozolyl or benzoisoxazolyl, each of which is optionally substituted with 1 or 2 substituents independently selected from halo and $C_{1-2}$alkyl.

4. A pharmaceutical composition comprising a compound of claim 1, or a pharmaceutically acceptable salt thereof, and a pharmaceutically acceptable excipient.

5. The compound of claim 1, wherein the compound is represented by formula (A-Ia):

(A-1a)

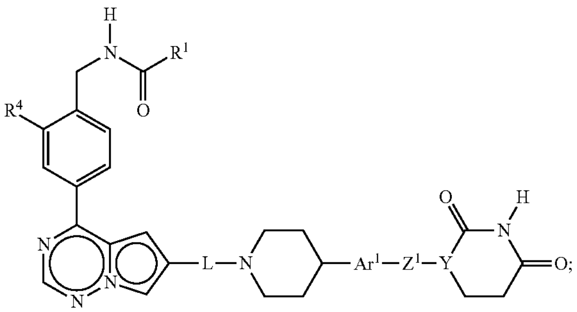

or a pharmaceutically acceptable salt thereof, wherein:

$R^1$ is phenyl, 1,2,4-oxadiazolyl, pyrazolyl, or azetidinyl, each of which is optionally substituted with 1 to 3 $R^{10}$;

$R^{10}$ is $C_{1-4}$ alkyl, $C_{1-4}$ haloalkyl or $C_{3-6}$ cycloalkyl optionally substituted with 1 to 3 halogen;

$R^4$ is selected from H, $C_{1-4}$ alkyl, halogen and —$OR^{4a}$, and $R^{4a}$ is $C_{1-4}$ alkyl;

$Ar^1$ is phenyl, pyrazoyl, pyridinyl, pyrimidinyl, pyridazinyl, or indazolyl, each or which is optionally substituted with 1 or 2 halogen;

$Z^1$ is a bond, NH or O; and

Y is CH, $C(CH_3)$ or —N—.

6. The compound of claim 1, or a pharmaceutically acceptable salt thereof, wherein $R^1$ is represented by the following formula:

(C4)

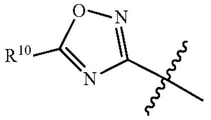

, or (C23)

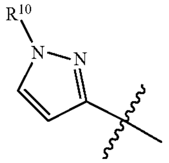

, and $Ar^1$ is 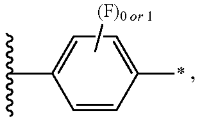 , 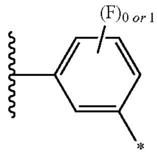 , or

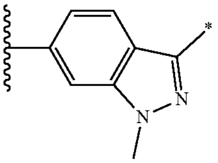

, wherein *— represents a bond to $Z^1$.

7. The compound of claim 1, or a pharmaceutically acceptable salt thereof, wherein:

$R^{10}$ is —$C(CH_3)_3$ or

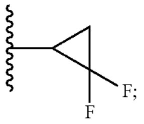 [SMILES: *C1CC1(F)F]

$R^4$ is F or —$CH_3$; and

Y is CH or N.

8. The compound of claim 3, or a pharmaceutically acceptable salt thereof, wherein:

(C4)

$R^1$ is 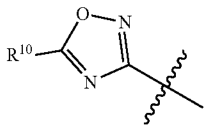 or (C26)

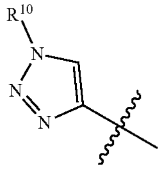

; and $Ar_1$ is 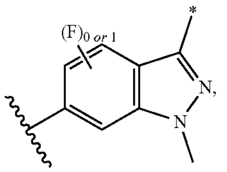 or 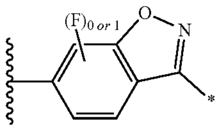 , wherein *— represents a bond to Y.

9. The compound of claim 3, or a pharmaceutically acceptable salt thereof, wherein $R^{10}$ is —$C(CH_3)_3$.
10. The compound of claim 8, or a pharmaceutically acceptable salt thereof, wherein $R^{10}$ is —$C(CH_3)_3$.
11. The compound of claim 1, wherein the compound is:
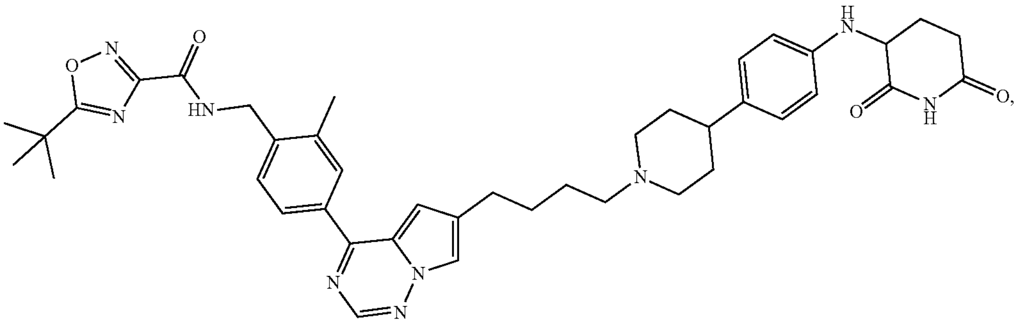
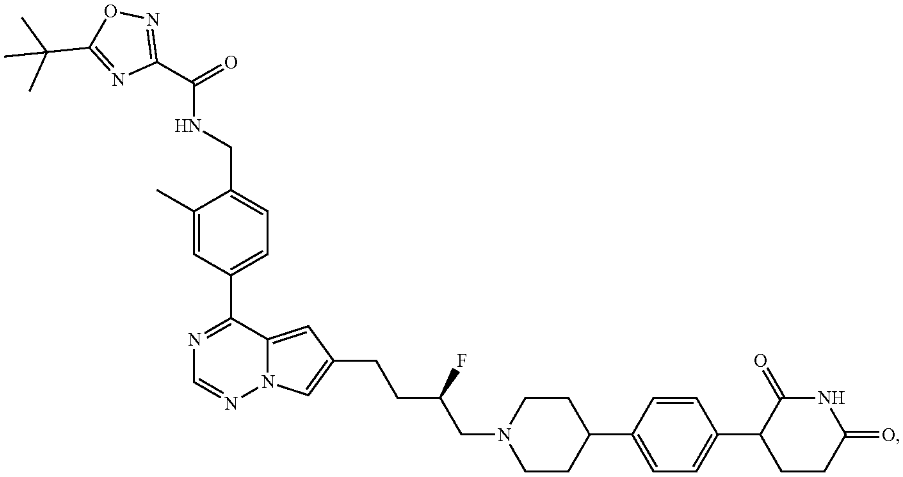
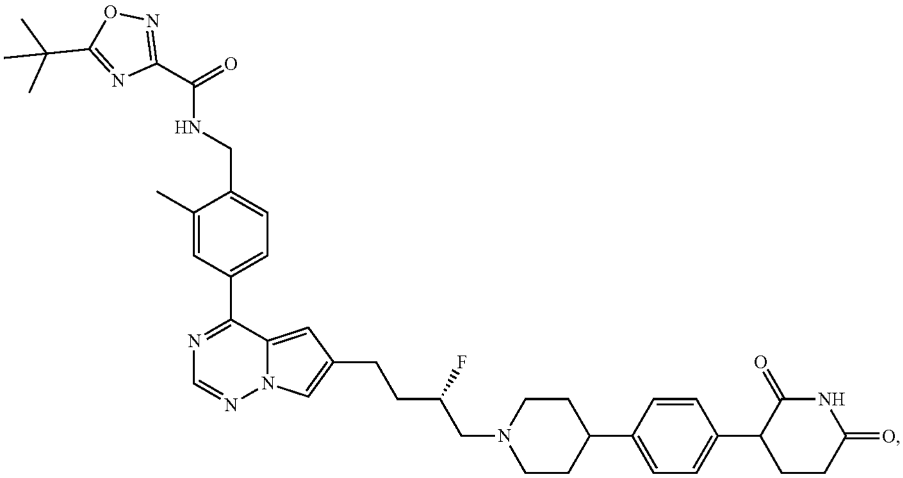

-continued
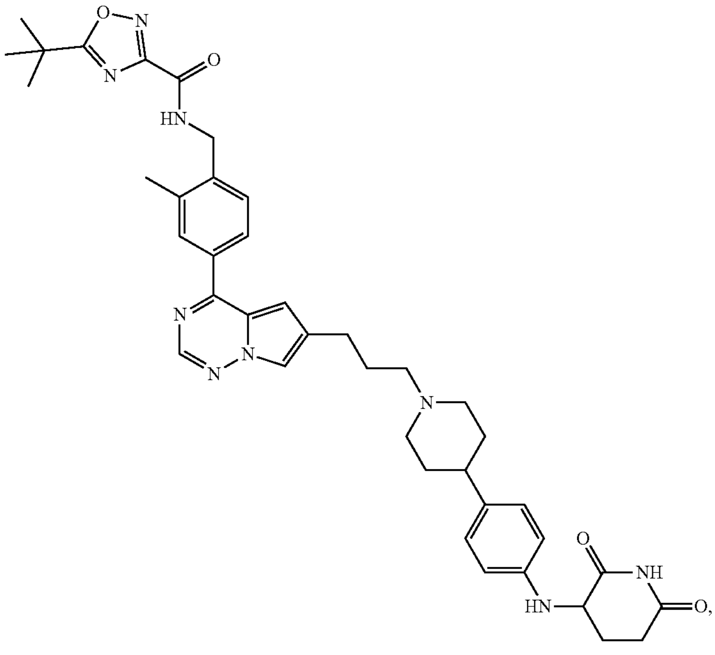
,
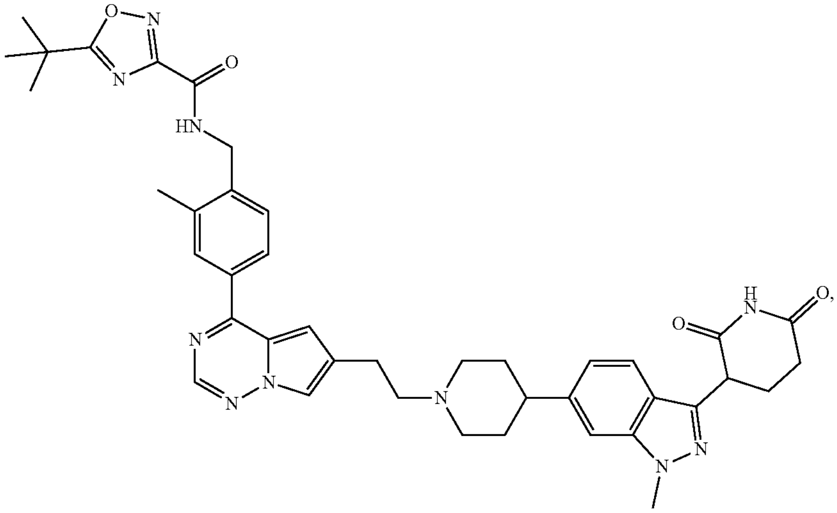
,
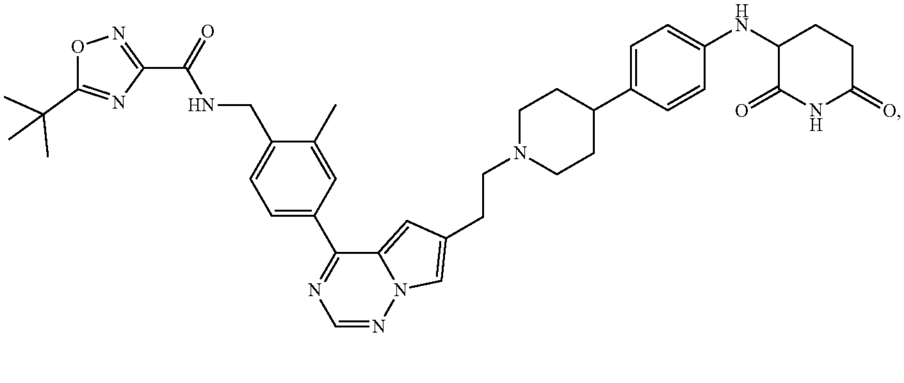
,

-continued
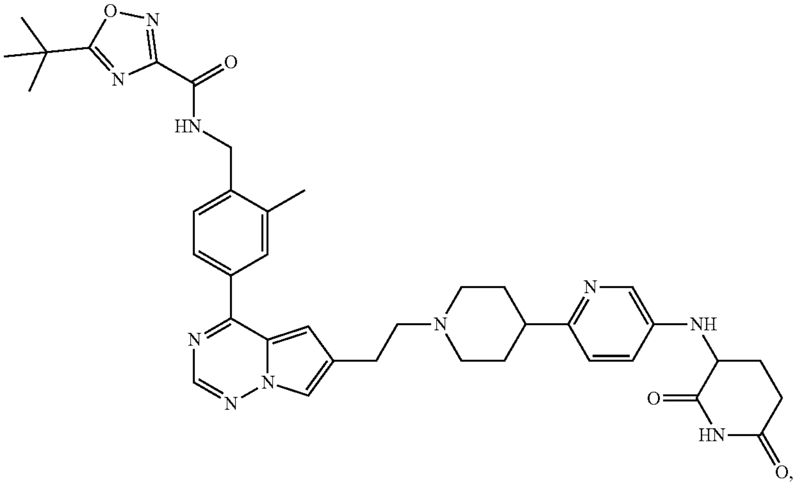
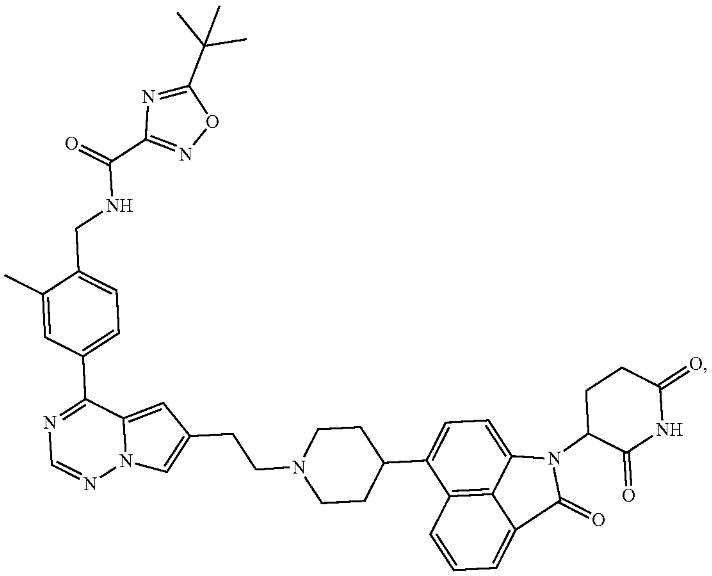
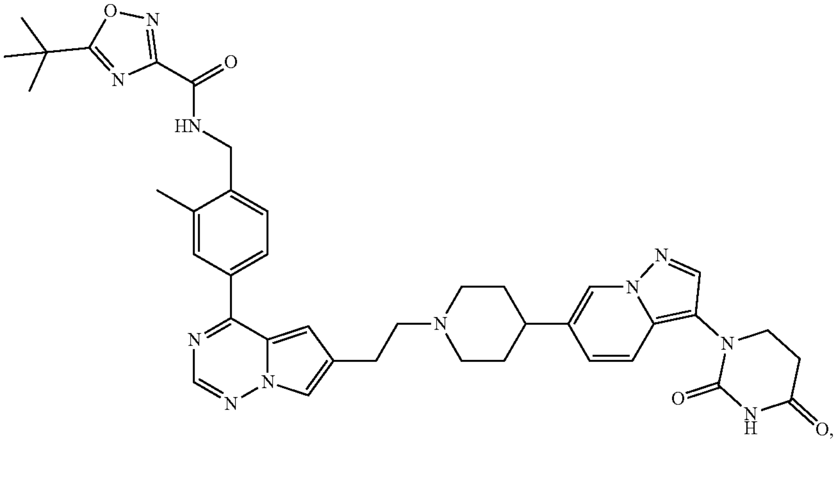

-continued
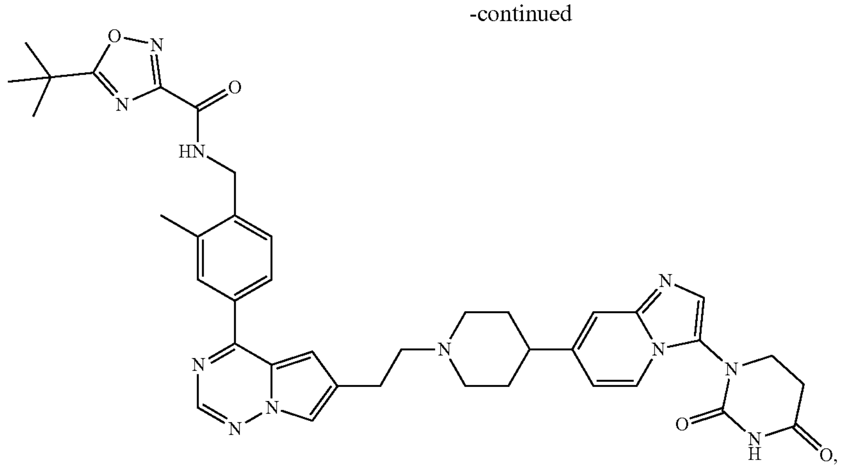
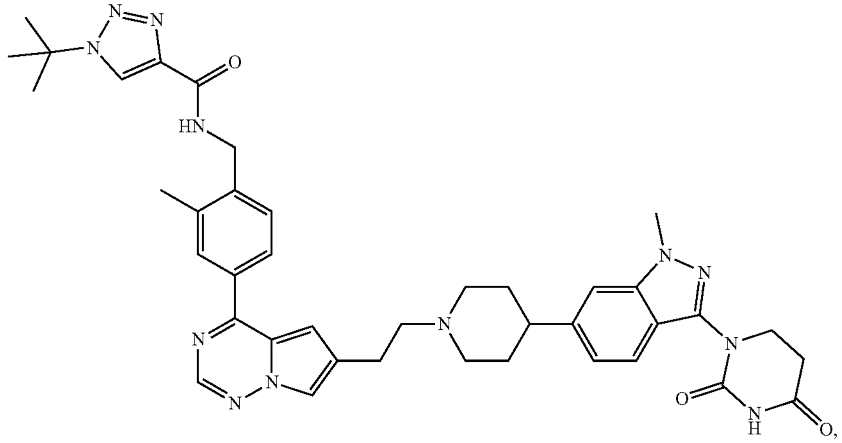
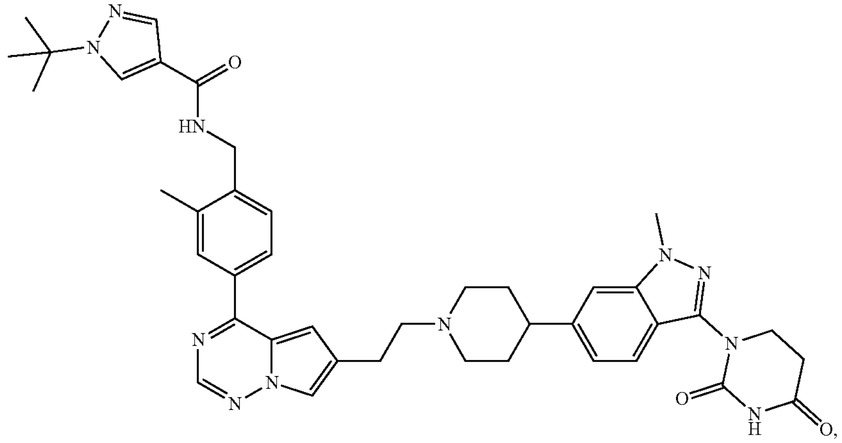

-continued
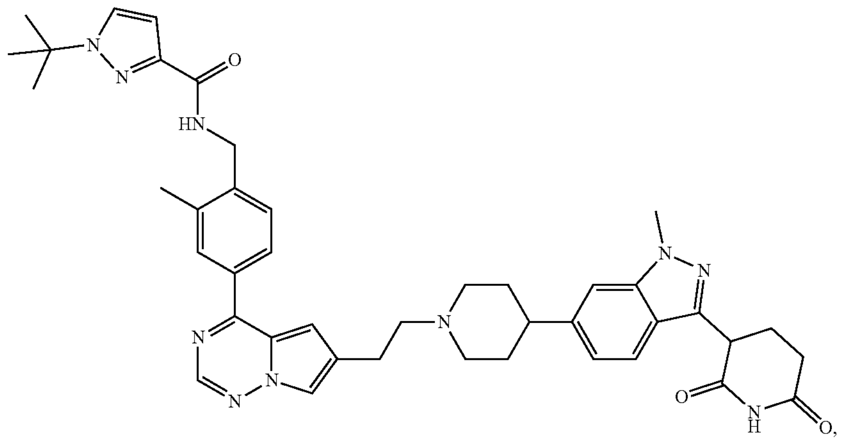
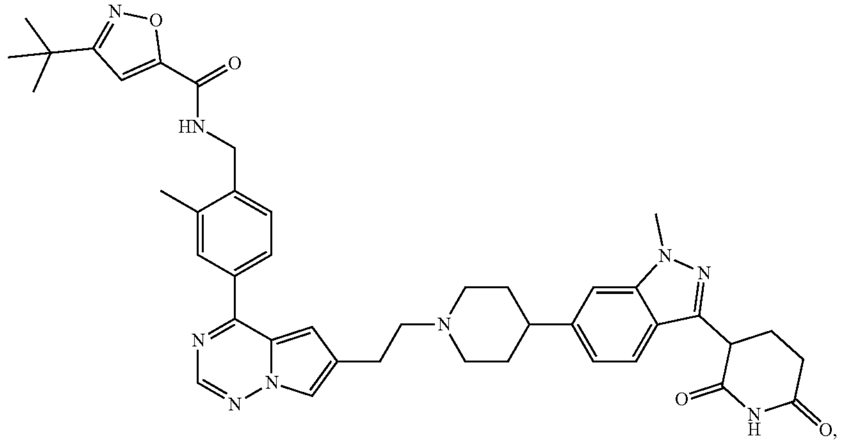
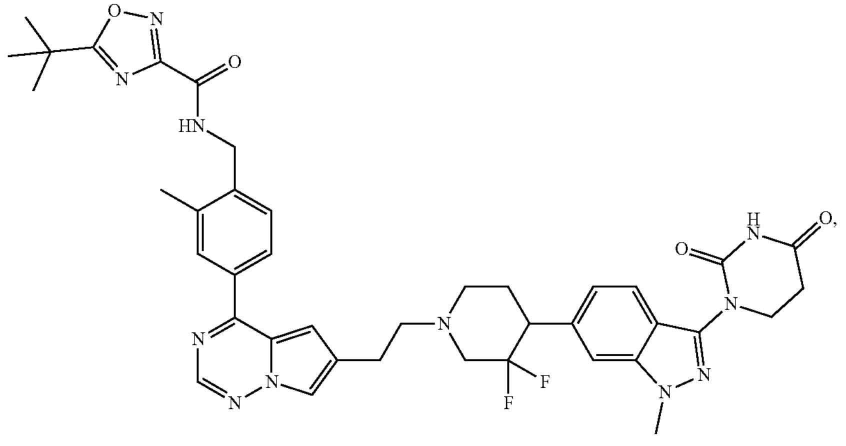

-continued
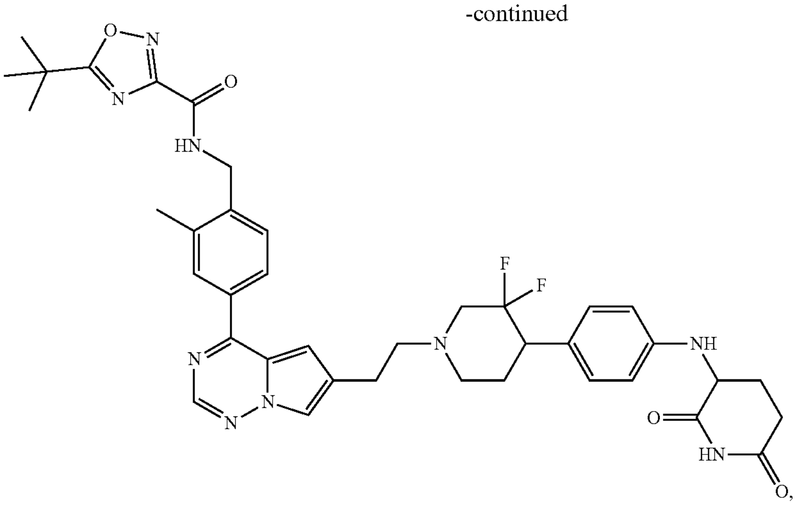
, or
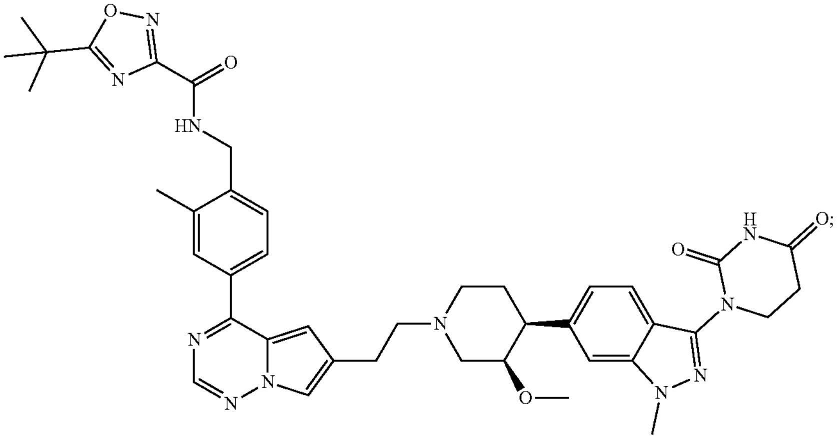
;
or a pharmaceutically acceptable salt thereof.
12. The compound of claim 1, wherein the compound is:
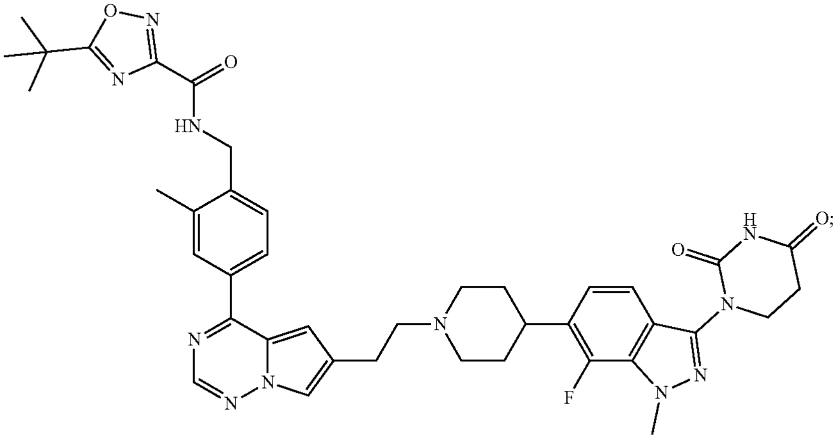 [SMILES: Cc1cc(-c2ncnn3cc(CCN4CCC(c5ccc6c(N7CCC(=O)NC7=O)nn(C)c6c5F)CC4)cc23)ccc1CNC(=O)c1noc(C(C)(C)C)n1]
;
or a pharmaceutically acceptable salt thereof.

13. The compound of claim 1, wherein the compound is:
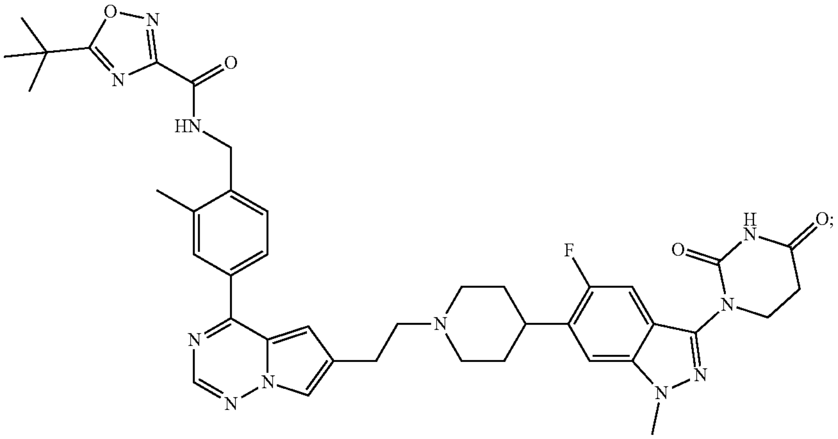 [SMILES: Cc1cc(-c2ncnn3cc(CCN4CCC(c5cc6c(cc5F)c(N5CCC(=O)NC5=O)nn6C)CC4)cc23)ccc1CNC(=O)c1noc(C(C)(C)C)n1]
or a pharmaceutically acceptable salt thereof.
14. The compound of claim 1, wherein the compound is:
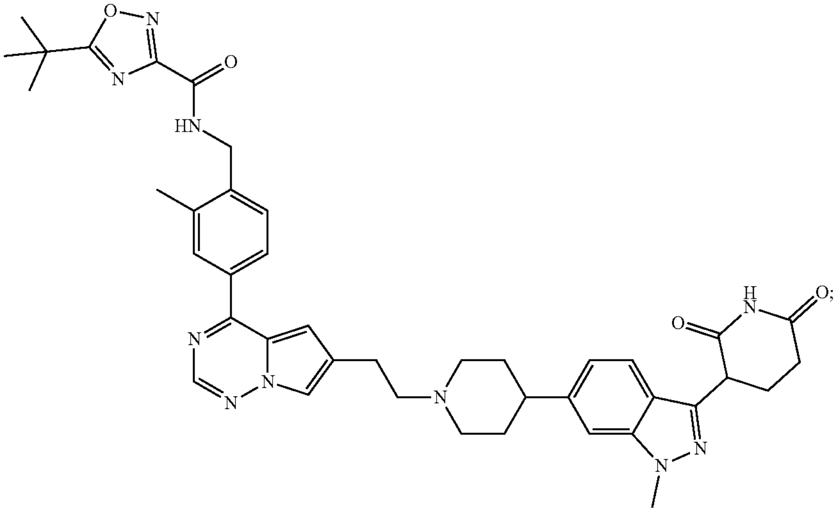 [SMILES: Cc1cc(-c2ncnn3cc(CCN4CCC(c5ccc6c(C7CCC(=O)NC7=O)nn(C)c6c5)CC4)cc23)ccc1CNC(=O)c1noc(C(C)(C)C)n1]
or a pharmaceutically acceptable salt thereof.
15. The compound of claim 1, wherein the compound is:
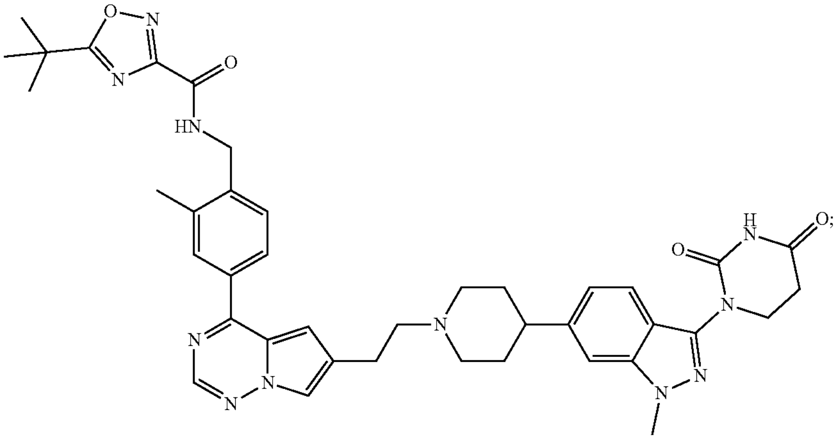 [SMILES: Cc1cc(-c2ncnn3cc(CCN4CCC(c5ccc6c(N7CCC(=O)NC7=O)nn(C)c6c5)CC4)cc23)ccc1CNC(=O)c1noc(C(C)(C)C)n1]
or a pharmaceutically acceptable salt thereof.

16. The compound of claim 1, wherein the compound is:
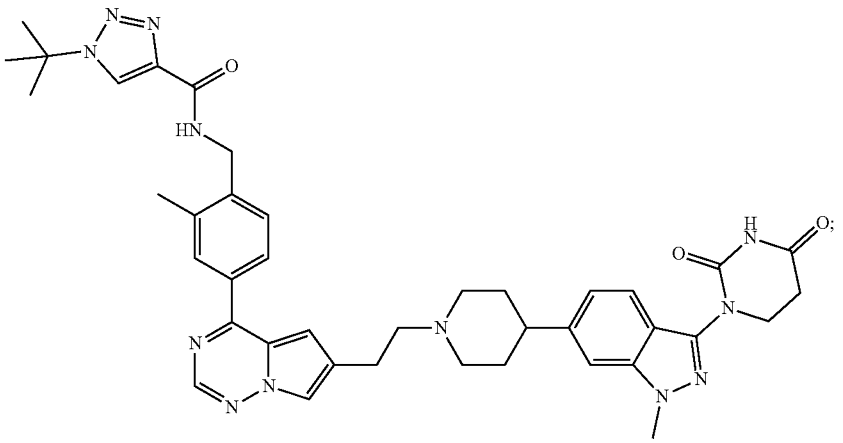 [SMILES: Cc1cc(-c2ncnn3cc(CCN4CCC(c5ccc6c(N7CCC(=O)NC7=O)nn(C)c6c5)CC4)cc23)ccc1CNC(=O)c1cn(C(C)(C)C)nn1]
or a pharmaceutically acceptable salt thereof.
17. The compound of claim 1, wherein the compound is:
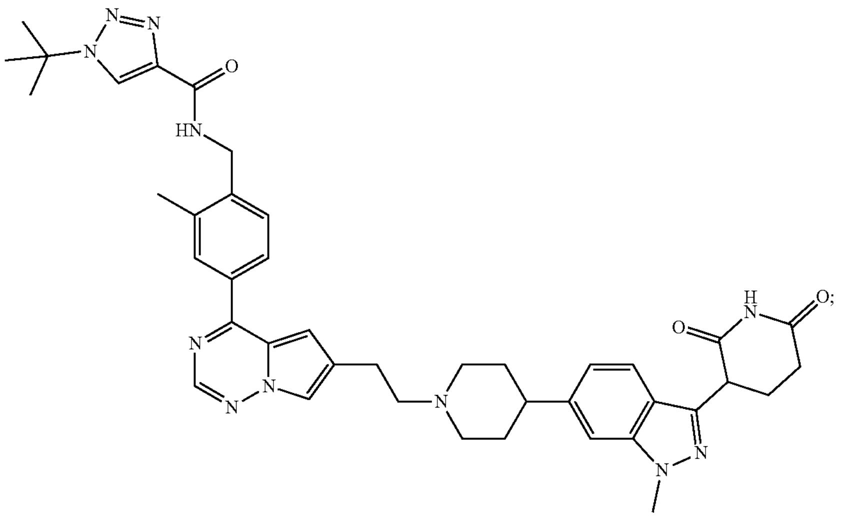 [SMILES: Cc1cc(-c2ncnn3cc(CCN4CCC(c5ccc6c(C7CCC(=O)NC7=O)nn(C)c6c5)CC4)cc23)ccc1CNC(=O)c1cn(C(C)(C)C)nn1]
or a pharmaceutically acceptable salt thereof.

18. The compound of claim 1, wherein the compound is:
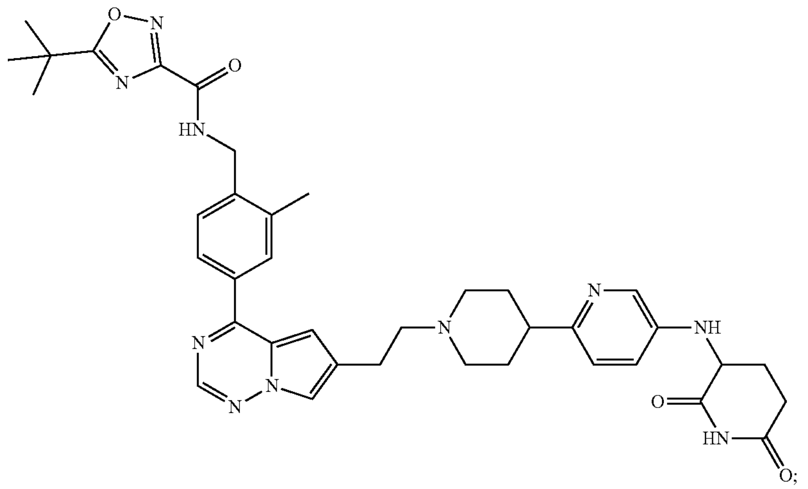 [SMILES: Cc1cc(-c2ncnn3cc(CCN4CCC(c5ccc(NC6CCC(=O)NC6=O)cn5)CC4)cc23)ccc1CNC(=O)c1noc(C(C)(C)C)n1]
or a pharmaceutically acceptable salt thereof.
19. The compound of claim 1, wherein the compound is:
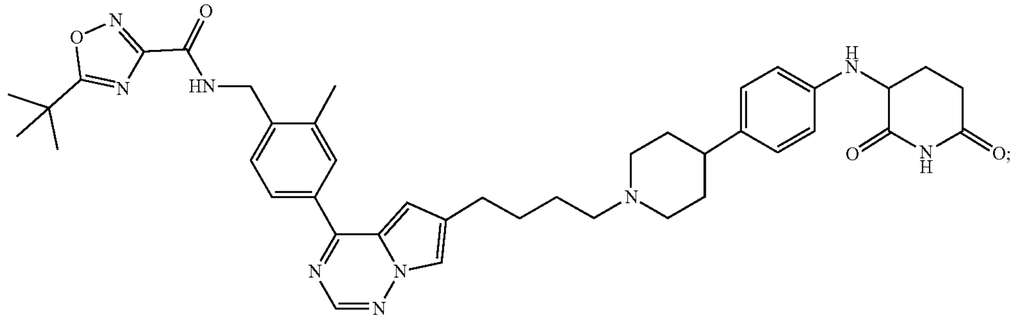 [SMILES: Cc1cc(-c2ncnn3cc(CCCCN4CCC(c5ccc(NC6CCC(=O)NC6=O)cc5)CC4)cc23)ccc1CNC(=O)c1noc(C(C)(C)C)n1]
or a pharmaceutically acceptable salt thereof.
20. The compound of claim 1, wherein the compound is:
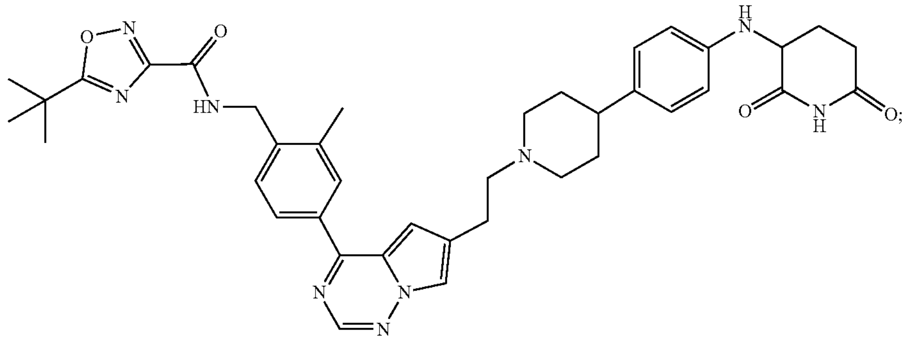 [SMILES: Cc1cc(-c2ncnn3cc(CCN4CCC(c5ccc(NC6CCC(=O)NC6=O)cc5)CC4)cc23)ccc1CNC(=O)c1noc(C(C)(C)C)n1]
or a pharmaceutically acceptable salt thereof.
* * * * *